US012551560B2

(12) United States Patent
Oakes et al.

(10) Patent No.: US 12,551,560 B2
(45) Date of Patent: Feb. 17, 2026

(54) COMPOSITIONS AND METHODS FOR USE IN IMMUNOTHERAPY

(71) Applicant: Scribe Therapeutics Inc., Alameda, CA (US)

(72) Inventors: Benjamin Oakes, El Cerrito, CA (US); Sean Higgins, Alameda, CA (US); Hannah Spinner, Boston, MA (US); Sarah Denny, San Francisco, CA (US); Brett T. Staahl, Tiburon, CA (US); Kian Taylor, Atlanta, GA (US); Katherine Baney, Berkeley, CA (US); Isabel Colin, Oakland, CA (US); Maroof Adil, Davis, CA (US); Cole Urnes, Los Alamitos, CA (US)

(73) Assignee: Scribe Therapeutics Inc., Alameda, CA (US)

( * ) Notice: Subject to any disclaimer, the term of this patent is extended or adjusted under 35 U.S.C. 154(b) by 1010 days.

(21) Appl. No.: 17/641,404

(22) PCT Filed: Sep. 9, 2020

(86) PCT No.: PCT/US2020/050008
§ 371 (c)(1),
(2) Date: Mar. 8, 2022

(87) PCT Pub. No.: WO2021/050601
PCT Pub. Date: Mar. 18, 2021

(65) Prior Publication Data

US 2023/0081117 A1 Mar. 16, 2023

Related U.S. Application Data

(60) Provisional application No. 63/075,041, filed on Sep. 4, 2020, provisional application No. 62/897,947, filed on Sep. 9, 2019.

(51) Int. Cl.

| | |
|---|---|
| ***A61K 45/06*** | (2006.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***A61K 48/00*** | (2006.01) |
| ***C07K 14/705*** | (2006.01) |
| ***C07K 14/715*** | (2006.01) |
| ***C07K 14/725*** | (2006.01) |
| ***C12N 9/22*** | (2006.01) |
| ***C12N 15/11*** | (2006.01) |

(52) U.S. Cl.

CPC .............. *A61K 45/06* (2013.01); *A61K 40/11* (2025.01); *A61K 40/31* (2025.01); *A61K 40/32* (2025.01); *A61K 40/4211* (2025.01); *A61K 48/005* (2013.01); *C07K 14/7051* (2013.01); *C07K 14/70517* (2013.01); *C07K 14/70521* (2013.01); *C07K 14/70578* (2013.01); *C07K 14/70596* (2013.01); *C07K 14/7151* (2013.01); *C12N 9/22* (2013.01); *C12N 15/11* (2013.01)

(58) Field of Classification Search

CPC ....................................................... C12N 9/22
See application file for complete search history.

(56) References Cited

U.S. PATENT DOCUMENTS

| | | | |
|---|---|---|---|
| 5,199,942 | A | 4/1993 | Gillis |
| 5,405,783 | A | 4/1995 | Pirrung et al. |
| 5,412,087 | A | 5/1995 | McGall et al. |
| 5,445,934 | A | 8/1995 | Fodor et al. |
| 5,641,870 | A | 6/1997 | Rinderknecht et al. |
| 5,695,937 | A | 12/1997 | Kinzler et al. |
| 6,410,319 | B1 | 6/2002 | Raubitschek et al. |
| 6,451,995 | B1 | 9/2002 | Cheung et al. |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen |
| 7,446,190 | B2 | 11/2008 | Sadelain et al. |
| 7,446,191 | B2 | 11/2008 | Jensen |
| 8,324,353 | B2 | 12/2012 | Jensen |
| 8,339,645 | B2 | 12/2012 | Nakawaki |

(Continued)

FOREIGN PATENT DOCUMENTS

| | | | |
|---|---|---|---|
| CN | 109312336 | A | 2/2019 |
| CN | 109688820 | A | 4/2019 |

(Continued)

OTHER PUBLICATIONS

US 8,252,592 B2, 08/2012, Sadelain et al. (withdrawn)

(Continued)

*Primary Examiner* — Christopher M Babic
*Assistant Examiner* — Jennifer S Spence
(74) *Attorney, Agent, or Firm* — COOLEY LLP

(57) ABSTRACT

Provided herein are CasX:gNA systems, and compositions and methods relating thereto, the systems comprising CasX proteins, guide nucleic acids (gNAs), and optionally donor template nucleic acids useful for the modification cell genes encoding proteins involved in antigen processing, antigen presentation, antigen recognition, and/or antigen response, as well as methods of producing and using populations of cells comprising these modified genes. In some embodiments, the modified cells further express chimeric antigen receptors (CAR) or engineered T cell receptors (TCR). Such systems are useful for preparing cells for immunotherapy.

37 Claims, 321 Drawing Sheets

Specification includes a Sequence Listing.

(56) References Cited

U.S. PATENT DOCUMENTS

| | | | |
|---|---|---|---|
| 8,398,282 B2 | 3/2013 | Kuhlman et al. | |
| 8,479,118 B2 | 7/2013 | Lyndersay et al. | |
| 9,855,297 B2 | 1/2018 | Duchateau et al. | |
| 9,890,393 B2 | 2/2018 | Duchateau et al. | |
| 10,570,415 B2 | 2/2020 | Doudna et al. | |
| 11,013,767 B2 | 5/2021 | Terrett et al. | |
| 11,560,555 B2 | 1/2023 | Oakes et al. | |
| 11,795,472 B2 | 10/2023 | Doudna et al. | |
| 11,873,504 B2 | 1/2024 | Doudna et al. | |
| 12,084,692 B2 | 9/2024 | Oakes et al. | |
| 12,163,125 B2 | 12/2024 | Vijayakumar et al. | |
| 2002/0131960 A1 | 9/2002 | Sadelain et al. | |
| 2013/0149337 A1 | 6/2013 | Cooper et al. | |
| 2013/0287748 A1 | 10/2013 | June et al. | |
| 2017/0369870 A1 | 12/2017 | Gill et al. | |
| 2018/0100158 A1 | 4/2018 | Del'guidice et al. | |
| 2018/0141992 A1 | 5/2018 | Cowan et al. | |
| 2018/0258424 A1 | 9/2018 | Greenberg et al. | |
| 2018/0325955 A1 | 11/2018 | Terrett et al. | |
| 2018/0362975 A1 | 12/2018 | Chen et al. | |
| 2019/0024075 A1 | 1/2019 | Gourguechon et al. | |
| 2019/0136230 A1 | 5/2019 | Sather et al. | |
| 2020/0181608 A1 | 6/2020 | Peng et al. | |
| 2020/0216805 A1 | 7/2020 | Yuan et al. | |
| 2020/0407737 A1* | 12/2020 | Hummel | C12N 9/22 |
| 2022/0081681 A1 | 3/2022 | Oakes et al. | |
| 2022/0220508 A1 | 7/2022 | Oakes et al. | |
| 2024/0026385 A1 | 1/2024 | Vijayakumar et al. | |
| 2024/0167052 A1 | 5/2024 | Doudna et al. | |
| 2024/0376462 A1 | 11/2024 | Vijayakumar et al. | |
| 2025/0011756 A1 | 1/2025 | Vijayakumar et al. | |
| 2025/0043262 A1 | 2/2025 | Oakes et al. | |
| 2025/0136962 A1 | 5/2025 | Oakes et al. | |

FOREIGN PATENT DOCUMENTS

| | | | | |
|---|---|---|---|---|
| CN | 110023494 A | 7/2019 | | |
| EP | 3 441 461 A1 | 2/2019 | | |
| KR | 10-2018-0051625 A | 5/2018 | | |
| WO | WO-2010/075303 A1 | 7/2010 | | |
| WO | WO-2012/068627 A1 | 5/2012 | | |
| WO | WO-2012/129514 A1 | 9/2012 | | |
| WO | WO-2013/071154 A1 | 5/2013 | | |
| WO | WO-2013/123061 A1 | 8/2013 | | |
| WO | WO-2013/126726 A1 | 8/2013 | | |
| WO | WO-2013/166321 A1 | 11/2013 | | |
| WO | WO-2014/031687 A1 | 2/2014 | | |
| WO | WO-2014/165707 A2 | 10/2014 | | |
| WO | WO-2014/165707 A3 | 10/2014 | | |
| WO | WO-2017/068077 A1 | 4/2017 | | |
| WO | WO-2018/064371 A1 | 4/2018 | | |
| WO | WO-2018/068135 A1 | 4/2018 | | |
| WO | WO-2018/132783 A1 | 7/2018 | | |
| WO | WO-2018/152418 A1 | 8/2018 | | |
| WO | WO-2018/195555 A1 | 10/2018 | | |
| WO | WO-2019/046285 A1 | 3/2019 | | |
| WO | WO-2019/051278 A1 | 3/2019 | | |
| WO | WO-2019084148 A1 * | 5/2019 | | C12N 15/102 |
| WO | WO-2019/118516 A1 | 6/2019 | | |
| WO | WO-2019/152519 A1 | 8/2019 | | |
| WO | WO-2020/023529 A1 | 1/2020 | | |
| WO | WO-2020/041456 A1 | 2/2020 | | |
| WO | WO-2020041387 A1 * | 2/2020 | | C12N 9/90 |
| WO | WO-2020/247882 A1 | 12/2020 | | |
| WO | WO-2021/050601 A1 | 3/2021 | | |

OTHER PUBLICATIONS

Aguilera, T.A. et al. (Jun. 2009). "Systemic in vivo distribution of activatable cell penetrating peptides is superior to that of cell penetrating peptides," Integr. Biol. (Camb) 1(5-6):371-381. Published online May 11, 2009.

Al-Lazikani, B. et al. (1997). "Standard conformations for the canonical structures of immunoglobulins," JMB 273:927-948.

Altschul, S.F. et al. (1990). "Basic local alignment search tool," J. Mol. Biol, 215:403-410.

Barrett, D.M. et al. (2015). "Chimeric antigen receptor and TCR Modified T cells Enter Main Street and Wall Street," J. Immunol. 195:755-761.

Bird, R.E. et al. (1988). "Single-chain antigen-binding proteins," Science 242:423-426.

Burstein, D. et al. (Feb. 2017). "New CRISPR-Cas systems from uncultivated microbes," Nature 542:237-241. Published online Dec. 22, 2016, with Supplemental Materials, 28 total pages.

Chen, B. et al. (2003). "Influence of histidine on the stability and physical properties of a fully human (antibody in aqueous and solid forms," Pharm. Res. 20:1952-1960.

Genbank Accession No. BAG36664.1 (2008). Unnamed protein product (*Homo sapiens*), 2 total pages.

Genbank Accession No. AAA62478.2 (1999). Induced by lymphocyte activation; similar to human receptor protein encoded by GenBank accession No. U03397 (*Homo sapiens*), 2 total pages.

Ghirlando, R. et al. (1999). "Glycosylation of human IgG-Fc: influences on structure revealed by differential scanning microcalorimetry," Immunol Letters 68:47-52.

Huston, J.S. et al. (1988). "Protein engineering of antibody binding sites: Recovery of specific activity in an anti-digoxin single-chain Fv analogue produced in *Escherichia coli*," PNAS 85:5879-5883.

International Search Report mailed on Feb. 10, 2021, for PCT Application No. PCT/US2020/050008, filed on Sep. 9, 2020, 11 pages.

Kotin, R.M. (1994). "Prospects for the use of adeno-associated virus as a vector for human gene therapy," Human Gene Therapy 5:793-801.

Kamiya, T. et al. (2018). "A novel method to generate T-cell receptor-deficient chimeric antigen receptor T cells," Blood Advances 2:517-528.

Liu, J.J. et al. "CasX enzymes comprise a distinct family of RNA-guided genome editors," Nature 566:218-223. Published online Feb. 4, 2019.

Liu, J.J. et al. CasX enzymes comprise a distinct family of RNA-guided genome editors, Nature 568:E8-E10. (Author correction: published online Apr. 3, 2019).

Mandal, P.K. et al. (2014). "Efficient ablation of genes in human hematopoietic stem and effector cells using CRISPR/Cas9," Cell Stem Cell. 15:643-652.

Murray, A. et al. (2002). "Epitope Affinity Chromatography and Biophysical Studies of Monoclonal Antibodies and Recombinant Antibody Fragments," J. Chromatogr Sci 40:343-349.

Noguchi, H. et al. (Jul. 2003). "PDX-1 protein containing its own antennapedia-like protein transduction domain can transduce pancreatic duct and islet cells," Diabetes 52:1732-1737.

Qi, L.S. et al. (Feb. 2013). "Repurposing CRISPR as an RNA-guided platform for sequence-specific control of gene expression," Cell 152:1173-1183.

Razeghian, E. et al. (2021). "A deep insight into CRISPR/Cas9 application in CAR-T cell-based tumor immunotherapies," Stem Cell Research & Therapy 12:428, 17 total pages.

Ren, J. et al. (2016). "Multiplex Genome Editing to Generate Universal CAR T Cells Resistant to PD1 Inhibition," Clinical Cancer Research 23:2255-2266.

Roberson, E.D.O. et al. (2019). "A catalog of CasX genome editing sites in common model organisms," BMC Genomics 20:1-5.

Roth, T.L. et al. (2018). "Reprogramming human T cell function and specificity with non-viral genome targeting," Nature 559(7714):405-409, with Extended Data, 41 total pages.

Rupp, L.J. et al. (2017). "CRISPR/Cas9-mediated PD-1 disruption enhances anti-tumor efficacy of human chimeric antigen receptor T cells," Sci. Rep. 7:737, 10 total pages.

Schumann, K. et al. (2015). "Generation of knock-in primary human T cells using Cas9 ribonucleoproteins," PNAS 112:10437-10442.

Smith, T.F. et al. (1981). "Comparison of biosequences," Adv. Appl. Math. 2:482-489.

(56) References Cited

OTHER PUBLICATIONS

Themeli, M. et al. (2013). "Generation of tumor-targeted human T lymphocytes from induced pluripotent stem cells for cancer therapy," Nat. Biotechnol. 31:928-933.
Tréhin, R. et al. (Jul. 2004). "Cellular uptake but low permeation of human calcitonin-derived cell penetrating peptides and Tat(47-57) through well-differentiated epithelial models," Pharm. Res. 21:1248-1256.
Wender, P.A. et al. (Nov. 2000). "The design, synthesis, and evaluation of molecules that enable or enhance cellular uptake: peptoid molecular transporters," PNAS 97:13003-13008.
Written Opinion of the International Searching Authority mailed on Feb. 10, 2021, for PCT Application No. PCT/US2020/050008, filed on Sep. 9, 2020, 13 pages.
Xu, H. et al. (2019). "Targeted Disruption of HLA Genes via CRISPR-Cas9 Generates IPSCs with Enhanced Immune Compatibility," Cell Stem Cell. 24:566-578.
Yang, H. et al. (May 2019). "CasX: a new and small CRISPR gene-editing protein," Cell Res. 29:345-1346. Published online Apr. 16, 2019.
Yoon, D.H. et al. (2018). "Incorporation of Immune Checkpoint Blockade into Chimeric Antigen Receptor T Cells (CAR-Ts): Combination or Built-In CAR-T," Int. J. Mol. Sci. 19:340, 16 total pages.
Zhang, J. et al. (Jun. 1997). "PowerBLAST: a new network BLAST application for interactive or automated sequence analysis and annotation," Genome Res. 7:649-656.
U.S. Appl. No. 18/869,765, filed Nov. 26, 2024, by Zhou et al. (Copy not attached).

* cited by examiner pSTX34 plasmid organization

FIG. 35: Table 3A: Targeting Sequences for B2M

| Name | SEQ ID NO. | Name | SEQ ID NO. |
|---|---|---|---|
| GTCN_0 | 725 | CTCN_844 | 3996 |
| GTCN_1 | 726 | TTCN_855 | 3997 |
| TTCN_0 | 727 | GTCN_456 | 3998 |
| GTCN_2 | 728 | TTCN_856 | 3999 |
| TTCN_1 | 729 | CTCN_845 | 4000 |
| ATCN_0 | 730 | GTCN_457 | 4001 |
| TTCN_2 | 731 | ATCN_517 | 4002 |
| GTCN_3 | 732 | ATCN_518 | 4003 |
| ATCN_1 | 733 | CTCN_846 | 4004 |
| CTCN_0 | 734 | ATCN_519 | 4005 |
| ATCN_2 | 735 | GTCN_458 | 4006 |
| GTCN_4 | 736 | CTCN_847 | 4007 |
| TTCN_3 | 737 | GTCN_459 | 4008 |
| GTCN_5 | 738 | TTCN_857 | 4009 |
| TTCN_4 | 739 | ATCN_520 | 4010 |
| TTCN_5 | 740 | CTCN_848 | 4011 |
| ATCN_3 | 741 | GTCN_460 | 4012 |
| ATCN_4 | 742 | CTCN_849 | 4013 |
| TTCN_6 | 743 | TTCN_858 | 4014 |
| GTCN_6 | 744 | TTCN_859 | 4015 |
| TTCN_7 | 745 | TTCN_860 | 4016 |
| TTCN_8 | 746 | TTCN_861 | 4017 |
| CTCN_1 | 747 | GTCN_461 | 4018 |
| TTCN_9 | 748 | CTCN_850 | 4019 |
| TTCN_10 | 749 | CTCN_851 | 4020 |
| TTCN_11 | 750 | CTCN_852 | 4021 |
| TTCN_12 | 751 | GTCN_462 | 4022 |
| GTCN_7 | 752 | CTCN_853 | 4023 |
| TTCN_13 | 753 | GTCN_463 | 4024 |
| GTCN_8 | 754 | GTCN_464 | 4025 |
| TTCN_18 | 755 | GTCN_465 | 4026 |
| TTCN_19 | 756 | GTCN_466 | 4027 |
| CTCN_6 | 757 | ATCN_521 | 4028 |
| ATCN_6 | 758 | CTCN_854 | 4029 |
| TTCN_20 | 759 | GTCN_467 | 4030 |
| TTCN_21 | 760 | TTCN_862 | 4031 |
| TTCN_22 | 761 | TTCN_863 | 4032 |
| CTCN_7 | 762 | GTCN_468 | 4033 |
| CTCN_8 | 763 | TTCN_864 | 4034 |
| CTCN_9 | 764 | CTCN_855 | 4035 |
| TTCN_23 | 765 | ATCN_522 | 4036 |
| ATCN_7 | 766 | GTCN_469 | 4037 |
| TTCN_24 | 767 | CTCN_856 | 4038 |
| CTCN_10 | 768 | CTCN_857 | 4039 |
| ATCN_8 | 769 | CTCN_858 | 4040 |
| TTCN_25 | 770 | CTCN_859 | 4041 |
| CTCN_11 | 771 | CTCN_860 | 4042 |
| TTCN_26 | 772 | CTCN_861 | 4043 |
| CTCN_12 | 773 | TTCN_865 | 4044 |
| GTCN_10 | 774 | CTCN_862 | 4045 |
| ATCN_9 | 775 | ATCN_523 | 4046 |

| | | | |
|---|---|---|---|
| CTCN_13 | 776 | CTCN_863 | 4047 |
| TTCN_27 | 777 | GTCN_470 | 4048 |
| GTCN_11 | 778 | CTCN_864 | 4049 |
| TTCN_28 | 779 | CTCN_865 | 4050 |
| CTCN_14 | 780 | CTCN_866 | 4051 |
| TTCN_29 | 781 | CTCN_867 | 4052 |
| ATCN_10 | 782 | GTCN_471 | 4053 |
| ATCN_11 | 783 | TTCN_866 | 4054 |
| TTCN_30 | 784 | CTCN_868 | 4055 |
| ATCN_12 | 785 | CTCN_869 | 4056 |
| CTCN_15 | 786 | CTCN_870 | 4057 |
| GTCN_12 | 787 | CTCN_871 | 4058 |
| CTCN_16 | 788 | CTCN_872 | 4059 |
| CTCN_17 | 789 | CTCN_873 | 4060 |
| CTCN_18 | 790 | CTCN_874 | 4061 |
| CTCN_19 | 791 | CTCN_875 | 4062 |
| ATCN_13 | 792 | CTCN_876 | 4063 |
| TTCN_31 | 793 | GTCN_472 | 4064 |
| ATCN_14 | 794 | TTCN_867 | 4065 |
| GTCN_13 | 795 | TTCN_868 | 4066 |
| CTCN_20 | 796 | CTCN_877 | 4067 |
| ATCN_15 | 797 | TTCN_869 | 4068 |
| TTCN_32 | 798 | CTCN_878 | 4069 |
| CTCN_21 | 799 | GTCN_473 | 4070 |
| TTCN_33 | 800 | ATCN_524 | 4071 |
| TTCN_34 | 801 | ATCN_525 | 4072 |
| GTCN_14 | 802 | CTCN_879 | 4073 |
| CTCN_22 | 803 | TTCN_870 | 4074 |
| CTCN_23 | 804 | CTCN_880 | 4075 |
| ATCN_16 | 805 | TTCN_871 | 4076 |
| CTCN_24 | 806 | GTCN_474 | 4077 |
| CTCN_25 | 807 | TTCN_872 | 4078 |
| ATCN_17 | 808 | CTCN_881 | 4079 |
| ATCN_18 | 809 | CTCN_882 | 4080 |
| CTCN_26 | 810 | GTCN_475 | 4081 |
| CTCN_27 | 811 | GTCN_476 | 4082 |
| CTCN_28 | 812 | CTCN_883 | 4083 |
| GTCN_15 | 813 | GTCN_477 | 4084 |
| CTCN_29 | 814 | GTCN_478 | 4085 |
| GTCN_16 | 815 | GTCN_479 | 4086 |
| CTCN_30 | 816 | ATCN_526 | 4087 |
| ATCN_19 | 817 | GTCN_480 | 4088 |
| CTCN_31 | 818 | CTCN_884 | 4089 |
| TTCN_35 | 819 | CTCN_885 | 4090 |
| GTCN_17 | 820 | CTCN_886 | 4091 |
| CTCN_32 | 821 | TTCN_873 | 4092 |
| CTCN_33 | 822 | CTCN_887 | 4093 |
| CTCN_34 | 823 | TTCN_874 | 4094 |
| GTCN_18 | 824 | CTCN_888 | 4095 |
| TTCN_36 | 825 | TTCN_875 | 4096 |
| GTCN_19 | 826 | CTCN_889 | 4097 |
| CTCN_35 | 827 | CTCN_890 | 4098 |
| CTCN_36 | 828 | CTCN_891 | 4099 |

FIG. 35 (continued)

| | | | |
|---|---|---|---|
| GTCN_20 | 829 | GTCN_481 | 4100 |
| GTCN_21 | 830 | CTCN_892 | 4101 |
| ATCN_20 | 831 | GTCN_482 | 4102 |
| CTCN_37 | 832 | CTCN_893 | 4103 |
| CTCN_38 | 833 | TTCN_876 | 4104 |
| TTCN_37 | 834 | CTCN_894 | 4105 |
| ATCN_21 | 835 | GTCN_483 | 4106 |
| CTCN_39 | 836 | CTCN_895 | 4107 |
| TTCN_38 | 837 | GTCN_484 | 4108 |
| CTCN_40 | 838 | GTCN_485 | 4109 |
| TTCN_39 | 839 | CTCN_896 | 4110 |
| ATCN_22 | 840 | TTCN_877 | 4111 |
| GTCN_22 | 841 | GTCN_486 | 4112 |
| TTCN_40 | 842 | CTCN_897 | 4113 |
| CTCN_41 | 843 | CTCN_898 | 4114 |
| TTCN_41 | 844 | GTCN_487 | 4115 |
| TTCN_42 | 845 | TTCN_878 | 4116 |
| GTCN_23 | 846 | GTCN_488 | 4117 |
| CTCN_42 | 847 | TTCN_879 | 4118 |
| CTCN_43 | 848 | GTCN_489 | 4119 |
| TTCN_43 | 849 | CTCN_899 | 4120 |
| TTCN_44 | 850 | GTCN_490 | 4121 |
| GTCN_24 | 851 | CTCN_900 | 4122 |
| GTCN_25 | 852 | TTCN_880 | 4123 |
| CTCN_44 | 853 | GTCN_491 | 4124 |
| GTCN_26 | 854 | TTCN_881 | 4125 |
| TTCN_45 | 855 | ATCN_527 | 4126 |
| TTCN_46 | 856 | TTCN_882 | 4127 |
| CTCN_45 | 857 | TTCN_883 | 4128 |
| GTCN_27 | 858 | TTCN_884 | 4129 |
| TTCN_47 | 859 | ATCN_528 | 4130 |
| TTCN_48 | 860 | GTCN_492 | 4131 |
| TTCN_49 | 861 | TTCN_885 | 4132 |
| TTCN_50 | 862 | GTCN_493 | 4133 |
| GTCN_28 | 863 | ATCN_529 | 4134 |
| TTCN_51 | 864 | TTCN_886 | 4135 |
| ATCN_23 | 865 | GTCN_494 | 4136 |
| ATCN_24 | 866 | GTCN_495 | 4137 |
| ATCN_25 | 867 | TTCN_887 | 4138 |
| TTCN_52 | 868 | ATCN_530 | 4139 |
| CTCN_46 | 869 | TTCN_888 | 4140 |
| ATCN_26 | 870 | ATCN_531 | 4141 |
| ATCN_27 | 871 | ATCN_532 | 4142 |
| ATCN_28 | 872 | TTCN_889 | 4143 |
| CTCN_47 | 873 | CTCN_901 | 4144 |
| ATCN_29 | 874 | CTCN_902 | 4145 |
| TTCN_53 | 875 | ATCN_533 | 4146 |
| TTCN_54 | 876 | TTCN_890 | 4147 |
| GTCN_29 | 877 | TTCN_891 | 4148 |
| CTCN_48 | 878 | CTCN_903 | 4149 |
| GTCN_30 | 879 | ATCN_534 | 4150 |
| GTCN_31 | 880 | TTCN_892 | 4151 |
| ATCN_30 | 881 | ATCN_535 | 4152 |

| | | | |
|---|---|---|---|
| TTCN_55 | 882 | ATCN_536 | 4153 |
| TTCN_56 | 883 | CTCN_904 | 4154 |
| TTCN_57 | 884 | ATCN_537 | 4155 |
| ATCN_31 | 885 | TTCN_893 | 4156 |
| CTCN_49 | 886 | GTCN_496 | 4157 |
| CTCN_50 | 887 | CTCN_905 | 4158 |
| GTCN_32 | 888 | TTCN_894 | 4159 |
| TTCN_58 | 889 | TTCN_895 | 4160 |
| TTCN_59 | 890 | TTCN_896 | 4161 |
| CTCN_51 | 891 | CTCN_906 | 4162 |
| GTCN_33 | 892 | ATCN_538 | 4163 |
| CTCN_52 | 893 | TTCN_897 | 4164 |
| TTCN_60 | 894 | CTCN_907 | 4165 |
| CTCN_53 | 895 | CTCN_908 | 4166 |
| CTCN_54 | 896 | GTCN_497 | 4167 |
| TTCN_61 | 897 | TTCN_898 | 4168 |
| CTCN_55 | 898 | CTCN_909 | 4169 |
| CTCN_56 | 899 | TTCN_899 | 4170 |
| TTCN_62 | 900 | CTCN_910 | 4171 |
| GTCN_34 | 901 | CTCN_911 | 4172 |
| TTCN_63 | 902 | TTCN_900 | 4173 |
| TTCN_64 | 903 | ATCN_539 | 4174 |
| CTCN_57 | 904 | CTCN_912 | 4175 |
| TTCN_65 | 905 | TTCN_901 | 4176 |
| CTCN_58 | 906 | TTCN_902 | 4177 |
| CTCN_59 | 907 | CTCN_913 | 4178 |
| TTCN_66 | 908 | ATCN_540 | 4179 |
| TTCN_67 | 909 | CTCN_914 | 4180 |
| CTCN_60 | 910 | CTCN_915 | 4181 |
| CTCN_61 | 911 | CTCN_916 | 4182 |
| CTCN_62 | 912 | ATCN_541 | 4183 |
| CTCN_63 | 913 | CTCN_917 | 4184 |
| CTCN_64 | 914 | GTCN_498 | 4185 |
| CTCN_65 | 915 | CTCN_918 | 4186 |
| GTCN_35 | 916 | GTCN_499 | 4187 |
| CTCN_66 | 917 | TTCN_903 | 4188 |
| CTCN_67 | 918 | GTCN_500 | 4189 |
| GTCN_36 | 919 | CTCN_919 | 4190 |
| CTCN_68 | 920 | CTCN_920 | 4191 |
| CTCN_69 | 921 | GTCN_501 | 4192 |
| CTCN_70 | 922 | CTCN_921 | 4193 |
| CTCN_71 | 923 | CTCN_922 | 4194 |
| TTCN_68 | 924 | CTCN_923 | 4195 |
| CTCN_72 | 925 | ATCN_542 | 4196 |
| GTCN_37 | 926 | ATCN_543 | 4197 |
| GTCN_38 | 927 | CTCN_924 | 4198 |
| TTCN_69 | 928 | CTCN_925 | 4199 |
| CTCN_73 | 929 | CTCN_926 | 4200 |
| GTCN_39 | 930 | ATCN_544 | 4201 |
| CTCN_74 | 931 | CTCN_927 | 4202 |
| CTCN_75 | 932 | CTCN_928 | 4203 |
| CTCN_76 | 933 | CTCN_929 | 4204 |
| CTCN_77 | 934 | GTCN_502 | 4205 |

FIG. 35 (continued)

| | | | |
|---|---|---|---|
| CTCN_78 | 935 | GTCN_503 | 4206 |
| ATCN_32 | 936 | CTCN_930 | 4207 |
| CTCN_79 | 937 | CTCN_931 | 4208 |
| GTCN_40 | 938 | TTCN_904 | 4209 |
| ATCN_33 | 939 | TTCN_905 | 4210 |
| TTCN_70 | 940 | CTCN_932 | 4211 |
| TTCN_71 | 941 | TTCN_906 | 4212 |
| CTCN_80 | 942 | TTCN_907 | 4213 |
| GTCN_41 | 943 | TTCN_908 | 4214 |
| TTCN_72 | 944 | TTCN_909 | 4215 |
| CTCN_81 | 945 | TTCN_910 | 4216 |
| ATCN_34 | 946 | TTCN_911 | 4217 |
| TTCN_73 | 947 | GTCN_504 | 4218 |
| GTCN_42 | 948 | GTCN_505 | 4219 |
| TTCN_74 | 949 | CTCN_933 | 4220 |
| TTCN_75 | 950 | ATCN_545 | 4221 |
| GTCN_43 | 951 | ATCN_546 | 4222 |
| GTCN_44 | 952 | ATCN_547 | 4223 |
| CTCN_82 | 953 | GTCN_506 | 4224 |
| CTCN_83 | 954 | CTCN_934 | 4225 |
| CTCN_84 | 955 | GTCN_507 | 4226 |
| GTCN_45 | 956 | CTCN_935 | 4227 |
| CTCN_85 | 957 | ATCN_548 | 4228 |
| CTCN_86 | 958 | ATCN_549 | 4229 |
| GTCN_46 | 959 | CTCN_936 | 4230 |
| CTCN_87 | 960 | TTCN_912 | 4231 |
| CTCN_88 | 961 | CTCN_937 | 4232 |
| GTCN_47 | 962 | TTCN_913 | 4233 |
| CTCN_89 | 963 | CTCN_938 | 4234 |
| GTCN_48 | 964 | ATCN_550 | 4235 |
| ATCN_35 | 965 | ATCN_551 | 4236 |
| TTCN_76 | 966 | TTCN_914 | 4237 |
| TTCN_77 | 967 | TTCN_915 | 4238 |
| TTCN_78 | 968 | ATCN_552 | 4239 |
| CTCN_90 | 969 | ATCN_553 | 4240 |
| CTCN_91 | 970 | CTCN_939 | 4241 |
| ATCN_36 | 971 | TTCN_916 | 4242 |
| GTCN_49 | 972 | TTCN_917 | 4243 |
| GTCN_50 | 973 | ATCN_554 | 4244 |
| CTCN_92 | 974 | ATCN_555 | 4245 |
| CTCN_93 | 975 | ATCN_556 | 4246 |
| TTCN_79 | 976 | GTCN_508 | 4247 |
| TTCN_80 | 977 | ATCN_557 | 4248 |
| CTCN_94 | 978 | ATCN_558 | 4249 |
| CTCN_95 | 979 | ATCN_559 | 4250 |
| CTCN_96 | 980 | TTCN_918 | 4251 |
| TTCN_81 | 981 | TTCN_919 | 4252 |
| GTCN_51 | 982 | GTCN_509 | 4253 |
| CTCN_97 | 983 | TTCN_920 | 4254 |
| CTCN_98 | 984 | TTCN_921 | 4255 |
| TTCN_82 | 985 | ATCN_560 | 4256 |
| TTCN_83 | 986 | TTCN_922 | 4257 |
| CTCN_99 | 987 | ATCN_561 | 4258 |

| | | | |
|---|---|---|---|
| TTCN_84 | 988 | ATCN_562 | 4259 |
| TTCN_85 | 989 | CTCN_940 | 4260 |
| TTCN_86 | 990 | TTCN_923 | 4261 |
| TTCN_87 | 991 | GTCN_510 | 4262 |
| CTCN_100 | 992 | TTCN_924 | 4263 |
| TTCN_88 | 993 | CTCN_941 | 4264 |
| GTCN_52 | 994 | CTCN_942 | 4265 |
| GTCN_53 | 995 | GTCN_511 | 4266 |
| ATCN_37 | 996 | TTCN_925 | 4267 |
| ATCN_38 | 997 | TTCN_926 | 4268 |
| GTCN_54 | 998 | CTCN_943 | 4269 |
| TTCN_89 | 999 | CTCN_944 | 4270 |
| TTCN_90 | 1000 | GTCN_512 | 4271 |
| GTCN_55 | 1001 | CTCN_945 | 4272 |
| ATCN_39 | 1002 | TTCN_927 | 4273 |
| GTCN_56 | 1003 | GTCN_513 | 4274 |
| CTCN_101 | 1004 | ATCN_563 | 4275 |
| CTCN_102 | 1005 | GTCN_514 | 4276 |
| GTCN_57 | 1006 | CTCN_946 | 4277 |
| CTCN_103 | 1007 | TTCN_928 | 4278 |
| ATCN_40 | 1008 | TTCN_929 | 4279 |
| CTCN_104 | 1009 | ATCN_564 | 4280 |
| CTCN_105 | 1010 | ATCN_565 | 4281 |
| CTCN_106 | 1011 | CTCN_947 | 4282 |
| GTCN_58 | 1012 | CTCN_948 | 4283 |
| TTCN_91 | 1013 | ATCN_566 | 4284 |
| CTCN_107 | 1014 | TTCN_930 | 4285 |
| TTCN_92 | 1015 | CTCN_949 | 4286 |
| ATCN_41 | 1016 | CTCN_950 | 4287 |
| ATCN_42 | 1017 | CTCN_951 | 4288 |
| ATCN_43 | 1018 | TTCN_931 | 4289 |
| ATCN_44 | 1019 | ATCN_567 | 4290 |
| CTCN_108 | 1020 | TTCN_932 | 4291 |
| TTCN_93 | 1021 | ATCN_568 | 4292 |
| CTCN_109 | 1022 | CTCN_952 | 4293 |
| CTCN_110 | 1023 | ATCN_569 | 4294 |
| CTCN_111 | 1024 | ATCN_570 | 4295 |
| CTCN_112 | 1025 | CTCN_953 | 4296 |
| CTCN_113 | 1026 | TTCN_933 | 4297 |
| CTCN_114 | 1027 | TTCN_934 | 4298 |
| TTCN_94 | 1028 | CTCN_954 | 4299 |
| CTCN_115 | 1029 | ATCN_571 | 4300 |
| TTCN_95 | 1030 | CTCN_955 | 4301 |
| GTCN_59 | 1031 | CTCN_956 | 4302 |
| CTCN_116 | 1032 | CTCN_957 | 4303 |
| GTCN_60 | 1033 | TTCN_935 | 4304 |
| TTCN_96 | 1034 | ATCN_572 | 4305 |
| ATCN_45 | 1035 | GTCN_515 | 4306 |
| TTCN_97 | 1036 | TTCN_936 | 4307 |
| TTCN_98 | 1037 | ATCN_573 | 4308 |
| TTCN_99 | 1038 | TTCN_937 | 4309 |
| TTCN_100 | 1039 | ATCN_574 | 4310 |
| CTCN_117 | 1040 | CTCN_958 | 4311 |

FIG. 35 (continued)

| | | | |
|---|---|---|---|
| GTCN_61 | 1041 | ATCN_575 | 4312 |
| CTCN_118 | 1042 | TTCN_938 | 4313 |
| TTCN_101 | 1043 | ATCN_576 | 4314 |
| GTCN_62 | 1044 | TTCN_939 | 4315 |
| TTCN_102 | 1045 | CTCN_959 | 4316 |
| GTCN_63 | 1046 | CTCN_960 | 4317 |
| CTCN_119 | 1047 | ATCN_577 | 4318 |
| CTCN_120 | 1048 | ATCN_578 | 4319 |
| ATCN_46 | 1049 | GTCN_516 | 4320 |
| ATCN_47 | 1050 | CTCN_961 | 4321 |
| ATCN_48 | 1051 | CTCN_962 | 4322 |
| TTCN_103 | 1052 | TTCN_940 | 4323 |
| TTCN_104 | 1053 | CTCN_963 | 4324 |
| GTCN_64 | 1054 | CTCN_964 | 4325 |
| TTCN_105 | 1055 | GTCN_517 | 4326 |
| TTCN_106 | 1056 | CTCN_965 | 4327 |
| CTCN_121 | 1057 | CTCN_966 | 4328 |
| GTCN_65 | 1058 | ATCN_579 | 4329 |
| CTCN_122 | 1059 | ATCN_580 | 4330 |
| GTCN_66 | 1060 | TTCN_941 | 4331 |
| TTCN_107 | 1061 | TTCN_942 | 4332 |
| TTCN_108 | 1062 | GTCN_518 | 4333 |
| CTCN_123 | 1063 | ATCN_581 | 4334 |
| ATCN_49 | 1064 | TTCN_943 | 4335 |
| ATCN_50 | 1065 | CTCN_967 | 4336 |
| GTCN_67 | 1066 | TTCN_944 | 4337 |
| GTCN_68 | 1067 | TTCN_945 | 4338 |
| TTCN_109 | 1068 | TTCN_946 | 4339 |
| CTCN_124 | 1069 | CTCN_968 | 4340 |
| ATCN_51 | 1070 | TTCN_947 | 4341 |
| CTCN_125 | 1071 | TTCN_948 | 4342 |
| GTCN_69 | 1072 | TTCN_949 | 4343 |
| CTCN_126 | 1073 | ATCN_582 | 4344 |
| GTCN_70 | 1074 | GTCN_519 | 4345 |
| CTCN_127 | 1075 | GTCN_520 | 4346 |
| CTCN_128 | 1076 | CTCN_969 | 4347 |
| ATCN_52 | 1077 | CTCN_970 | 4348 |
| ATCN_53 | 1078 | TTCN_950 | 4349 |
| CTCN_129 | 1079 | TTCN_951 | 4350 |
| CTCN_130 | 1080 | TTCN_952 | 4351 |
| CTCN_131 | 1081 | TTCN_953 | 4352 |
| CTCN_132 | 1082 | ATCN_583 | 4353 |
| CTCN_133 | 1083 | ATCN_584 | 4354 |
| TTCN_110 | 1084 | ATCN_585 | 4355 |
| CTCN_134 | 1085 | GTCN_521 | 4356 |
| TTCN_111 | 1086 | CTCN_971 | 4357 |
| ATCN_54 | 1087 | ATCN_586 | 4358 |
| CTCN_135 | 1088 | ATCN_587 | 4359 |
| GTCN_71 | 1089 | TTCN_954 | 4360 |
| TTCN_112 | 1090 | TTCN_955 | 4361 |
| TTCN_113 | 1091 | GTCN_522 | 4362 |
| TTCN_114 | 1092 | GTCN_523 | 4363 |
| TTCN_115 | 1093 | CTCN_972 | 4364 |

| | | | |
|---|---|---|---|
| GTCN_72 | 1094 | ATCN_588 | 4365 |
| CTCN_136 | 1095 | ATCN_589 | 4366 |
| ATCN_55 | 1096 | GTCN_524 | 4367 |
| GTCN_73 | 1097 | CTCN_973 | 4368 |
| TTCN_116 | 1098 | CTCN_974 | 4369 |
| ATCN_56 | 1099 | TTCN_956 | 4370 |
| GTCN_74 | 1100 | CTCN_975 | 4371 |
| CTCN_137 | 1101 | TTCN_957 | 4372 |
| TTCN_117 | 1102 | GTCN_525 | 4373 |
| TTCN_118 | 1103 | CTCN_976 | 4374 |
| ATCN_57 | 1104 | CTCN_977 | 4375 |
| CTCN_138 | 1105 | GTCN_526 | 4376 |
| ATCN_58 | 1106 | CTCN_978 | 4377 |
| TTCN_119 | 1107 | TTCN_958 | 4378 |
| TTCN_120 | 1108 | CTCN_979 | 4379 |
| TTCN_121 | 1109 | TTCN_959 | 4380 |
| TTCN_122 | 1110 | CTCN_980 | 4381 |
| TTCN_123 | 1111 | ATCN_590 | 4382 |
| GTCN_75 | 1112 | CTCN_981 | 4383 |
| ATCN_59 | 1113 | ATCN_591 | 4384 |
| GTCN_76 | 1114 | ATCN_592 | 4385 |
| GTCN_77 | 1115 | TTCN_960 | 4386 |
| TTCN_124 | 1116 | CTCN_982 | 4387 |
| CTCN_139 | 1117 | TTCN_961 | 4388 |
| ATCN_60 | 1118 | GTCN_527 | 4389 |
| CTCN_140 | 1119 | TTCN_962 | 4390 |
| CTCN_141 | 1120 | ATCN_593 | 4391 |
| ATCN_61 | 1121 | GTCN_528 | 4392 |
| ATCN_62 | 1122 | CTCN_983 | 4393 |
| CTCN_142 | 1123 | TTCN_963 | 4394 |
| CTCN_143 | 1124 | GTCN_529 | 4395 |
| GTCN_78 | 1125 | TTCN_964 | 4396 |
| GTCN_79 | 1126 | ATCN_594 | 4397 |
| CTCN_144 | 1127 | TTCN_965 | 4398 |
| ATCN_63 | 1128 | CTCN_984 | 4399 |
| CTCN_145 | 1129 | CTCN_985 | 4400 |
| CTCN_146 | 1130 | CTCN_986 | 4401 |
| CTCN_147 | 1131 | CTCN_987 | 4402 |
| GTCN_80 | 1132 | ATCN_595 | 4403 |
| CTCN_148 | 1133 | ATCN_596 | 4404 |
| GTCN_81 | 1134 | CTCN_988 | 4405 |
| CTCN_149 | 1135 | CTCN_989 | 4406 |
| CTCN_150 | 1136 | TTCN_966 | 4407 |
| CTCN_151 | 1137 | CTCN_990 | 4408 |
| CTCN_152 | 1138 | ATCN_597 | 4409 |
| TTCN_125 | 1139 | TTCN_967 | 4410 |
| ATCN_64 | 1140 | ATCN_598 | 4411 |
| TTCN_126 | 1141 | TTCN_968 | 4412 |
| CTCN_153 | 1142 | ATCN_599 | 4413 |
| CTCN_154 | 1143 | ATCN_600 | 4414 |
| CTCN_155 | 1144 | TTCN_969 | 4415 |
| ATCN_65 | 1145 | CTCN_991 | 4416 |
| ATCN_66 | 1146 | ATCN_601 | 4417 |

FIG. 35 (continued)

| | | | |
|---|---|---|---|
| CTCN_156 | 1147 | ATCN_602 | 4418 |
| GTCN_82 | 1148 | CTCN_992 | 4419 |
| TTCN_127 | 1149 | GTCN_530 | 4420 |
| TTCN_128 | 1150 | CTCN_993 | 4421 |
| GTCN_83 | 1151 | GTCN_531 | 4422 |
| TTCN_129 | 1152 | TTCN_970 | 4423 |
| CTCN_157 | 1153 | TTCN_971 | 4424 |
| CTCN_158 | 1154 | ATCN_603 | 4425 |
| GTCN_84 | 1155 | ATCN_604 | 4426 |
| CTCN_159 | 1156 | ATCN_605 | 4427 |
| ATCN_67 | 1157 | ATCN_606 | 4428 |
| ATCN_68 | 1158 | CTCN_994 | 4429 |
| CTCN_160 | 1159 | TTCN_972 | 4430 |
| CTCN_161 | 1160 | TTCN_973 | 4431 |
| CTCN_162 | 1161 | TTCN_974 | 4432 |
| ATCN_69 | 1162 | TTCN_975 | 4433 |
| CTCN_163 | 1163 | TTCN_976 | 4434 |
| GTCN_85 | 1164 | CTCN_995 | 4435 |
| ATCN_70 | 1165 | CTCN_996 | 4436 |
| CTCN_164 | 1166 | ATCN_607 | 4437 |
| TTCN_130 | 1167 | TTCN_977 | 4438 |
| GTCN_86 | 1168 | CTCN_997 | 4439 |
| CTCN_165 | 1169 | TTCN_978 | 4440 |
| CTCN_166 | 1170 | TTCN_979 | 4441 |
| ATCN_71 | 1171 | TTCN_980 | 4442 |
| ATCN_72 | 1172 | ATCN_608 | 4443 |
| CTCN_167 | 1173 | ATCN_609 | 4444 |
| CTCN_168 | 1174 | GTCN_532 | 4445 |
| GTCN_87 | 1175 | CTCN_998 | 4446 |
| ATCN_73 | 1176 | CTCN_999 | 4447 |
| CTCN_169 | 1177 | ATCN_610 | 4448 |
| GTCN_88 | 1178 | TTCN_981 | 4449 |
| CTCN_170 | 1179 | CTCN_1000 | 4450 |
| GTCN_89 | 1180 | CTCN_1001 | 4451 |
| GTCN_90 | 1181 | CTCN_1002 | 4452 |
| CTCN_171 | 1182 | ATCN_611 | 4453 |
| TTCN_131 | 1183 | TTCN_982 | 4454 |
| GTCN_91 | 1184 | GTCN_533 | 4455 |
| TTCN_132 | 1185 | CTCN_1003 | 4456 |
| CTCN_172 | 1186 | CTCN_1004 | 4457 |
| CTCN_173 | 1187 | CTCN_1005 | 4458 |
| ATCN_74 | 1188 | CTCN_1006 | 4459 |
| TTCN_133 | 1189 | TTCN_983 | 4460 |
| TTCN_134 | 1190 | CTCN_1007 | 4461 |
| ATCN_75 | 1191 | ATCN_612 | 4462 |
| TTCN_135 | 1192 | CTCN_1008 | 4463 |
| ATCN_76 | 1193 | GTCN_534 | 4464 |
| CTCN_174 | 1194 | TTCN_984 | 4465 |
| GTCN_92 | 1195 | ATCN_613 | 4466 |
| ATCN_77 | 1196 | TTCN_985 | 4467 |
| ATCN_78 | 1197 | ATCN_614 | 4468 |
| TTCN_136 | 1198 | TTCN_986 | 4469 |
| TTCN_137 | 1199 | CTCN_1009 | 4470 |

| | | | |
|---|---|---|---|
| ATCN_79 | 1200 | TTCN_987 | 4471 |
| TTCN_138 | 1201 | CTCN_1010 | 4472 |
| TTCN_139 | 1202 | TTCN_988 | 4473 |
| TTCN_140 | 1203 | ATCN_615 | 4474 |
| CTCN_175 | 1204 | GTCN_535 | 4475 |
| TTCN_141 | 1205 | TTCN_989 | 4476 |
| GTCN_93 | 1206 | TTCN_990 | 4477 |
| TTCN_142 | 1207 | CTCN_1011 | 4478 |
| GTCN_94 | 1208 | TTCN_991 | 4479 |
| CTCN_176 | 1209 | TTCN_992 | 4480 |
| CTCN_177 | 1210 | CTCN_1012 | 4481 |
| ATCN_80 | 1211 | CTCN_1013 | 4482 |
| ATCN_81 | 1212 | TTCN_993 | 4483 |
| GTCN_95 | 1213 | TTCN_994 | 4484 |
| GTCN_96 | 1214 | CTCN_1014 | 4485 |
| ATCN_82 | 1215 | TTCN_995 | 4486 |
| ATCN_83 | 1216 | ATCN_616 | 4487 |
| TTCN_143 | 1217 | ATCN_617 | 4488 |
| TTCN_144 | 1218 | GTCN_536 | 4489 |
| TTCN_145 | 1219 | ATCN_618 | 4490 |
| TTCN_146 | 1220 | GTCN_537 | 4491 |
| ATCN_84 | 1221 | TTCN_996 | 4492 |
| ATCN_85 | 1222 | GTCN_538 | 4493 |
| ATCN_86 | 1223 | TTCN_997 | 4494 |
| CTCN_178 | 1224 | ATCN_619 | 4495 |
| TTCN_147 | 1225 | TTCN_998 | 4496 |
| ATCN_87 | 1226 | CTCN_1015 | 4497 |
| TTCN_148 | 1227 | CTCN_1016 | 4498 |
| ATCN_88 | 1228 | ATCN_620 | 4499 |
| ATCN_89 | 1229 | TTCN_999 | 4500 |
| GTCN_97 | 1230 | CTCN_1017 | 4501 |
| CTCN_179 | 1231 | GTCN_539 | 4502 |
| TTCN_149 | 1232 | ATCN_621 | 4503 |
| TTCN_150 | 1233 | CTCN_1018 | 4504 |
| CTCN_180 | 1234 | TTCN_1000 | 4505 |
| GTCN_98 | 1235 | TTCN_1001 | 4506 |
| CTCN_181 | 1236 | GTCN_540 | 4507 |
| ATCN_90 | 1237 | TTCN_1002 | 4508 |
| GTCN_99 | 1238 | TTCN_1003 | 4509 |
| TTCN_151 | 1239 | GTCN_541 | 4510 |
| ATCN_91 | 1240 | TTCN_1004 | 4511 |
| TTCN_152 | 1241 | ATCN_622 | 4512 |
| GTCN_100 | 1242 | ATCN_623 | 4513 |
| CTCN_182 | 1243 | GTCN_542 | 4514 |
| TTCN_153 | 1244 | TTCN_1005 | 4515 |
| TTCN_154 | 1245 | GTCN_543 | 4516 |
| TTCN_155 | 1246 | TTCN_1006 | 4517 |
| TTCN_156 | 1247 | TTCN_1007 | 4518 |
| TTCN_157 | 1248 | CTCN_1019 | 4519 |
| TTCN_158 | 1249 | CTCN_1020 | 4520 |
| CTCN_183 | 1250 | CTCN_1021 | 4521 |
| GTCN_101 | 1251 | TTCN_1008 | 4522 |
| TTCN_159 | 1252 | TTCN_1009 | 4523 |

FIG. 35 (continued)

| | | | |
|---|---|---|---|
| TTCN_160 | 1253 | CTCN_1022 | 4524 |
| GTCN_102 | 1254 | TTCN_1010 | 4525 |
| GTCN_103 | 1255 | GTCN_544 | 4526 |
| TTCN_161 | 1256 | GTCN_545 | 4527 |
| CTCN_184 | 1257 | TTCN_1011 | 4528 |
| GTCN_104 | 1258 | GTCN_546 | 4529 |
| TTCN_162 | 1259 | GTCN_547 | 4530 |
| TTCN_163 | 1260 | TTCN_1012 | 4531 |
| ATCN_92 | 1261 | ATCN_624 | 4532 |
| ATCN_93 | 1262 | CTCN_1023 | 4533 |
| TTCN_164 | 1263 | TTCN_1013 | 4534 |
| CTCN_185 | 1264 | TTCN_1014 | 4535 |
| TTCN_165 | 1265 | TTCN_1015 | 4536 |
| TTCN_166 | 1266 | ATCN_625 | 4537 |
| TTCN_167 | 1267 | CTCN_1024 | 4538 |
| TTCN_168 | 1268 | TTCN_1016 | 4539 |
| TTCN_169 | 1269 | GTCN_548 | 4540 |
| ATCN_94 | 1270 | GTCN_549 | 4541 |
| TTCN_170 | 1271 | ATCN_626 | 4542 |
| GTCN_105 | 1272 | GTCN_550 | 4543 |
| TTCN_171 | 1273 | TTCN_1017 | 4544 |
| CTCN_186 | 1274 | TTCN_1018 | 4545 |
| ATCN_95 | 1275 | CTCN_1025 | 4546 |
| CTCN_187 | 1276 | GTCN_551 | 4547 |
| TTCN_172 | 1277 | ATCN_627 | 4548 |
| GTCN_106 | 1278 | ATCN_628 | 4549 |
| GTCN_107 | 1279 | GTCN_552 | 4550 |
| TTCN_173 | 1280 | TTCN_1019 | 4551 |
| TTCN_174 | 1281 | CTCN_1026 | 4552 |
| TTCN_175 | 1282 | GTCN_553 | 4553 |
| TTCN_176 | 1283 | ATCN_629 | 4554 |
| CTCN_188 | 1284 | ATCN_630 | 4555 |
| CTCN_189 | 1285 | ATCN_631 | 4556 |
| ATCN_96 | 1286 | ATCN_632 | 4557 |
| CTCN_190 | 1287 | ATCN_633 | 4558 |
| ATCN_97 | 1288 | GTCN_554 | 4559 |
| TTCN_177 | 1289 | TTCN_1020 | 4560 |
| GTCN_108 | 1290 | TTCN_1021 | 4561 |
| GTCN_109 | 1291 | ATCN_634 | 4562 |
| CTCN_191 | 1292 | ATCN_635 | 4563 |
| CTCN_192 | 1293 | ATCN_636 | 4564 |
| ATCN_98 | 1294 | CTCN_1027 | 4565 |
| TTCN_178 | 1295 | ATCN_637 | 4566 |
| GTCN_110 | 1296 | ATCN_638 | 4567 |
| CTCN_193 | 1297 | TTCN_1022 | 4568 |
| TTCN_179 | 1298 | TTCN_1023 | 4569 |
| ATCN_99 | 1299 | TTCN_1024 | 4570 |
| TTCN_180 | 1300 | CTCN_1028 | 4571 |
| GTCN_111 | 1301 | CTCN_1029 | 4572 |
| TTCN_181 | 1302 | CTCN_1030 | 4573 |
| CTCN_194 | 1303 | TTCN_1025 | 4574 |
| TTCN_182 | 1304 | TTCN_1026 | 4575 |
| TTCN_183 | 1305 | CTCN_1031 | 4576 |

| | | | |
|---|---|---|---|
| ATCN_100 | 1306 | TTCN_1027 | 4577 |
| TTCN_184 | 1307 | TTCN_1028 | 4578 |
| CTCN_195 | 1308 | TTCN_1029 | 4579 |
| ATCN_101 | 1309 | ATCN_639 | 4580 |
| ATCN_102 | 1310 | CTCN_1032 | 4581 |
| ATCN_103 | 1311 | TTCN_1030 | 4582 |
| TTCN_185 | 1312 | GTCN_555 | 4583 |
| CTCN_196 | 1313 | GTCN_556 | 4584 |
| TTCN_186 | 1314 | ATCN_640 | 4585 |
| CTCN_197 | 1315 | ATCN_641 | 4586 |
| TTCN_187 | 1316 | GTCN_557 | 4587 |
| TTCN_188 | 1317 | TTCN_1031 | 4588 |
| TTCN_189 | 1318 | CTCN_1033 | 4589 |
| ATCN_104 | 1319 | TTCN_1032 | 4590 |
| TTCN_190 | 1320 | ATCN_642 | 4591 |
| TTCN_191 | 1321 | ATCN_643 | 4592 |
| GTCN_112 | 1322 | CTCN_1034 | 4593 |
| ATCN_105 | 1323 | TTCN_1033 | 4594 |
| GTCN_113 | 1324 | TTCN_1034 | 4595 |
| CTCN_198 | 1325 | CTCN_1035 | 4596 |
| TTCN_192 | 1326 | TTCN_1035 | 4597 |
| TTCN_193 | 1327 | TTCN_1036 | 4598 |
| TTCN_194 | 1328 | TTCN_1037 | 4599 |
| CTCN_199 | 1329 | TTCN_1038 | 4600 |
| TTCN_195 | 1330 | GTCN_558 | 4601 |
| TTCN_196 | 1331 | GTCN_559 | 4602 |
| TTCN_197 | 1332 | TTCN_1039 | 4603 |
| CTCN_200 | 1333 | TTCN_1040 | 4604 |
| ATCN_106 | 1334 | CTCN_1036 | 4605 |
| CTCN_201 | 1335 | GTCN_560 | 4606 |
| TTCN_198 | 1336 | TTCN_1041 | 4607 |
| CTCN_202 | 1337 | ATCN_644 | 4608 |
| TTCN_199 | 1338 | ATCN_645 | 4609 |
| CTCN_203 | 1339 | CTCN_1037 | 4610 |
| TTCN_200 | 1340 | GTCN_561 | 4611 |
| TTCN_201 | 1341 | ATCN_646 | 4612 |
| CTCN_204 | 1342 | CTCN_1038 | 4613 |
| GTCN_114 | 1343 | GTCN_562 | 4614 |
| ATCN_107 | 1344 | CTCN_1039 | 4615 |
| CTCN_205 | 1345 | TTCN_1042 | 4616 |
| ATCN_108 | 1346 | TTCN_1043 | 4617 |
| ATCN_109 | 1347 | GTCN_563 | 4618 |
| ATCN_110 | 1348 | CTCN_1040 | 4619 |
| GTCN_115 | 1349 | GTCN_564 | 4620 |
| TTCN_202 | 1350 | GTCN_565 | 4621 |
| CTCN_206 | 1351 | CTCN_1041 | 4622 |
| TTCN_203 | 1352 | ATCN_647 | 4623 |
| TTCN_204 | 1353 | CTCN_1042 | 4624 |
| ATCN_111 | 1354 | CTCN_1043 | 4625 |
| CTCN_207 | 1355 | TTCN_1044 | 4626 |
| CTCN_208 | 1356 | GTCN_566 | 4627 |
| CTCN_209 | 1357 | CTCN_1044 | 4628 |
| ATCN_112 | 1358 | TTCN_1045 | 4629 |

FIG. 35 (continued)

| | | | |
|---|---|---|---|
| TTCN_205 | 1359 | TTCN_1046 | 4630 |
| GTCN_116 | 1360 | TTCN_1047 | 4631 |
| TTCN_206 | 1361 | ATCN_648 | 4632 |
| CTCN_210 | 1362 | GTCN_567 | 4633 |
| CTCN_211 | 1363 | TTCN_1048 | 4634 |
| TTCN_207 | 1364 | TTCN_1049 | 4635 |
| CTCN_212 | 1365 | CTCN_1045 | 4636 |
| TTCN_208 | 1366 | CTCN_1046 | 4637 |
| GTCN_117 | 1367 | TTCN_1050 | 4638 |
| CTCN_213 | 1368 | TTCN_1051 | 4639 |
| ATCN_113 | 1369 | GTCN_568 | 4640 |
| TTCN_209 | 1370 | CTCN_1047 | 4641 |
| GTCN_118 | 1371 | CTCN_1048 | 4642 |
| TTCN_210 | 1372 | CTCN_1049 | 4643 |
| CTCN_214 | 1373 | TTCN_1052 | 4644 |
| ATCN_114 | 1374 | ATCN_649 | 4645 |
| CTCN_215 | 1375 | ATCN_650 | 4646 |
| CTCN_216 | 1376 | ATCN_651 | 4647 |
| ATCN_115 | 1377 | TTCN_1053 | 4648 |
| GTCN_119 | 1378 | TTCN_1054 | 4649 |
| CTCN_217 | 1379 | TTCN_1055 | 4650 |
| TTCN_211 | 1380 | GTCN_569 | 4651 |
| CTCN_218 | 1381 | ATCN_652 | 4652 |
| CTCN_219 | 1382 | CTCN_1050 | 4653 |
| TTCN_212 | 1383 | CTCN_1051 | 4654 |
| TTCN_213 | 1384 | CTCN_1052 | 4655 |
| ATCN_116 | 1385 | CTCN_1053 | 4656 |
| CTCN_220 | 1386 | TTCN_1056 | 4657 |
| TTCN_214 | 1387 | TTCN_1057 | 4658 |
| TTCN_215 | 1388 | CTCN_1054 | 4659 |
| GTCN_120 | 1389 | TTCN_1058 | 4660 |
| CTCN_221 | 1390 | TTCN_1059 | 4661 |
| CTCN_222 | 1391 | TTCN_1060 | 4662 |
| CTCN_223 | 1392 | GTCN_570 | 4663 |
| ATCN_117 | 1393 | TTCN_1061 | 4664 |
| TTCN_216 | 1394 | CTCN_1055 | 4665 |
| CTCN_224 | 1395 | CTCN_1056 | 4666 |
| CTCN_225 | 1396 | CTCN_1057 | 4667 |
| CTCN_226 | 1397 | CTCN_1058 | 4668 |
| ATCN_118 | 1398 | GTCN_571 | 4669 |
| ATCN_119 | 1399 | ATCN_653 | 4670 |
| TTCN_217 | 1400 | TTCN_1062 | 4671 |
| ATCN_120 | 1401 | GTCN_572 | 4672 |
| TTCN_218 | 1402 | CTCN_1059 | 4673 |
| ATCN_121 | 1403 | CTCN_1060 | 4674 |
| CTCN_227 | 1404 | TTCN_1063 | 4675 |
| GTCN_121 | 1405 | CTCN_1061 | 4676 |
| GTCN_122 | 1406 | CTCN_1062 | 4677 |
| CTCN_228 | 1407 | ATCN_654 | 4678 |
| TTCN_219 | 1408 | TTCN_1064 | 4679 |
| GTCN_123 | 1409 | ATCN_655 | 4680 |
| TTCN_220 | 1410 | ATCN_656 | 4681 |
| CTCN_229 | 1411 | ATCN_657 | 4682 |

| | | | |
|---|---|---|---|
| ATCN_122 | 1412 | ATCN_658 | 4683 |
| ATCN_123 | 1413 | CTCN_1063 | 4684 |
| TTCN_221 | 1414 | CTCN_1064 | 4685 |
| CTCN_230 | 1415 | TTCN_1065 | 4686 |
| CTCN_231 | 1416 | CTCN_1065 | 4687 |
| ATCN_124 | 1417 | CTCN_1066 | 4688 |
| TTCN_222 | 1418 | CTCN_1067 | 4689 |
| ATCN_125 | 1419 | CTCN_1068 | 4690 |
| CTCN_232 | 1420 | TTCN_1066 | 4691 |
| GTCN_124 | 1421 | GTCN_573 | 4692 |
| CTCN_233 | 1422 | TTCN_1067 | 4693 |
| TTCN_223 | 1423 | CTCN_1069 | 4694 |
| TTCN_224 | 1424 | ATCN_659 | 4695 |
| GTCN_125 | 1425 | CTCN_1070 | 4696 |
| TTCN_225 | 1426 | GTCN_574 | 4697 |
| CTCN_234 | 1427 | TTCN_1068 | 4698 |
| GTCN_126 | 1428 | TTCN_1069 | 4699 |
| TTCN_226 | 1429 | TTCN_1070 | 4700 |
| GTCN_127 | 1430 | ATCN_660 | 4701 |
| CTCN_235 | 1431 | TTCN_1071 | 4702 |
| CTCN_236 | 1432 | TTCN_1072 | 4703 |
| CTCN_237 | 1433 | ATCN_661 | 4704 |
| CTCN_238 | 1434 | CTCN_1071 | 4705 |
| CTCN_239 | 1435 | TTCN_1073 | 4706 |
| TTCN_227 | 1436 | TTCN_1074 | 4707 |
| CTCN_240 | 1437 | TTCN_1075 | 4708 |
| CTCN_241 | 1438 | ATCN_662 | 4709 |
| TTCN_228 | 1439 | CTCN_1072 | 4710 |
| CTCN_242 | 1440 | CTCN_1073 | 4711 |
| GTCN_128 | 1441 | ATCN_663 | 4712 |
| TTCN_229 | 1442 | TTCN_1076 | 4713 |
| TTCN_230 | 1443 | ATCN_664 | 4714 |
| CTCN_243 | 1444 | ATCN_665 | 4715 |
| CTCN_244 | 1445 | ATCN_666 | 4716 |
| TTCN_231 | 1446 | GTCN_575 | 4717 |
| GTCN_129 | 1447 | CTCN_1074 | 4718 |
| TTCN_232 | 1448 | GTCN_576 | 4719 |
| ATCN_126 | 1449 | TTCN_1077 | 4720 |
| CTCN_245 | 1450 | CTCN_1075 | 4721 |
| CTCN_246 | 1451 | GTCN_577 | 4722 |
| ATCN_127 | 1452 | GTCN_578 | 4723 |
| TTCN_233 | 1453 | GTCN_579 | 4724 |
| GTCN_130 | 1454 | TTCN_1078 | 4725 |
| ATCN_128 | 1455 | CTCN_1076 | 4726 |
| ATCN_129 | 1456 | TTCN_1079 | 4727 |
| CTCN_247 | 1457 | CTCN_1077 | 4728 |
| CTCN_248 | 1458 | GTCN_580 | 4729 |
| CTCN_249 | 1459 | TTCN_1080 | 4730 |
| CTCN_250 | 1460 | ATCN_667 | 4731 |
| CTCN_251 | 1461 | TTCN_1081 | 4732 |
| TTCN_234 | 1462 | ATCN_668 | 4733 |
| GTCN_131 | 1463 | CTCN_1078 | 4734 |
| GTCN_132 | 1464 | GTCN_581 | 4735 |

FIG. 35 (continued)

| | | | |
|---|---|---|---|
| CTCN_252 | 1465 | GTCN_582 | 4736 |
| TTCN_235 | 1466 | GTCN_583 | 4737 |
| CTCN_253 | 1467 | ATCN_669 | 4738 |
| GTCN_133 | 1468 | GTCN_584 | 4739 |
| TTCN_236 | 1469 | ATCN_670 | 4740 |
| CTCN_254 | 1470 | ATCN_671 | 4741 |
| GTCN_134 | 1471 | TTCN_1082 | 4742 |
| ATCN_130 | 1472 | TTCN_1083 | 4743 |
| TTCN_237 | 1473 | ATCN_672 | 4744 |
| ATCN_131 | 1474 | CTCN_1079 | 4745 |
| TTCN_238 | 1475 | ATCN_673 | 4746 |
| ATCN_132 | 1476 | ATCN_674 | 4747 |
| CTCN_255 | 1477 | CTCN_1080 | 4748 |
| GTCN_135 | 1478 | CTCN_1081 | 4749 |
| GTCN_136 | 1479 | TTCN_1084 | 4750 |
| CTCN_256 | 1480 | GTCN_585 | 4751 |
| GTCN_137 | 1481 | TTCN_1085 | 4752 |
| CTCN_257 | 1482 | ATCN_675 | 4753 |
| ATCN_133 | 1483 | ATCN_676 | 4754 |
| CTCN_258 | 1484 | TTCN_1086 | 4755 |
| CTCN_259 | 1485 | GTCN_586 | 4756 |
| CTCN_260 | 1486 | CTCN_1082 | 4757 |
| CTCN_261 | 1487 | ATCN_677 | 4758 |
| CTCN_262 | 1488 | ATCN_678 | 4759 |
| ATCN_134 | 1489 | ATCN_679 | 4760 |
| CTCN_263 | 1490 | TTCN_1087 | 4761 |
| CTCN_264 | 1491 | TTCN_1088 | 4762 |
| GTCN_138 | 1492 | TTCN_1089 | 4763 |
| TTCN_239 | 1493 | TTCN_1090 | 4764 |
| CTCN_265 | 1494 | TTCN_1091 | 4765 |
| GTCN_139 | 1495 | ATCN_680 | 4766 |
| ATCN_135 | 1496 | ATCN_681 | 4767 |
| TTCN_240 | 1497 | ATCN_682 | 4768 |
| TTCN_241 | 1498 | TTCN_1092 | 4769 |
| GTCN_140 | 1499 | TTCN_1093 | 4770 |
| GTCN_141 | 1500 | TTCN_1094 | 4771 |
| TTCN_242 | 1501 | ATCN_683 | 4772 |
| GTCN_142 | 1502 | GTCN_587 | 4773 |
| CTCN_266 | 1503 | ATCN_684 | 4774 |
| CTCN_267 | 1504 | ATCN_685 | 4775 |
| ATCN_136 | 1505 | TTCN_1095 | 4776 |
| GTCN_143 | 1506 | TTCN_1096 | 4777 |
| TTCN_243 | 1507 | CTCN_1083 | 4778 |
| GTCN_144 | 1508 | GTCN_588 | 4779 |
| TTCN_244 | 1509 | CTCN_1084 | 4780 |
| TTCN_245 | 1510 | ATCN_686 | 4781 |
| TTCN_246 | 1511 | ATCN_687 | 4782 |
| TTCN_247 | 1512 | CTCN_1085 | 4783 |
| GTCN_145 | 1513 | CTCN_1086 | 4784 |
| CTCN_268 | 1514 | CTCN_1087 | 4785 |
| CTCN_269 | 1515 | CTCN_1088 | 4786 |
| TTCN_248 | 1516 | CTCN_1089 | 4787 |
| GTCN_146 | 1517 | CTCN_1090 | 4788 |

| | | | |
|---|---|---|---|
| GTCN_147 | 1518 | CTCN_1091 | 4789 |
| TTCN_249 | 1519 | TTCN_1097 | 4790 |
| TTCN_250 | 1520 | TTCN_1098 | 4791 |
| TTCN_251 | 1521 | CTCN_1092 | 4792 |
| GTCN_148 | 1522 | ATCN_688 | 4793 |
| TTCN_252 | 1523 | ATCN_689 | 4794 |
| TTCN_253 | 1524 | ATCN_690 | 4795 |
| TTCN_254 | 1525 | GTCN_589 | 4796 |
| TTCN_255 | 1526 | ATCN_691 | 4797 |
| ATCN_137 | 1527 | TTCN_1099 | 4798 |
| CTCN_270 | 1528 | CTCN_1093 | 4799 |
| ATCN_138 | 1529 | TTCN_1100 | 4800 |
| CTCN_271 | 1530 | ATCN_692 | 4801 |
| GTCN_149 | 1531 | CTCN_1094 | 4802 |
| GTCN_150 | 1532 | CTCN_1095 | 4803 |
| TTCN_256 | 1533 | ATCN_693 | 4804 |
| CTCN_272 | 1534 | TTCN_1101 | 4805 |
| ATCN_139 | 1535 | CTCN_1096 | 4806 |
| ATCN_140 | 1536 | TTCN_1102 | 4807 |
| TTCN_257 | 1537 | TTCN_1103 | 4808 |
| TTCN_258 | 1538 | TTCN_1104 | 4809 |
| GTCN_151 | 1539 | GTCN_590 | 4810 |
| CTCN_273 | 1540 | ATCN_694 | 4811 |
| GTCN_152 | 1541 | TTCN_1105 | 4812 |
| CTCN_274 | 1542 | TTCN_1106 | 4813 |
| ATCN_141 | 1543 | TTCN_1107 | 4814 |
| ATCN_142 | 1544 | GTCN_591 | 4815 |
| GTCN_153 | 1545 | ATCN_695 | 4816 |
| CTCN_275 | 1546 | TTCN_1108 | 4817 |
| ATCN_143 | 1547 | TTCN_1109 | 4818 |
| CTCN_276 | 1548 | ATCN_696 | 4819 |
| GTCN_154 | 1549 | ATCN_697 | 4820 |
| CTCN_277 | 1550 | TTCN_1110 | 4821 |
| TTCN_259 | 1551 | ATCN_698 | 4822 |
| ATCN_144 | 1552 | ATCN_699 | 4823 |
| TTCN_260 | 1553 | ATCN_700 | 4824 |
| TTCN_261 | 1554 | CTCN_1097 | 4825 |
| CTCN_278 | 1555 | ATCN_701 | 4826 |
| GTCN_155 | 1556 | CTCN_1098 | 4827 |
| CTCN_279 | 1557 | CTCN_1099 | 4828 |
| TTCN_262 | 1558 | TTCN_1111 | 4829 |
| CTCN_280 | 1559 | TTCN_1112 | 4830 |
| TTCN_263 | 1560 | GTCN_592 | 4831 |
| CTCN_281 | 1561 | TTCN_1113 | 4832 |
| CTCN_282 | 1562 | TTCN_1114 | 4833 |
| CTCN_283 | 1563 | TTCN_1115 | 4834 |
| GTCN_156 | 1564 | CTCN_1100 | 4835 |
| CTCN_284 | 1565 | CTCN_1101 | 4836 |
| TTCN_264 | 1566 | CTCN_1102 | 4837 |
| TTCN_265 | 1567 | ATCN_702 | 4838 |
| ATCN_145 | 1568 | TTCN_1116 | 4839 |
| TTCN_266 | 1569 | TTCN_1117 | 4840 |
| GTCN_157 | 1570 | ATCN_703 | 4841 |

FIG. 35 (continued)

| | | | |
|---|---|---|---|
| TTCN_267 | 1571 | TTCN_1118 | 4842 |
| TTCN_268 | 1572 | ATCN_704 | 4843 |
| CTCN_285 | 1573 | ATCN_705 | 4844 |
| TTCN_269 | 1574 | CTCN_1103 | 4845 |
| CTCN_286 | 1575 | TTCN_1119 | 4846 |
| TTCN_270 | 1576 | GTCN_593 | 4847 |
| GTCN_158 | 1577 | GTCN_594 | 4848 |
| CTCN_287 | 1578 | CTCN_1104 | 4849 |
| GTCN_159 | 1579 | TTCN_1120 | 4850 |
| TTCN_271 | 1580 | TTCN_1121 | 4851 |
| GTCN_160 | 1581 | TTCN_1122 | 4852 |
| CTCN_288 | 1582 | GTCN_595 | 4853 |
| CTCN_289 | 1583 | CTCN_1105 | 4854 |
| TTCN_272 | 1584 | CTCN_1106 | 4855 |
| TTCN_273 | 1585 | GTCN_596 | 4856 |
| GTCN_161 | 1586 | CTCN_1107 | 4857 |
| ATCN_146 | 1587 | CTCN_1108 | 4858 |
| ATCN_147 | 1588 | CTCN_1109 | 4859 |
| ATCN_148 | 1589 | ATCN_706 | 4860 |
| ATCN_149 | 1590 | TTCN_1123 | 4861 |
| TTCN_274 | 1591 | ATCN_707 | 4862 |
| CTCN_290 | 1592 | TTCN_1124 | 4863 |
| TTCN_275 | 1593 | ATCN_708 | 4864 |
| CTCN_291 | 1594 | ATCN_709 | 4865 |
| CTCN_292 | 1595 | ATCN_710 | 4866 |
| GTCN_162 | 1596 | GTCN_597 | 4867 |
| GTCN_163 | 1597 | CTCN_1110 | 4868 |
| ATCN_150 | 1598 | ATCN_711 | 4869 |
| ATCN_151 | 1599 | TTCN_1125 | 4870 |
| GTCN_164 | 1600 | GTCN_598 | 4871 |
| ATCN_152 | 1601 | TTCN_1126 | 4872 |
| ATCN_153 | 1602 | GTCN_599 | 4873 |
| CTCN_293 | 1603 | ATCN_712 | 4874 |
| CTCN_294 | 1604 | ATCN_713 | 4875 |
| GTCN_165 | 1605 | GTCN_600 | 4876 |
| CTCN_295 | 1606 | TTCN_1127 | 4877 |
| CTCN_296 | 1607 | ATCN_714 | 4878 |
| CTCN_297 | 1608 | ATCN_715 | 4879 |
| TTCN_276 | 1609 | CTCN_1111 | 4880 |
| CTCN_298 | 1610 | ATCN_716 | 4881 |
| CTCN_299 | 1611 | TTCN_1128 | 4882 |
| CTCN_300 | 1612 | ATCN_717 | 4883 |
| TTCN_277 | 1613 | TTCN_1129 | 4884 |
| TTCN_278 | 1614 | GTCN_601 | 4885 |
| CTCN_301 | 1615 | TTCN_1130 | 4886 |
| TTCN_279 | 1616 | GTCN_602 | 4887 |
| TTCN_280 | 1617 | CTCN_1112 | 4888 |
| TTCN_281 | 1618 | GTCN_603 | 4889 |
| GTCN_166 | 1619 | ATCN_718 | 4890 |
| CTCN_302 | 1620 | TTCN_1131 | 4891 |
| CTCN_303 | 1621 | ATCN_719 | 4892 |
| CTCN_304 | 1622 | ATCN_720 | 4893 |
| TTCN_282 | 1623 | TTCN_1132 | 4894 |

| | | | |
|---|---|---|---|
| GTCN_167 | 1624 | ATCN_721 | 4895 |
| CTCN_305 | 1625 | ATCN_722 | 4896 |
| CTCN_306 | 1626 | CTCN_1113 | 4897 |
| TTCN_283 | 1627 | ATCN_723 | 4898 |
| ATCN_154 | 1628 | TTCN_1133 | 4899 |
| CTCN_307 | 1629 | TTCN_1134 | 4900 |
| CTCN_308 | 1630 | GTCN_604 | 4901 |
| GTCN_168 | 1631 | ATCN_724 | 4902 |
| GTCN_169 | 1632 | TTCN_1135 | 4903 |
| CTCN_309 | 1633 | ATCN_725 | 4904 |
| CTCN_310 | 1634 | GTCN_605 | 4905 |
| CTCN_311 | 1635 | TTCN_1136 | 4906 |
| TTCN_284 | 1636 | ATCN_726 | 4907 |
| TTCN_285 | 1637 | CTCN_1114 | 4908 |
| ATCN_155 | 1638 | TTCN_1137 | 4909 |
| CTCN_312 | 1639 | GTCN_606 | 4910 |
| TTCN_286 | 1640 | ATCN_727 | 4911 |
| CTCN_313 | 1641 | CTCN_1115 | 4912 |
| TTCN_287 | 1642 | ATCN_728 | 4913 |
| CTCN_314 | 1643 | ATCN_729 | 4914 |
| CTCN_315 | 1644 | TTCN_1138 | 4915 |
| TTCN_288 | 1645 | CTCN_1116 | 4916 |
| CTCN_316 | 1646 | CTCN_1117 | 4917 |
| TTCN_289 | 1647 | GTCN_607 | 4918 |
| ATCN_156 | 1648 | ATCN_730 | 4919 |
| GTCN_170 | 1649 | CTCN_1118 | 4920 |
| TTCN_290 | 1650 | ATCN_731 | 4921 |
| CTCN_317 | 1651 | ATCN_732 | 4922 |
| CTCN_318 | 1652 | TTCN_1139 | 4923 |
| GTCN_171 | 1653 | TTCN_1140 | 4924 |
| CTCN_319 | 1654 | TTCN_1141 | 4925 |
| TTCN_291 | 1655 | ATCN_733 | 4926 |
| ATCN_157 | 1656 | TTCN_1142 | 4927 |
| ATCN_158 | 1657 | TTCN_1143 | 4928 |
| CTCN_320 | 1658 | CTCN_1119 | 4929 |
| CTCN_321 | 1659 | GTCN_608 | 4930 |
| ATCN_159 | 1660 | CTCN_1120 | 4931 |
| ATCN_160 | 1661 | GTCN_609 | 4932 |
| CTCN_322 | 1662 | ATCN_734 | 4933 |
| GTCN_172 | 1663 | CTCN_1121 | 4934 |
| GTCN_173 | 1664 | ATCN_735 | 4935 |
| CTCN_323 | 1665 | ATCN_736 | 4936 |
| TTCN_292 | 1666 | ATCN_737 | 4937 |
| ATCN_161 | 1667 | CTCN_1122 | 4938 |
| TTCN_293 | 1668 | CTCN_1123 | 4939 |
| TTCN_294 | 1669 | GTCN_610 | 4940 |
| ATCN_162 | 1670 | CTCN_1124 | 4941 |
| CTCN_324 | 1671 | GTCN_611 | 4942 |
| TTCN_295 | 1672 | GTCN_612 | 4943 |
| TTCN_296 | 1673 | GTCN_613 | 4944 |
| TTCN_297 | 1674 | CTCN_1125 | 4945 |
| TTCN_298 | 1675 | TTCN_1144 | 4946 |
| TTCN_299 | 1676 | TTCN_1145 | 4947 |

FIG. 35 (continued)

| | | | |
|---|---|---|---|
| ATCN_163 | 1677 | TTCN_1146 | 4948 |
| CTCN_325 | 1678 | TTCN_1147 | 4949 |
| TTCN_300 | 1679 | TTCN_1148 | 4950 |
| CTCN_326 | 1680 | TTCN_1149 | 4951 |
| TTCN_301 | 1681 | ATCN_738 | 4952 |
| TTCN_302 | 1682 | CTCN_1126 | 4953 |
| GTCN_174 | 1683 | CTCN_1127 | 4954 |
| CTCN_327 | 1684 | TTCN_1150 | 4955 |
| TTCN_303 | 1685 | CTCN_1128 | 4956 |
| CTCN_328 | 1686 | CTCN_1129 | 4957 |
| GTCN_175 | 1687 | CTCN_1130 | 4958 |
| ATCN_164 | 1688 | TTCN_1151 | 4959 |
| CTCN_329 | 1689 | CTCN_1131 | 4960 |
| TTCN_304 | 1690 | ATCN_739 | 4961 |
| TTCN_305 | 1691 | TTCN_1152 | 4962 |
| CTCN_330 | 1692 | TTCN_1153 | 4963 |
| GTCN_176 | 1693 | GTCN_614 | 4964 |
| TTCN_306 | 1694 | TTCN_1154 | 4965 |
| GTCN_177 | 1695 | CTCN_1132 | 4966 |
| ATCN_165 | 1696 | TTCN_1155 | 4967 |
| TTCN_307 | 1697 | GTCN_615 | 4968 |
| TTCN_308 | 1698 | TTCN_1156 | 4969 |
| TTCN_309 | 1699 | GTCN_616 | 4970 |
| TTCN_310 | 1700 | TTCN_1157 | 4971 |
| GTCN_178 | 1701 | CTCN_1133 | 4972 |
| CTCN_331 | 1702 | TTCN_1158 | 4973 |
| GTCN_179 | 1703 | ATCN_740 | 4974 |
| ATCN_166 | 1704 | ATCN_741 | 4975 |
| ATCN_167 | 1705 | CTCN_1134 | 4976 |
| TTCN_311 | 1706 | TTCN_1159 | 4977 |
| GTCN_180 | 1707 | TTCN_1160 | 4978 |
| CTCN_332 | 1708 | TTCN_1161 | 4979 |
| ATCN_168 | 1709 | CTCN_1135 | 4980 |
| ATCN_169 | 1710 | TTCN_1162 | 4981 |
| TTCN_312 | 1711 | GTCN_617 | 4982 |
| TTCN_313 | 1712 | ATCN_742 | 4983 |
| ATCN_170 | 1713 | TTCN_1163 | 4984 |
| GTCN_181 | 1714 | CTCN_1136 | 4985 |
| TTCN_314 | 1715 | CTCN_1137 | 4986 |
| TTCN_315 | 1716 | TTCN_1164 | 4987 |
| GTCN_182 | 1717 | GTCN_618 | 4988 |
| CTCN_333 | 1718 | ATCN_743 | 4989 |
| TTCN_316 | 1719 | CTCN_1138 | 4990 |
| CTCN_334 | 1720 | CTCN_1139 | 4991 |
| TTCN_317 | 1721 | ATCN_744 | 4992 |
| CTCN_335 | 1722 | TTCN_1165 | 4993 |
| GTCN_183 | 1723 | CTCN_1140 | 4994 |
| TTCN_318 | 1724 | TTCN_1166 | 4995 |
| CTCN_336 | 1725 | CTCN_1141 | 4996 |
| CTCN_337 | 1726 | TTCN_1167 | 4997 |
| ATCN_171 | 1727 | TTCN_1168 | 4998 |
| CTCN_338 | 1728 | GTCN_619 | 4999 |
| GTCN_184 | 1729 | CTCN_1142 | 5000 |

| | | | |
|---|---|---|---|
| ATCN_172 | 1730 | ATCN_745 | 5001 |
| GTCN_185 | 1731 | GTCN_620 | 5002 |
| TTCN_319 | 1732 | GTCN_621 | 5003 |
| ATCN_173 | 1733 | TTCN_1169 | 5004 |
| CTCN_339 | 1734 | TTCN_1170 | 5005 |
| ATCN_174 | 1735 | ATCN_746 | 5006 |
| CTCN_340 | 1736 | TTCN_1171 | 5007 |
| TTCN_320 | 1737 | TTCN_1172 | 5008 |
| TTCN_321 | 1738 | GTCN_622 | 5009 |
| GTCN_186 | 1739 | TTCN_1173 | 5010 |
| CTCN_341 | 1740 | ATCN_747 | 5011 |
| CTCN_342 | 1741 | TTCN_1174 | 5012 |
| CTCN_343 | 1742 | CTCN_1143 | 5013 |
| CTCN_344 | 1743 | TTCN_1175 | 5014 |
| GTCN_187 | 1744 | CTCN_1144 | 5015 |
| GTCN_188 | 1745 | ATCN_748 | 5016 |
| CTCN_345 | 1746 | CTCN_1145 | 5017 |
| GTCN_189 | 1747 | GTCN_623 | 5018 |
| CTCN_346 | 1748 | CTCN_1146 | 5019 |
| CTCN_347 | 1749 | CTCN_1147 | 5020 |
| CTCN_348 | 1750 | GTCN_624 | 5021 |
| CTCN_349 | 1751 | ATCN_749 | 5022 |
| GTCN_190 | 1752 | TTCN_1176 | 5023 |
| GTCN_191 | 1753 | CTCN_1148 | 5024 |
| TTCN_322 | 1754 | CTCN_1149 | 5025 |
| CTCN_350 | 1755 | TTCN_1177 | 5026 |
| TTCN_323 | 1756 | ATCN_750 | 5027 |
| TTCN_324 | 1757 | TTCN_1178 | 5028 |
| CTCN_351 | 1758 | CTCN_1150 | 5029 |
| TTCN_325 | 1759 | CTCN_1151 | 5030 |
| TTCN_326 | 1760 | GTCN_625 | 5031 |
| GTCN_192 | 1761 | GTCN_626 | 5032 |
| ATCN_175 | 1762 | CTCN_1152 | 5033 |
| GTCN_193 | 1763 | CTCN_1153 | 5034 |
| GTCN_194 | 1764 | GTCN_627 | 5035 |
| CTCN_352 | 1765 | CTCN_1154 | 5036 |
| ATCN_176 | 1766 | TTCN_1179 | 5037 |
| GTCN_195 | 1767 | ATCN_751 | 5038 |
| GTCN_196 | 1768 | ATCN_752 | 5039 |
| GTCN_197 | 1769 | CTCN_1155 | 5040 |
| TTCN_327 | 1770 | GTCN_628 | 5041 |
| TTCN_328 | 1771 | TTCN_1180 | 5042 |
| GTCN_198 | 1772 | CTCN_1156 | 5043 |
| CTCN_353 | 1773 | ATCN_753 | 5044 |
| GTCN_199 | 1774 | TTCN_1181 | 5045 |
| CTCN_354 | 1775 | CTCN_1157 | 5046 |
| CTCN_355 | 1776 | CTCN_1158 | 5047 |
| CTCN_356 | 1777 | CTCN_1159 | 5048 |
| ATCN_177 | 1778 | GTCN_629 | 5049 |
| CTCN_357 | 1779 | GTCN_630 | 5050 |
| ATCN_178 | 1780 | CTCN_1160 | 5051 |
| ATCN_179 | 1781 | ATCN_754 | 5052 |
| TTCN_329 | 1782 | TTCN_1182 | 5053 |

FIG. 35 (continued)

| | | | |
|---|---|---|---|
| CTCN_358 | 1783 | CTCN_1161 | 5054 |
| TTCN_330 | 1784 | TTCN_1183 | 5055 |
| ATCN_180 | 1785 | TTCN_1184 | 5056 |
| TTCN_331 | 1786 | CTCN_1162 | 5057 |
| CTCN_359 | 1787 | CTCN_1163 | 5058 |
| TTCN_332 | 1788 | TTCN_1185 | 5059 |
| GTCN_200 | 1789 | ATCN_755 | 5060 |
| ATCN_181 | 1790 | CTCN_1164 | 5061 |
| ATCN_182 | 1791 | CTCN_1165 | 5062 |
| ATCN_183 | 1792 | GTCN_631 | 5063 |
| ATCN_184 | 1793 | CTCN_1166 | 5064 |
| CTCN_360 | 1794 | TTCN_1186 | 5065 |
| ATCN_185 | 1795 | CTCN_1167 | 5066 |
| ATCN_186 | 1796 | CTCN_1168 | 5067 |
| TTCN_333 | 1797 | GTCN_632 | 5068 |
| TTCN_334 | 1798 | CTCN_1169 | 5069 |
| CTCN_361 | 1799 | ATCN_756 | 5070 |
| ATCN_187 | 1800 | CTCN_1170 | 5071 |
| TTCN_335 | 1801 | CTCN_1171 | 5072 |
| ATCN_188 | 1802 | CTCN_1172 | 5073 |
| TTCN_336 | 1803 | TTCN_1187 | 5074 |
| GTCN_201 | 1804 | ATCN_757 | 5075 |
| ATCN_189 | 1805 | TTCN_1188 | 5076 |
| ATCN_190 | 1806 | CTCN_1173 | 5077 |
| CTCN_362 | 1807 | TTCN_1189 | 5078 |
| ATCN_191 | 1808 | CTCN_1174 | 5079 |
| TTCN_337 | 1809 | CTCN_1175 | 5080 |
| TTCN_338 | 1810 | CTCN_1176 | 5081 |
| TTCN_339 | 1811 | ATCN_758 | 5082 |
| CTCN_363 | 1812 | CTCN_1177 | 5083 |
| GTCN_202 | 1813 | ATCN_759 | 5084 |
| ATCN_192 | 1814 | TTCN_1190 | 5085 |
| ATCN_193 | 1815 | GTCN_633 | 5086 |
| TTCN_340 | 1816 | GTCN_634 | 5087 |
| GTCN_203 | 1817 | CTCN_1178 | 5088 |
| CTCN_364 | 1818 | CTCN_1179 | 5089 |
| GTCN_204 | 1819 | CTCN_1180 | 5090 |
| CTCN_365 | 1820 | ATCN_760 | 5091 |
| CTCN_366 | 1821 | ATCN_761 | 5092 |
| GTCN_205 | 1822 | CTCN_1181 | 5093 |
| ATCN_194 | 1823 | CTCN_1182 | 5094 |
| CTCN_367 | 1824 | TTCN_1191 | 5095 |
| CTCN_368 | 1825 | CTCN_1183 | 5096 |
| GTCN_206 | 1826 | CTCN_1184 | 5097 |
| TTCN_341 | 1827 | ATCN_762 | 5098 |
| TTCN_342 | 1828 | CTCN_1185 | 5099 |
| GTCN_207 | 1829 | ATCN_763 | 5100 |
| ATCN_195 | 1830 | CTCN_1186 | 5101 |
| ATCN_196 | 1831 | GTCN_635 | 5102 |
| TTCN_343 | 1832 | ATCN_764 | 5103 |
| CTCN_369 | 1833 | TTCN_1192 | 5104 |
| ATCN_197 | 1834 | TTCN_1193 | 5105 |
| GTCN_208 | 1835 | ATCN_765 | 5106 |

| | | | |
|---|---|---|---|
| ATCN_198 | 1836 | ATCN_766 | 5107 |
| TTCN_344 | 1837 | ATCN_767 | 5108 |
| CTCN_370 | 1838 | ATCN_768 | 5109 |
| GTCN_209 | 1839 | CTCN_1187 | 5110 |
| TTCN_345 | 1840 | ATCN_769 | 5111 |
| CTCN_371 | 1841 | GTCN_636 | 5112 |
| CTCN_372 | 1842 | ATCN_770 | 5113 |
| ATCN_199 | 1843 | ATCN_771 | 5114 |
| CTCN_373 | 1844 | CTCN_1188 | 5115 |
| CTCN_374 | 1845 | TTCN_1194 | 5116 |
| GTCN_210 | 1846 | GTCN_637 | 5117 |
| CTCN_375 | 1847 | GTCN_638 | 5118 |
| ATCN_200 | 1848 | CTCN_1189 | 5119 |
| CTCN_376 | 1849 | TTCN_1195 | 5120 |
| TTCN_346 | 1850 | ATCN_772 | 5121 |
| ATCN_201 | 1851 | ATCN_773 | 5122 |
| TTCN_347 | 1852 | CTCN_1190 | 5123 |
| TTCN_348 | 1853 | TTCN_1196 | 5124 |
| GTCN_211 | 1854 | GTCN_639 | 5125 |
| TTCN_349 | 1855 | GTCN_640 | 5126 |
| TTCN_350 | 1856 | TTCN_1197 | 5127 |
| TTCN_351 | 1857 | TTCN_1198 | 5128 |
| TTCN_352 | 1858 | CTCN_1191 | 5129 |
| TTCN_353 | 1859 | GTCN_641 | 5130 |
| ATCN_202 | 1860 | CTCN_1192 | 5131 |
| TTCN_354 | 1861 | GTCN_642 | 5132 |
| GTCN_212 | 1862 | GTCN_643 | 5133 |
| CTCN_377 | 1863 | TTCN_1199 | 5134 |
| GTCN_213 | 1864 | ATCN_774 | 5135 |
| ATCN_203 | 1865 | ATCN_775 | 5136 |
| GTCN_214 | 1866 | GTCN_644 | 5137 |
| ATCN_204 | 1867 | TTCN_1200 | 5138 |
| TTCN_355 | 1868 | ATCN_776 | 5139 |
| TTCN_356 | 1869 | TTCN_1201 | 5140 |
| TTCN_357 | 1870 | ATCN_777 | 5141 |
| TTCN_358 | 1871 | TTCN_1202 | 5142 |
| GTCN_215 | 1872 | GTCN_645 | 5143 |
| TTCN_359 | 1873 | GTCN_646 | 5144 |
| TTCN_360 | 1874 | CTCN_1193 | 5145 |
| TTCN_361 | 1875 | CTCN_1194 | 5146 |
| TTCN_362 | 1876 | CTCN_1195 | 5147 |
| CTCN_378 | 1877 | CTCN_1196 | 5148 |
| ATCN_205 | 1878 | TTCN_1203 | 5149 |
| CTCN_379 | 1879 | TTCN_1204 | 5150 |
| ATCN_206 | 1880 | CTCN_1197 | 5151 |
| ATCN_207 | 1881 | ATCN_778 | 5152 |
| CTCN_380 | 1882 | TTCN_1205 | 5153 |
| GTCN_216 | 1883 | CTCN_1198 | 5154 |
| CTCN_381 | 1884 | CTCN_1199 | 5155 |
| ATCN_208 | 1885 | ATCN_779 | 5156 |
| ATCN_209 | 1886 | ATCN_780 | 5157 |
| CTCN_382 | 1887 | CTCN_1200 | 5158 |
| CTCN_383 | 1888 | CTCN_1201 | 5159 |

FIG. 35 (continued)

| | | | |
|---|---|---|---|
| TTCN_363 | 1889 | TTCN_1206 | 5160 |
| ATCN_210 | 1890 | TTCN_1207 | 5161 |
| TTCN_364 | 1891 | CTCN_1202 | 5162 |
| CTCN_384 | 1892 | ATCN_781 | 5163 |
| CTCN_385 | 1893 | TTCN_1208 | 5164 |
| CTCN_386 | 1894 | TTCN_1209 | 5165 |
| CTCN_387 | 1895 | ATCN_782 | 5166 |
| ATCN_211 | 1896 | TTCN_1210 | 5167 |
| TTCN_365 | 1897 | CTCN_1203 | 5168 |
| TTCN_366 | 1898 | ATCN_783 | 5169 |
| TTCN_367 | 1899 | GTCN_647 | 5170 |
| GTCN_217 | 1900 | TTCN_1211 | 5171 |
| CTCN_388 | 1901 | GTCN_648 | 5172 |
| CTCN_389 | 1902 | ATCN_784 | 5173 |
| GTCN_218 | 1903 | CTCN_1204 | 5174 |
| CTCN_390 | 1904 | ATCN_785 | 5175 |
| ATCN_212 | 1905 | CTCN_1205 | 5176 |
| CTCN_391 | 1906 | CTCN_1206 | 5177 |
| ATCN_213 | 1907 | CTCN_1207 | 5178 |
| TTCN_368 | 1908 | CTCN_1208 | 5179 |
| TTCN_369 | 1909 | GTCN_649 | 5180 |
| TTCN_370 | 1910 | CTCN_1209 | 5181 |
| CTCN_392 | 1911 | ATCN_786 | 5182 |
| CTCN_393 | 1912 | CTCN_1210 | 5183 |
| TTCN_371 | 1913 | TTCN_1212 | 5184 |
| TTCN_372 | 1914 | ATCN_787 | 5185 |
| GTCN_219 | 1915 | TTCN_1213 | 5186 |
| TTCN_373 | 1916 | TTCN_1214 | 5187 |
| TTCN_374 | 1917 | GTCN_650 | 5188 |
| TTCN_375 | 1918 | TTCN_1215 | 5189 |
| CTCN_394 | 1919 | GTCN_651 | 5190 |
| ATCN_214 | 1920 | GTCN_652 | 5191 |
| TTCN_376 | 1921 | TTCN_1216 | 5192 |
| CTCN_395 | 1922 | TTCN_1217 | 5193 |
| GTCN_220 | 1923 | CTCN_1211 | 5194 |
| ATCN_215 | 1924 | TTCN_1218 | 5195 |
| ATCN_216 | 1925 | CTCN_1212 | 5196 |
| CTCN_396 | 1926 | TTCN_1219 | 5197 |
| TTCN_377 | 1927 | GTCN_653 | 5198 |
| TTCN_378 | 1928 | CTCN_1213 | 5199 |
| ATCN_217 | 1929 | TTCN_1220 | 5200 |
| TTCN_379 | 1930 | GTCN_654 | 5201 |
| TTCN_380 | 1931 | CTCN_1214 | 5202 |
| TTCN_381 | 1932 | ATCN_788 | 5203 |
| GTCN_221 | 1933 | CTCN_1215 | 5204 |
| TTCN_382 | 1934 | CTCN_1216 | 5205 |
| GTCN_222 | 1935 | TTCN_1221 | 5206 |
| GTCN_223 | 1936 | GTCN_655 | 5207 |
| CTCN_397 | 1937 | TTCN_1222 | 5208 |
| GTCN_224 | 1938 | GTCN_656 | 5209 |
| ATCN_218 | 1939 | CTCN_1217 | 5210 |
| ATCN_219 | 1940 | TTCN_1223 | 5211 |
| CTCN_398 | 1941 | ATCN_789 | 5212 |

| | | | |
|---|---|---|---|
| TTCN_383 | 1942 | CTCN_1218 | 5213 |
| GTCN_225 | 1943 | CTCN_1219 | 5214 |
| TTCN_384 | 1944 | CTCN_1220 | 5215 |
| GTCN_226 | 1945 | CTCN_1221 | 5216 |
| ATCN_220 | 1946 | TTCN_1224 | 5217 |
| TTCN_385 | 1947 | ATCN_790 | 5218 |
| GTCN_227 | 1948 | TTCN_1225 | 5219 |
| CTCN_399 | 1949 | CTCN_1222 | 5220 |
| GTCN_228 | 1950 | CTCN_1223 | 5221 |
| ATCN_221 | 1951 | CTCN_1224 | 5222 |
| ATCN_222 | 1952 | CTCN_1225 | 5223 |
| ATCN_223 | 1953 | CTCN_1226 | 5224 |
| TTCN_386 | 1954 | ATCN_791 | 5225 |
| TTCN_387 | 1955 | ATCN_792 | 5226 |
| ATCN_224 | 1956 | CTCN_1227 | 5227 |
| TTCN_388 | 1957 | CTCN_1228 | 5228 |
| TTCN_389 | 1958 | GTCN_657 | 5229 |
| TTCN_390 | 1959 | CTCN_1229 | 5230 |
| ATCN_225 | 1960 | CTCN_1230 | 5231 |
| TTCN_391 | 1961 | GTCN_658 | 5232 |
| CTCN_400 | 1962 | CTCN_1231 | 5233 |
| TTCN_392 | 1963 | ATCN_793 | 5234 |
| TTCN_393 | 1964 | CTCN_1232 | 5235 |
| TTCN_394 | 1965 | CTCN_1233 | 5236 |
| TTCN_395 | 1966 | TTCN_1226 | 5237 |
| ATCN_226 | 1967 | GTCN_659 | 5238 |
| GTCN_229 | 1968 | CTCN_1234 | 5239 |
| ATCN_227 | 1969 | ATCN_794 | 5240 |
| GTCN_230 | 1970 | ATCN_795 | 5241 |
| CTCN_401 | 1971 | CTCN_1235 | 5242 |
| CTCN_402 | 1972 | CTCN_1236 | 5243 |
| ATCN_228 | 1973 | CTCN_1237 | 5244 |
| TTCN_396 | 1974 | CTCN_1238 | 5245 |
| CTCN_403 | 1975 | ATCN_796 | 5246 |
| CTCN_404 | 1976 | ATCN_797 | 5247 |
| ATCN_229 | 1977 | ATCN_798 | 5248 |
| CTCN_405 | 1978 | GTCN_660 | 5249 |
| CTCN_406 | 1979 | GTCN_661 | 5250 |
| TTCN_397 | 1980 | CTCN_1239 | 5251 |
| GTCN_231 | 1981 | TTCN_1227 | 5252 |
| GTCN_232 | 1982 | GTCN_662 | 5253 |
| CTCN_407 | 1983 | TTCN_1228 | 5254 |
| GTCN_233 | 1984 | CTCN_1240 | 5255 |
| ATCN_230 | 1985 | CTCN_1241 | 5256 |
| CTCN_408 | 1986 | CTCN_1242 | 5257 |
| TTCN_398 | 1987 | CTCN_1243 | 5258 |
| TTCN_399 | 1988 | TTCN_1229 | 5259 |
| GTCN_234 | 1989 | ATCN_799 | 5260 |
| TTCN_400 | 1990 | TTCN_1230 | 5261 |
| CTCN_409 | 1991 | CTCN_1244 | 5262 |
| CTCN_410 | 1992 | CTCN_1245 | 5263 |
| ATCN_231 | 1993 | CTCN_1246 | 5264 |
| ATCN_232 | 1994 | ATCN_800 | 5265 |

FIG. 35 (continued)

| | | | |
|---|---|---|---|
| TTCN_401 | 1995 | GTCN_663 | 5266 |
| TTCN_402 | 1996 | GTCN_664 | 5267 |
| ATCN_233 | 1997 | TTCN_1231 | 5268 |
| ATCN_234 | 1998 | CTCN_1247 | 5269 |
| GTCN_235 | 1999 | TTCN_1232 | 5270 |
| TTCN_403 | 2000 | ATCN_801 | 5271 |
| TTCN_404 | 2001 | CTCN_1248 | 5272 |
| TTCN_405 | 2002 | TTCN_1233 | 5273 |
| CTCN_411 | 2003 | CTCN_1249 | 5274 |
| ATCN_235 | 2004 | TTCN_1234 | 5275 |
| TTCN_406 | 2005 | TTCN_1235 | 5276 |
| TTCN_407 | 2006 | CTCN_1250 | 5277 |
| GTCN_236 | 2007 | GTCN_665 | 5278 |
| TTCN_408 | 2008 | GTCN_666 | 5279 |
| TTCN_409 | 2009 | GTCN_667 | 5280 |
| ATCN_236 | 2010 | TTCN_1236 | 5281 |
| GTCN_237 | 2011 | TTCN_1237 | 5282 |
| CTCN_412 | 2012 | ATCN_802 | 5283 |
| CTCN_413 | 2013 | CTCN_1251 | 5284 |
| TTCN_410 | 2014 | CTCN_1252 | 5285 |
| CTCN_414 | 2015 | TTCN_1238 | 5286 |
| GTCN_238 | 2016 | TTCN_1239 | 5287 |
| CTCN_415 | 2017 | CTCN_1253 | 5288 |
| GTCN_239 | 2018 | CTCN_1254 | 5289 |
| GTCN_240 | 2019 | ATCN_803 | 5290 |
| CTCN_416 | 2020 | ATCN_804 | 5291 |
| CTCN_417 | 2021 | GTCN_668 | 5292 |
| ATCN_237 | 2022 | TTCN_1240 | 5293 |
| ATCN_238 | 2023 | GTCN_669 | 5294 |
| CTCN_418 | 2024 | CTCN_1255 | 5295 |
| CTCN_419 | 2025 | CTCN_1256 | 5296 |
| CTCN_420 | 2026 | GTCN_670 | 5297 |
| CTCN_421 | 2027 | TTCN_1241 | 5298 |
| TTCN_411 | 2028 | TTCN_1242 | 5299 |
| TTCN_412 | 2029 | ATCN_805 | 5300 |
| CTCN_422 | 2030 | ATCN_806 | 5301 |
| CTCN_423 | 2031 | TTCN_1243 | 5302 |
| CTCN_424 | 2032 | TTCN_1244 | 5303 |
| CTCN_425 | 2033 | TTCN_1245 | 5304 |
| CTCN_426 | 2034 | ATCN_807 | 5305 |
| TTCN_413 | 2035 | TTCN_1246 | 5306 |
| CTCN_427 | 2036 | CTCN_1257 | 5307 |
| GTCN_241 | 2037 | TTCN_1247 | 5308 |
| CTCN_428 | 2038 | CTCN_1258 | 5309 |
| GTCN_242 | 2039 | TTCN_1248 | 5310 |
| CTCN_429 | 2040 | GTCN_671 | 5311 |
| GTCN_243 | 2041 | CTCN_1259 | 5312 |
| CTCN_430 | 2042 | CTCN_1260 | 5313 |
| ATCN_239 | 2043 | GTCN_672 | 5314 |
| CTCN_431 | 2044 | GTCN_673 | 5315 |
| CTCN_432 | 2045 | ATCN_808 | 5316 |
| CTCN_433 | 2046 | GTCN_674 | 5317 |
| CTCN_434 | 2047 | TTCN_1249 | 5318 |

| | | | |
|---|---|---|---|
| ATCN_240 | 2048 | TTCN_1250 | 5319 |
| ATCN_241 | 2049 | CTCN_1261 | 5320 |
| GTCN_244 | 2050 | TTCN_1251 | 5321 |
| CTCN_435 | 2051 | CTCN_1262 | 5322 |
| CTCN_436 | 2052 | TTCN_1252 | 5323 |
| TTCN_414 | 2053 | CTCN_1263 | 5324 |
| ATCN_242 | 2054 | CTCN_1264 | 5325 |
| TTCN_415 | 2055 | CTCN_1265 | 5326 |
| TTCN_416 | 2056 | CTCN_1266 | 5327 |
| GTCN_245 | 2057 | TTCN_1253 | 5328 |
| GTCN_246 | 2058 | TTCN_1254 | 5329 |
| TTCN_417 | 2059 | TTCN_1255 | 5330 |
| CTCN_437 | 2060 | GTCN_675 | 5331 |
| GTCN_247 | 2061 | ATCN_809 | 5332 |
| CTCN_438 | 2062 | CTCN_1267 | 5333 |
| ATCN_243 | 2063 | TTCN_1256 | 5334 |
| CTCN_439 | 2064 | ATCN_810 | 5335 |
| CTCN_440 | 2065 | ATCN_811 | 5336 |
| ATCN_244 | 2066 | GTCN_676 | 5337 |
| CTCN_441 | 2067 | TTCN_1257 | 5338 |
| TTCN_418 | 2068 | TTCN_1258 | 5339 |
| TTCN_419 | 2069 | TTCN_1259 | 5340 |
| TTCN_420 | 2070 | TTCN_1260 | 5341 |
| CTCN_442 | 2071 | CTCN_1268 | 5342 |
| ATCN_245 | 2072 | ATCN_812 | 5343 |
| GTCN_248 | 2073 | CTCN_1269 | 5344 |
| CTCN_443 | 2074 | CTCN_1270 | 5345 |
| CTCN_444 | 2075 | GTCN_677 | 5346 |
| TTCN_421 | 2076 | CTCN_1271 | 5347 |
| ATCN_246 | 2077 | TTCN_1261 | 5348 |
| ATCN_247 | 2078 | CTCN_1272 | 5349 |
| CTCN_445 | 2079 | GTCN_678 | 5350 |
| CTCN_446 | 2080 | CTCN_1273 | 5351 |
| CTCN_447 | 2081 | GTCN_679 | 5352 |
| ATCN_248 | 2082 | GTCN_680 | 5353 |
| CTCN_448 | 2083 | CTCN_1274 | 5354 |
| GTCN_249 | 2084 | CTCN_1275 | 5355 |
| GTCN_250 | 2085 | CTCN_1276 | 5356 |
| CTCN_449 | 2086 | CTCN_1277 | 5357 |
| TTCN_422 | 2087 | ATCN_813 | 5358 |
| TTCN_423 | 2088 | CTCN_1278 | 5359 |
| ATCN_249 | 2089 | GTCN_681 | 5360 |
| CTCN_450 | 2090 | CTCN_1279 | 5361 |
| CTCN_451 | 2091 | GTCN_682 | 5362 |
| TTCN_424 | 2092 | GTCN_683 | 5363 |
| TTCN_425 | 2093 | CTCN_1280 | 5364 |
| TTCN_426 | 2094 | GTCN_684 | 5365 |
| CTCN_452 | 2095 | ATCN_814 | 5366 |
| GTCN_251 | 2096 | ATCN_815 | 5367 |
| GTCN_252 | 2097 | CTCN_1281 | 5368 |
| TTCN_427 | 2098 | CTCN_1282 | 5369 |
| GTCN_253 | 2099 | CTCN_1283 | 5370 |
| TTCN_428 | 2100 | CTCN_1284 | 5371 |

FIG. 35 (continued)

| | | | |
|---|---|---|---|
| TTCN_429 | 2281 | TTCN_1262 | 5372 |
| TTCN_430 | 2282 | ATCN_816 | 5373 |
| ATCN_250 | 2283 | TTCN_1263 | 5374 |
| TTCN_431 | 2284 | CTCN_1285 | 5375 |
| ATCN_251 | 2285 | CTCN_1286 | 5376 |
| ATCN_252 | 2286 | CTCN_1287 | 5377 |
| TTCN_432 | 2287 | CTCN_1288 | 5378 |
| CTCN_453 | 2288 | TTCN_1264 | 5379 |
| TTCN_433 | 2289 | CTCN_1289 | 5380 |
| TTCN_434 | 2290 | GTCN_685 | 5381 |
| ATCN_253 | 2291 | ATCN_817 | 5382 |
| GTCN_254 | 2292 | TTCN_1265 | 5383 |
| GTCN_255 | 2293 | ATCN_818 | 5384 |
| CTCN_454 | 2294 | GTCN_686 | 5385 |
| ATCN_254 | 2295 | GTCN_687 | 5386 |
| CTCN_455 | 2296 | CTCN_1290 | 5387 |
| GTCN_256 | 2297 | CTCN_1291 | 5388 |
| TTCN_435 | 2298 | GTCN_688 | 5389 |
| CTCN_456 | 2299 | CTCN_1292 | 5390 |
| GTCN_257 | 2300 | ATCN_819 | 5391 |
| CTCN_457 | 2301 | ATCN_820 | 5392 |
| CTCN_458 | 2302 | CTCN_1293 | 5393 |
| TTCN_436 | 2303 | CTCN_1294 | 5394 |
| ATCN_255 | 2304 | ATCN_821 | 5395 |
| GTCN_258 | 2305 | CTCN_1295 | 5396 |
| ATCN_256 | 2306 | CTCN_1296 | 5397 |
| CTCN_459 | 2307 | GTCN_689 | 5398 |
| TTCN_437 | 2308 | GTCN_690 | 5399 |
| CTCN_460 | 2309 | CTCN_1297 | 5400 |
| CTCN_461 | 2310 | TTCN_1266 | 5401 |
| TTCN_438 | 2311 | ATCN_822 | 5402 |
| CTCN_462 | 2312 | CTCN_1298 | 5403 |
| ATCN_257 | 2313 | ATCN_823 | 5404 |
| ATCN_258 | 2314 | CTCN_1299 | 5405 |
| ATCN_259 | 2315 | CTCN_1300 | 5406 |
| ATCN_260 | 2316 | CTCN_1301 | 5407 |
| CTCN_463 | 2317 | TTCN_1267 | 5408 |
| CTCN_464 | 2318 | ATCN_824 | 5409 |
| CTCN_465 | 2319 | TTCN_1268 | 5410 |
| CTCN_466 | 2320 | CTCN_1302 | 5411 |
| GTCN_259 | 2321 | CTCN_1303 | 5412 |
| TTCN_439 | 2322 | CTCN_1304 | 5413 |
| CTCN_467 | 2323 | CTCN_1305 | 5414 |
| CTCN_468 | 2324 | ATCN_825 | 5415 |
| TTCN_440 | 2325 | ATCN_826 | 5416 |
| TTCN_441 | 2326 | GTCN_691 | 5417 |
| CTCN_469 | 2327 | CTCN_1306 | 5418 |
| TTCN_442 | 2328 | GTCN_692 | 5419 |
| TTCN_443 | 2329 | GTCN_693 | 5420 |
| TTCN_444 | 2330 | GTCN_694 | 5421 |
| TTCN_445 | 2331 | ATCN_827 | 5422 |
| TTCN_446 | 2332 | CTCN_1307 | 5423 |
| CTCN_470 | 2333 | CTCN_1308 | 5424 |

| | | | |
|---|---|---|---|
| TTCN_447 | 2334 | CTCN_1309 | 5425 |
| GTCN_260 | 2335 | CTCN_1310 | 5426 |
| CTCN_471 | 2336 | CTCN_1311 | 5427 |
| CTCN_472 | 2337 | ATCN_828 | 5428 |
| TTCN_448 | 2338 | ATCN_829 | 5429 |
| ATCN_261 | 2339 | GTCN_695 | 5430 |
| TTCN_449 | 2340 | CTCN_1312 | 5431 |
| GTCN_261 | 2341 | ATCN_830 | 5432 |
| GTCN_262 | 2342 | TTCN_1269 | 5433 |
| GTCN_263 | 2343 | GTCN_696 | 5434 |
| GTCN_264 | 2344 | CTCN_1313 | 5435 |
| CTCN_473 | 2345 | TTCN_1270 | 5436 |
| ATCN_262 | 2346 | GTCN_697 | 5437 |
| CTCN_474 | 2347 | ATCN_831 | 5438 |
| TTCN_450 | 2348 | TTCN_1271 | 5439 |
| GTCN_265 | 2349 | ATCN_832 | 5440 |
| TTCN_451 | 2350 | CTCN_1314 | 5441 |
| ATCN_263 | 2351 | ATCN_833 | 5442 |
| CTCN_475 | 2352 | TTCN_1272 | 5443 |
| ATCN_264 | 2353 | ATCN_834 | 5444 |
| ATCN_265 | 2354 | ATCN_835 | 5445 |
| TTCN_452 | 2355 | TTCN_1273 | 5446 |
| GTCN_266 | 2356 | GTCN_698 | 5447 |
| CTCN_476 | 2357 | ATCN_836 | 5448 |
| CTCN_477 | 2358 | GTCN_699 | 5449 |
| GTCN_267 | 2359 | TTCN_1274 | 5450 |
| TTCN_453 | 2360 | GTCN_700 | 5451 |
| CTCN_478 | 2361 | TTCN_1275 | 5452 |
| ATCN_266 | 2362 | GTCN_701 | 5453 |
| CTCN_479 | 2363 | TTCN_1276 | 5454 |
| CTCN_480 | 2364 | CTCN_1315 | 5455 |
| CTCN_481 | 2365 | GTCN_702 | 5456 |
| GTCN_268 | 2366 | TTCN_1277 | 5457 |
| CTCN_482 | 2367 | TTCN_1278 | 5458 |
| CTCN_483 | 2368 | TTCN_1279 | 5459 |
| TTCN_454 | 2369 | TTCN_1280 | 5460 |
| CTCN_484 | 2370 | TTCN_1281 | 5461 |
| ATCN_267 | 2371 | CTCN_1316 | 5462 |
| ATCN_268 | 2372 | GTCN_703 | 5463 |
| TTCN_455 | 2373 | GTCN_704 | 5464 |
| TTCN_456 | 2374 | CTCN_1317 | 5465 |
| CTCN_485 | 2375 | ATCN_837 | 5466 |
| TTCN_457 | 2376 | CTCN_1318 | 5467 |
| TTCN_458 | 2377 | CTCN_1319 | 5468 |
| CTCN_486 | 2378 | CTCN_1320 | 5469 |
| CTCN_487 | 2379 | GTCN_705 | 5470 |
| CTCN_488 | 2380 | CTCN_1321 | 5471 |
| CTCN_489 | 2381 | ATCN_838 | 5472 |
| TTCN_459 | 2382 | CTCN_1322 | 5473 |
| GTCN_269 | 2383 | ATCN_839 | 5474 |
| GTCN_270 | 2384 | CTCN_1323 | 5475 |
| CTCN_490 | 2385 | CTCN_1324 | 5476 |
| CTCN_491 | 2386 | CTCN_1325 | 5477 |

FIG. 35 (continued)

| | | | |
|---|---|---|---|
| TTCN_460 | 2387 | GTCN_706 | 5478 |
| ATCN_269 | 2388 | TTCN_1282 | 5479 |
| TTCN_461 | 2389 | CTCN_1326 | 5480 |
| TTCN_462 | 2390 | ATCN_840 | 5481 |
| CTCN_492 | 2391 | GTCN_707 | 5482 |
| GTCN_271 | 2392 | CTCN_1327 | 5483 |
| CTCN_493 | 2393 | TTCN_1283 | 5484 |
| CTCN_494 | 2394 | GTCN_708 | 5485 |
| CTCN_495 | 2395 | TTCN_1284 | 5486 |
| TTCN_463 | 2396 | CTCN_1328 | 5487 |
| TTCN_464 | 2397 | TTCN_1285 | 5488 |
| TTCN_465 | 2398 | ATCN_841 | 5489 |
| ATCN_270 | 2399 | ATCN_842 | 5490 |
| TTCN_466 | 2400 | CTCN_1329 | 5491 |
| ATCN_271 | 2401 | GTCN_709 | 5492 |
| ATCN_272 | 2402 | CTCN_1330 | 5493 |
| GTCN_272 | 2403 | CTCN_1331 | 5494 |
| TTCN_467 | 2404 | CTCN_1332 | 5495 |
| CTCN_496 | 2405 | ATCN_843 | 5496 |
| GTCN_273 | 2406 | CTCN_1333 | 5497 |
| ATCN_273 | 2407 | CTCN_1334 | 5498 |
| GTCN_274 | 2408 | TTCN_1286 | 5499 |
| TTCN_468 | 2409 | GTCN_710 | 5500 |
| TTCN_469 | 2410 | ATCN_844 | 5501 |
| GTCN_275 | 2411 | ATCN_845 | 5502 |
| CTCN_497 | 2412 | TTCN_1287 | 5503 |
| CTCN_498 | 2413 | GTCN_711 | 5504 |
| TTCN_470 | 2414 | TTCN_1288 | 5505 |
| CTCN_499 | 2415 | CTCN_1335 | 5506 |
| TTCN_471 | 2416 | GTCN_712 | 5507 |
| CTCN_500 | 2417 | GTCN_713 | 5508 |
| CTCN_501 | 2418 | TTCN_1289 | 5509 |
| GTCN_276 | 2419 | TTCN_1290 | 5510 |
| TTCN_472 | 2420 | TTCN_1291 | 5511 |
| ATCN_274 | 2421 | ATCN_846 | 5512 |
| CTCN_502 | 2422 | ATCN_847 | 5513 |
| TTCN_473 | 2423 | ATCN_848 | 5514 |
| TTCN_474 | 2424 | ATCN_849 | 5515 |
| TTCN_475 | 2425 | TTCN_1292 | 5516 |
| CTCN_503 | 2426 | TTCN_1293 | 5517 |
| TTCN_476 | 2427 | TTCN_1294 | 5518 |
| CTCN_504 | 2428 | CTCN_1336 | 5519 |
| CTCN_505 | 2429 | CTCN_1337 | 5520 |
| TTCN_477 | 2430 | TTCN_1295 | 5521 |
| TTCN_478 | 2431 | TTCN_1296 | 5522 |
| CTCN_506 | 2432 | ATCN_850 | 5523 |
| CTCN_507 | 2433 | GTCN_714 | 5524 |
| CTCN_508 | 2434 | CTCN_1338 | 5525 |
| ATCN_275 | 2435 | CTCN_1339 | 5526 |
| CTCN_509 | 2436 | ATCN_851 | 5527 |
| GTCN_277 | 2437 | CTCN_1340 | 5528 |
| CTCN_510 | 2438 | GTCN_715 | 5529 |
| CTCN_511 | 2439 | ATCN_852 | 5530 |

| | | | |
|---|---|---|---|
| GTCN_278 | 2440 | GTCN_716 | 5531 |
| GTCN_279 | 2441 | ATCN_853 | 5532 |
| CTCN_512 | 2442 | GTCN_717 | 5533 |
| CTCN_513 | 2443 | CTCN_1341 | 5534 |
| TTCN_479 | 2444 | ATCN_854 | 5535 |
| CTCN_514 | 2445 | TTCN_1297 | 5536 |
| GTCN_280 | 2446 | TTCN_1298 | 5537 |
| TTCN_480 | 2447 | ATCN_855 | 5538 |
| TTCN_481 | 2448 | GTCN_718 | 5539 |
| CTCN_515 | 2449 | GTCN_719 | 5540 |
| TTCN_482 | 2450 | TTCN_1299 | 5541 |
| ATCN_276 | 2451 | ATCN_856 | 5542 |
| CTCN_516 | 2452 | TTCN_1300 | 5543 |
| CTCN_517 | 2453 | CTCN_1342 | 5544 |
| GTCN_281 | 2454 | GTCN_720 | 5545 |
| CTCN_518 | 2455 | GTCN_721 | 5546 |
| CTCN_519 | 2456 | TTCN_1301 | 5547 |
| CTCN_520 | 2457 | CTCN_1343 | 5548 |
| ATCN_277 | 2458 | TTCN_1302 | 5549 |
| TTCN_483 | 2459 | GTCN_722 | 5550 |
| TTCN_484 | 2460 | CTCN_1344 | 5551 |
| ATCN_278 | 2461 | GTCN_723 | 5552 |
| CTCN_521 | 2462 | CTCN_1345 | 5553 |
| CTCN_522 | 2463 | ATCN_857 | 5554 |
| CTCN_523 | 2464 | CTCN_1346 | 5555 |
| GTCN_282 | 2465 | ATCN_858 | 5556 |
| ATCN_279 | 2466 | CTCN_1347 | 5557 |
| ATCN_280 | 2467 | CTCN_1348 | 5558 |
| CTCN_524 | 2468 | CTCN_1349 | 5559 |
| CTCN_525 | 2469 | TTCN_1303 | 5560 |
| TTCN_485 | 2470 | TTCN_1304 | 5561 |
| CTCN_526 | 2471 | ATCN_859 | 5562 |
| CTCN_527 | 2472 | TTCN_1305 | 5563 |
| GTCN_283 | 2473 | CTCN_1350 | 5564 |
| CTCN_528 | 2474 | CTCN_1351 | 5565 |
| ATCN_281 | 2475 | CTCN_1352 | 5566 |
| ATCN_282 | 2476 | CTCN_1353 | 5567 |
| ATCN_283 | 2477 | TTCN_1306 | 5568 |
| ATCN_284 | 2478 | GTCN_724 | 5569 |
| ATCN_285 | 2479 | CTCN_1354 | 5570 |
| CTCN_529 | 2480 | ATCN_860 | 5571 |
| ATCN_286 | 2481 | TTCN_1307 | 5572 |
| TTCN_486 | 2482 | GTCN_725 | 5573 |
| CTCN_530 | 2483 | CTCN_1355 | 5574 |
| ATCN_287 | 2484 | CTCN_1356 | 5575 |
| GTCN_284 | 2485 | GTCN_726 | 5576 |
| TTCN_487 | 2486 | CTCN_1357 | 5577 |
| ATCN_288 | 2487 | ATCN_861 | 5578 |
| TTCN_488 | 2488 | ATCN_862 | 5579 |
| TTCN_489 | 2489 | CTCN_1358 | 5580 |
| TTCN_490 | 2490 | CTCN_1359 | 5581 |
| TTCN_491 | 2491 | ATCN_863 | 5582 |
| GTCN_285 | 2492 | TTCN_1308 | 5583 |

FIG. 35 (continued)

| | | | |
|---|---|---|---|
| CTCN_531 | 2493 | CTCN_1360 | 5584 |
| GTCN_286 | 2494 | TTCN_1309 | 5585 |
| TTCN_492 | 2495 | TTCN_1310 | 5586 |
| GTCN_287 | 2496 | CTCN_1361 | 5587 |
| TTCN_493 | 2497 | CTCN_1362 | 5588 |
| ATCN_289 | 2498 | GTCN_727 | 5589 |
| TTCN_494 | 2499 | TTCN_1311 | 5590 |
| TTCN_495 | 2500 | GTCN_728 | 5591 |
| TTCN_496 | 2501 | TTCN_1312 | 5592 |
| ATCN_290 | 2502 | TTCN_1313 | 5593 |
| ATCN_291 | 2503 | CTCN_1363 | 5594 |
| GTCN_288 | 2504 | GTCN_729 | 5595 |
| TTCN_497 | 2505 | CTCN_1364 | 5596 |
| ATCN_292 | 2506 | TTCN_1314 | 5597 |
| TTCN_498 | 2507 | GTCN_730 | 5598 |
| TTCN_499 | 2508 | TTCN_1315 | 5599 |
| TTCN_500 | 2509 | TTCN_1316 | 5600 |
| CTCN_532 | 2510 | TTCN_1317 | 5601 |
| CTCN_533 | 2511 | TTCN_1318 | 5602 |
| ATCN_293 | 2512 | ATCN_864 | 5603 |
| ATCN_294 | 2513 | CTCN_1365 | 5604 |
| TTCN_501 | 2514 | TTCN_1319 | 5605 |
| TTCN_502 | 2515 | ATCN_865 | 5606 |
| ATCN_295 | 2516 | CTCN_1366 | 5607 |
| TTCN_503 | 2517 | CTCN_1367 | 5608 |
| TTCN_504 | 2518 | GTCN_731 | 5609 |
| ATCN_296 | 2519 | CTCN_1368 | 5610 |
| CTCN_534 | 2520 | ATCN_866 | 5611 |
| ATCN_297 | 2521 | ATCN_867 | 5612 |
| CTCN_535 | 2522 | CTCN_1369 | 5613 |
| GTCN_289 | 2523 | CTCN_1370 | 5614 |
| TTCN_505 | 2524 | CTCN_1371 | 5615 |
| CTCN_536 | 2525 | GTCN_732 | 5616 |
| CTCN_537 | 2526 | CTCN_1372 | 5617 |
| TTCN_506 | 2527 | GTCN_733 | 5618 |
| CTCN_538 | 2528 | CTCN_1373 | 5619 |
| GTCN_290 | 2529 | CTCN_1374 | 5620 |
| TTCN_507 | 2530 | CTCN_1375 | 5621 |
| ATCN_298 | 2531 | ATCN_868 | 5622 |
| GTCN_291 | 2532 | GTCN_734 | 5623 |
| TTCN_508 | 2533 | TTCN_1320 | 5624 |
| ATCN_299 | 2534 | CTCN_1376 | 5625 |
| ATCN_300 | 2535 | CTCN_1377 | 5626 |
| TTCN_509 | 2536 | ATCN_869 | 5627 |
| TTCN_510 | 2537 | TTCN_1321 | 5628 |
| TTCN_511 | 2538 | CTCN_1378 | 5629 |
| TTCN_512 | 2539 | CTCN_1379 | 5630 |
| TTCN_513 | 2540 | CTCN_1380 | 5631 |
| CTCN_539 | 2541 | GTCN_735 | 5632 |
| CTCN_540 | 2542 | CTCN_1381 | 5633 |
| ATCN_301 | 2543 | GTCN_736 | 5634 |
| TTCN_514 | 2544 | CTCN_1382 | 5635 |
| TTCN_515 | 2545 | ATCN_870 | 5636 |

| | | | |
|---|---|---|---|
| TTCN_516 | 2546 | GTCN_737 | 5637 |
| CTCN_541 | 2547 | ATCN_871 | 5638 |
| TTCN_517 | 2548 | ATCN_872 | 5639 |
| TTCN_518 | 2549 | ATCN_873 | 5640 |
| TTCN_519 | 2550 | ATCN_874 | 5641 |
| ATCN_302 | 2551 | ATCN_875 | 5642 |
| TTCN_520 | 2552 | ATCN_876 | 5643 |
| TTCN_521 | 2553 | ATCN_877 | 5644 |
| TTCN_522 | 2554 | ATCN_878 | 5645 |
| TTCN_523 | 2555 | ATCN_879 | 5646 |
| TTCN_524 | 2556 | ATCN_880 | 5647 |
| TTCN_525 | 2557 | CTCN_1383 | 5648 |
| CTCN_542 | 2558 | TTCN_1322 | 5649 |
| ATCN_303 | 2559 | TTCN_1323 | 5650 |
| TTCN_526 | 2560 | ATCN_881 | 5651 |
| ATCN_304 | 2561 | CTCN_1384 | 5652 |
| TTCN_527 | 2562 | TTCN_1324 | 5653 |
| TTCN_528 | 2563 | CTCN_1385 | 5654 |
| TTCN_529 | 2564 | GTCN_738 | 5655 |
| TTCN_530 | 2565 | GTCN_739 | 5656 |
| TTCN_531 | 2566 | CTCN_1386 | 5657 |
| GTCN_292 | 2567 | CTCN_1387 | 5658 |
| GTCN_293 | 2568 | TTCN_1325 | 5659 |
| CTCN_543 | 2569 | TTCN_1326 | 5660 |
| TTCN_532 | 2570 | ATCN_882 | 5661 |
| TTCN_533 | 2571 | ATCN_883 | 5662 |
| TTCN_534 | 2572 | ATCN_884 | 5663 |
| CTCN_544 | 2573 | CTCN_1388 | 5664 |
| ATCN_305 | 2574 | TTCN_1327 | 5665 |
| TTCN_535 | 2575 | GTCN_740 | 5666 |
| TTCN_536 | 2576 | TTCN_1328 | 5667 |
| GTCN_294 | 2577 | CTCN_1389 | 5668 |
| CTCN_545 | 2578 | TTCN_1329 | 5669 |
| TTCN_537 | 2579 | CTCN_1390 | 5670 |
| ATCN_306 | 2580 | CTCN_1391 | 5671 |
| ATCN_307 | 2581 | ATCN_885 | 5672 |
| TTCN_538 | 2582 | ATCN_886 | 5673 |
| GTCN_295 | 2583 | ATCN_887 | 5674 |
| GTCN_296 | 2584 | CTCN_1392 | 5675 |
| GTCN_297 | 2585 | CTCN_1393 | 5676 |
| ATCN_308 | 2586 | ATCN_888 | 5677 |
| CTCN_546 | 2587 | ATCN_889 | 5678 |
| TTCN_539 | 2588 | ATCN_890 | 5679 |
| ATCN_309 | 2589 | TTCN_1330 | 5680 |
| ATCN_310 | 2590 | CTCN_1394 | 5681 |
| CTCN_547 | 2591 | ATCN_891 | 5682 |
| CTCN_548 | 2592 | CTCN_1395 | 5683 |
| TTCN_540 | 2593 | TTCN_1331 | 5684 |
| TTCN_541 | 2594 | TTCN_1332 | 5685 |
| TTCN_542 | 2595 | CTCN_1396 | 5686 |
| ATCN_311 | 2596 | CTCN_1397 | 5687 |
| TTCN_543 | 2597 | TTCN_1333 | 5688 |
| ATCN_312 | 2598 | TTCN_1334 | 5689 |

FIG. 35 (continued)

| | | | |
|---|---|---|---|
| ATCN_313 | 2599 | TTCN_1335 | 5690 |
| ATCN_314 | 2600 | TTCN_1336 | 5691 |
| CTCN_549 | 2601 | CTCN_1398 | 5692 |
| CTCN_550 | 2602 | ATCN_892 | 5693 |
| CTCN_551 | 2603 | ATCN_893 | 5694 |
| ATCN_315 | 2604 | ATCN_894 | 5695 |
| ATCN_316 | 2605 | CTCN_1399 | 5696 |
| GTCN_298 | 2606 | CTCN_1400 | 5697 |
| CTCN_552 | 2607 | CTCN_1401 | 5698 |
| ATCN_317 | 2608 | CTCN_1402 | 5699 |
| ATCN_318 | 2609 | ATCN_895 | 5700 |
| GTCN_299 | 2610 | ATCN_896 | 5701 |
| ATCN_319 | 2611 | TTCN_1337 | 5702 |
| GTCN_300 | 2612 | ATCN_897 | 5703 |
| CTCN_553 | 2613 | CTCN_1403 | 5704 |
| TTCN_544 | 2614 | ATCN_898 | 5705 |
| ATCN_320 | 2615 | ATCN_899 | 5706 |
| CTCN_554 | 2616 | CTCN_1404 | 5707 |
| GTCN_301 | 2617 | ATCN_900 | 5708 |
| CTCN_555 | 2618 | CTCN_1405 | 5709 |
| CTCN_556 | 2619 | GTCN_741 | 5710 |
| CTCN_557 | 2620 | GTCN_742 | 5711 |
| CTCN_558 | 2621 | CTCN_1406 | 5712 |
| TTCN_545 | 2622 | ATCN_901 | 5713 |
| TTCN_546 | 2623 | ATCN_902 | 5714 |
| CTCN_559 | 2624 | CTCN_1407 | 5715 |
| CTCN_560 | 2625 | CTCN_1408 | 5716 |
| CTCN_561 | 2626 | CTCN_1409 | 5717 |
| ATCN_321 | 2627 | CTCN_1410 | 5718 |
| ATCN_322 | 2628 | TTCN_1338 | 5719 |
| CTCN_562 | 2629 | TTCN_1339 | 5720 |
| CTCN_563 | 2630 | CTCN_1411 | 5721 |
| GTCN_302 | 2631 | CTCN_1412 | 5722 |
| ATCN_323 | 2632 | CTCN_1413 | 5723 |
| CTCN_564 | 2633 | GTCN_743 | 5724 |
| TTCN_547 | 2634 | CTCN_1414 | 5725 |
| ATCN_324 | 2635 | GTCN_744 | 5726 |
| CTCN_565 | 2636 | TTCN_1340 | 5727 |
| ATCN_325 | 2637 | ATCN_903 | 5728 |
| ATCN_326 | 2638 | GTCN_745 | 5729 |
| ATCN_327 | 2639 | CTCN_1415 | 5730 |
| GTCN_303 | 2640 | ATCN_904 | 5731 |
| ATCN_328 | 2641 | ATCN_905 | 5732 |
| TTCN_548 | 2642 | CTCN_1416 | 5733 |
| ATCN_329 | 2643 | GTCN_746 | 5734 |
| TTCN_549 | 2644 | CTCN_1417 | 5735 |
| GTCN_304 | 2645 | ATCN_906 | 5736 |
| ATCN_330 | 2646 | ATCN_907 | 5737 |
| ATCN_331 | 2647 | ATCN_908 | 5738 |
| ATCN_332 | 2648 | CTCN_1418 | 5739 |
| GTCN_305 | 2649 | ATCN_909 | 5740 |
| TTCN_550 | 2650 | TTCN_1341 | 5741 |
| TTCN_551 | 2651 | ATCN_910 | 5742 |

| | | | |
|---|---|---|---|
| GTCN_306 | 2652 | CTCN_1419 | 5743 |
| CTCN_566 | 2653 | GTCN_747 | 5744 |
| GTCN_307 | 2654 | ATCN_911 | 5745 |
| ATCN_333 | 2655 | TTCN_1342 | 5746 |
| CTCN_567 | 2656 | GTCN_748 | 5747 |
| CTCN_568 | 2657 | CTCN_1420 | 5748 |
| CTCN_569 | 2658 | CTCN_1421 | 5749 |
| CTCN_570 | 2659 | CTCN_1422 | 5750 |
| CTCN_571 | 2660 | CTCN_1423 | 5751 |
| TTCN_552 | 2661 | ATCN_912 | 5752 |
| CTCN_572 | 2662 | ATCN_913 | 5753 |
| TTCN_553 | 2663 | CTCN_1424 | 5754 |
| CTCN_573 | 2664 | GTCN_749 | 5755 |
| TTCN_554 | 2665 | TTCN_1343 | 5756 |
| GTCN_308 | 2666 | CTCN_1425 | 5757 |
| TTCN_555 | 2667 | ATCN_914 | 5758 |
| GTCN_309 | 2668 | ATCN_915 | 5759 |
| CTCN_574 | 2669 | CTCN_1426 | 5760 |
| GTCN_310 | 2670 | CTCN_1427 | 5761 |
| TTCN_556 | 2671 | CTCN_1428 | 5762 |
| ATCN_334 | 2672 | ATCN_916 | 5763 |
| GTCN_311 | 2673 | ATCN_917 | 5764 |
| ATCN_335 | 2674 | CTCN_1429 | 5765 |
| TTCN_557 | 2675 | TTCN_1344 | 5766 |
| ATCN_336 | 2676 | TTCN_1345 | 5767 |
| ATCN_337 | 2677 | GTCN_750 | 5768 |
| TTCN_558 | 2678 | TTCN_1346 | 5769 |
| TTCN_559 | 2679 | GTCN_751 | 5770 |
| TTCN_560 | 2680 | TTCN_1347 | 5771 |
| TTCN_561 | 2681 | ATCN_918 | 5772 |
| ATCN_338 | 2682 | GTCN_752 | 5773 |
| GTCN_312 | 2683 | TTCN_1348 | 5774 |
| GTCN_313 | 2684 | ATCN_919 | 5775 |
| TTCN_562 | 2685 | ATCN_920 | 5776 |
| CTCN_575 | 2686 | TTCN_1349 | 5777 |
| ATCN_339 | 2687 | CTCN_1430 | 5778 |
| GTCN_314 | 2688 | GTCN_753 | 5779 |
| ATCN_340 | 2689 | CTCN_1431 | 5780 |
| TTCN_563 | 2690 | GTCN_754 | 5781 |
| CTCN_576 | 2691 | CTCN_1432 | 5782 |
| GTCN_315 | 2692 | GTCN_755 | 5783 |
| TTCN_564 | 2693 | CTCN_1433 | 5784 |
| CTCN_577 | 2694 | ATCN_921 | 5785 |
| CTCN_578 | 2695 | ATCN_922 | 5786 |
| GTCN_316 | 2696 | GTCN_756 | 5787 |
| ATCN_341 | 2697 | TTCN_1350 | 5788 |
| TTCN_565 | 2698 | CTCN_1434 | 5789 |
| ATCN_342 | 2699 | TTCN_1351 | 5790 |
| GTCN_317 | 2700 | CTCN_1435 | 5791 |
| CTCN_579 | 2701 | GTCN_757 | 5792 |
| TTCN_566 | 2702 | CTCN_1436 | 5793 |
| GTCN_318 | 2703 | TTCN_1352 | 5794 |
| CTCN_580 | 2704 | CTCN_1437 | 5795 |

FIG. 35 (continued)

| | | | |
|---|---|---|---|
| TTCN_567 | 2705 | TTCN_1353 | 5796 |
| TTCN_568 | 2706 | CTCN_1438 | 5797 |
| TTCN_569 | 2707 | TTCN_1354 | 5798 |
| TTCN_570 | 2708 | CTCN_1439 | 5799 |
| GTCN_319 | 2709 | TTCN_1355 | 5800 |
| TTCN_571 | 2710 | TTCN_1356 | 5801 |
| TTCN_572 | 2711 | CTCN_1440 | 5802 |
| TTCN_573 | 2712 | ATCN_923 | 5803 |
| ATCN_343 | 2713 | TTCN_1357 | 5804 |
| TTCN_574 | 2714 | GTCN_758 | 5805 |
| CTCN_581 | 2715 | TTCN_1358 | 5806 |
| TTCN_575 | 2716 | TTCN_1359 | 5807 |
| ATCN_344 | 2717 | TTCN_1360 | 5808 |
| GTCN_320 | 2718 | CTCN_1441 | 5809 |
| CTCN_582 | 2719 | CTCN_1442 | 5810 |
| ATCN_345 | 2720 | ATCN_924 | 5811 |
| ATCN_346 | 2721 | TTCN_1361 | 5812 |
| ATCN_347 | 2722 | TTCN_1362 | 5813 |
| CTCN_583 | 2723 | GTCN_759 | 5814 |
| GTCN_321 | 2724 | CTCN_1443 | 5815 |
| CTCN_584 | 2725 | ATCN_925 | 5816 |
| ATCN_348 | 2726 | ATCN_926 | 5817 |
| ATCN_349 | 2727 | TTCN_1363 | 5818 |
| CTCN_585 | 2728 | TTCN_1364 | 5819 |
| CTCN_586 | 2729 | TTCN_1365 | 5820 |
| TTCN_576 | 2730 | CTCN_1444 | 5821 |
| CTCN_587 | 2731 | CTCN_1445 | 5822 |
| ATCN_350 | 2732 | TTCN_1366 | 5823 |
| ATCN_351 | 2733 | CTCN_1446 | 5824 |
| ATCN_352 | 2734 | CTCN_1447 | 5825 |
| CTCN_588 | 2735 | CTCN_1448 | 5826 |
| CTCN_589 | 2736 | TTCN_1367 | 5827 |
| GTCN_322 | 2737 | ATCN_927 | 5828 |
| CTCN_590 | 2738 | GTCN_760 | 5829 |
| GTCN_323 | 2739 | ATCN_928 | 5830 |
| CTCN_591 | 2740 | TTCN_1368 | 5831 |
| GTCN_324 | 2741 | CTCN_1449 | 5832 |
| CTCN_592 | 2742 | TTCN_1369 | 5833 |
| GTCN_325 | 2743 | CTCN_1450 | 5834 |
| TTCN_577 | 2744 | CTCN_1451 | 5835 |
| TTCN_578 | 2745 | TTCN_1370 | 5836 |
| TTCN_579 | 2746 | CTCN_1452 | 5837 |
| CTCN_593 | 2747 | CTCN_1453 | 5838 |
| CTCN_594 | 2748 | GTCN_761 | 5839 |
| CTCN_595 | 2749 | CTCN_1454 | 5840 |
| CTCN_596 | 2750 | ATCN_929 | 5841 |
| ATCN_353 | 2751 | GTCN_762 | 5842 |
| CTCN_597 | 2752 | CTCN_1455 | 5843 |
| CTCN_598 | 2753 | ATCN_930 | 5844 |
| TTCN_580 | 2754 | CTCN_1456 | 5845 |
| TTCN_581 | 2755 | GTCN_763 | 5846 |
| TTCN_582 | 2756 | ATCN_931 | 5847 |
| ATCN_354 | 2757 | ATCN_932 | 5848 |

| | | | |
|---|---|---|---|
| TTCN_583 | 2758 | CTCN_1457 | 5849 |
| TTCN_584 | 2759 | GTCN_764 | 5850 |
| CTCN_599 | 2760 | TTCN_1371 | 5851 |
| GTCN_326 | 2761 | GTCN_765 | 5852 |
| CTCN_600 | 2762 | ATCN_933 | 5853 |
| TTCN_585 | 2763 | CTCN_1458 | 5854 |
| GTCN_327 | 2764 | TTCN_1372 | 5855 |
| GTCN_328 | 2765 | TTCN_1373 | 5856 |
| GTCN_329 | 2766 | TTCN_1374 | 5857 |
| TTCN_586 | 2767 | ATCN_934 | 5858 |
| GTCN_330 | 2768 | ATCN_935 | 5859 |
| TTCN_587 | 2769 | GTCN_766 | 5860 |
| GTCN_331 | 2770 | CTCN_1459 | 5861 |
| TTCN_588 | 2771 | GTCN_767 | 5862 |
| CTCN_601 | 2772 | CTCN_1460 | 5863 |
| ATCN_355 | 2773 | TTCN_1375 | 5864 |
| CTCN_602 | 2774 | ATCN_936 | 5865 |
| ATCN_356 | 2775 | TTCN_1376 | 5866 |
| TTCN_589 | 2776 | TTCN_1377 | 5867 |
| TTCN_590 | 2777 | TTCN_1378 | 5868 |
| TTCN_591 | 2778 | CTCN_1461 | 5869 |
| CTCN_603 | 2779 | GTCN_768 | 5870 |
| TTCN_592 | 2780 | GTCN_769 | 5871 |
| TTCN_593 | 2781 | GTCN_770 | 5872 |
| CTCN_604 | 2782 | GTCN_771 | 5873 |
| GTCN_332 | 2783 | ATCN_937 | 5874 |
| TTCN_594 | 2784 | ATCN_938 | 5875 |
| TTCN_595 | 2785 | TTCN_1379 | 5876 |
| ATCN_357 | 2786 | ATCN_939 | 5877 |
| TTCN_596 | 2787 | TTCN_1380 | 5878 |
| CTCN_605 | 2788 | GTCN_772 | 5879 |
| TTCN_597 | 2789 | CTCN_1462 | 5880 |
| TTCN_598 | 2790 | GTCN_773 | 5881 |
| GTCN_333 | 2791 | CTCN_1463 | 5882 |
| GTCN_334 | 2792 | TTCN_1381 | 5883 |
| ATCN_358 | 2793 | CTCN_1464 | 5884 |
| TTCN_599 | 2794 | TTCN_1382 | 5885 |
| ATCN_359 | 2795 | ATCN_940 | 5886 |
| CTCN_606 | 2796 | CTCN_1465 | 5887 |
| GTCN_335 | 2797 | TTCN_1383 | 5888 |
| TTCN_600 | 2798 | CTCN_1466 | 5889 |
| GTCN_336 | 2799 | CTCN_1467 | 5890 |
| TTCN_601 | 2800 | ATCN_941 | 5891 |
| CTCN_607 | 2801 | GTCN_774 | 5892 |
| TTCN_602 | 2802 | CTCN_1468 | 5893 |
| TTCN_603 | 2803 | TTCN_1384 | 5894 |
| ATCN_360 | 2804 | TTCN_1385 | 5895 |
| TTCN_604 | 2805 | TTCN_1386 | 5896 |
| CTCN_608 | 2806 | CTCN_1469 | 5897 |
| TTCN_605 | 2807 | CTCN_1470 | 5898 |
| TTCN_606 | 2808 | CTCN_1471 | 5899 |
| ATCN_361 | 2809 | ATCN_942 | 5900 |
| TTCN_607 | 2810 | CTCN_1472 | 5901 |

FIG. 35 (continued)

| | | | |
|---|---|---|---|
| TTCN_608 | 2811 | ATCN_943 | 5902 |
| GTCN_337 | 2812 | ATCN_944 | 5903 |
| GTCN_338 | 2813 | TTCN_1387 | 5904 |
| ATCN_362 | 2814 | TTCN_1388 | 5905 |
| CTCN_609 | 2815 | ATCN_945 | 5906 |
| CTCN_610 | 2816 | ATCN_946 | 5907 |
| TTCN_609 | 2817 | TTCN_1389 | 5908 |
| ATCN_363 | 2818 | ATCN_947 | 5909 |
| ATCN_364 | 2819 | CTCN_1473 | 5910 |
| TTCN_610 | 2820 | ATCN_948 | 5911 |
| TTCN_611 | 2821 | CTCN_1474 | 5912 |
| GTCN_339 | 2822 | TTCN_1390 | 5913 |
| CTCN_611 | 2823 | ATCN_949 | 5914 |
| CTCN_612 | 2824 | ATCN_950 | 5915 |
| GTCN_340 | 2825 | GTCN_775 | 5916 |
| ATCN_365 | 2826 | TTCN_1391 | 5917 |
| TTCN_612 | 2827 | CTCN_1475 | 5918 |
| TTCN_613 | 2828 | ATCN_951 | 5919 |
| TTCN_614 | 2829 | CTCN_1476 | 5920 |
| TTCN_615 | 2830 | CTCN_1477 | 5921 |
| TTCN_616 | 2831 | ATCN_952 | 5922 |
| ATCN_366 | 2832 | CTCN_1478 | 5923 |
| ATCN_367 | 2833 | ATCN_953 | 5924 |
| TTCN_617 | 2834 | TTCN_1392 | 5925 |
| TTCN_618 | 2835 | ATCN_954 | 5926 |
| GTCN_341 | 2836 | ATCN_955 | 5927 |
| ATCN_368 | 2837 | ATCN_956 | 5928 |
| TTCN_619 | 2838 | CTCN_1479 | 5929 |
| TTCN_620 | 2839 | TTCN_1393 | 5930 |
| ATCN_369 | 2840 | TTCN_1394 | 5931 |
| CTCN_613 | 2841 | ATCN_957 | 5932 |
| CTCN_614 | 2842 | ATCN_958 | 5933 |
| CTCN_615 | 2843 | TTCN_1395 | 5934 |
| CTCN_616 | 2844 | TTCN_1396 | 5935 |
| CTCN_617 | 2845 | TTCN_1397 | 5936 |
| CTCN_618 | 2846 | CTCN_1480 | 5937 |
| CTCN_619 | 2847 | TTCN_1398 | 5938 |
| TTCN_621 | 2848 | ATCN_959 | 5939 |
| CTCN_620 | 2849 | TTCN_1399 | 5940 |
| GTCN_342 | 2850 | TTCN_1400 | 5941 |
| CTCN_621 | 2851 | ATCN_960 | 5942 |
| GTCN_343 | 2852 | GTCN_776 | 5943 |
| CTCN_622 | 2853 | CTCN_1481 | 5944 |
| GTCN_344 | 2854 | TTCN_1401 | 5945 |
| CTCN_623 | 2855 | GTCN_777 | 5946 |
| ATCN_370 | 2856 | TTCN_1402 | 5947 |
| ATCN_371 | 2857 | CTCN_1482 | 5948 |
| TTCN_622 | 2858 | TTCN_1403 | 5949 |
| CTCN_624 | 2859 | CTCN_1483 | 5950 |
| TTCN_623 | 2860 | TTCN_1404 | 5951 |
| TTCN_624 | 2861 | TTCN_1405 | 5952 |
| TTCN_625 | 2862 | TTCN_1406 | 5953 |
| CTCN_625 | 2863 | TTCN_1407 | 5954 |

| | | | |
|---|---|---|---|
| CTCN_626 | 2864 | CTCN_1484 | 5955 |
| CTCN_627 | 2865 | TTCN_1408 | 5956 |
| CTCN_628 | 2866 | TTCN_1409 | 5957 |
| ATCN_372 | 2867 | CTCN_1485 | 5958 |
| GTCN_345 | 2868 | TTCN_1410 | 5959 |
| CTCN_629 | 2869 | TTCN_1411 | 5960 |
| GTCN_346 | 2870 | TTCN_1412 | 5961 |
| TTCN_626 | 2871 | GTCN_778 | 5962 |
| ATCN_373 | 2872 | ATCN_961 | 5963 |
| CTCN_630 | 2873 | GTCN_779 | 5964 |
| CTCN_631 | 2874 | CTCN_1486 | 5965 |
| CTCN_632 | 2875 | ATCN_962 | 5966 |
| TTCN_627 | 2876 | GTCN_780 | 5967 |
| CTCN_633 | 2877 | ATCN_963 | 5968 |
| GTCN_347 | 2878 | TTCN_1413 | 5969 |
| CTCN_634 | 2879 | ATCN_964 | 5970 |
| ATCN_374 | 2880 | TTCN_1414 | 5971 |
| ATCN_375 | 2881 | CTCN_1487 | 5972 |
| CTCN_635 | 2882 | ATCN_965 | 5973 |
| ATCN_376 | 2883 | CTCN_1488 | 5974 |
| CTCN_636 | 2884 | GTCN_781 | 5975 |
| CTCN_637 | 2885 | CTCN_1489 | 5976 |
| CTCN_638 | 2886 | GTCN_782 | 5977 |
| CTCN_639 | 2887 | ATCN_966 | 5978 |
| TTCN_628 | 2888 | ATCN_967 | 5979 |
| ATCN_377 | 2889 | CTCN_1490 | 5980 |
| ATCN_378 | 2890 | TTCN_1415 | 5981 |
| TTCN_629 | 2891 | ATCN_968 | 5982 |
| TTCN_630 | 2892 | TTCN_1416 | 5983 |
| TTCN_631 | 2893 | CTCN_1491 | 5984 |
| TTCN_632 | 2894 | TTCN_1417 | 5985 |
| ATCN_279 | 2895 | ATCN_969 | 5986 |
| ATCN_280 | 2896 | TTCN_1418 | 5987 |
| CTCN_524 | 2897 | ATCN_970 | 5988 |
| CTCN_525 | 2898 | ATCN_971 | 5989 |
| TTCN_485 | 2899 | TTCN_1419 | 5990 |
| CTCN_526 | 2900 | TTCN_1420 | 5991 |
| CTCN_527 | 2901 | CTCN_1492 | 5992 |
| GTCN_283 | 2902 | TTCN_1421 | 5993 |
| CTCN_528 | 2903 | GTCN_783 | 5994 |
| ATCN_281 | 2904 | ATCN_972 | 5995 |
| ATCN_282 | 2905 | ATCN_973 | 5996 |
| ATCN_283 | 2906 | CTCN_1493 | 5997 |
| ATCN_284 | 2907 | TTCN_1422 | 5998 |
| ATCN_285 | 2908 | TTCN_1423 | 5999 |
| CTCN_529 | 2909 | GTCN_784 | 6000 |
| ATCN_286 | 2910 | CTCN_1494 | 6001 |
| TTCN_486 | 2911 | CTCN_1495 | 6002 |
| CTCN_530 | 2912 | ATCN_974 | 6003 |
| ATCN_287 | 2913 | ATCN_975 | 6004 |
| GTCN_284 | 2914 | CTCN_1496 | 6005 |
| TTCN_487 | 2915 | ATCN_976 | 6006 |
| ATCN_288 | 2916 | TTCN_1424 | 6007 |

FIG. 35 (continued)

| | | | |
|---|---|---|---|
| TTCN_488 | 2917 | TTCN_1425 | 6008 |
| TTCN_489 | 2918 | TTCN_1426 | 6009 |
| TTCN_490 | 2919 | TTCN_1427 | 6010 |
| TTCN_491 | 2920 | ATCN_977 | 6011 |
| GTCN_285 | 2921 | CTCN_1497 | 6012 |
| CTCN_531 | 2922 | CTCN_1498 | 6013 |
| GTCN_286 | 2923 | ATCN_978 | 6014 |
| TTCN_492 | 2924 | TTCN_1428 | 6015 |
| GTCN_287 | 2925 | CTCN_1499 | 6016 |
| TTCN_493 | 2926 | TTCN_1429 | 6017 |
| ATCN_289 | 2927 | TTCN_1430 | 6018 |
| TTCN_494 | 2928 | TTCN_1431 | 6019 |
| TTCN_495 | 2929 | CTCN_1500 | 6020 |
| TTCN_496 | 2930 | CTCN_1501 | 6021 |
| ATCN_290 | 2931 | ATCN_979 | 6022 |
| ATCN_291 | 2932 | GTCN_785 | 6023 |
| GTCN_288 | 2933 | CTCN_1502 | 6024 |
| TTCN_497 | 2934 | TTCN_1432 | 6025 |
| ATCN_292 | 2935 | TTCN_1433 | 6026 |
| TTCN_498 | 2936 | GTCN_786 | 6027 |
| TTCN_499 | 2937 | ATCN_980 | 6028 |
| TTCN_500 | 2938 | GTCN_787 | 6029 |
| CTCN_532 | 2939 | CTCN_1503 | 6030 |
| CTCN_533 | 2940 | GTCN_788 | 6031 |
| ATCN_293 | 2941 | CTCN_1504 | 6032 |
| ATCN_294 | 2942 | CTCN_1505 | 6033 |
| TTCN_501 | 2943 | TTCN_1434 | 6034 |
| TTCN_502 | 2944 | CTCN_1506 | 6035 |
| ATCN_295 | 2945 | ATCN_981 | 6036 |
| TTCN_503 | 2946 | ATCN_982 | 6037 |
| TTCN_504 | 2947 | CTCN_1507 | 6038 |
| ATCN_296 | 2948 | CTCN_1508 | 6039 |
| CTCN_534 | 2949 | CTCN_1509 | 6040 |
| ATCN_297 | 2950 | TTCN_1435 | 6041 |
| CTCN_535 | 2951 | ATCN_983 | 6042 |
| GTCN_289 | 2952 | ATCN_984 | 6043 |
| TTCN_505 | 2953 | CTCN_1510 | 6044 |
| CTCN_536 | 2954 | CTCN_1511 | 6045 |
| CTCN_537 | 2955 | CTCN_1512 | 6046 |
| TTCN_506 | 2956 | CTCN_1513 | 6047 |
| CTCN_538 | 2957 | ATCN_985 | 6048 |
| GTCN_290 | 2958 | CTCN_1514 | 6049 |
| TTCN_507 | 2959 | ATCN_986 | 6050 |
| ATCN_298 | 2960 | ATCN_987 | 6051 |
| GTCN_291 | 2961 | CTCN_1515 | 6052 |
| TTCN_508 | 2962 | TTCN_1436 | 6053 |
| ATCN_299 | 2963 | TTCN_1437 | 6054 |
| ATCN_300 | 2964 | ATCN_988 | 6055 |
| TTCN_509 | 2965 | TTCN_1438 | 6056 |
| TTCN_510 | 2966 | CTCN_1516 | 6057 |
| TTCN_511 | 2967 | GTCN_789 | 6058 |
| TTCN_512 | 2968 | CTCN_1517 | 6059 |
| TTCN_513 | 2969 | ATCN_989 | 6060 |

| | | | |
|---|---|---|---|
| CTCN_539 | 2970 | ATCN_990 | 6061 |
| CTCN_540 | 2971 | CTCN_1518 | 6062 |
| ATCN_301 | 2972 | CTCN_1519 | 6063 |
| TTCN_514 | 2973 | ATCN_991 | 6064 |
| TTCN_515 | 2974 | CTCN_1520 | 6065 |
| TTCN_516 | 2975 | GTCN_790 | 6066 |
| CTCN_541 | 2976 | CTCN_1521 | 6067 |
| TTCN_517 | 2977 | GTCN_791 | 6068 |
| TTCN_518 | 2978 | GTCN_792 | 6069 |
| TTCN_519 | 2979 | CTCN_1522 | 6070 |
| ATCN_302 | 2980 | CTCN_1523 | 6071 |
| TTCN_520 | 2981 | CTCN_1524 | 6072 |
| TTCN_521 | 2982 | CTCN_1525 | 6073 |
| TTCN_522 | 2983 | GTCN_793 | 6074 |
| TTCN_523 | 2984 | TTCN_1439 | 6075 |
| TTCN_524 | 2985 | TTCN_1440 | 6076 |
| TTCN_525 | 2986 | CTCN_1526 | 6077 |
| CTCN_542 | 2987 | TTCN_1441 | 6078 |
| ATCN_303 | 2988 | ATCN_992 | 6079 |
| TTCN_526 | 2989 | ATCN_993 | 6080 |
| ATCN_304 | 2990 | CTCN_1527 | 6081 |
| TTCN_527 | 2991 | CTCN_1528 | 6082 |
| TTCN_528 | 2992 | TTCN_1442 | 6083 |
| TTCN_529 | 2993 | ATCN_994 | 6084 |
| TTCN_530 | 2994 | ATCN_995 | 6085 |
| TTCN_531 | 2995 | CTCN_1529 | 6086 |
| GTCN_292 | 2996 | ATCN_996 | 6087 |
| GTCN_293 | 2997 | CTCN_1530 | 6088 |
| CTCN_543 | 2998 | TTCN_1443 | 6089 |
| TTCN_532 | 2999 | TTCN_1444 | 6090 |
| TTCN_533 | 3000 | TTCN_1445 | 6091 |
| TTCN_534 | 3001 | CTCN_1531 | 6092 |
| CTCN_544 | 3002 | TTCN_1446 | 6093 |
| ATCN_305 | 3003 | TTCN_1447 | 6094 |
| TTCN_535 | 3004 | TTCN_1448 | 6095 |
| TTCN_536 | 3005 | CTCN_1532 | 6096 |
| GTCN_294 | 3006 | TTCN_1449 | 6097 |
| CTCN_545 | 3007 | GTCN_794 | 6098 |
| TTCN_537 | 3008 | TTCN_1450 | 6099 |
| ATCN_306 | 3009 | GTCN_795 | 6100 |
| ATCN_307 | 3010 | ATCN_997 | 6101 |
| TTCN_538 | 3011 | TTCN_1451 | 6102 |
| GTCN_295 | 3012 | ATCN_998 | 6103 |
| GTCN_296 | 3013 | TTCN_1452 | 6104 |
| GTCN_297 | 3014 | GTCN_796 | 6105 |
| ATCN_308 | 3015 | CTCN_1533 | 6106 |
| CTCN_546 | 3016 | GTCN_797 | 6107 |
| TTCN_539 | 3017 | GTCN_798 | 6108 |
| ATCN_309 | 3018 | CTCN_1534 | 6109 |
| ATCN_310 | 3019 | GTCN_799 | 6110 |
| CTCN_547 | 3020 | CTCN_1535 | 6111 |
| CTCN_548 | 3021 | ATCN_999 | 6112 |
| TTCN_540 | 3022 | TTCN_1453 | 6113 |

FIG. 35 (continued)

| | | | |
|---|---|---|---|
| TTCN_541 | 3023 | TTCN_1454 | 6114 |
| TTCN_542 | 3024 | TTCN_1455 | 6115 |
| ATCN_311 | 3025 | GTCN_800 | 6116 |
| TTCN_543 | 3026 | ATCN_1000 | 6117 |
| ATCN_312 | 3027 | TTCN_1456 | 6118 |
| ATCN_313 | 3028 | CTCN_1536 | 6119 |
| ATCN_314 | 3029 | GTCN_801 | 6120 |
| CTCN_549 | 3030 | CTCN_1537 | 6121 |
| CTCN_550 | 3031 | TTCN_1457 | 6122 |
| CTCN_551 | 3032 | GTCN_802 | 6123 |
| ATCN_315 | 3033 | CTCN_1538 | 6124 |
| ATCN_316 | 3034 | CTCN_1539 | 6125 |
| GTCN_298 | 3035 | GTCN_803 | 6126 |
| CTCN_552 | 3036 | ATCN_1001 | 6127 |
| ATCN_317 | 3037 | GTCN_804 | 6128 |
| ATCN_318 | 3038 | CTCN_1540 | 6129 |
| GTCN_299 | 3039 | TTCN_1458 | 6130 |
| ATCN_319 | 3040 | CTCN_1541 | 6131 |
| GTCN_300 | 3041 | CTCN_1542 | 6132 |
| CTCN_553 | 3042 | CTCN_1543 | 6133 |
| TTCN_544 | 3043 | CTCN_1544 | 6134 |
| ATCN_320 | 3044 | CTCN_1545 | 6135 |
| CTCN_554 | 3045 | TTCN_1459 | 6136 |
| GTCN_301 | 3046 | ATCN_1002 | 6137 |
| CTCN_555 | 3047 | CTCN_1546 | 6138 |
| CTCN_556 | 3048 | CTCN_1547 | 6139 |
| CTCN_557 | 3049 | CTCN_1548 | 6140 |
| CTCN_558 | 3050 | CTCN_1549 | 6141 |
| TTCN_545 | 3051 | GTCN_805 | 6142 |
| TTCN_546 | 3052 | CTCN_1550 | 6143 |
| CTCN_559 | 3053 | TTCN_1460 | 6144 |
| CTCN_560 | 3054 | TTCN_1461 | 6145 |
| CTCN_561 | 3055 | CTCN_1551 | 6146 |
| ATCN_321 | 3056 | GTCN_806 | 6147 |
| ATCN_322 | 3057 | CTCN_1552 | 6148 |
| CTCN_562 | 3058 | GTCN_807 | 6149 |
| CTCN_563 | 3059 | GTCN_808 | 6150 |
| GTCN_302 | 3060 | TTCN_1462 | 6151 |
| ATCN_323 | 3061 | CTCN_1553 | 6152 |
| CTCN_564 | 3062 | TTCN_1463 | 6153 |
| TTCN_547 | 3063 | CTCN_1554 | 6154 |
| ATCN_324 | 3064 | CTCN_1555 | 6155 |
| CTCN_565 | 3065 | CTCN_1556 | 6156 |
| ATCN_325 | 3066 | TTCN_1464 | 6157 |
| ATCN_326 | 3067 | CTCN_1557 | 6158 |
| ATCN_327 | 3068 | CTCN_1558 | 6159 |
| GTCN_303 | 3069 | CTCN_1559 | 6160 |
| ATCN_328 | 3070 | ATCN_1003 | 6161 |
| TTCN_548 | 3071 | TTCN_1465 | 6162 |
| ATCN_329 | 3072 | GTCN_809 | 6163 |
| TTCN_549 | 3073 | TTCN_1466 | 6164 |
| GTCN_304 | 3074 | GTCN_810 | 6165 |
| ATCN_330 | 3075 | GTCN_811 | 6166 |

| | | | |
|---|---|---|---|
| ATCN_331 | 3076 | ATCN_1004 | 6167 |
| ATCN_332 | 3077 | ATCN_1005 | 6168 |
| GTCN_305 | 3078 | CTCN_1560 | 6169 |
| TTCN_550 | 3079 | TTCN_1467 | 6170 |
| TTCN_551 | 3080 | ATCN_1006 | 6171 |
| GTCN_306 | 3081 | TTCN_1468 | 6172 |
| CTCN_566 | 3082 | TTCN_1469 | 6173 |
| GTCN_307 | 3083 | TTCN_1470 | 6174 |
| ATCN_333 | 3084 | CTCN_1561 | 6175 |
| CTCN_567 | 3085 | CTCN_1562 | 6176 |
| CTCN_568 | 3086 | TTCN_1471 | 6177 |
| CTCN_569 | 3087 | CTCN_1563 | 6178 |
| CTCN_570 | 3088 | TTCN_1472 | 6179 |
| CTCN_571 | 3089 | CTCN_1564 | 6180 |
| TTCN_552 | 3090 | CTCN_1565 | 6181 |
| CTCN_572 | 3091 | GTCN_812 | 6182 |
| TTCN_553 | 3092 | TTCN_1473 | 6183 |
| CTCN_573 | 3093 | GTCN_813 | 6184 |
| TTCN_554 | 3094 | CTCN_1566 | 6185 |
| GTCN_308 | 3095 | TTCN_1474 | 6186 |
| TTCN_555 | 3096 | ATCN_1007 | 6187 |
| GTCN_309 | 3097 | ATCN_1008 | 6188 |
| CTCN_574 | 3098 | CTCN_1567 | 6189 |
| GTCN_310 | 3099 | TTCN_1475 | 6190 |
| TTCN_556 | 3100 | GTCN_814 | 6191 |
| ATCN_334 | 3101 | CTCN_1568 | 6192 |
| GTCN_311 | 3102 | TTCN_1476 | 6193 |
| ATCN_335 | 3103 | ATCN_1009 | 6194 |
| TTCN_557 | 3104 | CTCN_1569 | 6195 |
| ATCN_336 | 3105 | CTCN_1570 | 6196 |
| ATCN_337 | 3106 | CTCN_1571 | 6197 |
| TTCN_558 | 3107 | TTCN_1477 | 6198 |
| TTCN_559 | 3108 | CTCN_1572 | 6199 |
| TTCN_560 | 3109 | GTCN_815 | 6200 |
| TTCN_561 | 3110 | TTCN_1478 | 6201 |
| ATCN_338 | 3111 | TTCN_1479 | 6202 |
| GTCN_312 | 3112 | CTCN_1573 | 6203 |
| GTCN_313 | 3113 | TTCN_1480 | 6204 |
| TTCN_562 | 3114 | CTCN_1574 | 6205 |
| CTCN_575 | 3115 | TTCN_1481 | 6206 |
| ATCN_339 | 3116 | ATCN_1010 | 6207 |
| GTCN_314 | 3117 | ATCN_1011 | 6208 |
| ATCN_340 | 3118 | ATCN_1012 | 6209 |
| TTCN_563 | 3119 | TTCN_1482 | 6210 |
| CTCN_576 | 3120 | GTCN_816 | 6211 |
| GTCN_315 | 3121 | ATCN_1013 | 6212 |
| TTCN_564 | 3122 | CTCN_1575 | 6213 |
| CTCN_577 | 3123 | ATCN_1014 | 6214 |
| CTCN_578 | 3124 | TTCN_1483 | 6215 |
| GTCN_316 | 3125 | TTCN_1484 | 6216 |
| ATCN_341 | 3126 | TTCN_1485 | 6217 |
| TTCN_565 | 3127 | CTCN_1576 | 6218 |
| ATCN_342 | 3128 | GTCN_817 | 6219 |

FIG. 35 (continued)

| | | | |
|---|---|---|---|
| GTCN_317 | 3129 | TTCN_1486 | 6220 |
| CTCN_579 | 3130 | GTCN_818 | 6221 |
| TTCN_566 | 3131 | CTCN_1577 | 6222 |
| GTCN_318 | 3132 | TTCN_1487 | 6223 |
| CTCN_580 | 3133 | TTCN_1488 | 6224 |
| TTCN_567 | 3134 | GTCN_819 | 6225 |
| TTCN_568 | 3135 | CTCN_1578 | 6226 |
| TTCN_569 | 3136 | TTCN_1489 | 6227 |
| TTCN_570 | 3137 | CTCN_1579 | 6228 |
| GTCN_319 | 3138 | GTCN_820 | 6229 |
| TTCN_571 | 3139 | TTCN_1490 | 6230 |
| TTCN_572 | 3140 | ATCN_1015 | 6231 |
| TTCN_573 | 3141 | TTCN_1491 | 6232 |
| ATCN_343 | 3142 | GTCN_821 | 6233 |
| TTCN_574 | 3143 | CTCN_1580 | 6234 |
| CTCN_581 | 3144 | TTCN_1492 | 6235 |
| TTCN_575 | 3145 | TTCN_1493 | 6236 |
| ATCN_344 | 3146 | TTCN_1494 | 6237 |
| GTCN_320 | 3147 | GTCN_822 | 6238 |
| CTCN_582 | 3148 | TTCN_1495 | 6239 |
| ATCN_345 | 3149 | TTCN_1496 | 6240 |
| ATCN_346 | 3150 | GTCN_823 | 6241 |
| ATCN_347 | 3151 | GTCN_824 | 6242 |
| CTCN_583 | 3152 | ATCN_1016 | 6243 |
| GTCN_321 | 3153 | ATCN_1017 | 6244 |
| CTCN_584 | 3154 | TTCN_1497 | 6245 |
| ATCN_348 | 3155 | TTCN_1498 | 6246 |
| ATCN_349 | 3156 | TTCN_1499 | 6247 |
| CTCN_585 | 3157 | ATCN_1018 | 6248 |
| CTCN_586 | 3158 | TTCN_1500 | 6249 |
| TTCN_576 | 3159 | CTCN_1581 | 6250 |
| CTCN_587 | 3160 | ATCN_1019 | 6251 |
| ATCN_350 | 3161 | ATCN_1020 | 6252 |
| ATCN_351 | 3162 | ATCN_1021 | 6253 |
| ATCN_352 | 3163 | ATCN_1022 | 6254 |
| CTCN_588 | 3164 | TTCN_1501 | 6255 |
| CTCN_589 | 3165 | CTCN_1582 | 6256 |
| GTCN_322 | 3166 | TTCN_1502 | 6257 |
| CTCN_590 | 3167 | CTCN_1583 | 6258 |
| GTCN_323 | 3168 | TTCN_1503 | 6259 |
| CTCN_591 | 3169 | ATCN_1023 | 6260 |
| GTCN_324 | 3170 | TTCN_1504 | 6261 |
| CTCN_592 | 3171 | GTCN_825 | 6262 |
| GTCN_325 | 3172 | ATCN_1024 | 6263 |
| TTCN_577 | 3173 | TTCN_1505 | 6264 |
| TTCN_578 | 3174 | TTCN_1506 | 6265 |
| TTCN_579 | 3175 | CTCN_1584 | 6266 |
| CTCN_593 | 3176 | CTCN_1585 | 6267 |
| CTCN_594 | 3177 | CTCN_1586 | 6268 |
| CTCN_595 | 3178 | TTCN_1507 | 6269 |
| CTCN_596 | 3179 | ATCN_1025 | 6270 |
| ATCN_353 | 3180 | CTCN_1587 | 6271 |
| CTCN_597 | 3181 | ATCN_1026 | 6272 |

| | | | |
|---|---|---|---|
| CTCN_598 | 3182 | TTCN_1508 | 6273 |
| TTCN_580 | 3183 | TTCN_1509 | 6274 |
| TTCN_581 | 3184 | CTCN_1588 | 6275 |
| TTCN_582 | 3185 | TTCN_1510 | 6276 |
| ATCN_354 | 3186 | CTCN_1589 | 6277 |
| TTCN_583 | 3187 | CTCN_1590 | 6278 |
| TTCN_584 | 3188 | TTCN_1511 | 6279 |
| CTCN_599 | 3189 | TTCN_1512 | 6280 |
| GTCN_326 | 3190 | ATCN_1027 | 6281 |
| CTCN_600 | 3191 | CTCN_1591 | 6282 |
| TTCN_585 | 3192 | ATCN_1028 | 6283 |
| GTCN_327 | 3193 | TTCN_1513 | 6284 |
| GTCN_328 | 3194 | ATCN_1029 | 6285 |
| GTCN_329 | 3195 | TTCN_1514 | 6286 |
| TTCN_586 | 3196 | ATCN_1030 | 6287 |
| GTCN_330 | 3197 | CTCN_1592 | 6288 |
| TTCN_587 | 3198 | ATCN_1031 | 6289 |
| GTCN_331 | 3199 | TTCN_1515 | 6290 |
| TTCN_588 | 3200 | GTCN_826 | 6291 |
| CTCN_601 | 3201 | ATCN_1032 | 6292 |
| ATCN_355 | 3202 | ATCN_1033 | 6293 |
| CTCN_602 | 3203 | GTCN_827 | 6294 |
| ATCN_356 | 3204 | TTCN_1516 | 6295 |
| TTCN_589 | 3205 | GTCN_828 | 6296 |
| TTCN_590 | 3206 | CTCN_1593 | 6297 |
| TTCN_591 | 3207 | GTCN_829 | 6298 |
| CTCN_603 | 3208 | CTCN_1594 | 6299 |
| TTCN_592 | 3209 | GTCN_830 | 6300 |
| TTCN_593 | 3210 | TTCN_1517 | 6301 |
| CTCN_604 | 3211 | CTCN_1595 | 6302 |
| GTCN_332 | 3212 | TTCN_1518 | 6303 |
| TTCN_594 | 3213 | CTCN_1596 | 6304 |
| TTCN_595 | 3214 | ATCN_1034 | 6305 |
| ATCN_357 | 3215 | CTCN_1597 | 6306 |
| TTCN_596 | 3216 | CTCN_1598 | 6307 |
| CTCN_605 | 3217 | TTCN_1519 | 6308 |
| TTCN_597 | 3218 | TTCN_1520 | 6309 |
| TTCN_598 | 3219 | ATCN_1035 | 6310 |
| GTCN_333 | 3220 | ATCN_1036 | 6311 |
| GTCN_334 | 3221 | TTCN_1521 | 6312 |
| ATCN_358 | 3222 | TTCN_1522 | 6313 |
| TTCN_599 | 3223 | CTCN_1599 | 6314 |
| ATCN_359 | 3224 | CTCN_1600 | 6315 |
| CTCN_606 | 3225 | TTCN_1523 | 6316 |
| GTCN_335 | 3226 | TTCN_1524 | 6317 |
| TTCN_600 | 3227 | ATCN_1037 | 6318 |
| GTCN_336 | 3228 | TTCN_1525 | 6319 |
| TTCN_601 | 3229 | CTCN_1601 | 6320 |
| CTCN_607 | 3230 | TTCN_1526 | 6321 |
| TTCN_602 | 3231 | CTCN_1602 | 6322 |
| TTCN_603 | 3232 | CTCN_1603 | 6323 |
| ATCN_360 | 3233 | ATCN_1038 | 6324 |
| TTCN_604 | 3234 | GTCN_831 | 6325 |

FIG. 35 (continued)

| | | | |
|---|---|---|---|
| CTCN_608 | 3235 | CTCN_1604 | 6326 |
| TTCN_605 | 3236 | CTCN_1605 | 6327 |
| TTCN_606 | 3237 | CTCN_1606 | 6328 |
| ATCN_361 | 3238 | CTCN_1607 | 6329 |
| TTCN_607 | 3239 | ATCN_1039 | 6330 |
| TTCN_608 | 3240 | ATCN_1040 | 6331 |
| GTCN_337 | 3241 | CTCN_1608 | 6332 |
| GTCN_338 | 3242 | GTCN_832 | 6333 |
| ATCN_362 | 3243 | CTCN_1609 | 6334 |
| CTCN_609 | 3244 | ATCN_1041 | 6335 |
| CTCN_610 | 3245 | ATCN_1042 | 6336 |
| TTCN_609 | 3246 | CTCN_1610 | 6337 |
| ATCN_363 | 3247 | GTCN_833 | 6338 |
| ATCN_364 | 3248 | CTCN_1611 | 6339 |
| TTCN_610 | 3249 | ATCN_1043 | 6340 |
| TTCN_611 | 3250 | ATCN_1044 | 6341 |
| GTCN_339 | 3251 | GTCN_834 | 6342 |
| CTCN_611 | 3252 | ATCN_1045 | 6343 |
| CTCN_612 | 3253 | CTCN_1612 | 6344 |
| GTCN_340 | 3254 | TTCN_1527 | 6345 |
| ATCN_365 | 3255 | CTCN_1613 | 6346 |
| TTCN_612 | 3256 | CTCN_1614 | 6347 |
| TTCN_613 | 3257 | TTCN_1528 | 6348 |
| TTCN_614 | 3258 | TTCN_1529 | 6349 |
| TTCN_615 | 3259 | CTCN_1615 | 6350 |
| TTCN_616 | 3260 | GTCN_835 | 6351 |
| ATCN_366 | 3261 | CTCN_1616 | 6352 |
| ATCN_367 | 3262 | CTCN_1617 | 6353 |
| TTCN_617 | 3263 | ATCN_1046 | 6354 |
| TTCN_618 | 3264 | CTCN_1618 | 6355 |
| GTCN_341 | 3265 | GTCN_836 | 6356 |
| ATCN_368 | 3266 | CTCN_1619 | 6357 |
| TTCN_619 | 3267 | CTCN_1620 | 6358 |
| TTCN_620 | 3268 | CTCN_1621 | 6359 |
| ATCN_369 | 3269 | TTCN_1530 | 6360 |
| CTCN_613 | 3270 | CTCN_1622 | 6361 |
| CTCN_614 | 3271 | TTCN_1531 | 6362 |
| CTCN_615 | 3272 | CTCN_1623 | 6363 |
| CTCN_616 | 3273 | TTCN_1532 | 6364 |
| CTCN_617 | 3274 | CTCN_1624 | 6365 |
| CTCN_618 | 3275 | TTCN_1533 | 6366 |
| CTCN_619 | 3276 | TTCN_1534 | 6367 |
| TTCN_621 | 3277 | TTCN_1535 | 6368 |
| CTCN_620 | 3278 | ATCN_1047 | 6369 |
| GTCN_342 | 3279 | TTCN_1536 | 6370 |
| CTCN_621 | 3280 | CTCN_1625 | 6371 |
| GTCN_343 | 3281 | TTCN_1537 | 6372 |
| CTCN_622 | 3282 | ATCN_1048 | 6373 |
| GTCN_344 | 3283 | TTCN_1538 | 6374 |
| CTCN_623 | 3284 | CTCN_1626 | 6375 |
| ATCN_370 | 3285 | CTCN_1627 | 6376 |
| ATCN_371 | 3286 | CTCN_1628 | 6377 |
| TTCN_622 | 3287 | ATCN_1049 | 6378 |

| | | | |
|---|---|---|---|
| CTCN_624 | 3288 | GTCN_837 | 6379 |
| TTCN_623 | 3289 | TTCN_1539 | 6380 |
| TTCN_624 | 3290 | CTCN_1629 | 6381 |
| TTCN_625 | 3291 | CTCN_1630 | 6382 |
| CTCN_625 | 3292 | TTCN_1540 | 6383 |
| CTCN_626 | 3293 | CTCN_1631 | 6384 |
| CTCN_627 | 3294 | TTCN_1541 | 6385 |
| CTCN_628 | 3295 | TTCN_1542 | 6386 |
| ATCN_372 | 3296 | CTCN_1632 | 6387 |
| GTCN_345 | 3297 | ATCN_1050 | 6388 |
| CTCN_629 | 3298 | GTCN_838 | 6389 |
| GTCN_346 | 3299 | ATCN_1051 | 6390 |
| TTCN_626 | 3300 | GTCN_839 | 6391 |
| ATCN_373 | 3301 | TTCN_1543 | 6392 |
| CTCN_630 | 3302 | CTCN_1633 | 6393 |
| CTCN_631 | 3303 | CTCN_1634 | 6394 |
| CTCN_632 | 3304 | TTCN_1544 | 6395 |
| TTCN_627 | 3305 | TTCN_1545 | 6396 |
| CTCN_633 | 3306 | ATCN_1052 | 6397 |
| GTCN_347 | 3307 | TTCN_1546 | 6398 |
| CTCN_634 | 3308 | ATCN_1053 | 6399 |
| ATCN_374 | 3309 | CTCN_1635 | 6400 |
| ATCN_375 | 3310 | TTCN_1547 | 6401 |
| CTCN_635 | 3311 | ATCN_1054 | 6402 |
| ATCN_376 | 3312 | ATCN_1055 | 6403 |
| CTCN_636 | 3313 | CTCN_1636 | 6404 |
| CTCN_637 | 3314 | TTCN_1548 | 6405 |
| CTCN_638 | 3315 | TTCN_1549 | 6406 |
| CTCN_639 | 3316 | TTCN_1550 | 6407 |
| TTCN_628 | 3317 | GTCN_840 | 6408 |
| ATCN_377 | 3318 | GTCN_841 | 6409 |
| ATCN_378 | 3319 | GTCN_842 | 6410 |
| TTCN_629 | 3320 | TTCN_1551 | 6411 |
| TTCN_630 | 3321 | TTCN_1552 | 6412 |
| TTCN_631 | 3322 | TTCN_1553 | 6413 |
| TTCN_632 | 3323 | ATCN_1056 | 6414 |
| GTCN_348 | 3324 | GTCN_843 | 6415 |
| CTCN_640 | 3325 | CTCN_1637 | 6416 |
| TTCN_633 | 3326 | TTCN_1554 | 6417 |
| ATCN_379 | 3327 | GTCN_844 | 6418 |
| TTCN_634 | 3328 | CTCN_1638 | 6419 |
| GTCN_349 | 3329 | CTCN_1639 | 6420 |
| TTCN_635 | 3330 | GTCN_845 | 6421 |
| CTCN_641 | 3331 | TTCN_1555 | 6422 |
| TTCN_636 | 3332 | CTCN_1640 | 6423 |
| TTCN_637 | 3333 | GTCN_846 | 6424 |
| TTCN_638 | 3334 | ATCN_1057 | 6425 |
| ATCN_380 | 3335 | TTCN_1556 | 6426 |
| ATCN_381 | 3336 | CTCN_1641 | 6427 |
| TTCN_639 | 3337 | ATCN_1058 | 6428 |
| ATCN_382 | 3338 | ATCN_1059 | 6429 |
| CTCN_642 | 3339 | ATCN_1060 | 6430 |
| CTCN_643 | 3340 | TTCN_1557 | 6431 |

FIG. 35 (continued)

| | | | |
|---|---|---|---|
| GTCN_350 | 3341 | CTCN_1642 | 6432 |
| ATCN_383 | 3342 | GTCN_847 | 6433 |
| GTCN_351 | 3343 | TTCN_1558 | 6434 |
| ATCN_384 | 3344 | ATCN_1061 | 6435 |
| TTCN_640 | 3345 | TTCN_1559 | 6436 |
| CTCN_644 | 3346 | CTCN_1643 | 6437 |
| ATCN_385 | 3347 | GTCN_848 | 6438 |
| TTCN_641 | 3348 | TTCN_1560 | 6439 |
| ATCN_386 | 3349 | TTCN_1561 | 6440 |
| CTCN_645 | 3350 | GTCN_849 | 6441 |
| ATCN_387 | 3351 | CTCN_1644 | 6442 |
| ATCN_388 | 3352 | TTCN_1562 | 6443 |
| TTCN_642 | 3353 | CTCN_1645 | 6444 |
| TTCN_643 | 3354 | TTCN_1563 | 6445 |
| TTCN_644 | 3355 | CTCN_1646 | 6446 |
| TTCN_645 | 3356 | ATCN_1062 | 6447 |
| CTCN_646 | 3357 | TTCN_1564 | 6448 |
| TTCN_646 | 3358 | ATCN_1063 | 6449 |
| CTCN_647 | 3359 | TTCN_1565 | 6450 |
| TTCN_647 | 3360 | TTCN_1566 | 6451 |
| CTCN_648 | 3361 | ATCN_1064 | 6452 |
| GTCN_352 | 3362 | TTCN_1567 | 6453 |
| CTCN_649 | 3363 | GTCN_850 | 6454 |
| GTCN_353 | 3364 | CTCN_1647 | 6455 |
| CTCN_650 | 3365 | TTCN_1568 | 6456 |
| CTCN_651 | 3366 | ATCN_1065 | 6457 |
| ATCN_389 | 3367 | CTCN_1648 | 6458 |
| ATCN_390 | 3368 | ATCN_1066 | 6459 |
| CTCN_652 | 3369 | GTCN_851 | 6460 |
| TTCN_648 | 3370 | CTCN_1649 | 6461 |
| ATCN_391 | 3371 | GTCN_852 | 6462 |
| CTCN_653 | 3372 | CTCN_1650 | 6463 |
| CTCN_654 | 3373 | ATCN_1067 | 6464 |
| TTCN_649 | 3374 | TTCN_1569 | 6465 |
| CTCN_655 | 3375 | CTCN_1651 | 6466 |
| CTCN_656 | 3376 | CTCN_1652 | 6467 |
| CTCN_657 | 3377 | CTCN_1653 | 6468 |
| CTCN_658 | 3378 | CTCN_1654 | 6469 |
| ATCN_392 | 3379 | GTCN_853 | 6470 |
| CTCN_659 | 3380 | TTCN_1570 | 6471 |
| ATCN_393 | 3381 | ATCN_1068 | 6472 |
| TTCN_650 | 3382 | CTCN_1655 | 6473 |
| GTCN_354 | 3383 | CTCN_1656 | 6474 |
| TTCN_651 | 3384 | CTCN_1657 | 6475 |
| CTCN_660 | 3385 | TTCN_1571 | 6476 |
| CTCN_661 | 3386 | GTCN_854 | 6477 |
| CTCN_662 | 3387 | CTCN_1658 | 6478 |
| ATCN_394 | 3388 | ATCN_1069 | 6479 |
| ATCN_395 | 3389 | TTCN_1572 | 6480 |
| CTCN_663 | 3390 | GTCN_855 | 6481 |
| TTCN_652 | 3391 | TTCN_1573 | 6482 |
| ATCN_396 | 3392 | GTCN_856 | 6483 |
| CTCN_664 | 3393 | ATCN_1070 | 6484 |

| | | | |
|---|---|---|---|
| GTCN_355 | 3394 | ATCN_1071 | 6485 |
| TTCN_653 | 3395 | CTCN_1659 | 6486 |
| TTCN_654 | 3396 | CTCN_1660 | 6487 |
| TTCN_655 | 3397 | ATCN_1072 | 6488 |
| GTCN_356 | 3398 | TTCN_1574 | 6489 |
| ATCN_397 | 3399 | ATCN_1073 | 6490 |
| CTCN_665 | 3400 | CTCN_1661 | 6491 |
| TTCN_656 | 3401 | TTCN_1575 | 6492 |
| CTCN_666 | 3402 | ATCN_1074 | 6493 |
| ATCN_398 | 3403 | GTCN_857 | 6494 |
| CTCN_667 | 3404 | TTCN_1576 | 6495 |
| TTCN_657 | 3405 | TTCN_1577 | 6496 |
| ATCN_399 | 3406 | TTCN_1578 | 6497 |
| CTCN_668 | 3407 | ATCN_1075 | 6498 |
| GTCN_357 | 3408 | CTCN_1662 | 6499 |
| TTCN_658 | 3409 | ATCN_1076 | 6500 |
| GTCN_358 | 3410 | ATCN_1077 | 6501 |
| ATCN_400 | 3411 | ATCN_1078 | 6502 |
| ATCN_401 | 3412 | CTCN_1663 | 6503 |
| TTCN_659 | 3413 | GTCN_858 | 6504 |
| ATCN_402 | 3414 | ATCN_1079 | 6505 |
| GTCN_359 | 3415 | ATCN_1080 | 6506 |
| CTCN_669 | 3416 | ATCN_1081 | 6507 |
| GTCN_360 | 3417 | TTCN_1579 | 6508 |
| GTCN_361 | 3418 | GTCN_859 | 6509 |
| ATCN_403 | 3419 | TTCN_1580 | 6510 |
| GTCN_362 | 3420 | ATCN_1082 | 6511 |
| TTCN_660 | 3421 | CTCN_1664 | 6512 |
| TTCN_661 | 3422 | CTCN_1665 | 6513 |
| TTCN_662 | 3423 | ATCN_1083 | 6514 |
| TTCN_663 | 3424 | ATCN_1084 | 6515 |
| TTCN_664 | 3425 | TTCN_1581 | 6516 |
| TTCN_665 | 3426 | CTCN_1666 | 6517 |
| ATCN_404 | 3427 | ATCN_1085 | 6518 |
| ATCN_405 | 3428 | TTCN_1582 | 6519 |
| GTCN_363 | 3429 | CTCN_1667 | 6520 |
| ATCN_406 | 3430 | CTCN_1668 | 6521 |
| CTCN_670 | 3431 | CTCN_1669 | 6522 |
| TTCN_666 | 3432 | GTCN_860 | 6523 |
| CTCN_671 | 3433 | TTCN_1583 | 6524 |
| TTCN_667 | 3434 | TTCN_1584 | 6525 |
| GTCN_364 | 3435 | CTCN_1670 | 6526 |
| ATCN_407 | 3436 | GTCN_861 | 6527 |
| ATCN_408 | 3437 | TTCN_1585 | 6528 |
| CTCN_672 | 3438 | CTCN_1671 | 6529 |
| CTCN_673 | 3439 | ATCN_1086 | 6530 |
| ATCN_409 | 3440 | GTCN_862 | 6531 |
| ATCN_410 | 3441 | GTCN_863 | 6532 |
| CTCN_674 | 3442 | TTCN_1586 | 6533 |
| GTCN_365 | 3443 | TTCN_1587 | 6534 |
| ATCN_411 | 3444 | GTCN_864 | 6535 |
| CTCN_675 | 3445 | ATCN_1087 | 6536 |
| CTCN_676 | 3446 | GTCN_865 | 6537 |

FIG. 35 (continued)

| | | | |
|---|---|---|---|
| GTCN_366 | 3447 | TTCN_1588 | 6538 |
| ATCN_412 | 3448 | GTCN_866 | 6539 |
| ATCN_413 | 3449 | GTCN_867 | 6540 |
| ATCN_414 | 3450 | CTCN_1672 | 6541 |
| TTCN_668 | 3451 | ATCN_1088 | 6542 |
| TTCN_669 | 3452 | TTCN_1589 | 6543 |
| TTCN_670 | 3453 | ATCN_1089 | 6544 |
| CTCN_677 | 3454 | GTCN_868 | 6545 |
| ATCN_415 | 3455 | TTCN_1590 | 6546 |
| CTCN_678 | 3456 | TTCN_1591 | 6547 |
| GTCN_367 | 3457 | CTCN_1673 | 6548 |
| CTCN_679 | 3458 | GTCN_869 | 6549 |
| GTCN_368 | 3459 | GTCN_870 | 6550 |
| TTCN_671 | 3460 | TTCN_1592 | 6551 |
| TTCN_672 | 3461 | CTCN_1674 | 6552 |
| GTCN_369 | 3462 | TTCN_1593 | 6553 |
| GTCN_370 | 3463 | GTCN_871 | 6554 |
| TTCN_673 | 3464 | ATCN_1090 | 6555 |
| ATCN_416 | 3465 | CTCN_1675 | 6556 |
| ATCN_417 | 3466 | GTCN_872 | 6557 |
| CTCN_680 | 3467 | GTCN_873 | 6558 |
| CTCN_681 | 3468 | TTCN_1594 | 6559 |
| TTCN_674 | 3469 | ATCN_1091 | 6560 |
| GTCN_371 | 3470 | CTCN_1676 | 6561 |
| GTCN_372 | 3471 | GTCN_874 | 6562 |
| GTCN_373 | 3472 | CTCN_1677 | 6563 |
| GTCN_374 | 3473 | GTCN_875 | 6564 |
| GTCN_375 | 3474 | GTCN_876 | 6565 |
| TTCN_675 | 3475 | GTCN_877 | 6566 |
| GTCN_376 | 3476 | ATCN_1092 | 6567 |
| TTCN_676 | 3477 | ATCN_1093 | 6568 |
| CTCN_682 | 3478 | GTCN_878 | 6569 |
| CTCN_683 | 3479 | TTCN_1595 | 6570 |
| ATCN_418 | 3480 | GTCN_879 | 6571 |
| GTCN_377 | 3481 | CTCN_1678 | 6572 |
| CTCN_684 | 3482 | TTCN_1596 | 6573 |
| CTCN_685 | 3483 | TTCN_1597 | 6574 |
| TTCN_677 | 3484 | TTCN_1598 | 6575 |
| TTCN_678 | 3485 | TTCN_1599 | 6576 |
| ATCN_419 | 3486 | TTCN_1600 | 6577 |
| CTCN_686 | 3487 | GTCN_880 | 6578 |
| ATCN_420 | 3488 | ATCN_1094 | 6579 |
| TTCN_679 | 3489 | TTCN_1601 | 6580 |
| TTCN_680 | 3490 | ATCN_1095 | 6581 |
| GTCN_378 | 3491 | ATCN_1096 | 6582 |
| TTCN_681 | 3492 | GTCN_881 | 6583 |
| TTCN_682 | 3493 | ATCN_1097 | 6584 |
| ATCN_421 | 3494 | ATCN_1098 | 6585 |
| CTCN_687 | 3495 | CTCN_1679 | 6586 |
| CTCN_688 | 3496 | TTCN_1602 | 6587 |
| TTCN_683 | 3497 | CTCN_1680 | 6588 |
| GTCN_379 | 3498 | CTCN_1681 | 6589 |
| GTCN_380 | 3499 | CTCN_1682 | 6590 |

| | | | |
|---|---|---|---|
| TTCN_684 | 3500 | TTCN_1603 | 6591 |
| TTCN_685 | 3501 | GTCN_882 | 6592 |
| CTCN_689 | 3502 | TTCN_1604 | 6593 |
| TTCN_686 | 3503 | TTCN_1605 | 6594 |
| CTCN_690 | 3504 | ATCN_1099 | 6595 |
| CTCN_691 | 3505 | TTCN_1606 | 6596 |
| GTCN_381 | 3506 | GTCN_883 | 6597 |
| CTCN_692 | 3507 | TTCN_1607 | 6598 |
| TTCN_687 | 3508 | CTCN_1683 | 6599 |
| GTCN_382 | 3509 | TTCN_1608 | 6600 |
| ATCN_422 | 3510 | ATCN_1100 | 6601 |
| CTCN_693 | 3511 | ATCN_1101 | 6602 |
| CTCN_694 | 3512 | TTCN_1609 | 6603 |
| TTCN_688 | 3513 | CTCN_1684 | 6604 |
| GTCN_383 | 3514 | CTCN_1685 | 6605 |
| CTCN_695 | 3515 | TTCN_1610 | 6606 |
| TTCN_689 | 3516 | GTCN_884 | 6607 |
| TTCN_690 | 3517 | ATCN_1102 | 6608 |
| CTCN_696 | 3518 | ATCN_1103 | 6609 |
| CTCN_697 | 3519 | GTCN_885 | 6610 |
| CTCN_698 | 3520 | CTCN_1686 | 6611 |
| GTCN_384 | 3521 | CTCN_1687 | 6612 |
| TTCN_691 | 3522 | CTCN_1688 | 6613 |
| ATCN_423 | 3523 | GTCN_886 | 6614 |
| CTCN_699 | 3524 | CTCN_1689 | 6615 |
| TTCN_692 | 3525 | CTCN_1690 | 6616 |
| ATCN_424 | 3526 | CTCN_1691 | 6617 |
| GTCN_385 | 3527 | GTCN_887 | 6618 |
| CTCN_700 | 3528 | GTCN_888 | 6619 |
| TTCN_693 | 3529 | GTCN_889 | 6620 |
| GTCN_386 | 3530 | TTCN_1611 | 6621 |
| CTCN_701 | 3531 | CTCN_1692 | 6622 |
| TTCN_694 | 3532 | CTCN_1693 | 6623 |
| TTCN_695 | 3533 | CTCN_1694 | 6624 |
| TTCN_696 | 3534 | CTCN_1695 | 6625 |
| CTCN_702 | 3535 | CTCN_1696 | 6626 |
| TTCN_697 | 3536 | ATCN_1104 | 6627 |
| TTCN_698 | 3537 | ATCN_1105 | 6628 |
| TTCN_699 | 3538 | TTCN_1612 | 6629 |
| CTCN_703 | 3539 | GTCN_890 | 6630 |
| GTCN_387 | 3540 | GTCN_891 | 6631 |
| GTCN_388 | 3541 | CTCN_1697 | 6632 |
| CTCN_704 | 3542 | TTCN_1613 | 6633 |
| CTCN_705 | 3543 | TTCN_1614 | 6634 |
| GTCN_389 | 3544 | GTCN_892 | 6635 |
| CTCN_706 | 3545 | GTCN_893 | 6636 |
| ATCN_425 | 3546 | GTCN_894 | 6637 |
| CTCN_707 | 3547 | CTCN_1698 | 6638 |
| TTCN_700 | 3548 | GTCN_895 | 6639 |
| ATCN_426 | 3549 | GTCN_896 | 6640 |
| TTCN_701 | 3550 | TTCN_1615 | 6641 |
| CTCN_708 | 3551 | CTCN_1699 | 6642 |
| GTCN_390 | 3552 | ATCN_1106 | 6643 |

FIG. 35 (continued)

| | | | |
|---|---|---|---|
| CTCN_709 | 3553 | CTCN_1700 | 6644 |
| TTCN_702 | 3554 | CTCN_1701 | 6645 |
| ATCN_427 | 3555 | GTCN_897 | 6646 |
| GTCN_391 | 3556 | ATCN_1107 | 6647 |
| GTCN_392 | 3557 | CTCN_1702 | 6648 |
| TTCN_703 | 3558 | ATCN_1108 | 6649 |
| TTCN_704 | 3559 | ATCN_1109 | 6650 |
| TTCN_705 | 3560 | GTCN_898 | 6651 |
| TTCN_706 | 3561 | CTCN_1703 | 6652 |
| TTCN_707 | 3562 | GTCN_899 | 6653 |
| GTCN_393 | 3563 | GTCN_900 | 6654 |
| CTCN_710 | 3564 | GTCN_901 | 6655 |
| TTCN_708 | 3565 | TTCN_1616 | 6656 |
| CTCN_711 | 3566 | CTCN_1704 | 6657 |
| GTCN_394 | 3567 | CTCN_1705 | 6658 |
| ATCN_428 | 3568 | CTCN_1706 | 6659 |
| CTCN_712 | 3569 | CTCN_1707 | 6660 |
| ATCN_429 | 3570 | CTCN_1708 | 6661 |
| GTCN_395 | 3571 | TTCN_1617 | 6662 |
| CTCN_713 | 3572 | GTCN_902 | 6663 |
| ATCN_430 | 3573 | TTCN_1618 | 6664 |
| TTCN_709 | 3574 | TTCN_1619 | 6665 |
| TTCN_710 | 3575 | CTCN_1709 | 6666 |
| CTCN_714 | 3576 | TTCN_1620 | 6667 |
| CTCN_715 | 3577 | TTCN_1621 | 6668 |
| CTCN_716 | 3578 | ATCN_1110 | 6669 |
| TTCN_711 | 3579 | ATCN_1111 | 6670 |
| CTCN_717 | 3580 | GTCN_903 | 6671 |
| CTCN_718 | 3581 | TTCN_1622 | 6672 |
| TTCN_712 | 3582 | ATCN_1112 | 6673 |
| TTCN_713 | 3583 | ATCN_1113 | 6674 |
| GTCN_396 | 3584 | CTCN_1710 | 6675 |
| CTCN_719 | 3585 | CTCN_1711 | 6676 |
| CTCN_720 | 3586 | CTCN_1712 | 6677 |
| CTCN_721 | 3587 | TTCN_1623 | 6678 |
| CTCN_722 | 3588 | TTCN_1624 | 6679 |
| CTCN_723 | 3589 | TTCN_1625 | 6680 |
| CTCN_724 | 3590 | CTCN_1713 | 6681 |
| CTCN_725 | 3591 | CTCN_1714 | 6682 |
| ATCN_431 | 3592 | GTCN_904 | 6683 |
| ATCN_432 | 3593 | TTCN_1626 | 6684 |
| GTCN_397 | 3594 | ATCN_1114 | 6685 |
| CTCN_726 | 3595 | CTCN_1715 | 6686 |
| TTCN_714 | 3596 | GTCN_905 | 6687 |
| CTCN_727 | 3597 | CTCN_1716 | 6688 |
| CTCN_728 | 3598 | ATCN_1115 | 6689 |
| GTCN_398 | 3599 | GTCN_906 | 6690 |
| TTCN_715 | 3600 | CTCN_1717 | 6691 |
| ATCN_433 | 3601 | CTCN_1718 | 6692 |
| GTCN_399 | 3602 | CTCN_1719 | 6693 |
| TTCN_716 | 3603 | CTCN_1720 | 6694 |
| TTCN_717 | 3604 | GTCN_907 | 6695 |
| CTCN_729 | 3605 | TTCN_1627 | 6696 |

| | | | |
|---|---|---|---|
| CTCN_730 | 3606 | CTCN_1721 | 6697 |
| TTCN_718 | 3607 | CTCN_1722 | 6698 |
| CTCN_731 | 3608 | TTCN_1628 | 6699 |
| TTCN_719 | 3609 | CTCN_1723 | 6700 |
| CTCN_732 | 3610 | GTCN_908 | 6701 |
| TTCN_720 | 3611 | CTCN_1724 | 6702 |
| ATCN_434 | 3612 | TTCN_1629 | 6703 |
| ATCN_435 | 3613 | GTCN_909 | 6704 |
| CTCN_733 | 3614 | TTCN_1630 | 6705 |
| GTCN_400 | 3615 | GTCN_910 | 6706 |
| ATCN_436 | 3616 | GTCN_911 | 6707 |
| ATCN_437 | 3617 | GTCN_912 | 6708 |
| CTCN_734 | 3618 | GTCN_913 | 6709 |
| GTCN_401 | 3619 | TTCN_1631 | 6710 |
| CTCN_735 | 3620 | GTCN_914 | 6711 |
| TTCN_721 | 3621 | CTCN_1725 | 6712 |
| TTCN_722 | 3622 | CTCN_1726 | 6713 |
| GTCN_402 | 3623 | GTCN_915 | 6714 |
| CTCN_736 | 3624 | TTCN_1632 | 6715 |
| TTCN_723 | 3625 | CTCN_1727 | 6716 |
| GTCN_403 | 3626 | GTCN_916 | 6717 |
| TTCN_724 | 3627 | TTCN_1633 | 6718 |
| ATCN_438 | 3628 | GTCN_917 | 6719 |
| CTCN_737 | 3629 | TTCN_1634 | 6720 |
| TTCN_725 | 3630 | CTCN_1728 | 6721 |
| CTCN_738 | 3631 | GTCN_918 | 6722 |
| CTCN_739 | 3632 | TTCN_1635 | 6723 |
| TTCN_726 | 3633 | CTCN_1729 | 6724 |
| TTCN_727 | 3634 | ATCN_1116 | 6725 |
| CTCN_740 | 3635 | CTCN_1730 | 6726 |
| CTCN_741 | 3636 | TTCN_1636 | 6727 |
| CTCN_742 | 3637 | ATCN_1117 | 6728 |
| TTCN_728 | 3638 | CTCN_1731 | 6729 |
| CTCN_743 | 3639 | TTCN_1637 | 6730 |
| CTCN_744 | 3640 | ATCN_1118 | 6731 |
| ATCN_439 | 3641 | TTCN_1638 | 6732 |
| TTCN_729 | 3642 | CTCN_1732 | 6733 |
| GTCN_404 | 3643 | ATCN_1119 | 6734 |
| GTCN_405 | 3644 | ATCN_1120 | 6735 |
| CTCN_745 | 3645 | TTCN_1639 | 6736 |
| TTCN_730 | 3646 | ATCN_1121 | 6737 |
| CTCN_746 | 3647 | ATCN_1122 | 6738 |
| TTCN_731 | 3648 | ATCN_1123 | 6739 |
| ATCN_440 | 3649 | ATCN_1124 | 6740 |
| TTCN_732 | 3650 | ATCN_1125 | 6741 |
| ATCN_441 | 3651 | TTCN_1640 | 6742 |
| ATCN_442 | 3652 | TTCN_1641 | 6743 |
| CTCN_747 | 3653 | TTCN_1642 | 6744 |
| ATCN_443 | 3654 | CTCN_1733 | 6745 |
| TTCN_733 | 3655 | GTCN_919 | 6746 |
| TTCN_734 | 3656 | CTCN_1734 | 6747 |
| ATCN_444 | 3657 | CTCN_1735 | 6748 |
| ATCN_445 | 3658 | CTCN_1736 | 6749 |

FIG. 35 (continued)

| | | | |
|---|---|---|---|
| TTCN_735 | 3659 | CTCN_1737 | 6750 |
| TTCN_736 | 3660 | GTCN_920 | 6751 |
| CTCN_748 | 3661 | TTCN_1643 | 6752 |
| ATCN_446 | 3662 | TTCN_1644 | 6753 |
| CTCN_749 | 3663 | CTCN_1738 | 6754 |
| GTCN_406 | 3664 | CTCN_1739 | 6755 |
| TTCN_737 | 3665 | CTCN_1740 | 6756 |
| ATCN_447 | 3666 | TTCN_1645 | 6757 |
| CTCN_750 | 3667 | GTCN_921 | 6758 |
| CTCN_751 | 3668 | CTCN_1741 | 6759 |
| GTCN_407 | 3669 | ATCN_1126 | 6760 |
| ATCN_448 | 3670 | CTCN_1742 | 6761 |
| GTCN_408 | 3671 | GTCN_922 | 6762 |
| TTCN_738 | 3672 | GTCN_923 | 6763 |
| TTCN_739 | 3673 | CTCN_1743 | 6764 |
| ATCN_449 | 3674 | TTCN_1646 | 6765 |
| ATCN_450 | 3675 | GTCN_924 | 6766 |
| ATCN_451 | 3676 | GTCN_925 | 6767 |
| TTCN_740 | 3677 | ATCN_1127 | 6768 |
| CTCN_752 | 3678 | GTCN_926 | 6769 |
| ATCN_452 | 3679 | TTCN_1647 | 6770 |
| ATCN_453 | 3680 | CTCN_1744 | 6771 |
| ATCN_454 | 3681 | ATCN_1128 | 6772 |
| TTCN_741 | 3682 | ATCN_1129 | 6773 |
| CTCN_753 | 3683 | GTCN_927 | 6774 |
| ATCN_455 | 3684 | TTCN_1648 | 6775 |
| ATCN_456 | 3685 | ATCN_1130 | 6776 |
| ATCN_457 | 3686 | ATCN_1131 | 6777 |
| CTCN_754 | 3687 | CTCN_1745 | 6778 |
| TTCN_742 | 3688 | TTCN_1649 | 6779 |
| CTCN_755 | 3689 | GTCN_928 | 6780 |
| TTCN_743 | 3690 | CTCN_1746 | 6781 |
| CTCN_756 | 3691 | TTCN_1650 | 6782 |
| ATCN_458 | 3692 | CTCN_1747 | 6783 |
| TTCN_744 | 3693 | GTCN_929 | 6784 |
| GTCN_409 | 3694 | CTCN_1748 | 6785 |
| ATCN_459 | 3695 | CTCN_1749 | 6786 |
| TTCN_745 | 3696 | TTCN_1651 | 6787 |
| CTCN_757 | 3697 | CTCN_1750 | 6788 |
| TTCN_746 | 3698 | TTCN_1652 | 6789 |
| ATCN_460 | 3699 | CTCN_1751 | 6790 |
| TTCN_747 | 3700 | GTCN_930 | 6791 |
| TTCN_748 | 3701 | ATCN_1132 | 6792 |
| GTCN_410 | 3702 | ATCN_1133 | 6793 |
| GTCN_411 | 3703 | GTCN_931 | 6794 |
| TTCN_749 | 3704 | TTCN_1653 | 6795 |
| ATCN_461 | 3705 | TTCN_1654 | 6796 |
| TTCN_750 | 3706 | CTCN_1752 | 6797 |
| ATCN_462 | 3707 | ATCN_1134 | 6798 |
| ATCN_463 | 3708 | GTCN_932 | 6799 |
| TTCN_751 | 3709 | TTCN_1655 | 6800 |
| ATCN_464 | 3710 | CTCN_1753 | 6801 |
| ATCN_465 | 3711 | TTCN_1656 | 6802 |

| | | | |
|---|---|---|---|
| TTCN_752 | 3712 | CTCN_1754 | 6803 |
| ATCN_466 | 3713 | TTCN_1657 | 6804 |
| CTCN_758 | 3714 | GTCN_933 | 6805 |
| TTCN_753 | 3715 | CTCN_1755 | 6806 |
| ATCN_467 | 3716 | TTCN_1658 | 6807 |
| ATCN_468 | 3717 | TTCN_1659 | 6808 |
| ATCN_469 | 3718 | CTCN_1756 | 6809 |
| TTCN_754 | 3719 | ATCN_1135 | 6810 |
| TTCN_755 | 3720 | TTCN_1660 | 6811 |
| ATCN_470 | 3721 | TTCN_1661 | 6812 |
| GTCN_412 | 3722 | CTCN_1757 | 6813 |
| GTCN_413 | 3723 | CTCN_1758 | 6814 |
| GTCN_414 | 3724 | GTCN_934 | 6815 |
| TTCN_756 | 3725 | CTCN_1759 | 6816 |
| TTCN_757 | 3726 | GTCN_935 | 6817 |
| CTCN_759 | 3727 | TTCN_1662 | 6818 |
| CTCN_760 | 3728 | GTCN_936 | 6819 |
| ATCN_471 | 3729 | CTCN_1760 | 6820 |
| CTCN_761 | 3730 | ATCN_1136 | 6821 |
| GTCN_415 | 3731 | TTCN_1663 | 6822 |
| TTCN_758 | 3732 | GTCN_937 | 6823 |
| TTCN_759 | 3733 | CTCN_1761 | 6824 |
| TTCN_760 | 3734 | ATCN_1137 | 6825 |
| TTCN_761 | 3735 | TTCN_1664 | 6826 |
| CTCN_762 | 3736 | GTCN_938 | 6827 |
| ATCN_472 | 3737 | CTCN_1762 | 6828 |
| TTCN_762 | 3738 | ATCN_1138 | 6829 |
| GTCN_416 | 3739 | ATCN_1139 | 6830 |
| CTCN_763 | 3740 | ATCN_1140 | 6831 |
| CTCN_764 | 3741 | ATCN_1141 | 6832 |
| ATCN_473 | 3742 | ATCN_1142 | 6833 |
| CTCN_765 | 3743 | TTCN_1665 | 6834 |
| CTCN_766 | 3744 | TTCN_1666 | 6835 |
| CTCN_767 | 3745 | CTCN_1763 | 6836 |
| CTCN_768 | 3746 | GTCN_939 | 6837 |
| TTCN_763 | 3747 | CTCN_1764 | 6838 |
| TTCN_764 | 3748 | TTCN_1667 | 6839 |
| CTCN_769 | 3749 | ATCN_1143 | 6840 |
| CTCN_770 | 3750 | TTCN_1668 | 6841 |
| CTCN_771 | 3751 | ATCN_1144 | 6842 |
| CTCN_772 | 3752 | TTCN_1669 | 6843 |
| ATCN_474 | 3753 | ATCN_1145 | 6844 |
| CTCN_773 | 3754 | ATCN_1146 | 6845 |
| GTCN_417 | 3755 | CTCN_1765 | 6846 |
| TTCN_765 | 3756 | ATCN_1147 | 6847 |
| GTCN_418 | 3757 | GTCN_940 | 6848 |
| CTCN_774 | 3758 | CTCN_1766 | 6849 |
| CTCN_775 | 3759 | TTCN_1670 | 6850 |
| ATCN_475 | 3760 | GTCN_941 | 6851 |
| ATCN_476 | 3761 | CTCN_1767 | 6852 |
| CTCN_776 | 3762 | TTCN_1671 | 6853 |
| ATCN_477 | 3763 | TTCN_1672 | 6854 |
| ATCN_478 | 3764 | GTCN_942 | 6855 |

FIG. 35 (continued)

| | | | |
|---|---|---|---|
| GTCN_419 | 3765 | GTCN_943 | 6856 |
| CTCN_777 | 3766 | TTCN_1673 | 6857 |
| CTCN_778 | 3767 | TTCN_1674 | 6858 |
| ATCN_479 | 3768 | TTCN_1675 | 6859 |
| CTCN_779 | 3769 | ATCN_1148 | 6860 |
| ATCN_480 | 3770 | GTCN_944 | 6861 |
| TTCN_766 | 3771 | GTCN_945 | 6862 |
| ATCN_481 | 3772 | TTCN_1676 | 6863 |
| CTCN_780 | 3773 | ATCN_1149 | 6864 |
| CTCN_781 | 3774 | TTCN_1677 | 6865 |
| TTCN_767 | 3775 | GTCN_946 | 6866 |
| TTCN_768 | 3776 | GTCN_947 | 6867 |
| TTCN_769 | 3777 | TTCN_1678 | 6868 |
| TTCN_770 | 3778 | CTCN_1768 | 6869 |
| TTCN_771 | 3779 | TTCN_1679 | 6870 |
| TTCN_772 | 3780 | GTCN_948 | 6871 |
| CTCN_782 | 3781 | GTCN_949 | 6872 |
| TTCN_773 | 3782 | ATCN_1150 | 6873 |
| ATCN_482 | 3783 | CTCN_1769 | 6874 |
| CTCN_783 | 3784 | TTCN_1680 | 6875 |
| ATCN_483 | 3785 | ATCN_1151 | 6876 |
| GTCN_420 | 3786 | ATCN_1152 | 6877 |
| ATCN_484 | 3787 | CTCN_1770 | 6878 |
| ATCN_485 | 3788 | CTCN_1771 | 6879 |
| CTCN_784 | 3789 | GTCN_950 | 6880 |
| TTCN_774 | 3790 | TTCN_1681 | 6881 |
| CTCN_785 | 3791 | CTCN_1772 | 6882 |
| ATCN_486 | 3792 | ATCN_1153 | 6883 |
| ATCN_487 | 3793 | GTCN_951 | 6884 |
| CTCN_786 | 3794 | ATCN_1154 | 6885 |
| GTCN_421 | 3795 | CTCN_1773 | 6886 |
| CTCN_787 | 3796 | CTCN_1774 | 6887 |
| TTCN_775 | 3797 | ATCN_1155 | 6888 |
| CTCN_788 | 3798 | CTCN_1775 | 6889 |
| GTCN_422 | 3799 | CTCN_1776 | 6890 |
| GTCN_423 | 3800 | GTCN_952 | 6891 |
| CTCN_789 | 3801 | ATCN_1156 | 6892 |
| GTCN_424 | 3802 | CTCN_1777 | 6893 |
| CTCN_790 | 3803 | GTCN_953 | 6894 |
| TTCN_776 | 3804 | ATCN_1157 | 6895 |
| GTCN_425 | 3805 | TTCN_1682 | 6896 |
| GTCN_426 | 3806 | GTCN_954 | 6897 |
| TTCN_777 | 3807 | CTCN_1778 | 6898 |
| ATCN_488 | 3808 | ATCN_1158 | 6899 |
| CTCN_791 | 3809 | GTCN_955 | 6900 |
| TTCN_778 | 3810 | GTCN_956 | 6901 |
| CTCN_792 | 3811 | GTCN_957 | 6902 |
| TTCN_779 | 3812 | GTCN_958 | 6903 |
| GTCN_427 | 3813 | ATCN_1159 | 6904 |
| GTCN_428 | 3814 | CTCN_1779 | 6905 |
| TTCN_780 | 3815 | GTCN_959 | 6906 |
| TTCN_781 | 3816 | ATCN_1160 | 6907 |
| TTCN_782 | 3817 | CTCN_1780 | 6908 |

| | | | |
|---|---|---|---|
| ATCN_489 | 3818 | TTCN_1683 | 6909 |
| GTCN_429 | 3819 | GTCN_960 | 6910 |
| TTCN_783 | 3820 | CTCN_1781 | 6911 |
| ATCN_490 | 3821 | GTCN_961 | 6912 |
| TTCN_784 | 3822 | TTCN_1684 | 6913 |
| CTCN_793 | 3823 | CTCN_1782 | 6914 |
| ATCN_491 | 3824 | GTCN_962 | 6915 |
| TTCN_785 | 3825 | CTCN_1783 | 6916 |
| ATCN_492 | 3826 | CTCN_1784 | 6917 |
| ATCN_493 | 3827 | TTCN_1685 | 6918 |
| ATCN_494 | 3828 | TTCN_1686 | 6919 |
| TTCN_786 | 3829 | TTCN_1687 | 6920 |
| CTCN_794 | 3830 | TTCN_1688 | 6921 |
| ATCN_495 | 3831 | TTCN_1689 | 6922 |
| TTCN_787 | 3832 | CTCN_1785 | 6923 |
| CTCN_795 | 3833 | CTCN_1786 | 6924 |
| GTCN_430 | 3834 | CTCN_1787 | 6925 |
| TTCN_788 | 3835 | CTCN_1788 | 6926 |
| TTCN_789 | 3836 | CTCN_1789 | 6927 |
| CTCN_796 | 3837 | TTCN_1690 | 6928 |
| TTCN_790 | 3838 | TTCN_1691 | 6929 |
| CTCN_797 | 3839 | TTCN_1692 | 6930 |
| TTCN_791 | 3840 | TTCN_1693 | 6931 |
| CTCN_798 | 3841 | ATCN_1161 | 6932 |
| CTCN_799 | 3842 | TTCN_1694 | 6933 |
| CTCN_800 | 3843 | ATCN_1162 | 6934 |
| GTCN_431 | 3844 | TTCN_1695 | 6935 |
| CTCN_801 | 3845 | ATCN_1163 | 6936 |
| TTCN_792 | 3846 | CTCN_1790 | 6937 |
| CTCN_802 | 3847 | GTCN_963 | 6938 |
| CTCN_803 | 3848 | TTCN_1696 | 6939 |
| CTCN_804 | 3849 | CTCN_1791 | 6940 |
| TTCN_793 | 3850 | TTCN_1697 | 6941 |
| TTCN_794 | 3851 | CTCN_1792 | 6942 |
| CTCN_805 | 3852 | CTCN_1793 | 6943 |
| CTCN_806 | 3853 | TTCN_1698 | 6944 |
| CTCN_807 | 3854 | CTCN_1794 | 6945 |
| CTCN_808 | 3855 | TTCN_1699 | 6946 |
| ATCN_496 | 3856 | CTCN_1795 | 6947 |
| CTCN_809 | 3857 | TTCN_1700 | 6948 |
| TTCN_795 | 3858 | TTCN_1701 | 6949 |
| GTCN_432 | 3859 | CTCN_1796 | 6950 |
| CTCN_810 | 3860 | ATCN_1164 | 6951 |
| CTCN_811 | 3861 | TTCN_1702 | 6952 |
| TTCN_796 | 3862 | TTCN_1703 | 6953 |
| CTCN_812 | 3863 | CTCN_1797 | 6954 |
| ATCN_497 | 3864 | TTCN_1704 | 6955 |
| ATCN_498 | 3865 | TTCN_1705 | 6956 |
| TTCN_797 | 3866 | ATCN_1165 | 6957 |
| TTCN_798 | 3867 | ATCN_1166 | 6958 |
| CTCN_813 | 3868 | TTCN_1706 | 6959 |
| TTCN_799 | 3869 | CTCN_1798 | 6960 |
| ATCN_499 | 3870 | TTCN_1707 | 6961 |

FIG. 35 (continued)

| | | | |
|---|---|---|---|
| TTCN_800 | 3871 | TTCN_1708 | 6962 |
| TTCN_801 | 3872 | GTCN_964 | 6963 |
| GTCN_433 | 3873 | TTCN_1709 | 6964 |
| TTCN_802 | 3874 | TTCN_1710 | 6965 |
| ATCN_500 | 3875 | CTCN_1799 | 6966 |
| ATCN_501 | 3876 | TTCN_1711 | 6967 |
| CTCN_814 | 3877 | CTCN_1800 | 6968 |
| CTCN_815 | 3878 | ATCN_1167 | 6969 |
| ATCN_502 | 3879 | CTCN_1801 | 6970 |
| GTCN_434 | 3880 | CTCN_1802 | 6971 |
| TTCN_803 | 3881 | CTCN_1803 | 6972 |
| CTCN_816 | 3882 | CTCN_1804 | 6973 |
| TTCN_804 | 3883 | GTCN_965 | 6974 |
| CTCN_817 | 3884 | CTCN_1805 | 6975 |
| TTCN_805 | 3885 | CTCN_1806 | 6976 |
| CTCN_818 | 3886 | ATCN_1168 | 6977 |
| TTCN_806 | 3887 | ATCN_1169 | 6978 |
| ATCN_503 | 3888 | CTCN_1807 | 6979 |
| ATCN_504 | 3889 | CTCN_1808 | 6980 |
| GTCN_435 | 3890 | TTCN_1712 | 6981 |
| CTCN_819 | 3891 | CTCN_1809 | 6982 |
| TTCN_807 | 3892 | GTCN_966 | 6983 |
| GTCN_436 | 3893 | TTCN_1713 | 6984 |
| CTCN_820 | 3894 | TTCN_1714 | 6985 |
| TTCN_808 | 3895 | ATCN_1170 | 6986 |
| GTCN_437 | 3896 | GTCN_967 | 6987 |
| GTCN_438 | 3897 | CTCN_1810 | 6988 |
| GTCN_439 | 3898 | TTCN_1715 | 6989 |
| GTCN_440 | 3899 | TTCN_1716 | 6990 |
| ATCN_505 | 3900 | GTCN_968 | 6991 |
| GTCN_441 | 3901 | TTCN_1717 | 6992 |
| CTCN_821 | 3902 | ATCN_1171 | 6993 |
| CTCN_822 | 3903 | CTCN_1811 | 6994 |
| CTCN_823 | 3904 | ATCN_1172 | 6995 |
| GTCN_442 | 3905 | CTCN_1812 | 6996 |
| TTCN_809 | 3906 | CTCN_1813 | 6997 |
| GTCN_443 | 3907 | TTCN_1718 | 6998 |
| GTCN_444 | 3908 | TTCN_1719 | 6999 |
| TTCN_810 | 3909 | GTCN_969 | 7000 |
| ATCN_506 | 3910 | ATCN_1173 | 7001 |
| CTCN_824 | 3911 | GTCN_970 | 7002 |
| TTCN_811 | 3912 | TTCN_1720 | 7003 |
| TTCN_812 | 3913 | CTCN_1814 | 7004 |
| GTCN_445 | 3914 | ATCN_1174 | 7005 |
| CTCN_825 | 3915 | GTCN_971 | 7006 |
| TTCN_813 | 3916 | ATCN_1175 | 7007 |
| GTCN_446 | 3917 | ATCN_1176 | 7008 |
| TTCN_814 | 3918 | GTCN_972 | 7009 |
| TTCN_815 | 3919 | CTCN_1815 | 7010 |
| TTCN_816 | 3920 | GTCN_973 | 7011 |
| CTCN_826 | 3921 | TTCN_1721 | 7012 |
| TTCN_817 | 3922 | TTCN_1722 | 7013 |
| TTCN_818 | 3923 | CTCN_1816 | 7014 |

| | | | |
|---|---|---|---|
| TTCN_819 | 3924 | CTCN_1817 | 7015 |
| TTCN_820 | 3925 | TTCN_1723 | 7016 |
| ATCN_507 | 3926 | TTCN_1724 | 7017 |
| ATCN_508 | 3927 | ATCN_1177 | 7018 |
| TTCN_821 | 3928 | ATCN_1178 | 7019 |
| TTCN_822 | 3929 | ATCN_1179 | 7020 |
| TTCN_823 | 3930 | ATCN_1180 | 7021 |
| CTCN_827 | 3931 | CTCN_1818 | 7022 |
| TTCN_824 | 3932 | TTCN_1725 | 7023 |
| TTCN_825 | 3933 | ATCN_1181 | 7024 |
| CTCN_828 | 3934 | ATCN_1182 | 7025 |
| TTCN_826 | 3935 | ATCN_1183 | 7026 |
| ATCN_509 | 3936 | ATCN_1184 | 7027 |
| CTCN_829 | 3937 | ATCN_1185 | 7028 |
| TTCN_827 | 3938 | CTCN_1819 | 7029 |
| CTCN_830 | 3939 | TTCN_1726 | 7030 |
| GTCN_447 | 3940 | TTCN_1727 | 7031 |
| TTCN_828 | 3941 | CTCN_1820 | 7032 |
| CTCN_831 | 3942 | CTCN_1821 | 7033 |
| GTCN_448 | 3943 | ATCN_1186 | 7034 |
| ATCN_510 | 3944 | ATCN_1187 | 7035 |
| TTCN_829 | 3945 | ATCN_1188 | 7036 |
| TTCN_830 | 3946 | TTCN_1728 | 7037 |
| GTCN_449 | 3947 | TTCN_1729 | 7038 |
| CTCN_832 | 3948 | GTCN_974 | 7039 |
| TTCN_831 | 3949 | CTCN_1822 | 7040 |
| TTCN_832 | 3950 | ATCN_1189 | 7041 |
| TTCN_833 | 3951 | TTCN_1730 | 7042 |
| TTCN_834 | 3952 | GTCN_975 | 7043 |
| TTCN_835 | 3953 | ATCN_1190 | 7044 |
| TTCN_836 | 3954 | TTCN_1731 | 7045 |
| ATCN_511 | 3955 | TTCN_1732 | 7046 |
| TTCN_837 | 3956 | CTCN_1823 | 7047 |
| TTCN_838 | 3957 | GTCN_976 | 7048 |
| CTCN_833 | 3958 | CTCN_1824 | 7049 |
| TTCN_839 | 3959 | GTCN_977 | 7050 |
| GTCN_450 | 3960 | ATCN_1191 | 7051 |
| TTCN_840 | 3961 | GTCN_978 | 7052 |
| CTCN_834 | 3962 | CTCN_1825 | 7053 |
| CTCN_835 | 3963 | GTCN_979 | 7054 |
| GTCN_451 | 3964 | ATCN_1192 | 7055 |
| CTCN_836 | 3965 | TTCN_1733 | 7056 |
| ATCN_512 | 3966 | TTCN_1734 | 7057 |
| GTCN_452 | 3967 | ATCN_1193 | 7058 |
| TTCN_841 | 3968 | TTCN_1735 | 7059 |
| CTCN_837 | 3969 | CTCN_1826 | 7060 |
| TTCN_842 | 3970 | CTCN_1827 | 7061 |
| CTCN_838 | 3971 | TTCN_1736 | 7062 |
| TTCN_843 | 3972 | TTCN_1737 | 7063 |
| TTCN_844 | 3973 | ATCN_1194 | 7064 |
| TTCN_845 | 3974 | GTCN_980 | 7065 |
| TTCN_846 | 3975 | TTCN_1738 | 7066 |
| TTCN_847 | 3976 | CTCN_1828 | 7067 |

FIG. 35 (continued)

| | | | |
|---|---|---|---|
| CTCN_839 | 3977 | GTCN_981 | 7068 |
| TTCN_848 | 3978 | CTCN_1829 | 7069 |
| TTCN_849 | 3979 | GTCN_982 | 7070 |
| ATCN_513 | 3980 | CTCN_1830 | 7071 |
| ATCN_514 | 3981 | CTCN_1831 | 7072 |
| ATCN_515 | 3982 | CTCN_1832 | 7073 |
| TTCN_850 | 3983 | CTCN_1833 | 7074 |
| TTCN_851 | 3984 | ATCN_1195 | 7075 |
| TTCN_852 | 3985 | CTCN_1834 | 7076 |
| CTCN_840 | 3986 | CTCN_1835 | 7077 |
| TTCN_853 | 3987 | CTCN_1836 | 7078 |
| TTCN_854 | 3988 | TTCN_1739 | 7079 |
| GTCN_453 | 3989 | TTCN_1740 | 7080 |
| CTCN_841 | 3990 | CTCN_1837 | 7081 |
| GTCN_454 | 3991 | CTCN_1838 | 7082 |
| ATCN_516 | 3992 | CTCN_1839 | 7083 |
| CTCN_842 | 3993 | CTCN_1840 | 7084 |
| GTCN_455 | 3994 | GTCN_983 | 7085 |
| CTCN_843 | 3995 | | |

FIG. 36: Table 3B: Targeting Sequences for TRAC

| Name | SEQ ID NO. | Name | SEQ ID NO. |
|---|---|---|---|
| GTCN_0 | 7086 | TTCN_3239 | 17273 |
| TTCN_0 | 7087 | CTCN_2822 | 17274 |
| CTCN_0 | 7088 | TTCN_3240 | 17275 |
| ATCN_0 | 7089 | ATCN_2005 | 17276 |
| ATCN_1 | 7090 | TTCN_3241 | 17277 |
| GTCN_1 | 7091 | ATCN_2006 | 17278 |
| GTCN_2 | 7092 | TTCN_3242 | 17279 |
| CTCN_1 | 7093 | ATCN_2007 | 17280 |
| CTCN_2 | 7094 | ATCN_2008 | 17281 |
| CTCN_3 | 7095 | CTCN_2823 | 17282 |
| ATCN_2 | 7096 | ATCN_2009 | 17283 |
| TTCN_1 | 7097 | TTCN_3243 | 17284 |
| TTCN_2 | 7098 | ATCN_2010 | 17285 |
| TTCN_3 | 7099 | GTCN_1701 | 17286 |
| ATCN_3 | 7100 | CTCN_2824 | 17287 |
| TTCN_4 | 7101 | TTCN_3244 | 17288 |
| TTCN_5 | 7102 | TTCN_3245 | 17289 |
| ATCN_4 | 7103 | GTCN_1702 | 17290 |
| TTCN_6 | 7104 | CTCN_2825 | 17291 |
| CTCN_4 | 7105 | TTCN_3246 | 17292 |
| CTCN_5 | 7106 | CTCN_2826 | 17293 |
| GTCN_3 | 7107 | CTCN_2827 | 17294 |
| CTCN_6 | 7108 | TTCN_3247 | 17295 |
| GTCN_4 | 7109 | TTCN_3248 | 17296 |
| TTCN_7 | 7110 | CTCN_2828 | 17297 |
| CTCN_7 | 7111 | TTCN_3249 | 17298 |
| ATCN_5 | 7112 | CTCN_2829 | 17299 |
| TTCN_8 | 7113 | CTCN_2830 | 17300 |
| TTCN_9 | 7114 | CTCN_2831 | 17301 |
| GTCN_5 | 7115 | TTCN_3250 | 17302 |
| CTCN_8 | 7116 | CTCN_2832 | 17303 |
| TTCN_10 | 7117 | GTCN_1703 | 17304 |
| GTCN_6 | 7118 | TTCN_3251 | 17305 |
| TTCN_11 | 7119 | TTCN_3252 | 17306 |
| CTCN_9 | 7120 | TTCN_3252 | 17307 |
| TTCN_12 | 7121 | TTCN_3253 | 17308 |
| CTCN_10 | 7122 | GTCN_1704 | 17309 |
| GTCN_7 | 7123 | TTCN_3254 | 17310 |
| TTCN_13 | 7124 | CTCN_2833 | 17311 |
| ATCN_6 | 7125 | CTCN_2834 | 17312 |
| TTCN_14 | 7126 | GTCN_1705 | 17313 |
| ATCN_7 | 7127 | CTCN_2835 | 17314 |
| ATCN_8 | 7128 | TTCN_3255 | 17315 |
| TTCN_15 | 7129 | TTCN_3256 | 17316 |
| GTCN_8 | 7130 | CTCN_2836 | 17317 |
| TTCN_16 | 7131 | ATCN_2011 | 17318 |
| GTCN_9 | 7132 | GTCN_1706 | 17319 |
| TTCN_17 | 7133 | CTCN_2837 | 17320 |
| CTCN_11 | 7134 | CTCN_2838 | 17321 |
| GTCN_10 | 7135 | GTCN_1707 | 17322 |
| GTCN_11 | 7136 | CTCN_2839 | 17323 |
| GTCN_12 | 7137 | TTCN_3257 | 17324 |
| ATCN_9 | 7138 | GTCN_1708 | 17325 |
| ATCN_10 | 7139 | CTCN_2840 | 17326 |
| CTCN_12 | 7140 | CTCN_2841 | 17327 |
| GTCN_13 | 7141 | GTCN_1709 | 17328 |
| CTCN_13 | 7142 | CTCN_2842 | 17329 |
| TTCN_18 | 7143 | TTCN_3258 | 17330 |
| ATCN_11 | 7144 | CTCN_2843 | 17331 |
| TTCN_19 | 7145 | ATCN_2012 | 17332 |
| ATCN_12 | 7146 | TTCN_3259 | 17333 |
| TTCN_20 | 7147 | TTCN_3260 | 17334 |
| CTCN_14 | 7148 | CTCN_2844 | 17335 |
| TTCN_21 | 7149 | CTCN_2845 | 17336 |
| CTCN_15 | 7150 | CTCN_2846 | 17337 |
| TTCN_22 | 7151 | GTCN_1710 | 17338 |
| CTCN_16 | 7152 | CTCN_2847 | 17339 |
| GTCN_14 | 7153 | CTCN_2848 | 17340 |
| ATCN_13 | 7154 | CTCN_2849 | 17341 |
| CTCN_17 | 7155 | CTCN_2850 | 17342 |
| GTCN_15 | 7156 | GTCN_1711 | 17343 |
| TTCN_23 | 7157 | CTCN_2851 | 17344 |
| ATCN_14 | 7158 | GTCN_1712 | 17345 |
| ATCN_15 | 7159 | TTCN_3261 | 17346 |
| CTCN_18 | 7160 | CTCN_2852 | 17347 |
| CTCN_19 | 7161 | CTCN_2853 | 17348 |
| CTCN_20 | 7162 | CTCN_2854 | 17349 |
| CTCN_21 | 7163 | TTCN_3262 | 17350 |
| CTCN_22 | 7164 | CTCN_2855 | 17351 |
| TTCN_24 | 7165 | TTCN_3263 | 17352 |
| TTCN_25 | 7166 | ATCN_2013 | 17353 |
| TTCN_26 | 7167 | CTCN_2856 | 17354 |
| CTCN_23 | 7168 | CTCN_2857 | 17355 |
| CTCN_24 | 7169 | GTCN_1713 | 17356 |
| CTCN_25 | 7170 | TTCN_3264 | 17357 |
| ATCN_16 | 7171 | ATCN_2014 | 17358 |
| CTCN_26 | 7172 | GTCN_1714 | 17359 |
| TTCN_27 | 7173 | CTCN_2858 | 17360 |
| CTCN_27 | 7174 | ATCN_2015 | 17361 |
| ATCN_17 | 7175 | CTCN_2859 | 17362 |
| TTCN_28 | 7176 | TTCN_3265 | 17363 |
| GTCN_16 | 7177 | TTCN_3266 | 17364 |
| TTCN_29 | 7178 | CTCN_2860 | 17365 |
| GTCN_17 | 7179 | TTCN_3267 | 17366 |
| CTCN_28 | 7180 | TTCN_3268 | 17367 |
| CTCN_29 | 7181 | ATCN_2016 | 17368 |
| GTCN_18 | 7182 | TTCN_3269 | 17369 |
| TTCN_30 | 7183 | ATCN_2017 | 17370 |
| TTCN_31 | 7184 | ATCN_2018 | 17371 |
| CTCN_30 | 7185 | TTCN_3270 | 17372 |
| CTCN_31 | 7186 | GTCN_1715 | 17373 |
| TTCN_32 | 7187 | ATCN_2019 | 17374 |
| GTCN_19 | 7188 | TTCN_3271 | 17375 |
| CTCN_32 | 7189 | ATCN_2020 | 17376 |
| GTCN_20 | 7190 | CTCN_2861 | 17377 |
| ATCN_18 | 7191 | CTCN_2862 | 17378 |

FIG. 36 (continued)

| | | | |
|---|---|---|---|
| CTCN_33 | 7192 | ATCN_2021 | 17379 |
| ATCN_19 | 7193 | ATCN_2022 | 17380 |
| TTCN_33 | 7194 | TTCN_3272 | 17381 |
| TTCN_34 | 7195 | ATCN_2023 | 17382 |
| GTCN_21 | 7196 | CTCN_2863 | 17383 |
| TTCN_35 | 7197 | GTCN_1716 | 17384 |
| CTCN_34 | 7198 | CTCN_2864 | 17385 |
| ATCN_20 | 7199 | ATCN_2024 | 17386 |
| TTCN_36 | 7200 | GTCN_1717 | 17387 |
| TTCN_37 | 7201 | GTCN_1718 | 17388 |
| CTCN_35 | 7202 | ATCN_2025 | 17389 |
| GTCN_22 | 7203 | CTCN_2865 | 17390 |
| CTCN_36 | 7204 | ATCN_2026 | 17391 |
| TTCN_38 | 7205 | ATCN_2027 | 17392 |
| CTCN_37 | 7206 | CTCN_2866 | 17393 |
| TTCN_39 | 7207 | GTCN_1719 | 17394 |
| ATCN_21 | 7208 | ATCN_2028 | 17395 |
| TTCN_40 | 7209 | TTCN_3273 | 17396 |
| CTCN_38 | 7210 | CTCN_2867 | 17397 |
| CTCN_39 | 7211 | GTCN_1720 | 17398 |
| CTCN_40 | 7212 | ATCN_2029 | 17399 |
| TTCN_41 | 7213 | TTCN_3274 | 17400 |
| GTCN_23 | 7214 | GTCN_1721 | 17401 |
| CTCN_41 | 7215 | TTCN_3275 | 17402 |
| TTCN_42 | 7216 | CTCN_2868 | 17403 |
| GTCN_24 | 7217 | TTCN_3276 | 17404 |
| TTCN_43 | 7218 | TTCN_3277 | 17405 |
| CTCN_42 | 7219 | TTCN_3278 | 17406 |
| GTCN_25 | 7220 | TTCN_3279 | 17407 |
| ATCN_22 | 7221 | GTCN_1722 | 17408 |
| TTCN_44 | 7222 | CTCN_2869 | 17409 |
| CTCN_43 | 7223 | CTCN_2870 | 17410 |
| TTCN_45 | 7224 | CTCN_2871 | 17411 |
| TTCN_46 | 7225 | GTCN_1723 | 17412 |
| TTCN_47 | 7226 | CTCN_2872 | 17413 |
| GTCN_26 | 7227 | TTCN_3280 | 17414 |
| TTCN_48 | 7228 | CTCN_2873 | 17415 |
| CTCN_44 | 7229 | GTCN_1724 | 17416 |
| TTCN_49 | 7230 | CTCN_2874 | 17417 |
| CTCN_45 | 7231 | GTCN_1725 | 17418 |
| TTCN_50 | 7232 | CTCN_2875 | 17419 |
| GTCN_27 | 7233 | TTCN_3281 | 17420 |
| TTCN_51 | 7234 | ATCN_2030 | 17421 |
| TTCN_52 | 7235 | CTCN_2876 | 17422 |
| CTCN_46 | 7236 | ATCN_2031 | 17423 |
| GTCN_28 | 7237 | TTCN_3282 | 17424 |
| ATCN_23 | 7238 | TTCN_3283 | 17425 |
| TTCN_53 | 7239 | CTCN_2877 | 17426 |
| GTCN_29 | 7240 | CTCN_2878 | 17427 |
| TTCN_54 | 7241 | CTCN_2879 | 17428 |
| TTCN_55 | 7242 | TTCN_3284 | 17429 |
| TTCN_56 | 7243 | ATCN_2032 | 17430 |
| TTCN_57 | 7244 | ATCN_2033 | 17431 |
| GTCN_30 | 7245 | TTCN_3285 | 17432 |
| CTCN_47 | 7246 | TTCN_3286 | 17433 |

| | | | |
|---|---|---|---|
| GTCN_31 | 7247 | TTCN_3287 | 17434 |
| CTCN_48 | 7248 | CTCN_2880 | 17435 |
| CTCN_49 | 7249 | ATCN_2034 | 17436 |
| TTCN_58 | 7250 | TTCN_3288 | 17437 |
| ATCN_24 | 7251 | TTCN_3289 | 17438 |
| GTCN_32 | 7252 | ATCN_2035 | 17439 |
| TTCN_59 | 7253 | ATCN_2036 | 17440 |
| GTCN_33 | 7254 | CTCN_2881 | 17441 |
| TTCN_60 | 7255 | TTCN_3290 | 17442 |
| TTCN_61 | 7256 | GTCN_1726 | 17443 |
| GTCN_34 | 7257 | TTCN_3291 | 17444 |
| GTCN_35 | 7258 | CTCN_2882 | 17445 |
| ATCN_25 | 7259 | GTCN_1727 | 17446 |
| ATCN_26 | 7260 | ATCN_2037 | 17447 |
| ATCN_27 | 7261 | CTCN_2883 | 17448 |
| ATCN_28 | 7262 | TTCN_3292 | 17449 |
| TTCN_62 | 7263 | ATCN_2038 | 17450 |
| ATCN_29 | 7264 | ATCN_2039 | 17451 |
| ATCN_30 | 7265 | ATCN_2040 | 17452 |
| TTCN_63 | 7266 | CTCN_2884 | 17453 |
| TTCN_64 | 7267 | TTCN_3293 | 17454 |
| TTCN_65 | 7268 | CTCN_2885 | 17455 |
| GTCN_36 | 7269 | ATCN_2041 | 17456 |
| ATCN_31 | 7270 | ATCN_2042 | 17457 |
| GTCN_37 | 7271 | ATCN_2043 | 17458 |
| GTCN_38 | 7272 | TTCN_3294 | 17459 |
| CTCN_50 | 7273 | GTCN_1728 | 17460 |
| ATCN_32 | 7274 | CTCN_2886 | 17461 |
| TTCN_66 | 7275 | CTCN_2887 | 17462 |
| TTCN_67 | 7276 | CTCN_2888 | 17463 |
| TTCN_68 | 7277 | ATCN_2044 | 17464 |
| TTCN_69 | 7278 | GTCN_1729 | 17465 |
| TTCN_70 | 7279 | CTCN_2889 | 17466 |
| ATCN_33 | 7280 | CTCN_2890 | 17467 |
| TTCN_71 | 7281 | TTCN_3295 | 17468 |
| TTCN_72 | 7282 | TTCN_3296 | 17469 |
| ATCN_34 | 7283 | TTCN_3297 | 17470 |
| CTCN_51 | 7284 | GTCN_1730 | 17471 |
| TTCN_73 | 7285 | TTCN_3298 | 17472 |
| ATCN_35 | 7286 | CTCN_2891 | 17473 |
| TTCN_74 | 7287 | ATCN_2045 | 17474 |
| TTCN_75 | 7288 | ATCN_2046 | 17475 |
| ATCN_36 | 7289 | CTCN_2892 | 17476 |
| CTCN_52 | 7290 | TTCN_3299 | 17477 |
| GTCN_39 | 7291 | GTCN_1731 | 17478 |
| ATCN_37 | 7292 | GTCN_1732 | 17479 |
| TTCN_76 | 7293 | CTCN_2893 | 17480 |
| CTCN_53 | 7294 | TTCN_3300 | 17481 |
| TTCN_77 | 7295 | TTCN_3301 | 17482 |
| ATCN_38 | 7296 | CTCN_2894 | 17483 |
| TTCN_78 | 7297 | ATCN_2047 | 17484 |
| CTCN_54 | 7298 | ATCN_2048 | 17485 |
| TTCN_79 | 7299 | CTCN_2895 | 17486 |
| TTCN_80 | 7300 | GTCN_1733 | 17487 |
| TTCN_81 | 7301 | TTCN_3302 | 17488 |

FIG. 36 (continued)

| | | | |
|---|---|---|---|
| CTCN_55 | 7302 | CTCN_2896 | 17489 |
| CTCN_56 | 7303 | TTCN_3303 | 17490 |
| GTCN_40 | 7304 | CTCN_2897 | 17491 |
| CTCN_57 | 7305 | TTCN_3304 | 17492 |
| ATCN_39 | 7306 | GTCN_1734 | 17493 |
| CTCN_58 | 7307 | CTCN_2898 | 17494 |
| CTCN_59 | 7308 | CTCN_2899 | 17495 |
| GTCN_41 | 7309 | TTCN_3305 | 17496 |
| TTCN_82 | 7310 | TTCN_3306 | 17497 |
| TTCN_83 | 7311 | ATCN_2049 | 17498 |
| CTCN_60 | 7312 | TTCN_3307 | 17499 |
| TTCN_84 | 7313 | TTCN_3308 | 17500 |
| GTCN_42 | 7314 | CTCN_2900 | 17501 |
| TTCN_85 | 7315 | TTCN_3309 | 17502 |
| CTCN_61 | 7316 | CTCN_2901 | 17503 |
| GTCN_43 | 7317 | CTCN_2902 | 17504 |
| ATCN_40 | 7318 | GTCN_1735 | 17505 |
| ATCN_41 | 7319 | CTCN_2903 | 17506 |
| TTCN_86 | 7320 | ATCN_2050 | 17507 |
| TTCN_87 | 7321 | ATCN_2051 | 17508 |
| ATCN_42 | 7322 | GTCN_1736 | 17509 |
| TTCN_88 | 7323 | CTCN_2904 | 17510 |
| CTCN_62 | 7324 | CTCN_2905 | 17511 |
| ATCN_43 | 7325 | CTCN_2906 | 17512 |
| ATCN_44 | 7326 | TTCN_3310 | 17513 |
| CTCN_63 | 7327 | GTCN_1737 | 17514 |
| TTCN_89 | 7328 | CTCN_2907 | 17515 |
| CTCN_64 | 7329 | CTCN_2908 | 17516 |
| GTCN_44 | 7330 | GTCN_1738 | 17517 |
| CTCN_65 | 7331 | TTCN_3311 | 17518 |
| TTCN_90 | 7332 | CTCN_2909 | 17519 |
| CTCN_66 | 7333 | TTCN_3312 | 17520 |
| CTCN_67 | 7334 | ATCN_2052 | 17521 |
| CTCN_68 | 7335 | ATCN_2053 | 17522 |
| CTCN_69 | 7336 | TTCN_3313 | 17523 |
| GTCN_45 | 7337 | ATCN_2054 | 17524 |
| CTCN_70 | 7338 | TTCN_3314 | 17525 |
| CTCN_71 | 7339 | TTCN_3315 | 17526 |
| GTCN_46 | 7340 | TTCN_3316 | 17527 |
| TTCN_91 | 7341 | TTCN_3317 | 17528 |
| TTCN_92 | 7342 | CTCN_2910 | 17529 |
| ATCN_45 | 7343 | TTCN_3318 | 17530 |
| TTCN_93 | 7344 | ATCN_2055 | 17531 |
| ATCN_46 | 7345 | TTCN_3319 | 17532 |
| CTCN_72 | 7346 | TTCN_3320 | 17533 |
| TTCN_94 | 7347 | GTCN_1739 | 17534 |
| GTCN_47 | 7348 | TTCN_3321 | 17535 |
| TTCN_95 | 7349 | TTCN_3322 | 17536 |
| TTCN_96 | 7350 | TTCN_3323 | 17537 |
| TTCN_97 | 7351 | ATCN_2056 | 17538 |
| TTCN_98 | 7352 | CTCN_2911 | 17539 |
| CTCN_73 | 7353 | GTCN_1740 | 17540 |
| TTCN_99 | 7354 | ATCN_2057 | 17541 |
| TTCN_100 | 7355 | TTCN_3324 | 17542 |
| ATCN_47 | 7356 | CTCN_2912 | 17543 |

| | | | |
|---|---|---|---|
| GTCN_48 | 7357 | GTCN_1741 | 17544 |
| TTCN_101 | 7358 | ATCN_2058 | 17545 |
| TTCN_102 | 7359 | ATCN_2059 | 17546 |
| TTCN_103 | 7360 | ATCN_2060 | 17547 |
| CTCN_74 | 7361 | TTCN_3325 | 17548 |
| TTCN_104 | 7362 | TTCN_3326 | 17549 |
| GTCN_49 | 7363 | GTCN_1742 | 17550 |
| ATCN_48 | 7364 | ATCN_2061 | 17551 |
| CTCN_75 | 7365 | ATCN_2062 | 17552 |
| GTCN_50 | 7366 | TTCN_3327 | 17553 |
| CTCN_76 | 7367 | TTCN_3328 | 17554 |
| GTCN_51 | 7368 | TTCN_3329 | 17555 |
| TTCN_105 | 7369 | ATCN_2063 | 17556 |
| CTCN_77 | 7370 | TTCN_3330 | 17557 |
| GTCN_52 | 7371 | TTCN_3331 | 17558 |
| TTCN_106 | 7372 | GTCN_1743 | 17559 |
| GTCN_53 | 7373 | CTCN_2913 | 17560 |
| CTCN_78 | 7374 | GTCN_1744 | 17561 |
| TTCN_107 | 7375 | TTCN_3332 | 17562 |
| GTCN_54 | 7376 | CTCN_2914 | 17563 |
| CTCN_79 | 7377 | ATCN_2064 | 17564 |
| CTCN_80 | 7378 | CTCN_2915 | 17565 |
| GTCN_55 | 7379 | CTCN_2916 | 17566 |
| CTCN_81 | 7380 | ATCN_2065 | 17567 |
| CTCN_82 | 7381 | TTCN_3333 | 17568 |
| CTCN_83 | 7382 | TTCN_3334 | 17569 |
| TTCN_108 | 7383 | CTCN_2917 | 17570 |
| ATCN_49 | 7384 | TTCN_3335 | 17571 |
| CTCN_84 | 7385 | TTCN_3336 | 17572 |
| GTCN_56 | 7386 | TTCN_3337 | 17573 |
| CTCN_85 | 7387 | TTCN_3338 | 17574 |
| CTCN_86 | 7388 | TTCN_3339 | 17575 |
| TTCN_109 | 7389 | GTCN_1745 | 17576 |
| ATCN_50 | 7390 | TTCN_3340 | 17577 |
| ATCN_51 | 7391 | TTCN_3341 | 17578 |
| ATCN_52 | 7392 | ATCN_2066 | 17579 |
| TTCN_110 | 7393 | TTCN_3342 | 17580 |
| ATCN_53 | 7394 | TTCN_3343 | 17581 |
| ATCN_54 | 7395 | TTCN_3344 | 17582 |
| CTCN_87 | 7396 | TTCN_3345 | 17583 |
| TTCN_111 | 7397 | CTCN_2918 | 17584 |
| CTCN_88 | 7398 | TTCN_3346 | 17585 |
| TTCN_112 | 7399 | GTCN_1746 | 17586 |
| ATCN_55 | 7400 | TTCN_3347 | 17587 |
| CTCN_89 | 7401 | CTCN_2919 | 17588 |
| CTCN_90 | 7402 | TTCN_3348 | 17589 |
| TTCN_113 | 7403 | TTCN_3349 | 17590 |
| TTCN_114 | 7404 | CTCN_2920 | 17591 |
| GTCN_57 | 7405 | TTCN_3350 | 17592 |
| TTCN_115 | 7406 | TTCN_3351 | 17593 |
| TTCN_116 | 7407 | TTCN_3352 | 17594 |
| ATCN_56 | 7408 | TTCN_3353 | 17595 |
| TTCN_117 | 7409 | TTCN_3354 | 17596 |
| CTCN_91 | 7410 | TTCN_3355 | 17597 |
| ATCN_57 | 7411 | CTCN_2921 | 17598 |

FIG. 36 (continued)

| | | | |
|---|---|---|---|
| ATCN_58 | 7412 | CTCN_2922 | 17599 |
| GTCN_58 | 7413 | TTCN_3356 | 17600 |
| ATCN_59 | 7414 | CTCN_2923 | 17601 |
| ATCN_60 | 7415 | TTCN_3357 | 17602 |
| ATCN_61 | 7416 | GTCN_1747 | 17603 |
| TTCN_118 | 7417 | CTCN_2924 | 17604 |
| ATCN_62 | 7418 | CTCN_2925 | 17605 |
| TTCN_119 | 7419 | TTCN_3358 | 17606 |
| CTCN_92 | 7420 | TTCN_3359 | 17607 |
| CTCN_93 | 7421 | TTCN_3360 | 17608 |
| GTCN_59 | 7422 | TTCN_3361 | 17609 |
| ATCN_63 | 7423 | CTCN_2926 | 17610 |
| CTCN_94 | 7424 | TTCN_3362 | 17611 |
| ATCN_64 | 7425 | CTCN_2927 | 17612 |
| TTCN_120 | 7426 | TTCN_3363 | 17613 |
| ATCN_65 | 7427 | CTCN_2928 | 17614 |
| TTCN_121 | 7428 | CTCN_2929 | 17615 |
| TTCN_122 | 7429 | TTCN_3364 | 17616 |
| GTCN_60 | 7430 | CTCN_2930 | 17617 |
| TTCN_123 | 7431 | TTCN_3365 | 17618 |
| CTCN_95 | 7432 | ATCN_2067 | 17619 |
| CTCN_96 | 7433 | TTCN_3366 | 17620 |
| GTCN_61 | 7434 | CTCN_2931 | 17621 |
| TTCN_124 | 7435 | CTCN_2932 | 17622 |
| ATCN_66 | 7436 | CTCN_2933 | 17623 |
| TTCN_125 | 7437 | GTCN_1748 | 17624 |
| ATCN_67 | 7438 | CTCN_2934 | 17625 |
| TTCN_126 | 7439 | ATCN_2068 | 17626 |
| TTCN_127 | 7440 | CTCN_2935 | 17627 |
| GTCN_62 | 7441 | CTCN_2936 | 17628 |
| CTCN_97 | 7442 | CTCN_2937 | 17629 |
| TTCN_128 | 7443 | GTCN_1749 | 17630 |
| CTCN_98 | 7444 | GTCN_1750 | 17631 |
| TTCN_129 | 7445 | GTCN_1751 | 17632 |
| CTCN_99 | 7446 | CTCN_2938 | 17633 |
| GTCN_63 | 7447 | TTCN_3367 | 17634 |
| TTCN_130 | 7448 | TTCN_3368 | 17635 |
| TTCN_131 | 7449 | GTCN_1752 | 17636 |
| TTCN_132 | 7450 | GTCN_1753 | 17637 |
| GTCN_64 | 7451 | CTCN_2939 | 17638 |
| ATCN_68 | 7452 | TTCN_3369 | 17639 |
| ATCN_69 | 7453 | CTCN_2940 | 17640 |
| TTCN_133 | 7454 | ATCN_2069 | 17641 |
| ATCN_70 | 7455 | CTCN_2941 | 17642 |
| CTCN_100 | 7456 | CTCN_2942 | 17643 |
| GTCN_65 | 7457 | CTCN_2943 | 17644 |
| CTCN_101 | 7458 | GTCN_1754 | 17645 |
| TTCN_134 | 7459 | TTCN_3370 | 17646 |
| ATCN_71 | 7460 | ATCN_2070 | 17647 |
| TTCN_135 | 7461 | CTCN_2944 | 17648 |
| ATCN_72 | 7462 | CTCN_2945 | 17649 |
| GTCN_66 | 7463 | CTCN_2946 | 17650 |
| GTCN_67 | 7464 | GTCN_1755 | 17651 |
| ATCN_73 | 7465 | ATCN_2071 | 17652 |
| ATCN_74 | 7466 | TTCN_3371 | 17653 |

| | | | |
|---|---|---|---|
| TTCN_136 | 7467 | TTCN_3372 | 17654 |
| ATCN_75 | 7468 | ATCN_2072 | 17655 |
| CTCN_102 | 7469 | CTCN_2947 | 17656 |
| TTCN_137 | 7470 | ATCN_2073 | 17657 |
| TTCN_138 | 7471 | TTCN_3373 | 17658 |
| GTCN_68 | 7472 | CTCN_2948 | 17659 |
| TTCN_139 | 7473 | CTCN_2949 | 17660 |
| GTCN_69 | 7474 | CTCN_2950 | 17661 |
| TTCN_140 | 7475 | CTCN_2951 | 17662 |
| ATCN_76 | 7476 | GTCN_1756 | 17663 |
| CTCN_103 | 7477 | CTCN_2952 | 17664 |
| TTCN_141 | 7478 | CTCN_2953 | 17665 |
| ATCN_77 | 7479 | ATCN_2074 | 17666 |
| GTCN_70 | 7480 | TTCN_3374 | 17667 |
| GTCN_71 | 7481 | ATCN_2075 | 17668 |
| GTCN_72 | 7482 | ATCN_2076 | 17669 |
| CTCN_104 | 7483 | ATCN_2077 | 17670 |
| GTCN_73 | 7484 | GTCN_1757 | 17671 |
| TTCN_142 | 7485 | CTCN_2954 | 17672 |
| ATCN_78 | 7486 | TTCN_3375 | 17673 |
| GTCN_74 | 7487 | ATCN_2078 | 17674 |
| TTCN_143 | 7488 | CTCN_2955 | 17675 |
| TTCN_144 | 7489 | CTCN_2956 | 17676 |
| CTCN_105 | 7490 | TTCN_3376 | 17677 |
| TTCN_145 | 7491 | CTCN_2957 | 17678 |
| TTCN_146 | 7492 | CTCN_2958 | 17679 |
| GTCN_75 | 7493 | ATCN_2079 | 17680 |
| GTCN_76 | 7494 | TTCN_3377 | 17681 |
| GTCN_77 | 7495 | TTCN_3378 | 17682 |
| CTCN_106 | 7496 | ATCN_2080 | 17683 |
| ATCN_79 | 7497 | CTCN_2959 | 17684 |
| ATCN_80 | 7498 | TTCN_3379 | 17685 |
| ATCN_81 | 7499 | CTCN_2960 | 17686 |
| ATCN_82 | 7500 | TTCN_3380 | 17687 |
| CTCN_107 | 7501 | TTCN_3381 | 17688 |
| CTCN_108 | 7502 | TTCN_3382 | 17689 |
| TTCN_147 | 7503 | ATCN_2081 | 17690 |
| CTCN_109 | 7504 | TTCN_3383 | 17691 |
| TTCN_148 | 7505 | CTCN_2961 | 17692 |
| TTCN_149 | 7506 | TTCN_3384 | 17693 |
| CTCN_110 | 7507 | ATCN_2082 | 17694 |
| TTCN_150 | 7508 | CTCN_2962 | 17695 |
| ATCN_83 | 7509 | ATCN_2083 | 17696 |
| TTCN_151 | 7510 | ATCN_2084 | 17697 |
| ATCN_84 | 7511 | CTCN_2963 | 17698 |
| ATCN_85 | 7512 | TTCN_3385 | 17699 |
| CTCN_111 | 7513 | ATCN_2085 | 17700 |
| CTCN_112 | 7514 | CTCN_2964 | 17701 |
| ATCN_86 | 7515 | ATCN_2086 | 17702 |
| CTCN_113 | 7516 | CTCN_2965 | 17703 |
| CTCN_114 | 7517 | TTCN_3386 | 17704 |
| ATCN_87 | 7518 | TTCN_3387 | 17705 |
| TTCN_152 | 7519 | CTCN_2966 | 17706 |
| ATCN_88 | 7520 | GTCN_1758 | 17707 |
| GTCN_78 | 7521 | ATCN_2087 | 17708 |

FIG. 36 (continued)

| | | | |
|---|---|---|---|
| GTCN_79 | 7522 | TTCN_3388 | 17709 |
| CTCN_115 | 7523 | GTCN_1759 | 17710 |
| TTCN_153 | 7524 | CTCN_2967 | 17711 |
| ATCN_89 | 7525 | CTCN_2968 | 17712 |
| GTCN_80 | 7526 | CTCN_2969 | 17713 |
| ATCN_90 | 7527 | GTCN_1760 | 17714 |
| CTCN_116 | 7528 | CTCN_2970 | 17715 |
| ATCN_91 | 7529 | TTCN_3389 | 17716 |
| ATCN_92 | 7530 | ATCN_2088 | 17717 |
| CTCN_117 | 7531 | TTCN_3390 | 17718 |
| TTCN_154 | 7532 | TTCN_3391 | 17719 |
| CTCN_118 | 7533 | TTCN_3392 | 17720 |
| GTCN_81 | 7534 | CTCN_2971 | 17721 |
| CTCN_119 | 7535 | CTCN_2972 | 17722 |
| TTCN_155 | 7536 | TTCN_3393 | 17723 |
| CTCN_120 | 7537 | ATCN_2089 | 17724 |
| TTCN_156 | 7538 | ATCN_2090 | 17725 |
| ATCN_93 | 7539 | TTCN_3394 | 17726 |
| TTCN_157 | 7540 | CTCN_2973 | 17727 |
| GTCN_82 | 7541 | TTCN_3395 | 17728 |
| GTCN_83 | 7542 | TTCN_3396 | 17729 |
| CTCN_121 | 7543 | GTCN_1761 | 17730 |
| TTCN_158 | 7544 | TTCN_3397 | 17731 |
| ATCN_94 | 7545 | TTCN_3398 | 17732 |
| GTCN_84 | 7546 | TTCN_3399 | 17733 |
| CTCN_122 | 7547 | TTCN_3400 | 17734 |
| TTCN_159 | 7548 | ATCN_2091 | 17735 |
| TTCN_160 | 7549 | ATCN_2092 | 17736 |
| TTCN_161 | 7550 | ATCN_2093 | 17737 |
| CTCN_123 | 7551 | GTCN_1762 | 17738 |
| ATCN_95 | 7552 | ATCN_2094 | 17739 |
| TTCN_162 | 7553 | CTCN_2974 | 17740 |
| CTCN_124 | 7554 | TTCN_3401 | 17741 |
| TTCN_163 | 7555 | GTCN_1763 | 17742 |
| CTCN_125 | 7556 | CTCN_2975 | 17743 |
| ATCN_96 | 7557 | TTCN_3402 | 17744 |
| TTCN_164 | 7558 | TTCN_3403 | 17745 |
| CTCN_126 | 7559 | TTCN_3404 | 17746 |
| TTCN_165 | 7560 | ATCN_2095 | 17747 |
| TTCN_166 | 7561 | ATCN_2096 | 17748 |
| TTCN_167 | 7562 | TTCN_3405 | 17749 |
| CTCN_127 | 7563 | TTCN_3406 | 17750 |
| TTCN_168 | 7564 | ATCN_2097 | 17751 |
| CTCN_128 | 7565 | ATCN_2098 | 17752 |
| TTCN_169 | 7566 | CTCN_2976 | 17753 |
| GTCN_85 | 7567 | CTCN_2977 | 17754 |
| CTCN_129 | 7568 | ATCN_2099 | 17755 |
| TTCN_170 | 7569 | ATCN_2100 | 17756 |
| TTCN_171 | 7570 | TTCN_3407 | 17757 |
| GTCN_86 | 7571 | CTCN_2978 | 17758 |
| GTCN_87 | 7572 | CTCN_2979 | 17759 |
| CTCN_130 | 7573 | TTCN_3408 | 17760 |
| TTCN_172 | 7574 | TTCN_3409 | 17761 |
| ATCN_97 | 7575 | GTCN_1764 | 17762 |
| TTCN_173 | 7576 | CTCN_2980 | 17763 |

| | | | |
|---|---|---|---|
| GTCN_88 | 7577 | GTCN_1765 | 17764 |
| GTCN_89 | 7578 | TTCN_3410 | 17765 |
| CTCN_131 | 7579 | CTCN_2981 | 17766 |
| TTCN_174 | 7580 | CTCN_2982 | 17767 |
| TTCN_175 | 7581 | GTCN_1766 | 17768 |
| GTCN_90 | 7582 | CTCN_2983 | 17769 |
| TTCN_176 | 7583 | TTCN_3411 | 17770 |
| GTCN_91 | 7584 | GTCN_1767 | 17771 |
| CTCN_132 | 7585 | CTCN_2984 | 17772 |
| CTCN_133 | 7586 | TTCN_3412 | 17773 |
| CTCN_134 | 7587 | GTCN_1768 | 17774 |
| ATCN_98 | 7588 | CTCN_2985 | 17775 |
| ATCN_99 | 7589 | ATCN_2101 | 17776 |
| TTCN_177 | 7590 | CTCN_2986 | 17777 |
| CTCN_135 | 7591 | GTCN_1769 | 17778 |
| TTCN_178 | 7592 | CTCN_2987 | 17779 |
| TTCN_179 | 7593 | TTCN_3413 | 17780 |
| CTCN_136 | 7594 | ATCN_2102 | 17781 |
| CTCN_137 | 7595 | ATCN_2103 | 17782 |
| TTCN_180 | 7596 | TTCN_3414 | 17783 |
| TTCN_181 | 7597 | ATCN_2104 | 17784 |
| CTCN_138 | 7598 | CTCN_2988 | 17785 |
| TTCN_182 | 7599 | GTCN_1770 | 17786 |
| ATCN_100 | 7600 | CTCN_2989 | 17787 |
| CTCN_139 | 7601 | GTCN_1771 | 17788 |
| CTCN_140 | 7602 | GTCN_1772 | 17789 |
| CTCN_141 | 7603 | TTCN_3415 | 17790 |
| CTCN_142 | 7604 | GTCN_1773 | 17791 |
| GTCN_92 | 7605 | GTCN_1774 | 17792 |
| CTCN_143 | 7606 | CTCN_2990 | 17793 |
| TTCN_183 | 7607 | TTCN_3416 | 17794 |
| CTCN_144 | 7608 | ATCN_2105 | 17795 |
| TTCN_184 | 7609 | ATCN_2106 | 17796 |
| TTCN_185 | 7610 | ATCN_2107 | 17797 |
| ATCN_101 | 7611 | ATCN_2108 | 17798 |
| GTCN_93 | 7612 | CTCN_2991 | 17799 |
| ATCN_102 | 7613 | TTCN_3417 | 17800 |
| GTCN_94 | 7614 | CTCN_2992 | 17801 |
| ATCN_103 | 7615 | TTCN_3418 | 17802 |
| ATCN_104 | 7616 | TTCN_3419 | 17803 |
| ATCN_105 | 7617 | CTCN_2993 | 17804 |
| CTCN_145 | 7618 | CTCN_2994 | 17805 |
| TTCN_186 | 7619 | GTCN_1775 | 17806 |
| TTCN_187 | 7620 | TTCN_3420 | 17807 |
| ATCN_106 | 7621 | TTCN_3421 | 17808 |
| TTCN_188 | 7622 | CTCN_2995 | 17809 |
| TTCN_189 | 7623 | TTCN_3422 | 17810 |
| TTCN_190 | 7624 | TTCN_3423 | 17811 |
| ATCN_107 | 7625 | CTCN_2996 | 17812 |
| TTCN_191 | 7626 | TTCN_3424 | 17813 |
| ATCN_108 | 7627 | ATCN_2109 | 17814 |
| ATCN_109 | 7628 | CTCN_2997 | 17815 |
| CTCN_146 | 7629 | TTCN_3425 | 17816 |
| CTCN_147 | 7630 | TTCN_3426 | 17817 |
| GTCN_95 | 7631 | CTCN_2998 | 17818 |

FIG. 36 (continued)

| | | | |
|---|---|---|---|
| TTCN_192 | 7632 | TTCN_3427 | 17819 |
| TTCN_193 | 7633 | CTCN_2999 | 17820 |
| TTCN_194 | 7634 | TTCN_3428 | 17821 |
| ATCN_110 | 7635 | TTCN_3429 | 17822 |
| TTCN_195 | 7636 | ATCN_2110 | 17823 |
| ATCN_111 | 7637 | ATCN_2111 | 17824 |
| CTCN_148 | 7638 | ATCN_2112 | 17825 |
| ATCN_112 | 7639 | ATCN_2113 | 17826 |
| GTCN_96 | 7640 | TTCN_3430 | 17827 |
| CTCN_149 | 7641 | TTCN_3431 | 17828 |
| ATCN_113 | 7642 | TTCN_3432 | 17829 |
| GTCN_97 | 7643 | TTCN_3433 | 17830 |
| CTCN_150 | 7644 | CTCN_3000 | 17831 |
| TTCN_196 | 7645 | ATCN_2114 | 17832 |
| TTCN_197 | 7646 | CTCN_3001 | 17833 |
| CTCN_151 | 7647 | TTCN_3434 | 17834 |
| TTCN_198 | 7648 | CTCN_3002 | 17835 |
| TTCN_199 | 7649 | TTCN_3435 | 17836 |
| CTCN_152 | 7650 | ATCN_2115 | 17837 |
| TTCN_200 | 7651 | ATCN_2116 | 17838 |
| ATCN_114 | 7652 | ATCN_2117 | 17839 |
| ATCN_115 | 7653 | CTCN_3003 | 17840 |
| TTCN_201 | 7654 | TTCN_3436 | 17841 |
| CTCN_153 | 7655 | ATCN_2118 | 17842 |
| ATCN_116 | 7656 | TTCN_3437 | 17843 |
| TTCN_202 | 7657 | CTCN_3004 | 17844 |
| TTCN_203 | 7658 | CTCN_3005 | 17845 |
| ATCN_117 | 7659 | CTCN_3006 | 17846 |
| GTCN_98 | 7660 | CTCN_3007 | 17847 |
| GTCN_99 | 7661 | CTCN_3008 | 17848 |
| TTCN_204 | 7662 | TTCN_3438 | 17849 |
| GTCN_100 | 7663 | TTCN_3439 | 17850 |
| TTCN_205 | 7664 | CTCN_3009 | 17851 |
| CTCN_154 | 7665 | GTCN_1776 | 17852 |
| CTCN_155 | 7666 | TTCN_3440 | 17853 |
| ATCN_118 | 7667 | CTCN_3010 | 17854 |
| ATCN_119 | 7668 | CTCN_3011 | 17855 |
| ATCN_120 | 7669 | CTCN_3012 | 17856 |
| ATCN_121 | 7670 | GTCN_1777 | 17857 |
| CTCN_156 | 7671 | TTCN_3441 | 17858 |
| CTCN_157 | 7672 | ATCN_2119 | 17859 |
| TTCN_206 | 7673 | CTCN_3013 | 17860 |
| GTCN_101 | 7674 | CTCN_3014 | 17861 |
| ATCN_122 | 7675 | CTCN_3015 | 17862 |
| GTCN_102 | 7676 | TTCN_3442 | 17863 |
| CTCN_158 | 7677 | CTCN_3016 | 17864 |
| TTCN_207 | 7678 | TTCN_3443 | 17865 |
| ATCN_123 | 7679 | CTCN_3017 | 17866 |
| ATCN_124 | 7680 | GTCN_1778 | 17867 |
| ATCN_125 | 7681 | ATCN_2120 | 17868 |
| CTCN_159 | 7682 | CTCN_3018 | 17869 |
| GTCN_103 | 7683 | ATCN_2121 | 17870 |
| CTCN_160 | 7684 | TTCN_3444 | 17871 |
| TTCN_208 | 7685 | ATCN_2122 | 17872 |
| TTCN_209 | 7686 | ATCN_2123 | 17873 |

| | | | |
|---|---|---|---|
| CTCN_161 | 7687 | TTCN_3445 | 17874 |
| GTCN_104 | 7688 | CTCN_3019 | 17875 |
| CTCN_162 | 7689 | ATCN_2124 | 17876 |
| CTCN_163 | 7690 | TTCN_3446 | 17877 |
| GTCN_105 | 7691 | CTCN_3020 | 17878 |
| TTCN_210 | 7692 | TTCN_3447 | 17879 |
| TTCN_211 | 7693 | ATCN_2125 | 17880 |
| CTCN_164 | 7694 | TTCN_3448 | 17881 |
| GTCN_106 | 7695 | TTCN_3449 | 17882 |
| TTCN_212 | 7696 | ATCN_2126 | 17883 |
| TTCN_213 | 7697 | GTCN_1779 | 17884 |
| CTCN_165 | 7698 | CTCN_3021 | 17885 |
| TTCN_214 | 7699 | TTCN_3450 | 17886 |
| TTCN_215 | 7700 | CTCN_3022 | 17887 |
| TTCN_216 | 7701 | GTCN_1780 | 17888 |
| CTCN_166 | 7702 | TTCN_3451 | 17889 |
| GTCN_107 | 7703 | ATCN_2127 | 17890 |
| CTCN_167 | 7704 | ATCN_2128 | 17891 |
| GTCN_108 | 7705 | TTCN_3452 | 17892 |
| CTCN_168 | 7706 | ATCN_2129 | 17893 |
| ATCN_126 | 7707 | CTCN_3023 | 17894 |
| TTCN_217 | 7708 | GTCN_1781 | 17895 |
| TTCN_218 | 7709 | TTCN_3453 | 17896 |
| ATCN_127 | 7710 | ATCN_2130 | 17897 |
| TTCN_219 | 7711 | ATCN_2131 | 17898 |
| GTCN_109 | 7712 | ATCN_2132 | 17899 |
| CTCN_169 | 7713 | ATCN_2133 | 17900 |
| TTCN_220 | 7714 | GTCN_1782 | 17901 |
| TTCN_221 | 7715 | GTCN_1783 | 17902 |
| CTCN_170 | 7716 | CTCN_3024 | 17903 |
| TTCN_222 | 7717 | ATCN_2134 | 17904 |
| TTCN_223 | 7718 | TTCN_3454 | 17905 |
| CTCN_171 | 7719 | TTCN_3455 | 17906 |
| TTCN_224 | 7720 | CTCN_3025 | 17907 |
| CTCN_172 | 7721 | CTCN_3026 | 17908 |
| CTCN_173 | 7722 | CTCN_3027 | 17909 |
| CTCN_174 | 7723 | GTCN_1784 | 17910 |
| CTCN_175 | 7724 | GTCN_1785 | 17911 |
| TTCN_225 | 7725 | TTCN_3456 | 17912 |
| GTCN_110 | 7726 | TTCN_3457 | 17913 |
| ATCN_128 | 7727 | GTCN_1786 | 17914 |
| ATCN_129 | 7728 | TTCN_3458 | 17915 |
| TTCN_226 | 7729 | TTCN_3459 | 17916 |
| ATCN_130 | 7730 | CTCN_3028 | 17917 |
| TTCN_227 | 7731 | CTCN_3029 | 17918 |
| GTCN_111 | 7732 | TTCN_3460 | 17919 |
| CTCN_176 | 7733 | TTCN_3461 | 17920 |
| TTCN_228 | 7734 | ATCN_2135 | 17921 |
| CTCN_177 | 7735 | TTCN_3462 | 17922 |
| CTCN_178 | 7736 | ATCN_2136 | 17923 |
| GTCN_112 | 7737 | CTCN_3030 | 17924 |
| CTCN_179 | 7738 | ATCN_2137 | 17925 |
| ATCN_131 | 7739 | CTCN_3031 | 17926 |
| ATCN_132 | 7740 | CTCN_3032 | 17927 |
| ATCN_133 | 7741 | CTCN_3033 | 17928 |

FIG. 36 (continued)

| | | | |
|---|---|---|---|
| CTCN_180 | 7742 | GTCN_1787 | 17929 |
| ATCN_134 | 7743 | ATCN_2138 | 17930 |
| CTCN_181 | 7744 | ATCN_2139 | 17931 |
| ATCN_135 | 7745 | GTCN_1788 | 17932 |
| TTCN_229 | 7746 | TTCN_3463 | 17933 |
| TTCN_230 | 7747 | CTCN_3034 | 17934 |
| TTCN_231 | 7748 | CTCN_3035 | 17935 |
| CTCN_182 | 7749 | CTCN_3036 | 17936 |
| GTCN_113 | 7750 | CTCN_3037 | 17937 |
| CTCN_183 | 7751 | TTCN_3464 | 17938 |
| CTCN_184 | 7752 | TTCN_3465 | 17939 |
| GTCN_114 | 7753 | ATCN_2140 | 17940 |
| CTCN_185 | 7754 | ATCN_2141 | 17941 |
| ATCN_136 | 7755 | TTCN_3466 | 17942 |
| CTCN_186 | 7756 | CTCN_3038 | 17943 |
| TTCN_232 | 7757 | TTCN_3467 | 17944 |
| CTCN_187 | 7758 | TTCN_3468 | 17945 |
| CTCN_188 | 7759 | TTCN_3469 | 17946 |
| GTCN_115 | 7760 | ATCN_2142 | 17947 |
| CTCN_189 | 7761 | TTCN_3470 | 17948 |
| CTCN_190 | 7762 | GTCN_1789 | 17949 |
| TTCN_233 | 7763 | CTCN_3039 | 17950 |
| CTCN_191 | 7764 | TTCN_3471 | 17951 |
| CTCN_192 | 7765 | ATCN_2143 | 17952 |
| ATCN_137 | 7766 | TTCN_3472 | 17953 |
| CTCN_193 | 7767 | TTCN_3473 | 17954 |
| CTCN_194 | 7768 | CTCN_3040 | 17955 |
| CTCN_195 | 7769 | CTCN_3041 | 17956 |
| GTCN_116 | 7770 | TTCN_3474 | 17957 |
| CTCN_196 | 7771 | ATCN_2144 | 17958 |
| GTCN_117 | 7772 | TTCN_3475 | 17959 |
| GTCN_118 | 7773 | TTCN_3476 | 17960 |
| ATCN_138 | 7774 | TTCN_3477 | 17961 |
| TTCN_234 | 7775 | CTCN_3042 | 17962 |
| TTCN_235 | 7776 | TTCN_3478 | 17963 |
| ATCN_139 | 7777 | CTCN_3043 | 17964 |
| CTCN_197 | 7778 | ATCN_2145 | 17965 |
| TTCN_236 | 7779 | CTCN_3044 | 17966 |
| CTCN_198 | 7780 | CTCN_3045 | 17967 |
| CTCN_199 | 7781 | CTCN_3046 | 17968 |
| ATCN_140 | 7782 | ATCN_2146 | 17969 |
| ATCN_141 | 7783 | ATCN_2147 | 17970 |
| TTCN_237 | 7784 | GTCN_1790 | 17971 |
| TTCN_238 | 7785 | CTCN_3047 | 17972 |
| ATCN_142 | 7786 | ATCN_2148 | 17973 |
| CTCN_200 | 7787 | ATCN_2149 | 17974 |
| GTCN_119 | 7788 | GTCN_1791 | 17975 |
| ATCN_143 | 7789 | ATCN_2150 | 17976 |
| TTCN_239 | 7790 | TTCN_3479 | 17977 |
| CTCN_201 | 7791 | ATCN_2151 | 17978 |
| GTCN_120 | 7792 | CTCN_3048 | 17979 |
| CTCN_202 | 7793 | ATCN_2152 | 17980 |
| ATCN_144 | 7794 | GTCN_1792 | 17981 |
| TTCN_240 | 7795 | CTCN_3049 | 17982 |
| GTCN_121 | 7796 | CTCN_3050 | 17983 |

| | | | |
|---|---|---|---|
| TTCN_241 | 7797 | CTCN_3051 | 17984 |
| TTCN_242 | 7798 | GTCN_1793 | 17985 |
| CTCN_203 | 7799 | CTCN_3052 | 17986 |
| GTCN_122 | 7800 | CTCN_3053 | 17987 |
| TTCN_243 | 7801 | TTCN_3480 | 17988 |
| ATCN_145 | 7802 | TTCN_3481 | 17989 |
| ATCN_146 | 7803 | CTCN_3054 | 17990 |
| GTCN_123 | 7804 | CTCN_3055 | 17991 |
| CTCN_204 | 7805 | ATCN_2153 | 17992 |
| TTCN_244 | 7806 | CTCN_3056 | 17993 |
| ATCN_147 | 7807 | CTCN_3057 | 17994 |
| GTCN_124 | 7808 | ATCN_2154 | 17995 |
| TTCN_245 | 7809 | ATCN_2155 | 17996 |
| TTCN_246 | 7810 | ATCN_2156 | 17997 |
| GTCN_125 | 7811 | CTCN_3058 | 17998 |
| TTCN_247 | 7812 | CTCN_3059 | 17999 |
| TTCN_248 | 7813 | GTCN_1794 | 18000 |
| TTCN_249 | 7814 | CTCN_3060 | 18001 |
| CTCN_205 | 7815 | TTCN_3482 | 18002 |
| TTCN_250 | 7816 | CTCN_3061 | 18003 |
| GTCN_126 | 7817 | TTCN_3483 | 18004 |
| GTCN_127 | 7818 | GTCN_1795 | 18005 |
| TTCN_251 | 7819 | CTCN_3062 | 18006 |
| TTCN_252 | 7820 | ATCN_2157 | 18007 |
| TTCN_253 | 7821 | ATCN_2158 | 18008 |
| GTCN_128 | 7822 | TTCN_3484 | 18009 |
| TTCN_254 | 7823 | CTCN_3063 | 18010 |
| GTCN_129 | 7824 | CTCN_3064 | 18011 |
| TTCN_255 | 7825 | ATCN_2159 | 18012 |
| TTCN_256 | 7826 | ATCN_2160 | 18013 |
| ATCN_148 | 7827 | TTCN_3485 | 18014 |
| ATCN_149 | 7828 | CTCN_3065 | 18015 |
| ATCN_150 | 7829 | GTCN_1796 | 18016 |
| ATCN_151 | 7830 | CTCN_3066 | 18017 |
| TTCN_257 | 7831 | GTCN_1797 | 18018 |
| GTCN_130 | 7832 | TTCN_3486 | 18019 |
| TTCN_258 | 7833 | CTCN_3067 | 18020 |
| TTCN_259 | 7834 | TTCN_3487 | 18021 |
| GTCN_131 | 7835 | ATCN_2161 | 18022 |
| TTCN_260 | 7836 | CTCN_3068 | 18023 |
| TTCN_261 | 7837 | TTCN_3488 | 18024 |
| CTCN_206 | 7838 | GTCN_1798 | 18025 |
| ATCN_152 | 7839 | TTCN_3489 | 18026 |
| TTCN_262 | 7840 | ATCN_2162 | 18027 |
| TTCN_263 | 7841 | CTCN_3069 | 18028 |
| ATCN_153 | 7842 | GTCN_1799 | 18029 |
| ATCN_154 | 7843 | ATCN_2163 | 18030 |
| CTCN_207 | 7844 | GTCN_1800 | 18031 |
| ATCN_155 | 7845 | ATCN_2164 | 18032 |
| TTCN_264 | 7846 | TTCN_3490 | 18033 |
| GTCN_132 | 7847 | CTCN_3070 | 18034 |
| CTCN_208 | 7848 | CTCN_3071 | 18035 |
| GTCN_133 | 7849 | ATCN_2165 | 18036 |
| CTCN_209 | 7850 | ATCN_2166 | 18037 |
| ATCN_156 | 7851 | CTCN_3072 | 18038 |

FIG. 36 (continued)

| | | | | | | | |
|---|---|---|---|---|---|---|---|
| GTCN_134 | 7852 | ATCN_2167 | 18039 | TTCN_284 | 7907 | ATCN_2181 | 18094 |
| TTCN_265 | 7853 | TTCN_3491 | 18040 | GTCN_143 | 7908 | ATCN_2182 | 18095 |
| TTCN_266 | 7854 | CTCN_3073 | 18041 | ATCN_170 | 7909 | CTCN_3084 | 18096 |
| GTCN_135 | 7855 | GTCN_1801 | 18042 | TTCN_285 | 7910 | TTCN_3509 | 18097 |
| ATCN_157 | 7856 | TTCN_3492 | 18043 | TTCN_286 | 7911 | CTCN_3085 | 18098 |
| GTCN_136 | 7857 | TTCN_3493 | 18044 | TTCN_287 | 7912 | CTCN_3086 | 18099 |
| TTCN_267 | 7858 | ATCN_2168 | 18045 | CTCN_224 | 7913 | TTCN_3510 | 18100 |
| TTCN_268 | 7859 | ATCN_2169 | 18046 | GTCN_144 | 7914 | TTCN_3511 | 18101 |
| CTCN_210 | 7860 | TTCN_3494 | 18047 | TTCN_288 | 7915 | TTCN_3512 | 18102 |
| ATCN_158 | 7861 | TTCN_3495 | 18048 | TTCN_289 | 7916 | TTCN_3513 | 18103 |
| CTCN_211 | 7862 | TTCN_3496 | 18049 | ATCN_171 | 7917 | GTCN_1813 | 18104 |
| ATCN_159 | 7863 | CTCN_3074 | 18050 | GTCN_145 | 7918 | TTCN_3514 | 18105 |
| ATCN_160 | 7864 | GTCN_1802 | 18051 | CTCN_225 | 7919 | TTCN_3515 | 18106 |
| GTCN_137 | 7865 | GTCN_1803 | 18052 | TTCN_290 | 7920 | ATCN_2183 | 18107 |
| ATCN_161 | 7866 | ATCN_2170 | 18053 | CTCN_226 | 7921 | ATCN_2184 | 18108 |
| TTCN_269 | 7867 | TTCN_3497 | 18054 | CTCN_227 | 7922 | TTCN_3516 | 18109 |
| TTCN_270 | 7868 | TTCN_3498 | 18055 | TTCN_291 | 7923 | ATCN_2185 | 18110 |
| ATCN_162 | 7869 | GTCN_1804 | 18056 | CTCN_228 | 7924 | ATCN_2186 | 18111 |
| ATCN_163 | 7870 | ATCN_2171 | 18057 | TTCN_292 | 7925 | ATCN_2187 | 18112 |
| GTCN_138 | 7871 | CTCN_3075 | 18058 | ATCN_172 | 7926 | TTCN_3517 | 18113 |
| ATCN_164 | 7872 | GTCN_1805 | 18059 | ATCN_173 | 7927 | GTCN_1814 | 18114 |
| CTCN_212 | 7873 | CTCN_3076 | 18060 | ATCN_174 | 7928 | CTCN_3087 | 18115 |
| ATCN_165 | 7874 | TTCN_3499 | 18061 | TTCN_293 | 7929 | TTCN_3518 | 18116 |
| CTCN_213 | 7875 | CTCN_3077 | 18062 | CTCN_229 | 7930 | ATCN_2188 | 18117 |
| CTCN_214 | 7876 | ATCN_2172 | 18063 | TTCN_294 | 7931 | GTCN_1815 | 18118 |
| ATCN_166 | 7877 | ATCN_2173 | 18064 | ATCN_175 | 7932 | TTCN_3519 | 18119 |
| GTCN_139 | 7878 | TTCN_3500 | 18065 | TTCN_295 | 7933 | TTCN_3520 | 18120 |
| TTCN_271 | 7879 | GTCN_1806 | 18066 | TTCN_296 | 7934 | CTCN_3088 | 18121 |
| CTCN_215 | 7880 | GTCN_1807 | 18067 | ATCN_176 | 7935 | TTCN_3521 | 18122 |
| TTCN_272 | 7881 | CTCN_3078 | 18068 | ATCN_177 | 7936 | TTCN_3522 | 18123 |
| GTCN_140 | 7882 | GTCN_1808 | 18069 | TTCN_297 | 7937 | TTCN_3523 | 18124 |
| CTCN_216 | 7883 | TTCN_3501 | 18070 | TTCN_298 | 7938 | TTCN_3524 | 18125 |
| GTCN_141 | 7884 | TTCN_3502 | 18071 | ATCN_178 | 7939 | CTCN_3089 | 18126 |
| CTCN_217 | 7885 | GTCN_1809 | 18072 | TTCN_299 | 7940 | TTCN_3525 | 18127 |
| GTCN_142 | 7886 | ATCN_2174 | 18073 | ATCN_179 | 7941 | ATCN_2189 | 18128 |
| ATCN_167 | 7887 | ATCN_2175 | 18074 | TTCN_300 | 7942 | ATCN_2190 | 18129 |
| CTCN_218 | 7888 | GTCN_1810 | 18075 | TTCN_301 | 7943 | CTCN_3090 | 18130 |
| TTCN_273 | 7889 | GTCN_1811 | 18076 | TTCN_302 | 7944 | ATCN_2191 | 18131 |
| TTCN_274 | 7890 | CTCN_3079 | 18077 | CTCN_230 | 7945 | GTCN_1816 | 18132 |
| CTCN_219 | 7891 | ATCN_2176 | 18078 | TTCN_303 | 7946 | TTCN_3526 | 18133 |
| CTCN_220 | 7892 | TTCN_3503 | 18079 | GTCN_146 | 7947 | TTCN_3527 | 18134 |
| CTCN_221 | 7893 | CTCN_3080 | 18080 | GTCN_147 | 7948 | CTCN_3091 | 18135 |
| TTCN_275 | 7894 | ATCN_2177 | 18081 | CTCN_231 | 7949 | CTCN_3092 | 18136 |
| CTCN_222 | 7895 | CTCN_3081 | 18082 | TTCN_304 | 7950 | GTCN_1817 | 18137 |
| ATCN_168 | 7896 | TTCN_3504 | 18083 | TTCN_305 | 7951 | CTCN_3093 | 18138 |
| TTCN_276 | 7897 | GTCN_1812 | 18084 | TTCN_306 | 7952 | CTCN_3094 | 18139 |
| ATCN_169 | 7898 | CTCN_3082 | 18085 | TTCN_307 | 7953 | CTCN_3095 | 18140 |
| TTCN_277 | 7899 | TTCN_3505 | 18086 | TTCN_308 | 7954 | TTCN_3528 | 18141 |
| TTCN_278 | 7900 | TTCN_3506 | 18087 | TTCN_309 | 7955 | CTCN_3096 | 18142 |
| TTCN_279 | 7901 | ATCN_2178 | 18088 | ATCN_180 | 7956 | CTCN_3097 | 18143 |
| TTCN_280 | 7902 | TTCN_3507 | 18089 | GTCN_148 | 7957 | CTCN_3098 | 18144 |
| CTCN_223 | 7903 | CTCN_3083 | 18090 | TTCN_310 | 7958 | CTCN_3099 | 18145 |
| TTCN_281 | 7904 | TTCN_3508 | 18091 | TTCN_311 | 7959 | GTCN_1818 | 18146 |
| TTCN_282 | 7905 | ATCN_2179 | 18092 | TTCN_312 | 7960 | ATCN_2192 | 18147 |
| TTCN_283 | 7906 | ATCN_2180 | 18093 | ATCN_181 | 7961 | CTCN_3100 | 18148 |

FIG. 36 (continued)

| | | | |
|---|---|---|---|
| ATCN_182 | 7962 | CTCN_3101 | 18149 |
| TTCN_313 | 7963 | CTCN_3102 | 18150 |
| CTCN_232 | 7964 | TTCN_3529 | 18151 |
| GTCN_149 | 7965 | ATCN_2193 | 18152 |
| ATCN_183 | 7966 | TTCN_3530 | 18153 |
| TTCN_314 | 7967 | CTCN_3103 | 18154 |
| ATCN_184 | 7968 | GTCN_1819 | 18155 |
| GTCN_150 | 7969 | TTCN_3531 | 18156 |
| GTCN_151 | 7970 | CTCN_3104 | 18157 |
| ATCN_185 | 7971 | TTCN_3532 | 18158 |
| TTCN_315 | 7972 | CTCN_3105 | 18159 |
| TTCN_316 | 7973 | TTCN_3533 | 18160 |
| CTCN_233 | 7974 | TTCN_3534 | 18161 |
| TTCN_317 | 7975 | CTCN_3106 | 18162 |
| TTCN_318 | 7976 | GTCN_1820 | 18163 |
| ATCN_186 | 7977 | TTCN_3535 | 18164 |
| ATCN_187 | 7978 | ATCN_2194 | 18165 |
| CTCN_234 | 7979 | CTCN_3107 | 18166 |
| CTCN_235 | 7980 | CTCN_3108 | 18167 |
| CTCN_236 | 7981 | GTCN_1821 | 18168 |
| TTCN_319 | 7982 | CTCN_3109 | 18169 |
| GTCN_152 | 7983 | GTCN_1822 | 18170 |
| GTCN_153 | 7984 | GTCN_1823 | 18171 |
| TTCN_320 | 7985 | TTCN_3536 | 18172 |
| TTCN_321 | 7986 | ATCN_2195 | 18173 |
| GTCN_154 | 7987 | TTCN_3537 | 18174 |
| TTCN_322 | 7988 | GTCN_1824 | 18175 |
| TTCN_323 | 7989 | GTCN_1825 | 18176 |
| TTCN_324 | 7990 | ATCN_2196 | 18177 |
| TTCN_325 | 7991 | TTCN_3538 | 18178 |
| GTCN_155 | 7992 | TTCN_3539 | 18179 |
| TTCN_326 | 7993 | ATCN_2197 | 18180 |
| TTCN_327 | 7994 | GTCN_1826 | 18181 |
| ATCN_188 | 7995 | ATCN_2198 | 18182 |
| ATCN_189 | 7996 | ATCN_2199 | 18183 |
| ATCN_190 | 7997 | CTCN_3110 | 18184 |
| CTCN_237 | 7998 | TTCN_3540 | 18185 |
| ATCN_191 | 7999 | TTCN_3541 | 18186 |
| GTCN_156 | 8000 | TTCN_3542 | 18187 |
| CTCN_238 | 8001 | GTCN_1827 | 18188 |
| TTCN_328 | 8002 | ATCN_2200 | 18189 |
| GTCN_157 | 8003 | ATCN_2201 | 18190 |
| GTCN_158 | 8004 | TTCN_3543 | 18191 |
| TTCN_329 | 8005 | TTCN_3544 | 18192 |
| TTCN_330 | 8006 | TTCN_3545 | 18193 |
| CTCN_239 | 8007 | CTCN_3111 | 18194 |
| ATCN_192 | 8008 | TTCN_3546 | 18195 |
| ATCN_193 | 8009 | GTCN_1828 | 18196 |
| TTCN_331 | 8010 | TTCN_3547 | 18197 |
| ATCN_194 | 8011 | ATCN_2202 | 18198 |
| ATCN_195 | 8012 | ATCN_2203 | 18199 |
| ATCN_196 | 8013 | ATCN_2204 | 18200 |
| TTCN_332 | 8014 | ATCN_2205 | 18201 |
| TTCN_333 | 8015 | ATCN_2206 | 18202 |
| GTCN_159 | 8016 | TTCN_3548 | 18203 |

| | | | |
|---|---|---|---|
| TTCN_334 | 8017 | TTCN_3549 | 18204 |
| ATCN_197 | 8018 | ATCN_2207 | 18205 |
| TTCN_335 | 8019 | GTCN_1829 | 18206 |
| ATCN_198 | 8020 | CTCN_3112 | 18207 |
| CTCN_240 | 8021 | CTCN_3113 | 18208 |
| CTCN_241 | 8022 | GTCN_1830 | 18209 |
| TTCN_336 | 8023 | CTCN_3114 | 18210 |
| GTCN_160 | 8024 | GTCN_1831 | 18211 |
| TTCN_337 | 8025 | GTCN_1832 | 18212 |
| TTCN_338 | 8026 | CTCN_3115 | 18213 |
| CTCN_242 | 8027 | CTCN_3116 | 18214 |
| GTCN_161 | 8028 | ATCN_2208 | 18215 |
| TTCN_339 | 8029 | TTCN_3550 | 18216 |
| CTCN_243 | 8030 | GTCN_1833 | 18217 |
| TTCN_340 | 8031 | ATCN_2209 | 18218 |
| ATCN_199 | 8032 | TTCN_3551 | 18219 |
| ATCN_200 | 8033 | TTCN_3552 | 18220 |
| CTCN_244 | 8034 | ATCN_2210 | 18221 |
| ATCN_201 | 8035 | CTCN_3117 | 18222 |
| TTCN_341 | 8036 | CTCN_3118 | 18223 |
| GTCN_162 | 8037 | TTCN_3553 | 18224 |
| CTCN_245 | 8038 | CTCN_3119 | 18225 |
| ATCN_202 | 8039 | CTCN_3120 | 18226 |
| GTCN_163 | 8040 | GTCN_1834 | 18227 |
| TTCN_342 | 8041 | TTCN_3554 | 18228 |
| TTCN_343 | 8042 | TTCN_3555 | 18229 |
| GTCN_164 | 8043 | GTCN_1835 | 18230 |
| GTCN_165 | 8044 | GTCN_1836 | 18231 |
| TTCN_344 | 8045 | TTCN_3556 | 18232 |
| TTCN_345 | 8046 | TTCN_3557 | 18233 |
| TTCN_346 | 8047 | TTCN_3558 | 18234 |
| ATCN_203 | 8048 | GTCN_1837 | 18235 |
| TTCN_347 | 8049 | GTCN_1838 | 18236 |
| ATCN_204 | 8050 | ATCN_2211 | 18237 |
| CTCN_246 | 8051 | GTCN_1839 | 18238 |
| GTCN_166 | 8052 | CTCN_3121 | 18239 |
| ATCN_205 | 8053 | CTCN_3122 | 18240 |
| TTCN_348 | 8054 | TTCN_3559 | 18241 |
| ATCN_206 | 8055 | TTCN_3560 | 18242 |
| CTCN_247 | 8056 | TTCN_3561 | 18243 |
| ATCN_207 | 8057 | TTCN_3562 | 18244 |
| ATCN_208 | 8058 | TTCN_3563 | 18245 |
| GTCN_167 | 8059 | GTCN_1840 | 18246 |
| ATCN_209 | 8060 | TTCN_3564 | 18247 |
| CTCN_248 | 8061 | CTCN_3123 | 18248 |
| CTCN_249 | 8062 | GTCN_1841 | 18249 |
| TTCN_349 | 8063 | GTCN_1842 | 18250 |
| GTCN_168 | 8064 | CTCN_3124 | 18251 |
| TTCN_350 | 8065 | ATCN_2212 | 18252 |
| ATCN_210 | 8066 | ATCN_2213 | 18253 |
| TTCN_351 | 8067 | TTCN_3565 | 18254 |
| TTCN_352 | 8068 | CTCN_3125 | 18255 |
| GTCN_169 | 8069 | GTCN_1843 | 18256 |
| TTCN_353 | 8070 | GTCN_1844 | 18257 |
| TTCN_354 | 8071 | GTCN_1845 | 18258 |

FIG. 36 (continued)

| | | | |
|---|---|---|---|
| GTCN_170 | 8072 | CTCN_3126 | 18259 |
| CTCN_250 | 8073 | CTCN_3127 | 18260 |
| GTCN_171 | 8074 | GTCN_1846 | 18261 |
| TTCN_355 | 8075 | CTCN_3128 | 18262 |
| TTCN_356 | 8076 | TTCN_3566 | 18263 |
| GTCN_172 | 8077 | TTCN_3567 | 18264 |
| ATCN_211 | 8078 | CTCN_3129 | 18265 |
| TTCN_357 | 8079 | ATCN_2214 | 18266 |
| TTCN_358 | 8080 | ATCN_2215 | 18267 |
| TTCN_359 | 8081 | ATCN_2216 | 18268 |
| CTCN_251 | 8082 | CTCN_3130 | 18269 |
| CTCN_252 | 8083 | ATCN_2217 | 18270 |
| ATCN_212 | 8084 | ATCN_2218 | 18271 |
| TTCN_360 | 8085 | TTCN_3568 | 18272 |
| TTCN_361 | 8086 | GTCN_1847 | 18273 |
| GTCN_173 | 8087 | CTCN_3131 | 18274 |
| TTCN_362 | 8088 | CTCN_3132 | 18275 |
| GTCN_174 | 8089 | CTCN_3133 | 18276 |
| ATCN_213 | 8090 | CTCN_3134 | 18277 |
| CTCN_253 | 8091 | GTCN_1848 | 18278 |
| GTCN_175 | 8092 | ATCN_2219 | 18279 |
| CTCN_254 | 8093 | GTCN_1849 | 18280 |
| TTCN_363 | 8094 | ATCN_2220 | 18281 |
| CTCN_255 | 8095 | ATCN_2221 | 18282 |
| GTCN_176 | 8096 | CTCN_3135 | 18283 |
| CTCN_256 | 8097 | TTCN_3569 | 18284 |
| CTCN_257 | 8098 | GTCN_1850 | 18285 |
| ATCN_214 | 8099 | GTCN_1851 | 18286 |
| CTCN_258 | 8100 | TTCN_3570 | 18287 |
| CTCN_259 | 8101 | TTCN_3571 | 18288 |
| TTCN_364 | 8102 | TTCN_3572 | 18289 |
| TTCN_365 | 8103 | CTCN_3136 | 18290 |
| GTCN_177 | 8104 | ATCN_2222 | 18291 |
| TTCN_366 | 8105 | GTCN_1852 | 18292 |
| ATCN_215 | 8106 | CTCN_3137 | 18293 |
| ATCN_216 | 8107 | CTCN_3138 | 18294 |
| TTCN_367 | 8108 | TTCN_3573 | 18295 |
| TTCN_368 | 8109 | TTCN_3574 | 18296 |
| TTCN_369 | 8110 | ATCN_2223 | 18297 |
| CTCN_260 | 8111 | CTCN_3139 | 18298 |
| TTCN_370 | 8112 | CTCN_3140 | 18299 |
| ATCN_217 | 8113 | CTCN_3141 | 18300 |
| TTCN_371 | 8114 | ATCN_2224 | 18301 |
| TTCN_372 | 8115 | GTCN_1853 | 18302 |
| ATCN_218 | 8116 | CTCN_3142 | 18303 |
| CTCN_261 | 8117 | CTCN_3143 | 18304 |
| GTCN_178 | 8118 | CTCN_3144 | 18305 |
| ATCN_219 | 8119 | GTCN_1854 | 18306 |
| ATCN_220 | 8120 | CTCN_3145 | 18307 |
| TTCN_373 | 8121 | CTCN_3146 | 18308 |
| TTCN_374 | 8122 | CTCN_3147 | 18309 |
| CTCN_262 | 8123 | GTCN_1855 | 18310 |
| TTCN_375 | 8124 | CTCN_3148 | 18311 |
| CTCN_263 | 8125 | CTCN_3149 | 18312 |
| CTCN_264 | 8126 | ATCN_2225 | 18313 |

| | | | |
|---|---|---|---|
| TTCN_376 | 8127 | ATCN_2226 | 18314 |
| CTCN_265 | 8128 | TTCN_3575 | 18315 |
| TTCN_377 | 8129 | ATCN_2227 | 18316 |
| TTCN_378 | 8130 | ATCN_2228 | 18317 |
| CTCN_266 | 8131 | ATCN_2229 | 18318 |
| TTCN_379 | 8132 | GTCN_1856 | 18319 |
| TTCN_380 | 8133 | CTCN_3150 | 18320 |
| ATCN_221 | 8134 | CTCN_3151 | 18321 |
| GTCN_179 | 8135 | GTCN_1857 | 18322 |
| CTCN_267 | 8136 | TTCN_3576 | 18323 |
| TTCN_381 | 8137 | ATCN_2230 | 18324 |
| GTCN_180 | 8138 | GTCN_1858 | 18325 |
| GTCN_181 | 8139 | CTCN_3152 | 18326 |
| TTCN_382 | 8140 | TTCN_3577 | 18327 |
| CTCN_268 | 8141 | ATCN_2231 | 18328 |
| GTCN_182 | 8142 | CTCN_3153 | 18329 |
| TTCN_383 | 8143 | CTCN_3154 | 18330 |
| TTCN_384 | 8144 | CTCN_3155 | 18331 |
| TTCN_385 | 8145 | TTCN_3578 | 18332 |
| TTCN_386 | 8146 | TTCN_3579 | 18333 |
| ATCN_222 | 8147 | TTCN_3580 | 18334 |
| CTCN_269 | 8148 | ATCN_2232 | 18335 |
| TTCN_387 | 8149 | TTCN_3581 | 18336 |
| ATCN_223 | 8150 | CTCN_3156 | 18337 |
| TTCN_388 | 8151 | CTCN_3157 | 18338 |
| TTCN_389 | 8152 | ATCN_2233 | 18339 |
| TTCN_390 | 8153 | CTCN_3158 | 18340 |
| TTCN_391 | 8154 | CTCN_3159 | 18341 |
| TTCN_392 | 8155 | TTCN_3582 | 18342 |
| CTCN_270 | 8156 | CTCN_3160 | 18343 |
| TTCN_393 | 8157 | CTCN_3161 | 18344 |
| ATCN_224 | 8158 | CTCN_3162 | 18345 |
| TTCN_394 | 8159 | GTCN_1859 | 18346 |
| CTCN_271 | 8160 | TTCN_3583 | 18347 |
| GTCN_183 | 8161 | TTCN_3584 | 18348 |
| GTCN_184 | 8162 | CTCN_3163 | 18349 |
| TTCN_395 | 8163 | CTCN_3164 | 18350 |
| CTCN_272 | 8164 | GTCN_1860 | 18351 |
| TTCN_396 | 8165 | ATCN_2234 | 18352 |
| CTCN_273 | 8166 | TTCN_3585 | 18353 |
| CTCN_274 | 8167 | TTCN_3586 | 18354 |
| TTCN_397 | 8168 | TTCN_3587 | 18355 |
| TTCN_398 | 8169 | CTCN_3165 | 18356 |
| ATCN_225 | 8170 | GTCN_1861 | 18357 |
| CTCN_275 | 8171 | CTCN_3166 | 18358 |
| TTCN_399 | 8172 | TTCN_3588 | 18359 |
| TTCN_400 | 8173 | CTCN_3167 | 18360 |
| ATCN_226 | 8174 | CTCN_3168 | 18361 |
| TTCN_401 | 8175 | TTCN_3589 | 18362 |
| TTCN_402 | 8176 | CTCN_3169 | 18363 |
| ATCN_227 | 8177 | TTCN_3590 | 18364 |
| GTCN_185 | 8178 | ATCN_2235 | 18365 |
| TTCN_403 | 8179 | GTCN_1862 | 18366 |
| GTCN_186 | 8180 | CTCN_3170 | 18367 |
| ATCN_228 | 8181 | GTCN_1863 | 18368 |

FIG. 36 (continued)

| | | | |
|---|---|---|---|
| CTCN_276 | 8182 | CTCN_3171 | 18369 |
| TTCN_404 | 8183 | CTCN_3172 | 18370 |
| TTCN_405 | 8184 | ATCN_2236 | 18371 |
| ATCN_229 | 8185 | TTCN_3591 | 18372 |
| GTCN_187 | 8186 | GTCN_1864 | 18373 |
| ATCN_230 | 8187 | CTCN_3173 | 18374 |
| CTCN_277 | 8188 | ATCN_2237 | 18375 |
| GTCN_188 | 8189 | CTCN_3174 | 18376 |
| TTCN_406 | 8190 | TTCN_3592 | 18377 |
| ATCN_231 | 8191 | CTCN_3175 | 18378 |
| ATCN_232 | 8192 | CTCN_3176 | 18379 |
| ATCN_233 | 8193 | TTCN_3593 | 18380 |
| ATCN_234 | 8194 | TTCN_3594 | 18381 |
| GTCN_189 | 8195 | CTCN_3177 | 18382 |
| TTCN_407 | 8196 | TTCN_3595 | 18383 |
| TTCN_408 | 8197 | CTCN_3178 | 18384 |
| TTCN_409 | 8198 | TTCN_3596 | 18385 |
| CTCN_278 | 8199 | ATCN_2238 | 18386 |
| ATCN_235 | 8200 | CTCN_3179 | 18387 |
| ATCN_236 | 8201 | TTCN_3597 | 18388 |
| GTCN_190 | 8202 | TTCN_3598 | 18389 |
| TTCN_410 | 8203 | TTCN_3599 | 18390 |
| GTCN_191 | 8204 | CTCN_3180 | 18391 |
| TTCN_411 | 8205 | ATCN_2239 | 18392 |
| TTCN_412 | 8206 | CTCN_3181 | 18393 |
| TTCN_413 | 8207 | GTCN_1865 | 18394 |
| GTCN_192 | 8208 | CTCN_3182 | 18395 |
| CTCN_279 | 8209 | ATCN_2240 | 18396 |
| TTCN_414 | 8210 | CTCN_3183 | 18397 |
| CTCN_280 | 8211 | GTCN_1866 | 18398 |
| TTCN_415 | 8212 | TTCN_3600 | 18399 |
| TTCN_416 | 8213 | ATCN_2241 | 18400 |
| ATCN_237 | 8214 | TTCN_3601 | 18401 |
| CTCN_281 | 8215 | CTCN_3184 | 18402 |
| TTCN_417 | 8216 | ATCN_2242 | 18403 |
| GTCN_193 | 8217 | CTCN_3185 | 18404 |
| TTCN_418 | 8218 | CTCN_3186 | 18405 |
| ATCN_238 | 8219 | CTCN_3187 | 18406 |
| TTCN_419 | 8220 | ATCN_2243 | 18407 |
| GTCN_194 | 8221 | CTCN_3188 | 18408 |
| GTCN_195 | 8222 | ATCN_2244 | 18409 |
| GTCN_196 | 8223 | ATCN_2245 | 18410 |
| CTCN_282 | 8224 | TTCN_3602 | 18411 |
| CTCN_283 | 8225 | CTCN_3189 | 18412 |
| ATCN_239 | 8226 | TTCN_3603 | 18413 |
| TTCN_420 | 8227 | CTCN_3190 | 18414 |
| ATCN_240 | 8228 | GTCN_1867 | 18415 |
| TTCN_421 | 8229 | CTCN_3191 | 18416 |
| GTCN_197 | 8230 | ATCN_2246 | 18417 |
| TTCN_422 | 8231 | TTCN_3604 | 18418 |
| TTCN_423 | 8232 | ATCN_2247 | 18419 |
| TTCN_424 | 8233 | TTCN_3605 | 18420 |
| TTCN_425 | 8234 | CTCN_3192 | 18421 |
| GTCN_198 | 8235 | CTCN_3193 | 18422 |
| TTCN_426 | 8236 | TTCN_3606 | 18423 |

| | | | |
|---|---|---|---|
| TTCN_427 | 8237 | TTCN_3607 | 18424 |
| CTCN_284 | 8238 | ATCN_2248 | 18425 |
| CTCN_285 | 8239 | ATCN_2249 | 18426 |
| CTCN_286 | 8240 | TTCN_3608 | 18427 |
| ATCN_241 | 8241 | TTCN_3609 | 18428 |
| TTCN_428 | 8242 | TTCN_3610 | 18429 |
| CTCN_287 | 8243 | CTCN_3194 | 18430 |
| CTCN_288 | 8244 | TTCN_3611 | 18431 |
| TTCN_429 | 8245 | TTCN_3612 | 18432 |
| ATCN_242 | 8246 | TTCN_3613 | 18433 |
| CTCN_289 | 8247 | ATCN_2250 | 18434 |
| ATCN_243 | 8248 | CTCN_3195 | 18435 |
| CTCN_290 | 8249 | ATCN_2251 | 18436 |
| CTCN_291 | 8250 | ATCN_2252 | 18437 |
| ATCN_244 | 8251 | GTCN_1868 | 18438 |
| ATCN_245 | 8252 | CTCN_3196 | 18439 |
| CTCN_292 | 8253 | GTCN_1869 | 18440 |
| CTCN_293 | 8254 | GTCN_1870 | 18441 |
| TTCN_430 | 8255 | ATCN_2253 | 18442 |
| TTCN_431 | 8256 | CTCN_3197 | 18443 |
| ATCN_246 | 8257 | TTCN_3614 | 18444 |
| TTCN_432 | 8258 | ATCN_2254 | 18445 |
| TTCN_433 | 8259 | TTCN_3615 | 18446 |
| TTCN_434 | 8260 | CTCN_3198 | 18447 |
| CTCN_294 | 8261 | GTCN_1871 | 18448 |
| CTCN_295 | 8262 | GTCN_1872 | 18449 |
| CTCN_296 | 8263 | CTCN_3199 | 18450 |
| CTCN_297 | 8264 | GTCN_1873 | 18451 |
| CTCN_298 | 8265 | ATCN_2255 | 18452 |
| CTCN_299 | 8266 | ATCN_2256 | 18453 |
| TTCN_435 | 8267 | GTCN_1874 | 18454 |
| GTCN_199 | 8268 | CTCN_3200 | 18455 |
| TTCN_436 | 8269 | CTCN_3201 | 18456 |
| CTCN_300 | 8270 | TTCN_3616 | 18457 |
| CTCN_301 | 8271 | CTCN_3202 | 18458 |
| CTCN_302 | 8272 | ATCN_2257 | 18459 |
| GTCN_200 | 8273 | ATCN_2258 | 18460 |
| CTCN_303 | 8274 | GTCN_1875 | 18461 |
| TTCN_437 | 8275 | ATCN_2259 | 18462 |
| CTCN_304 | 8276 | ATCN_2260 | 18463 |
| ATCN_247 | 8277 | CTCN_3203 | 18464 |
| CTCN_305 | 8278 | GTCN_1876 | 18465 |
| GTCN_201 | 8279 | ATCN_2261 | 18466 |
| CTCN_306 | 8280 | ATCN_2262 | 18467 |
| TTCN_438 | 8281 | TTCN_3617 | 18468 |
| TTCN_439 | 8282 | GTCN_1877 | 18469 |
| CTCN_307 | 8283 | CTCN_3204 | 18470 |
| CTCN_308 | 8284 | CTCN_3205 | 18471 |
| CTCN_309 | 8285 | GTCN_1878 | 18472 |
| TTCN_440 | 8286 | CTCN_3206 | 18473 |
| CTCN_310 | 8287 | ATCN_2263 | 18474 |
| CTCN_311 | 8288 | GTCN_1879 | 18475 |
| CTCN_312 | 8289 | GTCN_1880 | 18476 |
| CTCN_313 | 8290 | GTCN_1881 | 18477 |
| TTCN_441 | 8291 | TTCN_3618 | 18478 |

FIG. 36 (continued)

| | | | |
|---|---|---|---|
| TTCN_442 | 8292 | ATCN_2264 | 18479 |
| ATCN_248 | 8293 | ATCN_2265 | 18480 |
| ATCN_249 | 8294 | TTCN_3619 | 18481 |
| TTCN_443 | 8295 | CTCN_3207 | 18482 |
| CTCN_314 | 8296 | GTCN_1882 | 18483 |
| TTCN_444 | 8297 | ATCN_2266 | 18484 |
| ATCN_250 | 8298 | TTCN_3620 | 18485 |
| CTCN_315 | 8299 | ATCN_2267 | 18486 |
| CTCN_316 | 8300 | ATCN_2268 | 18487 |
| CTCN_317 | 8301 | GTCN_1883 | 18488 |
| CTCN_318 | 8302 | GTCN_1884 | 18489 |
| TTCN_445 | 8303 | CTCN_3208 | 18490 |
| CTCN_319 | 8304 | GTCN_1885 | 18491 |
| GTCN_202 | 8305 | GTCN_1886 | 18492 |
| TTCN_446 | 8306 | TTCN_3621 | 18493 |
| TTCN_447 | 8307 | CTCN_3209 | 18494 |
| TTCN_448 | 8308 | CTCN_3210 | 18495 |
| GTCN_203 | 8309 | ATCN_2269 | 18496 |
| TTCN_449 | 8310 | GTCN_1887 | 18497 |
| CTCN_320 | 8311 | TTCN_3622 | 18498 |
| CTCN_321 | 8312 | TTCN_3623 | 18499 |
| CTCN_322 | 8313 | TTCN_3624 | 18500 |
| TTCN_450 | 8314 | GTCN_1888 | 18501 |
| TTCN_451 | 8315 | TTCN_3625 | 18502 |
| GTCN_204 | 8316 | TTCN_3626 | 18503 |
| GTCN_205 | 8317 | TTCN_3627 | 18504 |
| TTCN_452 | 8318 | TTCN_3628 | 18505 |
| ATCN_251 | 8319 | TTCN_3629 | 18506 |
| GTCN_206 | 8320 | TTCN_3630 | 18507 |
| GTCN_207 | 8321 | TTCN_3631 | 18508 |
| GTCN_208 | 8322 | CTCN_3211 | 18509 |
| CTCN_323 | 8323 | CTCN_3212 | 18510 |
| ATCN_252 | 8324 | GTCN_1889 | 18511 |
| TTCN_453 | 8325 | ATCN_2270 | 18512 |
| CTCN_324 | 8326 | GTCN_1890 | 18513 |
| TTCN_454 | 8327 | CTCN_3213 | 18514 |
| GTCN_209 | 8328 | CTCN_3214 | 18515 |
| GTCN_210 | 8329 | ATCN_2271 | 18516 |
| TTCN_455 | 8330 | GTCN_1891 | 18517 |
| TTCN_456 | 8331 | CTCN_3215 | 18518 |
| CTCN_325 | 8332 | ATCN_2272 | 18519 |
| TTCN_457 | 8333 | CTCN_3216 | 18520 |
| ATCN_253 | 8334 | TTCN_3632 | 18521 |
| GTCN_211 | 8335 | CTCN_3217 | 18522 |
| GTCN_212 | 8336 | TTCN_3633 | 18523 |
| GTCN_213 | 8337 | GTCN_1892 | 18524 |
| CTCN_326 | 8338 | CTCN_3218 | 18525 |
| CTCN_327 | 8339 | TTCN_3634 | 18526 |
| CTCN_328 | 8340 | GTCN_1893 | 18527 |
| CTCN_329 | 8341 | TTCN_3635 | 18528 |
| GTCN_214 | 8342 | ATCN_2273 | 18529 |
| TTCN_458 | 8343 | TTCN_3636 | 18530 |
| ATCN_254 | 8344 | CTCN_3219 | 18531 |
| GTCN_215 | 8345 | TTCN_3637 | 18532 |
| TTCN_459 | 8346 | CTCN_3220 | 18533 |

| | | | |
|---|---|---|---|
| GTCN_216 | 8347 | CTCN_3221 | 18534 |
| CTCN_330 | 8348 | CTCN_3222 | 18535 |
| CTCN_331 | 8349 | GTCN_1894 | 18536 |
| ATCN_255 | 8350 | CTCN_3223 | 18537 |
| ATCN_256 | 8351 | CTCN_3224 | 18538 |
| TTCN_460 | 8352 | CTCN_3225 | 18539 |
| TTCN_461 | 8353 | TTCN_3638 | 18540 |
| GTCN_217 | 8354 | CTCN_3226 | 18541 |
| TTCN_462 | 8355 | GTCN_1895 | 18542 |
| TTCN_463 | 8356 | CTCN_3227 | 18543 |
| TTCN_464 | 8357 | TTCN_3639 | 18544 |
| GTCN_218 | 8358 | CTCN_3228 | 18545 |
| CTCN_332 | 8359 | TTCN_3640 | 18546 |
| ATCN_257 | 8360 | TTCN_3641 | 18547 |
| TTCN_465 | 8361 | CTCN_3229 | 18548 |
| ATCN_258 | 8362 | CTCN_3230 | 18549 |
| ATCN_259 | 8363 | CTCN_3231 | 18550 |
| ATCN_260 | 8364 | TTCN_3642 | 18551 |
| GTCN_219 | 8365 | CTCN_3232 | 18552 |
| TTCN_466 | 8366 | GTCN_1896 | 18553 |
| TTCN_467 | 8367 | ATCN_2274 | 18554 |
| ATCN_261 | 8368 | TTCN_3643 | 18555 |
| ATCN_262 | 8369 | CTCN_3233 | 18556 |
| TTCN_468 | 8370 | GTCN_1897 | 18557 |
| ATCN_263 | 8371 | GTCN_1898 | 18558 |
| ATCN_264 | 8372 | CTCN_3234 | 18559 |
| TTCN_469 | 8373 | GTCN_1899 | 18560 |
| GTCN_220 | 8374 | CTCN_3235 | 18561 |
| CTCN_333 | 8375 | ATCN_2275 | 18562 |
| CTCN_334 | 8376 | ATCN_2276 | 18563 |
| CTCN_335 | 8377 | TTCN_3644 | 18564 |
| GTCN_221 | 8378 | TTCN_3645 | 18565 |
| GTCN_222 | 8379 | CTCN_3236 | 18566 |
| TTCN_470 | 8380 | TTCN_3646 | 18567 |
| CTCN_336 | 8381 | GTCN_1900 | 18568 |
| GTCN_223 | 8382 | ATCN_2277 | 18569 |
| GTCN_224 | 8383 | CTCN_3237 | 18570 |
| TTCN_471 | 8384 | CTCN_3238 | 18571 |
| GTCN_225 | 8385 | TTCN_3647 | 18572 |
| CTCN_337 | 8386 | TTCN_3648 | 18573 |
| TTCN_472 | 8387 | CTCN_3239 | 18574 |
| TTCN_473 | 8388 | ATCN_2278 | 18575 |
| TTCN_474 | 8389 | GTCN_1901 | 18576 |
| CTCN_338 | 8390 | TTCN_3649 | 18577 |
| TTCN_475 | 8391 | GTCN_1902 | 18578 |
| TTCN_476 | 8392 | TTCN_3650 | 18579 |
| TTCN_477 | 8393 | ATCN_2279 | 18580 |
| TTCN_478 | 8394 | TTCN_3651 | 18581 |
| ATCN_265 | 8395 | CTCN_3240 | 18582 |
| ATCN_266 | 8396 | CTCN_3241 | 18583 |
| TTCN_479 | 8397 | TTCN_3652 | 18584 |
| TTCN_480 | 8398 | TTCN_3653 | 18585 |
| ATCN_267 | 8399 | GTCN_1903 | 18586 |
| CTCN_339 | 8400 | GTCN_1904 | 18587 |
| ATCN_268 | 8401 | TTCN_3654 | 18588 |

FIG. 36 (continued)

| | | | |
|---|---|---|---|
| CTCN_340 | 8402 | CTCN_3242 | 18589 |
| GTCN_226 | 8403 | CTCN_3243 | 18590 |
| ATCN_269 | 8404 | TTCN_3655 | 18591 |
| GTCN_227 | 8405 | TTCN_3656 | 18592 |
| TTCN_481 | 8406 | TTCN_3657 | 18593 |
| TTCN_482 | 8407 | ATCN_2280 | 18594 |
| TTCN_483 | 8408 | CTCN_3244 | 18595 |
| GTCN_228 | 8409 | CTCN_3245 | 18596 |
| CTCN_341 | 8410 | GTCN_1905 | 18597 |
| TTCN_484 | 8411 | CTCN_3246 | 18598 |
| CTCN_342 | 8412 | GTCN_1906 | 18599 |
| CTCN_343 | 8413 | CTCN_3247 | 18600 |
| GTCN_229 | 8414 | CTCN_3248 | 18601 |
| GTCN_230 | 8415 | CTCN_3249 | 18602 |
| GTCN_231 | 8416 | TTCN_3658 | 18603 |
| GTCN_232 | 8417 | CTCN_3250 | 18604 |
| ATCN_270 | 8418 | TTCN_3659 | 18605 |
| TTCN_485 | 8419 | CTCN_3251 | 18606 |
| GTCN_233 | 8420 | CTCN_3252 | 18607 |
| TTCN_486 | 8421 | TTCN_3660 | 18608 |
| CTCN_344 | 8422 | TTCN_3661 | 18609 |
| ATCN_271 | 8423 | CTCN_3253 | 18610 |
| CTCN_345 | 8424 | GTCN_1907 | 18611 |
| TTCN_487 | 8425 | TTCN_3662 | 18612 |
| TTCN_488 | 8426 | CTCN_3254 | 18613 |
| CTCN_346 | 8427 | CTCN_3255 | 18614 |
| ATCN_272 | 8428 | GTCN_1908 | 18615 |
| ATCN_273 | 8429 | TTCN_3663 | 18616 |
| TTCN_489 | 8430 | GTCN_1909 | 18617 |
| ATCN_274 | 8431 | TTCN_3664 | 18618 |
| ATCN_275 | 8432 | ATCN_2281 | 18619 |
| ATCN_276 | 8433 | ATCN_2282 | 18620 |
| TTCN_490 | 8434 | TTCN_3665 | 18621 |
| GTCN_234 | 8435 | CTCN_3256 | 18622 |
| CTCN_347 | 8436 | GTCN_1910 | 18623 |
| CTCN_348 | 8437 | TTCN_3666 | 18624 |
| ATCN_277 | 8438 | CTCN_3257 | 18625 |
| CTCN_349 | 8439 | ATCN_2283 | 18626 |
| CTCN_350 | 8440 | CTCN_3258 | 18627 |
| CTCN_351 | 8441 | CTCN_3259 | 18628 |
| ATCN_278 | 8442 | TTCN_3307 | 18629 |
| TTCN_491 | 8443 | TTCN_3308 | 18630 |
| CTCN_352 | 8444 | CTCN_2900 | 18631 |
| TTCN_492 | 8445 | TTCN_3309 | 18632 |
| ATCN_279 | 8446 | CTCN_2901 | 18633 |
| TTCN_493 | 8447 | CTCN_2902 | 18634 |
| GTCN_235 | 8448 | GTCN_1735 | 18635 |
| TTCN_494 | 8449 | CTCN_2903 | 18636 |
| TTCN_495 | 8450 | ATCN_2050 | 18637 |
| GTCN_236 | 8451 | ATCN_2051 | 18638 |
| TTCN_496 | 8452 | GTCN_1736 | 18639 |
| TTCN_497 | 8453 | CTCN_2904 | 18640 |
| ATCN_280 | 8454 | CTCN_2905 | 18641 |
| TTCN_498 | 8455 | CTCN_2906 | 18642 |
| TTCN_499 | 8456 | TTCN_3310 | 18643 |
| TTCN_500 | 8457 | GTCN_1737 | 18644 |
| GTCN_237 | 8458 | CTCN_2907 | 18645 |
| GTCN_238 | 8459 | CTCN_2908 | 18646 |
| CTCN_353 | 8460 | GTCN_1738 | 18647 |
| GTCN_239 | 8461 | TTCN_3311 | 18648 |
| ATCN_281 | 8462 | CTCN_2909 | 18649 |
| TTCN_501 | 8463 | TTCN_3312 | 18650 |
| CTCN_354 | 8464 | ATCN_2052 | 18651 |
| GTCN_240 | 8465 | ATCN_2053 | 18652 |
| TTCN_502 | 8466 | TTCN_3313 | 18653 |
| CTCN_355 | 8467 | ATCN_2054 | 18654 |
| GTCN_241 | 8468 | TTCN_3314 | 18655 |
| ATCN_282 | 8469 | TTCN_3315 | 18656 |
| ATCN_283 | 8470 | TTCN_3316 | 18657 |
| CTCN_356 | 8471 | TTCN_3317 | 18658 |
| TTCN_503 | 8472 | CTCN_2910 | 18659 |
| CTCN_357 | 8473 | TTCN_3318 | 18660 |
| CTCN_358 | 8474 | ATCN_2055 | 18661 |
| CTCN_359 | 8475 | TTCN_3319 | 18662 |
| ATCN_284 | 8476 | TTCN_3320 | 18663 |
| CTCN_360 | 8477 | GTCN_1739 | 18664 |
| TTCN_504 | 8478 | TTCN_3321 | 18665 |
| ATCN_285 | 8479 | TTCN_3322 | 18666 |
| CTCN_361 | 8480 | TTCN_3323 | 18667 |
| ATCN_286 | 8481 | ATCN_2056 | 18668 |
| ATCN_287 | 8482 | CTCN_2911 | 18669 |
| ATCN_288 | 8483 | GTCN_1740 | 18670 |
| ATCN_289 | 8484 | ATCN_2057 | 18671 |
| ATCN_290 | 8485 | TTCN_3324 | 18672 |
| ATCN_291 | 8486 | CTCN_2912 | 18673 |
| GTCN_242 | 8487 | GTCN_1741 | 18674 |
| GTCN_243 | 8488 | ATCN_2058 | 18675 |
| ATCN_292 | 8489 | ATCN_2059 | 18676 |
| TTCN_505 | 8490 | ATCN_2060 | 18677 |
| GTCN_244 | 8491 | TTCN_3325 | 18678 |
| CTCN_362 | 8492 | TTCN_3326 | 18679 |
| CTCN_363 | 8493 | GTCN_1742 | 18680 |
| ATCN_293 | 8494 | ATCN_2061 | 18681 |
| ATCN_294 | 8495 | ATCN_2062 | 18682 |
| CTCN_364 | 8496 | TTCN_3327 | 18683 |
| GTCN_245 | 8497 | TTCN_3328 | 18684 |
| ATCN_295 | 8498 | TTCN_3329 | 18685 |
| ATCN_296 | 8499 | ATCN_2063 | 18686 |
| CTCN_365 | 8500 | TTCN_3330 | 18687 |
| CTCN_366 | 8501 | TTCN_3331 | 18688 |
| GTCN_246 | 8502 | GTCN_1743 | 18689 |
| CTCN_367 | 8503 | CTCN_2913 | 18690 |
| CTCN_368 | 8504 | GTCN_1744 | 18691 |
| CTCN_369 | 8505 | TTCN_3332 | 18692 |
| GTCN_247 | 8506 | CTCN_2914 | 18693 |
| CTCN_370 | 8507 | ATCN_2064 | 18694 |
| CTCN_371 | 8508 | CTCN_2915 | 18695 |
| CTCN_372 | 8509 | CTCN_2916 | 18696 |
| TTCN_506 | 8510 | ATCN_2065 | 18697 |
| CTCN_373 | 8511 | TTCN_3333 | 18698 |

FIG. 36 (continued)

| | | | |
|---|---|---|---|
| TTCN_507 | 8512 | TTCN_3334 | 18699 |
| TTCN_508 | 8513 | CTCN_2917 | 18700 |
| GTCN_248 | 8514 | TTCN_3335 | 18701 |
| TTCN_509 | 8515 | TTCN_3336 | 18702 |
| TTCN_510 | 8516 | TTCN_3337 | 18703 |
| CTCN_374 | 8517 | TTCN_3338 | 18704 |
| CTCN_375 | 8518 | TTCN_3339 | 18705 |
| ATCN_297 | 8519 | GTCN_1745 | 18706 |
| ATCN_298 | 8520 | TTCN_3340 | 18707 |
| GTCN_249 | 8521 | TTCN_3341 | 18708 |
| CTCN_376 | 8522 | ATCN_2066 | 18709 |
| TTCN_511 | 8523 | TTCN_3342 | 18710 |
| CTCN_377 | 8524 | TTCN_3343 | 18711 |
| TTCN_512 | 8525 | TTCN_3344 | 18712 |
| CTCN_378 | 8526 | TTCN_3345 | 18713 |
| ATCN_299 | 8527 | CTCN_2918 | 18714 |
| TTCN_513 | 8528 | TTCN_3346 | 18715 |
| GTCN_250 | 8529 | GTCN_1746 | 18716 |
| TTCN_514 | 8530 | TTCN_3347 | 18717 |
| CTCN_379 | 8531 | CTCN_2919 | 18718 |
| ATCN_300 | 8532 | TTCN_3348 | 18719 |
| TTCN_515 | 8533 | TTCN_3349 | 18720 |
| ATCN_301 | 8534 | CTCN_2920 | 18721 |
| CTCN_380 | 8535 | TTCN_3350 | 18722 |
| GTCN_251 | 8536 | TTCN_3351 | 18723 |
| CTCN_381 | 8537 | TTCN_3352 | 18724 |
| TTCN_516 | 8538 | TTCN_3353 | 18725 |
| CTCN_382 | 8539 | TTCN_3354 | 18726 |
| GTCN_252 | 8540 | TTCN_3355 | 18727 |
| TTCN_517 | 8541 | CTCN_2921 | 18728 |
| TTCN_518 | 8542 | CTCN_2922 | 18729 |
| TTCN_519 | 8543 | TTCN_3356 | 18730 |
| CTCN_383 | 8544 | CTCN_2923 | 18731 |
| CTCN_384 | 8545 | TTCN_3357 | 18732 |
| GTCN_253 | 8546 | GTCN_1747 | 18733 |
| CTCN_385 | 8547 | CTCN_2924 | 18734 |
| GTCN_254 | 8548 | CTCN_2925 | 18735 |
| CTCN_386 | 8549 | TTCN_3358 | 18736 |
| CTCN_387 | 8550 | TTCN_3359 | 18737 |
| ATCN_302 | 8551 | TTCN_3360 | 18738 |
| TTCN_520 | 8552 | TTCN_3361 | 18739 |
| GTCN_255 | 8553 | CTCN_2926 | 18740 |
| GTCN_256 | 8554 | TTCN_3362 | 18741 |
| ATCN_303 | 8555 | CTCN_2927 | 18742 |
| ATCN_304 | 8556 | TTCN_3363 | 18743 |
| ATCN_305 | 8557 | CTCN_2928 | 18744 |
| ATCN_306 | 8558 | CTCN_2929 | 18745 |
| CTCN_388 | 8559 | TTCN_3364 | 18746 |
| ATCN_307 | 8560 | CTCN_2930 | 18747 |
| CTCN_389 | 8561 | TTCN_3365 | 18748 |
| TTCN_521 | 8562 | ATCN_2067 | 18749 |
| CTCN_390 | 8563 | TTCN_3366 | 18750 |
| GTCN_257 | 8564 | CTCN_2931 | 18751 |
| TTCN_522 | 8565 | CTCN_2932 | 18752 |
| CTCN_391 | 8566 | CTCN_2933 | 18753 |

| | | | |
|---|---|---|---|
| CTCN_392 | 8567 | GTCN_1748 | 18754 |
| TTCN_523 | 8568 | CTCN_2934 | 18755 |
| CTCN_393 | 8569 | ATCN_2068 | 18756 |
| GTCN_258 | 8570 | CTCN_2935 | 18757 |
| CTCN_394 | 8571 | CTCN_2936 | 18758 |
| ATCN_308 | 8572 | CTCN_2937 | 18759 |
| ATCN_309 | 8573 | GTCN_1749 | 18760 |
| CTCN_395 | 8574 | GTCN_1750 | 18761 |
| GTCN_259 | 8575 | GTCN_1751 | 18762 |
| CTCN_396 | 8576 | CTCN_2938 | 18763 |
| ATCN_310 | 8577 | TTCN_3367 | 18764 |
| TTCN_524 | 8578 | TTCN_3368 | 18765 |
| ATCN_311 | 8579 | GTCN_1752 | 18766 |
| ATCN_312 | 8580 | GTCN_1753 | 18767 |
| TTCN_525 | 8581 | CTCN_2939 | 18768 |
| TTCN_526 | 8582 | TTCN_3369 | 18769 |
| TTCN_527 | 8583 | CTCN_2940 | 18770 |
| TTCN_528 | 8584 | ATCN_2069 | 18771 |
| TTCN_529 | 8585 | CTCN_2941 | 18772 |
| GTCN_260 | 8586 | CTCN_2942 | 18773 |
| TTCN_530 | 8587 | CTCN_2943 | 18774 |
| GTCN_261 | 8588 | GTCN_1754 | 18775 |
| CTCN_397 | 8589 | TTCN_3370 | 18776 |
| TTCN_531 | 8590 | ATCN_2070 | 18777 |
| TTCN_532 | 8591 | CTCN_2944 | 18778 |
| CTCN_398 | 8592 | CTCN_2945 | 18779 |
| CTCN_399 | 8593 | CTCN_2946 | 18780 |
| GTCN_262 | 8594 | GTCN_1755 | 18781 |
| TTCN_533 | 8595 | ATCN_2071 | 18782 |
| CTCN_400 | 8596 | TTCN_3371 | 18783 |
| GTCN_263 | 8597 | TTCN_3372 | 18784 |
| ATCN_313 | 8598 | ATCN_2072 | 18785 |
| CTCN_401 | 8599 | CTCN_2947 | 18786 |
| GTCN_264 | 8600 | ATCN_2073 | 18787 |
| CTCN_402 | 8601 | TTCN_3373 | 18788 |
| GTCN_265 | 8602 | CTCN_2948 | 18789 |
| GTCN_266 | 8603 | CTCN_2949 | 18790 |
| ATCN_314 | 8604 | CTCN_2950 | 18791 |
| CTCN_403 | 8605 | CTCN_2951 | 18792 |
| ATCN_315 | 8606 | GTCN_1756 | 18793 |
| CTCN_404 | 8607 | CTCN_2952 | 18794 |
| ATCN_316 | 8608 | CTCN_2953 | 18795 |
| GTCN_267 | 8609 | ATCN_2074 | 18796 |
| TTCN_534 | 8610 | TTCN_3374 | 18797 |
| GTCN_268 | 8611 | ATCN_2075 | 18798 |
| CTCN_405 | 8612 | ATCN_2076 | 18799 |
| GTCN_269 | 8613 | ATCN_2077 | 18800 |
| TTCN_535 | 8614 | GTCN_1757 | 18801 |
| TTCN_536 | 8615 | CTCN_2954 | 18802 |
| ATCN_317 | 8616 | TTCN_3375 | 18803 |
| ATCN_318 | 8617 | ATCN_2078 | 18804 |
| CTCN_406 | 8618 | CTCN_2955 | 18805 |
| GTCN_270 | 8619 | CTCN_2956 | 18806 |
| ATCN_319 | 8620 | TTCN_3376 | 18807 |
| CTCN_407 | 8621 | CTCN_2957 | 18808 |

FIG. 36 (continued)

| | | | |
|---|---|---|---|
| TTCN_537 | 8622 | CTCN_2958 | 18809 |
| TTCN_538 | 8623 | ATCN_2079 | 18810 |
| TTCN_539 | 8624 | TTCN_3377 | 18811 |
| TTCN_540 | 8625 | TTCN_3378 | 18812 |
| ATCN_320 | 8626 | ATCN_2080 | 18813 |
| TTCN_541 | 8627 | CTCN_2959 | 18814 |
| TTCN_542 | 8628 | TTCN_3379 | 18815 |
| ATCN_321 | 8629 | CTCN_2960 | 18816 |
| TTCN_543 | 8630 | TTCN_3380 | 18817 |
| TTCN_544 | 8631 | TTCN_3381 | 18818 |
| CTCN_408 | 8632 | TTCN_3382 | 18819 |
| CTCN_409 | 8633 | ATCN_2081 | 18820 |
| TTCN_545 | 8634 | TTCN_3383 | 18821 |
| ATCN_322 | 8635 | CTCN_2961 | 18822 |
| TTCN_546 | 8636 | TTCN_3384 | 18823 |
| ATCN_323 | 8637 | ATCN_2082 | 18824 |
| TTCN_547 | 8638 | CTCN_2962 | 18825 |
| TTCN_548 | 8639 | ATCN_2083 | 18826 |
| TTCN_549 | 8640 | ATCN_2084 | 18827 |
| ATCN_324 | 8641 | CTCN_2963 | 18828 |
| CTCN_410 | 8642 | TTCN_3385 | 18829 |
| ATCN_325 | 8643 | ATCN_2085 | 18830 |
| ATCN_326 | 8644 | CTCN_2964 | 18831 |
| GTCN_271 | 8645 | ATCN_2086 | 18832 |
| GTCN_272 | 8646 | CTCN_2965 | 18833 |
| ATCN_327 | 8647 | TTCN_3386 | 18834 |
| TTCN_550 | 8648 | TTCN_3387 | 18835 |
| TTCN_551 | 8649 | CTCN_2966 | 18836 |
| CTCN_411 | 8650 | GTCN_1758 | 18837 |
| GTCN_273 | 8651 | ATCN_2087 | 18838 |
| GTCN_274 | 8652 | TTCN_3388 | 18839 |
| GTCN_275 | 8653 | GTCN_1759 | 18840 |
| TTCN_552 | 8654 | CTCN_2967 | 18841 |
| GTCN_276 | 8655 | CTCN_2968 | 18842 |
| GTCN_277 | 8656 | CTCN_2969 | 18843 |
| CTCN_412 | 8657 | GTCN_1760 | 18844 |
| TTCN_553 | 8658 | CTCN_2970 | 18845 |
| GTCN_278 | 8659 | TTCN_3389 | 18846 |
| CTCN_413 | 8660 | ATCN_2088 | 18847 |
| TTCN_554 | 8661 | TTCN_3390 | 18848 |
| TTCN_555 | 8662 | TTCN_3391 | 18849 |
| TTCN_556 | 8663 | TTCN_3392 | 18850 |
| CTCN_414 | 8664 | CTCN_2971 | 18851 |
| TTCN_557 | 8665 | CTCN_2972 | 18852 |
| TTCN_558 | 8666 | TTCN_3393 | 18853 |
| CTCN_415 | 8667 | ATCN_2089 | 18854 |
| TTCN_559 | 8668 | ATCN_2090 | 18855 |
| TTCN_560 | 8669 | TTCN_3394 | 18856 |
| GTCN_279 | 8670 | CTCN_2973 | 18857 |
| CTCN_416 | 8671 | TTCN_3395 | 18858 |
| CTCN_417 | 8672 | TTCN_3396 | 18859 |
| TTCN_561 | 8673 | GTCN_1761 | 18860 |
| GTCN_280 | 8674 | TTCN_3397 | 18861 |
| GTCN_281 | 8675 | TTCN_3398 | 18862 |
| GTCN_282 | 8676 | TTCN_3399 | 18863 |

| | | | |
|---|---|---|---|
| ATCN_328 | 8677 | TTCN_3400 | 18864 |
| ATCN_329 | 8678 | ATCN_2091 | 18865 |
| GTCN_283 | 8679 | ATCN_2092 | 18866 |
| GTCN_284 | 8680 | ATCN_2093 | 18867 |
| GTCN_285 | 8681 | GTCN_1762 | 18868 |
| CTCN_418 | 8682 | ATCN_2094 | 18869 |
| ATCN_330 | 8683 | CTCN_2974 | 18870 |
| TTCN_562 | 8684 | TTCN_3401 | 18871 |
| ATCN_331 | 8685 | GTCN_1763 | 18872 |
| GTCN_286 | 8686 | CTCN_2975 | 18873 |
| TTCN_563 | 8687 | TTCN_3402 | 18874 |
| CTCN_419 | 8688 | TTCN_3403 | 18875 |
| TTCN_564 | 8689 | TTCN_3404 | 18876 |
| CTCN_420 | 8690 | ATCN_2095 | 18877 |
| ATCN_332 | 8691 | ATCN_2096 | 18878 |
| ATCN_333 | 8692 | TTCN_3405 | 18879 |
| CTCN_421 | 8693 | TTCN_3406 | 18880 |
| ATCN_334 | 8694 | ATCN_2097 | 18881 |
| CTCN_422 | 8695 | ATCN_2098 | 18882 |
| CTCN_423 | 8696 | CTCN_2976 | 18883 |
| GTCN_287 | 8697 | CTCN_2977 | 18884 |
| CTCN_424 | 8698 | ATCN_2099 | 18885 |
| TTCN_565 | 8699 | ATCN_2100 | 18886 |
| ATCN_335 | 8700 | TTCN_3407 | 18887 |
| TTCN_566 | 8701 | CTCN_2978 | 18888 |
| CTCN_425 | 8702 | CTCN_2979 | 18889 |
| ATCN_336 | 8703 | TTCN_3408 | 18890 |
| CTCN_426 | 8704 | TTCN_3409 | 18891 |
| CTCN_427 | 8705 | GTCN_1764 | 18892 |
| TTCN_567 | 8706 | CTCN_2980 | 18893 |
| CTCN_428 | 8707 | GTCN_1765 | 18894 |
| CTCN_429 | 8708 | TTCN_3410 | 18895 |
| ATCN_337 | 8709 | CTCN_2981 | 18896 |
| CTCN_430 | 8710 | CTCN_2982 | 18897 |
| TTCN_568 | 8711 | GTCN_1766 | 18898 |
| CTCN_431 | 8712 | CTCN_2983 | 18899 |
| TTCN_569 | 8713 | TTCN_3411 | 18900 |
| TTCN_570 | 8714 | GTCN_1767 | 18901 |
| CTCN_432 | 8715 | CTCN_2984 | 18902 |
| CTCN_433 | 8716 | TTCN_3412 | 18903 |
| ATCN_338 | 8717 | GTCN_1768 | 18904 |
| GTCN_288 | 8718 | CTCN_2985 | 18905 |
| TTCN_571 | 8719 | ATCN_2101 | 18906 |
| TTCN_572 | 8720 | CTCN_2986 | 18907 |
| CTCN_434 | 8721 | GTCN_1769 | 18908 |
| GTCN_289 | 8722 | CTCN_2987 | 18909 |
| CTCN_435 | 8723 | TTCN_3413 | 18910 |
| TTCN_573 | 8724 | ATCN_2102 | 18911 |
| TTCN_574 | 8725 | ATCN_2103 | 18912 |
| ATCN_339 | 8726 | TTCN_3414 | 18913 |
| CTCN_436 | 8727 | ATCN_2104 | 18914 |
| TTCN_575 | 8728 | CTCN_2988 | 18915 |
| CTCN_437 | 8729 | GTCN_1770 | 18916 |
| ATCN_340 | 8730 | CTCN_2989 | 18917 |
| GTCN_290 | 8731 | GTCN_1771 | 18918 |

FIG. 36 (continued)

| | | | |
|---|---|---|---|
| TTCN_576 | 8732 | GTCN_1772 | 18919 |
| TTCN_577 | 8733 | TTCN_3415 | 18920 |
| GTCN_291 | 8734 | GTCN_1773 | 18921 |
| TTCN_578 | 8735 | GTCN_1774 | 18922 |
| GTCN_292 | 8736 | CTCN_2990 | 18923 |
| TTCN_579 | 8737 | TTCN_3416 | 18924 |
| ATCN_341 | 8738 | ATCN_2105 | 18925 |
| TTCN_580 | 8739 | ATCN_2106 | 18926 |
| CTCN_438 | 8740 | ATCN_2107 | 18927 |
| TTCN_581 | 8741 | ATCN_2108 | 18928 |
| TTCN_582 | 8742 | CTCN_2991 | 18929 |
| TTCN_583 | 8743 | TTCN_3417 | 18930 |
| CTCN_439 | 8744 | CTCN_2992 | 18931 |
| CTCN_440 | 8745 | TTCN_3418 | 18932 |
| ATCN_342 | 8746 | TTCN_3419 | 18933 |
| GTCN_293 | 8747 | CTCN_2993 | 18934 |
| TTCN_584 | 8748 | CTCN_2994 | 18935 |
| ATCN_343 | 8749 | GTCN_1775 | 18936 |
| TTCN_585 | 8750 | TTCN_3420 | 18937 |
| GTCN_294 | 8751 | TTCN_3421 | 18938 |
| CTCN_441 | 8752 | CTCN_2995 | 18939 |
| ATCN_344 | 8753 | TTCN_3422 | 18940 |
| TTCN_586 | 8754 | TTCN_3423 | 18941 |
| ATCN_345 | 8755 | CTCN_2996 | 18942 |
| CTCN_442 | 8756 | TTCN_3424 | 18943 |
| CTCN_443 | 8757 | ATCN_2109 | 18944 |
| GTCN_295 | 8758 | CTCN_2997 | 18945 |
| CTCN_444 | 8759 | TTCN_3425 | 18946 |
| GTCN_296 | 8760 | TTCN_3426 | 18947 |
| TTCN_587 | 8761 | CTCN_2998 | 18948 |
| GTCN_297 | 8762 | TTCN_3427 | 18949 |
| TTCN_588 | 8763 | CTCN_2999 | 18950 |
| CTCN_445 | 8764 | TTCN_3428 | 18951 |
| CTCN_446 | 8765 | TTCN_3429 | 18952 |
| GTCN_298 | 8766 | ATCN_2110 | 18953 |
| CTCN_447 | 8767 | ATCN_2111 | 18954 |
| GTCN_299 | 8768 | ATCN_2112 | 18955 |
| CTCN_448 | 8769 | ATCN_2113 | 18956 |
| TTCN_589 | 8770 | TTCN_3430 | 18957 |
| CTCN_449 | 8771 | TTCN_3431 | 18958 |
| GTCN_300 | 8772 | TTCN_3432 | 18959 |
| CTCN_450 | 8773 | TTCN_3433 | 18960 |
| TTCN_590 | 8774 | CTCN_3000 | 18961 |
| GTCN_301 | 8775 | ATCN_2114 | 18962 |
| CTCN_451 | 8776 | CTCN_3001 | 18963 |
| TTCN_591 | 8777 | TTCN_3434 | 18964 |
| ATCN_346 | 8778 | CTCN_3002 | 18965 |
| GTCN_302 | 8779 | TTCN_3435 | 18966 |
| CTCN_452 | 8780 | ATCN_2115 | 18967 |
| ATCN_347 | 8781 | ATCN_2116 | 18968 |
| CTCN_453 | 8782 | ATCN_2117 | 18969 |
| TTCN_592 | 8783 | CTCN_3003 | 18970 |
| TTCN_593 | 8784 | TTCN_3436 | 18971 |
| ATCN_348 | 8785 | ATCN_2118 | 18972 |
| CTCN_454 | 8786 | TTCN_3437 | 18973 |
| CTCN_455 | 8787 | CTCN_3004 | 18974 |
| TTCN_594 | 8788 | CTCN_3005 | 18975 |
| TTCN_595 | 8789 | CTCN_3006 | 18976 |
| GTCN_303 | 8790 | CTCN_3007 | 18977 |
| CTCN_456 | 8791 | CTCN_3008 | 18978 |
| TTCN_596 | 8792 | TTCN_3438 | 18979 |
| ATCN_349 | 8793 | TTCN_3439 | 18980 |
| TTCN_597 | 8794 | CTCN_3009 | 18981 |
| GTCN_304 | 8795 | GTCN_1776 | 18982 |
| CTCN_457 | 8796 | TTCN_3440 | 18983 |
| TTCN_598 | 8797 | CTCN_3010 | 18984 |
| ATCN_350 | 8798 | CTCN_3011 | 18985 |
| TTCN_599 | 8799 | CTCN_3012 | 18986 |
| CTCN_458 | 8800 | GTCN_1777 | 18987 |
| CTCN_459 | 8801 | TTCN_3441 | 18988 |
| CTCN_460 | 8802 | ATCN_2119 | 18989 |
| TTCN_600 | 8803 | CTCN_3013 | 18990 |
| TTCN_601 | 8804 | CTCN_3014 | 18991 |
| TTCN_602 | 8805 | CTCN_3015 | 18992 |
| TTCN_603 | 8806 | TTCN_3442 | 18993 |
| TTCN_604 | 8807 | CTCN_3016 | 18994 |
| GTCN_305 | 8808 | TTCN_3443 | 18995 |
| GTCN_306 | 8809 | CTCN_3017 | 18996 |
| CTCN_461 | 8810 | GTCN_1778 | 18997 |
| ATCN_351 | 8811 | ATCN_2120 | 18998 |
| CTCN_462 | 8812 | CTCN_3018 | 18999 |
| GTCN_307 | 8813 | ATCN_2121 | 19000 |
| TTCN_605 | 8814 | TTCN_3444 | 19001 |
| ATCN_352 | 8815 | ATCN_2122 | 19002 |
| ATCN_353 | 8816 | ATCN_2123 | 19003 |
| CTCN_463 | 8817 | TTCN_3445 | 19004 |
| CTCN_464 | 8818 | CTCN_3019 | 19005 |
| CTCN_465 | 8819 | ATCN_2124 | 19006 |
| TTCN_606 | 8820 | TTCN_3446 | 19007 |
| TTCN_607 | 8821 | CTCN_3020 | 19008 |
| GTCN_308 | 8822 | TTCN_3447 | 19009 |
| ATCN_354 | 8823 | ATCN_2125 | 19010 |
| ATCN_355 | 8824 | TTCN_3448 | 19011 |
| TTCN_608 | 8825 | TTCN_3449 | 19012 |
| TTCN_609 | 8826 | ATCN_2126 | 19013 |
| TTCN_610 | 8827 | GTCN_1779 | 19014 |
| TTCN_611 | 8828 | CTCN_3021 | 19015 |
| TTCN_612 | 8829 | TTCN_3450 | 19016 |
| CTCN_466 | 8830 | CTCN_3022 | 19017 |
| GTCN_309 | 8831 | GTCN_1780 | 19018 |
| ATCN_356 | 8832 | TTCN_3451 | 19019 |
| ATCN_357 | 8833 | ATCN_2127 | 19020 |
| TTCN_613 | 8834 | ATCN_2128 | 19021 |
| GTCN_310 | 8835 | TTCN_3452 | 19022 |
| TTCN_614 | 8836 | ATCN_2129 | 19023 |
| ATCN_358 | 8837 | CTCN_3023 | 19024 |
| TTCN_615 | 8838 | GTCN_1781 | 19025 |
| CTCN_467 | 8839 | TTCN_3453 | 19026 |
| CTCN_468 | 8840 | ATCN_2130 | 19027 |
| CTCN_469 | 8841 | ATCN_2131 | 19028 |

FIG. 36 (continued)

| | | | |
|---|---|---|---|
| CTCN_470 | 8842 | ATCN_2132 | 19029 |
| ATCN_359 | 8843 | ATCN_2133 | 19030 |
| CTCN_471 | 8844 | GTCN_1782 | 19031 |
| CTCN_472 | 8845 | GTCN_1783 | 19032 |
| TTCN_616 | 8846 | CTCN_3024 | 19033 |
| TTCN_617 | 8847 | ATCN_2134 | 19034 |
| CTCN_473 | 8848 | TTCN_3454 | 19035 |
| CTCN_474 | 8849 | TTCN_3455 | 19036 |
| CTCN_475 | 8850 | CTCN_3025 | 19037 |
| CTCN_476 | 8851 | CTCN_3026 | 19038 |
| TTCN_618 | 8852 | CTCN_3027 | 19039 |
| CTCN_477 | 8853 | GTCN_1784 | 19040 |
| CTCN_478 | 8854 | GTCN_1785 | 19041 |
| GTCN_311 | 8855 | TTCN_3456 | 19042 |
| ATCN_360 | 8856 | TTCN_3457 | 19043 |
| ATCN_361 | 8857 | GTCN_1786 | 19044 |
| TTCN_619 | 8858 | TTCN_3458 | 19045 |
| GTCN_312 | 8859 | TTCN_3459 | 19046 |
| CTCN_479 | 8860 | CTCN_3028 | 19047 |
| CTCN_480 | 8861 | CTCN_3029 | 19048 |
| TTCN_620 | 8862 | TTCN_3460 | 19049 |
| GTCN_313 | 8863 | TTCN_3461 | 19050 |
| CTCN_481 | 8864 | ATCN_2135 | 19051 |
| CTCN_482 | 8865 | TTCN_3462 | 19052 |
| TTCN_621 | 8866 | ATCN_2136 | 19053 |
| ATCN_362 | 8867 | CTCN_3030 | 19054 |
| TTCN_622 | 8868 | ATCN_2137 | 19055 |
| CTCN_483 | 8869 | CTCN_3031 | 19056 |
| TTCN_623 | 8870 | CTCN_3032 | 19057 |
| TTCN_624 | 8871 | CTCN_3033 | 19058 |
| ATCN_363 | 8872 | GTCN_1787 | 19059 |
| TTCN_625 | 8873 | ATCN_2138 | 19060 |
| ATCN_364 | 8874 | ATCN_2139 | 19061 |
| CTCN_484 | 8875 | GTCN_1788 | 19062 |
| CTCN_485 | 8876 | TTCN_3463 | 19063 |
| ATCN_365 | 8877 | CTCN_3034 | 19064 |
| TTCN_626 | 8878 | CTCN_3035 | 19065 |
| TTCN_627 | 8879 | CTCN_3036 | 19066 |
| ATCN_366 | 8880 | CTCN_3037 | 19067 |
| CTCN_486 | 8881 | TTCN_3464 | 19068 |
| TTCN_628 | 8882 | TTCN_3465 | 19069 |
| CTCN_487 | 8883 | ATCN_2140 | 19070 |
| TTCN_629 | 8884 | ATCN_2141 | 19071 |
| ATCN_367 | 8885 | TTCN_3466 | 19072 |
| ATCN_368 | 8886 | CTCN_3038 | 19073 |
| ATCN_369 | 8887 | TTCN_3467 | 19074 |
| CTCN_488 | 8888 | TTCN_3468 | 19075 |
| GTCN_314 | 8889 | TTCN_3469 | 19076 |
| TTCN_630 | 8890 | ATCN_2142 | 19077 |
| CTCN_489 | 8891 | TTCN_3470 | 19078 |
| TTCN_631 | 8892 | GTCN_1789 | 19079 |
| ATCN_370 | 8893 | CTCN_3039 | 19080 |
| CTCN_490 | 8894 | TTCN_3471 | 19081 |
| GTCN_315 | 8895 | ATCN_2143 | 19082 |
| CTCN_491 | 8896 | TTCN_3472 | 19083 |

| | | | |
|---|---|---|---|
| ATCN_371 | 8897 | TTCN_3473 | 19084 |
| TTCN_632 | 8898 | CTCN_3040 | 19085 |
| GTCN_316 | 8899 | CTCN_3041 | 19086 |
| ATCN_372 | 8900 | TTCN_3474 | 19087 |
| CTCN_492 | 8901 | ATCN_2144 | 19088 |
| GTCN_317 | 8902 | TTCN_3475 | 19089 |
| GTCN_318 | 8903 | TTCN_3476 | 19090 |
| TTCN_633 | 8904 | TTCN_3477 | 19091 |
| TTCN_634 | 8905 | CTCN_3042 | 19092 |
| TTCN_635 | 8906 | TTCN_3478 | 19093 |
| ATCN_373 | 8907 | CTCN_3043 | 19094 |
| TTCN_636 | 8908 | ATCN_2145 | 19095 |
| ATCN_374 | 8909 | CTCN_3044 | 19096 |
| TTCN_637 | 8910 | CTCN_3045 | 19097 |
| ATCN_375 | 8911 | CTCN_3046 | 19098 |
| CTCN_493 | 8912 | ATCN_2146 | 19099 |
| TTCN_638 | 8913 | ATCN_2147 | 19100 |
| GTCN_319 | 8914 | GTCN_1790 | 19101 |
| ATCN_376 | 8915 | CTCN_3047 | 19102 |
| TTCN_639 | 8916 | ATCN_2148 | 19103 |
| TTCN_640 | 8917 | ATCN_2149 | 19104 |
| TTCN_641 | 8918 | GTCN_1791 | 19105 |
| CTCN_494 | 8919 | ATCN_2150 | 19106 |
| GTCN_320 | 8920 | TTCN_3479 | 19107 |
| TTCN_642 | 8921 | ATCN_2151 | 19108 |
| GTCN_321 | 8922 | CTCN_3048 | 19109 |
| TTCN_643 | 8923 | ATCN_2152 | 19110 |
| ATCN_377 | 8924 | GTCN_1792 | 19111 |
| TTCN_644 | 8925 | CTCN_3049 | 19112 |
| TTCN_645 | 8926 | CTCN_3050 | 19113 |
| ATCN_378 | 8927 | CTCN_3051 | 19114 |
| GTCN_322 | 8928 | GTCN_1793 | 19115 |
| CTCN_495 | 8929 | CTCN_3052 | 19116 |
| TTCN_646 | 8930 | CTCN_3053 | 19117 |
| GTCN_323 | 8931 | TTCN_3480 | 19118 |
| TTCN_647 | 8932 | TTCN_3481 | 19119 |
| ATCN_379 | 8933 | CTCN_3054 | 19120 |
| ATCN_380 | 8934 | CTCN_3055 | 19121 |
| TTCN_648 | 8935 | ATCN_2153 | 19122 |
| ATCN_381 | 8936 | CTCN_3056 | 19123 |
| CTCN_496 | 8937 | CTCN_3057 | 19124 |
| GTCN_324 | 8938 | ATCN_2154 | 19125 |
| TTCN_649 | 8939 | ATCN_2155 | 19126 |
| TTCN_650 | 8940 | ATCN_2156 | 19127 |
| CTCN_497 | 8941 | CTCN_3058 | 19128 |
| TTCN_651 | 8942 | CTCN_3059 | 19129 |
| CTCN_498 | 8943 | GTCN_1794 | 19130 |
| TTCN_652 | 8944 | CTCN_3060 | 19131 |
| GTCN_325 | 8945 | TTCN_3482 | 19132 |
| ATCN_382 | 8946 | CTCN_3061 | 19133 |
| GTCN_326 | 8947 | TTCN_3483 | 19134 |
| GTCN_327 | 8948 | GTCN_1795 | 19135 |
| GTCN_328 | 8949 | CTCN_3062 | 19136 |
| CTCN_499 | 8950 | ATCN_2157 | 19137 |
| TTCN_653 | 8951 | ATCN_2158 | 19138 |

FIG. 36 (continued)

| | | | |
|---|---|---|---|
| ATCN_383 | 8952 | TTCN_3484 | 19139 |
| TTCN_654 | 8953 | CTCN_3063 | 19140 |
| CTCN_500 | 8954 | CTCN_3064 | 19141 |
| CTCN_501 | 8955 | ATCN_2159 | 19142 |
| TTCN_655 | 8956 | ATCN_2160 | 19143 |
| GTCN_329 | 8957 | TTCN_3485 | 19144 |
| ATCN_384 | 8958 | CTCN_3065 | 19145 |
| GTCN_330 | 8959 | GTCN_1796 | 19146 |
| TTCN_656 | 8960 | CTCN_3066 | 19147 |
| ATCN_385 | 8961 | GTCN_1797 | 19148 |
| GTCN_331 | 8962 | TTCN_3486 | 19149 |
| ATCN_386 | 8963 | CTCN_3067 | 19150 |
| ATCN_387 | 8964 | TTCN_3487 | 19151 |
| CTCN_502 | 8965 | ATCN_2161 | 19152 |
| GTCN_332 | 8966 | CTCN_3068 | 19153 |
| GTCN_333 | 8967 | TTCN_3488 | 19154 |
| GTCN_334 | 8968 | GTCN_1798 | 19155 |
| CTCN_503 | 8969 | TTCN_3489 | 19156 |
| CTCN_504 | 8970 | ATCN_2162 | 19157 |
| CTCN_505 | 8971 | CTCN_3069 | 19158 |
| TTCN_657 | 8972 | GTCN_1799 | 19159 |
| TTCN_658 | 8973 | ATCN_2163 | 19160 |
| ATCN_388 | 8974 | GTCN_1800 | 19161 |
| ATCN_389 | 8975 | ATCN_2164 | 19162 |
| ATCN_390 | 8976 | TTCN_3490 | 19163 |
| CTCN_506 | 8977 | CTCN_3070 | 19164 |
| TTCN_659 | 8978 | CTCN_3071 | 19165 |
| GTCN_335 | 8979 | ATCN_2165 | 19166 |
| CTCN_507 | 8980 | ATCN_2166 | 19167 |
| CTCN_508 | 8981 | CTCN_3072 | 19168 |
| CTCN_509 | 8982 | ATCN_2167 | 19169 |
| CTCN_510 | 8983 | TTCN_3491 | 19170 |
| CTCN_511 | 8984 | CTCN_3073 | 19171 |
| CTCN_512 | 8985 | GTCN_1801 | 19172 |
| TTCN_660 | 8986 | TTCN_3492 | 19173 |
| CTCN_513 | 8987 | TTCN_3493 | 19174 |
| ATCN_391 | 8988 | ATCN_2168 | 19175 |
| CTCN_514 | 8989 | ATCN_2169 | 19176 |
| TTCN_661 | 8990 | TTCN_3494 | 19177 |
| ATCN_392 | 8991 | TTCN_3495 | 19178 |
| TTCN_662 | 8992 | TTCN_3496 | 19179 |
| TTCN_663 | 8993 | CTCN_3074 | 19180 |
| CTCN_515 | 8994 | GTCN_1802 | 19181 |
| ATCN_393 | 8995 | GTCN_1803 | 19182 |
| TTCN_664 | 8996 | ATCN_2170 | 19183 |
| ATCN_394 | 8997 | TTCN_3497 | 19184 |
| ATCN_395 | 8998 | TTCN_3498 | 19185 |
| TTCN_665 | 8999 | GTCN_1804 | 19186 |
| CTCN_516 | 9000 | ATCN_2171 | 19187 |
| GTCN_336 | 9001 | CTCN_3075 | 19188 |
| CTCN_517 | 9002 | GTCN_1805 | 19189 |
| TTCN_666 | 9003 | CTCN_3076 | 19190 |
| TTCN_667 | 9004 | TTCN_3499 | 19191 |
| TTCN_668 | 9005 | CTCN_3077 | 19192 |
| TTCN_669 | 9006 | ATCN_2172 | 19193 |

| | | | |
|---|---|---|---|
| TTCN_670 | 9007 | ATCN_2173 | 19194 |
| GTCN_337 | 9008 | TTCN_3500 | 19195 |
| CTCN_518 | 9009 | GTCN_1806 | 19196 |
| CTCN_519 | 9010 | GTCN_1807 | 19197 |
| TTCN_671 | 9011 | CTCN_3078 | 19198 |
| ATCN_396 | 9012 | GTCN_1808 | 19199 |
| GTCN_338 | 9013 | TTCN_3501 | 19200 |
| TTCN_672 | 9014 | TTCN_3502 | 19201 |
| ATCN_397 | 9015 | GTCN_1809 | 19202 |
| TTCN_673 | 9016 | ATCN_2174 | 19203 |
| TTCN_674 | 9017 | ATCN_2175 | 19204 |
| TTCN_675 | 9018 | GTCN_1810 | 19205 |
| TTCN_676 | 9019 | GTCN_1811 | 19206 |
| TTCN_677 | 9020 | CTCN_3079 | 19207 |
| CTCN_520 | 9021 | ATCN_2176 | 19208 |
| CTCN_521 | 9022 | TTCN_3503 | 19209 |
| ATCN_398 | 9023 | CTCN_3080 | 19210 |
| ATCN_399 | 9024 | ATCN_2177 | 19211 |
| TTCN_678 | 9025 | CTCN_3081 | 19212 |
| GTCN_339 | 9026 | TTCN_3504 | 19213 |
| TTCN_679 | 9027 | GTCN_1812 | 19214 |
| TTCN_680 | 9028 | CTCN_3082 | 19215 |
| ATCN_400 | 9029 | TTCN_3505 | 19216 |
| ATCN_401 | 9030 | TTCN_3506 | 19217 |
| ATCN_402 | 9031 | ATCN_2178 | 19218 |
| ATCN_403 | 9032 | TTCN_3507 | 19219 |
| TTCN_681 | 9033 | CTCN_3083 | 19220 |
| CTCN_522 | 9034 | TTCN_3508 | 19221 |
| TTCN_682 | 9035 | ATCN_2179 | 19222 |
| CTCN_523 | 9036 | ATCN_2180 | 19223 |
| CTCN_524 | 9037 | ATCN_2181 | 19224 |
| TTCN_683 | 9038 | ATCN_2182 | 19225 |
| TTCN_684 | 9039 | CTCN_3084 | 19226 |
| ATCN_404 | 9040 | TTCN_3509 | 19227 |
| ATCN_405 | 9041 | CTCN_3085 | 19228 |
| TTCN_685 | 9042 | CTCN_3086 | 19229 |
| CTCN_525 | 9043 | TTCN_3510 | 19230 |
| ATCN_406 | 9044 | TTCN_3511 | 19231 |
| ATCN_407 | 9045 | TTCN_3512 | 19232 |
| CTCN_526 | 9046 | TTCN_3513 | 19233 |
| CTCN_527 | 9047 | GTCN_1813 | 19234 |
| GTCN_340 | 9048 | TTCN_3514 | 19235 |
| TTCN_686 | 9049 | TTCN_3515 | 19236 |
| ATCN_408 | 9050 | ATCN_2183 | 19237 |
| ATCN_409 | 9051 | ATCN_2184 | 19238 |
| ATCN_410 | 9052 | TTCN_3516 | 19239 |
| ATCN_411 | 9053 | ATCN_2185 | 19240 |
| ATCN_412 | 9054 | ATCN_2186 | 19241 |
| GTCN_341 | 9055 | ATCN_2187 | 19242 |
| CTCN_528 | 9056 | TTCN_3517 | 19243 |
| CTCN_529 | 9057 | GTCN_1814 | 19244 |
| CTCN_530 | 9058 | CTCN_3087 | 19245 |
| TTCN_687 | 9059 | TTCN_3518 | 19246 |
| ATCN_413 | 9060 | ATCN_2188 | 19247 |
| ATCN_414 | 9061 | GTCN_1815 | 19248 |

FIG. 36 (continued)

| | | | |
|---|---|---|---|
| CTCN_531 | 9062 | TTCN_3519 | 19249 |
| CTCN_532 | 9063 | TTCN_3520 | 19250 |
| CTCN_533 | 9064 | CTCN_3088 | 19251 |
| TTCN_688 | 9065 | TTCN_3521 | 19252 |
| GTCN_342 | 9066 | TTCN_3522 | 19253 |
| TTCN_689 | 9067 | TTCN_3523 | 19254 |
| CTCN_534 | 9068 | TTCN_3524 | 19255 |
| CTCN_535 | 9069 | CTCN_3089 | 19256 |
| CTCN_536 | 9070 | TTCN_3525 | 19257 |
| TTCN_690 | 9071 | ATCN_2189 | 19258 |
| CTCN_537 | 9072 | ATCN_2190 | 19259 |
| GTCN_343 | 9073 | CTCN_3090 | 19260 |
| ATCN_415 | 9074 | ATCN_2191 | 19261 |
| ATCN_416 | 9075 | GTCN_1816 | 19262 |
| ATCN_417 | 9076 | TTCN_3526 | 19263 |
| ATCN_418 | 9077 | TTCN_3527 | 19264 |
| GTCN_344 | 9078 | CTCN_3091 | 19265 |
| GTCN_345 | 9079 | CTCN_3092 | 19266 |
| CTCN_538 | 9080 | GTCN_1817 | 19267 |
| TTCN_691 | 9081 | CTCN_3093 | 19268 |
| CTCN_539 | 9082 | CTCN_3094 | 19269 |
| GTCN_346 | 9083 | CTCN_3095 | 19270 |
| CTCN_540 | 9084 | TTCN_3528 | 19271 |
| TTCN_692 | 9085 | CTCN_3096 | 19272 |
| ATCN_419 | 9086 | CTCN_3097 | 19273 |
| GTCN_347 | 9087 | CTCN_3098 | 19274 |
| ATCN_420 | 9088 | CTCN_3099 | 19275 |
| ATCN_421 | 9089 | GTCN_1818 | 19276 |
| TTCN_693 | 9090 | ATCN_2192 | 19277 |
| GTCN_348 | 9091 | CTCN_3100 | 19278 |
| TTCN_694 | 9092 | CTCN_3101 | 19279 |
| CTCN_541 | 9093 | CTCN_3102 | 19280 |
| TTCN_695 | 9094 | TTCN_3529 | 19281 |
| ATCN_422 | 9095 | ATCN_2193 | 19282 |
| CTCN_542 | 9096 | TTCN_3530 | 19283 |
| TTCN_696 | 9097 | CTCN_3103 | 19284 |
| TTCN_697 | 9098 | GTCN_1819 | 19285 |
| ATCN_423 | 9099 | TTCN_3531 | 19286 |
| TTCN_698 | 9100 | CTCN_3104 | 19287 |
| GTCN_349 | 9101 | TTCN_3532 | 19288 |
| TTCN_699 | 9102 | CTCN_3105 | 19289 |
| TTCN_700 | 9103 | TTCN_3533 | 19290 |
| TTCN_701 | 9104 | TTCN_3534 | 19291 |
| ATCN_424 | 9105 | CTCN_3106 | 19292 |
| TTCN_702 | 9106 | GTCN_1820 | 19293 |
| ATCN_425 | 9107 | TTCN_3535 | 19294 |
| GTCN_350 | 9108 | ATCN_2194 | 19295 |
| CTCN_543 | 9109 | CTCN_3107 | 19296 |
| CTCN_544 | 9110 | CTCN_3108 | 19297 |
| TTCN_703 | 9111 | GTCN_1821 | 19298 |
| TTCN_704 | 9112 | CTCN_3109 | 19299 |
| TTCN_705 | 9113 | GTCN_1822 | 19300 |
| GTCN_351 | 9114 | GTCN_1823 | 19301 |
| TTCN_706 | 9115 | TTCN_3536 | 19302 |
| GTCN_352 | 9116 | ATCN_2195 | 19303 |
| ATCN_426 | 9117 | TTCN_3537 | 19304 |
| GTCN_353 | 9118 | GTCN_1824 | 19305 |
| TTCN_707 | 9119 | GTCN_1825 | 19306 |
| TTCN_708 | 9120 | ATCN_2196 | 19307 |
| CTCN_545 | 9121 | TTCN_3538 | 19308 |
| TTCN_709 | 9122 | TTCN_3539 | 19309 |
| TTCN_710 | 9123 | ATCN_2197 | 19310 |
| ATCN_427 | 9124 | GTCN_1826 | 19311 |
| TTCN_711 | 9125 | ATCN_2198 | 19312 |
| ATCN_428 | 9126 | ATCN_2199 | 19313 |
| ATCN_429 | 9127 | CTCN_3110 | 19314 |
| ATCN_430 | 9128 | TTCN_3540 | 19315 |
| ATCN_431 | 9129 | TTCN_3541 | 19316 |
| GTCN_354 | 9130 | TTCN_3542 | 19317 |
| TTCN_712 | 9131 | GTCN_1827 | 19318 |
| TTCN_713 | 9132 | ATCN_2200 | 19319 |
| CTCN_546 | 9133 | ATCN_2201 | 19320 |
| TTCN_714 | 9134 | TTCN_3543 | 19321 |
| GTCN_355 | 9135 | TTCN_3544 | 19322 |
| TTCN_715 | 9136 | TTCN_3545 | 19323 |
| TTCN_716 | 9137 | CTCN_3111 | 19324 |
| ATCN_432 | 9138 | TTCN_3546 | 19325 |
| ATCN_433 | 9139 | GTCN_1828 | 19326 |
| CTCN_547 | 9140 | TTCN_3547 | 19327 |
| GTCN_356 | 9141 | ATCN_2202 | 19328 |
| ATCN_434 | 9142 | ATCN_2203 | 19329 |
| GTCN_357 | 9143 | ATCN_2204 | 19330 |
| TTCN_717 | 9144 | ATCN_2205 | 19331 |
| TTCN_718 | 9145 | ATCN_2206 | 19332 |
| TTCN_719 | 9146 | TTCN_3548 | 19333 |
| ATCN_435 | 9147 | TTCN_3549 | 19334 |
| GTCN_358 | 9148 | ATCN_2207 | 19335 |
| ATCN_436 | 9149 | GTCN_1829 | 19336 |
| TTCN_720 | 9150 | CTCN_3112 | 19337 |
| CTCN_548 | 9151 | CTCN_3113 | 19338 |
| TTCN_721 | 9152 | GTCN_1830 | 19339 |
| CTCN_549 | 9153 | CTCN_3114 | 19340 |
| TTCN_722 | 9154 | GTCN_1831 | 19341 |
| TTCN_723 | 9155 | GTCN_1832 | 19342 |
| TTCN_724 | 9156 | CTCN_3115 | 19343 |
| TTCN_725 | 9157 | CTCN_3116 | 19344 |
| CTCN_550 | 9158 | ATCN_2208 | 19345 |
| TTCN_726 | 9159 | TTCN_3550 | 19346 |
| ATCN_437 | 9160 | GTCN_1833 | 19347 |
| CTCN_551 | 9161 | ATCN_2209 | 19348 |
| TTCN_727 | 9162 | TTCN_3551 | 19349 |
| CTCN_552 | 9163 | TTCN_3552 | 19350 |
| GTCN_359 | 9164 | ATCN_2210 | 19351 |
| TTCN_728 | 9165 | CTCN_3117 | 19352 |
| TTCN_729 | 9166 | CTCN_3118 | 19353 |
| CTCN_553 | 9167 | TTCN_3553 | 19354 |
| TTCN_730 | 9168 | CTCN_3119 | 19355 |
| ATCN_438 | 9169 | CTCN_3120 | 19356 |
| CTCN_554 | 9170 | GTCN_1834 | 19357 |
| CTCN_555 | 9171 | TTCN_3554 | 19358 |

FIG. 36 (continued)

| | | | |
|---|---|---|---|
| TTCN_731 | 9172 | TTCN_3555 | 19359 |
| ATCN_439 | 9173 | GTCN_1835 | 19360 |
| CTCN_556 | 9174 | GTCN_1836 | 19361 |
| TTCN_732 | 9175 | TTCN_3556 | 19362 |
| ATCN_440 | 9176 | TTCN_3557 | 19363 |
| TTCN_733 | 9177 | TTCN_3558 | 19364 |
| CTCN_557 | 9178 | GTCN_1837 | 19365 |
| ATCN_441 | 9179 | GTCN_1838 | 19366 |
| TTCN_734 | 9180 | ATCN_2211 | 19367 |
| ATCN_442 | 9181 | GTCN_1839 | 19368 |
| CTCN_558 | 9182 | CTCN_3121 | 19369 |
| TTCN_735 | 9183 | CTCN_3122 | 19370 |
| GTCN_360 | 9184 | TTCN_3559 | 19371 |
| CTCN_559 | 9185 | TTCN_3560 | 19372 |
| ATCN_443 | 9186 | TTCN_3561 | 19373 |
| ATCN_444 | 9187 | TTCN_3562 | 19374 |
| TTCN_736 | 9188 | TTCN_3563 | 19375 |
| CTCN_560 | 9189 | GTCN_1840 | 19376 |
| CTCN_561 | 9190 | TTCN_3564 | 19377 |
| ATCN_445 | 9191 | CTCN_3123 | 19378 |
| TTCN_737 | 9192 | GTCN_1841 | 19379 |
| CTCN_562 | 9193 | GTCN_1842 | 19380 |
| TTCN_738 | 9194 | CTCN_3124 | 19381 |
| CTCN_563 | 9195 | ATCN_2212 | 19382 |
| TTCN_739 | 9196 | ATCN_2213 | 19383 |
| CTCN_564 | 9197 | TTCN_3565 | 19384 |
| TTCN_740 | 9198 | CTCN_3125 | 19385 |
| GTCN_361 | 9199 | GTCN_1843 | 19386 |
| TTCN_741 | 9200 | GTCN_1844 | 19387 |
| CTCN_565 | 9201 | GTCN_1845 | 19388 |
| GTCN_362 | 9202 | CTCN_3126 | 19389 |
| TTCN_742 | 9203 | CTCN_3127 | 19390 |
| CTCN_566 | 9204 | GTCN_1846 | 19391 |
| TTCN_743 | 9205 | CTCN_3128 | 19392 |
| ATCN_446 | 9206 | TTCN_3566 | 19393 |
| CTCN_567 | 9207 | TTCN_3567 | 19394 |
| TTCN_744 | 9208 | CTCN_3129 | 19395 |
| ATCN_447 | 9209 | ATCN_2214 | 19396 |
| ATCN_448 | 9210 | ATCN_2215 | 19397 |
| CTCN_568 | 9211 | ATCN_2216 | 19398 |
| TTCN_745 | 9212 | CTCN_3130 | 19399 |
| ATCN_449 | 9213 | ATCN_2217 | 19400 |
| TTCN_746 | 9214 | ATCN_2218 | 19401 |
| TTCN_747 | 9215 | TTCN_3568 | 19402 |
| CTCN_569 | 9216 | GTCN_1847 | 19403 |
| ATCN_450 | 9217 | CTCN_3131 | 19404 |
| ATCN_451 | 9218 | CTCN_3132 | 19405 |
| GTCN_363 | 9219 | CTCN_3133 | 19406 |
| CTCN_570 | 9220 | CTCN_3134 | 19407 |
| ATCN_452 | 9221 | GTCN_1848 | 19408 |
| CTCN_571 | 9222 | ATCN_2219 | 19409 |
| TTCN_748 | 9223 | GTCN_1849 | 19410 |
| CTCN_572 | 9224 | ATCN_2220 | 19411 |
| ATCN_453 | 9225 | ATCN_2221 | 19412 |
| TTCN_749 | 9226 | CTCN_3135 | 19413 |

| | | | |
|---|---|---|---|
| TTCN_750 | 9227 | TTCN_3569 | 19414 |
| CTCN_573 | 9228 | GTCN_1850 | 19415 |
| ATCN_454 | 9229 | GTCN_1851 | 19416 |
| TTCN_751 | 9230 | TTCN_3570 | 19417 |
| TTCN_752 | 9231 | TTCN_3571 | 19418 |
| ATCN_455 | 9232 | TTCN_3572 | 19419 |
| TTCN_753 | 9233 | CTCN_3136 | 19420 |
| TTCN_754 | 9234 | ATCN_2222 | 19421 |
| CTCN_574 | 9235 | GTCN_1852 | 19422 |
| TTCN_755 | 9236 | CTCN_3137 | 19423 |
| CTCN_575 | 9237 | CTCN_3138 | 19424 |
| TTCN_756 | 9238 | TTCN_3573 | 19425 |
| CTCN_576 | 9239 | TTCN_3574 | 19426 |
| ATCN_456 | 9240 | ATCN_2223 | 19427 |
| TTCN_757 | 9241 | CTCN_3139 | 19428 |
| CTCN_577 | 9242 | CTCN_3140 | 19429 |
| TTCN_758 | 9243 | CTCN_3141 | 19430 |
| CTCN_578 | 9244 | ATCN_2224 | 19431 |
| ATCN_457 | 9245 | GTCN_1853 | 19432 |
| GTCN_364 | 9246 | CTCN_3142 | 19433 |
| CTCN_579 | 9247 | CTCN_3143 | 19434 |
| TTCN_759 | 9248 | CTCN_3144 | 19435 |
| GTCN_365 | 9249 | GTCN_1854 | 19436 |
| ATCN_458 | 9250 | CTCN_3145 | 19437 |
| CTCN_580 | 9251 | CTCN_3146 | 19438 |
| GTCN_366 | 9252 | CTCN_3147 | 19439 |
| CTCN_581 | 9253 | GTCN_1855 | 19440 |
| ATCN_459 | 9254 | CTCN_3148 | 19441 |
| ATCN_460 | 9255 | CTCN_3149 | 19442 |
| TTCN_760 | 9256 | ATCN_2225 | 19443 |
| CTCN_582 | 9257 | ATCN_2226 | 19444 |
| CTCN_583 | 9258 | TTCN_3575 | 19445 |
| GTCN_367 | 9259 | ATCN_2227 | 19446 |
| GTCN_368 | 9260 | ATCN_2228 | 19447 |
| GTCN_369 | 9261 | ATCN_2229 | 19448 |
| TTCN_761 | 9262 | GTCN_1856 | 19449 |
| ATCN_461 | 9263 | CTCN_3150 | 19450 |
| ATCN_462 | 9264 | CTCN_3151 | 19451 |
| ATCN_463 | 9265 | GTCN_1857 | 19452 |
| TTCN_762 | 9266 | TTCN_3576 | 19453 |
| CTCN_584 | 9267 | ATCN_2230 | 19454 |
| TTCN_763 | 9268 | GTCN_1858 | 19455 |
| CTCN_585 | 9269 | CTCN_3152 | 19456 |
| TTCN_764 | 9270 | TTCN_3577 | 19457 |
| GTCN_370 | 9271 | ATCN_2231 | 19458 |
| CTCN_586 | 9272 | CTCN_3153 | 19459 |
| CTCN_587 | 9273 | CTCN_3154 | 19460 |
| CTCN_588 | 9274 | CTCN_3155 | 19461 |
| CTCN_589 | 9275 | TTCN_3578 | 19462 |
| GTCN_371 | 9276 | TTCN_3579 | 19463 |
| ATCN_464 | 9277 | TTCN_3580 | 19464 |
| ATCN_465 | 9278 | ATCN_2232 | 19465 |
| ATCN_466 | 9279 | TTCN_3581 | 19466 |
| ATCN_467 | 9280 | CTCN_3156 | 19467 |
| TTCN_765 | 9281 | CTCN_3157 | 19468 |

FIG. 36 (continued)

| | | | |
|---|---|---|---|
| GTCN_372 | 9282 | ATCN_2233 | 19469 |
| CTCN_590 | 9283 | CTCN_3158 | 19470 |
| TTCN_766 | 9284 | CTCN_3159 | 19471 |
| TTCN_767 | 9285 | TTCN_3582 | 19472 |
| TTCN_768 | 9286 | CTCN_3160 | 19473 |
| CTCN_591 | 9287 | CTCN_3161 | 19474 |
| CTCN_592 | 9288 | CTCN_3162 | 19475 |
| CTCN_593 | 9289 | GTCN_1859 | 19476 |
| CTCN_594 | 9290 | TTCN_3583 | 19477 |
| ATCN_468 | 9291 | TTCN_3584 | 19478 |
| TTCN_769 | 9292 | CTCN_3163 | 19479 |
| GTCN_373 | 9293 | CTCN_3164 | 19480 |
| GTCN_374 | 9294 | GTCN_1860 | 19481 |
| CTCN_595 | 9295 | ATCN_2234 | 19482 |
| ATCN_469 | 9296 | TTCN_3585 | 19483 |
| ATCN_470 | 9297 | TTCN_3586 | 19484 |
| TTCN_770 | 9298 | TTCN_3587 | 19485 |
| GTCN_375 | 9299 | CTCN_3165 | 19486 |
| TTCN_771 | 9300 | GTCN_1861 | 19487 |
| TTCN_772 | 9301 | CTCN_3166 | 19488 |
| TTCN_773 | 9302 | TTCN_3588 | 19489 |
| GTCN_376 | 9303 | CTCN_3167 | 19490 |
| GTCN_377 | 9304 | CTCN_3168 | 19491 |
| TTCN_774 | 9305 | TTCN_3589 | 19492 |
| TTCN_775 | 9306 | CTCN_3169 | 19493 |
| TTCN_776 | 9307 | TTCN_3590 | 19494 |
| CTCN_596 | 9308 | ATCN_2235 | 19495 |
| TTCN_777 | 9309 | GTCN_1862 | 19496 |
| ATCN_471 | 9310 | CTCN_3170 | 19497 |
| TTCN_778 | 9311 | GTCN_1863 | 19498 |
| TTCN_779 | 9312 | CTCN_3171 | 19499 |
| TTCN_780 | 9313 | CTCN_3172 | 19500 |
| GTCN_378 | 9314 | ATCN_2236 | 19501 |
| GTCN_379 | 9315 | TTCN_3591 | 19502 |
| ATCN_472 | 9316 | GTCN_1864 | 19503 |
| TTCN_781 | 9317 | CTCN_3173 | 19504 |
| TTCN_782 | 9318 | ATCN_2237 | 19505 |
| GTCN_380 | 9319 | CTCN_3174 | 19506 |
| CTCN_597 | 9320 | TTCN_3592 | 19507 |
| CTCN_598 | 9321 | CTCN_3175 | 19508 |
| ATCN_473 | 9322 | CTCN_3176 | 19509 |
| CTCN_599 | 9323 | TTCN_3593 | 19510 |
| TTCN_783 | 9324 | TTCN_3594 | 19511 |
| GTCN_381 | 9325 | CTCN_3177 | 19512 |
| CTCN_600 | 9326 | TTCN_3595 | 19513 |
| CTCN_601 | 9327 | CTCN_3178 | 19514 |
| CTCN_602 | 9328 | TTCN_3596 | 19515 |
| GTCN_382 | 9329 | ATCN_2238 | 19516 |
| GTCN_383 | 9330 | CTCN_3179 | 19517 |
| TTCN_784 | 9331 | TTCN_3597 | 19518 |
| TTCN_785 | 9332 | TTCN_3598 | 19519 |
| TTCN_786 | 9333 | TTCN_3599 | 19520 |
| TTCN_787 | 9334 | CTCN_3180 | 19521 |
| TTCN_788 | 9335 | ATCN_2239 | 19522 |
| CTCN_603 | 9336 | CTCN_3181 | 19523 |

| | | | |
|---|---|---|---|
| ATCN_474 | 9337 | GTCN_1865 | 19524 |
| TTCN_789 | 9338 | CTCN_3182 | 19525 |
| GTCN_384 | 9339 | ATCN_2240 | 19526 |
| CTCN_604 | 9340 | CTCN_3183 | 19527 |
| TTCN_790 | 9341 | GTCN_1866 | 19528 |
| ATCN_475 | 9342 | TTCN_3600 | 19529 |
| CTCN_605 | 9343 | ATCN_2241 | 19530 |
| CTCN_606 | 9344 | TTCN_3601 | 19531 |
| CTCN_607 | 9345 | CTCN_3184 | 19532 |
| CTCN_608 | 9346 | ATCN_2242 | 19533 |
| TTCN_791 | 9347 | CTCN_3185 | 19534 |
| CTCN_609 | 9348 | CTCN_3186 | 19535 |
| CTCN_610 | 9349 | CTCN_3187 | 19536 |
| TTCN_792 | 9350 | ATCN_2243 | 19537 |
| CTCN_611 | 9351 | CTCN_3188 | 19538 |
| TTCN_793 | 9352 | ATCN_2244 | 19539 |
| TTCN_794 | 9353 | ATCN_2245 | 19540 |
| CTCN_612 | 9354 | TTCN_3602 | 19541 |
| ATCN_476 | 9355 | CTCN_3189 | 19542 |
| TTCN_795 | 9356 | TTCN_3603 | 19543 |
| GTCN_385 | 9357 | CTCN_3190 | 19544 |
| CTCN_613 | 9358 | GTCN_1867 | 19545 |
| TTCN_796 | 9359 | CTCN_3191 | 19546 |
| CTCN_614 | 9360 | ATCN_2246 | 19547 |
| TTCN_797 | 9361 | TTCN_3604 | 19548 |
| TTCN_798 | 9362 | ATCN_2247 | 19549 |
| GTCN_386 | 9363 | TTCN_3605 | 19550 |
| CTCN_615 | 9364 | CTCN_3192 | 19551 |
| TTCN_799 | 9365 | CTCN_3193 | 19552 |
| GTCN_387 | 9366 | TTCN_3606 | 19553 |
| ATCN_477 | 9367 | TTCN_3607 | 19554 |
| ATCN_478 | 9368 | ATCN_2248 | 19555 |
| TTCN_800 | 9369 | ATCN_2249 | 19556 |
| ATCN_479 | 9370 | TTCN_3608 | 19557 |
| GTCN_388 | 9371 | TTCN_3609 | 19558 |
| ATCN_480 | 9372 | TTCN_3610 | 19559 |
| CTCN_616 | 9373 | CTCN_3194 | 19560 |
| GTCN_389 | 9374 | TTCN_3611 | 19561 |
| CTCN_617 | 9375 | TTCN_3612 | 19562 |
| ATCN_481 | 9376 | TTCN_3613 | 19563 |
| ATCN_482 | 9377 | ATCN_2250 | 19564 |
| CTCN_618 | 9378 | CTCN_3195 | 19565 |
| GTCN_390 | 9379 | ATCN_2251 | 19566 |
| CTCN_619 | 9380 | ATCN_2252 | 19567 |
| GTCN_391 | 9381 | GTCN_1868 | 19568 |
| TTCN_801 | 9382 | CTCN_3196 | 19569 |
| TTCN_802 | 9383 | GTCN_1869 | 19570 |
| CTCN_620 | 9384 | GTCN_1870 | 19571 |
| CTCN_621 | 9385 | ATCN_2253 | 19572 |
| GTCN_392 | 9386 | CTCN_3197 | 19573 |
| TTCN_803 | 9387 | TTCN_3614 | 19574 |
| TTCN_804 | 9388 | ATCN_2254 | 19575 |
| ATCN_483 | 9389 | TTCN_3615 | 19576 |
| TTCN_805 | 9390 | CTCN_3198 | 19577 |
| TTCN_806 | 9391 | GTCN_1871 | 19578 |

FIG. 36 (continued)

| | | | |
|---|---|---|---|
| TTCN_807 | 9392 | GTCN_1872 | 19579 |
| ATCN_484 | 9393 | CTCN_3199 | 19580 |
| TTCN_808 | 9394 | GTCN_1873 | 19581 |
| ATCN_485 | 9395 | ATCN_2255 | 19582 |
| CTCN_622 | 9396 | ATCN_2256 | 19583 |
| ATCN_486 | 9397 | GTCN_1874 | 19584 |
| TTCN_809 | 9398 | CTCN_3200 | 19585 |
| GTCN_393 | 9399 | CTCN_3201 | 19586 |
| TTCN_810 | 9400 | TTCN_3616 | 19587 |
| CTCN_623 | 9401 | CTCN_3202 | 19588 |
| TTCN_811 | 9402 | ATCN_2257 | 19589 |
| GTCN_394 | 9403 | ATCN_2258 | 19590 |
| GTCN_395 | 9404 | GTCN_1875 | 19591 |
| GTCN_396 | 9405 | ATCN_2259 | 19592 |
| TTCN_812 | 9406 | ATCN_2260 | 19593 |
| TTCN_813 | 9407 | CTCN_3203 | 19594 |
| TTCN_814 | 9408 | GTCN_1876 | 19595 |
| CTCN_624 | 9409 | ATCN_2261 | 19596 |
| ATCN_487 | 9410 | ATCN_2262 | 19597 |
| GTCN_397 | 9411 | TTCN_3617 | 19598 |
| GTCN_398 | 9412 | GTCN_1877 | 19599 |
| TTCN_815 | 9413 | CTCN_3204 | 19600 |
| ATCN_488 | 9414 | CTCN_3205 | 19601 |
| TTCN_816 | 9415 | GTCN_1878 | 19602 |
| TTCN_817 | 9416 | CTCN_3206 | 19603 |
| TTCN_818 | 9417 | ATCN_2263 | 19604 |
| TTCN_819 | 9418 | GTCN_1879 | 19605 |
| GTCN_399 | 9419 | GTCN_1880 | 19606 |
| TTCN_820 | 9420 | GTCN_1881 | 19607 |
| GTCN_400 | 9421 | TTCN_3618 | 19608 |
| ATCN_489 | 9422 | ATCN_2264 | 19609 |
| GTCN_401 | 9423 | ATCN_2265 | 19610 |
| CTCN_625 | 9424 | TTCN_3619 | 19611 |
| ATCN_490 | 9425 | CTCN_3207 | 19612 |
| TTCN_821 | 9426 | GTCN_1882 | 19613 |
| CTCN_626 | 9427 | ATCN_2266 | 19614 |
| ATCN_491 | 9428 | TTCN_3620 | 19615 |
| ATCN_492 | 9429 | ATCN_2267 | 19616 |
| CTCN_627 | 9430 | ATCN_2268 | 19617 |
| CTCN_628 | 9431 | GTCN_1883 | 19618 |
| GTCN_402 | 9432 | GTCN_1884 | 19619 |
| GTCN_403 | 9433 | CTCN_3208 | 19620 |
| GTCN_404 | 9434 | GTCN_1885 | 19621 |
| TTCN_822 | 9435 | GTCN_1886 | 19622 |
| TTCN_823 | 9436 | TTCN_3621 | 19623 |
| TTCN_824 | 9437 | CTCN_3209 | 19624 |
| TTCN_825 | 9438 | CTCN_3210 | 19625 |
| GTCN_405 | 9439 | ATCN_2269 | 19626 |
| ATCN_493 | 9440 | GTCN_1887 | 19627 |
| CTCN_629 | 9441 | TTCN_3622 | 19628 |
| ATCN_494 | 9442 | TTCN_3623 | 19629 |
| CTCN_630 | 9443 | TTCN_3624 | 19630 |
| ATCN_495 | 9444 | GTCN_1888 | 19631 |
| TTCN_826 | 9445 | TTCN_3625 | 19632 |
| GTCN_406 | 9446 | TTCN_3626 | 19633 |

| | | | |
|---|---|---|---|
| GTCN_407 | 9447 | TTCN_3627 | 19634 |
| ATCN_496 | 9448 | TTCN_3628 | 19635 |
| TTCN_827 | 9449 | TTCN_3629 | 19636 |
| ATCN_497 | 9450 | TTCN_3630 | 19637 |
| TTCN_828 | 9451 | TTCN_3631 | 19638 |
| TTCN_829 | 9452 | CTCN_3211 | 19639 |
| GTCN_408 | 9453 | CTCN_3212 | 19640 |
| TTCN_830 | 9454 | GTCN_1889 | 19641 |
| GTCN_409 | 9455 | ATCN_2270 | 19642 |
| TTCN_831 | 9456 | GTCN_1890 | 19643 |
| TTCN_832 | 9457 | CTCN_3213 | 19644 |
| TTCN_833 | 9458 | CTCN_3214 | 19645 |
| TTCN_834 | 9459 | ATCN_2271 | 19646 |
| GTCN_410 | 9460 | GTCN_1891 | 19647 |
| CTCN_631 | 9461 | CTCN_3215 | 19648 |
| TTCN_835 | 9462 | ATCN_2272 | 19649 |
| TTCN_836 | 9463 | CTCN_3216 | 19650 |
| ATCN_498 | 9464 | TTCN_3632 | 19651 |
| CTCN_632 | 9465 | CTCN_3217 | 19652 |
| GTCN_411 | 9466 | TTCN_3633 | 19653 |
| CTCN_633 | 9467 | GTCN_1892 | 19654 |
| TTCN_837 | 9468 | CTCN_3218 | 19655 |
| CTCN_634 | 9469 | TTCN_3634 | 19656 |
| TTCN_838 | 9470 | GTCN_1893 | 19657 |
| ATCN_499 | 9471 | TTCN_3635 | 19658 |
| CTCN_635 | 9472 | ATCN_2273 | 19659 |
| TTCN_839 | 9473 | TTCN_3636 | 19660 |
| CTCN_636 | 9474 | CTCN_3219 | 19661 |
| GTCN_412 | 9475 | TTCN_3637 | 19662 |
| CTCN_637 | 9476 | CTCN_3220 | 19663 |
| TTCN_840 | 9477 | CTCN_3221 | 19664 |
| CTCN_638 | 9478 | CTCN_3222 | 19665 |
| TTCN_841 | 9479 | GTCN_1894 | 19666 |
| ATCN_500 | 9480 | CTCN_3223 | 19667 |
| TTCN_842 | 9481 | CTCN_3224 | 19668 |
| ATCN_501 | 9482 | CTCN_3225 | 19669 |
| TTCN_843 | 9483 | TTCN_3638 | 19670 |
| CTCN_639 | 9484 | CTCN_3226 | 19671 |
| CTCN_640 | 9485 | GTCN_1895 | 19672 |
| TTCN_844 | 9486 | CTCN_3227 | 19673 |
| CTCN_641 | 9487 | TTCN_3639 | 19674 |
| TTCN_845 | 9488 | CTCN_3228 | 19675 |
| TTCN_846 | 9489 | TTCN_3640 | 19676 |
| TTCN_847 | 9490 | TTCN_3641 | 19677 |
| TTCN_848 | 9491 | CTCN_3229 | 19678 |
| CTCN_642 | 9492 | CTCN_3230 | 19679 |
| TTCN_849 | 9493 | CTCN_3231 | 19680 |
| ATCN_502 | 9494 | TTCN_3642 | 19681 |
| CTCN_643 | 9495 | CTCN_3232 | 19682 |
| TTCN_850 | 9496 | GTCN_1896 | 19683 |
| ATCN_503 | 9497 | ATCN_2274 | 19684 |
| CTCN_644 | 9498 | TTCN_3643 | 19685 |
| TTCN_851 | 9499 | CTCN_3233 | 19686 |
| ATCN_504 | 9500 | GTCN_1897 | 19687 |
| CTCN_645 | 9501 | GTCN_1898 | 19688 |

FIG. 36 (continued)

| | | | |
|---|---|---|---|
| TTCN_852 | 9502 | CTCN_3234 | 19689 |
| ATCN_505 | 9503 | GTCN_1899 | 19690 |
| TTCN_853 | 9504 | CTCN_3235 | 19691 |
| CTCN_646 | 9505 | ATCN_2275 | 19692 |
| ATCN_506 | 9506 | ATCN_2276 | 19693 |
| GTCN_413 | 9507 | TTCN_3644 | 19694 |
| ATCN_507 | 9508 | TTCN_3645 | 19695 |
| TTCN_854 | 9509 | CTCN_3236 | 19696 |
| TTCN_855 | 9510 | TTCN_3646 | 19697 |
| ATCN_508 | 9511 | GTCN_1900 | 19698 |
| TTCN_856 | 9512 | ATCN_2277 | 19699 |
| GTCN_414 | 9513 | CTCN_3237 | 19700 |
| TTCN_857 | 9514 | CTCN_3238 | 19701 |
| GTCN_415 | 9515 | TTCN_3647 | 19702 |
| TTCN_858 | 9516 | TTCN_3648 | 19703 |
| TTCN_859 | 9517 | CTCN_3239 | 19704 |
| CTCN_647 | 9518 | ATCN_2278 | 19705 |
| CTCN_648 | 9519 | GTCN_1901 | 19706 |
| TTCN_860 | 9520 | TTCN_3649 | 19707 |
| TTCN_861 | 9521 | GTCN_1902 | 19708 |
| TTCN_862 | 9522 | TTCN_3650 | 19709 |
| GTCN_416 | 9523 | ATCN_2279 | 19710 |
| CTCN_649 | 9524 | TTCN_3651 | 19711 |
| CTCN_650 | 9525 | CTCN_3240 | 19712 |
| GTCN_417 | 9526 | CTCN_3241 | 19713 |
| CTCN_651 | 9527 | TTCN_3652 | 19714 |
| TTCN_863 | 9528 | TTCN_3653 | 19715 |
| GTCN_418 | 9529 | GTCN_1903 | 19716 |
| GTCN_419 | 9530 | GTCN_1904 | 19717 |
| GTCN_420 | 9531 | TTCN_3654 | 19718 |
| ATCN_509 | 9532 | CTCN_3242 | 19719 |
| ATCN_510 | 9533 | CTCN_3243 | 19720 |
| ATCN_511 | 9534 | TTCN_3655 | 19721 |
| TTCN_864 | 9535 | TTCN_3656 | 19722 |
| TTCN_865 | 9536 | TTCN_3657 | 19723 |
| TTCN_866 | 9537 | ATCN_2280 | 19724 |
| TTCN_867 | 9538 | CTCN_3244 | 19725 |
| ATCN_512 | 9539 | CTCN_3245 | 19726 |
| TTCN_868 | 9540 | GTCN_1905 | 19727 |
| TTCN_869 | 9541 | CTCN_3246 | 19728 |
| TTCN_870 | 9542 | GTCN_1906 | 19729 |
| CTCN_652 | 9543 | CTCN_3247 | 19730 |
| CTCN_653 | 9544 | CTCN_3248 | 19731 |
| TTCN_871 | 9545 | CTCN_3249 | 19732 |
| ATCN_513 | 9546 | TTCN_3658 | 19733 |
| TTCN_872 | 9547 | CTCN_3250 | 19734 |
| CTCN_654 | 9548 | TTCN_3659 | 19735 |
| ATCN_514 | 9549 | CTCN_3251 | 19736 |
| CTCN_655 | 9550 | CTCN_3252 | 19737 |
| TTCN_873 | 9551 | TTCN_3660 | 19738 |
| CTCN_656 | 9552 | TTCN_3661 | 19739 |
| ATCN_515 | 9553 | CTCN_3253 | 19740 |
| TTCN_874 | 9554 | GTCN_1907 | 19741 |
| CTCN_657 | 9555 | TTCN_3662 | 19742 |
| ATCN_516 | 9556 | CTCN_3254 | 19743 |

| | | | |
|---|---|---|---|
| TTCN_875 | 9557 | CTCN_3255 | 19744 |
| GTCN_421 | 9558 | GTCN_1908 | 19745 |
| CTCN_658 | 9559 | TTCN_3663 | 19746 |
| CTCN_659 | 9560 | GTCN_1909 | 19747 |
| ATCN_517 | 9561 | TTCN_3664 | 19748 |
| TTCN_876 | 9562 | ATCN_2281 | 19749 |
| CTCN_660 | 9563 | ATCN_2282 | 19750 |
| ATCN_518 | 9564 | TTCN_3665 | 19751 |
| TTCN_877 | 9565 | CTCN_3256 | 19752 |
| TTCN_878 | 9566 | GTCN_1910 | 19753 |
| ATCN_519 | 9567 | TTCN_3666 | 19754 |
| TTCN_879 | 9568 | CTCN_3257 | 19755 |
| ATCN_520 | 9569 | ATCN_2283 | 19756 |
| ATCN_521 | 9570 | CTCN_3258 | 19757 |
| CTCN_661 | 9571 | CTCN_3259 | 19758 |
| CTCN_662 | 9572 | CTCN_3260 | 19759 |
| ATCN_522 | 9573 | ATCN_2284 | 19760 |
| GTCN_422 | 9574 | CTCN_3261 | 19761 |
| GTCN_423 | 9575 | CTCN_3262 | 19762 |
| CTCN_663 | 9576 | CTCN_3263 | 19763 |
| GTCN_424 | 9577 | TTCN_3667 | 19764 |
| ATCN_523 | 9578 | ATCN_2285 | 19765 |
| GTCN_425 | 9579 | TTCN_3668 | 19766 |
| TTCN_880 | 9580 | CTCN_3264 | 19767 |
| CTCN_664 | 9581 | CTCN_3265 | 19768 |
| TTCN_881 | 9582 | CTCN_3266 | 19769 |
| GTCN_426 | 9583 | CTCN_3267 | 19770 |
| CTCN_665 | 9584 | CTCN_3268 | 19771 |
| TTCN_882 | 9585 | ATCN_2286 | 19772 |
| GTCN_427 | 9586 | CTCN_3269 | 19773 |
| CTCN_666 | 9587 | GTCN_1911 | 19774 |
| GTCN_428 | 9588 | TTCN_3669 | 19775 |
| TTCN_883 | 9589 | GTCN_1912 | 19776 |
| TTCN_884 | 9590 | CTCN_3270 | 19777 |
| ATCN_524 | 9591 | TTCN_3670 | 19778 |
| TTCN_885 | 9592 | CTCN_3271 | 19779 |
| CTCN_667 | 9593 | GTCN_1913 | 19780 |
| TTCN_886 | 9594 | CTCN_3272 | 19781 |
| TTCN_887 | 9595 | ATCN_2287 | 19782 |
| CTCN_668 | 9596 | ATCN_2288 | 19783 |
| TTCN_888 | 9597 | TTCN_3671 | 19784 |
| TTCN_889 | 9598 | CTCN_3273 | 19785 |
| CTCN_669 | 9599 | ATCN_2289 | 19786 |
| TTCN_890 | 9600 | CTCN_3274 | 19787 |
| TTCN_891 | 9601 | TTCN_3672 | 19788 |
| ATCN_525 | 9602 | ATCN_2290 | 19789 |
| GTCN_429 | 9603 | ATCN_2291 | 19790 |
| ATCN_526 | 9604 | ATCN_2292 | 19791 |
| TTCN_892 | 9605 | CTCN_3275 | 19792 |
| ATCN_527 | 9606 | CTCN_3276 | 19793 |
| TTCN_893 | 9607 | CTCN_3277 | 19794 |
| CTCN_670 | 9608 | CTCN_3278 | 19795 |
| ATCN_528 | 9609 | TTCN_3673 | 19796 |
| TTCN_894 | 9610 | TTCN_3674 | 19797 |
| TTCN_895 | 9611 | CTCN_3279 | 19798 |

FIG. 36 (continued)

| | | | |
|---|---|---|---|
| CTCN_671 | 9612 | CTCN_3280 | 19799 |
| ATCN_529 | 9613 | CTCN_3281 | 19800 |
| TTCN_896 | 9614 | ATCN_2293 | 19801 |
| TTCN_897 | 9615 | ATCN_2294 | 19802 |
| GTCN_430 | 9616 | CTCN_3282 | 19803 |
| TTCN_898 | 9617 | CTCN_3283 | 19804 |
| CTCN_672 | 9618 | TTCN_3675 | 19805 |
| CTCN_673 | 9619 | TTCN_3676 | 19806 |
| TTCN_899 | 9620 | TTCN_3677 | 19807 |
| CTCN_674 | 9621 | ATCN_2295 | 19808 |
| TTCN_900 | 9622 | CTCN_3284 | 19809 |
| CTCN_675 | 9623 | TTCN_3678 | 19810 |
| ATCN_530 | 9624 | CTCN_3285 | 19811 |
| TTCN_901 | 9625 | ATCN_2296 | 19812 |
| CTCN_676 | 9626 | ATCN_2297 | 19813 |
| ATCN_531 | 9627 | TTCN_3679 | 19814 |
| TTCN_902 | 9628 | ATCN_2298 | 19815 |
| TTCN_903 | 9629 | CTCN_3286 | 19816 |
| TTCN_904 | 9630 | CTCN_3287 | 19817 |
| TTCN_905 | 9631 | GTCN_1914 | 19818 |
| CTCN_677 | 9632 | ATCN_2299 | 19819 |
| CTCN_678 | 9633 | TTCN_3680 | 19820 |
| TTCN_906 | 9634 | TTCN_3681 | 19821 |
| TTCN_907 | 9635 | TTCN_3682 | 19822 |
| GTCN_431 | 9636 | ATCN_2300 | 19823 |
| TTCN_908 | 9637 | ATCN_2301 | 19824 |
| TTCN_909 | 9638 | TTCN_3683 | 19825 |
| CTCN_679 | 9639 | TTCN_3684 | 19826 |
| GTCN_432 | 9640 | CTCN_3288 | 19827 |
| CTCN_680 | 9641 | GTCN_1915 | 19828 |
| CTCN_681 | 9642 | CTCN_3289 | 19829 |
| ATCN_532 | 9643 | CTCN_3290 | 19830 |
| CTCN_682 | 9644 | GTCN_1916 | 19831 |
| ATCN_533 | 9645 | CTCN_3291 | 19832 |
| ATCN_534 | 9646 | TTCN_3685 | 19833 |
| ATCN_535 | 9647 | TTCN_3686 | 19834 |
| GTCN_433 | 9648 | CTCN_3292 | 19835 |
| CTCN_683 | 9649 | GTCN_1917 | 19836 |
| TTCN_910 | 9650 | ATCN_2302 | 19837 |
| ATCN_536 | 9651 | GTCN_1918 | 19838 |
| CTCN_684 | 9652 | CTCN_3293 | 19839 |
| ATCN_537 | 9653 | TTCN_3687 | 19840 |
| CTCN_685 | 9654 | GTCN_1919 | 19841 |
| GTCN_434 | 9655 | CTCN_3294 | 19842 |
| TTCN_911 | 9656 | CTCN_3295 | 19843 |
| ATCN_538 | 9657 | ATCN_2303 | 19844 |
| ATCN_539 | 9658 | GTCN_1920 | 19845 |
| CTCN_686 | 9659 | CTCN_3296 | 19846 |
| ATCN_540 | 9660 | CTCN_3297 | 19847 |
| TTCN_912 | 9661 | CTCN_3298 | 19848 |
| ATCN_541 | 9662 | TTCN_3688 | 19849 |
| TTCN_913 | 9663 | CTCN_3299 | 19850 |
| TTCN_914 | 9664 | ATCN_2304 | 19851 |
| TTCN_915 | 9665 | ATCN_2305 | 19852 |
| GTCN_435 | 9666 | CTCN_3300 | 19853 |

| | | | |
|---|---|---|---|
| GTCN_436 | 9667 | CTCN_3301 | 19854 |
| GTCN_437 | 9668 | CTCN_3302 | 19855 |
| ATCN_542 | 9669 | TTCN_3689 | 19856 |
| CTCN_687 | 9670 | TTCN_3690 | 19857 |
| CTCN_688 | 9671 | TTCN_3691 | 19858 |
| TTCN_916 | 9672 | CTCN_3303 | 19859 |
| TTCN_917 | 9673 | GTCN_1921 | 19860 |
| CTCN_689 | 9674 | CTCN_3304 | 19861 |
| TTCN_918 | 9675 | CTCN_3305 | 19862 |
| ATCN_543 | 9676 | GTCN_1922 | 19863 |
| CTCN_690 | 9677 | CTCN_3306 | 19864 |
| CTCN_691 | 9678 | ATCN_2306 | 19865 |
| GTCN_438 | 9679 | TTCN_3692 | 19866 |
| GTCN_439 | 9680 | TTCN_3693 | 19867 |
| CTCN_692 | 9681 | GTCN_1923 | 19868 |
| GTCN_440 | 9682 | TTCN_3694 | 19869 |
| ATCN_544 | 9683 | TTCN_3695 | 19870 |
| TTCN_919 | 9684 | TTCN_3696 | 19871 |
| ATCN_545 | 9685 | ATCN_2307 | 19872 |
| CTCN_693 | 9686 | GTCN_1924 | 19873 |
| CTCN_694 | 9687 | GTCN_1925 | 19874 |
| CTCN_695 | 9688 | CTCN_3307 | 19875 |
| ATCN_546 | 9689 | TTCN_3697 | 19876 |
| TTCN_920 | 9690 | TTCN_3698 | 19877 |
| TTCN_921 | 9691 | GTCN_1926 | 19878 |
| TTCN_922 | 9692 | GTCN_1927 | 19879 |
| TTCN_923 | 9693 | ATCN_2308 | 19880 |
| ATCN_547 | 9694 | TTCN_3699 | 19881 |
| ATCN_548 | 9695 | ATCN_2309 | 19882 |
| TTCN_924 | 9696 | TTCN_3700 | 19883 |
| ATCN_549 | 9697 | ATCN_2310 | 19884 |
| GTCN_441 | 9698 | CTCN_3308 | 19885 |
| GTCN_442 | 9699 | CTCN_3309 | 19886 |
| CTCN_696 | 9700 | TTCN_3701 | 19887 |
| TTCN_925 | 9701 | TTCN_3702 | 19888 |
| CTCN_697 | 9702 | ATCN_2311 | 19889 |
| TTCN_926 | 9703 | TTCN_3703 | 19890 |
| CTCN_698 | 9704 | TTCN_3704 | 19891 |
| CTCN_699 | 9705 | ATCN_2312 | 19892 |
| ATCN_550 | 9706 | CTCN_3310 | 19893 |
| ATCN_551 | 9707 | TTCN_3705 | 19894 |
| GTCN_443 | 9708 | TTCN_3706 | 19895 |
| TTCN_927 | 9709 | TTCN_3707 | 19896 |
| CTCN_700 | 9710 | GTCN_1928 | 19897 |
| TTCN_928 | 9711 | CTCN_3311 | 19898 |
| TTCN_929 | 9712 | GTCN_1929 | 19899 |
| TTCN_930 | 9713 | CTCN_3312 | 19900 |
| CTCN_701 | 9714 | CTCN_3313 | 19901 |
| GTCN_444 | 9715 | TTCN_3708 | 19902 |
| CTCN_702 | 9716 | ATCN_2313 | 19903 |
| ATCN_552 | 9717 | CTCN_3314 | 19904 |
| ATCN_553 | 9718 | CTCN_3315 | 19905 |
| GTCN_445 | 9719 | ATCN_2314 | 19906 |
| TTCN_931 | 9720 | CTCN_3316 | 19907 |
| CTCN_703 | 9721 | GTCN_1930 | 19908 |

FIG. 36 (continued)

| | | | |
|---|---|---|---|
| CTCN_704 | 9722 | TTCN_3709 | 19909 |
| CTCN_705 | 9723 | TTCN_3710 | 19910 |
| CTCN_706 | 9724 | CTCN_3317 | 19911 |
| TTCN_932 | 9725 | ATCN_2315 | 19912 |
| CTCN_707 | 9726 | CTCN_3318 | 19913 |
| TTCN_933 | 9727 | TTCN_3711 | 19914 |
| CTCN_708 | 9728 | TTCN_3712 | 19915 |
| TTCN_934 | 9729 | GTCN_1931 | 19916 |
| TTCN_935 | 9730 | GTCN_1932 | 19917 |
| GTCN_446 | 9731 | CTCN_3319 | 19918 |
| ATCN_554 | 9732 | CTCN_3320 | 19919 |
| GTCN_447 | 9733 | CTCN_3321 | 19920 |
| TTCN_936 | 9734 | CTCN_3322 | 19921 |
| CTCN_709 | 9735 | TTCN_3713 | 19922 |
| GTCN_448 | 9736 | TTCN_3714 | 19923 |
| TTCN_937 | 9737 | CTCN_3323 | 19924 |
| TTCN_938 | 9738 | GTCN_1933 | 19925 |
| GTCN_449 | 9739 | CTCN_3324 | 19926 |
| GTCN_450 | 9740 | CTCN_3325 | 19927 |
| CTCN_710 | 9741 | CTCN_3326 | 19928 |
| CTCN_711 | 9742 | CTCN_3327 | 19929 |
| CTCN_712 | 9743 | CTCN_3328 | 19930 |
| GTCN_451 | 9744 | TTCN_3715 | 19931 |
| CTCN_713 | 9745 | TTCN_3716 | 19932 |
| GTCN_452 | 9746 | TTCN_3717 | 19933 |
| CTCN_714 | 9747 | CTCN_3329 | 19934 |
| TTCN_939 | 9748 | GTCN_1934 | 19935 |
| GTCN_453 | 9749 | ATCN_2316 | 19936 |
| TTCN_940 | 9750 | TTCN_3718 | 19937 |
| GTCN_454 | 9751 | ATCN_2317 | 19938 |
| TTCN_941 | 9752 | ATCN_2318 | 19939 |
| CTCN_715 | 9753 | ATCN_2319 | 19940 |
| TTCN_942 | 9754 | CTCN_3330 | 19941 |
| CTCN_716 | 9755 | GTCN_1935 | 19942 |
| GTCN_455 | 9756 | CTCN_3331 | 19943 |
| CTCN_717 | 9757 | TTCN_3719 | 19944 |
| TTCN_943 | 9758 | TTCN_3720 | 19945 |
| CTCN_718 | 9759 | GTCN_1936 | 19946 |
| TTCN_944 | 9760 | CTCN_3332 | 19947 |
| ATCN_555 | 9761 | GTCN_1937 | 19948 |
| TTCN_945 | 9762 | GTCN_1938 | 19949 |
| ATCN_556 | 9763 | CTCN_3333 | 19950 |
| TTCN_946 | 9764 | CTCN_3334 | 19951 |
| ATCN_557 | 9765 | TTCN_3721 | 19952 |
| TTCN_947 | 9766 | ATCN_2320 | 19953 |
| ATCN_558 | 9767 | CTCN_3335 | 19954 |
| TTCN_948 | 9768 | CTCN_3336 | 19955 |
| TTCN_949 | 9769 | TTCN_3722 | 19956 |
| CTCN_719 | 9770 | TTCN_3723 | 19957 |
| TTCN_950 | 9771 | CTCN_3337 | 19958 |
| TTCN_951 | 9772 | TTCN_3724 | 19959 |
| ATCN_559 | 9773 | CTCN_3338 | 19960 |
| CTCN_720 | 9774 | GTCN_1939 | 19961 |
| TTCN_952 | 9775 | ATCN_2321 | 19962 |
| ATCN_560 | 9776 | TTCN_3725 | 19963 |

| | | | |
|---|---|---|---|
| TTCN_953 | 9777 | TTCN_3726 | 19964 |
| TTCN_954 | 9778 | CTCN_3339 | 19965 |
| TTCN_955 | 9779 | ATCN_2322 | 19966 |
| TTCN_956 | 9780 | GTCN_1940 | 19967 |
| ATCN_561 | 9781 | CTCN_3340 | 19968 |
| TTCN_957 | 9782 | ATCN_2323 | 19969 |
| ATCN_562 | 9783 | ATCN_2324 | 19970 |
| GTCN_456 | 9784 | TTCN_3727 | 19971 |
| TTCN_958 | 9785 | CTCN_3341 | 19972 |
| ATCN_563 | 9786 | ATCN_2325 | 19973 |
| TTCN_959 | 9787 | TTCN_3728 | 19974 |
| ATCN_564 | 9788 | CTCN_3342 | 19975 |
| ATCN_565 | 9789 | TTCN_3729 | 19976 |
| ATCN_566 | 9790 | CTCN_3343 | 19977 |
| GTCN_457 | 9791 | GTCN_1941 | 19978 |
| CTCN_721 | 9792 | GTCN_1942 | 19979 |
| TTCN_960 | 9793 | TTCN_3730 | 19980 |
| CTCN_722 | 9794 | GTCN_1943 | 19981 |
| CTCN_723 | 9795 | TTCN_3731 | 19982 |
| TTCN_961 | 9796 | TTCN_3732 | 19983 |
| GTCN_458 | 9797 | TTCN_3733 | 19984 |
| ATCN_567 | 9798 | TTCN_3734 | 19985 |
| TTCN_962 | 9799 | ATCN_2326 | 19986 |
| CTCN_724 | 9800 | ATCN_2327 | 19987 |
| CTCN_725 | 9801 | TTCN_3735 | 19988 |
| ATCN_568 | 9802 | GTCN_1944 | 19989 |
| GTCN_459 | 9803 | CTCN_3344 | 19990 |
| GTCN_460 | 9804 | CTCN_3345 | 19991 |
| GTCN_461 | 9805 | CTCN_3346 | 19992 |
| TTCN_963 | 9806 | CTCN_3347 | 19993 |
| CTCN_726 | 9807 | TTCN_3736 | 19994 |
| TTCN_964 | 9808 | GTCN_1945 | 19995 |
| TTCN_965 | 9809 | GTCN_1946 | 19996 |
| TTCN_966 | 9810 | CTCN_3348 | 19997 |
| TTCN_967 | 9811 | ATCN_2328 | 19998 |
| CTCN_727 | 9812 | TTCN_3737 | 19999 |
| TTCN_968 | 9813 | TTCN_3738 | 20000 |
| CTCN_728 | 9814 | GTCN_1947 | 20001 |
| GTCN_462 | 9815 | ATCN_2329 | 20002 |
| TTCN_969 | 9816 | TTCN_3739 | 20003 |
| TTCN_970 | 9817 | TTCN_3740 | 20004 |
| CTCN_729 | 9818 | ATCN_2330 | 20005 |
| CTCN_730 | 9819 | CTCN_3349 | 20006 |
| TTCN_971 | 9820 | CTCN_3350 | 20007 |
| ATCN_569 | 9821 | TTCN_3741 | 20008 |
| TTCN_972 | 9822 | ATCN_2331 | 20009 |
| CTCN_731 | 9823 | CTCN_3351 | 20010 |
| TTCN_973 | 9824 | GTCN_1948 | 20011 |
| TTCN_974 | 9825 | GTCN_1949 | 20012 |
| TTCN_975 | 9826 | CTCN_3352 | 20013 |
| TTCN_976 | 9827 | CTCN_3353 | 20014 |
| ATCN_570 | 9828 | TTCN_3742 | 20015 |
| CTCN_732 | 9829 | CTCN_3354 | 20016 |
| TTCN_977 | 9830 | GTCN_1950 | 20017 |
| TTCN_978 | 9831 | GTCN_1951 | 20018 |

FIG. 36 (continued)

| | | | |
|---|---|---|---|
| ATCN_571 | 9832 | CTCN_3355 | 20019 |
| ATCN_572 | 9833 | ATCN_2332 | 20020 |
| ATCN_573 | 9834 | CTCN_3356 | 20021 |
| CTCN_733 | 9835 | CTCN_3357 | 20022 |
| ATCN_574 | 9836 | CTCN_3358 | 20023 |
| TTCN_979 | 9837 | CTCN_3359 | 20024 |
| CTCN_734 | 9838 | GTCN_1952 | 20025 |
| GTCN_463 | 9839 | GTCN_1953 | 20026 |
| TTCN_980 | 9840 | CTCN_3360 | 20027 |
| TTCN_981 | 9841 | CTCN_3361 | 20028 |
| ATCN_575 | 9842 | CTCN_3362 | 20029 |
| TTCN_982 | 9843 | TTCN_3743 | 20030 |
| ATCN_576 | 9844 | TTCN_3744 | 20031 |
| ATCN_577 | 9845 | TTCN_3745 | 20032 |
| CTCN_735 | 9846 | CTCN_3363 | 20033 |
| TTCN_983 | 9847 | TTCN_3746 | 20034 |
| TTCN_984 | 9848 | ATCN_2333 | 20035 |
| TTCN_985 | 9849 | CTCN_3364 | 20036 |
| ATCN_578 | 9850 | TTCN_3747 | 20037 |
| CTCN_736 | 9851 | CTCN_3365 | 20038 |
| ATCN_579 | 9852 | TTCN_3748 | 20039 |
| ATCN_580 | 9853 | CTCN_3366 | 20040 |
| GTCN_464 | 9854 | CTCN_3367 | 20041 |
| TTCN_986 | 9855 | TTCN_3749 | 20042 |
| TTCN_987 | 9856 | TTCN_3750 | 20043 |
| ATCN_581 | 9857 | TTCN_3751 | 20044 |
| CTCN_737 | 9858 | TTCN_3752 | 20045 |
| TTCN_988 | 9859 | TTCN_3753 | 20046 |
| ATCN_582 | 9860 | CTCN_3368 | 20047 |
| GTCN_465 | 9861 | CTCN_3369 | 20048 |
| GTCN_466 | 9862 | CTCN_3370 | 20049 |
| GTCN_467 | 9863 | TTCN_3754 | 20050 |
| GTCN_468 | 9864 | CTCN_3371 | 20051 |
| ATCN_583 | 9865 | CTCN_3372 | 20052 |
| CTCN_738 | 9866 | GTCN_1954 | 20053 |
| CTCN_739 | 9867 | TTCN_3755 | 20054 |
| ATCN_584 | 9868 | CTCN_3373 | 20055 |
| TTCN_989 | 9869 | CTCN_3374 | 20056 |
| TTCN_990 | 9870 | CTCN_3375 | 20057 |
| TTCN_991 | 9871 | CTCN_3376 | 20058 |
| TTCN_992 | 9872 | GTCN_1955 | 20059 |
| TTCN_993 | 9873 | CTCN_3377 | 20060 |
| CTCN_740 | 9874 | CTCN_3378 | 20061 |
| TTCN_994 | 9875 | CTCN_3379 | 20062 |
| TTCN_995 | 9876 | CTCN_3380 | 20063 |
| TTCN_996 | 9877 | CTCN_3381 | 20064 |
| CTCN_741 | 9878 | CTCN_3382 | 20065 |
| CTCN_742 | 9879 | TTCN_3756 | 20066 |
| TTCN_997 | 9880 | TTCN_3757 | 20067 |
| TTCN_998 | 9881 | GTCN_1956 | 20068 |
| TTCN_999 | 9882 | CTCN_3383 | 20069 |
| CTCN_743 | 9883 | ATCN_2334 | 20070 |
| ATCN_585 | 9884 | CTCN_3384 | 20071 |
| GTCN_469 | 9885 | GTCN_1957 | 20072 |
| CTCN_744 | 9886 | CTCN_3385 | 20073 |

| | | | |
|---|---|---|---|
| GTCN_470 | 9887 | CTCN_3386 | 20074 |
| GTCN_471 | 9888 | CTCN_3387 | 20075 |
| GTCN_472 | 9889 | GTCN_1958 | 20076 |
| CTCN_745 | 9890 | GTCN_1959 | 20077 |
| CTCN_746 | 9891 | GTCN_1960 | 20078 |
| TTCN_1000 | 9892 | GTCN_1961 | 20079 |
| ATCN_586 | 9893 | ATCN_2335 | 20080 |
| TTCN_1001 | 9894 | TTCN_3758 | 20081 |
| CTCN_747 | 9895 | ATCN_2336 | 20082 |
| TTCN_1002 | 9896 | ATCN_2337 | 20083 |
| CTCN_748 | 9897 | CTCN_3388 | 20084 |
| TTCN_1003 | 9898 | CTCN_3389 | 20085 |
| TTCN_1004 | 9899 | ATCN_2338 | 20086 |
| TTCN_1005 | 9900 | CTCN_3390 | 20087 |
| ATCN_587 | 9901 | CTCN_3391 | 20088 |
| GTCN_473 | 9902 | CTCN_3392 | 20089 |
| CTCN_749 | 9903 | CTCN_3393 | 20090 |
| CTCN_750 | 9904 | CTCN_3394 | 20091 |
| GTCN_474 | 9905 | CTCN_3395 | 20092 |
| CTCN_751 | 9906 | GTCN_1962 | 20093 |
| TTCN_1006 | 9907 | CTCN_3396 | 20094 |
| CTCN_752 | 9908 | GTCN_1963 | 20095 |
| TTCN_1007 | 9909 | CTCN_3397 | 20096 |
| CTCN_753 | 9910 | TTCN_3759 | 20097 |
| CTCN_754 | 9911 | GTCN_1964 | 20098 |
| TTCN_1008 | 9912 | CTCN_3398 | 20099 |
| TTCN_1009 | 9913 | CTCN_3399 | 20100 |
| CTCN_755 | 9914 | ATCN_2339 | 20101 |
| TTCN_1010 | 9915 | CTCN_3400 | 20102 |
| ATCN_588 | 9916 | ATCN_2340 | 20103 |
| TTCN_1011 | 9917 | ATCN_2341 | 20104 |
| TTCN_1012 | 9918 | CTCN_3401 | 20105 |
| ATCN_589 | 9919 | TTCN_3760 | 20106 |
| GTCN_475 | 9920 | CTCN_3402 | 20107 |
| TTCN_1013 | 9921 | CTCN_3403 | 20108 |
| TTCN_1014 | 9922 | ATCN_2342 | 20109 |
| CTCN_756 | 9923 | GTCN_1965 | 20110 |
| TTCN_1015 | 9924 | CTCN_3404 | 20111 |
| GTCN_476 | 9925 | TTCN_3761 | 20112 |
| GTCN_477 | 9926 | GTCN_1966 | 20113 |
| TTCN_1016 | 9927 | ATCN_2343 | 20114 |
| ATCN_590 | 9928 | ATCN_2344 | 20115 |
| TTCN_1017 | 9929 | GTCN_1967 | 20116 |
| TTCN_1018 | 9930 | CTCN_3405 | 20117 |
| ATCN_591 | 9931 | TTCN_3762 | 20118 |
| GTCN_478 | 9932 | CTCN_3406 | 20119 |
| CTCN_757 | 9933 | CTCN_3407 | 20120 |
| ATCN_592 | 9934 | TTCN_3763 | 20121 |
| CTCN_758 | 9935 | CTCN_3408 | 20122 |
| CTCN_759 | 9936 | CTCN_3409 | 20123 |
| ATCN_593 | 9937 | ATCN_2345 | 20124 |
| ATCN_594 | 9938 | ATCN_2346 | 20125 |
| TTCN_1019 | 9939 | ATCN_2347 | 20126 |
| ATCN_595 | 9940 | GTCN_1968 | 20127 |
| TTCN_1020 | 9941 | GTCN_1969 | 20128 |

FIG. 36 (continued)

| | | | |
|---|---|---|---|
| CTCN_760 | 9942 | TTCN_3764 | 20129 |
| ATCN_596 | 9943 | CTCN_3410 | 20130 |
| CTCN_761 | 9944 | GTCN_1970 | 20131 |
| CTCN_762 | 9945 | GTCN_1971 | 20132 |
| CTCN_763 | 9946 | TTCN_3765 | 20133 |
| TTCN_1021 | 9947 | TTCN_3766 | 20134 |
| TTCN_1022 | 9948 | TTCN_3767 | 20135 |
| GTCN_479 | 9949 | CTCN_3411 | 20136 |
| CTCN_764 | 9950 | TTCN_3768 | 20137 |
| TTCN_1023 | 9951 | ATCN_2348 | 20138 |
| GTCN_480 | 9952 | ATCN_2349 | 20139 |
| CTCN_765 | 9953 | ATCN_2350 | 20140 |
| GTCN_481 | 9954 | GTCN_1972 | 20141 |
| CTCN_766 | 9955 | CTCN_3412 | 20142 |
| CTCN_767 | 9956 | CTCN_3413 | 20143 |
| GTCN_482 | 9957 | CTCN_3414 | 20144 |
| GTCN_483 | 9958 | TTCN_3769 | 20145 |
| TTCN_1024 | 9959 | CTCN_3415 | 20146 |
| TTCN_1025 | 9960 | CTCN_3416 | 20147 |
| ATCN_597 | 9961 | TTCN_3770 | 20148 |
| TTCN_1026 | 9962 | CTCN_3417 | 20149 |
| TTCN_1027 | 9963 | CTCN_3418 | 20150 |
| ATCN_598 | 9964 | CTCN_3419 | 20151 |
| TTCN_1028 | 9965 | CTCN_3420 | 20152 |
| TTCN_1029 | 9966 | TTCN_3771 | 20153 |
| CTCN_768 | 9967 | CTCN_3421 | 20154 |
| ATCN_599 | 9968 | CTCN_3422 | 20155 |
| GTCN_484 | 9969 | CTCN_3423 | 20156 |
| TTCN_1030 | 9970 | TTCN_3772 | 20157 |
| ATCN_600 | 9971 | CTCN_3424 | 20158 |
| ATCN_601 | 9972 | ATCN_2351 | 20159 |
| TTCN_1031 | 9973 | ATCN_2352 | 20160 |
| GTCN_485 | 9974 | TTCN_3773 | 20161 |
| CTCN_769 | 9975 | ATCN_2353 | 20162 |
| CTCN_770 | 9976 | ATCN_2354 | 20163 |
| GTCN_486 | 9977 | TTCN_3774 | 20164 |
| ATCN_602 | 9978 | CTCN_3425 | 20165 |
| TTCN_1032 | 9979 | CTCN_3426 | 20166 |
| ATCN_603 | 9980 | TTCN_3775 | 20167 |
| TTCN_1033 | 9981 | GTCN_1973 | 20168 |
| TTCN_1034 | 9982 | GTCN_1974 | 20169 |
| ATCN_604 | 9983 | TTCN_3776 | 20170 |
| CTCN_771 | 9984 | CTCN_3427 | 20171 |
| GTCN_487 | 9985 | CTCN_3428 | 20172 |
| CTCN_772 | 9986 | TTCN_3777 | 20173 |
| GTCN_488 | 9987 | CTCN_3429 | 20174 |
| CTCN_773 | 9988 | CTCN_3430 | 20175 |
| GTCN_489 | 9989 | CTCN_3431 | 20176 |
| TTCN_1035 | 9990 | GTCN_1975 | 20177 |
| CTCN_774 | 9991 | CTCN_3432 | 20178 |
| GTCN_490 | 9992 | ATCN_2355 | 20179 |
| GTCN_491 | 9993 | ATCN_2356 | 20180 |
| TTCN_1036 | 9994 | ATCN_2357 | 20181 |
| TTCN_1037 | 9995 | ATCN_2358 | 20182 |
| TTCN_1038 | 9996 | ATCN_2359 | 20183 |

| | | | |
|---|---|---|---|
| CTCN_775 | 9997 | TTCN_3778 | 20184 |
| TTCN_1039 | 9998 | TTCN_3779 | 20185 |
| TTCN_1040 | 9999 | CTCN_3433 | 20186 |
| CTCN_776 | 10000 | CTCN_3434 | 20187 |
| TTCN_1041 | 10001 | GTCN_1976 | 20188 |
| CTCN_777 | 10002 | TTCN_3780 | 20189 |
| CTCN_778 | 10003 | CTCN_3435 | 20190 |
| CTCN_779 | 10004 | TTCN_3781 | 20191 |
| GTCN_492 | 10005 | TTCN_3782 | 20192 |
| CTCN_780 | 10006 | TTCN_3783 | 20193 |
| GTCN_493 | 10007 | TTCN_3784 | 20194 |
| CTCN_781 | 10008 | TTCN_3785 | 20195 |
| TTCN_1042 | 10009 | CTCN_3436 | 20196 |
| CTCN_782 | 10010 | GTCN_1977 | 20197 |
| GTCN_494 | 10011 | TTCN_3786 | 20198 |
| CTCN_783 | 10012 | ATCN_2360 | 20199 |
| GTCN_495 | 10013 | CTCN_3437 | 20200 |
| GTCN_496 | 10014 | ATCN_2361 | 20201 |
| TTCN_1043 | 10015 | CTCN_3438 | 20202 |
| ATCN_605 | 10016 | ATCN_2362 | 20203 |
| TTCN_1044 | 10017 | GTCN_1978 | 20204 |
| TTCN_1045 | 10018 | ATCN_2363 | 20205 |
| CTCN_784 | 10019 | TTCN_3787 | 20206 |
| CTCN_785 | 10020 | ATCN_2364 | 20207 |
| GTCN_497 | 10021 | TTCN_3788 | 20208 |
| ATCN_606 | 10022 | CTCN_3439 | 20209 |
| ATCN_607 | 10023 | CTCN_3440 | 20210 |
| TTCN_1046 | 10024 | GTCN_1979 | 20211 |
| ATCN_608 | 10025 | CTCN_3441 | 20212 |
| TTCN_1047 | 10026 | GTCN_1980 | 20213 |
| TTCN_1048 | 10027 | CTCN_3442 | 20214 |
| CTCN_786 | 10028 | GTCN_1981 | 20215 |
| GTCN_498 | 10029 | TTCN_3789 | 20216 |
| TTCN_1049 | 10030 | ATCN_2365 | 20217 |
| ATCN_609 | 10031 | ATCN_2366 | 20218 |
| TTCN_1050 | 10032 | CTCN_3443 | 20219 |
| TTCN_1051 | 10033 | TTCN_3790 | 20220 |
| TTCN_1052 | 10034 | GTCN_1982 | 20221 |
| CTCN_787 | 10035 | ATCN_2367 | 20222 |
| ATCN_610 | 10036 | GTCN_1983 | 20223 |
| GTCN_499 | 10037 | TTCN_3791 | 20224 |
| CTCN_788 | 10038 | CTCN_3444 | 20225 |
| GTCN_500 | 10039 | TTCN_3792 | 20226 |
| CTCN_789 | 10040 | GTCN_1984 | 20227 |
| CTCN_790 | 10041 | CTCN_3445 | 20228 |
| ATCN_611 | 10042 | TTCN_3793 | 20229 |
| GTCN_501 | 10043 | TTCN_3794 | 20230 |
| CTCN_791 | 10044 | CTCN_3446 | 20231 |
| TTCN_1053 | 10045 | TTCN_3795 | 20232 |
| CTCN_792 | 10046 | CTCN_3447 | 20233 |
| CTCN_793 | 10047 | TTCN_3796 | 20234 |
| TTCN_1054 | 10048 | GTCN_1985 | 20235 |
| GTCN_502 | 10049 | CTCN_3448 | 20236 |
| TTCN_1055 | 10050 | CTCN_3449 | 20237 |
| TTCN_1056 | 10051 | CTCN_3450 | 20238 |

FIG. 36 (continued)

| | | | |
|---|---|---|---|
| TTCN_1057 | 10052 | CTCN_3451 | 20239 |
| CTCN_794 | 10053 | CTCN_3452 | 20240 |
| ATCN_612 | 10054 | GTCN_1986 | 20241 |
| TTCN_1058 | 10055 | CTCN_3453 | 20242 |
| GTCN_503 | 10056 | GTCN_1987 | 20243 |
| TTCN_1059 | 10057 | GTCN_1988 | 20244 |
| ATCN_613 | 10058 | GTCN_1989 | 20245 |
| GTCN_504 | 10059 | GTCN_1990 | 20246 |
| GTCN_505 | 10060 | GTCN_1991 | 20247 |
| ATCN_614 | 10061 | CTCN_3454 | 20248 |
| GTCN_506 | 10062 | CTCN_3455 | 20249 |
| TTCN_1060 | 10063 | CTCN_3456 | 20250 |
| TTCN_1061 | 10064 | TTCN_3797 | 20251 |
| CTCN_795 | 10065 | CTCN_3457 | 20252 |
| CTCN_796 | 10066 | CTCN_3458 | 20253 |
| TTCN_1062 | 10067 | CTCN_3459 | 20254 |
| ATCN_615 | 10068 | CTCN_3460 | 20255 |
| TTCN_1063 | 10069 | GTCN_1992 | 20256 |
| GTCN_507 | 10070 | TTCN_3798 | 20257 |
| GTCN_508 | 10071 | TTCN_3799 | 20258 |
| TTCN_1064 | 10072 | GTCN_1993 | 20259 |
| GTCN_509 | 10073 | CTCN_3461 | 20260 |
| CTCN_797 | 10074 | TTCN_3800 | 20261 |
| TTCN_1065 | 10075 | GTCN_1994 | 20262 |
| TTCN_1066 | 10076 | CTCN_3462 | 20263 |
| CTCN_798 | 10077 | ATCN_2368 | 20264 |
| GTCN_510 | 10078 | ATCN_2369 | 20265 |
| TTCN_1067 | 10079 | CTCN_3463 | 20266 |
| GTCN_511 | 10080 | GTCN_1995 | 20267 |
| ATCN_616 | 10081 | CTCN_3464 | 20268 |
| ATCN_617 | 10082 | CTCN_3465 | 20269 |
| ATCN_618 | 10083 | CTCN_3466 | 20270 |
| ATCN_619 | 10084 | TTCN_3801 | 20271 |
| TTCN_1068 | 10085 | GTCN_1996 | 20272 |
| ATCN_620 | 10086 | GTCN_1997 | 20273 |
| CTCN_799 | 10087 | TTCN_3802 | 20274 |
| TTCN_1069 | 10088 | ATCN_2370 | 20275 |
| GTCN_512 | 10089 | ATCN_2371 | 20276 |
| ATCN_621 | 10090 | CTCN_3467 | 20277 |
| GTCN_513 | 10091 | TTCN_3803 | 20278 |
| GTCN_514 | 10092 | CTCN_3468 | 20279 |
| CTCN_800 | 10093 | TTCN_3804 | 20280 |
| ATCN_622 | 10094 | CTCN_3469 | 20281 |
| TTCN_1070 | 10095 | ATCN_2372 | 20282 |
| GTCN_515 | 10096 | CTCN_3470 | 20283 |
| TTCN_1071 | 10097 | GTCN_1998 | 20284 |
| GTCN_516 | 10098 | CTCN_3471 | 20285 |
| ATCN_623 | 10099 | CTCN_3472 | 20286 |
| TTCN_1072 | 10100 | ATCN_2373 | 20287 |
| TTCN_1073 | 10101 | GTCN_1999 | 20288 |
| CTCN_801 | 10102 | CTCN_3473 | 20289 |
| GTCN_517 | 10103 | CTCN_3474 | 20290 |
| CTCN_802 | 10104 | CTCN_3475 | 20291 |
| GTCN_518 | 10105 | CTCN_3476 | 20292 |
| CTCN_803 | 10106 | CTCN_3477 | 20293 |
| CTCN_804 | 10107 | CTCN_3478 | 20294 |
| GTCN_519 | 10108 | CTCN_3479 | 20295 |
| TTCN_1074 | 10109 | CTCN_3480 | 20296 |
| CTCN_805 | 10110 | CTCN_3481 | 20297 |
| CTCN_806 | 10111 | TTCN_3805 | 20298 |
| GTCN_520 | 10112 | GTCN_2000 | 20299 |
| CTCN_807 | 10113 | TTCN_3806 | 20300 |
| ATCN_624 | 10114 | GTCN_2001 | 20301 |
| GTCN_521 | 10115 | CTCN_3482 | 20302 |
| TTCN_1075 | 10116 | CTCN_3483 | 20303 |
| TTCN_1076 | 10117 | CTCN_3484 | 20304 |
| TTCN_1077 | 10118 | CTCN_3485 | 20305 |
| GTCN_522 | 10119 | CTCN_3486 | 20306 |
| GTCN_523 | 10120 | GTCN_2002 | 20307 |
| TTCN_1078 | 10121 | CTCN_3487 | 20308 |
| TTCN_1079 | 10122 | CTCN_3488 | 20309 |
| ATCN_625 | 10123 | TTCN_3807 | 20310 |
| ATCN_626 | 10124 | GTCN_2003 | 20311 |
| ATCN_627 | 10125 | ATCN_2374 | 20312 |
| ATCN_628 | 10126 | CTCN_3489 | 20313 |
| TTCN_1080 | 10127 | TTCN_3808 | 20314 |
| ATCN_629 | 10128 | CTCN_3490 | 20315 |
| TTCN_1081 | 10129 | GTCN_2004 | 20316 |
| CTCN_808 | 10130 | CTCN_3491 | 20317 |
| TTCN_1082 | 10131 | ATCN_2375 | 20318 |
| TTCN_1083 | 10132 | GTCN_2005 | 20319 |
| GTCN_524 | 10133 | CTCN_3492 | 20320 |
| GTCN_525 | 10134 | CTCN_3493 | 20321 |
| TTCN_1084 | 10135 | TTCN_3809 | 20322 |
| CTCN_809 | 10136 | ATCN_2376 | 20323 |
| ATCN_630 | 10137 | TTCN_3810 | 20324 |
| TTCN_1085 | 10138 | CTCN_3494 | 20325 |
| TTCN_1086 | 10139 | TTCN_3811 | 20326 |
| TTCN_1087 | 10140 | GTCN_2006 | 20327 |
| CTCN_810 | 10141 | GTCN_2007 | 20328 |
| CTCN_811 | 10142 | ATCN_2377 | 20329 |
| ATCN_631 | 10143 | TTCN_3812 | 20330 |
| ATCN_632 | 10144 | ATCN_2378 | 20331 |
| TTCN_1088 | 10145 | ATCN_2379 | 20332 |
| CTCN_812 | 10146 | CTCN_3495 | 20333 |
| GTCN_526 | 10147 | TTCN_3813 | 20334 |
| ATCN_633 | 10148 | TTCN_3814 | 20335 |
| CTCN_813 | 10149 | TTCN_3815 | 20336 |
| ATCN_634 | 10150 | ATCN_2380 | 20337 |
| TTCN_1089 | 10151 | TTCN_3816 | 20338 |
| GTCN_527 | 10152 | CTCN_3496 | 20339 |
| TTCN_1090 | 10153 | ATCN_2381 | 20340 |
| CTCN_814 | 10154 | ATCN_2382 | 20341 |
| TTCN_1091 | 10155 | TTCN_3817 | 20342 |
| CTCN_815 | 10156 | TTCN_3818 | 20343 |
| CTCN_816 | 10157 | TTCN_3819 | 20344 |
| CTCN_817 | 10158 | ATCN_2383 | 20345 |
| GTCN_528 | 10159 | CTCN_3497 | 20346 |
| CTCN_818 | 10160 | TTCN_3820 | 20347 |
| ATCN_635 | 10161 | TTCN_3821 | 20348 |

FIG. 36 (continued)

| | | | |
|---|---|---|---|
| TTCN_1092 | 10162 | ATCN_2384 | 20349 |
| GTCN_529 | 10163 | ATCN_2385 | 20350 |
| ATCN_636 | 10164 | ATCN_2386 | 20351 |
| TTCN_1093 | 10165 | TTCN_3822 | 20352 |
| GTCN_530 | 10166 | ATCN_2387 | 20353 |
| CTCN_819 | 10167 | ATCN_2388 | 20354 |
| CTCN_820 | 10168 | CTCN_3498 | 20355 |
| CTCN_821 | 10169 | CTCN_3499 | 20356 |
| CTCN_822 | 10170 | TTCN_3823 | 20357 |
| GTCN_531 | 10171 | CTCN_3500 | 20358 |
| GTCN_532 | 10172 | ATCN_2389 | 20359 |
| TTCN_1094 | 10173 | TTCN_3824 | 20360 |
| ATCN_637 | 10174 | ATCN_2390 | 20361 |
| ATCN_638 | 10175 | CTCN_3501 | 20362 |
| CTCN_823 | 10176 | TTCN_3825 | 20363 |
| TTCN_1095 | 10177 | TTCN_3826 | 20364 |
| GTCN_533 | 10178 | ATCN_2391 | 20365 |
| TTCN_1096 | 10179 | TTCN_3827 | 20366 |
| ATCN_639 | 10180 | ATCN_2392 | 20367 |
| TTCN_1097 | 10181 | GTCN_2008 | 20368 |
| CTCN_824 | 10182 | CTCN_3502 | 20369 |
| GTCN_534 | 10183 | ATCN_2393 | 20370 |
| TTCN_1098 | 10184 | CTCN_3503 | 20371 |
| CTCN_825 | 10185 | CTCN_3504 | 20372 |
| CTCN_826 | 10186 | TTCN_3828 | 20373 |
| ATCN_640 | 10187 | GTCN_2009 | 20374 |
| TTCN_1099 | 10188 | GTCN_2010 | 20375 |
| CTCN_827 | 10189 | CTCN_3505 | 20376 |
| TTCN_1100 | 10190 | CTCN_3506 | 20377 |
| ATCN_641 | 10191 | CTCN_3507 | 20378 |
| CTCN_828 | 10192 | CTCN_3508 | 20379 |
| GTCN_535 | 10193 | ATCN_2394 | 20380 |
| CTCN_829 | 10194 | TTCN_3829 | 20381 |
| TTCN_1101 | 10195 | GTCN_2011 | 20382 |
| CTCN_830 | 10196 | TTCN_3830 | 20383 |
| CTCN_831 | 10197 | TTCN_3831 | 20384 |
| CTCN_832 | 10198 | GTCN_2012 | 20385 |
| ATCN_642 | 10199 | TTCN_3832 | 20386 |
| CTCN_833 | 10200 | CTCN_3509 | 20387 |
| TTCN_1102 | 10201 | GTCN_2013 | 20388 |
| GTCN_536 | 10202 | GTCN_2014 | 20389 |
| CTCN_834 | 10203 | CTCN_3510 | 20390 |
| GTCN_537 | 10204 | GTCN_2015 | 20391 |
| GTCN_538 | 10205 | TTCN_3833 | 20392 |
| GTCN_539 | 10206 | ATCN_2395 | 20393 |
| GTCN_540 | 10207 | TTCN_3834 | 20394 |
| CTCN_835 | 10208 | TTCN_3835 | 20395 |
| TTCN_1103 | 10209 | ATCN_2396 | 20396 |
| GTCN_541 | 10210 | CTCN_3511 | 20397 |
| TTCN_1104 | 10211 | CTCN_3512 | 20398 |
| ATCN_643 | 10212 | ATCN_2397 | 20399 |
| TTCN_1105 | 10213 | TTCN_3836 | 20400 |
| CTCN_836 | 10214 | CTCN_3513 | 20401 |
| CTCN_837 | 10215 | GTCN_2016 | 20402 |
| GTCN_542 | 10216 | CTCN_3514 | 20403 |

| | | | |
|---|---|---|---|
| CTCN_838 | 10217 | ATCN_2398 | 20404 |
| TTCN_1106 | 10218 | GTCN_2017 | 20405 |
| CTCN_839 | 10219 | CTCN_3515 | 20406 |
| TTCN_1107 | 10220 | CTCN_3516 | 20407 |
| CTCN_840 | 10221 | GTCN_2018 | 20408 |
| CTCN_841 | 10222 | TTCN_3837 | 20409 |
| TTCN_1108 | 10223 | CTCN_3517 | 20410 |
| GTCN_543 | 10224 | CTCN_3518 | 20411 |
| CTCN_842 | 10225 | CTCN_3519 | 20412 |
| TTCN_1109 | 10226 | CTCN_3520 | 20413 |
| TTCN_1110 | 10227 | CTCN_3521 | 20414 |
| GTCN_544 | 10228 | GTCN_2019 | 20415 |
| TTCN_1111 | 10229 | GTCN_2020 | 20416 |
| CTCN_843 | 10230 | CTCN_3522 | 20417 |
| TTCN_1112 | 10231 | ATCN_2399 | 20418 |
| GTCN_545 | 10232 | TTCN_3838 | 20419 |
| GTCN_546 | 10233 | TTCN_3839 | 20420 |
| GTCN_547 | 10234 | TTCN_3840 | 20421 |
| ATCN_644 | 10235 | TTCN_3841 | 20422 |
| GTCN_548 | 10236 | CTCN_3523 | 20423 |
| GTCN_549 | 10237 | TTCN_3842 | 20424 |
| ATCN_645 | 10238 | TTCN_3843 | 20425 |
| GTCN_550 | 10239 | CTCN_3524 | 20426 |
| TTCN_1113 | 10240 | CTCN_3525 | 20427 |
| TTCN_1114 | 10241 | CTCN_3526 | 20428 |
| TTCN_1115 | 10242 | ATCN_2400 | 20429 |
| GTCN_551 | 10243 | CTCN_3527 | 20430 |
| GTCN_552 | 10244 | TTCN_3844 | 20431 |
| TTCN_1116 | 10245 | CTCN_3528 | 20432 |
| ATCN_646 | 10246 | TTCN_3845 | 20433 |
| GTCN_553 | 10247 | TTCN_3846 | 20434 |
| CTCN_844 | 10248 | TTCN_3847 | 20435 |
| CTCN_845 | 10249 | TTCN_3848 | 20436 |
| GTCN_554 | 10250 | TTCN_3849 | 20437 |
| TTCN_1117 | 10251 | ATCN_2401 | 20438 |
| CTCN_846 | 10252 | TTCN_3850 | 20439 |
| TTCN_1118 | 10253 | TTCN_3851 | 20440 |
| CTCN_847 | 10254 | CTCN_3529 | 20441 |
| TTCN_1119 | 10255 | GTCN_2021 | 20442 |
| ATCN_647 | 10256 | CTCN_3530 | 20443 |
| TTCN_1120 | 10257 | CTCN_3531 | 20444 |
| GTCN_555 | 10258 | GTCN_2022 | 20445 |
| CTCN_848 | 10259 | TTCN_3852 | 20446 |
| GTCN_556 | 10260 | GTCN_2023 | 20447 |
| GTCN_557 | 10261 | CTCN_3532 | 20448 |
| CTCN_849 | 10262 | TTCN_3853 | 20449 |
| GTCN_558 | 10263 | CTCN_3533 | 20450 |
| GTCN_559 | 10264 | GTCN_2024 | 20451 |
| TTCN_1121 | 10265 | CTCN_3534 | 20452 |
| GTCN_560 | 10266 | GTCN_2025 | 20453 |
| TTCN_1122 | 10267 | TTCN_3854 | 20454 |
| ATCN_648 | 10268 | GTCN_2026 | 20455 |
| TTCN_1123 | 10269 | GTCN_2027 | 20456 |
| TTCN_1124 | 10270 | GTCN_2028 | 20457 |
| GTCN_561 | 10271 | CTCN_3535 | 20458 |

FIG. 36 (continued)

| | | | |
|---|---|---|---|
| TTCN_1125 | 10272 | TTCN_3855 | 20459 |
| CTCN_850 | 10273 | CTCN_3536 | 20460 |
| CTCN_851 | 10274 | CTCN_3537 | 20461 |
| ATCN_649 | 10275 | CTCN_3538 | 20462 |
| CTCN_852 | 10276 | GTCN_2029 | 20463 |
| CTCN_853 | 10277 | GTCN_2030 | 20464 |
| GTCN_562 | 10278 | CTCN_3539 | 20465 |
| ATCN_650 | 10279 | GTCN_2031 | 20466 |
| TTCN_1126 | 10280 | CTCN_3540 | 20467 |
| GTCN_563 | 10281 | CTCN_3541 | 20468 |
| CTCN_854 | 10282 | CTCN_3542 | 20469 |
| CTCN_855 | 10283 | CTCN_3543 | 20470 |
| TTCN_1127 | 10284 | CTCN_3544 | 20471 |
| TTCN_1128 | 10285 | CTCN_3545 | 20472 |
| GTCN_564 | 10286 | CTCN_3546 | 20473 |
| TTCN_1129 | 10287 | CTCN_3547 | 20474 |
| GTCN_565 | 10288 | CTCN_3548 | 20475 |
| TTCN_1130 | 10289 | CTCN_3549 | 20476 |
| CTCN_856 | 10290 | CTCN_3550 | 20477 |
| ATCN_651 | 10291 | GTCN_2032 | 20478 |
| TTCN_1131 | 10292 | CTCN_3551 | 20479 |
| CTCN_857 | 10293 | CTCN_3552 | 20480 |
| TTCN_1132 | 10294 | CTCN_3553 | 20481 |
| ATCN_652 | 10295 | CTCN_3554 | 20482 |
| ATCN_653 | 10296 | CTCN_3555 | 20483 |
| CTCN_858 | 10297 | CTCN_3556 | 20484 |
| TTCN_1133 | 10298 | CTCN_3557 | 20485 |
| CTCN_859 | 10299 | GTCN_2033 | 20486 |
| CTCN_860 | 10300 | CTCN_3558 | 20487 |
| CTCN_861 | 10301 | CTCN_3559 | 20488 |
| TTCN_1134 | 10302 | GTCN_2034 | 20489 |
| TTCN_1135 | 10303 | CTCN_3560 | 20490 |
| TTCN_1136 | 10304 | CTCN_3561 | 20491 |
| TTCN_1137 | 10305 | CTCN_3562 | 20492 |
| CTCN_862 | 10306 | CTCN_3563 | 20493 |
| CTCN_863 | 10307 | CTCN_3564 | 20494 |
| TTCN_1138 | 10308 | CTCN_3565 | 20495 |
| TTCN_1139 | 10309 | GTCN_2035 | 20496 |
| TTCN_1140 | 10310 | CTCN_3566 | 20497 |
| TTCN_1141 | 10311 | CTCN_3567 | 20498 |
| ATCN_654 | 10312 | CTCN_3568 | 20499 |
| CTCN_864 | 10313 | CTCN_3569 | 20500 |
| GTCN_566 | 10314 | GTCN_2036 | 20501 |
| TTCN_1142 | 10315 | CTCN_3570 | 20502 |
| ATCN_655 | 10316 | CTCN_3571 | 20503 |
| CTCN_865 | 10317 | CTCN_3572 | 20504 |
| CTCN_866 | 10318 | CTCN_3573 | 20505 |
| TTCN_1143 | 10319 | GTCN_2037 | 20506 |
| GTCN_567 | 10320 | CTCN_3574 | 20507 |
| GTCN_568 | 10321 | CTCN_3575 | 20508 |
| ATCN_656 | 10322 | CTCN_3576 | 20509 |
| CTCN_867 | 10323 | CTCN_3577 | 20510 |
| TTCN_1144 | 10324 | GTCN_2038 | 20511 |
| ATCN_657 | 10325 | GTCN_2039 | 20512 |
| CTCN_868 | 10326 | ATCN_2402 | 20513 |

| | | | |
|---|---|---|---|
| CTCN_869 | 10327 | ATCN_2403 | 20514 |
| CTCN_870 | 10328 | ATCN_2404 | 20515 |
| CTCN_871 | 10329 | GTCN_2040 | 20516 |
| CTCN_872 | 10330 | CTCN_3578 | 20517 |
| CTCN_873 | 10331 | ATCN_2405 | 20518 |
| TTCN_1145 | 10332 | GTCN_2041 | 20519 |
| ATCN_658 | 10333 | GTCN_2042 | 20520 |
| GTCN_569 | 10334 | ATCN_2406 | 20521 |
| TTCN_1146 | 10335 | TTCN_3856 | 20522 |
| ATCN_659 | 10336 | CTCN_3579 | 20523 |
| GTCN_570 | 10337 | CTCN_3580 | 20524 |
| TTCN_1147 | 10338 | CTCN_3581 | 20525 |
| GTCN_571 | 10339 | TTCN_3857 | 20526 |
| TTCN_1148 | 10340 | TTCN_3858 | 20527 |
| ATCN_660 | 10341 | GTCN_2043 | 20528 |
| TTCN_1149 | 10342 | ATCN_2407 | 20529 |
| CTCN_874 | 10343 | CTCN_3582 | 20530 |
| TTCN_1150 | 10344 | ATCN_2408 | 20531 |
| ATCN_661 | 10345 | ATCN_2409 | 20532 |
| TTCN_1151 | 10346 | ATCN_2410 | 20533 |
| CTCN_875 | 10347 | TTCN_3859 | 20534 |
| GTCN_572 | 10348 | TTCN_3860 | 20535 |
| ATCN_662 | 10349 | TTCN_3861 | 20536 |
| ATCN_663 | 10350 | CTCN_3583 | 20537 |
| CTCN_876 | 10351 | GTCN_2044 | 20538 |
| ATCN_664 | 10352 | CTCN_3584 | 20539 |
| TTCN_1152 | 10353 | CTCN_3585 | 20540 |
| ATCN_665 | 10354 | GTCN_2045 | 20541 |
| TTCN_1153 | 10355 | CTCN_3586 | 20542 |
| CTCN_877 | 10356 | GTCN_2046 | 20543 |
| GTCN_573 | 10357 | CTCN_3587 | 20544 |
| TTCN_1154 | 10358 | GTCN_2047 | 20545 |
| GTCN_574 | 10359 | CTCN_3588 | 20546 |
| ATCN_666 | 10360 | CTCN_3589 | 20547 |
| TTCN_1155 | 10361 | CTCN_3590 | 20548 |
| TTCN_1156 | 10362 | ATCN_2411 | 20549 |
| TTCN_1157 | 10363 | TTCN_3862 | 20550 |
| GTCN_575 | 10364 | CTCN_3591 | 20551 |
| GTCN_576 | 10365 | ATCN_2412 | 20552 |
| CTCN_878 | 10366 | ATCN_2413 | 20553 |
| TTCN_1158 | 10367 | CTCN_3592 | 20554 |
| CTCN_879 | 10368 | GTCN_2048 | 20555 |
| ATCN_667 | 10369 | CTCN_3593 | 20556 |
| GTCN_577 | 10370 | CTCN_3594 | 20557 |
| CTCN_880 | 10371 | ATCN_2414 | 20558 |
| TTCN_1159 | 10372 | CTCN_3595 | 20559 |
| ATCN_668 | 10373 | GTCN_2049 | 20560 |
| TTCN_1160 | 10374 | CTCN_3596 | 20561 |
| CTCN_881 | 10375 | TTCN_3863 | 20562 |
| GTCN_578 | 10376 | TTCN_3864 | 20563 |
| GTCN_579 | 10377 | CTCN_3597 | 20564 |
| TTCN_1161 | 10378 | CTCN_3598 | 20565 |
| TTCN_1162 | 10379 | CTCN_3599 | 20566 |
| GTCN_580 | 10380 | CTCN_3600 | 20567 |
| CTCN_882 | 10381 | TTCN_3865 | 20568 |

FIG. 36 (continued)

| | | | |
|---|---|---|---|
| TTCN_1163 | 10382 | CTCN_3601 | 20569 |
| CTCN_883 | 10383 | GTCN_2050 | 20570 |
| TTCN_1164 | 10384 | CTCN_3602 | 20571 |
| TTCN_1165 | 10385 | CTCN_3603 | 20572 |
| TTCN_1166 | 10386 | TTCN_3866 | 20573 |
| ATCN_669 | 10387 | CTCN_3604 | 20574 |
| TTCN_1167 | 10388 | TTCN_3867 | 20575 |
| CTCN_884 | 10389 | CTCN_3605 | 20576 |
| CTCN_885 | 10390 | CTCN_3606 | 20577 |
| GTCN_581 | 10391 | GTCN_2051 | 20578 |
| TTCN_1168 | 10392 | TTCN_3868 | 20579 |
| ATCN_670 | 10393 | GTCN_2052 | 20580 |
| TTCN_1169 | 10394 | TTCN_3869 | 20581 |
| CTCN_886 | 10395 | CTCN_3607 | 20582 |
| CTCN_887 | 10396 | GTCN_2053 | 20583 |
| GTCN_582 | 10397 | TTCN_3870 | 20584 |
| TTCN_1170 | 10398 | GTCN_2054 | 20585 |
| CTCN_888 | 10399 | GTCN_2055 | 20586 |
| TTCN_1171 | 10400 | CTCN_3608 | 20587 |
| ATCN_671 | 10401 | CTCN_3609 | 20588 |
| TTCN_1172 | 10402 | GTCN_2056 | 20589 |
| TTCN_1173 | 10403 | CTCN_3610 | 20590 |
| CTCN_889 | 10404 | GTCN_2057 | 20591 |
| GTCN_583 | 10405 | ATCN_2415 | 20592 |
| TTCN_1174 | 10406 | TTCN_3871 | 20593 |
| TTCN_1175 | 10407 | TTCN_3872 | 20594 |
| TTCN_1176 | 10408 | GTCN_2058 | 20595 |
| TTCN_1177 | 10409 | TTCN_3873 | 20596 |
| GTCN_584 | 10410 | CTCN_3611 | 20597 |
| TTCN_1178 | 10411 | GTCN_2059 | 20598 |
| ATCN_672 | 10412 | CTCN_3612 | 20599 |
| GTCN_585 | 10413 | CTCN_3613 | 20600 |
| CTCN_890 | 10414 | GTCN_2060 | 20601 |
| ATCN_673 | 10415 | GTCN_2061 | 20602 |
| CTCN_891 | 10416 | TTCN_3874 | 20603 |
| GTCN_586 | 10417 | TTCN_3875 | 20604 |
| CTCN_892 | 10418 | GTCN_2062 | 20605 |
| TTCN_1179 | 10419 | CTCN_3614 | 20606 |
| ATCN_674 | 10420 | CTCN_3615 | 20607 |
| ATCN_675 | 10421 | ATCN_2416 | 20608 |
| CTCN_893 | 10422 | TTCN_3876 | 20609 |
| TTCN_1180 | 10423 | CTCN_3616 | 20610 |
| CTCN_894 | 10424 | GTCN_2063 | 20611 |
| TTCN_1181 | 10425 | CTCN_3617 | 20612 |
| ATCN_676 | 10426 | CTCN_3618 | 20613 |
| ATCN_677 | 10427 | TTCN_3877 | 20614 |
| CTCN_895 | 10428 | TTCN_3878 | 20615 |
| ATCN_678 | 10429 | TTCN_3879 | 20616 |
| GTCN_587 | 10430 | GTCN_2064 | 20617 |
| CTCN_896 | 10431 | GTCN_2065 | 20618 |
| ATCN_679 | 10432 | CTCN_3619 | 20619 |
| CTCN_897 | 10433 | CTCN_3620 | 20620 |
| GTCN_588 | 10434 | CTCN_3621 | 20621 |
| GTCN_589 | 10435 | GTCN_2066 | 20622 |
| TTCN_1182 | 10436 | CTCN_3622 | 20623 |

| | | | |
|---|---|---|---|
| CTCN_898 | 10437 | CTCN_3623 | 20624 |
| GTCN_590 | 10438 | TTCN_3880 | 20625 |
| GTCN_591 | 10439 | TTCN_3881 | 20626 |
| ATCN_680 | 10440 | CTCN_3624 | 20627 |
| CTCN_899 | 10441 | ATCN_2417 | 20628 |
| CTCN_900 | 10442 | CTCN_3625 | 20629 |
| CTCN_901 | 10443 | GTCN_2067 | 20630 |
| GTCN_592 | 10444 | TTCN_3882 | 20631 |
| ATCN_681 | 10445 | CTCN_3626 | 20632 |
| CTCN_902 | 10446 | GTCN_2068 | 20633 |
| TTCN_1183 | 10447 | CTCN_3627 | 20634 |
| ATCN_682 | 10448 | CTCN_3628 | 20635 |
| ATCN_683 | 10449 | CTCN_3629 | 20636 |
| TTCN_1184 | 10450 | ATCN_2418 | 20637 |
| TTCN_1185 | 10451 | CTCN_3630 | 20638 |
| CTCN_903 | 10452 | GTCN_2069 | 20639 |
| ATCN_684 | 10453 | CTCN_3631 | 20640 |
| ATCN_685 | 10454 | GTCN_2070 | 20641 |
| ATCN_686 | 10455 | TTCN_3883 | 20642 |
| TTCN_1186 | 10456 | CTCN_3632 | 20643 |
| CTCN_904 | 10457 | ATCN_2419 | 20644 |
| ATCN_687 | 10458 | ATCN_2420 | 20645 |
| CTCN_905 | 10459 | GTCN_2071 | 20646 |
| TTCN_1187 | 10460 | ATCN_2421 | 20647 |
| GTCN_593 | 10461 | ATCN_2422 | 20648 |
| TTCN_1188 | 10462 | TTCN_3884 | 20649 |
| CTCN_906 | 10463 | GTCN_2072 | 20650 |
| GTCN_594 | 10464 | CTCN_3633 | 20651 |
| TTCN_1189 | 10465 | ATCN_2423 | 20652 |
| CTCN_907 | 10466 | TTCN_3885 | 20653 |
| TTCN_1190 | 10467 | GTCN_2073 | 20654 |
| CTCN_908 | 10468 | GTCN_2074 | 20655 |
| CTCN_909 | 10469 | ATCN_2424 | 20656 |
| CTCN_910 | 10470 | GTCN_2075 | 20657 |
| CTCN_911 | 10471 | TTCN_3886 | 20658 |
| GTCN_595 | 10472 | TTCN_3887 | 20659 |
| GTCN_596 | 10473 | ATCN_2425 | 20660 |
| CTCN_912 | 10474 | TTCN_3888 | 20661 |
| ATCN_688 | 10475 | TTCN_3889 | 20662 |
| ATCN_689 | 10476 | GTCN_2076 | 20663 |
| GTCN_597 | 10477 | CTCN_3634 | 20664 |
| TTCN_1191 | 10478 | CTCN_3635 | 20665 |
| ATCN_690 | 10479 | CTCN_3636 | 20666 |
| ATCN_691 | 10480 | CTCN_3637 | 20667 |
| TTCN_1192 | 10481 | CTCN_3638 | 20668 |
| GTCN_598 | 10482 | CTCN_3639 | 20669 |
| TTCN_1193 | 10483 | CTCN_3640 | 20670 |
| CTCN_913 | 10484 | CTCN_3641 | 20671 |
| CTCN_914 | 10485 | TTCN_3890 | 20672 |
| ATCN_692 | 10486 | TTCN_3891 | 20673 |
| CTCN_915 | 10487 | ATCN_2426 | 20674 |
| CTCN_916 | 10488 | CTCN_3642 | 20675 |
| GTCN_599 | 10489 | TTCN_3892 | 20676 |
| TTCN_1194 | 10490 | GTCN_2077 | 20677 |
| ATCN_693 | 10491 | CTCN_3643 | 20678 |

FIG. 36 (continued)

| | | | |
|---|---|---|---|
| TTCN_1195 | 10492 | GTCN_2078 | 20679 |
| CTCN_917 | 10493 | TTCN_3893 | 20680 |
| CTCN_918 | 10494 | CTCN_3644 | 20681 |
| TTCN_1196 | 10495 | GTCN_2079 | 20682 |
| GTCN_600 | 10496 | TTCN_3894 | 20683 |
| CTCN_919 | 10497 | TTCN_3895 | 20684 |
| TTCN_1197 | 10498 | TTCN_3896 | 20685 |
| GTCN_601 | 10499 | TTCN_3897 | 20686 |
| CTCN_920 | 10500 | CTCN_3645 | 20687 |
| ATCN_694 | 10501 | CTCN_3646 | 20688 |
| CTCN_921 | 10502 | ATCN_2427 | 20689 |
| CTCN_922 | 10503 | ATCN_2428 | 20690 |
| ATCN_695 | 10504 | CTCN_3647 | 20691 |
| ATCN_696 | 10505 | GTCN_2080 | 20692 |
| CTCN_923 | 10506 | GTCN_2081 | 20693 |
| CTCN_924 | 10507 | ATCN_2429 | 20694 |
| CTCN_925 | 10508 | CTCN_3648 | 20695 |
| CTCN_926 | 10509 | GTCN_2082 | 20696 |
| TTCN_1198 | 10510 | GTCN_2083 | 20697 |
| TTCN_1199 | 10511 | CTCN_3649 | 20698 |
| ATCN_697 | 10512 | GTCN_2084 | 20699 |
| CTCN_927 | 10513 | CTCN_3650 | 20700 |
| CTCN_928 | 10514 | GTCN_2085 | 20701 |
| ATCN_698 | 10515 | CTCN_3651 | 20702 |
| CTCN_929 | 10516 | GTCN_2086 | 20703 |
| CTCN_930 | 10517 | TTCN_3898 | 20704 |
| TTCN_1200 | 10518 | CTCN_3652 | 20705 |
| ATCN_699 | 10519 | TTCN_3899 | 20706 |
| ATCN_700 | 10520 | CTCN_3653 | 20707 |
| CTCN_931 | 10521 | CTCN_3654 | 20708 |
| GTCN_602 | 10522 | GTCN_2087 | 20709 |
| GTCN_603 | 10523 | CTCN_3655 | 20710 |
| CTCN_932 | 10524 | ATCN_2430 | 20711 |
| GTCN_604 | 10525 | CTCN_3656 | 20712 |
| TTCN_1201 | 10526 | CTCN_3657 | 20713 |
| CTCN_933 | 10527 | TTCN_3900 | 20714 |
| ATCN_701 | 10528 | GTCN_2088 | 20715 |
| ATCN_702 | 10529 | CTCN_3658 | 20716 |
| ATCN_703 | 10530 | TTCN_3901 | 20717 |
| TTCN_1202 | 10531 | GTCN_2089 | 20718 |
| TTCN_1203 | 10532 | ATCN_2431 | 20719 |
| CTCN_934 | 10533 | CTCN_3659 | 20720 |
| TTCN_1204 | 10534 | GTCN_2090 | 20721 |
| CTCN_935 | 10535 | CTCN_3660 | 20722 |
| CTCN_936 | 10536 | CTCN_3661 | 20723 |
| CTCN_937 | 10537 | GTCN_2091 | 20724 |
| GTCN_605 | 10538 | GTCN_2092 | 20725 |
| CTCN_938 | 10539 | TTCN_3902 | 20726 |
| TTCN_1205 | 10540 | TTCN_3903 | 20727 |
| ATCN_704 | 10541 | GTCN_2093 | 20728 |
| CTCN_939 | 10542 | GTCN_2094 | 20729 |
| TTCN_1206 | 10543 | GTCN_2095 | 20730 |
| GTCN_606 | 10544 | CTCN_3662 | 20731 |
| TTCN_1207 | 10545 | CTCN_3663 | 20732 |
| TTCN_1208 | 10546 | CTCN_3664 | 20733 |

| | | | |
|---|---|---|---|
| ATCN_705 | 10547 | TTCN_3904 | 20734 |
| TTCN_1209 | 10548 | CTCN_3665 | 20735 |
| TTCN_1210 | 10549 | GTCN_2096 | 20736 |
| TTCN_1211 | 10550 | CTCN_3666 | 20737 |
| ATCN_706 | 10551 | CTCN_3667 | 20738 |
| CTCN_940 | 10552 | CTCN_3668 | 20739 |
| CTCN_941 | 10553 | CTCN_3669 | 20740 |
| CTCN_942 | 10554 | GTCN_2097 | 20741 |
| ATCN_707 | 10555 | GTCN_2098 | 20742 |
| ATCN_708 | 10556 | CTCN_3670 | 20743 |
| TTCN_1212 | 10557 | GTCN_2099 | 20744 |
| ATCN_709 | 10558 | TTCN_3905 | 20745 |
| CTCN_943 | 10559 | TTCN_3906 | 20746 |
| ATCN_710 | 10560 | TTCN_3907 | 20747 |
| TTCN_1213 | 10561 | GTCN_2100 | 20748 |
| ATCN_711 | 10562 | CTCN_3671 | 20749 |
| GTCN_607 | 10563 | TTCN_3908 | 20750 |
| CTCN_944 | 10564 | CTCN_3672 | 20751 |
| ATCN_712 | 10565 | GTCN_2101 | 20752 |
| CTCN_945 | 10566 | CTCN_3673 | 20753 |
| GTCN_608 | 10567 | TTCN_3909 | 20754 |
| GTCN_609 | 10568 | GTCN_2102 | 20755 |
| ATCN_713 | 10569 | GTCN_2103 | 20756 |
| TTCN_1214 | 10570 | CTCN_3674 | 20757 |
| CTCN_946 | 10571 | TTCN_3910 | 20758 |
| GTCN_610 | 10572 | CTCN_3675 | 20759 |
| ATCN_714 | 10573 | CTCN_3676 | 20760 |
| GTCN_611 | 10574 | TTCN_3911 | 20761 |
| ATCN_715 | 10575 | ATCN_2432 | 20762 |
| GTCN_612 | 10576 | CTCN_3677 | 20763 |
| TTCN_1215 | 10577 | TTCN_3912 | 20764 |
| GTCN_613 | 10578 | TTCN_3913 | 20765 |
| CTCN_947 | 10579 | CTCN_3678 | 20766 |
| GTCN_614 | 10580 | CTCN_3679 | 20767 |
| CTCN_948 | 10581 | CTCN_3680 | 20768 |
| GTCN_615 | 10582 | ATCN_2433 | 20769 |
| ATCN_716 | 10583 | ATCN_2434 | 20770 |
| ATCN_717 | 10584 | CTCN_3681 | 20771 |
| CTCN_949 | 10585 | CTCN_3682 | 20772 |
| GTCN_616 | 10586 | CTCN_3683 | 20773 |
| CTCN_950 | 10587 | CTCN_3684 | 20774 |
| CTCN_951 | 10588 | GTCN_2104 | 20775 |
| TTCN_1216 | 10589 | CTCN_3685 | 20776 |
| ATCN_718 | 10590 | CTCN_3686 | 20777 |
| CTCN_952 | 10591 | CTCN_3687 | 20778 |
| ATCN_719 | 10592 | CTCN_3688 | 20779 |
| GTCN_617 | 10593 | CTCN_3689 | 20780 |
| CTCN_953 | 10594 | CTCN_3690 | 20781 |
| ATCN_720 | 10595 | ATCN_2435 | 20782 |
| ATCN_721 | 10596 | ATCN_2436 | 20783 |
| TTCN_1217 | 10597 | GTCN_2105 | 20784 |
| GTCN_618 | 10598 | ATCN_2437 | 20785 |
| TTCN_1218 | 10599 | ATCN_2438 | 20786 |
| GTCN_619 | 10600 | CTCN_3691 | 20787 |
| ATCN_722 | 10601 | ATCN_2439 | 20788 |

FIG. 36 (continued)

| | | | |
|---|---|---|---|
| GTCN_620 | 10602 | GTCN_2106 | 20789 |
| TTCN_1219 | 10603 | CTCN_3692 | 20790 |
| TTCN_1220 | 10604 | CTCN_3693 | 20791 |
| GTCN_621 | 10605 | GTCN_2107 | 20792 |
| ATCN_723 | 10606 | CTCN_3694 | 20793 |
| TTCN_1221 | 10607 | GTCN_2108 | 20794 |
| CTCN_954 | 10608 | CTCN_3695 | 20795 |
| ATCN_724 | 10609 | CTCN_3696 | 20796 |
| TTCN_1222 | 10610 | TTCN_3914 | 20797 |
| GTCN_622 | 10611 | CTCN_3697 | 20798 |
| ATCN_725 | 10612 | CTCN_3698 | 20799 |
| TTCN_1223 | 10613 | CTCN_3699 | 20800 |
| CTCN_955 | 10614 | ATCN_2440 | 20801 |
| GTCN_623 | 10615 | TTCN_3915 | 20802 |
| TTCN_1224 | 10616 | CTCN_3700 | 20803 |
| TTCN_1225 | 10617 | CTCN_3701 | 20804 |
| TTCN_1226 | 10618 | GTCN_2109 | 20805 |
| ATCN_726 | 10619 | CTCN_3702 | 20806 |
| ATCN_727 | 10620 | ATCN_2441 | 20807 |
| CTCN_956 | 10621 | GTCN_2110 | 20808 |
| CTCN_957 | 10622 | ATCN_2442 | 20809 |
| CTCN_958 | 10623 | GTCN_2111 | 20810 |
| ATCN_728 | 10624 | ATCN_2443 | 20811 |
| CTCN_959 | 10625 | GTCN_2112 | 20812 |
| TTCN_1227 | 10626 | GTCN_2113 | 20813 |
| ATCN_729 | 10627 | GTCN_2114 | 20814 |
| TTCN_1228 | 10628 | GTCN_2115 | 20815 |
| TTCN_1229 | 10629 | CTCN_3703 | 20816 |
| TTCN_1230 | 10630 | GTCN_2116 | 20817 |
| TTCN_1231 | 10631 | TTCN_3916 | 20818 |
| GTCN_624 | 10632 | ATCN_2444 | 20819 |
| ATCN_730 | 10633 | GTCN_2117 | 20820 |
| TTCN_1232 | 10634 | CTCN_3704 | 20821 |
| GTCN_625 | 10635 | CTCN_3705 | 20822 |
| ATCN_731 | 10636 | TTCN_3917 | 20823 |
| ATCN_732 | 10637 | TTCN_3918 | 20824 |
| TTCN_1233 | 10638 | ATCN_2445 | 20825 |
| TTCN_1234 | 10639 | ATCN_2446 | 20826 |
| ATCN_733 | 10640 | CTCN_3706 | 20827 |
| ATCN_734 | 10641 | TTCN_3919 | 20828 |
| ATCN_735 | 10642 | GTCN_2118 | 20829 |
| ATCN_736 | 10643 | ATCN_2447 | 20830 |
| CTCN_960 | 10644 | CTCN_3707 | 20831 |
| CTCN_961 | 10645 | GTCN_2119 | 20832 |
| TTCN_1235 | 10646 | CTCN_3708 | 20833 |
| GTCN_626 | 10647 | TTCN_3920 | 20834 |
| TTCN_1236 | 10648 | CTCN_3709 | 20835 |
| TTCN_1237 | 10649 | GTCN_2120 | 20836 |
| GTCN_627 | 10650 | TTCN_3921 | 20837 |
| GTCN_628 | 10651 | CTCN_3710 | 20838 |
| GTCN_629 | 10652 | ATCN_2448 | 20839 |
| ATCN_737 | 10653 | TTCN_3922 | 20840 |
| TTCN_1238 | 10654 | TTCN_3923 | 20841 |
| ATCN_738 | 10655 | CTCN_3711 | 20842 |
| CTCN_962 | 10656 | TTCN_3924 | 20843 |

| | | | |
|---|---|---|---|
| CTCN_963 | 10657 | CTCN_3712 | 20844 |
| CTCN_964 | 10658 | TTCN_3925 | 20845 |
| TTCN_1239 | 10659 | GTCN_2121 | 20846 |
| ATCN_739 | 10660 | ATCN_2449 | 20847 |
| GTCN_630 | 10661 | GTCN_2122 | 20848 |
| CTCN_965 | 10662 | GTCN_2123 | 20849 |
| GTCN_631 | 10663 | GTCN_2124 | 20850 |
| CTCN_966 | 10664 | ATCN_2450 | 20851 |
| CTCN_967 | 10665 | GTCN_2125 | 20852 |
| CTCN_968 | 10666 | ATCN_2451 | 20853 |
| TTCN_1240 | 10667 | CTCN_3713 | 20854 |
| CTCN_969 | 10668 | CTCN_3714 | 20855 |
| TTCN_1241 | 10669 | CTCN_3715 | 20856 |
| CTCN_970 | 10670 | TTCN_3926 | 20857 |
| ATCN_740 | 10671 | GTCN_2126 | 20858 |
| GTCN_632 | 10672 | ATCN_2452 | 20859 |
| GTCN_633 | 10673 | ATCN_2453 | 20860 |
| CTCN_971 | 10674 | GTCN_2127 | 20861 |
| GTCN_634 | 10675 | GTCN_2128 | 20862 |
| CTCN_972 | 10676 | CTCN_3716 | 20863 |
| TTCN_1242 | 10677 | CTCN_3717 | 20864 |
| CTCN_973 | 10678 | CTCN_3718 | 20865 |
| TTCN_1243 | 10679 | TTCN_3927 | 20866 |
| ATCN_741 | 10680 | CTCN_3719 | 20867 |
| TTCN_1244 | 10681 | CTCN_3720 | 20868 |
| TTCN_1245 | 10682 | CTCN_3721 | 20869 |
| GTCN_635 | 10683 | TTCN_3928 | 20870 |
| GTCN_636 | 10684 | TTCN_3929 | 20871 |
| GTCN_637 | 10685 | CTCN_3722 | 20872 |
| GTCN_638 | 10686 | GTCN_2129 | 20873 |
| TTCN_1246 | 10687 | ATCN_2454 | 20874 |
| GTCN_639 | 10688 | ATCN_2455 | 20875 |
| TTCN_1247 | 10689 | ATCN_2456 | 20876 |
| TTCN_1248 | 10690 | CTCN_3723 | 20877 |
| ATCN_742 | 10691 | GTCN_2130 | 20878 |
| CTCN_974 | 10692 | CTCN_3724 | 20879 |
| TTCN_1249 | 10693 | TTCN_3930 | 20880 |
| CTCN_975 | 10694 | GTCN_2131 | 20881 |
| GTCN_640 | 10695 | TTCN_3931 | 20882 |
| GTCN_641 | 10696 | CTCN_3725 | 20883 |
| CTCN_976 | 10697 | CTCN_3726 | 20884 |
| TTCN_1250 | 10698 | CTCN_3727 | 20885 |
| CTCN_977 | 10699 | CTCN_3728 | 20886 |
| TTCN_1251 | 10700 | TTCN_3932 | 20887 |
| ATCN_743 | 10701 | TTCN_3933 | 20888 |
| GTCN_642 | 10702 | GTCN_2132 | 20889 |
| CTCN_978 | 10703 | CTCN_3729 | 20890 |
| CTCN_979 | 10704 | ATCN_2457 | 20891 |
| GTCN_643 | 10705 | TTCN_3934 | 20892 |
| CTCN_980 | 10706 | GTCN_2133 | 20893 |
| TTCN_1252 | 10707 | CTCN_3730 | 20894 |
| ATCN_744 | 10708 | GTCN_2134 | 20895 |
| GTCN_644 | 10709 | CTCN_3731 | 20896 |
| GTCN_645 | 10710 | ATCN_2458 | 20897 |
| TTCN_1253 | 10711 | TTCN_3935 | 20898 |

FIG. 36 (continued)

| | | | |
|---|---|---|---|
| TTCN_1254 | 10712 | GTCN_2135 | 20899 |
| TTCN_1255 | 10713 | TTCN_3936 | 20900 |
| ATCN_745 | 10714 | ATCN_2459 | 20901 |
| ATCN_746 | 10715 | ATCN_2460 | 20902 |
| GTCN_646 | 10716 | TTCN_3937 | 20903 |
| ATCN_747 | 10717 | CTCN_3732 | 20904 |
| ATCN_748 | 10718 | TTCN_3938 | 20905 |
| ATCN_749 | 10719 | ATCN_2461 | 20906 |
| ATCN_750 | 10720 | ATCN_2462 | 20907 |
| ATCN_751 | 10721 | TTCN_3939 | 20908 |
| ATCN_752 | 10722 | CTCN_3733 | 20909 |
| ATCN_753 | 10723 | TTCN_3940 | 20910 |
| ATCN_754 | 10724 | TTCN_3941 | 20911 |
| ATCN_755 | 10725 | TTCN_3942 | 20912 |
| ATCN_756 | 10726 | TTCN_3943 | 20913 |
| CTCN_981 | 10727 | ATCN_2463 | 20914 |
| TTCN_1256 | 10728 | ATCN_2464 | 20915 |
| ATCN_757 | 10729 | ATCN_2465 | 20916 |
| TTCN_1257 | 10730 | ATCN_2466 | 20917 |
| CTCN_982 | 10731 | ATCN_2467 | 20918 |
| GTCN_647 | 10732 | TTCN_3944 | 20919 |
| ATCN_758 | 10733 | CTCN_3734 | 20920 |
| ATCN_759 | 10734 | TTCN_3945 | 20921 |
| TTCN_1258 | 10735 | CTCN_3735 | 20922 |
| TTCN_1259 | 10736 | CTCN_3736 | 20923 |
| TTCN_1260 | 10737 | TTCN_3946 | 20924 |
| CTCN_983 | 10738 | GTCN_2136 | 20925 |
| TTCN_1261 | 10739 | TTCN_3947 | 20926 |
| TTCN_1262 | 10740 | CTCN_3737 | 20927 |
| TTCN_1263 | 10741 | GTCN_2137 | 20928 |
| TTCN_1264 | 10742 | CTCN_3738 | 20929 |
| TTCN_1265 | 10743 | TTCN_3948 | 20930 |
| ATCN_760 | 10744 | CTCN_3739 | 20931 |
| GTCN_648 | 10745 | ATCN_2468 | 20932 |
| GTCN_649 | 10746 | GTCN_2138 | 20933 |
| CTCN_984 | 10747 | CTCN_3740 | 20934 |
| CTCN_985 | 10748 | TTCN_3949 | 20935 |
| CTCN_986 | 10749 | CTCN_3741 | 20936 |
| ATCN_761 | 10750 | CTCN_3742 | 20937 |
| CTCN_987 | 10751 | CTCN_3743 | 20938 |
| TTCN_1266 | 10752 | GTCN_2139 | 20939 |
| CTCN_988 | 10753 | CTCN_3744 | 20940 |
| CTCN_989 | 10754 | CTCN_3745 | 20941 |
| CTCN_990 | 10755 | CTCN_3746 | 20942 |
| TTCN_1267 | 10756 | TTCN_3950 | 20943 |
| CTCN_991 | 10757 | GTCN_2140 | 20944 |
| GTCN_650 | 10758 | GTCN_2141 | 20945 |
| TTCN_1268 | 10759 | CTCN_3747 | 20946 |
| CTCN_992 | 10760 | TTCN_3951 | 20947 |
| CTCN_993 | 10761 | CTCN_3748 | 20948 |
| CTCN_994 | 10762 | CTCN_3749 | 20949 |
| CTCN_995 | 10763 | TTCN_3952 | 20950 |
| CTCN_996 | 10764 | CTCN_3750 | 20951 |
| GTCN_651 | 10765 | GTCN_2142 | 20952 |
| CTCN_997 | 10766 | TTCN_3953 | 20953 |

| | | | |
|---|---|---|---|
| ATCN_762 | 10767 | CTCN_3751 | 20954 |
| TTCN_1269 | 10768 | ATCN_2469 | 20955 |
| CTCN_998 | 10769 | TTCN_3954 | 20956 |
| GTCN_652 | 10770 | CTCN_3752 | 20957 |
| CTCN_999 | 10771 | TTCN_3955 | 20958 |
| TTCN_1270 | 10772 | ATCN_2470 | 20959 |
| ATCN_763 | 10773 | TTCN_3956 | 20960 |
| TTCN_1271 | 10774 | TTCN_3957 | 20961 |
| ATCN_764 | 10775 | TTCN_3958 | 20962 |
| ATCN_765 | 10776 | ATCN_2471 | 20963 |
| CTCN_1000 | 10777 | TTCN_3959 | 20964 |
| TTCN_1272 | 10778 | TTCN_3960 | 20965 |
| ATCN_766 | 10779 | ATCN_2472 | 20966 |
| GTCN_653 | 10780 | TTCN_3961 | 20967 |
| ATCN_767 | 10781 | TTCN_3962 | 20968 |
| ATCN_768 | 10782 | GTCN_2143 | 20969 |
| CTCN_1001 | 10783 | TTCN_3963 | 20970 |
| GTCN_654 | 10784 | GTCN_2144 | 20971 |
| ATCN_769 | 10785 | TTCN_3964 | 20972 |
| ATCN_770 | 10786 | ATCN_2473 | 20973 |
| ATCN_771 | 10787 | GTCN_2145 | 20974 |
| CTCN_1002 | 10788 | ATCN_2474 | 20975 |
| CTCN_1003 | 10789 | CTCN_3753 | 20976 |
| CTCN_1004 | 10790 | TTCN_3965 | 20977 |
| TTCN_1273 | 10791 | TTCN_3966 | 20978 |
| CTCN_1005 | 10792 | CTCN_3754 | 20979 |
| ATCN_772 | 10793 | CTCN_3755 | 20980 |
| TTCN_1274 | 10794 | CTCN_3756 | 20981 |
| TTCN_1275 | 10795 | TTCN_3967 | 20982 |
| CTCN_1006 | 10796 | CTCN_3757 | 20983 |
| TTCN_1276 | 10797 | TTCN_3968 | 20984 |
| TTCN_1277 | 10798 | CTCN_3758 | 20985 |
| TTCN_1278 | 10799 | CTCN_3759 | 20986 |
| ATCN_773 | 10800 | CTCN_3760 | 20987 |
| ATCN_774 | 10801 | GTCN_2146 | 20988 |
| ATCN_775 | 10802 | TTCN_3969 | 20989 |
| GTCN_655 | 10803 | CTCN_3761 | 20990 |
| CTCN_1007 | 10804 | TTCN_3970 | 20991 |
| CTCN_1008 | 10805 | ATCN_2475 | 20992 |
| TTCN_1279 | 10806 | GTCN_2147 | 20993 |
| TTCN_1280 | 10807 | CTCN_3762 | 20994 |
| TTCN_1281 | 10808 | TTCN_3971 | 20995 |
| CTCN_1009 | 10809 | CTCN_3763 | 20996 |
| CTCN_1010 | 10810 | TTCN_3972 | 20997 |
| TTCN_1282 | 10811 | TTCN_3973 | 20998 |
| TTCN_1283 | 10812 | TTCN_3974 | 20999 |
| TTCN_1284 | 10813 | TTCN_3975 | 21000 |
| GTCN_656 | 10814 | ATCN_2476 | 21001 |
| ATCN_776 | 10815 | CTCN_3764 | 21002 |
| TTCN_1285 | 10816 | TTCN_3976 | 21003 |
| TTCN_1286 | 10817 | GTCN_2148 | 21004 |
| CTCN_1011 | 10818 | CTCN_3765 | 21005 |
| ATCN_777 | 10819 | GTCN_2149 | 21006 |
| TTCN_1287 | 10820 | CTCN_3766 | 21007 |
| CTCN_1012 | 10821 | TTCN_3977 | 21008 |

FIG. 36 (continued)

| | | | |
|---|---|---|---|
| GTCN_657 | 10822 | GTCN_2150 | 21009 |
| CTCN_1013 | 10823 | TTCN_3978 | 21010 |
| CTCN_1014 | 10824 | TTCN_3979 | 21011 |
| TTCN_1288 | 10825 | CTCN_3767 | 21012 |
| ATCN_778 | 10826 | CTCN_3768 | 21013 |
| GTCN_658 | 10827 | GTCN_2151 | 21014 |
| TTCN_1289 | 10828 | CTCN_3769 | 21015 |
| ATCN_779 | 10829 | CTCN_3770 | 21016 |
| TTCN_1290 | 10830 | ATCN_2477 | 21017 |
| CTCN_1015 | 10831 | TTCN_3980 | 21018 |
| TTCN_1291 | 10832 | CTCN_3771 | 21019 |
| GTCN_659 | 10833 | GTCN_2152 | 21020 |
| TTCN_1292 | 10834 | ATCN_2478 | 21021 |
| GTCN_660 | 10835 | CTCN_3772 | 21022 |
| CTCN_1016 | 10836 | CTCN_3773 | 21023 |
| ATCN_780 | 10837 | CTCN_3774 | 21024 |
| TTCN_1293 | 10838 | CTCN_3775 | 21025 |
| TTCN_1294 | 10839 | TTCN_3981 | 21026 |
| ATCN_781 | 10840 | CTCN_3776 | 21027 |
| GTCN_661 | 10841 | TTCN_3982 | 21028 |
| TTCN_1295 | 10842 | TTCN_3983 | 21029 |
| ATCN_782 | 10843 | CTCN_3777 | 21030 |
| ATCN_783 | 10844 | CTCN_3778 | 21031 |
| TTCN_1296 | 10845 | TTCN_3984 | 21032 |
| ATCN_784 | 10846 | ATCN_2479 | 21033 |
| ATCN_785 | 10847 | TTCN_3985 | 21034 |
| CTCN_1017 | 10848 | CTCN_3779 | 21035 |
| ATCN_786 | 10849 | GTCN_2153 | 21036 |
| CTCN_1018 | 10850 | CTCN_3780 | 21037 |
| TTCN_1297 | 10851 | CTCN_3781 | 21038 |
| TTCN_1298 | 10852 | TTCN_3986 | 21039 |
| ATCN_787 | 10853 | ATCN_2480 | 21040 |
| GTCN_662 | 10854 | CTCN_3782 | 21041 |
| TTCN_1299 | 10855 | CTCN_3783 | 21042 |
| CTCN_1019 | 10856 | TTCN_3987 | 21043 |
| GTCN_663 | 10857 | GTCN_2154 | 21044 |
| ATCN_788 | 10858 | CTCN_3784 | 21045 |
| CTCN_1020 | 10859 | GTCN_2155 | 21046 |
| TTCN_1300 | 10860 | TTCN_3988 | 21047 |
| TTCN_1301 | 10861 | CTCN_3785 | 21048 |
| CTCN_1021 | 10862 | TTCN_3989 | 21049 |
| GTCN_664 | 10863 | CTCN_3786 | 21050 |
| GTCN_665 | 10864 | CTCN_3787 | 21051 |
| TTCN_1302 | 10865 | GTCN_2156 | 21052 |
| TTCN_1303 | 10866 | CTCN_3788 | 21053 |
| ATCN_789 | 10867 | GTCN_2157 | 21054 |
| TTCN_1304 | 10868 | TTCN_3990 | 21055 |
| TTCN_1305 | 10869 | CTCN_3789 | 21056 |
| GTCN_666 | 10870 | TTCN_3991 | 21057 |
| TTCN_1306 | 10871 | TTCN_3992 | 21058 |
| CTCN_1022 | 10872 | TTCN_3993 | 21059 |
| TTCN_1307 | 10873 | ATCN_2481 | 21060 |
| TTCN_1308 | 10874 | ATCN_2482 | 21061 |
| TTCN_1309 | 10875 | ATCN_2483 | 21062 |
| GTCN_667 | 10876 | CTCN_3790 | 21063 |

| | | | |
|---|---|---|---|
| ATCN_790 | 10877 | CTCN_3791 | 21064 |
| TTCN_1310 | 10878 | ATCN_2484 | 21065 |
| TTCN_1311 | 10879 | ATCN_2485 | 21066 |
| ATCN_791 | 10880 | TTCN_3994 | 21067 |
| ATCN_792 | 10881 | TTCN_3995 | 21068 |
| CTCN_1023 | 10882 | TTCN_3996 | 21069 |
| CTCN_1024 | 10883 | ATCN_2486 | 21070 |
| TTCN_1312 | 10884 | ATCN_2487 | 21071 |
| TTCN_1313 | 10885 | CTCN_3792 | 21072 |
| TTCN_1314 | 10886 | CTCN_3793 | 21073 |
| ATCN_793 | 10887 | GTCN_2158 | 21074 |
| CTCN_1025 | 10888 | TTCN_3997 | 21075 |
| GTCN_668 | 10889 | TTCN_3998 | 21076 |
| CTCN_1026 | 10890 | TTCN_3999 | 21077 |
| GTCN_669 | 10891 | TTCN_4000 | 21078 |
| CTCN_1027 | 10892 | CTCN_3794 | 21079 |
| CTCN_1028 | 10893 | TTCN_4001 | 21080 |
| GTCN_670 | 10894 | ATCN_2488 | 21081 |
| TTCN_1315 | 10895 | ATCN_2489 | 21082 |
| GTCN_671 | 10896 | TTCN_4002 | 21083 |
| TTCN_1316 | 10897 | GTCN_2159 | 21084 |
| GTCN_672 | 10898 | GTCN_2160 | 21085 |
| CTCN_1029 | 10899 | CTCN_3795 | 21086 |
| CTCN_1030 | 10900 | CTCN_3796 | 21087 |
| CTCN_1031 | 10901 | GTCN_2161 | 21088 |
| ATCN_794 | 10902 | ATCN_2490 | 21089 |
| TTCN_1317 | 10903 | TTCN_4003 | 21090 |
| CTCN_1032 | 10904 | TTCN_4004 | 21091 |
| CTCN_1033 | 10905 | CTCN_3797 | 21092 |
| ATCN_795 | 10906 | GTCN_2162 | 21093 |
| ATCN_796 | 10907 | CTCN_3798 | 21094 |
| TTCN_1318 | 10908 | TTCN_4005 | 21095 |
| ATCN_797 | 10909 | TTCN_4006 | 21096 |
| ATCN_798 | 10910 | ATCN_2491 | 21097 |
| CTCN_1034 | 10911 | CTCN_3799 | 21098 |
| TTCN_1319 | 10912 | TTCN_4007 | 21099 |
| TTCN_1320 | 10913 | GTCN_2163 | 21100 |
| ATCN_799 | 10914 | TTCN_4008 | 21101 |
| CTCN_1035 | 10915 | TTCN_4009 | 21102 |
| TTCN_1321 | 10916 | CTCN_3800 | 21103 |
| TTCN_1322 | 10917 | ATCN_2492 | 21104 |
| ATCN_800 | 10918 | TTCN_4010 | 21105 |
| ATCN_801 | 10919 | CTCN_3801 | 21106 |
| GTCN_673 | 10920 | GTCN_2164 | 21107 |
| CTCN_1036 | 10921 | ATCN_2493 | 21108 |
| TTCN_1323 | 10922 | GTCN_2165 | 21109 |
| TTCN_1324 | 10923 | TTCN_4011 | 21110 |
| ATCN_802 | 10924 | ATCN_2494 | 21111 |
| CTCN_1037 | 10925 | TTCN_4012 | 21112 |
| TTCN_1325 | 10926 | TTCN_4013 | 21113 |
| GTCN_674 | 10927 | GTCN_2166 | 21114 |
| GTCN_675 | 10928 | ATCN_2495 | 21115 |
| ATCN_803 | 10929 | ATCN_2496 | 21116 |
| TTCN_1326 | 10930 | GTCN_2167 | 21117 |
| TTCN_1327 | 10931 | CTCN_3802 | 21118 |

FIG. 36 (continued)

| | | | |
|---|---|---|---|
| ATCN_804 | 10932 | ATCN_2497 | 21119 |
| ATCN_805 | 10933 | ATCN_2498 | 21120 |
| TTCN_1328 | 10934 | ATCN_2499 | 21121 |
| CTCN_1038 | 10935 | CTCN_3803 | 21122 |
| ATCN_806 | 10936 | ATCN_2500 | 21123 |
| TTCN_1329 | 10937 | ATCN_2501 | 21124 |
| TTCN_1330 | 10938 | ATCN_2502 | 21125 |
| CTCN_1039 | 10939 | GTCN_2168 | 21126 |
| CTCN_1040 | 10940 | CTCN_3804 | 21127 |
| TTCN_1331 | 10941 | TTCN_4014 | 21128 |
| TTCN_1332 | 10942 | CTCN_3805 | 21129 |
| CTCN_1041 | 10943 | CTCN_3806 | 21130 |
| ATCN_807 | 10944 | CTCN_3807 | 21131 |
| ATCN_808 | 10945 | ATCN_2503 | 21132 |
| GTCN_676 | 10946 | TTCN_4015 | 21133 |
| TTCN_1333 | 10947 | CTCN_3808 | 21134 |
| TTCN_1334 | 10948 | ATCN_2504 | 21135 |
| ATCN_809 | 10949 | ATCN_2505 | 21136 |
| CTCN_1042 | 10950 | TTCN_4016 | 21137 |
| GTCN_677 | 10951 | ATCN_2506 | 21138 |
| CTCN_1043 | 10952 | ATCN_2507 | 21139 |
| CTCN_1044 | 10953 | GTCN_2169 | 21140 |
| ATCN_810 | 10954 | CTCN_3809 | 21141 |
| CTCN_1045 | 10955 | ATCN_2508 | 21142 |
| ATCN_811 | 10956 | ATCN_2509 | 21143 |
| GTCN_678 | 10957 | TTCN_4017 | 21144 |
| CTCN_1046 | 10958 | CTCN_3810 | 21145 |
| TTCN_1335 | 10959 | GTCN_2170 | 21146 |
| CTCN_1047 | 10960 | CTCN_3811 | 21147 |
| ATCN_812 | 10961 | TTCN_4018 | 21148 |
| ATCN_813 | 10962 | TTCN_4019 | 21149 |
| ATCN_814 | 10963 | ATCN_2510 | 21150 |
| CTCN_1048 | 10964 | TTCN_4020 | 21151 |
| CTCN_1049 | 10965 | ATCN_2511 | 21152 |
| CTCN_1050 | 10966 | CTCN_3812 | 21153 |
| CTCN_1051 | 10967 | TTCN_4021 | 21154 |
| ATCN_815 | 10968 | CTCN_3813 | 21155 |
| ATCN_816 | 10969 | TTCN_4022 | 21156 |
| GTCN_679 | 10970 | GTCN_2171 | 21157 |
| CTCN_1052 | 10971 | TTCN_4023 | 21158 |
| TTCN_1336 | 10972 | GTCN_2172 | 21159 |
| TTCN_1337 | 10973 | GTCN_2173 | 21160 |
| CTCN_1053 | 10974 | TTCN_4024 | 21161 |
| ATCN_817 | 10975 | CTCN_3814 | 21162 |
| CTCN_1054 | 10976 | TTCN_4025 | 21163 |
| CTCN_1055 | 10977 | CTCN_3815 | 21164 |
| TTCN_1338 | 10978 | TTCN_4026 | 21165 |
| CTCN_1056 | 10979 | GTCN_2174 | 21166 |
| CTCN_1057 | 10980 | CTCN_3816 | 21167 |
| CTCN_1058 | 10981 | ATCN_2512 | 21168 |
| ATCN_818 | 10982 | ATCN_2513 | 21169 |
| ATCN_819 | 10983 | ATCN_2514 | 21170 |
| TTCN_1339 | 10984 | TTCN_4027 | 21171 |
| TTCN_1340 | 10985 | ATCN_2515 | 21172 |
| CTCN_1059 | 10986 | CTCN_3817 | 21173 |

| | | | |
|---|---|---|---|
| CTCN_1060 | 10987 | ATCN_2516 | 21174 |
| TTCN_1341 | 10988 | ATCN_2517 | 21175 |
| TTCN_1342 | 10989 | TTCN_4028 | 21176 |
| TTCN_1343 | 10990 | CTCN_3818 | 21177 |
| TTCN_1344 | 10991 | CTCN_3819 | 21178 |
| TTCN_1345 | 10992 | CTCN_3820 | 21179 |
| GTCN_680 | 10993 | CTCN_3821 | 21180 |
| TTCN_1346 | 10994 | CTCN_3822 | 21181 |
| TTCN_1347 | 10995 | ATCN_2518 | 21182 |
| CTCN_1061 | 10996 | CTCN_3823 | 21183 |
| TTCN_1348 | 10997 | ATCN_2519 | 21184 |
| TTCN_1349 | 10998 | TTCN_4029 | 21185 |
| TTCN_1350 | 10999 | ATCN_2520 | 21186 |
| TTCN_1351 | 11000 | ATCN_2521 | 21187 |
| GTCN_681 | 11001 | CTCN_3824 | 21188 |
| CTCN_1062 | 11002 | GTCN_2175 | 21189 |
| TTCN_1352 | 11003 | CTCN_3825 | 21190 |
| TTCN_1353 | 11004 | TTCN_4030 | 21191 |
| ATCN_820 | 11005 | GTCN_2176 | 21192 |
| TTCN_1354 | 11006 | TTCN_4031 | 21193 |
| TTCN_1355 | 11007 | ATCN_2522 | 21194 |
| CTCN_1063 | 11008 | CTCN_3826 | 21195 |
| CTCN_1064 | 11009 | ATCN_2523 | 21196 |
| ATCN_821 | 11010 | CTCN_3827 | 21197 |
| GTCN_682 | 11011 | CTCN_3828 | 21198 |
| GTCN_683 | 11012 | CTCN_3829 | 21199 |
| GTCN_684 | 11013 | TTCN_4032 | 21200 |
| ATCN_822 | 11014 | TTCN_4033 | 21201 |
| CTCN_1065 | 11015 | TTCN_4034 | 21202 |
| ATCN_823 | 11016 | CTCN_3830 | 21203 |
| ATCN_824 | 11017 | ATCN_2524 | 21204 |
| GTCN_685 | 11018 | CTCN_3831 | 21205 |
| TTCN_1356 | 11019 | CTCN_3832 | 21206 |
| TTCN_1357 | 11020 | ATCN_2525 | 21207 |
| TTCN_1358 | 11021 | ATCN_2526 | 21208 |
| ATCN_825 | 11022 | CTCN_3833 | 21209 |
| CTCN_1066 | 11023 | CTCN_3834 | 21210 |
| ATCN_826 | 11024 | GTCN_2177 | 21211 |
| TTCN_1359 | 11025 | CTCN_3835 | 21212 |
| GTCN_686 | 11026 | ATCN_2527 | 21213 |
| CTCN_1067 | 11027 | ATCN_2528 | 21214 |
| CTCN_1068 | 11028 | CTCN_3836 | 21215 |
| CTCN_1069 | 11029 | ATCN_2529 | 21216 |
| CTCN_1070 | 11030 | CTCN_3837 | 21217 |
| ATCN_827 | 11031 | ATCN_2530 | 21218 |
| GTCN_687 | 11032 | ATCN_2531 | 21219 |
| CTCN_1071 | 11033 | GTCN_2178 | 21220 |
| CTCN_1072 | 11034 | CTCN_3838 | 21221 |
| CTCN_1073 | 11035 | GTCN_2179 | 21222 |
| TTCN_1360 | 11036 | TTCN_4035 | 21223 |
| GTCN_688 | 11037 | GTCN_2180 | 21224 |
| CTCN_1074 | 11038 | CTCN_3839 | 21225 |
| GTCN_689 | 11039 | TTCN_4036 | 21226 |
| CTCN_1075 | 11040 | GTCN_2181 | 21227 |
| CTCN_1076 | 11041 | ATCN_2532 | 21228 |

FIG. 36 (continued)

| | | | |
|---|---|---|---|
| GTCN_690 | 11042 | ATCN_2533 | 21229 |
| CTCN_1077 | 11043 | CTCN_3840 | 21230 |
| GTCN_691 | 11044 | GTCN_2182 | 21231 |
| GTCN_692 | 11045 | GTCN_2183 | 21232 |
| GTCN_693 | 11046 | CTCN_3841 | 21233 |
| CTCN_1078 | 11047 | CTCN_3842 | 21234 |
| CTCN_1079 | 11048 | GTCN_2184 | 21235 |
| TTCN_1361 | 11049 | TTCN_4037 | 21236 |
| TTCN_1362 | 11050 | CTCN_3843 | 21237 |
| GTCN_694 | 11051 | CTCN_3844 | 21238 |
| CTCN_1080 | 11052 | GTCN_2185 | 21239 |
| TTCN_1363 | 11053 | TTCN_4038 | 21240 |
| TTCN_1364 | 11054 | TTCN_4039 | 21241 |
| ATCN_828 | 11055 | TTCN_4040 | 21242 |
| CTCN_1081 | 11056 | CTCN_3845 | 21243 |
| CTCN_1082 | 11057 | CTCN_3846 | 21244 |
| TTCN_1365 | 11058 | TTCN_4041 | 21245 |
| GTCN_695 | 11059 | CTCN_3847 | 21246 |
| GTCN_696 | 11060 | CTCN_3848 | 21247 |
| CTCN_1083 | 11061 | TTCN_4042 | 21248 |
| CTCN_1084 | 11062 | TTCN_4043 | 21249 |
| CTCN_1085 | 11063 | CTCN_3849 | 21250 |
| TTCN_1366 | 11064 | TTCN_4044 | 21251 |
| TTCN_1367 | 11065 | CTCN_3850 | 21252 |
| TTCN_1368 | 11066 | GTCN_2186 | 21253 |
| TTCN_1369 | 11067 | GTCN_2187 | 21254 |
| TTCN_1370 | 11068 | TTCN_4045 | 21255 |
| TTCN_1371 | 11069 | TTCN_4046 | 21256 |
| TTCN_1372 | 11070 | TTCN_4047 | 21257 |
| CTCN_1086 | 11071 | CTCN_3851 | 21258 |
| GTCN_697 | 11072 | TTCN_4048 | 21259 |
| ATCN_829 | 11073 | CTCN_3852 | 21260 |
| CTCN_1087 | 11074 | TTCN_4049 | 21261 |
| TTCN_1373 | 11075 | TTCN_4050 | 21262 |
| ATCN_830 | 11076 | CTCN_3853 | 21263 |
| TTCN_1374 | 11077 | CTCN_3854 | 21264 |
| CTCN_1088 | 11078 | ATCN_2534 | 21265 |
| ATCN_831 | 11079 | ATCN_2535 | 21266 |
| TTCN_1375 | 11080 | GTCN_2188 | 21267 |
| TTCN_1376 | 11081 | ATCN_2536 | 21268 |
| TTCN_1377 | 11082 | GTCN_2189 | 21269 |
| TTCN_1378 | 11083 | ATCN_2537 | 21270 |
| GTCN_698 | 11084 | TTCN_4051 | 21271 |
| TTCN_1379 | 11085 | GTCN_2190 | 21272 |
| ATCN_832 | 11086 | CTCN_3855 | 21273 |
| TTCN_1380 | 11087 | CTCN_3856 | 21274 |
| TTCN_1381 | 11088 | GTCN_2191 | 21275 |
| ATCN_833 | 11089 | CTCN_3857 | 21276 |
| CTCN_1089 | 11090 | TTCN_4052 | 21277 |
| ATCN_834 | 11091 | TTCN_4053 | 21278 |
| GTCN_699 | 11092 | ATCN_2538 | 21279 |
| CTCN_1090 | 11093 | ATCN_2539 | 21280 |
| GTCN_700 | 11094 | TTCN_4054 | 21281 |
| TTCN_1382 | 11095 | GTCN_2192 | 21282 |
| TTCN_1383 | 11096 | CTCN_3858 | 21283 |

| | | | |
|---|---|---|---|
| TTCN_1384 | 11097 | CTCN_3859 | 21284 |
| ATCN_835 | 11098 | CTCN_3860 | 21285 |
| GTCN_701 | 11099 | GTCN_2193 | 21286 |
| TTCN_1385 | 11100 | CTCN_3861 | 21287 |
| TTCN_1386 | 11101 | CTCN_3862 | 21288 |
| ATCN_836 | 11102 | TTCN_4055 | 21289 |
| GTCN_702 | 11103 | CTCN_3863 | 21290 |
| TTCN_1387 | 11104 | TTCN_4056 | 21291 |
| GTCN_703 | 11105 | CTCN_3864 | 21292 |
| CTCN_1091 | 11106 | GTCN_2194 | 21293 |
| TTCN_1388 | 11107 | CTCN_3865 | 21294 |
| TTCN_1389 | 11108 | CTCN_3866 | 21295 |
| CTCN_1092 | 11109 | GTCN_2195 | 21296 |
| CTCN_1093 | 11110 | TTCN_4057 | 21297 |
| CTCN_1094 | 11111 | ATCN_2540 | 21298 |
| CTCN_1095 | 11112 | CTCN_3867 | 21299 |
| GTCN_704 | 11113 | CTCN_3868 | 21300 |
| TTCN_1390 | 11114 | TTCN_4058 | 21301 |
| TTCN_1391 | 11115 | GTCN_2196 | 21302 |
| GTCN_705 | 11116 | TTCN_4059 | 21303 |
| TTCN_1392 | 11117 | CTCN_3869 | 21304 |
| TTCN_1393 | 11118 | CTCN_3870 | 21305 |
| CTCN_1096 | 11119 | TTCN_4060 | 21306 |
| CTCN_1097 | 11120 | CTCN_3871 | 21307 |
| GTCN_706 | 11121 | TTCN_4061 | 21308 |
| GTCN_707 | 11122 | TTCN_4062 | 21309 |
| CTCN_1098 | 11123 | ATCN_2541 | 21310 |
| CTCN_1099 | 11124 | CTCN_3872 | 21311 |
| GTCN_708 | 11125 | TTCN_4063 | 21312 |
| TTCN_1394 | 11126 | ATCN_2542 | 21313 |
| TTCN_1395 | 11127 | TTCN_4064 | 21314 |
| TTCN_1396 | 11128 | ATCN_2543 | 21315 |
| ATCN_837 | 11129 | TTCN_4065 | 21316 |
| TTCN_1397 | 11130 | ATCN_2544 | 21317 |
| TTCN_1398 | 11131 | CTCN_3873 | 21318 |
| TTCN_1399 | 11132 | GTCN_2197 | 21319 |
| TTCN_1400 | 11133 | ATCN_2545 | 21320 |
| TTCN_1401 | 11134 | CTCN_3874 | 21321 |
| TTCN_1402 | 11135 | TTCN_4066 | 21322 |
| ATCN_838 | 11136 | TTCN_4067 | 21323 |
| TTCN_1403 | 11137 | GTCN_2198 | 21324 |
| TTCN_1404 | 11138 | TTCN_4068 | 21325 |
| TTCN_1405 | 11139 | ATCN_2546 | 21326 |
| TTCN_1406 | 11140 | TTCN_4069 | 21327 |
| CTCN_1100 | 11141 | CTCN_3875 | 21328 |
| CTCN_1101 | 11142 | GTCN_2199 | 21329 |
| ATCN_839 | 11143 | CTCN_3876 | 21330 |
| ATCN_840 | 11144 | TTCN_4070 | 21331 |
| TTCN_1407 | 11145 | CTCN_3877 | 21332 |
| CTCN_1102 | 11146 | ATCN_2547 | 21333 |
| GTCN_709 | 11147 | TTCN_4071 | 21334 |
| TTCN_1408 | 11148 | ATCN_2548 | 21335 |
| CTCN_1103 | 11149 | TTCN_4072 | 21336 |
| TTCN_1409 | 11150 | CTCN_3878 | 21337 |
| GTCN_710 | 11151 | TTCN_4073 | 21338 |

FIG. 36 (continued)

| | | | |
|---|---|---|---|
| ATCN_841 | 11152 | ATCN_2549 | 21339 |
| CTCN_1104 | 11153 | TTCN_4074 | 21340 |
| GTCN_711 | 11154 | CTCN_3879 | 21341 |
| GTCN_712 | 11155 | GTCN_2200 | 21342 |
| GTCN_713 | 11156 | CTCN_3880 | 21343 |
| TTCN_1410 | 11157 | CTCN_3881 | 21344 |
| TTCN_1411 | 11158 | CTCN_3882 | 21345 |
| CTCN_1105 | 11159 | GTCN_2201 | 21346 |
| ATCN_842 | 11160 | ATCN_2550 | 21347 |
| TTCN_1412 | 11161 | GTCN_2202 | 21348 |
| CTCN_1106 | 11162 | ATCN_2551 | 21349 |
| CTCN_1107 | 11163 | TTCN_4075 | 21350 |
| ATCN_843 | 11164 | CTCN_3883 | 21351 |
| ATCN_844 | 11165 | GTCN_2203 | 21352 |
| CTCN_1108 | 11166 | GTCN_2204 | 21353 |
| GTCN_714 | 11167 | GTCN_2205 | 21354 |
| CTCN_1109 | 11168 | TTCN_4076 | 21355 |
| ATCN_845 | 11169 | GTCN_2206 | 21356 |
| TTCN_1413 | 11170 | TTCN_4077 | 21357 |
| ATCN_846 | 11171 | ATCN_2552 | 21358 |
| ATCN_847 | 11172 | TTCN_4078 | 21359 |
| GTCN_715 | 11173 | ATCN_2553 | 21360 |
| TTCN_1414 | 11174 | ATCN_2554 | 21361 |
| GTCN_716 | 11175 | TTCN_4079 | 21362 |
| CTCN_1110 | 11176 | CTCN_3884 | 21363 |
| CTCN_1111 | 11177 | CTCN_3885 | 21364 |
| GTCN_717 | 11178 | TTCN_4080 | 21365 |
| GTCN_718 | 11179 | ATCN_2555 | 21366 |
| GTCN_719 | 11180 | GTCN_2207 | 21367 |
| TTCN_1415 | 11181 | TTCN_4081 | 21368 |
| GTCN_720 | 11182 | GTCN_2208 | 21369 |
| CTCN_1112 | 11183 | ATCN_2556 | 21370 |
| TTCN_1416 | 11184 | GTCN_2209 | 21371 |
| TTCN_1417 | 11185 | TTCN_4082 | 21372 |
| CTCN_1113 | 11186 | TTCN_4083 | 21373 |
| GTCN_721 | 11187 | TTCN_4084 | 21374 |
| GTCN_722 | 11188 | CTCN_3886 | 21375 |
| GTCN_723 | 11189 | TTCN_4085 | 21376 |
| GTCN_724 | 11190 | CTCN_3887 | 21377 |
| CTCN_1114 | 11191 | CTCN_3888 | 21378 |
| GTCN_725 | 11192 | CTCN_3889 | 21379 |
| CTCN_1115 | 11193 | CTCN_3890 | 21380 |
| TTCN_1418 | 11194 | ATCN_2557 | 21381 |
| ATCN_848 | 11195 | ATCN_2558 | 21382 |
| TTCN_1419 | 11196 | TTCN_4086 | 21383 |
| TTCN_1420 | 11197 | TTCN_4087 | 21384 |
| GTCN_726 | 11198 | TTCN_4088 | 21385 |
| CTCN_1116 | 11199 | CTCN_3891 | 21386 |
| GTCN_727 | 11200 | CTCN_3892 | 21387 |
| CTCN_1117 | 11201 | TTCN_4089 | 21388 |
| ATCN_849 | 11202 | ATCN_2559 | 21389 |
| TTCN_1421 | 11203 | GTCN_2210 | 21390 |
| ATCN_850 | 11204 | TTCN_4090 | 21391 |
| ATCN_851 | 11205 | GTCN_2211 | 21392 |
| GTCN_728 | 11206 | CTCN_3893 | 21393 |

| | | | |
|---|---|---|---|
| TTCN_1422 | 11207 | CTCN_3894 | 21394 |
| CTCN_1118 | 11208 | ATCN_2560 | 21395 |
| CTCN_1119 | 11209 | CTCN_3895 | 21396 |
| TTCN_1423 | 11210 | CTCN_3896 | 21397 |
| TTCN_1424 | 11211 | CTCN_3897 | 21398 |
| ATCN_852 | 11212 | GTCN_2212 | 21399 |
| GTCN_729 | 11213 | CTCN_3898 | 21400 |
| CTCN_1120 | 11214 | CTCN_3899 | 21401 |
| GTCN_730 | 11215 | CTCN_3900 | 21402 |
| GTCN_731 | 11216 | CTCN_3901 | 21403 |
| TTCN_1425 | 11217 | CTCN_3902 | 21404 |
| TTCN_1426 | 11218 | CTCN_3903 | 21405 |
| ATCN_853 | 11219 | GTCN_2213 | 21406 |
| GTCN_732 | 11220 | CTCN_3904 | 21407 |
| TTCN_1427 | 11221 | TTCN_4091 | 21408 |
| GTCN_733 | 11222 | ATCN_2561 | 21409 |
| ATCN_854 | 11223 | TTCN_4092 | 21410 |
| ATCN_855 | 11224 | ATCN_2562 | 21411 |
| CTCN_1121 | 11225 | TTCN_4093 | 21412 |
| CTCN_1122 | 11226 | ATCN_2563 | 21413 |
| TTCN_1428 | 11227 | ATCN_2564 | 21414 |
| CTCN_1123 | 11228 | ATCN_2565 | 21415 |
| CTCN_1124 | 11229 | CTCN_3905 | 21416 |
| CTCN_1125 | 11230 | TTCN_4094 | 21417 |
| CTCN_1126 | 11231 | CTCN_3906 | 21418 |
| TTCN_1429 | 11232 | TTCN_4095 | 21419 |
| GTCN_734 | 11233 | TTCN_4096 | 21420 |
| GTCN_735 | 11234 | CTCN_3907 | 21421 |
| GTCN_736 | 11235 | CTCN_3908 | 21422 |
| TTCN_1430 | 11236 | ATCN_2566 | 21423 |
| CTCN_1127 | 11237 | TTCN_4097 | 21424 |
| CTCN_1128 | 11238 | ATCN_2567 | 21425 |
| CTCN_1129 | 11239 | TTCN_4098 | 21426 |
| TTCN_1431 | 11240 | CTCN_3909 | 21427 |
| CTCN_1130 | 11241 | CTCN_3910 | 21428 |
| TTCN_1432 | 11242 | TTCN_4099 | 21429 |
| CTCN_1131 | 11243 | TTCN_4100 | 21430 |
| CTCN_1132 | 11244 | TTCN_4101 | 21431 |
| CTCN_1133 | 11245 | GTCN_2214 | 21432 |
| TTCN_1433 | 11246 | TTCN_4102 | 21433 |
| CTCN_1134 | 11247 | TTCN_4103 | 21434 |
| CTCN_1135 | 11248 | TTCN_4104 | 21435 |
| GTCN_737 | 11249 | CTCN_3911 | 21436 |
| GTCN_738 | 11250 | TTCN_4105 | 21437 |
| CTCN_1136 | 11251 | CTCN_3912 | 21438 |
| GTCN_739 | 11252 | CTCN_3913 | 21439 |
| CTCN_1137 | 11253 | CTCN_3914 | 21440 |
| ATCN_856 | 11254 | TTCN_4106 | 21441 |
| ATCN_857 | 11255 | GTCN_2215 | 21442 |
| ATCN_858 | 11256 | CTCN_3915 | 21443 |
| CTCN_1138 | 11257 | CTCN_3916 | 21444 |
| TTCN_1434 | 11258 | CTCN_3917 | 21445 |
| GTCN_740 | 11259 | CTCN_3918 | 21446 |
| CTCN_1139 | 11260 | ATCN_2568 | 21447 |
| GTCN_741 | 11261 | CTCN_3919 | 21448 |

FIG. 36 (continued)

| | | | |
|---|---|---|---|
| TTCN_1435 | 11262 | TTCN_4107 | 21449 |
| CTCN_1140 | 11263 | TTCN_4108 | 21450 |
| TTCN_1436 | 11264 | TTCN_4109 | 21451 |
| ATCN_859 | 11265 | TTCN_4110 | 21452 |
| CTCN_1141 | 11266 | ATCN_2569 | 21453 |
| CTCN_1142 | 11267 | TTCN_4111 | 21454 |
| GTCN_742 | 11268 | GTCN_2216 | 21455 |
| CTCN_1143 | 11269 | TTCN_4112 | 21456 |
| ATCN_860 | 11270 | GTCN_2217 | 21457 |
| CTCN_1144 | 11271 | GTCN_2218 | 21458 |
| GTCN_743 | 11272 | TTCN_4113 | 21459 |
| CTCN_1145 | 11273 | GTCN_2219 | 21460 |
| CTCN_1146 | 11274 | TTCN_4114 | 21461 |
| ATCN_861 | 11275 | ATCN_2570 | 21462 |
| ATCN_862 | 11276 | GTCN_2220 | 21463 |
| CTCN_1147 | 11277 | CTCN_3920 | 21464 |
| CTCN_1148 | 11278 | CTCN_3921 | 21465 |
| GTCN_744 | 11279 | ATCN_2571 | 21466 |
| CTCN_1149 | 11280 | ATCN_2572 | 21467 |
| TTCN_1437 | 11281 | GTCN_2221 | 21468 |
| ATCN_863 | 11282 | CTCN_3922 | 21469 |
| ATCN_864 | 11283 | CTCN_3923 | 21470 |
| GTCN_745 | 11284 | CTCN_3924 | 21471 |
| ATCN_865 | 11285 | CTCN_3925 | 21472 |
| CTCN_1150 | 11286 | CTCN_3926 | 21473 |
| ATCN_866 | 11287 | GTCN_2222 | 21474 |
| GTCN_746 | 11288 | CTCN_3927 | 21475 |
| CTCN_1151 | 11289 | CTCN_3928 | 21476 |
| TTCN_1438 | 11290 | GTCN_2223 | 21477 |
| TTCN_1439 | 11291 | GTCN_2224 | 21478 |
| TTCN_1440 | 11292 | CTCN_3929 | 21479 |
| TTCN_1441 | 11293 | GTCN_2225 | 21480 |
| ATCN_867 | 11294 | TTCN_4115 | 21481 |
| CTCN_1152 | 11295 | CTCN_3930 | 21482 |
| ATCN_868 | 11296 | TTCN_4116 | 21483 |
| TTCN_1442 | 11297 | TTCN_4117 | 21484 |
| CTCN_1153 | 11298 | TTCN_4118 | 21485 |
| TTCN_1443 | 11299 | CTCN_3931 | 21486 |
| GTCN_747 | 11300 | TTCN_4119 | 21487 |
| CTCN_1154 | 11301 | ATCN_2573 | 21488 |
| TTCN_1444 | 11302 | CTCN_3932 | 21489 |
| CTCN_1155 | 11303 | TTCN_4120 | 21490 |
| GTCN_748 | 11304 | GTCN_2226 | 21491 |
| GTCN_749 | 11305 | TTCN_4121 | 21492 |
| CTCN_1156 | 11306 | ATCN_2574 | 21493 |
| ATCN_869 | 11307 | TTCN_4122 | 21494 |
| ATCN_870 | 11308 | TTCN_4123 | 21495 |
| TTCN_1445 | 11309 | TTCN_4124 | 21496 |
| CTCN_1157 | 11310 | CTCN_3933 | 21497 |
| ATCN_871 | 11311 | ATCN_2575 | 21498 |
| CTCN_1158 | 11312 | CTCN_3934 | 21499 |
| ATCN_872 | 11313 | CTCN_3935 | 21500 |
| GTCN_750 | 11314 | CTCN_3936 | 21501 |
| CTCN_1159 | 11315 | TTCN_4125 | 21502 |
| ATCN_873 | 11316 | TTCN_4126 | 21503 |

| | | | |
|---|---|---|---|
| TTCN_1446 | 11317 | CTCN_3937 | 21504 |
| ATCN_874 | 11318 | GTCN_2227 | 21505 |
| TTCN_1447 | 11319 | CTCN_3938 | 21506 |
| TTCN_1448 | 11320 | GTCN_2228 | 21507 |
| GTCN_751 | 11321 | CTCN_3939 | 21508 |
| TTCN_1449 | 11322 | CTCN_3940 | 21509 |
| TTCN_1450 | 11323 | ATCN_2576 | 21510 |
| TTCN_1451 | 11324 | CTCN_3941 | 21511 |
| CTCN_1160 | 11325 | CTCN_3942 | 21512 |
| GTCN_752 | 11326 | GTCN_2229 | 21513 |
| TTCN_1452 | 11327 | TTCN_4127 | 21514 |
| CTCN_1161 | 11328 | ATCN_2577 | 21515 |
| TTCN_1453 | 11329 | GTCN_2230 | 21516 |
| GTCN_753 | 11330 | GTCN_2231 | 21517 |
| CTCN_1162 | 11331 | CTCN_3943 | 21518 |
| CTCN_1163 | 11332 | GTCN_2232 | 21519 |
| ATCN_875 | 11333 | CTCN_3944 | 21520 |
| GTCN_754 | 11334 | ATCN_2578 | 21521 |
| GTCN_755 | 11335 | ATCN_2579 | 21522 |
| CTCN_1164 | 11336 | CTCN_3945 | 21523 |
| GTCN_756 | 11337 | CTCN_3946 | 21524 |
| CTCN_1165 | 11338 | ATCN_2580 | 21525 |
| GTCN_757 | 11339 | TTCN_4128 | 21526 |
| CTCN_1166 | 11340 | CTCN_3947 | 21527 |
| ATCN_876 | 11341 | TTCN_4129 | 21528 |
| CTCN_1167 | 11342 | GTCN_2233 | 21529 |
| CTCN_1168 | 11343 | CTCN_3948 | 21530 |
| TTCN_1454 | 11344 | CTCN_3949 | 21531 |
| CTCN_1169 | 11345 | GTCN_2234 | 21532 |
| TTCN_1455 | 11346 | TTCN_4130 | 21533 |
| TTCN_1456 | 11347 | TTCN_4131 | 21534 |
| ATCN_877 | 11348 | GTCN_2235 | 21535 |
| CTCN_1170 | 11349 | CTCN_3950 | 21536 |
| CTCN_1171 | 11350 | TTCN_4132 | 21537 |
| ATCN_878 | 11351 | ATCN_2581 | 21538 |
| CTCN_1172 | 11352 | TTCN_4133 | 21539 |
| CTCN_1173 | 11353 | CTCN_3951 | 21540 |
| ATCN_879 | 11354 | CTCN_3952 | 21541 |
| ATCN_880 | 11355 | ATCN_2582 | 21542 |
| CTCN_1174 | 11356 | ATCN_2583 | 21543 |
| CTCN_1175 | 11357 | CTCN_3953 | 21544 |
| TTCN_1457 | 11358 | GTCN_2236 | 21545 |
| CTCN_1176 | 11359 | TTCN_4134 | 21546 |
| CTCN_1177 | 11360 | TTCN_4135 | 21547 |
| CTCN_1178 | 11361 | GTCN_2237 | 21548 |
| TTCN_1458 | 11362 | TTCN_4136 | 21549 |
| ATCN_881 | 11363 | TTCN_4137 | 21550 |
| TTCN_1459 | 11364 | TTCN_4138 | 21551 |
| GTCN_758 | 11365 | ATCN_2584 | 21552 |
| TTCN_1460 | 11366 | ATCN_2585 | 21553 |
| TTCN_1461 | 11367 | CTCN_3954 | 21554 |
| ATCN_882 | 11368 | CTCN_3955 | 21555 |
| CTCN_1179 | 11369 | GTCN_2238 | 21556 |
| CTCN_1180 | 11370 | GTCN_2239 | 21557 |
| GTCN_759 | 11371 | TTCN_4139 | 21558 |

FIG. 36 (continued)

| | | | |
|---|---|---|---|
| TTCN_1462 | 11372 | GTCN_2240 | 21559 |
| GTCN_760 | 11373 | ATCN_2586 | 21560 |
| TTCN_1463 | 11374 | CTCN_3956 | 21561 |
| GTCN_761 | 11375 | ATCN_2587 | 21562 |
| CTCN_1181 | 11376 | ATCN_2588 | 21563 |
| TTCN_1464 | 11377 | TTCN_4140 | 21564 |
| CTCN_1182 | 11378 | GTCN_2241 | 21565 |
| TTCN_1465 | 11379 | GTCN_2242 | 21566 |
| ATCN_883 | 11380 | TTCN_4141 | 21567 |
| CTCN_1183 | 11381 | TTCN_4142 | 21568 |
| ATCN_884 | 11382 | TTCN_4143 | 21569 |
| ATCN_885 | 11383 | TTCN_4144 | 21570 |
| ATCN_886 | 11384 | GTCN_2243 | 21571 |
| GTCN_762 | 11385 | CTCN_3957 | 21572 |
| TTCN_1466 | 11386 | GTCN_2244 | 21573 |
| TTCN_1467 | 11387 | ATCN_2589 | 21574 |
| TTCN_1468 | 11388 | TTCN_4145 | 21575 |
| CTCN_1184 | 11389 | TTCN_4146 | 21576 |
| ATCN_887 | 11390 | TTCN_4147 | 21577 |
| ATCN_888 | 11391 | TTCN_4148 | 21578 |
| CTCN_1185 | 11392 | CTCN_3958 | 21579 |
| CTCN_1186 | 11393 | GTCN_2245 | 21580 |
| GTCN_763 | 11394 | ATCN_2590 | 21581 |
| TTCN_1469 | 11395 | TTCN_4149 | 21582 |
| GTCN_764 | 11396 | CTCN_3959 | 21583 |
| TTCN_1470 | 11397 | ATCN_2591 | 21584 |
| CTCN_1187 | 11398 | GTCN_2246 | 21585 |
| TTCN_1471 | 11399 | GTCN_2247 | 21586 |
| TTCN_1472 | 11400 | ATCN_2592 | 21587 |
| TTCN_1473 | 11401 | TTCN_4150 | 21588 |
| TTCN_1474 | 11402 | ATCN_2593 | 21589 |
| CTCN_1188 | 11403 | CTCN_3960 | 21590 |
| CTCN_1189 | 11404 | ATCN_2594 | 21591 |
| CTCN_1190 | 11405 | CTCN_3961 | 21592 |
| TTCN_1475 | 11406 | CTCN_3962 | 21593 |
| TTCN_1476 | 11407 | ATCN_2595 | 21594 |
| GTCN_765 | 11408 | ATCN_2596 | 21595 |
| TTCN_1477 | 11409 | CTCN_3963 | 21596 |
| TTCN_1478 | 11410 | GTCN_2248 | 21597 |
| TTCN_1479 | 11411 | CTCN_3964 | 21598 |
| ATCN_889 | 11412 | CTCN_3965 | 21599 |
| ATCN_890 | 11413 | GTCN_2249 | 21600 |
| GTCN_766 | 11414 | GTCN_2250 | 21601 |
| GTCN_767 | 11415 | CTCN_3966 | 21602 |
| CTCN_1191 | 11416 | TTCN_4151 | 21603 |
| ATCN_891 | 11417 | GTCN_2251 | 21604 |
| ATCN_892 | 11418 | CTCN_3967 | 21605 |
| ATCN_893 | 11419 | ATCN_2597 | 21606 |
| CTCN_1192 | 11420 | CTCN_3968 | 21607 |
| TTCN_1480 | 11421 | CTCN_3969 | 21608 |
| CTCN_1193 | 11422 | CTCN_3970 | 21609 |
| CTCN_1194 | 11423 | TTCN_4152 | 21610 |
| CTCN_1195 | 11424 | TTCN_4153 | 21611 |
| TTCN_1481 | 11425 | CTCN_3971 | 21612 |
| CTCN_1196 | 11426 | CTCN_3972 | 21613 |
| CTCN_1197 | 11427 | CTCN_3973 | 21614 |
| GTCN_768 | 11428 | CTCN_3974 | 21615 |
| TTCN_1482 | 11429 | ATCN_2598 | 21616 |
| CTCN_1198 | 11430 | ATCN_2599 | 21617 |
| ATCN_894 | 11431 | CTCN_3975 | 21618 |
| TTCN_1483 | 11432 | CTCN_3976 | 21619 |
| CTCN_1199 | 11433 | CTCN_3977 | 21620 |
| ATCN_895 | 11434 | CTCN_3978 | 21621 |
| ATCN_896 | 11435 | ATCN_2600 | 21622 |
| TTCN_1484 | 11436 | CTCN_3979 | 21623 |
| TTCN_1485 | 11437 | TTCN_4154 | 21624 |
| GTCN_769 | 11438 | ATCN_2601 | 21625 |
| TTCN_1486 | 11439 | CTCN_3980 | 21626 |
| GTCN_770 | 11440 | ATCN_2602 | 21627 |
| CTCN_1200 | 11441 | CTCN_3981 | 21628 |
| GTCN_771 | 11442 | TTCN_4155 | 21629 |
| TTCN_1487 | 11443 | ATCN_2603 | 21630 |
| ATCN_897 | 11444 | TTCN_4156 | 21631 |
| ATCN_898 | 11445 | GTCN_2252 | 21632 |
| TTCN_1488 | 11446 | ATCN_2604 | 21633 |
| TTCN_1489 | 11447 | TTCN_4157 | 21634 |
| ATCN_899 | 11448 | TTCN_4158 | 21635 |
| GTCN_772 | 11449 | GTCN_2253 | 21636 |
| CTCN_1201 | 11450 | CTCN_3982 | 21637 |
| TTCN_1490 | 11451 | GTCN_2254 | 21638 |
| CTCN_1202 | 11452 | CTCN_3983 | 21639 |
| CTCN_1203 | 11453 | CTCN_3984 | 21640 |
| CTCN_1204 | 11454 | CTCN_3985 | 21641 |
| TTCN_1491 | 11455 | TTCN_4159 | 21642 |
| TTCN_1492 | 11456 | TTCN_4160 | 21643 |
| ATCN_900 | 11457 | TTCN_4161 | 21644 |
| TTCN_1493 | 11458 | ATCN_2605 | 21645 |
| ATCN_901 | 11459 | CTCN_3986 | 21646 |
| CTCN_1205 | 11460 | GTCN_2255 | 21647 |
| CTCN_1206 | 11461 | CTCN_3987 | 21648 |
| GTCN_773 | 11462 | TTCN_4162 | 21649 |
| CTCN_1207 | 11463 | ATCN_2606 | 21650 |
| ATCN_902 | 11464 | CTCN_3988 | 21651 |
| TTCN_1494 | 11465 | CTCN_3989 | 21652 |
| TTCN_1495 | 11466 | ATCN_2607 | 21653 |
| CTCN_1208 | 11467 | TTCN_4163 | 21654 |
| TTCN_1496 | 11468 | CTCN_3990 | 21655 |
| TTCN_1497 | 11469 | ATCN_2608 | 21656 |
| GTCN_774 | 11470 | ATCN_2609 | 21657 |
| TTCN_1498 | 11471 | CTCN_3991 | 21658 |
| GTCN_775 | 11472 | GTCN_2256 | 21659 |
| GTCN_776 | 11473 | TTCN_4164 | 21660 |
| TTCN_1499 | 11474 | ATCN_2610 | 21661 |
| ATCN_903 | 11475 | TTCN_4165 | 21662 |
| GTCN_777 | 11476 | CTCN_3992 | 21663 |
| GTCN_778 | 11477 | CTCN_3993 | 21664 |
| CTCN_1209 | 11478 | ATCN_2611 | 21665 |
| CTCN_1210 | 11479 | GTCN_2257 | 21666 |
| ATCN_904 | 11480 | GTCN_2258 | 21667 |
| GTCN_779 | 11481 | CTCN_3994 | 21668 |

FIG. 36 (continued)

| | | | |
|---|---|---|---|
| TTCN_1500 | 11482 | TTCN_4166 | 21669 |
| GTCN_780 | 11483 | ATCN_2612 | 21670 |
| GTCN_781 | 11484 | CTCN_3995 | 21671 |
| TTCN_1501 | 11485 | TTCN_4167 | 21672 |
| TTCN_1502 | 11486 | CTCN_3996 | 21673 |
| CTCN_1211 | 11487 | CTCN_3997 | 21674 |
| TTCN_1503 | 11488 | TTCN_4168 | 21675 |
| TTCN_1504 | 11489 | ATCN_2613 | 21676 |
| GTCN_782 | 11490 | TTCN_4169 | 21677 |
| CTCN_1212 | 11491 | CTCN_3998 | 21678 |
| GTCN_783 | 11492 | ATCN_2614 | 21679 |
| CTCN_1213 | 11493 | GTCN_2259 | 21680 |
| TTCN_1505 | 11494 | ATCN_2615 | 21681 |
| CTCN_1214 | 11495 | TTCN_4170 | 21682 |
| CTCN_1215 | 11496 | GTCN_2260 | 21683 |
| GTCN_784 | 11497 | CTCN_3999 | 21684 |
| GTCN_785 | 11498 | TTCN_4171 | 21685 |
| CTCN_1216 | 11499 | TTCN_4172 | 21686 |
| GTCN_786 | 11500 | CTCN_4000 | 21687 |
| GTCN_787 | 11501 | ATCN_2616 | 21688 |
| GTCN_788 | 11502 | TTCN_4173 | 21689 |
| TTCN_1506 | 11503 | CTCN_4001 | 21690 |
| GTCN_789 | 11504 | TTCN_4174 | 21691 |
| ATCN_905 | 11505 | CTCN_4002 | 21692 |
| GTCN_790 | 11506 | TTCN_4175 | 21693 |
| CTCN_1217 | 11507 | ATCN_2617 | 21694 |
| CTCN_1218 | 11508 | TTCN_4176 | 21695 |
| TTCN_1507 | 11509 | TTCN_4177 | 21696 |
| TTCN_1508 | 11510 | GTCN_2261 | 21697 |
| GTCN_791 | 11511 | GTCN_2262 | 21698 |
| CTCN_1219 | 11512 | TTCN_4178 | 21699 |
| CTCN_1220 | 11513 | GTCN_2263 | 21700 |
| ATCN_906 | 11514 | TTCN_4179 | 21701 |
| ATCN_907 | 11515 | ATCN_2618 | 21702 |
| TTCN_1509 | 11516 | GTCN_2264 | 21703 |
| CTCN_1221 | 11517 | TTCN_4180 | 21704 |
| GTCN_792 | 11518 | CTCN_4003 | 21705 |
| CTCN_1222 | 11519 | ATCN_2619 | 21706 |
| TTCN_1510 | 11520 | ATCN_2620 | 21707 |
| GTCN_793 | 11521 | GTCN_2265 | 21708 |
| ATCN_908 | 11522 | ATCN_2621 | 21709 |
| TTCN_1511 | 11523 | CTCN_4004 | 21710 |
| TTCN_1512 | 11524 | TTCN_4181 | 21711 |
| ATCN_909 | 11525 | TTCN_4182 | 21712 |
| ATCN_910 | 11526 | TTCN_4183 | 21713 |
| GTCN_794 | 11527 | CTCN_4005 | 21714 |
| TTCN_1513 | 11528 | GTCN_2266 | 21715 |
| TTCN_1514 | 11529 | TTCN_4184 | 21716 |
| TTCN_1515 | 11530 | ATCN_2622 | 21717 |
| TTCN_1516 | 11531 | TTCN_4185 | 21718 |
| TTCN_1517 | 11532 | CTCN_4006 | 21719 |
| TTCN_1518 | 11533 | CTCN_4007 | 21720 |
| CTCN_1223 | 11534 | TTCN_4186 | 21721 |
| ATCN_911 | 11535 | TTCN_4187 | 21722 |
| CTCN_1224 | 11536 | TTCN_4188 | 21723 |

| | | | |
|---|---|---|---|
| CTCN_1225 | 11537 | ATCN_2623 | 21724 |
| ATCN_912 | 11538 | GTCN_2267 | 21725 |
| CTCN_1226 | 11539 | TTCN_4189 | 21726 |
| CTCN_1227 | 11540 | CTCN_4008 | 21727 |
| TTCN_1519 | 11541 | GTCN_2268 | 21728 |
| ATCN_913 | 11542 | CTCN_4009 | 21729 |
| ATCN_914 | 11543 | TTCN_4190 | 21730 |
| CTCN_1228 | 11544 | TTCN_4191 | 21731 |
| GTCN_795 | 11545 | TTCN_4192 | 21732 |
| CTCN_1229 | 11546 | ATCN_2624 | 21733 |
| ATCN_915 | 11547 | TTCN_4193 | 21734 |
| GTCN_796 | 11548 | TTCN_4194 | 21735 |
| ATCN_916 | 11549 | CTCN_4010 | 21736 |
| TTCN_1520 | 11550 | ATCN_2625 | 21737 |
| ATCN_917 | 11551 | TTCN_4195 | 21738 |
| CTCN_1230 | 11552 | TTCN_4196 | 21739 |
| GTCN_797 | 11553 | GTCN_2269 | 21740 |
| CTCN_1231 | 11554 | CTCN_4011 | 21741 |
| CTCN_1232 | 11555 | TTCN_4197 | 21742 |
| CTCN_1233 | 11556 | ATCN_2626 | 21743 |
| CTCN_1234 | 11557 | TTCN_4198 | 21744 |
| TTCN_1521 | 11558 | ATCN_2627 | 21745 |
| ATCN_918 | 11559 | ATCN_2628 | 21746 |
| TTCN_1522 | 11560 | CTCN_4012 | 21747 |
| TTCN_1523 | 11561 | TTCN_4199 | 21748 |
| CTCN_1235 | 11562 | TTCN_4200 | 21749 |
| CTCN_1236 | 11563 | GTCN_2270 | 21750 |
| ATCN_919 | 11564 | GTCN_2271 | 21751 |
| ATCN_920 | 11565 | TTCN_4201 | 21752 |
| CTCN_1237 | 11566 | GTCN_2272 | 21753 |
| GTCN_798 | 11567 | TTCN_4202 | 21754 |
| CTCN_1238 | 11568 | TTCN_4203 | 21755 |
| CTCN_1239 | 11569 | CTCN_4013 | 21756 |
| GTCN_799 | 11570 | TTCN_4204 | 21757 |
| ATCN_921 | 11571 | CTCN_4014 | 21758 |
| CTCN_1240 | 11572 | CTCN_4015 | 21759 |
| TTCN_1524 | 11573 | TTCN_4205 | 21760 |
| TTCN_1525 | 11574 | CTCN_4016 | 21761 |
| TTCN_1526 | 11575 | GTCN_2273 | 21762 |
| CTCN_1241 | 11576 | TTCN_4206 | 21763 |
| TTCN_1527 | 11577 | CTCN_4017 | 21764 |
| CTCN_1242 | 11578 | TTCN_4207 | 21765 |
| GTCN_800 | 11579 | ATCN_2629 | 21766 |
| GTCN_801 | 11580 | TTCN_4208 | 21767 |
| CTCN_1243 | 11581 | ATCN_2630 | 21768 |
| GTCN_802 | 11582 | TTCN_4209 | 21769 |
| CTCN_1244 | 11583 | CTCN_4018 | 21770 |
| ATCN_922 | 11584 | CTCN_4019 | 21771 |
| TTCN_1528 | 11585 | CTCN_4020 | 21772 |
| CTCN_1245 | 11586 | CTCN_4021 | 21773 |
| TTCN_1529 | 11587 | CTCN_4022 | 21774 |
| GTCN_803 | 11588 | TTCN_4210 | 21775 |
| TTCN_1530 | 11589 | TTCN_4211 | 21776 |
| GTCN_804 | 11590 | TTCN_4212 | 21777 |
| TTCN_1531 | 11591 | CTCN_4023 | 21778 |

FIG. 36 (continued)

| | | | |
|---|---|---|---|
| ATCN_923 | 11592 | ATCN_2631 | 21779 |
| ATCN_924 | 11593 | TTCN_4213 | 21780 |
| ATCN_925 | 11594 | TTCN_4214 | 21781 |
| TTCN_1532 | 11595 | GTCN_2274 | 21782 |
| ATCN_926 | 11596 | TTCN_4215 | 21783 |
| ATCN_927 | 11597 | CTCN_4024 | 21784 |
| ATCN_928 | 11598 | TTCN_4216 | 21785 |
| CTCN_1246 | 11599 | CTCN_4025 | 21786 |
| TTCN_1533 | 11600 | CTCN_4026 | 21787 |
| GTCN_805 | 11601 | ATCN_2632 | 21788 |
| GTCN_806 | 11602 | TTCN_4217 | 21789 |
| TTCN_1534 | 11603 | TTCN_4218 | 21790 |
| TTCN_1535 | 11604 | ATCN_2633 | 21791 |
| CTCN_1247 | 11605 | GTCN_2275 | 21792 |
| CTCN_1248 | 11606 | ATCN_2634 | 21793 |
| GTCN_807 | 11607 | CTCN_4027 | 21794 |
| TTCN_1536 | 11608 | TTCN_4219 | 21795 |
| CTCN_1249 | 11609 | CTCN_4028 | 21796 |
| TTCN_1537 | 11610 | ATCN_2635 | 21797 |
| ATCN_929 | 11611 | TTCN_4220 | 21798 |
| ATCN_930 | 11612 | TTCN_4221 | 21799 |
| CTCN_1250 | 11613 | CTCN_4029 | 21800 |
| CTCN_1251 | 11614 | TTCN_4222 | 21801 |
| TTCN_1538 | 11615 | TTCN_4223 | 21802 |
| CTCN_1252 | 11616 | TTCN_4224 | 21803 |
| ATCN_931 | 11617 | GTCN_2276 | 21804 |
| TTCN_1539 | 11618 | ATCN_2636 | 21805 |
| ATCN_932 | 11619 | CTCN_4030 | 21806 |
| GTCN_808 | 11620 | GTCN_2277 | 21807 |
| TTCN_1540 | 11621 | ATCN_2637 | 21808 |
| CTCN_1253 | 11622 | TTCN_4225 | 21809 |
| TTCN_1541 | 11623 | ATCN_2638 | 21810 |
| TTCN_1542 | 11624 | TTCN_4226 | 21811 |
| ATCN_933 | 11625 | GTCN_2278 | 21812 |
| CTCN_1254 | 11626 | TTCN_4227 | 21813 |
| ATCN_934 | 11627 | CTCN_4031 | 21814 |
| TTCN_1543 | 11628 | GTCN_2279 | 21815 |
| CTCN_1255 | 11629 | CTCN_4032 | 21816 |
| CTCN_1256 | 11630 | TTCN_4228 | 21817 |
| ATCN_935 | 11631 | TTCN_4229 | 21818 |
| TTCN_1544 | 11632 | TTCN_4230 | 21819 |
| GTCN_809 | 11633 | TTCN_4231 | 21820 |
| ATCN_936 | 11634 | TTCN_4232 | 21821 |
| ATCN_937 | 11635 | CTCN_4033 | 21822 |
| ATCN_938 | 11636 | ATCN_2639 | 21823 |
| GTCN_810 | 11637 | TTCN_4233 | 21824 |
| CTCN_1257 | 11638 | GTCN_2280 | 21825 |
| TTCN_1545 | 11639 | TTCN_4234 | 21826 |
| TTCN_1546 | 11640 | TTCN_4235 | 21827 |
| CTCN_1258 | 11641 | ATCN_2640 | 21828 |
| CTCN_1259 | 11642 | TTCN_4236 | 21829 |
| CTCN_1260 | 11643 | TTCN_4237 | 21830 |
| TTCN_1547 | 11644 | CTCN_4034 | 21831 |
| CTCN_1261 | 11645 | GTCN_2281 | 21832 |
| CTCN_1262 | 11646 | GTCN_2282 | 21833 |

| | | | |
|---|---|---|---|
| GTCN_811 | 11647 | CTCN_4035 | 21834 |
| TTCN_1548 | 11648 | CTCN_4036 | 21835 |
| CTCN_1263 | 11649 | GTCN_2283 | 21836 |
| ATCN_939 | 11650 | TTCN_4238 | 21837 |
| TTCN_1549 | 11651 | GTCN_2284 | 21838 |
| CTCN_1264 | 11652 | GTCN_2285 | 21839 |
| ATCN_940 | 11653 | TTCN_4239 | 21840 |
| ATCN_941 | 11654 | TTCN_4240 | 21841 |
| TTCN_1550 | 11655 | CTCN_4037 | 21842 |
| TTCN_1551 | 11656 | CTCN_4038 | 21843 |
| GTCN_812 | 11657 | CTCN_4039 | 21844 |
| TTCN_1552 | 11658 | CTCN_4040 | 21845 |
| GTCN_813 | 11659 | TTCN_4241 | 21846 |
| CTCN_1265 | 11660 | TTCN_4242 | 21847 |
| GTCN_814 | 11661 | ATCN_2641 | 21848 |
| TTCN_1553 | 11662 | TTCN_4243 | 21849 |
| ATCN_942 | 11663 | ATCN_2642 | 21850 |
| TTCN_1554 | 11664 | TTCN_4244 | 21851 |
| TTCN_1555 | 11665 | CTCN_4041 | 21852 |
| TTCN_1556 | 11666 | TTCN_4245 | 21853 |
| CTCN_1266 | 11667 | ATCN_2643 | 21854 |
| CTCN_1267 | 11668 | TTCN_4246 | 21855 |
| CTCN_1268 | 11669 | TTCN_4247 | 21856 |
| TTCN_1557 | 11670 | TTCN_4248 | 21857 |
| CTCN_1269 | 11671 | TTCN_4249 | 21858 |
| GTCN_815 | 11672 | TTCN_4250 | 21859 |
| CTCN_1270 | 11673 | ATCN_2644 | 21860 |
| TTCN_1558 | 11674 | CTCN_4042 | 21861 |
| CTCN_1271 | 11675 | GTCN_2286 | 21862 |
| ATCN_943 | 11676 | TTCN_4251 | 21863 |
| ATCN_944 | 11677 | TTCN_4252 | 21864 |
| TTCN_1559 | 11678 | ATCN_2645 | 21865 |
| TTCN_1560 | 11679 | TTCN_4253 | 21866 |
| TTCN_1561 | 11680 | TTCN_4254 | 21867 |
| TTCN_1562 | 11681 | TTCN_4255 | 21868 |
| TTCN_1563 | 11682 | CTCN_4043 | 21869 |
| GTCN_816 | 11683 | TTCN_4256 | 21870 |
| TTCN_1564 | 11684 | CTCN_4044 | 21871 |
| GTCN_817 | 11685 | TTCN_4257 | 21872 |
| GTCN_818 | 11686 | CTCN_4045 | 21873 |
| GTCN_819 | 11687 | ATCN_2646 | 21874 |
| TTCN_1565 | 11688 | ATCN_2647 | 21875 |
| GTCN_820 | 11689 | CTCN_4046 | 21876 |
| TTCN_1566 | 11690 | TTCN_4258 | 21877 |
| CTCN_1272 | 11691 | CTCN_4047 | 21878 |
| GTCN_821 | 11692 | ATCN_2648 | 21879 |
| TTCN_1567 | 11693 | TTCN_4259 | 21880 |
| GTCN_822 | 11694 | GTCN_2287 | 21881 |
| CTCN_1273 | 11695 | CTCN_4048 | 21882 |
| CTCN_1274 | 11696 | CTCN_4049 | 21883 |
| ATCN_945 | 11697 | GTCN_2288 | 21884 |
| ATCN_946 | 11698 | CTCN_4050 | 21885 |
| ATCN_947 | 11699 | CTCN_4051 | 21886 |
| CTCN_1275 | 11700 | TTCN_4260 | 21887 |
| ATCN_948 | 11701 | GTCN_2289 | 21888 |

FIG. 36 (continued)

| | | | |
|---|---|---|---|
| ATCN_949 | 11702 | CTCN_4052 | 21889 |
| ATCN_950 | 11703 | CTCN_4053 | 21890 |
| CTCN_1276 | 11704 | GTCN_2290 | 21891 |
| GTCN_823 | 11705 | CTCN_4054 | 21892 |
| GTCN_824 | 11706 | ATCN_2649 | 21893 |
| GTCN_825 | 11707 | TTCN_4261 | 21894 |
| CTCN_1277 | 11708 | ATCN_2650 | 21895 |
| TTCN_1568 | 11709 | CTCN_4055 | 21896 |
| CTCN_1278 | 11710 | GTCN_2291 | 21897 |
| TTCN_1569 | 11711 | CTCN_4056 | 21898 |
| ATCN_951 | 11712 | CTCN_4057 | 21899 |
| ATCN_952 | 11713 | TTCN_4262 | 21900 |
| GTCN_826 | 11714 | TTCN_4263 | 21901 |
| GTCN_827 | 11715 | TTCN_4264 | 21902 |
| GTCN_828 | 11716 | TTCN_4265 | 21903 |
| ATCN_953 | 11717 | CTCN_4058 | 21904 |
| TTCN_1570 | 11718 | TTCN_4266 | 21905 |
| GTCN_829 | 11719 | GTCN_2292 | 21906 |
| TTCN_1571 | 11720 | CTCN_4059 | 21907 |
| ATCN_954 | 11721 | ATCN_2651 | 21908 |
| CTCN_1279 | 11722 | TTCN_4267 | 21909 |
| TTCN_1572 | 11723 | ATCN_2652 | 21910 |
| GTCN_830 | 11724 | TTCN_4268 | 21911 |
| CTCN_1280 | 11725 | CTCN_4060 | 21912 |
| TTCN_1573 | 11726 | CTCN_4061 | 21913 |
| TTCN_1574 | 11727 | ATCN_2653 | 21914 |
| CTCN_1281 | 11728 | GTCN_2293 | 21915 |
| TTCN_1575 | 11729 | TTCN_4269 | 21916 |
| CTCN_1282 | 11730 | TTCN_4270 | 21917 |
| TTCN_1576 | 11731 | TTCN_4271 | 21918 |
| CTCN_1283 | 11732 | TTCN_4272 | 21919 |
| GTCN_831 | 11733 | TTCN_4273 | 21920 |
| CTCN_1284 | 11734 | TTCN_4274 | 21921 |
| GTCN_832 | 11735 | TTCN_4275 | 21922 |
| CTCN_1285 | 11736 | ATCN_2654 | 21923 |
| CTCN_1286 | 11737 | TTCN_4276 | 21924 |
| TTCN_1577 | 11738 | TTCN_4277 | 21925 |
| TTCN_1578 | 11739 | CTCN_4062 | 21926 |
| ATCN_955 | 11740 | TTCN_4278 | 21927 |
| GTCN_833 | 11741 | TTCN_4279 | 21928 |
| TTCN_1579 | 11742 | GTCN_2294 | 21929 |
| TTCN_1580 | 11743 | TTCN_4280 | 21930 |
| GTCN_834 | 11744 | CTCN_4063 | 21931 |
| ATCN_956 | 11745 | TTCN_4281 | 21932 |
| CTCN_1287 | 11746 | TTCN_4282 | 21933 |
| ATCN_957 | 11747 | ATCN_2655 | 21934 |
| TTCN_1581 | 11748 | TTCN_4283 | 21935 |
| TTCN_1582 | 11749 | CTCN_4064 | 21936 |
| CTCN_1288 | 11750 | CTCN_4065 | 21937 |
| ATCN_958 | 11751 | GTCN_2295 | 21938 |
| ATCN_959 | 11752 | ATCN_2656 | 21939 |
| GTCN_835 | 11753 | TTCN_4284 | 21940 |
| CTCN_1289 | 11754 | GTCN_2296 | 21941 |
| ATCN_960 | 11755 | CTCN_4066 | 21942 |
| ATCN_961 | 11756 | GTCN_2297 | 21943 |

| | | | |
|---|---|---|---|
| TTCN_1583 | 11757 | CTCN_4067 | 21944 |
| GTCN_836 | 11758 | ATCN_2657 | 21945 |
| TTCN_1584 | 11759 | ATCN_2658 | 21946 |
| CTCN_1290 | 11760 | CTCN_4068 | 21947 |
| ATCN_962 | 11761 | GTCN_2298 | 21948 |
| TTCN_1585 | 11762 | CTCN_4069 | 21949 |
| ATCN_963 | 11763 | CTCN_4070 | 21950 |
| CTCN_1291 | 11764 | TTCN_4285 | 21951 |
| GTCN_837 | 11765 | ATCN_2659 | 21952 |
| TTCN_1586 | 11766 | TTCN_4286 | 21953 |
| TTCN_1587 | 11767 | CTCN_4071 | 21954 |
| TTCN_1588 | 11768 | TTCN_4287 | 21955 |
| TTCN_1589 | 11769 | CTCN_4072 | 21956 |
| GTCN_838 | 11770 | ATCN_2660 | 21957 |
| CTCN_1292 | 11771 | CTCN_4073 | 21958 |
| ATCN_964 | 11772 | ATCN_2661 | 21959 |
| GTCN_839 | 11773 | TTCN_4288 | 21960 |
| CTCN_1293 | 11774 | GTCN_2299 | 21961 |
| ATCN_965 | 11775 | GTCN_2300 | 21962 |
| GTCN_840 | 11776 | CTCN_4074 | 21963 |
| TTCN_1590 | 11777 | TTCN_4289 | 21964 |
| ATCN_966 | 11778 | CTCN_4075 | 21965 |
| CTCN_1294 | 11779 | GTCN_2301 | 21966 |
| CTCN_1295 | 11780 | CTCN_4076 | 21967 |
| TTCN_1591 | 11781 | ATCN_2662 | 21968 |
| ATCN_967 | 11782 | ATCN_2663 | 21969 |
| CTCN_1296 | 11783 | CTCN_4077 | 21970 |
| CTCN_1297 | 11784 | ATCN_2664 | 21971 |
| ATCN_968 | 11785 | ATCN_2665 | 21972 |
| CTCN_1298 | 11786 | TTCN_4290 | 21973 |
| GTCN_841 | 11787 | CTCN_4078 | 21974 |
| CTCN_1299 | 11788 | CTCN_4079 | 21975 |
| TTCN_1592 | 11789 | CTCN_4080 | 21976 |
| GTCN_842 | 11790 | GTCN_2302 | 21977 |
| ATCN_969 | 11791 | ATCN_2666 | 21978 |
| ATCN_970 | 11792 | ATCN_2667 | 21979 |
| TTCN_1593 | 11793 | TTCN_4291 | 21980 |
| ATCN_971 | 11794 | TTCN_4292 | 21981 |
| CTCN_1300 | 11795 | GTCN_2303 | 21982 |
| TTCN_1594 | 11796 | TTCN_4293 | 21983 |
| TTCN_1595 | 11797 | TTCN_4294 | 21984 |
| CTCN_1301 | 11798 | ATCN_2668 | 21985 |
| TTCN_1596 | 11799 | ATCN_2669 | 21986 |
| ATCN_972 | 11800 | ATCN_2670 | 21987 |
| CTCN_1302 | 11801 | ATCN_2671 | 21988 |
| TTCN_1597 | 11802 | ATCN_2672 | 21989 |
| CTCN_1303 | 11803 | CTCN_4081 | 21990 |
| CTCN_1304 | 11804 | GTCN_2304 | 21991 |
| ATCN_973 | 11805 | TTCN_4295 | 21992 |
| CTCN_1305 | 11806 | GTCN_2305 | 21993 |
| ATCN_974 | 11807 | CTCN_4082 | 21994 |
| ATCN_975 | 11808 | CTCN_4083 | 21995 |
| TTCN_1598 | 11809 | CTCN_4084 | 21996 |
| ATCN_976 | 11810 | GTCN_2306 | 21997 |
| CTCN_1306 | 11811 | CTCN_4085 | 21998 |

FIG. 36 (continued)

| | | | |
|---|---|---|---|
| CTCN_1307 | 11812 | ATCN_2673 | 21999 |
| GTCN_843 | 11813 | TTCN_4296 | 22000 |
| CTCN_1308 | 11814 | TTCN_4297 | 22001 |
| GTCN_844 | 11815 | TTCN_4298 | 22002 |
| CTCN_1309 | 11816 | ATCN_2674 | 22003 |
| TTCN_1599 | 11817 | ATCN_2675 | 22004 |
| TTCN_1600 | 11818 | TTCN_4299 | 22005 |
| TTCN_1601 | 11819 | CTCN_4086 | 22006 |
| CTCN_1310 | 11820 | ATCN_2676 | 22007 |
| GTCN_845 | 11821 | ATCN_2677 | 22008 |
| CTCN_1311 | 11822 | GTCN_2307 | 22009 |
| GTCN_846 | 11823 | TTCN_4300 | 22010 |
| CTCN_1312 | 11824 | CTCN_4087 | 22011 |
| TTCN_1602 | 11825 | TTCN_4301 | 22012 |
| CTCN_1313 | 11826 | ATCN_2678 | 22013 |
| CTCN_1314 | 11827 | TTCN_4302 | 22014 |
| TTCN_1603 | 11828 | TTCN_4303 | 22015 |
| TTCN_1604 | 11829 | CTCN_4088 | 22016 |
| TTCN_1605 | 11830 | GTCN_2308 | 22017 |
| CTCN_1315 | 11831 | CTCN_4089 | 22018 |
| CTCN_1316 | 11832 | TTCN_4304 | 22019 |
| TTCN_1606 | 11833 | TTCN_4305 | 22020 |
| TTCN_1607 | 11834 | TTCN_4306 | 22021 |
| TTCN_1608 | 11835 | TTCN_4307 | 22022 |
| CTCN_1317 | 11836 | TTCN_4308 | 22023 |
| CTCN_1318 | 11837 | GTCN_2309 | 22024 |
| CTCN_1319 | 11838 | ATCN_2679 | 22025 |
| CTCN_1320 | 11839 | CTCN_4090 | 22026 |
| TTCN_1609 | 11840 | CTCN_4091 | 22027 |
| CTCN_1321 | 11841 | ATCN_2680 | 22028 |
| ATCN_977 | 11842 | ATCN_2681 | 22029 |
| ATCN_978 | 11843 | GTCN_2310 | 22030 |
| ATCN_979 | 11844 | TTCN_4309 | 22031 |
| TTCN_1610 | 11845 | GTCN_2311 | 22032 |
| TTCN_1611 | 11846 | CTCN_4092 | 22033 |
| CTCN_1322 | 11847 | TTCN_4310 | 22034 |
| GTCN_847 | 11848 | GTCN_2312 | 22035 |
| GTCN_848 | 11849 | TTCN_4311 | 22036 |
| TTCN_1612 | 11850 | GTCN_2313 | 22037 |
| CTCN_1323 | 11851 | TTCN_4312 | 22038 |
| CTCN_1324 | 11852 | TTCN_4313 | 22039 |
| CTCN_1325 | 11853 | GTCN_2314 | 22040 |
| TTCN_1613 | 11854 | ATCN_2682 | 22041 |
| ATCN_980 | 11855 | TTCN_4314 | 22042 |
| GTCN_849 | 11856 | ATCN_2683 | 22043 |
| CTCN_1326 | 11857 | ATCN_2684 | 22044 |
| CTCN_1327 | 11858 | TTCN_4315 | 22045 |
| GTCN_850 | 11859 | TTCN_4316 | 22046 |
| ATCN_981 | 11860 | GTCN_2315 | 22047 |
| ATCN_982 | 11861 | CTCN_4093 | 22048 |
| TTCN_1614 | 11862 | ATCN_2685 | 22049 |
| ATCN_983 | 11863 | TTCN_4317 | 22050 |
| TTCN_1615 | 11864 | ATCN_2686 | 22051 |
| CTCN_1328 | 11865 | GTCN_2316 | 22052 |
| CTCN_1329 | 11866 | TTCN_4318 | 22053 |

| | | | |
|---|---|---|---|
| CTCN_1330 | 11867 | TTCN_4319 | 22054 |
| ATCN_984 | 11868 | ATCN_2687 | 22055 |
| ATCN_985 | 11869 | TTCN_4320 | 22056 |
| ATCN_986 | 11870 | TTCN_4321 | 22057 |
| TTCN_1616 | 11871 | CTCN_4094 | 22058 |
| GTCN_851 | 11872 | ATCN_2688 | 22059 |
| CTCN_1331 | 11873 | CTCN_4095 | 22060 |
| TTCN_1617 | 11874 | TTCN_4322 | 22061 |
| TTCN_1618 | 11875 | GTCN_2317 | 22062 |
| TTCN_1619 | 11876 | ATCN_2689 | 22063 |
| TTCN_1620 | 11877 | TTCN_4323 | 22064 |
| TTCN_1621 | 11878 | ATCN_2690 | 22065 |
| TTCN_1622 | 11879 | TTCN_4324 | 22066 |
| GTCN_852 | 11880 | TTCN_4325 | 22067 |
| ATCN_987 | 11881 | TTCN_4326 | 22068 |
| CTCN_1332 | 11882 | ATCN_2691 | 22069 |
| TTCN_1623 | 11883 | CTCN_4096 | 22070 |
| TTCN_1624 | 11884 | ATCN_2692 | 22071 |
| ATCN_988 | 11885 | ATCN_2693 | 22072 |
| ATCN_989 | 11886 | TTCN_4327 | 22073 |
| TTCN_1625 | 11887 | GTCN_2318 | 22074 |
| TTCN_1626 | 11888 | TTCN_4328 | 22075 |
| GTCN_853 | 11889 | TTCN_4329 | 22076 |
| ATCN_990 | 11890 | TTCN_4330 | 22077 |
| ATCN_991 | 11891 | ATCN_2694 | 22078 |
| CTCN_1333 | 11892 | GTCN_2319 | 22079 |
| TTCN_1627 | 11893 | TTCN_4331 | 22080 |
| CTCN_1334 | 11894 | TTCN_4332 | 22081 |
| GTCN_854 | 11895 | TTCN_4333 | 22082 |
| CTCN_1335 | 11896 | CTCN_4097 | 22083 |
| TTCN_1628 | 11897 | TTCN_4334 | 22084 |
| ATCN_992 | 11898 | ATCN_2695 | 22085 |
| GTCN_855 | 11899 | TTCN_4335 | 22086 |
| TTCN_1629 | 11900 | GTCN_2320 | 22087 |
| CTCN_1336 | 11901 | TTCN_4336 | 22088 |
| TTCN_1630 | 11902 | TTCN_4337 | 22089 |
| CTCN_1337 | 11903 | CTCN_4098 | 22090 |
| TTCN_1631 | 11904 | CTCN_4099 | 22091 |
| ATCN_993 | 11905 | ATCN_2696 | 22092 |
| ATCN_994 | 11906 | ATCN_2697 | 22093 |
| ATCN_995 | 11907 | TTCN_4338 | 22094 |
| ATCN_996 | 11908 | ATCN_2698 | 22095 |
| CTCN_1338 | 11909 | TTCN_4339 | 22096 |
| ATCN_997 | 11910 | CTCN_4100 | 22097 |
| ATCN_998 | 11911 | ATCN_2699 | 22098 |
| ATCN_999 | 11912 | CTCN_4101 | 22099 |
| TTCN_1632 | 11913 | TTCN_4340 | 22100 |
| TTCN_1633 | 11914 | ATCN_2700 | 22101 |
| CTCN_1339 | 11915 | GTCN_2321 | 22102 |
| CTCN_1340 | 11916 | ATCN_2701 | 22103 |
| CTCN_1341 | 11917 | GTCN_2322 | 22104 |
| TTCN_1634 | 11918 | CTCN_4102 | 22105 |
| ATCN_1000 | 11919 | GTCN_2323 | 22106 |
| GTCN_856 | 11920 | GTCN_2324 | 22107 |
| ATCN_1001 | 11921 | GTCN_2325 | 22108 |

FIG. 36 (continued)

| | | | |
|---|---|---|---|
| ATCN_1002 | 11922 | GTCN_2326 | 22109 |
| ATCN_1003 | 11923 | TTCN_4341 | 22110 |
| ATCN_1004 | 11924 | TTCN_4342 | 22111 |
| GTCN_857 | 11925 | TTCN_4343 | 22112 |
| CTCN_1342 | 11926 | GTCN_2327 | 22113 |
| CTCN_1343 | 11927 | TTCN_4344 | 22114 |
| CTCN_1344 | 11928 | TTCN_4345 | 22115 |
| TTCN_1635 | 11929 | GTCN_2328 | 22116 |
| ATCN_1005 | 11930 | TTCN_4346 | 22117 |
| ATCN_1006 | 11931 | TTCN_4347 | 22118 |
| TTCN_1636 | 11932 | CTCN_4103 | 22119 |
| TTCN_1637 | 11933 | GTCN_2329 | 22120 |
| CTCN_1345 | 11934 | GTCN_2330 | 22121 |
| TTCN_1638 | 11935 | ATCN_2702 | 22122 |
| GTCN_858 | 11936 | ATCN_2703 | 22123 |
| ATCN_1007 | 11937 | CTCN_4104 | 22124 |
| GTCN_859 | 11938 | GTCN_2331 | 22125 |
| CTCN_1346 | 11939 | GTCN_2332 | 22126 |
| TTCN_1639 | 11940 | CTCN_4105 | 22127 |
| ATCN_1008 | 11941 | GTCN_2333 | 22128 |
| GTCN_860 | 11942 | TTCN_4348 | 22129 |
| CTCN_1347 | 11943 | CTCN_4106 | 22130 |
| ATCN_1009 | 11944 | CTCN_4107 | 22131 |
| CTCN_1348 | 11945 | TTCN_4349 | 22132 |
| ATCN_1010 | 11946 | CTCN_4108 | 22133 |
| TTCN_1640 | 11947 | GTCN_2334 | 22134 |
| TTCN_1641 | 11948 | TTCN_4350 | 22135 |
| CTCN_1349 | 11949 | CTCN_4109 | 22136 |
| GTCN_861 | 11950 | ATCN_2704 | 22137 |
| TTCN_1642 | 11951 | TTCN_4351 | 22138 |
| TTCN_1643 | 11952 | ATCN_2705 | 22139 |
| GTCN_862 | 11953 | TTCN_4352 | 22140 |
| TTCN_1644 | 11954 | ATCN_2706 | 22141 |
| TTCN_1645 | 11955 | ATCN_2707 | 22142 |
| ATCN_1011 | 11956 | CTCN_4110 | 22143 |
| ATCN_1012 | 11957 | TTCN_4353 | 22144 |
| TTCN_1646 | 11958 | TTCN_4354 | 22145 |
| TTCN_1647 | 11959 | TTCN_4355 | 22146 |
| CTCN_1350 | 11960 | ATCN_2708 | 22147 |
| GTCN_863 | 11961 | GTCN_2335 | 22148 |
| TTCN_1648 | 11962 | ATCN_2709 | 22149 |
| TTCN_1649 | 11963 | CTCN_4111 | 22150 |
| TTCN_1650 | 11964 | ATCN_2710 | 22151 |
| CTCN_1351 | 11965 | TTCN_4356 | 22152 |
| CTCN_1352 | 11966 | TTCN_4357 | 22153 |
| TTCN_1651 | 11967 | TTCN_4358 | 22154 |
| CTCN_1353 | 11968 | TTCN_4359 | 22155 |
| GTCN_864 | 11969 | CTCN_4112 | 22156 |
| GTCN_865 | 11970 | GTCN_2336 | 22157 |
| CTCN_1354 | 11971 | ATCN_2711 | 22158 |
| TTCN_1652 | 11972 | ATCN_2712 | 22159 |
| ATCN_1013 | 11973 | CTCN_4113 | 22160 |
| TTCN_1653 | 11974 | CTCN_4114 | 22161 |
| TTCN_1654 | 11975 | GTCN_2337 | 22162 |
| CTCN_1355 | 11976 | TTCN_4360 | 22163 |

| | | | |
|---|---|---|---|
| GTCN_866 | 11977 | TTCN_4361 | 22164 |
| GTCN_867 | 11978 | CTCN_4115 | 22165 |
| TTCN_1655 | 11979 | GTCN_2338 | 22166 |
| CTCN_1356 | 11980 | GTCN_2339 | 22167 |
| GTCN_868 | 11981 | ATCN_2713 | 22168 |
| TTCN_1656 | 11982 | TTCN_4362 | 22169 |
| GTCN_869 | 11983 | CTCN_4116 | 22170 |
| TTCN_1657 | 11984 | GTCN_2340 | 22171 |
| ATCN_1014 | 11985 | TTCN_4363 | 22172 |
| ATCN_1015 | 11986 | ATCN_2714 | 22173 |
| TTCN_1658 | 11987 | ATCN_2715 | 22174 |
| TTCN_1659 | 11988 | TTCN_4364 | 22175 |
| GTCN_870 | 11989 | CTCN_4117 | 22176 |
| CTCN_1357 | 11990 | TTCN_4365 | 22177 |
| CTCN_1358 | 11991 | GTCN_2341 | 22178 |
| GTCN_871 | 11992 | GTCN_2342 | 22179 |
| CTCN_1359 | 11993 | CTCN_4118 | 22180 |
| TTCN_1660 | 11994 | ATCN_2716 | 22181 |
| CTCN_1360 | 11995 | TTCN_4366 | 22182 |
| CTCN_1361 | 11996 | TTCN_4367 | 22183 |
| CTCN_1362 | 11997 | ATCN_2717 | 22184 |
| CTCN_1363 | 11998 | ATCN_2718 | 22185 |
| ATCN_1016 | 11999 | CTCN_4119 | 22186 |
| GTCN_872 | 12000 | ATCN_2719 | 22187 |
| ATCN_1017 | 12001 | TTCN_4368 | 22188 |
| TTCN_1661 | 12002 | TTCN_4369 | 22189 |
| TTCN_1662 | 12003 | ATCN_2720 | 22190 |
| ATCN_1018 | 12004 | TTCN_4370 | 22191 |
| ATCN_1019 | 12005 | TTCN_4371 | 22192 |
| GTCN_873 | 12006 | GTCN_2343 | 22193 |
| TTCN_1663 | 12007 | TTCN_4372 | 22194 |
| CTCN_1364 | 12008 | ATCN_2721 | 22195 |
| TTCN_1664 | 12009 | ATCN_2722 | 22196 |
| CTCN_1365 | 12010 | TTCN_4373 | 22197 |
| CTCN_1366 | 12011 | CTCN_4120 | 22198 |
| TTCN_1665 | 12012 | ATCN_2723 | 22199 |
| TTCN_1666 | 12013 | TTCN_4374 | 22200 |
| TTCN_1667 | 12014 | ATCN_2724 | 22201 |
| TTCN_1668 | 12015 | TTCN_4375 | 22202 |
| CTCN_1367 | 12016 | TTCN_4376 | 22203 |
| TTCN_1669 | 12017 | ATCN_2725 | 22204 |
| CTCN_1368 | 12018 | CTCN_4121 | 22205 |
| TTCN_1670 | 12019 | TTCN_4377 | 22206 |
| GTCN_874 | 12020 | TTCN_4378 | 22207 |
| CTCN_1369 | 12021 | CTCN_4122 | 22208 |
| CTCN_1370 | 12022 | ATCN_2726 | 22209 |
| CTCN_1371 | 12023 | ATCN_2727 | 22210 |
| CTCN_1372 | 12024 | ATCN_2728 | 22211 |
| TTCN_1671 | 12025 | CTCN_4123 | 22212 |
| ATCN_1020 | 12026 | CTCN_4124 | 22213 |
| TTCN_1672 | 12027 | TTCN_4379 | 22214 |
| CTCN_1373 | 12028 | ATCN_2729 | 22215 |
| TTCN_1673 | 12029 | TTCN_4380 | 22216 |
| ATCN_1021 | 12030 | ATCN_2730 | 22217 |
| ATCN_1022 | 12031 | CTCN_4125 | 22218 |

FIG. 36 (continued)

| | | | |
|---|---|---|---|
| CTCN_1374 | 12032 | CTCN_4126 | 22219 |
| CTCN_1375 | 12033 | CTCN_4127 | 22220 |
| TTCN_1674 | 12034 | GTCN_2344 | 22221 |
| ATCN_1023 | 12035 | ATCN_2731 | 22222 |
| GTCN_875 | 12036 | TTCN_4381 | 22223 |
| ATCN_1024 | 12037 | ATCN_2732 | 22224 |
| ATCN_1025 | 12038 | GTCN_2345 | 22225 |
| GTCN_876 | 12039 | ATCN_2733 | 22226 |
| CTCN_1376 | 12040 | CTCN_4128 | 22227 |
| CTCN_1377 | 12041 | CTCN_4129 | 22228 |
| CTCN_1378 | 12042 | GTCN_2346 | 22229 |
| TTCN_1675 | 12043 | CTCN_4130 | 22230 |
| ATCN_1026 | 12044 | TTCN_4382 | 22231 |
| TTCN_1676 | 12045 | CTCN_4131 | 22232 |
| TTCN_1677 | 12046 | CTCN_4132 | 22233 |
| CTCN_1379 | 12047 | CTCN_4133 | 22234 |
| TTCN_1678 | 12048 | GTCN_2347 | 22235 |
| ATCN_1027 | 12049 | TTCN_4383 | 22236 |
| TTCN_1679 | 12050 | CTCN_4134 | 22237 |
| TTCN_1680 | 12051 | GTCN_2348 | 22238 |
| TTCN_1681 | 12052 | TTCN_4384 | 22239 |
| CTCN_1380 | 12053 | ATCN_2734 | 22240 |
| CTCN_1381 | 12054 | CTCN_4135 | 22241 |
| TTCN_1682 | 12055 | GTCN_2349 | 22242 |
| ATCN_1028 | 12056 | TTCN_4385 | 22243 |
| CTCN_1382 | 12057 | CTCN_4136 | 22244 |
| CTCN_1383 | 12058 | CTCN_4137 | 22245 |
| TTCN_1683 | 12059 | GTCN_2350 | 22246 |
| GTCN_877 | 12060 | CTCN_4138 | 22247 |
| ATCN_1029 | 12061 | CTCN_4139 | 22248 |
| GTCN_878 | 12062 | ATCN_2735 | 22249 |
| ATCN_1030 | 12063 | ATCN_2736 | 22250 |
| GTCN_879 | 12064 | TTCN_4386 | 22251 |
| GTCN_880 | 12065 | GTCN_2351 | 22252 |
| CTCN_1384 | 12066 | CTCN_4140 | 22253 |
| ATCN_1031 | 12067 | CTCN_4141 | 22254 |
| ATCN_1032 | 12068 | ATCN_2737 | 22255 |
| CTCN_1385 | 12069 | TTCN_4387 | 22256 |
| CTCN_1386 | 12070 | CTCN_4142 | 22257 |
| CTCN_1387 | 12071 | TTCN_4388 | 22258 |
| GTCN_881 | 12072 | CTCN_4143 | 22259 |
| ATCN_1033 | 12073 | GTCN_2352 | 22260 |
| ATCN_1034 | 12074 | CTCN_4144 | 22261 |
| TTCN_1684 | 12075 | TTCN_4389 | 22262 |
| TTCN_1685 | 12076 | ATCN_2738 | 22263 |
| CTCN_1388 | 12077 | CTCN_4145 | 22264 |
| TTCN_1686 | 12078 | GTCN_2353 | 22265 |
| ATCN_1035 | 12079 | GTCN_2354 | 22266 |
| ATCN_1036 | 12080 | ATCN_2739 | 22267 |
| CTCN_1389 | 12081 | GTCN_2355 | 22268 |
| ATCN_1037 | 12082 | CTCN_4146 | 22269 |
| ATCN_1038 | 12083 | CTCN_4147 | 22270 |
| ATCN_1039 | 12084 | CTCN_4148 | 22271 |
| GTCN_882 | 12085 | ATCN_2740 | 22272 |
| TTCN_1687 | 12086 | ATCN_2741 | 22273 |

| | | | |
|---|---|---|---|
| TTCN_1688 | 12087 | CTCN_4149 | 22274 |
| CTCN_1390 | 12088 | CTCN_4150 | 22275 |
| CTCN_1391 | 12089 | ATCN_2742 | 22276 |
| CTCN_1392 | 12090 | CTCN_4151 | 22277 |
| ATCN_1040 | 12091 | CTCN_4152 | 22278 |
| TTCN_1689 | 12092 | GTCN_2356 | 22279 |
| CTCN_1393 | 12093 | TTCN_4390 | 22280 |
| CTCN_1394 | 12094 | GTCN_2357 | 22281 |
| CTCN_1395 | 12095 | CTCN_4153 | 22282 |
| GTCN_883 | 12096 | CTCN_4154 | 22283 |
| TTCN_1690 | 12097 | TTCN_4391 | 22284 |
| ATCN_1041 | 12098 | CTCN_4155 | 22285 |
| CTCN_1396 | 12099 | CTCN_4156 | 22286 |
| ATCN_1042 | 12100 | TTCN_4392 | 22287 |
| TTCN_1691 | 12101 | ATCN_2743 | 22288 |
| TTCN_1692 | 12102 | TTCN_4393 | 22289 |
| CTCN_1397 | 12103 | TTCN_4394 | 22290 |
| CTCN_1398 | 12104 | TTCN_4395 | 22291 |
| TTCN_1693 | 12105 | ATCN_2744 | 22292 |
| GTCN_884 | 12106 | TTCN_4396 | 22293 |
| TTCN_1694 | 12107 | CTCN_4157 | 22294 |
| CTCN_1399 | 12108 | TTCN_4397 | 22295 |
| TTCN_1695 | 12109 | CTCN_4158 | 22296 |
| CTCN_1400 | 12110 | ATCN_2745 | 22297 |
| CTCN_1401 | 12111 | ATCN_2746 | 22298 |
| GTCN_885 | 12112 | GTCN_2358 | 22299 |
| CTCN_1402 | 12113 | ATCN_2747 | 22300 |
| CTCN_1403 | 12114 | CTCN_4159 | 22301 |
| TTCN_1696 | 12115 | GTCN_2359 | 22302 |
| CTCN_1404 | 12116 | TTCN_4398 | 22303 |
| GTCN_886 | 12117 | GTCN_2360 | 22304 |
| TTCN_1697 | 12118 | CTCN_4160 | 22305 |
| CTCN_1405 | 12119 | CTCN_4161 | 22306 |
| ATCN_1043 | 12120 | CTCN_4162 | 22307 |
| CTCN_1406 | 12121 | GTCN_2361 | 22308 |
| CTCN_1407 | 12122 | CTCN_4163 | 22309 |
| CTCN_1408 | 12123 | CTCN_4164 | 22310 |
| TTCN_1698 | 12124 | CTCN_4165 | 22311 |
| CTCN_1409 | 12125 | CTCN_4166 | 22312 |
| ATCN_1044 | 12126 | TTCN_4399 | 22313 |
| ATCN_1045 | 12127 | CTCN_4167 | 22314 |
| CTCN_1410 | 12128 | CTCN_4168 | 22315 |
| TTCN_1699 | 12129 | CTCN_4169 | 22316 |
| GTCN_887 | 12130 | ATCN_2748 | 22317 |
| TTCN_1700 | 12131 | ATCN_2749 | 22318 |
| GTCN_888 | 12132 | GTCN_2362 | 22319 |
| CTCN_1411 | 12133 | CTCN_4170 | 22320 |
| ATCN_1046 | 12134 | GTCN_2363 | 22321 |
| TTCN_1701 | 12135 | CTCN_4171 | 22322 |
| ATCN_1047 | 12136 | GTCN_2364 | 22323 |
| GTCN_889 | 12137 | CTCN_4172 | 22324 |
| CTCN_1412 | 12138 | TTCN_4400 | 22325 |
| GTCN_890 | 12139 | TTCN_4401 | 22326 |
| TTCN_1702 | 12140 | CTCN_4173 | 22327 |
| GTCN_891 | 12141 | TTCN_4402 | 22328 |

FIG. 36 (continued)

| | | | |
|---|---|---|---|
| CTCN_1413 | 12142 | TTCN_4403 | 22329 |
| TTCN_1703 | 12143 | CTCN_4174 | 22330 |
| GTCN_892 | 12144 | GTCN_2365 | 22331 |
| CTCN_1414 | 12145 | CTCN_4175 | 22332 |
| CTCN_1415 | 12146 | CTCN_4176 | 22333 |
| GTCN_893 | 12147 | CTCN_4177 | 22334 |
| ATCN_1048 | 12148 | TTCN_4404 | 22335 |
| TTCN_1704 | 12149 | TTCN_4405 | 22336 |
| TTCN_1705 | 12150 | TTCN_4406 | 22337 |
| GTCN_894 | 12151 | TTCN_4407 | 22338 |
| TTCN_1706 | 12152 | TTCN_4408 | 22339 |
| GTCN_895 | 12153 | ATCN_2750 | 22340 |
| ATCN_1049 | 12154 | CTCN_4178 | 22341 |
| TTCN_1707 | 12155 | TTCN_4409 | 22342 |
| ATCN_1050 | 12156 | GTCN_2366 | 22343 |
| ATCN_1051 | 12157 | CTCN_4179 | 22344 |
| CTCN_1416 | 12158 | CTCN_4180 | 22345 |
| CTCN_1417 | 12159 | TTCN_4410 | 22346 |
| GTCN_896 | 12160 | GTCN_2367 | 22347 |
| ATCN_1052 | 12161 | TTCN_4411 | 22348 |
| TTCN_1708 | 12162 | CTCN_4181 | 22349 |
| GTCN_897 | 12163 | GTCN_2368 | 22350 |
| GTCN_898 | 12164 | ATCN_2751 | 22351 |
| GTCN_899 | 12165 | CTCN_4182 | 22352 |
| CTCN_1418 | 12166 | ATCN_2752 | 22353 |
| CTCN_1419 | 12167 | CTCN_4183 | 22354 |
| TTCN_1709 | 12168 | TTCN_4412 | 22355 |
| ATCN_1053 | 12169 | TTCN_4413 | 22356 |
| TTCN_1710 | 12170 | TTCN_4414 | 22357 |
| ATCN_1054 | 12171 | TTCN_4281 | 22358 |
| TTCN_1711 | 12172 | TTCN_4282 | 22359 |
| ATCN_1055 | 12173 | ATCN_2655 | 22360 |
| TTCN_1712 | 12174 | TTCN_4283 | 22361 |
| CTCN_1420 | 12175 | CTCN_4064 | 22362 |
| GTCN_900 | 12176 | CTCN_4065 | 22363 |
| CTCN_1421 | 12177 | GTCN_2295 | 22364 |
| GTCN_901 | 12178 | ATCN_2656 | 22365 |
| CTCN_1422 | 12179 | TTCN_4284 | 22366 |
| CTCN_1423 | 12180 | GTCN_2296 | 22367 |
| TTCN_1713 | 12181 | CTCN_4066 | 22368 |
| GTCN_902 | 12182 | GTCN_2297 | 22369 |
| CTCN_1424 | 12183 | CTCN_4067 | 22370 |
| CTCN_1425 | 12184 | ATCN_2657 | 22371 |
| GTCN_903 | 12185 | ATCN_2658 | 22372 |
| TTCN_1714 | 12186 | CTCN_4068 | 22373 |
| CTCN_1426 | 12187 | GTCN_2298 | 22374 |
| ATCN_1056 | 12188 | CTCN_4069 | 22375 |
| CTCN_1427 | 12189 | CTCN_4070 | 22376 |
| CTCN_1428 | 12190 | TTCN_4285 | 22377 |
| GTCN_904 | 12191 | ATCN_2659 | 22378 |
| GTCN_905 | 12192 | TTCN_4286 | 22379 |
| CTCN_1429 | 12193 | CTCN_4071 | 22380 |
| CTCN_1430 | 12194 | TTCN_4287 | 22381 |
| ATCN_1057 | 12195 | CTCN_4072 | 22382 |
| CTCN_1431 | 12196 | ATCN_2660 | 22383 |

| | | | |
|---|---|---|---|
| GTCN_906 | 12197 | CTCN_4073 | 22384 |
| TTCN_1715 | 12198 | ATCN_2661 | 22385 |
| GTCN_907 | 12199 | TTCN_4288 | 22386 |
| CTCN_1432 | 12200 | GTCN_2299 | 22387 |
| TTCN_1716 | 12201 | GTCN_2300 | 22388 |
| TTCN_1717 | 12202 | CTCN_4074 | 22389 |
| CTCN_1433 | 12203 | TTCN_4289 | 22390 |
| TTCN_1718 | 12204 | CTCN_4075 | 22391 |
| ATCN_1058 | 12205 | GTCN_2301 | 22392 |
| ATCN_1059 | 12206 | CTCN_4076 | 22393 |
| TTCN_1719 | 12207 | ATCN_2662 | 22394 |
| TTCN_1720 | 12208 | ATCN_2663 | 22395 |
| TTCN_1721 | 12209 | CTCN_4077 | 22396 |
| CTCN_1434 | 12210 | ATCN_2664 | 22397 |
| TTCN_1722 | 12211 | ATCN_2665 | 22398 |
| TTCN_1723 | 12212 | TTCN_4290 | 22399 |
| TTCN_1724 | 12213 | CTCN_4078 | 22400 |
| GTCN_908 | 12214 | CTCN_4079 | 22401 |
| ATCN_1060 | 12215 | CTCN_4080 | 22402 |
| ATCN_1061 | 12216 | GTCN_2302 | 22403 |
| TTCN_1725 | 12217 | ATCN_2666 | 22404 |
| GTCN_909 | 12218 | ATCN_2667 | 22405 |
| TTCN_1726 | 12219 | TTCN_4291 | 22406 |
| ATCN_1062 | 12220 | TTCN_4292 | 22407 |
| ATCN_1063 | 12221 | GTCN_2303 | 22408 |
| ATCN_1064 | 12222 | TTCN_4293 | 22409 |
| ATCN_1065 | 12223 | TTCN_4294 | 22410 |
| GTCN_910 | 12224 | ATCN_2668 | 22411 |
| TTCN_1727 | 12225 | ATCN_2669 | 22412 |
| CTCN_1435 | 12226 | ATCN_2670 | 22413 |
| CTCN_1436 | 12227 | ATCN_2671 | 22414 |
| ATCN_1066 | 12228 | ATCN_2672 | 22415 |
| ATCN_1067 | 12229 | CTCN_4081 | 22416 |
| CTCN_1437 | 12230 | GTCN_2304 | 22417 |
| TTCN_1728 | 12231 | TTCN_4295 | 22418 |
| TTCN_1729 | 12232 | GTCN_2305 | 22419 |
| ATCN_1068 | 12233 | CTCN_4082 | 22420 |
| ATCN_1069 | 12234 | CTCN_4083 | 22421 |
| TTCN_1730 | 12235 | CTCN_4084 | 22422 |
| TTCN_1731 | 12236 | GTCN_2306 | 22423 |
| TTCN_1732 | 12237 | CTCN_4085 | 22424 |
| CTCN_1438 | 12238 | ATCN_2673 | 22425 |
| CTCN_1439 | 12239 | TTCN_4296 | 22426 |
| TTCN_1733 | 12240 | TTCN_4297 | 22427 |
| ATCN_1070 | 12241 | TTCN_4298 | 22428 |
| ATCN_1071 | 12242 | ATCN_2674 | 22429 |
| TTCN_1734 | 12243 | ATCN_2675 | 22430 |
| CTCN_1440 | 12244 | TTCN_4299 | 22431 |
| CTCN_1441 | 12245 | CTCN_4086 | 22432 |
| TTCN_1735 | 12246 | ATCN_2676 | 22433 |
| GTCN_911 | 12247 | ATCN_2677 | 22434 |
| CTCN_1442 | 12248 | GTCN_2307 | 22435 |
| ATCN_1072 | 12249 | TTCN_4300 | 22436 |
| CTCN_1443 | 12250 | CTCN_4087 | 22437 |
| TTCN_1736 | 12251 | TTCN_4301 | 22438 |

FIG. 36 (continued)

| | | | |
|---|---|---|---|
| ATCN_1073 | 12252 | ATCN_2678 | 22439 |
| TTCN_1737 | 12253 | TTCN_4302 | 22440 |
| CTCN_1444 | 12254 | TTCN_4303 | 22441 |
| TTCN_1738 | 12255 | CTCN_4088 | 22442 |
| TTCN_1739 | 12256 | GTCN_2308 | 22443 |
| CTCN_1445 | 12257 | CTCN_4089 | 22444 |
| CTCN_1446 | 12258 | TTCN_4304 | 22445 |
| TTCN_1740 | 12259 | TTCN_4305 | 22446 |
| TTCN_1741 | 12260 | TTCN_4306 | 22447 |
| CTCN_1447 | 12261 | TTCN_4307 | 22448 |
| ATCN_1074 | 12262 | TTCN_4308 | 22449 |
| TTCN_1742 | 12263 | GTCN_2309 | 22450 |
| ATCN_1075 | 12264 | ATCN_2679 | 22451 |
| ATCN_1076 | 12265 | CTCN_4090 | 22452 |
| TTCN_1743 | 12266 | CTCN_4091 | 22453 |
| GTCN_912 | 12267 | ATCN_2680 | 22454 |
| GTCN_913 | 12268 | ATCN_2681 | 22455 |
| TTCN_1744 | 12269 | GTCN_2310 | 22456 |
| CTCN_1448 | 12270 | TTCN_4309 | 22457 |
| TTCN_1745 | 12271 | GTCN_2311 | 22458 |
| ATCN_1077 | 12272 | CTCN_4092 | 22459 |
| TTCN_1746 | 12273 | TTCN_4310 | 22460 |
| GTCN_914 | 12274 | GTCN_2312 | 22461 |
| GTCN_915 | 12275 | TTCN_4311 | 22462 |
| GTCN_916 | 12276 | GTCN_2313 | 22463 |
| TTCN_1747 | 12277 | TTCN_4312 | 22464 |
| GTCN_917 | 12278 | TTCN_4313 | 22465 |
| GTCN_918 | 12279 | GTCN_2314 | 22466 |
| CTCN_1449 | 12280 | ATCN_2682 | 22467 |
| TTCN_1748 | 12281 | TTCN_4314 | 22468 |
| CTCN_1450 | 12282 | ATCN_2683 | 22469 |
| TTCN_1749 | 12283 | ATCN_2684 | 22470 |
| ATCN_1078 | 12284 | TTCN_4315 | 22471 |
| TTCN_1750 | 12285 | TTCN_4316 | 22472 |
| CTCN_1451 | 12286 | GTCN_2315 | 22473 |
| GTCN_919 | 12287 | CTCN_4093 | 22474 |
| TTCN_1751 | 12288 | ATCN_2685 | 22475 |
| CTCN_1452 | 12289 | TTCN_4317 | 22476 |
| GTCN_920 | 12290 | ATCN_2686 | 22477 |
| TTCN_1752 | 12291 | GTCN_2316 | 22478 |
| GTCN_921 | 12292 | TTCN_4318 | 22479 |
| CTCN_1453 | 12293 | TTCN_4319 | 22480 |
| TTCN_1753 | 12294 | ATCN_2687 | 22481 |
| ATCN_1079 | 12295 | TTCN_4320 | 22482 |
| TTCN_1754 | 12296 | TTCN_4321 | 22483 |
| CTCN_1454 | 12297 | CTCN_4094 | 22484 |
| TTCN_1755 | 12298 | ATCN_2688 | 22485 |
| CTCN_1455 | 12299 | CTCN_4095 | 22486 |
| TTCN_1756 | 12300 | TTCN_4322 | 22487 |
| CTCN_1456 | 12301 | GTCN_2317 | 22488 |
| GTCN_922 | 12302 | ATCN_2689 | 22489 |
| TTCN_1757 | 12303 | TTCN_4323 | 22490 |
| GTCN_923 | 12304 | ATCN_2690 | 22491 |
| GTCN_924 | 12305 | TTCN_4324 | 22492 |
| TTCN_1758 | 12306 | TTCN_4325 | 22493 |

| | | | |
|---|---|---|---|
| CTCN_1457 | 12307 | TTCN_4326 | 22494 |
| GTCN_925 | 12308 | ATCN_2691 | 22495 |
| CTCN_1458 | 12309 | CTCN_4096 | 22496 |
| CTCN_1459 | 12310 | ATCN_2692 | 22497 |
| ATCN_1080 | 12311 | ATCN_2693 | 22498 |
| ATCN_1081 | 12312 | TTCN_4327 | 22499 |
| TTCN_1759 | 12313 | GTCN_2318 | 22500 |
| ATCN_1082 | 12314 | TTCN_4328 | 22501 |
| TTCN_1760 | 12315 | TTCN_4329 | 22502 |
| ATCN_1083 | 12316 | TTCN_4330 | 22503 |
| GTCN_926 | 12317 | ATCN_2694 | 22504 |
| TTCN_1761 | 12318 | GTCN_2319 | 22505 |
| GTCN_927 | 12319 | TTCN_4331 | 22506 |
| ATCN_1084 | 12320 | TTCN_4332 | 22507 |
| ATCN_1085 | 12321 | TTCN_4333 | 22508 |
| TTCN_1762 | 12322 | CTCN_4097 | 22509 |
| ATCN_1086 | 12323 | TTCN_4334 | 22510 |
| CTCN_1460 | 12324 | ATCN_2695 | 22511 |
| CTCN_1461 | 12325 | TTCN_4335 | 22512 |
| GTCN_928 | 12326 | GTCN_2320 | 22513 |
| TTCN_1763 | 12327 | TTCN_4336 | 22514 |
| CTCN_1462 | 12328 | TTCN_4337 | 22515 |
| GTCN_929 | 12329 | CTCN_4098 | 22516 |
| GTCN_930 | 12330 | CTCN_4099 | 22517 |
| TTCN_1764 | 12331 | ATCN_2696 | 22518 |
| ATCN_1087 | 12332 | ATCN_2697 | 22519 |
| CTCN_1463 | 12333 | TTCN_4338 | 22520 |
| TTCN_1765 | 12334 | ATCN_2698 | 22521 |
| CTCN_1464 | 12335 | TTCN_4339 | 22522 |
| TTCN_1766 | 12336 | CTCN_4100 | 22523 |
| CTCN_1465 | 12337 | ATCN_2699 | 22524 |
| ATCN_1088 | 12338 | CTCN_4101 | 22525 |
| ATCN_1089 | 12339 | TTCN_4340 | 22526 |
| TTCN_1767 | 12340 | ATCN_2700 | 22527 |
| TTCN_1768 | 12341 | GTCN_2321 | 22528 |
| GTCN_931 | 12342 | ATCN_2701 | 22529 |
| TTCN_1769 | 12343 | GTCN_2322 | 22530 |
| CTCN_1466 | 12344 | CTCN_4102 | 22531 |
| ATCN_1090 | 12345 | GTCN_2323 | 22532 |
| ATCN_1091 | 12346 | GTCN_2324 | 22533 |
| CTCN_1467 | 12347 | GTCN_2325 | 22534 |
| ATCN_1092 | 12348 | GTCN_2326 | 22535 |
| ATCN_1093 | 12349 | TTCN_4341 | 22536 |
| CTCN_1468 | 12350 | TTCN_4342 | 22537 |
| TTCN_1770 | 12351 | TTCN_4343 | 22538 |
| CTCN_1469 | 12352 | GTCN_2327 | 22539 |
| TTCN_1771 | 12353 | TTCN_4344 | 22540 |
| TTCN_1772 | 12354 | TTCN_4345 | 22541 |
| CTCN_1470 | 12355 | GTCN_2328 | 22542 |
| CTCN_1471 | 12356 | TTCN_4346 | 22543 |
| TTCN_1773 | 12357 | TTCN_4347 | 22544 |
| TTCN_1774 | 12358 | CTCN_4103 | 22545 |
| CTCN_1472 | 12359 | GTCN_2329 | 22546 |
| TTCN_1775 | 12360 | GTCN_2330 | 22547 |
| TTCN_1776 | 12361 | ATCN_2702 | 22548 |

FIG. 36 (continued)

| | | | |
|---|---|---|---|
| CTCN_1473 | 12362 | ATCN_2703 | 22549 |
| TTCN_1777 | 12363 | CTCN_4104 | 22550 |
| GTCN_932 | 12364 | GTCN_2331 | 22551 |
| CTCN_1474 | 12365 | GTCN_2332 | 22552 |
| TTCN_1778 | 12366 | CTCN_4105 | 22553 |
| GTCN_933 | 12367 | GTCN_2333 | 22554 |
| GTCN_934 | 12368 | TTCN_4348 | 22555 |
| TTCN_1779 | 12369 | CTCN_4106 | 22556 |
| CTCN_1475 | 12370 | CTCN_4107 | 22557 |
| CTCN_1476 | 12371 | TTCN_4349 | 22558 |
| GTCN_935 | 12372 | CTCN_4108 | 22559 |
| CTCN_1477 | 12373 | GTCN_2334 | 22560 |
| GTCN_936 | 12374 | TTCN_4350 | 22561 |
| GTCN_937 | 12375 | CTCN_4109 | 22562 |
| CTCN_1478 | 12376 | ATCN_2704 | 22563 |
| ATCN_1094 | 12377 | TTCN_4351 | 22564 |
| CTCN_1479 | 12378 | ATCN_2705 | 22565 |
| ATCN_1095 | 12379 | TTCN_4352 | 22566 |
| ATCN_1096 | 12380 | ATCN_2706 | 22567 |
| TTCN_1780 | 12381 | ATCN_2707 | 22568 |
| GTCN_938 | 12382 | CTCN_4110 | 22569 |
| CTCN_1480 | 12383 | TTCN_4353 | 22570 |
| ATCN_1097 | 12384 | TTCN_4354 | 22571 |
| CTCN_1481 | 12385 | TTCN_4355 | 22572 |
| ATCN_1098 | 12386 | ATCN_2708 | 22573 |
| CTCN_1482 | 12387 | GTCN_2335 | 22574 |
| CTCN_1483 | 12388 | ATCN_2709 | 22575 |
| TTCN_1781 | 12389 | CTCN_4111 | 22576 |
| CTCN_1484 | 12390 | ATCN_2710 | 22577 |
| CTCN_1485 | 12391 | TTCN_4356 | 22578 |
| ATCN_1099 | 12392 | TTCN_4357 | 22579 |
| CTCN_1486 | 12393 | TTCN_4358 | 22580 |
| TTCN_1782 | 12394 | TTCN_4359 | 22581 |
| TTCN_1783 | 12395 | CTCN_4112 | 22582 |
| ATCN_1100 | 12396 | GTCN_2336 | 22583 |
| TTCN_1784 | 12397 | ATCN_2711 | 22584 |
| ATCN_1101 | 12398 | ATCN_2712 | 22585 |
| TTCN_1785 | 12399 | CTCN_4113 | 22586 |
| CTCN_1487 | 12400 | CTCN_4114 | 22587 |
| TTCN_1786 | 12401 | GTCN_2337 | 22588 |
| CTCN_1488 | 12402 | TTCN_4360 | 22589 |
| TTCN_1787 | 12403 | TTCN_4361 | 22590 |
| TTCN_1788 | 12404 | CTCN_4115 | 22591 |
| CTCN_1489 | 12405 | GTCN_2338 | 22592 |
| CTCN_1490 | 12406 | GTCN_2339 | 22593 |
| GTCN_939 | 12407 | ATCN_2713 | 22594 |
| TTCN_1789 | 12408 | TTCN_4362 | 22595 |
| CTCN_1491 | 12409 | CTCN_4116 | 22596 |
| ATCN_1102 | 12410 | GTCN_2340 | 22597 |
| GTCN_940 | 12411 | TTCN_4363 | 22598 |
| TTCN_1790 | 12412 | ATCN_2714 | 22599 |
| TTCN_1791 | 12413 | ATCN_2715 | 22600 |
| TTCN_1792 | 12414 | TTCN_4364 | 22601 |
| TTCN_1793 | 12415 | CTCN_4117 | 22602 |
| GTCN_941 | 12416 | TTCN_4365 | 22603 |

| | | | |
|---|---|---|---|
| CTCN_1492 | 12417 | GTCN_2341 | 22604 |
| GTCN_942 | 12418 | GTCN_2342 | 22605 |
| TTCN_1794 | 12419 | CTCN_4118 | 22606 |
| CTCN_1493 | 12420 | ATCN_2716 | 22607 |
| CTCN_1494 | 12421 | TTCN_4366 | 22608 |
| ATCN_1103 | 12422 | TTCN_4367 | 22609 |
| CTCN_1495 | 12423 | ATCN_2717 | 22610 |
| TTCN_1795 | 12424 | ATCN_2718 | 22611 |
| TTCN_1796 | 12425 | CTCN_4119 | 22612 |
| TTCN_1797 | 12426 | ATCN_2719 | 22613 |
| GTCN_943 | 12427 | TTCN_4368 | 22614 |
| ATCN_1104 | 12428 | TTCN_4369 | 22615 |
| ATCN_1105 | 12429 | ATCN_2720 | 22616 |
| GTCN_944 | 12430 | TTCN_4370 | 22617 |
| TTCN_1798 | 12431 | TTCN_4371 | 22618 |
| TTCN_1799 | 12432 | GTCN_2343 | 22619 |
| TTCN_1800 | 12433 | TTCN_4372 | 22620 |
| ATCN_1106 | 12434 | ATCN_2721 | 22621 |
| GTCN_945 | 12435 | ATCN_2722 | 22622 |
| CTCN_1496 | 12436 | TTCN_4373 | 22623 |
| CTCN_1497 | 12437 | CTCN_4120 | 22624 |
| CTCN_1498 | 12438 | ATCN_2723 | 22625 |
| TTCN_1801 | 12439 | TTCN_4374 | 22626 |
| GTCN_946 | 12440 | ATCN_2724 | 22627 |
| TTCN_1802 | 12441 | TTCN_4375 | 22628 |
| CTCN_1499 | 12442 | TTCN_4376 | 22629 |
| GTCN_947 | 12443 | ATCN_2725 | 22630 |
| TTCN_1803 | 12444 | CTCN_4121 | 22631 |
| TTCN_1804 | 12445 | TTCN_4377 | 22632 |
| TTCN_1805 | 12446 | TTCN_4378 | 22633 |
| GTCN_948 | 12447 | CTCN_4122 | 22634 |
| TTCN_1806 | 12448 | ATCN_2726 | 22635 |
| ATCN_1107 | 12449 | ATCN_2727 | 22636 |
| ATCN_1108 | 12450 | ATCN_2728 | 22637 |
| ATCN_1109 | 12451 | CTCN_4123 | 22638 |
| GTCN_949 | 12452 | CTCN_4124 | 22639 |
| TTCN_1807 | 12453 | TTCN_4379 | 22640 |
| GTCN_950 | 12454 | ATCN_2729 | 22641 |
| TTCN_1808 | 12455 | TTCN_4380 | 22642 |
| TTCN_1809 | 12456 | ATCN_2730 | 22643 |
| TTCN_1810 | 12457 | CTCN_4125 | 22644 |
| ATCN_1110 | 12458 | CTCN_4126 | 22645 |
| CTCN_1500 | 12459 | CTCN_4127 | 22646 |
| ATCN_1111 | 12460 | GTCN_2344 | 22647 |
| GTCN_951 | 12461 | ATCN_2731 | 22648 |
| TTCN_1811 | 12462 | TTCN_4381 | 22649 |
| ATCN_1112 | 12463 | ATCN_2732 | 22650 |
| GTCN_952 | 12464 | GTCN_2345 | 22651 |
| TTCN_1812 | 12465 | ATCN_2733 | 22652 |
| CTCN_1501 | 12466 | CTCN_4128 | 22653 |
| TTCN_1813 | 12467 | CTCN_4129 | 22654 |
| CTCN_1502 | 12468 | GTCN_2346 | 22655 |
| TTCN_1814 | 12469 | CTCN_4130 | 22656 |
| TTCN_1815 | 12470 | TTCN_4382 | 22657 |
| TTCN_1816 | 12471 | CTCN_4131 | 22658 |

FIG. 36 (continued)

| | | | |
|---|---|---|---|
| TTCN_1817 | 12472 | CTCN_4132 | 22659 |
| ATCN_1113 | 12473 | CTCN_4133 | 22660 |
| TTCN_1818 | 12474 | GTCN_2347 | 22661 |
| TTCN_1819 | 12475 | TTCN_4383 | 22662 |
| ATCN_1114 | 12476 | CTCN_4134 | 22663 |
| CTCN_1503 | 12477 | GTCN_2348 | 22664 |
| CTCN_1504 | 12478 | TTCN_4384 | 22665 |
| TTCN_1820 | 12479 | ATCN_2734 | 22666 |
| CTCN_1505 | 12480 | CTCN_4135 | 22667 |
| ATCN_1115 | 12481 | GTCN_2349 | 22668 |
| ATCN_1116 | 12482 | TTCN_4385 | 22669 |
| CTCN_1506 | 12483 | CTCN_4136 | 22670 |
| CTCN_1507 | 12484 | CTCN_4137 | 22671 |
| ATCN_1117 | 12485 | GTCN_2350 | 22672 |
| CTCN_1508 | 12486 | CTCN_4138 | 22673 |
| ATCN_1118 | 12487 | CTCN_4139 | 22674 |
| CTCN_1509 | 12488 | ATCN_2735 | 22675 |
| GTCN_953 | 12489 | ATCN_2736 | 22676 |
| ATCN_1119 | 12490 | TTCN_4386 | 22677 |
| TTCN_1821 | 12491 | GTCN_2351 | 22678 |
| TTCN_1822 | 12492 | CTCN_4140 | 22679 |
| GTCN_954 | 12493 | CTCN_4141 | 22680 |
| CTCN_1510 | 12494 | ATCN_2737 | 22681 |
| TTCN_1823 | 12495 | TTCN_4387 | 22682 |
| TTCN_1824 | 12496 | CTCN_4142 | 22683 |
| TTCN_1825 | 12497 | TTCN_4388 | 22684 |
| TTCN_1826 | 12498 | CTCN_4143 | 22685 |
| ATCN_1120 | 12499 | GTCN_2352 | 22686 |
| ATCN_1121 | 12500 | CTCN_4144 | 22687 |
| CTCN_1511 | 12501 | TTCN_4389 | 22688 |
| CTCN_1512 | 12502 | ATCN_2738 | 22689 |
| ATCN_1122 | 12503 | CTCN_4145 | 22690 |
| GTCN_955 | 12504 | GTCN_2353 | 22691 |
| GTCN_956 | 12505 | GTCN_2354 | 22692 |
| ATCN_1123 | 12506 | ATCN_2739 | 22693 |
| TTCN_1827 | 12507 | GTCN_2355 | 22694 |
| TTCN_1828 | 12508 | CTCN_4146 | 22695 |
| ATCN_1124 | 12509 | CTCN_4147 | 22696 |
| CTCN_1513 | 12510 | CTCN_4148 | 22697 |
| TTCN_1829 | 12511 | ATCN_2740 | 22698 |
| ATCN_1125 | 12512 | ATCN_2741 | 22699 |
| TTCN_1830 | 12513 | CTCN_4149 | 22700 |
| CTCN_1514 | 12514 | CTCN_4150 | 22701 |
| GTCN_957 | 12515 | ATCN_2742 | 22702 |
| CTCN_1515 | 12516 | CTCN_4151 | 22703 |
| TTCN_1831 | 12517 | CTCN_4152 | 22704 |
| CTCN_1516 | 12518 | GTCN_2356 | 22705 |
| CTCN_1517 | 12519 | TTCN_4390 | 22706 |
| TTCN_1832 | 12520 | GTCN_2357 | 22707 |
| TTCN_1833 | 12521 | CTCN_4153 | 22708 |
| GTCN_958 | 12522 | CTCN_4154 | 22709 |
| ATCN_1126 | 12523 | TTCN_4391 | 22710 |
| ATCN_1127 | 12524 | CTCN_4155 | 22711 |
| ATCN_1128 | 12525 | CTCN_4156 | 22712 |
| TTCN_1834 | 12526 | TTCN_4392 | 22713 |

| | | | |
|---|---|---|---|
| CTCN_1518 | 12527 | ATCN_2743 | 22714 |
| TTCN_1835 | 12528 | TTCN_4393 | 22715 |
| TTCN_1836 | 12529 | TTCN_4394 | 22716 |
| ATCN_1129 | 12530 | TTCN_4395 | 22717 |
| ATCN_1130 | 12531 | ATCN_2744 | 22718 |
| TTCN_1837 | 12532 | TTCN_4396 | 22719 |
| TTCN_1838 | 12533 | CTCN_4157 | 22720 |
| CTCN_1519 | 12534 | TTCN_4397 | 22721 |
| CTCN_1520 | 12535 | CTCN_4158 | 22722 |
| TTCN_1839 | 12536 | ATCN_2745 | 22723 |
| CTCN_1521 | 12537 | ATCN_2746 | 22724 |
| GTCN_959 | 12538 | GTCN_2358 | 22725 |
| TTCN_1840 | 12539 | ATCN_2747 | 22726 |
| TTCN_1841 | 12540 | CTCN_4159 | 22727 |
| ATCN_1131 | 12541 | GTCN_2359 | 22728 |
| TTCN_1842 | 12542 | TTCN_4398 | 22729 |
| TTCN_1843 | 12543 | GTCN_2360 | 22730 |
| ATCN_1132 | 12544 | CTCN_4160 | 22731 |
| TTCN_1844 | 12545 | CTCN_4161 | 22732 |
| TTCN_1845 | 12546 | CTCN_4162 | 22733 |
| ATCN_1133 | 12547 | GTCN_2361 | 22734 |
| GTCN_960 | 12548 | CTCN_4163 | 22735 |
| TTCN_1846 | 12549 | CTCN_4164 | 22736 |
| TTCN_1847 | 12550 | CTCN_4165 | 22737 |
| GTCN_961 | 12551 | CTCN_4166 | 22738 |
| TTCN_1848 | 12552 | TTCN_4399 | 22739 |
| GTCN_962 | 12553 | CTCN_4167 | 22740 |
| TTCN_1849 | 12554 | CTCN_4168 | 22741 |
| ATCN_1134 | 12555 | CTCN_4169 | 22742 |
| TTCN_1850 | 12556 | ATCN_2748 | 22743 |
| CTCN_1522 | 12557 | ATCN_2749 | 22744 |
| CTCN_1523 | 12558 | GTCN_2362 | 22745 |
| CTCN_1524 | 12559 | CTCN_4170 | 22746 |
| CTCN_1525 | 12560 | GTCN_2363 | 22747 |
| CTCN_1526 | 12561 | CTCN_4171 | 22748 |
| TTCN_1851 | 12562 | GTCN_2364 | 22749 |
| GTCN_963 | 12563 | CTCN_4172 | 22750 |
| GTCN_964 | 12564 | TTCN_4400 | 22751 |
| ATCN_1135 | 12565 | TTCN_4401 | 22752 |
| TTCN_1852 | 12566 | CTCN_4173 | 22753 |
| TTCN_1853 | 12567 | TTCN_4402 | 22754 |
| GTCN_965 | 12568 | TTCN_4403 | 22755 |
| TTCN_1854 | 12569 | CTCN_4174 | 22756 |
| ATCN_1136 | 12570 | GTCN_2365 | 22757 |
| TTCN_1855 | 12571 | CTCN_4175 | 22758 |
| GTCN_966 | 12572 | CTCN_4176 | 22759 |
| TTCN_1856 | 12573 | CTCN_4177 | 22760 |
| TTCN_1857 | 12574 | TTCN_4404 | 22761 |
| TTCN_1858 | 12575 | TTCN_4405 | 22762 |
| CTCN_1527 | 12576 | TTCN_4406 | 22763 |
| ATCN_1137 | 12577 | TTCN_4407 | 22764 |
| CTCN_1528 | 12578 | TTCN_4408 | 22765 |
| CTCN_1529 | 12579 | ATCN_2750 | 22766 |
| ATCN_1138 | 12580 | CTCN_4178 | 22767 |
| ATCN_1139 | 12581 | TTCN_4409 | 22768 |

FIG. 36 (continued)

| | | | |
|---|---|---|---|
| CTCN_1530 | 12582 | GTCN_2366 | 22769 |
| GTCN_967 | 12583 | CTCN_4179 | 22770 |
| CTCN_1531 | 12584 | CTCN_4180 | 22771 |
| TTCN_1859 | 12585 | TTCN_4410 | 22772 |
| CTCN_1532 | 12586 | GTCN_2367 | 22773 |
| GTCN_968 | 12587 | TTCN_4411 | 22774 |
| ATCN_1140 | 12588 | CTCN_4181 | 22775 |
| TTCN_1860 | 12589 | GTCN_2368 | 22776 |
| GTCN_969 | 12590 | ATCN_2751 | 22777 |
| CTCN_1533 | 12591 | CTCN_4182 | 22778 |
| GTCN_970 | 12592 | ATCN_2752 | 22779 |
| CTCN_1534 | 12593 | CTCN_4183 | 22780 |
| CTCN_1535 | 12594 | TTCN_4412 | 22781 |
| CTCN_1536 | 12595 | TTCN_4413 | 22782 |
| TTCN_1861 | 12596 | TTCN_4414 | 22783 |
| TTCN_1862 | 12597 | ATCN_2753 | 22784 |
| CTCN_1537 | 12598 | TTCN_4415 | 22785 |
| CTCN_1538 | 12599 | ATCN_2754 | 22786 |
| CTCN_1539 | 12600 | TTCN_4416 | 22787 |
| ATCN_1141 | 12601 | TTCN_4417 | 22788 |
| ATCN_1142 | 12602 | CTCN_4184 | 22789 |
| CTCN_1540 | 12603 | TTCN_4418 | 22790 |
| GTCN_971 | 12604 | GTCN_2369 | 22791 |
| CTCN_1541 | 12605 | ATCN_2755 | 22792 |
| CTCN_1542 | 12606 | ATCN_2756 | 22793 |
| GTCN_972 | 12607 | TTCN_4419 | 22794 |
| CTCN_1543 | 12608 | TTCN_4420 | 22795 |
| ATCN_1143 | 12609 | TTCN_4421 | 22796 |
| CTCN_1544 | 12610 | TTCN_4422 | 22797 |
| TTCN_1863 | 12611 | ATCN_2757 | 22798 |
| TTCN_1864 | 12612 | CTCN_4185 | 22799 |
| TTCN_1865 | 12613 | CTCN_4186 | 22800 |
| CTCN_1545 | 12614 | GTCN_2370 | 22801 |
| GTCN_973 | 12615 | GTCN_2371 | 22802 |
| CTCN_1546 | 12616 | TTCN_4423 | 22803 |
| CTCN_1547 | 12617 | CTCN_4187 | 22804 |
| ATCN_1144 | 12618 | CTCN_4188 | 22805 |
| CTCN_1548 | 12619 | ATCN_2758 | 22806 |
| TTCN_1866 | 12620 | ATCN_2759 | 22807 |
| CTCN_1549 | 12621 | GTCN_2372 | 22808 |
| CTCN_1550 | 12622 | CTCN_4189 | 22809 |
| ATCN_1145 | 12623 | TTCN_4424 | 22810 |
| ATCN_1146 | 12624 | CTCN_4190 | 22811 |
| CTCN_1551 | 12625 | GTCN_2373 | 22812 |
| CTCN_1552 | 12626 | ATCN_2760 | 22813 |
| TTCN_1867 | 12627 | CTCN_4191 | 22814 |
| GTCN_974 | 12628 | TTCN_4425 | 22815 |
| CTCN_1553 | 12629 | CTCN_4192 | 22816 |
| GTCN_975 | 12630 | TTCN_4426 | 22817 |
| ATCN_1147 | 12631 | CTCN_4193 | 22818 |
| CTCN_1554 | 12632 | TTCN_4427 | 22819 |
| GTCN_976 | 12633 | ATCN_2761 | 22820 |
| ATCN_1148 | 12634 | GTCN_2374 | 22821 |
| TTCN_1868 | 12635 | CTCN_4194 | 22822 |
| CTCN_1555 | 12636 | ATCN_2762 | 22823 |

| | | | |
|---|---|---|---|
| CTCN_1556 | 12637 | TTCN_4428 | 22824 |
| CTCN_1557 | 12638 | GTCN_2375 | 22825 |
| ATCN_1149 | 12639 | TTCN_4429 | 22826 |
| ATCN_1150 | 12640 | CTCN_4195 | 22827 |
| CTCN_1558 | 12641 | CTCN_4196 | 22828 |
| GTCN_977 | 12642 | CTCN_4197 | 22829 |
| CTCN_1559 | 12643 | CTCN_4198 | 22830 |
| TTCN_1869 | 12644 | GTCN_2376 | 22831 |
| CTCN_1560 | 12645 | TTCN_4430 | 22832 |
| GTCN_978 | 12646 | TTCN_4431 | 22833 |
| ATCN_1151 | 12647 | ATCN_2763 | 22834 |
| ATCN_1152 | 12648 | CTCN_4199 | 22835 |
| GTCN_979 | 12649 | TTCN_4432 | 22836 |
| CTCN_1561 | 12650 | TTCN_4433 | 22837 |
| TTCN_1870 | 12651 | CTCN_4200 | 22838 |
| CTCN_1562 | 12652 | ATCN_2764 | 22839 |
| TTCN_1871 | 12653 | CTCN_4201 | 22840 |
| CTCN_1563 | 12654 | GTCN_2377 | 22841 |
| ATCN_1153 | 12655 | CTCN_4202 | 22842 |
| TTCN_1872 | 12656 | TTCN_4434 | 22843 |
| TTCN_1873 | 12657 | GTCN_2378 | 22844 |
| TTCN_1874 | 12658 | TTCN_4435 | 22845 |
| TTCN_1875 | 12659 | TTCN_4436 | 22846 |
| GTCN_980 | 12660 | CTCN_4203 | 22847 |
| CTCN_1564 | 12661 | CTCN_4204 | 22848 |
| TTCN_1876 | 12662 | CTCN_4205 | 22849 |
| GTCN_981 | 12663 | TTCN_4437 | 22850 |
| TTCN_1877 | 12664 | TTCN_4438 | 22851 |
| CTCN_1565 | 12665 | ATCN_2765 | 22852 |
| GTCN_982 | 12666 | TTCN_4439 | 22853 |
| CTCN_1566 | 12667 | GTCN_2379 | 22854 |
| TTCN_1878 | 12668 | GTCN_2380 | 22855 |
| GTCN_983 | 12669 | GTCN_2381 | 22856 |
| CTCN_1567 | 12670 | TTCN_4440 | 22857 |
| GTCN_984 | 12671 | ATCN_2766 | 22858 |
| CTCN_1568 | 12672 | TTCN_4441 | 22859 |
| GTCN_985 | 12673 | TTCN_4442 | 22860 |
| GTCN_986 | 12674 | CTCN_4206 | 22861 |
| TTCN_1879 | 12675 | GTCN_2382 | 22862 |
| CTCN_1569 | 12676 | TTCN_4443 | 22863 |
| ATCN_1154 | 12677 | TTCN_4444 | 22864 |
| GTCN_987 | 12678 | ATCN_2767 | 22865 |
| TTCN_1880 | 12679 | CTCN_4207 | 22866 |
| TTCN_1881 | 12680 | GTCN_2383 | 22867 |
| CTCN_1570 | 12681 | CTCN_4208 | 22868 |
| TTCN_1882 | 12682 | GTCN_2384 | 22869 |
| ATCN_1155 | 12683 | TTCN_4445 | 22870 |
| CTCN_1571 | 12684 | TTCN_4446 | 22871 |
| CTCN_1572 | 12685 | ATCN_2768 | 22872 |
| CTCN_1573 | 12686 | TTCN_4447 | 22873 |
| TTCN_1883 | 12687 | TTCN_4448 | 22874 |
| GTCN_988 | 12688 | CTCN_4209 | 22875 |
| CTCN_1574 | 12689 | CTCN_4210 | 22876 |
| GTCN_989 | 12690 | CTCN_4211 | 22877 |
| TTCN_1884 | 12691 | CTCN_4212 | 22878 |

FIG. 36 (continued)

| | | | |
|---|---|---|---|
| TTCN_1885 | 12692 | TTCN_4449 | 22879 |
| TTCN_1886 | 12693 | ATCN_2769 | 22880 |
| GTCN_990 | 12694 | TTCN_4450 | 22881 |
| ATCN_1156 | 12695 | ATCN_2770 | 22882 |
| ATCN_1157 | 12696 | TTCN_4451 | 22883 |
| TTCN_1887 | 12697 | TTCN_4452 | 22884 |
| TTCN_1888 | 12698 | CTCN_4213 | 22885 |
| ATCN_1158 | 12699 | TTCN_4453 | 22886 |
| CTCN_1575 | 12700 | ATCN_2771 | 22887 |
| GTCN_991 | 12701 | TTCN_4454 | 22888 |
| GTCN_992 | 12702 | TTCN_4455 | 22889 |
| ATCN_1159 | 12703 | TTCN_4456 | 22890 |
| ATCN_1160 | 12704 | TTCN_4457 | 22891 |
| ATCN_1161 | 12705 | GTCN_2385 | 22892 |
| GTCN_993 | 12706 | CTCN_4214 | 22893 |
| TTCN_1889 | 12707 | TTCN_4458 | 22894 |
| CTCN_1576 | 12708 | TTCN_4459 | 22895 |
| TTCN_1890 | 12709 | ATCN_2772 | 22896 |
| TTCN_1891 | 12710 | ATCN_2773 | 22897 |
| CTCN_1577 | 12711 | TTCN_4460 | 22898 |
| TTCN_1892 | 12712 | GTCN_2386 | 22899 |
| TTCN_1893 | 12713 | CTCN_4215 | 22900 |
| ATCN_1162 | 12714 | CTCN_4216 | 22901 |
| TTCN_1894 | 12715 | TTCN_4461 | 22902 |
| GTCN_994 | 12716 | GTCN_2387 | 22903 |
| CTCN_1578 | 12717 | CTCN_4217 | 22904 |
| TTCN_1895 | 12718 | ATCN_2774 | 22905 |
| GTCN_995 | 12719 | CTCN_4218 | 22906 |
| GTCN_996 | 12720 | CTCN_4219 | 22907 |
| CTCN_1579 | 12721 | CTCN_4220 | 22908 |
| CTCN_1580 | 12722 | TTCN_4462 | 22909 |
| CTCN_1581 | 12723 | GTCN_2388 | 22910 |
| TTCN_1896 | 12724 | TTCN_4463 | 22911 |
| TTCN_1897 | 12725 | TTCN_4464 | 22912 |
| TTCN_1898 | 12726 | TTCN_4465 | 22913 |
| ATCN_1163 | 12727 | GTCN_2389 | 22914 |
| CTCN_1582 | 12728 | TTCN_4466 | 22915 |
| TTCN_1899 | 12729 | ATCN_2775 | 22916 |
| TTCN_1900 | 12730 | TTCN_4467 | 22917 |
| TTCN_1901 | 12731 | TTCN_4468 | 22918 |
| ATCN_1164 | 12732 | CTCN_4221 | 22919 |
| GTCN_997 | 12733 | ATCN_2776 | 22920 |
| GTCN_998 | 12734 | ATCN_2777 | 22921 |
| CTCN_1583 | 12735 | TTCN_4469 | 22922 |
| TTCN_1902 | 12736 | GTCN_2390 | 22923 |
| TTCN_1903 | 12737 | TTCN_4470 | 22924 |
| ATCN_1165 | 12738 | TTCN_4471 | 22925 |
| TTCN_1904 | 12739 | CTCN_4222 | 22926 |
| GTCN_999 | 12740 | TTCN_4472 | 22927 |
| GTCN_1000 | 12741 | TTCN_4473 | 22928 |
| ATCN_1166 | 12742 | CTCN_4223 | 22929 |
| GTCN_1001 | 12743 | ATCN_2778 | 22930 |
| TTCN_1905 | 12744 | GTCN_2391 | 22931 |
| CTCN_1584 | 12745 | CTCN_4224 | 22932 |
| CTCN_1585 | 12746 | ATCN_2779 | 22933 |

| | | | |
|---|---|---|---|
| TTCN_1906 | 12747 | CTCN_4225 | 22934 |
| ATCN_1167 | 12748 | TTCN_4344 | 22935 |
| TTCN_1907 | 12749 | TTCN_4345 | 22936 |
| CTCN_1586 | 12750 | GTCN_2328 | 22937 |
| ATCN_1168 | 12751 | TTCN_4346 | 22938 |
| TTCN_1908 | 12752 | TTCN_4347 | 22939 |
| CTCN_1587 | 12753 | CTCN_4103 | 22940 |
| TTCN_1909 | 12754 | GTCN_2329 | 22941 |
| GTCN_1002 | 12755 | GTCN_2330 | 22942 |
| ATCN_1169 | 12756 | ATCN_2702 | 22943 |
| CTCN_1588 | 12757 | ATCN_2703 | 22944 |
| CTCN_1589 | 12758 | CTCN_4104 | 22945 |
| GTCN_1003 | 12759 | GTCN_2331 | 22946 |
| TTCN_1910 | 12760 | GTCN_2332 | 22947 |
| GTCN_1004 | 12761 | CTCN_4105 | 22948 |
| GTCN_1005 | 12762 | GTCN_2333 | 22949 |
| GTCN_1006 | 12763 | TTCN_4348 | 22950 |
| CTCN_1590 | 12764 | CTCN_4106 | 22951 |
| GTCN_1007 | 12765 | CTCN_4107 | 22952 |
| GTCN_1008 | 12766 | TTCN_4349 | 22953 |
| CTCN_1591 | 12767 | CTCN_4108 | 22954 |
| CTCN_1592 | 12768 | GTCN_2334 | 22955 |
| GTCN_1009 | 12769 | TTCN_4350 | 22956 |
| CTCN_1593 | 12770 | CTCN_4109 | 22957 |
| GTCN_1010 | 12771 | ATCN_2704 | 22958 |
| GTCN_1011 | 12772 | TTCN_4351 | 22959 |
| TTCN_1911 | 12773 | ATCN_2705 | 22960 |
| TTCN_1912 | 12774 | TTCN_4352 | 22961 |
| TTCN_1913 | 12775 | ATCN_2706 | 22962 |
| TTCN_1914 | 12776 | ATCN_2707 | 22963 |
| CTCN_1594 | 12777 | CTCN_4110 | 22964 |
| GTCN_1012 | 12778 | TTCN_4353 | 22965 |
| GTCN_1013 | 12779 | TTCN_4354 | 22966 |
| ATCN_1170 | 12780 | TTCN_4355 | 22967 |
| GTCN_1014 | 12781 | ATCN_2708 | 22968 |
| TTCN_1915 | 12782 | GTCN_2335 | 22969 |
| TTCN_1916 | 12783 | ATCN_2709 | 22970 |
| GTCN_1015 | 12784 | CTCN_4111 | 22971 |
| TTCN_1917 | 12785 | ATCN_2710 | 22972 |
| CTCN_1595 | 12786 | TTCN_4356 | 22973 |
| CTCN_1596 | 12787 | TTCN_4357 | 22974 |
| ATCN_1171 | 12788 | TTCN_4358 | 22975 |
| ATCN_1172 | 12789 | TTCN_4359 | 22976 |
| TTCN_1918 | 12790 | CTCN_4112 | 22977 |
| TTCN_1919 | 12791 | GTCN_2336 | 22978 |
| ATCN_1173 | 12792 | ATCN_2711 | 22979 |
| CTCN_1597 | 12793 | ATCN_2712 | 22980 |
| CTCN_1598 | 12794 | CTCN_4113 | 22981 |
| ATCN_1174 | 12795 | CTCN_4114 | 22982 |
| CTCN_1599 | 12796 | GTCN_2337 | 22983 |
| CTCN_1600 | 12797 | TTCN_4360 | 22984 |
| CTCN_1601 | 12798 | TTCN_4361 | 22985 |
| TTCN_1920 | 12799 | CTCN_4115 | 22986 |
| TTCN_1921 | 12800 | GTCN_2338 | 22987 |
| GTCN_1016 | 12801 | GTCN_2339 | 22988 |

FIG. 36 (continued)

| | | | |
|---|---|---|---|
| CTCN_1602 | 12802 | ATCN_2713 | 22989 |
| ATCN_1175 | 12803 | TTCN_4362 | 22990 |
| TTCN_1922 | 12804 | CTCN_4116 | 22991 |
| CTCN_1603 | 12805 | GTCN_2340 | 22992 |
| GTCN_1017 | 12806 | TTCN_4363 | 22993 |
| TTCN_1923 | 12807 | ATCN_2714 | 22994 |
| CTCN_1604 | 12808 | ATCN_2715 | 22995 |
| CTCN_1605 | 12809 | TTCN_4364 | 22996 |
| ATCN_1176 | 12810 | CTCN_4117 | 22997 |
| ATCN_1177 | 12811 | TTCN_4365 | 22998 |
| CTCN_1606 | 12812 | GTCN_2341 | 22999 |
| CTCN_1607 | 12813 | GTCN_2342 | 23000 |
| CTCN_1608 | 12814 | CTCN_4118 | 23001 |
| TTCN_1924 | 12815 | ATCN_2716 | 23002 |
| ATCN_1178 | 12816 | TTCN_4366 | 23003 |
| CTCN_1609 | 12817 | TTCN_4367 | 23004 |
| CTCN_1610 | 12818 | ATCN_2717 | 23005 |
| CTCN_1611 | 12819 | ATCN_2718 | 23006 |
| CTCN_1612 | 12820 | CTCN_4119 | 23007 |
| GTCN_1018 | 12821 | ATCN_2719 | 23008 |
| GTCN_1019 | 12822 | TTCN_4368 | 23009 |
| TTCN_1925 | 12823 | TTCN_4369 | 23010 |
| CTCN_1613 | 12824 | ATCN_2720 | 23011 |
| ATCN_1179 | 12825 | TTCN_4370 | 23012 |
| CTCN_1614 | 12826 | TTCN_4371 | 23013 |
| TTCN_1926 | 12827 | GTCN_2343 | 23014 |
| CTCN_1615 | 12828 | TTCN_4372 | 23015 |
| TTCN_1927 | 12829 | ATCN_2721 | 23016 |
| CTCN_1616 | 12830 | ATCN_2722 | 23017 |
| GTCN_1020 | 12831 | TTCN_4373 | 23018 |
| TTCN_1928 | 12832 | CTCN_4120 | 23019 |
| TTCN_1929 | 12833 | ATCN_2723 | 23020 |
| TTCN_1930 | 12834 | TTCN_4374 | 23021 |
| CTCN_1617 | 12835 | ATCN_2724 | 23022 |
| ATCN_1180 | 12836 | TTCN_4375 | 23023 |
| GTCN_1021 | 12837 | TTCN_4376 | 23024 |
| TTCN_1931 | 12838 | ATCN_2725 | 23025 |
| ATCN_1181 | 12839 | CTCN_4121 | 23026 |
| CTCN_1618 | 12840 | TTCN_4377 | 23027 |
| CTCN_1619 | 12841 | TTCN_4378 | 23028 |
| CTCN_1620 | 12842 | CTCN_4122 | 23029 |
| CTCN_1621 | 12843 | ATCN_2726 | 23030 |
| TTCN_1932 | 12844 | ATCN_2727 | 23031 |
| TTCN_1933 | 12845 | ATCN_2728 | 23032 |
| CTCN_1622 | 12846 | CTCN_4123 | 23033 |
| GTCN_1022 | 12847 | CTCN_4124 | 23034 |
| GTCN_0 | 12848 | TTCN_4379 | 23035 |
| TTCN_0 | 12849 | ATCN_2729 | 23036 |
| CTCN_0 | 12850 | TTCN_4380 | 23037 |
| ATCN_0 | 12851 | ATCN_2730 | 23038 |
| ATCN_1 | 12852 | CTCN_4125 | 23039 |
| GTCN_1 | 12853 | CTCN_4126 | 23040 |
| GTCN_2 | 12854 | CTCN_4127 | 23041 |
| CTCN_1 | 12855 | GTCN_2344 | 23042 |
| CTCN_2 | 12856 | ATCN_2731 | 23043 |

| | | | |
|---|---|---|---|
| CTCN_3 | 12857 | TTCN_4381 | 23044 |
| ATCN_2 | 12858 | ATCN_2732 | 23045 |
| TTCN_1 | 12859 | GTCN_2345 | 23046 |
| TTCN_2 | 12860 | ATCN_2733 | 23047 |
| TTCN_3 | 12861 | CTCN_4128 | 23048 |
| ATCN_3 | 12862 | CTCN_4129 | 23049 |
| TTCN_4 | 12863 | GTCN_2346 | 23050 |
| TTCN_5 | 12864 | CTCN_4130 | 23051 |
| ATCN_4 | 12865 | TTCN_4382 | 23052 |
| TTCN_6 | 12866 | CTCN_4131 | 23053 |
| CTCN_4 | 12867 | CTCN_4132 | 23054 |
| CTCN_5 | 12868 | CTCN_4133 | 23055 |
| GTCN_3 | 12869 | GTCN_2347 | 23056 |
| CTCN_6 | 12870 | TTCN_4383 | 23057 |
| GTCN_4 | 12871 | CTCN_4134 | 23058 |
| TTCN_7 | 12872 | GTCN_2348 | 23059 |
| CTCN_7 | 12873 | TTCN_4384 | 23060 |
| ATCN_5 | 12874 | ATCN_2734 | 23061 |
| TTCN_8 | 12875 | CTCN_4135 | 23062 |
| TTCN_9 | 12876 | GTCN_2349 | 23063 |
| GTCN_5 | 12877 | TTCN_4385 | 23064 |
| CTCN_8 | 12878 | CTCN_4136 | 23065 |
| TTCN_10 | 12879 | CTCN_4137 | 23066 |
| GTCN_6 | 12880 | GTCN_2350 | 23067 |
| TTCN_11 | 12881 | CTCN_4138 | 23068 |
| CTCN_9 | 12882 | CTCN_4139 | 23069 |
| TTCN_12 | 12883 | ATCN_2735 | 23070 |
| CTCN_10 | 12884 | ATCN_2736 | 23071 |
| GTCN_7 | 12885 | TTCN_4386 | 23072 |
| TTCN_13 | 12886 | GTCN_2351 | 23073 |
| ATCN_6 | 12887 | CTCN_4140 | 23074 |
| TTCN_14 | 12888 | CTCN_4141 | 23075 |
| ATCN_7 | 12889 | ATCN_2737 | 23076 |
| ATCN_8 | 12890 | TTCN_4387 | 23077 |
| TTCN_15 | 12891 | CTCN_4142 | 23078 |
| GTCN_8 | 12892 | TTCN_4388 | 23079 |
| TTCN_16 | 12893 | CTCN_4143 | 23080 |
| GTCN_9 | 12894 | GTCN_2352 | 23081 |
| TTCN_17 | 12895 | CTCN_4144 | 23082 |
| CTCN_11 | 12896 | TTCN_4389 | 23083 |
| GTCN_10 | 12897 | ATCN_2738 | 23084 |
| GTCN_11 | 12898 | CTCN_4145 | 23085 |
| GTCN_12 | 12899 | GTCN_2353 | 23086 |
| ATCN_9 | 12900 | GTCN_2354 | 23087 |
| ATCN_10 | 12901 | ATCN_2739 | 23088 |
| CTCN_12 | 12902 | GTCN_2355 | 23089 |
| GTCN_13 | 12903 | CTCN_4146 | 23090 |
| CTCN_13 | 12904 | CTCN_4147 | 23091 |
| TTCN_18 | 12905 | CTCN_4148 | 23092 |
| ATCN_11 | 12906 | ATCN_2740 | 23093 |
| TTCN_19 | 12907 | ATCN_2741 | 23094 |
| ATCN_12 | 12908 | CTCN_4149 | 23095 |
| TTCN_20 | 12909 | CTCN_4150 | 23096 |
| CTCN_14 | 12910 | ATCN_2742 | 23097 |
| TTCN_21 | 12911 | CTCN_4151 | 23098 |

FIG. 36 (continued)

| | | | |
|---|---|---|---|
| CTCN_15 | 12912 | CTCN_4152 | 23099 |
| TTCN_22 | 12913 | GTCN_2356 | 23100 |
| CTCN_16 | 12914 | TTCN_4390 | 23101 |
| GTCN_14 | 12915 | GTCN_2357 | 23102 |
| ATCN_13 | 12916 | CTCN_4153 | 23103 |
| CTCN_17 | 12917 | CTCN_4154 | 23104 |
| GTCN_15 | 12918 | TTCN_4391 | 23105 |
| TTCN_23 | 12919 | CTCN_4155 | 23106 |
| ATCN_14 | 12920 | CTCN_4156 | 23107 |
| ATCN_15 | 12921 | TTCN_4392 | 23108 |
| CTCN_18 | 12922 | ATCN_2743 | 23109 |
| CTCN_19 | 12923 | TTCN_4393 | 23110 |
| CTCN_20 | 12924 | TTCN_4394 | 23111 |
| CTCN_21 | 12925 | TTCN_4395 | 23112 |
| CTCN_22 | 12926 | ATCN_2744 | 23113 |
| TTCN_24 | 12927 | TTCN_4396 | 23114 |
| TTCN_25 | 12928 | CTCN_4157 | 23115 |
| TTCN_26 | 12929 | TTCN_4397 | 23116 |
| CTCN_23 | 12930 | CTCN_4158 | 23117 |
| CTCN_24 | 12931 | ATCN_2745 | 23118 |
| CTCN_25 | 12932 | ATCN_2746 | 23119 |
| ATCN_16 | 12933 | GTCN_2358 | 23120 |
| CTCN_26 | 12934 | ATCN_2747 | 23121 |
| TTCN_27 | 12935 | CTCN_4159 | 23122 |
| CTCN_27 | 12936 | GTCN_2359 | 23123 |
| ATCN_17 | 12937 | TTCN_4398 | 23124 |
| TTCN_28 | 12938 | GTCN_2360 | 23125 |
| GTCN_16 | 12939 | CTCN_4160 | 23126 |
| TTCN_29 | 12940 | CTCN_4161 | 23127 |
| GTCN_17 | 12941 | CTCN_4162 | 23128 |
| CTCN_28 | 12942 | GTCN_2361 | 23129 |
| CTCN_29 | 12943 | CTCN_4163 | 23130 |
| GTCN_18 | 12944 | CTCN_4164 | 23131 |
| TTCN_30 | 12945 | CTCN_4165 | 23132 |
| TTCN_31 | 12946 | CTCN_4166 | 23133 |
| CTCN_30 | 12947 | TTCN_4399 | 23134 |
| CTCN_31 | 12948 | CTCN_4167 | 23135 |
| TTCN_32 | 12949 | CTCN_4168 | 23136 |
| GTCN_19 | 12950 | CTCN_4169 | 23137 |
| CTCN_32 | 12951 | ATCN_2748 | 23138 |
| GTCN_20 | 12952 | ATCN_2749 | 23139 |
| ATCN_18 | 12953 | GTCN_2362 | 23140 |
| CTCN_33 | 12954 | CTCN_4170 | 23141 |
| ATCN_19 | 12955 | GTCN_2363 | 23142 |
| TTCN_33 | 12956 | CTCN_4171 | 23143 |
| TTCN_34 | 12957 | GTCN_2364 | 23144 |
| GTCN_21 | 12958 | CTCN_4172 | 23145 |
| TTCN_35 | 12959 | TTCN_4400 | 23146 |
| CTCN_34 | 12960 | TTCN_4401 | 23147 |
| ATCN_20 | 12961 | CTCN_4173 | 23148 |
| TTCN_36 | 12962 | TTCN_4402 | 23149 |
| TTCN_37 | 12963 | TTCN_4403 | 23150 |
| CTCN_35 | 12964 | CTCN_4174 | 23151 |
| GTCN_22 | 12965 | GTCN_2365 | 23152 |
| CTCN_36 | 12966 | CTCN_4175 | 23153 |

| | | | |
|---|---|---|---|
| TTCN_38 | 12967 | CTCN_4176 | 23154 |
| CTCN_37 | 12968 | CTCN_4177 | 23155 |
| TTCN_39 | 12969 | TTCN_4404 | 23156 |
| ATCN_21 | 12970 | TTCN_4405 | 23157 |
| TTCN_40 | 12971 | TTCN_4406 | 23158 |
| CTCN_38 | 12972 | TTCN_4407 | 23159 |
| CTCN_39 | 12973 | TTCN_4408 | 23160 |
| CTCN_40 | 12974 | ATCN_2750 | 23161 |
| TTCN_41 | 12975 | CTCN_4178 | 23162 |
| GTCN_23 | 12976 | TTCN_4409 | 23163 |
| CTCN_41 | 12977 | GTCN_2366 | 23164 |
| TTCN_42 | 12978 | CTCN_4179 | 23165 |
| GTCN_24 | 12979 | CTCN_4180 | 23166 |
| TTCN_43 | 12980 | TTCN_4410 | 23167 |
| CTCN_42 | 12981 | GTCN_2367 | 23168 |
| GTCN_25 | 12982 | TTCN_4411 | 23169 |
| ATCN_22 | 12983 | CTCN_4181 | 23170 |
| TTCN_44 | 12984 | GTCN_2368 | 23171 |
| CTCN_43 | 12985 | ATCN_2751 | 23172 |
| TTCN_45 | 12986 | CTCN_4182 | 23173 |
| TTCN_46 | 12987 | ATCN_2752 | 23174 |
| TTCN_47 | 12988 | CTCN_4183 | 23175 |
| GTCN_26 | 12989 | TTCN_4412 | 23176 |
| TTCN_48 | 12990 | TTCN_4413 | 23177 |
| CTCN_44 | 12991 | TTCN_4414 | 23178 |
| TTCN_49 | 12992 | ATCN_2753 | 23179 |
| CTCN_45 | 12993 | TTCN_4415 | 23180 |
| TTCN_50 | 12994 | ATCN_2754 | 23181 |
| GTCN_27 | 12995 | TTCN_4416 | 23182 |
| TTCN_51 | 12996 | TTCN_4417 | 23183 |
| TTCN_52 | 12997 | CTCN_4184 | 23184 |
| CTCN_46 | 12998 | TTCN_4418 | 23185 |
| GTCN_28 | 12999 | GTCN_2369 | 23186 |
| ATCN_23 | 13000 | ATCN_2755 | 23187 |
| TTCN_53 | 13001 | ATCN_2756 | 23188 |
| GTCN_29 | 13002 | TTCN_4419 | 23189 |
| TTCN_54 | 13003 | TTCN_4420 | 23190 |
| TTCN_55 | 13004 | TTCN_4421 | 23191 |
| TTCN_56 | 13005 | TTCN_4422 | 23192 |
| TTCN_57 | 13006 | ATCN_2757 | 23193 |
| GTCN_30 | 13007 | CTCN_4185 | 23194 |
| CTCN_47 | 13008 | CTCN_4186 | 23195 |
| GTCN_31 | 13009 | GTCN_2370 | 23196 |
| CTCN_48 | 13010 | GTCN_2371 | 23197 |
| CTCN_49 | 13011 | TTCN_4423 | 23198 |
| TTCN_58 | 13012 | CTCN_4187 | 23199 |
| ATCN_24 | 13013 | CTCN_4188 | 23200 |
| GTCN_32 | 13014 | ATCN_2758 | 23201 |
| TTCN_59 | 13015 | ATCN_2759 | 23202 |
| GTCN_33 | 13016 | GTCN_2372 | 23203 |
| TTCN_60 | 13017 | CTCN_4189 | 23204 |
| TTCN_61 | 13018 | TTCN_4424 | 23205 |
| GTCN_34 | 13019 | CTCN_4190 | 23206 |
| GTCN_35 | 13020 | GTCN_2373 | 23207 |
| ATCN_25 | 13021 | ATCN_2760 | 23208 |

FIG. 36 (continued)

| | | | | | | | |
|---|---|---|---|---|---|---|---|
| ATCN_26 | 13022 | CTCN_4191 | 23209 | TTCN_85 | 13077 | GTCN_2384 | 23264 |
| ATCN_27 | 13023 | TTCN_4425 | 23210 | CTCN_61 | 13078 | TTCN_4445 | 23265 |
| ATCN_28 | 13024 | CTCN_4192 | 23211 | GTCN_43 | 13079 | TTCN_4446 | 23266 |
| TTCN_62 | 13025 | TTCN_4426 | 23212 | ATCN_40 | 13080 | ATCN_2768 | 23267 |
| ATCN_29 | 13026 | CTCN_4193 | 23213 | ATCN_41 | 13081 | TTCN_4447 | 23268 |
| ATCN_30 | 13027 | TTCN_4427 | 23214 | TTCN_86 | 13082 | TTCN_4448 | 23269 |
| TTCN_63 | 13028 | ATCN_2761 | 23215 | TTCN_87 | 13083 | CTCN_4209 | 23270 |
| TTCN_64 | 13029 | GTCN_2374 | 23216 | ATCN_42 | 13084 | CTCN_4210 | 23271 |
| TTCN_65 | 13030 | CTCN_4194 | 23217 | TTCN_88 | 13085 | CTCN_4211 | 23272 |
| GTCN_36 | 13031 | ATCN_2762 | 23218 | CTCN_62 | 13086 | CTCN_4212 | 23273 |
| ATCN_31 | 13032 | TTCN_4428 | 23219 | ATCN_43 | 13087 | TTCN_4449 | 23274 |
| GTCN_37 | 13033 | GTCN_2375 | 23220 | ATCN_44 | 13088 | ATCN_2769 | 23275 |
| GTCN_38 | 13034 | TTCN_4429 | 23221 | CTCN_63 | 13089 | TTCN_4450 | 23276 |
| CTCN_50 | 13035 | CTCN_4195 | 23222 | TTCN_89 | 13090 | ATCN_2770 | 23277 |
| ATCN_32 | 13036 | CTCN_4196 | 23223 | CTCN_64 | 13091 | TTCN_4451 | 23278 |
| TTCN_66 | 13037 | CTCN_4197 | 23224 | GTCN_44 | 13092 | TTCN_4452 | 23279 |
| TTCN_67 | 13038 | CTCN_4198 | 23225 | CTCN_65 | 13093 | CTCN_4213 | 23280 |
| TTCN_68 | 13039 | GTCN_2376 | 23226 | TTCN_90 | 13094 | TTCN_4453 | 23281 |
| TTCN_69 | 13040 | TTCN_4430 | 23227 | CTCN_66 | 13095 | ATCN_2771 | 23282 |
| TTCN_70 | 13041 | TTCN_4431 | 23228 | CTCN_67 | 13096 | TTCN_4454 | 23283 |
| ATCN_33 | 13042 | ATCN_2763 | 23229 | CTCN_68 | 13097 | TTCN_4455 | 23284 |
| TTCN_71 | 13043 | CTCN_4199 | 23230 | CTCN_69 | 13098 | TTCN_4456 | 23285 |
| TTCN_72 | 13044 | TTCN_4432 | 23231 | GTCN_45 | 13099 | TTCN_4457 | 23286 |
| ATCN_34 | 13045 | TTCN_4433 | 23232 | CTCN_70 | 13100 | GTCN_2385 | 23287 |
| CTCN_51 | 13046 | CTCN_4200 | 23233 | CTCN_71 | 13101 | CTCN_4214 | 23288 |
| TTCN_73 | 13047 | ATCN_2764 | 23234 | GTCN_46 | 13102 | TTCN_4458 | 23289 |
| ATCN_35 | 13048 | CTCN_4201 | 23235 | TTCN_91 | 13103 | TTCN_4459 | 23290 |
| TTCN_74 | 13049 | GTCN_2377 | 23236 | TTCN_92 | 13104 | ATCN_2772 | 23291 |
| TTCN_75 | 13050 | CTCN_4202 | 23237 | ATCN_45 | 13105 | ATCN_2773 | 23292 |
| ATCN_36 | 13051 | TTCN_4434 | 23238 | TTCN_93 | 13106 | TTCN_4460 | 23293 |
| CTCN_52 | 13052 | GTCN_2378 | 23239 | ATCN_46 | 13107 | GTCN_2386 | 23294 |
| GTCN_39 | 13053 | TTCN_4435 | 23240 | CTCN_72 | 13108 | CTCN_4215 | 23295 |
| ATCN_37 | 13054 | TTCN_4436 | 23241 | TTCN_94 | 13109 | CTCN_4216 | 23296 |
| TTCN_76 | 13055 | CTCN_4203 | 23242 | GTCN_47 | 13110 | TTCN_4461 | 23297 |
| CTCN_53 | 13056 | CTCN_4204 | 23243 | TTCN_95 | 13111 | GTCN_2387 | 23298 |
| TTCN_77 | 13057 | CTCN_4205 | 23244 | TTCN_96 | 13112 | CTCN_4217 | 23299 |
| ATCN_38 | 13058 | TTCN_4437 | 23245 | TTCN_97 | 13113 | ATCN_2774 | 23300 |
| TTCN_78 | 13059 | TTCN_4438 | 23246 | TTCN_98 | 13114 | CTCN_4218 | 23301 |
| CTCN_54 | 13060 | ATCN_2765 | 23247 | CTCN_73 | 13115 | CTCN_4219 | 23302 |
| TTCN_79 | 13061 | TTCN_4439 | 23248 | TTCN_99 | 13116 | CTCN_4220 | 23303 |
| TTCN_80 | 13062 | GTCN_2379 | 23249 | TTCN_100 | 13117 | TTCN_4462 | 23304 |
| TTCN_81 | 13063 | GTCN_2380 | 23250 | ATCN_47 | 13118 | GTCN_2388 | 23305 |
| CTCN_55 | 13064 | GTCN_2381 | 23251 | GTCN_48 | 13119 | TTCN_4463 | 23306 |
| CTCN_56 | 13065 | TTCN_4440 | 23252 | TTCN_101 | 13120 | TTCN_4464 | 23307 |
| GTCN_40 | 13066 | ATCN_2766 | 23253 | TTCN_102 | 13121 | TTCN_4465 | 23308 |
| CTCN_57 | 13067 | TTCN_4441 | 23254 | TTCN_103 | 13122 | GTCN_2389 | 23309 |
| ATCN_39 | 13068 | TTCN_4442 | 23255 | CTCN_74 | 13123 | TTCN_4466 | 23310 |
| CTCN_58 | 13069 | CTCN_4206 | 23256 | TTCN_104 | 13124 | ATCN_2775 | 23311 |
| CTCN_59 | 13070 | GTCN_2382 | 23257 | GTCN_49 | 13125 | TTCN_4467 | 23312 |
| GTCN_41 | 13071 | TTCN_4443 | 23258 | ATCN_48 | 13126 | TTCN_4468 | 23313 |
| TTCN_82 | 13072 | TTCN_4444 | 23259 | CTCN_75 | 13127 | CTCN_4221 | 23314 |
| TTCN_83 | 13073 | ATCN_2767 | 23260 | GTCN_50 | 13128 | ATCN_2776 | 23315 |
| CTCN_60 | 13074 | CTCN_4207 | 23261 | CTCN_76 | 13129 | ATCN_2777 | 23316 |
| TTCN_84 | 13075 | GTCN_2383 | 23262 | GTCN_51 | 13130 | TTCN_4469 | 23317 |
| GTCN_42 | 13076 | CTCN_4208 | 23263 | TTCN_105 | 13131 | GTCN_2390 | 23318 |

FIG. 36 (continued)

| | | | |
|---|---|---|---|
| CTCN_77 | 13132 | TTCN_4470 | 23319 |
| GTCN_52 | 13133 | TTCN_4471 | 23320 |
| TTCN_106 | 13134 | CTCN_4222 | 23321 |
| GTCN_53 | 13135 | TTCN_4472 | 23322 |
| CTCN_78 | 13136 | TTCN_4473 | 23323 |
| TTCN_107 | 13137 | CTCN_4223 | 23324 |
| GTCN_54 | 13138 | ATCN_2778 | 23325 |
| CTCN_79 | 13139 | GTCN_2391 | 23326 |
| CTCN_80 | 13140 | CTCN_4224 | 23327 |
| GTCN_55 | 13141 | ATCN_2779 | 23328 |
| CTCN_81 | 13142 | CTCN_4225 | 23329 |
| CTCN_82 | 13143 | TTCN_4474 | 23330 |
| CTCN_83 | 13144 | CTCN_4226 | 23331 |
| TTCN_108 | 13145 | ATCN_2780 | 23332 |
| ATCN_49 | 13146 | CTCN_4227 | 23333 |
| CTCN_84 | 13147 | CTCN_4228 | 23334 |
| GTCN_56 | 13148 | ATCN_2781 | 23335 |
| CTCN_85 | 13149 | ATCN_2782 | 23336 |
| CTCN_86 | 13150 | CTCN_4229 | 23337 |
| TTCN_109 | 13151 | GTCN_2392 | 23338 |
| ATCN_50 | 13152 | CTCN_4230 | 23339 |
| ATCN_51 | 13153 | TTCN_4475 | 23340 |
| ATCN_52 | 13154 | CTCN_4231 | 23341 |
| TTCN_110 | 13155 | TTCN_4476 | 23342 |
| ATCN_53 | 13156 | ATCN_2783 | 23343 |
| ATCN_54 | 13157 | CTCN_4232 | 23344 |
| CTCN_87 | 13158 | GTCN_2393 | 23345 |
| TTCN_111 | 13159 | CTCN_4233 | 23346 |
| CTCN_88 | 13160 | CTCN_4234 | 23347 |
| TTCN_112 | 13161 | CTCN_4235 | 23348 |
| ATCN_55 | 13162 | TTCN_4477 | 23349 |
| CTCN_89 | 13163 | TTCN_4478 | 23350 |
| CTCN_90 | 13164 | CTCN_4236 | 23351 |
| TTCN_113 | 13165 | CTCN_4237 | 23352 |
| TTCN_114 | 13166 | GTCN_2394 | 23353 |
| GTCN_57 | 13167 | CTCN_4238 | 23354 |
| TTCN_115 | 13168 | GTCN_2395 | 23355 |
| TTCN_116 | 13169 | GTCN_2396 | 23356 |
| ATCN_56 | 13170 | CTCN_4239 | 23357 |
| TTCN_117 | 13171 | GTCN_2397 | 23358 |
| CTCN_91 | 13172 | CTCN_4240 | 23359 |
| ATCN_57 | 13173 | TTCN_4479 | 23360 |
| ATCN_58 | 13174 | TTCN_4480 | 23361 |
| GTCN_58 | 13175 | TTCN_4481 | 23362 |
| ATCN_59 | 13176 | TTCN_4482 | 23363 |
| ATCN_60 | 13177 | TTCN_4483 | 23364 |
| ATCN_61 | 13178 | TTCN_4484 | 23365 |
| TTCN_118 | 13179 | TTCN_4485 | 23366 |
| ATCN_62 | 13180 | ATCN_2784 | 23367 |
| TTCN_119 | 13181 | CTCN_4241 | 23368 |
| CTCN_92 | 13182 | TTCN_4486 | 23369 |
| CTCN_93 | 13183 | TTCN_4487 | 23370 |
| GTCN_59 | 13184 | GTCN_2398 | 23371 |
| ATCN_63 | 13185 | TTCN_4374 | 23372 |
| CTCN_94 | 13186 | ATCN_2724 | 23373 |

| | | | |
|---|---|---|---|
| ATCN_64 | 13187 | TTCN_4375 | 23374 |
| TTCN_120 | 13188 | TTCN_4376 | 23375 |
| ATCN_65 | 13189 | ATCN_2725 | 23376 |
| TTCN_121 | 13190 | CTCN_4121 | 23377 |
| TTCN_122 | 13191 | TTCN_4377 | 23378 |
| GTCN_60 | 13192 | TTCN_4378 | 23379 |
| TTCN_123 | 13193 | CTCN_4122 | 23380 |
| CTCN_95 | 13194 | ATCN_2726 | 23381 |
| CTCN_96 | 13195 | ATCN_2727 | 23382 |
| GTCN_61 | 13196 | ATCN_2728 | 23383 |
| TTCN_124 | 13197 | CTCN_4123 | 23384 |
| ATCN_66 | 13198 | CTCN_4124 | 23385 |
| TTCN_125 | 13199 | TTCN_4379 | 23386 |
| ATCN_67 | 13200 | ATCN_2729 | 23387 |
| TTCN_126 | 13201 | TTCN_4380 | 23388 |
| TTCN_127 | 13202 | ATCN_2730 | 23389 |
| GTCN_62 | 13203 | CTCN_4125 | 23390 |
| CTCN_97 | 13204 | CTCN_4126 | 23391 |
| TTCN_128 | 13205 | CTCN_4127 | 23392 |
| CTCN_98 | 13206 | GTCN_2344 | 23393 |
| TTCN_129 | 13207 | ATCN_2731 | 23394 |
| CTCN_99 | 13208 | TTCN_4381 | 23395 |
| GTCN_63 | 13209 | ATCN_2732 | 23396 |
| TTCN_130 | 13210 | GTCN_2345 | 23397 |
| TTCN_131 | 13211 | ATCN_2733 | 23398 |
| TTCN_132 | 13212 | CTCN_4128 | 23399 |
| GTCN_64 | 13213 | CTCN_4129 | 23400 |
| ATCN_68 | 13214 | GTCN_2346 | 23401 |
| ATCN_69 | 13215 | CTCN_4130 | 23402 |
| TTCN_133 | 13216 | TTCN_4382 | 23403 |
| ATCN_70 | 13217 | CTCN_4131 | 23404 |
| CTCN_100 | 13218 | CTCN_4132 | 23405 |
| GTCN_65 | 13219 | CTCN_4133 | 23406 |
| CTCN_101 | 13220 | GTCN_2347 | 23407 |
| TTCN_134 | 13221 | TTCN_4383 | 23408 |
| ATCN_71 | 13222 | CTCN_4134 | 23409 |
| TTCN_135 | 13223 | GTCN_2348 | 23410 |
| ATCN_72 | 13224 | TTCN_4384 | 23411 |
| GTCN_66 | 13225 | ATCN_2734 | 23412 |
| GTCN_67 | 13226 | CTCN_4135 | 23413 |
| ATCN_73 | 13227 | GTCN_2349 | 23414 |
| ATCN_74 | 13228 | TTCN_4385 | 23415 |
| TTCN_136 | 13229 | CTCN_4136 | 23416 |
| ATCN_75 | 13230 | CTCN_4137 | 23417 |
| CTCN_102 | 13231 | GTCN_2350 | 23418 |
| TTCN_137 | 13232 | CTCN_4138 | 23419 |
| TTCN_138 | 13233 | CTCN_4139 | 23420 |
| GTCN_68 | 13234 | ATCN_2735 | 23421 |
| TTCN_139 | 13235 | ATCN_2736 | 23422 |
| GTCN_69 | 13236 | TTCN_4386 | 23423 |
| TTCN_140 | 13237 | GTCN_2351 | 23424 |
| ATCN_76 | 13238 | CTCN_4140 | 23425 |
| CTCN_103 | 13239 | CTCN_4141 | 23426 |
| TTCN_141 | 13240 | ATCN_2737 | 23427 |
| ATCN_77 | 13241 | TTCN_4387 | 23428 |

FIG. 36 (continued)

| | | | |
|---|---|---|---|
| GTCN_70 | 13242 | CTCN_4142 | 23429 |
| GTCN_71 | 13243 | TTCN_4388 | 23430 |
| GTCN_72 | 13244 | CTCN_4143 | 23431 |
| CTCN_104 | 13245 | GTCN_2352 | 23432 |
| GTCN_73 | 13246 | CTCN_4144 | 23433 |
| TTCN_142 | 13247 | TTCN_4389 | 23434 |
| ATCN_78 | 13248 | ATCN_2738 | 23435 |
| GTCN_74 | 13249 | CTCN_4145 | 23436 |
| TTCN_143 | 13250 | GTCN_2353 | 23437 |
| TTCN_144 | 13251 | GTCN_2354 | 23438 |
| CTCN_105 | 13252 | ATCN_2739 | 23439 |
| TTCN_145 | 13253 | GTCN_2355 | 23440 |
| TTCN_146 | 13254 | CTCN_4146 | 23441 |
| GTCN_75 | 13255 | CTCN_4147 | 23442 |
| GTCN_76 | 13256 | CTCN_4148 | 23443 |
| GTCN_77 | 13257 | ATCN_2740 | 23444 |
| CTCN_106 | 13258 | ATCN_2741 | 23445 |
| ATCN_79 | 13259 | CTCN_4149 | 23446 |
| ATCN_80 | 13260 | CTCN_4150 | 23447 |
| ATCN_81 | 13261 | ATCN_2742 | 23448 |
| ATCN_82 | 13262 | CTCN_4151 | 23449 |
| CTCN_107 | 13263 | CTCN_4152 | 23450 |
| CTCN_108 | 13264 | GTCN_2356 | 23451 |
| TTCN_147 | 13265 | TTCN_4390 | 23452 |
| CTCN_109 | 13266 | GTCN_2357 | 23453 |
| GTCN_1022 | 13267 | CTCN_4153 | 23454 |
| TTCN_1934 | 13268 | CTCN_4154 | 23455 |
| CTCN_1623 | 13269 | TTCN_4391 | 23456 |
| ATCN_1182 | 13270 | CTCN_4155 | 23457 |
| GTCN_1023 | 13271 | CTCN_4156 | 23458 |
| TTCN_1935 | 13272 | TTCN_4392 | 23459 |
| CTCN_1624 | 13273 | ATCN_2743 | 23460 |
| ATCN_1183 | 13274 | TTCN_4393 | 23461 |
| TTCN_1936 | 13275 | TTCN_4394 | 23462 |
| GTCN_1024 | 13276 | TTCN_4395 | 23463 |
| CTCN_1625 | 13277 | ATCN_2744 | 23464 |
| ATCN_1184 | 13278 | TTCN_4396 | 23465 |
| ATCN_1185 | 13279 | CTCN_4157 | 23466 |
| TTCN_1937 | 13280 | TTCN_4397 | 23467 |
| CTCN_1626 | 13281 | CTCN_4158 | 23468 |
| TTCN_1938 | 13282 | ATCN_2745 | 23469 |
| GTCN_1025 | 13283 | ATCN_2746 | 23470 |
| ATCN_1186 | 13284 | GTCN_2358 | 23471 |
| TTCN_1939 | 13285 | ATCN_2747 | 23472 |
| TTCN_1940 | 13286 | CTCN_4159 | 23473 |
| TTCN_1941 | 13287 | GTCN_2359 | 23474 |
| TTCN_1942 | 13288 | TTCN_4398 | 23475 |
| GTCN_1026 | 13289 | GTCN_2360 | 23476 |
| CTCN_1627 | 13290 | CTCN_4160 | 23477 |
| CTCN_1628 | 13291 | CTCN_4161 | 23478 |
| TTCN_1943 | 13292 | CTCN_4162 | 23479 |
| GTCN_1027 | 13293 | GTCN_2361 | 23480 |
| CTCN_1629 | 13294 | CTCN_4163 | 23481 |
| GTCN_1028 | 13295 | CTCN_4164 | 23482 |
| GTCN_1029 | 13296 | CTCN_4165 | 23483 |

| | | | |
|---|---|---|---|
| ATCN_1187 | 13297 | CTCN_4166 | 23484 |
| GTCN_1030 | 13298 | TTCN_4399 | 23485 |
| TTCN_1944 | 13299 | CTCN_4167 | 23486 |
| TTCN_1945 | 13300 | CTCN_4168 | 23487 |
| ATCN_1188 | 13301 | CTCN_4169 | 23488 |
| TTCN_1946 | 13302 | ATCN_2748 | 23489 |
| GTCN_1031 | 13303 | ATCN_2749 | 23490 |
| TTCN_1947 | 13304 | GTCN_2362 | 23491 |
| ATCN_1189 | 13305 | CTCN_4170 | 23492 |
| TTCN_1948 | 13306 | GTCN_2363 | 23493 |
| CTCN_1630 | 13307 | CTCN_4171 | 23494 |
| CTCN_1631 | 13308 | GTCN_2364 | 23495 |
| GTCN_1032 | 13309 | CTCN_4172 | 23496 |
| GTCN_1033 | 13310 | TTCN_4400 | 23497 |
| TTCN_1949 | 13311 | TTCN_4401 | 23498 |
| TTCN_1950 | 13312 | CTCN_4173 | 23499 |
| TTCN_1951 | 13313 | TTCN_4402 | 23500 |
| CTCN_1632 | 13314 | TTCN_4403 | 23501 |
| GTCN_1034 | 13315 | CTCN_4174 | 23502 |
| GTCN_1035 | 13316 | GTCN_2365 | 23503 |
| TTCN_1952 | 13317 | CTCN_4175 | 23504 |
| TTCN_1953 | 13318 | CTCN_4176 | 23505 |
| ATCN_1190 | 13319 | CTCN_4177 | 23506 |
| GTCN_1036 | 13320 | TTCN_4404 | 23507 |
| TTCN_1954 | 13321 | TTCN_4405 | 23508 |
| GTCN_1037 | 13322 | TTCN_4406 | 23509 |
| CTCN_1633 | 13323 | TTCN_4407 | 23510 |
| TTCN_1955 | 13324 | TTCN_4408 | 23511 |
| ATCN_1191 | 13325 | ATCN_2750 | 23512 |
| TTCN_1956 | 13326 | CTCN_4178 | 23513 |
| TTCN_1957 | 13327 | TTCN_4409 | 23514 |
| TTCN_1958 | 13328 | GTCN_2366 | 23515 |
| GTCN_1038 | 13329 | CTCN_4179 | 23516 |
| ATCN_1192 | 13330 | CTCN_4180 | 23517 |
| TTCN_1959 | 13331 | TTCN_4410 | 23518 |
| CTCN_1634 | 13332 | GTCN_2367 | 23519 |
| TTCN_1960 | 13333 | TTCN_4411 | 23520 |
| TTCN_1961 | 13334 | CTCN_4181 | 23521 |
| ATCN_1193 | 13335 | GTCN_2368 | 23522 |
| GTCN_1039 | 13336 | ATCN_2751 | 23523 |
| TTCN_1962 | 13337 | CTCN_4182 | 23524 |
| GTCN_1040 | 13338 | ATCN_2752 | 23525 |
| TTCN_1963 | 13339 | CTCN_4183 | 23526 |
| ATCN_1194 | 13340 | TTCN_4412 | 23527 |
| GTCN_1041 | 13341 | TTCN_4413 | 23528 |
| TTCN_1964 | 13342 | TTCN_4414 | 23529 |
| ATCN_1195 | 13343 | ATCN_2753 | 23530 |
| TTCN_1965 | 13344 | TTCN_4415 | 23531 |
| ATCN_1196 | 13345 | ATCN_2754 | 23532 |
| TTCN_1966 | 13346 | TTCN_4416 | 23533 |
| TTCN_1967 | 13347 | TTCN_4417 | 23534 |
| ATCN_1197 | 13348 | CTCN_4184 | 23535 |
| ATCN_1198 | 13349 | TTCN_4418 | 23536 |
| TTCN_1968 | 13350 | GTCN_2369 | 23537 |
| TTCN_1969 | 13351 | ATCN_2755 | 23538 |

FIG. 36 (continued)

| | | | |
|---|---|---|---|
| CTCN_1635 | 13352 | ATCN_2756 | 23539 |
| ATCN_1199 | 13353 | TTCN_4419 | 23540 |
| ATCN_1200 | 13354 | TTCN_4420 | 23541 |
| ATCN_1201 | 13355 | TTCN_4421 | 23542 |
| ATCN_1202 | 13356 | TTCN_4422 | 23543 |
| GTCN_1042 | 13357 | ATCN_2757 | 23544 |
| GTCN_1043 | 13358 | CTCN_4185 | 23545 |
| TTCN_1970 | 13359 | CTCN_4186 | 23546 |
| GTCN_1044 | 13360 | GTCN_2370 | 23547 |
| GTCN_1045 | 13361 | GTCN_2371 | 23548 |
| GTCN_1046 | 13362 | TTCN_4423 | 23549 |
| ATCN_1203 | 13363 | CTCN_4187 | 23550 |
| ATCN_1204 | 13364 | CTCN_4188 | 23551 |
| CTCN_1636 | 13365 | ATCN_2758 | 23552 |
| CTCN_1637 | 13366 | ATCN_2759 | 23553 |
| ATCN_1205 | 13367 | GTCN_2372 | 23554 |
| TTCN_1971 | 13368 | CTCN_4189 | 23555 |
| TTCN_1972 | 13369 | TTCN_4424 | 23556 |
| TTCN_1973 | 13370 | CTCN_4190 | 23557 |
| GTCN_1047 | 13371 | GTCN_2373 | 23558 |
| CTCN_1638 | 13372 | ATCN_2760 | 23559 |
| GTCN_1048 | 13373 | CTCN_4191 | 23560 |
| TTCN_1974 | 13374 | TTCN_4425 | 23561 |
| TTCN_1975 | 13375 | CTCN_4192 | 23562 |
| TTCN_1976 | 13376 | TTCN_4426 | 23563 |
| TTCN_1977 | 13377 | CTCN_4193 | 23564 |
| GTCN_1049 | 13378 | TTCN_4427 | 23565 |
| TTCN_1978 | 13379 | ATCN_2761 | 23566 |
| GTCN_1050 | 13380 | GTCN_2374 | 23567 |
| ATCN_1206 | 13381 | CTCN_4194 | 23568 |
| ATCN_1207 | 13382 | ATCN_2762 | 23569 |
| ATCN_1208 | 13383 | TTCN_4428 | 23570 |
| CTCN_1639 | 13384 | GTCN_2375 | 23571 |
| ATCN_1209 | 13385 | TTCN_4429 | 23572 |
| GTCN_1051 | 13386 | CTCN_4195 | 23573 |
| GTCN_1052 | 13387 | CTCN_4196 | 23574 |
| TTCN_1979 | 13388 | CTCN_4197 | 23575 |
| CTCN_1640 | 13389 | CTCN_4198 | 23576 |
| CTCN_1641 | 13390 | GTCN_2376 | 23577 |
| CTCN_1642 | 13391 | TTCN_4430 | 23578 |
| ATCN_1210 | 13392 | TTCN_4431 | 23579 |
| ATCN_1211 | 13393 | ATCN_2763 | 23580 |
| CTCN_1643 | 13394 | CTCN_4199 | 23581 |
| ATCN_1212 | 13395 | TTCN_4432 | 23582 |
| GTCN_1053 | 13396 | TTCN_4433 | 23583 |
| GTCN_1054 | 13397 | CTCN_4200 | 23584 |
| CTCN_1644 | 13398 | ATCN_2764 | 23585 |
| ATCN_1213 | 13399 | CTCN_4201 | 23586 |
| GTCN_1055 | 13400 | GTCN_2377 | 23587 |
| GTCN_1056 | 13401 | CTCN_4202 | 23588 |
| ATCN_1214 | 13402 | TTCN_4434 | 23589 |
| GTCN_1057 | 13403 | GTCN_2378 | 23590 |
| TTCN_1980 | 13404 | TTCN_4435 | 23591 |
| TTCN_1981 | 13405 | TTCN_4436 | 23592 |
| CTCN_1645 | 13406 | CTCN_4203 | 23593 |

| | | | |
|---|---|---|---|
| TTCN_1982 | 13407 | CTCN_4204 | 23594 |
| TTCN_1983 | 13408 | CTCN_4205 | 23595 |
| TTCN_1984 | 13409 | TTCN_4437 | 23596 |
| TTCN_1985 | 13410 | TTCN_4438 | 23597 |
| TTCN_1986 | 13411 | ATCN_2765 | 23598 |
| CTCN_1646 | 13412 | TTCN_4439 | 23599 |
| CTCN_1647 | 13413 | GTCN_2379 | 23600 |
| ATCN_1215 | 13414 | GTCN_2380 | 23601 |
| ATCN_1216 | 13415 | GTCN_2381 | 23602 |
| CTCN_1648 | 13416 | TTCN_4440 | 23603 |
| CTCN_1649 | 13417 | ATCN_2766 | 23604 |
| CTCN_1650 | 13418 | TTCN_4441 | 23605 |
| CTCN_1651 | 13419 | TTCN_4442 | 23606 |
| TTCN_1987 | 13420 | CTCN_4206 | 23607 |
| ATCN_1217 | 13421 | GTCN_2382 | 23608 |
| TTCN_1988 | 13422 | TTCN_4443 | 23609 |
| CTCN_1652 | 13423 | TTCN_4444 | 23610 |
| GTCN_1058 | 13424 | ATCN_2767 | 23611 |
| CTCN_1653 | 13425 | CTCN_4207 | 23612 |
| CTCN_1654 | 13426 | GTCN_2383 | 23613 |
| CTCN_1655 | 13427 | CTCN_4208 | 23614 |
| ATCN_1218 | 13428 | GTCN_2384 | 23615 |
| TTCN_1989 | 13429 | TTCN_4445 | 23616 |
| TTCN_1990 | 13430 | TTCN_4446 | 23617 |
| GTCN_1059 | 13431 | ATCN_2768 | 23618 |
| TTCN_1991 | 13432 | TTCN_4447 | 23619 |
| CTCN_1656 | 13433 | TTCN_4448 | 23620 |
| GTCN_1060 | 13434 | CTCN_4209 | 23621 |
| CTCN_1657 | 13435 | CTCN_4210 | 23622 |
| ATCN_1219 | 13436 | CTCN_4211 | 23623 |
| ATCN_1220 | 13437 | CTCN_4212 | 23624 |
| CTCN_1658 | 13438 | TTCN_4449 | 23625 |
| ATCN_1221 | 13439 | ATCN_2769 | 23626 |
| TTCN_1992 | 13440 | TTCN_4450 | 23627 |
| TTCN_1993 | 13441 | ATCN_2770 | 23628 |
| TTCN_1994 | 13442 | TTCN_4451 | 23629 |
| CTCN_1659 | 13443 | TTCN_4452 | 23630 |
| CTCN_1660 | 13444 | CTCN_4213 | 23631 |
| CTCN_1661 | 13445 | TTCN_4453 | 23632 |
| CTCN_1662 | 13446 | ATCN_2771 | 23633 |
| TTCN_1995 | 13447 | TTCN_4454 | 23634 |
| TTCN_1996 | 13448 | TTCN_4455 | 23635 |
| ATCN_1222 | 13449 | TTCN_4456 | 23636 |
| TTCN_1997 | 13450 | TTCN_4457 | 23637 |
| TTCN_1998 | 13451 | GTCN_2385 | 23638 |
| CTCN_1663 | 13452 | CTCN_4214 | 23639 |
| ATCN_1223 | 13453 | TTCN_4458 | 23640 |
| TTCN_1999 | 13454 | TTCN_4459 | 23641 |
| TTCN_2000 | 13455 | ATCN_2772 | 23642 |
| CTCN_1664 | 13456 | ATCN_2773 | 23643 |
| GTCN_1061 | 13457 | TTCN_4460 | 23644 |
| ATCN_1224 | 13458 | GTCN_2386 | 23645 |
| GTCN_1062 | 13459 | CTCN_4215 | 23646 |
| CTCN_1665 | 13460 | CTCN_4216 | 23647 |
| ATCN_1225 | 13461 | TTCN_4461 | 23648 |

FIG. 36 (continued)

| | | | |
|---|---|---|---|
| ATCN_1226 | 13462 | GTCN_2387 | 23649 |
| TTCN_2001 | 13463 | CTCN_4217 | 23650 |
| CTCN_1666 | 13464 | ATCN_2774 | 23651 |
| ATCN_1227 | 13465 | CTCN_4218 | 23652 |
| TTCN_2002 | 13466 | CTCN_4219 | 23653 |
| TTCN_2003 | 13467 | CTCN_4220 | 23654 |
| TTCN_2004 | 13468 | TTCN_4462 | 23655 |
| TTCN_2005 | 13469 | GTCN_2388 | 23656 |
| CTCN_1667 | 13470 | TTCN_4463 | 23657 |
| TTCN_2006 | 13471 | TTCN_4464 | 23658 |
| TTCN_2007 | 13472 | TTCN_4465 | 23659 |
| TTCN_2008 | 13473 | GTCN_2389 | 23660 |
| TTCN_2009 | 13474 | TTCN_4466 | 23661 |
| CTCN_1668 | 13475 | ATCN_2775 | 23662 |
| CTCN_1669 | 13476 | TTCN_4467 | 23663 |
| GTCN_1063 | 13477 | TTCN_4468 | 23664 |
| ATCN_1228 | 13478 | CTCN_4221 | 23665 |
| GTCN_1064 | 13479 | ATCN_2776 | 23666 |
| ATCN_1229 | 13480 | ATCN_2777 | 23667 |
| GTCN_1065 | 13481 | TTCN_4469 | 23668 |
| TTCN_2010 | 13482 | GTCN_2390 | 23669 |
| ATCN_1230 | 13483 | TTCN_4470 | 23670 |
| ATCN_1231 | 13484 | TTCN_4471 | 23671 |
| CTCN_1670 | 13485 | CTCN_4222 | 23672 |
| ATCN_1232 | 13486 | TTCN_4472 | 23673 |
| CTCN_1671 | 13487 | TTCN_4473 | 23674 |
| TTCN_2011 | 13488 | CTCN_4223 | 23675 |
| TTCN_2012 | 13489 | ATCN_2778 | 23676 |
| CTCN_1672 | 13490 | GTCN_2391 | 23677 |
| GTCN_1066 | 13491 | CTCN_4224 | 23678 |
| GTCN_1067 | 13492 | ATCN_2779 | 23679 |
| GTCN_1068 | 13493 | CTCN_4225 | 23680 |
| CTCN_1673 | 13494 | TTCN_4474 | 23681 |
| ATCN_1233 | 13495 | CTCN_4226 | 23682 |
| ATCN_1234 | 13496 | ATCN_2780 | 23683 |
| TTCN_2013 | 13497 | CTCN_4227 | 23684 |
| GTCN_1069 | 13498 | CTCN_4228 | 23685 |
| TTCN_2014 | 13499 | ATCN_2781 | 23686 |
| GTCN_1070 | 13500 | ATCN_2782 | 23687 |
| ATCN_1235 | 13501 | CTCN_4229 | 23688 |
| ATCN_1236 | 13502 | GTCN_2392 | 23689 |
| ATCN_1237 | 13503 | CTCN_4230 | 23690 |
| GTCN_1071 | 13504 | TTCN_4475 | 23691 |
| GTCN_1072 | 13505 | CTCN_4231 | 23692 |
| CTCN_1674 | 13506 | TTCN_4476 | 23693 |
| CTCN_1675 | 13507 | ATCN_2783 | 23694 |
| ATCN_1238 | 13508 | CTCN_4232 | 23695 |
| GTCN_1073 | 13509 | GTCN_2393 | 23696 |
| CTCN_1676 | 13510 | CTCN_4233 | 23697 |
| CTCN_1677 | 13511 | CTCN_4234 | 23698 |
| CTCN_1678 | 13512 | CTCN_4235 | 23699 |
| GTCN_1074 | 13513 | TTCN_4477 | 23700 |
| TTCN_2015 | 13514 | TTCN_4478 | 23701 |
| ATCN_1239 | 13515 | CTCN_4236 | 23702 |
| TTCN_2016 | 13516 | CTCN_4237 | 23703 |

| | | | |
|---|---|---|---|
| GTCN_1075 | 13517 | GTCN_2394 | 23704 |
| CTCN_1679 | 13518 | CTCN_4238 | 23705 |
| GTCN_1076 | 13519 | GTCN_2395 | 23706 |
| CTCN_1680 | 13520 | GTCN_2396 | 23707 |
| GTCN_1077 | 13521 | CTCN_4239 | 23708 |
| CTCN_1681 | 13522 | GTCN_2397 | 23709 |
| CTCN_1682 | 13523 | CTCN_4240 | 23710 |
| CTCN_1683 | 13524 | TTCN_4479 | 23711 |
| TTCN_2017 | 13525 | TTCN_4480 | 23712 |
| GTCN_1078 | 13526 | TTCN_4481 | 23713 |
| CTCN_1684 | 13527 | TTCN_4482 | 23714 |
| GTCN_1079 | 13528 | TTCN_4483 | 23715 |
| TTCN_2018 | 13529 | TTCN_4484 | 23716 |
| TTCN_2019 | 13530 | TTCN_4485 | 23717 |
| TTCN_2020 | 13531 | ATCN_2784 | 23718 |
| CTCN_1685 | 13532 | CTCN_4241 | 23719 |
| CTCN_1686 | 13533 | TTCN_4486 | 23720 |
| CTCN_1687 | 13534 | TTCN_4487 | 23721 |
| CTCN_1688 | 13535 | GTCN_2398 | 23722 |
| TTCN_2021 | 13536 | ATCN_2785 | 23723 |
| ATCN_1240 | 13537 | TTCN_4488 | 23724 |
| TTCN_2022 | 13538 | TTCN_4489 | 23725 |
| CTCN_1689 | 13539 | ATCN_2786 | 23726 |
| ATCN_1241 | 13540 | ATCN_2787 | 23727 |
| CTCN_1690 | 13541 | TTCN_4490 | 23728 |
| TTCN_2023 | 13542 | ATCN_2788 | 23729 |
| CTCN_1691 | 13543 | TTCN_4491 | 23730 |
| TTCN_2024 | 13544 | GTCN_2399 | 23731 |
| TTCN_2025 | 13545 | TTCN_4492 | 23732 |
| CTCN_1692 | 13546 | CTCN_4242 | 23733 |
| TTCN_2026 | 13547 | CTCN_4243 | 23734 |
| CTCN_1693 | 13548 | TTCN_4493 | 23735 |
| TTCN_2027 | 13549 | TTCN_4494 | 23736 |
| TTCN_2028 | 13550 | GTCN_2400 | 23737 |
| GTCN_1080 | 13551 | CTCN_4244 | 23738 |
| GTCN_1081 | 13552 | GTCN_2401 | 23739 |
| TTCN_2029 | 13553 | TTCN_4495 | 23740 |
| TTCN_2030 | 13554 | ATCN_2789 | 23741 |
| GTCN_1082 | 13555 | ATCN_2790 | 23742 |
| CTCN_1694 | 13556 | ATCN_2791 | 23743 |
| CTCN_1695 | 13557 | ATCN_2792 | 23744 |
| GTCN_1083 | 13558 | ATCN_2793 | 23745 |
| ATCN_1242 | 13559 | TTCN_4496 | 23746 |
| CTCN_1696 | 13560 | CTCN_4245 | 23747 |
| GTCN_1084 | 13561 | TTCN_4497 | 23748 |
| CTCN_1697 | 13562 | CTCN_4246 | 23749 |
| CTCN_1698 | 13563 | GTCN_2402 | 23750 |
| ATCN_1243 | 13564 | CTCN_4247 | 23751 |
| CTCN_1699 | 13565 | CTCN_4248 | 23752 |
| CTCN_1700 | 13566 | TTCN_4498 | 23753 |
| GTCN_1085 | 13567 | CTCN_4249 | 23754 |
| CTCN_1701 | 13568 | CTCN_4250 | 23755 |
| GTCN_1086 | 13569 | CTCN_4251 | 23756 |
| CTCN_1702 | 13570 | TTCN_4499 | 23757 |
| TTCN_2031 | 13571 | ATCN_2794 | 23758 |

FIG. 36 (continued)

| | | | |
|---|---|---|---|
| ATCN_1244 | 13572 | TTCN_4500 | 23759 |
| GTCN_1087 | 13573 | CTCN_4252 | 23760 |
| GTCN_1088 | 13574 | CTCN_4253 | 23761 |
| GTCN_1089 | 13575 | CTCN_4254 | 23762 |
| CTCN_1703 | 13576 | ATCN_2795 | 23763 |
| TTCN_2032 | 13577 | GTCN_2403 | 23764 |
| TTCN_2033 | 13578 | CTCN_4255 | 23765 |
| ATCN_1245 | 13579 | GTCN_2404 | 23766 |
| GTCN_1090 | 13580 | CTCN_4256 | 23767 |
| GTCN_1091 | 13581 | TTCN_4501 | 23768 |
| CTCN_1704 | 13582 | GTCN_2405 | 23769 |
| TTCN_2034 | 13583 | CTCN_4257 | 23770 |
| TTCN_2035 | 13584 | CTCN_4258 | 23771 |
| GTCN_1092 | 13585 | GTCN_2406 | 23772 |
| GTCN_1093 | 13586 | CTCN_4259 | 23773 |
| CTCN_1705 | 13587 | ATCN_2796 | 23774 |
| ATCN_1246 | 13588 | ATCN_2797 | 23775 |
| CTCN_1706 | 13589 | CTCN_4260 | 23776 |
| CTCN_1707 | 13590 | CTCN_4261 | 23777 |
| CTCN_1708 | 13591 | ATCN_2798 | 23778 |
| TTCN_2036 | 13592 | ATCN_2799 | 23779 |
| GTCN_1094 | 13593 | CTCN_4262 | 23780 |
| TTCN_2037 | 13594 | ATCN_2800 | 23781 |
| CTCN_1709 | 13595 | CTCN_4263 | 23782 |
| ATCN_1247 | 13596 | CTCN_4264 | 23783 |
| TTCN_2038 | 13597 | CTCN_4265 | 23784 |
| CTCN_1710 | 13598 | TTCN_4502 | 23785 |
| GTCN_1095 | 13599 | TTCN_4503 | 23786 |
| GTCN_1096 | 13600 | CTCN_4266 | 23787 |
| ATCN_1248 | 13601 | ATCN_2801 | 23788 |
| TTCN_2039 | 13602 | CTCN_4267 | 23789 |
| GTCN_1097 | 13603 | TTCN_4504 | 23790 |
| TTCN_2040 | 13604 | ATCN_2802 | 23791 |
| GTCN_1098 | 13605 | CTCN_4268 | 23792 |
| TTCN_2041 | 13606 | TTCN_4505 | 23793 |
| ATCN_1249 | 13607 | TTCN_4506 | 23794 |
| TTCN_2042 | 13608 | TTCN_4507 | 23795 |
| GTCN_1099 | 13609 | ATCN_2803 | 23796 |
| TTCN_2043 | 13610 | TTCN_4508 | 23797 |
| GTCN_1100 | 13611 | TTCN_4509 | 23798 |
| ATCN_1250 | 13612 | CTCN_4269 | 23799 |
| CTCN_1711 | 13613 | CTCN_4270 | 23800 |
| ATCN_1251 | 13614 | ATCN_2804 | 23801 |
| ATCN_1252 | 13615 | TTCN_4510 | 23802 |
| GTCN_1101 | 13616 | TTCN_4511 | 23803 |
| TTCN_2044 | 13617 | TTCN_4512 | 23804 |
| TTCN_2045 | 13618 | TTCN_4513 | 23805 |
| CTCN_1712 | 13619 | GTCN_2407 | 23806 |
| ATCN_1253 | 13620 | CTCN_4271 | 23807 |
| GTCN_1102 | 13621 | TTCN_4514 | 23808 |
| CTCN_1713 | 13622 | CTCN_4272 | 23809 |
| TTCN_2046 | 13623 | CTCN_4273 | 23810 |
| ATCN_1254 | 13624 | GTCN_2408 | 23811 |
| CTCN_1714 | 13625 | TTCN_4515 | 23812 |
| TTCN_2047 | 13626 | ATCN_2805 | 23813 |

| | | | |
|---|---|---|---|
| GTCN_1103 | 13627 | ATCN_2806 | 23814 |
| TTCN_2048 | 13628 | TTCN_4516 | 23815 |
| CTCN_1715 | 13629 | ATCN_2807 | 23816 |
| TTCN_2049 | 13630 | CTCN_4274 | 23817 |
| ATCN_1255 | 13631 | CTCN_4275 | 23818 |
| TTCN_2050 | 13632 | TTCN_4517 | 23819 |
| CTCN_1716 | 13633 | GTCN_2409 | 23820 |
| TTCN_2051 | 13634 | TTCN_4518 | 23821 |
| TTCN_2052 | 13635 | ATCN_2808 | 23822 |
| TTCN_2053 | 13636 | TTCN_4519 | 23823 |
| TTCN_2054 | 13637 | TTCN_4520 | 23824 |
| GTCN_1104 | 13638 | CTCN_4276 | 23825 |
| TTCN_2055 | 13639 | CTCN_4277 | 23826 |
| ATCN_1256 | 13640 | TTCN_4521 | 23827 |
| CTCN_1717 | 13641 | TTCN_4522 | 23828 |
| CTCN_1718 | 13642 | CTCN_4278 | 23829 |
| GTCN_1105 | 13643 | TTCN_4523 | 23830 |
| GTCN_1106 | 13644 | CTCN_4279 | 23831 |
| TTCN_2056 | 13645 | CTCN_4280 | 23832 |
| TTCN_2057 | 13646 | CTCN_4281 | 23833 |
| TTCN_2058 | 13647 | GTCN_2410 | 23834 |
| CTCN_1719 | 13648 | TTCN_4524 | 23835 |
| TTCN_2059 | 13649 | TTCN_4525 | 23836 |
| CTCN_1720 | 13650 | ATCN_2809 | 23837 |
| GTCN_1107 | 13651 | ATCN_2810 | 23838 |
| CTCN_1721 | 13652 | CTCN_4282 | 23839 |
| CTCN_1722 | 13653 | TTCN_4526 | 23840 |
| ATCN_1257 | 13654 | ATCN_2811 | 23841 |
| TTCN_2060 | 13655 | ATCN_2812 | 23842 |
| CTCN_1723 | 13656 | CTCN_4283 | 23843 |
| CTCN_1724 | 13657 | CTCN_4284 | 23844 |
| TTCN_2061 | 13658 | TTCN_4527 | 23845 |
| GTCN_1108 | 13659 | ATCN_2813 | 23846 |
| CTCN_1725 | 13660 | ATCN_2814 | 23847 |
| GTCN_1109 | 13661 | ATCN_2815 | 23848 |
| CTCN_1726 | 13662 | CTCN_4285 | 23849 |
| TTCN_2062 | 13663 | ATCN_2816 | 23850 |
| CTCN_1727 | 13664 | TTCN_4528 | 23851 |
| TTCN_2063 | 13665 | CTCN_4286 | 23852 |
| CTCN_1728 | 13666 | GTCN_2411 | 23853 |
| TTCN_2064 | 13667 | GTCN_2412 | 23854 |
| ATCN_1258 | 13668 | TTCN_4529 | 23855 |
| ATCN_1259 | 13669 | CTCN_4287 | 23856 |
| ATCN_1260 | 13670 | GTCN_2413 | 23857 |
| GTCN_1110 | 13671 | GTCN_2414 | 23858 |
| CTCN_1729 | 13672 | GTCN_2415 | 23859 |
| TTCN_2065 | 13673 | TTCN_4530 | 23860 |
| TTCN_2066 | 13674 | CTCN_4288 | 23861 |
| TTCN_2067 | 13675 | CTCN_4289 | 23862 |
| CTCN_1730 | 13676 | CTCN_4290 | 23863 |
| TTCN_2068 | 13677 | GTCN_2416 | 23864 |
| TTCN_2069 | 13678 | TTCN_4531 | 23865 |
| CTCN_1731 | 13679 | CTCN_4291 | 23866 |
| GTCN_1111 | 13680 | ATCN_2817 | 23867 |
| CTCN_1732 | 13681 | GTCN_2417 | 23868 |

FIG. 36 (continued)

| | | | |
|---|---|---|---|
| ATCN_1261 | 13682 | TTCN_4532 | 23869 |
| TTCN_2070 | 13683 | TTCN_4533 | 23870 |
| CTCN_1733 | 13684 | ATCN_2818 | 23871 |
| CTCN_1734 | 13685 | ATCN_2819 | 23872 |
| TTCN_2071 | 13686 | CTCN_4292 | 23873 |
| CTCN_1735 | 13687 | CTCN_4293 | 23874 |
| ATCN_1262 | 13688 | TTCN_4534 | 23875 |
| ATCN_1263 | 13689 | ATCN_2820 | 23876 |
| TTCN_2072 | 13690 | TTCN_4535 | 23877 |
| TTCN_2073 | 13691 | GTCN_2418 | 23878 |
| CTCN_1736 | 13692 | TTCN_4536 | 23879 |
| TTCN_2074 | 13693 | GTCN_2419 | 23880 |
| TTCN_2075 | 13694 | CTCN_4294 | 23881 |
| ATCN_1264 | 13695 | ATCN_2821 | 23882 |
| GTCN_1112 | 13696 | TTCN_4537 | 23883 |
| GTCN_1113 | 13697 | TTCN_4538 | 23884 |
| TTCN_2076 | 13698 | TTCN_4539 | 23885 |
| TTCN_2077 | 13699 | TTCN_4540 | 23886 |
| CTCN_1737 | 13700 | ATCN_2822 | 23887 |
| CTCN_1738 | 13701 | CTCN_4295 | 23888 |
| CTCN_1739 | 13702 | ATCN_2823 | 23889 |
| TTCN_2078 | 13703 | TTCN_4541 | 23890 |
| TTCN_2079 | 13704 | GTCN_2420 | 23891 |
| GTCN_1114 | 13705 | GTCN_2421 | 23892 |
| ATCN_1265 | 13706 | TTCN_4542 | 23893 |
| GTCN_1115 | 13707 | TTCN_4543 | 23894 |
| ATCN_1266 | 13708 | CTCN_4296 | 23895 |
| CTCN_1740 | 13709 | ATCN_2824 | 23896 |
| CTCN_1741 | 13710 | TTCN_4544 | 23897 |
| CTCN_1742 | 13711 | TTCN_4545 | 23898 |
| CTCN_1743 | 13712 | CTCN_4297 | 23899 |
| TTCN_2080 | 13713 | TTCN_4546 | 23900 |
| CTCN_1744 | 13714 | CTCN_4298 | 23901 |
| ATCN_1267 | 13715 | GTCN_2422 | 23902 |
| CTCN_1745 | 13716 | TTCN_4547 | 23903 |
| CTCN_1746 | 13717 | TTCN_4548 | 23904 |
| CTCN_1747 | 13718 | TTCN_4549 | 23905 |
| ATCN_1268 | 13719 | TTCN_4550 | 23906 |
| CTCN_1748 | 13720 | CTCN_4299 | 23907 |
| GTCN_1116 | 13721 | GTCN_2423 | 23908 |
| ATCN_1269 | 13722 | ATCN_2825 | 23909 |
| CTCN_1749 | 13723 | TTCN_4551 | 23910 |
| ATCN_1270 | 13724 | TTCN_4552 | 23911 |
| GTCN_1117 | 13725 | CTCN_4300 | 23912 |
| TTCN_2081 | 13726 | ATCN_2826 | 23913 |
| TTCN_2082 | 13727 | ATCN_2827 | 23914 |
| TTCN_2083 | 13728 | GTCN_2424 | 23915 |
| CTCN_1750 | 13729 | TTCN_4553 | 23916 |
| TTCN_2084 | 13730 | CTCN_4301 | 23917 |
| GTCN_1118 | 13731 | TTCN_4554 | 23918 |
| CTCN_1751 | 13732 | TTCN_4555 | 23919 |
| CTCN_1752 | 13733 | GTCN_2425 | 23920 |
| TTCN_2085 | 13734 | TTCN_4556 | 23921 |
| TTCN_2086 | 13735 | ATCN_2828 | 23922 |
| GTCN_1119 | 13736 | ATCN_2829 | 23923 |

| | | | |
|---|---|---|---|
| TTCN_2087 | 13737 | ATCN_2830 | 23924 |
| TTCN_2088 | 13738 | GTCN_2426 | 23925 |
| TTCN_2089 | 13739 | GTCN_2427 | 23926 |
| TTCN_2090 | 13740 | ATCN_2831 | 23927 |
| GTCN_1120 | 13741 | CTCN_4302 | 23928 |
| CTCN_1753 | 13742 | ATCN_2832 | 23929 |
| TTCN_2091 | 13743 | ATCN_2833 | 23930 |
| CTCN_1754 | 13744 | ATCN_2834 | 23931 |
| TTCN_2092 | 13745 | TTCN_4557 | 23932 |
| ATCN_1271 | 13746 | ATCN_2835 | 23933 |
| CTCN_1755 | 13747 | GTCN_2428 | 23934 |
| TTCN_2093 | 13748 | CTCN_4303 | 23935 |
| TTCN_2094 | 13749 | TTCN_4558 | 23936 |
| ATCN_1272 | 13750 | ATCN_2836 | 23937 |
| ATCN_1273 | 13751 | CTCN_4304 | 23938 |
| CTCN_1756 | 13752 | CTCN_4305 | 23939 |
| GTCN_1121 | 13753 | TTCN_4559 | 23940 |
| CTCN_1757 | 13754 | CTCN_4306 | 23941 |
| CTCN_1758 | 13755 | TTCN_4560 | 23942 |
| ATCN_1274 | 13756 | TTCN_4561 | 23943 |
| CTCN_1759 | 13757 | ATCN_2837 | 23944 |
| TTCN_2095 | 13758 | TTCN_4562 | 23945 |
| ATCN_1275 | 13759 | TTCN_4563 | 23946 |
| TTCN_2096 | 13760 | TTCN_4564 | 23947 |
| GTCN_1122 | 13761 | GTCN_2429 | 23948 |
| TTCN_2097 | 13762 | GTCN_2430 | 23949 |
| CTCN_1760 | 13763 | CTCN_4307 | 23950 |
| CTCN_1761 | 13764 | ATCN_2838 | 23951 |
| GTCN_1123 | 13765 | TTCN_4565 | 23952 |
| CTCN_1762 | 13766 | ATCN_2839 | 23953 |
| ATCN_1276 | 13767 | ATCN_2840 | 23954 |
| TTCN_2098 | 13768 | GTCN_2431 | 23955 |
| TTCN_2099 | 13769 | TTCN_4566 | 23956 |
| TTCN_2100 | 13770 | TTCN_4567 | 23957 |
| CTCN_1763 | 13771 | GTCN_2432 | 23958 |
| CTCN_1764 | 13772 | CTCN_4308 | 23959 |
| GTCN_1124 | 13773 | ATCN_2841 | 23960 |
| CTCN_1765 | 13774 | ATCN_2842 | 23961 |
| TTCN_2101 | 13775 | GTCN_2433 | 23962 |
| TTCN_2102 | 13776 | ATCN_2843 | 23963 |
| ATCN_1277 | 13777 | TTCN_4568 | 23964 |
| TTCN_2103 | 13778 | CTCN_4309 | 23965 |
| CTCN_1766 | 13779 | TTCN_4569 | 23966 |
| TTCN_2104 | 13780 | ATCN_2844 | 23967 |
| TTCN_2105 | 13781 | GTCN_2434 | 23968 |
| CTCN_1767 | 13782 | GTCN_2435 | 23969 |
| CTCN_1768 | 13783 | ATCN_2845 | 23970 |
| GTCN_1125 | 13784 | ATCN_2846 | 23971 |
| CTCN_1769 | 13785 | ATCN_2847 | 23972 |
| TTCN_2106 | 13786 | TTCN_4570 | 23973 |
| TTCN_2107 | 13787 | GTCN_2436 | 23974 |
| TTCN_2108 | 13788 | CTCN_4310 | 23975 |
| GTCN_1126 | 13789 | CTCN_4311 | 23976 |
| CTCN_1770 | 13790 | CTCN_4312 | 23977 |
| CTCN_1771 | 13791 | CTCN_4313 | 23978 |

FIG. 36 (continued)

| | | | |
|---|---|---|---|
| ATCN_1278 | 13792 | TTCN_4571 | 23979 |
| TTCN_2109 | 13793 | ATCN_2848 | 23980 |
| CTCN_1772 | 13794 | TTCN_4572 | 23981 |
| TTCN_2110 | 13795 | TTCN_4573 | 23982 |
| ATCN_1279 | 13796 | GTCN_2437 | 23983 |
| GTCN_1127 | 13797 | ATCN_2849 | 23984 |
| ATCN_1280 | 13798 | CTCN_4314 | 23985 |
| TTCN_2111 | 13799 | TTCN_4574 | 23986 |
| CTCN_1773 | 13800 | ATCN_2850 | 23987 |
| ATCN_1281 | 13801 | CTCN_4315 | 23988 |
| ATCN_1282 | 13802 | CTCN_4316 | 23989 |
| TTCN_2112 | 13803 | CTCN_4317 | 23990 |
| TTCN_2113 | 13804 | ATCN_2851 | 23991 |
| GTCN_1128 | 13805 | TTCN_4575 | 23992 |
| TTCN_2114 | 13806 | ATCN_2852 | 23993 |
| TTCN_2115 | 13807 | TTCN_4576 | 23994 |
| CTCN_1774 | 13808 | ATCN_2853 | 23995 |
| ATCN_1283 | 13809 | ATCN_2854 | 23996 |
| CTCN_1775 | 13810 | TTCN_4577 | 23997 |
| GTCN_1129 | 13811 | CTCN_4318 | 23998 |
| CTCN_1776 | 13812 | TTCN_4578 | 23999 |
| ATCN_1284 | 13813 | ATCN_2855 | 24000 |
| CTCN_1777 | 13814 | TTCN_4579 | 24001 |
| GTCN_1130 | 13815 | GTCN_2438 | 24002 |
| ATCN_1285 | 13816 | CTCN_4319 | 24003 |
| CTCN_1778 | 13817 | GTCN_2439 | 24004 |
| TTCN_2116 | 13818 | TTCN_4580 | 24005 |
| TTCN_2117 | 13819 | CTCN_4320 | 24006 |
| CTCN_1779 | 13820 | TTCN_4581 | 24007 |
| CTCN_1780 | 13821 | TTCN_4582 | 24008 |
| ATCN_1286 | 13822 | ATCN_2856 | 24009 |
| CTCN_1781 | 13823 | TTCN_4583 | 24010 |
| ATCN_1287 | 13824 | ATCN_2857 | 24011 |
| CTCN_1782 | 13825 | TTCN_4584 | 24012 |
| TTCN_2118 | 13826 | ATCN_2858 | 24013 |
| GTCN_1131 | 13827 | GTCN_2440 | 24014 |
| CTCN_1783 | 13828 | TTCN_4585 | 24015 |
| ATCN_1288 | 13829 | GTCN_2441 | 24016 |
| TTCN_2119 | 13830 | TTCN_4586 | 24017 |
| TTCN_2120 | 13831 | TTCN_4587 | 24018 |
| TTCN_2121 | 13832 | ATCN_2859 | 24019 |
| CTCN_1784 | 13833 | TTCN_4588 | 24020 |
| TTCN_2122 | 13834 | TTCN_4589 | 24021 |
| ATCN_1289 | 13835 | TTCN_4590 | 24022 |
| ATCN_1290 | 13836 | CTCN_4321 | 24023 |
| CTCN_1785 | 13837 | TTCN_4591 | 24024 |
| TTCN_2123 | 13838 | ATCN_2860 | 24025 |
| GTCN_1132 | 13839 | ATCN_2861 | 24026 |
| CTCN_1786 | 13840 | TTCN_4592 | 24027 |
| TTCN_2124 | 13841 | TTCN_4593 | 24028 |
| TTCN_2125 | 13842 | ATCN_2862 | 24029 |
| ATCN_1291 | 13843 | TTCN_4594 | 24030 |
| ATCN_1292 | 13844 | TTCN_4595 | 24031 |
| CTCN_1787 | 13845 | ATCN_2863 | 24032 |
| TTCN_2126 | 13846 | ATCN_2864 | 24033 |

| | | | |
|---|---|---|---|
| GTCN_1133 | 13847 | CTCN_4322 | 24034 |
| GTCN_1134 | 13848 | GTCN_2442 | 24035 |
| GTCN_1135 | 13849 | TTCN_4596 | 24036 |
| ATCN_1293 | 13850 | GTCN_2443 | 24037 |
| GTCN_1136 | 13851 | CTCN_4323 | 24038 |
| GTCN_1137 | 13852 | ATCN_2865 | 24039 |
| TTCN_2127 | 13853 | GTCN_2444 | 24040 |
| GTCN_1138 | 13854 | GTCN_2445 | 24041 |
| TTCN_2128 | 13855 | TTCN_4597 | 24042 |
| TTCN_2129 | 13856 | GTCN_2446 | 24043 |
| TTCN_2130 | 13857 | ATCN_2866 | 24044 |
| TTCN_2131 | 13858 | CTCN_4324 | 24045 |
| ATCN_1294 | 13859 | GTCN_2447 | 24046 |
| GTCN_1139 | 13860 | CTCN_4325 | 24047 |
| CTCN_1788 | 13861 | TTCN_4598 | 24048 |
| TTCN_2132 | 13862 | TTCN_4599 | 24049 |
| ATCN_1295 | 13863 | TTCN_4600 | 24050 |
| CTCN_1789 | 13864 | ATCN_2867 | 24051 |
| TTCN_2133 | 13865 | GTCN_2448 | 24052 |
| ATCN_1296 | 13866 | GTCN_2449 | 24053 |
| ATCN_1297 | 13867 | CTCN_4326 | 24054 |
| ATCN_1298 | 13868 | CTCN_4327 | 24055 |
| ATCN_1299 | 13869 | GTCN_2450 | 24056 |
| TTCN_2134 | 13870 | CTCN_4328 | 24057 |
| CTCN_1790 | 13871 | GTCN_2451 | 24058 |
| TTCN_2135 | 13872 | CTCN_4329 | 24059 |
| CTCN_1791 | 13873 | ATCN_2868 | 24060 |
| TTCN_2136 | 13874 | TTCN_4601 | 24061 |
| CTCN_1792 | 13875 | ATCN_2869 | 24062 |
| TTCN_2137 | 13876 | ATCN_2870 | 24063 |
| CTCN_1793 | 13877 | ATCN_2871 | 24064 |
| TTCN_2138 | 13878 | ATCN_2872 | 24065 |
| CTCN_1794 | 13879 | GTCN_2452 | 24066 |
| TTCN_2139 | 13880 | ATCN_2873 | 24067 |
| CTCN_1795 | 13881 | TTCN_4602 | 24068 |
| GTCN_1140 | 13882 | CTCN_4330 | 24069 |
| TTCN_2140 | 13883 | TTCN_4603 | 24070 |
| CTCN_1796 | 13884 | TTCN_4604 | 24071 |
| CTCN_1797 | 13885 | CTCN_4331 | 24072 |
| GTCN_1141 | 13886 | CTCN_4332 | 24073 |
| GTCN_1142 | 13887 | TTCN_4605 | 24074 |
| ATCN_1300 | 13888 | CTCN_4333 | 24075 |
| GTCN_1143 | 13889 | TTCN_4606 | 24076 |
| CTCN_1798 | 13890 | CTCN_4334 | 24077 |
| CTCN_1799 | 13891 | TTCN_4607 | 24078 |
| GTCN_1144 | 13892 | CTCN_4335 | 24079 |
| GTCN_1145 | 13893 | CTCN_4336 | 24080 |
| GTCN_1146 | 13894 | ATCN_2874 | 24081 |
| ATCN_1301 | 13895 | ATCN_2875 | 24082 |
| TTCN_2141 | 13896 | TTCN_4608 | 24083 |
| GTCN_1147 | 13897 | ATCN_2876 | 24084 |
| CTCN_1800 | 13898 | ATCN_2877 | 24085 |
| ATCN_1302 | 13899 | CTCN_4337 | 24086 |
| TTCN_2142 | 13900 | GTCN_2453 | 24087 |
| TTCN_2143 | 13901 | TTCN_4609 | 24088 |

FIG. 36 (continued)

| | | | |
|---|---|---|---|
| TTCN_2144 | 13902 | ATCN_2878 | 24089 |
| GTCN_1148 | 13903 | TTCN_4610 | 24090 |
| TTCN_2145 | 13904 | TTCN_4611 | 24091 |
| CTCN_1801 | 13905 | CTCN_4338 | 24092 |
| ATCN_1303 | 13906 | TTCN_4612 | 24093 |
| ATCN_1304 | 13907 | CTCN_4339 | 24094 |
| GTCN_1149 | 13908 | ATCN_2879 | 24095 |
| CTCN_1802 | 13909 | ATCN_2880 | 24096 |
| GTCN_1150 | 13910 | ATCN_2881 | 24097 |
| TTCN_2146 | 13911 | ATCN_2882 | 24098 |
| ATCN_1305 | 13912 | CTCN_4340 | 24099 |
| ATCN_1306 | 13913 | TTCN_4613 | 24100 |
| GTCN_1151 | 13914 | TTCN_4614 | 24101 |
| ATCN_1307 | 13915 | GTCN_2454 | 24102 |
| CTCN_1803 | 13916 | CTCN_4341 | 24103 |
| TTCN_2147 | 13917 | TTCN_4615 | 24104 |
| GTCN_1152 | 13918 | GTCN_2455 | 24105 |
| TTCN_2148 | 13919 | CTCN_4342 | 24106 |
| CTCN_1804 | 13920 | CTCN_4343 | 24107 |
| TTCN_2149 | 13921 | ATCN_2883 | 24108 |
| CTCN_1805 | 13922 | CTCN_4344 | 24109 |
| TTCN_2150 | 13923 | CTCN_4345 | 24110 |
| GTCN_1153 | 13924 | TTCN_4616 | 24111 |
| TTCN_2151 | 13925 | CTCN_4346 | 24112 |
| GTCN_1154 | 13926 | CTCN_4347 | 24113 |
| ATCN_1308 | 13927 | CTCN_4348 | 24114 |
| ATCN_1309 | 13928 | ATCN_2884 | 24115 |
| CTCN_1806 | 13929 | TTCN_4617 | 24116 |
| TTCN_2152 | 13930 | ATCN_2885 | 24117 |
| CTCN_1807 | 13931 | TTCN_4618 | 24118 |
| CTCN_1808 | 13932 | GTCN_2456 | 24119 |
| CTCN_1809 | 13933 | GTCN_2457 | 24120 |
| CTCN_1810 | 13934 | TTCN_4619 | 24121 |
| GTCN_1155 | 13935 | TTCN_4620 | 24122 |
| ATCN_1310 | 13936 | CTCN_4349 | 24123 |
| GTCN_1156 | 13937 | TTCN_4621 | 24124 |
| TTCN_2153 | 13938 | TTCN_4622 | 24125 |
| CTCN_1811 | 13939 | ATCN_2886 | 24126 |
| TTCN_2154 | 13940 | ATCN_2887 | 24127 |
| TTCN_2155 | 13941 | TTCN_4623 | 24128 |
| GTCN_1157 | 13942 | CTCN_4350 | 24129 |
| ATCN_1311 | 13943 | TTCN_4624 | 24130 |
| ATCN_1312 | 13944 | ATCN_2888 | 24131 |
| TTCN_2156 | 13945 | ATCN_2889 | 24132 |
| ATCN_1313 | 13946 | ATCN_2890 | 24133 |
| CTCN_1812 | 13947 | TTCN_4625 | 24134 |
| GTCN_1158 | 13948 | ATCN_2891 | 24135 |
| CTCN_1813 | 13949 | ATCN_2892 | 24136 |
| ATCN_1314 | 13950 | TTCN_4626 | 24137 |
| CTCN_1814 | 13951 | ATCN_2893 | 24138 |
| TTCN_2157 | 13952 | GTCN_2458 | 24139 |
| GTCN_1159 | 13953 | TTCN_4627 | 24140 |
| TTCN_2158 | 13954 | CTCN_4351 | 24141 |
| TTCN_2159 | 13955 | CTCN_4352 | 24142 |
| CTCN_1815 | 13956 | GTCN_2459 | 24143 |

| | | | |
|---|---|---|---|
| TTCN_2160 | 13957 | TTCN_4628 | 24144 |
| TTCN_2161 | 13958 | TTCN_4629 | 24145 |
| GTCN_1160 | 13959 | ATCN_2894 | 24146 |
| CTCN_1816 | 13960 | ATCN_2895 | 24147 |
| TTCN_2162 | 13961 | TTCN_4630 | 24148 |
| TTCN_2163 | 13962 | ATCN_2896 | 24149 |
| CTCN_1817 | 13963 | GTCN_2460 | 24150 |
| TTCN_2164 | 13964 | GTCN_2461 | 24151 |
| ATCN_1315 | 13965 | GTCN_2462 | 24152 |
| ATCN_1316 | 13966 | TTCN_4631 | 24153 |
| GTCN_1161 | 13967 | TTCN_4632 | 24154 |
| TTCN_2165 | 13968 | ATCN_2897 | 24155 |
| CTCN_1818 | 13969 | TTCN_4633 | 24156 |
| TTCN_2166 | 13970 | TTCN_4634 | 24157 |
| ATCN_1317 | 13971 | ATCN_2898 | 24158 |
| TTCN_2167 | 13972 | CTCN_4353 | 24159 |
| CTCN_1819 | 13973 | CTCN_4354 | 24160 |
| GTCN_1162 | 13974 | ATCN_2899 | 24161 |
| ATCN_1318 | 13975 | ATCN_2900 | 24162 |
| TTCN_2168 | 13976 | GTCN_2463 | 24163 |
| TTCN_2169 | 13977 | TTCN_4635 | 24164 |
| ATCN_1319 | 13978 | ATCN_2901 | 24165 |
| TTCN_2170 | 13979 | TTCN_4636 | 24166 |
| CTCN_1820 | 13980 | GTCN_2464 | 24167 |
| TTCN_2171 | 13981 | TTCN_4637 | 24168 |
| CTCN_1821 | 13982 | TTCN_4638 | 24169 |
| CTCN_1822 | 13983 | TTCN_4639 | 24170 |
| GTCN_1163 | 13984 | GTCN_2465 | 24171 |
| CTCN_1823 | 13985 | ATCN_2902 | 24172 |
| GTCN_1164 | 13986 | ATCN_2903 | 24173 |
| TTCN_2172 | 13987 | TTCN_4640 | 24174 |
| TTCN_2173 | 13988 | ATCN_2904 | 24175 |
| CTCN_1824 | 13989 | TTCN_4641 | 24176 |
| CTCN_1825 | 13990 | TTCN_4642 | 24177 |
| TTCN_2174 | 13991 | TTCN_4643 | 24178 |
| TTCN_2175 | 13992 | CTCN_4355 | 24179 |
| TTCN_2176 | 13993 | GTCN_2466 | 24180 |
| TTCN_2177 | 13994 | ATCN_2905 | 24181 |
| GTCN_1165 | 13995 | GTCN_2467 | 24182 |
| CTCN_1826 | 13996 | CTCN_4356 | 24183 |
| TTCN_2178 | 13997 | CTCN_4357 | 24184 |
| ATCN_1320 | 13998 | TTCN_4644 | 24185 |
| CTCN_1827 | 13999 | CTCN_4358 | 24186 |
| ATCN_1321 | 14000 | TTCN_4645 | 24187 |
| CTCN_1828 | 14001 | TTCN_4646 | 24188 |
| CTCN_1829 | 14002 | ATCN_2906 | 24189 |
| TTCN_2179 | 14003 | TTCN_4647 | 24190 |
| CTCN_1830 | 14004 | ATCN_2907 | 24191 |
| GTCN_1166 | 14005 | ATCN_2908 | 24192 |
| TTCN_2180 | 14006 | CTCN_4359 | 24193 |
| ATCN_1322 | 14007 | ATCN_2909 | 24194 |
| GTCN_1167 | 14008 | TTCN_4648 | 24195 |
| CTCN_1831 | 14009 | TTCN_4649 | 24196 |
| TTCN_2181 | 14010 | CTCN_4360 | 24197 |
| ATCN_1323 | 14011 | TTCN_4650 | 24198 |

FIG. 36 (continued)

| | | | |
|---|---|---|---|
| GTCN_1168 | 14012 | ATCN_2910 | 24199 |
| GTCN_1169 | 14013 | CTCN_4361 | 24200 |
| CTCN_1832 | 14014 | TTCN_4651 | 24201 |
| GTCN_1170 | 14015 | CTCN_4362 | 24202 |
| ATCN_1324 | 14016 | ATCN_2911 | 24203 |
| TTCN_2182 | 14017 | ATCN_2912 | 24204 |
| CTCN_1833 | 14018 | TTCN_4652 | 24205 |
| ATCN_1325 | 14019 | GTCN_2468 | 24206 |
| GTCN_1171 | 14020 | CTCN_4363 | 24207 |
| ATCN_1326 | 14021 | CTCN_4364 | 24208 |
| ATCN_1327 | 14022 | TTCN_4653 | 24209 |
| ATCN_1328 | 14023 | ATCN_2913 | 24210 |
| TTCN_2183 | 14024 | TTCN_4654 | 24211 |
| GTCN_1172 | 14025 | CTCN_4365 | 24212 |
| GTCN_1173 | 14026 | TTCN_4655 | 24213 |
| TTCN_2184 | 14027 | GTCN_2469 | 24214 |
| TTCN_2185 | 14028 | TTCN_4656 | 24215 |
| CTCN_1834 | 14029 | TTCN_4657 | 24216 |
| ATCN_1329 | 14030 | ATCN_2914 | 24217 |
| TTCN_2186 | 14031 | CTCN_4366 | 24218 |
| GTCN_1174 | 14032 | ATCN_2915 | 24219 |
| CTCN_1835 | 14033 | GTCN_2470 | 24220 |
| CTCN_1836 | 14034 | TTCN_4658 | 24221 |
| TTCN_2187 | 14035 | ATCN_2916 | 24222 |
| CTCN_1837 | 14036 | GTCN_2471 | 24223 |
| CTCN_1838 | 14037 | ATCN_2917 | 24224 |
| TTCN_2188 | 14038 | TTCN_4659 | 24225 |
| TTCN_2189 | 14039 | TTCN_4660 | 24226 |
| TTCN_2190 | 14040 | TTCN_4661 | 24227 |
| GTCN_1175 | 14041 | GTCN_2472 | 24228 |
| GTCN_1176 | 14042 | CTCN_4367 | 24229 |
| CTCN_1839 | 14043 | CTCN_4368 | 24230 |
| TTCN_2191 | 14044 | TTCN_4662 | 24231 |
| CTCN_1840 | 14045 | CTCN_4369 | 24232 |
| CTCN_1841 | 14046 | CTCN_4370 | 24233 |
| GTCN_1177 | 14047 | CTCN_4371 | 24234 |
| GTCN_1178 | 14048 | TTCN_4663 | 24235 |
| CTCN_1842 | 14049 | GTCN_2473 | 24236 |
| TTCN_2192 | 14050 | TTCN_4664 | 24237 |
| CTCN_1843 | 14051 | ATCN_2918 | 24238 |
| TTCN_2193 | 14052 | TTCN_4665 | 24239 |
| CTCN_1844 | 14053 | ATCN_2919 | 24240 |
| CTCN_1845 | 14054 | CTCN_4372 | 24241 |
| TTCN_2194 | 14055 | TTCN_4666 | 24242 |
| GTCN_1179 | 14056 | GTCN_2474 | 24243 |
| CTCN_1846 | 14057 | TTCN_4667 | 24244 |
| TTCN_2195 | 14058 | CTCN_4373 | 24245 |
| CTCN_1847 | 14059 | ATCN_2920 | 24246 |
| TTCN_2196 | 14060 | CTCN_4374 | 24247 |
| ATCN_1330 | 14061 | ATCN_2921 | 24248 |
| GTCN_1180 | 14062 | GTCN_2475 | 24249 |
| GTCN_1181 | 14063 | GTCN_2476 | 24250 |
| TTCN_2197 | 14064 | GTCN_2477 | 24251 |
| TTCN_2198 | 14065 | ATCN_2922 | 24252 |
| GTCN_1182 | 14066 | ATCN_2923 | 24253 |

| | | | |
|---|---|---|---|
| TTCN_2199 | 14067 | TTCN_4668 | 24254 |
| GTCN_1183 | 14068 | GTCN_2478 | 24255 |
| CTCN_1848 | 14069 | GTCN_2479 | 24256 |
| GTCN_1184 | 14070 | TTCN_4669 | 24257 |
| CTCN_1849 | 14071 | GTCN_2480 | 24258 |
| ATCN_1331 | 14072 | CTCN_4375 | 24259 |
| CTCN_1850 | 14073 | TTCN_4670 | 24260 |
| ATCN_1332 | 14074 | GTCN_2481 | 24261 |
| TTCN_2200 | 14075 | CTCN_4376 | 24262 |
| GTCN_1185 | 14076 | ATCN_2924 | 24263 |
| CTCN_1851 | 14077 | TTCN_4671 | 24264 |
| GTCN_1186 | 14078 | ATCN_2925 | 24265 |
| CTCN_1852 | 14079 | CTCN_4377 | 24266 |
| CTCN_1853 | 14080 | ATCN_2926 | 24267 |
| TTCN_2201 | 14081 | CTCN_4378 | 24268 |
| CTCN_1854 | 14082 | TTCN_4672 | 24269 |
| ATCN_1333 | 14083 | ATCN_2927 | 24270 |
| TTCN_2202 | 14084 | GTCN_2482 | 24271 |
| CTCN_1855 | 14085 | TTCN_4673 | 24272 |
| CTCN_1856 | 14086 | TTCN_4674 | 24273 |
| ATCN_1334 | 14087 | TTCN_4675 | 24274 |
| TTCN_2203 | 14088 | CTCN_4379 | 24275 |
| ATCN_1335 | 14089 | ATCN_2928 | 24276 |
| ATCN_1336 | 14090 | CTCN_4380 | 24277 |
| ATCN_1337 | 14091 | CTCN_4381 | 24278 |
| CTCN_1857 | 14092 | CTCN_4382 | 24279 |
| CTCN_1858 | 14093 | CTCN_4383 | 24280 |
| TTCN_2204 | 14094 | TTCN_4676 | 24281 |
| TTCN_2205 | 14095 | CTCN_4384 | 24282 |
| ATCN_1338 | 14096 | ATCN_2929 | 24283 |
| CTCN_1859 | 14097 | CTCN_4385 | 24284 |
| CTCN_1860 | 14098 | GTCN_2483 | 24285 |
| ATCN_1339 | 14099 | CTCN_4386 | 24286 |
| GTCN_1187 | 14100 | CTCN_4387 | 24287 |
| CTCN_1861 | 14101 | GTCN_2484 | 24288 |
| TTCN_2206 | 14102 | GTCN_2485 | 24289 |
| ATCN_1340 | 14103 | CTCN_4388 | 24290 |
| CTCN_1862 | 14104 | GTCN_2486 | 24291 |
| GTCN_1188 | 14105 | TTCN_4677 | 24292 |
| CTCN_1863 | 14106 | TTCN_4678 | 24293 |
| CTCN_1864 | 14107 | GTCN_2487 | 24294 |
| CTCN_1865 | 14108 | TTCN_4679 | 24295 |
| ATCN_1341 | 14109 | CTCN_4389 | 24296 |
| CTCN_1866 | 14110 | ATCN_2930 | 24297 |
| TTCN_2207 | 14111 | CTCN_4390 | 24298 |
| CTCN_1867 | 14112 | CTCN_4391 | 24299 |
| CTCN_1868 | 14113 | GTCN_2488 | 24300 |
| TTCN_2208 | 14114 | CTCN_4392 | 24301 |
| ATCN_1342 | 14115 | TTCN_4680 | 24302 |
| TTCN_2209 | 14116 | TTCN_4681 | 24303 |
| ATCN_1343 | 14117 | TTCN_4682 | 24304 |
| GTCN_1189 | 14118 | CTCN_4393 | 24305 |
| CTCN_1869 | 14119 | CTCN_4394 | 24306 |
| TTCN_2210 | 14120 | GTCN_2489 | 24307 |
| CTCN_1870 | 14121 | TTCN_4683 | 24308 |

FIG. 36 (continued)

| | | | |
|---|---|---|---|
| ATCN_1344 | 14122 | CTCN_4395 | 24309 |
| ATCN_1345 | 14123 | CTCN_4396 | 24310 |
| GTCN_1190 | 14124 | TTCN_4684 | 24311 |
| TTCN_2211 | 14125 | TTCN_4685 | 24312 |
| ATCN_1346 | 14126 | TTCN_4686 | 24313 |
| TTCN_2212 | 14127 | TTCN_4687 | 24314 |
| TTCN_2213 | 14128 | TTCN_4688 | 24315 |
| TTCN_2214 | 14129 | TTCN_4689 | 24316 |
| TTCN_2215 | 14130 | CTCN_4397 | 24317 |
| GTCN_1191 | 14131 | GTCN_2490 | 24318 |
| TTCN_2216 | 14132 | GTCN_2491 | 24319 |
| TTCN_2217 | 14133 | CTCN_4398 | 24320 |
| ATCN_1347 | 14134 | TTCN_4690 | 24321 |
| CTCN_1871 | 14135 | TTCN_4691 | 24322 |
| CTCN_1872 | 14136 | TTCN_4692 | 24323 |
| TTCN_2218 | 14137 | TTCN_4693 | 24324 |
| CTCN_1873 | 14138 | TTCN_4694 | 24325 |
| ATCN_1348 | 14139 | TTCN_4695 | 24326 |
| GTCN_1192 | 14140 | ATCN_2931 | 24327 |
| TTCN_2219 | 14141 | TTCN_4696 | 24328 |
| CTCN_1874 | 14142 | TTCN_4697 | 24329 |
| ATCN_1349 | 14143 | ATCN_2932 | 24330 |
| CTCN_1875 | 14144 | TTCN_4698 | 24331 |
| TTCN_2220 | 14145 | ATCN_2933 | 24332 |
| TTCN_2221 | 14146 | ATCN_2934 | 24333 |
| CTCN_1876 | 14147 | GTCN_2492 | 24334 |
| ATCN_1350 | 14148 | ATCN_2935 | 24335 |
| TTCN_2222 | 14149 | TTCN_4699 | 24336 |
| ATCN_1351 | 14150 | ATCN_2936 | 24337 |
| TTCN_2223 | 14151 | ATCN_2937 | 24338 |
| TTCN_2224 | 14152 | CTCN_4399 | 24339 |
| TTCN_2225 | 14153 | CTCN_4400 | 24340 |
| GTCN_1193 | 14154 | TTCN_4700 | 24341 |
| CTCN_1877 | 14155 | TTCN_4701 | 24342 |
| TTCN_2226 | 14156 | GTCN_2493 | 24343 |
| TTCN_2227 | 14157 | TTCN_4702 | 24344 |
| TTCN_2228 | 14158 | CTCN_4401 | 24345 |
| TTCN_2229 | 14159 | TTCN_4703 | 24346 |
| CTCN_1878 | 14160 | TTCN_4704 | 24347 |
| TTCN_2230 | 14161 | TTCN_4705 | 24348 |
| ATCN_1352 | 14162 | ATCN_2938 | 24349 |
| TTCN_2231 | 14163 | ATCN_2939 | 24350 |
| TTCN_2232 | 14164 | TTCN_4706 | 24351 |
| TTCN_2233 | 14165 | TTCN_4707 | 24352 |
| CTCN_1879 | 14166 | CTCN_4402 | 24353 |
| GTCN_1194 | 14167 | TTCN_4708 | 24354 |
| TTCN_2234 | 14168 | CTCN_4403 | 24355 |
| GTCN_1195 | 14169 | ATCN_2940 | 24356 |
| TTCN_2235 | 14170 | TTCN_4709 | 24357 |
| ATCN_1353 | 14171 | TTCN_4710 | 24358 |
| TTCN_2236 | 14172 | TTCN_4711 | 24359 |
| ATCN_1354 | 14173 | CTCN_4404 | 24360 |
| ATCN_1355 | 14174 | TTCN_4712 | 24361 |
| ATCN_1356 | 14175 | TTCN_4713 | 24362 |
| ATCN_1357 | 14176 | TTCN_4714 | 24363 |

| | | | |
|---|---|---|---|
| TTCN_2237 | 14177 | TTCN_4715 | 24364 |
| TTCN_2238 | 14178 | CTCN_4405 | 24365 |
| TTCN_2239 | 14179 | TTCN_4716 | 24366 |
| TTCN_2240 | 14180 | ATCN_2941 | 24367 |
| TTCN_2241 | 14181 | CTCN_4406 | 24368 |
| TTCN_2242 | 14182 | TTCN_4717 | 24369 |
| TTCN_2243 | 14183 | GTCN_2494 | 24370 |
| CTCN_1880 | 14184 | GTCN_2495 | 24371 |
| GTCN_1196 | 14185 | TTCN_4718 | 24372 |
| TTCN_2244 | 14186 | GTCN_2496 | 24373 |
| TTCN_2245 | 14187 | CTCN_4407 | 24374 |
| TTCN_2246 | 14188 | CTCN_4408 | 24375 |
| TTCN_2247 | 14189 | TTCN_4719 | 24376 |
| GTCN_1197 | 14190 | CTCN_4409 | 24377 |
| GTCN_1198 | 14191 | CTCN_4410 | 24378 |
| TTCN_2248 | 14192 | TTCN_4720 | 24379 |
| ATCN_1358 | 14193 | GTCN_2497 | 24380 |
| ATCN_1359 | 14194 | GTCN_2498 | 24381 |
| CTCN_1881 | 14195 | CTCN_4411 | 24382 |
| TTCN_2249 | 14196 | ATCN_2942 | 24383 |
| GTCN_1199 | 14197 | CTCN_4412 | 24384 |
| ATCN_1360 | 14198 | CTCN_4413 | 24385 |
| TTCN_2250 | 14199 | GTCN_2499 | 24386 |
| CTCN_1882 | 14200 | TTCN_4721 | 24387 |
| CTCN_1883 | 14201 | TTCN_4722 | 24388 |
| ATCN_1361 | 14202 | TTCN_4723 | 24389 |
| ATCN_1362 | 14203 | CTCN_4414 | 24390 |
| CTCN_1884 | 14204 | CTCN_4415 | 24391 |
| GTCN_1200 | 14205 | TTCN_4724 | 24392 |
| CTCN_1885 | 14206 | GTCN_2500 | 24393 |
| TTCN_2251 | 14207 | TTCN_4725 | 24394 |
| GTCN_1201 | 14208 | TTCN_4726 | 24395 |
| TTCN_2252 | 14209 | TTCN_4727 | 24396 |
| GTCN_1202 | 14210 | GTCN_2501 | 24397 |
| CTCN_1886 | 14211 | GTCN_2502 | 24398 |
| ATCN_1363 | 14212 | CTCN_4416 | 24399 |
| ATCN_1364 | 14213 | CTCN_4417 | 24400 |
| TTCN_2253 | 14214 | CTCN_4418 | 24401 |
| TTCN_2254 | 14215 | GTCN_2503 | 24402 |
| CTCN_1887 | 14216 | ATCN_2943 | 24403 |
| GTCN_1203 | 14217 | ATCN_2944 | 24404 |
| CTCN_1888 | 14218 | GTCN_2504 | 24405 |
| GTCN_1204 | 14219 | ATCN_2945 | 24406 |
| CTCN_1889 | 14220 | TTCN_4728 | 24407 |
| CTCN_1890 | 14221 | ATCN_2946 | 24408 |
| GTCN_1205 | 14222 | GTCN_2505 | 24409 |
| CTCN_1891 | 14223 | TTCN_4729 | 24410 |
| ATCN_1365 | 14224 | CTCN_4419 | 24411 |
| ATCN_1366 | 14225 | ATCN_2947 | 24412 |
| CTCN_1892 | 14226 | TTCN_4730 | 24413 |
| CTCN_1893 | 14227 | ATCN_2948 | 24414 |
| CTCN_1894 | 14228 | TTCN_4731 | 24415 |
| CTCN_1895 | 14229 | ATCN_2949 | 24416 |
| TTCN_2255 | 14230 | TTCN_4732 | 24417 |
| TTCN_2256 | 14231 | GTCN_2506 | 24418 |

FIG. 36 (continued)

| | | | |
|---|---|---|---|
| CTCN_1896 | 14232 | ATCN_2950 | 24419 |
| CTCN_1897 | 14233 | TTCN_4733 | 24420 |
| CTCN_1898 | 14234 | GTCN_2507 | 24421 |
| GTCN_1206 | 14235 | CTCN_4420 | 24422 |
| CTCN_1899 | 14236 | CTCN_4421 | 24423 |
| GTCN_1207 | 14237 | GTCN_2508 | 24424 |
| CTCN_1900 | 14238 | TTCN_4734 | 24425 |
| GTCN_1208 | 14239 | CTCN_4422 | 24426 |
| TTCN_2257 | 14240 | GTCN_2509 | 24427 |
| ATCN_1367 | 14241 | CTCN_4423 | 24428 |
| ATCN_1368 | 14242 | ATCN_2951 | 24429 |
| ATCN_1369 | 14243 | TTCN_4735 | 24430 |
| CTCN_1901 | 14244 | TTCN_4736 | 24431 |
| ATCN_1370 | 14245 | TTCN_4737 | 24432 |
| ATCN_1371 | 14246 | CTCN_4424 | 24433 |
| CTCN_1902 | 14247 | ATCN_2952 | 24434 |
| GTCN_1209 | 14248 | CTCN_4425 | 24435 |
| CTCN_1903 | 14249 | TTCN_4738 | 24436 |
| ATCN_1372 | 14250 | TTCN_4739 | 24437 |
| ATCN_1373 | 14251 | ATCN_2953 | 24438 |
| CTCN_1904 | 14252 | TTCN_4740 | 24439 |
| CTCN_1905 | 14253 | TTCN_4741 | 24440 |
| ATCN_1374 | 14254 | TTCN_4742 | 24441 |
| CTCN_1906 | 14255 | TTCN_4743 | 24442 |
| TTCN_2258 | 14256 | GTCN_2510 | 24443 |
| TTCN_2259 | 14257 | GTCN_2511 | 24444 |
| ATCN_1375 | 14258 | CTCN_4426 | 24445 |
| TTCN_2260 | 14259 | GTCN_2512 | 24446 |
| CTCN_1907 | 14260 | GTCN_2513 | 24447 |
| TTCN_2261 | 14261 | TTCN_4744 | 24448 |
| ATCN_1376 | 14262 | ATCN_2954 | 24449 |
| GTCN_1210 | 14263 | CTCN_4427 | 24450 |
| CTCN_1908 | 14264 | CTCN_4428 | 24451 |
| ATCN_1377 | 14265 | TTCN_4745 | 24452 |
| TTCN_2262 | 14266 | TTCN_4746 | 24453 |
| CTCN_1909 | 14267 | TTCN_4747 | 24454 |
| ATCN_1378 | 14268 | CTCN_4429 | 24455 |
| CTCN_1910 | 14269 | GTCN_2514 | 24456 |
| GTCN_1211 | 14270 | ATCN_2955 | 24457 |
| CTCN_1911 | 14271 | GTCN_2515 | 24458 |
| CTCN_1912 | 14272 | CTCN_4430 | 24459 |
| GTCN_1212 | 14273 | TTCN_4748 | 24460 |
| GTCN_1213 | 14274 | CTCN_4431 | 24461 |
| ATCN_1379 | 14275 | ATCN_2956 | 24462 |
| TTCN_2263 | 14276 | ATCN_2957 | 24463 |
| ATCN_1380 | 14277 | ATCN_2958 | 24464 |
| ATCN_1381 | 14278 | GTCN_2516 | 24465 |
| CTCN_1913 | 14279 | ATCN_2959 | 24466 |
| TTCN_2264 | 14280 | TTCN_4749 | 24467 |
| GTCN_1214 | 14281 | ATCN_2960 | 24468 |
| ATCN_1382 | 14282 | GTCN_2517 | 24469 |
| ATCN_1383 | 14283 | CTCN_4432 | 24470 |
| CTCN_1914 | 14284 | TTCN_4750 | 24471 |
| CTCN_1915 | 14285 | ATCN_2961 | 24472 |
| CTCN_1916 | 14286 | ATCN_2962 | 24473 |

| | | | |
|---|---|---|---|
| ATCN_1384 | 14287 | CTCN_4433 | 24474 |
| ATCN_1385 | 14288 | CTCN_4434 | 24475 |
| TTCN_2265 | 14289 | GTCN_2518 | 24476 |
| CTCN_1917 | 14290 | TTCN_4751 | 24477 |
| CTCN_1918 | 14291 | CTCN_4435 | 24478 |
| CTCN_1919 | 14292 | TTCN_4752 | 24479 |
| CTCN_1920 | 14293 | TTCN_4753 | 24480 |
| ATCN_1386 | 14294 | TTCN_4754 | 24481 |
| ATCN_1387 | 14295 | GTCN_2519 | 24482 |
| CTCN_1921 | 14296 | CTCN_4436 | 24483 |
| GTCN_1215 | 14297 | CTCN_4437 | 24484 |
| CTCN_1922 | 14298 | CTCN_4438 | 24485 |
| CTCN_1923 | 14299 | TTCN_4755 | 24486 |
| GTCN_1216 | 14300 | TTCN_4756 | 24487 |
| CTCN_1924 | 14301 | TTCN_4757 | 24488 |
| ATCN_1388 | 14302 | CTCN_4439 | 24489 |
| CTCN_1925 | 14303 | TTCN_4758 | 24490 |
| ATCN_1389 | 14304 | ATCN_2963 | 24491 |
| TTCN_2266 | 14305 | ATCN_2964 | 24492 |
| TTCN_2267 | 14306 | TTCN_4759 | 24493 |
| TTCN_2268 | 14307 | TTCN_4760 | 24494 |
| ATCN_1390 | 14308 | CTCN_4440 | 24495 |
| TTCN_2269 | 14309 | ATCN_2965 | 24496 |
| CTCN_1926 | 14310 | TTCN_4761 | 24497 |
| CTCN_1927 | 14311 | TTCN_4762 | 24498 |
| GTCN_1217 | 14312 | ATCN_2966 | 24499 |
| TTCN_2270 | 14313 | GTCN_2520 | 24500 |
| ATCN_1391 | 14314 | TTCN_4763 | 24501 |
| CTCN_1928 | 14315 | GTCN_2521 | 24502 |
| TTCN_2271 | 14316 | CTCN_4441 | 24503 |
| CTCN_1929 | 14317 | TTCN_4764 | 24504 |
| TTCN_2272 | 14318 | TTCN_4765 | 24505 |
| TTCN_2273 | 14319 | ATCN_2967 | 24506 |
| ATCN_1392 | 14320 | ATCN_2968 | 24507 |
| ATCN_1393 | 14321 | GTCN_2522 | 24508 |
| TTCN_2274 | 14322 | TTCN_4766 | 24509 |
| TTCN_2275 | 14323 | CTCN_4442 | 24510 |
| CTCN_1930 | 14324 | ATCN_2969 | 24511 |
| CTCN_1931 | 14325 | TTCN_4767 | 24512 |
| TTCN_2276 | 14326 | GTCN_2523 | 24513 |
| CTCN_1932 | 14327 | GTCN_2524 | 24514 |
| GTCN_1218 | 14328 | TTCN_4768 | 24515 |
| ATCN_1394 | 14329 | ATCN_2970 | 24516 |
| TTCN_2277 | 14330 | TTCN_4769 | 24517 |
| ATCN_1395 | 14331 | TTCN_4770 | 24518 |
| TTCN_2278 | 14332 | ATCN_2971 | 24519 |
| ATCN_1396 | 14333 | TTCN_4771 | 24520 |
| ATCN_1397 | 14334 | ATCN_2972 | 24521 |
| CTCN_1933 | 14335 | TTCN_4772 | 24522 |
| TTCN_2279 | 14336 | CTCN_4443 | 24523 |
| CTCN_1934 | 14337 | CTCN_4444 | 24524 |
| CTCN_1935 | 14338 | TTCN_4773 | 24525 |
| GTCN_1219 | 14339 | GTCN_2525 | 24526 |
| GTCN_1220 | 14340 | TTCN_4774 | 24527 |
| GTCN_1221 | 14341 | ATCN_2973 | 24528 |

FIG. 36 (continued)

| | | | |
|---|---|---|---|
| GTCN_1222 | 14342 | ATCN_2974 | 24529 |
| GTCN_1223 | 14343 | TTCN_4775 | 24530 |
| CTCN_1936 | 14344 | CTCN_4445 | 24531 |
| GTCN_1224 | 14345 | ATCN_2975 | 24532 |
| CTCN_1937 | 14346 | TTCN_4776 | 24533 |
| ATCN_1398 | 14347 | GTCN_2526 | 24534 |
| ATCN_1399 | 14348 | GTCN_2527 | 24535 |
| TTCN_2280 | 14349 | GTCN_2528 | 24536 |
| ATCN_1400 | 14350 | GTCN_2529 | 24537 |
| GTCN_1225 | 14351 | ATCN_2976 | 24538 |
| CTCN_1938 | 14352 | GTCN_2530 | 24539 |
| TTCN_2281 | 14353 | GTCN_2531 | 24540 |
| GTCN_1226 | 14354 | ATCN_2977 | 24541 |
| GTCN_1227 | 14355 | TTCN_4777 | 24542 |
| CTCN_1939 | 14356 | GTCN_2532 | 24543 |
| CTCN_1940 | 14357 | ATCN_2978 | 24544 |
| GTCN_1228 | 14358 | ATCN_2979 | 24545 |
| CTCN_1941 | 14359 | CTCN_4446 | 24546 |
| CTCN_1942 | 14360 | GTCN_2533 | 24547 |
| TTCN_2282 | 14361 | TTCN_4778 | 24548 |
| GTCN_1229 | 14362 | TTCN_4779 | 24549 |
| TTCN_2283 | 14363 | ATCN_2980 | 24550 |
| CTCN_1943 | 14364 | CTCN_4447 | 24551 |
| TTCN_2284 | 14365 | GTCN_2534 | 24552 |
| CTCN_1944 | 14366 | TTCN_4780 | 24553 |
| CTCN_1945 | 14367 | TTCN_4781 | 24554 |
| GTCN_1230 | 14368 | GTCN_2535 | 24555 |
| GTCN_1231 | 14369 | GTCN_2536 | 24556 |
| CTCN_1946 | 14370 | GTCN_2537 | 24557 |
| GTCN_1232 | 14371 | ATCN_2981 | 24558 |
| CTCN_1947 | 14372 | ATCN_2982 | 24559 |
| CTCN_1948 | 14373 | TTCN_4782 | 24560 |
| CTCN_1949 | 14374 | TTCN_4783 | 24561 |
| GTCN_1233 | 14375 | TTCN_4784 | 24562 |
| ATCN_1401 | 14376 | TTCN_4785 | 24563 |
| TTCN_2285 | 14377 | GTCN_2538 | 24564 |
| CTCN_1950 | 14378 | ATCN_2983 | 24565 |
| ATCN_1402 | 14379 | ATCN_2984 | 24566 |
| CTCN_1951 | 14380 | CTCN_4448 | 24567 |
| TTCN_2286 | 14381 | ATCN_2985 | 24568 |
| CTCN_1952 | 14382 | TTCN_4786 | 24569 |
| CTCN_1953 | 14383 | GTCN_2539 | 24570 |
| CTCN_1954 | 14384 | ATCN_2986 | 24571 |
| CTCN_1955 | 14385 | ATCN_2987 | 24572 |
| TTCN_2287 | 14386 | CTCN_4449 | 24573 |
| TTCN_2288 | 14387 | GTCN_2540 | 24574 |
| GTCN_1234 | 14388 | TTCN_4787 | 24575 |
| CTCN_1956 | 14389 | CTCN_4450 | 24576 |
| CTCN_1957 | 14390 | GTCN_2541 | 24577 |
| GTCN_1235 | 14391 | ATCN_2988 | 24578 |
| TTCN_2289 | 14392 | TTCN_4788 | 24579 |
| TTCN_2290 | 14393 | ATCN_2989 | 24580 |
| TTCN_2291 | 14394 | TTCN_4789 | 24581 |
| TTCN_2292 | 14395 | CTCN_4451 | 24582 |
| TTCN_2293 | 14396 | TTCN_4790 | 24583 |

| | | | |
|---|---|---|---|
| CTCN_1958 | 14397 | TTCN_4791 | 24584 |
| TTCN_2294 | 14398 | TTCN_4792 | 24585 |
| GTCN_1236 | 14399 | GTCN_2542 | 24586 |
| TTCN_2295 | 14400 | CTCN_4452 | 24587 |
| ATCN_1403 | 14401 | TTCN_4793 | 24588 |
| TTCN_2296 | 14402 | TTCN_4794 | 24589 |
| GTCN_1237 | 14403 | TTCN_4795 | 24590 |
| TTCN_2297 | 14404 | GTCN_2543 | 24591 |
| ATCN_1404 | 14405 | ATCN_2990 | 24592 |
| TTCN_2298 | 14406 | CTCN_4453 | 24593 |
| TTCN_2299 | 14407 | TTCN_4796 | 24594 |
| TTCN_2300 | 14408 | ATCN_2991 | 24595 |
| GTCN_1238 | 14409 | ATCN_2992 | 24596 |
| ATCN_1405 | 14410 | TTCN_4797 | 24597 |
| GTCN_1239 | 14411 | ATCN_2993 | 24598 |
| CTCN_1959 | 14412 | TTCN_4798 | 24599 |
| CTCN_1960 | 14413 | CTCN_4454 | 24600 |
| TTCN_2301 | 14414 | CTCN_4455 | 24601 |
| TTCN_2302 | 14415 | ATCN_2994 | 24602 |
| CTCN_1961 | 14416 | TTCN_4799 | 24603 |
| TTCN_2303 | 14417 | CTCN_4456 | 24604 |
| TTCN_2304 | 14418 | CTCN_4457 | 24605 |
| GTCN_1240 | 14419 | TTCN_4800 | 24606 |
| TTCN_2305 | 14420 | CTCN_4458 | 24607 |
| TTCN_2306 | 14421 | TTCN_4801 | 24608 |
| TTCN_2307 | 14422 | TTCN_4802 | 24609 |
| ATCN_1406 | 14423 | GTCN_2544 | 24610 |
| TTCN_2308 | 14424 | CTCN_4459 | 24611 |
| CTCN_1962 | 14425 | CTCN_4460 | 24612 |
| TTCN_2309 | 14426 | GTCN_2545 | 24613 |
| ATCN_1407 | 14427 | TTCN_4803 | 24614 |
| ATCN_1408 | 14428 | GTCN_2546 | 24615 |
| CTCN_1963 | 14429 | GTCN_2547 | 24616 |
| GTCN_1241 | 14430 | TTCN_4804 | 24617 |
| CTCN_1964 | 14431 | GTCN_2548 | 24618 |
| CTCN_1965 | 14432 | CTCN_4461 | 24619 |
| TTCN_2310 | 14433 | CTCN_4462 | 24620 |
| TTCN_2311 | 14434 | CTCN_4463 | 24621 |
| CTCN_1966 | 14435 | CTCN_4464 | 24622 |
| CTCN_1967 | 14436 | TTCN_4805 | 24623 |
| TTCN_2312 | 14437 | TTCN_4806 | 24624 |
| TTCN_2313 | 14438 | TTCN_4807 | 24625 |
| TTCN_2314 | 14439 | GTCN_2549 | 24626 |
| CTCN_1968 | 14440 | GTCN_2550 | 24627 |
| TTCN_2315 | 14441 | GTCN_2551 | 24628 |
| CTCN_1969 | 14442 | GTCN_2552 | 24629 |
| TTCN_2316 | 14443 | CTCN_4465 | 24630 |
| CTCN_1970 | 14444 | GTCN_2553 | 24631 |
| GTCN_1242 | 14445 | CTCN_4466 | 24632 |
| ATCN_1409 | 14446 | CTCN_4467 | 24633 |
| CTCN_1971 | 14447 | GTCN_2554 | 24634 |
| TTCN_2317 | 14448 | GTCN_2555 | 24635 |
| TTCN_2318 | 14449 | GTCN_2556 | 24636 |
| CTCN_1972 | 14450 | ATCN_2995 | 24637 |
| CTCN_1973 | 14451 | CTCN_4468 | 24638 |

FIG. 36 (continued)

| | | | |
|---|---|---|---|
| GTCN_1243 | 14452 | GTCN_2557 | 24639 |
| TTCN_2319 | 14453 | CTCN_4469 | 24640 |
| CTCN_1974 | 14454 | CTCN_4470 | 24641 |
| CTCN_1975 | 14455 | CTCN_4471 | 24642 |
| GTCN_1244 | 14456 | GTCN_2558 | 24643 |
| GTCN_1245 | 14457 | GTCN_2559 | 24644 |
| ATCN_1410 | 14458 | ATCN_2996 | 24645 |
| ATCN_1411 | 14459 | GTCN_2560 | 24646 |
| GTCN_1246 | 14460 | CTCN_4472 | 24647 |
| CTCN_1976 | 14461 | CTCN_4473 | 24648 |
| TTCN_2320 | 14462 | TTCN_4808 | 24649 |
| TTCN_2321 | 14463 | GTCN_2561 | 24650 |
| TTCN_2322 | 14464 | ATCN_2997 | 24651 |
| TTCN_2323 | 14465 | CTCN_4474 | 24652 |
| ATCN_1412 | 14466 | GTCN_2562 | 24653 |
| ATCN_1413 | 14467 | CTCN_4475 | 24654 |
| TTCN_2324 | 14468 | TTCN_4809 | 24655 |
| GTCN_1247 | 14469 | TTCN_4810 | 24656 |
| ATCN_1414 | 14470 | TTCN_4811 | 24657 |
| ATCN_1415 | 14471 | GTCN_2563 | 24658 |
| CTCN_1977 | 14472 | CTCN_4476 | 24659 |
| TTCN_2325 | 14473 | GTCN_2564 | 24660 |
| TTCN_2326 | 14474 | CTCN_4477 | 24661 |
| CTCN_1978 | 14475 | GTCN_2565 | 24662 |
| CTCN_1979 | 14476 | CTCN_4478 | 24663 |
| TTCN_2327 | 14477 | TTCN_4812 | 24664 |
| CTCN_1980 | 14478 | CTCN_4479 | 24665 |
| TTCN_2328 | 14479 | TTCN_4813 | 24666 |
| CTCN_1981 | 14480 | GTCN_2566 | 24667 |
| ATCN_1416 | 14481 | CTCN_4480 | 24668 |
| CTCN_1982 | 14482 | TTCN_4814 | 24669 |
| GTCN_1248 | 14483 | CTCN_4481 | 24670 |
| CTCN_1983 | 14484 | CTCN_4482 | 24671 |
| CTCN_1984 | 14485 | CTCN_4483 | 24672 |
| CTCN_1985 | 14486 | CTCN_4484 | 24673 |
| TTCN_2329 | 14487 | TTCN_4815 | 24674 |
| CTCN_1986 | 14488 | TTCN_4816 | 24675 |
| CTCN_1987 | 14489 | TTCN_4817 | 24676 |
| TTCN_2330 | 14490 | TTCN_4818 | 24677 |
| TTCN_2331 | 14491 | ATCN_2998 | 24678 |
| CTCN_1988 | 14492 | CTCN_4485 | 24679 |
| TTCN_2332 | 14493 | CTCN_4486 | 24680 |
| CTCN_1989 | 14494 | TTCN_4819 | 24681 |
| CTCN_1990 | 14495 | GTCN_2567 | 24682 |
| GTCN_1249 | 14496 | TTCN_4820 | 24683 |
| TTCN_2333 | 14497 | CTCN_4487 | 24684 |
| TTCN_2334 | 14498 | ATCN_2999 | 24685 |
| CTCN_1991 | 14499 | TTCN_4821 | 24686 |
| GTCN_1250 | 14500 | ATCN_3000 | 24687 |
| TTCN_2335 | 14501 | TTCN_4822 | 24688 |
| ATCN_1417 | 14502 | CTCN_4488 | 24689 |
| ATCN_1418 | 14503 | GTCN_2568 | 24690 |
| CTCN_1992 | 14504 | TTCN_4823 | 24691 |
| ATCN_1419 | 14505 | TTCN_4824 | 24692 |
| ATCN_1420 | 14506 | CTCN_4489 | 24693 |

| | | | |
|---|---|---|---|
| ATCN_1421 | 14507 | CTCN_4490 | 24694 |
| GTCN_1251 | 14508 | CTCN_4491 | 24695 |
| ATCN_1422 | 14509 | ATCN_3001 | 24696 |
| TTCN_2336 | 14510 | CTCN_4492 | 24697 |
| ATCN_1423 | 14511 | TTCN_4825 | 24698 |
| CTCN_1993 | 14512 | TTCN_4826 | 24699 |
| CTCN_1994 | 14513 | TTCN_4827 | 24700 |
| TTCN_2337 | 14514 | ATCN_3002 | 24701 |
| TTCN_2338 | 14515 | ATCN_3003 | 24702 |
| TTCN_2339 | 14516 | TTCN_4828 | 24703 |
| CTCN_1995 | 14517 | ATCN_3004 | 24704 |
| ATCN_1424 | 14518 | TTCN_4829 | 24705 |
| ATCN_1425 | 14519 | TTCN_4830 | 24706 |
| ATCN_1426 | 14520 | CTCN_4493 | 24707 |
| CTCN_1996 | 14521 | TTCN_4831 | 24708 |
| ATCN_1427 | 14522 | TTCN_4832 | 24709 |
| ATCN_1428 | 14523 | ATCN_3005 | 24710 |
| TTCN_2340 | 14524 | CTCN_4494 | 24711 |
| TTCN_2341 | 14525 | TTCN_4833 | 24712 |
| TTCN_2342 | 14526 | TTCN_4834 | 24713 |
| CTCN_1997 | 14527 | CTCN_4495 | 24714 |
| ATCN_1429 | 14528 | GTCN_2569 | 24715 |
| ATCN_1430 | 14529 | ATCN_3006 | 24716 |
| CTCN_1998 | 14530 | ATCN_3007 | 24717 |
| TTCN_2343 | 14531 | GTCN_2570 | 24718 |
| ATCN_1431 | 14532 | ATCN_3008 | 24719 |
| TTCN_2344 | 14533 | ATCN_3009 | 24720 |
| CTCN_1999 | 14534 | ATCN_3010 | 24721 |
| CTCN_2000 | 14535 | ATCN_3011 | 24722 |
| CTCN_2001 | 14536 | CTCN_4496 | 24723 |
| CTCN_2002 | 14537 | TTCN_4835 | 24724 |
| GTCN_1252 | 14538 | CTCN_4497 | 24725 |
| GTCN_1253 | 14539 | CTCN_4498 | 24726 |
| GTCN_1254 | 14540 | CTCN_4499 | 24727 |
| CTCN_2003 | 14541 | CTCN_4500 | 24728 |
| GTCN_1255 | 14542 | TTCN_4836 | 24729 |
| CTCN_2004 | 14543 | TTCN_4837 | 24730 |
| CTCN_2005 | 14544 | CTCN_4501 | 24731 |
| ATCN_1432 | 14545 | ATCN_3012 | 24732 |
| ATCN_1433 | 14546 | TTCN_4838 | 24733 |
| TTCN_2345 | 14547 | GTCN_2571 | 24734 |
| TTCN_2346 | 14548 | TTCN_4839 | 24735 |
| TTCN_2347 | 14549 | TTCN_4840 | 24736 |
| TTCN_2348 | 14550 | CTCN_4502 | 24737 |
| GTCN_1256 | 14551 | GTCN_2572 | 24738 |
| CTCN_2006 | 14552 | GTCN_2573 | 24739 |
| GTCN_1257 | 14553 | TTCN_4841 | 24740 |
| TTCN_2349 | 14554 | TTCN_4842 | 24741 |
| ATCN_1434 | 14555 | TTCN_4843 | 24742 |
| CTCN_2007 | 14556 | TTCN_4844 | 24743 |
| CTCN_2008 | 14557 | CTCN_4503 | 24744 |
| CTCN_2009 | 14558 | TTCN_4845 | 24745 |
| CTCN_2010 | 14559 | ATCN_3013 | 24746 |
| TTCN_2350 | 14560 | TTCN_4846 | 24747 |
| ATCN_1435 | 14561 | ATCN_3014 | 24748 |

FIG. 36 (continued)

| | | | | | | | |
|---|---|---|---|---|---|---|---|
| TTCN_2351 | 14562 | TTCN_4847 | 24749 | ATCN_1450 | 14617 | TTCN_4866 | 24804 |
| ATCN_1436 | 14563 | ATCN_3015 | 24750 | TTCN_2369 | 14618 | TTCN_4867 | 24805 |
| TTCN_2352 | 14564 | ATCN_3016 | 24751 | TTCN_2370 | 14619 | GTCN_2584 | 24806 |
| CTCN_2011 | 14565 | GTCN_2574 | 24752 | TTCN_2371 | 14620 | ATCN_3028 | 24807 |
| CTCN_2012 | 14566 | TTCN_4848 | 24753 | ATCN_1451 | 14621 | TTCN_4868 | 24808 |
| GTCN_1258 | 14567 | ATCN_3017 | 24754 | GTCN_1263 | 14622 | CTCN_4517 | 24809 |
| ATCN_1437 | 14568 | TTCN_4849 | 24755 | ATCN_1452 | 14623 | TTCN_4869 | 24810 |
| ATCN_1438 | 14569 | ATCN_3018 | 24756 | TTCN_2372 | 14624 | TTCN_4870 | 24811 |
| TTCN_2353 | 14570 | TTCN_4850 | 24757 | GTCN_1264 | 14625 | CTCN_4518 | 24812 |
| CTCN_2013 | 14571 | TTCN_4851 | 24758 | CTCN_2029 | 14626 | TTCN_4871 | 24813 |
| TTCN_2354 | 14572 | GTCN_2575 | 24759 | TTCN_2373 | 14627 | ATCN_3029 | 24814 |
| TTCN_2355 | 14573 | CTCN_4504 | 24760 | GTCN_1265 | 14628 | GTCN_2585 | 24815 |
| CTCN_2014 | 14574 | ATCN_3019 | 24761 | CTCN_2030 | 14629 | ATCN_3030 | 24816 |
| CTCN_2015 | 14575 | CTCN_4505 | 24762 | CTCN_2031 | 14630 | TTCN_4872 | 24817 |
| ATCN_1439 | 14576 | GTCN_2576 | 24763 | GTCN_1266 | 14631 | ATCN_3031 | 24818 |
| ATCN_1440 | 14577 | ATCN_3020 | 24764 | CTCN_2032 | 14632 | ATCN_3032 | 24819 |
| ATCN_1441 | 14578 | TTCN_4852 | 24765 | TTCN_2374 | 14633 | GTCN_2586 | 24820 |
| CTCN_2016 | 14579 | CTCN_4506 | 24766 | ATCN_1453 | 14634 | TTCN_4873 | 24821 |
| CTCN_2017 | 14580 | GTCN_2577 | 24767 | TTCN_2375 | 14635 | ATCN_3033 | 24822 |
| CTCN_2018 | 14581 | GTCN_2578 | 24768 | TTCN_2376 | 14636 | ATCN_3034 | 24823 |
| TTCN_2356 | 14582 | GTCN_2579 | 24769 | ATCN_1454 | 14637 | CTCN_4519 | 24824 |
| GTCN_1259 | 14583 | CTCN_4507 | 24770 | ATCN_1455 | 14638 | TTCN_4874 | 24825 |
| TTCN_2357 | 14584 | TTCN_4853 | 24771 | ATCN_1456 | 14639 | TTCN_4875 | 24826 |
| ATCN_1442 | 14585 | TTCN_4854 | 24772 | GTCN_1267 | 14640 | ATCN_3035 | 24827 |
| CTCN_2019 | 14586 | TTCN_4855 | 24773 | TTCN_2377 | 14641 | GTCN_2587 | 24828 |
| TTCN_2358 | 14587 | CTCN_4508 | 24774 | CTCN_2033 | 14642 | CTCN_4520 | 24829 |
| CTCN_2020 | 14588 | TTCN_4856 | 24775 | CTCN_2034 | 14643 | CTCN_4521 | 24830 |
| CTCN_2021 | 14589 | CTCN_4509 | 24776 | TTCN_2378 | 14644 | GTCN_2588 | 24831 |
| TTCN_2359 | 14590 | ATCN_3021 | 24777 | TTCN_2379 | 14645 | CTCN_4522 | 24832 |
| GTCN_1260 | 14591 | CTCN_4510 | 24778 | CTCN_2035 | 14646 | CTCN_4523 | 24833 |
| TTCN_2360 | 14592 | ATCN_3022 | 24779 | CTCN_2036 | 14647 | ATCN_3036 | 24834 |
| TTCN_2361 | 14593 | ATCN_3023 | 24780 | TTCN_2380 | 14648 | ATCN_3037 | 24835 |
| TTCN_2362 | 14594 | GTCN_2580 | 24781 | CTCN_2037 | 14649 | TTCN_4876 | 24836 |
| TTCN_2363 | 14595 | TTCN_4857 | 24782 | TTCN_2381 | 14650 | ATCN_3038 | 24837 |
| ATCN_1443 | 14596 | CTCN_4511 | 24783 | TTCN_2382 | 14651 | TTCN_4877 | 24838 |
| TTCN_2364 | 14597 | TTCN_4858 | 24784 | CTCN_2038 | 14652 | CTCN_4524 | 24839 |
| TTCN_2365 | 14598 | CTCN_4512 | 24785 | CTCN_2039 | 14653 | TTCN_4878 | 24840 |
| TTCN_2366 | 14599 | TTCN_4859 | 24786 | CTCN_2040 | 14654 | TTCN_4879 | 24841 |
| ATCN_1444 | 14600 | ATCN_3024 | 24787 | CTCN_2041 | 14655 | TTCN_4880 | 24842 |
| GTCN_1261 | 14601 | ATCN_3025 | 24788 | ATCN_1457 | 14656 | TTCN_4881 | 24843 |
| ATCN_1445 | 14602 | CTCN_4513 | 24789 | ATCN_1458 | 14657 | GTCN_2589 | 24844 |
| ATCN_1446 | 14603 | GTCN_2581 | 24790 | GTCN_1268 | 14658 | CTCN_4525 | 24845 |
| GTCN_1262 | 14604 | CTCN_4514 | 24791 | CTCN_2042 | 14659 | ATCN_3039 | 24846 |
| CTCN_2022 | 14605 | CTCN_4515 | 24792 | CTCN_2043 | 14660 | TTCN_4882 | 24847 |
| CTCN_2023 | 14606 | ATCN_3026 | 24793 | TTCN_2383 | 14661 | TTCN_4883 | 24848 |
| CTCN_2024 | 14607 | ATCN_3027 | 24794 | TTCN_2384 | 14662 | ATCN_3040 | 24849 |
| TTCN_2367 | 14608 | TTCN_4860 | 24795 | CTCN_2044 | 14663 | TTCN_4884 | 24850 |
| CTCN_2025 | 14609 | TTCN_4861 | 24796 | CTCN_2045 | 14664 | TTCN_4885 | 24851 |
| CTCN_2026 | 14610 | GTCN_2582 | 24797 | CTCN_2046 | 14665 | ATCN_3041 | 24852 |
| ATCN_1447 | 14611 | CTCN_4516 | 24798 | GTCN_1269 | 14666 | CTCN_4526 | 24853 |
| ATCN_1448 | 14612 | TTCN_4862 | 24799 | ATCN_1459 | 14667 | ATCN_3042 | 24854 |
| CTCN_2027 | 14613 | TTCN_4863 | 24800 | ATCN_1460 | 14668 | ATCN_3043 | 24855 |
| CTCN_2028 | 14614 | TTCN_4864 | 24801 | TTCN_2385 | 14669 | CTCN_4527 | 24856 |
| ATCN_1449 | 14615 | GTCN_2583 | 24802 | TTCN_2386 | 14670 | TTCN_4886 | 24857 |
| TTCN_2368 | 14616 | TTCN_4865 | 24803 | TTCN_2387 | 14671 | CTCN_4528 | 24858 |

FIG. 36 (continued)

| | | | |
|---|---|---|---|
| GTCN_1270 | 14672 | ATCN_3044 | 24859 |
| CTCN_2047 | 14673 | GTCN_2590 | 24860 |
| CTCN_2048 | 14674 | GTCN_2591 | 24861 |
| CTCN_2049 | 14675 | TTCN_4887 | 24862 |
| CTCN_2050 | 14676 | CTCN_4529 | 24863 |
| CTCN_2051 | 14677 | CTCN_4530 | 24864 |
| ATCN_1461 | 14678 | CTCN_4531 | 24865 |
| TTCN_2388 | 14679 | TTCN_4888 | 24866 |
| GTCN_1271 | 14680 | TTCN_4889 | 24867 |
| GTCN_1272 | 14681 | ATCN_3045 | 24868 |
| TTCN_2389 | 14682 | GTCN_2592 | 24869 |
| CTCN_2052 | 14683 | TTCN_4890 | 24870 |
| TTCN_2390 | 14684 | CTCN_4532 | 24871 |
| TTCN_2391 | 14685 | TTCN_4891 | 24872 |
| TTCN_2392 | 14686 | TTCN_4892 | 24873 |
| CTCN_2053 | 14687 | TTCN_4893 | 24874 |
| GTCN_1273 | 14688 | GTCN_2593 | 24875 |
| CTCN_2054 | 14689 | TTCN_4894 | 24876 |
| TTCN_2393 | 14690 | CTCN_4533 | 24877 |
| CTCN_2055 | 14691 | ATCN_3046 | 24878 |
| CTCN_2056 | 14692 | CTCN_4534 | 24879 |
| CTCN_2057 | 14693 | GTCN_2594 | 24880 |
| TTCN_2394 | 14694 | ATCN_3047 | 24881 |
| CTCN_2058 | 14695 | ATCN_3048 | 24882 |
| ATCN_1462 | 14696 | CTCN_4535 | 24883 |
| GTCN_1274 | 14697 | TTCN_4895 | 24884 |
| ATCN_1463 | 14698 | GTCN_2595 | 24885 |
| CTCN_2059 | 14699 | CTCN_4536 | 24886 |
| ATCN_1464 | 14700 | GTCN_2596 | 24887 |
| CTCN_2060 | 14701 | ATCN_3049 | 24888 |
| CTCN_2061 | 14702 | TTCN_4896 | 24889 |
| CTCN_2062 | 14703 | ATCN_3050 | 24890 |
| CTCN_2063 | 14704 | GTCN_2597 | 24891 |
| CTCN_2064 | 14705 | TTCN_4897 | 24892 |
| TTCN_2395 | 14706 | ATCN_3051 | 24893 |
| CTCN_2065 | 14707 | CTCN_4537 | 24894 |
| CTCN_2066 | 14708 | GTCN_2598 | 24895 |
| TTCN_2396 | 14709 | CTCN_4538 | 24896 |
| CTCN_2067 | 14710 | CTCN_4539 | 24897 |
| CTCN_2068 | 14711 | ATCN_3052 | 24898 |
| TTCN_2397 | 14712 | ATCN_3053 | 24899 |
| CTCN_2069 | 14713 | CTCN_4540 | 24900 |
| GTCN_1275 | 14714 | TTCN_4898 | 24901 |
| CTCN_2070 | 14715 | TTCN_4899 | 24902 |
| TTCN_2398 | 14716 | CTCN_4541 | 24903 |
| CTCN_2071 | 14717 | CTCN_4542 | 24904 |
| CTCN_2072 | 14718 | CTCN_4543 | 24905 |
| ATCN_1465 | 14719 | CTCN_4544 | 24906 |
| CTCN_2073 | 14720 | CTCN_4545 | 24907 |
| GTCN_1276 | 14721 | CTCN_4546 | 24908 |
| TTCN_2399 | 14722 | GTCN_2599 | 24909 |
| CTCN_2074 | 14723 | TTCN_4900 | 24910 |
| TTCN_2400 | 14724 | TTCN_4901 | 24911 |
| CTCN_2075 | 14725 | TTCN_4902 | 24912 |
| GTCN_1277 | 14726 | TTCN_4903 | 24913 |

| | | | |
|---|---|---|---|
| GTCN_1278 | 14727 | CTCN_4547 | 24914 |
| ATCN_1466 | 14728 | ATCN_3054 | 24915 |
| ATCN_1467 | 14729 | TTCN_4904 | 24916 |
| TTCN_2401 | 14730 | TTCN_4905 | 24917 |
| CTCN_2076 | 14731 | TTCN_4906 | 24918 |
| CTCN_2077 | 14732 | GTCN_2600 | 24919 |
| ATCN_1468 | 14733 | GTCN_2601 | 24920 |
| CTCN_2078 | 14734 | CTCN_4548 | 24921 |
| CTCN_2079 | 14735 | ATCN_3055 | 24922 |
| TTCN_2402 | 14736 | TTCN_4907 | 24923 |
| CTCN_2080 | 14737 | TTCN_4908 | 24924 |
| CTCN_2081 | 14738 | TTCN_4909 | 24925 |
| TTCN_2403 | 14739 | CTCN_4549 | 24926 |
| ATCN_1469 | 14740 | GTCN_2602 | 24927 |
| GTCN_1279 | 14741 | TTCN_4910 | 24928 |
| TTCN_2404 | 14742 | TTCN_4911 | 24929 |
| GTCN_1280 | 14743 | CTCN_4550 | 24930 |
| GTCN_1281 | 14744 | TTCN_4912 | 24931 |
| TTCN_2405 | 14745 | GTCN_2603 | 24932 |
| ATCN_1470 | 14746 | CTCN_4551 | 24933 |
| GTCN_1282 | 14747 | CTCN_4552 | 24934 |
| CTCN_2082 | 14748 | TTCN_4913 | 24935 |
| ATCN_1471 | 14749 | CTCN_4553 | 24936 |
| TTCN_2406 | 14750 | ATCN_3056 | 24937 |
| CTCN_2083 | 14751 | GTCN_2604 | 24938 |
| GTCN_1283 | 14752 | CTCN_4554 | 24939 |
| ATCN_1472 | 14753 | CTCN_4555 | 24940 |
| CTCN_2084 | 14754 | GTCN_2605 | 24941 |
| TTCN_2407 | 14755 | TTCN_4914 | 24942 |
| GTCN_1284 | 14756 | ATCN_3057 | 24943 |
| CTCN_2085 | 14757 | TTCN_4915 | 24944 |
| CTCN_2086 | 14758 | ATCN_3058 | 24945 |
| GTCN_1285 | 14759 | TTCN_4916 | 24946 |
| GTCN_1286 | 14760 | TTCN_4917 | 24947 |
| CTCN_2087 | 14761 | GTCN_2606 | 24948 |
| CTCN_2088 | 14762 | CTCN_4556 | 24949 |
| ATCN_1473 | 14763 | ATCN_3059 | 24950 |
| CTCN_2089 | 14764 | ATCN_3060 | 24951 |
| TTCN_2408 | 14765 | CTCN_4557 | 24952 |
| TTCN_2409 | 14766 | TTCN_4918 | 24953 |
| TTCN_2410 | 14767 | CTCN_4558 | 24954 |
| CTCN_2090 | 14768 | CTCN_4559 | 24955 |
| TTCN_2411 | 14769 | CTCN_4560 | 24956 |
| TTCN_2412 | 14770 | TTCN_4919 | 24957 |
| GTCN_1287 | 14771 | ATCN_3061 | 24958 |
| CTCN_2091 | 14772 | CTCN_4561 | 24959 |
| TTCN_2413 | 14773 | TTCN_4920 | 24960 |
| TTCN_2414 | 14774 | ATCN_3062 | 24961 |
| TTCN_2415 | 14775 | CTCN_4562 | 24962 |
| TTCN_2416 | 14776 | ATCN_3063 | 24963 |
| TTCN_2417 | 14777 | CTCN_4563 | 24964 |
| ATCN_1474 | 14778 | GTCN_2607 | 24965 |
| ATCN_1475 | 14779 | ATCN_3064 | 24966 |
| CTCN_2092 | 14780 | ATCN_3065 | 24967 |
| TTCN_2418 | 14781 | CTCN_4564 | 24968 |

FIG. 36 (continued)

| | | | |
|---|---|---|---|
| CTCN_2093 | 14782 | TTCN_4921 | 24969 |
| CTCN_2094 | 14783 | TTCN_4922 | 24970 |
| GTCN_1288 | 14784 | TTCN_4923 | 24971 |
| TTCN_2419 | 14785 | ATCN_3066 | 24972 |
| CTCN_2095 | 14786 | TTCN_4924 | 24973 |
| CTCN_2096 | 14787 | ATCN_3067 | 24974 |
| GTCN_1289 | 14788 | TTCN_4925 | 24975 |
| TTCN_2420 | 14789 | CTCN_4565 | 24976 |
| CTCN_2097 | 14790 | ATCN_3068 | 24977 |
| ATCN_1476 | 14791 | CTCN_4566 | 24978 |
| CTCN_2098 | 14792 | TTCN_4926 | 24979 |
| ATCN_1477 | 14793 | TTCN_4927 | 24980 |
| ATCN_1478 | 14794 | CTCN_4567 | 24981 |
| TTCN_2421 | 14795 | ATCN_3069 | 24982 |
| GTCN_1290 | 14796 | ATCN_3070 | 24983 |
| TTCN_2422 | 14797 | ATCN_3071 | 24984 |
| CTCN_2099 | 14798 | TTCN_4928 | 24985 |
| ATCN_1479 | 14799 | TTCN_4929 | 24986 |
| TTCN_2423 | 14800 | ATCN_3072 | 24987 |
| GTCN_1291 | 14801 | TTCN_4930 | 24988 |
| GTCN_1292 | 14802 | ATCN_3073 | 24989 |
| GTCN_1293 | 14803 | TTCN_4931 | 24990 |
| TTCN_2424 | 14804 | ATCN_3074 | 24991 |
| ATCN_1480 | 14805 | CTCN_4568 | 24992 |
| ATCN_1481 | 14806 | CTCN_4569 | 24993 |
| CTCN_2100 | 14807 | TTCN_4932 | 24994 |
| CTCN_2101 | 14808 | CTCN_4570 | 24995 |
| TTCN_2425 | 14809 | TTCN_4933 | 24996 |
| CTCN_2102 | 14810 | CTCN_4571 | 24997 |
| TTCN_2426 | 14811 | GTCN_2608 | 24998 |
| CTCN_2103 | 14812 | ATCN_3075 | 24999 |
| GTCN_1294 | 14813 | ATCN_3076 | 25000 |
| CTCN_2104 | 14814 | TTCN_4934 | 25001 |
| GTCN_1295 | 14815 | TTCN_4935 | 25002 |
| CTCN_2105 | 14816 | ATCN_3077 | 25003 |
| GTCN_1296 | 14817 | CTCN_4572 | 25004 |
| CTCN_2106 | 14818 | TTCN_4936 | 25005 |
| GTCN_1297 | 14819 | ATCN_3078 | 25006 |
| TTCN_2427 | 14820 | ATCN_3079 | 25007 |
| TTCN_2428 | 14821 | GTCN_2609 | 25008 |
| ATCN_1482 | 14822 | TTCN_4937 | 25009 |
| TTCN_2429 | 14823 | TTCN_4938 | 25010 |
| CTCN_2107 | 14824 | CTCN_4573 | 25011 |
| CTCN_2108 | 14825 | GTCN_2610 | 25012 |
| CTCN_2109 | 14826 | ATCN_3080 | 25013 |
| TTCN_2430 | 14827 | ATCN_3081 | 25014 |
| TTCN_2431 | 14828 | ATCN_3082 | 25015 |
| GTCN_1298 | 14829 | TTCN_4939 | 25016 |
| CTCN_2110 | 14830 | ATCN_3083 | 25017 |
| GTCN_1299 | 14831 | GTCN_2611 | 25018 |
| CTCN_2111 | 14832 | TTCN_4940 | 25019 |
| CTCN_2112 | 14833 | CTCN_4574 | 25020 |
| GTCN_1300 | 14834 | GTCN_2612 | 25021 |
| GTCN_1301 | 14835 | GTCN_2613 | 25022 |
| TTCN_2432 | 14836 | CTCN_4575 | 25023 |

| | | | |
|---|---|---|---|
| TTCN_2433 | 14837 | CTCN_4576 | 25024 |
| ATCN_1483 | 14838 | CTCN_4577 | 25025 |
| CTCN_2113 | 14839 | GTCN_2614 | 25026 |
| TTCN_2434 | 14840 | GTCN_2615 | 25027 |
| GTCN_1302 | 14841 | CTCN_4578 | 25028 |
| TTCN_2435 | 14842 | GTCN_2616 | 25029 |
| CTCN_2114 | 14843 | ATCN_3084 | 25030 |
| TTCN_2436 | 14844 | ATCN_3085 | 25031 |
| GTCN_1303 | 14845 | ATCN_3086 | 25032 |
| CTCN_2115 | 14846 | CTCN_4579 | 25033 |
| GTCN_1304 | 14847 | CTCN_4580 | 25034 |
| ATCN_1484 | 14848 | ATCN_3087 | 25035 |
| ATCN_1485 | 14849 | GTCN_2617 | 25036 |
| ATCN_1486 | 14850 | TTCN_4941 | 25037 |
| TTCN_2437 | 14851 | CTCN_4581 | 25038 |
| CTCN_2116 | 14852 | CTCN_4582 | 25039 |
| CTCN_2117 | 14853 | TTCN_4942 | 25040 |
| CTCN_2118 | 14854 | CTCN_4583 | 25041 |
| ATCN_1487 | 14855 | CTCN_4584 | 25042 |
| TTCN_2438 | 14856 | CTCN_4585 | 25043 |
| CTCN_2119 | 14857 | CTCN_4586 | 25044 |
| ATCN_1488 | 14858 | CTCN_4587 | 25045 |
| ATCN_1489 | 14859 | CTCN_4588 | 25046 |
| TTCN_2439 | 14860 | ATCN_3088 | 25047 |
| GTCN_1305 | 14861 | ATCN_3089 | 25048 |
| CTCN_2120 | 14862 | GTCN_2618 | 25049 |
| TTCN_2440 | 14863 | GTCN_2619 | 25050 |
| CTCN_2121 | 14864 | CTCN_4589 | 25051 |
| GTCN_1306 | 14865 | TTCN_4943 | 25052 |
| TTCN_2441 | 14866 | GTCN_2620 | 25053 |
| GTCN_1307 | 14867 | TTCN_4944 | 25054 |
| CTCN_2122 | 14868 | CTCN_4590 | 25055 |
| ATCN_1490 | 14869 | TTCN_4945 | 25056 |
| CTCN_2123 | 14870 | TTCN_4946 | 25057 |
| TTCN_2442 | 14871 | GTCN_2621 | 25058 |
| CTCN_2124 | 14872 | CTCN_4591 | 25059 |
| CTCN_2125 | 14873 | CTCN_4592 | 25060 |
| TTCN_2443 | 14874 | TTCN_4947 | 25061 |
| ATCN_1491 | 14875 | CTCN_4593 | 25062 |
| TTCN_2444 | 14876 | CTCN_4594 | 25063 |
| CTCN_2126 | 14877 | CTCN_4595 | 25064 |
| CTCN_2127 | 14878 | CTCN_4596 | 25065 |
| CTCN_2128 | 14879 | GTCN_2622 | 25066 |
| ATCN_1492 | 14880 | CTCN_4597 | 25067 |
| ATCN_1493 | 14881 | ATCN_3090 | 25068 |
| CTCN_2129 | 14882 | CTCN_4598 | 25069 |
| TTCN_2445 | 14883 | ATCN_3091 | 25070 |
| TTCN_2446 | 14884 | CTCN_4599 | 25071 |
| ATCN_1494 | 14885 | TTCN_4948 | 25072 |
| CTCN_2130 | 14886 | ATCN_3092 | 25073 |
| CTCN_2131 | 14887 | ATCN_3093 | 25074 |
| CTCN_2132 | 14888 | GTCN_2623 | 25075 |
| ATCN_1495 | 14889 | TTCN_4949 | 25076 |
| CTCN_2133 | 14890 | ATCN_3094 | 25077 |
| TTCN_2447 | 14891 | ATCN_3095 | 25078 |

FIG. 36 (continued)

| | | | |
|---|---|---|---|
| TTCN_2448 | 14892 | CTCN_4600 | 25079 |
| ATCN_1496 | 14893 | TTCN_4950 | 25080 |
| ATCN_1497 | 14894 | CTCN_4601 | 25081 |
| TTCN_2449 | 14895 | TTCN_4951 | 25082 |
| CTCN_2134 | 14896 | TTCN_4952 | 25083 |
| TTCN_2450 | 14897 | GTCN_2624 | 25084 |
| CTCN_2135 | 14898 | CTCN_4602 | 25085 |
| GTCN_1308 | 14899 | CTCN_4603 | 25086 |
| ATCN_1498 | 14900 | CTCN_4604 | 25087 |
| ATCN_1499 | 14901 | TTCN_4953 | 25088 |
| GTCN_1309 | 14902 | TTCN_4954 | 25089 |
| CTCN_2136 | 14903 | TTCN_4955 | 25090 |
| CTCN_2137 | 14904 | GTCN_2625 | 25091 |
| GTCN_1310 | 14905 | ATCN_3096 | 25092 |
| GTCN_1311 | 14906 | TTCN_4956 | 25093 |
| GTCN_1312 | 14907 | GTCN_2626 | 25094 |
| CTCN_2138 | 14908 | TTCN_4957 | 25095 |
| TTCN_2451 | 14909 | GTCN_2627 | 25096 |
| ATCN_1500 | 14910 | TTCN_4958 | 25097 |
| ATCN_1501 | 14911 | TTCN_4959 | 25098 |
| GTCN_1313 | 14912 | ATCN_3097 | 25099 |
| TTCN_2452 | 14913 | GTCN_2628 | 25100 |
| GTCN_1314 | 14914 | TTCN_4960 | 25101 |
| GTCN_1315 | 14915 | CTCN_4605 | 25102 |
| TTCN_2453 | 14916 | TTCN_4961 | 25103 |
| CTCN_2139 | 14917 | GTCN_2629 | 25104 |
| CTCN_2140 | 14918 | CTCN_4606 | 25105 |
| ATCN_1502 | 14919 | TTCN_4962 | 25106 |
| GTCN_1316 | 14920 | CTCN_4607 | 25107 |
| TTCN_2454 | 14921 | GTCN_2630 | 25108 |
| TTCN_2455 | 14922 | TTCN_4963 | 25109 |
| CTCN_2141 | 14923 | CTCN_4608 | 25110 |
| TTCN_2456 | 14924 | TTCN_4964 | 25111 |
| CTCN_2142 | 14925 | TTCN_4965 | 25112 |
| TTCN_2457 | 14926 | GTCN_2631 | 25113 |
| TTCN_2458 | 14927 | TTCN_4966 | 25114 |
| ATCN_1503 | 14928 | CTCN_4609 | 25115 |
| CTCN_2143 | 14929 | GTCN_2632 | 25116 |
| ATCN_1504 | 14930 | TTCN_4967 | 25117 |
| CTCN_2144 | 14931 | TTCN_4968 | 25118 |
| ATCN_1505 | 14932 | TTCN_4969 | 25119 |
| TTCN_2459 | 14933 | TTCN_4970 | 25120 |
| CTCN_2145 | 14934 | TTCN_4971 | 25121 |
| GTCN_1317 | 14935 | CTCN_4610 | 25122 |
| TTCN_2460 | 14936 | GTCN_2633 | 25123 |
| TTCN_2461 | 14937 | CTCN_4611 | 25124 |
| GTCN_1318 | 14938 | CTCN_4612 | 25125 |
| TTCN_2462 | 14939 | CTCN_4613 | 25126 |
| CTCN_2146 | 14940 | TTCN_4972 | 25127 |
| TTCN_2463 | 14941 | CTCN_4614 | 25128 |
| CTCN_2147 | 14942 | GTCN_2634 | 25129 |
| GTCN_1319 | 14943 | ATCN_3098 | 25130 |
| GTCN_1320 | 14944 | ATCN_3099 | 25131 |
| GTCN_1321 | 14945 | ATCN_3100 | 25132 |
| TTCN_2464 | 14946 | ATCN_3101 | 25133 |

| | | | |
|---|---|---|---|
| TTCN_2465 | 14947 | GTCN_2635 | 25134 |
| CTCN_2148 | 14948 | GTCN_2636 | 25135 |
| GTCN_1322 | 14949 | GTCN_2637 | 25136 |
| GTCN_1323 | 14950 | GTCN_2638 | 25137 |
| TTCN_2466 | 14951 | GTCN_2639 | 25138 |
| CTCN_2149 | 14952 | TTCN_4973 | 25139 |
| CTCN_2150 | 14953 | TTCN_4974 | 25140 |
| TTCN_2467 | 14954 | TTCN_4975 | 25141 |
| CTCN_2151 | 14955 | TTCN_4976 | 25142 |
| GTCN_1324 | 14956 | ATCN_3102 | 25143 |
| CTCN_2152 | 14957 | TTCN_4977 | 25144 |
| TTCN_2468 | 14958 | CTCN_4615 | 25145 |
| ATCN_1506 | 14959 | GTCN_2640 | 25146 |
| TTCN_2469 | 14960 | CTCN_4616 | 25147 |
| TTCN_2470 | 14961 | ATCN_3103 | 25148 |
| TTCN_2471 | 14962 | ATCN_3104 | 25149 |
| TTCN_2472 | 14963 | CTCN_4617 | 25150 |
| CTCN_2153 | 14964 | TTCN_4978 | 25151 |
| CTCN_2154 | 14965 | TTCN_4979 | 25152 |
| ATCN_1507 | 14966 | TTCN_4980 | 25153 |
| ATCN_1508 | 14967 | ATCN_3105 | 25154 |
| GTCN_1325 | 14968 | CTCN_4618 | 25155 |
| TTCN_2473 | 14969 | CTCN_4619 | 25156 |
| ATCN_1509 | 14970 | TTCN_4981 | 25157 |
| TTCN_2474 | 14971 | ATCN_3106 | 25158 |
| CTCN_2155 | 14972 | ATCN_3107 | 25159 |
| TTCN_2475 | 14973 | CTCN_4620 | 25160 |
| CTCN_2156 | 14974 | ATCN_3108 | 25161 |
| ATCN_1510 | 14975 | CTCN_4621 | 25162 |
| GTCN_1326 | 14976 | TTCN_4982 | 25163 |
| CTCN_2157 | 14977 | CTCN_4622 | 25164 |
| TTCN_2476 | 14978 | ATCN_3109 | 25165 |
| TTCN_2477 | 14979 | ATCN_3110 | 25166 |
| TTCN_2478 | 14980 | CTCN_4623 | 25167 |
| ATCN_1511 | 14981 | CTCN_4624 | 25168 |
| ATCN_1512 | 14982 | TTCN_4983 | 25169 |
| TTCN_2479 | 14983 | GTCN_2641 | 25170 |
| CTCN_2158 | 14984 | TTCN_4984 | 25171 |
| ATCN_1513 | 14985 | TTCN_4985 | 25172 |
| ATCN_1514 | 14986 | TTCN_4986 | 25173 |
| CTCN_2159 | 14987 | CTCN_4625 | 25174 |
| ATCN_1515 | 14988 | CTCN_4626 | 25175 |
| TTCN_2480 | 14989 | TTCN_4987 | 25176 |
| TTCN_2481 | 14990 | ATCN_3111 | 25177 |
| GTCN_1327 | 14991 | CTCN_4627 | 25178 |
| ATCN_1516 | 14992 | ATCN_3112 | 25179 |
| GTCN_1328 | 14993 | CTCN_4628 | 25180 |
| ATCN_1517 | 14994 | TTCN_4988 | 25181 |
| ATCN_1518 | 14995 | TTCN_4989 | 25182 |
| CTCN_2160 | 14996 | TTCN_4990 | 25183 |
| TTCN_2482 | 14997 | GTCN_2642 | 25184 |
| ATCN_1519 | 14998 | CTCN_4629 | 25185 |
| TTCN_2483 | 14999 | ATCN_3113 | 25186 |
| GTCN_1329 | 15000 | CTCN_4630 | 25187 |
| TTCN_2484 | 15001 | TTCN_4991 | 25188 |

FIG. 36 (continued)

| | | | |
|---|---|---|---|
| CTCN_2161 | 15002 | ATCN_3114 | 25189 |
| ATCN_1520 | 15003 | ATCN_3115 | 25190 |
| TTCN_2485 | 15004 | GTCN_2643 | 25191 |
| ATCN_1521 | 15005 | CTCN_4631 | 25192 |
| ATCN_1522 | 15006 | CTCN_4632 | 25193 |
| GTCN_1330 | 15007 | TTCN_4992 | 25194 |
| ATCN_1523 | 15008 | TTCN_4993 | 25195 |
| ATCN_1524 | 15009 | CTCN_4633 | 25196 |
| GTCN_1331 | 15010 | TTCN_4994 | 25197 |
| TTCN_2486 | 15011 | ATCN_3116 | 25198 |
| TTCN_2487 | 15012 | TTCN_4995 | 25199 |
| CTCN_2162 | 15013 | GTCN_2644 | 25200 |
| CTCN_2163 | 15014 | TTCN_4996 | 25201 |
| ATCN_1525 | 15015 | CTCN_4634 | 25202 |
| CTCN_2164 | 15016 | ATCN_3117 | 25203 |
| ATCN_1526 | 15017 | CTCN_4635 | 25204 |
| TTCN_2488 | 15018 | ATCN_3118 | 25205 |
| ATCN_1527 | 15019 | GTCN_2645 | 25206 |
| GTCN_1332 | 15020 | TTCN_4997 | 25207 |
| GTCN_1333 | 15021 | CTCN_4636 | 25208 |
| ATCN_1528 | 15022 | TTCN_4998 | 25209 |
| ATCN_1529 | 15023 | ATCN_3119 | 25210 |
| ATCN_1530 | 15024 | CTCN_4637 | 25211 |
| CTCN_2165 | 15025 | ATCN_3120 | 25212 |
| CTCN_2166 | 15026 | GTCN_2646 | 25213 |
| TTCN_2489 | 15027 | CTCN_4638 | 25214 |
| CTCN_2167 | 15028 | CTCN_4639 | 25215 |
| TTCN_2490 | 15029 | GTCN_2647 | 25216 |
| GTCN_1334 | 15030 | CTCN_4640 | 25217 |
| GTCN_1335 | 15031 | TTCN_4999 | 25218 |
| ATCN_1531 | 15032 | CTCN_4641 | 25219 |
| ATCN_1532 | 15033 | ATCN_3121 | 25220 |
| ATCN_1533 | 15034 | TTCN_5000 | 25221 |
| ATCN_1534 | 15035 | GTCN_2648 | 25222 |
| GTCN_1336 | 15036 | CTCN_4642 | 25223 |
| ATCN_1535 | 15037 | TTCN_5001 | 25224 |
| TTCN_2491 | 15038 | GTCN_2649 | 25225 |
| TTCN_2492 | 15039 | GTCN_2650 | 25226 |
| TTCN_2493 | 15040 | TTCN_5002 | 25227 |
| TTCN_2494 | 15041 | TTCN_5003 | 25228 |
| ATCN_1536 | 15042 | TTCN_5004 | 25229 |
| GTCN_1337 | 15043 | ATCN_3122 | 25230 |
| TTCN_2495 | 15044 | GTCN_2651 | 25231 |
| TTCN_2496 | 15045 | CTCN_4643 | 25232 |
| TTCN_2497 | 15046 | CTCN_4644 | 25233 |
| ATCN_1537 | 15047 | CTCN_4645 | 25234 |
| ATCN_1538 | 15048 | CTCN_4646 | 25235 |
| ATCN_1539 | 15049 | CTCN_4647 | 25236 |
| GTCN_1338 | 15050 | TTCN_5005 | 25237 |
| CTCN_2168 | 15051 | CTCN_4648 | 25238 |
| CTCN_2169 | 15052 | ATCN_3123 | 25239 |
| CTCN_2170 | 15053 | TTCN_5006 | 25240 |
| GTCN_1339 | 15054 | GTCN_2652 | 25241 |
| TTCN_2498 | 15055 | TTCN_5007 | 25242 |
| CTCN_2171 | 15056 | GTCN_2653 | 25243 |

| | | | |
|---|---|---|---|
| GTCN_1340 | 15057 | ATCN_3124 | 25244 |
| CTCN_2172 | 15058 | TTCN_5008 | 25245 |
| GTCN_1341 | 15059 | ATCN_3125 | 25246 |
| TTCN_2499 | 15060 | CTCN_4649 | 25247 |
| TTCN_2500 | 15061 | CTCN_4650 | 25248 |
| CTCN_2173 | 15062 | ATCN_3126 | 25249 |
| GTCN_1342 | 15063 | CTCN_4651 | 25250 |
| TTCN_2501 | 15064 | TTCN_5009 | 25251 |
| TTCN_2502 | 15065 | ATCN_3127 | 25252 |
| CTCN_2174 | 15066 | ATCN_3128 | 25253 |
| CTCN_2175 | 15067 | CTCN_4652 | 25254 |
| CTCN_2176 | 15068 | TTCN_5010 | 25255 |
| CTCN_2177 | 15069 | TTCN_5011 | 25256 |
| TTCN_2503 | 15070 | CTCN_4653 | 25257 |
| GTCN_1343 | 15071 | ATCN_3129 | 25258 |
| TTCN_2504 | 15072 | GTCN_2654 | 25259 |
| GTCN_1344 | 15073 | CTCN_4654 | 25260 |
| TTCN_2505 | 15074 | CTCN_4655 | 25261 |
| CTCN_2178 | 15075 | ATCN_3130 | 25262 |
| ATCN_1540 | 15076 | TTCN_5012 | 25263 |
| CTCN_2179 | 15077 | TTCN_5013 | 25264 |
| TTCN_2506 | 15078 | ATCN_3131 | 25265 |
| CTCN_2180 | 15079 | TTCN_5014 | 25266 |
| CTCN_2181 | 15080 | TTCN_5015 | 25267 |
| TTCN_2507 | 15081 | ATCN_3132 | 25268 |
| CTCN_2182 | 15082 | ATCN_3133 | 25269 |
| GTCN_1345 | 15083 | TTCN_5016 | 25270 |
| ATCN_1541 | 15084 | GTCN_2655 | 25271 |
| ATCN_1542 | 15085 | CTCN_4656 | 25272 |
| GTCN_1346 | 15086 | CTCN_4657 | 25273 |
| CTCN_2183 | 15087 | TTCN_5017 | 25274 |
| TTCN_2508 | 15088 | TTCN_5018 | 25275 |
| ATCN_1543 | 15089 | CTCN_4658 | 25276 |
| GTCN_1347 | 15090 | TTCN_5019 | 25277 |
| CTCN_2184 | 15091 | CTCN_4659 | 25278 |
| GTCN_1348 | 15092 | CTCN_4660 | 25279 |
| CTCN_2185 | 15093 | CTCN_4661 | 25280 |
| TTCN_2509 | 15094 | CTCN_4662 | 25281 |
| TTCN_2510 | 15095 | ATCN_3134 | 25282 |
| CTCN_2186 | 15096 | TTCN_5020 | 25283 |
| GTCN_1349 | 15097 | TTCN_5021 | 25284 |
| ATCN_1544 | 15098 | CTCN_4663 | 25285 |
| TTCN_2511 | 15099 | GTCN_2656 | 25286 |
| ATCN_1545 | 15100 | CTCN_4664 | 25287 |
| GTCN_1350 | 15101 | GTCN_2657 | 25288 |
| TTCN_2512 | 15102 | CTCN_4665 | 25289 |
| CTCN_2187 | 15103 | CTCN_4666 | 25290 |
| CTCN_2188 | 15104 | CTCN_4667 | 25291 |
| TTCN_2513 | 15105 | GTCN_2658 | 25292 |
| ATCN_1546 | 15106 | CTCN_4668 | 25293 |
| ATCN_1547 | 15107 | CTCN_4669 | 25294 |
| TTCN_2514 | 15108 | TTCN_5022 | 25295 |
| CTCN_2189 | 15109 | GTCN_2659 | 25296 |
| ATCN_1548 | 15110 | CTCN_4670 | 25297 |
| TTCN_2515 | 15111 | TTCN_5023 | 25298 |

FIG. 36 (continued)

| | | | |
|---|---|---|---|
| TTCN_2516 | 15112 | TTCN_5024 | 25299 |
| TTCN_2517 | 15113 | TTCN_5025 | 25300 |
| CTCN_2190 | 15114 | ATCN_3135 | 25301 |
| ATCN_1549 | 15115 | ATCN_3136 | 25302 |
| TTCN_2518 | 15116 | CTCN_4671 | 25303 |
| TTCN_2519 | 15117 | TTCN_5026 | 25304 |
| TTCN_2520 | 15118 | GTCN_2660 | 25305 |
| ATCN_1550 | 15119 | GTCN_2661 | 25306 |
| GTCN_1351 | 15120 | CTCN_4672 | 25307 |
| ATCN_1551 | 15121 | CTCN_4673 | 25308 |
| TTCN_2521 | 15122 | CTCN_4674 | 25309 |
| CTCN_2191 | 15123 | GTCN_2662 | 25310 |
| CTCN_2192 | 15124 | ATCN_3137 | 25311 |
| CTCN_2193 | 15125 | TTCN_5027 | 25312 |
| ATCN_1552 | 15126 | TTCN_5028 | 25313 |
| ATCN_1553 | 15127 | CTCN_4675 | 25314 |
| TTCN_2522 | 15128 | GTCN_2663 | 25315 |
| TTCN_2523 | 15129 | CTCN_4676 | 25316 |
| GTCN_1352 | 15130 | TTCN_5029 | 25317 |
| CTCN_2194 | 15131 | TTCN_5030 | 25318 |
| ATCN_1554 | 15132 | ATCN_3138 | 25319 |
| GTCN_1353 | 15133 | ATCN_3139 | 25320 |
| CTCN_2195 | 15134 | CTCN_4677 | 25321 |
| TTCN_2524 | 15135 | TTCN_5031 | 25322 |
| TTCN_2525 | 15136 | ATCN_3140 | 25323 |
| TTCN_2526 | 15137 | ATCN_3141 | 25324 |
| TTCN_2527 | 15138 | GTCN_2664 | 25325 |
| TTCN_2528 | 15139 | GTCN_2665 | 25326 |
| GTCN_1354 | 15140 | CTCN_4678 | 25327 |
| ATCN_1555 | 15141 | CTCN_4679 | 25328 |
| ATCN_1556 | 15142 | GTCN_2666 | 25329 |
| ATCN_1557 | 15143 | ATCN_3142 | 25330 |
| TTCN_2529 | 15144 | GTCN_2667 | 25331 |
| CTCN_2196 | 15145 | CTCN_4680 | 25332 |
| GTCN_1355 | 15146 | ATCN_3143 | 25333 |
| CTCN_2197 | 15147 | ATCN_3144 | 25334 |
| CTCN_2198 | 15148 | CTCN_4681 | 25335 |
| ATCN_1558 | 15149 | GTCN_2668 | 25336 |
| TTCN_2530 | 15150 | CTCN_4682 | 25337 |
| GTCN_1356 | 15151 | CTCN_4683 | 25338 |
| CTCN_2199 | 15152 | TTCN_5032 | 25339 |
| GTCN_1357 | 15153 | ATCN_3145 | 25340 |
| CTCN_2200 | 15154 | ATCN_3146 | 25341 |
| CTCN_2201 | 15155 | TTCN_5033 | 25342 |
| ATCN_1559 | 15156 | TTCN_5034 | 25343 |
| TTCN_2531 | 15157 | CTCN_4684 | 25344 |
| TTCN_2532 | 15158 | TTCN_5035 | 25345 |
| TTCN_2533 | 15159 | GTCN_2669 | 25346 |
| GTCN_1358 | 15160 | CTCN_4685 | 25347 |
| TTCN_2534 | 15161 | CTCN_4686 | 25348 |
| CTCN_2202 | 15162 | ATCN_3147 | 25349 |
| ATCN_1560 | 15163 | CTCN_4687 | 25350 |
| GTCN_1359 | 15164 | GTCN_2670 | 25351 |
| ATCN_1561 | 15165 | ATCN_3148 | 25352 |
| ATCN_1562 | 15166 | ATCN_3149 | 25353 |
| CTCN_2203 | 15167 | CTCN_4688 | 25354 |
| CTCN_2204 | 15168 | GTCN_2671 | 25355 |
| TTCN_2535 | 15169 | CTCN_4689 | 25356 |
| CTCN_2205 | 15170 | GTCN_2672 | 25357 |
| TTCN_2536 | 15171 | ATCN_3150 | 25358 |
| GTCN_1360 | 15172 | ATCN_3151 | 25359 |
| CTCN_2206 | 15173 | ATCN_3152 | 25360 |
| GTCN_1361 | 15174 | ATCN_3153 | 25361 |
| CTCN_2207 | 15175 | CTCN_4690 | 25362 |
| ATCN_1563 | 15176 | CTCN_4691 | 25363 |
| TTCN_2537 | 15177 | ATCN_3154 | 25364 |
| ATCN_1564 | 15178 | TTCN_5036 | 25365 |
| TTCN_2538 | 15179 | TTCN_5037 | 25366 |
| GTCN_1362 | 15180 | CTCN_4692 | 25367 |
| ATCN_1565 | 15181 | ATCN_3155 | 25368 |
| CTCN_2208 | 15182 | ATCN_3156 | 25369 |
| CTCN_2209 | 15183 | CTCN_4693 | 25370 |
| CTCN_2210 | 15184 | ATCN_3157 | 25371 |
| ATCN_1566 | 15185 | CTCN_4694 | 25372 |
| TTCN_2539 | 15186 | ATCN_3158 | 25373 |
| TTCN_2540 | 15187 | CTCN_4695 | 25374 |
| TTCN_2541 | 15188 | GTCN_2673 | 25375 |
| TTCN_2542 | 15189 | TTCN_5038 | 25376 |
| GTCN_1363 | 15190 | TTCN_5039 | 25377 |
| TTCN_2543 | 15191 | TTCN_5040 | 25378 |
| ATCN_1567 | 15192 | TTCN_5041 | 25379 |
| GTCN_1364 | 15193 | TTCN_5042 | 25380 |
| TTCN_2544 | 15194 | TTCN_5043 | 25381 |
| CTCN_2211 | 15195 | CTCN_4696 | 25382 |
| ATCN_1568 | 15196 | CTCN_4697 | 25383 |
| TTCN_2545 | 15197 | TTCN_5044 | 25384 |
| GTCN_1365 | 15198 | ATCN_3159 | 25385 |
| CTCN_2212 | 15199 | GTCN_2674 | 25386 |
| GTCN_1366 | 15200 | TTCN_5045 | 25387 |
| ATCN_1569 | 15201 | CTCN_4698 | 25388 |
| ATCN_1570 | 15202 | CTCN_4699 | 25389 |
| TTCN_2546 | 15203 | TTCN_5046 | 25390 |
| TTCN_2547 | 15204 | CTCN_4700 | 25391 |
| CTCN_2213 | 15205 | CTCN_4701 | 25392 |
| TTCN_2548 | 15206 | ATCN_3160 | 25393 |
| ATCN_1571 | 15207 | GTCN_2675 | 25394 |
| ATCN_1572 | 15208 | TTCN_5047 | 25395 |
| CTCN_2214 | 15209 | CTCN_4702 | 25396 |
| ATCN_1573 | 15210 | GTCN_2676 | 25397 |
| TTCN_2549 | 15211 | CTCN_4703 | 25398 |
| TTCN_2550 | 15212 | ATCN_3161 | 25399 |
| TTCN_2551 | 15213 | ATCN_3162 | 25400 |
| GTCN_1367 | 15214 | GTCN_2677 | 25401 |
| ATCN_1574 | 15215 | ATCN_3163 | 25402 |
| ATCN_1575 | 15216 | GTCN_2678 | 25403 |
| GTCN_1368 | 15217 | GTCN_2679 | 25404 |
| GTCN_1369 | 15218 | TTCN_5048 | 25405 |
| CTCN_2215 | 15219 | ATCN_3164 | 25406 |
| ATCN_1576 | 15220 | TTCN_5049 | 25407 |
| ATCN_1577 | 15221 | TTCN_5050 | 25408 |

FIG. 36 (continued)

| | | | |
|---|---|---|---|
| TTCN_2552 | 15222 | CTCN_4704 | 25409 |
| CTCN_2216 | 15223 | CTCN_4705 | 25410 |
| TTCN_2553 | 15224 | ATCN_3165 | 25411 |
| ATCN_1578 | 15225 | CTCN_4706 | 25412 |
| CTCN_2217 | 15226 | TTCN_5051 | 25413 |
| CTCN_2218 | 15227 | TTCN_5052 | 25414 |
| GTCN_1370 | 15228 | TTCN_5053 | 25415 |
| TTCN_2554 | 15229 | GTCN_2680 | 25416 |
| CTCN_2219 | 15230 | TTCN_5054 | 25417 |
| CTCN_2220 | 15231 | TTCN_5055 | 25418 |
| TTCN_2555 | 15232 | ATCN_3166 | 25419 |
| ATCN_1579 | 15233 | TTCN_5056 | 25420 |
| CTCN_2221 | 15234 | ATCN_3167 | 25421 |
| GTCN_1371 | 15235 | ATCN_3168 | 25422 |
| TTCN_2556 | 15236 | TTCN_5057 | 25423 |
| CTCN_2222 | 15237 | CTCN_4707 | 25424 |
| TTCN_2557 | 15238 | TTCN_5058 | 25425 |
| CTCN_2223 | 15239 | CTCN_4708 | 25426 |
| TTCN_2558 | 15240 | TTCN_5059 | 25427 |
| CTCN_2224 | 15241 | ATCN_3169 | 25428 |
| TTCN_2559 | 15242 | TTCN_5060 | 25429 |
| TTCN_2560 | 15243 | TTCN_5061 | 25430 |
| TTCN_2561 | 15244 | TTCN_5062 | 25431 |
| TTCN_2562 | 15245 | CTCN_4709 | 25432 |
| TTCN_2563 | 15246 | TTCN_5063 | 25433 |
| TTCN_2564 | 15247 | CTCN_4710 | 25434 |
| TTCN_2565 | 15248 | GTCN_2681 | 25435 |
| TTCN_2566 | 15249 | CTCN_4711 | 25436 |
| ATCN_1580 | 15250 | CTCN_4712 | 25437 |
| TTCN_2567 | 15251 | ATCN_3170 | 25438 |
| TTCN_2568 | 15252 | CTCN_4713 | 25439 |
| CTCN_2225 | 15253 | ATCN_3171 | 25440 |
| TTCN_2569 | 15254 | ATCN_3172 | 25441 |
| TTCN_2570 | 15255 | ATCN_3173 | 25442 |
| GTCN_1372 | 15256 | CTCN_4714 | 25443 |
| GTCN_1373 | 15257 | CTCN_4715 | 25444 |
| CTCN_2226 | 15258 | ATCN_3174 | 25445 |
| GTCN_1374 | 15259 | ATCN_3175 | 25446 |
| GTCN_1375 | 15260 | ATCN_3176 | 25447 |
| TTCN_2571 | 15261 | TTCN_5064 | 25448 |
| TTCN_2572 | 15262 | CTCN_4716 | 25449 |
| GTCN_1376 | 15263 | CTCN_4717 | 25450 |
| CTCN_2227 | 15264 | GTCN_2682 | 25451 |
| ATCN_1581 | 15265 | TTCN_5065 | 25452 |
| CTCN_2228 | 15266 | CTCN_4718 | 25453 |
| CTCN_2229 | 15267 | CTCN_4719 | 25454 |
| TTCN_2573 | 15268 | ATCN_3177 | 25455 |
| CTCN_2230 | 15269 | CTCN_4720 | 25456 |
| CTCN_2231 | 15270 | ATCN_3178 | 25457 |
| TTCN_2574 | 15271 | CTCN_4721 | 25458 |
| ATCN_1582 | 15272 | CTCN_4722 | 25459 |
| TTCN_2575 | 15273 | GTCN_2683 | 25460 |
| CTCN_2232 | 15274 | TTCN_5066 | 25461 |
| TTCN_2576 | 15275 | TTCN_5067 | 25462 |
| CTCN_2233 | 15276 | TTCN_5068 | 25463 |

| | | | |
|---|---|---|---|
| CTCN_2234 | 15277 | ATCN_3179 | 25464 |
| ATCN_1583 | 15278 | TTCN_5069 | 25465 |
| TTCN_2577 | 15279 | ATCN_3180 | 25466 |
| GTCN_1377 | 15280 | TTCN_5070 | 25467 |
| TTCN_2578 | 15281 | ATCN_3181 | 25468 |
| TTCN_2579 | 15282 | TTCN_5071 | 25469 |
| CTCN_2235 | 15283 | ATCN_3182 | 25470 |
| TTCN_2580 | 15284 | CTCN_4723 | 25471 |
| CTCN_2236 | 15285 | GTCN_2684 | 25472 |
| ATCN_1584 | 15286 | CTCN_4724 | 25473 |
| ATCN_1585 | 15287 | CTCN_4725 | 25474 |
| CTCN_2237 | 15288 | CTCN_4726 | 25475 |
| GTCN_1378 | 15289 | CTCN_4727 | 25476 |
| TTCN_2581 | 15290 | TTCN_5072 | 25477 |
| TTCN_2582 | 15291 | CTCN_4728 | 25478 |
| CTCN_2238 | 15292 | CTCN_4729 | 25479 |
| TTCN_2583 | 15293 | CTCN_4730 | 25480 |
| TTCN_2584 | 15294 | CTCN_4731 | 25481 |
| ATCN_1586 | 15295 | ATCN_3183 | 25482 |
| GTCN_1379 | 15296 | CTCN_4732 | 25483 |
| GTCN_1380 | 15297 | ATCN_3184 | 25484 |
| CTCN_2239 | 15298 | TTCN_5073 | 25485 |
| TTCN_2585 | 15299 | CTCN_4733 | 25486 |
| TTCN_2586 | 15300 | GTCN_2685 | 25487 |
| TTCN_2587 | 15301 | CTCN_4734 | 25488 |
| TTCN_2588 | 15302 | CTCN_4735 | 25489 |
| TTCN_2589 | 15303 | TTCN_5074 | 25490 |
| TTCN_2590 | 15304 | CTCN_4736 | 25491 |
| GTCN_1381 | 15305 | CTCN_4737 | 25492 |
| GTCN_1382 | 15306 | TTCN_5075 | 25493 |
| CTCN_2240 | 15307 | CTCN_4738 | 25494 |
| CTCN_2241 | 15308 | CTCN_4739 | 25495 |
| CTCN_2242 | 15309 | CTCN_4740 | 25496 |
| GTCN_1383 | 15310 | TTCN_5076 | 25497 |
| ATCN_1587 | 15311 | GTCN_2686 | 25498 |
| GTCN_1384 | 15312 | CTCN_4741 | 25499 |
| CTCN_2243 | 15313 | CTCN_4742 | 25500 |
| CTCN_2244 | 15314 | TTCN_5077 | 25501 |
| ATCN_1588 | 15315 | CTCN_4743 | 25502 |
| ATCN_1589 | 15316 | CTCN_4744 | 25503 |
| ATCN_1590 | 15317 | CTCN_4745 | 25504 |
| ATCN_1591 | 15318 | ATCN_3185 | 25505 |
| CTCN_2245 | 15319 | ATCN_3186 | 25506 |
| GTCN_1385 | 15320 | ATCN_3187 | 25507 |
| CTCN_2246 | 15321 | ATCN_3188 | 25508 |
| GTCN_1386 | 15322 | TTCN_5078 | 25509 |
| TTCN_2591 | 15323 | GTCN_2687 | 25510 |
| CTCN_2247 | 15324 | GTCN_2688 | 25511 |
| GTCN_1387 | 15325 | CTCN_4746 | 25512 |
| GTCN_1388 | 15326 | TTCN_5079 | 25513 |
| ATCN_1592 | 15327 | CTCN_4747 | 25514 |
| TTCN_2592 | 15328 | CTCN_4748 | 25515 |
| ATCN_1593 | 15329 | TTCN_5080 | 25516 |
| CTCN_2248 | 15330 | TTCN_5081 | 25517 |
| GTCN_1389 | 15331 | CTCN_4749 | 25518 |

FIG. 36 (continued)

| | | | |
|---|---|---|---|
| CTCN_2249 | 15332 | CTCN_4750 | 25519 |
| CTCN_2250 | 15333 | GTCN_2689 | 25520 |
| CTCN_2251 | 15334 | CTCN_4751 | 25521 |
| TTCN_2593 | 15335 | GTCN_2690 | 25522 |
| TTCN_2594 | 15336 | TTCN_5082 | 25523 |
| ATCN_1594 | 15337 | ATCN_3189 | 25524 |
| ATCN_1595 | 15338 | ATCN_3190 | 25525 |
| CTCN_2252 | 15339 | TTCN_5083 | 25526 |
| TTCN_2595 | 15340 | ATCN_3191 | 25527 |
| TTCN_2596 | 15341 | GTCN_2691 | 25528 |
| TTCN_2597 | 15342 | CTCN_4752 | 25529 |
| GTCN_1390 | 15343 | TTCN_5084 | 25530 |
| CTCN_2253 | 15344 | CTCN_4753 | 25531 |
| TTCN_2598 | 15345 | ATCN_3192 | 25532 |
| TTCN_2599 | 15346 | CTCN_4754 | 25533 |
| TTCN_2600 | 15347 | ATCN_3193 | 25534 |
| CTCN_2254 | 15348 | TTCN_5085 | 25535 |
| TTCN_2601 | 15349 | ATCN_3194 | 25536 |
| TTCN_2602 | 15350 | CTCN_4755 | 25537 |
| GTCN_1391 | 15351 | ATCN_3195 | 25538 |
| TTCN_2603 | 15352 | TTCN_5086 | 25539 |
| CTCN_2255 | 15353 | TTCN_5087 | 25540 |
| CTCN_2256 | 15354 | ATCN_3196 | 25541 |
| GTCN_1392 | 15355 | ATCN_3197 | 25542 |
| TTCN_2604 | 15356 | CTCN_4756 | 25543 |
| TTCN_2605 | 15357 | TTCN_5088 | 25544 |
| TTCN_2606 | 15358 | CTCN_4757 | 25545 |
| TTCN_2607 | 15359 | TTCN_5089 | 25546 |
| TTCN_2608 | 15360 | CTCN_4758 | 25547 |
| ATCN_1596 | 15361 | TTCN_5090 | 25548 |
| TTCN_2609 | 15362 | TTCN_5091 | 25549 |
| TTCN_2610 | 15363 | CTCN_4759 | 25550 |
| ATCN_1597 | 15364 | GTCN_2692 | 25551 |
| GTCN_1393 | 15365 | TTCN_5092 | 25552 |
| CTCN_2257 | 15366 | ATCN_3198 | 25553 |
| ATCN_1598 | 15367 | CTCN_4760 | 25554 |
| TTCN_2611 | 15368 | GTCN_2693 | 25555 |
| TTCN_2612 | 15369 | ATCN_3199 | 25556 |
| CTCN_2258 | 15370 | TTCN_5093 | 25557 |
| TTCN_2613 | 15371 | GTCN_2694 | 25558 |
| CTCN_2259 | 15372 | TTCN_5094 | 25559 |
| TTCN_2614 | 15373 | GTCN_2695 | 25560 |
| CTCN_2260 | 15374 | TTCN_5095 | 25561 |
| TTCN_2615 | 15375 | TTCN_5096 | 25562 |
| TTCN_2616 | 15376 | ATCN_3200 | 25563 |
| TTCN_2617 | 15377 | ATCN_3201 | 25564 |
| GTCN_1394 | 15378 | ATCN_3202 | 25565 |
| GTCN_1395 | 15379 | CTCN_4761 | 25566 |
| GTCN_1396 | 15380 | TTCN_5097 | 25567 |
| ATCN_1599 | 15381 | ATCN_3203 | 25568 |
| CTCN_2261 | 15382 | CTCN_4762 | 25569 |
| ATCN_1600 | 15383 | CTCN_4763 | 25570 |
| GTCN_1397 | 15384 | GTCN_2696 | 25571 |
| CTCN_2262 | 15385 | CTCN_4764 | 25572 |
| TTCN_2618 | 15386 | ATCN_3204 | 25573 |

| | | | |
|---|---|---|---|
| ATCN_1601 | 15387 | CTCN_4765 | 25574 |
| TTCN_2619 | 15388 | CTCN_4766 | 25575 |
| ATCN_1602 | 15389 | TTCN_5098 | 25576 |
| ATCN_1603 | 15390 | ATCN_3205 | 25577 |
| GTCN_1398 | 15391 | ATCN_3206 | 25578 |
| CTCN_2263 | 15392 | TTCN_5099 | 25579 |
| TTCN_2620 | 15393 | CTCN_4767 | 25580 |
| TTCN_2621 | 15394 | CTCN_4768 | 25581 |
| TTCN_2622 | 15395 | TTCN_5100 | 25582 |
| TTCN_2623 | 15396 | GTCN_2697 | 25583 |
| TTCN_2624 | 15397 | GTCN_2698 | 25584 |
| GTCN_1399 | 15398 | TTCN_5101 | 25585 |
| TTCN_2625 | 15399 | TTCN_5102 | 25586 |
| TTCN_2626 | 15400 | ATCN_3207 | 25587 |
| GTCN_1400 | 15401 | ATCN_3208 | 25588 |
| ATCN_1604 | 15402 | ATCN_3209 | 25589 |
| GTCN_1401 | 15403 | CTCN_4769 | 25590 |
| TTCN_2627 | 15404 | CTCN_4770 | 25591 |
| GTCN_1402 | 15405 | TTCN_5103 | 25592 |
| TTCN_2628 | 15406 | CTCN_4771 | 25593 |
| ATCN_1605 | 15407 | TTCN_5104 | 25594 |
| ATCN_1606 | 15408 | ATCN_3210 | 25595 |
| CTCN_2264 | 15409 | TTCN_5105 | 25596 |
| ATCN_1607 | 15410 | CTCN_4772 | 25597 |
| ATCN_1608 | 15411 | GTCN_2699 | 25598 |
| CTCN_2265 | 15412 | TTCN_5106 | 25599 |
| GTCN_1403 | 15413 | ATCN_3211 | 25600 |
| TTCN_2629 | 15414 | TTCN_5107 | 25601 |
| TTCN_2630 | 15415 | ATCN_3212 | 25602 |
| CTCN_2266 | 15416 | TTCN_5108 | 25603 |
| TTCN_2631 | 15417 | ATCN_3213 | 25604 |
| TTCN_2632 | 15418 | CTCN_4773 | 25605 |
| TTCN_2633 | 15419 | TTCN_5109 | 25606 |
| CTCN_2267 | 15420 | GTCN_2700 | 25607 |
| ATCN_1609 | 15421 | ATCN_3214 | 25608 |
| TTCN_2634 | 15422 | CTCN_4774 | 25609 |
| GTCN_1404 | 15423 | GTCN_2701 | 25610 |
| ATCN_1610 | 15424 | CTCN_4775 | 25611 |
| TTCN_2635 | 15425 | CTCN_4776 | 25612 |
| CTCN_2268 | 15426 | CTCN_4777 | 25613 |
| CTCN_2269 | 15427 | TTCN_5110 | 25614 |
| CTCN_2270 | 15428 | CTCN_4778 | 25615 |
| GTCN_1405 | 15429 | ATCN_3215 | 25616 |
| GTCN_1406 | 15430 | TTCN_5111 | 25617 |
| ATCN_1611 | 15431 | GTCN_2702 | 25618 |
| TTCN_2636 | 15432 | TTCN_5112 | 25619 |
| TTCN_2637 | 15433 | CTCN_4779 | 25620 |
| ATCN_1612 | 15434 | CTCN_4780 | 25621 |
| ATCN_1613 | 15435 | GTCN_2703 | 25622 |
| CTCN_2271 | 15436 | GTCN_2704 | 25623 |
| TTCN_2638 | 15437 | TTCN_5113 | 25624 |
| CTCN_2272 | 15438 | CTCN_4781 | 25625 |
| TTCN_2639 | 15439 | CTCN_4782 | 25626 |
| TTCN_2640 | 15440 | TTCN_5114 | 25627 |
| TTCN_2641 | 15441 | TTCN_5115 | 25628 |

FIG. 36 (continued)

| | | | |
|---|---|---|---|
| TTCN_2642 | 15442 | ATCN_3216 | 25629 |
| GTCN_1407 | 15443 | ATCN_3217 | 25630 |
| CTCN_2273 | 15444 | TTCN_5116 | 25631 |
| ATCN_1614 | 15445 | CTCN_4783 | 25632 |
| GTCN_1408 | 15446 | CTCN_4784 | 25633 |
| CTCN_2274 | 15447 | GTCN_2705 | 25634 |
| CTCN_2275 | 15448 | ATCN_3218 | 25635 |
| ATCN_1615 | 15449 | TTCN_5117 | 25636 |
| ATCN_1616 | 15450 | GTCN_2706 | 25637 |
| ATCN_1617 | 15451 | TTCN_5118 | 25638 |
| CTCN_2276 | 15452 | TTCN_5119 | 25639 |
| TTCN_2643 | 15453 | CTCN_4785 | 25640 |
| ATCN_1618 | 15454 | CTCN_4786 | 25641 |
| CTCN_2277 | 15455 | CTCN_4787 | 25642 |
| TTCN_2644 | 15456 | GTCN_2707 | 25643 |
| TTCN_2645 | 15457 | CTCN_4788 | 25644 |
| CTCN_2278 | 15458 | GTCN_2708 | 25645 |
| TTCN_2646 | 15459 | CTCN_4789 | 25646 |
| CTCN_2279 | 15460 | CTCN_4790 | 25647 |
| ATCN_1619 | 15461 | ATCN_3219 | 25648 |
| CTCN_2280 | 15462 | TTCN_5120 | 25649 |
| CTCN_2281 | 15463 | TTCN_5121 | 25650 |
| ATCN_1620 | 15464 | TTCN_5122 | 25651 |
| CTCN_2282 | 15465 | GTCN_2709 | 25652 |
| GTCN_1409 | 15466 | CTCN_4791 | 25653 |
| CTCN_2283 | 15467 | ATCN_3220 | 25654 |
| CTCN_2284 | 15468 | TTCN_5123 | 25655 |
| GTCN_1410 | 15469 | TTCN_5124 | 25656 |
| CTCN_2285 | 15470 | GTCN_2710 | 25657 |
| GTCN_1411 | 15471 | CTCN_4792 | 25658 |
| CTCN_2286 | 15472 | GTCN_2711 | 25659 |
| TTCN_2647 | 15473 | TTCN_5125 | 25660 |
| GTCN_1412 | 15474 | ATCN_3221 | 25661 |
| CTCN_2287 | 15475 | CTCN_4793 | 25662 |
| CTCN_2288 | 15476 | GTCN_2712 | 25663 |
| TTCN_2648 | 15477 | CTCN_4794 | 25664 |
| CTCN_2289 | 15478 | TTCN_5126 | 25665 |
| TTCN_2649 | 15479 | TTCN_5127 | 25666 |
| TTCN_2650 | 15480 | ATCN_3222 | 25667 |
| GTCN_1413 | 15481 | TTCN_5128 | 25668 |
| TTCN_2651 | 15482 | TTCN_5129 | 25669 |
| TTCN_2652 | 15483 | ATCN_3223 | 25670 |
| TTCN_2653 | 15484 | ATCN_3224 | 25671 |
| TTCN_2654 | 15485 | ATCN_3225 | 25672 |
| GTCN_1414 | 15486 | ATCN_3226 | 25673 |
| TTCN_2655 | 15487 | GTCN_2713 | 25674 |
| TTCN_2656 | 15488 | GTCN_2714 | 25675 |
| CTCN_2290 | 15489 | ATCN_3227 | 25676 |
| TTCN_2657 | 15490 | ATCN_3228 | 25677 |
| TTCN_2658 | 15491 | TTCN_5130 | 25678 |
| TTCN_2659 | 15492 | TTCN_5131 | 25679 |
| CTCN_2291 | 15493 | ATCN_3229 | 25680 |
| GTCN_1415 | 15494 | ATCN_3230 | 25681 |
| CTCN_2292 | 15495 | TTCN_5132 | 25682 |
| CTCN_2293 | 15496 | GTCN_2715 | 25683 |

| | | | |
|---|---|---|---|
| TTCN_2660 | 15497 | CTCN_4795 | 25684 |
| CTCN_2294 | 15498 | GTCN_2716 | 25685 |
| GTCN_1416 | 15499 | CTCN_4796 | 25686 |
| CTCN_2295 | 15500 | TTCN_5133 | 25687 |
| TTCN_2661 | 15501 | ATCN_3231 | 25688 |
| CTCN_2296 | 15502 | GTCN_2717 | 25689 |
| CTCN_2297 | 15503 | CTCN_4797 | 25690 |
| GTCN_1417 | 15504 | CTCN_4798 | 25691 |
| TTCN_2662 | 15505 | CTCN_4799 | 25692 |
| GTCN_1418 | 15506 | TTCN_5134 | 25693 |
| GTCN_1419 | 15507 | GTCN_2718 | 25694 |
| ATCN_1621 | 15508 | GTCN_2719 | 25695 |
| CTCN_2298 | 15509 | CTCN_4800 | 25696 |
| ATCN_1622 | 15510 | ATCN_3232 | 25697 |
| TTCN_2663 | 15511 | CTCN_4801 | 25698 |
| ATCN_1623 | 15512 | ATCN_3233 | 25699 |
| CTCN_2299 | 15513 | CTCN_4802 | 25700 |
| GTCN_1420 | 15514 | TTCN_5135 | 25701 |
| CTCN_2300 | 15515 | TTCN_5136 | 25702 |
| CTCN_2301 | 15516 | CTCN_4803 | 25703 |
| CTCN_2302 | 15517 | CTCN_4804 | 25704 |
| CTCN_2303 | 15518 | TTCN_5137 | 25705 |
| CTCN_2304 | 15519 | ATCN_3234 | 25706 |
| TTCN_2664 | 15520 | CTCN_4805 | 25707 |
| TTCN_2665 | 15521 | CTCN_4806 | 25708 |
| TTCN_2666 | 15522 | TTCN_5025 | 25709 |
| ATCN_1624 | 15523 | ATCN_3135 | 25710 |
| GTCN_1421 | 15524 | ATCN_3136 | 25711 |
| CTCN_2305 | 15525 | CTCN_4671 | 25712 |
| CTCN_2306 | 15526 | TTCN_5026 | 25713 |
| ATCN_1625 | 15527 | GTCN_2660 | 25714 |
| CTCN_2307 | 15528 | GTCN_2661 | 25715 |
| ATCN_1626 | 15529 | CTCN_4672 | 25716 |
| CTCN_2308 | 15530 | CTCN_4673 | 25717 |
| CTCN_2309 | 15531 | CTCN_4674 | 25718 |
| TTCN_2667 | 15532 | GTCN_2662 | 25719 |
| TTCN_2668 | 15533 | ATCN_3137 | 25720 |
| TTCN_2669 | 15534 | TTCN_5027 | 25721 |
| TTCN_2670 | 15535 | TTCN_5028 | 25722 |
| TTCN_2671 | 15536 | CTCN_4675 | 25723 |
| TTCN_2672 | 15537 | GTCN_2663 | 25724 |
| TTCN_2673 | 15538 | CTCN_4676 | 25725 |
| ATCN_1627 | 15539 | TTCN_5029 | 25726 |
| ATCN_1628 | 15540 | TTCN_5030 | 25727 |
| TTCN_2674 | 15541 | ATCN_3138 | 25728 |
| GTCN_1422 | 15542 | ATCN_3139 | 25729 |
| CTCN_2310 | 15543 | CTCN_4677 | 25730 |
| ATCN_1629 | 15544 | TTCN_5031 | 25731 |
| TTCN_2675 | 15545 | ATCN_3140 | 25732 |
| TTCN_2676 | 15546 | ATCN_3141 | 25733 |
| ATCN_1630 | 15547 | GTCN_2664 | 25734 |
| TTCN_2677 | 15548 | GTCN_2665 | 25735 |
| ATCN_1631 | 15549 | CTCN_4678 | 25736 |
| CTCN_2311 | 15550 | CTCN_4679 | 25737 |
| CTCN_2312 | 15551 | GTCN_2666 | 25738 |

FIG. 36 (continued)

| | | | |
|---|---|---|---|
| TTCN_2678 | 15552 | ATCN_3142 | 25739 |
| ATCN_1632 | 15553 | GTCN_2667 | 25740 |
| ATCN_1633 | 15554 | CTCN_4680 | 25741 |
| ATCN_1634 | 15555 | ATCN_3143 | 25742 |
| GTCN_1423 | 15556 | ATCN_3144 | 25743 |
| CTCN_2313 | 15557 | CTCN_4681 | 25744 |
| CTCN_2314 | 15558 | GTCN_2668 | 25745 |
| ATCN_1635 | 15559 | CTCN_4682 | 25746 |
| CTCN_2315 | 15560 | CTCN_4683 | 25747 |
| CTCN_2316 | 15561 | TTCN_5032 | 25748 |
| GTCN_1424 | 15562 | ATCN_3145 | 25749 |
| TTCN_2679 | 15563 | ATCN_3146 | 25750 |
| TTCN_2680 | 15564 | TTCN_5033 | 25751 |
| ATCN_1636 | 15565 | TTCN_5034 | 25752 |
| TTCN_2681 | 15566 | CTCN_4684 | 25753 |
| TTCN_2682 | 15567 | TTCN_5035 | 25754 |
| ATCN_1637 | 15568 | GTCN_2669 | 25755 |
| TTCN_2683 | 15569 | CTCN_4685 | 25756 |
| ATCN_1638 | 15570 | CTCN_4686 | 25757 |
| TTCN_2684 | 15571 | ATCN_3147 | 25758 |
| ATCN_1639 | 15572 | CTCN_4687 | 25759 |
| ATCN_1640 | 15573 | GTCN_2670 | 25760 |
| TTCN_2685 | 15574 | ATCN_3148 | 25761 |
| CTCN_2317 | 15575 | ATCN_3149 | 25762 |
| TTCN_2686 | 15576 | CTCN_4688 | 25763 |
| CTCN_2318 | 15577 | GTCN_2671 | 25764 |
| GTCN_1425 | 15578 | CTCN_4689 | 25765 |
| ATCN_1641 | 15579 | GTCN_2672 | 25766 |
| CTCN_2319 | 15580 | ATCN_3150 | 25767 |
| TTCN_2687 | 15581 | ATCN_3151 | 25768 |
| TTCN_2688 | 15582 | ATCN_3152 | 25769 |
| TTCN_2689 | 15583 | ATCN_3153 | 25770 |
| CTCN_2320 | 15584 | CTCN_4690 | 25771 |
| ATCN_1642 | 15585 | CTCN_4691 | 25772 |
| TTCN_2690 | 15586 | ATCN_3154 | 25773 |
| GTCN_1426 | 15587 | TTCN_5036 | 25774 |
| CTCN_2321 | 15588 | TTCN_5037 | 25775 |
| CTCN_2322 | 15589 | CTCN_4692 | 25776 |
| CTCN_2323 | 15590 | ATCN_3155 | 25777 |
| TTCN_2691 | 15591 | ATCN_3156 | 25778 |
| TTCN_2692 | 15592 | CTCN_4693 | 25779 |
| TTCN_2693 | 15593 | ATCN_3157 | 25780 |
| CTCN_2324 | 15594 | CTCN_4694 | 25781 |
| ATCN_1643 | 15595 | ATCN_3158 | 25782 |
| CTCN_2325 | 15596 | CTCN_4695 | 25783 |
| GTCN_1427 | 15597 | GTCN_2673 | 25784 |
| ATCN_1644 | 15598 | TTCN_5038 | 25785 |
| ATCN_1645 | 15599 | TTCN_5039 | 25786 |
| ATCN_1646 | 15600 | TTCN_5040 | 25787 |
| TTCN_2694 | 15601 | TTCN_5041 | 25788 |
| TTCN_2695 | 15602 | TTCN_5042 | 25789 |
| ATCN_1647 | 15603 | TTCN_5043 | 25790 |
| ATCN_1648 | 15604 | CTCN_4696 | 25791 |
| GTCN_1428 | 15605 | CTCN_4697 | 25792 |
| CTCN_2326 | 15606 | TTCN_5044 | 25793 |

| | | | |
|---|---|---|---|
| CTCN_2327 | 15607 | ATCN_3159 | 25794 |
| CTCN_2328 | 15608 | GTCN_2674 | 25795 |
| TTCN_2696 | 15609 | TTCN_5045 | 25796 |
| CTCN_2329 | 15610 | CTCN_4698 | 25797 |
| TTCN_2697 | 15611 | CTCN_4699 | 25798 |
| TTCN_2698 | 15612 | TTCN_5046 | 25799 |
| CTCN_2330 | 15613 | CTCN_4700 | 25800 |
| ATCN_1649 | 15614 | CTCN_4701 | 25801 |
| TTCN_2699 | 15615 | ATCN_3160 | 25802 |
| ATCN_1650 | 15616 | GTCN_2675 | 25803 |
| CTCN_2331 | 15617 | TTCN_5047 | 25804 |
| TTCN_2700 | 15618 | CTCN_4702 | 25805 |
| CTCN_2332 | 15619 | GTCN_2676 | 25806 |
| TTCN_2701 | 15620 | CTCN_4703 | 25807 |
| TTCN_2702 | 15621 | ATCN_3161 | 25808 |
| GTCN_1429 | 15622 | ATCN_3162 | 25809 |
| ATCN_1651 | 15623 | GTCN_2677 | 25810 |
| ATCN_1652 | 15624 | ATCN_3163 | 25811 |
| GTCN_1430 | 15625 | GTCN_2678 | 25812 |
| CTCN_2333 | 15626 | GTCN_2679 | 25813 |
| ATCN_1653 | 15627 | TTCN_5048 | 25814 |
| ATCN_1654 | 15628 | ATCN_3164 | 25815 |
| CTCN_2334 | 15629 | TTCN_5049 | 25816 |
| GTCN_1431 | 15630 | TTCN_5050 | 25817 |
| GTCN_1432 | 15631 | CTCN_4704 | 25818 |
| GTCN_1433 | 15632 | CTCN_4705 | 25819 |
| GTCN_1434 | 15633 | ATCN_3165 | 25820 |
| GTCN_1435 | 15634 | CTCN_4706 | 25821 |
| TTCN_2703 | 15635 | TTCN_5051 | 25822 |
| TTCN_2704 | 15636 | TTCN_5052 | 25823 |
| GTCN_1436 | 15637 | TTCN_5053 | 25824 |
| ATCN_1655 | 15638 | GTCN_2680 | 25825 |
| CTCN_2335 | 15639 | TTCN_5054 | 25826 |
| ATCN_1656 | 15640 | TTCN_5055 | 25827 |
| CTCN_2336 | 15641 | ATCN_3166 | 25828 |
| TTCN_2705 | 15642 | TTCN_5056 | 25829 |
| CTCN_2337 | 15643 | ATCN_3167 | 25830 |
| CTCN_2338 | 15644 | ATCN_3168 | 25831 |
| CTCN_2339 | 15645 | TTCN_5057 | 25832 |
| CTCN_2340 | 15646 | CTCN_4707 | 25833 |
| ATCN_1657 | 15647 | TTCN_5058 | 25834 |
| TTCN_2706 | 15648 | CTCN_4708 | 25835 |
| TTCN_2707 | 15649 | TTCN_5059 | 25836 |
| GTCN_1437 | 15650 | ATCN_3169 | 25837 |
| GTCN_1438 | 15651 | TTCN_5060 | 25838 |
| CTCN_2341 | 15652 | TTCN_5061 | 25839 |
| CTCN_2342 | 15653 | TTCN_5062 | 25840 |
| CTCN_2343 | 15654 | CTCN_4709 | 25841 |
| TTCN_2708 | 15655 | TTCN_5063 | 25842 |
| CTCN_2344 | 15656 | CTCN_4710 | 25843 |
| TTCN_2709 | 15657 | GTCN_2681 | 25844 |
| CTCN_2345 | 15658 | CTCN_4711 | 25845 |
| GTCN_1439 | 15659 | CTCN_4712 | 25846 |
| GTCN_1440 | 15660 | ATCN_3170 | 25847 |
| CTCN_2346 | 15661 | CTCN_4713 | 25848 |

FIG. 36 (continued)

| | | | | | | | |
|---|---|---|---|---|---|---|---|
| CTCN_2347 | 15662 | ATCN_3171 | 25849 | GTCN_1455 | 15717 | CTCN_4739 | 25904 |
| GTCN_1441 | 15663 | ATCN_3172 | 25850 | CTCN_2364 | 15718 | CTCN_4740 | 25905 |
| TTCN_2710 | 15664 | ATCN_3173 | 25851 | GTCN_1456 | 15719 | TTCN_5076 | 25906 |
| TTCN_2711 | 15665 | CTCN_4714 | 25852 | CTCN_2365 | 15720 | GTCN_2686 | 25907 |
| TTCN_2712 | 15666 | CTCN_4715 | 25853 | CTCN_2366 | 15721 | CTCN_4741 | 25908 |
| CTCN_2348 | 15667 | ATCN_3174 | 25854 | ATCN_1665 | 15722 | CTCN_4742 | 25909 |
| TTCN_2713 | 15668 | ATCN_3175 | 25855 | GTCN_1457 | 15723 | TTCN_5077 | 25910 |
| CTCN_2349 | 15669 | ATCN_3176 | 25856 | CTCN_2367 | 15724 | CTCN_4743 | 25911 |
| ATCN_1658 | 15670 | TTCN_5064 | 25857 | TTCN_2727 | 15725 | CTCN_4744 | 25912 |
| TTCN_2714 | 15671 | CTCN_4716 | 25858 | CTCN_2368 | 15726 | CTCN_4745 | 25913 |
| CTCN_2350 | 15672 | CTCN_4717 | 25859 | TTCN_2728 | 15727 | ATCN_3185 | 25914 |
| GTCN_1442 | 15673 | GTCN_2682 | 25860 | CTCN_2369 | 15728 | ATCN_3186 | 25915 |
| TTCN_2715 | 15674 | TTCN_5065 | 25861 | CTCN_2370 | 15729 | ATCN_3187 | 25916 |
| CTCN_2351 | 15675 | CTCN_4718 | 25862 | TTCN_2729 | 15730 | ATCN_3188 | 25917 |
| ATCN_1659 | 15676 | CTCN_4719 | 25863 | CTCN_2371 | 15731 | TTCN_5078 | 25918 |
| TTCN_2716 | 15677 | ATCN_3177 | 25864 | TTCN_2730 | 15732 | GTCN_2687 | 25919 |
| CTCN_2352 | 15678 | CTCN_4720 | 25865 | TTCN_2731 | 15733 | GTCN_2688 | 25920 |
| CTCN_2353 | 15679 | ATCN_3178 | 25866 | TTCN_2732 | 15734 | CTCN_4746 | 25921 |
| GTCN_1443 | 15680 | CTCN_4721 | 25867 | TTCN_2733 | 15735 | TTCN_5079 | 25922 |
| GTCN_1444 | 15681 | CTCN_4722 | 25868 | CTCN_2372 | 15736 | CTCN_4747 | 25923 |
| ATCN_1660 | 15682 | GTCN_2683 | 25869 | CTCN_2373 | 15737 | CTCN_4748 | 25924 |
| GTCN_1445 | 15683 | TTCN_5066 | 25870 | ATCN_1666 | 15738 | TTCN_5080 | 25925 |
| CTCN_2354 | 15684 | TTCN_5067 | 25871 | ATCN_1667 | 15739 | TTCN_5081 | 25926 |
| TTCN_2717 | 15685 | TTCN_5068 | 25872 | CTCN_2374 | 15740 | CTCN_4749 | 25927 |
| CTCN_2355 | 15686 | ATCN_3179 | 25873 | CTCN_2375 | 15741 | CTCN_4750 | 25928 |
| CTCN_2356 | 15687 | TTCN_5069 | 25874 | CTCN_2376 | 15742 | GTCN_2689 | 25929 |
| GTCN_1446 | 15688 | ATCN_3180 | 25875 | CTCN_2377 | 15743 | CTCN_4751 | 25930 |
| ATCN_1661 | 15689 | TTCN_5070 | 25876 | GTCN_1458 | 15744 | GTCN_2690 | 25931 |
| TTCN_2718 | 15690 | ATCN_3181 | 25877 | GTCN_1459 | 15745 | TTCN_5082 | 25932 |
| GTCN_1447 | 15691 | TTCN_5071 | 25878 | TTCN_2734 | 15746 | ATCN_3189 | 25933 |
| TTCN_2719 | 15692 | ATCN_3182 | 25879 | TTCN_2735 | 15747 | ATCN_3190 | 25934 |
| TTCN_2720 | 15693 | CTCN_4723 | 25880 | CTCN_2378 | 15748 | TTCN_5083 | 25935 |
| ATCN_1662 | 15694 | GTCN_2684 | 25881 | TTCN_2736 | 15749 | ATCN_3191 | 25936 |
| CTCN_2357 | 15695 | CTCN_4724 | 25882 | ATCN_1668 | 15750 | GTCN_2691 | 25937 |
| CTCN_2358 | 15696 | CTCN_4725 | 25883 | ATCN_1669 | 15751 | CTCN_4752 | 25938 |
| TTCN_2721 | 15697 | CTCN_4726 | 25884 | ATCN_1670 | 15752 | TTCN_5084 | 25939 |
| ATCN_1663 | 15698 | CTCN_4727 | 25885 | ATCN_1671 | 15753 | CTCN_4753 | 25940 |
| GTCN_1448 | 15699 | TTCN_5072 | 25886 | CTCN_2379 | 15754 | ATCN_3192 | 25941 |
| TTCN_2722 | 15700 | CTCN_4728 | 25887 | GTCN_1460 | 15755 | CTCN_4754 | 25942 |
| CTCN_2359 | 15701 | CTCN_4729 | 25888 | GTCN_1461 | 15756 | ATCN_3193 | 25943 |
| GTCN_1449 | 15702 | CTCN_4730 | 25889 | TTCN_2737 | 15757 | TTCN_5085 | 25944 |
| CTCN_2360 | 15703 | CTCN_4731 | 25890 | CTCN_2380 | 15758 | ATCN_3194 | 25945 |
| ATCN_1664 | 15704 | ATCN_3183 | 25891 | GTCN_1462 | 15759 | CTCN_4755 | 25946 |
| CTCN_2361 | 15705 | CTCN_4732 | 25892 | CTCN_2381 | 15760 | ATCN_3195 | 25947 |
| GTCN_1450 | 15706 | ATCN_3184 | 25893 | CTCN_2382 | 15761 | TTCN_5086 | 25948 |
| TTCN_2723 | 15707 | TTCN_5073 | 25894 | TTCN_2738 | 15762 | TTCN_5087 | 25949 |
| GTCN_1451 | 15708 | CTCN_4733 | 25895 | CTCN_2383 | 15763 | ATCN_3196 | 25950 |
| CTCN_2362 | 15709 | GTCN_2685 | 25896 | ATCN_1672 | 15764 | ATCN_3197 | 25951 |
| TTCN_2724 | 15710 | CTCN_4734 | 25897 | TTCN_2739 | 15765 | CTCN_4756 | 25952 |
| GTCN_1452 | 15711 | CTCN_4735 | 25898 | TTCN_2740 | 15766 | TTCN_5088 | 25953 |
| TTCN_2725 | 15712 | TTCN_5074 | 25899 | CTCN_2384 | 15767 | CTCN_4757 | 25954 |
| TTCN_2726 | 15713 | CTCN_4736 | 25900 | TTCN_2741 | 15768 | TTCN_5089 | 25955 |
| GTCN_1453 | 15714 | CTCN_4737 | 25901 | TTCN_2742 | 15769 | CTCN_4758 | 25956 |
| GTCN_1454 | 15715 | TTCN_5075 | 25902 | TTCN_2743 | 15770 | TTCN_5090 | 25957 |
| CTCN_2363 | 15716 | CTCN_4738 | 25903 | TTCN_2744 | 15771 | TTCN_5091 | 25958 |

FIG. 36 (continued)

| | | | |
|---|---|---|---|
| TTCN_2745 | 15772 | CTCN_4759 | 25959 |
| TTCN_2746 | 15773 | GTCN_2692 | 25960 |
| CTCN_2385 | 15774 | TTCN_5092 | 25961 |
| TTCN_2747 | 15775 | ATCN_3198 | 25962 |
| GTCN_1463 | 15776 | CTCN_4760 | 25963 |
| CTCN_2386 | 15777 | GTCN_2693 | 25964 |
| CTCN_2387 | 15778 | ATCN_3199 | 25965 |
| TTCN_2748 | 15779 | TTCN_5093 | 25966 |
| TTCN_2749 | 15780 | GTCN_2694 | 25967 |
| CTCN_2388 | 15781 | TTCN_5094 | 25968 |
| TTCN_2750 | 15782 | GTCN_2695 | 25969 |
| CTCN_2389 | 15783 | TTCN_5095 | 25970 |
| GTCN_1464 | 15784 | TTCN_5096 | 25971 |
| TTCN_2751 | 15785 | ATCN_3200 | 25972 |
| CTCN_2390 | 15786 | ATCN_3201 | 25973 |
| CTCN_2391 | 15787 | ATCN_3202 | 25974 |
| CTCN_2392 | 15788 | CTCN_4761 | 25975 |
| ATCN_1673 | 15789 | TTCN_5097 | 25976 |
| TTCN_2752 | 15790 | ATCN_3203 | 25977 |
| CTCN_2393 | 15791 | CTCN_4762 | 25978 |
| ATCN_1674 | 15792 | CTCN_4763 | 25979 |
| ATCN_1675 | 15793 | GTCN_2696 | 25980 |
| TTCN_2753 | 15794 | CTCN_4764 | 25981 |
| TTCN_2754 | 15795 | ATCN_3204 | 25982 |
| CTCN_2394 | 15796 | CTCN_4765 | 25983 |
| GTCN_1465 | 15797 | CTCN_4766 | 25984 |
| TTCN_2755 | 15798 | TTCN_5098 | 25985 |
| GTCN_1466 | 15799 | ATCN_3205 | 25986 |
| TTCN_2756 | 15800 | ATCN_3206 | 25987 |
| CTCN_2395 | 15801 | TTCN_5099 | 25988 |
| TTCN_2757 | 15802 | CTCN_4767 | 25989 |
| CTCN_2396 | 15803 | CTCN_4768 | 25990 |
| ATCN_1676 | 15804 | TTCN_5100 | 25991 |
| CTCN_2397 | 15805 | GTCN_2697 | 25992 |
| ATCN_1677 | 15806 | GTCN_2698 | 25993 |
| ATCN_1678 | 15807 | TTCN_5101 | 25994 |
| CTCN_2398 | 15808 | TTCN_5102 | 25995 |
| TTCN_2758 | 15809 | ATCN_3207 | 25996 |
| GTCN_1467 | 15810 | ATCN_3208 | 25997 |
| TTCN_2759 | 15811 | ATCN_3209 | 25998 |
| GTCN_1468 | 15812 | CTCN_4769 | 25999 |
| CTCN_2399 | 15813 | CTCN_4770 | 26000 |
| CTCN_2400 | 15814 | TTCN_5103 | 26001 |
| TTCN_2760 | 15815 | CTCN_4771 | 26002 |
| GTCN_1469 | 15816 | TTCN_5104 | 26003 |
| ATCN_1679 | 15817 | ATCN_3210 | 26004 |
| ATCN_1680 | 15818 | TTCN_5105 | 26005 |
| ATCN_1681 | 15819 | CTCN_4772 | 26006 |
| CTCN_2401 | 15820 | GTCN_2699 | 26007 |
| CTCN_2402 | 15821 | TTCN_5106 | 26008 |
| TTCN_2761 | 15822 | ATCN_3211 | 26009 |
| CTCN_2403 | 15823 | TTCN_5107 | 26010 |
| GTCN_1470 | 15824 | ATCN_3212 | 26011 |
| CTCN_2404 | 15825 | TTCN_5108 | 26012 |
| GTCN_1471 | 15826 | ATCN_3213 | 26013 |

| | | | |
|---|---|---|---|
| ATCN_1682 | 15827 | CTCN_4773 | 26014 |
| TTCN_2762 | 15828 | TTCN_5109 | 26015 |
| GTCN_1472 | 15829 | GTCN_2700 | 26016 |
| CTCN_2405 | 15830 | ATCN_3214 | 26017 |
| GTCN_1473 | 15831 | CTCN_4774 | 26018 |
| TTCN_2763 | 15832 | GTCN_2701 | 26019 |
| CTCN_2406 | 15833 | CTCN_4775 | 26020 |
| TTCN_2764 | 15834 | CTCN_4776 | 26021 |
| ATCN_1683 | 15835 | CTCN_4777 | 26022 |
| ATCN_1684 | 15836 | TTCN_5110 | 26023 |
| GTCN_1474 | 15837 | CTCN_4778 | 26024 |
| ATCN_1685 | 15838 | ATCN_3215 | 26025 |
| GTCN_1475 | 15839 | TTCN_5111 | 26026 |
| TTCN_2765 | 15840 | GTCN_2702 | 26027 |
| TTCN_2766 | 15841 | TTCN_5112 | 26028 |
| ATCN_1686 | 15842 | CTCN_4779 | 26029 |
| TTCN_2767 | 15843 | CTCN_4780 | 26030 |
| CTCN_2407 | 15844 | GTCN_2703 | 26031 |
| TTCN_2768 | 15845 | GTCN_2704 | 26032 |
| TTCN_2769 | 15846 | TTCN_5113 | 26033 |
| TTCN_2770 | 15847 | CTCN_4781 | 26034 |
| TTCN_2771 | 15848 | CTCN_4782 | 26035 |
| TTCN_2772 | 15849 | TTCN_5114 | 26036 |
| ATCN_1687 | 15850 | TTCN_5115 | 26037 |
| TTCN_2773 | 15851 | ATCN_3216 | 26038 |
| CTCN_2408 | 15852 | ATCN_3217 | 26039 |
| CTCN_2409 | 15853 | TTCN_5116 | 26040 |
| TTCN_2774 | 15854 | CTCN_4783 | 26041 |
| GTCN_1476 | 15855 | CTCN_4784 | 26042 |
| TTCN_2775 | 15856 | GTCN_2705 | 26043 |
| GTCN_1477 | 15857 | ATCN_3218 | 26044 |
| TTCN_2776 | 15858 | TTCN_5117 | 26045 |
| CTCN_2410 | 15859 | GTCN_2706 | 26046 |
| ATCN_1688 | 15860 | TTCN_5118 | 26047 |
| TTCN_2777 | 15861 | TTCN_5119 | 26048 |
| CTCN_2411 | 15862 | CTCN_4785 | 26049 |
| GTCN_1478 | 15863 | CTCN_4786 | 26050 |
| TTCN_2778 | 15864 | CTCN_4787 | 26051 |
| TTCN_2779 | 15865 | GTCN_2707 | 26052 |
| GTCN_1479 | 15866 | CTCN_4788 | 26053 |
| CTCN_2412 | 15867 | GTCN_2708 | 26054 |
| TTCN_2780 | 15868 | CTCN_4789 | 26055 |
| ATCN_1689 | 15869 | CTCN_4790 | 26056 |
| TTCN_2781 | 15870 | ATCN_3219 | 26057 |
| CTCN_2413 | 15871 | TTCN_5120 | 26058 |
| CTCN_2414 | 15872 | TTCN_5121 | 26059 |
| TTCN_2782 | 15873 | TTCN_5122 | 26060 |
| TTCN_2783 | 15874 | GTCN_2709 | 26061 |
| ATCN_1690 | 15875 | CTCN_4791 | 26062 |
| TTCN_2784 | 15876 | ATCN_3220 | 26063 |
| TTCN_2785 | 15877 | TTCN_5123 | 26064 |
| TTCN_2786 | 15878 | TTCN_5124 | 26065 |
| CTCN_2415 | 15879 | GTCN_2710 | 26066 |
| ATCN_1691 | 15880 | CTCN_4792 | 26067 |
| GTCN_1480 | 15881 | GTCN_2711 | 26068 |

FIG. 36 (continued)

| | | | |
|---|---|---|---|
| CTCN_2416 | 15882 | TTCN_5125 | 26069 |
| TTCN_2787 | 15883 | ATCN_3221 | 26070 |
| TTCN_2788 | 15884 | CTCN_4793 | 26071 |
| CTCN_2417 | 15885 | GTCN_2712 | 26072 |
| CTCN_2418 | 15886 | CTCN_4794 | 26073 |
| TTCN_2789 | 15887 | TTCN_5126 | 26074 |
| ATCN_1692 | 15888 | TTCN_5127 | 26075 |
| ATCN_1693 | 15889 | ATCN_3222 | 26076 |
| GTCN_1481 | 15890 | TTCN_5128 | 26077 |
| CTCN_2419 | 15891 | TTCN_5129 | 26078 |
| TTCN_2790 | 15892 | ATCN_3223 | 26079 |
| CTCN_2420 | 15893 | ATCN_3224 | 26080 |
| CTCN_2421 | 15894 | ATCN_3225 | 26081 |
| CTCN_2422 | 15895 | ATCN_3226 | 26082 |
| TTCN_2791 | 15896 | GTCN_2713 | 26083 |
| TTCN_2792 | 15897 | GTCN_2714 | 26084 |
| CTCN_2423 | 15898 | ATCN_3227 | 26085 |
| TTCN_2793 | 15899 | ATCN_3228 | 26086 |
| ATCN_1694 | 15900 | TTCN_5130 | 26087 |
| ATCN_1695 | 15901 | TTCN_5131 | 26088 |
| TTCN_2794 | 15902 | ATCN_3229 | 26089 |
| ATCN_1696 | 15903 | ATCN_3230 | 26090 |
| TTCN_2795 | 15904 | TTCN_5132 | 26091 |
| TTCN_2796 | 15905 | GTCN_2715 | 26092 |
| GTCN_1482 | 15906 | CTCN_4795 | 26093 |
| CTCN_2424 | 15907 | GTCN_2716 | 26094 |
| CTCN_2425 | 15908 | CTCN_4796 | 26095 |
| CTCN_2426 | 15909 | TTCN_5133 | 26096 |
| CTCN_2427 | 15910 | ATCN_3231 | 26097 |
| TTCN_2797 | 15911 | GTCN_2717 | 26098 |
| ATCN_1697 | 15912 | CTCN_4797 | 26099 |
| ATCN_1698 | 15913 | CTCN_4798 | 26100 |
| CTCN_2428 | 15914 | CTCN_4799 | 26101 |
| CTCN_2429 | 15915 | TTCN_5134 | 26102 |
| CTCN_2430 | 15916 | GTCN_2718 | 26103 |
| CTCN_2431 | 15917 | GTCN_2719 | 26104 |
| ATCN_1699 | 15918 | CTCN_4800 | 26105 |
| TTCN_2798 | 15919 | ATCN_3232 | 26106 |
| GTCN_1483 | 15920 | CTCN_4801 | 26107 |
| TTCN_2799 | 15921 | ATCN_3233 | 26108 |
| ATCN_1700 | 15922 | CTCN_4802 | 26109 |
| TTCN_2800 | 15923 | TTCN_5135 | 26110 |
| TTCN_2801 | 15924 | TTCN_5136 | 26111 |
| ATCN_1701 | 15925 | CTCN_4803 | 26112 |
| CTCN_2432 | 15926 | CTCN_4804 | 26113 |
| ATCN_1702 | 15927 | TTCN_5137 | 26114 |
| TTCN_2802 | 15928 | ATCN_3234 | 26115 |
| ATCN_1703 | 15929 | CTCN_4805 | 26116 |
| CTCN_2433 | 15930 | CTCN_4806 | 26117 |
| TTCN_2803 | 15931 | TTCN_5138 | 26118 |
| ATCN_1704 | 15932 | CTCN_4807 | 26119 |
| GTCN_1484 | 15933 | CTCN_4808 | 26120 |
| ATCN_1705 | 15934 | CTCN_4809 | 26121 |
| TTCN_2804 | 15935 | CTCN_4810 | 26122 |
| ATCN_1706 | 15936 | CTCN_4811 | 26123 |

| | | | |
|---|---|---|---|
| CTCN_2434 | 15937 | ATCN_3235 | 26124 |
| GTCN_1485 | 15938 | ATCN_3236 | 26125 |
| CTCN_2435 | 15939 | TTCN_5139 | 26126 |
| GTCN_1486 | 15940 | TTCN_5140 | 26127 |
| CTCN_2436 | 15941 | GTCN_2720 | 26128 |
| CTCN_2437 | 15942 | TTCN_5141 | 26129 |
| GTCN_1487 | 15943 | ATCN_3237 | 26130 |
| CTCN_2438 | 15944 | TTCN_5142 | 26131 |
| ATCN_1707 | 15945 | TTCN_5143 | 26132 |
| ATCN_1708 | 15946 | GTCN_2721 | 26133 |
| CTCN_2439 | 15947 | TTCN_5144 | 26134 |
| CTCN_2440 | 15948 | ATCN_3238 | 26135 |
| CTCN_2441 | 15949 | ATCN_3239 | 26136 |
| CTCN_2442 | 15950 | TTCN_5145 | 26137 |
| TTCN_2805 | 15951 | TTCN_5146 | 26138 |
| TTCN_2806 | 15952 | TTCN_5147 | 26139 |
| CTCN_2443 | 15953 | TTCN_5148 | 26140 |
| CTCN_2444 | 15954 | ATCN_3240 | 26141 |
| CTCN_2445 | 15955 | TTCN_5149 | 26142 |
| GTCN_1488 | 15956 | CTCN_4812 | 26143 |
| CTCN_2446 | 15957 | CTCN_4813 | 26144 |
| GTCN_1489 | 15958 | CTCN_4814 | 26145 |
| CTCN_2447 | 15959 | CTCN_4815 | 26146 |
| TTCN_2807 | 15960 | ATCN_3241 | 26147 |
| ATCN_1709 | 15961 | CTCN_4816 | 26148 |
| GTCN_1490 | 15962 | GTCN_2722 | 26149 |
| CTCN_2448 | 15963 | GTCN_2723 | 26150 |
| ATCN_1710 | 15964 | ATCN_3242 | 26151 |
| ATCN_1711 | 15965 | TTCN_5150 | 26152 |
| CTCN_2449 | 15966 | CTCN_4817 | 26153 |
| GTCN_1491 | 15967 | CTCN_4818 | 26154 |
| CTCN_2450 | 15968 | ATCN_3243 | 26155 |
| ATCN_1712 | 15969 | ATCN_3244 | 26156 |
| ATCN_1713 | 15970 | GTCN_2724 | 26157 |
| CTCN_2451 | 15971 | CTCN_4819 | 26158 |
| CTCN_2452 | 15972 | ATCN_3245 | 26159 |
| ATCN_1714 | 15973 | CTCN_4820 | 26160 |
| CTCN_2453 | 15974 | CTCN_4821 | 26161 |
| CTCN_2454 | 15975 | CTCN_4822 | 26162 |
| ATCN_1715 | 15976 | TTCN_5151 | 26163 |
| ATCN_1716 | 15977 | CTCN_4823 | 26164 |
| TTCN_2808 | 15978 | TTCN_5152 | 26165 |
| CTCN_2455 | 15979 | CTCN_4824 | 26166 |
| TTCN_2809 | 15980 | CTCN_4825 | 26167 |
| GTCN_1492 | 15981 | TTCN_5153 | 26168 |
| CTCN_2456 | 15982 | CTCN_4826 | 26169 |
| TTCN_2810 | 15983 | CTCN_4827 | 26170 |
| ATCN_1717 | 15984 | GTCN_2725 | 26171 |
| GTCN_1493 | 15985 | CTCN_4828 | 26172 |
| CTCN_2457 | 15986 | CTCN_4829 | 26173 |
| CTCN_2458 | 15987 | GTCN_2726 | 26174 |
| TTCN_2811 | 15988 | CTCN_4830 | 26175 |
| TTCN_2812 | 15989 | CTCN_4831 | 26176 |
| CTCN_2459 | 15990 | GTCN_2727 | 26177 |
| TTCN_2813 | 15991 | TTCN_5154 | 26178 |

FIG. 36 (continued)

| | | | |
|---|---|---|---|
| TTCN_2814 | 15992 | CTCN_4832 | 26179 |
| GTCN_1494 | 15993 | CTCN_4833 | 26180 |
| TTCN_2815 | 15994 | GTCN_2728 | 26181 |
| CTCN_2460 | 15995 | TTCN_5155 | 26182 |
| ATCN_1718 | 15996 | TTCN_5156 | 26183 |
| ATCN_1719 | 15997 | GTCN_2729 | 26184 |
| TTCN_2816 | 15998 | GTCN_2730 | 26185 |
| TTCN_2817 | 15999 | TTCN_5157 | 26186 |
| CTCN_2461 | 16000 | TTCN_5158 | 26187 |
| GTCN_1495 | 16001 | CTCN_4834 | 26188 |
| CTCN_2462 | 16002 | GTCN_2731 | 26189 |
| CTCN_2463 | 16003 | TTCN_5159 | 26190 |
| CTCN_2464 | 16004 | TTCN_5160 | 26191 |
| TTCN_2818 | 16005 | TTCN_5161 | 26192 |
| TTCN_2819 | 16006 | CTCN_4835 | 26193 |
| CTCN_2465 | 16007 | CTCN_4836 | 26194 |
| CTCN_2466 | 16008 | TTCN_5162 | 26195 |
| GTCN_1496 | 16009 | TTCN_5163 | 26196 |
| CTCN_2467 | 16010 | ATCN_3246 | 26197 |
| TTCN_2820 | 16011 | CTCN_4837 | 26198 |
| TTCN_2821 | 16012 | ATCN_3247 | 26199 |
| TTCN_2822 | 16013 | CTCN_4838 | 26200 |
| CTCN_2468 | 16014 | ATCN_3248 | 26201 |
| CTCN_2469 | 16015 | TTCN_5164 | 26202 |
| TTCN_2823 | 16016 | ATCN_3249 | 26203 |
| CTCN_2470 | 16017 | CTCN_4839 | 26204 |
| ATCN_1720 | 16018 | GTCN_2732 | 26205 |
| TTCN_2824 | 16019 | TTCN_5165 | 26206 |
| TTCN_2825 | 16020 | GTCN_2733 | 26207 |
| CTCN_2471 | 16021 | CTCN_4840 | 26208 |
| TTCN_2826 | 16022 | GTCN_2734 | 26209 |
| CTCN_2472 | 16023 | TTCN_5166 | 26210 |
| TTCN_2827 | 16024 | CTCN_4841 | 26211 |
| TTCN_2828 | 16025 | GTCN_2735 | 26212 |
| ATCN_1721 | 16026 | CTCN_4842 | 26213 |
| ATCN_1722 | 16027 | CTCN_4843 | 26214 |
| ATCN_1723 | 16028 | TTCN_5167 | 26215 |
| TTCN_2829 | 16029 | GTCN_2736 | 26216 |
| ATCN_1724 | 16030 | GTCN_2737 | 26217 |
| TTCN_2830 | 16031 | ATCN_3250 | 26218 |
| CTCN_2473 | 16032 | CTCN_4844 | 26219 |
| GTCN_1497 | 16033 | ATCN_3251 | 26220 |
| ATCN_1725 | 16034 | TTCN_5168 | 26221 |
| ATCN_1726 | 16035 | TTCN_5169 | 26222 |
| TTCN_2831 | 16036 | CTCN_4845 | 26223 |
| TTCN_2832 | 16037 | CTCN_4846 | 26224 |
| ATCN_1727 | 16038 | GTCN_2738 | 26225 |
| CTCN_2474 | 16039 | GTCN_2739 | 26226 |
| GTCN_1498 | 16040 | ATCN_3252 | 26227 |
| TTCN_2833 | 16041 | CTCN_4847 | 26228 |
| ATCN_1728 | 16042 | GTCN_2740 | 26229 |
| GTCN_1499 | 16043 | GTCN_2741 | 26230 |
| TTCN_2834 | 16044 | GTCN_2742 | 26231 |
| CTCN_2475 | 16045 | CTCN_4848 | 26232 |
| ATCN_1729 | 16046 | ATCN_3253 | 26233 |

| | | | |
|---|---|---|---|
| ATCN_1730 | 16047 | GTCN_2743 | 26234 |
| CTCN_2476 | 16048 | GTCN_2744 | 26235 |
| CTCN_2477 | 16049 | GTCN_2745 | 26236 |
| TTCN_2835 | 16050 | CTCN_4849 | 26237 |
| TTCN_2836 | 16051 | ATCN_3254 | 26238 |
| TTCN_2837 | 16052 | GTCN_2746 | 26239 |
| CTCN_2478 | 16053 | CTCN_4850 | 26240 |
| ATCN_1731 | 16054 | TTCN_5170 | 26241 |
| CTCN_2479 | 16055 | TTCN_5171 | 26242 |
| TTCN_2838 | 16056 | ATCN_3255 | 26243 |
| TTCN_2839 | 16057 | TTCN_5172 | 26244 |
| TTCN_2840 | 16058 | CTCN_4851 | 26245 |
| TTCN_2841 | 16059 | CTCN_4852 | 26246 |
| CTCN_2480 | 16060 | CTCN_4853 | 26247 |
| TTCN_2842 | 16061 | CTCN_4854 | 26248 |
| TTCN_2843 | 16062 | CTCN_4855 | 26249 |
| GTCN_1500 | 16063 | TTCN_5173 | 26250 |
| GTCN_1501 | 16064 | CTCN_4856 | 26251 |
| CTCN_2481 | 16065 | CTCN_4857 | 26252 |
| GTCN_1502 | 16066 | TTCN_5174 | 26253 |
| ATCN_1732 | 16067 | CTCN_4858 | 26254 |
| CTCN_2482 | 16068 | CTCN_4859 | 26255 |
| TTCN_2844 | 16069 | TTCN_5175 | 26256 |
| GTCN_1503 | 16070 | TTCN_5176 | 26257 |
| CTCN_2483 | 16071 | GTCN_2747 | 26258 |
| TTCN_2845 | 16072 | TTCN_5177 | 26259 |
| TTCN_2846 | 16073 | CTCN_4860 | 26260 |
| TTCN_2847 | 16074 | ATCN_3256 | 26261 |
| CTCN_2484 | 16075 | GTCN_2748 | 26262 |
| CTCN_2485 | 16076 | CTCN_4861 | 26263 |
| CTCN_2486 | 16077 | TTCN_5178 | 26264 |
| TTCN_2848 | 16078 | CTCN_4862 | 26265 |
| ATCN_1733 | 16079 | CTCN_4863 | 26266 |
| ATCN_1734 | 16080 | CTCN_4864 | 26267 |
| GTCN_1504 | 16081 | ATCN_3257 | 26268 |
| CTCN_2487 | 16082 | CTCN_4865 | 26269 |
| CTCN_2488 | 16083 | CTCN_4866 | 26270 |
| CTCN_2489 | 16084 | TTCN_5179 | 26271 |
| TTCN_2849 | 16085 | GTCN_2749 | 26272 |
| CTCN_2490 | 16086 | ATCN_3258 | 26273 |
| CTCN_2491 | 16087 | TTCN_5180 | 26274 |
| TTCN_2850 | 16088 | GTCN_2750 | 26275 |
| ATCN_1735 | 16089 | CTCN_4867 | 26276 |
| GTCN_1505 | 16090 | ATCN_3259 | 26277 |
| TTCN_2851 | 16091 | ATCN_3260 | 26278 |
| TTCN_2852 | 16092 | GTCN_2751 | 26279 |
| ATCN_1736 | 16093 | TTCN_5181 | 26280 |
| TTCN_2853 | 16094 | CTCN_4868 | 26281 |
| CTCN_2492 | 16095 | ATCN_3261 | 26282 |
| TTCN_2854 | 16096 | GTCN_2752 | 26283 |
| GTCN_1506 | 16097 | ATCN_3262 | 26284 |
| ATCN_1737 | 16098 | GTCN_2753 | 26285 |
| ATCN_1738 | 16099 | TTCN_5182 | 26286 |
| GTCN_1507 | 16100 | CTCN_4869 | 26287 |
| GTCN_1508 | 16101 | TTCN_5183 | 26288 |

FIG. 36 (continued)

| | | | | | | | |
|---|---|---|---|---|---|---|---|
| CTCN_2493 | 16102 | TTCN_5184 | 26289 | CTCN_2509 | 16157 | GTCN_2762 | 26344 |
| GTCN_1509 | 16103 | CTCN_4870 | 26290 | TTCN_2867 | 16158 | TTCN_5207 | 26345 |
| CTCN_2494 | 16104 | TTCN_5185 | 26291 | CTCN_2510 | 16159 | ATCN_3270 | 26346 |
| ATCN_1739 | 16105 | CTCN_4871 | 26292 | ATCN_1755 | 16160 | TTCN_5208 | 26347 |
| ATCN_1740 | 16106 | CTCN_4872 | 26293 | TTCN_2868 | 16161 | CTCN_4887 | 26348 |
| ATCN_1741 | 16107 | TTCN_5186 | 26294 | ATCN_1756 | 16162 | ATCN_3271 | 26349 |
| ATCN_1742 | 16108 | ATCN_3263 | 26295 | ATCN_1757 | 16163 | TTCN_5209 | 26350 |
| CTCN_2495 | 16109 | TTCN_5187 | 26296 | ATCN_1758 | 16164 | TTCN_5210 | 26351 |
| TTCN_2855 | 16110 | TTCN_5188 | 26297 | CTCN_2511 | 16165 | CTCN_4888 | 26352 |
| CTCN_2496 | 16111 | CTCN_4873 | 26298 | CTCN_2512 | 16166 | CTCN_4889 | 26353 |
| ATCN_1743 | 16112 | GTCN_2754 | 26299 | CTCN_2513 | 16167 | TTCN_5211 | 26354 |
| ATCN_1744 | 16113 | CTCN_4874 | 26300 | CTCN_2514 | 16168 | TTCN_5212 | 26355 |
| ATCN_1745 | 16114 | TTCN_5189 | 26301 | TTCN_2869 | 16169 | CTCN_4890 | 26356 |
| ATCN_1746 | 16115 | TTCN_5190 | 26302 | TTCN_2870 | 16170 | GTCN_2763 | 26357 |
| TTCN_2856 | 16116 | CTCN_4875 | 26303 | CTCN_2515 | 16171 | TTCN_5213 | 26358 |
| CTCN_2497 | 16117 | ATCN_3264 | 26304 | ATCN_1759 | 16172 | CTCN_4891 | 26359 |
| GTCN_1510 | 16118 | ATCN_3265 | 26305 | ATCN_1760 | 16173 | GTCN_2764 | 26360 |
| TTCN_2857 | 16119 | CTCN_4876 | 26306 | TTCN_2871 | 16174 | CTCN_4892 | 26361 |
| GTCN_1511 | 16120 | GTCN_2755 | 26307 | TTCN_2872 | 16175 | TTCN_5214 | 26362 |
| ATCN_1747 | 16121 | ATCN_3266 | 26308 | ATCN_1761 | 16176 | GTCN_2765 | 26363 |
| CTCN_2498 | 16122 | TTCN_5191 | 26309 | CTCN_2516 | 16177 | CTCN_4893 | 26364 |
| CTCN_2499 | 16123 | TTCN_5192 | 26310 | TTCN_2873 | 16178 | TTCN_5215 | 26365 |
| CTCN_2500 | 16124 | TTCN_5193 | 26311 | ATCN_1762 | 16179 | TTCN_5216 | 26366 |
| GTCN_1512 | 16125 | ATCN_3267 | 26312 | ATCN_1763 | 16180 | TTCN_5217 | 26367 |
| ATCN_1748 | 16126 | TTCN_5194 | 26313 | ATCN_1764 | 16181 | GTCN_2766 | 26368 |
| ATCN_1749 | 16127 | GTCN_2756 | 26314 | ATCN_1765 | 16182 | TTCN_5218 | 26369 |
| CTCN_2501 | 16128 | TTCN_5195 | 26315 | GTCN_1520 | 16183 | TTCN_5219 | 26370 |
| CTCN_2502 | 16129 | TTCN_5196 | 26316 | GTCN_1521 | 16184 | TTCN_5220 | 26371 |
| ATCN_1750 | 16130 | GTCN_2757 | 26317 | CTCN_2517 | 16185 | ATCN_3272 | 26372 |
| TTCN_2858 | 16131 | GTCN_2758 | 26318 | TTCN_2874 | 16186 | ATCN_3273 | 26373 |
| TTCN_2859 | 16132 | CTCN_4877 | 26319 | CTCN_2518 | 16187 | CTCN_4894 | 26374 |
| ATCN_1751 | 16133 | CTCN_4878 | 26320 | TTCN_2875 | 16188 | CTCN_4895 | 26375 |
| ATCN_1752 | 16134 | CTCN_4879 | 26321 | GTCN_1522 | 16189 | CTCN_4896 | 26376 |
| TTCN_2860 | 16135 | GTCN_2759 | 26322 | ATCN_1766 | 16190 | CTCN_4897 | 26377 |
| TTCN_2861 | 16136 | CTCN_4880 | 26323 | CTCN_2519 | 16191 | ATCN_3274 | 26378 |
| GTCN_1513 | 16137 | CTCN_4881 | 26324 | TTCN_2876 | 16192 | TTCN_5221 | 26379 |
| GTCN_1514 | 16138 | CTCN_4882 | 26325 | TTCN_2877 | 16193 | GTCN_2767 | 26380 |
| CTCN_2503 | 16139 | ATCN_3268 | 26326 | ATCN_1767 | 16194 | GTCN_2768 | 26381 |
| GTCN_1515 | 16140 | ATCN_3269 | 26327 | GTCN_1523 | 16195 | GTCN_2769 | 26382 |
| GTCN_1516 | 16141 | CTCN_4883 | 26328 | CTCN_2520 | 16196 | GTCN_2770 | 26383 |
| GTCN_1517 | 16142 | TTCN_5197 | 26329 | CTCN_2521 | 16197 | CTCN_4898 | 26384 |
| CTCN_2504 | 16143 | TTCN_5198 | 26330 | CTCN_2522 | 16198 | GTCN_2771 | 26385 |
| CTCN_2505 | 16144 | TTCN_5199 | 26331 | GTCN_1524 | 16199 | TTCN_5222 | 26386 |
| ATCN_1753 | 16145 | TTCN_5200 | 26332 | TTCN_2878 | 16200 | GTCN_2772 | 26387 |
| GTCN_1518 | 16146 | TTCN_5201 | 26333 | CTCN_2523 | 16201 | TTCN_5223 | 26388 |
| ATCN_1754 | 16147 | TTCN_5202 | 26334 | ATCN_1768 | 16202 | TTCN_5224 | 26389 |
| CTCN_2506 | 16148 | TTCN_5203 | 26335 | TTCN_2879 | 16203 | CTCN_4899 | 26390 |
| TTCN_2862 | 16149 | CTCN_4884 | 26336 | TTCN_2880 | 16204 | CTCN_4900 | 26391 |
| TTCN_2863 | 16150 | TTCN_5204 | 26337 | TTCN_2881 | 16205 | GTCN_2773 | 26392 |
| CTCN_2507 | 16151 | TTCN_5205 | 26338 | ATCN_1769 | 16206 | GTCN_2774 | 26393 |
| TTCN_2864 | 16152 | CTCN_4885 | 26339 | ATCN_1770 | 16207 | TTCN_5225 | 26394 |
| GTCN_1519 | 16153 | GTCN_2760 | 26340 | ATCN_1771 | 16208 | TTCN_5226 | 26395 |
| CTCN_2508 | 16154 | TTCN_5206 | 26341 | CTCN_2524 | 16209 | ATCN_3275 | 26396 |
| TTCN_2865 | 16155 | CTCN_4886 | 26342 | CTCN_2525 | 16210 | ATCN_3276 | 26397 |
| TTCN_2866 | 16156 | GTCN_2761 | 26343 | ATCN_1772 | 16211 | CTCN_4901 | 26398 |

FIG. 36 (continued)

| | | | |
|---|---|---|---|
| ATCN_1773 | 16212 | CTCN_4902 | 26399 |
| TTCN_2882 | 16213 | TTCN_5227 | 26400 |
| GTCN_1525 | 16214 | TTCN_5228 | 26401 |
| CTCN_2526 | 16215 | ATCN_3277 | 26402 |
| ATCN_1774 | 16216 | ATCN_3278 | 26403 |
| ATCN_1775 | 16217 | GTCN_2775 | 26404 |
| TTCN_2883 | 16218 | TTCN_5229 | 26405 |
| ATCN_1776 | 16219 | ATCN_3279 | 26406 |
| CTCN_2527 | 16220 | TTCN_5230 | 26407 |
| CTCN_2528 | 16221 | GTCN_2776 | 26408 |
| TTCN_2884 | 16222 | CTCN_4903 | 26409 |
| TTCN_2885 | 16223 | GTCN_2777 | 26410 |
| TTCN_2886 | 16224 | GTCN_2778 | 26411 |
| CTCN_2529 | 16225 | ATCN_3280 | 26412 |
| GTCN_1526 | 16226 | TTCN_5231 | 26413 |
| CTCN_2530 | 16227 | TTCN_5232 | 26414 |
| TTCN_2887 | 16228 | CTCN_4904 | 26415 |
| ATCN_1777 | 16229 | ATCN_3281 | 26416 |
| GTCN_1527 | 16230 | TTCN_5233 | 26417 |
| TTCN_2888 | 16231 | CTCN_4905 | 26418 |
| CTCN_2531 | 16232 | GTCN_2779 | 26419 |
| TTCN_2889 | 16233 | GTCN_2780 | 26420 |
| ATCN_1778 | 16234 | CTCN_4906 | 26421 |
| TTCN_2890 | 16235 | ATCN_3282 | 26422 |
| CTCN_2532 | 16236 | TTCN_5234 | 26423 |
| TTCN_2891 | 16237 | ATCN_3283 | 26424 |
| CTCN_2533 | 16238 | GTCN_2781 | 26425 |
| TTCN_2892 | 16239 | CTCN_4907 | 26426 |
| GTCN_1528 | 16240 | CTCN_4908 | 26427 |
| TTCN_2893 | 16241 | CTCN_4909 | 26428 |
| ATCN_1779 | 16242 | CTCN_4910 | 26429 |
| TTCN_2894 | 16243 | TTCN_5235 | 26430 |
| ATCN_1780 | 16244 | ATCN_3284 | 26431 |
| CTCN_2534 | 16245 | TTCN_5236 | 26432 |
| CTCN_2535 | 16246 | CTCN_4911 | 26433 |
| CTCN_2536 | 16247 | CTCN_4912 | 26434 |
| CTCN_2537 | 16248 | CTCN_4913 | 26435 |
| ATCN_1781 | 16249 | GTCN_2782 | 26436 |
| ATCN_1782 | 16250 | ATCN_3285 | 26437 |
| ATCN_1783 | 16251 | ATCN_3286 | 26438 |
| CTCN_2538 | 16252 | GTCN_2783 | 26439 |
| GTCN_1529 | 16253 | TTCN_5237 | 26440 |
| GTCN_1530 | 16254 | TTCN_5238 | 26441 |
| ATCN_1784 | 16255 | TTCN_5239 | 26442 |
| TTCN_2895 | 16256 | ATCN_3287 | 26443 |
| ATCN_1785 | 16257 | ATCN_3288 | 26444 |
| CTCN_2539 | 16258 | CTCN_4914 | 26445 |
| GTCN_1531 | 16259 | TTCN_5240 | 26446 |
| ATCN_1786 | 16260 | ATCN_3289 | 26447 |
| ATCN_1787 | 16261 | GTCN_2784 | 26448 |
| GTCN_1532 | 16262 | GTCN_2785 | 26449 |
| CTCN_2540 | 16263 | TTCN_5241 | 26450 |
| CTCN_2541 | 16264 | TTCN_5242 | 26451 |
| GTCN_1533 | 16265 | CTCN_4915 | 26452 |
| TTCN_2896 | 16266 | ATCN_3290 | 26453 |

| | | | |
|---|---|---|---|
| GTCN_1534 | 16267 | CTCN_4916 | 26454 |
| TTCN_2897 | 16268 | CTCN_4917 | 26455 |
| GTCN_1535 | 16269 | TTCN_5243 | 26456 |
| ATCN_1788 | 16270 | GTCN_2786 | 26457 |
| TTCN_2898 | 16271 | ATCN_3291 | 26458 |
| TTCN_2899 | 16272 | ATCN_3292 | 26459 |
| TTCN_2900 | 16273 | TTCN_5244 | 26460 |
| TTCN_2901 | 16274 | CTCN_4918 | 26461 |
| CTCN_2542 | 16275 | ATCN_3293 | 26462 |
| ATCN_1789 | 16276 | ATCN_3294 | 26463 |
| TTCN_2902 | 16277 | CTCN_4919 | 26464 |
| CTCN_2543 | 16278 | ATCN_3295 | 26465 |
| TTCN_2903 | 16279 | TTCN_5245 | 26466 |
| ATCN_1790 | 16280 | CTCN_4920 | 26467 |
| TTCN_2904 | 16281 | ATCN_3296 | 26468 |
| GTCN_1536 | 16282 | ATCN_3297 | 26469 |
| TTCN_2905 | 16283 | ATCN_3298 | 26470 |
| CTCN_2544 | 16284 | CTCN_4921 | 26471 |
| CTCN_2545 | 16285 | TTCN_5246 | 26472 |
| CTCN_2546 | 16286 | GTCN_2787 | 26473 |
| ATCN_1791 | 16287 | TTCN_5247 | 26474 |
| ATCN_1792 | 16288 | CTCN_4922 | 26475 |
| TTCN_2906 | 16289 | ATCN_3299 | 26476 |
| TTCN_2907 | 16290 | TTCN_5248 | 26477 |
| GTCN_1537 | 16291 | GTCN_2788 | 26478 |
| CTCN_2547 | 16292 | TTCN_5249 | 26479 |
| TTCN_2908 | 16293 | ATCN_3300 | 26480 |
| TTCN_2909 | 16294 | ATCN_3301 | 26481 |
| GTCN_1538 | 16295 | ATCN_3302 | 26482 |
| ATCN_1793 | 16296 | CTCN_4923 | 26483 |
| TTCN_2910 | 16297 | GTCN_2789 | 26484 |
| ATCN_1794 | 16298 | TTCN_5250 | 26485 |
| ATCN_1795 | 16299 | ATCN_3303 | 26486 |
| ATCN_1796 | 16300 | CTCN_4924 | 26487 |
| TTCN_2911 | 16301 | ATCN_3304 | 26488 |
| ATCN_1797 | 16302 | CTCN_4925 | 26489 |
| CTCN_2548 | 16303 | GTCN_2790 | 26490 |
| ATCN_1798 | 16304 | ATCN_3305 | 26491 |
| ATCN_1799 | 16305 | TTCN_5251 | 26492 |
| TTCN_2912 | 16306 | ATCN_3306 | 26493 |
| TTCN_2913 | 16307 | ATCN_3307 | 26494 |
| ATCN_1800 | 16308 | ATCN_3308 | 26495 |
| TTCN_2914 | 16309 | GTCN_2791 | 26496 |
| GTCN_1539 | 16310 | CTCN_4926 | 26497 |
| ATCN_1801 | 16311 | ATCN_3309 | 26498 |
| TTCN_2915 | 16312 | ATCN_3310 | 26499 |
| TTCN_2916 | 16313 | ATCN_3311 | 26500 |
| CTCN_2549 | 16314 | CTCN_4927 | 26501 |
| TTCN_2917 | 16315 | CTCN_4928 | 26502 |
| TTCN_2918 | 16316 | CTCN_4929 | 26503 |
| TTCN_2919 | 16317 | ATCN_3312 | 26504 |
| ATCN_1802 | 16318 | TTCN_5252 | 26505 |
| ATCN_1803 | 16319 | CTCN_4930 | 26506 |
| TTCN_2920 | 16320 | TTCN_5253 | 26507 |
| CTCN_2550 | 16321 | ATCN_3313 | 26508 |

FIG. 36 (continued)

| | | | |
|---|---|---|---|
| TTCN_2921 | 16322 | TTCN_5254 | 26509 |
| TTCN_2922 | 16323 | TTCN_5255 | 26510 |
| CTCN_2551 | 16324 | TTCN_5256 | 26511 |
| TTCN_2923 | 16325 | TTCN_5257 | 26512 |
| TTCN_2924 | 16326 | CTCN_4931 | 26513 |
| TTCN_2925 | 16327 | CTCN_4932 | 26514 |
| GTCN_1540 | 16328 | CTCN_4933 | 26515 |
| TTCN_2926 | 16329 | TTCN_5258 | 26516 |
| TTCN_2927 | 16330 | TTCN_5259 | 26517 |
| TTCN_2928 | 16331 | TTCN_5260 | 26518 |
| TTCN_2929 | 16332 | ATCN_3314 | 26519 |
| TTCN_2930 | 16333 | ATCN_3315 | 26520 |
| CTCN_2552 | 16334 | GTCN_2792 | 26521 |
| GTCN_1541 | 16335 | GTCN_2793 | 26522 |
| ATCN_1804 | 16336 | CTCN_4934 | 26523 |
| CTCN_2553 | 16337 | TTCN_5261 | 26524 |
| GTCN_1542 | 16338 | GTCN_2794 | 26525 |
| TTCN_2931 | 16339 | GTCN_2795 | 26526 |
| TTCN_2932 | 16340 | ATCN_3316 | 26527 |
| CTCN_2554 | 16341 | CTCN_4935 | 26528 |
| TTCN_2933 | 16342 | ATCN_3317 | 26529 |
| GTCN_1543 | 16343 | TTCN_5262 | 26530 |
| TTCN_2934 | 16344 | CTCN_4936 | 26531 |
| CTCN_2555 | 16345 | GTCN_2796 | 26532 |
| CTCN_2556 | 16346 | GTCN_2797 | 26533 |
| GTCN_1544 | 16347 | CTCN_4937 | 26534 |
| CTCN_2557 | 16348 | GTCN_2798 | 26535 |
| CTCN_2558 | 16349 | CTCN_4938 | 26536 |
| ATCN_1805 | 16350 | GTCN_2799 | 26537 |
| CTCN_2559 | 16351 | TTCN_5263 | 26538 |
| TTCN_2935 | 16352 | ATCN_3318 | 26539 |
| TTCN_2936 | 16353 | CTCN_4939 | 26540 |
| CTCN_2560 | 16354 | ATCN_3319 | 26541 |
| GTCN_1545 | 16355 | CTCN_4940 | 26542 |
| TTCN_2937 | 16356 | TTCN_5264 | 26543 |
| ATCN_1806 | 16357 | TTCN_5265 | 26544 |
| TTCN_2938 | 16358 | ATCN_3320 | 26545 |
| ATCN_1807 | 16359 | ATCN_3321 | 26546 |
| TTCN_2939 | 16360 | TTCN_5266 | 26547 |
| GTCN_1546 | 16361 | GTCN_2800 | 26548 |
| TTCN_2940 | 16362 | CTCN_4941 | 26549 |
| TTCN_2941 | 16363 | ATCN_3322 | 26550 |
| ATCN_1808 | 16364 | ATCN_3323 | 26551 |
| GTCN_1547 | 16365 | GTCN_2801 | 26552 |
| TTCN_2942 | 16366 | ATCN_3324 | 26553 |
| TTCN_2943 | 16367 | TTCN_5267 | 26554 |
| ATCN_1809 | 16368 | ATCN_3325 | 26555 |
| TTCN_2944 | 16369 | TTCN_5268 | 26556 |
| TTCN_2945 | 16370 | CTCN_4942 | 26557 |
| CTCN_2561 | 16371 | CTCN_4943 | 26558 |
| TTCN_2946 | 16372 | CTCN_4944 | 26559 |
| GTCN_1548 | 16373 | TTCN_5269 | 26560 |
| CTCN_2562 | 16374 | CTCN_4945 | 26561 |
| GTCN_1549 | 16375 | CTCN_4946 | 26562 |
| ATCN_1810 | 16376 | CTCN_4947 | 26563 |

| | | | |
|---|---|---|---|
| CTCN_2563 | 16377 | CTCN_4948 | 26564 |
| ATCN_1811 | 16378 | CTCN_4949 | 26565 |
| TTCN_2947 | 16379 | ATCN_3326 | 26566 |
| ATCN_1812 | 16380 | TTCN_5270 | 26567 |
| GTCN_1550 | 16381 | TTCN_5271 | 26568 |
| CTCN_2564 | 16382 | CTCN_4950 | 26569 |
| CTCN_2565 | 16383 | ATCN_3327 | 26570 |
| GTCN_1551 | 16384 | ATCN_3328 | 26571 |
| CTCN_2566 | 16385 | GTCN_2802 | 26572 |
| TTCN_2948 | 16386 | ATCN_3329 | 26573 |
| CTCN_2567 | 16387 | ATCN_3330 | 26574 |
| GTCN_1552 | 16388 | ATCN_3331 | 26575 |
| CTCN_2568 | 16389 | ATCN_3332 | 26576 |
| CTCN_2569 | 16390 | ATCN_3333 | 26577 |
| TTCN_2949 | 16391 | GTCN_2803 | 26578 |
| CTCN_2570 | 16392 | TTCN_5272 | 26579 |
| ATCN_1813 | 16393 | TTCN_5273 | 26580 |
| ATCN_1814 | 16394 | TTCN_5274 | 26581 |
| ATCN_1815 | 16395 | GTCN_2804 | 26582 |
| TTCN_2950 | 16396 | GTCN_2805 | 26583 |
| TTCN_2951 | 16397 | CTCN_4951 | 26584 |
| TTCN_2952 | 16398 | GTCN_2806 | 26585 |
| TTCN_2953 | 16399 | CTCN_4952 | 26586 |
| ATCN_1816 | 16400 | CTCN_4953 | 26587 |
| ATCN_1817 | 16401 | TTCN_5275 | 26588 |
| TTCN_2954 | 16402 | TTCN_5276 | 26589 |
| GTCN_1553 | 16403 | ATCN_3334 | 26590 |
| GTCN_1554 | 16404 | CTCN_4954 | 26591 |
| TTCN_2955 | 16405 | TTCN_5277 | 26592 |
| ATCN_1818 | 16406 | TTCN_5278 | 26593 |
| ATCN_1819 | 16407 | GTCN_2807 | 26594 |
| TTCN_2956 | 16408 | ATCN_3335 | 26595 |
| TTCN_2957 | 16409 | ATCN_3336 | 26596 |
| TTCN_2958 | 16410 | GTCN_2808 | 26597 |
| ATCN_1820 | 16411 | ATCN_3337 | 26598 |
| ATCN_1821 | 16412 | ATCN_3338 | 26599 |
| CTCN_2571 | 16413 | ATCN_3339 | 26600 |
| TTCN_2959 | 16414 | CTCN_4955 | 26601 |
| ATCN_1822 | 16415 | TTCN_5279 | 26602 |
| TTCN_2960 | 16416 | CTCN_4956 | 26603 |
| ATCN_1823 | 16417 | TTCN_5280 | 26604 |
| GTCN_1555 | 16418 | GTCN_2809 | 26605 |
| GTCN_1556 | 16419 | TTCN_5281 | 26606 |
| CTCN_2572 | 16420 | CTCN_4957 | 26607 |
| CTCN_2573 | 16421 | TTCN_5282 | 26608 |
| TTCN_2961 | 16422 | CTCN_4958 | 26609 |
| TTCN_2962 | 16423 | CTCN_4959 | 26610 |
| TTCN_2963 | 16424 | TTCN_5283 | 26611 |
| ATCN_1824 | 16425 | CTCN_4960 | 26612 |
| CTCN_2574 | 16426 | ATCN_3340 | 26613 |
| GTCN_1557 | 16427 | ATCN_3341 | 26614 |
| TTCN_2964 | 16428 | ATCN_3342 | 26615 |
| TTCN_2965 | 16429 | CTCN_4961 | 26616 |
| ATCN_1825 | 16430 | TTCN_5284 | 26617 |
| CTCN_2575 | 16431 | TTCN_5285 | 26618 |

FIG. 36 (continued)

| | | | |
|---|---|---|---|
| TTCN_2966 | 16432 | TTCN_5286 | 26619 |
| ATCN_1826 | 16433 | TTCN_5287 | 26620 |
| CTCN_2576 | 16434 | CTCN_4962 | 26621 |
| GTCN_1558 | 16435 | CTCN_4963 | 26622 |
| TTCN_2967 | 16436 | CTCN_4964 | 26623 |
| ATCN_1827 | 16437 | ATCN_3343 | 26624 |
| TTCN_2968 | 16438 | TTCN_5288 | 26625 |
| GTCN_1559 | 16439 | GTCN_2810 | 26626 |
| GTCN_1560 | 16440 | GTCN_2811 | 26627 |
| TTCN_2969 | 16441 | TTCN_5289 | 26628 |
| ATCN_1828 | 16442 | TTCN_5290 | 26629 |
| ATCN_1829 | 16443 | CTCN_4965 | 26630 |
| ATCN_1830 | 16444 | ATCN_3344 | 26631 |
| ATCN_1831 | 16445 | TTCN_5291 | 26632 |
| TTCN_2970 | 16446 | ATCN_3345 | 26633 |
| CTCN_2577 | 16447 | TTCN_5292 | 26634 |
| GTCN_1561 | 16448 | CTCN_4966 | 26635 |
| GTCN_1562 | 16449 | GTCN_2812 | 26636 |
| GTCN_1563 | 16450 | GTCN_2813 | 26637 |
| GTCN_1564 | 16451 | GTCN_2814 | 26638 |
| CTCN_2578 | 16452 | TTCN_5293 | 26639 |
| CTCN_2579 | 16453 | TTCN_5294 | 26640 |
| TTCN_2971 | 16454 | ATCN_3346 | 26641 |
| ATCN_1832 | 16455 | TTCN_5295 | 26642 |
| CTCN_2580 | 16456 | TTCN_5296 | 26643 |
| GTCN_1565 | 16457 | ATCN_3347 | 26644 |
| TTCN_2972 | 16458 | GTCN_2815 | 26645 |
| GTCN_1566 | 16459 | CTCN_4967 | 26646 |
| CTCN_2581 | 16460 | TTCN_5297 | 26647 |
| TTCN_2973 | 16461 | GTCN_2816 | 26648 |
| ATCN_1833 | 16462 | CTCN_4968 | 26649 |
| CTCN_2582 | 16463 | CTCN_4969 | 26650 |
| CTCN_2583 | 16464 | CTCN_4970 | 26651 |
| CTCN_2584 | 16465 | TTCN_5298 | 26652 |
| CTCN_2585 | 16466 | TTCN_5299 | 26653 |
| TTCN_2974 | 16467 | GTCN_2817 | 26654 |
| ATCN_1834 | 16468 | TTCN_5300 | 26655 |
| GTCN_1567 | 16469 | ATCN_3348 | 26656 |
| TTCN_2975 | 16470 | ATCN_3349 | 26657 |
| TTCN_2976 | 16471 | GTCN_2818 | 26658 |
| ATCN_1835 | 16472 | ATCN_3350 | 26659 |
| CTCN_2586 | 16473 | ATCN_3351 | 26660 |
| CTCN_2587 | 16474 | ATCN_3352 | 26661 |
| TTCN_2977 | 16475 | TTCN_5301 | 26662 |
| TTCN_2978 | 16476 | GTCN_2819 | 26663 |
| TTCN_2979 | 16477 | CTCN_4971 | 26664 |
| CTCN_2588 | 16478 | TTCN_5302 | 26665 |
| ATCN_1836 | 16479 | TTCN_5303 | 26666 |
| TTCN_2980 | 16480 | TTCN_5304 | 26667 |
| TTCN_2981 | 16481 | TTCN_5305 | 26668 |
| CTCN_2589 | 16482 | ATCN_3353 | 26669 |
| TTCN_2982 | 16483 | ATCN_3354 | 26670 |
| CTCN_2590 | 16484 | CTCN_4972 | 26671 |
| CTCN_2591 | 16485 | ATCN_3355 | 26672 |
| ATCN_1837 | 16486 | GTCN_2820 | 26673 |

| | | | |
|---|---|---|---|
| ATCN_1838 | 16487 | ATCN_3356 | 26674 |
| ATCN_1839 | 16488 | ATCN_3357 | 26675 |
| CTCN_2592 | 16489 | TTCN_5306 | 26676 |
| GTCN_1568 | 16490 | TTCN_5307 | 26677 |
| ATCN_1840 | 16491 | GTCN_2821 | 26678 |
| ATCN_1841 | 16492 | ATCN_3358 | 26679 |
| ATCN_1842 | 16493 | TTCN_5308 | 26680 |
| ATCN_1843 | 16494 | TTCN_5309 | 26681 |
| CTCN_2593 | 16495 | TTCN_5310 | 26682 |
| CTCN_2594 | 16496 | TTCN_5311 | 26683 |
| ATCN_1844 | 16497 | ATCN_3359 | 26684 |
| ATCN_1845 | 16498 | TTCN_5312 | 26685 |
| ATCN_1846 | 16499 | CTCN_4973 | 26686 |
| CTCN_2595 | 16500 | TTCN_5313 | 26687 |
| CTCN_2596 | 16501 | TTCN_5314 | 26688 |
| ATCN_1847 | 16502 | ATCN_3360 | 26689 |
| CTCN_2597 | 16503 | CTCN_4974 | 26690 |
| TTCN_2983 | 16504 | GTCN_2822 | 26691 |
| CTCN_2598 | 16505 | CTCN_4975 | 26692 |
| TTCN_2984 | 16506 | TTCN_5315 | 26693 |
| ATCN_1848 | 16507 | TTCN_5316 | 26694 |
| ATCN_1849 | 16508 | TTCN_5317 | 26695 |
| CTCN_2599 | 16509 | TTCN_5318 | 26696 |
| TTCN_2985 | 16510 | ATCN_3361 | 26697 |
| TTCN_2986 | 16511 | TTCN_5319 | 26698 |
| TTCN_2987 | 16512 | TTCN_5320 | 26699 |
| TTCN_2988 | 16513 | ATCN_3362 | 26700 |
| ATCN_1850 | 16514 | CTCN_4976 | 26701 |
| ATCN_1851 | 16515 | TTCN_5321 | 26702 |
| TTCN_2989 | 16516 | TTCN_5322 | 26703 |
| ATCN_1852 | 16517 | CTCN_4977 | 26704 |
| ATCN_1853 | 16518 | TTCN_5323 | 26705 |
| TTCN_2990 | 16519 | TTCN_5324 | 26706 |
| TTCN_2991 | 16520 | GTCN_2823 | 26707 |
| ATCN_1854 | 16521 | GTCN_2824 | 26708 |
| CTCN_2600 | 16522 | TTCN_5325 | 26709 |
| TTCN_2992 | 16523 | TTCN_5326 | 26710 |
| GTCN_1569 | 16524 | CTCN_4978 | 26711 |
| TTCN_2993 | 16525 | ATCN_3363 | 26712 |
| GTCN_1570 | 16526 | ATCN_3364 | 26713 |
| CTCN_2601 | 16527 | TTCN_5327 | 26714 |
| CTCN_2602 | 16528 | ATCN_3365 | 26715 |
| GTCN_1571 | 16529 | CTCN_4979 | 26716 |
| ATCN_1855 | 16530 | TTCN_5328 | 26717 |
| TTCN_2994 | 16531 | ATCN_3366 | 26718 |
| ATCN_1856 | 16532 | ATCN_3367 | 26719 |
| TTCN_2995 | 16533 | TTCN_5329 | 26720 |
| ATCN_1857 | 16534 | TTCN_5330 | 26721 |
| CTCN_2603 | 16535 | CTCN_4980 | 26722 |
| ATCN_1858 | 16536 | TTCN_5331 | 26723 |
| TTCN_2996 | 16537 | TTCN_5332 | 26724 |
| ATCN_1859 | 16538 | TTCN_5333 | 26725 |
| ATCN_1860 | 16539 | TTCN_5334 | 26726 |
| ATCN_1861 | 16540 | TTCN_5335 | 26727 |
| TTCN_2997 | 16541 | ATCN_3368 | 26728 |

FIG. 36 (continued)

| | | | |
|---|---|---|---|
| TTCN_2998 | 16542 | GTCN_2825 | 26729 |
| ATCN_1862 | 16543 | TTCN_5336 | 26730 |
| CTCN_2604 | 16544 | ATCN_3369 | 26731 |
| CTCN_2605 | 16545 | ATCN_3370 | 26732 |
| GTCN_1572 | 16546 | TTCN_5337 | 26733 |
| CTCN_2606 | 16547 | CTCN_4981 | 26734 |
| TTCN_2999 | 16548 | CTCN_4982 | 26735 |
| TTCN_3000 | 16549 | CTCN_4983 | 26736 |
| TTCN_3001 | 16550 | TTCN_5338 | 26737 |
| CTCN_2607 | 16551 | TTCN_5339 | 26738 |
| TTCN_3002 | 16552 | ATCN_3371 | 26739 |
| TTCN_3003 | 16553 | GTCN_2826 | 26740 |
| TTCN_3004 | 16554 | ATCN_3372 | 26741 |
| GTCN_1573 | 16555 | GTCN_2827 | 26742 |
| ATCN_1863 | 16556 | TTCN_5340 | 26743 |
| CTCN_2608 | 16557 | TTCN_5341 | 26744 |
| TTCN_3005 | 16558 | ATCN_3373 | 26745 |
| CTCN_2609 | 16559 | CTCN_4984 | 26746 |
| GTCN_1574 | 16560 | CTCN_4985 | 26747 |
| GTCN_1575 | 16561 | TTCN_5342 | 26748 |
| TTCN_3006 | 16562 | TTCN_5343 | 26749 |
| TTCN_3007 | 16563 | CTCN_4986 | 26750 |
| GTCN_1576 | 16564 | TTCN_5344 | 26751 |
| CTCN_2610 | 16565 | ATCN_3374 | 26752 |
| TTCN_3008 | 16566 | TTCN_5345 | 26753 |
| GTCN_1577 | 16567 | GTCN_2828 | 26754 |
| GTCN_1578 | 16568 | GTCN_2829 | 26755 |
| CTCN_2611 | 16569 | TTCN_5346 | 26756 |
| CTCN_2612 | 16570 | TTCN_5347 | 26757 |
| TTCN_3009 | 16571 | TTCN_5348 | 26758 |
| TTCN_3010 | 16572 | TTCN_5349 | 26759 |
| CTCN_2613 | 16573 | GTCN_2830 | 26760 |
| CTCN_2614 | 16574 | ATCN_3375 | 26761 |
| ATCN_1864 | 16575 | TTCN_5350 | 26762 |
| TTCN_3011 | 16576 | TTCN_5351 | 26763 |
| ATCN_1865 | 16577 | TTCN_5352 | 26764 |
| GTCN_1579 | 16578 | CTCN_4987 | 26765 |
| ATCN_1866 | 16579 | CTCN_4988 | 26766 |
| GTCN_1580 | 16580 | CTCN_4989 | 26767 |
| TTCN_3012 | 16581 | GTCN_2831 | 26768 |
| ATCN_1867 | 16582 | TTCN_5353 | 26769 |
| TTCN_3013 | 16583 | TTCN_5354 | 26770 |
| CTCN_2615 | 16584 | TTCN_5355 | 26771 |
| TTCN_3014 | 16585 | ATCN_3376 | 26772 |
| ATCN_1868 | 16586 | CTCN_4990 | 26773 |
| TTCN_3015 | 16587 | TTCN_5356 | 26774 |
| ATCN_1869 | 16588 | GTCN_2832 | 26775 |
| ATCN_1870 | 16589 | GTCN_2833 | 26776 |
| CTCN_2616 | 16590 | CTCN_4991 | 26777 |
| TTCN_3016 | 16591 | TTCN_5357 | 26778 |
| GTCN_1581 | 16592 | CTCN_4992 | 26779 |
| GTCN_1582 | 16593 | TTCN_5358 | 26780 |
| CTCN_2617 | 16594 | TTCN_5359 | 26781 |
| TTCN_3017 | 16595 | GTCN_2834 | 26782 |
| TTCN_3018 | 16596 | GTCN_2835 | 26783 |

| | | | |
|---|---|---|---|
| GTCN_1583 | 16597 | GTCN_2836 | 26784 |
| ATCN_1871 | 16598 | ATCN_3377 | 26785 |
| GTCN_1584 | 16599 | TTCN_5360 | 26786 |
| ATCN_1872 | 16600 | ATCN_3378 | 26787 |
| TTCN_3019 | 16601 | GTCN_2837 | 26788 |
| TTCN_3020 | 16602 | ATCN_3379 | 26789 |
| TTCN_3021 | 16603 | TTCN_5361 | 26790 |
| ATCN_1873 | 16604 | TTCN_5362 | 26791 |
| TTCN_3022 | 16605 | CTCN_4993 | 26792 |
| TTCN_3023 | 16606 | CTCN_4994 | 26793 |
| TTCN_3024 | 16607 | GTCN_2838 | 26794 |
| TTCN_3025 | 16608 | TTCN_5363 | 26795 |
| GTCN_1585 | 16609 | GTCN_2839 | 26796 |
| CTCN_2618 | 16610 | CTCN_4995 | 26797 |
| CTCN_2619 | 16611 | GTCN_2840 | 26798 |
| TTCN_3026 | 16612 | GTCN_2841 | 26799 |
| TTCN_3027 | 16613 | ATCN_3380 | 26800 |
| ATCN_1874 | 16614 | ATCN_3381 | 26801 |
| ATCN_1875 | 16615 | ATCN_3382 | 26802 |
| TTCN_3028 | 16616 | CTCN_4996 | 26803 |
| CTCN_2620 | 16617 | GTCN_2842 | 26804 |
| GTCN_1586 | 16618 | GTCN_2843 | 26805 |
| CTCN_2621 | 16619 | CTCN_4997 | 26806 |
| GTCN_1587 | 16620 | CTCN_4998 | 26807 |
| ATCN_1876 | 16621 | TTCN_5364 | 26808 |
| ATCN_1877 | 16622 | ATCN_3383 | 26809 |
| CTCN_2622 | 16623 | CTCN_4999 | 26810 |
| CTCN_2623 | 16624 | TTCN_5365 | 26811 |
| CTCN_2624 | 16625 | TTCN_5366 | 26812 |
| TTCN_3029 | 16626 | GTCN_2844 | 26813 |
| ATCN_1878 | 16627 | CTCN_5000 | 26814 |
| TTCN_3030 | 16628 | TTCN_5367 | 26815 |
| GTCN_1588 | 16629 | GTCN_2845 | 26816 |
| CTCN_2625 | 16630 | GTCN_2846 | 26817 |
| CTCN_2626 | 16631 | TTCN_5368 | 26818 |
| CTCN_2627 | 16632 | ATCN_3384 | 26819 |
| GTCN_1589 | 16633 | ATCN_3385 | 26820 |
| TTCN_3031 | 16634 | GTCN_2847 | 26821 |
| ATCN_1879 | 16635 | TTCN_5369 | 26822 |
| TTCN_3032 | 16636 | TTCN_5370 | 26823 |
| CTCN_2628 | 16637 | TTCN_5371 | 26824 |
| CTCN_2629 | 16638 | TTCN_5372 | 26825 |
| CTCN_2630 | 16639 | TTCN_5373 | 26826 |
| CTCN_2631 | 16640 | GTCN_2848 | 26827 |
| TTCN_3033 | 16641 | CTCN_5001 | 26828 |
| CTCN_2632 | 16642 | CTCN_5002 | 26829 |
| CTCN_2633 | 16643 | GTCN_2849 | 26830 |
| ATCN_1880 | 16644 | CTCN_5003 | 26831 |
| TTCN_3034 | 16645 | GTCN_2850 | 26832 |
| CTCN_2634 | 16646 | CTCN_5004 | 26833 |
| TTCN_3035 | 16647 | TTCN_5374 | 26834 |
| GTCN_1590 | 16648 | ATCN_3386 | 26835 |
| CTCN_2635 | 16649 | TTCN_5375 | 26836 |
| CTCN_2636 | 16650 | TTCN_5376 | 26837 |
| ATCN_1881 | 16651 | ATCN_3387 | 26838 |

FIG. 36 (continued)

| | | | |
|---|---|---|---|
| ATCN_1882 | 16652 | TTCN_5377 | 26839 |
| CTCN_2637 | 16653 | CTCN_5005 | 26840 |
| CTCN_2638 | 16654 | CTCN_5006 | 26841 |
| CTCN_2639 | 16655 | TTCN_5378 | 26842 |
| TTCN_3036 | 16656 | TTCN_5379 | 26843 |
| CTCN_2640 | 16657 | CTCN_5007 | 26844 |
| GTCN_1591 | 16658 | GTCN_2851 | 26845 |
| CTCN_2641 | 16659 | CTCN_5008 | 26846 |
| TTCN_3037 | 16660 | TTCN_5380 | 26847 |
| CTCN_2642 | 16661 | ATCN_3388 | 26848 |
| CTCN_2643 | 16662 | CTCN_5009 | 26849 |
| ATCN_1883 | 16663 | TTCN_5381 | 26850 |
| TTCN_3038 | 16664 | TTCN_5382 | 26851 |
| TTCN_3039 | 16665 | GTCN_2852 | 26852 |
| GTCN_1592 | 16666 | TTCN_5383 | 26853 |
| TTCN_3040 | 16667 | GTCN_2853 | 26854 |
| TTCN_3041 | 16668 | TTCN_5384 | 26855 |
| ATCN_1884 | 16669 | ATCN_3389 | 26856 |
| GTCN_1593 | 16670 | CTCN_5010 | 26857 |
| ATCN_1885 | 16671 | TTCN_5385 | 26858 |
| ATCN_1886 | 16672 | ATCN_3390 | 26859 |
| TTCN_3042 | 16673 | ATCN_3391 | 26860 |
| TTCN_3043 | 16674 | TTCN_5386 | 26861 |
| GTCN_1594 | 16675 | ATCN_3392 | 26862 |
| ATCN_1887 | 16676 | CTCN_5011 | 26863 |
| ATCN_1888 | 16677 | CTCN_5012 | 26864 |
| TTCN_3044 | 16678 | ATCN_3393 | 26865 |
| TTCN_3045 | 16679 | TTCN_5387 | 26866 |
| TTCN_3046 | 16680 | GTCN_2854 | 26867 |
| TTCN_3047 | 16681 | ATCN_3394 | 26868 |
| GTCN_1595 | 16682 | TTCN_5388 | 26869 |
| TTCN_3048 | 16683 | ATCN_3395 | 26870 |
| ATCN_1889 | 16684 | ATCN_3396 | 26871 |
| CTCN_2644 | 16685 | TTCN_5389 | 26872 |
| ATCN_1890 | 16686 | TTCN_5390 | 26873 |
| TTCN_3049 | 16687 | CTCN_5013 | 26874 |
| CTCN_2645 | 16688 | GTCN_2855 | 26875 |
| CTCN_2646 | 16689 | GTCN_2856 | 26876 |
| TTCN_3050 | 16690 | GTCN_2857 | 26877 |
| CTCN_2647 | 16691 | CTCN_5014 | 26878 |
| CTCN_2648 | 16692 | GTCN_2858 | 26879 |
| ATCN_1891 | 16693 | ATCN_3397 | 26880 |
| CTCN_2649 | 16694 | CTCN_5015 | 26881 |
| TTCN_3051 | 16695 | TTCN_5391 | 26882 |
| TTCN_3052 | 16696 | TTCN_5392 | 26883 |
| CTCN_2650 | 16697 | GTCN_2859 | 26884 |
| TTCN_3053 | 16698 | ATCN_3398 | 26885 |
| CTCN_2651 | 16699 | GTCN_2860 | 26886 |
| TTCN_3054 | 16700 | GTCN_2861 | 26887 |
| GTCN_1596 | 16701 | CTCN_5016 | 26888 |
| ATCN_1892 | 16702 | CTCN_5017 | 26889 |
| ATCN_1893 | 16703 | GTCN_2862 | 26890 |
| ATCN_1894 | 16704 | GTCN_2863 | 26891 |
| ATCN_1895 | 16705 | GTCN_2864 | 26892 |
| TTCN_3055 | 16706 | CTCN_5018 | 26893 |

| | | | |
|---|---|---|---|
| TTCN_3056 | 16707 | ATCN_3399 | 26894 |
| GTCN_1597 | 16708 | GTCN_2865 | 26895 |
| CTCN_2652 | 16709 | TTCN_5393 | 26896 |
| TTCN_3057 | 16710 | GTCN_2866 | 26897 |
| CTCN_2653 | 16711 | GTCN_2867 | 26898 |
| TTCN_3058 | 16712 | CTCN_5019 | 26899 |
| GTCN_1598 | 16713 | GTCN_2868 | 26900 |
| CTCN_2654 | 16714 | CTCN_5020 | 26901 |
| TTCN_3059 | 16715 | GTCN_2869 | 26902 |
| TTCN_3060 | 16716 | TTCN_5394 | 26903 |
| CTCN_2655 | 16717 | CTCN_5021 | 26904 |
| ATCN_1896 | 16718 | TTCN_5395 | 26905 |
| ATCN_1897 | 16719 | TTCN_5396 | 26906 |
| ATCN_1898 | 16720 | TTCN_5397 | 26907 |
| TTCN_3061 | 16721 | CTCN_5022 | 26908 |
| CTCN_2656 | 16722 | TTCN_5398 | 26909 |
| GTCN_1599 | 16723 | GTCN_2870 | 26910 |
| TTCN_3062 | 16724 | TTCN_5399 | 26911 |
| CTCN_2657 | 16725 | TTCN_5400 | 26912 |
| TTCN_3063 | 16726 | CTCN_5023 | 26913 |
| TTCN_3064 | 16727 | TTCN_5401 | 26914 |
| TTCN_3065 | 16728 | TTCN_5402 | 26915 |
| TTCN_3066 | 16729 | TTCN_5403 | 26916 |
| GTCN_1600 | 16730 | TTCN_5404 | 26917 |
| CTCN_2658 | 16731 | ATCN_3400 | 26918 |
| TTCN_3067 | 16732 | TTCN_5405 | 26919 |
| ATCN_1899 | 16733 | GTCN_2871 | 26920 |
| GTCN_1601 | 16734 | TTCN_5406 | 26921 |
| ATCN_1900 | 16735 | GTCN_2872 | 26922 |
| ATCN_1901 | 16736 | TTCN_5407 | 26923 |
| TTCN_3068 | 16737 | CTCN_5024 | 26924 |
| CTCN_2659 | 16738 | GTCN_2873 | 26925 |
| GTCN_1602 | 16739 | GTCN_2874 | 26926 |
| CTCN_2660 | 16740 | CTCN_5025 | 26927 |
| CTCN_2661 | 16741 | TTCN_5408 | 26928 |
| CTCN_2662 | 16742 | CTCN_5026 | 26929 |
| GTCN_1603 | 16743 | TTCN_5409 | 26930 |
| CTCN_2663 | 16744 | TTCN_5410 | 26931 |
| CTCN_2664 | 16745 | TTCN_5411 | 26932 |
| ATCN_1902 | 16746 | CTCN_5027 | 26933 |
| CTCN_2665 | 16747 | TTCN_5412 | 26934 |
| GTCN_1604 | 16748 | CTCN_5028 | 26935 |
| CTCN_2666 | 16749 | ATCN_3401 | 26936 |
| ATCN_1903 | 16750 | CTCN_5029 | 26937 |
| TTCN_3069 | 16751 | CTCN_5030 | 26938 |
| ATCN_1904 | 16752 | GTCN_2875 | 26939 |
| TTCN_3070 | 16753 | TTCN_5413 | 26940 |
| CTCN_2667 | 16754 | ATCN_3402 | 26941 |
| CTCN_2668 | 16755 | CTCN_5031 | 26942 |
| GTCN_1605 | 16756 | GTCN_2876 | 26943 |
| CTCN_2669 | 16757 | ATCN_3403 | 26944 |
| CTCN_2670 | 16758 | CTCN_5032 | 26945 |
| CTCN_2671 | 16759 | CTCN_5033 | 26946 |
| TTCN_3071 | 16760 | CTCN_5034 | 26947 |
| ATCN_1905 | 16761 | TTCN_5414 | 26948 |

FIG. 36 (continued)

| | | | |
|---|---|---|---|
| CTCN_2672 | 16762 | ATCN_3404 | 26949 |
| TTCN_3072 | 16763 | ATCN_3405 | 26950 |
| TTCN_3073 | 16764 | TTCN_5415 | 26951 |
| GTCN_1606 | 16765 | CTCN_5035 | 26952 |
| CTCN_2673 | 16766 | ATCN_3406 | 26953 |
| TTCN_3074 | 16767 | ATCN_3407 | 26954 |
| ATCN_1906 | 16768 | CTCN_5036 | 26955 |
| TTCN_3075 | 16769 | TTCN_5416 | 26956 |
| ATCN_1907 | 16770 | TTCN_5417 | 26957 |
| CTCN_2674 | 16771 | GTCN_2877 | 26958 |
| GTCN_1607 | 16772 | TTCN_5418 | 26959 |
| ATCN_1908 | 16773 | GTCN_2878 | 26960 |
| ATCN_1909 | 16774 | CTCN_5037 | 26961 |
| ATCN_1910 | 16775 | TTCN_5419 | 26962 |
| GTCN_1608 | 16776 | TTCN_5420 | 26963 |
| TTCN_3076 | 16777 | TTCN_5421 | 26964 |
| TTCN_3077 | 16778 | TTCN_5422 | 26965 |
| ATCN_1911 | 16779 | TTCN_5423 | 26966 |
| TTCN_3078 | 16780 | CTCN_5038 | 26967 |
| CTCN_2675 | 16781 | GTCN_2879 | 26968 |
| CTCN_2676 | 16782 | ATCN_3408 | 26969 |
| TTCN_3079 | 16783 | GTCN_2880 | 26970 |
| ATCN_1912 | 16784 | TTCN_5424 | 26971 |
| TTCN_3080 | 16785 | ATCN_3409 | 26972 |
| TTCN_3081 | 16786 | ATCN_3410 | 26973 |
| CTCN_2677 | 16787 | GTCN_2881 | 26974 |
| CTCN_2678 | 16788 | TTCN_5425 | 26975 |
| CTCN_2679 | 16789 | ATCN_3411 | 26976 |
| TTCN_3082 | 16790 | CTCN_5039 | 26977 |
| TTCN_3083 | 16791 | GTCN_2882 | 26978 |
| ATCN_1913 | 16792 | CTCN_5040 | 26979 |
| ATCN_1914 | 16793 | CTCN_5041 | 26980 |
| GTCN_1609 | 16794 | ATCN_3412 | 26981 |
| GTCN_1610 | 16795 | GTCN_2883 | 26982 |
| CTCN_2680 | 16796 | CTCN_5042 | 26983 |
| TTCN_3084 | 16797 | ATCN_3413 | 26984 |
| TTCN_3085 | 16798 | CTCN_5043 | 26985 |
| CTCN_2681 | 16799 | TTCN_5426 | 26986 |
| GTCN_1611 | 16800 | ATCN_3414 | 26987 |
| CTCN_2682 | 16801 | CTCN_5044 | 26988 |
| GTCN_1612 | 16802 | GTCN_2884 | 26989 |
| CTCN_2683 | 16803 | TTCN_5427 | 26990 |
| GTCN_1613 | 16804 | GTCN_2885 | 26991 |
| CTCN_2684 | 16805 | TTCN_5428 | 26992 |
| GTCN_1614 | 16806 | CTCN_5045 | 26993 |
| CTCN_2685 | 16807 | TTCN_5429 | 26994 |
| CTCN_2686 | 16808 | GTCN_2886 | 26995 |
| CTCN_2687 | 16809 | TTCN_5430 | 26996 |
| CTCN_2688 | 16810 | GTCN_2887 | 26997 |
| TTCN_3086 | 16811 | TTCN_5431 | 26998 |
| ATCN_1915 | 16812 | CTCN_5046 | 26999 |
| TTCN_3087 | 16813 | CTCN_5047 | 27000 |
| ATCN_1916 | 16814 | GTCN_2888 | 27001 |
| TTCN_3088 | 16815 | ATCN_3415 | 27002 |
| CTCN_2689 | 16816 | GTCN_2889 | 27003 |

| | | | |
|---|---|---|---|
| CTCN_2690 | 16817 | TTCN_5432 | 27004 |
| CTCN_2691 | 16818 | TTCN_5433 | 27005 |
| TTCN_3089 | 16819 | GTCN_2890 | 27006 |
| CTCN_2692 | 16820 | TTCN_5434 | 27007 |
| TTCN_3090 | 16821 | ATCN_3416 | 27008 |
| ATCN_1917 | 16822 | ATCN_3417 | 27009 |
| GTCN_1615 | 16823 | ATCN_3418 | 27010 |
| CTCN_2693 | 16824 | CTCN_5048 | 27011 |
| CTCN_2694 | 16825 | TTCN_5435 | 27012 |
| TTCN_3091 | 16826 | TTCN_5436 | 27013 |
| CTCN_2695 | 16827 | TTCN_5437 | 27014 |
| CTCN_2696 | 16828 | ATCN_3419 | 27015 |
| ATCN_1918 | 16829 | ATCN_3420 | 27016 |
| ATCN_1919 | 16830 | CTCN_5049 | 27017 |
| GTCN_1616 | 16831 | ATCN_3421 | 27018 |
| TTCN_3092 | 16832 | TTCN_5438 | 27019 |
| TTCN_3093 | 16833 | TTCN_5439 | 27020 |
| ATCN_1920 | 16834 | CTCN_5050 | 27021 |
| TTCN_3094 | 16835 | GTCN_2891 | 27022 |
| ATCN_1921 | 16836 | ATCN_3422 | 27023 |
| CTCN_2697 | 16837 | CTCN_5051 | 27024 |
| CTCN_2698 | 16838 | GTCN_2892 | 27025 |
| CTCN_2699 | 16839 | CTCN_5052 | 27026 |
| TTCN_3095 | 16840 | GTCN_2893 | 27027 |
| TTCN_3096 | 16841 | TTCN_5440 | 27028 |
| ATCN_1922 | 16842 | CTCN_5053 | 27029 |
| GTCN_1617 | 16843 | CTCN_5054 | 27030 |
| ATCN_1923 | 16844 | CTCN_5055 | 27031 |
| GTCN_1618 | 16845 | TTCN_5441 | 27032 |
| CTCN_2700 | 16846 | CTCN_5056 | 27033 |
| TTCN_3097 | 16847 | GTCN_2894 | 27034 |
| CTCN_2701 | 16848 | CTCN_5057 | 27035 |
| CTCN_2702 | 16849 | TTCN_5442 | 27036 |
| TTCN_3098 | 16850 | ATCN_3423 | 27037 |
| GTCN_1619 | 16851 | ATCN_3424 | 27038 |
| CTCN_2703 | 16852 | ATCN_3425 | 27039 |
| CTCN_2704 | 16853 | ATCN_3426 | 27040 |
| CTCN_2705 | 16854 | TTCN_5443 | 27041 |
| TTCN_3099 | 16855 | ATCN_3427 | 27042 |
| CTCN_2706 | 16856 | GTCN_2895 | 27043 |
| CTCN_2707 | 16857 | GTCN_2896 | 27044 |
| CTCN_2708 | 16858 | TTCN_5444 | 27045 |
| CTCN_2709 | 16859 | TTCN_5445 | 27046 |
| TTCN_3100 | 16860 | TTCN_5446 | 27047 |
| GTCN_1620 | 16861 | TTCN_5447 | 27048 |
| GTCN_1621 | 16862 | TTCN_5448 | 27049 |
| TTCN_3101 | 16863 | TTCN_5449 | 27050 |
| TTCN_3102 | 16864 | GTCN_2897 | 27051 |
| TTCN_3103 | 16865 | ATCN_3428 | 27052 |
| TTCN_3104 | 16866 | ATCN_3429 | 27053 |
| GTCN_1622 | 16867 | TTCN_5450 | 27054 |
| ATCN_1924 | 16868 | CTCN_5058 | 27055 |
| ATCN_1925 | 16869 | GTCN_2898 | 27056 |
| CTCN_2710 | 16870 | CTCN_5059 | 27057 |
| GTCN_1623 | 16871 | ATCN_3430 | 27058 |

FIG. 36 (continued)

| | | | |
|---|---|---|---|
| CTCN_2711 | 16872 | GTCN_2899 | 27059 |
| CTCN_2712 | 16873 | ATCN_3431 | 27060 |
| CTCN_2713 | 16874 | ATCN_3432 | 27061 |
| TTCN_3105 | 16875 | CTCN_5060 | 27062 |
| TTCN_3106 | 16876 | ATCN_3433 | 27063 |
| TTCN_3107 | 16877 | GTCN_2900 | 27064 |
| CTCN_2714 | 16878 | GTCN_2901 | 27065 |
| CTCN_2715 | 16879 | GTCN_2902 | 27066 |
| CTCN_2716 | 16880 | TTCN_5451 | 27067 |
| GTCN_1624 | 16881 | TTCN_5452 | 27068 |
| CTCN_2717 | 16882 | ATCN_3434 | 27069 |
| ATCN_1926 | 16883 | CTCN_5061 | 27070 |
| TTCN_3108 | 16884 | TTCN_5453 | 27071 |
| CTCN_2718 | 16885 | CTCN_5062 | 27072 |
| TTCN_3109 | 16886 | ATCN_3435 | 27073 |
| TTCN_3110 | 16887 | CTCN_5063 | 27074 |
| GTCN_1625 | 16888 | ATCN_3436 | 27075 |
| CTCN_2719 | 16889 | TTCN_5454 | 27076 |
| CTCN_2720 | 16890 | CTCN_5064 | 27077 |
| TTCN_3111 | 16891 | GTCN_2903 | 27078 |
| GTCN_1626 | 16892 | TTCN_5455 | 27079 |
| GTCN_1627 | 16893 | GTCN_2904 | 27080 |
| TTCN_3112 | 16894 | CTCN_5065 | 27081 |
| GTCN_1628 | 16895 | ATCN_3437 | 27082 |
| TTCN_3113 | 16896 | ATCN_3438 | 27083 |
| CTCN_2721 | 16897 | GTCN_2905 | 27084 |
| ATCN_1927 | 16898 | GTCN_2906 | 27085 |
| ATCN_1928 | 16899 | GTCN_2907 | 27086 |
| GTCN_1629 | 16900 | GTCN_2908 | 27087 |
| TTCN_3114 | 16901 | CTCN_5066 | 27088 |
| GTCN_1630 | 16902 | TTCN_5456 | 27089 |
| TTCN_3115 | 16903 | CTCN_5067 | 27090 |
| TTCN_3116 | 16904 | TTCN_5457 | 27091 |
| ATCN_1929 | 16905 | TTCN_5458 | 27092 |
| TTCN_3117 | 16906 | ATCN_3439 | 27093 |
| CTCN_2722 | 16907 | ATCN_3440 | 27094 |
| CTCN_2723 | 16908 | CTCN_5068 | 27095 |
| TTCN_3118 | 16909 | ATCN_3441 | 27096 |
| CTCN_2724 | 16910 | ATCN_3442 | 27097 |
| GTCN_1631 | 16911 | ATCN_3443 | 27098 |
| CTCN_2725 | 16912 | ATCN_3444 | 27099 |
| CTCN_2726 | 16913 | CTCN_5069 | 27100 |
| GTCN_1632 | 16914 | CTCN_5070 | 27101 |
| CTCN_2727 | 16915 | ATCN_3445 | 27102 |
| TTCN_3119 | 16916 | GTCN_2909 | 27103 |
| CTCN_2728 | 16917 | CTCN_5071 | 27104 |
| TTCN_3120 | 16918 | TTCN_5459 | 27105 |
| TTCN_3121 | 16919 | CTCN_5072 | 27106 |
| GTCN_1633 | 16920 | ATCN_3446 | 27107 |
| ATCN_1930 | 16921 | GTCN_2910 | 27108 |
| TTCN_3122 | 16922 | ATCN_3447 | 27109 |
| CTCN_2729 | 16923 | CTCN_5073 | 27110 |
| TTCN_3123 | 16924 | CTCN_5074 | 27111 |
| ATCN_1931 | 16925 | TTCN_5460 | 27112 |
| CTCN_2730 | 16926 | TTCN_5461 | 27113 |

| | | | |
|---|---|---|---|
| TTCN_3124 | 16927 | CTCN_5075 | 27114 |
| GTCN_1634 | 16928 | CTCN_5076 | 27115 |
| TTCN_3125 | 16929 | GTCN_2911 | 27116 |
| TTCN_3126 | 16930 | CTCN_5077 | 27117 |
| ATCN_1932 | 16931 | ATCN_3448 | 27118 |
| TTCN_3127 | 16932 | ATCN_3449 | 27119 |
| TTCN_3128 | 16933 | CTCN_5078 | 27120 |
| ATCN_1933 | 16934 | TTCN_5462 | 27121 |
| TTCN_3129 | 16935 | TTCN_5463 | 27122 |
| ATCN_1934 | 16936 | CTCN_5079 | 27123 |
| TTCN_3130 | 16937 | GTCN_2912 | 27124 |
| TTCN_3131 | 16938 | TTCN_5464 | 27125 |
| GTCN_1635 | 16939 | CTCN_5080 | 27126 |
| GTCN_1636 | 16940 | CTCN_5081 | 27127 |
| TTCN_3132 | 16941 | CTCN_5082 | 27128 |
| ATCN_1935 | 16942 | CTCN_5083 | 27129 |
| ATCN_1936 | 16943 | CTCN_5084 | 27130 |
| ATCN_1937 | 16944 | TTCN_5465 | 27131 |
| CTCN_2731 | 16945 | TTCN_5466 | 27132 |
| TTCN_3133 | 16946 | CTCN_5085 | 27133 |
| ATCN_1938 | 16947 | GTCN_2913 | 27134 |
| ATCN_1939 | 16948 | GTCN_2914 | 27135 |
| TTCN_3134 | 16949 | GTCN_2915 | 27136 |
| GTCN_1637 | 16950 | TTCN_5467 | 27137 |
| ATCN_1940 | 16951 | CTCN_5086 | 27138 |
| TTCN_3135 | 16952 | ATCN_3450 | 27139 |
| TTCN_3136 | 16953 | CTCN_5087 | 27140 |
| CTCN_2732 | 16954 | GTCN_2916 | 27141 |
| TTCN_3137 | 16955 | TTCN_5468 | 27142 |
| GTCN_1638 | 16956 | ATCN_3451 | 27143 |
| TTCN_3138 | 16957 | ATCN_3452 | 27144 |
| ATCN_1941 | 16958 | TTCN_5469 | 27145 |
| TTCN_3139 | 16959 | TTCN_5470 | 27146 |
| TTCN_3140 | 16960 | TTCN_5471 | 27147 |
| ATCN_1942 | 16961 | GTCN_2917 | 27148 |
| ATCN_1943 | 16962 | TTCN_5472 | 27149 |
| GTCN_1639 | 16963 | ATCN_3453 | 27150 |
| ATCN_1944 | 16964 | TTCN_5473 | 27151 |
| TTCN_3141 | 16965 | ATCN_3454 | 27152 |
| GTCN_1640 | 16966 | CTCN_5088 | 27153 |
| TTCN_3142 | 16967 | ATCN_3455 | 27154 |
| ATCN_1945 | 16968 | GTCN_2918 | 27155 |
| ATCN_1946 | 16969 | ATCN_3456 | 27156 |
| CTCN_2733 | 16970 | CTCN_5089 | 27157 |
| GTCN_1641 | 16971 | ATCN_3457 | 27158 |
| TTCN_3143 | 16972 | GTCN_2919 | 27159 |
| GTCN_1642 | 16973 | ATCN_3458 | 27160 |
| ATCN_1947 | 16974 | ATCN_3459 | 27161 |
| GTCN_1643 | 16975 | ATCN_3460 | 27162 |
| GTCN_1644 | 16976 | TTCN_5474 | 27163 |
| CTCN_2734 | 16977 | TTCN_5475 | 27164 |
| GTCN_1645 | 16978 | CTCN_5090 | 27165 |
| CTCN_2735 | 16979 | CTCN_5091 | 27166 |
| TTCN_3144 | 16980 | TTCN_5476 | 27167 |
| TTCN_3145 | 16981 | TTCN_5477 | 27168 |

FIG. 36 (continued)

| | | | |
|---|---|---|---|
| TTCN_3146 | 16982 | GTCN_2920 | 27169 |
| TTCN_3147 | 16983 | TTCN_5478 | 27170 |
| GTCN_1646 | 16984 | TTCN_5479 | 27171 |
| TTCN_3148 | 16985 | TTCN_5480 | 27172 |
| GTCN_1647 | 16986 | TTCN_5481 | 27173 |
| GTCN_1648 | 16987 | TTCN_5482 | 27174 |
| GTCN_1649 | 16988 | TTCN_5483 | 27175 |
| ATCN_1948 | 16989 | CTCN_5092 | 27176 |
| TTCN_3149 | 16990 | CTCN_5093 | 27177 |
| ATCN_1949 | 16991 | TTCN_5484 | 27178 |
| CTCN_2736 | 16992 | ATCN_3461 | 27179 |
| ATCN_1950 | 16993 | ATCN_3462 | 27180 |
| TTCN_3150 | 16994 | ATCN_3463 | 27181 |
| GTCN_1650 | 16995 | CTCN_5094 | 27182 |
| ATCN_1951 | 16996 | TTCN_5485 | 27183 |
| TTCN_3151 | 16997 | GTCN_2921 | 27184 |
| ATCN_1952 | 16998 | CTCN_5095 | 27185 |
| TTCN_3152 | 16999 | CTCN_5096 | 27186 |
| TTCN_3153 | 17000 | CTCN_5097 | 27187 |
| CTCN_2737 | 17001 | CTCN_5098 | 27188 |
| TTCN_3154 | 17002 | CTCN_5099 | 27189 |
| GTCN_1651 | 17003 | CTCN_5100 | 27190 |
| ATCN_1953 | 17004 | CTCN_5101 | 27191 |
| ATCN_1954 | 17005 | CTCN_5102 | 27192 |
| CTCN_2738 | 17006 | CTCN_5103 | 27193 |
| TTCN_3155 | 17007 | CTCN_5104 | 27194 |
| TTCN_3156 | 17008 | CTCN_5105 | 27195 |
| TTCN_3157 | 17009 | TTCN_5486 | 27196 |
| CTCN_2739 | 17010 | GTCN_2922 | 27197 |
| GTCN_1652 | 17011 | ATCN_3464 | 27198 |
| TTCN_3158 | 17012 | TTCN_5487 | 27199 |
| TTCN_3159 | 17013 | TTCN_5488 | 27200 |
| GTCN_1653 | 17014 | CTCN_5106 | 27201 |
| TTCN_3160 | 17015 | CTCN_5107 | 27202 |
| CTCN_2740 | 17016 | GTCN_2923 | 27203 |
| CTCN_2741 | 17017 | TTCN_5489 | 27204 |
| CTCN_2742 | 17018 | TTCN_5490 | 27205 |
| GTCN_1654 | 17019 | CTCN_5108 | 27206 |
| TTCN_3161 | 17020 | CTCN_5109 | 27207 |
| CTCN_2743 | 17021 | CTCN_5110 | 27208 |
| ATCN_1955 | 17022 | CTCN_5111 | 27209 |
| TTCN_3162 | 17023 | TTCN_5491 | 27210 |
| ATCN_1956 | 17024 | CTCN_5112 | 27211 |
| CTCN_2744 | 17025 | CTCN_5113 | 27212 |
| CTCN_2745 | 17026 | CTCN_5114 | 27213 |
| TTCN_3163 | 17027 | CTCN_5115 | 27214 |
| TTCN_3164 | 17028 | TTCN_5492 | 27215 |
| TTCN_3165 | 17029 | TTCN_5493 | 27216 |
| ATCN_1957 | 17030 | CTCN_5116 | 27217 |
| CTCN_2746 | 17031 | CTCN_5117 | 27218 |
| CTCN_2747 | 17032 | TTCN_5494 | 27219 |
| CTCN_2748 | 17033 | CTCN_5118 | 27220 |
| CTCN_2749 | 17034 | GTCN_2924 | 27221 |
| CTCN_2750 | 17035 | GTCN_2925 | 27222 |
| GTCN_1655 | 17036 | CTCN_5119 | 27223 |

| | | | |
|---|---|---|---|
| GTCN_1656 | 17037 | GTCN_2926 | 27224 |
| TTCN_3166 | 17038 | CTCN_5120 | 27225 |
| TTCN_3167 | 17039 | CTCN_5121 | 27226 |
| ATCN_1958 | 17040 | TTCN_5495 | 27227 |
| CTCN_2751 | 17041 | ATCN_3465 | 27228 |
| ATCN_1959 | 17042 | TTCN_5496 | 27229 |
| ATCN_1960 | 17043 | TTCN_5497 | 27230 |
| TTCN_3168 | 17044 | TTCN_5498 | 27231 |
| ATCN_1961 | 17045 | TTCN_5499 | 27232 |
| ATCN_1962 | 17046 | ATCN_3466 | 27233 |
| TTCN_3169 | 17047 | TTCN_5500 | 27234 |
| TTCN_3170 | 17048 | CTCN_5122 | 27235 |
| TTCN_3171 | 17049 | CTCN_5123 | 27236 |
| TTCN_3172 | 17050 | ATCN_3467 | 27237 |
| ATCN_1963 | 17051 | GTCN_2927 | 27238 |
| TTCN_3173 | 17052 | GTCN_2928 | 27239 |
| ATCN_1964 | 17053 | CTCN_5124 | 27240 |
| ATCN_1965 | 17054 | CTCN_5125 | 27241 |
| CTCN_2752 | 17055 | GTCN_2929 | 27242 |
| TTCN_3174 | 17056 | TTCN_5501 | 27243 |
| TTCN_3175 | 17057 | CTCN_5126 | 27244 |
| GTCN_1657 | 17058 | CTCN_5127 | 27245 |
| ATCN_1966 | 17059 | TTCN_5502 | 27246 |
| CTCN_2753 | 17060 | GTCN_2930 | 27247 |
| TTCN_3176 | 17061 | TTCN_5503 | 27248 |
| CTCN_2754 | 17062 | CTCN_5128 | 27249 |
| GTCN_1658 | 17063 | TTCN_5504 | 27250 |
| ATCN_1967 | 17064 | ATCN_3468 | 27251 |
| TTCN_3177 | 17065 | CTCN_5129 | 27252 |
| CTCN_2755 | 17066 | CTCN_5130 | 27253 |
| CTCN_2756 | 17067 | TTCN_5505 | 27254 |
| GTCN_1659 | 17068 | CTCN_5131 | 27255 |
| GTCN_1660 | 17069 | ATCN_3469 | 27256 |
| GTCN_1661 | 17070 | ATCN_3470 | 27257 |
| TTCN_3178 | 17071 | CTCN_5132 | 27258 |
| CTCN_2757 | 17072 | GTCN_2931 | 27259 |
| TTCN_3179 | 17073 | CTCN_5133 | 27260 |
| ATCN_1968 | 17074 | CTCN_5134 | 27261 |
| TTCN_3180 | 17075 | GTCN_2932 | 27262 |
| TTCN_3181 | 17076 | CTCN_5135 | 27263 |
| TTCN_3182 | 17077 | TTCN_5506 | 27264 |
| TTCN_3183 | 17078 | TTCN_5507 | 27265 |
| CTCN_2758 | 17079 | TTCN_5508 | 27266 |
| GTCN_1662 | 17080 | CTCN_5136 | 27267 |
| TTCN_3184 | 17081 | CTCN_5137 | 27268 |
| CTCN_2759 | 17082 | CTCN_5138 | 27269 |
| ATCN_1969 | 17083 | CTCN_5139 | 27270 |
| ATCN_1970 | 17084 | CTCN_5140 | 27271 |
| GTCN_1663 | 17085 | CTCN_5141 | 27272 |
| TTCN_3185 | 17086 | TTCN_5509 | 27273 |
| CTCN_2760 | 17087 | CTCN_5142 | 27274 |
| GTCN_1664 | 17088 | CTCN_5143 | 27275 |
| ATCN_1971 | 17089 | GTCN_2933 | 27276 |
| CTCN_2761 | 17090 | CTCN_5144 | 27277 |
| CTCN_2762 | 17091 | CTCN_5145 | 27278 |

FIG. 36 (continued)

| | | | |
|---|---|---|---|
| GTCN_1665 | 17092 | CTCN_5146 | 27279 |
| TTCN_3186 | 17093 | CTCN_5147 | 27280 |
| TTCN_3187 | 17094 | TTCN_5510 | 27281 |
| CTCN_2763 | 17095 | ATCN_3471 | 27282 |
| GTCN_1666 | 17096 | TTCN_5511 | 27283 |
| CTCN_2764 | 17097 | TTCN_5512 | 27284 |
| GTCN_1667 | 17098 | TTCN_5513 | 27285 |
| GTCN_1668 | 17099 | TTCN_5514 | 27286 |
| CTCN_2765 | 17100 | TTCN_5515 | 27287 |
| CTCN_2766 | 17101 | TTCN_5516 | 27288 |
| CTCN_2767 | 17102 | TTCN_5517 | 27289 |
| CTCN_2768 | 17103 | TTCN_5518 | 27290 |
| ATCN_1972 | 17104 | TTCN_5519 | 27291 |
| CTCN_2769 | 17105 | TTCN_5520 | 27292 |
| GTCN_1669 | 17106 | TTCN_5521 | 27293 |
| CTCN_2770 | 17107 | TTCN_5522 | 27294 |
| CTCN_2771 | 17108 | TTCN_5523 | 27295 |
| GTCN_1670 | 17109 | CTCN_5148 | 27296 |
| CTCN_2772 | 17110 | TTCN_5524 | 27297 |
| GTCN_1671 | 17111 | GTCN_2934 | 27298 |
| CTCN_2773 | 17112 | CTCN_5149 | 27299 |
| TTCN_3188 | 17113 | ATCN_3472 | 27300 |
| GTCN_1672 | 17114 | TTCN_5525 | 27301 |
| TTCN_3189 | 17115 | TTCN_5526 | 27302 |
| TTCN_3190 | 17116 | ATCN_3473 | 27303 |
| TTCN_3191 | 17117 | TTCN_5527 | 27304 |
| CTCN_2774 | 17118 | TTCN_5528 | 27305 |
| ATCN_1973 | 17119 | ATCN_3474 | 27306 |
| TTCN_3192 | 17120 | TTCN_5529 | 27307 |
| TTCN_3193 | 17121 | CTCN_5150 | 27308 |
| CTCN_2775 | 17122 | TTCN_5530 | 27309 |
| CTCN_2776 | 17123 | GTCN_2935 | 27310 |
| ATCN_1974 | 17124 | TTCN_5531 | 27311 |
| TTCN_3194 | 17125 | ATCN_3475 | 27312 |
| CTCN_2777 | 17126 | GTCN_2936 | 27313 |
| ATCN_1975 | 17127 | GTCN_2937 | 27314 |
| ATCN_1976 | 17128 | TTCN_5532 | 27315 |
| TTCN_3195 | 17129 | TTCN_5533 | 27316 |
| TTCN_3196 | 17130 | ATCN_3476 | 27317 |
| TTCN_3197 | 17131 | ATCN_3477 | 27318 |
| ATCN_1977 | 17132 | TTCN_5534 | 27319 |
| TTCN_3198 | 17133 | GTCN_2938 | 27320 |
| TTCN_3199 | 17134 | GTCN_2939 | 27321 |
| CTCN_2778 | 17135 | TTCN_5535 | 27322 |
| TTCN_3200 | 17136 | TTCN_5536 | 27323 |
| ATCN_1978 | 17137 | GTCN_2940 | 27324 |
| ATCN_1979 | 17138 | ATCN_3478 | 27325 |
| CTCN_2779 | 17139 | ATCN_3479 | 27326 |
| TTCN_3201 | 17140 | TTCN_5537 | 27327 |
| TTCN_3202 | 17141 | CTCN_5151 | 27328 |
| GTCN_1673 | 17142 | ATCN_3480 | 27329 |
| CTCN_2780 | 17143 | CTCN_5152 | 27330 |
| TTCN_3203 | 17144 | GTCN_2941 | 27331 |
| TTCN_3204 | 17145 | CTCN_5153 | 27332 |
| GTCN_1674 | 17146 | CTCN_5154 | 27333 |

| | | | |
|---|---|---|---|
| TTCN_3205 | 17147 | GTCN_2942 | 27334 |
| TTCN_3206 | 17148 | TTCN_5538 | 27335 |
| ATCN_1980 | 17149 | TTCN_5539 | 27336 |
| TTCN_3207 | 17150 | GTCN_2943 | 27337 |
| TTCN_3208 | 17151 | ATCN_3481 | 27338 |
| ATCN_1981 | 17152 | TTCN_5540 | 27339 |
| ATCN_1982 | 17153 | GTCN_2944 | 27340 |
| CTCN_2781 | 17154 | TTCN_5541 | 27341 |
| TTCN_3209 | 17155 | TTCN_5542 | 27342 |
| ATCN_1983 | 17156 | ATCN_3482 | 27343 |
| GTCN_1675 | 17157 | GTCN_2945 | 27344 |
| TTCN_3210 | 17158 | ATCN_3483 | 27345 |
| CTCN_2782 | 17159 | TTCN_5543 | 27346 |
| TTCN_3211 | 17160 | TTCN_5544 | 27347 |
| CTCN_2783 | 17161 | TTCN_5545 | 27348 |
| GTCN_1676 | 17162 | ATCN_3484 | 27349 |
| TTCN_3212 | 17163 | TTCN_5546 | 27350 |
| GTCN_1677 | 17164 | CTCN_5155 | 27351 |
| CTCN_2784 | 17165 | ATCN_3485 | 27352 |
| TTCN_3213 | 17166 | TTCN_5547 | 27353 |
| TTCN_3214 | 17167 | TTCN_5548 | 27354 |
| GTCN_1678 | 17168 | TTCN_5549 | 27355 |
| CTCN_2785 | 17169 | ATCN_3486 | 27356 |
| ATCN_1984 | 17170 | CTCN_5156 | 27357 |
| ATCN_1985 | 17171 | ATCN_3487 | 27358 |
| CTCN_2786 | 17172 | TTCN_5550 | 27359 |
| ATCN_1986 | 17173 | ATCN_3488 | 27360 |
| CTCN_2787 | 17174 | GTCN_2946 | 27361 |
| CTCN_2788 | 17175 | ATCN_3489 | 27362 |
| CTCN_2789 | 17176 | TTCN_5551 | 27363 |
| ATCN_1987 | 17177 | TTCN_5552 | 27364 |
| TTCN_3215 | 17178 | CTCN_5157 | 27365 |
| CTCN_2790 | 17179 | GTCN_2947 | 27366 |
| TTCN_3216 | 17180 | CTCN_5158 | 27367 |
| GTCN_1679 | 17181 | ATCN_3490 | 27368 |
| TTCN_3217 | 17182 | ATCN_3491 | 27369 |
| ATCN_1988 | 17183 | TTCN_5553 | 27370 |
| ATCN_1989 | 17184 | CTCN_5159 | 27371 |
| TTCN_3218 | 17185 | GTCN_2948 | 27372 |
| TTCN_3219 | 17186 | GTCN_2949 | 27373 |
| GTCN_1680 | 17187 | GTCN_2950 | 27374 |
| ATCN_1990 | 17188 | TTCN_5554 | 27375 |
| GTCN_1681 | 17189 | CTCN_5160 | 27376 |
| TTCN_3220 | 17190 | TTCN_5555 | 27377 |
| TTCN_3221 | 17191 | CTCN_5161 | 27378 |
| CTCN_2791 | 17192 | CTCN_5162 | 27379 |
| CTCN_2792 | 17193 | TTCN_5556 | 27380 |
| TTCN_3222 | 17194 | CTCN_5163 | 27381 |
| CTCN_2793 | 17195 | CTCN_5164 | 27382 |
| ATCN_1991 | 17196 | CTCN_5165 | 27383 |
| CTCN_2794 | 17197 | TTCN_5557 | 27384 |
| GTCN_1682 | 17198 | TTCN_5558 | 27385 |
| CTCN_2795 | 17199 | ATCN_3492 | 27386 |
| TTCN_3223 | 17200 | CTCN_5166 | 27387 |
| CTCN_2796 | 17201 | ATCN_3493 | 27388 |

FIG. 36 (continued)

| | | | |
|---|---|---|---|
| ATCN_1992 | 17202 | ATCN_3494 | 27389 |
| ATCN_1993 | 17203 | ATCN_3495 | 27390 |
| TTCN_3224 | 17204 | ATCN_3496 | 27391 |
| CTCN_2797 | 17205 | ATCN_3497 | 27392 |
| ATCN_1994 | 17206 | ATCN_3498 | 27393 |
| TTCN_3225 | 17207 | TTCN_5559 | 27394 |
| ATCN_1995 | 17208 | TTCN_5560 | 27395 |
| TTCN_3226 | 17209 | CTCN_5167 | 27396 |
| GTCN_1683 | 17210 | TTCN_5561 | 27397 |
| CTCN_2798 | 17211 | TTCN_5562 | 27398 |
| CTCN_2799 | 17212 | TTCN_5563 | 27399 |
| CTCN_2800 | 17213 | ATCN_3499 | 27400 |
| GTCN_1684 | 17214 | TTCN_5564 | 27401 |
| GTCN_1685 | 17215 | GTCN_2951 | 27402 |
| ATCN_1996 | 17216 | CTCN_5168 | 27403 |
| CTCN_2801 | 17217 | ATCN_3500 | 27404 |
| CTCN_2802 | 17218 | ATCN_3501 | 27405 |
| GTCN_1686 | 17219 | ATCN_3502 | 27406 |
| ATCN_1997 | 17220 | ATCN_3503 | 27407 |
| GTCN_1687 | 17221 | CTCN_5169 | 27408 |
| ATCN_1998 | 17222 | TTCN_5565 | 27409 |
| GTCN_1688 | 17223 | TTCN_5566 | 27410 |
| GTCN_1689 | 17224 | GTCN_2952 | 27411 |
| ATCN_1999 | 17225 | TTCN_5567 | 27412 |
| GTCN_1690 | 17226 | ATCN_3504 | 27413 |
| CTCN_2803 | 17227 | TTCN_5568 | 27414 |
| CTCN_2804 | 17228 | CTCN_5170 | 27415 |
| CTCN_2805 | 17229 | GTCN_2953 | 27416 |
| CTCN_2806 | 17230 | CTCN_5171 | 27417 |
| CTCN_2807 | 17231 | TTCN_5569 | 27418 |
| GTCN_1691 | 17232 | CTCN_5172 | 27419 |
| CTCN_2808 | 17233 | CTCN_5173 | 27420 |
| CTCN_2809 | 17234 | CTCN_5174 | 27421 |
| ATCN_2000 | 17235 | CTCN_5175 | 27422 |
| CTCN_2810 | 17236 | CTCN_5176 | 27423 |
| GTCN_1692 | 17237 | TTCN_5570 | 27424 |
| TTCN_3227 | 17238 | GTCN_2954 | 27425 |
| CTCN_2811 | 17239 | TTCN_5571 | 27426 |
| TTCN_3228 | 17240 | CTCN_5177 | 27427 |
| CTCN_2812 | 17241 | GTCN_2955 | 27428 |
| GTCN_1693 | 17242 | ATCN_3505 | 27429 |
| GTCN_1694 | 17243 | CTCN_5178 | 27430 |
| CTCN_2813 | 17244 | TTCN_5572 | 27431 |
| CTCN_2814 | 17245 | ATCN_3506 | 27432 |
| CTCN_2815 | 17246 | ATCN_3507 | 27433 |
| TTCN_3229 | 17247 | TTCN_5573 | 27434 |
| ATCN_2001 | 17248 | TTCN_5574 | 27435 |
| CTCN_2816 | 17249 | CTCN_5179 | 27436 |
| TTCN_3230 | 17250 | CTCN_5180 | 27437 |
| GTCN_1695 | 17251 | ATCN_3508 | 27438 |
| GTCN_1696 | 17252 | ATCN_3509 | 27439 |
| CTCN_2817 | 17253 | TTCN_5575 | 27440 |
| TTCN_3231 | 17254 | TTCN_5576 | 27441 |
| CTCN_2818 | 17255 | ATCN_3510 | 27442 |
| ATCN_2002 | 17256 | TTCN_5577 | 27443 |

| | | | |
|---|---|---|---|
| TTCN_3232 | 17257 | ATCN_3511 | 27444 |
| TTCN_3233 | 17258 | TTCN_5578 | 27445 |
| TTCN_3234 | 17259 | CTCN_5181 | 27446 |
| GTCN_1697 | 17260 | TTCN_5579 | 27447 |
| TTCN_3235 | 17261 | TTCN_5580 | 27448 |
| CTCN_2819 | 17262 | ATCN_3512 | 27449 |
| TTCN_3236 | 17263 | TTCN_5581 | 27450 |
| CTCN_2820 | 17264 | CTCN_5182 | 27451 |
| GTCN_1698 | 17265 | TTCN_5582 | 27452 |
| CTCN_2821 | 17266 | GTCN_2956 | 27453 |
| GTCN_1699 | 17267 | TTCN_5583 | 27454 |
| GTCN_1700 | 17268 | | |
| TTCN_3237 | 17269 | | |
| TTCN_3238 | 17270 | | |
| ATCN_2003 | 17271 | | |
| ATCN_2004 | 17272 | | |

232782441 v1

FIG. 37: Table 3C

| Spacer | SEQ ID NO. | Spacer | SEQ ID NO. |
|---|---|---|---|
| CTCN_0 | 27455 | CTCN_4863 | 41514 |
| TTCN_0 | 27456 | TTCN_3918 | 41515 |
| ATCN_0 | 27457 | GTCN_2506 | 41516 |
| CTCN_1 | 27458 | CTCN_4864 | 41517 |
| GTCN_0 | 27459 | CTCN_4865 | 41518 |
| GTCN_1 | 27460 | GTCN_2507 | 41519 |
| TTCN_1 | 27461 | CTCN_4866 | 41520 |
| GTCN_2 | 27462 | TTCN_3919 | 41521 |
| TTCN_2 | 27463 | ATCN_2772 | 41522 |
| TTCN_3 | 27464 | GTCN_2508 | 41523 |
| ATCN_1 | 27465 | TTCN_3920 | 41524 |
| GTCN_3 | 27466 | TTCN_3921 | 41525 |
| TTCN_4 | 27467 | TTCN_3922 | 41526 |
| GTCN_4 | 27468 | TTCN_3923 | 41527 |
| ATCN_2 | 27469 | ATCN_2773 | 41528 |
| TTCN_5 | 27470 | ATCN_2774 | 41529 |
| CTCN_2 | 27471 | TTCN_3924 | 41530 |
| CTCN_3 | 27472 | CTCN_4867 | 41531 |
| ATCN_3 | 27473 | CTCN_4868 | 41532 |
| CTCN_4 | 27474 | GTCN_2509 | 41533 |
| ATCN_4 | 27475 | CTCN_4869 | 41534 |
| ATCN_5 | 27476 | ATCN_2775 | 41535 |
| CTCN_5 | 27477 | ATCN_2776 | 41536 |
| GTCN_5 | 27478 | CTCN_4870 | 41537 |
| CTCN_6 | 27479 | GTCN_2510 | 41538 |
| ATCN_6 | 27480 | CTCN_4871 | 41539 |
| ATCN_7 | 27481 | TTCN_3925 | 41540 |
| CTCN_7 | 27482 | CTCN_4872 | 41541 |
| GTCN_6 | 27483 | CTCN_4873 | 41542 |
| TTCN_6 | 27484 | GTCN_2511 | 41543 |
| TTCN_7 | 27485 | CTCN_4874 | 41544 |
| GTCN_7 | 27486 | ATCN_2777 | 41545 |
| CTCN_8 | 27487 | TTCN_3926 | 41546 |
| GTCN_8 | 27488 | TTCN_3927 | 41547 |
| CTCN_9 | 27489 | TTCN_3928 | 41548 |
| CTCN_10 | 27490 | GTCN_2512 | 41549 |
| CTCN_11 | 27491 | TTCN_3929 | 41550 |
| CTCN_12 | 27492 | TTCN_3930 | 41551 |
| TTCN_8 | 27493 | GTCN_2513 | 41552 |
| GTCN_9 | 27494 | TTCN_3931 | 41553 |
| TTCN_9 | 27495 | GTCN_2514 | 41554 |
| TTCN_10 | 27496 | TTCN_3932 | 41555 |
| CTCN_13 | 27497 | CTCN_4875 | 41556 |
| CTCN_14 | 27498 | GTCN_2515 | 41557 |
| CTCN_15 | 27499 | CTCN_4876 | 41558 |
| ATCN_8 | 27500 | TTCN_3933 | 41559 |
| ATCN_9 | 27501 | GTCN_2516 | 41560 |
| CTCN_16 | 27502 | CTCN_4877 | 41561 |
| GTCN_10 | 27503 | CTCN_4878 | 41562 |
| CTCN_17 | 27504 | CTCN_4879 | 41563 |
| CTCN_18 | 27505 | GTCN_2517 | 41564 |
| TTCN_11 | 27506 | GTCN_2518 | 41565 |
| ATCN_10 | 27507 | ATCN_2778 | 41566 |
| CTCN_19 | 27508 | GTCN_2519 | 41567 |
| TTCN_12 | 27509 | CTCN_4880 | 41568 |
| TTCN_13 | 27510 | GTCN_2520 | 41569 |
| GTCN_11 | 27511 | CTCN_4881 | 41570 |
| TTCN_14 | 27512 | GTCN_2521 | 41571 |
| CTCN_20 | 27513 | CTCN_4882 | 41572 |
| TTCN_15 | 27514 | ATCN_2779 | 41573 |
| CTCN_21 | 27515 | ATCN_2780 | 41574 |
| GTCN_12 | 27516 | TTCN_3934 | 41575 |
| CTCN_22 | 27517 | ATCN_2781 | 41576 |
| CTCN_23 | 27518 | TTCN_3935 | 41577 |
| ATCN_11 | 27519 | CTCN_4883 | 41578 |
| ATCN_12 | 27520 | TTCN_3936 | 41579 |
| TTCN_16 | 27521 | GTCN_2522 | 41580 |
| TTCN_17 | 27522 | GTCN_2523 | 41581 |
| GTCN_13 | 27523 | TTCN_3937 | 41582 |
| CTCN_24 | 27524 | CTCN_4884 | 41583 |
| TTCN_18 | 27525 | GTCN_2524 | 41584 |
| TTCN_19 | 27526 | TTCN_3938 | 41585 |
| GTCN_14 | 27527 | TTCN_3939 | 41586 |
| CTCN_25 | 27528 | CTCN_4885 | 41587 |
| TTCN_20 | 27529 | TTCN_3940 | 41588 |
| ATCN_13 | 27530 | ATCN_2782 | 41589 |
| GTCN_15 | 27531 | TTCN_3941 | 41590 |
| TTCN_21 | 27532 | TTCN_3942 | 41591 |
| ATCN_14 | 27533 | ATCN_2783 | 41592 |
| ATCN_15 | 27534 | CTCN_4886 | 41593 |
| TTCN_22 | 27535 | ATCN_2784 | 41594 |
| TTCN_23 | 27536 | TTCN_3943 | 41595 |

FIG. 37 (continued)

| | | | |
|---|---|---|---|
| CTCN_26 | 27537 | TTCN_3944 | 41596 |
| TTCN_24 | 27538 | ATCN_2785 | 41597 |
| ATCN_16 | 27539 | GTCN_2525 | 41598 |
| TTCN_25 | 27540 | TTCN_3945 | 41599 |
| TTCN_26 | 27541 | TTCN_3946 | 41600 |
| GTCN_16 | 27542 | ATCN_2786 | 41601 |
| TTCN_27 | 27543 | ATCN_2787 | 41602 |
| TTCN_28 | 27544 | TTCN_3947 | 41603 |
| ATCN_17 | 27545 | TTCN_3948 | 41604 |
| TTCN_29 | 27546 | GTCN_2526 | 41605 |
| ATCN_18 | 27547 | CTCN_4887 | 41606 |
| GTCN_17 | 27548 | ATCN_2788 | 41607 |
| TTCN_30 | 27549 | CTCN_4888 | 41608 |
| TTCN_31 | 27550 | CTCN_4889 | 41609 |
| ATCN_19 | 27551 | TTCN_3949 | 41610 |
| GTCN_18 | 27552 | GTCN_2527 | 41611 |
| ATCN_20 | 27553 | ATCN_2789 | 41612 |
| TTCN_32 | 27554 | GTCN_2528 | 41613 |
| ATCN_21 | 27555 | CTCN_4890 | 41614 |
| CTCN_27 | 27556 | CTCN_4891 | 41615 |
| GTCN_19 | 27557 | CTCN_4892 | 41616 |
| TTCN_33 | 27558 | CTCN_4893 | 41617 |
| TTCN_34 | 27559 | TTCN_3950 | 41618 |
| TTCN_35 | 27560 | GTCN_2529 | 41619 |
| CTCN_28 | 27561 | GTCN_2530 | 41620 |
| CTCN_29 | 27562 | CTCN_4894 | 41621 |
| ATCN_22 | 27563 | ATCN_2790 | 41622 |
| ATCN_23 | 27564 | CTCN_4895 | 41623 |
| ATCN_24 | 27565 | CTCN_4896 | 41624 |
| ATCN_25 | 27566 | CTCN_4897 | 41625 |
| CTCN_30 | 27567 | GTCN_2531 | 41626 |
| TTCN_36 | 27568 | CTCN_4898 | 41627 |
| ATCN_26 | 27569 | CTCN_4899 | 41628 |
| CTCN_31 | 27570 | GTCN_2532 | 41629 |
| TTCN_37 | 27571 | TTCN_3951 | 41630 |
| TTCN_38 | 27572 | GTCN_2533 | 41631 |
| ATCN_27 | 27573 | CTCN_4900 | 41632 |
| GTCN_20 | 27574 | CTCN_4901 | 41633 |
| CTCN_32 | 27575 | GTCN_2534 | 41634 |
| CTCN_33 | 27576 | TTCN_3952 | 41635 |
| TTCN_39 | 27577 | CTCN_4902 | 41636 |
| TTCN_40 | 27578 | ATCN_2791 | 41637 |
| TTCN_41 | 27579 | GTCN_2535 | 41638 |
| CTCN_34 | 27580 | CTCN_4903 | 41639 |
| TTCN_42 | 27581 | CTCN_4904 | 41640 |
| GTCN_21 | 27582 | GTCN_2536 | 41641 |
| ATCN_28 | 27583 | CTCN_4905 | 41642 |
| ATCN_29 | 27584 | TTCN_3953 | 41643 |
| TTCN_43 | 27585 | CTCN_4906 | 41644 |
| GTCN_22 | 27586 | GTCN_2537 | 41645 |
| GTCN_23 | 27587 | TTCN_3954 | 41646 |
| ATCN_30 | 27588 | CTCN_4907 | 41647 |
| TTCN_44 | 27589 | TTCN_3955 | 41648 |
| TTCN_45 | 27590 | CTCN_4908 | 41649 |
| TTCN_46 | 27591 | GTCN_2538 | 41650 |
| ATCN_31 | 27592 | CTCN_4909 | 41651 |
| CTCN_35 | 27593 | CTCN_4910 | 41652 |
| CTCN_36 | 27594 | GTCN_2539 | 41653 |
| CTCN_37 | 27595 | GTCN_2540 | 41654 |
| ATCN_32 | 27596 | CTCN_4911 | 41655 |
| GTCN_24 | 27597 | TTCN_3956 | 41656 |
| ATCN_33 | 27598 | CTCN_4912 | 41657 |
| TTCN_47 | 27599 | CTCN_4913 | 41658 |
| ATCN_34 | 27600 | GTCN_2541 | 41659 |
| TTCN_48 | 27601 | CTCN_4914 | 41660 |
| GTCN_25 | 27602 | CTCN_4915 | 41661 |
| GTCN_26 | 27603 | ATCN_2792 | 41662 |
| GTCN_27 | 27604 | CTCN_4916 | 41663 |
| ATCN_35 | 27605 | TTCN_3957 | 41664 |
| ATCN_36 | 27606 | TTCN_3958 | 41665 |
| CTCN_38 | 27607 | ATCN_2793 | 41666 |
| GTCN_28 | 27608 | CTCN_4917 | 41667 |
| TTCN_49 | 27609 | GTCN_2542 | 41668 |
| GTCN_29 | 27610 | TTCN_3959 | 41669 |
| ATCN_37 | 27611 | CTCN_4918 | 41670 |
| ATCN_38 | 27612 | TTCN_3960 | 41671 |
| TTCN_50 | 27613 | TTCN_3961 | 41672 |
| CTCN_39 | 27614 | TTCN_3962 | 41673 |
| GTCN_30 | 27615 | ATCN_2794 | 41674 |
| TTCN_51 | 27616 | GTCN_2543 | 41675 |
| CTCN_40 | 27617 | ATCN_2795 | 41676 |
| TTCN_52 | 27618 | CTCN_4919 | 41677 |
| CTCN_41 | 27619 | CTCN_4920 | 41678 |
| CTCN_42 | 27620 | ATCN_2796 | 41679 |
| TTCN_53 | 27621 | CTCN_4921 | 41680 |
| ATCN_39 | 27622 | TTCN_3963 | 41681 |

FIG. 37 (continued)

| | | | |
|---|---|---|---|
| CTCN_43 | 27623 | TTCN_3964 | 41682 |
| GTCN_31 | 27624 | GTCN_2544 | 41683 |
| TTCN_54 | 27625 | ATCN_2797 | 41684 |
| TTCN_55 | 27626 | GTCN_2545 | 41685 |
| GTCN_32 | 27627 | TTCN_3965 | 41686 |
| ATCN_40 | 27628 | TTCN_3966 | 41687 |
| ATCN_41 | 27629 | ATCN_2798 | 41688 |
| ATCN_42 | 27630 | GTCN_2546 | 41689 |
| CTCN_44 | 27631 | ATCN_2799 | 41690 |
| TTCN_56 | 27632 | GTCN_2547 | 41691 |
| ATCN_43 | 27633 | TTCN_3967 | 41692 |
| GTCN_33 | 27634 | TTCN_3968 | 41693 |
| TTCN_57 | 27635 | ATCN_2800 | 41694 |
| TTCN_58 | 27636 | CTCN_4922 | 41695 |
| TTCN_59 | 27637 | ATCN_2801 | 41696 |
| CTCN_45 | 27638 | CTCN_4923 | 41697 |
| ATCN_44 | 27639 | CTCN_4924 | 41698 |
| TTCN_60 | 27640 | TTCN_3969 | 41699 |
| ATCN_45 | 27641 | GTCN_2548 | 41700 |
| TTCN_61 | 27642 | GTCN_2549 | 41701 |
| ATCN_46 | 27643 | GTCN_2550 | 41702 |
| CTCN_46 | 27644 | ATCN_2802 | 41703 |
| TTCN_62 | 27645 | CTCN_4925 | 41704 |
| TTCN_63 | 27646 | TTCN_3970 | 41705 |
| GTCN_34 | 27647 | CTCN_4926 | 41706 |
| CTCN_47 | 27648 | TTCN_3971 | 41707 |
| GTCN_35 | 27649 | GTCN_2551 | 41708 |
| GTCN_36 | 27650 | GTCN_2552 | 41709 |
| TTCN_64 | 27651 | TTCN_3972 | 41710 |
| TTCN_65 | 27652 | TTCN_3973 | 41711 |
| TTCN_66 | 27653 | ATCN_2803 | 41712 |
| CTCN_48 | 27654 | CTCN_4927 | 41713 |
| GTCN_37 | 27655 | CTCN_4928 | 41714 |
| TTCN_67 | 27656 | TTCN_3974 | 41715 |
| GTCN_38 | 27657 | CTCN_4929 | 41716 |
| CTCN_49 | 27658 | TTCN_3975 | 41717 |
| TTCN_68 | 27659 | GTCN_2553 | 41718 |
| ATCN_47 | 27660 | GTCN_2554 | 41719 |
| ATCN_48 | 27661 | ATCN_2804 | 41720 |
| TTCN_69 | 27662 | TTCN_3976 | 41721 |
| GTCN_39 | 27663 | GTCN_2555 | 41722 |
| TTCN_70 | 27664 | TTCN_3977 | 41723 |
| GTCN_40 | 27665 | TTCN_3978 | 41724 |

| | | | |
|---|---|---|---|
| TTCN_71 | 27666 | CTCN_4930 | 41725 |
| GTCN_41 | 27667 | ATCN_2805 | 41726 |
| TTCN_72 | 27668 | GTCN_2556 | 41727 |
| CTCN_50 | 27669 | CTCN_4931 | 41728 |
| CTCN_51 | 27670 | CTCN_4932 | 41729 |
| CTCN_52 | 27671 | CTCN_4933 | 41730 |
| CTCN_53 | 27672 | CTCN_4934 | 41731 |
| CTCN_54 | 27673 | CTCN_4935 | 41732 |
| GTCN_42 | 27674 | CTCN_4936 | 41733 |
| TTCN_73 | 27675 | GTCN_2557 | 41734 |
| GTCN_43 | 27676 | ATCN_2806 | 41735 |
| CTCN_55 | 27677 | ATCN_2807 | 41736 |
| CTCN_56 | 27678 | GTCN_2558 | 41737 |
| GTCN_44 | 27679 | ATCN_2808 | 41738 |
| GTCN_45 | 27680 | TTCN_3979 | 41739 |
| CTCN_57 | 27681 | GTCN_2559 | 41740 |
| GTCN_46 | 27682 | TTCN_3980 | 41741 |
| GTCN_47 | 27683 | ATCN_2809 | 41742 |
| GTCN_48 | 27684 | TTCN_3981 | 41743 |
| CTCN_58 | 27685 | ATCN_2810 | 41744 |
| TTCN_74 | 27686 | ATCN_2811 | 41745 |
| GTCN_49 | 27687 | CTCN_4937 | 41746 |
| ATCN_49 | 27688 | ATCN_2812 | 41747 |
| TTCN_75 | 27689 | ATCN_2813 | 41748 |
| CTCN_59 | 27690 | ATCN_2814 | 41749 |
| CTCN_60 | 27691 | CTCN_4938 | 41750 |
| GTCN_50 | 27692 | GTCN_2560 | 41751 |
| CTCN_61 | 27693 | CTCN_4939 | 41752 |
| TTCN_76 | 27694 | CTCN_4940 | 41753 |
| CTCN_62 | 27695 | CTCN_4941 | 41754 |
| TTCN_77 | 27696 | GTCN_2561 | 41755 |
| CTCN_63 | 27697 | TTCN_3982 | 41756 |
| TTCN_78 | 27698 | TTCN_3983 | 41757 |
| CTCN_64 | 27699 | GTCN_2562 | 41758 |
| CTCN_65 | 27700 | GTCN_2563 | 41759 |
| ATCN_50 | 27701 | GTCN_2564 | 41760 |
| ATCN_51 | 27702 | ATCN_2815 | 41761 |
| TTCN_79 | 27703 | CTCN_4942 | 41762 |
| GTCN_51 | 27704 | GTCN_2565 | 41763 |
| GTCN_52 | 27705 | ATCN_2816 | 41764 |
| TTCN_80 | 27706 | CTCN_4943 | 41765 |
| TTCN_81 | 27707 | ATCN_2817 | 41766 |
| CTCN_66 | 27708 | CTCN_4944 | 41767 |

FIG. 37 (continued)

| | | | |
|---|---|---|---|
| CTCN_67 | 27709 | CTCN_4945 | 41768 |
| TTCN_82 | 27710 | CTCN_4946 | 41769 |
| TTCN_83 | 27711 | GTCN_2566 | 41770 |
| CTCN_68 | 27712 | CTCN_4947 | 41771 |
| CTCN_69 | 27713 | CTCN_4948 | 41772 |
| TTCN_84 | 27714 | GTCN_2567 | 41773 |
| GTCN_53 | 27715 | GTCN_2568 | 41774 |
| GTCN_54 | 27716 | CTCN_4949 | 41775 |
| TTCN_85 | 27717 | ATCN_2818 | 41776 |
| CTCN_70 | 27718 | ATCN_2819 | 41777 |
| TTCN_86 | 27719 | GTCN_2569 | 41778 |
| CTCN_71 | 27720 | TTCN_3984 | 41779 |
| TTCN_87 | 27721 | ATCN_2820 | 41780 |
| GTCN_55 | 27722 | ATCN_2821 | 41781 |
| ATCN_52 | 27723 | CTCN_4950 | 41782 |
| CTCN_72 | 27724 | TTCN_3985 | 41783 |
| CTCN_73 | 27725 | CTCN_4951 | 41784 |
| GTCN_56 | 27726 | TTCN_3986 | 41785 |
| GTCN_57 | 27727 | GTCN_2570 | 41786 |
| CTCN_74 | 27728 | CTCN_4952 | 41787 |
| GTCN_58 | 27729 | TTCN_3987 | 41788 |
| TTCN_88 | 27730 | TTCN_3988 | 41789 |
| GTCN_59 | 27731 | ATCN_2822 | 41790 |
| CTCN_75 | 27732 | CTCN_4953 | 41791 |
| GTCN_60 | 27733 | GTCN_2571 | 41792 |
| CTCN_76 | 27734 | CTCN_4954 | 41793 |
| CTCN_77 | 27735 | ATCN_2823 | 41794 |
| GTCN_61 | 27736 | TTCN_3989 | 41795 |
| GTCN_62 | 27737 | GTCN_2572 | 41796 |
| CTCN_78 | 27738 | GTCN_2573 | 41797 |
| TTCN_89 | 27739 | CTCN_4955 | 41798 |
| ATCN_53 | 27740 | CTCN_4956 | 41799 |
| TTCN_90 | 27741 | CTCN_4957 | 41800 |
| TTCN_91 | 27742 | TTCN_3990 | 41801 |
| GTCN_63 | 27743 | ATCN_2824 | 41802 |
| CTCN_79 | 27744 | ATCN_2825 | 41803 |
| GTCN_64 | 27745 | GTCN_2574 | 41804 |
| TTCN_92 | 27746 | CTCN_4958 | 41805 |
| GTCN_65 | 27747 | GTCN_2575 | 41806 |
| ATCN_54 | 27748 | CTCN_4959 | 41807 |
| CTCN_80 | 27749 | TTCN_3991 | 41808 |
| TTCN_93 | 27750 | CTCN_4960 | 41809 |
| GTCN_66 | 27751 | ATCN_2826 | 41810 |

| | | | |
|---|---|---|---|
| TTCN_94 | 27752 | ATCN_2827 | 41811 |
| TTCN_95 | 27753 | ATCN_2828 | 41812 |
| CTCN_81 | 27754 | TTCN_3992 | 41813 |
| CTCN_82 | 27755 | GTCN_2576 | 41814 |
| ATCN_55 | 27756 | CTCN_4961 | 41815 |
| TTCN_96 | 27757 | CTCN_4962 | 41816 |
| CTCN_83 | 27758 | GTCN_2577 | 41817 |
| CTCN_84 | 27759 | CTCN_4963 | 41818 |
| TTCN_97 | 27760 | CTCN_4964 | 41819 |
| TTCN_98 | 27761 | CTCN_4965 | 41820 |
| ATCN_56 | 27762 | CTCN_4966 | 41821 |
| ATCN_57 | 27763 | TTCN_3993 | 41822 |
| CTCN_85 | 27764 | CTCN_4967 | 41823 |
| GTCN_67 | 27765 | CTCN_4968 | 41824 |
| GTCN_68 | 27766 | GTCN_2578 | 41825 |
| ATCN_58 | 27767 | GTCN_2579 | 41826 |
| ATCN_59 | 27768 | TTCN_3994 | 41827 |
| GTCN_69 | 27769 | GTCN_2580 | 41828 |
| CTCN_86 | 27770 | CTCN_4969 | 41829 |
| CTCN_87 | 27771 | TTCN_3995 | 41830 |
| TTCN_99 | 27772 | CTCN_4970 | 41831 |
| CTCN_88 | 27773 | ATCN_2829 | 41832 |
| TTCN_100 | 27774 | CTCN_4971 | 41833 |
| ATCN_60 | 27775 | CTCN_4972 | 41834 |
| TTCN_101 | 27776 | ATCN_2830 | 41835 |
| ATCN_61 | 27777 | TTCN_3996 | 41836 |
| CTCN_89 | 27778 | TTCN_3997 | 41837 |
| CTCN_90 | 27779 | TTCN_3998 | 41838 |
| GTCN_70 | 27780 | ATCN_2831 | 41839 |
| CTCN_91 | 27781 | CTCN_4973 | 41840 |
| CTCN_92 | 27782 | GTCN_2581 | 41841 |
| TTCN_102 | 27783 | GTCN_2582 | 41842 |
| GTCN_71 | 27784 | CTCN_4974 | 41843 |
| CTCN_93 | 27785 | CTCN_4975 | 41844 |
| CTCN_94 | 27786 | ATCN_2832 | 41845 |
| GTCN_72 | 27787 | GTCN_2583 | 41846 |
| TTCN_103 | 27788 | CTCN_4976 | 41847 |
| TTCN_104 | 27789 | CTCN_4977 | 41848 |
| GTCN_73 | 27790 | TTCN_3999 | 41849 |
| CTCN_95 | 27791 | CTCN_4978 | 41850 |
| GTCN_74 | 27792 | TTCN_4000 | 41851 |
| GTCN_75 | 27793 | GTCN_2584 | 41852 |
| CTCN_96 | 27794 | GTCN_2585 | 41853 |

FIG. 37 (continued)

| | | | |
|---|---|---|---|
| ATCN_62 | 27795 | CTCN_4979 | 41854 |
| ATCN_63 | 27796 | CTCN_4980 | 41855 |
| CTCN_97 | 27797 | GTCN_2586 | 41856 |
| CTCN_98 | 27798 | CTCN_4981 | 41857 |
| TTCN_105 | 27799 | TTCN_4001 | 41858 |
| CTCN_99 | 27800 | CTCN_4982 | 41859 |
| CTCN_100 | 27801 | TTCN_4002 | 41860 |
| TTCN_106 | 27802 | TTCN_4003 | 41861 |
| ATCN_64 | 27803 | GTCN_2587 | 41862 |
| TTCN_107 | 27804 | CTCN_4983 | 41863 |
| CTCN_101 | 27805 | GTCN_2588 | 41864 |
| CTCN_102 | 27806 | CTCN_4984 | 41865 |
| GTCN_76 | 27807 | ATCN_2833 | 41866 |
| CTCN_103 | 27808 | ATCN_2834 | 41867 |
| CTCN_104 | 27809 | TTCN_4004 | 41868 |
| GTCN_77 | 27810 | CTCN_4985 | 41869 |
| TTCN_108 | 27811 | CTCN_4986 | 41870 |
| CTCN_105 | 27812 | TTCN_4005 | 41871 |
| TTCN_109 | 27813 | ATCN_2835 | 41872 |
| GTCN_78 | 27814 | TTCN_4006 | 41873 |
| GTCN_79 | 27815 | TTCN_4007 | 41874 |
| CTCN_106 | 27816 | TTCN_4008 | 41875 |
| TTCN_110 | 27817 | CTCN_4987 | 41876 |
| CTCN_107 | 27818 | CTCN_4988 | 41877 |
| GTCN_80 | 27819 | GTCN_2589 | 41878 |
| CTCN_108 | 27820 | ATCN_2836 | 41879 |
| ATCN_65 | 27821 | GTCN_2590 | 41880 |
| ATCN_66 | 27822 | TTCN_4009 | 41881 |
| CTCN_109 | 27823 | CTCN_4989 | 41882 |
| ATCN_67 | 27824 | GTCN_2591 | 41883 |
| CTCN_110 | 27825 | GTCN_2592 | 41884 |
| CTCN_111 | 27826 | CTCN_4990 | 41885 |
| TTCN_111 | 27827 | CTCN_4991 | 41886 |
| ATCN_68 | 27828 | GTCN_2593 | 41887 |
| TTCN_112 | 27829 | CTCN_4992 | 41888 |
| CTCN_112 | 27830 | ATCN_2837 | 41889 |
| TTCN_113 | 27831 | ATCN_2838 | 41890 |
| CTCN_113 | 27832 | CTCN_4993 | 41891 |
| CTCN_114 | 27833 | CTCN_4994 | 41892 |
| CTCN_115 | 27834 | ATCN_2839 | 41893 |
| GTCN_81 | 27835 | CTCN_4995 | 41894 |
| ATCN_69 | 27836 | CTCN_4996 | 41895 |
| ATCN_70 | 27837 | TTCN_4010 | 41896 |

| | | | |
|---|---|---|---|
| TTCN_114 | 27838 | TTCN_4011 | 41897 |
| ATCN_71 | 27839 | CTCN_4997 | 41898 |
| ATCN_72 | 27840 | CTCN_4998 | 41899 |
| GTCN_82 | 27841 | CTCN_4999 | 41900 |
| TTCN_115 | 27842 | GTCN_2594 | 41901 |
| GTCN_83 | 27843 | GTCN_2595 | 41902 |
| CTCN_116 | 27844 | GTCN_2596 | 41903 |
| CTCN_117 | 27845 | CTCN_5000 | 41904 |
| CTCN_118 | 27846 | TTCN_4012 | 41905 |
| TTCN_116 | 27847 | GTCN_2597 | 41906 |
| TTCN_117 | 27848 | ATCN_2840 | 41907 |
| CTCN_119 | 27849 | TTCN_4013 | 41908 |
| ATCN_73 | 27850 | ATCN_2841 | 41909 |
| CTCN_120 | 27851 | TTCN_4014 | 41910 |
| GTCN_84 | 27852 | GTCN_2598 | 41911 |
| CTCN_121 | 27853 | GTCN_2599 | 41912 |
| ATCN_74 | 27854 | CTCN_5001 | 41913 |
| CTCN_122 | 27855 | GTCN_2600 | 41914 |
| CTCN_123 | 27856 | ATCN_2842 | 41915 |
| ATCN_75 | 27857 | TTCN_4015 | 41916 |
| ATCN_76 | 27858 | GTCN_2601 | 41917 |
| ATCN_77 | 27859 | CTCN_5002 | 41918 |
| CTCN_124 | 27860 | CTCN_5003 | 41919 |
| GTCN_85 | 27861 | TTCN_4016 | 41920 |
| CTCN_125 | 27862 | GTCN_2602 | 41921 |
| TTCN_118 | 27863 | TTCN_4017 | 41922 |
| CTCN_126 | 27864 | TTCN_4018 | 41923 |
| GTCN_86 | 27865 | TTCN_4019 | 41924 |
| TTCN_119 | 27866 | GTCN_2603 | 41925 |
| GTCN_87 | 27867 | TTCN_4020 | 41926 |
| CTCN_127 | 27868 | GTCN_2604 | 41927 |
| CTCN_128 | 27869 | CTCN_5004 | 41928 |
| CTCN_129 | 27870 | GTCN_2605 | 41929 |
| CTCN_130 | 27871 | GTCN_2606 | 41930 |
| CTCN_131 | 27872 | CTCN_5005 | 41931 |
| ATCN_78 | 27873 | TTCN_4021 | 41932 |
| ATCN_79 | 27874 | CTCN_5006 | 41933 |
| TTCN_120 | 27875 | ATCN_2843 | 41934 |
| CTCN_132 | 27876 | ATCN_2844 | 41935 |
| CTCN_133 | 27877 | CTCN_5007 | 41936 |
| CTCN_134 | 27878 | TTCN_4022 | 41937 |
| CTCN_135 | 27879 | CTCN_5008 | 41938 |
| ATCN_80 | 27880 | ATCN_2845 | 41939 |

FIG. 37 (continued)

| | | | |
|---|---|---|---|
| ATCN_81 | 27881 | GTCN_2607 | 41940 |
| CTCN_136 | 27882 | CTCN_5009 | 41941 |
| GTCN_88 | 27883 | CTCN_5010 | 41942 |
| CTCN_137 | 27884 | GTCN_2608 | 41943 |
| CTCN_138 | 27885 | CTCN_5011 | 41944 |
| GTCN_89 | 27886 | TTCN_4023 | 41945 |
| GTCN_90 | 27887 | GTCN_2609 | 41946 |
| CTCN_139 | 27888 | CTCN_5012 | 41947 |
| TTCN_121 | 27889 | GTCN_2610 | 41948 |
| TTCN_122 | 27890 | CTCN_5013 | 41949 |
| CTCN_140 | 27891 | GTCN_2611 | 41950 |
| TTCN_123 | 27892 | TTCN_4024 | 41951 |
| ATCN_82 | 27893 | GTCN_2612 | 41952 |
| CTCN_141 | 27894 | CTCN_5014 | 41953 |
| GTCN_91 | 27895 | TTCN_4025 | 41954 |
| CTCN_142 | 27896 | TTCN_4026 | 41955 |
| CTCN_143 | 27897 | GTCN_2613 | 41956 |
| GTCN_92 | 27898 | GTCN_2614 | 41957 |
| TTCN_124 | 27899 | CTCN_5015 | 41958 |
| CTCN_144 | 27900 | TTCN_4027 | 41959 |
| CTCN_145 | 27901 | GTCN_2615 | 41960 |
| CTCN_146 | 27902 | CTCN_5016 | 41961 |
| CTCN_147 | 27903 | TTCN_4028 | 41962 |
| CTCN_148 | 27904 | CTCN_5017 | 41963 |
| TTCN_125 | 27905 | CTCN_5018 | 41964 |
| GTCN_93 | 27906 | GTCN_2616 | 41965 |
| TTCN_126 | 27907 | TTCN_4029 | 41966 |
| ATCN_83 | 27908 | CTCN_5019 | 41967 |
| CTCN_149 | 27909 | ATCN_2846 | 41968 |
| ATCN_84 | 27910 | CTCN_5020 | 41969 |
| CTCN_150 | 27911 | CTCN_5021 | 41970 |
| TTCN_127 | 27912 | CTCN_5022 | 41971 |
| TTCN_128 | 27913 | GTCN_2617 | 41972 |
| TTCN_129 | 27914 | TTCN_4030 | 41973 |
| TTCN_130 | 27915 | TTCN_4031 | 41974 |
| TTCN_131 | 27916 | GTCN_2618 | 41975 |
| CTCN_151 | 27917 | TTCN_4032 | 41976 |
| TTCN_132 | 27918 | CTCN_5023 | 41977 |
| CTCN_152 | 27919 | GTCN_2619 | 41978 |
| TTCN_133 | 27920 | CTCN_5024 | 41979 |
| ATCN_85 | 27921 | CTCN_5025 | 41980 |
| TTCN_134 | 27922 | GTCN_2620 | 41981 |
| TTCN_135 | 27923 | GTCN_2621 | 41982 |

| | | | |
|---|---|---|---|
| TTCN_136 | 27924 | TTCN_4033 | 41983 |
| CTCN_153 | 27925 | ATCN_2847 | 41984 |
| TTCN_137 | 27926 | ATCN_2848 | 41985 |
| TTCN_138 | 27927 | CTCN_5026 | 41986 |
| TTCN_139 | 27928 | CTCN_5027 | 41987 |
| GTCN_94 | 27929 | CTCN_5028 | 41988 |
| GTCN_95 | 27930 | ATCN_2849 | 41989 |
| CTCN_154 | 27931 | ATCN_2850 | 41990 |
| CTCN_155 | 27932 | CTCN_5029 | 41991 |
| CTCN_156 | 27933 | CTCN_5030 | 41992 |
| TTCN_140 | 27934 | CTCN_5031 | 41993 |
| GTCN_96 | 27935 | TTCN_4034 | 41994 |
| ATCN_86 | 27936 | GTCN_2622 | 41995 |
| CTCN_157 | 27937 | CTCN_5032 | 41996 |
| ATCN_87 | 27938 | GTCN_2623 | 41997 |
| ATCN_88 | 27939 | ATCN_2851 | 41998 |
| CTCN_158 | 27940 | CTCN_5033 | 41999 |
| ATCN_89 | 27941 | GTCN_2624 | 42000 |
| GTCN_97 | 27942 | CTCN_5034 | 42001 |
| GTCN_98 | 27943 | GTCN_2625 | 42002 |
| GTCN_99 | 27944 | TTCN_4035 | 42003 |
| ATCN_90 | 27945 | CTCN_5035 | 42004 |
| TTCN_141 | 27946 | CTCN_5036 | 42005 |
| CTCN_159 | 27947 | ATCN_2852 | 42006 |
| GTCN_100 | 27948 | TTCN_4036 | 42007 |
| CTCN_160 | 27949 | CTCN_5037 | 42008 |
| GTCN_101 | 27950 | CTCN_5038 | 42009 |
| GTCN_102 | 27951 | CTCN_5039 | 42010 |
| CTCN_161 | 27952 | ATCN_2853 | 42011 |
| ATCN_91 | 27953 | TTCN_4037 | 42012 |
| CTCN_162 | 27954 | TTCN_4038 | 42013 |
| ATCN_92 | 27955 | TTCN_4039 | 42014 |
| TTCN_142 | 27956 | GTCN_2626 | 42015 |
| ATCN_93 | 27957 | ATCN_2854 | 42016 |
| CTCN_163 | 27958 | GTCN_2627 | 42017 |
| TTCN_143 | 27959 | CTCN_5040 | 42018 |
| CTCN_164 | 27960 | TTCN_4040 | 42019 |
| CTCN_165 | 27961 | CTCN_5041 | 42020 |
| GTCN_103 | 27962 | CTCN_5042 | 42021 |
| ATCN_94 | 27963 | GTCN_2628 | 42022 |
| ATCN_95 | 27964 | CTCN_5043 | 42023 |
| GTCN_104 | 27965 | TTCN_4041 | 42024 |
| TTCN_144 | 27966 | CTCN_5044 | 42025 |

FIG. 37 (continued)

| | | | |
|---|---|---|---|
| GTCN_105 | 27967 | CTCN_5045 | 42026 |
| TTCN_145 | 27968 | GTCN_2629 | 42027 |
| GTCN_106 | 27969 | TTCN_4042 | 42028 |
| ATCN_96 | 27970 | TTCN_4043 | 42029 |
| CTCN_166 | 27971 | TTCN_4044 | 42030 |
| CTCN_167 | 27972 | TTCN_4045 | 42031 |
| GTCN_107 | 27973 | ATCN_2855 | 42032 |
| ATCN_97 | 27974 | CTCN_5046 | 42033 |
| GTCN_108 | 27975 | TTCN_4046 | 42034 |
| CTCN_168 | 27976 | TTCN_4047 | 42035 |
| CTCN_169 | 27977 | TTCN_4048 | 42036 |
| TTCN_146 | 27978 | CTCN_5047 | 42037 |
| CTCN_170 | 27979 | CTCN_5048 | 42038 |
| ATCN_98 | 27980 | GTCN_2630 | 42039 |
| GTCN_109 | 27981 | CTCN_5049 | 42040 |
| CTCN_171 | 27982 | GTCN_2631 | 42041 |
| GTCN_110 | 27983 | CTCN_5050 | 42042 |
| CTCN_172 | 27984 | CTCN_5051 | 42043 |
| CTCN_173 | 27985 | CTCN_5052 | 42044 |
| ATCN_99 | 27986 | GTCN_2632 | 42045 |
| GTCN_111 | 27987 | CTCN_5053 | 42046 |
| TTCN_147 | 27988 | GTCN_2633 | 42047 |
| GTCN_112 | 27989 | CTCN_5054 | 42048 |
| CTCN_174 | 27990 | GTCN_2634 | 42049 |
| GTCN_113 | 27991 | TTCN_4049 | 42050 |
| ATCN_100 | 27992 | GTCN_2635 | 42051 |
| TTCN_148 | 27993 | TTCN_4050 | 42052 |
| CTCN_175 | 27994 | CTCN_5055 | 42053 |
| CTCN_176 | 27995 | TTCN_4051 | 42054 |
| ATCN_101 | 27996 | CTCN_5056 | 42055 |
| TTCN_149 | 27997 | GTCN_2636 | 42056 |
| ATCN_102 | 27998 | TTCN_4052 | 42057 |
| ATCN_103 | 27999 | CTCN_5057 | 42058 |
| ATCN_104 | 28000 | GTCN_2637 | 42059 |
| ATCN_105 | 28001 | CTCN_5058 | 42060 |
| CTCN_177 | 28002 | TTCN_4053 | 42061 |
| ATCN_106 | 28003 | TTCN_4054 | 42062 |
| CTCN_178 | 28004 | GTCN_2638 | 42063 |
| ATCN_107 | 28005 | ATCN_2856 | 42064 |
| TTCN_150 | 28006 | CTCN_5059 | 42065 |
| ATCN_108 | 28007 | CTCN_5060 | 42066 |
| CTCN_179 | 28008 | TTCN_4055 | 42067 |
| CTCN_180 | 28009 | CTCN_5061 | 42068 |

| | | | |
|---|---|---|---|
| ATCN_109 | 28010 | CTCN_5062 | 42069 |
| ATCN_110 | 28011 | ATCN_2857 | 42070 |
| CTCN_181 | 28012 | ATCN_2858 | 42071 |
| GTCN_114 | 28013 | GTCN_2639 | 42072 |
| CTCN_182 | 28014 | ATCN_2859 | 42073 |
| CTCN_183 | 28015 | TTCN_4056 | 42074 |
| GTCN_115 | 28016 | CTCN_5063 | 42075 |
| TTCN_151 | 28017 | CTCN_5064 | 42076 |
| GTCN_116 | 28018 | CTCN_5065 | 42077 |
| CTCN_184 | 28019 | CTCN_5066 | 42078 |
| GTCN_117 | 28020 | CTCN_5067 | 42079 |
| CTCN_185 | 28021 | CTCN_5068 | 42080 |
| CTCN_186 | 28022 | GTCN_2640 | 42081 |
| CTCN_187 | 28023 | CTCN_5069 | 42082 |
| CTCN_188 | 28024 | GTCN_2641 | 42083 |
| TTCN_152 | 28025 | CTCN_5070 | 42084 |
| ATCN_111 | 28026 | TTCN_4057 | 42085 |
| TTCN_153 | 28027 | ATCN_2860 | 42086 |
| CTCN_189 | 28028 | GTCN_2642 | 42087 |
| CTCN_190 | 28029 | ATCN_2861 | 42088 |
| GTCN_118 | 28030 | ATCN_2862 | 42089 |
| ATCN_112 | 28031 | ATCN_2863 | 42090 |
| CTCN_191 | 28032 | GTCN_2643 | 42091 |
| GTCN_119 | 28033 | CTCN_5071 | 42092 |
| GTCN_120 | 28034 | CTCN_5072 | 42093 |
| GTCN_121 | 28035 | TTCN_4058 | 42094 |
| CTCN_192 | 28036 | ATCN_2864 | 42095 |
| ATCN_113 | 28037 | ATCN_2865 | 42096 |
| ATCN_114 | 28038 | TTCN_4059 | 42097 |
| ATCN_115 | 28039 | CTCN_5073 | 42098 |
| GTCN_122 | 28040 | GTCN_2644 | 42099 |
| ATCN_116 | 28041 | ATCN_2866 | 42100 |
| TTCN_154 | 28042 | ATCN_2867 | 42101 |
| GTCN_123 | 28043 | GTCN_2645 | 42102 |
| TTCN_155 | 28044 | CTCN_5074 | 42103 |
| CTCN_193 | 28045 | CTCN_5075 | 42104 |
| GTCN_124 | 28046 | CTCN_5076 | 42105 |
| ATCN_117 | 28047 | CTCN_5077 | 42106 |
| ATCN_118 | 28048 | CTCN_5078 | 42107 |
| CTCN_194 | 28049 | CTCN_5079 | 42108 |
| CTCN_195 | 28050 | ATCN_2868 | 42109 |
| GTCN_125 | 28051 | ATCN_2869 | 42110 |
| ATCN_119 | 28052 | ATCN_2870 | 42111 |

FIG. 37 (continued)

| | | | |
|---|---|---|---|
| TTCN_156 | 28053 | GTCN_2646 | 42112 |
| ATCN_120 | 28054 | GTCN_2647 | 42113 |
| TTCN_157 | 28055 | GTCN_2648 | 42114 |
| CTCN_196 | 28056 | ATCN_2871 | 42115 |
| ATCN_121 | 28057 | ATCN_2872 | 42116 |
| GTCN_126 | 28058 | TTCN_4060 | 42117 |
| ATCN_122 | 28059 | CTCN_5080 | 42118 |
| TTCN_158 | 28060 | GTCN_2649 | 42119 |
| TTCN_159 | 28061 | CTCN_5081 | 42120 |
| ATCN_123 | 28062 | ATCN_2873 | 42121 |
| TTCN_160 | 28063 | ATCN_2874 | 42122 |
| TTCN_161 | 28064 | CTCN_5082 | 42123 |
| GTCN_127 | 28065 | GTCN_2650 | 42124 |
| TTCN_162 | 28066 | CTCN_5083 | 42125 |
| TTCN_163 | 28067 | TTCN_4061 | 42126 |
| CTCN_197 | 28068 | CTCN_5084 | 42127 |
| CTCN_198 | 28069 | CTCN_5085 | 42128 |
| ATCN_124 | 28070 | ATCN_2875 | 42129 |
| TTCN_164 | 28071 | ATCN_2876 | 42130 |
| ATCN_125 | 28072 | CTCN_5086 | 42131 |
| CTCN_199 | 28073 | CTCN_5087 | 42132 |
| CTCN_200 | 28074 | CTCN_5088 | 42133 |
| GTCN_128 | 28075 | CTCN_5089 | 42134 |
| ATCN_126 | 28076 | TTCN_4062 | 42135 |
| TTCN_165 | 28077 | TTCN_4063 | 42136 |
| TTCN_166 | 28078 | CTCN_5090 | 42137 |
| TTCN_167 | 28079 | CTCN_5091 | 42138 |
| TTCN_168 | 28080 | CTCN_5092 | 42139 |
| GTCN_129 | 28081 | ATCN_2877 | 42140 |
| GTCN_130 | 28082 | CTCN_5093 | 42141 |
| GTCN_131 | 28083 | ATCN_2878 | 42142 |
| TTCN_169 | 28084 | CTCN_5094 | 42143 |
| TTCN_170 | 28085 | TTCN_4064 | 42144 |
| TTCN_171 | 28086 | ATCN_2879 | 42145 |
| TTCN_172 | 28087 | CTCN_5095 | 42146 |
| ATCN_127 | 28088 | ATCN_2880 | 42147 |
| ATCN_128 | 28089 | CTCN_5096 | 42148 |
| TTCN_173 | 28090 | CTCN_5097 | 42149 |
| GTCN_132 | 28091 | ATCN_2881 | 42150 |
| TTCN_174 | 28092 | ATCN_2882 | 42151 |
| TTCN_175 | 28093 | TTCN_4065 | 42152 |
| GTCN_133 | 28094 | TTCN_4066 | 42153 |
| CTCN_201 | 28095 | CTCN_5098 | 42154 |

| | | | |
|---|---|---|---|
| GTCN_134 | 28096 | TTCN_4067 | 42155 |
| GTCN_135 | 28097 | CTCN_5099 | 42156 |
| ATCN_129 | 28098 | ATCN_2883 | 42157 |
| ATCN_130 | 28099 | GTCN_2651 | 42158 |
| GTCN_136 | 28100 | GTCN_2652 | 42159 |
| TTCN_176 | 28101 | CTCN_5100 | 42160 |
| TTCN_177 | 28102 | CTCN_5101 | 42161 |
| GTCN_137 | 28103 | CTCN_5102 | 42162 |
| ATCN_131 | 28104 | ATCN_2884 | 42163 |
| GTCN_138 | 28105 | CTCN_5103 | 42164 |
| ATCN_132 | 28106 | GTCN_2653 | 42165 |
| TTCN_178 | 28107 | CTCN_5104 | 42166 |
| CTCN_202 | 28108 | GTCN_2654 | 42167 |
| ATCN_133 | 28109 | CTCN_5105 | 42168 |
| GTCN_139 | 28110 | TTCN_4068 | 42169 |
| GTCN_140 | 28111 | CTCN_5106 | 42170 |
| TTCN_179 | 28112 | ATCN_2885 | 42171 |
| ATCN_134 | 28113 | CTCN_5107 | 42172 |
| TTCN_180 | 28114 | CTCN_5108 | 42173 |
| CTCN_203 | 28115 | TTCN_4069 | 42174 |
| CTCN_204 | 28116 | CTCN_5109 | 42175 |
| GTCN_141 | 28117 | CTCN_5110 | 42176 |
| TTCN_181 | 28118 | GTCN_2655 | 42177 |
| CTCN_205 | 28119 | CTCN_5111 | 42178 |
| GTCN_142 | 28120 | CTCN_5112 | 42179 |
| ATCN_135 | 28121 | TTCN_4070 | 42180 |
| CTCN_206 | 28122 | ATCN_2886 | 42181 |
| ATCN_136 | 28123 | TTCN_4071 | 42182 |
| ATCN_137 | 28124 | CTCN_5113 | 42183 |
| CTCN_207 | 28125 | TTCN_4072 | 42184 |
| CTCN_208 | 28126 | CTCN_5114 | 42185 |
| CTCN_209 | 28127 | CTCN_5115 | 42186 |
| TTCN_182 | 28128 | GTCN_2656 | 42187 |
| TTCN_183 | 28129 | ATCN_2887 | 42188 |
| GTCN_143 | 28130 | TTCN_4073 | 42189 |
| CTCN_210 | 28131 | TTCN_4074 | 42190 |
| GTCN_144 | 28132 | CTCN_5116 | 42191 |
| CTCN_211 | 28133 | TTCN_4075 | 42192 |
| TTCN_184 | 28134 | TTCN_4076 | 42193 |
| TTCN_185 | 28135 | TTCN_4077 | 42194 |
| CTCN_212 | 28136 | CTCN_5117 | 42195 |
| CTCN_213 | 28137 | CTCN_5118 | 42196 |
| CTCN_214 | 28138 | ATCN_2888 | 42197 |

FIG. 37 (continued)

| | | | |
|---|---|---|---|
| CTCN_215 | 28139 | TTCN_4078 | 42198 |
| GTCN_145 | 28140 | CTCN_5119 | 42199 |
| CTCN_216 | 28141 | ATCN_2889 | 42200 |
| GTCN_146 | 28142 | TTCN_4079 | 42201 |
| GTCN_147 | 28143 | GTCN_2657 | 42202 |
| TTCN_186 | 28144 | TTCN_4080 | 42203 |
| GTCN_148 | 28145 | CTCN_5120 | 42204 |
| GTCN_149 | 28146 | ATCN_2890 | 42205 |
| CTCN_217 | 28147 | ATCN_2891 | 42206 |
| TTCN_187 | 28148 | TTCN_4081 | 42207 |
| CTCN_218 | 28149 | GTCN_2658 | 42208 |
| GTCN_150 | 28150 | CTCN_5121 | 42209 |
| GTCN_151 | 28151 | GTCN_2659 | 42210 |
| CTCN_219 | 28152 | GTCN_2660 | 42211 |
| GTCN_152 | 28153 | CTCN_5122 | 42212 |
| CTCN_220 | 28154 | CTCN_5123 | 42213 |
| CTCN_221 | 28155 | CTCN_5124 | 42214 |
| GTCN_153 | 28156 | TTCN_4082 | 42215 |
| TTCN_188 | 28157 | ATCN_2892 | 42216 |
| TTCN_189 | 28158 | CTCN_5125 | 42217 |
| CTCN_222 | 28159 | CTCN_5126 | 42218 |
| TTCN_190 | 28160 | CTCN_5127 | 42219 |
| ATCN_138 | 28161 | TTCN_4083 | 42220 |
| TTCN_191 | 28162 | ATCN_2893 | 42221 |
| TTCN_192 | 28163 | CTCN_5128 | 42222 |
| CTCN_223 | 28164 | TTCN_4084 | 42223 |
| GTCN_154 | 28165 | TTCN_4085 | 42224 |
| CTCN_224 | 28166 | TTCN_4086 | 42225 |
| GTCN_155 | 28167 | GTCN_2661 | 42226 |
| TTCN_193 | 28168 | GTCN_2662 | 42227 |
| CTCN_225 | 28169 | TTCN_4087 | 42228 |
| CTCN_226 | 28170 | ATCN_2894 | 42229 |
| ATCN_139 | 28171 | TTCN_4088 | 42230 |
| CTCN_227 | 28172 | CTCN_5129 | 42231 |
| TTCN_194 | 28173 | GTCN_2663 | 42232 |
| GTCN_156 | 28174 | CTCN_5130 | 42233 |
| CTCN_228 | 28175 | GTCN_2664 | 42234 |
| ATCN_140 | 28176 | CTCN_5131 | 42235 |
| GTCN_157 | 28177 | GTCN_2665 | 42236 |
| ATCN_141 | 28178 | GTCN_2666 | 42237 |
| GTCN_158 | 28179 | TTCN_4089 | 42238 |
| TTCN_195 | 28180 | GTCN_2667 | 42239 |
| ATCN_142 | 28181 | TTCN_4090 | 42240 |

| | | | |
|---|---|---|---|
| ATCN_143 | 28182 | CTCN_5132 | 42241 |
| GTCN_159 | 28183 | GTCN_2668 | 42242 |
| ATCN_144 | 28184 | CTCN_5133 | 42243 |
| GTCN_160 | 28185 | CTCN_5134 | 42244 |
| ATCN_145 | 28186 | ATCN_2895 | 42245 |
| GTCN_161 | 28187 | TTCN_4091 | 42246 |
| CTCN_229 | 28188 | GTCN_2669 | 42247 |
| CTCN_230 | 28189 | ATCN_2896 | 42248 |
| CTCN_231 | 28190 | ATCN_2897 | 42249 |
| GTCN_162 | 28191 | ATCN_2898 | 42250 |
| TTCN_196 | 28192 | GTCN_2670 | 42251 |
| ATCN_146 | 28193 | CTCN_5135 | 42252 |
| ATCN_147 | 28194 | GTCN_2671 | 42253 |
| GTCN_163 | 28195 | ATCN_2899 | 42254 |
| CTCN_232 | 28196 | ATCN_2900 | 42255 |
| TTCN_197 | 28197 | ATCN_2901 | 42256 |
| CTCN_233 | 28198 | GTCN_2672 | 42257 |
| ATCN_148 | 28199 | CTCN_5136 | 42258 |
| CTCN_234 | 28200 | TTCN_4092 | 42259 |
| CTCN_235 | 28201 | GTCN_2673 | 42260 |
| CTCN_236 | 28202 | TTCN_4093 | 42261 |
| GTCN_164 | 28203 | GTCN_2674 | 42262 |
| ATCN_149 | 28204 | TTCN_4094 | 42263 |
| TTCN_198 | 28205 | CTCN_5137 | 42264 |
| CTCN_237 | 28206 | GTCN_2675 | 42265 |
| GTCN_165 | 28207 | CTCN_5138 | 42266 |
| CTCN_238 | 28208 | CTCN_5139 | 42267 |
| TTCN_199 | 28209 | GTCN_2676 | 42268 |
| CTCN_239 | 28210 | TTCN_4095 | 42269 |
| CTCN_240 | 28211 | TTCN_4096 | 42270 |
| CTCN_241 | 28212 | GTCN_2677 | 42271 |
| ATCN_150 | 28213 | CTCN_5140 | 42272 |
| TTCN_200 | 28214 | CTCN_5141 | 42273 |
| CTCN_242 | 28215 | TTCN_4097 | 42274 |
| TTCN_201 | 28216 | ATCN_2902 | 42275 |
| TTCN_202 | 28217 | ATCN_2903 | 42276 |
| GTCN_166 | 28218 | TTCN_4098 | 42277 |
| CTCN_243 | 28219 | GTCN_2678 | 42278 |
| ATCN_151 | 28220 | ATCN_2904 | 42279 |
| ATCN_152 | 28221 | GTCN_2679 | 42280 |
| CTCN_244 | 28222 | TTCN_4099 | 42281 |
| GTCN_167 | 28223 | GTCN_2680 | 42282 |
| ATCN_153 | 28224 | CTCN_5142 | 42283 |

FIG. 37 (continued)

| | | | |
|---|---|---|---|
| TTCN_203 | 28225 | TTCN_4100 | 42284 |
| CTCN_245 | 28226 | CTCN_5143 | 42285 |
| CTCN_246 | 28227 | CTCN_5144 | 42286 |
| TTCN_204 | 28228 | CTCN_5145 | 42287 |
| CTCN_247 | 28229 | CTCN_5146 | 42288 |
| TTCN_205 | 28230 | GTCN_2681 | 42289 |
| TTCN_206 | 28231 | CTCN_5147 | 42290 |
| CTCN_248 | 28232 | CTCN_5148 | 42291 |
| CTCN_249 | 28233 | GTCN_2682 | 42292 |
| TTCN_207 | 28234 | CTCN_5149 | 42293 |
| GTCN_168 | 28235 | TTCN_4101 | 42294 |
| CTCN_250 | 28236 | CTCN_5150 | 42295 |
| CTCN_251 | 28237 | CTCN_5151 | 42296 |
| CTCN_252 | 28238 | GTCN_2683 | 42297 |
| CTCN_253 | 28239 | TTCN_4102 | 42298 |
| GTCN_169 | 28240 | TTCN_4103 | 42299 |
| GTCN_170 | 28241 | ATCN_2905 | 42300 |
| CTCN_254 | 28242 | TTCN_4104 | 42301 |
| CTCN_255 | 28243 | TTCN_4105 | 42302 |
| GTCN_171 | 28244 | TTCN_4106 | 42303 |
| CTCN_256 | 28245 | ATCN_2906 | 42304 |
| CTCN_257 | 28246 | CTCN_5152 | 42305 |
| CTCN_258 | 28247 | CTCN_5153 | 42306 |
| CTCN_259 | 28248 | GTCN_2684 | 42307 |
| CTCN_260 | 28249 | CTCN_5154 | 42308 |
| TTCN_208 | 28250 | CTCN_5155 | 42309 |
| ATCN_154 | 28251 | TTCN_4107 | 42310 |
| TTCN_209 | 28252 | CTCN_5156 | 42311 |
| CTCN_261 | 28253 | CTCN_5157 | 42312 |
| CTCN_262 | 28254 | CTCN_5158 | 42313 |
| CTCN_263 | 28255 | GTCN_2685 | 42314 |
| GTCN_172 | 28256 | CTCN_5159 | 42315 |
| ATCN_155 | 28257 | CTCN_5160 | 42316 |
| CTCN_264 | 28258 | TTCN_4108 | 42317 |
| GTCN_173 | 28259 | GTCN_2686 | 42318 |
| TTCN_210 | 28260 | ATCN_2907 | 42319 |
| CTCN_265 | 28261 | TTCN_4109 | 42320 |
| CTCN_266 | 28262 | TTCN_4110 | 42321 |
| GTCN_174 | 28263 | TTCN_4111 | 42322 |
| CTCN_267 | 28264 | TTCN_4112 | 42323 |
| ATCN_156 | 28265 | ATCN_2908 | 42324 |
| ATCN_157 | 28266 | CTCN_5161 | 42325 |
| CTCN_268 | 28267 | CTCN_5162 | 42326 |

| | | | |
|---|---|---|---|
| CTCN_269 | 28268 | CTCN_5163 | 42327 |
| ATCN_158 | 28269 | TTCN_4113 | 42328 |
| CTCN_270 | 28270 | TTCN_4114 | 42329 |
| GTCN_175 | 28271 | TTCN_4115 | 42330 |
| CTCN_271 | 28272 | CTCN_5164 | 42331 |
| CTCN_272 | 28273 | TTCN_4116 | 42332 |
| CTCN_273 | 28274 | CTCN_5165 | 42333 |
| CTCN_274 | 28275 | ATCN_2909 | 42334 |
| GTCN_176 | 28276 | CTCN_5166 | 42335 |
| ATCN_159 | 28277 | CTCN_5167 | 42336 |
| GTCN_177 | 28278 | CTCN_5168 | 42337 |
| CTCN_275 | 28279 | TTCN_4117 | 42338 |
| GTCN_178 | 28280 | ATCN_2910 | 42339 |
| CTCN_276 | 28281 | ATCN_2911 | 42340 |
| ATCN_160 | 28282 | CTCN_5169 | 42341 |
| TTCN_211 | 28283 | CTCN_5170 | 42342 |
| GTCN_179 | 28284 | CTCN_5171 | 42343 |
| GTCN_180 | 28285 | CTCN_5172 | 42344 |
| CTCN_277 | 28286 | TTCN_4118 | 42345 |
| TTCN_212 | 28287 | TTCN_4119 | 42346 |
| TTCN_213 | 28288 | CTCN_5173 | 42347 |
| ATCN_161 | 28289 | CTCN_5174 | 42348 |
| CTCN_278 | 28290 | CTCN_5175 | 42349 |
| CTCN_279 | 28291 | CTCN_5176 | 42350 |
| CTCN_280 | 28292 | GTCN_2687 | 42351 |
| TTCN_214 | 28293 | CTCN_5177 | 42352 |
| TTCN_215 | 28294 | ATCN_2912 | 42353 |
| TTCN_216 | 28295 | TTCN_4120 | 42354 |
| TTCN_217 | 28296 | GTCN_2688 | 42355 |
| GTCN_181 | 28297 | CTCN_5178 | 42356 |
| TTCN_218 | 28298 | TTCN_4121 | 42357 |
| CTCN_281 | 28299 | CTCN_5179 | 42358 |
| GTCN_182 | 28300 | CTCN_5180 | 42359 |
| TTCN_219 | 28301 | ATCN_2913 | 42360 |
| GTCN_183 | 28302 | ATCN_2914 | 42361 |
| GTCN_184 | 28303 | CTCN_5181 | 42362 |
| TTCN_220 | 28304 | TTCN_4122 | 42363 |
| TTCN_221 | 28305 | ATCN_2915 | 42364 |
| TTCN_222 | 28306 | CTCN_5182 | 42365 |
| GTCN_185 | 28307 | TTCN_4123 | 42366 |
| CTCN_282 | 28308 | ATCN_2916 | 42367 |
| TTCN_223 | 28309 | TTCN_4124 | 42368 |
| CTCN_283 | 28310 | GTCN_2689 | 42369 |

FIG. 37 (continued)

| | | | |
|---|---|---|---|
| GTCN_186 | 28311 | GTCN_2690 | 42370 |
| CTCN_284 | 28312 | ATCN_2917 | 42371 |
| ATCN_162 | 28313 | TTCN_4125 | 42372 |
| GTCN_187 | 28314 | ATCN_2918 | 42373 |
| CTCN_285 | 28315 | TTCN_4126 | 42374 |
| TTCN_224 | 28316 | TTCN_4127 | 42375 |
| TTCN_225 | 28317 | TTCN_4128 | 42376 |
| CTCN_286 | 28318 | TTCN_4129 | 42377 |
| CTCN_287 | 28319 | GTCN_2691 | 42378 |
| CTCN_288 | 28320 | CTCN_5183 | 42379 |
| CTCN_289 | 28321 | GTCN_2692 | 42380 |
| ATCN_163 | 28322 | TTCN_4130 | 42381 |
| TTCN_226 | 28323 | GTCN_2693 | 42382 |
| TTCN_227 | 28324 | GTCN_2694 | 42383 |
| ATCN_164 | 28325 | CTCN_5184 | 42384 |
| GTCN_188 | 28326 | CTCN_5185 | 42385 |
| CTCN_290 | 28327 | CTCN_5186 | 42386 |
| CTCN_291 | 28328 | ATCN_2919 | 42387 |
| GTCN_189 | 28329 | ATCN_2920 | 42388 |
| CTCN_292 | 28330 | TTCN_4131 | 42389 |
| ATCN_165 | 28331 | GTCN_2695 | 42390 |
| TTCN_228 | 28332 | TTCN_4132 | 42391 |
| TTCN_229 | 28333 | TTCN_4133 | 42392 |
| TTCN_230 | 28334 | CTCN_5187 | 42393 |
| ATCN_166 | 28335 | TTCN_4134 | 42394 |
| ATCN_167 | 28336 | TTCN_4135 | 42395 |
| TTCN_231 | 28337 | ATCN_2921 | 42396 |
| GTCN_190 | 28338 | CTCN_5188 | 42397 |
| TTCN_232 | 28339 | CTCN_5189 | 42398 |
| GTCN_191 | 28340 | ATCN_2922 | 42399 |
| GTCN_192 | 28341 | TTCN_4136 | 42400 |
| CTCN_293 | 28342 | CTCN_5190 | 42401 |
| TTCN_233 | 28343 | GTCN_2696 | 42402 |
| ATCN_168 | 28344 | ATCN_2923 | 42403 |
| ATCN_169 | 28345 | TTCN_4137 | 42404 |
| TTCN_234 | 28346 | CTCN_5191 | 42405 |
| CTCN_294 | 28347 | TTCN_4138 | 42406 |
| CTCN_295 | 28348 | TTCN_4139 | 42407 |
| ATCN_170 | 28349 | TTCN_4140 | 42408 |
| GTCN_193 | 28350 | CTCN_5192 | 42409 |
| CTCN_296 | 28351 | CTCN_5193 | 42410 |
| GTCN_194 | 28352 | ATCN_2924 | 42411 |
| CTCN_297 | 28353 | GTCN_2697 | 42412 |

| | | | |
|---|---|---|---|
| CTCN_298 | 28354 | TTCN_4141 | 42413 |
| GTCN_195 | 28355 | TTCN_4142 | 42414 |
| CTCN_299 | 28356 | CTCN_5194 | 42415 |
| CTCN_300 | 28357 | TTCN_4143 | 42416 |
| ATCN_171 | 28358 | TTCN_4144 | 42417 |
| CTCN_301 | 28359 | CTCN_5195 | 42418 |
| CTCN_302 | 28360 | CTCN_5196 | 42419 |
| ATCN_172 | 28361 | TTCN_4145 | 42420 |
| GTCN_196 | 28362 | ATCN_2925 | 42421 |
| CTCN_303 | 28363 | CTCN_5197 | 42422 |
| CTCN_304 | 28364 | TTCN_4146 | 42423 |
| CTCN_305 | 28365 | CTCN_5198 | 42424 |
| TTCN_235 | 28366 | TTCN_4147 | 42425 |
| TTCN_236 | 28367 | TTCN_4148 | 42426 |
| CTCN_306 | 28368 | TTCN_4149 | 42427 |
| GTCN_197 | 28369 | CTCN_5199 | 42428 |
| GTCN_198 | 28370 | GTCN_2698 | 42429 |
| GTCN_199 | 28371 | TTCN_4150 | 42430 |
| CTCN_307 | 28372 | GTCN_2699 | 42431 |
| CTCN_308 | 28373 | ATCN_2926 | 42432 |
| GTCN_200 | 28374 | GTCN_2700 | 42433 |
| CTCN_309 | 28375 | CTCN_5200 | 42434 |
| CTCN_310 | 28376 | TTCN_4151 | 42435 |
| TTCN_237 | 28377 | CTCN_5201 | 42436 |
| ATCN_173 | 28378 | CTCN_5202 | 42437 |
| TTCN_238 | 28379 | ATCN_2927 | 42438 |
| TTCN_239 | 28380 | CTCN_5203 | 42439 |
| CTCN_311 | 28381 | CTCN_5204 | 42440 |
| CTCN_312 | 28382 | GTCN_2701 | 42441 |
| TTCN_240 | 28383 | GTCN_2702 | 42442 |
| CTCN_313 | 28384 | TTCN_4152 | 42443 |
| CTCN_314 | 28385 | GTCN_2703 | 42444 |
| ATCN_174 | 28386 | CTCN_5205 | 42445 |
| GTCN_201 | 28387 | CTCN_5206 | 42446 |
| CTCN_315 | 28388 | TTCN_4153 | 42447 |
| GTCN_202 | 28389 | TTCN_4154 | 42448 |
| ATCN_175 | 28390 | TTCN_4155 | 42449 |
| TTCN_241 | 28391 | CTCN_5207 | 42450 |
| GTCN_203 | 28392 | ATCN_2928 | 42451 |
| ATCN_176 | 28393 | TTCN_4156 | 42452 |
| TTCN_242 | 28394 | CTCN_5208 | 42453 |
| TTCN_243 | 28395 | CTCN_5209 | 42454 |
| TTCN_244 | 28396 | TTCN_4157 | 42455 |

FIG. 37 (continued)

| | | | |
|---|---|---|---|
| TTCN_245 | 28397 | ATCN_2929 | 42456 |
| TTCN_246 | 28398 | ATCN_2930 | 42457 |
| TTCN_247 | 28399 | ATCN_2931 | 42458 |
| TTCN_248 | 28400 | TTCN_4158 | 42459 |
| TTCN_249 | 28401 | ATCN_2932 | 42460 |
| CTCN_316 | 28402 | ATCN_2933 | 42461 |
| ATCN_177 | 28403 | GTCN_2704 | 42462 |
| ATCN_178 | 28404 | ATCN_2934 | 42463 |
| ATCN_179 | 28405 | CTCN_5210 | 42464 |
| GTCN_204 | 28406 | GTCN_2705 | 42465 |
| GTCN_205 | 28407 | ATCN_2935 | 42466 |
| GTCN_206 | 28408 | CTCN_5211 | 42467 |
| ATCN_180 | 28409 | TTCN_4159 | 42468 |
| CTCN_317 | 28410 | TTCN_4160 | 42469 |
| ATCN_181 | 28411 | CTCN_5212 | 42470 |
| GTCN_207 | 28412 | TTCN_4161 | 42471 |
| TTCN_250 | 28413 | CTCN_5213 | 42472 |
| CTCN_318 | 28414 | CTCN_5214 | 42473 |
| TTCN_251 | 28415 | GTCN_2706 | 42474 |
| CTCN_319 | 28416 | ATCN_2936 | 42475 |
| GTCN_208 | 28417 | CTCN_5215 | 42476 |
| GTCN_209 | 28418 | CTCN_5216 | 42477 |
| TTCN_252 | 28419 | TTCN_4162 | 42478 |
| ATCN_182 | 28420 | CTCN_5217 | 42479 |
| GTCN_210 | 28421 | CTCN_5218 | 42480 |
| CTCN_320 | 28422 | TTCN_4163 | 42481 |
| ATCN_183 | 28423 | TTCN_4164 | 42482 |
| CTCN_321 | 28424 | CTCN_5219 | 42483 |
| TTCN_253 | 28425 | CTCN_5220 | 42484 |
| TTCN_254 | 28426 | TTCN_4165 | 42485 |
| ATCN_184 | 28427 | CTCN_5221 | 42486 |
| TTCN_255 | 28428 | CTCN_5222 | 42487 |
| TTCN_256 | 28429 | GTCN_2707 | 42488 |
| GTCN_211 | 28430 | TTCN_4166 | 42489 |
| TTCN_257 | 28431 | TTCN_4167 | 42490 |
| CTCN_322 | 28432 | TTCN_4168 | 42491 |
| GTCN_212 | 28433 | GTCN_2708 | 42492 |
| TTCN_258 | 28434 | GTCN_2709 | 42493 |
| ATCN_185 | 28435 | ATCN_2937 | 42494 |
| TTCN_259 | 28436 | CTCN_5223 | 42495 |
| CTCN_323 | 28437 | CTCN_5224 | 42496 |
| TTCN_260 | 28438 | TTCN_4169 | 42497 |
| ATCN_186 | 28439 | GTCN_2710 | 42498 |

| | | | |
|---|---|---|---|
| CTCN_324 | 28440 | TTCN_4170 | 42499 |
| TTCN_261 | 28441 | CTCN_5225 | 42500 |
| TTCN_262 | 28442 | ATCN_2938 | 42501 |
| TTCN_263 | 28443 | CTCN_5226 | 42502 |
| CTCN_325 | 28444 | TTCN_4171 | 42503 |
| GTCN_213 | 28445 | CTCN_5227 | 42504 |
| TTCN_264 | 28446 | GTCN_2711 | 42505 |
| CTCN_326 | 28447 | CTCN_5228 | 42506 |
| TTCN_265 | 28448 | TTCN_4172 | 42507 |
| ATCN_187 | 28449 | GTCN_2712 | 42508 |
| TTCN_266 | 28450 | TTCN_4173 | 42509 |
| TTCN_267 | 28451 | CTCN_5229 | 42510 |
| TTCN_268 | 28452 | TTCN_4174 | 42511 |
| TTCN_269 | 28453 | TTCN_4175 | 42512 |
| ATCN_188 | 28454 | CTCN_5230 | 42513 |
| TTCN_270 | 28455 | CTCN_5231 | 42514 |
| CTCN_327 | 28456 | GTCN_2713 | 42515 |
| CTCN_328 | 28457 | CTCN_5232 | 42516 |
| CTCN_329 | 28458 | TTCN_4176 | 42517 |
| CTCN_330 | 28459 | GTCN_2714 | 42518 |
| CTCN_331 | 28460 | CTCN_5233 | 42519 |
| CTCN_332 | 28461 | CTCN_5234 | 42520 |
| TTCN_271 | 28462 | TTCN_4177 | 42521 |
| GTCN_214 | 28463 | GTCN_2715 | 42522 |
| ATCN_189 | 28464 | GTCN_2716 | 42523 |
| ATCN_190 | 28465 | CTCN_5235 | 42524 |
| ATCN_191 | 28466 | CTCN_5236 | 42525 |
| CTCN_333 | 28467 | CTCN_5237 | 42526 |
| TTCN_272 | 28468 | ATCN_2939 | 42527 |
| CTCN_334 | 28469 | CTCN_5238 | 42528 |
| ATCN_192 | 28470 | CTCN_5239 | 42529 |
| CTCN_335 | 28471 | GTCN_2717 | 42530 |
| GTCN_215 | 28472 | GTCN_2718 | 42531 |
| TTCN_273 | 28473 | CTCN_5240 | 42532 |
| ATCN_193 | 28474 | GTCN_2719 | 42533 |
| ATCN_194 | 28475 | CTCN_5241 | 42534 |
| ATCN_195 | 28476 | CTCN_5242 | 42535 |
| CTCN_336 | 28477 | TTCN_4178 | 42536 |
| TTCN_274 | 28478 | TTCN_4179 | 42537 |
| TTCN_275 | 28479 | TTCN_4180 | 42538 |
| ATCN_196 | 28480 | CTCN_5243 | 42539 |
| ATCN_197 | 28481 | CTCN_5244 | 42540 |
| ATCN_198 | 28482 | TTCN_4181 | 42541 |

FIG. 37 (continued)

| | | | |
|---|---|---|---|
| ATCN_199 | 28483 | CTCN_5245 | 42542 |
| TTCN_276 | 28484 | ATCN_2940 | 42543 |
| CTCN_337 | 28485 | ATCN_2941 | 42544 |
| CTCN_338 | 28486 | ATCN_2942 | 42545 |
| ATCN_200 | 28487 | CTCN_5246 | 42546 |
| ATCN_201 | 28488 | GTCN_2720 | 42547 |
| GTCN_216 | 28489 | TTCN_4182 | 42548 |
| CTCN_339 | 28490 | TTCN_4183 | 42549 |
| ATCN_202 | 28491 | CTCN_5247 | 42550 |
| TTCN_277 | 28492 | GTCN_2721 | 42551 |
| CTCN_340 | 28493 | CTCN_5248 | 42552 |
| ATCN_203 | 28494 | CTCN_5249 | 42553 |
| ATCN_204 | 28495 | TTCN_4184 | 42554 |
| ATCN_205 | 28496 | CTCN_5250 | 42555 |
| ATCN_206 | 28497 | CTCN_5251 | 42556 |
| ATCN_207 | 28498 | CTCN_5252 | 42557 |
| CTCN_341 | 28499 | ATCN_2943 | 42558 |
| GTCN_217 | 28500 | TTCN_4185 | 42559 |
| TTCN_278 | 28501 | CTCN_5253 | 42560 |
| TTCN_279 | 28502 | ATCN_2944 | 42561 |
| CTCN_342 | 28503 | CTCN_5254 | 42562 |
| ATCN_208 | 28504 | CTCN_5255 | 42563 |
| TTCN_280 | 28505 | ATCN_2945 | 42564 |
| ATCN_209 | 28506 | TTCN_4186 | 42565 |
| GTCN_218 | 28507 | TTCN_4187 | 42566 |
| TTCN_281 | 28508 | TTCN_4188 | 42567 |
| TTCN_282 | 28509 | ATCN_2946 | 42568 |
| CTCN_343 | 28510 | CTCN_5256 | 42569 |
| GTCN_219 | 28511 | TTCN_4189 | 42570 |
| CTCN_344 | 28512 | GTCN_2722 | 42571 |
| ATCN_210 | 28513 | GTCN_2723 | 42572 |
| GTCN_220 | 28514 | GTCN_2724 | 42573 |
| TTCN_283 | 28515 | GTCN_2725 | 42574 |
| TTCN_284 | 28516 | TTCN_4190 | 42575 |
| ATCN_211 | 28517 | CTCN_5257 | 42576 |
| TTCN_285 | 28518 | TTCN_4191 | 42577 |
| TTCN_286 | 28519 | CTCN_5258 | 42578 |
| ATCN_212 | 28520 | ATCN_2947 | 42579 |
| ATCN_213 | 28521 | CTCN_5259 | 42580 |
| CTCN_345 | 28522 | CTCN_5260 | 42581 |
| TTCN_287 | 28523 | TTCN_4192 | 42582 |
| CTCN_346 | 28524 | CTCN_5261 | 42583 |
| TTCN_288 | 28525 | TTCN_4193 | 42584 |
| ATCN_214 | 28526 | GTCN_2726 | 42585 |
| GTCN_221 | 28527 | GTCN_2727 | 42586 |
| CTCN_347 | 28528 | TTCN_4194 | 42587 |
| CTCN_348 | 28529 | TTCN_4195 | 42588 |
| ATCN_215 | 28530 | CTCN_5262 | 42589 |
| ATCN_216 | 28531 | GTCN_2728 | 42590 |
| CTCN_349 | 28532 | ATCN_2948 | 42591 |
| CTCN_350 | 28533 | ATCN_2949 | 42592 |
| ATCN_217 | 28534 | TTCN_4196 | 42593 |
| CTCN_351 | 28535 | CTCN_5263 | 42594 |
| TTCN_289 | 28536 | TTCN_4197 | 42595 |
| ATCN_218 | 28537 | ATCN_2950 | 42596 |
| ATCN_219 | 28538 | ATCN_2951 | 42597 |
| TTCN_290 | 28539 | TTCN_4198 | 42598 |
| CTCN_352 | 28540 | CTCN_5264 | 42599 |
| TTCN_291 | 28541 | TTCN_4199 | 42600 |
| TTCN_292 | 28542 | CTCN_5265 | 42601 |
| GTCN_222 | 28543 | TTCN_4200 | 42602 |
| TTCN_293 | 28544 | ATCN_2952 | 42603 |
| TTCN_294 | 28545 | CTCN_5266 | 42604 |
| ATCN_220 | 28546 | CTCN_5267 | 42605 |
| ATCN_221 | 28547 | ATCN_2953 | 42606 |
| TTCN_295 | 28548 | TTCN_4201 | 42607 |
| GTCN_223 | 28549 | GTCN_2729 | 42608 |
| TTCN_296 | 28550 | TTCN_4202 | 42609 |
| TTCN_297 | 28551 | CTCN_5268 | 42610 |
| TTCN_298 | 28552 | CTCN_5269 | 42611 |
| TTCN_299 | 28553 | TTCN_4203 | 42612 |
| TTCN_300 | 28554 | CTCN_5270 | 42613 |
| GTCN_224 | 28555 | CTCN_5271 | 42614 |
| ATCN_222 | 28556 | GTCN_2730 | 42615 |
| ATCN_223 | 28557 | CTCN_5272 | 42616 |
| TTCN_301 | 28558 | GTCN_2731 | 42617 |
| TTCN_302 | 28559 | CTCN_5273 | 42618 |
| CTCN_353 | 28560 | GTCN_2732 | 42619 |
| TTCN_303 | 28561 | CTCN_5274 | 42620 |
| TTCN_304 | 28562 | TTCN_4204 | 42621 |
| TTCN_305 | 28563 | CTCN_5275 | 42622 |
| ATCN_224 | 28564 | CTCN_5276 | 42623 |
| CTCN_354 | 28565 | CTCN_5277 | 42624 |
| ATCN_225 | 28566 | TTCN_4205 | 42625 |
| TTCN_306 | 28567 | GTCN_2733 | 42626 |
| CTCN_355 | 28568 | GTCN_2734 | 42627 |

FIG. 37 (continued)

| | | | |
|---|---|---|---|
| CTCN_356 | 28569 | TTCN_4206 | 42628 |
| CTCN_357 | 28570 | CTCN_5278 | 42629 |
| GTCN_225 | 28571 | TTCN_4207 | 42630 |
| CTCN_358 | 28572 | CTCN_5279 | 42631 |
| GTCN_226 | 28573 | CTCN_5280 | 42632 |
| CTCN_359 | 28574 | CTCN_5281 | 42633 |
| CTCN_360 | 28575 | GTCN_2735 | 42634 |
| CTCN_361 | 28576 | CTCN_5282 | 42635 |
| CTCN_362 | 28577 | CTCN_5283 | 42636 |
| ATCN_226 | 28578 | GTCN_2736 | 42637 |
| ATCN_227 | 28579 | CTCN_5284 | 42638 |
| CTCN_363 | 28580 | CTCN_5285 | 42639 |
| GTCN_227 | 28581 | CTCN_5286 | 42640 |
| CTCN_364 | 28582 | CTCN_5287 | 42641 |
| CTCN_365 | 28583 | CTCN_5288 | 42642 |
| CTCN_366 | 28584 | GTCN_2737 | 42643 |
| GTCN_228 | 28585 | TTCN_4208 | 42644 |
| GTCN_229 | 28586 | TTCN_4209 | 42645 |
| CTCN_367 | 28587 | ATCN_2954 | 42646 |
| CTCN_368 | 28588 | CTCN_5289 | 42647 |
| TTCN_307 | 28589 | ATCN_2955 | 42648 |
| CTCN_369 | 28590 | TTCN_4210 | 42649 |
| CTCN_370 | 28591 | ATCN_2956 | 42650 |
| GTCN_230 | 28592 | CTCN_5290 | 42651 |
| CTCN_371 | 28593 | CTCN_5291 | 42652 |
| GTCN_231 | 28594 | ATCN_2957 | 42653 |
| CTCN_372 | 28595 | ATCN_2958 | 42654 |
| CTCN_373 | 28596 | CTCN_5292 | 42655 |
| CTCN_374 | 28597 | GTCN_2738 | 42656 |
| CTCN_375 | 28598 | ATCN_2959 | 42657 |
| CTCN_376 | 28599 | CTCN_5293 | 42658 |
| CTCN_377 | 28600 | ATCN_2960 | 42659 |
| GTCN_232 | 28601 | CTCN_5294 | 42660 |
| CTCN_378 | 28602 | ATCN_2961 | 42661 |
| CTCN_379 | 28603 | ATCN_2962 | 42662 |
| CTCN_380 | 28604 | CTCN_5295 | 42663 |
| CTCN_381 | 28605 | TTCN_4211 | 42664 |
| TTCN_308 | 28606 | TTCN_4212 | 42665 |
| TTCN_309 | 28607 | ATCN_2963 | 42666 |
| CTCN_382 | 28608 | ATCN_2964 | 42667 |
| CTCN_383 | 28609 | CTCN_5296 | 42668 |
| GTCN_233 | 28610 | TTCN_4213 | 42669 |
| CTCN_384 | 28611 | ATCN_2965 | 42670 |

| | | | |
|---|---|---|---|
| CTCN_385 | 28612 | CTCN_5297 | 42671 |
| ATCN_228 | 28613 | CTCN_5298 | 42672 |
| CTCN_386 | 28614 | ATCN_2966 | 42673 |
| CTCN_387 | 28615 | ATCN_2967 | 42674 |
| ATCN_229 | 28616 | CTCN_5299 | 42675 |
| GTCN_234 | 28617 | CTCN_5300 | 42676 |
| CTCN_388 | 28618 | CTCN_5301 | 42677 |
| TTCN_310 | 28619 | GTCN_2739 | 42678 |
| CTCN_389 | 28620 | CTCN_5302 | 42679 |
| TTCN_311 | 28621 | GTCN_2740 | 42680 |
| ATCN_230 | 28622 | GTCN_2741 | 42681 |
| TTCN_312 | 28623 | CTCN_5303 | 42682 |
| CTCN_390 | 28624 | GTCN_2742 | 42683 |
| CTCN_391 | 28625 | CTCN_5304 | 42684 |
| TTCN_313 | 28626 | TTCN_4214 | 42685 |
| ATCN_231 | 28627 | CTCN_5305 | 42686 |
| CTCN_392 | 28628 | CTCN_5306 | 42687 |
| GTCN_235 | 28629 | ATCN_2968 | 42688 |
| CTCN_393 | 28630 | CTCN_5307 | 42689 |
| GTCN_236 | 28631 | TTCN_4215 | 42690 |
| GTCN_237 | 28632 | TTCN_4216 | 42691 |
| TTCN_314 | 28633 | GTCN_2743 | 42692 |
| ATCN_232 | 28634 | GTCN_2744 | 42693 |
| ATCN_233 | 28635 | CTCN_5308 | 42694 |
| CTCN_394 | 28636 | GTCN_2745 | 42695 |
| TTCN_315 | 28637 | GTCN_2746 | 42696 |
| CTCN_395 | 28638 | CTCN_5309 | 42697 |
| TTCN_316 | 28639 | CTCN_5310 | 42698 |
| GTCN_238 | 28640 | TTCN_4217 | 42699 |
| CTCN_396 | 28641 | ATCN_2969 | 42700 |
| ATCN_234 | 28642 | TTCN_4218 | 42701 |
| ATCN_235 | 28643 | ATCN_2970 | 42702 |
| CTCN_397 | 28644 | CTCN_5311 | 42703 |
| ATCN_236 | 28645 | CTCN_5312 | 42704 |
| CTCN_398 | 28646 | GTCN_2747 | 42705 |
| CTCN_399 | 28647 | CTCN_5313 | 42706 |
| CTCN_400 | 28648 | CTCN_5314 | 42707 |
| TTCN_317 | 28649 | CTCN_5315 | 42708 |
| CTCN_401 | 28650 | CTCN_5316 | 42709 |
| GTCN_239 | 28651 | GTCN_2748 | 42710 |
| TTCN_318 | 28652 | GTCN_2749 | 42711 |
| GTCN_240 | 28653 | ATCN_2971 | 42712 |
| CTCN_402 | 28654 | GTCN_2750 | 42713 |

FIG. 37 (continued)

| | | | |
|---|---|---|---|
| CTCN_403 | 28655 | GTCN_2751 | 42714 |
| CTCN_404 | 28656 | GTCN_2752 | 42715 |
| TTCN_319 | 28657 | CTCN_5317 | 42716 |
| CTCN_405 | 28658 | ATCN_2972 | 42717 |
| CTCN_406 | 28659 | ATCN_2973 | 42718 |
| GTCN_241 | 28660 | CTCN_5318 | 42719 |
| GTCN_242 | 28661 | GTCN_2753 | 42720 |
| CTCN_407 | 28662 | TTCN_4219 | 42721 |
| CTCN_408 | 28663 | TTCN_4220 | 42722 |
| CTCN_409 | 28664 | CTCN_5319 | 42723 |
| GTCN_243 | 28665 | TTCN_4221 | 42724 |
| CTCN_410 | 28666 | ATCN_2974 | 42725 |
| GTCN_244 | 28667 | TTCN_4222 | 42726 |
| CTCN_411 | 28668 | ATCN_2975 | 42727 |
| CTCN_412 | 28669 | TTCN_4223 | 42728 |
| TTCN_320 | 28670 | TTCN_4224 | 42729 |
| CTCN_413 | 28671 | TTCN_4225 | 42730 |
| CTCN_414 | 28672 | TTCN_4226 | 42731 |
| CTCN_415 | 28673 | GTCN_2754 | 42732 |
| TTCN_321 | 28674 | CTCN_5320 | 42733 |
| CTCN_416 | 28675 | ATCN_2976 | 42734 |
| CTCN_417 | 28676 | CTCN_5321 | 42735 |
| ATCN_237 | 28677 | ATCN_2977 | 42736 |
| ATCN_238 | 28678 | ATCN_2978 | 42737 |
| CTCN_418 | 28679 | CTCN_5322 | 42738 |
| CTCN_419 | 28680 | ATCN_2979 | 42739 |
| TTCN_322 | 28681 | ATCN_2980 | 42740 |
| TTCN_323 | 28682 | CTCN_5323 | 42741 |
| CTCN_420 | 28683 | CTCN_5324 | 42742 |
| GTCN_245 | 28684 | GTCN_2755 | 42743 |
| TTCN_324 | 28685 | TTCN_4227 | 42744 |
| CTCN_421 | 28686 | CTCN_5325 | 42745 |
| GTCN_246 | 28687 | GTCN_2756 | 42746 |
| GTCN_247 | 28688 | GTCN_2757 | 42747 |
| CTCN_422 | 28689 | TTCN_4228 | 42748 |
| CTCN_423 | 28690 | GTCN_2758 | 42749 |
| CTCN_424 | 28691 | CTCN_5326 | 42750 |
| TTCN_325 | 28692 | TTCN_4229 | 42751 |
| CTCN_425 | 28693 | CTCN_5327 | 42752 |
| CTCN_426 | 28694 | GTCN_2759 | 42753 |
| CTCN_427 | 28695 | CTCN_5328 | 42754 |
| CTCN_428 | 28696 | CTCN_5329 | 42755 |
| CTCN_429 | 28697 | CTCN_5330 | 42756 |

| | | | |
|---|---|---|---|
| CTCN_430 | 28698 | TTCN_4230 | 42757 |
| CTCN_431 | 28699 | TTCN_4231 | 42758 |
| CTCN_432 | 28700 | ATCN_2981 | 42759 |
| CTCN_433 | 28701 | CTCN_5331 | 42760 |
| CTCN_434 | 28702 | CTCN_5332 | 42761 |
| TTCN_326 | 28703 | CTCN_5333 | 42762 |
| CTCN_435 | 28704 | CTCN_5334 | 42763 |
| TTCN_327 | 28705 | CTCN_5335 | 42764 |
| CTCN_436 | 28706 | ATCN_2982 | 42765 |
| TTCN_328 | 28707 | ATCN_2983 | 42766 |
| GTCN_248 | 28708 | GTCN_2760 | 42767 |
| GTCN_249 | 28709 | CTCN_5336 | 42768 |
| GTCN_250 | 28710 | CTCN_5337 | 42769 |
| TTCN_329 | 28711 | GTCN_2761 | 42770 |
| CTCN_437 | 28712 | CTCN_5338 | 42771 |
| CTCN_438 | 28713 | GTCN_2762 | 42772 |
| CTCN_439 | 28714 | CTCN_5339 | 42773 |
| ATCN_239 | 28715 | TTCN_4232 | 42774 |
| TTCN_330 | 28716 | CTCN_5340 | 42775 |
| ATCN_240 | 28717 | TTCN_4233 | 42776 |
| CTCN_440 | 28718 | CTCN_5341 | 42777 |
| TTCN_331 | 28719 | TTCN_4234 | 42778 |
| TTCN_332 | 28720 | TTCN_4235 | 42779 |
| TTCN_333 | 28721 | ATCN_2984 | 42780 |
| GTCN_251 | 28722 | TTCN_4236 | 42781 |
| CTCN_441 | 28723 | GTCN_2763 | 42782 |
| CTCN_442 | 28724 | CTCN_5342 | 42783 |
| TTCN_334 | 28725 | CTCN_5343 | 42784 |
| GTCN_252 | 28726 | ATCN_2985 | 42785 |
| ATCN_241 | 28727 | ATCN_2986 | 42786 |
| CTCN_443 | 28728 | ATCN_2987 | 42787 |
| GTCN_253 | 28729 | GTCN_2764 | 42788 |
| GTCN_254 | 28730 | CTCN_5344 | 42789 |
| GTCN_255 | 28731 | GTCN_2765 | 42790 |
| CTCN_444 | 28732 | CTCN_5345 | 42791 |
| CTCN_445 | 28733 | TTCN_4237 | 42792 |
| GTCN_256 | 28734 | TTCN_4238 | 42793 |
| GTCN_257 | 28735 | CTCN_5346 | 42794 |
| CTCN_446 | 28736 | CTCN_5347 | 42795 |
| CTCN_447 | 28737 | GTCN_2766 | 42796 |
| GTCN_258 | 28738 | CTCN_5348 | 42797 |
| TTCN_335 | 28739 | TTCN_4239 | 42798 |
| CTCN_448 | 28740 | GTCN_2767 | 42799 |

FIG. 37 (continued)

| | | | |
|---|---|---|---|
| CTCN_449 | 28741 | CTCN_5349 | 42800 |
| CTCN_450 | 28742 | GTCN_2768 | 42801 |
| CTCN_451 | 28743 | CTCN_5350 | 42802 |
| CTCN_452 | 28744 | GTCN_2769 | 42803 |
| GTCN_259 | 28745 | CTCN_5351 | 42804 |
| TTCN_336 | 28746 | GTCN_2770 | 42805 |
| GTCN_260 | 28747 | TTCN_4240 | 42806 |
| GTCN_261 | 28748 | CTCN_5352 | 42807 |
| CTCN_453 | 28749 | ATCN_2988 | 42808 |
| TTCN_337 | 28750 | TTCN_4241 | 42809 |
| TTCN_338 | 28751 | GTCN_2771 | 42810 |
| GTCN_262 | 28752 | TTCN_4242 | 42811 |
| CTCN_454 | 28753 | TTCN_4243 | 42812 |
| TTCN_339 | 28754 | CTCN_5353 | 42813 |
| GTCN_263 | 28755 | GTCN_2772 | 42814 |
| GTCN_264 | 28756 | CTCN_5354 | 42815 |
| ATCN_242 | 28757 | ATCN_2989 | 42816 |
| TTCN_340 | 28758 | ATCN_2990 | 42817 |
| CTCN_455 | 28759 | TTCN_4244 | 42818 |
| CTCN_456 | 28760 | CTCN_5355 | 42819 |
| GTCN_265 | 28761 | GTCN_2773 | 42820 |
| ATCN_243 | 28762 | TTCN_4245 | 42821 |
| CTCN_457 | 28763 | ATCN_2991 | 42822 |
| CTCN_458 | 28764 | GTCN_2774 | 42823 |
| TTCN_341 | 28765 | TTCN_4246 | 42824 |
| CTCN_459 | 28766 | TTCN_4247 | 42825 |
| CTCN_460 | 28767 | CTCN_5356 | 42826 |
| TTCN_342 | 28768 | TTCN_4248 | 42827 |
| ATCN_244 | 28769 | CTCN_5357 | 42828 |
| TTCN_343 | 28770 | GTCN_2775 | 42829 |
| CTCN_461 | 28771 | CTCN_5358 | 42830 |
| TTCN_344 | 28772 | ATCN_2992 | 42831 |
| CTCN_462 | 28773 | CTCN_5359 | 42832 |
| GTCN_266 | 28774 | CTCN_5360 | 42833 |
| CTCN_463 | 28775 | CTCN_5361 | 42834 |
| GTCN_267 | 28776 | GTCN_2776 | 42835 |
| ATCN_245 | 28777 | ATCN_2993 | 42836 |
| TTCN_345 | 28778 | ATCN_2994 | 42837 |
| TTCN_346 | 28779 | TTCN_4249 | 42838 |
| ATCN_246 | 28780 | CTCN_5362 | 42839 |
| TTCN_347 | 28781 | CTCN_5363 | 42840 |
| CTCN_464 | 28782 | CTCN_5364 | 42841 |
| ATCN_247 | 28783 | CTCN_5365 | 42842 |

| | | | |
|---|---|---|---|
| TTCN_348 | 28784 | CTCN_5366 | 42843 |
| TTCN_349 | 28785 | CTCN_5367 | 42844 |
| TTCN_350 | 28786 | ATCN_2995 | 42845 |
| CTCN_465 | 28787 | TTCN_4250 | 42846 |
| TTCN_351 | 28788 | GTCN_2777 | 42847 |
| ATCN_248 | 28789 | TTCN_4251 | 42848 |
| CTCN_466 | 28790 | CTCN_5368 | 42849 |
| TTCN_352 | 28791 | TTCN_4252 | 42850 |
| ATCN_249 | 28792 | GTCN_2778 | 42851 |
| CTCN_467 | 28793 | TTCN_4253 | 42852 |
| CTCN_468 | 28794 | CTCN_5369 | 42853 |
| CTCN_469 | 28795 | CTCN_5370 | 42854 |
| CTCN_470 | 28796 | ATCN_2996 | 42855 |
| CTCN_471 | 28797 | ATCN_2997 | 42856 |
| TTCN_353 | 28798 | ATCN_2998 | 42857 |
| ATCN_250 | 28799 | TTCN_4254 | 42858 |
| ATCN_251 | 28800 | TTCN_4255 | 42859 |
| GTCN_268 | 28801 | TTCN_4256 | 42860 |
| CTCN_472 | 28802 | GTCN_2779 | 42861 |
| ATCN_252 | 28803 | ATCN_2999 | 42862 |
| TTCN_354 | 28804 | CTCN_5371 | 42863 |
| CTCN_473 | 28805 | CTCN_5372 | 42864 |
| TTCN_355 | 28806 | ATCN_3000 | 42865 |
| CTCN_474 | 28807 | TTCN_4257 | 42866 |
| CTCN_475 | 28808 | CTCN_5373 | 42867 |
| ATCN_253 | 28809 | GTCN_2780 | 42868 |
| ATCN_254 | 28810 | GTCN_2781 | 42869 |
| GTCN_269 | 28811 | GTCN_2782 | 42870 |
| GTCN_270 | 28812 | CTCN_5374 | 42871 |
| TTCN_356 | 28813 | ATCN_3001 | 42872 |
| ATCN_255 | 28814 | ATCN_3002 | 42873 |
| CTCN_476 | 28815 | CTCN_5375 | 42874 |
| TTCN_357 | 28816 | TTCN_4258 | 42875 |
| GTCN_271 | 28817 | TTCN_4259 | 42876 |
| CTCN_477 | 28818 | TTCN_4260 | 42877 |
| CTCN_478 | 28819 | CTCN_5376 | 42878 |
| ATCN_256 | 28820 | CTCN_5377 | 42879 |
| TTCN_358 | 28821 | CTCN_5378 | 42880 |
| CTCN_479 | 28822 | CTCN_5379 | 42881 |
| TTCN_359 | 28823 | GTCN_2783 | 42882 |
| TTCN_360 | 28824 | GTCN_2784 | 42883 |
| GTCN_272 | 28825 | ATCN_3003 | 42884 |
| GTCN_273 | 28826 | CTCN_5380 | 42885 |

FIG. 37 (continued)

| | | | |
|---|---|---|---|
| CTCN_480 | 28827 | ATCN_3004 | 42886 |
| ATCN_257 | 28828 | TTCN_4261 | 42887 |
| CTCN_481 | 28829 | ATCN_3005 | 42888 |
| GTCN_274 | 28830 | CTCN_5381 | 42889 |
| CTCN_482 | 28831 | TTCN_4262 | 42890 |
| GTCN_275 | 28832 | TTCN_4263 | 42891 |
| GTCN_276 | 28833 | ATCN_3006 | 42892 |
| CTCN_483 | 28834 | GTCN_2785 | 42893 |
| ATCN_258 | 28835 | GTCN_2786 | 42894 |
| CTCN_484 | 28836 | CTCN_5382 | 42895 |
| GTCN_277 | 28837 | ATCN_3007 | 42896 |
| CTCN_485 | 28838 | TTCN_4264 | 42897 |
| GTCN_278 | 28839 | TTCN_4265 | 42898 |
| GTCN_279 | 28840 | TTCN_4266 | 42899 |
| CTCN_486 | 28841 | ATCN_3008 | 42900 |
| ATCN_259 | 28842 | CTCN_5383 | 42901 |
| CTCN_487 | 28843 | TTCN_4267 | 42902 |
| GTCN_280 | 28844 | CTCN_5384 | 42903 |
| CTCN_488 | 28845 | CTCN_5385 | 42904 |
| GTCN_281 | 28846 | TTCN_4268 | 42905 |
| CTCN_489 | 28847 | TTCN_4269 | 42906 |
| ATCN_260 | 28848 | CTCN_5386 | 42907 |
| CTCN_490 | 28849 | TTCN_4270 | 42908 |
| GTCN_282 | 28850 | GTCN_2787 | 42909 |
| CTCN_491 | 28851 | ATCN_3009 | 42910 |
| GTCN_283 | 28852 | ATCN_3010 | 42911 |
| GTCN_284 | 28853 | CTCN_5387 | 42912 |
| CTCN_492 | 28854 | GTCN_2788 | 42913 |
| ATCN_261 | 28855 | ATCN_3011 | 42914 |
| CTCN_493 | 28856 | ATCN_3012 | 42915 |
| GTCN_285 | 28857 | TTCN_4271 | 42916 |
| CTCN_494 | 28858 | TTCN_4272 | 42917 |
| GTCN_286 | 28859 | TTCN_4273 | 42918 |
| GTCN_287 | 28860 | TTCN_4274 | 42919 |
| CTCN_495 | 28861 | TTCN_4275 | 42920 |
| ATCN_262 | 28862 | TTCN_4276 | 42921 |
| CTCN_496 | 28863 | CTCN_5388 | 42922 |
| GTCN_288 | 28864 | GTCN_2789 | 42923 |
| CTCN_497 | 28865 | CTCN_5389 | 42924 |
| GTCN_289 | 28866 | GTCN_2790 | 42925 |
| GTCN_290 | 28867 | TTCN_4277 | 42926 |
| CTCN_498 | 28868 | GTCN_2791 | 42927 |
| ATCN_263 | 28869 | TTCN_4278 | 42928 |

| | | | |
|---|---|---|---|
| CTCN_499 | 28870 | GTCN_2792 | 42929 |
| GTCN_291 | 28871 | ATCN_3013 | 42930 |
| CTCN_500 | 28872 | ATCN_3014 | 42931 |
| GTCN_292 | 28873 | TTCN_4279 | 42932 |
| GTCN_293 | 28874 | TTCN_4280 | 42933 |
| CTCN_501 | 28875 | GTCN_2793 | 42934 |
| ATCN_264 | 28876 | CTCN_5390 | 42935 |
| GTCN_294 | 28877 | CTCN_5391 | 42936 |
| CTCN_502 | 28878 | CTCN_5392 | 42937 |
| GTCN_295 | 28879 | TTCN_4281 | 42938 |
| GTCN_296 | 28880 | TTCN_4282 | 42939 |
| CTCN_503 | 28881 | ATCN_3015 | 42940 |
| ATCN_265 | 28882 | TTCN_4283 | 42941 |
| CTCN_504 | 28883 | ATCN_3016 | 42942 |
| GTCN_297 | 28884 | CTCN_5393 | 42943 |
| CTCN_505 | 28885 | CTCN_5394 | 42944 |
| GTCN_298 | 28886 | TTCN_4284 | 42945 |
| GTCN_299 | 28887 | TTCN_4285 | 42946 |
| CTCN_506 | 28888 | TTCN_4286 | 42947 |
| ATCN_266 | 28889 | TTCN_4287 | 42948 |
| GTCN_300 | 28890 | TTCN_4288 | 42949 |
| CTCN_507 | 28891 | CTCN_5395 | 42950 |
| GTCN_301 | 28892 | TTCN_4289 | 42951 |
| GTCN_302 | 28893 | GTCN_2794 | 42952 |
| CTCN_508 | 28894 | CTCN_5396 | 42953 |
| TTCN_361 | 28895 | CTCN_5397 | 42954 |
| TTCN_362 | 28896 | CTCN_5398 | 42955 |
| CTCN_509 | 28897 | ATCN_3017 | 42956 |
| ATCN_267 | 28898 | ATCN_3018 | 42957 |
| CTCN_510 | 28899 | GTCN_2795 | 42958 |
| ATCN_268 | 28900 | ATCN_3019 | 42959 |
| CTCN_511 | 28901 | TTCN_4290 | 42960 |
| TTCN_363 | 28902 | TTCN_4291 | 42961 |
| CTCN_512 | 28903 | GTCN_2796 | 42962 |
| CTCN_513 | 28904 | CTCN_5399 | 42963 |
| GTCN_303 | 28905 | GTCN_2797 | 42964 |
| CTCN_514 | 28906 | GTCN_2798 | 42965 |
| GTCN_304 | 28907 | CTCN_5400 | 42966 |
| CTCN_515 | 28908 | CTCN_5401 | 42967 |
| CTCN_516 | 28909 | TTCN_4292 | 42968 |
| CTCN_517 | 28910 | CTCN_5402 | 42969 |
| ATCN_269 | 28911 | ATCN_3020 | 42970 |
| CTCN_518 | 28912 | TTCN_4293 | 42971 |

FIG. 37 (continued)

| | | | |
|---|---|---|---|
| CTCN_519 | 28913 | GTCN_2799 | 42972 |
| ATCN_270 | 28914 | GTCN_2800 | 42973 |
| ATCN_271 | 28915 | CTCN_5403 | 42974 |
| CTCN_520 | 28916 | GTCN_2801 | 42975 |
| GTCN_305 | 28917 | CTCN_5404 | 42976 |
| ATCN_272 | 28918 | GTCN_2802 | 42977 |
| TTCN_364 | 28919 | ATCN_3021 | 42978 |
| TTCN_365 | 28920 | TTCN_4294 | 42979 |
| CTCN_521 | 28921 | TTCN_4295 | 42980 |
| TTCN_366 | 28922 | CTCN_5405 | 42981 |
| ATCN_273 | 28923 | TTCN_4296 | 42982 |
| ATCN_274 | 28924 | TTCN_4297 | 42983 |
| GTCN_306 | 28925 | TTCN_4298 | 42984 |
| CTCN_522 | 28926 | TTCN_4299 | 42985 |
| ATCN_275 | 28927 | CTCN_5406 | 42986 |
| ATCN_276 | 28928 | TTCN_4300 | 42987 |
| CTCN_523 | 28929 | TTCN_4301 | 42988 |
| CTCN_524 | 28930 | TTCN_4302 | 42989 |
| TTCN_367 | 28931 | CTCN_5407 | 42990 |
| ATCN_277 | 28932 | TTCN_4303 | 42991 |
| CTCN_525 | 28933 | GTCN_2803 | 42992 |
| ATCN_278 | 28934 | TTCN_4304 | 42993 |
| CTCN_526 | 28935 | TTCN_4305 | 42994 |
| TTCN_368 | 28936 | CTCN_5408 | 42995 |
| TTCN_369 | 28937 | TTCN_4306 | 42996 |
| GTCN_307 | 28938 | TTCN_4307 | 42997 |
| CTCN_527 | 28939 | CTCN_5409 | 42998 |
| CTCN_528 | 28940 | ATCN_3022 | 42999 |
| CTCN_529 | 28941 | GTCN_2804 | 43000 |
| ATCN_279 | 28942 | GTCN_2805 | 43001 |
| ATCN_280 | 28943 | GTCN_2806 | 43002 |
| CTCN_530 | 28944 | CTCN_5410 | 43003 |
| CTCN_531 | 28945 | CTCN_5411 | 43004 |
| CTCN_532 | 28946 | TTCN_4308 | 43005 |
| CTCN_533 | 28947 | ATCN_3023 | 43006 |
| ATCN_281 | 28948 | ATCN_3024 | 43007 |
| ATCN_282 | 28949 | CTCN_5412 | 43008 |
| CTCN_534 | 28950 | GTCN_2807 | 43009 |
| GTCN_308 | 28951 | CTCN_5413 | 43010 |
| CTCN_535 | 28952 | GTCN_2808 | 43011 |
| TTCN_370 | 28953 | CTCN_5414 | 43012 |
| GTCN_309 | 28954 | ATCN_3025 | 43013 |
| CTCN_536 | 28955 | CTCN_5415 | 43014 |

| | | | |
|---|---|---|---|
| GTCN_310 | 28956 | TTCN_4309 | 43015 |
| GTCN_311 | 28957 | TTCN_4310 | 43016 |
| GTCN_312 | 28958 | GTCN_2809 | 43017 |
| GTCN_313 | 28959 | GTCN_2810 | 43018 |
| ATCN_283 | 28960 | CTCN_5416 | 43019 |
| ATCN_284 | 28961 | TTCN_4311 | 43020 |
| TTCN_371 | 28962 | CTCN_5417 | 43021 |
| GTCN_314 | 28963 | GTCN_2811 | 43022 |
| ATCN_285 | 28964 | GTCN_2812 | 43023 |
| ATCN_286 | 28965 | CTCN_5418 | 43024 |
| ATCN_287 | 28966 | TTCN_4312 | 43025 |
| TTCN_372 | 28967 | GTCN_2813 | 43026 |
| TTCN_373 | 28968 | CTCN_5419 | 43027 |
| CTCN_537 | 28969 | GTCN_2814 | 43028 |
| CTCN_538 | 28970 | GTCN_2815 | 43029 |
| ATCN_288 | 28971 | CTCN_5420 | 43030 |
| TTCN_374 | 28972 | TTCN_4313 | 43031 |
| CTCN_539 | 28973 | GTCN_2816 | 43032 |
| CTCN_540 | 28974 | CTCN_5421 | 43033 |
| GTCN_315 | 28975 | TTCN_4314 | 43034 |
| TTCN_375 | 28976 | ATCN_3026 | 43035 |
| TTCN_376 | 28977 | GTCN_2817 | 43036 |
| TTCN_377 | 28978 | TTCN_4315 | 43037 |
| TTCN_378 | 28979 | CTCN_5422 | 43038 |
| TTCN_379 | 28980 | TTCN_4316 | 43039 |
| TTCN_380 | 28981 | ATCN_3027 | 43040 |
| CTCN_541 | 28982 | ATCN_3028 | 43041 |
| TTCN_381 | 28983 | ATCN_3029 | 43042 |
| CTCN_542 | 28984 | TTCN_4317 | 43043 |
| CTCN_543 | 28985 | ATCN_3030 | 43044 |
| GTCN_316 | 28986 | GTCN_2818 | 43045 |
| CTCN_544 | 28987 | CTCN_5423 | 43046 |
| CTCN_545 | 28988 | GTCN_2819 | 43047 |
| TTCN_382 | 28989 | GTCN_2820 | 43048 |
| CTCN_546 | 28990 | CTCN_5424 | 43049 |
| CTCN_547 | 28991 | CTCN_5425 | 43050 |
| TTCN_383 | 28992 | CTCN_5426 | 43051 |
| TTCN_384 | 28993 | TTCN_4318 | 43052 |
| GTCN_317 | 28994 | CTCN_5427 | 43053 |
| GTCN_318 | 28995 | CTCN_5428 | 43054 |
| TTCN_385 | 28996 | GTCN_2821 | 43055 |
| CTCN_548 | 28997 | ATCN_3031 | 43056 |
| CTCN_549 | 28998 | TTCN_4319 | 43057 |

FIG. 37 (continued)

| | | | |
|---|---|---|---|
| TTCN_386 | 28999 | GTCN_2822 | 43058 |
| ATCN_289 | 29000 | CTCN_5429 | 43059 |
| CTCN_550 | 29001 | ATCN_3032 | 43060 |
| TTCN_387 | 29002 | ATCN_3033 | 43061 |
| TTCN_388 | 29003 | GTCN_2823 | 43062 |
| GTCN_319 | 29004 | TTCN_4320 | 43063 |
| CTCN_551 | 29005 | GTCN_2824 | 43064 |
| CTCN_552 | 29006 | TTCN_4321 | 43065 |
| CTCN_553 | 29007 | TTCN_4322 | 43066 |
| GTCN_320 | 29008 | TTCN_4323 | 43067 |
| GTCN_321 | 29009 | TTCN_4324 | 43068 |
| ATCN_290 | 29010 | GTCN_2825 | 43069 |
| GTCN_322 | 29011 | ATCN_3034 | 43070 |
| GTCN_323 | 29012 | CTCN_5430 | 43071 |
| CTCN_554 | 29013 | CTCN_5431 | 43072 |
| TTCN_389 | 29014 | GTCN_2826 | 43073 |
| TTCN_390 | 29015 | CTCN_5432 | 43074 |
| TTCN_391 | 29016 | CTCN_5433 | 43075 |
| GTCN_324 | 29017 | ATCN_3035 | 43076 |
| TTCN_392 | 29018 | ATCN_3036 | 43077 |
| CTCN_555 | 29019 | ATCN_3037 | 43078 |
| GTCN_325 | 29020 | ATCN_3038 | 43079 |
| TTCN_393 | 29021 | TTCN_4325 | 43080 |
| GTCN_326 | 29022 | GTCN_2827 | 43081 |
| CTCN_556 | 29023 | CTCN_5434 | 43082 |
| CTCN_557 | 29024 | GTCN_2828 | 43083 |
| GTCN_327 | 29025 | CTCN_5435 | 43084 |
| CTCN_558 | 29026 | TTCN_4326 | 43085 |
| ATCN_291 | 29027 | ATCN_3039 | 43086 |
| CTCN_559 | 29028 | GTCN_2829 | 43087 |
| GTCN_328 | 29029 | CTCN_5436 | 43088 |
| GTCN_329 | 29030 | CTCN_5437 | 43089 |
| CTCN_560 | 29031 | ATCN_3040 | 43090 |
| ATCN_292 | 29032 | ATCN_3041 | 43091 |
| ATCN_293 | 29033 | CTCN_5438 | 43092 |
| TTCN_394 | 29034 | ATCN_3042 | 43093 |
| CTCN_561 | 29035 | CTCN_5439 | 43094 |
| CTCN_562 | 29036 | GTCN_2830 | 43095 |
| CTCN_563 | 29037 | ATCN_3043 | 43096 |
| GTCN_330 | 29038 | TTCN_4327 | 43097 |
| GTCN_331 | 29039 | TTCN_4328 | 43098 |
| TTCN_395 | 29040 | CTCN_5440 | 43099 |
| CTCN_564 | 29041 | TTCN_4329 | 43100 |

| | | | |
|---|---|---|---|
| CTCN_565 | 29042 | CTCN_5441 | 43101 |
| CTCN_566 | 29043 | GTCN_2831 | 43102 |
| ATCN_294 | 29044 | TTCN_4330 | 43103 |
| GTCN_332 | 29045 | CTCN_5442 | 43104 |
| CTCN_567 | 29046 | TTCN_4331 | 43105 |
| CTCN_568 | 29047 | ATCN_3044 | 43106 |
| ATCN_295 | 29048 | ATCN_3045 | 43107 |
| ATCN_296 | 29049 | CTCN_5443 | 43108 |
| CTCN_569 | 29050 | ATCN_3046 | 43109 |
| CTCN_570 | 29051 | CTCN_5444 | 43110 |
| ATCN_297 | 29052 | CTCN_5445 | 43111 |
| ATCN_298 | 29053 | CTCN_5446 | 43112 |
| ATCN_299 | 29054 | GTCN_2832 | 43113 |
| CTCN_571 | 29055 | CTCN_5447 | 43114 |
| TTCN_396 | 29056 | TTCN_4332 | 43115 |
| CTCN_572 | 29057 | TTCN_4333 | 43116 |
| TTCN_397 | 29058 | CTCN_5448 | 43117 |
| ATCN_300 | 29059 | CTCN_5449 | 43118 |
| TTCN_398 | 29060 | TTCN_4334 | 43119 |
| CTCN_573 | 29061 | CTCN_5450 | 43120 |
| CTCN_574 | 29062 | ATCN_3047 | 43121 |
| CTCN_575 | 29063 | CTCN_5451 | 43122 |
| TTCN_399 | 29064 | ATCN_3048 | 43123 |
| TTCN_400 | 29065 | GTCN_2833 | 43124 |
| TTCN_401 | 29066 | CTCN_5452 | 43125 |
| CTCN_576 | 29067 | ATCN_3049 | 43126 |
| CTCN_577 | 29068 | TTCN_4335 | 43127 |
| CTCN_578 | 29069 | GTCN_2834 | 43128 |
| TTCN_402 | 29070 | CTCN_5453 | 43129 |
| CTCN_579 | 29071 | GTCN_2835 | 43130 |
| GTCN_333 | 29072 | CTCN_5454 | 43131 |
| TTCN_403 | 29073 | CTCN_5455 | 43132 |
| GTCN_334 | 29074 | TTCN_4336 | 43133 |
| GTCN_335 | 29075 | TTCN_4337 | 43134 |
| TTCN_404 | 29076 | TTCN_4338 | 43135 |
| GTCN_336 | 29077 | TTCN_4339 | 43136 |
| TTCN_405 | 29078 | CTCN_5456 | 43137 |
| ATCN_301 | 29079 | TTCN_4340 | 43138 |
| ATCN_302 | 29080 | GTCN_2836 | 43139 |
| CTCN_580 | 29081 | GTCN_2837 | 43140 |
| GTCN_337 | 29082 | GTCN_2838 | 43141 |
| TTCN_406 | 29083 | GTCN_2839 | 43142 |
| CTCN_581 | 29084 | GTCN_2840 | 43143 |

FIG. 37 (continued)

| | | | |
|---|---|---|---|
| CTCN_582 | 29085 | TTCN_4341 | 43144 |
| ATCN_303 | 29086 | ATCN_3050 | 43145 |
| TTCN_407 | 29087 | TTCN_4342 | 43146 |
| TTCN_408 | 29088 | ATCN_3051 | 43147 |
| GTCN_338 | 29089 | ATCN_3052 | 43148 |
| TTCN_409 | 29090 | ATCN_3053 | 43149 |
| TTCN_410 | 29091 | CTCN_5457 | 43150 |
| GTCN_339 | 29092 | TTCN_4343 | 43151 |
| CTCN_583 | 29093 | TTCN_4344 | 43152 |
| ATCN_304 | 29094 | CTCN_5458 | 43153 |
| CTCN_584 | 29095 | CTCN_5459 | 43154 |
| GTCN_340 | 29096 | ATCN_3054 | 43155 |
| CTCN_585 | 29097 | TTCN_4345 | 43156 |
| TTCN_411 | 29098 | GTCN_2841 | 43157 |
| TTCN_412 | 29099 | CTCN_5460 | 43158 |
| ATCN_305 | 29100 | CTCN_5461 | 43159 |
| TTCN_413 | 29101 | ATCN_3055 | 43160 |
| CTCN_586 | 29102 | GTCN_2842 | 43161 |
| TTCN_414 | 29103 | CTCN_5462 | 43162 |
| GTCN_341 | 29104 | CTCN_5463 | 43163 |
| TTCN_415 | 29105 | GTCN_2843 | 43164 |
| GTCN_342 | 29106 | TTCN_4346 | 43165 |
| TTCN_416 | 29107 | ATCN_3056 | 43166 |
| TTCN_417 | 29108 | CTCN_5464 | 43167 |
| TTCN_418 | 29109 | TTCN_4347 | 43168 |
| GTCN_343 | 29110 | GTCN_2844 | 43169 |
| GTCN_344 | 29111 | ATCN_3057 | 43170 |
| TTCN_419 | 29112 | ATCN_3058 | 43171 |
| GTCN_345 | 29113 | CTCN_5465 | 43172 |
| ATCN_306 | 29114 | CTCN_5466 | 43173 |
| TTCN_420 | 29115 | TTCN_4348 | 43174 |
| TTCN_421 | 29116 | TTCN_4349 | 43175 |
| TTCN_422 | 29117 | ATCN_3059 | 43176 |
| CTCN_587 | 29118 | ATCN_3060 | 43177 |
| TTCN_423 | 29119 | GTCN_2845 | 43178 |
| CTCN_588 | 29120 | ATCN_3061 | 43179 |
| ATCN_307 | 29121 | CTCN_5467 | 43180 |
| CTCN_589 | 29122 | TTCN_4350 | 43181 |
| TTCN_424 | 29123 | GTCN_2846 | 43182 |
| TTCN_425 | 29124 | GTCN_2847 | 43183 |
| ATCN_308 | 29125 | ATCN_3062 | 43184 |
| ATCN_309 | 29126 | ATCN_3063 | 43185 |
| TTCN_426 | 29127 | ATCN_3064 | 43186 |

| | | | |
|---|---|---|---|
| CTCN_590 | 29128 | ATCN_3065 | 43187 |
| GTCN_346 | 29129 | TTCN_4351 | 43188 |
| GTCN_347 | 29130 | CTCN_5468 | 43189 |
| TTCN_427 | 29131 | GTCN_2848 | 43190 |
| TTCN_428 | 29132 | GTCN_2849 | 43191 |
| ATCN_310 | 29133 | TTCN_4352 | 43192 |
| CTCN_591 | 29134 | ATCN_3066 | 43193 |
| ATCN_311 | 29135 | TTCN_4353 | 43194 |
| CTCN_592 | 29136 | TTCN_4354 | 43195 |
| ATCN_312 | 29137 | ATCN_3067 | 43196 |
| GTCN_348 | 29138 | TTCN_4355 | 43197 |
| TTCN_429 | 29139 | GTCN_2850 | 43198 |
| CTCN_593 | 29140 | CTCN_5469 | 43199 |
| TTCN_430 | 29141 | CTCN_5470 | 43200 |
| CTCN_594 | 29142 | GTCN_2851 | 43201 |
| ATCN_313 | 29143 | GTCN_2852 | 43202 |
| TTCN_431 | 29144 | TTCN_4356 | 43203 |
| TTCN_432 | 29145 | ATCN_3068 | 43204 |
| CTCN_595 | 29146 | ATCN_3069 | 43205 |
| CTCN_596 | 29147 | ATCN_3070 | 43206 |
| TTCN_433 | 29148 | TTCN_4357 | 43207 |
| TTCN_434 | 29149 | GTCN_2853 | 43208 |
| GTCN_349 | 29150 | ATCN_3071 | 43209 |
| CTCN_597 | 29151 | CTCN_5471 | 43210 |
| ATCN_314 | 29152 | CTCN_5472 | 43211 |
| GTCN_350 | 29153 | ATCN_3072 | 43212 |
| TTCN_435 | 29154 | ATCN_3073 | 43213 |
| TTCN_436 | 29155 | TTCN_4358 | 43214 |
| CTCN_598 | 29156 | GTCN_2854 | 43215 |
| CTCN_599 | 29157 | CTCN_5473 | 43216 |
| GTCN_351 | 29158 | TTCN_4359 | 43217 |
| ATCN_315 | 29159 | TTCN_4360 | 43218 |
| CTCN_600 | 29160 | TTCN_4361 | 43219 |
| TTCN_437 | 29161 | CTCN_5474 | 43220 |
| TTCN_438 | 29162 | ATCN_3074 | 43221 |
| CTCN_601 | 29163 | TTCN_4362 | 43222 |
| TTCN_439 | 29164 | ATCN_3075 | 43223 |
| CTCN_602 | 29165 | ATCN_3076 | 43224 |
| ATCN_316 | 29166 | CTCN_5475 | 43225 |
| CTCN_603 | 29167 | CTCN_5476 | 43226 |
| CTCN_604 | 29168 | ATCN_3077 | 43227 |
| CTCN_605 | 29169 | GTCN_2855 | 43228 |
| TTCN_440 | 29170 | CTCN_5477 | 43229 |

FIG. 37 (continued)

| | | | |
|---|---|---|---|
| ATCN_317 | 29171 | CTCN_5478 | 43230 |
| CTCN_606 | 29172 | GTCN_2856 | 43231 |
| CTCN_607 | 29173 | CTCN_5479 | 43232 |
| TTCN_441 | 29174 | GTCN_2857 | 43233 |
| TTCN_442 | 29175 | GTCN_2858 | 43234 |
| ATCN_318 | 29176 | CTCN_5480 | 43235 |
| GTCN_352 | 29177 | CTCN_5481 | 43236 |
| GTCN_353 | 29178 | TTCN_4363 | 43237 |
| ATCN_319 | 29179 | GTCN_2859 | 43238 |
| TTCN_443 | 29180 | GTCN_2860 | 43239 |
| CTCN_608 | 29181 | TTCN_4364 | 43240 |
| GTCN_354 | 29182 | CTCN_5482 | 43241 |
| TTCN_444 | 29183 | ATCN_3078 | 43242 |
| ATCN_320 | 29184 | ATCN_3079 | 43243 |
| GTCN_355 | 29185 | GTCN_2861 | 43244 |
| TTCN_445 | 29186 | TTCN_4365 | 43245 |
| GTCN_356 | 29187 | TTCN_4366 | 43246 |
| TTCN_446 | 29188 | CTCN_5483 | 43247 |
| ATCN_321 | 29189 | CTCN_5484 | 43248 |
| GTCN_357 | 29190 | ATCN_3080 | 43249 |
| GTCN_358 | 29191 | ATCN_3081 | 43250 |
| TTCN_447 | 29192 | ATCN_3082 | 43251 |
| CTCN_609 | 29193 | ATCN_3083 | 43252 |
| GTCN_359 | 29194 | ATCN_3084 | 43253 |
| ATCN_322 | 29195 | GTCN_2862 | 43254 |
| CTCN_610 | 29196 | CTCN_5485 | 43255 |
| ATCN_323 | 29197 | CTCN_5486 | 43256 |
| ATCN_324 | 29198 | CTCN_5487 | 43257 |
| ATCN_325 | 29199 | GTCN_2863 | 43258 |
| CTCN_611 | 29200 | GTCN_2864 | 43259 |
| CTCN_612 | 29201 | TTCN_4367 | 43260 |
| CTCN_613 | 29202 | CTCN_5488 | 43261 |
| CTCN_614 | 29203 | GTCN_2865 | 43262 |
| GTCN_360 | 29204 | GTCN_2866 | 43263 |
| ATCN_326 | 29205 | CTCN_5489 | 43264 |
| ATCN_327 | 29206 | CTCN_5490 | 43265 |
| CTCN_615 | 29207 | GTCN_2867 | 43266 |
| GTCN_361 | 29208 | CTCN_5491 | 43267 |
| CTCN_616 | 29209 | TTCN_4368 | 43268 |
| TTCN_448 | 29210 | CTCN_5492 | 43269 |
| CTCN_617 | 29211 | TTCN_4369 | 43270 |
| TTCN_449 | 29212 | CTCN_5493 | 43271 |
| TTCN_450 | 29213 | GTCN_2868 | 43272 |

| | | | |
|---|---|---|---|
| CTCN_618 | 29214 | CTCN_5494 | 43273 |
| CTCN_619 | 29215 | ATCN_3085 | 43274 |
| TTCN_451 | 29216 | CTCN_5495 | 43275 |
| TTCN_452 | 29217 | CTCN_5496 | 43276 |
| ATCN_328 | 29218 | TTCN_4370 | 43277 |
| TTCN_453 | 29219 | CTCN_5497 | 43278 |
| TTCN_454 | 29220 | GTCN_2869 | 43279 |
| CTCN_620 | 29221 | CTCN_5498 | 43280 |
| GTCN_362 | 29222 | TTCN_4371 | 43281 |
| CTCN_621 | 29223 | CTCN_5499 | 43282 |
| TTCN_455 | 29224 | GTCN_2870 | 43283 |
| CTCN_622 | 29225 | GTCN_2871 | 43284 |
| TTCN_456 | 29226 | CTCN_5500 | 43285 |
| GTCN_363 | 29227 | TTCN_4372 | 43286 |
| ATCN_329 | 29228 | CTCN_5501 | 43287 |
| ATCN_330 | 29229 | ATCN_3086 | 43288 |
| ATCN_331 | 29230 | ATCN_3087 | 43289 |
| TTCN_457 | 29231 | TTCN_4373 | 43290 |
| CTCN_623 | 29232 | CTCN_5502 | 43291 |
| TTCN_458 | 29233 | CTCN_5503 | 43292 |
| GTCN_364 | 29234 | TTCN_4374 | 43293 |
| CTCN_624 | 29235 | ATCN_3088 | 43294 |
| GTCN_365 | 29236 | CTCN_5504 | 43295 |
| CTCN_625 | 29237 | ATCN_3089 | 43296 |
| CTCN_626 | 29238 | GTCN_2872 | 43297 |
| CTCN_627 | 29239 | ATCN_3090 | 43298 |
| CTCN_628 | 29240 | ATCN_3091 | 43299 |
| GTCN_366 | 29241 | ATCN_3092 | 43300 |
| TTCN_459 | 29242 | ATCN_3093 | 43301 |
| GTCN_367 | 29243 | GTCN_2873 | 43302 |
| TTCN_460 | 29244 | GTCN_2874 | 43303 |
| TTCN_461 | 29245 | TTCN_4375 | 43304 |
| GTCN_368 | 29246 | TTCN_4376 | 43305 |
| CTCN_629 | 29247 | TTCN_4377 | 43306 |
| TTCN_462 | 29248 | CTCN_5505 | 43307 |
| TTCN_463 | 29249 | TTCN_4378 | 43308 |
| TTCN_464 | 29250 | TTCN_4379 | 43309 |
| TTCN_465 | 29251 | TTCN_4380 | 43310 |
| CTCN_630 | 29252 | CTCN_5506 | 43311 |
| ATCN_332 | 29253 | TTCN_4381 | 43312 |
| ATCN_333 | 29254 | CTCN_5507 | 43313 |
| TTCN_466 | 29255 | CTCN_5508 | 43314 |
| CTCN_631 | 29256 | CTCN_5509 | 43315 |

FIG. 37 (continued)

| | | | |
|---|---|---|---|
| TTCN_467 | 29257 | CTCN_5510 | 43316 |
| ATCN_334 | 29258 | TTCN_4382 | 43317 |
| CTCN_632 | 29259 | TTCN_4383 | 43318 |
| CTCN_633 | 29260 | TTCN_4384 | 43319 |
| CTCN_634 | 29261 | CTCN_5511 | 43320 |
| TTCN_468 | 29262 | TTCN_4385 | 43321 |
| TTCN_469 | 29263 | TTCN_4386 | 43322 |
| GTCN_369 | 29264 | TTCN_4387 | 43323 |
| TTCN_470 | 29265 | CTCN_5512 | 43324 |
| GTCN_370 | 29266 | TTCN_4388 | 43325 |
| TTCN_471 | 29267 | TTCN_4389 | 43326 |
| GTCN_371 | 29268 | CTCN_5513 | 43327 |
| CTCN_635 | 29269 | TTCN_4390 | 43328 |
| ATCN_335 | 29270 | GTCN_2875 | 43329 |
| ATCN_336 | 29271 | ATCN_3094 | 43330 |
| ATCN_337 | 29272 | CTCN_5514 | 43331 |
| TTCN_472 | 29273 | CTCN_5515 | 43332 |
| CTCN_636 | 29274 | CTCN_5516 | 43333 |
| TTCN_473 | 29275 | CTCN_5517 | 43334 |
| TTCN_474 | 29276 | CTCN_5518 | 43335 |
| TTCN_475 | 29277 | TTCN_4391 | 43336 |
| ATCN_338 | 29278 | GTCN_2876 | 43337 |
| GTCN_372 | 29279 | TTCN_4392 | 43338 |
| TTCN_476 | 29280 | CTCN_5519 | 43339 |
| GTCN_373 | 29281 | CTCN_5520 | 43340 |
| TTCN_477 | 29282 | TTCN_4393 | 43341 |
| TTCN_478 | 29283 | TTCN_4394 | 43342 |
| ATCN_339 | 29284 | CTCN_5521 | 43343 |
| TTCN_479 | 29285 | CTCN_5522 | 43344 |
| GTCN_374 | 29286 | GTCN_2877 | 43345 |
| TTCN_480 | 29287 | ATCN_3095 | 43346 |
| GTCN_375 | 29288 | CTCN_5523 | 43347 |
| TTCN_481 | 29289 | GTCN_2878 | 43348 |
| GTCN_376 | 29290 | ATCN_3096 | 43349 |
| CTCN_637 | 29291 | ATCN_3097 | 43350 |
| CTCN_638 | 29292 | TTCN_4395 | 43351 |
| TTCN_482 | 29293 | CTCN_5524 | 43352 |
| ATCN_340 | 29294 | TTCN_4396 | 43353 |
| CTCN_639 | 29295 | TTCN_4397 | 43354 |
| ATCN_341 | 29296 | TTCN_4398 | 43355 |
| CTCN_640 | 29297 | CTCN_5525 | 43356 |
| ATCN_342 | 29298 | TTCN_4399 | 43357 |
| ATCN_343 | 29299 | ATCN_3098 | 43358 |

| | | | |
|---|---|---|---|
| CTCN_641 | 29300 | TTCN_4400 | 43359 |
| CTCN_642 | 29301 | TTCN_4401 | 43360 |
| TTCN_483 | 29302 | ATCN_3099 | 43361 |
| CTCN_643 | 29303 | CTCN_5526 | 43362 |
| GTCN_377 | 29304 | CTCN_5527 | 43363 |
| GTCN_378 | 29305 | TTCN_4402 | 43364 |
| CTCN_644 | 29306 | CTCN_5528 | 43365 |
| CTCN_645 | 29307 | TTCN_4403 | 43366 |
| GTCN_379 | 29308 | TTCN_4404 | 43367 |
| GTCN_380 | 29309 | GTCN_2879 | 43368 |
| ATCN_344 | 29310 | CTCN_5529 | 43369 |
| CTCN_646 | 29311 | GTCN_2880 | 43370 |
| CTCN_647 | 29312 | TTCN_4405 | 43371 |
| CTCN_648 | 29313 | TTCN_4406 | 43372 |
| TTCN_484 | 29314 | ATCN_3100 | 43373 |
| ATCN_345 | 29315 | CTCN_5530 | 43374 |
| TTCN_485 | 29316 | TTCN_4407 | 43375 |
| CTCN_649 | 29317 | CTCN_5531 | 43376 |
| CTCN_650 | 29318 | CTCN_5532 | 43377 |
| CTCN_651 | 29319 | GTCN_2881 | 43378 |
| CTCN_652 | 29320 | CTCN_5533 | 43379 |
| CTCN_653 | 29321 | GTCN_2882 | 43380 |
| CTCN_654 | 29322 | ATCN_3101 | 43381 |
| CTCN_655 | 29323 | CTCN_5534 | 43382 |
| GTCN_381 | 29324 | GTCN_2883 | 43383 |
| CTCN_656 | 29325 | CTCN_5535 | 43384 |
| ATCN_346 | 29326 | GTCN_2884 | 43385 |
| CTCN_657 | 29327 | TTCN_4408 | 43386 |
| TTCN_486 | 29328 | CTCN_5536 | 43387 |
| GTCN_382 | 29329 | GTCN_2885 | 43388 |
| CTCN_658 | 29330 | TTCN_4409 | 43389 |
| TTCN_487 | 29331 | GTCN_2886 | 43390 |
| TTCN_488 | 29332 | GTCN_2887 | 43391 |
| ATCN_347 | 29333 | TTCN_4410 | 43392 |
| TTCN_489 | 29334 | CTCN_5537 | 43393 |
| GTCN_383 | 29335 | CTCN_5538 | 43394 |
| GTCN_384 | 29336 | GTCN_2888 | 43395 |
| CTCN_659 | 29337 | CTCN_5539 | 43396 |
| GTCN_385 | 29338 | CTCN_5540 | 43397 |
| GTCN_386 | 29339 | CTCN_5541 | 43398 |
| ATCN_348 | 29340 | CTCN_5542 | 43399 |
| TTCN_490 | 29341 | CTCN_5543 | 43400 |
| TTCN_491 | 29342 | GTCN_2889 | 43401 |

FIG. 37 (continued)

| | | | |
|---|---|---|---|
| CTCN_660 | 29343 | GTCN_2890 | 43402 |
| CTCN_661 | 29344 | GTCN_2891 | 43403 |
| CTCN_662 | 29345 | CTCN_5544 | 43404 |
| CTCN_663 | 29346 | ATCN_3102 | 43405 |
| CTCN_664 | 29347 | GTCN_2892 | 43406 |
| CTCN_665 | 29348 | TTCN_4411 | 43407 |
| ATCN_349 | 29349 | TTCN_4412 | 43408 |
| TTCN_492 | 29350 | ATCN_3103 | 43409 |
| TTCN_493 | 29351 | GTCN_2893 | 43410 |
| CTCN_666 | 29352 | ATCN_3104 | 43411 |
| TTCN_494 | 29353 | ATCN_3105 | 43412 |
| TTCN_495 | 29354 | CTCN_5545 | 43413 |
| ATCN_350 | 29355 | CTCN_5546 | 43414 |
| CTCN_667 | 29356 | ATCN_3106 | 43415 |
| CTCN_668 | 29357 | GTCN_2894 | 43416 |
| ATCN_351 | 29358 | GTCN_2895 | 43417 |
| CTCN_669 | 29359 | TTCN_4413 | 43418 |
| CTCN_670 | 29360 | TTCN_4414 | 43419 |
| CTCN_671 | 29361 | GTCN_2896 | 43420 |
| CTCN_672 | 29362 | CTCN_5547 | 43421 |
| TTCN_496 | 29363 | GTCN_2897 | 43422 |
| CTCN_673 | 29364 | TTCN_4415 | 43423 |
| TTCN_497 | 29365 | ATCN_3107 | 43424 |
| GTCN_387 | 29366 | ATCN_3108 | 43425 |
| CTCN_674 | 29367 | CTCN_5548 | 43426 |
| GTCN_388 | 29368 | GTCN_2898 | 43427 |
| CTCN_675 | 29369 | TTCN_4416 | 43428 |
| CTCN_676 | 29370 | CTCN_5549 | 43429 |
| CTCN_677 | 29371 | TTCN_4417 | 43430 |
| ATCN_352 | 29372 | CTCN_5550 | 43431 |
| ATCN_353 | 29373 | ATCN_3109 | 43432 |
| CTCN_678 | 29374 | TTCN_4418 | 43433 |
| CTCN_679 | 29375 | TTCN_4419 | 43434 |
| ATCN_354 | 29376 | ATCN_3110 | 43435 |
| CTCN_680 | 29377 | TTCN_4420 | 43436 |
| ATCN_355 | 29378 | ATCN_3111 | 43437 |
| ATCN_356 | 29379 | GTCN_2899 | 43438 |
| CTCN_681 | 29380 | ATCN_3112 | 43439 |
| GTCN_389 | 29381 | ATCN_3113 | 43440 |
| CTCN_682 | 29382 | CTCN_5551 | 43441 |
| CTCN_683 | 29383 | CTCN_5552 | 43442 |
| ATCN_357 | 29384 | ATCN_3114 | 43443 |
| ATCN_358 | 29385 | CTCN_5553 | 43444 |

| | | | |
|---|---|---|---|
| GTCN_390 | 29386 | GTCN_2900 | 43445 |
| CTCN_684 | 29387 | GTCN_2901 | 43446 |
| ATCN_359 | 29388 | CTCN_5554 | 43447 |
| GTCN_391 | 29389 | TTCN_4421 | 43448 |
| GTCN_392 | 29390 | CTCN_5555 | 43449 |
| CTCN_685 | 29391 | GTCN_2902 | 43450 |
| CTCN_686 | 29392 | CTCN_5556 | 43451 |
| CTCN_687 | 29393 | TTCN_4422 | 43452 |
| GTCN_393 | 29394 | CTCN_5557 | 43453 |
| CTCN_688 | 29395 | CTCN_5558 | 43454 |
| GTCN_394 | 29396 | CTCN_5559 | 43455 |
| GTCN_395 | 29397 | TTCN_4423 | 43456 |
| CTCN_689 | 29398 | TTCN_4424 | 43457 |
| CTCN_690 | 29399 | TTCN_4425 | 43458 |
| GTCN_396 | 29400 | GTCN_2903 | 43459 |
| TTCN_498 | 29401 | TTCN_4426 | 43460 |
| GTCN_397 | 29402 | ATCN_3115 | 43461 |
| GTCN_398 | 29403 | CTCN_5560 | 43462 |
| TTCN_499 | 29404 | CTCN_5561 | 43463 |
| GTCN_399 | 29405 | TTCN_4427 | 43464 |
| GTCN_400 | 29406 | GTCN_2904 | 43465 |
| CTCN_691 | 29407 | TTCN_4428 | 43466 |
| ATCN_360 | 29408 | GTCN_2905 | 43467 |
| ATCN_361 | 29409 | CTCN_5562 | 43468 |
| CTCN_692 | 29410 | CTCN_5563 | 43469 |
| CTCN_693 | 29411 | CTCN_5564 | 43470 |
| CTCN_694 | 29412 | TTCN_4429 | 43471 |
| ATCN_362 | 29413 | CTCN_5565 | 43472 |
| ATCN_363 | 29414 | TTCN_4430 | 43473 |
| CTCN_695 | 29415 | CTCN_5566 | 43474 |
| CTCN_696 | 29416 | CTCN_5567 | 43475 |
| GTCN_401 | 29417 | CTCN_5568 | 43476 |
| TTCN_500 | 29418 | ATCN_3116 | 43477 |
| GTCN_402 | 29419 | TTCN_4431 | 43478 |
| CTCN_697 | 29420 | TTCN_4432 | 43479 |
| GTCN_403 | 29421 | CTCN_5569 | 43480 |
| CTCN_698 | 29422 | CTCN_5570 | 43481 |
| TTCN_501 | 29423 | TTCN_4433 | 43482 |
| CTCN_699 | 29424 | CTCN_5571 | 43483 |
| GTCN_404 | 29425 | ATCN_3117 | 43484 |
| CTCN_700 | 29426 | TTCN_4434 | 43485 |
| ATCN_364 | 29427 | GTCN_2906 | 43486 |
| ATCN_365 | 29428 | TTCN_4435 | 43487 |

FIG. 37 (continued)

| | | | |
|---|---|---|---|
| CTCN_701 | 29429 | TTCN_4436 | 43488 |
| CTCN_702 | 29430 | CTCN_5572 | 43489 |
| TTCN_502 | 29431 | GTCN_2907 | 43490 |
| CTCN_703 | 29432 | TTCN_4437 | 43491 |
| TTCN_503 | 29433 | CTCN_5573 | 43492 |
| TTCN_504 | 29434 | TTCN_4438 | 43493 |
| CTCN_704 | 29435 | GTCN_2908 | 43494 |
| CTCN_705 | 29436 | CTCN_5574 | 43495 |
| CTCN_706 | 29437 | GTCN_2909 | 43496 |
| CTCN_707 | 29438 | GTCN_2910 | 43497 |
| GTCN_405 | 29439 | CTCN_5575 | 43498 |
| GTCN_406 | 29440 | CTCN_5576 | 43499 |
| CTCN_708 | 29441 | GTCN_2911 | 43500 |
| GTCN_407 | 29442 | CTCN_5577 | 43501 |
| TTCN_505 | 29443 | TTCN_4439 | 43502 |
| ATCN_366 | 29444 | CTCN_5578 | 43503 |
| GTCN_408 | 29445 | ATCN_3118 | 43504 |
| CTCN_709 | 29446 | TTCN_4440 | 43505 |
| ATCN_367 | 29447 | CTCN_5579 | 43506 |
| GTCN_409 | 29448 | TTCN_4441 | 43507 |
| GTCN_410 | 29449 | ATCN_3119 | 43508 |
| TTCN_506 | 29450 | GTCN_2912 | 43509 |
| CTCN_710 | 29451 | TTCN_4442 | 43510 |
| TTCN_507 | 29452 | CTCN_5580 | 43511 |
| CTCN_711 | 29453 | ATCN_3120 | 43512 |
| CTCN_712 | 29454 | CTCN_5581 | 43513 |
| TTCN_508 | 29455 | CTCN_5582 | 43514 |
| CTCN_713 | 29456 | ATCN_3121 | 43515 |
| TTCN_509 | 29457 | ATCN_3122 | 43516 |
| CTCN_714 | 29458 | ATCN_3123 | 43517 |
| GTCN_411 | 29459 | CTCN_5583 | 43518 |
| CTCN_715 | 29460 | ATCN_3124 | 43519 |
| TTCN_510 | 29461 | CTCN_5584 | 43520 |
| ATCN_368 | 29462 | CTCN_5585 | 43521 |
| CTCN_716 | 29463 | ATCN_3125 | 43522 |
| CTCN_717 | 29464 | TTCN_4443 | 43523 |
| ATCN_369 | 29465 | TTCN_4444 | 43524 |
| ATCN_370 | 29466 | ATCN_3126 | 43525 |
| ATCN_371 | 29467 | TTCN_4445 | 43526 |
| CTCN_718 | 29468 | TTCN_4446 | 43527 |
| TTCN_511 | 29469 | CTCN_5586 | 43528 |
| CTCN_719 | 29470 | TTCN_4447 | 43529 |
| CTCN_720 | 29471 | CTCN_5587 | 43530 |

| | | | |
|---|---|---|---|
| TTCN_512 | 29472 | GTCN_2913 | 43531 |
| GTCN_412 | 29473 | ATCN_3127 | 43532 |
| TTCN_513 | 29474 | TTCN_4448 | 43533 |
| GTCN_413 | 29475 | CTCN_5588 | 43534 |
| CTCN_721 | 29476 | GTCN_2914 | 43535 |
| CTCN_722 | 29477 | CTCN_5589 | 43536 |
| GTCN_414 | 29478 | CTCN_5590 | 43537 |
| CTCN_723 | 29479 | CTCN_5591 | 43538 |
| ATCN_372 | 29480 | CTCN_5592 | 43539 |
| ATCN_373 | 29481 | TTCN_4449 | 43540 |
| TTCN_514 | 29482 | TTCN_4450 | 43541 |
| TTCN_515 | 29483 | GTCN_2915 | 43542 |
| GTCN_415 | 29484 | CTCN_5593 | 43543 |
| ATCN_374 | 29485 | TTCN_4451 | 43544 |
| TTCN_516 | 29486 | CTCN_5594 | 43545 |
| CTCN_724 | 29487 | CTCN_5595 | 43546 |
| ATCN_375 | 29488 | TTCN_4452 | 43547 |
| GTCN_416 | 29489 | ATCN_3128 | 43548 |
| CTCN_725 | 29490 | CTCN_5596 | 43549 |
| CTCN_726 | 29491 | ATCN_3129 | 43550 |
| CTCN_727 | 29492 | TTCN_4453 | 43551 |
| GTCN_417 | 29493 | ATCN_3130 | 43552 |
| TTCN_517 | 29494 | GTCN_2916 | 43553 |
| ATCN_376 | 29495 | CTCN_5597 | 43554 |
| ATCN_377 | 29496 | GTCN_2917 | 43555 |
| CTCN_728 | 29497 | TTCN_4454 | 43556 |
| CTCN_729 | 29498 | ATCN_3131 | 43557 |
| CTCN_730 | 29499 | TTCN_4455 | 43558 |
| TTCN_518 | 29500 | GTCN_2918 | 43559 |
| ATCN_378 | 29501 | CTCN_5598 | 43560 |
| TTCN_519 | 29502 | TTCN_4456 | 43561 |
| CTCN_731 | 29503 | CTCN_5599 | 43562 |
| CTCN_732 | 29504 | TTCN_4457 | 43563 |
| CTCN_733 | 29505 | CTCN_5600 | 43564 |
| CTCN_734 | 29506 | GTCN_2919 | 43565 |
| ATCN_379 | 29507 | GTCN_2920 | 43566 |
| ATCN_380 | 29508 | TTCN_4458 | 43567 |
| GTCN_418 | 29509 | TTCN_4459 | 43568 |
| GTCN_419 | 29510 | CTCN_5601 | 43569 |
| CTCN_735 | 29511 | ATCN_3132 | 43570 |
| CTCN_736 | 29512 | CTCN_5602 | 43571 |
| GTCN_420 | 29513 | CTCN_5603 | 43572 |
| CTCN_737 | 29514 | GTCN_2921 | 43573 |

FIG. 37 (continued)

| | | | |
|---|---|---|---|
| ATCN_381 | 29515 | ATCN_3133 | 43574 |
| TTCN_520 | 29516 | ATCN_3134 | 43575 |
| CTCN_738 | 29517 | ATCN_3135 | 43576 |
| ATCN_382 | 29518 | CTCN_5604 | 43577 |
| ATCN_383 | 29519 | GTCN_2922 | 43578 |
| CTCN_739 | 29520 | TTCN_4460 | 43579 |
| CTCN_740 | 29521 | TTCN_4461 | 43580 |
| GTCN_421 | 29522 | CTCN_5605 | 43581 |
| TTCN_521 | 29523 | CTCN_5606 | 43582 |
| TTCN_522 | 29524 | TTCN_4462 | 43583 |
| ATCN_384 | 29525 | CTCN_5607 | 43584 |
| TTCN_523 | 29526 | TTCN_4463 | 43585 |
| TTCN_524 | 29527 | CTCN_5608 | 43586 |
| CTCN_741 | 29528 | CTCN_5609 | 43587 |
| TTCN_525 | 29529 | ATCN_3136 | 43588 |
| TTCN_526 | 29530 | CTCN_5610 | 43589 |
| TTCN_527 | 29531 | CTCN_5611 | 43590 |
| GTCN_422 | 29532 | CTCN_5612 | 43591 |
| TTCN_528 | 29533 | TTCN_4464 | 43592 |
| TTCN_529 | 29534 | TTCN_4465 | 43593 |
| ATCN_385 | 29535 | TTCN_4466 | 43594 |
| TTCN_530 | 29536 | CTCN_5613 | 43595 |
| TTCN_531 | 29537 | CTCN_5614 | 43596 |
| ATCN_386 | 29538 | TTCN_4467 | 43597 |
| CTCN_742 | 29539 | GTCN_2923 | 43598 |
| GTCN_423 | 29540 | GTCN_2924 | 43599 |
| TTCN_532 | 29541 | CTCN_5615 | 43600 |
| TTCN_533 | 29542 | CTCN_5616 | 43601 |
| TTCN_534 | 29543 | GTCN_2925 | 43602 |
| CTCN_743 | 29544 | CTCN_5617 | 43603 |
| GTCN_424 | 29545 | CTCN_5618 | 43604 |
| GTCN_425 | 29546 | ATCN_3137 | 43605 |
| CTCN_744 | 29547 | TTCN_4468 | 43606 |
| CTCN_745 | 29548 | TTCN_4469 | 43607 |
| CTCN_746 | 29549 | GTCN_2926 | 43608 |
| ATCN_387 | 29550 | TTCN_4470 | 43609 |
| CTCN_747 | 29551 | ATCN_3138 | 43610 |
| TTCN_535 | 29552 | TTCN_4471 | 43611 |
| CTCN_748 | 29553 | TTCN_4472 | 43612 |
| ATCN_388 | 29554 | TTCN_4473 | 43613 |
| CTCN_749 | 29555 | TTCN_4474 | 43614 |
| ATCN_389 | 29556 | TTCN_4475 | 43615 |
| GTCN_426 | 29557 | TTCN_4476 | 43616 |

| | | | |
|---|---|---|---|
| CTCN_750 | 29558 | TTCN_4477 | 43617 |
| TTCN_536 | 29559 | ATCN_3139 | 43618 |
| CTCN_751 | 29560 | CTCN_5619 | 43619 |
| CTCN_752 | 29561 | ATCN_3140 | 43620 |
| CTCN_753 | 29562 | GTCN_2927 | 43621 |
| ATCN_390 | 29563 | TTCN_4478 | 43622 |
| TTCN_537 | 29564 | CTCN_5620 | 43623 |
| CTCN_754 | 29565 | TTCN_4479 | 43624 |
| ATCN_391 | 29566 | GTCN_2928 | 43625 |
| TTCN_538 | 29567 | CTCN_5621 | 43626 |
| ATCN_392 | 29568 | GTCN_2929 | 43627 |
| CTCN_755 | 29569 | ATCN_3141 | 43628 |
| ATCN_393 | 29570 | ATCN_3142 | 43629 |
| ATCN_394 | 29571 | ATCN_3143 | 43630 |
| ATCN_395 | 29572 | ATCN_3144 | 43631 |
| ATCN_396 | 29573 | TTCN_4480 | 43632 |
| CTCN_756 | 29574 | CTCN_5622 | 43633 |
| GTCN_427 | 29575 | GTCN_2930 | 43634 |
| ATCN_397 | 29576 | GTCN_2931 | 43635 |
| TTCN_539 | 29577 | TTCN_4481 | 43636 |
| GTCN_428 | 29578 | CTCN_5623 | 43637 |
| ATCN_398 | 29579 | CTCN_5624 | 43638 |
| ATCN_399 | 29580 | GTCN_2932 | 43639 |
| TTCN_540 | 29581 | CTCN_5625 | 43640 |
| TTCN_541 | 29582 | ATCN_3145 | 43641 |
| ATCN_400 | 29583 | ATCN_3146 | 43642 |
| ATCN_401 | 29584 | CTCN_5626 | 43643 |
| ATCN_402 | 29585 | ATCN_3147 | 43644 |
| CTCN_757 | 29586 | TTCN_4482 | 43645 |
| TTCN_542 | 29587 | ATCN_3148 | 43646 |
| ATCN_403 | 29588 | TTCN_4483 | 43647 |
| TTCN_543 | 29589 | TTCN_4484 | 43648 |
| TTCN_544 | 29590 | CTCN_5627 | 43649 |
| TTCN_545 | 29591 | CTCN_5628 | 43650 |
| TTCN_546 | 29592 | TTCN_4485 | 43651 |
| CTCN_758 | 29593 | CTCN_5629 | 43652 |
| CTCN_759 | 29594 | GTCN_2933 | 43653 |
| GTCN_429 | 29595 | TTCN_4486 | 43654 |
| TTCN_547 | 29596 | TTCN_4487 | 43655 |
| TTCN_548 | 29597 | CTCN_5630 | 43656 |
| GTCN_430 | 29598 | ATCN_3149 | 43657 |
| TTCN_549 | 29599 | TTCN_4488 | 43658 |
| CTCN_760 | 29600 | CTCN_5631 | 43659 |

FIG. 37 (continued)

| | | | | | | | |
|---|---|---|---|---|---|---|---|
| CTCN_761 | 29601 | CTCN_5632 | 43660 | ATCN_412 | 29644 | TTCN_4500 | 43703 |
| TTCN_550 | 29602 | ATCN_3150 | 43661 | ATCN_413 | 29645 | CTCN_5651 | 43704 |
| ATCN_404 | 29603 | CTCN_5633 | 43662 | CTCN_781 | 29646 | GTCN_2942 | 43705 |
| ATCN_405 | 29604 | GTCN_2934 | 43663 | TTCN_558 | 29647 | TTCN_4501 | 43706 |
| CTCN_762 | 29605 | CTCN_5634 | 43664 | TTCN_559 | 29648 | CTCN_5652 | 43707 |
| GTCN_431 | 29606 | GTCN_2935 | 43665 | TTCN_560 | 29649 | ATCN_3155 | 43708 |
| GTCN_432 | 29607 | ATCN_3151 | 43666 | ATCN_414 | 29650 | ATCN_3156 | 43709 |
| CTCN_763 | 29608 | CTCN_5635 | 43667 | CTCN_782 | 29651 | TTCN_4502 | 43710 |
| GTCN_433 | 29609 | TTCN_4489 | 43668 | TTCN_561 | 29652 | ATCN_3157 | 43711 |
| CTCN_764 | 29610 | CTCN_5636 | 43669 | CTCN_783 | 29653 | CTCN_5653 | 43712 |
| ATCN_406 | 29611 | CTCN_5637 | 43670 | GTCN_438 | 29654 | CTCN_5654 | 43713 |
| ATCN_407 | 29612 | CTCN_5638 | 43671 | CTCN_784 | 29655 | ATCN_3158 | 43714 |
| CTCN_765 | 29613 | TTCN_4490 | 43672 | TTCN_562 | 29656 | ATCN_3159 | 43715 |
| TTCN_551 | 29614 | GTCN_2936 | 43673 | TTCN_563 | 29657 | CTCN_5655 | 43716 |
| CTCN_766 | 29615 | CTCN_5639 | 43674 | TTCN_564 | 29658 | CTCN_5656 | 43717 |
| CTCN_767 | 29616 | GTCN_2937 | 43675 | ATCN_415 | 29659 | CTCN_5657 | 43718 |
| TTCN_552 | 29617 | TTCN_4491 | 43676 | ATCN_416 | 29660 | TTCN_4503 | 43719 |
| ATCN_408 | 29618 | ATCN_3152 | 43677 | CTCN_785 | 29661 | CTCN_5658 | 43720 |
| TTCN_553 | 29619 | GTCN_2938 | 43678 | TTCN_565 | 29662 | GTCN_2943 | 43721 |
| CTCN_768 | 29620 | ATCN_3153 | 43679 | ATCN_417 | 29663 | CTCN_5659 | 43722 |
| CTCN_769 | 29621 | CTCN_5640 | 43680 | TTCN_566 | 29664 | ATCN_3160 | 43723 |
| CTCN_770 | 29622 | TTCN_4492 | 43681 | ATCN_418 | 29665 | CTCN_5660 | 43724 |
| CTCN_771 | 29623 | TTCN_4493 | 43682 | ATCN_419 | 29666 | ATCN_3161 | 43725 |
| TTCN_554 | 29624 | TTCN_4494 | 43683 | TTCN_567 | 29667 | TTCN_4504 | 43726 |
| CTCN_772 | 29625 | CTCN_5641 | 43684 | ATCN_420 | 29668 | TTCN_4505 | 43727 |
| GTCN_434 | 29626 | TTCN_4495 | 43685 | TTCN_568 | 29669 | TTCN_4506 | 43728 |
| TTCN_555 | 29627 | GTCN_2939 | 43686 | CTCN_786 | 29670 | CTCN_5661 | 43729 |
| GTCN_435 | 29628 | CTCN_5642 | 43687 | GTCN_439 | 29671 | GTCN_2944 | 43730 |
| CTCN_773 | 29629 | CTCN_5643 | 43688 | TTCN_569 | 29672 | CTCN_5662 | 43731 |
| CTCN_774 | 29630 | CTCN_5644 | 43689 | TTCN_570 | 29673 | GTCN_2945 | 43732 |
| CTCN_775 | 29631 | GTCN_2940 | 43690 | CTCN_787 | 29674 | GTCN_2946 | 43733 |
| ATCN_409 | 29632 | TTCN_4496 | 43691 | TTCN_571 | 29675 | CTCN_5663 | 43734 |
| ATCN_410 | 29633 | TTCN_4497 | 43692 | GTCN_440 | 29676 | CTCN_5664 | 43735 |
| CTCN_776 | 29634 | CTCN_5645 | 43693 | GTCN_441 | 29677 | GTCN_2947 | 43736 |
| CTCN_777 | 29635 | CTCN_5646 | 43694 | CTCN_788 | 29678 | TTCN_4507 | 43737 |
| ATCN_411 | 29636 | TTCN_4498 | 43695 | CTCN_789 | 29679 | TTCN_4508 | 43738 |
| CTCN_778 | 29637 | CTCN_5647 | 43696 | GTCN_442 | 29680 | CTCN_5665 | 43739 |
| GTCN_436 | 29638 | CTCN_5648 | 43697 | CTCN_790 | 29681 | GTCN_2948 | 43740 |
| CTCN_779 | 29639 | CTCN_5649 | 43698 | TTCN_572 | 29682 | TTCN_4509 | 43741 |
| GTCN_437 | 29640 | CTCN_5650 | 43699 | ATCN_421 | 29683 | TTCN_4510 | 43742 |
| TTCN_556 | 29641 | TTCN_4499 | 43700 | TTCN_573 | 29684 | TTCN_4511 | 43743 |
| CTCN_780 | 29642 | GTCN_2941 | 43701 | ATCN_422 | 29685 | TTCN_4512 | 43744 |
| TTCN_557 | 29643 | ATCN_3154 | 43702 | TTCN_574 | 29686 | ATCN_3162 | 43745 |

FIG. 37 (continued)

| | | | |
|---|---|---|---|
| TTCN_575 | 29687 | ATCN_3163 | 43746 |
| GTCN_443 | 29688 | TTCN_4513 | 43747 |
| CTCN_791 | 29689 | CTCN_5666 | 43748 |
| CTCN_792 | 29690 | TTCN_4514 | 43749 |
| CTCN_793 | 29691 | GTCN_2949 | 43750 |
| CTCN_794 | 29692 | TTCN_4515 | 43751 |
| TTCN_576 | 29693 | CTCN_5667 | 43752 |
| CTCN_795 | 29694 | GTCN_2950 | 43753 |
| CTCN_796 | 29695 | GTCN_2951 | 43754 |
| CTCN_797 | 29696 | TTCN_4516 | 43755 |
| TTCN_577 | 29697 | TTCN_4517 | 43756 |
| CTCN_798 | 29698 | ATCN_3164 | 43757 |
| GTCN_444 | 29699 | TTCN_4518 | 43758 |
| CTCN_799 | 29700 | TTCN_4519 | 43759 |
| GTCN_445 | 29701 | TTCN_4520 | 43760 |
| CTCN_800 | 29702 | TTCN_4521 | 43761 |
| GTCN_446 | 29703 | GTCN_2952 | 43762 |
| ATCN_423 | 29704 | ATCN_3165 | 43763 |
| CTCN_801 | 29705 | ATCN_3166 | 43764 |
| GTCN_447 | 29706 | CTCN_5668 | 43765 |
| TTCN_578 | 29707 | CTCN_5669 | 43766 |
| CTCN_802 | 29708 | CTCN_5670 | 43767 |
| TTCN_579 | 29709 | TTCN_4522 | 43768 |
| TTCN_580 | 29710 | CTCN_5671 | 43769 |
| TTCN_581 | 29711 | ATCN_3167 | 43770 |
| ATCN_424 | 29712 | CTCN_5672 | 43771 |
| GTCN_448 | 29713 | CTCN_5673 | 43772 |
| ATCN_425 | 29714 | TTCN_4523 | 43773 |
| TTCN_582 | 29715 | TTCN_4524 | 43774 |
| CTCN_803 | 29716 | TTCN_4525 | 43775 |
| TTCN_583 | 29717 | TTCN_4526 | 43776 |
| GTCN_449 | 29718 | ATCN_3168 | 43777 |
| TTCN_584 | 29719 | CTCN_5674 | 43778 |
| GTCN_450 | 29720 | TTCN_4527 | 43779 |
| GTCN_451 | 29721 | CTCN_5675 | 43780 |
| CTCN_804 | 29722 | CTCN_5676 | 43781 |
| CTCN_805 | 29723 | CTCN_5677 | 43782 |
| GTCN_452 | 29724 | GTCN_2953 | 43783 |
| CTCN_806 | 29725 | GTCN_2954 | 43784 |
| TTCN_585 | 29726 | ATCN_3169 | 43785 |
| GTCN_453 | 29727 | GTCN_2955 | 43786 |
| CTCN_807 | 29728 | CTCN_5678 | 43787 |
| GTCN_454 | 29729 | GTCN_2956 | 43788 |

| | | | |
|---|---|---|---|
| ATCN_426 | 29730 | CTCN_5679 | 43789 |
| CTCN_808 | 29731 | CTCN_5680 | 43790 |
| CTCN_809 | 29732 | TTCN_4528 | 43791 |
| TTCN_586 | 29733 | TTCN_4529 | 43792 |
| TTCN_587 | 29734 | CTCN_5681 | 43793 |
| GTCN_455 | 29735 | ATCN_3170 | 43794 |
| TTCN_588 | 29736 | ATCN_3171 | 43795 |
| GTCN_456 | 29737 | ATCN_3172 | 43796 |
| TTCN_589 | 29738 | CTCN_5682 | 43797 |
| CTCN_810 | 29739 | ATCN_3173 | 43798 |
| CTCN_811 | 29740 | GTCN_2957 | 43799 |
| CTCN_812 | 29741 | TTCN_4530 | 43800 |
| TTCN_590 | 29742 | CTCN_5683 | 43801 |
| TTCN_591 | 29743 | TTCN_4531 | 43802 |
| CTCN_813 | 29744 | ATCN_3174 | 43803 |
| GTCN_457 | 29745 | TTCN_4532 | 43804 |
| TTCN_592 | 29746 | CTCN_5684 | 43805 |
| CTCN_814 | 29747 | ATCN_3175 | 43806 |
| GTCN_458 | 29748 | GTCN_2958 | 43807 |
| ATCN_427 | 29749 | TTCN_4533 | 43808 |
| GTCN_459 | 29750 | GTCN_2959 | 43809 |
| GTCN_460 | 29751 | TTCN_4534 | 43810 |
| GTCN_461 | 29752 | GTCN_2960 | 43811 |
| TTCN_593 | 29753 | CTCN_5685 | 43812 |
| CTCN_815 | 29754 | GTCN_2961 | 43813 |
| TTCN_594 | 29755 | CTCN_5686 | 43814 |
| TTCN_595 | 29756 | CTCN_5687 | 43815 |
| TTCN_596 | 29757 | GTCN_2962 | 43816 |
| ATCN_428 | 29758 | CTCN_5688 | 43817 |
| TTCN_597 | 29759 | TTCN_4535 | 43818 |
| GTCN_462 | 29760 | GTCN_2963 | 43819 |
| CTCN_816 | 29761 | TTCN_4536 | 43820 |
| ATCN_429 | 29762 | CTCN_5689 | 43821 |
| CTCN_817 | 29763 | ATCN_3176 | 43822 |
| TTCN_598 | 29764 | CTCN_5690 | 43823 |
| TTCN_599 | 29765 | ATCN_3177 | 43824 |
| GTCN_463 | 29766 | CTCN_5691 | 43825 |
| ATCN_430 | 29767 | TTCN_4537 | 43826 |
| TTCN_600 | 29768 | GTCN_2964 | 43827 |
| TTCN_601 | 29769 | GTCN_2965 | 43828 |
| GTCN_464 | 29770 | CTCN_5692 | 43829 |
| GTCN_465 | 29771 | GTCN_2966 | 43830 |
| TTCN_602 | 29772 | GTCN_2967 | 43831 |

FIG. 37 (continued)

| | | | | | | | |
|---|---|---|---|---|---|---|---|
| CTCN_818 | 29773 | CTCN_5693 | 43832 | TTCN_616 | 29816 | CTCN_5711 | 43875 |
| ATCN_431 | 29774 | CTCN_5694 | 43833 | TTCN_617 | 29817 | GTCN_2983 | 43876 |
| GTCN_466 | 29775 | TTCN_4538 | 43834 | TTCN_618 | 29818 | CTCN_5712 | 43877 |
| TTCN_603 | 29776 | GTCN_2968 | 43835 | CTCN_834 | 29819 | CTCN_5713 | 43878 |
| TTCN_604 | 29777 | CTCN_5695 | 43836 | CTCN_835 | 29820 | TTCN_4545 | 43879 |
| GTCN_467 | 29778 | GTCN_2969 | 43837 | TTCN_619 | 29821 | TTCN_4546 | 43880 |
| CTCN_819 | 29779 | GTCN_2970 | 43838 | ATCN_437 | 29822 | CTCN_5714 | 43881 |
| CTCN_820 | 29780 | GTCN_2971 | 43839 | CTCN_836 | 29823 | TTCN_4547 | 43882 |
| CTCN_821 | 29781 | CTCN_5696 | 43840 | ATCN_438 | 29824 | CTCN_5715 | 43883 |
| GTCN_468 | 29782 | TTCN_4539 | 43841 | ATCN_439 | 29825 | TTCN_4548 | 43884 |
| CTCN_822 | 29783 | CTCN_5697 | 43842 | TTCN_620 | 29826 | ATCN_3181 | 43885 |
| TTCN_605 | 29784 | CTCN_5698 | 43843 | ATCN_440 | 29827 | CTCN_5716 | 43886 |
| GTCN_469 | 29785 | CTCN_5699 | 43844 | CTCN_837 | 29828 | TTCN_4549 | 43887 |
| TTCN_606 | 29786 | GTCN_2972 | 43845 | TTCN_621 | 29829 | GTCN_2984 | 43888 |
| TTCN_607 | 29787 | CTCN_5700 | 43846 | TTCN_622 | 29830 | CTCN_5717 | 43889 |
| CTCN_823 | 29788 | CTCN_5701 | 43847 | ATCN_441 | 29831 | TTCN_4550 | 43890 |
| CTCN_824 | 29789 | TTCN_4540 | 43848 | ATCN_442 | 29832 | TTCN_4551 | 43891 |
| TTCN_608 | 29790 | GTCN_2973 | 43849 | GTCN_474 | 29833 | ATCN_3182 | 43892 |
| CTCN_825 | 29791 | GTCN_2974 | 43850 | CTCN_838 | 29834 | TTCN_4552 | 43893 |
| CTCN_826 | 29792 | GTCN_2975 | 43851 | CTCN_839 | 29835 | CTCN_5718 | 43894 |
| TTCN_609 | 29793 | CTCN_5702 | 43852 | TTCN_623 | 29836 | CTCN_5719 | 43895 |
| ATCN_432 | 29794 | TTCN_4541 | 43853 | ATCN_443 | 29837 | CTCN_5720 | 43896 |
| TTCN_610 | 29795 | GTCN_2976 | 43854 | ATCN_444 | 29838 | CTCN_5721 | 43897 |
| CTCN_827 | 29796 | TTCN_4542 | 43855 | CTCN_840 | 29839 | ATCN_3183 | 43898 |
| CTCN_828 | 29797 | TTCN_4543 | 43856 | TTCN_624 | 29840 | ATCN_3184 | 43899 |
| CTCN_829 | 29798 | CTCN_5703 | 43857 | TTCN_625 | 29841 | TTCN_4553 | 43900 |
| ATCN_433 | 29799 | CTCN_5704 | 43858 | TTCN_626 | 29842 | CTCN_5722 | 43901 |
| ATCN_434 | 29800 | ATCN_3178 | 43859 | GTCN_475 | 29843 | GTCN_2985 | 43902 |
| CTCN_830 | 29801 | ATCN_3179 | 43860 | CTCN_841 | 29844 | TTCN_4554 | 43903 |
| TTCN_611 | 29802 | CTCN_5705 | 43861 | TTCN_627 | 29845 | GTCN_2986 | 43904 |
| GTCN_470 | 29803 | CTCN_5706 | 43862 | TTCN_628 | 29846 | ATCN_3185 | 43905 |
| GTCN_471 | 29804 | GTCN_2977 | 43863 | TTCN_629 | 29847 | ATCN_3186 | 43906 |
| CTCN_831 | 29805 | GTCN_2978 | 43864 | TTCN_630 | 29848 | TTCN_4555 | 43907 |
| CTCN_832 | 29806 | GTCN_2979 | 43865 | GTCN_476 | 29849 | GTCN_2987 | 43908 |
| TTCN_612 | 29807 | GTCN_2980 | 43866 | ATCN_445 | 29850 | CTCN_5723 | 43909 |
| TTCN_613 | 29808 | ATCN_3180 | 43867 | CTCN_842 | 29851 | TTCN_4556 | 43910 |
| CTCN_833 | 29809 | CTCN_5707 | 43868 | GTCN_477 | 29852 | ATCN_3187 | 43911 |
| ATCN_435 | 29810 | GTCN_2981 | 43869 | GTCN_478 | 29853 | GTCN_2988 | 43912 |
| ATCN_436 | 29811 | TTCN_4544 | 43870 | CTCN_843 | 29854 | ATCN_3188 | 43913 |
| GTCN_472 | 29812 | CTCN_5708 | 43871 | ATCN_446 | 29855 | ATCN_3189 | 43914 |
| TTCN_614 | 29813 | CTCN_5709 | 43872 | TTCN_631 | 29856 | ATCN_3190 | 43915 |
| GTCN_473 | 29814 | GTCN_2982 | 43873 | CTCN_844 | 29857 | CTCN_5724 | 43916 |
| TTCN_615 | 29815 | CTCN_5710 | 43874 | TTCN_632 | 29858 | GTCN_2989 | 43917 |

FIG. 37 (continued)

| | | | |
|---|---|---|---|
| GTCN_479 | 29859 | CTCN_5725 | 43918 |
| TTCN_633 | 29860 | CTCN_5726 | 43919 |
| ATCN_447 | 29861 | CTCN_5727 | 43920 |
| GTCN_480 | 29862 | GTCN_2990 | 43921 |
| TTCN_634 | 29863 | CTCN_5728 | 43922 |
| ATCN_448 | 29864 | CTCN_5729 | 43923 |
| ATCN_449 | 29865 | ATCN_3191 | 43924 |
| ATCN_450 | 29866 | CTCN_5730 | 43925 |
| ATCN_451 | 29867 | TTCN_4557 | 43926 |
| TTCN_635 | 29868 | TTCN_4558 | 43927 |
| TTCN_636 | 29869 | GTCN_2991 | 43928 |
| CTCN_845 | 29870 | CTCN_5731 | 43929 |
| TTCN_637 | 29871 | GTCN_2992 | 43930 |
| TTCN_638 | 29872 | CTCN_5732 | 43931 |
| ATCN_452 | 29873 | GTCN_2993 | 43932 |
| GTCN_481 | 29874 | CTCN_5733 | 43933 |
| CTCN_846 | 29875 | TTCN_4559 | 43934 |
| GTCN_482 | 29876 | TTCN_4560 | 43935 |
| CTCN_847 | 29877 | GTCN_2994 | 43936 |
| ATCN_453 | 29878 | CTCN_5734 | 43937 |
| GTCN_483 | 29879 | TTCN_4561 | 43938 |
| CTCN_848 | 29880 | TTCN_4562 | 43939 |
| TTCN_639 | 29881 | TTCN_4563 | 43940 |
| ATCN_454 | 29882 | CTCN_5735 | 43941 |
| CTCN_849 | 29883 | CTCN_5736 | 43942 |
| GTCN_484 | 29884 | GTCN_2995 | 43943 |
| ATCN_455 | 29885 | TTCN_4564 | 43944 |
| CTCN_850 | 29886 | ATCN_3192 | 43945 |
| CTCN_851 | 29887 | GTCN_2996 | 43946 |
| ATCN_456 | 29888 | CTCN_5737 | 43947 |
| ATCN_457 | 29889 | CTCN_5738 | 43948 |
| TTCN_640 | 29890 | TTCN_4565 | 43949 |
| GTCN_485 | 29891 | CTCN_5739 | 43950 |
| CTCN_852 | 29892 | CTCN_5740 | 43951 |
| TTCN_641 | 29893 | TTCN_4566 | 43952 |
| CTCN_853 | 29894 | CTCN_5741 | 43953 |
| CTCN_854 | 29895 | CTCN_5742 | 43954 |
| GTCN_486 | 29896 | ATCN_3193 | 43955 |
| TTCN_642 | 29897 | TTCN_4567 | 43956 |
| TTCN_643 | 29898 | TTCN_4568 | 43957 |
| TTCN_644 | 29899 | CTCN_5743 | 43958 |
| ATCN_458 | 29900 | CTCN_5744 | 43959 |
| TTCN_645 | 29901 | CTCN_5745 | 43960 |

| | | | |
|---|---|---|---|
| TTCN_646 | 29902 | CTCN_5746 | 43961 |
| TTCN_647 | 29903 | ATCN_3194 | 43962 |
| CTCN_855 | 29904 | TTCN_4569 | 43963 |
| CTCN_856 | 29905 | CTCN_5747 | 43964 |
| TTCN_648 | 29906 | CTCN_5748 | 43965 |
| TTCN_649 | 29907 | CTCN_5749 | 43966 |
| ATCN_459 | 29908 | CTCN_5750 | 43967 |
| TTCN_650 | 29909 | CTCN_5751 | 43968 |
| ATCN_460 | 29910 | GTCN_2997 | 43969 |
| ATCN_461 | 29911 | CTCN_5752 | 43970 |
| ATCN_462 | 29912 | CTCN_5753 | 43971 |
| CTCN_857 | 29913 | TTCN_4570 | 43972 |
| GTCN_487 | 29914 | ATCN_3195 | 43973 |
| TTCN_651 | 29915 | GTCN_2998 | 43974 |
| GTCN_488 | 29916 | ATCN_3196 | 43975 |
| TTCN_652 | 29917 | ATCN_3197 | 43976 |
| CTCN_858 | 29918 | ATCN_3198 | 43977 |
| CTCN_859 | 29919 | GTCN_2999 | 43978 |
| CTCN_860 | 29920 | ATCN_3199 | 43979 |
| ATCN_463 | 29921 | ATCN_3200 | 43980 |
| GTCN_489 | 29922 | TTCN_4571 | 43981 |
| ATCN_464 | 29923 | CTCN_5754 | 43982 |
| ATCN_465 | 29924 | TTCN_4572 | 43983 |
| GTCN_490 | 29925 | GTCN_3000 | 43984 |
| CTCN_861 | 29926 | CTCN_5755 | 43985 |
| ATCN_466 | 29927 | GTCN_3001 | 43986 |
| GTCN_491 | 29928 | CTCN_5756 | 43987 |
| CTCN_862 | 29929 | ATCN_3201 | 43988 |
| GTCN_492 | 29930 | GTCN_3002 | 43989 |
| TTCN_653 | 29931 | GTCN_3003 | 43990 |
| CTCN_863 | 29932 | CTCN_5757 | 43991 |
| CTCN_864 | 29933 | CTCN_5758 | 43992 |
| CTCN_865 | 29934 | CTCN_5759 | 43993 |
| TTCN_654 | 29935 | GTCN_3004 | 43994 |
| CTCN_866 | 29936 | ATCN_3202 | 43995 |
| TTCN_655 | 29937 | CTCN_5760 | 43996 |
| CTCN_867 | 29938 | GTCN_3005 | 43997 |
| GTCN_493 | 29939 | CTCN_5761 | 43998 |
| CTCN_868 | 29940 | CTCN_5762 | 43999 |
| TTCN_656 | 29941 | CTCN_5763 | 44000 |
| CTCN_869 | 29942 | GTCN_3006 | 44001 |
| TTCN_657 | 29943 | CTCN_5764 | 44002 |
| TTCN_658 | 29944 | GTCN_3007 | 44003 |

FIG. 37 (continued)

| | | | |
|---|---|---|---|
| CTCN_870 | 29945 | GTCN_3008 | 44004 |
| GTCN_494 | 29946 | CTCN_5765 | 44005 |
| TTCN_659 | 29947 | TTCN_4573 | 44006 |
| CTCN_871 | 29948 | GTCN_3009 | 44007 |
| CTCN_872 | 29949 | CTCN_5766 | 44008 |
| CTCN_873 | 29950 | CTCN_5767 | 44009 |
| CTCN_874 | 29951 | GTCN_3010 | 44010 |
| GTCN_495 | 29952 | ATCN_3203 | 44011 |
| GTCN_496 | 29953 | CTCN_5768 | 44012 |
| ATCN_467 | 29954 | CTCN_5769 | 44013 |
| ATCN_468 | 29955 | TTCN_4574 | 44014 |
| CTCN_875 | 29956 | ATCN_3204 | 44015 |
| GTCN_497 | 29957 | ATCN_3205 | 44016 |
| CTCN_876 | 29958 | GTCN_3011 | 44017 |
| CTCN_877 | 29959 | TTCN_4575 | 44018 |
| TTCN_660 | 29960 | TTCN_4576 | 44019 |
| ATCN_469 | 29961 | TTCN_4577 | 44020 |
| TTCN_661 | 29962 | CTCN_5770 | 44021 |
| CTCN_878 | 29963 | GTCN_3012 | 44022 |
| TTCN_662 | 29964 | GTCN_3013 | 44023 |
| ATCN_470 | 29965 | GTCN_3014 | 44024 |
| TTCN_663 | 29966 | CTCN_5771 | 44025 |
| ATCN_471 | 29967 | ATCN_3206 | 44026 |
| TTCN_664 | 29968 | ATCN_3207 | 44027 |
| GTCN_498 | 29969 | TTCN_4578 | 44028 |
| CTCN_879 | 29970 | CTCN_5772 | 44029 |
| CTCN_880 | 29971 | CTCN_5773 | 44030 |
| CTCN_881 | 29972 | ATCN_3208 | 44031 |
| CTCN_882 | 29973 | CTCN_5774 | 44032 |
| TTCN_665 | 29974 | GTCN_3015 | 44033 |
| TTCN_666 | 29975 | TTCN_4579 | 44034 |
| ATCN_472 | 29976 | CTCN_5775 | 44035 |
| CTCN_883 | 29977 | ATCN_3209 | 44036 |
| ATCN_473 | 29978 | GTCN_3016 | 44037 |
| ATCN_474 | 29979 | GTCN_3017 | 44038 |
| TTCN_667 | 29980 | TTCN_4580 | 44039 |
| ATCN_475 | 29981 | GTCN_3018 | 44040 |
| ATCN_476 | 29982 | CTCN_5776 | 44041 |
| GTCN_499 | 29983 | ATCN_3210 | 44042 |
| TTCN_668 | 29984 | ATCN_3211 | 44043 |
| GTCN_500 | 29985 | ATCN_3212 | 44044 |
| ATCN_477 | 29986 | CTCN_5777 | 44045 |
| TTCN_669 | 29987 | CTCN_5778 | 44046 |

| | | | |
|---|---|---|---|
| ATCN_478 | 29988 | GTCN_3019 | 44047 |
| CTCN_884 | 29989 | CTCN_5779 | 44048 |
| GTCN_501 | 29990 | TTCN_4581 | 44049 |
| GTCN_502 | 29991 | CTCN_5780 | 44050 |
| CTCN_885 | 29992 | CTCN_5781 | 44051 |
| TTCN_670 | 29993 | CTCN_5782 | 44052 |
| TTCN_671 | 29994 | CTCN_5783 | 44053 |
| CTCN_886 | 29995 | CTCN_5784 | 44054 |
| TTCN_672 | 29996 | CTCN_5785 | 44055 |
| CTCN_887 | 29997 | ATCN_3213 | 44056 |
| CTCN_888 | 29998 | ATCN_3214 | 44057 |
| ATCN_479 | 29999 | CTCN_5786 | 44058 |
| ATCN_480 | 30000 | GTCN_3020 | 44059 |
| GTCN_503 | 30001 | GTCN_3021 | 44060 |
| CTCN_889 | 30002 | TTCN_4582 | 44061 |
| GTCN_504 | 30003 | CTCN_5787 | 44062 |
| CTCN_890 | 30004 | CTCN_5788 | 44063 |
| GTCN_505 | 30005 | GTCN_3022 | 44064 |
| ATCN_481 | 30006 | CTCN_5789 | 44065 |
| ATCN_482 | 30007 | CTCN_5790 | 44066 |
| TTCN_673 | 30008 | CTCN_5791 | 44067 |
| GTCN_506 | 30009 | CTCN_5792 | 44068 |
| TTCN_674 | 30010 | CTCN_5793 | 44069 |
| TTCN_675 | 30011 | CTCN_5794 | 44070 |
| TTCN_676 | 30012 | CTCN_5795 | 44071 |
| ATCN_483 | 30013 | CTCN_5796 | 44072 |
| TTCN_677 | 30014 | CTCN_5797 | 44073 |
| CTCN_891 | 30015 | CTCN_5798 | 44074 |
| ATCN_484 | 30016 | ATCN_3215 | 44075 |
| ATCN_485 | 30017 | CTCN_5799 | 44076 |
| ATCN_486 | 30018 | TTCN_4583 | 44077 |
| TTCN_678 | 30019 | CTCN_5800 | 44078 |
| GTCN_507 | 30020 | CTCN_5801 | 44079 |
| TTCN_679 | 30021 | GTCN_3023 | 44080 |
| TTCN_680 | 30022 | CTCN_5802 | 44081 |
| CTCN_892 | 30023 | TTCN_4584 | 44082 |
| TTCN_681 | 30024 | TTCN_4585 | 44083 |
| TTCN_682 | 30025 | GTCN_3024 | 44084 |
| TTCN_683 | 30026 | CTCN_5803 | 44085 |
| TTCN_684 | 30027 | ATCN_3216 | 44086 |
| TTCN_685 | 30028 | ATCN_3217 | 44087 |
| ATCN_487 | 30029 | CTCN_5804 | 44088 |
| TTCN_686 | 30030 | ATCN_3218 | 44089 |

FIG. 37 (continued)

| | | | |
|---|---|---|---|
| ATCN_488 | 30031 | TTCN_4586 | 44090 |
| TTCN_687 | 30032 | TTCN_4587 | 44091 |
| ATCN_489 | 30033 | CTCN_5805 | 44092 |
| GTCN_508 | 30034 | ATCN_3219 | 44093 |
| GTCN_509 | 30035 | TTCN_4588 | 44094 |
| ATCN_490 | 30036 | CTCN_5806 | 44095 |
| CTCN_893 | 30037 | CTCN_5807 | 44096 |
| GTCN_510 | 30038 | GTCN_3025 | 44097 |
| ATCN_491 | 30039 | TTCN_4589 | 44098 |
| TTCN_688 | 30040 | TTCN_4590 | 44099 |
| TTCN_689 | 30041 | GTCN_3026 | 44100 |
| TTCN_690 | 30042 | TTCN_4591 | 44101 |
| TTCN_691 | 30043 | TTCN_4592 | 44102 |
| GTCN_511 | 30044 | CTCN_5808 | 44103 |
| TTCN_692 | 30045 | GTCN_3027 | 44104 |
| TTCN_693 | 30046 | CTCN_5809 | 44105 |
| TTCN_694 | 30047 | TTCN_4593 | 44106 |
| CTCN_894 | 30048 | CTCN_5810 | 44107 |
| CTCN_895 | 30049 | CTCN_5811 | 44108 |
| TTCN_695 | 30050 | GTCN_3028 | 44109 |
| CTCN_896 | 30051 | CTCN_5812 | 44110 |
| ATCN_492 | 30052 | GTCN_3029 | 44111 |
| ATCN_493 | 30053 | GTCN_3030 | 44112 |
| CTCN_897 | 30054 | TTCN_4594 | 44113 |
| TTCN_696 | 30055 | GTCN_3031 | 44114 |
| CTCN_898 | 30056 | TTCN_4595 | 44115 |
| ATCN_494 | 30057 | TTCN_4596 | 44116 |
| CTCN_899 | 30058 | CTCN_5813 | 44117 |
| GTCN_512 | 30059 | ATCN_3220 | 44118 |
| ATCN_495 | 30060 | ATCN_3221 | 44119 |
| ATCN_496 | 30061 | GTCN_3032 | 44120 |
| TTCN_697 | 30062 | TTCN_4597 | 44121 |
| ATCN_497 | 30063 | TTCN_4598 | 44122 |
| ATCN_498 | 30064 | CTCN_5814 | 44123 |
| TTCN_698 | 30065 | CTCN_5815 | 44124 |
| ATCN_499 | 30066 | TTCN_4599 | 44125 |
| CTCN_900 | 30067 | GTCN_3033 | 44126 |
| CTCN_901 | 30068 | TTCN_4600 | 44127 |
| ATCN_500 | 30069 | ATCN_3222 | 44128 |
| ATCN_501 | 30070 | CTCN_5816 | 44129 |
| CTCN_902 | 30071 | TTCN_4601 | 44130 |
| GTCN_513 | 30072 | TTCN_4602 | 44131 |
| ATCN_502 | 30073 | CTCN_5817 | 44132 |

| | | | |
|---|---|---|---|
| TTCN_699 | 30074 | ATCN_3223 | 44133 |
| ATCN_503 | 30075 | TTCN_4603 | 44134 |
| TTCN_700 | 30076 | CTCN_5818 | 44135 |
| CTCN_903 | 30077 | TTCN_4604 | 44136 |
| GTCN_514 | 30078 | ATCN_3224 | 44137 |
| CTCN_904 | 30079 | ATCN_3225 | 44138 |
| TTCN_701 | 30080 | TTCN_4605 | 44139 |
| TTCN_702 | 30081 | ATCN_3226 | 44140 |
| TTCN_703 | 30082 | TTCN_4606 | 44141 |
| TTCN_704 | 30083 | TTCN_4607 | 44142 |
| TTCN_705 | 30084 | ATCN_3227 | 44143 |
| TTCN_706 | 30085 | TTCN_4608 | 44144 |
| GTCN_515 | 30086 | TTCN_4609 | 44145 |
| CTCN_905 | 30087 | TTCN_4610 | 44146 |
| TTCN_707 | 30088 | CTCN_5819 | 44147 |
| CTCN_906 | 30089 | GTCN_3034 | 44148 |
| ATCN_504 | 30090 | CTCN_5820 | 44149 |
| CTCN_907 | 30091 | CTCN_5821 | 44150 |
| TTCN_708 | 30092 | TTCN_4611 | 44151 |
| TTCN_709 | 30093 | CTCN_5822 | 44152 |
| TTCN_710 | 30094 | GTCN_3035 | 44153 |
| TTCN_711 | 30095 | TTCN_4612 | 44154 |
| TTCN_712 | 30096 | TTCN_4613 | 44155 |
| ATCN_505 | 30097 | ATCN_3228 | 44156 |
| TTCN_713 | 30098 | ATCN_3229 | 44157 |
| TTCN_714 | 30099 | CTCN_5823 | 44158 |
| CTCN_908 | 30100 | CTCN_5824 | 44159 |
| ATCN_506 | 30101 | TTCN_4614 | 44160 |
| GTCN_516 | 30102 | TTCN_4615 | 44161 |
| GTCN_517 | 30103 | TTCN_4616 | 44162 |
| TTCN_715 | 30104 | ATCN_3230 | 44163 |
| TTCN_716 | 30105 | CTCN_5825 | 44164 |
| TTCN_717 | 30106 | CTCN_5826 | 44165 |
| CTCN_909 | 30107 | CTCN_5827 | 44166 |
| ATCN_507 | 30108 | ATCN_3231 | 44167 |
| CTCN_910 | 30109 | ATCN_3232 | 44168 |
| TTCN_718 | 30110 | CTCN_5828 | 44169 |
| TTCN_719 | 30111 | ATCN_3233 | 44170 |
| GTCN_518 | 30112 | TTCN_4617 | 44171 |
| CTCN_911 | 30113 | CTCN_5829 | 44172 |
| TTCN_720 | 30114 | ATCN_3234 | 44173 |
| TTCN_721 | 30115 | ATCN_3235 | 44174 |
| TTCN_722 | 30116 | TTCN_4618 | 44175 |

FIG. 37 (continued)

| | | | |
|---|---|---|---|
| TTCN_723 | 30117 | CTCN_5830 | 44176 |
| CTCN_912 | 30118 | TTCN_4619 | 44177 |
| TTCN_724 | 30119 | CTCN_5831 | 44178 |
| CTCN_913 | 30120 | ATCN_3236 | 44179 |
| TTCN_725 | 30121 | ATCN_3237 | 44180 |
| TTCN_726 | 30122 | TTCN_4620 | 44181 |
| TTCN_727 | 30123 | CTCN_5832 | 44182 |
| CTCN_914 | 30124 | GTCN_3036 | 44183 |
| GTCN_519 | 30125 | GTCN_3037 | 44184 |
| CTCN_915 | 30126 | CTCN_5833 | 44185 |
| CTCN_916 | 30127 | TTCN_4621 | 44186 |
| ATCN_508 | 30128 | GTCN_3038 | 44187 |
| TTCN_728 | 30129 | CTCN_5834 | 44188 |
| TTCN_729 | 30130 | CTCN_5835 | 44189 |
| CTCN_917 | 30131 | CTCN_5836 | 44190 |
| CTCN_918 | 30132 | ATCN_3238 | 44191 |
| TTCN_730 | 30133 | TTCN_4622 | 44192 |
| CTCN_919 | 30134 | CTCN_5837 | 44193 |
| ATCN_509 | 30135 | TTCN_4623 | 44194 |
| GTCN_520 | 30136 | TTCN_4624 | 44195 |
| CTCN_920 | 30137 | CTCN_5838 | 44196 |
| CTCN_921 | 30138 | TTCN_4625 | 44197 |
| TTCN_731 | 30139 | CTCN_5839 | 44198 |
| CTCN_922 | 30140 | CTCN_5840 | 44199 |
| TTCN_732 | 30141 | TTCN_4626 | 44200 |
| CTCN_923 | 30142 | CTCN_5841 | 44201 |
| GTCN_521 | 30143 | TTCN_4627 | 44202 |
| GTCN_522 | 30144 | TTCN_4628 | 44203 |
| TTCN_733 | 30145 | CTCN_5842 | 44204 |
| ATCN_510 | 30146 | CTCN_5843 | 44205 |
| CTCN_924 | 30147 | GTCN_3039 | 44206 |
| CTCN_925 | 30148 | GTCN_3040 | 44207 |
| CTCN_926 | 30149 | ATCN_3239 | 44208 |
| TTCN_734 | 30150 | TTCN_4629 | 44209 |
| ATCN_511 | 30151 | GTCN_3041 | 44210 |
| CTCN_927 | 30152 | TTCN_4630 | 44211 |
| GTCN_523 | 30153 | TTCN_4631 | 44212 |
| TTCN_735 | 30154 | TTCN_4632 | 44213 |
| TTCN_736 | 30155 | ATCN_3240 | 44214 |
| TTCN_737 | 30156 | CTCN_5844 | 44215 |
| GTCN_524 | 30157 | TTCN_4633 | 44216 |
| CTCN_928 | 30158 | GTCN_3042 | 44217 |
| GTCN_525 | 30159 | TTCN_4634 | 44218 |

| | | | |
|---|---|---|---|
| TTCN_738 | 30160 | TTCN_4635 | 44219 |
| CTCN_929 | 30161 | ATCN_3241 | 44220 |
| GTCN_526 | 30162 | TTCN_4636 | 44221 |
| ATCN_512 | 30163 | ATCN_3242 | 44222 |
| GTCN_527 | 30164 | TTCN_4637 | 44223 |
| CTCN_930 | 30165 | CTCN_5845 | 44224 |
| CTCN_931 | 30166 | TTCN_4638 | 44225 |
| GTCN_528 | 30167 | TTCN_4639 | 44226 |
| TTCN_739 | 30168 | TTCN_4640 | 44227 |
| ATCN_513 | 30169 | TTCN_4641 | 44228 |
| GTCN_529 | 30170 | ATCN_3243 | 44229 |
| CTCN_932 | 30171 | TTCN_4642 | 44230 |
| CTCN_933 | 30172 | TTCN_4643 | 44231 |
| GTCN_530 | 30173 | GTCN_3043 | 44232 |
| CTCN_934 | 30174 | CTCN_5846 | 44233 |
| CTCN_935 | 30175 | TTCN_4644 | 44234 |
| ATCN_514 | 30176 | ATCN_3244 | 44235 |
| GTCN_531 | 30177 | CTCN_5847 | 44236 |
| TTCN_740 | 30178 | TTCN_4645 | 44237 |
| CTCN_936 | 30179 | TTCN_4646 | 44238 |
| CTCN_937 | 30180 | ATCN_3245 | 44239 |
| CTCN_938 | 30181 | TTCN_4647 | 44240 |
| CTCN_939 | 30182 | TTCN_4648 | 44241 |
| GTCN_532 | 30183 | TTCN_4649 | 44242 |
| GTCN_533 | 30184 | TTCN_4650 | 44243 |
| TTCN_741 | 30185 | GTCN_3044 | 44244 |
| TTCN_742 | 30186 | GTCN_3045 | 44245 |
| GTCN_534 | 30187 | ATCN_3246 | 44246 |
| CTCN_940 | 30188 | TTCN_4651 | 44247 |
| TTCN_743 | 30189 | TTCN_4652 | 44248 |
| ATCN_515 | 30190 | TTCN_4653 | 44249 |
| GTCN_535 | 30191 | ATCN_3247 | 44250 |
| TTCN_744 | 30192 | ATCN_3248 | 44251 |
| TTCN_745 | 30193 | GTCN_3046 | 44252 |
| TTCN_746 | 30194 | CTCN_5848 | 44253 |
| CTCN_941 | 30195 | CTCN_5849 | 44254 |
| TTCN_747 | 30196 | GTCN_3047 | 44255 |
| ATCN_516 | 30197 | CTCN_5850 | 44256 |
| TTCN_748 | 30198 | TTCN_4654 | 44257 |
| TTCN_749 | 30199 | ATCN_3249 | 44258 |
| ATCN_517 | 30200 | ATCN_3250 | 44259 |
| GTCN_536 | 30201 | TTCN_4655 | 44260 |
| TTCN_750 | 30202 | ATCN_3251 | 44261 |

FIG. 37 (continued)

| | | | |
|---|---|---|---|
| TTCN_751 | 30203 | TTCN_4656 | 44262 |
| ATCN_518 | 30204 | ATCN_3252 | 44263 |
| TTCN_752 | 30205 | TTCN_4657 | 44264 |
| ATCN_519 | 30206 | ATCN_3253 | 44265 |
| CTCN_942 | 30207 | ATCN_3254 | 44266 |
| TTCN_753 | 30208 | TTCN_4658 | 44267 |
| GTCN_537 | 30209 | TTCN_4659 | 44268 |
| ATCN_520 | 30210 | ATCN_3255 | 44269 |
| CTCN_943 | 30211 | GTCN_3048 | 44270 |
| GTCN_538 | 30212 | TTCN_4660 | 44271 |
| TTCN_754 | 30213 | GTCN_3049 | 44272 |
| CTCN_944 | 30214 | ATCN_3256 | 44273 |
| ATCN_521 | 30215 | ATCN_3257 | 44274 |
| CTCN_945 | 30216 | TTCN_4661 | 44275 |
| ATCN_522 | 30217 | CTCN_5851 | 44276 |
| ATCN_523 | 30218 | CTCN_5852 | 44277 |
| GTCN_539 | 30219 | GTCN_3050 | 44278 |
| TTCN_755 | 30220 | TTCN_4662 | 44279 |
| CTCN_946 | 30221 | TTCN_4663 | 44280 |
| CTCN_947 | 30222 | CTCN_5853 | 44281 |
| CTCN_948 | 30223 | ATCN_3258 | 44282 |
| CTCN_949 | 30224 | TTCN_4664 | 44283 |
| TTCN_756 | 30225 | GTCN_3051 | 44284 |
| ATCN_524 | 30226 | CTCN_5854 | 44285 |
| GTCN_540 | 30227 | CTCN_5855 | 44286 |
| CTCN_950 | 30228 | CTCN_5856 | 44287 |
| TTCN_757 | 30229 | CTCN_5857 | 44288 |
| ATCN_525 | 30230 | ATCN_3259 | 44289 |
| TTCN_758 | 30231 | ATCN_3260 | 44290 |
| ATCN_526 | 30232 | GTCN_3052 | 44291 |
| GTCN_541 | 30233 | TTCN_4665 | 44292 |
| CTCN_951 | 30234 | CTCN_5858 | 44293 |
| CTCN_952 | 30235 | GTCN_3053 | 44294 |
| GTCN_542 | 30236 | TTCN_4666 | 44295 |
| ATCN_527 | 30237 | TTCN_4667 | 44296 |
| CTCN_953 | 30238 | TTCN_4668 | 44297 |
| TTCN_759 | 30239 | GTCN_3054 | 44298 |
| CTCN_954 | 30240 | TTCN_4669 | 44299 |
| GTCN_543 | 30241 | TTCN_4670 | 44300 |
| CTCN_955 | 30242 | TTCN_4671 | 44301 |
| TTCN_760 | 30243 | GTCN_3055 | 44302 |
| GTCN_544 | 30244 | CTCN_5859 | 44303 |
| CTCN_956 | 30245 | TTCN_4672 | 44304 |

| | | | |
|---|---|---|---|
| GTCN_545 | 30246 | CTCN_5860 | 44305 |
| GTCN_546 | 30247 | TTCN_4673 | 44306 |
| ATCN_528 | 30248 | CTCN_5861 | 44307 |
| CTCN_957 | 30249 | CTCN_5862 | 44308 |
| ATCN_529 | 30250 | ATCN_3261 | 44309 |
| TTCN_761 | 30251 | CTCN_5863 | 44310 |
| ATCN_530 | 30252 | CTCN_5864 | 44311 |
| GTCN_547 | 30253 | GTCN_3056 | 44312 |
| GTCN_548 | 30254 | CTCN_5865 | 44313 |
| TTCN_762 | 30255 | GTCN_3057 | 44314 |
| ATCN_531 | 30256 | CTCN_5866 | 44315 |
| TTCN_763 | 30257 | GTCN_3058 | 44316 |
| ATCN_532 | 30258 | CTCN_5867 | 44317 |
| TTCN_764 | 30259 | CTCN_5868 | 44318 |
| ATCN_533 | 30260 | GTCN_3059 | 44319 |
| GTCN_549 | 30261 | GTCN_3060 | 44320 |
| TTCN_765 | 30262 | GTCN_3061 | 44321 |
| TTCN_766 | 30263 | CTCN_5869 | 44322 |
| TTCN_767 | 30264 | CTCN_5870 | 44323 |
| CTCN_958 | 30265 | GTCN_3062 | 44324 |
| TTCN_768 | 30266 | TTCN_4674 | 44325 |
| ATCN_534 | 30267 | ATCN_3262 | 44326 |
| CTCN_959 | 30268 | CTCN_5871 | 44327 |
| TTCN_769 | 30269 | GTCN_3063 | 44328 |
| TTCN_770 | 30270 | CTCN_5872 | 44329 |
| ATCN_535 | 30271 | CTCN_5873 | 44330 |
| CTCN_960 | 30272 | CTCN_5874 | 44331 |
| TTCN_771 | 30273 | CTCN_5875 | 44332 |
| TTCN_772 | 30274 | GTCN_3064 | 44333 |
| GTCN_550 | 30275 | GTCN_3065 | 44334 |
| TTCN_773 | 30276 | CTCN_5876 | 44335 |
| ATCN_536 | 30277 | CTCN_5877 | 44336 |
| TTCN_774 | 30278 | GTCN_3066 | 44337 |
| TTCN_775 | 30279 | CTCN_5878 | 44338 |
| ATCN_537 | 30280 | CTCN_5879 | 44339 |
| GTCN_551 | 30281 | CTCN_5880 | 44340 |
| TTCN_776 | 30282 | CTCN_5881 | 44341 |
| ATCN_538 | 30283 | TTCN_4675 | 44342 |
| CTCN_961 | 30284 | TTCN_4676 | 44343 |
| ATCN_539 | 30285 | CTCN_5882 | 44344 |
| GTCN_552 | 30286 | CTCN_5883 | 44345 |
| GTCN_553 | 30287 | CTCN_5884 | 44346 |
| TTCN_777 | 30288 | CTCN_5885 | 44347 |

FIG. 37 (continued)

| | | | |
|---|---|---|---|
| TTCN_778 | 30289 | GTCN_3067 | 44348 |
| ATCN_540 | 30290 | TTCN_4677 | 44349 |
| CTCN_962 | 30291 | TTCN_4678 | 44350 |
| CTCN_963 | 30292 | GTCN_3068 | 44351 |
| GTCN_554 | 30293 | GTCN_3069 | 44352 |
| TTCN_779 | 30294 | CTCN_5886 | 44353 |
| TTCN_780 | 30295 | GTCN_3070 | 44354 |
| GTCN_555 | 30296 | GTCN_3071 | 44355 |
| CTCN_964 | 30297 | GTCN_3072 | 44356 |
| GTCN_556 | 30298 | TTCN_4679 | 44357 |
| CTCN_965 | 30299 | CTCN_5887 | 44358 |
| GTCN_557 | 30300 | CTCN_5888 | 44359 |
| ATCN_541 | 30301 | GTCN_3073 | 44360 |
| ATCN_542 | 30302 | CTCN_5889 | 44361 |
| TTCN_781 | 30303 | ATCN_3263 | 44362 |
| ATCN_543 | 30304 | CTCN_5890 | 44363 |
| TTCN_782 | 30305 | CTCN_5891 | 44364 |
| TTCN_783 | 30306 | ATCN_3264 | 44365 |
| TTCN_784 | 30307 | ATCN_3265 | 44366 |
| GTCN_558 | 30308 | TTCN_4680 | 44367 |
| GTCN_559 | 30309 | GTCN_3074 | 44368 |
| TTCN_785 | 30310 | GTCN_3075 | 44369 |
| ATCN_544 | 30311 | TTCN_4681 | 44370 |
| TTCN_786 | 30312 | GTCN_3076 | 44371 |
| TTCN_787 | 30313 | GTCN_3077 | 44372 |
| CTCN_966 | 30314 | TTCN_4682 | 44373 |
| TTCN_788 | 30315 | TTCN_4683 | 44374 |
| ATCN_545 | 30316 | TTCN_4684 | 44375 |
| ATCN_546 | 30317 | CTCN_5892 | 44376 |
| ATCN_547 | 30318 | GTCN_3078 | 44377 |
| TTCN_789 | 30319 | GTCN_3079 | 44378 |
| TTCN_790 | 30320 | CTCN_5893 | 44379 |
| TTCN_791 | 30321 | GTCN_3080 | 44380 |
| ATCN_548 | 30322 | ATCN_3266 | 44381 |
| CTCN_967 | 30323 | ATCN_3267 | 44382 |
| CTCN_968 | 30324 | GTCN_3081 | 44383 |
| ATCN_549 | 30325 | TTCN_4685 | 44384 |
| TTCN_792 | 30326 | ATCN_3268 | 44385 |
| CTCN_969 | 30327 | ATCN_3269 | 44386 |
| CTCN_970 | 30328 | TTCN_4686 | 44387 |
| CTCN_971 | 30329 | CTCN_5894 | 44388 |
| TTCN_793 | 30330 | TTCN_4687 | 44389 |
| ATCN_550 | 30331 | CTCN_5895 | 44390 |

| | | | |
|---|---|---|---|
| TTCN_794 | 30332 | CTCN_5896 | 44391 |
| CTCN_972 | 30333 | GTCN_3082 | 44392 |
| TTCN_795 | 30334 | TTCN_4688 | 44393 |
| TTCN_796 | 30335 | CTCN_5897 | 44394 |
| CTCN_973 | 30336 | CTCN_5898 | 44395 |
| GTCN_560 | 30337 | ATCN_3270 | 44396 |
| TTCN_797 | 30338 | CTCN_5899 | 44397 |
| GTCN_561 | 30339 | TTCN_4689 | 44398 |
| TTCN_798 | 30340 | TTCN_4690 | 44399 |
| CTCN_974 | 30341 | CTCN_5900 | 44400 |
| CTCN_975 | 30342 | TTCN_4691 | 44401 |
| GTCN_562 | 30343 | CTCN_5901 | 44402 |
| CTCN_976 | 30344 | TTCN_4692 | 44403 |
| CTCN_977 | 30345 | ATCN_3271 | 44404 |
| ATCN_551 | 30346 | TTCN_4693 | 44405 |
| ATCN_552 | 30347 | CTCN_5902 | 44406 |
| GTCN_563 | 30348 | CTCN_5903 | 44407 |
| CTCN_978 | 30349 | GTCN_3083 | 44408 |
| GTCN_564 | 30350 | CTCN_5904 | 44409 |
| GTCN_565 | 30351 | GTCN_3084 | 44410 |
| ATCN_553 | 30352 | ATCN_3272 | 44411 |
| CTCN_979 | 30353 | ATCN_3273 | 44412 |
| GTCN_566 | 30354 | CTCN_5905 | 44413 |
| ATCN_554 | 30355 | ATCN_3274 | 44414 |
| ATCN_555 | 30356 | ATCN_3275 | 44415 |
| TTCN_799 | 30357 | TTCN_4694 | 44416 |
| CTCN_980 | 30358 | CTCN_5906 | 44417 |
| TTCN_800 | 30359 | GTCN_3085 | 44418 |
| CTCN_981 | 30360 | CTCN_5907 | 44419 |
| TTCN_801 | 30361 | CTCN_5908 | 44420 |
| ATCN_556 | 30362 | CTCN_5909 | 44421 |
| TTCN_802 | 30363 | TTCN_4695 | 44422 |
| TTCN_803 | 30364 | GTCN_3086 | 44423 |
| ATCN_557 | 30365 | CTCN_5910 | 44424 |
| TTCN_804 | 30366 | CTCN_5911 | 44425 |
| ATCN_558 | 30367 | CTCN_5912 | 44426 |
| TTCN_805 | 30368 | GTCN_3087 | 44427 |
| TTCN_806 | 30369 | ATCN_3276 | 44428 |
| TTCN_807 | 30370 | GTCN_3088 | 44429 |
| ATCN_559 | 30371 | GTCN_3089 | 44430 |
| TTCN_808 | 30372 | CTCN_5913 | 44431 |
| GTCN_567 | 30373 | TTCN_4696 | 44432 |
| TTCN_809 | 30374 | CTCN_5914 | 44433 |

FIG. 37 (continued)

| | | | |
|---|---|---|---|
| ATCN_560 | 30375 | TTCN_4697 | 44434 |
| ATCN_561 | 30376 | ATCN_3277 | 44435 |
| ATCN_562 | 30377 | TTCN_4698 | 44436 |
| TTCN_810 | 30378 | GTCN_3090 | 44437 |
| CTCN_982 | 30379 | TTCN_4699 | 44438 |
| TTCN_811 | 30380 | CTCN_5915 | 44439 |
| ATCN_563 | 30381 | CTCN_5916 | 44440 |
| GTCN_568 | 30382 | CTCN_5917 | 44441 |
| ATCN_564 | 30383 | CTCN_5918 | 44442 |
| CTCN_983 | 30384 | ATCN_3278 | 44443 |
| ATCN_565 | 30385 | TTCN_4700 | 44444 |
| TTCN_812 | 30386 | ATCN_3279 | 44445 |
| TTCN_813 | 30387 | ATCN_3280 | 44446 |
| GTCN_569 | 30388 | TTCN_4701 | 44447 |
| GTCN_570 | 30389 | TTCN_4702 | 44448 |
| TTCN_814 | 30390 | TTCN_4703 | 44449 |
| CTCN_984 | 30391 | GTCN_3091 | 44450 |
| CTCN_985 | 30392 | GTCN_3092 | 44451 |
| CTCN_986 | 30393 | ATCN_3281 | 44452 |
| ATCN_566 | 30394 | CTCN_5919 | 44453 |
| TTCN_815 | 30395 | CTCN_5920 | 44454 |
| GTCN_571 | 30396 | TTCN_4704 | 44455 |
| CTCN_987 | 30397 | GTCN_3093 | 44456 |
| ATCN_567 | 30398 | CTCN_5921 | 44457 |
| ATCN_568 | 30399 | ATCN_3282 | 44458 |
| ATCN_569 | 30400 | TTCN_4705 | 44459 |
| TTCN_816 | 30401 | ATCN_3283 | 44460 |
| CTCN_988 | 30402 | ATCN_3284 | 44461 |
| CTCN_989 | 30403 | ATCN_3285 | 44462 |
| CTCN_990 | 30404 | TTCN_4706 | 44463 |
| TTCN_817 | 30405 | CTCN_5922 | 44464 |
| GTCN_572 | 30406 | TTCN_4707 | 44465 |
| GTCN_573 | 30407 | CTCN_5923 | 44466 |
| ATCN_570 | 30408 | TTCN_4708 | 44467 |
| CTCN_991 | 30409 | CTCN_5924 | 44468 |
| ATCN_571 | 30410 | CTCN_5925 | 44469 |
| GTCN_574 | 30411 | CTCN_5926 | 44470 |
| CTCN_992 | 30412 | ATCN_3286 | 44471 |
| CTCN_993 | 30413 | TTCN_4709 | 44472 |
| CTCN_994 | 30414 | TTCN_4710 | 44473 |
| CTCN_995 | 30415 | GTCN_3094 | 44474 |
| ATCN_572 | 30416 | TTCN_4711 | 44475 |
| CTCN_996 | 30417 | TTCN_4712 | 44476 |

| | | | |
|---|---|---|---|
| TTCN_818 | 30418 | CTCN_5927 | 44477 |
| ATCN_573 | 30419 | GTCN_3095 | 44478 |
| CTCN_997 | 30420 | TTCN_4713 | 44479 |
| CTCN_998 | 30421 | TTCN_4714 | 44480 |
| CTCN_999 | 30422 | ATCN_3287 | 44481 |
| TTCN_819 | 30423 | GTCN_3096 | 44482 |
| CTCN_1000 | 30424 | CTCN_5928 | 44483 |
| CTCN_1001 | 30425 | CTCN_5929 | 44484 |
| GTCN_575 | 30426 | CTCN_5930 | 44485 |
| CTCN_1002 | 30427 | TTCN_4715 | 44486 |
| CTCN_1003 | 30428 | TTCN_4716 | 44487 |
| CTCN_1004 | 30429 | ATCN_3288 | 44488 |
| GTCN_576 | 30430 | TTCN_4717 | 44489 |
| CTCN_1005 | 30431 | CTCN_5931 | 44490 |
| CTCN_1006 | 30432 | CTCN_5932 | 44491 |
| TTCN_820 | 30433 | ATCN_3289 | 44492 |
| GTCN_577 | 30434 | TTCN_4718 | 44493 |
| TTCN_821 | 30435 | CTCN_5933 | 44494 |
| TTCN_822 | 30436 | GTCN_3097 | 44495 |
| TTCN_823 | 30437 | ATCN_3290 | 44496 |
| GTCN_578 | 30438 | CTCN_5934 | 44497 |
| TTCN_824 | 30439 | ATCN_3291 | 44498 |
| CTCN_1007 | 30440 | ATCN_3292 | 44499 |
| TTCN_825 | 30441 | TTCN_4719 | 44500 |
| TTCN_826 | 30442 | CTCN_5935 | 44501 |
| GTCN_579 | 30443 | ATCN_3293 | 44502 |
| CTCN_1008 | 30444 | ATCN_3294 | 44503 |
| GTCN_580 | 30445 | TTCN_4720 | 44504 |
| TTCN_827 | 30446 | TTCN_4721 | 44505 |
| GTCN_581 | 30447 | CTCN_5936 | 44506 |
| GTCN_582 | 30448 | TTCN_4722 | 44507 |
| CTCN_1009 | 30449 | ATCN_3295 | 44508 |
| CTCN_1010 | 30450 | TTCN_4723 | 44509 |
| CTCN_1011 | 30451 | CTCN_5937 | 44510 |
| CTCN_1012 | 30452 | CTCN_5938 | 44511 |
| CTCN_1013 | 30453 | GTCN_3098 | 44512 |
| CTCN_1014 | 30454 | ATCN_3296 | 44513 |
| GTCN_583 | 30455 | TTCN_4724 | 44514 |
| ATCN_574 | 30456 | GTCN_3099 | 44515 |
| ATCN_575 | 30457 | TTCN_4725 | 44516 |
| GTCN_584 | 30458 | TTCN_4726 | 44517 |
| CTCN_1015 | 30459 | TTCN_4727 | 44518 |
| CTCN_1016 | 30460 | CTCN_5939 | 44519 |

FIG. 37 (continued)

| | | | |
|---|---|---|---|
| ATCN_576 | 30461 | ATCN_3297 | 44520 |
| CTCN_1017 | 30462 | ATCN_3298 | 44521 |
| ATCN_577 | 30463 | CTCN_5940 | 44522 |
| GTCN_585 | 30464 | GTCN_3100 | 44523 |
| CTCN_1018 | 30465 | TTCN_4728 | 44524 |
| GTCN_586 | 30466 | CTCN_5941 | 44525 |
| GTCN_587 | 30467 | TTCN_4729 | 44526 |
| GTCN_588 | 30468 | ATCN_3299 | 44527 |
| CTCN_1019 | 30469 | ATCN_3300 | 44528 |
| CTCN_1020 | 30470 | TTCN_4730 | 44529 |
| GTCN_589 | 30471 | TTCN_4731 | 44530 |
| TTCN_828 | 30472 | CTCN_5942 | 44531 |
| GTCN_590 | 30473 | GTCN_3101 | 44532 |
| CTCN_1021 | 30474 | TTCN_4732 | 44533 |
| CTCN_1022 | 30475 | ATCN_3301 | 44534 |
| CTCN_1023 | 30476 | CTCN_5943 | 44535 |
| CTCN_1024 | 30477 | TTCN_4733 | 44536 |
| GTCN_591 | 30478 | ATCN_3302 | 44537 |
| CTCN_1025 | 30479 | GTCN_3102 | 44538 |
| ATCN_578 | 30480 | TTCN_4734 | 44539 |
| CTCN_1026 | 30481 | CTCN_5944 | 44540 |
| ATCN_579 | 30482 | GTCN_3103 | 44541 |
| ATCN_580 | 30483 | CTCN_5945 | 44542 |
| TTCN_829 | 30484 | TTCN_4735 | 44543 |
| TTCN_830 | 30485 | CTCN_5946 | 44544 |
| GTCN_592 | 30486 | GTCN_3104 | 44545 |
| CTCN_1027 | 30487 | TTCN_4736 | 44546 |
| TTCN_831 | 30488 | CTCN_5947 | 44547 |
| GTCN_593 | 30489 | CTCN_5948 | 44548 |
| CTCN_1028 | 30490 | GTCN_3105 | 44549 |
| TTCN_832 | 30491 | TTCN_4737 | 44550 |
| TTCN_833 | 30492 | CTCN_5949 | 44551 |
| CTCN_1029 | 30493 | CTCN_5950 | 44552 |
| TTCN_834 | 30494 | CTCN_5951 | 44553 |
| CTCN_1030 | 30495 | TTCN_4738 | 44554 |
| CTCN_1031 | 30496 | CTCN_5952 | 44555 |
| ATCN_581 | 30497 | CTCN_5953 | 44556 |
| CTCN_1032 | 30498 | CTCN_5954 | 44557 |
| TTCN_835 | 30499 | CTCN_5955 | 44558 |
| CTCN_1033 | 30500 | CTCN_5956 | 44559 |
| GTCN_594 | 30501 | TTCN_4739 | 44560 |
| CTCN_1034 | 30502 | GTCN_3106 | 44561 |
| ATCN_582 | 30503 | CTCN_5957 | 44562 |

| | | | |
|---|---|---|---|
| ATCN_583 | 30504 | TTCN_4740 | 44563 |
| CTCN_1035 | 30505 | CTCN_5958 | 44564 |
| CTCN_1036 | 30506 | GTCN_3107 | 44565 |
| CTCN_1037 | 30507 | GTCN_3108 | 44566 |
| TTCN_836 | 30508 | CTCN_5959 | 44567 |
| TTCN_837 | 30509 | ATCN_3303 | 44568 |
| CTCN_1038 | 30510 | ATCN_3304 | 44569 |
| CTCN_1039 | 30511 | ATCN_3305 | 44570 |
| CTCN_1040 | 30512 | CTCN_5960 | 44571 |
| GTCN_595 | 30513 | TTCN_4741 | 44572 |
| ATCN_584 | 30514 | CTCN_5961 | 44573 |
| CTCN_1041 | 30515 | TTCN_4742 | 44574 |
| CTCN_1042 | 30516 | ATCN_3306 | 44575 |
| TTCN_838 | 30517 | TTCN_4743 | 44576 |
| GTCN_596 | 30518 | TTCN_4744 | 44577 |
| CTCN_1043 | 30519 | ATCN_3307 | 44578 |
| CTCN_1044 | 30520 | CTCN_5962 | 44579 |
| GTCN_597 | 30521 | CTCN_5963 | 44580 |
| ATCN_585 | 30522 | CTCN_5964 | 44581 |
| ATCN_586 | 30523 | CTCN_5965 | 44582 |
| CTCN_1045 | 30524 | CTCN_5966 | 44583 |
| CTCN_1046 | 30525 | CTCN_5967 | 44584 |
| ATCN_587 | 30526 | ATCN_3308 | 44585 |
| TTCN_839 | 30527 | CTCN_5968 | 44586 |
| CTCN_1047 | 30528 | CTCN_5969 | 44587 |
| ATCN_588 | 30529 | CTCN_5970 | 44588 |
| ATCN_589 | 30530 | ATCN_3309 | 44589 |
| TTCN_840 | 30531 | CTCN_5971 | 44590 |
| TTCN_841 | 30532 | TTCN_4745 | 44591 |
| ATCN_590 | 30533 | CTCN_5972 | 44592 |
| CTCN_1048 | 30534 | CTCN_5973 | 44593 |
| ATCN_591 | 30535 | CTCN_5974 | 44594 |
| ATCN_592 | 30536 | ATCN_3310 | 44595 |
| TTCN_842 | 30537 | TTCN_4746 | 44596 |
| GTCN_598 | 30538 | TTCN_4747 | 44597 |
| ATCN_593 | 30539 | GTCN_3109 | 44598 |
| GTCN_599 | 30540 | TTCN_4748 | 44599 |
| ATCN_594 | 30541 | GTCN_3110 | 44600 |
| CTCN_1049 | 30542 | CTCN_5975 | 44601 |
| CTCN_1050 | 30543 | GTCN_3111 | 44602 |
| ATCN_595 | 30544 | CTCN_5976 | 44603 |
| GTCN_600 | 30545 | TTCN_4749 | 44604 |
| CTCN_1051 | 30546 | TTCN_4750 | 44605 |

FIG. 37 (continued)

| | | | |
|---|---|---|---|
| TTCN_843 | 30547 | TTCN_4751 | 44606 |
| ATCN_596 | 30548 | TTCN_4752 | 44607 |
| CTCN_1052 | 30549 | TTCN_4753 | 44608 |
| TTCN_844 | 30550 | TTCN_4754 | 44609 |
| GTCN_601 | 30551 | GTCN_3112 | 44610 |
| CTCN_1053 | 30552 | GTCN_3113 | 44611 |
| ATCN_597 | 30553 | TTCN_4755 | 44612 |
| TTCN_845 | 30554 | CTCN_5977 | 44613 |
| ATCN_598 | 30555 | ATCN_3311 | 44614 |
| CTCN_1054 | 30556 | GTCN_3114 | 44615 |
| TTCN_846 | 30557 | CTCN_5978 | 44616 |
| ATCN_599 | 30558 | CTCN_5979 | 44617 |
| GTCN_602 | 30559 | CTCN_5980 | 44618 |
| CTCN_1055 | 30560 | GTCN_3115 | 44619 |
| TTCN_847 | 30561 | TTCN_4756 | 44620 |
| GTCN_603 | 30562 | TTCN_4757 | 44621 |
| GTCN_604 | 30563 | TTCN_4758 | 44622 |
| CTCN_1056 | 30564 | GTCN_3116 | 44623 |
| ATCN_600 | 30565 | CTCN_5981 | 44624 |
| TTCN_848 | 30566 | TTCN_4759 | 44625 |
| TTCN_849 | 30567 | GTCN_3117 | 44626 |
| TTCN_850 | 30568 | CTCN_5982 | 44627 |
| TTCN_851 | 30569 | GTCN_3118 | 44628 |
| TTCN_852 | 30570 | CTCN_5983 | 44629 |
| TTCN_853 | 30571 | ATCN_3312 | 44630 |
| TTCN_854 | 30572 | ATCN_3313 | 44631 |
| TTCN_855 | 30573 | TTCN_4760 | 44632 |
| TTCN_856 | 30574 | GTCN_3119 | 44633 |
| CTCN_1057 | 30575 | CTCN_5984 | 44634 |
| TTCN_857 | 30576 | TTCN_4761 | 44635 |
| TTCN_858 | 30577 | ATCN_3314 | 44636 |
| TTCN_859 | 30578 | TTCN_4762 | 44637 |
| TTCN_860 | 30579 | TTCN_4763 | 44638 |
| TTCN_861 | 30580 | ATCN_3315 | 44639 |
| TTCN_862 | 30581 | ATCN_3316 | 44640 |
| CTCN_1058 | 30582 | GTCN_3120 | 44641 |
| ATCN_601 | 30583 | ATCN_3317 | 44642 |
| CTCN_1059 | 30584 | ATCN_3318 | 44643 |
| GTCN_605 | 30585 | TTCN_4764 | 44644 |
| ATCN_602 | 30586 | TTCN_4765 | 44645 |
| ATCN_603 | 30587 | TTCN_4766 | 44646 |
| CTCN_1060 | 30588 | ATCN_3319 | 44647 |
| CTCN_1061 | 30589 | ATCN_3320 | 44648 |

| | | | |
|---|---|---|---|
| CTCN_1062 | 30590 | ATCN_3321 | 44649 |
| CTCN_1063 | 30591 | ATCN_3322 | 44650 |
| TTCN_863 | 30592 | TTCN_4767 | 44651 |
| ATCN_604 | 30593 | CTCN_5985 | 44652 |
| TTCN_864 | 30594 | ATCN_3323 | 44653 |
| CTCN_1064 | 30595 | TTCN_4768 | 44654 |
| GTCN_606 | 30596 | ATCN_3324 | 44655 |
| TTCN_865 | 30597 | ATCN_3325 | 44656 |
| CTCN_1065 | 30598 | GTCN_3121 | 44657 |
| GTCN_607 | 30599 | TTCN_4769 | 44658 |
| TTCN_866 | 30600 | CTCN_5986 | 44659 |
| GTCN_608 | 30601 | CTCN_5987 | 44660 |
| CTCN_1066 | 30602 | CTCN_5988 | 44661 |
| TTCN_867 | 30603 | ATCN_3326 | 44662 |
| CTCN_1067 | 30604 | GTCN_3122 | 44663 |
| GTCN_609 | 30605 | TTCN_4770 | 44664 |
| CTCN_1068 | 30606 | CTCN_5989 | 44665 |
| ATCN_605 | 30607 | TTCN_4771 | 44666 |
| ATCN_606 | 30608 | CTCN_5990 | 44667 |
| TTCN_868 | 30609 | CTCN_5991 | 44668 |
| CTCN_1069 | 30610 | CTCN_5992 | 44669 |
| TTCN_869 | 30611 | GTCN_3123 | 44670 |
| CTCN_1070 | 30612 | CTCN_5993 | 44671 |
| ATCN_607 | 30613 | GTCN_3124 | 44672 |
| CTCN_1071 | 30614 | ATCN_3327 | 44673 |
| ATCN_608 | 30615 | CTCN_5994 | 44674 |
| ATCN_609 | 30616 | ATCN_3328 | 44675 |
| TTCN_870 | 30617 | ATCN_3329 | 44676 |
| CTCN_1072 | 30618 | GTCN_3125 | 44677 |
| CTCN_1073 | 30619 | TTCN_4772 | 44678 |
| CTCN_1074 | 30620 | TTCN_4773 | 44679 |
| TTCN_871 | 30621 | CTCN_5995 | 44680 |
| ATCN_610 | 30622 | TTCN_4774 | 44681 |
| CTCN_1075 | 30623 | CTCN_5996 | 44682 |
| GTCN_610 | 30624 | CTCN_5997 | 44683 |
| TTCN_872 | 30625 | GTCN_3126 | 44684 |
| ATCN_611 | 30626 | TTCN_4775 | 44685 |
| ATCN_612 | 30627 | CTCN_5998 | 44686 |
| TTCN_873 | 30628 | TTCN_4776 | 44687 |
| TTCN_874 | 30629 | TTCN_4777 | 44688 |
| CTCN_1076 | 30630 | TTCN_4778 | 44689 |
| CTCN_1077 | 30631 | CTCN_5999 | 44690 |
| TTCN_875 | 30632 | CTCN_6000 | 44691 |

FIG. 37 (continued)

| | | | |
|---|---|---|---|
| TTCN_876 | 30633 | GTCN_3127 | 44692 |
| TTCN_877 | 30634 | GTCN_3128 | 44693 |
| CTCN_1078 | 30635 | GTCN_3129 | 44694 |
| CTCN_1079 | 30636 | ATCN_3330 | 44695 |
| CTCN_1080 | 30637 | TTCN_4779 | 44696 |
| TTCN_878 | 30638 | TTCN_4780 | 44697 |
| ATCN_613 | 30639 | TTCN_4781 | 44698 |
| CTCN_1081 | 30640 | ATCN_3331 | 44699 |
| TTCN_879 | 30641 | ATCN_3332 | 44700 |
| CTCN_1082 | 30642 | GTCN_3130 | 44701 |
| CTCN_1083 | 30643 | TTCN_4782 | 44702 |
| CTCN_1084 | 30644 | GTCN_3131 | 44703 |
| TTCN_880 | 30645 | GTCN_3132 | 44704 |
| TTCN_881 | 30646 | CTCN_6001 | 44705 |
| TTCN_882 | 30647 | TTCN_4783 | 44706 |
| TTCN_883 | 30648 | ATCN_3333 | 44707 |
| CTCN_1085 | 30649 | GTCN_3133 | 44708 |
| GTCN_611 | 30650 | TTCN_4784 | 44709 |
| TTCN_884 | 30651 | TTCN_4785 | 44710 |
| ATCN_614 | 30652 | GTCN_3134 | 44711 |
| GTCN_612 | 30653 | GTCN_3135 | 44712 |
| CTCN_1086 | 30654 | GTCN_3136 | 44713 |
| TTCN_885 | 30655 | GTCN_3137 | 44714 |
| CTCN_1087 | 30656 | GTCN_3138 | 44715 |
| GTCN_613 | 30657 | TTCN_4786 | 44716 |
| TTCN_886 | 30658 | CTCN_6002 | 44717 |
| TTCN_887 | 30659 | GTCN_3139 | 44718 |
| ATCN_615 | 30660 | CTCN_6003 | 44719 |
| GTCN_614 | 30661 | ATCN_3334 | 44720 |
| GTCN_615 | 30662 | CTCN_6004 | 44721 |
| GTCN_616 | 30663 | CTCN_6005 | 44722 |
| TTCN_888 | 30664 | TTCN_4787 | 44723 |
| CTCN_1088 | 30665 | ATCN_3335 | 44724 |
| CTCN_1089 | 30666 | TTCN_4788 | 44725 |
| TTCN_889 | 30667 | ATCN_3336 | 44726 |
| CTCN_1090 | 30668 | TTCN_4789 | 44727 |
| TTCN_890 | 30669 | CTCN_6006 | 44728 |
| ATCN_616 | 30670 | TTCN_4790 | 44729 |
| CTCN_1091 | 30671 | CTCN_6007 | 44730 |
| CTCN_1092 | 30672 | ATCN_3337 | 44731 |
| ATCN_617 | 30673 | CTCN_6008 | 44732 |
| CTCN_1093 | 30674 | GTCN_3140 | 44733 |
| CTCN_1094 | 30675 | CTCN_6009 | 44734 |

| | | | |
|---|---|---|---|
| GTCN_617 | 30676 | CTCN_6010 | 44735 |
| TTCN_891 | 30677 | ATCN_3338 | 44736 |
| ATCN_618 | 30678 | ATCN_3339 | 44737 |
| CTCN_1095 | 30679 | CTCN_6011 | 44738 |
| GTCN_618 | 30680 | CTCN_6012 | 44739 |
| GTCN_619 | 30681 | CTCN_6013 | 44740 |
| CTCN_1096 | 30682 | TTCN_4791 | 44741 |
| CTCN_1097 | 30683 | TTCN_4792 | 44742 |
| ATCN_619 | 30684 | CTCN_6014 | 44743 |
| ATCN_620 | 30685 | CTCN_6015 | 44744 |
| TTCN_892 | 30686 | CTCN_6016 | 44745 |
| TTCN_893 | 30687 | CTCN_6017 | 44746 |
| CTCN_1098 | 30688 | GTCN_3141 | 44747 |
| TTCN_894 | 30689 | CTCN_6018 | 44748 |
| TTCN_895 | 30690 | GTCN_3142 | 44749 |
| CTCN_1099 | 30691 | TTCN_4793 | 44750 |
| CTCN_1100 | 30692 | ATCN_3340 | 44751 |
| GTCN_620 | 30693 | GTCN_3143 | 44752 |
| CTCN_1101 | 30694 | CTCN_6019 | 44753 |
| GTCN_621 | 30695 | ATCN_3341 | 44754 |
| TTCN_896 | 30696 | ATCN_3342 | 44755 |
| TTCN_897 | 30697 | CTCN_6020 | 44756 |
| ATCN_621 | 30698 | GTCN_3144 | 44757 |
| CTCN_1102 | 30699 | ATCN_3343 | 44758 |
| CTCN_1103 | 30700 | ATCN_3344 | 44759 |
| CTCN_1104 | 30701 | CTCN_6021 | 44760 |
| CTCN_1105 | 30702 | GTCN_3145 | 44761 |
| TTCN_898 | 30703 | CTCN_6022 | 44762 |
| CTCN_1106 | 30704 | ATCN_3345 | 44763 |
| ATCN_622 | 30705 | CTCN_6023 | 44764 |
| CTCN_1107 | 30706 | GTCN_3146 | 44765 |
| GTCN_622 | 30707 | TTCN_4794 | 44766 |
| TTCN_899 | 30708 | CTCN_6024 | 44767 |
| ATCN_623 | 30709 | ATCN_3346 | 44768 |
| CTCN_1108 | 30710 | TTCN_4795 | 44769 |
| ATCN_624 | 30711 | CTCN_6025 | 44770 |
| CTCN_1109 | 30712 | TTCN_4796 | 44771 |
| CTCN_1110 | 30713 | ATCN_3347 | 44772 |
| ATCN_625 | 30714 | CTCN_6026 | 44773 |
| ATCN_626 | 30715 | CTCN_6027 | 44774 |
| TTCN_900 | 30716 | TTCN_4797 | 44775 |
| GTCN_623 | 30717 | TTCN_4798 | 44776 |
| CTCN_1111 | 30718 | TTCN_4799 | 44777 |

FIG. 37 (continued)

| | | | |
|---|---|---|---|
| CTCN_1112 | 30719 | CTCN_6028 | 44778 |
| ATCN_627 | 30720 | TTCN_4800 | 44779 |
| ATCN_628 | 30721 | TTCN_4801 | 44780 |
| TTCN_901 | 30722 | TTCN_4802 | 44781 |
| ATCN_629 | 30723 | TTCN_4803 | 44782 |
| CTCN_1113 | 30724 | TTCN_4804 | 44783 |
| CTCN_1114 | 30725 | GTCN_3147 | 44784 |
| ATCN_630 | 30726 | CTCN_6029 | 44785 |
| CTCN_1115 | 30727 | GTCN_3148 | 44786 |
| CTCN_1116 | 30728 | TTCN_4805 | 44787 |
| CTCN_1117 | 30729 | CTCN_6030 | 44788 |
| CTCN_1118 | 30730 | ATCN_3348 | 44789 |
| CTCN_1119 | 30731 | CTCN_6031 | 44790 |
| TTCN_902 | 30732 | ATCN_3349 | 44791 |
| ATCN_631 | 30733 | TTCN_4806 | 44792 |
| TTCN_903 | 30734 | GTCN_3149 | 44793 |
| TTCN_904 | 30735 | CTCN_6032 | 44794 |
| CTCN_1120 | 30736 | GTCN_3150 | 44795 |
| CTCN_1121 | 30737 | ATCN_3350 | 44796 |
| ATCN_632 | 30738 | GTCN_3151 | 44797 |
| CTCN_1122 | 30739 | GTCN_3152 | 44798 |
| CTCN_1123 | 30740 | GTCN_3153 | 44799 |
| ATCN_633 | 30741 | GTCN_3154 | 44800 |
| TTCN_905 | 30742 | TTCN_4807 | 44801 |
| GTCN_624 | 30743 | CTCN_6033 | 44802 |
| CTCN_1124 | 30744 | ATCN_3351 | 44803 |
| TTCN_906 | 30745 | TTCN_4808 | 44804 |
| ATCN_634 | 30746 | ATCN_3352 | 44805 |
| ATCN_635 | 30747 | ATCN_3353 | 44806 |
| ATCN_636 | 30748 | TTCN_4809 | 44807 |
| CTCN_1125 | 30749 | ATCN_3354 | 44808 |
| CTCN_1126 | 30750 | ATCN_3355 | 44809 |
| TTCN_907 | 30751 | GTCN_3155 | 44810 |
| TTCN_908 | 30752 | GTCN_3156 | 44811 |
| CTCN_1127 | 30753 | TTCN_4810 | 44812 |
| CTCN_1128 | 30754 | GTCN_3157 | 44813 |
| ATCN_637 | 30755 | TTCN_4811 | 44814 |
| ATCN_638 | 30756 | TTCN_4812 | 44815 |
| CTCN_1129 | 30757 | GTCN_3158 | 44816 |
| CTCN_1130 | 30758 | GTCN_3159 | 44817 |
| CTCN_1131 | 30759 | ATCN_3356 | 44818 |
| TTCN_909 | 30760 | TTCN_4813 | 44819 |
| GTCN_625 | 30761 | GTCN_3160 | 44820 |

| | | | |
|---|---|---|---|
| TTCN_910 | 30762 | TTCN_4814 | 44821 |
| CTCN_1132 | 30763 | TTCN_4815 | 44822 |
| CTCN_1133 | 30764 | CTCN_6034 | 44823 |
| CTCN_1134 | 30765 | ATCN_3357 | 44824 |
| GTCN_626 | 30766 | TTCN_4816 | 44825 |
| TTCN_911 | 30767 | CTCN_6035 | 44826 |
| ATCN_639 | 30768 | GTCN_3161 | 44827 |
| CTCN_1135 | 30769 | TTCN_4817 | 44828 |
| GTCN_627 | 30770 | GTCN_3162 | 44829 |
| CTCN_1136 | 30771 | GTCN_3163 | 44830 |
| TTCN_912 | 30772 | TTCN_4818 | 44831 |
| ATCN_640 | 30773 | ATCN_3358 | 44832 |
| CTCN_1137 | 30774 | CTCN_6036 | 44833 |
| ATCN_641 | 30775 | GTCN_3164 | 44834 |
| ATCN_642 | 30776 | TTCN_4819 | 44835 |
| GTCN_628 | 30777 | ATCN_3359 | 44836 |
| TTCN_913 | 30778 | TTCN_4820 | 44837 |
| TTCN_914 | 30779 | TTCN_4821 | 44838 |
| TTCN_915 | 30780 | CTCN_6037 | 44839 |
| CTCN_1138 | 30781 | TTCN_4822 | 44840 |
| GTCN_629 | 30782 | GTCN_3165 | 44841 |
| CTCN_1139 | 30783 | TTCN_4823 | 44842 |
| CTCN_1140 | 30784 | ATCN_3360 | 44843 |
| GTCN_630 | 30785 | ATCN_3361 | 44844 |
| CTCN_1141 | 30786 | TTCN_4824 | 44845 |
| GTCN_631 | 30787 | CTCN_6038 | 44846 |
| ATCN_643 | 30788 | TTCN_4825 | 44847 |
| CTCN_1142 | 30789 | CTCN_6039 | 44848 |
| GTCN_632 | 30790 | CTCN_6040 | 44849 |
| ATCN_644 | 30791 | TTCN_4826 | 44850 |
| ATCN_645 | 30792 | TTCN_4827 | 44851 |
| TTCN_916 | 30793 | CTCN_6041 | 44852 |
| TTCN_917 | 30794 | TTCN_4828 | 44853 |
| ATCN_646 | 30795 | GTCN_3166 | 44854 |
| TTCN_918 | 30796 | TTCN_4829 | 44855 |
| GTCN_633 | 30797 | CTCN_6042 | 44856 |
| CTCN_1143 | 30798 | ATCN_3362 | 44857 |
| ATCN_647 | 30799 | CTCN_6043 | 44858 |
| ATCN_648 | 30800 | ATCN_3363 | 44859 |
| GTCN_634 | 30801 | GTCN_3167 | 44860 |
| CTCN_1144 | 30802 | GTCN_3168 | 44861 |
| ATCN_649 | 30803 | CTCN_6044 | 44862 |
| TTCN_919 | 30804 | TTCN_4830 | 44863 |

FIG. 37 (continued)

| | | | | | | | |
|---|---|---|---|---|---|---|---|
| TTCN_920 | 30805 | GTCN_3169 | 44864 | GTCN_645 | 30848 | GTCN_3175 | 44907 |
| GTCN_635 | 30806 | CTCN_6045 | 44865 | TTCN_930 | 30849 | GTCN_3176 | 44908 |
| TTCN_921 | 30807 | ATCN_3364 | 44866 | ATCN_654 | 30850 | TTCN_4844 | 44909 |
| TTCN_922 | 30808 | ATCN_3365 | 44867 | CTCN_1164 | 30851 | TTCN_4845 | 44910 |
| TTCN_923 | 30809 | ATCN_3366 | 44868 | CTCN_1165 | 30852 | TTCN_4846 | 44911 |
| TTCN_924 | 30810 | TTCN_4831 | 44869 | CTCN_1166 | 30853 | ATCN_3373 | 44912 |
| CTCN_1145 | 30811 | CTCN_6046 | 44870 | TTCN_931 | 30854 | CTCN_6060 | 44913 |
| CTCN_1146 | 30812 | CTCN_6047 | 44871 | ATCN_655 | 30855 | CTCN_6061 | 44914 |
| GTCN_636 | 30813 | TTCN_4832 | 44872 | ATCN_656 | 30856 | TTCN_4847 | 44915 |
| TTCN_925 | 30814 | TTCN_4833 | 44873 | GTCN_646 | 30857 | ATCN_3374 | 44916 |
| CTCN_1147 | 30815 | CTCN_6048 | 44874 | CTCN_1167 | 30858 | GTCN_3177 | 44917 |
| GTCN_637 | 30816 | CTCN_6049 | 44875 | ATCN_657 | 30859 | CTCN_6062 | 44918 |
| TTCN_926 | 30817 | ATCN_3367 | 44876 | ATCN_658 | 30860 | GTCN_3178 | 44919 |
| CTCN_1148 | 30818 | CTCN_6050 | 44877 | CTCN_1168 | 30861 | CTCN_6063 | 44920 |
| ATCN_650 | 30819 | CTCN_6051 | 44878 | TTCN_932 | 30862 | GTCN_3179 | 44921 |
| ATCN_651 | 30820 | TTCN_4834 | 44879 | GTCN_647 | 30863 | GTCN_3180 | 44922 |
| CTCN_1149 | 30821 | TTCN_4835 | 44880 | CTCN_1169 | 30864 | TTCN_4848 | 44923 |
| GTCN_638 | 30822 | CTCN_6052 | 44881 | GTCN_648 | 30865 | TTCN_4849 | 44924 |
| TTCN_927 | 30823 | CTCN_6053 | 44882 | ATCN_659 | 30866 | ATCN_3375 | 44925 |
| CTCN_1150 | 30824 | TTCN_4836 | 44883 | TTCN_933 | 30867 | TTCN_4850 | 44926 |
| GTCN_639 | 30825 | CTCN_6054 | 44884 | CTCN_1170 | 30868 | CTCN_6064 | 44927 |
| CTCN_1151 | 30826 | TTCN_4837 | 44885 | TTCN_934 | 30869 | TTCN_4851 | 44928 |
| GTCN_640 | 30827 | CTCN_6055 | 44886 | TTCN_935 | 30870 | CTCN_6065 | 44929 |
| GTCN_641 | 30828 | TTCN_4838 | 44887 | TTCN_936 | 30871 | TTCN_4852 | 44930 |
| CTCN_1152 | 30829 | ATCN_3368 | 44888 | ATCN_660 | 30872 | CTCN_6066 | 44931 |
| CTCN_1153 | 30830 | TTCN_4839 | 44889 | ATCN_661 | 30873 | TTCN_4853 | 44932 |
| CTCN_1154 | 30831 | CTCN_6056 | 44890 | CTCN_1171 | 30874 | CTCN_6067 | 44933 |
| CTCN_1155 | 30832 | TTCN_4840 | 44891 | CTCN_1172 | 30875 | TTCN_4854 | 44934 |
| CTCN_1156 | 30833 | ATCN_3369 | 44892 | CTCN_1173 | 30876 | CTCN_6068 | 44935 |
| CTCN_1157 | 30834 | ATCN_3370 | 44893 | GTCN_649 | 30877 | TTCN_4855 | 44936 |
| ATCN_652 | 30835 | GTCN_3170 | 44894 | CTCN_1174 | 30878 | TTCN_4856 | 44937 |
| ATCN_653 | 30836 | GTCN_3171 | 44895 | TTCN_937 | 30879 | CTCN_6069 | 44938 |
| CTCN_1158 | 30837 | CTCN_6057 | 44896 | TTCN_938 | 30880 | TTCN_4857 | 44939 |
| CTCN_1159 | 30838 | TTCN_4841 | 44897 | GTCN_650 | 30881 | CTCN_6070 | 44940 |
| CTCN_1160 | 30839 | GTCN_3172 | 44898 | CTCN_1175 | 30882 | GTCN_3181 | 44941 |
| GTCN_642 | 30840 | CTCN_6058 | 44899 | CTCN_1176 | 30883 | CTCN_6071 | 44942 |
| CTCN_1161 | 30841 | ATCN_3371 | 44900 | TTCN_939 | 30884 | CTCN_6072 | 44943 |
| GTCN_643 | 30842 | TTCN_4842 | 44901 | CTCN_1177 | 30885 | GTCN_3182 | 44944 |
| GTCN_644 | 30843 | ATCN_3372 | 44902 | ATCN_662 | 30886 | CTCN_6073 | 44945 |
| CTCN_1162 | 30844 | GTCN_3173 | 44903 | ATCN_663 | 30887 | CTCN_6074 | 44946 |
| TTCN_928 | 30845 | TTCN_4843 | 44904 | GTCN_651 | 30888 | GTCN_3183 | 44947 |
| TTCN_929 | 30846 | GTCN_3174 | 44905 | CTCN_1178 | 30889 | ATCN_3376 | 44948 |
| CTCN_1163 | 30847 | CTCN_6059 | 44906 | TTCN_940 | 30890 | TTCN_4858 | 44949 |

FIG. 37 (continued)

| | | | |
|---|---|---|---|
| CTCN_1179 | 30891 | TTCN_4859 | 44950 |
| GTCN_652 | 30892 | GTCN_3184 | 44951 |
| ATCN_664 | 30893 | CTCN_6075 | 44952 |
| TTCN_941 | 30894 | CTCN_6076 | 44953 |
| GTCN_653 | 30895 | TTCN_4860 | 44954 |
| CTCN_1180 | 30896 | CTCN_6077 | 44955 |
| ATCN_665 | 30897 | TTCN_4861 | 44956 |
| CTCN_1181 | 30898 | TTCN_4862 | 44957 |
| CTCN_1182 | 30899 | GTCN_3185 | 44958 |
| GTCN_654 | 30900 | TTCN_4863 | 44959 |
| CTCN_1183 | 30901 | TTCN_4864 | 44960 |
| TTCN_942 | 30902 | ATCN_3377 | 44961 |
| ATCN_666 | 30903 | ATCN_3378 | 44962 |
| TTCN_943 | 30904 | CTCN_6078 | 44963 |
| CTCN_1184 | 30905 | GTCN_3186 | 44964 |
| CTCN_1185 | 30906 | CTCN_6079 | 44965 |
| CTCN_1186 | 30907 | CTCN_6080 | 44966 |
| CTCN_1187 | 30908 | CTCN_6081 | 44967 |
| ATCN_667 | 30909 | CTCN_6082 | 44968 |
| ATCN_668 | 30910 | GTCN_3187 | 44969 |
| CTCN_1188 | 30911 | CTCN_6083 | 44970 |
| CTCN_1189 | 30912 | GTCN_3188 | 44971 |
| CTCN_1190 | 30913 | ATCN_3379 | 44972 |
| GTCN_655 | 30914 | ATCN_3380 | 44973 |
| CTCN_1191 | 30915 | CTCN_6084 | 44974 |
| GTCN_656 | 30916 | GTCN_3189 | 44975 |
| CTCN_1192 | 30917 | CTCN_6085 | 44976 |
| TTCN_944 | 30918 | CTCN_6086 | 44977 |
| CTCN_1193 | 30919 | CTCN_6087 | 44978 |
| GTCN_657 | 30920 | GTCN_3190 | 44979 |
| CTCN_1194 | 30921 | CTCN_6088 | 44980 |
| GTCN_658 | 30922 | TTCN_4865 | 44981 |
| ATCN_669 | 30923 | CTCN_6089 | 44982 |
| CTCN_1195 | 30924 | ATCN_3381 | 44983 |
| GTCN_659 | 30925 | ATCN_3382 | 44984 |
| CTCN_1196 | 30926 | CTCN_6090 | 44985 |
| TTCN_945 | 30927 | ATCN_3383 | 44986 |
| ATCN_670 | 30928 | TTCN_4866 | 44987 |
| TTCN_946 | 30929 | TTCN_4867 | 44988 |
| GTCN_660 | 30930 | TTCN_4868 | 44989 |
| GTCN_661 | 30931 | GTCN_3191 | 44990 |
| ATCN_671 | 30932 | TTCN_4869 | 44991 |
| GTCN_662 | 30933 | CTCN_6091 | 44992 |

| | | | |
|---|---|---|---|
| TTCN_947 | 30934 | GTCN_3192 | 44993 |
| GTCN_663 | 30935 | TTCN_4870 | 44994 |
| TTCN_948 | 30936 | CTCN_6092 | 44995 |
| CTCN_1197 | 30937 | TTCN_4871 | 44996 |
| GTCN_664 | 30938 | TTCN_4872 | 44997 |
| ATCN_672 | 30939 | TTCN_4873 | 44998 |
| CTCN_1198 | 30940 | GTCN_3193 | 44999 |
| CTCN_1199 | 30941 | TTCN_4874 | 45000 |
| CTCN_1200 | 30942 | CTCN_6093 | 45001 |
| GTCN_665 | 30943 | ATCN_3384 | 45002 |
| GTCN_666 | 30944 | CTCN_6094 | 45003 |
| TTCN_949 | 30945 | GTCN_3194 | 45004 |
| CTCN_1201 | 30946 | CTCN_6095 | 45005 |
| TTCN_950 | 30947 | TTCN_4875 | 45006 |
| GTCN_667 | 30948 | TTCN_4876 | 45007 |
| CTCN_1202 | 30949 | ATCN_3385 | 45008 |
| ATCN_673 | 30950 | CTCN_6096 | 45009 |
| ATCN_674 | 30951 | CTCN_6097 | 45010 |
| CTCN_1203 | 30952 | GTCN_3195 | 45011 |
| GTCN_668 | 30953 | CTCN_6098 | 45012 |
| CTCN_1204 | 30954 | TTCN_4877 | 45013 |
| GTCN_669 | 30955 | TTCN_4878 | 45014 |
| CTCN_1205 | 30956 | GTCN_3196 | 45015 |
| GTCN_670 | 30957 | ATCN_3386 | 45016 |
| CTCN_1206 | 30958 | GTCN_3197 | 45017 |
| ATCN_675 | 30959 | GTCN_3198 | 45018 |
| CTCN_1207 | 30960 | TTCN_4879 | 45019 |
| ATCN_676 | 30961 | ATCN_3387 | 45020 |
| ATCN_677 | 30962 | TTCN_4880 | 45021 |
| CTCN_1208 | 30963 | CTCN_6099 | 45022 |
| CTCN_1209 | 30964 | TTCN_4881 | 45023 |
| CTCN_1210 | 30965 | TTCN_4882 | 45024 |
| GTCN_671 | 30966 | ATCN_3388 | 45025 |
| CTCN_1211 | 30967 | TTCN_4883 | 45026 |
| ATCN_678 | 30968 | TTCN_4884 | 45027 |
| CTCN_1212 | 30969 | GTCN_3199 | 45028 |
| GTCN_672 | 30970 | ATCN_3389 | 45029 |
| CTCN_1213 | 30971 | ATCN_3390 | 45030 |
| GTCN_673 | 30972 | GTCN_3200 | 45031 |
| CTCN_1214 | 30973 | ATCN_3391 | 45032 |
| GTCN_674 | 30974 | TTCN_4885 | 45033 |
| CTCN_1215 | 30975 | CTCN_6100 | 45034 |
| ATCN_679 | 30976 | CTCN_6101 | 45035 |

FIG. 37 (continued)

| | | | |
|---|---|---|---|
| CTCN_1216 | 30977 | GTCN_3201 | 45036 |
| CTCN_1217 | 30978 | CTCN_6102 | 45037 |
| ATCN_680 | 30979 | TTCN_4886 | 45038 |
| CTCN_1218 | 30980 | TTCN_4887 | 45039 |
| CTCN_1219 | 30981 | GTCN_3202 | 45040 |
| TTCN_951 | 30982 | TTCN_4888 | 45041 |
| TTCN_952 | 30983 | TTCN_4889 | 45042 |
| CTCN_1220 | 30984 | CTCN_6103 | 45043 |
| CTCN_1221 | 30985 | GTCN_3203 | 45044 |
| CTCN_1222 | 30986 | GTCN_3204 | 45045 |
| ATCN_681 | 30987 | TTCN_4890 | 45046 |
| CTCN_1223 | 30988 | CTCN_6104 | 45047 |
| ATCN_682 | 30989 | TTCN_4891 | 45048 |
| TTCN_953 | 30990 | ATCN_3392 | 45049 |
| GTCN_675 | 30991 | CTCN_6105 | 45050 |
| TTCN_954 | 30992 | GTCN_3205 | 45051 |
| CTCN_1224 | 30993 | ATCN_3393 | 45052 |
| GTCN_676 | 30994 | ATCN_3394 | 45053 |
| CTCN_1225 | 30995 | ATCN_3395 | 45054 |
| ATCN_683 | 30996 | TTCN_4892 | 45055 |
| ATCN_684 | 30997 | TTCN_4893 | 45056 |
| CTCN_1226 | 30998 | TTCN_4894 | 45057 |
| GTCN_677 | 30999 | TTCN_4895 | 45058 |
| CTCN_1227 | 31000 | CTCN_6106 | 45059 |
| CTCN_1228 | 31001 | ATCN_3396 | 45060 |
| ATCN_685 | 31002 | CTCN_6107 | 45061 |
| ATCN_686 | 31003 | ATCN_3397 | 45062 |
| CTCN_1229 | 31004 | TTCN_4896 | 45063 |
| GTCN_678 | 31005 | CTCN_6108 | 45064 |
| ATCN_687 | 31006 | TTCN_4897 | 45065 |
| TTCN_955 | 31007 | TTCN_4898 | 45066 |
| CTCN_1230 | 31008 | CTCN_6109 | 45067 |
| CTCN_1231 | 31009 | GTCN_3206 | 45068 |
| TTCN_956 | 31010 | TTCN_4899 | 45069 |
| TTCN_957 | 31011 | TTCN_4900 | 45070 |
| GTCN_679 | 31012 | GTCN_3207 | 45071 |
| TTCN_958 | 31013 | ATCN_3398 | 45072 |
| GTCN_680 | 31014 | TTCN_4901 | 45073 |
| ATCN_688 | 31015 | CTCN_6110 | 45074 |
| CTCN_1232 | 31016 | GTCN_3208 | 45075 |
| GTCN_681 | 31017 | TTCN_4902 | 45076 |
| GTCN_682 | 31018 | GTCN_3209 | 45077 |
| CTCN_1233 | 31019 | CTCN_6111 | 45078 |

| | | | |
|---|---|---|---|
| TTCN_959 | 31020 | CTCN_6112 | 45079 |
| GTCN_683 | 31021 | TTCN_4903 | 45080 |
| TTCN_960 | 31022 | GTCN_3210 | 45081 |
| CTCN_1234 | 31023 | ATCN_3399 | 45082 |
| GTCN_684 | 31024 | CTCN_6113 | 45083 |
| CTCN_1235 | 31025 | GTCN_3211 | 45084 |
| GTCN_685 | 31026 | CTCN_6114 | 45085 |
| CTCN_1236 | 31027 | ATCN_3400 | 45086 |
| GTCN_686 | 31028 | CTCN_6115 | 45087 |
| TTCN_961 | 31029 | CTCN_6116 | 45088 |
| GTCN_687 | 31030 | GTCN_3212 | 45089 |
| GTCN_688 | 31031 | CTCN_6117 | 45090 |
| TTCN_962 | 31032 | GTCN_3213 | 45091 |
| CTCN_1237 | 31033 | TTCN_4904 | 45092 |
| ATCN_689 | 31034 | GTCN_3214 | 45093 |
| GTCN_689 | 31035 | CTCN_6118 | 45094 |
| GTCN_690 | 31036 | ATCN_3401 | 45095 |
| GTCN_691 | 31037 | TTCN_4905 | 45096 |
| ATCN_690 | 31038 | ATCN_3402 | 45097 |
| GTCN_692 | 31039 | TTCN_4906 | 45098 |
| CTCN_1238 | 31040 | CTCN_6119 | 45099 |
| CTCN_1239 | 31041 | TTCN_4907 | 45100 |
| CTCN_1240 | 31042 | ATCN_3403 | 45101 |
| CTCN_1241 | 31043 | TTCN_4908 | 45102 |
| GTCN_693 | 31044 | CTCN_6120 | 45103 |
| CTCN_1242 | 31045 | CTCN_6121 | 45104 |
| CTCN_1243 | 31046 | ATCN_3404 | 45105 |
| CTCN_1244 | 31047 | CTCN_6122 | 45106 |
| GTCN_694 | 31048 | TTCN_4909 | 45107 |
| GTCN_695 | 31049 | GTCN_3215 | 45108 |
| GTCN_696 | 31050 | TTCN_4910 | 45109 |
| CTCN_1245 | 31051 | TTCN_4911 | 45110 |
| GTCN_697 | 31052 | GTCN_3216 | 45111 |
| TTCN_963 | 31053 | TTCN_4912 | 45112 |
| GTCN_698 | 31054 | GTCN_3217 | 45113 |
| CTCN_1246 | 31055 | CTCN_6123 | 45114 |
| TTCN_964 | 31056 | TTCN_4913 | 45115 |
| GTCN_699 | 31057 | GTCN_3218 | 45116 |
| GTCN_700 | 31058 | TTCN_4914 | 45117 |
| TTCN_965 | 31059 | TTCN_4915 | 45118 |
| ATCN_691 | 31060 | ATCN_3405 | 45119 |
| ATCN_692 | 31061 | TTCN_4916 | 45120 |
| TTCN_966 | 31062 | GTCN_3219 | 45121 |

FIG. 37 (continued)

| | | | | | | | |
|---|---|---|---|---|---|---|---|
| TTCN_967 | 31063 | CTCN_6124 | 45122 | GTCN_709 | 31106 | ATCN_3415 | 45165 |
| CTCN_1247 | 31064 | CTCN_6125 | 45123 | TTCN_980 | 31107 | TTCN_4925 | 45166 |
| CTCN_1248 | 31065 | TTCN_4917 | 45124 | TTCN_981 | 31108 | ATCN_3416 | 45167 |
| ATCN_693 | 31066 | CTCN_6126 | 45125 | TTCN_982 | 31109 | TTCN_4926 | 45168 |
| CTCN_1249 | 31067 | CTCN_6127 | 45126 | ATCN_698 | 31110 | CTCN_6144 | 45169 |
| GTCN_701 | 31068 | ATCN_3406 | 45127 | ATCN_699 | 31111 | TTCN_4927 | 45170 |
| GTCN_702 | 31069 | GTCN_3220 | 45128 | CTCN_1264 | 31112 | TTCN_4928 | 45171 |
| CTCN_1250 | 31070 | GTCN_3221 | 45129 | TTCN_983 | 31113 | TTCN_4929 | 45172 |
| ATCN_694 | 31071 | ATCN_3407 | 45130 | CTCN_1265 | 31114 | GTCN_3226 | 45173 |
| TTCN_968 | 31072 | ATCN_3408 | 45131 | TTCN_984 | 31115 | TTCN_4930 | 45174 |
| TTCN_969 | 31073 | CTCN_6128 | 45132 | ATCN_700 | 31116 | ATCN_3417 | 45175 |
| TTCN_970 | 31074 | CTCN_6129 | 45133 | TTCN_985 | 31117 | GTCN_3227 | 45176 |
| CTCN_1251 | 31075 | TTCN_4918 | 45134 | CTCN_1266 | 31118 | CTCN_6145 | 45177 |
| TTCN_971 | 31076 | CTCN_6130 | 45135 | CTCN_1267 | 31119 | TTCN_4931 | 45178 |
| CTCN_1252 | 31077 | TTCN_4919 | 45136 | GTCN_710 | 31120 | GTCN_3228 | 45179 |
| TTCN_972 | 31078 | CTCN_6131 | 45137 | CTCN_1268 | 31121 | CTCN_6146 | 45180 |
| CTCN_1253 | 31079 | TTCN_4920 | 45138 | GTCN_711 | 31122 | ATCN_3418 | 45181 |
| GTCN_703 | 31080 | CTCN_6132 | 45139 | CTCN_1269 | 31123 | CTCN_6147 | 45182 |
| CTCN_1254 | 31081 | TTCN_4921 | 45140 | TTCN_986 | 31124 | CTCN_6148 | 45183 |
| TTCN_973 | 31082 | CTCN_6133 | 45141 | CTCN_1270 | 31125 | CTCN_6149 | 45184 |
| TTCN_974 | 31083 | ATCN_3409 | 45142 | TTCN_987 | 31126 | ATCN_3419 | 45185 |
| CTCN_1255 | 31084 | GTCN_3222 | 45143 | CTCN_1271 | 31127 | ATCN_3420 | 45186 |
| CTCN_1256 | 31085 | CTCN_6134 | 45144 | CTCN_1272 | 31128 | GTCN_3229 | 45187 |
| ATCN_695 | 31086 | CTCN_6135 | 45145 | TTCN_988 | 31129 | ATCN_3421 | 45188 |
| TTCN_975 | 31087 | CTCN_6136 | 45146 | ATCN_701 | 31130 | TTCN_4932 | 45189 |
| CTCN_1257 | 31088 | ATCN_3410 | 45147 | CTCN_1273 | 31131 | ATCN_3422 | 45190 |
| TTCN_976 | 31089 | CTCN_6137 | 45148 | GTCN_712 | 31132 | TTCN_4933 | 45191 |
| CTCN_1258 | 31090 | GTCN_3223 | 45149 | CTCN_1274 | 31133 | CTCN_6150 | 45192 |
| GTCN_704 | 31091 | ATCN_3411 | 45150 | TTCN_989 | 31134 | GTCN_3230 | 45193 |
| CTCN_1259 | 31092 | CTCN_6138 | 45151 | TTCN_990 | 31135 | CTCN_6151 | 45194 |
| TTCN_977 | 31093 | CTCN_6139 | 45152 | ATCN_702 | 31136 | GTCN_3231 | 45195 |
| TTCN_978 | 31094 | ATCN_3412 | 45153 | CTCN_1275 | 31137 | TTCN_4934 | 45196 |
| CTCN_1260 | 31095 | CTCN_6140 | 45154 | CTCN_1276 | 31138 | TTCN_4935 | 45197 |
| GTCN_705 | 31096 | TTCN_4922 | 45155 | GTCN_713 | 31139 | ATCN_3423 | 45198 |
| TTCN_979 | 31097 | CTCN_6141 | 45156 | ATCN_703 | 31140 | CTCN_6152 | 45199 |
| CTCN_1261 | 31098 | TTCN_4923 | 45157 | CTCN_1277 | 31141 | CTCN_6153 | 45200 |
| GTCN_706 | 31099 | GTCN_3224 | 45158 | GTCN_714 | 31142 | TTCN_4936 | 45201 |
| CTCN_1262 | 31100 | CTCN_6142 | 45159 | TTCN_991 | 31143 | GTCN_3232 | 45202 |
| CTCN_1263 | 31101 | CTCN_6143 | 45160 | GTCN_715 | 31144 | TTCN_4937 | 45203 |
| GTCN_707 | 31102 | GTCN_3225 | 45161 | CTCN_1278 | 31145 | ATCN_3424 | 45204 |
| ATCN_696 | 31103 | TTCN_4924 | 45162 | GTCN_716 | 31146 | CTCN_6154 | 45205 |
| ATCN_697 | 31104 | ATCN_3413 | 45163 | ATCN_704 | 31147 | TTCN_4938 | 45206 |
| GTCN_708 | 31105 | ATCN_3414 | 45164 | CTCN_1279 | 31148 | TTCN_4939 | 45207 |

FIG. 37 (continued)

| | | | |
|---|---|---|---|
| CTCN_1280 | 31149 | GTCN_3233 | 45208 |
| GTCN_717 | 31150 | TTCN_4940 | 45209 |
| GTCN_718 | 31151 | TTCN_4941 | 45210 |
| CTCN_1281 | 31152 | CTCN_6155 | 45211 |
| ATCN_705 | 31153 | ATCN_3425 | 45212 |
| TTCN_992 | 31154 | GTCN_3234 | 45213 |
| CTCN_1282 | 31155 | TTCN_4942 | 45214 |
| CTCN_1283 | 31156 | ATCN_3426 | 45215 |
| TTCN_993 | 31157 | GTCN_3235 | 45216 |
| TTCN_994 | 31158 | ATCN_3427 | 45217 |
| GTCN_719 | 31159 | CTCN_6156 | 45218 |
| ATCN_706 | 31160 | TTCN_4943 | 45219 |
| CTCN_1284 | 31161 | ATCN_3428 | 45220 |
| GTCN_720 | 31162 | TTCN_4944 | 45221 |
| CTCN_1285 | 31163 | CTCN_6157 | 45222 |
| GTCN_721 | 31164 | GTCN_3236 | 45223 |
| CTCN_1286 | 31165 | TTCN_4945 | 45224 |
| CTCN_1287 | 31166 | GTCN_3237 | 45225 |
| CTCN_1288 | 31167 | ATCN_3429 | 45226 |
| CTCN_1289 | 31168 | GTCN_3238 | 45227 |
| CTCN_1290 | 31169 | CTCN_6158 | 45228 |
| GTCN_722 | 31170 | TTCN_4946 | 45229 |
| ATCN_707 | 31171 | ATCN_3430 | 45230 |
| GTCN_723 | 31172 | TTCN_4947 | 45231 |
| ATCN_708 | 31173 | ATCN_3431 | 45232 |
| CTCN_1291 | 31174 | GTCN_3239 | 45233 |
| CTCN_1292 | 31175 | CTCN_6159 | 45234 |
| CTCN_1293 | 31176 | ATCN_3432 | 45235 |
| CTCN_1294 | 31177 | TTCN_4948 | 45236 |
| GTCN_724 | 31178 | GTCN_3240 | 45237 |
| CTCN_1295 | 31179 | CTCN_6160 | 45238 |
| TTCN_995 | 31180 | TTCN_4949 | 45239 |
| CTCN_1296 | 31181 | ATCN_3433 | 45240 |
| CTCN_1297 | 31182 | CTCN_6161 | 45241 |
| CTCN_1298 | 31183 | GTCN_3241 | 45242 |
| TTCN_996 | 31184 | ATCN_3434 | 45243 |
| CTCN_1299 | 31185 | CTCN_6162 | 45244 |
| GTCN_725 | 31186 | TTCN_4950 | 45245 |
| GTCN_726 | 31187 | CTCN_6163 | 45246 |
| GTCN_727 | 31188 | TTCN_4951 | 45247 |
| TTCN_997 | 31189 | GTCN_3242 | 45248 |
| GTCN_728 | 31190 | TTCN_4952 | 45249 |
| CTCN_1300 | 31191 | TTCN_4953 | 45250 |

| | | | |
|---|---|---|---|
| TTCN_998 | 31192 | CTCN_6164 | 45251 |
| CTCN_1301 | 31193 | TTCN_4954 | 45252 |
| GTCN_729 | 31194 | ATCN_3435 | 45253 |
| GTCN_730 | 31195 | TTCN_4955 | 45254 |
| CTCN_1302 | 31196 | CTCN_6165 | 45255 |
| GTCN_731 | 31197 | CTCN_6166 | 45256 |
| CTCN_1303 | 31198 | ATCN_3436 | 45257 |
| GTCN_732 | 31199 | TTCN_4956 | 45258 |
| ATCN_709 | 31200 | CTCN_6167 | 45259 |
| CTCN_1304 | 31201 | ATCN_3437 | 45260 |
| CTCN_1305 | 31202 | ATCN_3438 | 45261 |
| CTCN_1306 | 31203 | CTCN_6168 | 45262 |
| TTCN_999 | 31204 | GTCN_3243 | 45263 |
| ATCN_710 | 31205 | CTCN_6169 | 45264 |
| GTCN_733 | 31206 | TTCN_4957 | 45265 |
| CTCN_1307 | 31207 | GTCN_3244 | 45266 |
| GTCN_734 | 31208 | ATCN_3439 | 45267 |
| GTCN_735 | 31209 | CTCN_6170 | 45268 |
| TTCN_1000 | 31210 | CTCN_6171 | 45269 |
| CTCN_1308 | 31211 | TTCN_4958 | 45270 |
| CTCN_1309 | 31212 | ATCN_3440 | 45271 |
| CTCN_1310 | 31213 | CTCN_6172 | 45272 |
| ATCN_711 | 31214 | CTCN_6173 | 45273 |
| TTCN_1001 | 31215 | TTCN_4959 | 45274 |
| GTCN_736 | 31216 | ATCN_3441 | 45275 |
| CTCN_1311 | 31217 | TTCN_4960 | 45276 |
| CTCN_1312 | 31218 | CTCN_6174 | 45277 |
| TTCN_1002 | 31219 | CTCN_6175 | 45278 |
| CTCN_1313 | 31220 | CTCN_6176 | 45279 |
| TTCN_1003 | 31221 | ATCN_3442 | 45280 |
| TTCN_1004 | 31222 | ATCN_3443 | 45281 |
| TTCN_1005 | 31223 | CTCN_6177 | 45282 |
| CTCN_1314 | 31224 | ATCN_3444 | 45283 |
| TTCN_1006 | 31225 | GTCN_3245 | 45284 |
| ATCN_712 | 31226 | CTCN_6178 | 45285 |
| GTCN_737 | 31227 | GTCN_3246 | 45286 |
| TTCN_1007 | 31228 | CTCN_6179 | 45287 |
| CTCN_1315 | 31229 | ATCN_3445 | 45288 |
| TTCN_1008 | 31230 | CTCN_6180 | 45289 |
| GTCN_738 | 31231 | TTCN_4961 | 45290 |
| ATCN_713 | 31232 | GTCN_3247 | 45291 |
| GTCN_739 | 31233 | ATCN_3446 | 45292 |
| CTCN_1316 | 31234 | CTCN_6181 | 45293 |

FIG. 37 (continued)

| | | | |
|---|---|---|---|
| GTCN_740 | 31235 | CTCN_6182 | 45294 |
| CTCN_1317 | 31236 | TTCN_4962 | 45295 |
| TTCN_1009 | 31237 | ATCN_3447 | 45296 |
| TTCN_1010 | 31238 | TTCN_4963 | 45297 |
| GTCN_741 | 31239 | TTCN_4964 | 45298 |
| CTCN_1318 | 31240 | ATCN_3448 | 45299 |
| GTCN_742 | 31241 | ATCN_3449 | 45300 |
| CTCN_1319 | 31242 | ATCN_3450 | 45301 |
| TTCN_1011 | 31243 | TTCN_4965 | 45302 |
| GTCN_743 | 31244 | TTCN_4966 | 45303 |
| CTCN_1320 | 31245 | TTCN_4967 | 45304 |
| GTCN_744 | 31246 | CTCN_6183 | 45305 |
| GTCN_745 | 31247 | ATCN_3451 | 45306 |
| CTCN_1321 | 31248 | CTCN_6184 | 45307 |
| CTCN_1322 | 31249 | TTCN_4968 | 45308 |
| TTCN_1012 | 31250 | GTCN_3248 | 45309 |
| CTCN_1323 | 31251 | TTCN_4969 | 45310 |
| ATCN_714 | 31252 | GTCN_3249 | 45311 |
| ATCN_715 | 31253 | CTCN_6185 | 45312 |
| ATCN_716 | 31254 | TTCN_4970 | 45313 |
| TTCN_1013 | 31255 | CTCN_6186 | 45314 |
| TTCN_1014 | 31256 | CTCN_6187 | 45315 |
| TTCN_1015 | 31257 | CTCN_6188 | 45316 |
| CTCN_1324 | 31258 | GTCN_3250 | 45317 |
| ATCN_717 | 31259 | CTCN_6189 | 45318 |
| CTCN_1325 | 31260 | TTCN_4971 | 45319 |
| TTCN_1016 | 31261 | GTCN_3251 | 45320 |
| ATCN_718 | 31262 | TTCN_4972 | 45321 |
| ATCN_719 | 31263 | TTCN_4973 | 45322 |
| CTCN_1326 | 31264 | TTCN_4974 | 45323 |
| TTCN_1017 | 31265 | ATCN_3452 | 45324 |
| ATCN_720 | 31266 | GTCN_3252 | 45325 |
| GTCN_746 | 31267 | GTCN_3253 | 45326 |
| TTCN_1018 | 31268 | CTCN_6190 | 45327 |
| TTCN_1019 | 31269 | ATCN_3453 | 45328 |
| TTCN_1020 | 31270 | ATCN_3454 | 45329 |
| GTCN_747 | 31271 | ATCN_3455 | 45330 |
| GTCN_748 | 31272 | TTCN_4975 | 45331 |
| ATCN_721 | 31273 | GTCN_3254 | 45332 |
| TTCN_1021 | 31274 | CTCN_6191 | 45333 |
| CTCN_1327 | 31275 | TTCN_4976 | 45334 |
| CTCN_1328 | 31276 | ATCN_3456 | 45335 |
| ATCN_722 | 31277 | TTCN_4977 | 45336 |

| | | | |
|---|---|---|---|
| CTCN_1329 | 31278 | GTCN_3255 | 45337 |
| CTCN_1330 | 31279 | TTCN_4978 | 45338 |
| TTCN_1022 | 31280 | CTCN_6192 | 45339 |
| GTCN_749 | 31281 | CTCN_6193 | 45340 |
| CTCN_1331 | 31282 | ATCN_3457 | 45341 |
| CTCN_1332 | 31283 | GTCN_3256 | 45342 |
| TTCN_1023 | 31284 | TTCN_4979 | 45343 |
| CTCN_1333 | 31285 | TTCN_4980 | 45344 |
| CTCN_1334 | 31286 | TTCN_4981 | 45345 |
| ATCN_723 | 31287 | TTCN_4982 | 45346 |
| CTCN_1335 | 31288 | ATCN_3458 | 45347 |
| TTCN_1024 | 31289 | TTCN_4983 | 45348 |
| TTCN_1025 | 31290 | CTCN_6194 | 45349 |
| ATCN_724 | 31291 | ATCN_3459 | 45350 |
| CTCN_1336 | 31292 | TTCN_4984 | 45351 |
| GTCN_750 | 31293 | TTCN_4985 | 45352 |
| TTCN_1026 | 31294 | TTCN_4986 | 45353 |
| TTCN_1027 | 31295 | TTCN_4987 | 45354 |
| CTCN_1337 | 31296 | TTCN_4988 | 45355 |
| GTCN_751 | 31297 | TTCN_4989 | 45356 |
| TTCN_1028 | 31298 | GTCN_3257 | 45357 |
| CTCN_1338 | 31299 | ATCN_3460 | 45358 |
| ATCN_725 | 31300 | ATCN_3461 | 45359 |
| CTCN_1339 | 31301 | GTCN_3258 | 45360 |
| CTCN_1340 | 31302 | GTCN_3259 | 45361 |
| TTCN_1029 | 31303 | ATCN_3462 | 45362 |
| CTCN_1341 | 31304 | ATCN_3463 | 45363 |
| CTCN_1342 | 31305 | GTCN_3260 | 45364 |
| GTCN_752 | 31306 | ATCN_3464 | 45365 |
| CTCN_1343 | 31307 | ATCN_3465 | 45366 |
| GTCN_753 | 31308 | TTCN_4990 | 45367 |
| GTCN_754 | 31309 | CTCN_6195 | 45368 |
| GTCN_755 | 31310 | ATCN_3466 | 45369 |
| GTCN_756 | 31311 | TTCN_4991 | 45370 |
| GTCN_757 | 31312 | CTCN_6196 | 45371 |
| TTCN_1030 | 31313 | GTCN_3261 | 45372 |
| CTCN_1344 | 31314 | GTCN_3262 | 45373 |
| ATCN_726 | 31315 | ATCN_3467 | 45374 |
| CTCN_1345 | 31316 | GTCN_3263 | 45375 |
| GTCN_758 | 31317 | CTCN_6197 | 45376 |
| TTCN_1031 | 31318 | CTCN_6198 | 45377 |
| GTCN_759 | 31319 | TTCN_4992 | 45378 |
| ATCN_727 | 31320 | CTCN_6199 | 45379 |

FIG. 37 (continued)

| | | | |
|---|---|---|---|
| CTCN_1346 | 31321 | TTCN_4993 | 45380 |
| TTCN_1032 | 31322 | GTCN_3264 | 45381 |
| GTCN_760 | 31323 | ATCN_3468 | 45382 |
| TTCN_1033 | 31324 | TTCN_4994 | 45383 |
| CTCN_1347 | 31325 | TTCN_4995 | 45384 |
| GTCN_761 | 31326 | CTCN_6200 | 45385 |
| TTCN_1034 | 31327 | ATCN_3469 | 45386 |
| CTCN_1348 | 31328 | TTCN_4996 | 45387 |
| GTCN_762 | 31329 | ATCN_3470 | 45388 |
| CTCN_1349 | 31330 | TTCN_4997 | 45389 |
| TTCN_1035 | 31331 | ATCN_3471 | 45390 |
| GTCN_763 | 31332 | CTCN_6201 | 45391 |
| ATCN_728 | 31333 | GTCN_3265 | 45392 |
| ATCN_729 | 31334 | TTCN_4998 | 45393 |
| ATCN_730 | 31335 | TTCN_4999 | 45394 |
| TTCN_1036 | 31336 | CTCN_6202 | 45395 |
| CTCN_1350 | 31337 | TTCN_5000 | 45396 |
| CTCN_1351 | 31338 | TTCN_5001 | 45397 |
| GTCN_764 | 31339 | TTCN_5002 | 45398 |
| ATCN_731 | 31340 | CTCN_6203 | 45399 |
| CTCN_1352 | 31341 | ATCN_3472 | 45400 |
| GTCN_765 | 31342 | TTCN_5003 | 45401 |
| TTCN_1037 | 31343 | ATCN_3473 | 45402 |
| CTCN_1353 | 31344 | TTCN_5004 | 45403 |
| GTCN_766 | 31345 | ATCN_3474 | 45404 |
| CTCN_1354 | 31346 | TTCN_5005 | 45405 |
| GTCN_767 | 31347 | TTCN_5006 | 45406 |
| TTCN_1038 | 31348 | CTCN_6204 | 45407 |
| TTCN_1039 | 31349 | CTCN_6205 | 45408 |
| GTCN_768 | 31350 | ATCN_3475 | 45409 |
| GTCN_769 | 31351 | GTCN_3266 | 45410 |
| ATCN_732 | 31352 | TTCN_5007 | 45411 |
| ATCN_733 | 31353 | TTCN_5008 | 45412 |
| CTCN_1355 | 31354 | ATCN_3476 | 45413 |
| CTCN_1356 | 31355 | CTCN_6206 | 45414 |
| TTCN_1040 | 31356 | TTCN_5009 | 45415 |
| TTCN_1041 | 31357 | ATCN_3477 | 45416 |
| ATCN_734 | 31358 | CTCN_6207 | 45417 |
| TTCN_1042 | 31359 | GTCN_3267 | 45418 |
| CTCN_1357 | 31360 | CTCN_6208 | 45419 |
| TTCN_1043 | 31361 | TTCN_5010 | 45420 |
| TTCN_1044 | 31362 | TTCN_5011 | 45421 |
| ATCN_735 | 31363 | CTCN_6209 | 45422 |

| | | | |
|---|---|---|---|
| GTCN_770 | 31364 | ATCN_3478 | 45423 |
| CTCN_1358 | 31365 | CTCN_6210 | 45424 |
| GTCN_771 | 31366 | CTCN_6211 | 45425 |
| CTCN_1359 | 31367 | ATCN_3479 | 45426 |
| ATCN_736 | 31368 | ATCN_3480 | 45427 |
| GTCN_772 | 31369 | CTCN_6212 | 45428 |
| CTCN_1360 | 31370 | GTCN_3268 | 45429 |
| CTCN_1361 | 31371 | CTCN_6213 | 45430 |
| TTCN_1045 | 31372 | ATCN_3481 | 45431 |
| CTCN_1362 | 31373 | ATCN_3482 | 45432 |
| ATCN_737 | 31374 | CTCN_6214 | 45433 |
| CTCN_1363 | 31375 | GTCN_3269 | 45434 |
| CTCN_1364 | 31376 | ATCN_3483 | 45435 |
| GTCN_773 | 31377 | TTCN_5012 | 45436 |
| TTCN_1046 | 31378 | GTCN_3270 | 45437 |
| CTCN_1365 | 31379 | CTCN_6215 | 45438 |
| CTCN_1366 | 31380 | GTCN_3271 | 45439 |
| GTCN_774 | 31381 | TTCN_5013 | 45440 |
| GTCN_775 | 31382 | TTCN_5014 | 45441 |
| GTCN_776 | 31383 | CTCN_6216 | 45442 |
| TTCN_1047 | 31384 | TTCN_5015 | 45443 |
| GTCN_777 | 31385 | TTCN_5016 | 45444 |
| CTCN_1367 | 31386 | CTCN_6217 | 45445 |
| ATCN_738 | 31387 | CTCN_6218 | 45446 |
| ATCN_739 | 31388 | CTCN_6219 | 45447 |
| CTCN_1368 | 31389 | CTCN_6220 | 45448 |
| CTCN_1369 | 31390 | ATCN_3484 | 45449 |
| GTCN_778 | 31391 | ATCN_3485 | 45450 |
| TTCN_1048 | 31392 | CTCN_6221 | 45451 |
| CTCN_1370 | 31393 | GTCN_3272 | 45452 |
| GTCN_779 | 31394 | CTCN_6222 | 45453 |
| CTCN_1371 | 31395 | GTCN_3273 | 45454 |
| TTCN_1049 | 31396 | CTCN_6223 | 45455 |
| TTCN_1050 | 31397 | GTCN_3274 | 45456 |
| CTCN_1372 | 31398 | CTCN_6224 | 45457 |
| CTCN_1373 | 31399 | GTCN_3275 | 45458 |
| ATCN_740 | 31400 | CTCN_6225 | 45459 |
| ATCN_741 | 31401 | TTCN_5017 | 45460 |
| CTCN_1374 | 31402 | ATCN_3486 | 45461 |
| TTCN_1051 | 31403 | TTCN_5018 | 45462 |
| GTCN_780 | 31404 | GTCN_3276 | 45463 |
| TTCN_1052 | 31405 | TTCN_5019 | 45464 |
| ATCN_742 | 31406 | TTCN_5020 | 45465 |

FIG. 37 (continued)

| | | | |
|---|---|---|---|
| TTCN_1053 | 31407 | TTCN_5021 | 45466 |
| CTCN_1375 | 31408 | TTCN_5022 | 45467 |
| CTCN_1376 | 31409 | ATCN_3487 | 45468 |
| GTCN_781 | 31410 | ATCN_3488 | 45469 |
| ATCN_743 | 31411 | GTCN_3277 | 45470 |
| TTCN_1054 | 31412 | TTCN_5023 | 45471 |
| TTCN_1055 | 31413 | CTCN_6226 | 45472 |
| CTCN_1377 | 31414 | CTCN_6227 | 45473 |
| CTCN_1378 | 31415 | TTCN_5024 | 45474 |
| CTCN_1379 | 31416 | CTCN_6228 | 45475 |
| CTCN_1380 | 31417 | TTCN_5025 | 45476 |
| GTCN_782 | 31418 | CTCN_6229 | 45477 |
| TTCN_1056 | 31419 | GTCN_3278 | 45478 |
| TTCN_1057 | 31420 | TTCN_5026 | 45479 |
| CTCN_1381 | 31421 | TTCN_5027 | 45480 |
| TTCN_1058 | 31422 | GTCN_3279 | 45481 |
| TTCN_1059 | 31423 | CTCN_6230 | 45482 |
| CTCN_1382 | 31424 | TTCN_5028 | 45483 |
| TTCN_1060 | 31425 | GTCN_3280 | 45484 |
| CTCN_1383 | 31426 | CTCN_6231 | 45485 |
| TTCN_1061 | 31427 | GTCN_3281 | 45486 |
| GTCN_783 | 31428 | GTCN_3282 | 45487 |
| GTCN_784 | 31429 | ATCN_3489 | 45488 |
| TTCN_1062 | 31430 | TTCN_5029 | 45489 |
| GTCN_785 | 31431 | CTCN_6232 | 45490 |
| CTCN_1384 | 31432 | GTCN_3283 | 45491 |
| TTCN_1063 | 31433 | GTCN_3284 | 45492 |
| CTCN_1385 | 31434 | TTCN_5030 | 45493 |
| GTCN_786 | 31435 | CTCN_6233 | 45494 |
| TTCN_1064 | 31436 | CTCN_6234 | 45495 |
| ATCN_744 | 31437 | TTCN_5031 | 45496 |
| GTCN_787 | 31438 | CTCN_6235 | 45497 |
| TTCN_1065 | 31439 | TTCN_5032 | 45498 |
| CTCN_1386 | 31440 | ATCN_3490 | 45499 |
| CTCN_1387 | 31441 | TTCN_5033 | 45500 |
| GTCN_788 | 31442 | GTCN_3285 | 45501 |
| TTCN_1066 | 31443 | CTCN_6236 | 45502 |
| CTCN_1388 | 31444 | CTCN_6237 | 45503 |
| GTCN_789 | 31445 | TTCN_5034 | 45504 |
| CTCN_1389 | 31446 | GTCN_3286 | 45505 |
| CTCN_1390 | 31447 | TTCN_5035 | 45506 |
| ATCN_745 | 31448 | TTCN_5036 | 45507 |
| TTCN_1067 | 31449 | ATCN_3491 | 45508 |

| | | | |
|---|---|---|---|
| CTCN_1391 | 31450 | ATCN_3492 | 45509 |
| CTCN_1392 | 31451 | ATCN_3493 | 45510 |
| TTCN_1068 | 31452 | CTCN_6238 | 45511 |
| TTCN_1069 | 31453 | ATCN_3494 | 45512 |
| CTCN_1393 | 31454 | TTCN_5037 | 45513 |
| CTCN_1394 | 31455 | CTCN_6239 | 45514 |
| GTCN_790 | 31456 | GTCN_3287 | 45515 |
| GTCN_791 | 31457 | CTCN_6240 | 45516 |
| ATCN_746 | 31458 | CTCN_6241 | 45517 |
| TTCN_1070 | 31459 | TTCN_5038 | 45518 |
| TTCN_1071 | 31460 | CTCN_6242 | 45519 |
| TTCN_1072 | 31461 | ATCN_3495 | 45520 |
| GTCN_792 | 31462 | ATCN_3496 | 45521 |
| CTCN_1395 | 31463 | ATCN_3497 | 45522 |
| CTCN_1396 | 31464 | CTCN_6243 | 45523 |
| ATCN_747 | 31465 | CTCN_6244 | 45524 |
| GTCN_793 | 31466 | GTCN_3288 | 45525 |
| TTCN_1073 | 31467 | TTCN_5039 | 45526 |
| TTCN_1074 | 31468 | GTCN_3289 | 45527 |
| TTCN_1075 | 31469 | ATCN_3498 | 45528 |
| ATCN_748 | 31470 | TTCN_5040 | 45529 |
| CTCN_1397 | 31471 | CTCN_6245 | 45530 |
| CTCN_1398 | 31472 | CTCN_6246 | 45531 |
| TTCN_1076 | 31473 | CTCN_6247 | 45532 |
| CTCN_1399 | 31474 | TTCN_5041 | 45533 |
| TTCN_1077 | 31475 | GTCN_3290 | 45534 |
| CTCN_1400 | 31476 | TTCN_5042 | 45535 |
| CTCN_1401 | 31477 | CTCN_6248 | 45536 |
| CTCN_1402 | 31478 | TTCN_5043 | 45537 |
| ATCN_749 | 31479 | CTCN_6249 | 45538 |
| GTCN_794 | 31480 | TTCN_5044 | 45539 |
| GTCN_795 | 31481 | TTCN_5045 | 45540 |
| CTCN_1403 | 31482 | TTCN_5046 | 45541 |
| GTCN_796 | 31483 | ATCN_3499 | 45542 |
| GTCN_797 | 31484 | GTCN_3291 | 45543 |
| ATCN_750 | 31485 | CTCN_6250 | 45544 |
| CTCN_1404 | 31486 | TTCN_5047 | 45545 |
| CTCN_1405 | 31487 | CTCN_6251 | 45546 |
| TTCN_1078 | 31488 | TTCN_5048 | 45547 |
| TTCN_1079 | 31489 | TTCN_5049 | 45548 |
| CTCN_1406 | 31490 | ATCN_3500 | 45549 |
| TTCN_1080 | 31491 | ATCN_3501 | 45550 |
| ATCN_751 | 31492 | ATCN_3502 | 45551 |

FIG. 37 (continued)

| | | | |
|---|---|---|---|
| CTCN_1407 | 31493 | CTCN_6252 | 45552 |
| TTCN_1081 | 31494 | TTCN_5050 | 45553 |
| TTCN_1082 | 31495 | TTCN_5051 | 45554 |
| GTCN_798 | 31496 | TTCN_5052 | 45555 |
| ATCN_752 | 31497 | TTCN_5053 | 45556 |
| TTCN_1083 | 31498 | ATCN_3503 | 45557 |
| ATCN_753 | 31499 | TTCN_5054 | 45558 |
| GTCN_799 | 31500 | GTCN_3292 | 45559 |
| CTCN_1408 | 31501 | ATCN_3504 | 45560 |
| ATCN_754 | 31502 | ATCN_3505 | 45561 |
| GTCN_800 | 31503 | TTCN_5055 | 45562 |
| TTCN_1084 | 31504 | CTCN_6253 | 45563 |
| CTCN_1409 | 31505 | CTCN_6254 | 45564 |
| TTCN_1085 | 31506 | CTCN_6255 | 45565 |
| GTCN_801 | 31507 | TTCN_5056 | 45566 |
| CTCN_1410 | 31508 | GTCN_3293 | 45567 |
| GTCN_802 | 31509 | CTCN_6256 | 45568 |
| CTCN_1411 | 31510 | CTCN_6257 | 45569 |
| TTCN_1086 | 31511 | TTCN_5057 | 45570 |
| CTCN_1412 | 31512 | CTCN_6258 | 45571 |
| CTCN_1413 | 31513 | TTCN_5058 | 45572 |
| ATCN_755 | 31514 | GTCN_3294 | 45573 |
| TTCN_1087 | 31515 | TTCN_5059 | 45574 |
| TTCN_1088 | 31516 | TTCN_5060 | 45575 |
| ATCN_756 | 31517 | ATCN_3506 | 45576 |
| TTCN_1089 | 31518 | CTCN_6259 | 45577 |
| CTCN_1414 | 31519 | CTCN_6260 | 45578 |
| GTCN_803 | 31520 | CTCN_6261 | 45579 |
| TTCN_1090 | 31521 | TTCN_5061 | 45580 |
| CTCN_1415 | 31522 | GTCN_3295 | 45581 |
| CTCN_1416 | 31523 | CTCN_6262 | 45582 |
| CTCN_1417 | 31524 | GTCN_3296 | 45583 |
| ATCN_757 | 31525 | GTCN_3297 | 45584 |
| CTCN_1418 | 31526 | GTCN_3298 | 45585 |
| TTCN_1091 | 31527 | GTCN_3299 | 45586 |
| CTCN_1419 | 31528 | CTCN_6263 | 45587 |
| TTCN_1092 | 31529 | TTCN_5062 | 45588 |
| ATCN_758 | 31530 | GTCN_3300 | 45589 |
| GTCN_804 | 31531 | CTCN_6264 | 45590 |
| CTCN_1420 | 31532 | TTCN_5063 | 45591 |
| CTCN_1421 | 31533 | CTCN_6265 | 45592 |
| ATCN_759 | 31534 | CTCN_6266 | 45593 |
| CTCN_1422 | 31535 | GTCN_3301 | 45594 |

| | | | |
|---|---|---|---|
| TTCN_1093 | 31536 | GTCN_3302 | 45595 |
| CTCN_1423 | 31537 | ATCN_3507 | 45596 |
| TTCN_1094 | 31538 | ATCN_3508 | 45597 |
| CTCN_1424 | 31539 | TTCN_5064 | 45598 |
| ATCN_760 | 31540 | GTCN_3303 | 45599 |
| GTCN_805 | 31541 | ATCN_3509 | 45600 |
| CTCN_1425 | 31542 | ATCN_3510 | 45601 |
| ATCN_761 | 31543 | GTCN_3304 | 45602 |
| CTCN_1426 | 31544 | ATCN_3511 | 45603 |
| CTCN_1427 | 31545 | TTCN_5065 | 45604 |
| TTCN_1095 | 31546 | TTCN_5066 | 45605 |
| CTCN_1428 | 31547 | ATCN_3512 | 45606 |
| CTCN_1429 | 31548 | GTCN_3305 | 45607 |
| CTCN_1430 | 31549 | CTCN_6267 | 45608 |
| ATCN_762 | 31550 | GTCN_3306 | 45609 |
| TTCN_1096 | 31551 | ATCN_3513 | 45610 |
| GTCN_806 | 31552 | ATCN_3514 | 45611 |
| TTCN_1097 | 31553 | ATCN_3515 | 45612 |
| TTCN_1098 | 31554 | GTCN_3307 | 45613 |
| TTCN_1099 | 31555 | CTCN_6268 | 45614 |
| ATCN_763 | 31556 | CTCN_6269 | 45615 |
| ATCN_764 | 31557 | CTCN_6270 | 45616 |
| CTCN_1431 | 31558 | GTCN_3308 | 45617 |
| TTCN_1100 | 31559 | CTCN_6271 | 45618 |
| ATCN_765 | 31560 | ATCN_3516 | 45619 |
| ATCN_766 | 31561 | ATCN_3517 | 45620 |
| CTCN_1432 | 31562 | CTCN_6272 | 45621 |
| ATCN_767 | 31563 | CTCN_6273 | 45622 |
| ATCN_768 | 31564 | CTCN_6274 | 45623 |
| TTCN_1101 | 31565 | CTCN_6275 | 45624 |
| TTCN_1102 | 31566 | TTCN_5067 | 45625 |
| ATCN_769 | 31567 | ATCN_3518 | 45626 |
| ATCN_770 | 31568 | CTCN_6276 | 45627 |
| TTCN_1103 | 31569 | TTCN_5068 | 45628 |
| TTCN_1104 | 31570 | CTCN_6277 | 45629 |
| ATCN_771 | 31571 | ATCN_3519 | 45630 |
| TTCN_1105 | 31572 | CTCN_6278 | 45631 |
| CTCN_1433 | 31573 | TTCN_5069 | 45632 |
| ATCN_772 | 31574 | ATCN_3520 | 45633 |
| ATCN_773 | 31575 | GTCN_3309 | 45634 |
| CTCN_1434 | 31576 | GTCN_3310 | 45635 |
| TTCN_1106 | 31577 | TTCN_5070 | 45636 |
| CTCN_1435 | 31578 | TTCN_5071 | 45637 |

FIG. 37 (continued)

| | | | |
|---|---|---|---|
| TTCN_1107 | 31579 | ATCN_3521 | 45638 |
| GTCN_807 | 31580 | TTCN_5072 | 45639 |
| GTCN_808 | 31581 | GTCN_3311 | 45640 |
| GTCN_809 | 31582 | GTCN_3312 | 45641 |
| CTCN_1436 | 31583 | TTCN_5073 | 45642 |
| TTCN_1108 | 31584 | TTCN_5074 | 45643 |
| TTCN_1109 | 31585 | TTCN_5075 | 45644 |
| TTCN_1110 | 31586 | TTCN_5076 | 45645 |
| TTCN_1111 | 31587 | ATCN_3522 | 45646 |
| TTCN_1112 | 31588 | ATCN_3523 | 45647 |
| ATCN_774 | 31589 | TTCN_5077 | 45648 |
| TTCN_1113 | 31590 | CTCN_6279 | 45649 |
| GTCN_810 | 31591 | GTCN_3313 | 45650 |
| ATCN_775 | 31592 | GTCN_3314 | 45651 |
| TTCN_1114 | 31593 | CTCN_6280 | 45652 |
| GTCN_811 | 31594 | GTCN_3315 | 45653 |
| TTCN_1115 | 31595 | CTCN_6281 | 45654 |
| TTCN_1116 | 31596 | ATCN_3524 | 45655 |
| TTCN_1117 | 31597 | ATCN_3525 | 45656 |
| ATCN_776 | 31598 | ATCN_3526 | 45657 |
| TTCN_1118 | 31599 | TTCN_5078 | 45658 |
| TTCN_1119 | 31600 | CTCN_6282 | 45659 |
| ATCN_777 | 31601 | CTCN_6283 | 45660 |
| ATCN_778 | 31602 | CTCN_6284 | 45661 |
| ATCN_779 | 31603 | CTCN_6285 | 45662 |
| ATCN_780 | 31604 | TTCN_5079 | 45663 |
| TTCN_1120 | 31605 | ATCN_3527 | 45664 |
| ATCN_781 | 31606 | TTCN_5080 | 45665 |
| ATCN_782 | 31607 | CTCN_6286 | 45666 |
| ATCN_783 | 31608 | ATCN_3528 | 45667 |
| TTCN_1121 | 31609 | GTCN_3316 | 45668 |
| ATCN_784 | 31610 | GTCN_3317 | 45669 |
| TTCN_1122 | 31611 | GTCN_3318 | 45670 |
| TTCN_1123 | 31612 | CTCN_6287 | 45671 |
| ATCN_785 | 31613 | CTCN_6288 | 45672 |
| TTCN_1124 | 31614 | GTCN_3319 | 45673 |
| GTCN_812 | 31615 | ATCN_3529 | 45674 |
| CTCN_1437 | 31616 | CTCN_6289 | 45675 |
| ATCN_786 | 31617 | GTCN_3320 | 45676 |
| TTCN_1125 | 31618 | GTCN_3321 | 45677 |
| CTCN_1438 | 31619 | GTCN_3322 | 45678 |
| ATCN_787 | 31620 | TTCN_5081 | 45679 |
| ATCN_788 | 31621 | ATCN_3530 | 45680 |

| | | | |
|---|---|---|---|
| TTCN_1126 | 31622 | GTCN_3323 | 45681 |
| GTCN_813 | 31623 | TTCN_5082 | 45682 |
| TTCN_1127 | 31624 | GTCN_3324 | 45683 |
| TTCN_1128 | 31625 | GTCN_3325 | 45684 |
| TTCN_1129 | 31626 | ATCN_3531 | 45685 |
| ATCN_789 | 31627 | TTCN_5083 | 45686 |
| TTCN_1130 | 31628 | ATCN_3532 | 45687 |
| ATCN_790 | 31629 | ATCN_3533 | 45688 |
| TTCN_1131 | 31630 | TTCN_5084 | 45689 |
| TTCN_1132 | 31631 | TTCN_5085 | 45690 |
| ATCN_791 | 31632 | CTCN_6290 | 45691 |
| TTCN_1133 | 31633 | TTCN_5086 | 45692 |
| ATCN_792 | 31634 | CTCN_6291 | 45693 |
| CTCN_1439 | 31635 | TTCN_5087 | 45694 |
| TTCN_1134 | 31636 | ATCN_3534 | 45695 |
| ATCN_793 | 31637 | CTCN_6292 | 45696 |
| TTCN_1135 | 31638 | ATCN_3535 | 45697 |
| TTCN_1136 | 31639 | TTCN_5088 | 45698 |
| ATCN_794 | 31640 | ATCN_3536 | 45699 |
| TTCN_1137 | 31641 | ATCN_3537 | 45700 |
| TTCN_1138 | 31642 | CTCN_6293 | 45701 |
| GTCN_814 | 31643 | GTCN_3326 | 45702 |
| CTCN_1440 | 31644 | CTCN_6294 | 45703 |
| CTCN_1441 | 31645 | ATCN_3538 | 45704 |
| GTCN_815 | 31646 | TTCN_5089 | 45705 |
| ATCN_795 | 31647 | ATCN_3539 | 45706 |
| ATCN_796 | 31648 | TTCN_5090 | 45707 |
| TTCN_1139 | 31649 | CTCN_6295 | 45708 |
| TTCN_1140 | 31650 | CTCN_6296 | 45709 |
| ATCN_797 | 31651 | TTCN_5091 | 45710 |
| TTCN_1141 | 31652 | CTCN_6297 | 45711 |
| TTCN_1142 | 31653 | ATCN_3540 | 45712 |
| TTCN_1143 | 31654 | CTCN_6298 | 45713 |
| TTCN_1144 | 31655 | ATCN_3541 | 45714 |
| GTCN_816 | 31656 | CTCN_6299 | 45715 |
| CTCN_1442 | 31657 | CTCN_6300 | 45716 |
| TTCN_1145 | 31658 | TTCN_5092 | 45717 |
| CTCN_1443 | 31659 | TTCN_5093 | 45718 |
| GTCN_817 | 31660 | ATCN_3542 | 45719 |
| GTCN_818 | 31661 | GTCN_3327 | 45720 |
| ATCN_798 | 31662 | TTCN_5094 | 45721 |
| TTCN_1146 | 31663 | ATCN_3543 | 45722 |
| ATCN_799 | 31664 | TTCN_5095 | 45723 |

FIG. 37 (continued)

| | | | |
|---|---|---|---|
| CTCN_1444 | 31665 | TTCN_5096 | 45724 |
| TTCN_1147 | 31666 | ATCN_3544 | 45725 |
| GTCN_819 | 31667 | TTCN_5097 | 45726 |
| CTCN_1445 | 31668 | TTCN_5098 | 45727 |
| TTCN_1148 | 31669 | CTCN_6301 | 45728 |
| TTCN_1149 | 31670 | GTCN_3328 | 45729 |
| CTCN_1446 | 31671 | CTCN_6302 | 45730 |
| TTCN_1150 | 31672 | ATCN_3545 | 45731 |
| TTCN_1151 | 31673 | ATCN_3546 | 45732 |
| TTCN_1152 | 31674 | GTCN_3329 | 45733 |
| CTCN_1447 | 31675 | ATCN_3547 | 45734 |
| GTCN_820 | 31676 | ATCN_3548 | 45735 |
| GTCN_821 | 31677 | GTCN_3330 | 45736 |
| TTCN_1153 | 31678 | TTCN_5099 | 45737 |
| TTCN_1154 | 31679 | TTCN_5100 | 45738 |
| TTCN_1155 | 31680 | CTCN_6303 | 45739 |
| TTCN_1156 | 31681 | CTCN_6304 | 45740 |
| TTCN_1157 | 31682 | GTCN_3331 | 45741 |
| GTCN_822 | 31683 | TTCN_5101 | 45742 |
| GTCN_823 | 31684 | TTCN_5102 | 45743 |
| GTCN_824 | 31685 | TTCN_5103 | 45744 |
| GTCN_825 | 31686 | ATCN_3549 | 45745 |
| TTCN_1158 | 31687 | CTCN_6305 | 45746 |
| CTCN_1448 | 31688 | CTCN_6306 | 45747 |
| GTCN_826 | 31689 | CTCN_6307 | 45748 |
| TTCN_1159 | 31690 | TTCN_5104 | 45749 |
| CTCN_1449 | 31691 | CTCN_6308 | 45750 |
| ATCN_800 | 31692 | GTCN_3332 | 45751 |
| ATCN_801 | 31693 | TTCN_5105 | 45752 |
| CTCN_1450 | 31694 | CTCN_6309 | 45753 |
| TTCN_1160 | 31695 | GTCN_3333 | 45754 |
| CTCN_1451 | 31696 | TTCN_5106 | 45755 |
| GTCN_827 | 31697 | TTCN_5107 | 45756 |
| CTCN_1452 | 31698 | CTCN_6310 | 45757 |
| TTCN_1161 | 31699 | CTCN_6311 | 45758 |
| GTCN_828 | 31700 | CTCN_6312 | 45759 |
| CTCN_1453 | 31701 | GTCN_3334 | 45760 |
| ATCN_802 | 31702 | TTCN_5108 | 45761 |
| TTCN_1162 | 31703 | CTCN_6313 | 45762 |
| GTCN_829 | 31704 | TTCN_5109 | 45763 |
| CTCN_1454 | 31705 | ATCN_3550 | 45764 |
| TTCN_1163 | 31706 | CTCN_6314 | 45765 |
| TTCN_1164 | 31707 | ATCN_3551 | 45766 |

| | | | |
|---|---|---|---|
| ATCN_803 | 31708 | TTCN_5110 | 45767 |
| TTCN_1165 | 31709 | GTCN_3335 | 45768 |
| CTCN_1455 | 31710 | CTCN_6315 | 45769 |
| CTCN_1456 | 31711 | GTCN_3336 | 45770 |
| CTCN_1457 | 31712 | CTCN_6316 | 45771 |
| CTCN_1458 | 31713 | ATCN_3552 | 45772 |
| CTCN_1459 | 31714 | TTCN_5111 | 45773 |
| TTCN_1166 | 31715 | GTCN_3337 | 45774 |
| TTCN_1167 | 31716 | CTCN_6317 | 45775 |
| ATCN_804 | 31717 | CTCN_6318 | 45776 |
| TTCN_1168 | 31718 | CTCN_6319 | 45777 |
| ATCN_805 | 31719 | GTCN_3338 | 45778 |
| CTCN_1460 | 31720 | TTCN_5112 | 45779 |
| CTCN_1461 | 31721 | GTCN_3339 | 45780 |
| GTCN_830 | 31722 | GTCN_3340 | 45781 |
| TTCN_1169 | 31723 | CTCN_6320 | 45782 |
| GTCN_831 | 31724 | CTCN_6321 | 45783 |
| TTCN_1170 | 31725 | TTCN_5113 | 45784 |
| ATCN_806 | 31726 | ATCN_3553 | 45785 |
| TTCN_1171 | 31727 | TTCN_5114 | 45786 |
| CTCN_1462 | 31728 | CTCN_6322 | 45787 |
| GTCN_832 | 31729 | GTCN_3341 | 45788 |
| ATCN_807 | 31730 | CTCN_6323 | 45789 |
| CTCN_1463 | 31731 | CTCN_6324 | 45790 |
| GTCN_833 | 31732 | CTCN_6325 | 45791 |
| CTCN_1464 | 31733 | GTCN_3342 | 45792 |
| ATCN_808 | 31734 | CTCN_6326 | 45793 |
| ATCN_809 | 31735 | ATCN_3554 | 45794 |
| TTCN_1172 | 31736 | ATCN_3555 | 45795 |
| TTCN_1173 | 31737 | CTCN_6327 | 45796 |
| ATCN_810 | 31738 | CTCN_6328 | 45797 |
| TTCN_1174 | 31739 | CTCN_6329 | 45798 |
| TTCN_1175 | 31740 | CTCN_6330 | 45799 |
| ATCN_811 | 31741 | TTCN_5115 | 45800 |
| ATCN_812 | 31742 | TTCN_5116 | 45801 |
| CTCN_1465 | 31743 | CTCN_6331 | 45802 |
| GTCN_834 | 31744 | CTCN_6332 | 45803 |
| CTCN_1466 | 31745 | TTCN_5117 | 45804 |
| GTCN_835 | 31746 | CTCN_6333 | 45805 |
| TTCN_1176 | 31747 | ATCN_3556 | 45806 |
| TTCN_1177 | 31748 | GTCN_3343 | 45807 |
| ATCN_813 | 31749 | TTCN_5118 | 45808 |
| TTCN_1178 | 31750 | CTCN_6334 | 45809 |

FIG. 37 (continued)

| | | | | | | | |
|---|---|---|---|---|---|---|---|
| TTCN_1179 | 31751 | GTCN_3344 | 45810 | TTCN_1196 | 31794 | GTCN_3351 | 45853 |
| TTCN_1180 | 31752 | TTCN_5119 | 45811 | GTCN_841 | 31795 | CTCN_6352 | 45854 |
| CTCN_1467 | 31753 | GTCN_3345 | 45812 | TTCN_1197 | 31796 | TTCN_5127 | 45855 |
| TTCN_1181 | 31754 | GTCN_3346 | 45813 | TTCN_1198 | 31797 | ATCN_3568 | 45856 |
| ATCN_814 | 31755 | CTCN_6335 | 45814 | CTCN_1481 | 31798 | ATCN_3569 | 45857 |
| CTCN_1468 | 31756 | CTCN_6336 | 45815 | TTCN_1199 | 31799 | TTCN_5128 | 45858 |
| GTCN_836 | 31757 | GTCN_3347 | 45816 | GTCN_842 | 31800 | TTCN_5129 | 45859 |
| TTCN_1182 | 31758 | CTCN_6337 | 45817 | TTCN_1200 | 31801 | CTCN_6353 | 45860 |
| GTCN_837 | 31759 | ATCN_3557 | 45818 | TTCN_1201 | 31802 | TTCN_5130 | 45861 |
| GTCN_838 | 31760 | ATCN_3558 | 45819 | ATCN_821 | 31803 | CTCN_6354 | 45862 |
| TTCN_1183 | 31761 | CTCN_6338 | 45820 | ATCN_822 | 31804 | CTCN_6355 | 45863 |
| ATCN_815 | 31762 | ATCN_3559 | 45821 | TTCN_1202 | 31805 | GTCN_3352 | 45864 |
| CTCN_1469 | 31763 | CTCN_6339 | 45822 | TTCN_1203 | 31806 | TTCN_5131 | 45865 |
| ATCN_816 | 31764 | CTCN_6340 | 45823 | CTCN_1482 | 31807 | ATCN_3570 | 45866 |
| TTCN_1184 | 31765 | CTCN_6341 | 45824 | GTCN_843 | 31808 | TTCN_5132 | 45867 |
| CTCN_1470 | 31766 | TTCN_5120 | 45825 | GTCN_844 | 31809 | TTCN_5133 | 45868 |
| CTCN_1471 | 31767 | ATCN_3560 | 45826 | CTCN_1483 | 31810 | CTCN_6356 | 45869 |
| TTCN_1185 | 31768 | TTCN_5121 | 45827 | GTCN_845 | 31811 | CTCN_6357 | 45870 |
| ATCN_817 | 31769 | CTCN_6342 | 45828 | CTCN_1484 | 31812 | CTCN_6358 | 45871 |
| ATCN_818 | 31770 | GTCN_3348 | 45829 | CTCN_1485 | 31813 | ATCN_3571 | 45872 |
| CTCN_1472 | 31771 | ATCN_3561 | 45830 | GTCN_846 | 31814 | TTCN_5134 | 45873 |
| TTCN_1186 | 31772 | ATCN_3562 | 45831 | CTCN_1486 | 31815 | TTCN_5135 | 45874 |
| TTCN_1187 | 31773 | CTCN_6343 | 45832 | CTCN_1487 | 31816 | CTCN_6359 | 45875 |
| CTCN_1473 | 31774 | TTCN_5122 | 45833 | GTCN_847 | 31817 | TTCN_5136 | 45876 |
| GTCN_839 | 31775 | ATCN_3563 | 45834 | CTCN_1488 | 31818 | CTCN_6360 | 45877 |
| CTCN_1474 | 31776 | CTCN_6344 | 45835 | GTCN_848 | 31819 | CTCN_6361 | 45878 |
| ATCN_819 | 31777 | CTCN_6345 | 45836 | GTCN_849 | 31820 | CTCN_6362 | 45879 |
| ATCN_820 | 31778 | TTCN_5123 | 45837 | GTCN_850 | 31821 | GTCN_3353 | 45880 |
| TTCN_1188 | 31779 | ATCN_3564 | 45838 | ATCN_823 | 31822 | TTCN_5137 | 45881 |
| CTCN_1475 | 31780 | CTCN_6346 | 45839 | TTCN_1204 | 31823 | GTCN_3354 | 45882 |
| TTCN_1189 | 31781 | TTCN_5124 | 45840 | ATCN_824 | 31824 | ATCN_3572 | 45883 |
| TTCN_1190 | 31782 | TTCN_5125 | 45841 | CTCN_1489 | 31825 | TTCN_5138 | 45884 |
| TTCN_1191 | 31783 | ATCN_3565 | 45842 | ATCN_825 | 31826 | GTCN_3355 | 45885 |
| TTCN_1192 | 31784 | GTCN_3349 | 45843 | GTCN_851 | 31827 | CTCN_6363 | 45886 |
| TTCN_1193 | 31785 | GTCN_3350 | 45844 | CTCN_1490 | 31828 | GTCN_3356 | 45887 |
| CTCN_1476 | 31786 | TTCN_5126 | 45845 | TTCN_1205 | 31829 | GTCN_3357 | 45888 |
| CTCN_1477 | 31787 | CTCN_6347 | 45846 | TTCN_1206 | 31830 | TTCN_5139 | 45889 |
| GTCN_840 | 31788 | ATCN_3566 | 45847 | TTCN_1207 | 31831 | GTCN_3358 | 45890 |
| TTCN_1194 | 31789 | CTCN_6348 | 45848 | TTCN_1208 | 31832 | TTCN_5140 | 45891 |
| CTCN_1478 | 31790 | CTCN_6349 | 45849 | CTCN_1491 | 31833 | CTCN_6364 | 45892 |
| TTCN_1195 | 31791 | CTCN_6350 | 45850 | TTCN_1209 | 31834 | ATCN_3573 | 45893 |
| CTCN_1479 | 31792 | ATCN_3567 | 45851 | CTCN_1492 | 31835 | ATCN_3574 | 45894 |
| CTCN_1480 | 31793 | CTCN_6351 | 45852 | ATCN_826 | 31836 | TTCN_5141 | 45895 |

FIG. 37 (continued)

| | | | |
|---|---|---|---|
| CTCN_1493 | 31837 | TTCN_5142 | 45896 |
| CTCN_1494 | 31838 | TTCN_5143 | 45897 |
| ATCN_827 | 31839 | GTCN_3359 | 45898 |
| ATCN_828 | 31840 | CTCN_6365 | 45899 |
| CTCN_1495 | 31841 | GTCN_3360 | 45900 |
| CTCN_1496 | 31842 | TTCN_5144 | 45901 |
| CTCN_1497 | 31843 | TTCN_5145 | 45902 |
| CTCN_1498 | 31844 | TTCN_5146 | 45903 |
| CTCN_1499 | 31845 | TTCN_5147 | 45904 |
| CTCN_1500 | 31846 | CTCN_6366 | 45905 |
| CTCN_1501 | 31847 | CTCN_6367 | 45906 |
| GTCN_852 | 31848 | TTCN_5148 | 45907 |
| CTCN_1502 | 31849 | CTCN_6368 | 45908 |
| CTCN_1503 | 31850 | CTCN_6369 | 45909 |
| GTCN_853 | 31851 | ATCN_3575 | 45910 |
| CTCN_1504 | 31852 | GTCN_3361 | 45911 |
| CTCN_1505 | 31853 | GTCN_3362 | 45912 |
| TTCN_1210 | 31854 | TTCN_5149 | 45913 |
| TTCN_1211 | 31855 | TTCN_5150 | 45914 |
| TTCN_1212 | 31856 | TTCN_5151 | 45915 |
| CTCN_1506 | 31857 | CTCN_6370 | 45916 |
| ATCN_829 | 31858 | GTCN_3363 | 45917 |
| CTCN_1507 | 31859 | ATCN_3576 | 45918 |
| TTCN_1213 | 31860 | TTCN_5152 | 45919 |
| CTCN_1508 | 31861 | ATCN_3577 | 45920 |
| TTCN_1214 | 31862 | CTCN_6371 | 45921 |
| CTCN_1509 | 31863 | ATCN_3578 | 45922 |
| CTCN_1510 | 31864 | ATCN_3579 | 45923 |
| CTCN_1511 | 31865 | ATCN_3580 | 45924 |
| CTCN_1512 | 31866 | ATCN_3581 | 45925 |
| ATCN_830 | 31867 | CTCN_6372 | 45926 |
| GTCN_854 | 31868 | ATCN_3582 | 45927 |
| TTCN_1215 | 31869 | ATCN_3583 | 45928 |
| CTCN_1513 | 31870 | GTCN_3364 | 45929 |
| TTCN_1216 | 31871 | CTCN_6373 | 45930 |
| CTCN_1514 | 31872 | CTCN_6374 | 45931 |
| ATCN_831 | 31873 | TTCN_5153 | 45932 |
| ATCN_832 | 31874 | ATCN_3584 | 45933 |
| TTCN_1217 | 31875 | TTCN_5154 | 45934 |
| CTCN_1515 | 31876 | ATCN_3585 | 45935 |
| CTCN_1516 | 31877 | TTCN_5155 | 45936 |
| CTCN_1517 | 31878 | TTCN_5156 | 45937 |
| CTCN_1518 | 31879 | TTCN_5157 | 45938 |

| | | | |
|---|---|---|---|
| GTCN_855 | 31880 | TTCN_5158 | 45939 |
| CTCN_1519 | 31881 | CTCN_6375 | 45940 |
| TTCN_1218 | 31882 | GTCN_3365 | 45941 |
| CTCN_1520 | 31883 | TTCN_5159 | 45942 |
| CTCN_1521 | 31884 | ATCN_3586 | 45943 |
| TTCN_1219 | 31885 | ATCN_3587 | 45944 |
| CTCN_1522 | 31886 | GTCN_3366 | 45945 |
| TTCN_1220 | 31887 | ATCN_3588 | 45946 |
| CTCN_1523 | 31888 | GTCN_3367 | 45947 |
| TTCN_1221 | 31889 | ATCN_3589 | 45948 |
| GTCN_856 | 31890 | ATCN_3590 | 45949 |
| TTCN_1222 | 31891 | ATCN_3591 | 45950 |
| CTCN_1524 | 31892 | ATCN_3592 | 45951 |
| GTCN_857 | 31893 | ATCN_3593 | 45952 |
| CTCN_1525 | 31894 | CTCN_6376 | 45953 |
| GTCN_858 | 31895 | GTCN_3368 | 45954 |
| TTCN_1223 | 31896 | TTCN_5160 | 45955 |
| TTCN_1224 | 31897 | TTCN_5161 | 45956 |
| GTCN_859 | 31898 | TTCN_5162 | 45957 |
| TTCN_1225 | 31899 | TTCN_5163 | 45958 |
| ATCN_833 | 31900 | CTCN_6377 | 45959 |
| GTCN_860 | 31901 | GTCN_3369 | 45960 |
| CTCN_1526 | 31902 | CTCN_6378 | 45961 |
| TTCN_1226 | 31903 | TTCN_5164 | 45962 |
| CTCN_1527 | 31904 | TTCN_5165 | 45963 |
| ATCN_834 | 31905 | GTCN_3370 | 45964 |
| GTCN_861 | 31906 | TTCN_5166 | 45965 |
| GTCN_862 | 31907 | TTCN_5167 | 45966 |
| GTCN_863 | 31908 | GTCN_3371 | 45967 |
| ATCN_835 | 31909 | ATCN_3594 | 45968 |
| GTCN_864 | 31910 | TTCN_5168 | 45969 |
| ATCN_836 | 31911 | TTCN_5169 | 45970 |
| TTCN_1227 | 31912 | CTCN_6379 | 45971 |
| CTCN_1528 | 31913 | TTCN_5170 | 45972 |
| CTCN_1529 | 31914 | GTCN_3372 | 45973 |
| GTCN_865 | 31915 | ATCN_3595 | 45974 |
| GTCN_866 | 31916 | GTCN_3373 | 45975 |
| CTCN_1530 | 31917 | TTCN_5171 | 45976 |
| GTCN_867 | 31918 | TTCN_5172 | 45977 |
| TTCN_1228 | 31919 | CTCN_6380 | 45978 |
| TTCN_1229 | 31920 | GTCN_3374 | 45979 |
| CTCN_1531 | 31921 | CTCN_6381 | 45980 |
| TTCN_1230 | 31922 | CTCN_6382 | 45981 |

FIG. 37 (continued)

| | | | |
|---|---|---|---|
| TTCN_1231 | 31923 | ATCN_3596 | 45982 |
| CTCN_1532 | 31924 | GTCN_3375 | 45983 |
| GTCN_868 | 31925 | CTCN_6383 | 45984 |
| TTCN_1232 | 31926 | CTCN_6384 | 45985 |
| TTCN_1233 | 31927 | ATCN_3597 | 45986 |
| GTCN_869 | 31928 | CTCN_6385 | 45987 |
| GTCN_870 | 31929 | ATCN_3598 | 45988 |
| GTCN_871 | 31930 | GTCN_3376 | 45989 |
| CTCN_1533 | 31931 | TTCN_5173 | 45990 |
| ATCN_837 | 31932 | CTCN_6386 | 45991 |
| CTCN_1534 | 31933 | GTCN_3377 | 45992 |
| GTCN_872 | 31934 | CTCN_6387 | 45993 |
| CTCN_1535 | 31935 | GTCN_3378 | 45994 |
| CTCN_1536 | 31936 | TTCN_5174 | 45995 |
| ATCN_838 | 31937 | GTCN_3379 | 45996 |
| ATCN_839 | 31938 | TTCN_5175 | 45997 |
| TTCN_1234 | 31939 | ATCN_3599 | 45998 |
| TTCN_1235 | 31940 | CTCN_6388 | 45999 |
| CTCN_1537 | 31941 | GTCN_3380 | 46000 |
| GTCN_873 | 31942 | CTCN_6389 | 46001 |
| CTCN_1538 | 31943 | TTCN_5176 | 46002 |
| GTCN_874 | 31944 | CTCN_6390 | 46003 |
| ATCN_840 | 31945 | GTCN_3381 | 46004 |
| CTCN_1539 | 31946 | CTCN_6391 | 46005 |
| ATCN_841 | 31947 | CTCN_6392 | 46006 |
| ATCN_842 | 31948 | TTCN_5177 | 46007 |
| TTCN_1236 | 31949 | ATCN_3600 | 46008 |
| GTCN_875 | 31950 | CTCN_6393 | 46009 |
| CTCN_1540 | 31951 | CTCN_6394 | 46010 |
| CTCN_1541 | 31952 | TTCN_5178 | 46011 |
| CTCN_1542 | 31953 | CTCN_6395 | 46012 |
| ATCN_843 | 31954 | CTCN_6396 | 46013 |
| ATCN_844 | 31955 | CTCN_6397 | 46014 |
| CTCN_1543 | 31956 | TTCN_5179 | 46015 |
| CTCN_1544 | 31957 | TTCN_5180 | 46016 |
| ATCN_845 | 31958 | CTCN_6398 | 46017 |
| ATCN_846 | 31959 | GTCN_3382 | 46018 |
| ATCN_847 | 31960 | TTCN_5181 | 46019 |
| TTCN_1237 | 31961 | ATCN_3601 | 46020 |
| GTCN_876 | 31962 | ATCN_3602 | 46021 |
| GTCN_877 | 31963 | GTCN_3383 | 46022 |
| ATCN_848 | 31964 | GTCN_3384 | 46023 |
| GTCN_878 | 31965 | CTCN_6399 | 46024 |

| | | | |
|---|---|---|---|
| ATCN_849 | 31966 | GTCN_3385 | 46025 |
| CTCN_1545 | 31967 | CTCN_6400 | 46026 |
| TTCN_1238 | 31968 | ATCN_3603 | 46027 |
| TTCN_1239 | 31969 | CTCN_6401 | 46028 |
| TTCN_1240 | 31970 | CTCN_6402 | 46029 |
| CTCN_1546 | 31971 | CTCN_6403 | 46030 |
| CTCN_1547 | 31972 | ATCN_3604 | 46031 |
| ATCN_850 | 31973 | ATCN_3605 | 46032 |
| TTCN_1241 | 31974 | CTCN_6404 | 46033 |
| CTCN_1548 | 31975 | CTCN_6405 | 46034 |
| TTCN_1242 | 31976 | CTCN_6406 | 46035 |
| CTCN_1549 | 31977 | GTCN_3386 | 46036 |
| TTCN_1243 | 31978 | CTCN_6407 | 46037 |
| TTCN_1244 | 31979 | GTCN_3387 | 46038 |
| GTCN_879 | 31980 | CTCN_6408 | 46039 |
| ATCN_851 | 31981 | GTCN_3388 | 46040 |
| GTCN_880 | 31982 | CTCN_6409 | 46041 |
| CTCN_1550 | 31983 | GTCN_3389 | 46042 |
| ATCN_852 | 31984 | TTCN_5182 | 46043 |
| CTCN_1551 | 31985 | CTCN_6410 | 46044 |
| GTCN_881 | 31986 | TTCN_5183 | 46045 |
| CTCN_1552 | 31987 | CTCN_6411 | 46046 |
| ATCN_853 | 31988 | CTCN_6412 | 46047 |
| TTCN_1245 | 31989 | ATCN_3606 | 46048 |
| CTCN_1553 | 31990 | CTCN_6413 | 46049 |
| CTCN_1554 | 31991 | CTCN_6414 | 46050 |
| TTCN_1246 | 31992 | GTCN_3390 | 46051 |
| CTCN_1555 | 31993 | CTCN_6415 | 46052 |
| CTCN_1556 | 31994 | ATCN_3607 | 46053 |
| CTCN_1557 | 31995 | ATCN_3608 | 46054 |
| ATCN_854 | 31996 | CTCN_6416 | 46055 |
| ATCN_855 | 31997 | GTCN_3391 | 46056 |
| CTCN_1558 | 31998 | CTCN_6417 | 46057 |
| TTCN_1247 | 31999 | CTCN_6418 | 46058 |
| CTCN_1559 | 32000 | GTCN_3392 | 46059 |
| GTCN_882 | 32001 | GTCN_3393 | 46060 |
| TTCN_1248 | 32002 | CTCN_6419 | 46061 |
| GTCN_883 | 32003 | TTCN_5184 | 46062 |
| CTCN_1560 | 32004 | CTCN_6420 | 46063 |
| CTCN_1561 | 32005 | ATCN_3609 | 46064 |
| GTCN_884 | 32006 | ATCN_3610 | 46065 |
| TTCN_1249 | 32007 | ATCN_3611 | 46066 |
| TTCN_1250 | 32008 | GTCN_3394 | 46067 |

FIG. 37 (continued)

| | | | |
|---|---|---|---|
| CTCN_1562 | 32009 | TTCN_5185 | 46068 |
| ATCN_856 | 32010 | ATCN_3612 | 46069 |
| TTCN_1251 | 32011 | GTCN_3395 | 46070 |
| ATCN_857 | 32012 | GTCN_3396 | 46071 |
| TTCN_1252 | 32013 | CTCN_6421 | 46072 |
| TTCN_1253 | 32014 | CTCN_6422 | 46073 |
| TTCN_1254 | 32015 | TTCN_5186 | 46074 |
| GTCN_885 | 32016 | TTCN_5187 | 46075 |
| GTCN_886 | 32017 | TTCN_5188 | 46076 |
| CTCN_1563 | 32018 | ATCN_3613 | 46077 |
| ATCN_858 | 32019 | ATCN_3614 | 46078 |
| TTCN_1255 | 32020 | TTCN_5189 | 46079 |
| CTCN_1564 | 32021 | TTCN_5190 | 46080 |
| CTCN_1565 | 32022 | ATCN_3615 | 46081 |
| TTCN_1256 | 32023 | TTCN_5191 | 46082 |
| CTCN_1566 | 32024 | ATCN_3616 | 46083 |
| TTCN_1257 | 32025 | TTCN_5192 | 46084 |
| TTCN_1258 | 32026 | GTCN_3397 | 46085 |
| CTCN_1567 | 32027 | TTCN_5193 | 46086 |
| TTCN_1259 | 32028 | CTCN_6423 | 46087 |
| TTCN_1260 | 32029 | TTCN_5194 | 46088 |
| ATCN_859 | 32030 | TTCN_5195 | 46089 |
| TTCN_1261 | 32031 | TTCN_5196 | 46090 |
| TTCN_1262 | 32032 | TTCN_5197 | 46091 |
| TTCN_1263 | 32033 | ATCN_3617 | 46092 |
| TTCN_1264 | 32034 | ATCN_3618 | 46093 |
| TTCN_1265 | 32035 | TTCN_5198 | 46094 |
| TTCN_1266 | 32036 | GTCN_3398 | 46095 |
| CTCN_1568 | 32037 | CTCN_6424 | 46096 |
| ATCN_860 | 32038 | ATCN_3619 | 46097 |
| TTCN_1267 | 32039 | ATCN_3620 | 46098 |
| TTCN_1268 | 32040 | CTCN_6425 | 46099 |
| TTCN_1269 | 32041 | TTCN_5199 | 46100 |
| GTCN_887 | 32042 | CTCN_6426 | 46101 |
| TTCN_1270 | 32043 | GTCN_3399 | 46102 |
| TTCN_1271 | 32044 | TTCN_5200 | 46103 |
| CTCN_1569 | 32045 | GTCN_3400 | 46104 |
| ATCN_861 | 32046 | TTCN_5201 | 46105 |
| CTCN_1570 | 32047 | ATCN_3621 | 46106 |
| ATCN_862 | 32048 | ATCN_3622 | 46107 |
| CTCN_1571 | 32049 | TTCN_5202 | 46108 |
| GTCN_888 | 32050 | CTCN_6427 | 46109 |
| TTCN_1272 | 32051 | ATCN_3623 | 46110 |

| | | | |
|---|---|---|---|
| ATCN_863 | 32052 | CTCN_6428 | 46111 |
| GTCN_889 | 32053 | GTCN_3401 | 46112 |
| TTCN_1273 | 32054 | CTCN_6429 | 46113 |
| CTCN_1572 | 32055 | GTCN_3402 | 46114 |
| GTCN_890 | 32056 | ATCN_3624 | 46115 |
| CTCN_1573 | 32057 | CTCN_6430 | 46116 |
| GTCN_891 | 32058 | ATCN_3625 | 46117 |
| TTCN_1274 | 32059 | ATCN_3626 | 46118 |
| CTCN_1574 | 32060 | CTCN_6431 | 46119 |
| GTCN_892 | 32061 | CTCN_6432 | 46120 |
| TTCN_1275 | 32062 | CTCN_6433 | 46121 |
| TTCN_1276 | 32063 | TTCN_5203 | 46122 |
| GTCN_893 | 32064 | TTCN_5204 | 46123 |
| CTCN_1575 | 32065 | CTCN_6434 | 46124 |
| TTCN_1277 | 32066 | CTCN_6435 | 46125 |
| TTCN_1278 | 32067 | CTCN_6436 | 46126 |
| TTCN_1279 | 32068 | CTCN_6437 | 46127 |
| GTCN_894 | 32069 | ATCN_3627 | 46128 |
| TTCN_1280 | 32070 | CTCN_6438 | 46129 |
| TTCN_1281 | 32071 | ATCN_3628 | 46130 |
| TTCN_1282 | 32072 | TTCN_5205 | 46131 |
| TTCN_1283 | 32073 | GTCN_3403 | 46132 |
| CTCN_1576 | 32074 | CTCN_6439 | 46133 |
| GTCN_895 | 32075 | CTCN_6440 | 46134 |
| ATCN_864 | 32076 | GTCN_3404 | 46135 |
| CTCN_1577 | 32077 | CTCN_6441 | 46136 |
| TTCN_1284 | 32078 | ATCN_3629 | 46137 |
| GTCN_896 | 32079 | ATCN_3630 | 46138 |
| CTCN_1578 | 32080 | CTCN_6442 | 46139 |
| TTCN_1285 | 32081 | TTCN_5206 | 46140 |
| ATCN_865 | 32082 | ATCN_3631 | 46141 |
| ATCN_866 | 32083 | CTCN_6443 | 46142 |
| ATCN_867 | 32084 | TTCN_5207 | 46143 |
| ATCN_868 | 32085 | ATCN_3632 | 46144 |
| CTCN_1579 | 32086 | TTCN_5208 | 46145 |
| CTCN_1580 | 32087 | ATCN_3633 | 46146 |
| TTCN_1286 | 32088 | GTCN_3405 | 46147 |
| GTCN_897 | 32089 | ATCN_3634 | 46148 |
| CTCN_1581 | 32090 | CTCN_6444 | 46149 |
| ATCN_869 | 32091 | TTCN_5209 | 46150 |
| CTCN_1582 | 32092 | GTCN_3406 | 46151 |
| GTCN_898 | 32093 | GTCN_3407 | 46152 |
| CTCN_1583 | 32094 | TTCN_5210 | 46153 |

FIG. 37 (continued)

| | | | |
|---|---|---|---|
| CTCN_1584 | 32095 | GTCN_3408 | 46154 |
| TTCN_1287 | 32096 | CTCN_6445 | 46155 |
| TTCN_1288 | 32097 | GTCN_3409 | 46156 |
| TTCN_1289 | 32098 | GTCN_3410 | 46157 |
| CTCN_1585 | 32099 | GTCN_3411 | 46158 |
| GTCN_899 | 32100 | CTCN_6446 | 46159 |
| CTCN_1586 | 32101 | CTCN_6447 | 46160 |
| CTCN_1587 | 32102 | CTCN_6448 | 46161 |
| CTCN_1588 | 32103 | CTCN_6449 | 46162 |
| TTCN_1290 | 32104 | ATCN_3635 | 46163 |
| CTCN_1589 | 32105 | TTCN_5211 | 46164 |
| TTCN_1291 | 32106 | TTCN_5212 | 46165 |
| ATCN_870 | 32107 | CTCN_6450 | 46166 |
| TTCN_1292 | 32108 | CTCN_6451 | 46167 |
| TTCN_1293 | 32109 | CTCN_6452 | 46168 |
| GTCN_900 | 32110 | ATCN_3636 | 46169 |
| TTCN_1294 | 32111 | CTCN_6453 | 46170 |
| TTCN_1295 | 32112 | TTCN_5213 | 46171 |
| TTCN_1296 | 32113 | GTCN_3412 | 46172 |
| ATCN_871 | 32114 | GTCN_3413 | 46173 |
| CTCN_1590 | 32115 | TTCN_5214 | 46174 |
| TTCN_1297 | 32116 | GTCN_3414 | 46175 |
| TTCN_1298 | 32117 | ATCN_3637 | 46176 |
| ATCN_872 | 32118 | GTCN_3415 | 46177 |
| GTCN_901 | 32119 | GTCN_3416 | 46178 |
| TTCN_1299 | 32120 | ATCN_3638 | 46179 |
| CTCN_1591 | 32121 | GTCN_3417 | 46180 |
| TTCN_1300 | 32122 | ATCN_3639 | 46181 |
| ATCN_873 | 32123 | TTCN_5215 | 46182 |
| TTCN_1301 | 32124 | CTCN_6454 | 46183 |
| CTCN_1592 | 32125 | CTCN_6455 | 46184 |
| TTCN_1302 | 32126 | GTCN_3418 | 46185 |
| TTCN_1303 | 32127 | CTCN_6456 | 46186 |
| CTCN_1593 | 32128 | ATCN_3640 | 46187 |
| GTCN_902 | 32129 | TTCN_5216 | 46188 |
| CTCN_1594 | 32130 | ATCN_3641 | 46189 |
| TTCN_1304 | 32131 | GTCN_3419 | 46190 |
| TTCN_1305 | 32132 | TTCN_5217 | 46191 |
| TTCN_1306 | 32133 | TTCN_5218 | 46192 |
| TTCN_1307 | 32134 | ATCN_3642 | 46193 |
| TTCN_1308 | 32135 | TTCN_5219 | 46194 |
| TTCN_1309 | 32136 | TTCN_5220 | 46195 |
| TTCN_1310 | 32137 | ATCN_3643 | 46196 |

| | | | |
|---|---|---|---|
| ATCN_874 | 32138 | TTCN_5221 | 46197 |
| ATCN_875 | 32139 | TTCN_5222 | 46198 |
| ATCN_876 | 32140 | GTCN_3420 | 46199 |
| ATCN_877 | 32141 | TTCN_5223 | 46200 |
| CTCN_1595 | 32142 | TTCN_5224 | 46201 |
| GTCN_903 | 32143 | GTCN_3421 | 46202 |
| TTCN_1311 | 32144 | CTCN_6457 | 46203 |
| CTCN_1596 | 32145 | GTCN_3422 | 46204 |
| GTCN_904 | 32146 | TTCN_5225 | 46205 |
| CTCN_1597 | 32147 | CTCN_6458 | 46206 |
| CTCN_1598 | 32148 | ATCN_3644 | 46207 |
| TTCN_1312 | 32149 | TTCN_5226 | 46208 |
| GTCN_905 | 32150 | ATCN_3645 | 46209 |
| TTCN_1313 | 32151 | CTCN_6459 | 46210 |
| GTCN_906 | 32152 | TTCN_5227 | 46211 |
| ATCN_878 | 32153 | GTCN_3423 | 46212 |
| ATCN_879 | 32154 | ATCN_3646 | 46213 |
| ATCN_880 | 32155 | ATCN_3647 | 46214 |
| CTCN_1599 | 32156 | TTCN_5228 | 46215 |
| CTCN_1600 | 32157 | GTCN_3424 | 46216 |
| CTCN_1601 | 32158 | ATCN_3648 | 46217 |
| CTCN_1602 | 32159 | CTCN_6460 | 46218 |
| TTCN_1314 | 32160 | ATCN_3649 | 46219 |
| CTCN_1603 | 32161 | ATCN_3650 | 46220 |
| GTCN_907 | 32162 | GTCN_3425 | 46221 |
| TTCN_1315 | 32163 | CTCN_6461 | 46222 |
| TTCN_1316 | 32164 | GTCN_3426 | 46223 |
| ATCN_881 | 32165 | TTCN_5229 | 46224 |
| CTCN_1604 | 32166 | TTCN_5230 | 46225 |
| CTCN_1605 | 32167 | CTCN_6462 | 46226 |
| CTCN_1606 | 32168 | TTCN_5231 | 46227 |
| TTCN_1317 | 32169 | GTCN_3427 | 46228 |
| CTCN_1607 | 32170 | CTCN_6463 | 46229 |
| TTCN_1318 | 32171 | TTCN_5232 | 46230 |
| CTCN_1608 | 32172 | GTCN_3428 | 46231 |
| TTCN_1319 | 32173 | CTCN_6464 | 46232 |
| TTCN_1320 | 32174 | ATCN_3651 | 46233 |
| TTCN_1321 | 32175 | GTCN_3429 | 46234 |
| TTCN_1322 | 32176 | CTCN_6465 | 46235 |
| CTCN_1609 | 32177 | TTCN_5233 | 46236 |
| ATCN_882 | 32178 | CTCN_6466 | 46237 |
| ATCN_883 | 32179 | ATCN_3652 | 46238 |
| TTCN_1323 | 32180 | TTCN_5234 | 46239 |

FIG. 37 (continued)

| | | | |
|---|---|---|---|
| GTCN_908 | 32181 | TTCN_5235 | 46240 |
| CTCN_1610 | 32182 | CTCN_6467 | 46241 |
| ATCN_884 | 32183 | TTCN_5236 | 46242 |
| TTCN_1324 | 32184 | CTCN_6468 | 46243 |
| CTCN_1611 | 32185 | CTCN_6469 | 46244 |
| TTCN_1325 | 32186 | ATCN_3653 | 46245 |
| GTCN_909 | 32187 | ATCN_3654 | 46246 |
| CTCN_1612 | 32188 | TTCN_5237 | 46247 |
| ATCN_885 | 32189 | ATCN_3655 | 46248 |
| ATCN_886 | 32190 | GTCN_3430 | 46249 |
| TTCN_1326 | 32191 | ATCN_3656 | 46250 |
| ATCN_887 | 32192 | ATCN_3657 | 46251 |
| ATCN_888 | 32193 | ATCN_3658 | 46252 |
| TTCN_1327 | 32194 | GTCN_3431 | 46253 |
| TTCN_1328 | 32195 | TTCN_5238 | 46254 |
| ATCN_889 | 32196 | CTCN_6470 | 46255 |
| CTCN_1613 | 32197 | GTCN_3432 | 46256 |
| GTCN_910 | 32198 | TTCN_5239 | 46257 |
| TTCN_1329 | 32199 | CTCN_6471 | 46258 |
| CTCN_1614 | 32200 | TTCN_5240 | 46259 |
| GTCN_911 | 32201 | TTCN_5241 | 46260 |
| TTCN_1330 | 32202 | TTCN_5242 | 46261 |
| TTCN_1331 | 32203 | CTCN_6472 | 46262 |
| ATCN_890 | 32204 | CTCN_6473 | 46263 |
| CTCN_1615 | 32205 | GTCN_3433 | 46264 |
| TTCN_1332 | 32206 | GTCN_3434 | 46265 |
| ATCN_891 | 32207 | TTCN_5243 | 46266 |
| TTCN_1333 | 32208 | ATCN_3659 | 46267 |
| TTCN_1334 | 32209 | CTCN_6474 | 46268 |
| ATCN_892 | 32210 | GTCN_3435 | 46269 |
| ATCN_893 | 32211 | TTCN_5244 | 46270 |
| TTCN_1335 | 32212 | TTCN_5245 | 46271 |
| TTCN_1336 | 32213 | ATCN_3660 | 46272 |
| TTCN_1337 | 32214 | TTCN_5246 | 46273 |
| ATCN_894 | 32215 | TTCN_5247 | 46274 |
| CTCN_1616 | 32216 | TTCN_5248 | 46275 |
| ATCN_895 | 32217 | TTCN_5249 | 46276 |
| TTCN_1338 | 32218 | ATCN_3661 | 46277 |
| TTCN_1339 | 32219 | TTCN_5250 | 46278 |
| CTCN_1617 | 32220 | ATCN_3662 | 46279 |
| TTCN_1340 | 32221 | CTCN_6475 | 46280 |
| ATCN_896 | 32222 | TTCN_5251 | 46281 |
| TTCN_1341 | 32223 | CTCN_6476 | 46282 |

| | | | |
|---|---|---|---|
| CTCN_1618 | 32224 | CTCN_6477 | 46283 |
| TTCN_1342 | 32225 | CTCN_6478 | 46284 |
| GTCN_912 | 32226 | GTCN_3436 | 46285 |
| CTCN_1619 | 32227 | GTCN_3437 | 46286 |
| GTCN_913 | 32228 | CTCN_6479 | 46287 |
| ATCN_897 | 32229 | ATCN_3663 | 46288 |
| CTCN_1620 | 32230 | TTCN_5252 | 46289 |
| ATCN_898 | 32231 | CTCN_6480 | 46290 |
| ATCN_899 | 32232 | TTCN_5253 | 46291 |
| GTCN_914 | 32233 | CTCN_6481 | 46292 |
| GTCN_915 | 32234 | CTCN_6482 | 46293 |
| TTCN_1343 | 32235 | TTCN_5254 | 46294 |
| ATCN_900 | 32236 | TTCN_5255 | 46295 |
| CTCN_1621 | 32237 | ATCN_3664 | 46296 |
| CTCN_1622 | 32238 | CTCN_6483 | 46297 |
| ATCN_901 | 32239 | ATCN_3665 | 46298 |
| CTCN_1623 | 32240 | CTCN_6484 | 46299 |
| CTCN_1624 | 32241 | CTCN_6485 | 46300 |
| TTCN_1344 | 32242 | TTCN_5256 | 46301 |
| ATCN_902 | 32243 | CTCN_6486 | 46302 |
| CTCN_1625 | 32244 | TTCN_5257 | 46303 |
| GTCN_916 | 32245 | TTCN_5258 | 46304 |
| GTCN_917 | 32246 | CTCN_6487 | 46305 |
| GTCN_918 | 32247 | GTCN_3438 | 46306 |
| GTCN_919 | 32248 | ATCN_3666 | 46307 |
| CTCN_1626 | 32249 | TTCN_5259 | 46308 |
| TTCN_1345 | 32250 | TTCN_5260 | 46309 |
| GTCN_920 | 32251 | CTCN_6488 | 46310 |
| CTCN_1627 | 32252 | CTCN_6489 | 46311 |
| CTCN_1628 | 32253 | ATCN_3667 | 46312 |
| CTCN_1629 | 32254 | TTCN_5261 | 46313 |
| ATCN_903 | 32255 | ATCN_3668 | 46314 |
| ATCN_904 | 32256 | GTCN_3439 | 46315 |
| CTCN_1630 | 32257 | GTCN_3440 | 46316 |
| CTCN_1631 | 32258 | ATCN_3669 | 46317 |
| CTCN_1632 | 32259 | ATCN_3670 | 46318 |
| CTCN_1633 | 32260 | ATCN_3671 | 46319 |
| ATCN_905 | 32261 | TTCN_5262 | 46320 |
| ATCN_906 | 32262 | GTCN_3441 | 46321 |
| CTCN_1634 | 32263 | CTCN_6490 | 46322 |
| GTCN_921 | 32264 | CTCN_6491 | 46323 |
| CTCN_1635 | 32265 | GTCN_3442 | 46324 |
| GTCN_922 | 32266 | ATCN_3672 | 46325 |

FIG. 37 (continued)

| | | | |
|---|---|---|---|
| CTCN_1636 | 32267 | TTCN_5263 | 46326 |
| CTCN_1637 | 32268 | TTCN_5264 | 46327 |
| GTCN_923 | 32269 | GTCN_3443 | 46328 |
| TTCN_1346 | 32270 | GTCN_3444 | 46329 |
| GTCN_924 | 32271 | TTCN_5265 | 46330 |
| GTCN_925 | 32272 | CTCN_6492 | 46331 |
| CTCN_1638 | 32273 | CTCN_6493 | 46332 |
| TTCN_1347 | 32274 | GTCN_3445 | 46333 |
| TTCN_1348 | 32275 | TTCN_5266 | 46334 |
| CTCN_1639 | 32276 | ATCN_3673 | 46335 |
| TTCN_1349 | 32277 | CTCN_6494 | 46336 |
| TTCN_1350 | 32278 | CTCN_6495 | 46337 |
| TTCN_1351 | 32279 | CTCN_6496 | 46338 |
| ATCN_907 | 32280 | TTCN_5267 | 46339 |
| CTCN_1640 | 32281 | ATCN_3674 | 46340 |
| CTCN_1641 | 32282 | GTCN_3446 | 46341 |
| TTCN_1352 | 32283 | TTCN_5268 | 46342 |
| GTCN_926 | 32284 | ATCN_3675 | 46343 |
| CTCN_1642 | 32285 | TTCN_5269 | 46344 |
| CTCN_1643 | 32286 | ATCN_3676 | 46345 |
| CTCN_1644 | 32287 | TTCN_5270 | 46346 |
| ATCN_908 | 32288 | GTCN_3447 | 46347 |
| ATCN_909 | 32289 | TTCN_5271 | 46348 |
| TTCN_1353 | 32290 | ATCN_3677 | 46349 |
| CTCN_1645 | 32291 | CTCN_6497 | 46350 |
| ATCN_910 | 32292 | TTCN_5272 | 46351 |
| GTCN_927 | 32293 | GTCN_3448 | 46352 |
| TTCN_1354 | 32294 | CTCN_6498 | 46353 |
| TTCN_1355 | 32295 | CTCN_6499 | 46354 |
| TTCN_1356 | 32296 | ATCN_3678 | 46355 |
| GTCN_928 | 32297 | GTCN_3449 | 46356 |
| GTCN_929 | 32298 | CTCN_6500 | 46357 |
| CTCN_1646 | 32299 | GTCN_3450 | 46358 |
| TTCN_1357 | 32300 | CTCN_6501 | 46359 |
| CTCN_1647 | 32301 | CTCN_6502 | 46360 |
| ATCN_911 | 32302 | CTCN_6503 | 46361 |
| ATCN_912 | 32303 | GTCN_3451 | 46362 |
| CTCN_1648 | 32304 | CTCN_6504 | 46363 |
| TTCN_1358 | 32305 | TTCN_5273 | 46364 |
| TTCN_1359 | 32306 | TTCN_5274 | 46365 |
| TTCN_1360 | 32307 | GTCN_3452 | 46366 |
| TTCN_1361 | 32308 | ATCN_3679 | 46367 |
| ATCN_913 | 32309 | ATCN_3680 | 46368 |

| | | | |
|---|---|---|---|
| TTCN_1362 | 32310 | ATCN_3681 | 46369 |
| ATCN_914 | 32311 | CTCN_6505 | 46370 |
| ATCN_915 | 32312 | CTCN_6506 | 46371 |
| CTCN_1649 | 32313 | TTCN_5275 | 46372 |
| TTCN_1363 | 32314 | TTCN_5276 | 46373 |
| CTCN_1650 | 32315 | GTCN_3453 | 46374 |
| CTCN_1651 | 32316 | TTCN_5277 | 46375 |
| GTCN_930 | 32317 | CTCN_6507 | 46376 |
| TTCN_1364 | 32318 | TTCN_5278 | 46377 |
| GTCN_931 | 32319 | CTCN_6508 | 46378 |
| GTCN_932 | 32320 | TTCN_5279 | 46379 |
| ATCN_916 | 32321 | ATCN_3682 | 46380 |
| GTCN_933 | 32322 | GTCN_3454 | 46381 |
| ATCN_917 | 32323 | TTCN_5280 | 46382 |
| ATCN_918 | 32324 | TTCN_5281 | 46383 |
| TTCN_1365 | 32325 | GTCN_3455 | 46384 |
| TTCN_1366 | 32326 | TTCN_5282 | 46385 |
| TTCN_1367 | 32327 | CTCN_6509 | 46386 |
| CTCN_1652 | 32328 | TTCN_5283 | 46387 |
| TTCN_1368 | 32329 | GTCN_3456 | 46388 |
| TTCN_1369 | 32330 | ATCN_3683 | 46389 |
| CTCN_1653 | 32331 | ATCN_3684 | 46390 |
| ATCN_919 | 32332 | CTCN_6510 | 46391 |
| CTCN_1654 | 32333 | TTCN_5284 | 46392 |
| CTCN_1655 | 32334 | TTCN_5285 | 46393 |
| CTCN_1656 | 32335 | GTCN_3457 | 46394 |
| CTCN_1657 | 32336 | ATCN_3685 | 46395 |
| ATCN_920 | 32337 | TTCN_5286 | 46396 |
| ATCN_921 | 32338 | CTCN_6511 | 46397 |
| CTCN_1658 | 32339 | ATCN_3686 | 46398 |
| CTCN_1659 | 32340 | TTCN_5287 | 46399 |
| CTCN_1660 | 32341 | TTCN_5288 | 46400 |
| GTCN_934 | 32342 | TTCN_5289 | 46401 |
| TTCN_1370 | 32343 | TTCN_5290 | 46402 |
| TTCN_1371 | 32344 | GTCN_3458 | 46403 |
| ATCN_922 | 32345 | CTCN_6512 | 46404 |
| CTCN_1661 | 32346 | GTCN_3459 | 46405 |
| CTCN_1662 | 32347 | ATCN_3687 | 46406 |
| GTCN_935 | 32348 | CTCN_6513 | 46407 |
| CTCN_1663 | 32349 | CTCN_6514 | 46408 |
| TTCN_1372 | 32350 | CTCN_6515 | 46409 |
| ATCN_923 | 32351 | TTCN_5291 | 46410 |
| TTCN_1373 | 32352 | GTCN_3460 | 46411 |

FIG. 37 (continued)

| | | | |
|---|---|---|---|
| CTCN_1664 | 32353 | CTCN_6516 | 46412 |
| GTCN_936 | 32354 | GTCN_3461 | 46413 |
| CTCN_1665 | 32355 | TTCN_5292 | 46414 |
| TTCN_1374 | 32356 | GTCN_3462 | 46415 |
| CTCN_1666 | 32357 | TTCN_5293 | 46416 |
| TTCN_1375 | 32358 | CTCN_6517 | 46417 |
| GTCN_937 | 32359 | TTCN_5294 | 46418 |
| CTCN_1667 | 32360 | GTCN_3463 | 46419 |
| TTCN_1376 | 32361 | TTCN_5295 | 46420 |
| ATCN_924 | 32362 | TTCN_5296 | 46421 |
| ATCN_925 | 32363 | GTCN_3464 | 46422 |
| CTCN_1668 | 32364 | GTCN_3465 | 46423 |
| CTCN_1669 | 32365 | CTCN_6518 | 46424 |
| CTCN_1670 | 32366 | TTCN_5297 | 46425 |
| TTCN_1377 | 32367 | CTCN_6519 | 46426 |
| ATCN_926 | 32368 | ATCN_3688 | 46427 |
| TTCN_1378 | 32369 | TTCN_5298 | 46428 |
| ATCN_927 | 32370 | TTCN_5299 | 46429 |
| CTCN_1671 | 32371 | TTCN_5300 | 46430 |
| CTCN_1672 | 32372 | TTCN_5301 | 46431 |
| CTCN_1673 | 32373 | TTCN_5302 | 46432 |
| CTCN_1674 | 32374 | CTCN_6520 | 46433 |
| ATCN_928 | 32375 | GTCN_3466 | 46434 |
| ATCN_929 | 32376 | CTCN_6521 | 46435 |
| CTCN_1675 | 32377 | ATCN_3689 | 46436 |
| CTCN_1676 | 32378 | ATCN_3690 | 46437 |
| TTCN_1379 | 32379 | ATCN_3691 | 46438 |
| ATCN_930 | 32380 | CTCN_6522 | 46439 |
| CTCN_1677 | 32381 | TTCN_5303 | 46440 |
| CTCN_1678 | 32382 | CTCN_6523 | 46441 |
| CTCN_1679 | 32383 | CTCN_6524 | 46442 |
| CTCN_1680 | 32384 | GTCN_3467 | 46443 |
| TTCN_1380 | 32385 | CTCN_6525 | 46444 |
| CTCN_1681 | 32386 | CTCN_6526 | 46445 |
| CTCN_1682 | 32387 | CTCN_6527 | 46446 |
| TTCN_1381 | 32388 | TTCN_5304 | 46447 |
| CTCN_1683 | 32389 | TTCN_5305 | 46448 |
| CTCN_1684 | 32390 | TTCN_5306 | 46449 |
| CTCN_1685 | 32391 | CTCN_6528 | 46450 |
| TTCN_1382 | 32392 | CTCN_6529 | 46451 |
| CTCN_1686 | 32393 | GTCN_3468 | 46452 |
| ATCN_931 | 32394 | GTCN_3469 | 46453 |
| CTCN_1687 | 32395 | TTCN_5307 | 46454 |

| | | | |
|---|---|---|---|
| TTCN_1383 | 32396 | CTCN_6530 | 46455 |
| CTCN_1688 | 32397 | ATCN_3692 | 46456 |
| CTCN_1689 | 32398 | ATCN_3693 | 46457 |
| TTCN_1384 | 32399 | ATCN_3694 | 46458 |
| TTCN_1385 | 32400 | CTCN_6531 | 46459 |
| TTCN_1386 | 32401 | CTCN_6532 | 46460 |
| CTCN_1690 | 32402 | ATCN_3695 | 46461 |
| GTCN_938 | 32403 | CTCN_6533 | 46462 |
| ATCN_932 | 32404 | ATCN_3696 | 46463 |
| TTCN_1387 | 32405 | ATCN_3697 | 46464 |
| ATCN_933 | 32406 | CTCN_6534 | 46465 |
| GTCN_939 | 32407 | CTCN_6535 | 46466 |
| CTCN_1691 | 32408 | ATCN_3698 | 46467 |
| CTCN_1692 | 32409 | TTCN_5308 | 46468 |
| CTCN_1693 | 32410 | TTCN_5309 | 46469 |
| CTCN_1694 | 32411 | TTCN_5310 | 46470 |
| CTCN_1695 | 32412 | GTCN_3470 | 46471 |
| CTCN_1696 | 32413 | GTCN_3471 | 46472 |
| ATCN_934 | 32414 | ATCN_3699 | 46473 |
| CTCN_1697 | 32415 | CTCN_6536 | 46474 |
| CTCN_1698 | 32416 | CTCN_6537 | 46475 |
| TTCN_1388 | 32417 | TTCN_5311 | 46476 |
| GTCN_940 | 32418 | ATCN_3700 | 46477 |
| CTCN_1699 | 32419 | TTCN_5312 | 46478 |
| ATCN_935 | 32420 | TTCN_5313 | 46479 |
| CTCN_1700 | 32421 | ATCN_3701 | 46480 |
| CTCN_1701 | 32422 | TTCN_5314 | 46481 |
| CTCN_1702 | 32423 | TTCN_5315 | 46482 |
| TTCN_1389 | 32424 | TTCN_5316 | 46483 |
| ATCN_936 | 32425 | ATCN_3702 | 46484 |
| ATCN_937 | 32426 | TTCN_5317 | 46485 |
| TTCN_1390 | 32427 | TTCN_5318 | 46486 |
| CTCN_1703 | 32428 | CTCN_6538 | 46487 |
| GTCN_941 | 32429 | CTCN_6539 | 46488 |
| CTCN_1704 | 32430 | TTCN_5319 | 46489 |
| CTCN_1705 | 32431 | TTCN_5320 | 46490 |
| GTCN_942 | 32432 | CTCN_6540 | 46491 |
| ATCN_938 | 32433 | TTCN_5321 | 46492 |
| CTCN_1706 | 32434 | TTCN_5322 | 46493 |
| GTCN_943 | 32435 | TTCN_5323 | 46494 |
| CTCN_1707 | 32436 | TTCN_5324 | 46495 |
| CTCN_1708 | 32437 | TTCN_5325 | 46496 |
| GTCN_944 | 32438 | ATCN_3703 | 46497 |

FIG. 37 (continued)

| | | | |
|---|---|---|---|
| ATCN_939 | 32439 | GTCN_3472 | 46498 |
| CTCN_1709 | 32440 | TTCN_5326 | 46499 |
| ATCN_940 | 32441 | GTCN_3473 | 46500 |
| GTCN_945 | 32442 | TTCN_5327 | 46501 |
| CTCN_1710 | 32443 | ATCN_3704 | 46502 |
| GTCN_946 | 32444 | CTCN_6541 | 46503 |
| CTCN_1711 | 32445 | CTCN_6542 | 46504 |
| CTCN_1712 | 32446 | TTCN_5328 | 46505 |
| GTCN_947 | 32447 | ATCN_3705 | 46506 |
| GTCN_948 | 32448 | GTCN_3474 | 46507 |
| CTCN_1713 | 32449 | CTCN_6543 | 46508 |
| GTCN_949 | 32450 | GTCN_3475 | 46509 |
| TTCN_1391 | 32451 | CTCN_6544 | 46510 |
| CTCN_1714 | 32452 | GTCN_3476 | 46511 |
| GTCN_950 | 32453 | TTCN_5329 | 46512 |
| TTCN_1392 | 32454 | CTCN_6545 | 46513 |
| CTCN_1715 | 32455 | TTCN_5330 | 46514 |
| GTCN_951 | 32456 | TTCN_5331 | 46515 |
| CTCN_1716 | 32457 | GTCN_3477 | 46516 |
| ATCN_941 | 32458 | TTCN_5332 | 46517 |
| CTCN_1717 | 32459 | GTCN_3478 | 46518 |
| TTCN_1393 | 32460 | CTCN_6546 | 46519 |
| GTCN_952 | 32461 | ATCN_3706 | 46520 |
| TTCN_1394 | 32462 | GTCN_3479 | 46521 |
| TTCN_1395 | 32463 | CTCN_6547 | 46522 |
| TTCN_1396 | 32464 | CTCN_6548 | 46523 |
| TTCN_1397 | 32465 | ATCN_3707 | 46524 |
| TTCN_1398 | 32466 | TTCN_5333 | 46525 |
| TTCN_1399 | 32467 | CTCN_6549 | 46526 |
| TTCN_1400 | 32468 | TTCN_5334 | 46527 |
| CTCN_1718 | 32469 | CTCN_6550 | 46528 |
| TTCN_1401 | 32470 | TTCN_5335 | 46529 |
| CTCN_1719 | 32471 | GTCN_3480 | 46530 |
| TTCN_1402 | 32472 | ATCN_3708 | 46531 |
| TTCN_1403 | 32473 | ATCN_3709 | 46532 |
| ATCN_942 | 32474 | CTCN_6551 | 46533 |
| CTCN_1720 | 32475 | ATCN_3710 | 46534 |
| GTCN_953 | 32476 | CTCN_6552 | 46535 |
| CTCN_1721 | 32477 | ATCN_3711 | 46536 |
| CTCN_1722 | 32478 | ATCN_3712 | 46537 |
| ATCN_943 | 32479 | CTCN_6553 | 46538 |
| TTCN_1404 | 32480 | CTCN_6554 | 46539 |
| CTCN_1723 | 32481 | CTCN_6555 | 46540 |

| | | | |
|---|---|---|---|
| GTCN_954 | 32482 | CTCN_6556 | 46541 |
| CTCN_1724 | 32483 | TTCN_5336 | 46542 |
| CTCN_1725 | 32484 | GTCN_3481 | 46543 |
| CTCN_1726 | 32485 | TTCN_5337 | 46544 |
| CTCN_1727 | 32486 | GTCN_3482 | 46545 |
| ATCN_944 | 32487 | CTCN_6557 | 46546 |
| TTCN_1405 | 32488 | GTCN_3483 | 46547 |
| ATCN_945 | 32489 | CTCN_6558 | 46548 |
| CTCN_1728 | 32490 | CTCN_6559 | 46549 |
| CTCN_1729 | 32491 | CTCN_6560 | 46550 |
| TTCN_1406 | 32492 | TTCN_5338 | 46551 |
| CTCN_1730 | 32493 | ATCN_3713 | 46552 |
| GTCN_955 | 32494 | GTCN_3484 | 46553 |
| CTCN_1731 | 32495 | TTCN_5339 | 46554 |
| CTCN_1732 | 32496 | GTCN_3485 | 46555 |
| ATCN_946 | 32497 | CTCN_6561 | 46556 |
| GTCN_956 | 32498 | CTCN_6562 | 46557 |
| GTCN_957 | 32499 | ATCN_3714 | 46558 |
| CTCN_1733 | 32500 | CTCN_6563 | 46559 |
| ATCN_947 | 32501 | GTCN_3486 | 46560 |
| ATCN_948 | 32502 | CTCN_6564 | 46561 |
| CTCN_1734 | 32503 | TTCN_5340 | 46562 |
| ATCN_949 | 32504 | GTCN_3487 | 46563 |
| TTCN_1407 | 32505 | TTCN_5341 | 46564 |
| CTCN_1735 | 32506 | ATCN_3715 | 46565 |
| CTCN_1736 | 32507 | CTCN_6565 | 46566 |
| ATCN_950 | 32508 | TTCN_5342 | 46567 |
| CTCN_1737 | 32509 | CTCN_6566 | 46568 |
| TTCN_1408 | 32510 | ATCN_3716 | 46569 |
| TTCN_1409 | 32511 | ATCN_3717 | 46570 |
| CTCN_1738 | 32512 | TTCN_5343 | 46571 |
| CTCN_1739 | 32513 | TTCN_5344 | 46572 |
| TTCN_1410 | 32514 | GTCN_3488 | 46573 |
| TTCN_1411 | 32515 | CTCN_6567 | 46574 |
| TTCN_1412 | 32516 | GTCN_3489 | 46575 |
| ATCN_951 | 32517 | TTCN_5345 | 46576 |
| ATCN_952 | 32518 | ATCN_3718 | 46577 |
| ATCN_953 | 32519 | ATCN_3719 | 46578 |
| CTCN_1740 | 32520 | TTCN_5346 | 46579 |
| ATCN_954 | 32521 | TTCN_5347 | 46580 |
| TTCN_1413 | 32522 | TTCN_5348 | 46581 |
| TTCN_1414 | 32523 | GTCN_3490 | 46582 |
| CTCN_1741 | 32524 | TTCN_5349 | 46583 |

FIG. 37 (continued)

| | | | |
|---|---|---|---|
| ATCN_955 | 32525 | ATCN_3720 | 46584 |
| TTCN_1415 | 32526 | ATCN_3721 | 46585 |
| GTCN_958 | 32527 | CTCN_6568 | 46586 |
| CTCN_1742 | 32528 | CTCN_6569 | 46587 |
| TTCN_1416 | 32529 | CTCN_6570 | 46588 |
| ATCN_956 | 32530 | TTCN_5350 | 46589 |
| CTCN_1743 | 32531 | GTCN_3491 | 46590 |
| TTCN_1417 | 32532 | CTCN_6571 | 46591 |
| CTCN_1744 | 32533 | CTCN_6572 | 46592 |
| ATCN_957 | 32534 | GTCN_3492 | 46593 |
| TTCN_1418 | 32535 | CTCN_6573 | 46594 |
| TTCN_1419 | 32536 | TTCN_5351 | 46595 |
| TTCN_1420 | 32537 | TTCN_5352 | 46596 |
| TTCN_1421 | 32538 | CTCN_6574 | 46597 |
| GTCN_959 | 32539 | CTCN_6575 | 46598 |
| TTCN_1422 | 32540 | TTCN_5353 | 46599 |
| TTCN_1423 | 32541 | GTCN_3493 | 46600 |
| CTCN_1745 | 32542 | ATCN_3722 | 46601 |
| ATCN_958 | 32543 | CTCN_6576 | 46602 |
| ATCN_959 | 32544 | CTCN_6577 | 46603 |
| CTCN_1746 | 32545 | ATCN_3723 | 46604 |
| TTCN_1424 | 32546 | TTCN_5354 | 46605 |
| GTCN_960 | 32547 | CTCN_6578 | 46606 |
| TTCN_1425 | 32548 | TTCN_5355 | 46607 |
| GTCN_961 | 32549 | CTCN_6579 | 46608 |
| CTCN_1747 | 32550 | TTCN_5356 | 46609 |
| GTCN_962 | 32551 | TTCN_5357 | 46610 |
| CTCN_1748 | 32552 | ATCN_3724 | 46611 |
| CTCN_1749 | 32553 | ATCN_3725 | 46612 |
| TTCN_1426 | 32554 | CTCN_6580 | 46613 |
| ATCN_960 | 32555 | GTCN_3494 | 46614 |
| TTCN_1427 | 32556 | TTCN_5358 | 46615 |
| CTCN_1750 | 32557 | CTCN_6581 | 46616 |
| TTCN_1428 | 32558 | GTCN_3495 | 46617 |
| ATCN_961 | 32559 | ATCN_3726 | 46618 |
| GTCN_963 | 32560 | ATCN_3727 | 46619 |
| CTCN_1751 | 32561 | TTCN_5359 | 46620 |
| CTCN_1752 | 32562 | GTCN_3496 | 46621 |
| TTCN_1429 | 32563 | ATCN_3728 | 46622 |
| ATCN_962 | 32564 | CTCN_6582 | 46623 |
| ATCN_963 | 32565 | GTCN_3497 | 46624 |
| ATCN_964 | 32566 | TTCN_5360 | 46625 |
| GTCN_964 | 32567 | GTCN_3498 | 46626 |
| CTCN_1753 | 32568 | CTCN_6583 | 46627 |
| CTCN_1754 | 32569 | CTCN_6584 | 46628 |
| CTCN_1755 | 32570 | TTCN_5361 | 46629 |
| GTCN_965 | 32571 | TTCN_5362 | 46630 |
| TTCN_1430 | 32572 | ATCN_3729 | 46631 |
| CTCN_1756 | 32573 | CTCN_6585 | 46632 |
| TTCN_1431 | 32574 | GTCN_3499 | 46633 |
| TTCN_1432 | 32575 | TTCN_5363 | 46634 |
| GTCN_966 | 32576 | GTCN_3500 | 46635 |
| ATCN_965 | 32577 | TTCN_5364 | 46636 |
| TTCN_1433 | 32578 | TTCN_5365 | 46637 |
| ATCN_966 | 32579 | GTCN_3501 | 46638 |
| GTCN_967 | 32580 | GTCN_3502 | 46639 |
| TTCN_1434 | 32581 | ATCN_3730 | 46640 |
| GTCN_968 | 32582 | CTCN_6586 | 46641 |
| GTCN_969 | 32583 | CTCN_6587 | 46642 |
| ATCN_967 | 32584 | GTCN_3503 | 46643 |
| ATCN_968 | 32585 | GTCN_3504 | 46644 |
| GTCN_970 | 32586 | GTCN_3505 | 46645 |
| GTCN_971 | 32587 | TTCN_5366 | 46646 |
| GTCN_972 | 32588 | GTCN_3506 | 46647 |
| ATCN_969 | 32589 | TTCN_5367 | 46648 |
| TTCN_1435 | 32590 | CTCN_6588 | 46649 |
| CTCN_1757 | 32591 | CTCN_6589 | 46650 |
| TTCN_1436 | 32592 | ATCN_3731 | 46651 |
| TTCN_1437 | 32593 | TTCN_5368 | 46652 |
| TTCN_1438 | 32594 | CTCN_6590 | 46653 |
| TTCN_1439 | 32595 | CTCN_6591 | 46654 |
| ATCN_970 | 32596 | CTCN_6592 | 46655 |
| GTCN_973 | 32597 | CTCN_6593 | 46656 |
| TTCN_1440 | 32598 | TTCN_5369 | 46657 |
| GTCN_974 | 32599 | CTCN_6594 | 46658 |
| TTCN_1441 | 32600 | ATCN_3732 | 46659 |
| CTCN_1758 | 32601 | CTCN_6595 | 46660 |
| CTCN_1759 | 32602 | CTCN_6596 | 46661 |
| GTCN_975 | 32603 | CTCN_6597 | 46662 |
| TTCN_1442 | 32604 | CTCN_6598 | 46663 |
| ATCN_971 | 32605 | GTCN_3507 | 46664 |
| ATCN_972 | 32606 | TTCN_5370 | 46665 |
| TTCN_1443 | 32607 | GTCN_3508 | 46666 |
| ATCN_973 | 32608 | GTCN_3509 | 46667 |
| CTCN_1760 | 32609 | GTCN_3510 | 46668 |
| TTCN_1444 | 32610 | CTCN_6599 | 46669 |

FIG. 37 (continued)

| | | | |
|---|---|---|---|
| CTCN_1761 | 32611 | GTCN_3511 | 46670 |
| CTCN_1762 | 32612 | CTCN_6600 | 46671 |
| GTCN_976 | 32613 | TTCN_5371 | 46672 |
| GTCN_977 | 32614 | TTCN_5372 | 46673 |
| ATCN_974 | 32615 | ATCN_3733 | 46674 |
| TTCN_1445 | 32616 | TTCN_5373 | 46675 |
| TTCN_1446 | 32617 | GTCN_3512 | 46676 |
| CTCN_1763 | 32618 | TTCN_5374 | 46677 |
| TTCN_1447 | 32619 | CTCN_6601 | 46678 |
| TTCN_1448 | 32620 | CTCN_6602 | 46679 |
| CTCN_1764 | 32621 | TTCN_5375 | 46680 |
| TTCN_1449 | 32622 | ATCN_3734 | 46681 |
| GTCN_978 | 32623 | ATCN_3735 | 46682 |
| TTCN_1450 | 32624 | CTCN_6603 | 46683 |
| TTCN_1451 | 32625 | GTCN_3513 | 46684 |
| CTCN_1765 | 32626 | CTCN_6604 | 46685 |
| TTCN_1452 | 32627 | GTCN_3514 | 46686 |
| ATCN_975 | 32628 | TTCN_5376 | 46687 |
| CTCN_1766 | 32629 | GTCN_3515 | 46688 |
| TTCN_1453 | 32630 | TTCN_5377 | 46689 |
| TTCN_1454 | 32631 | CTCN_6605 | 46690 |
| TTCN_1455 | 32632 | GTCN_3516 | 46691 |
| CTCN_1767 | 32633 | TTCN_5378 | 46692 |
| TTCN_1456 | 32634 | CTCN_6606 | 46693 |
| CTCN_1768 | 32635 | CTCN_6607 | 46694 |
| TTCN_1457 | 32636 | ATCN_3736 | 46695 |
| ATCN_976 | 32637 | GTCN_3517 | 46696 |
| CTCN_1769 | 32638 | CTCN_6608 | 46697 |
| CTCN_1770 | 32639 | CTCN_6609 | 46698 |
| TTCN_1458 | 32640 | CTCN_6610 | 46699 |
| CTCN_1771 | 32641 | CTCN_6611 | 46700 |
| TTCN_1459 | 32642 | CTCN_6612 | 46701 |
| TTCN_1460 | 32643 | CTCN_6613 | 46702 |
| CTCN_1772 | 32644 | CTCN_6614 | 46703 |
| GTCN_979 | 32645 | TTCN_5379 | 46704 |
| CTCN_1773 | 32646 | CTCN_6615 | 46705 |
| GTCN_980 | 32647 | CTCN_6616 | 46706 |
| CTCN_1774 | 32648 | GTCN_3518 | 46707 |
| CTCN_1775 | 32649 | ATCN_3737 | 46708 |
| CTCN_1776 | 32650 | GTCN_3519 | 46709 |
| CTCN_1777 | 32651 | GTCN_3520 | 46710 |
| ATCN_977 | 32652 | ATCN_3738 | 46711 |
| ATCN_978 | 32653 | ATCN_3739 | 46712 |

| | | | |
|---|---|---|---|
| CTCN_1778 | 32654 | CTCN_6617 | 46713 |
| CTCN_1779 | 32655 | GTCN_3521 | 46714 |
| CTCN_1780 | 32656 | TTCN_5380 | 46715 |
| CTCN_1781 | 32657 | CTCN_6618 | 46716 |
| TTCN_1461 | 32658 | CTCN_6619 | 46717 |
| TTCN_1462 | 32659 | GTCN_3522 | 46718 |
| CTCN_1782 | 32660 | GTCN_3523 | 46719 |
| CTCN_1783 | 32661 | ATCN_3740 | 46720 |
| CTCN_1784 | 32662 | CTCN_6620 | 46721 |
| ATCN_979 | 32663 | ATCN_3741 | 46722 |
| CTCN_1785 | 32664 | ATCN_3742 | 46723 |
| GTCN_981 | 32665 | ATCN_3743 | 46724 |
| TTCN_1463 | 32666 | CTCN_6621 | 46725 |
| GTCN_982 | 32667 | TTCN_5381 | 46726 |
| CTCN_1786 | 32668 | CTCN_6622 | 46727 |
| TTCN_1464 | 32669 | TTCN_5382 | 46728 |
| CTCN_1787 | 32670 | ATCN_3744 | 46729 |
| GTCN_983 | 32671 | TTCN_5383 | 46730 |
| CTCN_1788 | 32672 | ATCN_3745 | 46731 |
| ATCN_980 | 32673 | ATCN_3746 | 46732 |
| ATCN_981 | 32674 | TTCN_5384 | 46733 |
| CTCN_1789 | 32675 | ATCN_3747 | 46734 |
| ATCN_982 | 32676 | ATCN_3748 | 46735 |
| CTCN_1790 | 32677 | CTCN_6623 | 46736 |
| ATCN_983 | 32678 | ATCN_3749 | 46737 |
| CTCN_1791 | 32679 | TTCN_5385 | 46738 |
| TTCN_1465 | 32680 | ATCN_3750 | 46739 |
| TTCN_1466 | 32681 | ATCN_3751 | 46740 |
| ATCN_984 | 32682 | ATCN_3752 | 46741 |
| TTCN_1467 | 32683 | TTCN_5386 | 46742 |
| ATCN_985 | 32684 | GTCN_3524 | 46743 |
| GTCN_984 | 32685 | ATCN_3753 | 46744 |
| TTCN_1468 | 32686 | GTCN_3525 | 46745 |
| CTCN_1792 | 32687 | GTCN_3526 | 46746 |
| ATCN_986 | 32688 | CTCN_6624 | 46747 |
| TTCN_1469 | 32689 | CTCN_6625 | 46748 |
| TTCN_1470 | 32690 | CTCN_6626 | 46749 |
| CTCN_1793 | 32691 | TTCN_5387 | 46750 |
| TTCN_1471 | 32692 | CTCN_6627 | 46751 |
| TTCN_1472 | 32693 | ATCN_3754 | 46752 |
| CTCN_1794 | 32694 | GTCN_3527 | 46753 |
| CTCN_1795 | 32695 | ATCN_3755 | 46754 |
| ATCN_987 | 32696 | ATCN_3756 | 46755 |

FIG. 37 (continued)

| | | | |
|---|---|---|---|
| TTCN_1473 | 32697 | GTCN_3528 | 46756 |
| CTCN_1796 | 32698 | CTCN_6628 | 46757 |
| CTCN_1797 | 32699 | TTCN_5388 | 46758 |
| GTCN_985 | 32700 | CTCN_6629 | 46759 |
| ATCN_988 | 32701 | CTCN_6630 | 46760 |
| CTCN_1798 | 32702 | GTCN_3529 | 46761 |
| TTCN_1474 | 32703 | GTCN_3530 | 46762 |
| TTCN_1475 | 32704 | CTCN_6631 | 46763 |
| ATCN_989 | 32705 | CTCN_6632 | 46764 |
| ATCN_990 | 32706 | TTCN_5389 | 46765 |
| TTCN_1476 | 32707 | TTCN_5390 | 46766 |
| TTCN_1477 | 32708 | GTCN_3531 | 46767 |
| TTCN_1478 | 32709 | GTCN_3532 | 46768 |
| CTCN_1799 | 32710 | ATCN_3757 | 46769 |
| TTCN_1479 | 32711 | TTCN_5391 | 46770 |
| TTCN_1480 | 32712 | CTCN_6633 | 46771 |
| GTCN_986 | 32713 | CTCN_6634 | 46772 |
| ATCN_991 | 32714 | ATCN_3758 | 46773 |
| CTCN_1800 | 32715 | ATCN_3759 | 46774 |
| TTCN_1481 | 32716 | TTCN_5392 | 46775 |
| TTCN_1482 | 32717 | GTCN_3533 | 46776 |
| TTCN_1483 | 32718 | TTCN_5393 | 46777 |
| TTCN_1484 | 32719 | TTCN_5394 | 46778 |
| TTCN_1485 | 32720 | ATCN_3760 | 46779 |
| TTCN_1486 | 32721 | TTCN_5395 | 46780 |
| ATCN_992 | 32722 | TTCN_5396 | 46781 |
| ATCN_993 | 32723 | ATCN_3761 | 46782 |
| TTCN_1487 | 32724 | TTCN_5397 | 46783 |
| TTCN_1488 | 32725 | ATCN_3762 | 46784 |
| GTCN_987 | 32726 | CTCN_6635 | 46785 |
| GTCN_988 | 32727 | CTCN_6636 | 46786 |
| TTCN_1489 | 32728 | ATCN_3763 | 46787 |
| TTCN_1490 | 32729 | TTCN_5398 | 46788 |
| CTCN_1801 | 32730 | GTCN_3534 | 46789 |
| GTCN_989 | 32731 | TTCN_5399 | 46790 |
| CTCN_1802 | 32732 | ATCN_3764 | 46791 |
| TTCN_1491 | 32733 | TTCN_5400 | 46792 |
| GTCN_990 | 32734 | TTCN_5401 | 46793 |
| TTCN_1492 | 32735 | GTCN_3535 | 46794 |
| TTCN_1493 | 32736 | CTCN_6637 | 46795 |
| GTCN_991 | 32737 | TTCN_5402 | 46796 |
| TTCN_1494 | 32738 | TTCN_5403 | 46797 |
| ATCN_994 | 32739 | GTCN_3536 | 46798 |

| | | | |
|---|---|---|---|
| TTCN_1495 | 32740 | TTCN_5404 | 46799 |
| ATCN_995 | 32741 | TTCN_5405 | 46800 |
| TTCN_1496 | 32742 | TTCN_5406 | 46801 |
| ATCN_996 | 32743 | ATCN_3765 | 46802 |
| ATCN_997 | 32744 | ATCN_3766 | 46803 |
| GTCN_992 | 32745 | TTCN_5407 | 46804 |
| TTCN_1497 | 32746 | TTCN_5408 | 46805 |
| GTCN_993 | 32747 | TTCN_5409 | 46806 |
| TTCN_1498 | 32748 | TTCN_5410 | 46807 |
| TTCN_1499 | 32749 | ATCN_3767 | 46808 |
| TTCN_1500 | 32750 | ATCN_3768 | 46809 |
| TTCN_1501 | 32751 | ATCN_3769 | 46810 |
| GTCN_994 | 32752 | CTCN_6638 | 46811 |
| CTCN_1803 | 32753 | GTCN_3537 | 46812 |
| TTCN_1502 | 32754 | TTCN_5411 | 46813 |
| GTCN_995 | 32755 | CTCN_6639 | 46814 |
| CTCN_1804 | 32756 | ATCN_3770 | 46815 |
| GTCN_996 | 32757 | GTCN_3538 | 46816 |
| CTCN_1805 | 32758 | TTCN_5412 | 46817 |
| GTCN_997 | 32759 | TTCN_5413 | 46818 |
| ATCN_998 | 32760 | TTCN_5414 | 46819 |
| TTCN_1503 | 32761 | GTCN_3539 | 46820 |
| CTCN_1806 | 32762 | GTCN_3540 | 46821 |
| TTCN_1504 | 32763 | CTCN_6640 | 46822 |
| TTCN_1505 | 32764 | GTCN_3541 | 46823 |
| ATCN_999 | 32765 | CTCN_6641 | 46824 |
| CTCN_1807 | 32766 | CTCN_6642 | 46825 |
| TTCN_1506 | 32767 | GTCN_3542 | 46826 |
| GTCN_998 | 32768 | CTCN_6643 | 46827 |
| ATCN_1000 | 32769 | ATCN_3771 | 46828 |
| GTCN_999 | 32770 | CTCN_6644 | 46829 |
| TTCN_1507 | 32771 | TTCN_5415 | 46830 |
| GTCN_1000 | 32772 | ATCN_3772 | 46831 |
| CTCN_1808 | 32773 | TTCN_5416 | 46832 |
| GTCN_1001 | 32774 | GTCN_3543 | 46833 |
| TTCN_1508 | 32775 | CTCN_6645 | 46834 |
| TTCN_1509 | 32776 | TTCN_5417 | 46835 |
| TTCN_1510 | 32777 | ATCN_3773 | 46836 |
| GTCN_1002 | 32778 | ATCN_3774 | 46837 |
| CTCN_1809 | 32779 | CTCN_6646 | 46838 |
| GTCN_1003 | 32780 | CTCN_6647 | 46839 |
| ATCN_1001 | 32781 | GTCN_3544 | 46840 |
| ATCN_1002 | 32782 | CTCN_6648 | 46841 |

FIG. 37 (continued)

| | | | |
|---|---|---|---|
| CTCN_1810 | 32783 | GTCN_3545 | 46842 |
| GTCN_1004 | 32784 | ATCN_3775 | 46843 |
| GTCN_1005 | 32785 | CTCN_6649 | 46844 |
| GTCN_1006 | 32786 | CTCN_6650 | 46845 |
| CTCN_1811 | 32787 | TTCN_5418 | 46846 |
| CTCN_1812 | 32788 | GTCN_3546 | 46847 |
| ATCN_1003 | 32789 | CTCN_6651 | 46848 |
| TTCN_1511 | 32790 | CTCN_6652 | 46849 |
| ATCN_1004 | 32791 | CTCN_6653 | 46850 |
| TTCN_1512 | 32792 | GTCN_3547 | 46851 |
| TTCN_1513 | 32793 | TTCN_5419 | 46852 |
| TTCN_1514 | 32794 | CTCN_6654 | 46853 |
| GTCN_1007 | 32795 | CTCN_6655 | 46854 |
| ATCN_1005 | 32796 | CTCN_6656 | 46855 |
| ATCN_1006 | 32797 | GTCN_3548 | 46856 |
| ATCN_1007 | 32798 | CTCN_6657 | 46857 |
| ATCN_1008 | 32799 | ATCN_3776 | 46858 |
| GTCN_1008 | 32800 | TTCN_5420 | 46859 |
| TTCN_1515 | 32801 | CTCN_6658 | 46860 |
| CTCN_1813 | 32802 | GTCN_3549 | 46861 |
| TTCN_1516 | 32803 | GTCN_3550 | 46862 |
| CTCN_1814 | 32804 | TTCN_5421 | 46863 |
| TTCN_1517 | 32805 | GTCN_3551 | 46864 |
| GTCN_1009 | 32806 | CTCN_6659 | 46865 |
| TTCN_1518 | 32807 | GTCN_3552 | 46866 |
| GTCN_1010 | 32808 | CTCN_6660 | 46867 |
| GTCN_1011 | 32809 | ATCN_3777 | 46868 |
| ATCN_1009 | 32810 | CTCN_6661 | 46869 |
| TTCN_1519 | 32811 | TTCN_5422 | 46870 |
| TTCN_1520 | 32812 | CTCN_6662 | 46871 |
| GTCN_1012 | 32813 | CTCN_6663 | 46872 |
| TTCN_1521 | 32814 | TTCN_5423 | 46873 |
| GTCN_1013 | 32815 | GTCN_3553 | 46874 |
| TTCN_1522 | 32816 | TTCN_5424 | 46875 |
| TTCN_1523 | 32817 | TTCN_5425 | 46876 |
| GTCN_1014 | 32818 | TTCN_5426 | 46877 |
| TTCN_1524 | 32819 | CTCN_6664 | 46878 |
| TTCN_1525 | 32820 | ATCN_3778 | 46879 |
| ATCN_1010 | 32821 | TTCN_5427 | 46880 |
| ATCN_1011 | 32822 | ATCN_3779 | 46881 |
| TTCN_1526 | 32823 | GTCN_3554 | 46882 |
| TTCN_1527 | 32824 | ATCN_3780 | 46883 |
| GTCN_1015 | 32825 | GTCN_3555 | 46884 |

| | | | |
|---|---|---|---|
| ATCN_1012 | 32826 | CTCN_6665 | 46885 |
| TTCN_1528 | 32827 | ATCN_3781 | 46886 |
| ATCN_1013 | 32828 | GTCN_3556 | 46887 |
| TTCN_1529 | 32829 | TTCN_5428 | 46888 |
| TTCN_1530 | 32830 | CTCN_6666 | 46889 |
| ATCN_1014 | 32831 | TTCN_5429 | 46890 |
| CTCN_1815 | 32832 | TTCN_5430 | 46891 |
| TTCN_1531 | 32833 | TTCN_5431 | 46892 |
| CTCN_1816 | 32834 | TTCN_5432 | 46893 |
| TTCN_1532 | 32835 | TTCN_5433 | 46894 |
| TTCN_1533 | 32836 | TTCN_5434 | 46895 |
| TTCN_1534 | 32837 | TTCN_5435 | 46896 |
| GTCN_1016 | 32838 | TTCN_5436 | 46897 |
| TTCN_1535 | 32839 | TTCN_5437 | 46898 |
| GTCN_1017 | 32840 | CTCN_6667 | 46899 |
| TTCN_1536 | 32841 | ATCN_3782 | 46900 |
| TTCN_1537 | 32842 | TTCN_5438 | 46901 |
| CTCN_1817 | 32843 | CTCN_6668 | 46902 |
| GTCN_1018 | 32844 | GTCN_3557 | 46903 |
| CTCN_1818 | 32845 | TTCN_5439 | 46904 |
| ATCN_1015 | 32846 | GTCN_3558 | 46905 |
| ATCN_1016 | 32847 | TTCN_5440 | 46906 |
| ATCN_1017 | 32848 | ATCN_3783 | 46907 |
| TTCN_1538 | 32849 | TTCN_5441 | 46908 |
| CTCN_1819 | 32850 | GTCN_3559 | 46909 |
| TTCN_1539 | 32851 | CTCN_6669 | 46910 |
| GTCN_1019 | 32852 | GTCN_3560 | 46911 |
| TTCN_1540 | 32853 | ATCN_3784 | 46912 |
| GTCN_1020 | 32854 | TTCN_5442 | 46913 |
| ATCN_1018 | 32855 | TTCN_5443 | 46914 |
| GTCN_1021 | 32856 | GTCN_3561 | 46915 |
| TTCN_1541 | 32857 | CTCN_6670 | 46916 |
| CTCN_1820 | 32858 | TTCN_5444 | 46917 |
| ATCN_1019 | 32859 | GTCN_3562 | 46918 |
| ATCN_1020 | 32860 | TTCN_5445 | 46919 |
| TTCN_1542 | 32861 | CTCN_6671 | 46920 |
| ATCN_1021 | 32862 | CTCN_6672 | 46921 |
| ATCN_1022 | 32863 | TTCN_5446 | 46922 |
| GTCN_1022 | 32864 | GTCN_3563 | 46923 |
| TTCN_1543 | 32865 | ATCN_3785 | 46924 |
| TTCN_1544 | 32866 | ATCN_3786 | 46925 |
| CTCN_1821 | 32867 | ATCN_3787 | 46926 |
| TTCN_1545 | 32868 | ATCN_3788 | 46927 |

FIG. 37 (continued)

| | | | |
|---|---|---|---|
| TTCN_1546 | 32869 | TTCN_5447 | 46928 |
| TTCN_1547 | 32870 | ATCN_3789 | 46929 |
| ATCN_1023 | 32871 | ATCN_3790 | 46930 |
| CTCN_1822 | 32872 | ATCN_3791 | 46931 |
| TTCN_1548 | 32873 | CTCN_6673 | 46932 |
| TTCN_1549 | 32874 | TTCN_5448 | 46933 |
| TTCN_1550 | 32875 | CTCN_6674 | 46934 |
| CTCN_1823 | 32876 | TTCN_5449 | 46935 |
| TTCN_1551 | 32877 | GTCN_3564 | 46936 |
| ATCN_1024 | 32878 | CTCN_6675 | 46937 |
| CTCN_1824 | 32879 | CTCN_6676 | 46938 |
| TTCN_1552 | 32880 | CTCN_6677 | 46939 |
| GTCN_1023 | 32881 | TTCN_5450 | 46940 |
| CTCN_1825 | 32882 | ATCN_3792 | 46941 |
| GTCN_1024 | 32883 | TTCN_5451 | 46942 |
| CTCN_1826 | 32884 | TTCN_5452 | 46943 |
| TTCN_1553 | 32885 | ATCN_3793 | 46944 |
| GTCN_1025 | 32886 | TTCN_5453 | 46945 |
| CTCN_1827 | 32887 | TTCN_5454 | 46946 |
| TTCN_1554 | 32888 | CTCN_6678 | 46947 |
| TTCN_1555 | 32889 | TTCN_5455 | 46948 |
| TTCN_1556 | 32890 | TTCN_5456 | 46949 |
| ATCN_1025 | 32891 | CTCN_6679 | 46950 |
| GTCN_1026 | 32892 | CTCN_6680 | 46951 |
| CTCN_1828 | 32893 | TTCN_5457 | 46952 |
| CTCN_1829 | 32894 | ATCN_3794 | 46953 |
| TTCN_1557 | 32895 | ATCN_3795 | 46954 |
| TTCN_1558 | 32896 | CTCN_6681 | 46955 |
| TTCN_1559 | 32897 | CTCN_6682 | 46956 |
| TTCN_1560 | 32898 | TTCN_5458 | 46957 |
| TTCN_1561 | 32899 | CTCN_6683 | 46958 |
| ATCN_1026 | 32900 | ATCN_3796 | 46959 |
| ATCN_1027 | 32901 | CTCN_6684 | 46960 |
| CTCN_1830 | 32902 | TTCN_5459 | 46961 |
| TTCN_1562 | 32903 | ATCN_3797 | 46962 |
| CTCN_1831 | 32904 | TTCN_5460 | 46963 |
| GTCN_1027 | 32905 | ATCN_3798 | 46964 |
| TTCN_1563 | 32906 | TTCN_5461 | 46965 |
| CTCN_1832 | 32907 | ATCN_3799 | 46966 |
| GTCN_1028 | 32908 | CTCN_6685 | 46967 |
| TTCN_1564 | 32909 | ATCN_3800 | 46968 |
| ATCN_1028 | 32910 | ATCN_3801 | 46969 |
| TTCN_1565 | 32911 | CTCN_6686 | 46970 |

| | | | |
|---|---|---|---|
| CTCN_1833 | 32912 | ATCN_3802 | 46971 |
| ATCN_1029 | 32913 | TTCN_5462 | 46972 |
| CTCN_1834 | 32914 | TTCN_5463 | 46973 |
| GTCN_1029 | 32915 | ATCN_3803 | 46974 |
| GTCN_1030 | 32916 | CTCN_6687 | 46975 |
| TTCN_1566 | 32917 | GTCN_3565 | 46976 |
| ATCN_1030 | 32918 | GTCN_3566 | 46977 |
| ATCN_1031 | 32919 | ATCN_3804 | 46978 |
| CTCN_1835 | 32920 | TTCN_5464 | 46979 |
| ATCN_1032 | 32921 | GTCN_3567 | 46980 |
| GTCN_1031 | 32922 | GTCN_3568 | 46981 |
| TTCN_1567 | 32923 | ATCN_3805 | 46982 |
| TTCN_1568 | 32924 | ATCN_3806 | 46983 |
| CTCN_1836 | 32925 | ATCN_3807 | 46984 |
| GTCN_1032 | 32926 | ATCN_3808 | 46985 |
| CTCN_1837 | 32927 | TTCN_5465 | 46986 |
| GTCN_1033 | 32928 | ATCN_3809 | 46987 |
| CTCN_1838 | 32929 | TTCN_5466 | 46988 |
| GTCN_1034 | 32930 | GTCN_3569 | 46989 |
| CTCN_1839 | 32931 | GTCN_3570 | 46990 |
| ATCN_1033 | 32932 | CTCN_6688 | 46991 |
| ATCN_1034 | 32933 | CTCN_6689 | 46992 |
| CTCN_1840 | 32934 | TTCN_5467 | 46993 |
| CTCN_1841 | 32935 | GTCN_3571 | 46994 |
| CTCN_1842 | 32936 | TTCN_5468 | 46995 |
| TTCN_1569 | 32937 | CTCN_6690 | 46996 |
| TTCN_1570 | 32938 | ATCN_3810 | 46997 |
| CTCN_1843 | 32939 | TTCN_5469 | 46998 |
| TTCN_1571 | 32940 | CTCN_6691 | 46999 |
| CTCN_1844 | 32941 | GTCN_3572 | 47000 |
| GTCN_1035 | 32942 | GTCN_3573 | 47001 |
| TTCN_1572 | 32943 | CTCN_6692 | 47002 |
| TTCN_1573 | 32944 | GTCN_3574 | 47003 |
| CTCN_1845 | 32945 | GTCN_3575 | 47004 |
| GTCN_1036 | 32946 | CTCN_6693 | 47005 |
| TTCN_1574 | 32947 | ATCN_3811 | 47006 |
| GTCN_1037 | 32948 | ATCN_3812 | 47007 |
| CTCN_1846 | 32949 | ATCN_3813 | 47008 |
| TTCN_1575 | 32950 | CTCN_6694 | 47009 |
| CTCN_1847 | 32951 | TTCN_5470 | 47010 |
| GTCN_1038 | 32952 | CTCN_6695 | 47011 |
| CTCN_1848 | 32953 | CTCN_6696 | 47012 |
| ATCN_1035 | 32954 | ATCN_3814 | 47013 |

FIG. 37 (continued)

| | | | |
|---|---|---|---|
| ATCN_1036 | 32955 | CTCN_6697 | 47014 |
| CTCN_1849 | 32956 | CTCN_6698 | 47015 |
| ATCN_1037 | 32957 | TTCN_5471 | 47016 |
| CTCN_1850 | 32958 | ATCN_3815 | 47017 |
| TTCN_1576 | 32959 | ATCN_3816 | 47018 |
| CTCN_1851 | 32960 | TTCN_5472 | 47019 |
| ATCN_1038 | 32961 | GTCN_3576 | 47020 |
| CTCN_1852 | 32962 | TTCN_5473 | 47021 |
| GTCN_1039 | 32963 | ATCN_3817 | 47022 |
| CTCN_1853 | 32964 | CTCN_6699 | 47023 |
| ATCN_1039 | 32965 | CTCN_6700 | 47024 |
| CTCN_1854 | 32966 | ATCN_3818 | 47025 |
| GTCN_1040 | 32967 | ATCN_3819 | 47026 |
| CTCN_1855 | 32968 | TTCN_5474 | 47027 |
| GTCN_1041 | 32969 | TTCN_5475 | 47028 |
| CTCN_1856 | 32970 | TTCN_5476 | 47029 |
| GTCN_1042 | 32971 | CTCN_6701 | 47030 |
| GTCN_1043 | 32972 | GTCN_3577 | 47031 |
| CTCN_1857 | 32973 | TTCN_5477 | 47032 |
| ATCN_1040 | 32974 | CTCN_6702 | 47033 |
| CTCN_1858 | 32975 | CTCN_6703 | 47034 |
| CTCN_1859 | 32976 | TTCN_5478 | 47035 |
| TTCN_1577 | 32977 | TTCN_5479 | 47036 |
| TTCN_1578 | 32978 | CTCN_6704 | 47037 |
| ATCN_1041 | 32979 | GTCN_3578 | 47038 |
| TTCN_1579 | 32980 | GTCN_3579 | 47039 |
| ATCN_1042 | 32981 | TTCN_5480 | 47040 |
| ATCN_1043 | 32982 | GTCN_3580 | 47041 |
| ATCN_1044 | 32983 | GTCN_3581 | 47042 |
| CTCN_1860 | 32984 | TTCN_5481 | 47043 |
| GTCN_1044 | 32985 | GTCN_3582 | 47044 |
| TTCN_1580 | 32986 | TTCN_5482 | 47045 |
| GTCN_1045 | 32987 | GTCN_3583 | 47046 |
| GTCN_1046 | 32988 | GTCN_3584 | 47047 |
| CTCN_1861 | 32989 | TTCN_5483 | 47048 |
| TTCN_1581 | 32990 | TTCN_5484 | 47049 |
| ATCN_1045 | 32991 | CTCN_6705 | 47050 |
| CTCN_1862 | 32992 | TTCN_5485 | 47051 |
| TTCN_1582 | 32993 | CTCN_6706 | 47052 |
| GTCN_1047 | 32994 | ATCN_3820 | 47053 |
| TTCN_1583 | 32995 | CTCN_6707 | 47054 |
| CTCN_1863 | 32996 | TTCN_5486 | 47055 |
| TTCN_1584 | 32997 | ATCN_3821 | 47056 |

| | | | |
|---|---|---|---|
| ATCN_1046 | 32998 | TTCN_5487 | 47057 |
| ATCN_1047 | 32999 | ATCN_3822 | 47058 |
| CTCN_1864 | 33000 | ATCN_3823 | 47059 |
| ATCN_1048 | 33001 | ATCN_3824 | 47060 |
| CTCN_1865 | 33002 | GTCN_3585 | 47061 |
| TTCN_1585 | 33003 | GTCN_3586 | 47062 |
| ATCN_1049 | 33004 | TTCN_5488 | 47063 |
| ATCN_1050 | 33005 | CTCN_6708 | 47064 |
| CTCN_1866 | 33006 | TTCN_5489 | 47065 |
| GTCN_1048 | 33007 | TTCN_5490 | 47066 |
| CTCN_1867 | 33008 | ATCN_3825 | 47067 |
| TTCN_1586 | 33009 | CTCN_6709 | 47068 |
| GTCN_1049 | 33010 | TTCN_5491 | 47069 |
| GTCN_1050 | 33011 | CTCN_6710 | 47070 |
| ATCN_1051 | 33012 | GTCN_3587 | 47071 |
| TTCN_1587 | 33013 | ATCN_3826 | 47072 |
| GTCN_1051 | 33014 | CTCN_6711 | 47073 |
| CTCN_1868 | 33015 | ATCN_3827 | 47074 |
| CTCN_1869 | 33016 | ATCN_3828 | 47075 |
| ATCN_1052 | 33017 | TTCN_5492 | 47076 |
| CTCN_1870 | 33018 | TTCN_5493 | 47077 |
| CTCN_1871 | 33019 | GTCN_3588 | 47078 |
| ATCN_1053 | 33020 | TTCN_5494 | 47079 |
| ATCN_1054 | 33021 | TTCN_5495 | 47080 |
| TTCN_1588 | 33022 | TTCN_5496 | 47081 |
| GTCN_1052 | 33023 | CTCN_6712 | 47082 |
| CTCN_1872 | 33024 | TTCN_5497 | 47083 |
| ATCN_1055 | 33025 | TTCN_5498 | 47084 |
| ATCN_1056 | 33026 | CTCN_6713 | 47085 |
| CTCN_1873 | 33027 | TTCN_5499 | 47086 |
| GTCN_1053 | 33028 | CTCN_6714 | 47087 |
| ATCN_1057 | 33029 | TTCN_5500 | 47088 |
| TTCN_1589 | 33030 | TTCN_5501 | 47089 |
| ATCN_1058 | 33031 | TTCN_5502 | 47090 |
| CTCN_1874 | 33032 | GTCN_3589 | 47091 |
| CTCN_1875 | 33033 | TTCN_5503 | 47092 |
| GTCN_1054 | 33034 | ATCN_3829 | 47093 |
| CTCN_1876 | 33035 | TTCN_5504 | 47094 |
| CTCN_1877 | 33036 | TTCN_5505 | 47095 |
| CTCN_1878 | 33037 | TTCN_5506 | 47096 |
| CTCN_1879 | 33038 | TTCN_5507 | 47097 |
| TTCN_1590 | 33039 | TTCN_5508 | 47098 |
| TTCN_1591 | 33040 | GTCN_3590 | 47099 |

FIG. 37 (continued)

| | | | |
|---|---|---|---|
| CTCN_1880 | 33041 | GTCN_3591 | 47100 |
| CTCN_1881 | 33042 | CTCN_6715 | 47101 |
| CTCN_1882 | 33043 | GTCN_3592 | 47102 |
| CTCN_1883 | 33044 | CTCN_6716 | 47103 |
| ATCN_1059 | 33045 | ATCN_3830 | 47104 |
| ATCN_1060 | 33046 | TTCN_5509 | 47105 |
| CTCN_1884 | 33047 | GTCN_3593 | 47106 |
| GTCN_1055 | 33048 | GTCN_3594 | 47107 |
| CTCN_1885 | 33049 | TTCN_5510 | 47108 |
| GTCN_1056 | 33050 | TTCN_5511 | 47109 |
| CTCN_1886 | 33051 | TTCN_5512 | 47110 |
| GTCN_1057 | 33052 | CTCN_6717 | 47111 |
| CTCN_1887 | 33053 | GTCN_3595 | 47112 |
| ATCN_1061 | 33054 | CTCN_6718 | 47113 |
| TTCN_1592 | 33055 | CTCN_6719 | 47114 |
| CTCN_1888 | 33056 | TTCN_5513 | 47115 |
| CTCN_1889 | 33057 | TTCN_5514 | 47116 |
| CTCN_1890 | 33058 | CTCN_6720 | 47117 |
| TTCN_1593 | 33059 | TTCN_5515 | 47118 |
| ATCN_1062 | 33060 | CTCN_6721 | 47119 |
| CTCN_1891 | 33061 | CTCN_6722 | 47120 |
| TTCN_1594 | 33062 | TTCN_5516 | 47121 |
| CTCN_1892 | 33063 | CTCN_6723 | 47122 |
| GTCN_1058 | 33064 | GTCN_3596 | 47123 |
| CTCN_1893 | 33065 | CTCN_6724 | 47124 |
| CTCN_1894 | 33066 | TTCN_5517 | 47125 |
| GTCN_1059 | 33067 | ATCN_3831 | 47126 |
| CTCN_1895 | 33068 | CTCN_6725 | 47127 |
| CTCN_1896 | 33069 | CTCN_6726 | 47128 |
| CTCN_1897 | 33070 | ATCN_3832 | 47129 |
| GTCN_1060 | 33071 | CTCN_6727 | 47130 |
| TTCN_1595 | 33072 | GTCN_3597 | 47131 |
| GTCN_1061 | 33073 | CTCN_6728 | 47132 |
| CTCN_1898 | 33074 | CTCN_6729 | 47133 |
| ATCN_1063 | 33075 | CTCN_6730 | 47134 |
| ATCN_1064 | 33076 | CTCN_6731 | 47135 |
| CTCN_1899 | 33077 | CTCN_6732 | 47136 |
| ATCN_1065 | 33078 | CTCN_6733 | 47137 |
| TTCN_1596 | 33079 | CTCN_6734 | 47138 |
| ATCN_1066 | 33080 | CTCN_6735 | 47139 |
| CTCN_1900 | 33081 | TTCN_5518 | 47140 |
| TTCN_1597 | 33082 | GTCN_3598 | 47141 |
| CTCN_1901 | 33083 | GTCN_3599 | 47142 |

| | | | |
|---|---|---|---|
| GTCN_1062 | 33084 | TTCN_5519 | 47143 |
| CTCN_1902 | 33085 | TTCN_5520 | 47144 |
| TTCN_1598 | 33086 | GTCN_3600 | 47145 |
| ATCN_1067 | 33087 | ATCN_3833 | 47146 |
| TTCN_1599 | 33088 | TTCN_5521 | 47147 |
| ATCN_1068 | 33089 | TTCN_5522 | 47148 |
| CTCN_1903 | 33090 | TTCN_5523 | 47149 |
| GTCN_1063 | 33091 | GTCN_3601 | 47150 |
| TTCN_1600 | 33092 | CTCN_6736 | 47151 |
| ATCN_1069 | 33093 | TTCN_5524 | 47152 |
| CTCN_1904 | 33094 | TTCN_5525 | 47153 |
| GTCN_1064 | 33095 | ATCN_3834 | 47154 |
| TTCN_1601 | 33096 | CTCN_6737 | 47155 |
| ATCN_1070 | 33097 | TTCN_5526 | 47156 |
| ATCN_1071 | 33098 | TTCN_5527 | 47157 |
| TTCN_1602 | 33099 | CTCN_6738 | 47158 |
| GTCN_1065 | 33100 | ATCN_3835 | 47159 |
| CTCN_1905 | 33101 | TTCN_5528 | 47160 |
| GTCN_1066 | 33102 | ATCN_3836 | 47161 |
| CTCN_1906 | 33103 | GTCN_3602 | 47162 |
| TTCN_1603 | 33104 | TTCN_5529 | 47163 |
| TTCN_1604 | 33105 | ATCN_3837 | 47164 |
| ATCN_1072 | 33106 | TTCN_5530 | 47165 |
| TTCN_1605 | 33107 | TTCN_5531 | 47166 |
| GTCN_1067 | 33108 | GTCN_3603 | 47167 |
| CTCN_1907 | 33109 | GTCN_3604 | 47168 |
| TTCN_1606 | 33110 | TTCN_5532 | 47169 |
| ATCN_1073 | 33111 | ATCN_3838 | 47170 |
| CTCN_1908 | 33112 | CTCN_6739 | 47171 |
| GTCN_1068 | 33113 | TTCN_5533 | 47172 |
| CTCN_1909 | 33114 | ATCN_3839 | 47173 |
| TTCN_1607 | 33115 | TTCN_5534 | 47174 |
| CTCN_1910 | 33116 | GTCN_3605 | 47175 |
| ATCN_1074 | 33117 | TTCN_5535 | 47176 |
| CTCN_1911 | 33118 | TTCN_5536 | 47177 |
| TTCN_1608 | 33119 | TTCN_5537 | 47178 |
| GTCN_1069 | 33120 | TTCN_5538 | 47179 |
| TTCN_1609 | 33121 | CTCN_6740 | 47180 |
| ATCN_1075 | 33122 | ATCN_3840 | 47181 |
| ATCN_1076 | 33123 | ATCN_3841 | 47182 |
| TTCN_1610 | 33124 | CTCN_6741 | 47183 |
| ATCN_1077 | 33125 | ATCN_3842 | 47184 |
| CTCN_1912 | 33126 | TTCN_5539 | 47185 |

FIG. 37 (continued)

| | | | |
|---|---|---|---|
| TTCN_1611 | 33127 | TTCN_5540 | 47186 |
| TTCN_1612 | 33128 | CTCN_6742 | 47187 |
| CTCN_1913 | 33129 | GTCN_3606 | 47188 |
| ATCN_1078 | 33130 | TTCN_5541 | 47189 |
| CTCN_1914 | 33131 | CTCN_6743 | 47190 |
| TTCN_1613 | 33132 | ATCN_3843 | 47191 |
| CTCN_1915 | 33133 | ATCN_3844 | 47192 |
| CTCN_1916 | 33134 | TTCN_5542 | 47193 |
| GTCN_1070 | 33135 | CTCN_6744 | 47194 |
| CTCN_1917 | 33136 | ATCN_3845 | 47195 |
| CTCN_1918 | 33137 | GTCN_3607 | 47196 |
| CTCN_1919 | 33138 | GTCN_3608 | 47197 |
| TTCN_1614 | 33139 | ATCN_3846 | 47198 |
| ATCN_1079 | 33140 | CTCN_6745 | 47199 |
| TTCN_1615 | 33141 | CTCN_6746 | 47200 |
| CTCN_1920 | 33142 | GTCN_3609 | 47201 |
| CTCN_1921 | 33143 | CTCN_6747 | 47202 |
| CTCN_1922 | 33144 | ATCN_3847 | 47203 |
| TTCN_1616 | 33145 | GTCN_3610 | 47204 |
| CTCN_1923 | 33146 | TTCN_5543 | 47205 |
| GTCN_1071 | 33147 | CTCN_6748 | 47206 |
| TTCN_1617 | 33148 | TTCN_5544 | 47207 |
| GTCN_1072 | 33149 | TTCN_5545 | 47208 |
| CTCN_1924 | 33150 | TTCN_5546 | 47209 |
| TTCN_1618 | 33151 | ATCN_3848 | 47210 |
| CTCN_1925 | 33152 | TTCN_5547 | 47211 |
| GTCN_1073 | 33153 | ATCN_3849 | 47212 |
| CTCN_1926 | 33154 | TTCN_5548 | 47213 |
| ATCN_1080 | 33155 | GTCN_3611 | 47214 |
| ATCN_1081 | 33156 | ATCN_3850 | 47215 |
| CTCN_1927 | 33157 | CTCN_6749 | 47216 |
| GTCN_1074 | 33158 | GTCN_3612 | 47217 |
| CTCN_1928 | 33159 | CTCN_6750 | 47218 |
| ATCN_1082 | 33160 | GTCN_3613 | 47219 |
| CTCN_1929 | 33161 | TTCN_5549 | 47220 |
| CTCN_1930 | 33162 | TTCN_5550 | 47221 |
| TTCN_1619 | 33163 | TTCN_5551 | 47222 |
| GTCN_1075 | 33164 | TTCN_5552 | 47223 |
| ATCN_1083 | 33165 | ATCN_3851 | 47224 |
| TTCN_1620 | 33166 | GTCN_3614 | 47225 |
| TTCN_1621 | 33167 | CTCN_6751 | 47226 |
| GTCN_1076 | 33168 | CTCN_6752 | 47227 |
| ATCN_1084 | 33169 | CTCN_6753 | 47228 |

| | | | |
|---|---|---|---|
| CTCN_1931 | 33170 | CTCN_6754 | 47229 |
| CTCN_1932 | 33171 | TTCN_5553 | 47230 |
| TTCN_1622 | 33172 | GTCN_3615 | 47231 |
| CTCN_1933 | 33173 | ATCN_3852 | 47232 |
| CTCN_1934 | 33174 | CTCN_6755 | 47233 |
| GTCN_1077 | 33175 | GTCN_3616 | 47234 |
| CTCN_1935 | 33176 | ATCN_3853 | 47235 |
| CTCN_1936 | 33177 | TTCN_5554 | 47236 |
| CTCN_1937 | 33178 | TTCN_5555 | 47237 |
| CTCN_1938 | 33179 | CTCN_6756 | 47238 |
| TTCN_1623 | 33180 | ATCN_3854 | 47239 |
| GTCN_1078 | 33181 | CTCN_6757 | 47240 |
| CTCN_1939 | 33182 | GTCN_3617 | 47241 |
| TTCN_1624 | 33183 | CTCN_6758 | 47242 |
| TTCN_1625 | 33184 | GTCN_3618 | 47243 |
| ATCN_1085 | 33185 | CTCN_6759 | 47244 |
| GTCN_1079 | 33186 | ATCN_3855 | 47245 |
| GTCN_1080 | 33187 | GTCN_3619 | 47246 |
| GTCN_1081 | 33188 | CTCN_6760 | 47247 |
| TTCN_1626 | 33189 | TTCN_5556 | 47248 |
| TTCN_1627 | 33190 | CTCN_6761 | 47249 |
| CTCN_1940 | 33191 | GTCN_3620 | 47250 |
| ATCN_1086 | 33192 | ATCN_3856 | 47251 |
| ATCN_1087 | 33193 | CTCN_6762 | 47252 |
| TTCN_1628 | 33194 | ATCN_3857 | 47253 |
| GTCN_1082 | 33195 | GTCN_3621 | 47254 |
| CTCN_1941 | 33196 | CTCN_6763 | 47255 |
| CTCN_1942 | 33197 | TTCN_5557 | 47256 |
| CTCN_1943 | 33198 | ATCN_3858 | 47257 |
| TTCN_1629 | 33199 | CTCN_6764 | 47258 |
| ATCN_1088 | 33200 | CTCN_6765 | 47259 |
| ATCN_1089 | 33201 | TTCN_5558 | 47260 |
| CTCN_1944 | 33202 | ATCN_3859 | 47261 |
| ATCN_1090 | 33203 | ATCN_3860 | 47262 |
| CTCN_1945 | 33204 | CTCN_6766 | 47263 |
| GTCN_1083 | 33205 | GTCN_3622 | 47264 |
| CTCN_1946 | 33206 | CTCN_6767 | 47265 |
| CTCN_1947 | 33207 | CTCN_6768 | 47266 |
| ATCN_1091 | 33208 | GTCN_3623 | 47267 |
| CTCN_1948 | 33209 | CTCN_6769 | 47268 |
| CTCN_1949 | 33210 | GTCN_3624 | 47269 |
| CTCN_1950 | 33211 | CTCN_6770 | 47270 |
| CTCN_1951 | 33212 | CTCN_6771 | 47271 |

FIG. 37 (continued)

| | | | |
|---|---|---|---|
| ATCN_1092 | 33213 | GTCN_3625 | 47272 |
| ATCN_1093 | 33214 | TTCN_5559 | 47273 |
| ATCN_1094 | 33215 | TTCN_5560 | 47274 |
| CTCN_1952 | 33216 | GTCN_3626 | 47275 |
| TTCN_1630 | 33217 | ATCN_3861 | 47276 |
| GTCN_1084 | 33218 | ATCN_3862 | 47277 |
| CTCN_1953 | 33219 | ATCN_3863 | 47278 |
| GTCN_1085 | 33220 | CTCN_6772 | 47279 |
| CTCN_1954 | 33221 | CTCN_6773 | 47280 |
| GTCN_1086 | 33222 | TTCN_5561 | 47281 |
| TTCN_1631 | 33223 | CTCN_6774 | 47282 |
| ATCN_1095 | 33224 | TTCN_5562 | 47283 |
| CTCN_1955 | 33225 | CTCN_6775 | 47284 |
| ATCN_1096 | 33226 | CTCN_6776 | 47285 |
| ATCN_1097 | 33227 | CTCN_6777 | 47286 |
| CTCN_1956 | 33228 | ATCN_3864 | 47287 |
| CTCN_1957 | 33229 | CTCN_6778 | 47288 |
| GTCN_1087 | 33230 | ATCN_3865 | 47289 |
| ATCN_1098 | 33231 | CTCN_6779 | 47290 |
| ATCN_1099 | 33232 | ATCN_3866 | 47291 |
| ATCN_1100 | 33233 | ATCN_3867 | 47292 |
| CTCN_1958 | 33234 | CTCN_6780 | 47293 |
| CTCN_1959 | 33235 | CTCN_6781 | 47294 |
| CTCN_1960 | 33236 | CTCN_6782 | 47295 |
| TTCN_1632 | 33237 | CTCN_6783 | 47296 |
| TTCN_1633 | 33238 | GTCN_3627 | 47297 |
| CTCN_1961 | 33239 | TTCN_5563 | 47298 |
| GTCN_1088 | 33240 | CTCN_6784 | 47299 |
| CTCN_1962 | 33241 | ATCN_3868 | 47300 |
| CTCN_1963 | 33242 | TTCN_5564 | 47301 |
| CTCN_1964 | 33243 | ATCN_3869 | 47302 |
| ATCN_1101 | 33244 | CTCN_6785 | 47303 |
| CTCN_1965 | 33245 | ATCN_3870 | 47304 |
| CTCN_1966 | 33246 | ATCN_3871 | 47305 |
| GTCN_1089 | 33247 | CTCN_6786 | 47306 |
| CTCN_1967 | 33248 | GTCN_3628 | 47307 |
| GTCN_1090 | 33249 | ATCN_3872 | 47308 |
| CTCN_1968 | 33250 | CTCN_6787 | 47309 |
| GTCN_1091 | 33251 | GTCN_3629 | 47310 |
| ATCN_1102 | 33252 | ATCN_3873 | 47311 |
| CTCN_1969 | 33253 | ATCN_3874 | 47312 |
| ATCN_1103 | 33254 | ATCN_3875 | 47313 |
| ATCN_1104 | 33255 | ATCN_3876 | 47314 |

| | | | |
|---|---|---|---|
| TTCN_1634 | 33256 | CTCN_6788 | 47315 |
| TTCN_1635 | 33257 | TTCN_5565 | 47316 |
| CTCN_1970 | 33258 | CTCN_6789 | 47317 |
| CTCN_1971 | 33259 | ATCN_3877 | 47318 |
| TTCN_1636 | 33260 | CTCN_6790 | 47319 |
| TTCN_1637 | 33261 | GTCN_3630 | 47320 |
| TTCN_1638 | 33262 | CTCN_6791 | 47321 |
| ATCN_1105 | 33263 | CTCN_6792 | 47322 |
| CTCN_1972 | 33264 | TTCN_5566 | 47323 |
| CTCN_1973 | 33265 | CTCN_6793 | 47324 |
| TTCN_1639 | 33266 | CTCN_6794 | 47325 |
| CTCN_1974 | 33267 | CTCN_6795 | 47326 |
| TTCN_1640 | 33268 | TTCN_5567 | 47327 |
| CTCN_1975 | 33269 | GTCN_3631 | 47328 |
| TTCN_1641 | 33270 | GTCN_3632 | 47329 |
| CTCN_1976 | 33271 | CTCN_6796 | 47330 |
| CTCN_1977 | 33272 | TTCN_5568 | 47331 |
| TTCN_1642 | 33273 | ATCN_3878 | 47332 |
| CTCN_1978 | 33274 | CTCN_6797 | 47333 |
| CTCN_1979 | 33275 | GTCN_3633 | 47334 |
| TTCN_1643 | 33276 | CTCN_6798 | 47335 |
| TTCN_1644 | 33277 | CTCN_6799 | 47336 |
| CTCN_1980 | 33278 | TTCN_5569 | 47337 |
| GTCN_1092 | 33279 | GTCN_3634 | 47338 |
| GTCN_1093 | 33280 | TTCN_5570 | 47339 |
| CTCN_1981 | 33281 | CTCN_6800 | 47340 |
| CTCN_1982 | 33282 | TTCN_5571 | 47341 |
| ATCN_1106 | 33283 | ATCN_3879 | 47342 |
| CTCN_1983 | 33284 | GTCN_3635 | 47343 |
| TTCN_1645 | 33285 | ATCN_3880 | 47344 |
| TTCN_1646 | 33286 | CTCN_6801 | 47345 |
| CTCN_1984 | 33287 | TTCN_5572 | 47346 |
| CTCN_1985 | 33288 | TTCN_5573 | 47347 |
| ATCN_1107 | 33289 | ATCN_3881 | 47348 |
| ATCN_1108 | 33290 | TTCN_5574 | 47349 |
| CTCN_1986 | 33291 | TTCN_5575 | 47350 |
| CTCN_1987 | 33292 | CTCN_6802 | 47351 |
| CTCN_1988 | 33293 | CTCN_6803 | 47352 |
| CTCN_1989 | 33294 | TTCN_5576 | 47353 |
| GTCN_1094 | 33295 | TTCN_5577 | 47354 |
| CTCN_1990 | 33296 | CTCN_6804 | 47355 |
| CTCN_1991 | 33297 | CTCN_6805 | 47356 |
| GTCN_1095 | 33298 | CTCN_6806 | 47357 |

FIG. 37 (continued)

| | | | |
|---|---|---|---|
| TTCN_1647 | 33299 | TTCN_5578 | 47358 |
| GTCN_1096 | 33300 | CTCN_6807 | 47359 |
| CTCN_1992 | 33301 | TTCN_5579 | 47360 |
| ATCN_1109 | 33302 | CTCN_6808 | 47361 |
| CTCN_1993 | 33303 | GTCN_3636 | 47362 |
| CTCN_1994 | 33304 | CTCN_6809 | 47363 |
| ATCN_1110 | 33305 | CTCN_6810 | 47364 |
| ATCN_1111 | 33306 | ATCN_3882 | 47365 |
| ATCN_1112 | 33307 | CTCN_6811 | 47366 |
| ATCN_1113 | 33308 | ATCN_3883 | 47367 |
| CTCN_1995 | 33309 | ATCN_3884 | 47368 |
| GTCN_1097 | 33310 | CTCN_6812 | 47369 |
| ATCN_1114 | 33311 | CTCN_6813 | 47370 |
| GTCN_1098 | 33312 | CTCN_6814 | 47371 |
| CTCN_1996 | 33313 | CTCN_6815 | 47372 |
| GTCN_1099 | 33314 | CTCN_6816 | 47373 |
| ATCN_1115 | 33315 | CTCN_6817 | 47374 |
| ATCN_1116 | 33316 | CTCN_6818 | 47375 |
| TTCN_1648 | 33317 | CTCN_6819 | 47376 |
| TTCN_1649 | 33318 | CTCN_6820 | 47377 |
| CTCN_1997 | 33319 | TTCN_5580 | 47378 |
| GTCN_1100 | 33320 | TTCN_5581 | 47379 |
| TTCN_1650 | 33321 | GTCN_3637 | 47380 |
| CTCN_1998 | 33322 | CTCN_6821 | 47381 |
| CTCN_1999 | 33323 | ATCN_3885 | 47382 |
| CTCN_2000 | 33324 | TTCN_5582 | 47383 |
| TTCN_1651 | 33325 | GTCN_3638 | 47384 |
| TTCN_1652 | 33326 | ATCN_3886 | 47385 |
| GTCN_1101 | 33327 | ATCN_3887 | 47386 |
| ATCN_1117 | 33328 | TTCN_5583 | 47387 |
| TTCN_1653 | 33329 | GTCN_3639 | 47388 |
| TTCN_1654 | 33330 | ATCN_3888 | 47389 |
| TTCN_1655 | 33331 | TTCN_5584 | 47390 |
| ATCN_1118 | 33332 | TTCN_5585 | 47391 |
| CTCN_2001 | 33333 | ATCN_3889 | 47392 |
| TTCN_1656 | 33334 | TTCN_5586 | 47393 |
| GTCN_1102 | 33335 | TTCN_5587 | 47394 |
| GTCN_1103 | 33336 | ATCN_3890 | 47395 |
| CTCN_2002 | 33337 | CTCN_6822 | 47396 |
| GTCN_1104 | 33338 | CTCN_6823 | 47397 |
| TTCN_1657 | 33339 | ATCN_3891 | 47398 |
| TTCN_1658 | 33340 | GTCN_3640 | 47399 |
| ATCN_1119 | 33341 | CTCN_6824 | 47400 |

| | | | |
|---|---|---|---|
| ATCN_1120 | 33342 | ATCN_3892 | 47401 |
| TTCN_1659 | 33343 | CTCN_6825 | 47402 |
| ATCN_1121 | 33344 | CTCN_6826 | 47403 |
| CTCN_2003 | 33345 | CTCN_6827 | 47404 |
| CTCN_2004 | 33346 | TTCN_5588 | 47405 |
| GTCN_1105 | 33347 | TTCN_5589 | 47406 |
| CTCN_2005 | 33348 | TTCN_5590 | 47407 |
| CTCN_2006 | 33349 | TTCN_5591 | 47408 |
| CTCN_2007 | 33350 | TTCN_5592 | 47409 |
| TTCN_1660 | 33351 | CTCN_6828 | 47410 |
| TTCN_1661 | 33352 | GTCN_3641 | 47411 |
| ATCN_1122 | 33353 | GTCN_3642 | 47412 |
| TTCN_1662 | 33354 | GTCN_3643 | 47413 |
| GTCN_1106 | 33355 | CTCN_6829 | 47414 |
| TTCN_1663 | 33356 | CTCN_6830 | 47415 |
| TTCN_1664 | 33357 | ATCN_3893 | 47416 |
| TTCN_1665 | 33358 | CTCN_6831 | 47417 |
| TTCN_1666 | 33359 | GTCN_3644 | 47418 |
| CTCN_2008 | 33360 | GTCN_3645 | 47419 |
| CTCN_2009 | 33361 | TTCN_5593 | 47420 |
| TTCN_1667 | 33362 | TTCN_5594 | 47421 |
| ATCN_1123 | 33363 | TTCN_5595 | 47422 |
| CTCN_2010 | 33364 | ATCN_3894 | 47423 |
| TTCN_1668 | 33365 | CTCN_6832 | 47424 |
| TTCN_1669 | 33366 | CTCN_6833 | 47425 |
| GTCN_1107 | 33367 | GTCN_3646 | 47426 |
| CTCN_2011 | 33368 | TTCN_5596 | 47427 |
| GTCN_1108 | 33369 | CTCN_6834 | 47428 |
| CTCN_2012 | 33370 | CTCN_6835 | 47429 |
| CTCN_2013 | 33371 | CTCN_6836 | 47430 |
| CTCN_2014 | 33372 | CTCN_6837 | 47431 |
| GTCN_1109 | 33373 | GTCN_3647 | 47432 |
| TTCN_1670 | 33374 | TTCN_5597 | 47433 |
| ATCN_1124 | 33375 | CTCN_6838 | 47434 |
| ATCN_1125 | 33376 | GTCN_3648 | 47435 |
| TTCN_1671 | 33377 | CTCN_6839 | 47436 |
| GTCN_1110 | 33378 | CTCN_6840 | 47437 |
| CTCN_2015 | 33379 | CTCN_6841 | 47438 |
| ATCN_1126 | 33380 | CTCN_6842 | 47439 |
| CTCN_2016 | 33381 | TTCN_5598 | 47440 |
| ATCN_1127 | 33382 | GTCN_3649 | 47441 |
| CTCN_2017 | 33383 | ATCN_3895 | 47442 |
| CTCN_2018 | 33384 | CTCN_6843 | 47443 |

FIG. 37 (continued)

| | | | |
|---|---|---|---|
| CTCN_2019 | 33385 | CTCN_6844 | 47444 |
| ATCN_1128 | 33386 | ATCN_3896 | 47445 |
| CTCN_2020 | 33387 | TTCN_5599 | 47446 |
| CTCN_2021 | 33388 | CTCN_6845 | 47447 |
| TTCN_1672 | 33389 | CTCN_6846 | 47448 |
| TTCN_1673 | 33390 | GTCN_3650 | 47449 |
| ATCN_1129 | 33391 | GTCN_3651 | 47450 |
| TTCN_1674 | 33392 | TTCN_5600 | 47451 |
| TTCN_1675 | 33393 | CTCN_6847 | 47452 |
| CTCN_2022 | 33394 | TTCN_5601 | 47453 |
| TTCN_1676 | 33395 | ATCN_3897 | 47454 |
| TTCN_1677 | 33396 | TTCN_5602 | 47455 |
| CTCN_2023 | 33397 | ATCN_3898 | 47456 |
| GTCN_1111 | 33398 | CTCN_6848 | 47457 |
| CTCN_2024 | 33399 | GTCN_3652 | 47458 |
| GTCN_1112 | 33400 | TTCN_5603 | 47459 |
| CTCN_2025 | 33401 | TTCN_5604 | 47460 |
| GTCN_1113 | 33402 | TTCN_5605 | 47461 |
| CTCN_2026 | 33403 | GTCN_3653 | 47462 |
| GTCN_1114 | 33404 | TTCN_5606 | 47463 |
| TTCN_1678 | 33405 | ATCN_3899 | 47464 |
| ATCN_1130 | 33406 | ATCN_3900 | 47465 |
| TTCN_1679 | 33407 | GTCN_3654 | 47466 |
| CTCN_2027 | 33408 | TTCN_5607 | 47467 |
| ATCN_1131 | 33409 | CTCN_6849 | 47468 |
| ATCN_1132 | 33410 | GTCN_3655 | 47469 |
| ATCN_1133 | 33411 | ATCN_3901 | 47470 |
| CTCN_2028 | 33412 | CTCN_6850 | 47471 |
| CTCN_2029 | 33413 | GTCN_3656 | 47472 |
| CTCN_2030 | 33414 | ATCN_3902 | 47473 |
| CTCN_2031 | 33415 | CTCN_6851 | 47474 |
| ATCN_1134 | 33416 | GTCN_3657 | 47475 |
| ATCN_1135 | 33417 | GTCN_3658 | 47476 |
| CTCN_2032 | 33418 | ATCN_3903 | 47477 |
| TTCN_1680 | 33419 | CTCN_6852 | 47478 |
| CTCN_2033 | 33420 | GTCN_3659 | 47479 |
| ATCN_1136 | 33421 | CTCN_6853 | 47480 |
| GTCN_1115 | 33422 | ATCN_3904 | 47481 |
| GTCN_1116 | 33423 | TTCN_5608 | 47482 |
| TTCN_1681 | 33424 | TTCN_5609 | 47483 |
| CTCN_2034 | 33425 | CTCN_6854 | 47484 |
| CTCN_2035 | 33426 | GTCN_3660 | 47485 |
| TTCN_1682 | 33427 | ATCN_3905 | 47486 |

| | | | |
|---|---|---|---|
| CTCN_2036 | 33428 | CTCN_6855 | 47487 |
| GTCN_1117 | 33429 | ATCN_3906 | 47488 |
| ATCN_1137 | 33430 | TTCN_5610 | 47489 |
| TTCN_1683 | 33431 | ATCN_3907 | 47490 |
| GTCN_1118 | 33432 | CTCN_6856 | 47491 |
| TTCN_1684 | 33433 | CTCN_6857 | 47492 |
| TTCN_1685 | 33434 | GTCN_3661 | 47493 |
| CTCN_2037 | 33435 | ATCN_3908 | 47494 |
| ATCN_1138 | 33436 | TTCN_5611 | 47495 |
| ATCN_1139 | 33437 | CTCN_6858 | 47496 |
| TTCN_1686 | 33438 | CTCN_6859 | 47497 |
| TTCN_1687 | 33439 | TTCN_5612 | 47498 |
| ATCN_1140 | 33440 | TTCN_5613 | 47499 |
| CTCN_2038 | 33441 | GTCN_3662 | 47500 |
| TTCN_1688 | 33442 | TTCN_5614 | 47501 |
| ATCN_1141 | 33443 | GTCN_3663 | 47502 |
| TTCN_1689 | 33444 | TTCN_5615 | 47503 |
| GTCN_1119 | 33445 | CTCN_6860 | 47504 |
| TTCN_1690 | 33446 | GTCN_3664 | 47505 |
| GTCN_1120 | 33447 | TTCN_5616 | 47506 |
| TTCN_1691 | 33448 | TTCN_5617 | 47507 |
| TTCN_1692 | 33449 | CTCN_6861 | 47508 |
| CTCN_2039 | 33450 | TTCN_5618 | 47509 |
| CTCN_2040 | 33451 | TTCN_5619 | 47510 |
| CTCN_2041 | 33452 | CTCN_6862 | 47511 |
| GTCN_1121 | 33453 | TTCN_5620 | 47512 |
| CTCN_2042 | 33454 | ATCN_3909 | 47513 |
| GTCN_1122 | 33455 | TTCN_5621 | 47514 |
| TTCN_1693 | 33456 | CTCN_6863 | 47515 |
| GTCN_1123 | 33457 | GTCN_3665 | 47516 |
| GTCN_1124 | 33458 | GTCN_3666 | 47517 |
| CTCN_2043 | 33459 | CTCN_6864 | 47518 |
| CTCN_2044 | 33460 | TTCN_5622 | 47519 |
| CTCN_2045 | 33461 | TTCN_5623 | 47520 |
| TTCN_1694 | 33462 | CTCN_6865 | 47521 |
| CTCN_2046 | 33463 | TTCN_5624 | 47522 |
| CTCN_2047 | 33464 | CTCN_6866 | 47523 |
| CTCN_2048 | 33465 | GTCN_3667 | 47524 |
| CTCN_2049 | 33466 | TTCN_5625 | 47525 |
| CTCN_2050 | 33467 | CTCN_6867 | 47526 |
| ATCN_1142 | 33468 | CTCN_6868 | 47527 |
| CTCN_2051 | 33469 | GTCN_3668 | 47528 |
| GTCN_1125 | 33470 | GTCN_3669 | 47529 |

FIG. 37 (continued)

| | | | |
|---|---|---|---|
| CTCN_2052 | 33471 | TTCN_5626 | 47530 |
| GTCN_1126 | 33472 | ATCN_3910 | 47531 |
| CTCN_2053 | 33473 | TTCN_5627 | 47532 |
| TTCN_1695 | 33474 | TTCN_5628 | 47533 |
| GTCN_1127 | 33475 | GTCN_3670 | 47534 |
| TTCN_1696 | 33476 | TTCN_5629 | 47535 |
| TTCN_1697 | 33477 | ATCN_3911 | 47536 |
| TTCN_1698 | 33478 | TTCN_5630 | 47537 |
| TTCN_1699 | 33479 | CTCN_6869 | 47538 |
| ATCN_1143 | 33480 | TTCN_5631 | 47539 |
| TTCN_1700 | 33481 | GTCN_3671 | 47540 |
| ATCN_1144 | 33482 | TTCN_5632 | 47541 |
| TTCN_1701 | 33483 | TTCN_5633 | 47542 |
| TTCN_1702 | 33484 | ATCN_3912 | 47543 |
| TTCN_1703 | 33485 | ATCN_3913 | 47544 |
| TTCN_1704 | 33486 | GTCN_3672 | 47545 |
| TTCN_1705 | 33487 | CTCN_6870 | 47546 |
| ATCN_1145 | 33488 | ATCN_3914 | 47547 |
| CTCN_2054 | 33489 | GTCN_3673 | 47548 |
| ATCN_1146 | 33490 | TTCN_5634 | 47549 |
| GTCN_1128 | 33491 | ATCN_3915 | 47550 |
| TTCN_1706 | 33492 | TTCN_5635 | 47551 |
| GTCN_1129 | 33493 | CTCN_6871 | 47552 |
| CTCN_2055 | 33494 | TTCN_5636 | 47553 |
| TTCN_1707 | 33495 | TTCN_5637 | 47554 |
| TTCN_1708 | 33496 | GTCN_3674 | 47555 |
| CTCN_2056 | 33497 | TTCN_5638 | 47556 |
| TTCN_1709 | 33498 | GTCN_3675 | 47557 |
| TTCN_1710 | 33499 | GTCN_3676 | 47558 |
| ATCN_1147 | 33500 | TTCN_5639 | 47559 |
| GTCN_1130 | 33501 | CTCN_6872 | 47560 |
| ATCN_1148 | 33502 | ATCN_3916 | 47561 |
| CTCN_2057 | 33503 | TTCN_5640 | 47562 |
| TTCN_1711 | 33504 | CTCN_6873 | 47563 |
| CTCN_2058 | 33505 | ATCN_3917 | 47564 |
| TTCN_1712 | 33506 | TTCN_5641 | 47565 |
| ATCN_1149 | 33507 | TTCN_5642 | 47566 |
| TTCN_1713 | 33508 | TTCN_5643 | 47567 |
| CTCN_2059 | 33509 | ATCN_3918 | 47568 |
| ATCN_1150 | 33510 | ATCN_3919 | 47569 |
| GTCN_1131 | 33511 | ATCN_3920 | 47570 |
| TTCN_1714 | 33512 | CTCN_6874 | 47571 |
| TTCN_1715 | 33513 | GTCN_3677 | 47572 |

| | | | |
|---|---|---|---|
| TTCN_1716 | 33514 | ATCN_3921 | 47573 |
| CTCN_2060 | 33515 | GTCN_3678 | 47574 |
| GTCN_1132 | 33516 | CTCN_6875 | 47575 |
| TTCN_1717 | 33517 | TTCN_5644 | 47576 |
| ATCN_1151 | 33518 | ATCN_3922 | 47577 |
| ATCN_1152 | 33519 | CTCN_6876 | 47578 |
| GTCN_1133 | 33520 | TTCN_5645 | 47579 |
| GTCN_1134 | 33521 | GTCN_3679 | 47580 |
| GTCN_1135 | 33522 | TTCN_5646 | 47581 |
| GTCN_1136 | 33523 | CTCN_6877 | 47582 |
| TTCN_1718 | 33524 | CTCN_6878 | 47583 |
| TTCN_1719 | 33525 | CTCN_6879 | 47584 |
| CTCN_2061 | 33526 | CTCN_6880 | 47585 |
| CTCN_2062 | 33527 | TTCN_5647 | 47586 |
| ATCN_1153 | 33528 | TTCN_5648 | 47587 |
| GTCN_1137 | 33529 | CTCN_6881 | 47588 |
| TTCN_1720 | 33530 | ATCN_3923 | 47589 |
| CTCN_2063 | 33531 | ATCN_3924 | 47590 |
| TTCN_1721 | 33532 | CTCN_6882 | 47591 |
| CTCN_2064 | 33533 | CTCN_6883 | 47592 |
| ATCN_1154 | 33534 | CTCN_6884 | 47593 |
| ATCN_1155 | 33535 | ATCN_3925 | 47594 |
| CTCN_2065 | 33536 | CTCN_6885 | 47595 |
| ATCN_1156 | 33537 | TTCN_5649 | 47596 |
| ATCN_1157 | 33538 | TTCN_5650 | 47597 |
| CTCN_2066 | 33539 | CTCN_6886 | 47598 |
| GTCN_1138 | 33540 | CTCN_6887 | 47599 |
| ATCN_1158 | 33541 | CTCN_6888 | 47600 |
| GTCN_1139 | 33542 | CTCN_6889 | 47601 |
| GTCN_1140 | 33543 | GTCN_3680 | 47602 |
| TTCN_1722 | 33544 | TTCN_5651 | 47603 |
| TTCN_1723 | 33545 | CTCN_6890 | 47604 |
| ATCN_1159 | 33546 | CTCN_6891 | 47605 |
| TTCN_1724 | 33547 | TTCN_5652 | 47606 |
| ATCN_1160 | 33548 | TTCN_5653 | 47607 |
| TTCN_1725 | 33549 | TTCN_5654 | 47608 |
| TTCN_1726 | 33550 | CTCN_6892 | 47609 |
| ATCN_1161 | 33551 | GTCN_3681 | 47610 |
| TTCN_1727 | 33552 | TTCN_5655 | 47611 |
| TTCN_1728 | 33553 | ATCN_3926 | 47612 |
| TTCN_1729 | 33554 | TTCN_5656 | 47613 |
| CTCN_2067 | 33555 | GTCN_3682 | 47614 |
| ATCN_1162 | 33556 | ATCN_3927 | 47615 |

FIG. 37 (continued)

| | | | |
|---|---|---|---|
| GTCN_1141 | 33557 | TTCN_5657 | 47616 |
| ATCN_1163 | 33558 | ATCN_3928 | 47617 |
| TTCN_1730 | 33559 | GTCN_3683 | 47618 |
| ATCN_1164 | 33560 | CTCN_6893 | 47619 |
| TTCN_1731 | 33561 | GTCN_3684 | 47620 |
| CTCN_2068 | 33562 | TTCN_5658 | 47621 |
| TTCN_1732 | 33563 | CTCN_6894 | 47622 |
| GTCN_1142 | 33564 | CTCN_6895 | 47623 |
| TTCN_1733 | 33565 | CTCN_6896 | 47624 |
| ATCN_1165 | 33566 | GTCN_3685 | 47625 |
| TTCN_1734 | 33567 | ATCN_3929 | 47626 |
| ATCN_1166 | 33568 | ATCN_3930 | 47627 |
| GTCN_1143 | 33569 | ATCN_3931 | 47628 |
| CTCN_2069 | 33570 | TTCN_5659 | 47629 |
| GTCN_1144 | 33571 | ATCN_3932 | 47630 |
| ATCN_1167 | 33572 | TTCN_5660 | 47631 |
| CTCN_2070 | 33573 | CTCN_6897 | 47632 |
| CTCN_2071 | 33574 | GTCN_3686 | 47633 |
| CTCN_2072 | 33575 | TTCN_5661 | 47634 |
| GTCN_1145 | 33576 | ATCN_3933 | 47635 |
| TTCN_1735 | 33577 | ATCN_3934 | 47636 |
| GTCN_1146 | 33578 | GTCN_3687 | 47637 |
| CTCN_2073 | 33579 | ATCN_3935 | 47638 |
| CTCN_2074 | 33580 | TTCN_5662 | 47639 |
| ATCN_1168 | 33581 | TTCN_5663 | 47640 |
| ATCN_1169 | 33582 | TTCN_5664 | 47641 |
| CTCN_2075 | 33583 | GTCN_3688 | 47642 |
| CTCN_2076 | 33584 | CTCN_6898 | 47643 |
| CTCN_2077 | 33585 | GTCN_3689 | 47644 |
| TTCN_1736 | 33586 | ATCN_3936 | 47645 |
| ATCN_1170 | 33587 | TTCN_5665 | 47646 |
| TTCN_1737 | 33588 | CTCN_6899 | 47647 |
| CTCN_2078 | 33589 | ATCN_3937 | 47648 |
| CTCN_2079 | 33590 | TTCN_5666 | 47649 |
| CTCN_2080 | 33591 | ATCN_3938 | 47650 |
| CTCN_2081 | 33592 | CTCN_6900 | 47651 |
| ATCN_1171 | 33593 | CTCN_6901 | 47652 |
| ATCN_1172 | 33594 | ATCN_3939 | 47653 |
| CTCN_2082 | 33595 | TTCN_5667 | 47654 |
| GTCN_1147 | 33596 | ATCN_3940 | 47655 |
| GTCN_1148 | 33597 | TTCN_5668 | 47656 |
| GTCN_1149 | 33598 | ATCN_3941 | 47657 |
| CTCN_2083 | 33599 | TTCN_5669 | 47658 |

| | | | |
|---|---|---|---|
| CTCN_2084 | 33600 | CTCN_6902 | 47659 |
| CTCN_2085 | 33601 | CTCN_6903 | 47660 |
| CTCN_2086 | 33602 | CTCN_6904 | 47661 |
| TTCN_1738 | 33603 | CTCN_6905 | 47662 |
| TTCN_1739 | 33604 | GTCN_3690 | 47663 |
| TTCN_1740 | 33605 | ATCN_3942 | 47664 |
| ATCN_1173 | 33606 | CTCN_6906 | 47665 |
| TTCN_1741 | 33607 | TTCN_5670 | 47666 |
| ATCN_1174 | 33608 | ATCN_3943 | 47667 |
| ATCN_1175 | 33609 | TTCN_5671 | 47668 |
| ATCN_1176 | 33610 | CTCN_6907 | 47669 |
| GTCN_1150 | 33611 | ATCN_3944 | 47670 |
| ATCN_1177 | 33612 | ATCN_3945 | 47671 |
| ATCN_1178 | 33613 | GTCN_3691 | 47672 |
| ATCN_1179 | 33614 | ATCN_3946 | 47673 |
| ATCN_1180 | 33615 | ATCN_3947 | 47674 |
| ATCN_1181 | 33616 | CTCN_6908 | 47675 |
| ATCN_1182 | 33617 | CTCN_6909 | 47676 |
| ATCN_1183 | 33618 | CTCN_6910 | 47677 |
| ATCN_1184 | 33619 | GTCN_3692 | 47678 |
| ATCN_1185 | 33620 | GTCN_3693 | 47679 |
| ATCN_1186 | 33621 | CTCN_6911 | 47680 |
| ATCN_1187 | 33622 | CTCN_6912 | 47681 |
| ATCN_1188 | 33623 | TTCN_5672 | 47682 |
| GTCN_1151 | 33624 | GTCN_3694 | 47683 |
| ATCN_1189 | 33625 | TTCN_5673 | 47684 |
| ATCN_1190 | 33626 | TTCN_5674 | 47685 |
| ATCN_1191 | 33627 | TTCN_5675 | 47686 |
| ATCN_1192 | 33628 | CTCN_6913 | 47687 |
| ATCN_1193 | 33629 | CTCN_6914 | 47688 |
| GTCN_1152 | 33630 | TTCN_5676 | 47689 |
| ATCN_1194 | 33631 | ATCN_3948 | 47690 |
| ATCN_1195 | 33632 | ATCN_3949 | 47691 |
| ATCN_1196 | 33633 | GTCN_3695 | 47692 |
| ATCN_1197 | 33634 | ATCN_3950 | 47693 |
| ATCN_1198 | 33635 | TTCN_5677 | 47694 |
| ATCN_1199 | 33636 | TTCN_5678 | 47695 |
| ATCN_1200 | 33637 | CTCN_6915 | 47696 |
| ATCN_1201 | 33638 | TTCN_5679 | 47697 |
| ATCN_1202 | 33639 | TTCN_5680 | 47698 |
| ATCN_1203 | 33640 | TTCN_5681 | 47699 |
| ATCN_1204 | 33641 | GTCN_3696 | 47700 |
| ATCN_1205 | 33642 | ATCN_3951 | 47701 |

FIG. 37 (continued)

| | | | |
|---|---|---|---|
| ATCN_1206 | 33643 | GTCN_3697 | 47702 |
| ATCN_1207 | 33644 | ATCN_3952 | 47703 |
| ATCN_1208 | 33645 | TTCN_5682 | 47704 |
| ATCN_1209 | 33646 | TTCN_5683 | 47705 |
| ATCN_1210 | 33647 | CTCN_6916 | 47706 |
| ATCN_1211 | 33648 | CTCN_6917 | 47707 |
| ATCN_1212 | 33649 | TTCN_5684 | 47708 |
| ATCN_1213 | 33650 | GTCN_3698 | 47709 |
| ATCN_1214 | 33651 | CTCN_6918 | 47710 |
| ATCN_1215 | 33652 | TTCN_5685 | 47711 |
| ATCN_1216 | 33653 | CTCN_6919 | 47712 |
| ATCN_1217 | 33654 | ATCN_3953 | 47713 |
| ATCN_1218 | 33655 | ATCN_3954 | 47714 |
| ATCN_1219 | 33656 | TTCN_5686 | 47715 |
| ATCN_1220 | 33657 | GTCN_3699 | 47716 |
| GTCN_1153 | 33658 | TTCN_5687 | 47717 |
| ATCN_1221 | 33659 | CTCN_6920 | 47718 |
| ATCN_1222 | 33660 | TTCN_5688 | 47719 |
| ATCN_1223 | 33661 | ATCN_3955 | 47720 |
| ATCN_1224 | 33662 | CTCN_6921 | 47721 |
| ATCN_1225 | 33663 | GTCN_3700 | 47722 |
| ATCN_1226 | 33664 | TTCN_5689 | 47723 |
| ATCN_1227 | 33665 | TTCN_5690 | 47724 |
| ATCN_1228 | 33666 | CTCN_6922 | 47725 |
| GTCN_1154 | 33667 | CTCN_6923 | 47726 |
| ATCN_1229 | 33668 | CTCN_6924 | 47727 |
| ATCN_1230 | 33669 | TTCN_5691 | 47728 |
| ATCN_1231 | 33670 | CTCN_6925 | 47729 |
| ATCN_1232 | 33671 | CTCN_6926 | 47730 |
| ATCN_1233 | 33672 | ATCN_3956 | 47731 |
| ATCN_1234 | 33673 | ATCN_3957 | 47732 |
| ATCN_1235 | 33674 | TTCN_5692 | 47733 |
| ATCN_1236 | 33675 | GTCN_3701 | 47734 |
| CTCN_2087 | 33676 | TTCN_5693 | 47735 |
| ATCN_1237 | 33677 | ATCN_3958 | 47736 |
| GTCN_1155 | 33678 | ATCN_3959 | 47737 |
| CTCN_2088 | 33679 | TTCN_5694 | 47738 |
| ATCN_1238 | 33680 | GTCN_3702 | 47739 |
| GTCN_1156 | 33681 | TTCN_5695 | 47740 |
| ATCN_1239 | 33682 | TTCN_5696 | 47741 |
| GTCN_1157 | 33683 | ATCN_3960 | 47742 |
| GTCN_1158 | 33684 | ATCN_3961 | 47743 |
| CTCN_2089 | 33685 | TTCN_5697 | 47744 |

| | | | |
|---|---|---|---|
| CTCN_2090 | 33686 | TTCN_5698 | 47745 |
| TTCN_1742 | 33687 | TTCN_5699 | 47746 |
| GTCN_1159 | 33688 | TTCN_5700 | 47747 |
| CTCN_2091 | 33689 | CTCN_6927 | 47748 |
| TTCN_1743 | 33690 | ATCN_3962 | 47749 |
| CTCN_2092 | 33691 | TTCN_5701 | 47750 |
| GTCN_1160 | 33692 | TTCN_5702 | 47751 |
| TTCN_1744 | 33693 | ATCN_3963 | 47752 |
| GTCN_1161 | 33694 | CTCN_6928 | 47753 |
| CTCN_2093 | 33695 | GTCN_3703 | 47754 |
| GTCN_1162 | 33696 | TTCN_5703 | 47755 |
| CTCN_2094 | 33697 | TTCN_5704 | 47756 |
| CTCN_2095 | 33698 | ATCN_3964 | 47757 |
| ATCN_1240 | 33699 | CTCN_6929 | 47758 |
| GTCN_1163 | 33700 | TTCN_5705 | 47759 |
| GTCN_1164 | 33701 | TTCN_5706 | 47760 |
| GTCN_1165 | 33702 | CTCN_6930 | 47761 |
| ATCN_1241 | 33703 | GTCN_3704 | 47762 |
| ATCN_1242 | 33704 | CTCN_6931 | 47763 |
| CTCN_2096 | 33705 | CTCN_6932 | 47764 |
| ATCN_1243 | 33706 | GTCN_3705 | 47765 |
| ATCN_1244 | 33707 | TTCN_5707 | 47766 |
| CTCN_2097 | 33708 | GTCN_3706 | 47767 |
| TTCN_1745 | 33709 | CTCN_6933 | 47768 |
| CTCN_2098 | 33710 | CTCN_6934 | 47769 |
| CTCN_2099 | 33711 | CTCN_6935 | 47770 |
| TTCN_1746 | 33712 | TTCN_5708 | 47771 |
| CTCN_2100 | 33713 | GTCN_3707 | 47772 |
| ATCN_1245 | 33714 | TTCN_5709 | 47773 |
| TTCN_1747 | 33715 | TTCN_5710 | 47774 |
| CTCN_2101 | 33716 | CTCN_6936 | 47775 |
| TTCN_1748 | 33717 | GTCN_3708 | 47776 |
| CTCN_2102 | 33718 | CTCN_6937 | 47777 |
| TTCN_1749 | 33719 | CTCN_6938 | 47778 |
| ATCN_1246 | 33720 | TTCN_5711 | 47779 |
| TTCN_1750 | 33721 | ATCN_3965 | 47780 |
| CTCN_2103 | 33722 | ATCN_3966 | 47781 |
| TTCN_1751 | 33723 | TTCN_5712 | 47782 |
| GTCN_1166 | 33724 | TTCN_5713 | 47783 |
| TTCN_1752 | 33725 | TTCN_5714 | 47784 |
| ATCN_1247 | 33726 | TTCN_5715 | 47785 |
| CTCN_2104 | 33727 | TTCN_5716 | 47786 |
| ATCN_1248 | 33728 | TTCN_5717 | 47787 |

FIG. 37 (continued)

| | | | | | | | |
|---|---|---|---|---|---|---|---|
| ATCN_1249 | 33729 | TTCN_5718 | 47788 | TTCN_1766 | 33772 | GTCN_3718 | 47831 |
| ATCN_1250 | 33730 | CTCN_6939 | 47789 | CTCN_2118 | 33773 | CTCN_6951 | 47832 |
| TTCN_1753 | 33731 | TTCN_5719 | 47790 | CTCN_2119 | 33774 | CTCN_6952 | 47833 |
| TTCN_1754 | 33732 | ATCN_3967 | 47791 | TTCN_1767 | 33775 | CTCN_6953 | 47834 |
| ATCN_1251 | 33733 | TTCN_5720 | 47792 | CTCN_2120 | 33776 | CTCN_6954 | 47835 |
| ATCN_1252 | 33734 | ATCN_3968 | 47793 | ATCN_1263 | 33777 | TTCN_5733 | 47836 |
| ATCN_1253 | 33735 | ATCN_3969 | 47794 | GTCN_1170 | 33778 | ATCN_3974 | 47837 |
| ATCN_1254 | 33736 | GTCN_3709 | 47795 | TTCN_1768 | 33779 | CTCN_6955 | 47838 |
| TTCN_1755 | 33737 | TTCN_5721 | 47796 | CTCN_2121 | 33780 | ATCN_3975 | 47839 |
| ATCN_1255 | 33738 | GTCN_3710 | 47797 | GTCN_1171 | 33781 | ATCN_3976 | 47840 |
| CTCN_2105 | 33739 | GTCN_3711 | 47798 | GTCN_1172 | 33782 | TTCN_5734 | 47841 |
| TTCN_1756 | 33740 | CTCN_6940 | 47799 | ATCN_1264 | 33783 | TTCN_5735 | 47842 |
| CTCN_2106 | 33741 | TTCN_5722 | 47800 | ATCN_1265 | 33784 | TTCN_5736 | 47843 |
| CTCN_2107 | 33742 | ATCN_3970 | 47801 | ATCN_1266 | 33785 | CTCN_6956 | 47844 |
| TTCN_1757 | 33743 | CTCN_6941 | 47802 | TTCN_1769 | 33786 | TTCN_5737 | 47845 |
| ATCN_1256 | 33744 | TTCN_5723 | 47803 | GTCN_1173 | 33787 | ATCN_3977 | 47846 |
| ATCN_1257 | 33745 | TTCN_5724 | 47804 | TTCN_1770 | 33788 | CTCN_6957 | 47847 |
| TTCN_1758 | 33746 | CTCN_6942 | 47805 | TTCN_1771 | 33789 | TTCN_5738 | 47848 |
| ATCN_1258 | 33747 | GTCN_3712 | 47806 | GTCN_1174 | 33790 | CTCN_6958 | 47849 |
| ATCN_1259 | 33748 | CTCN_6943 | 47807 | TTCN_1772 | 33791 | ATCN_3978 | 47850 |
| ATCN_1260 | 33749 | TTCN_5725 | 47808 | ATCN_1267 | 33792 | CTCN_6959 | 47851 |
| TTCN_1759 | 33750 | GTCN_3713 | 47809 | TTCN_1773 | 33793 | GTCN_3719 | 47852 |
| CTCN_2108 | 33751 | TTCN_5726 | 47810 | TTCN_1774 | 33794 | ATCN_3979 | 47853 |
| CTCN_2109 | 33752 | GTCN_3714 | 47811 | ATCN_1268 | 33795 | ATCN_3980 | 47854 |
| TTCN_1760 | 33753 | CTCN_6944 | 47812 | TTCN_1775 | 33796 | ATCN_3981 | 47855 |
| CTCN_2110 | 33754 | ATCN_3971 | 47813 | CTCN_2122 | 33797 | CTCN_6960 | 47856 |
| TTCN_1761 | 33755 | TTCN_5727 | 47814 | CTCN_2123 | 33798 | TTCN_5739 | 47857 |
| GTCN_1167 | 33756 | CTCN_6945 | 47815 | ATCN_1269 | 33799 | CTCN_6961 | 47858 |
| GTCN_1168 | 33757 | TTCN_5728 | 47816 | ATCN_1270 | 33800 | CTCN_6962 | 47859 |
| GTCN_1169 | 33758 | TTCN_5729 | 47817 | ATCN_1271 | 33801 | TTCN_5740 | 47860 |
| CTCN_2111 | 33759 | TTCN_5730 | 47818 | ATCN_1272 | 33802 | TTCN_5741 | 47861 |
| TTCN_1762 | 33760 | CTCN_6946 | 47819 | TTCN_1776 | 33803 | CTCN_6963 | 47862 |
| TTCN_1763 | 33761 | TTCN_5731 | 47820 | ATCN_1273 | 33804 | GTCN_3720 | 47863 |
| CTCN_2112 | 33762 | CTCN_6947 | 47821 | TTCN_1777 | 33805 | CTCN_6964 | 47864 |
| TTCN_1764 | 33763 | CTCN_6948 | 47822 | TTCN_1778 | 33806 | CTCN_6965 | 47865 |
| CTCN_2113 | 33764 | ATCN_3972 | 47823 | ATCN_1274 | 33807 | GTCN_3721 | 47866 |
| CTCN_2114 | 33765 | CTCN_6949 | 47824 | ATCN_1275 | 33808 | GTCN_3722 | 47867 |
| ATCN_1261 | 33766 | GTCN_3715 | 47825 | GTCN_1175 | 33809 | TTCN_5742 | 47868 |
| ATCN_1262 | 33767 | ATCN_3973 | 47826 | CTCN_2124 | 33810 | GTCN_3723 | 47869 |
| CTCN_2115 | 33768 | TTCN_5732 | 47827 | ATCN_1276 | 33811 | ATCN_3982 | 47870 |
| CTCN_2116 | 33769 | GTCN_3716 | 47828 | ATCN_1277 | 33812 | CTCN_6966 | 47871 |
| CTCN_2117 | 33770 | CTCN_6950 | 47829 | TTCN_1779 | 33813 | CTCN_6967 | 47872 |
| TTCN_1765 | 33771 | GTCN_3717 | 47830 | GTCN_1176 | 33814 | GTCN_3724 | 47873 |

FIG. 37 (continued)

| | | | |
|---|---|---|---|
| TTCN_1780 | 33815 | GTCN_3725 | 47874 |
| ATCN_1278 | 33816 | GTCN_3726 | 47875 |
| CTCN_2125 | 33817 | TTCN_5743 | 47876 |
| TTCN_1781 | 33818 | CTCN_6968 | 47877 |
| CTCN_2126 | 33819 | CTCN_6969 | 47878 |
| GTCN_1177 | 33820 | CTCN_6970 | 47879 |
| CTCN_2127 | 33821 | TTCN_5744 | 47880 |
| ATCN_1279 | 33822 | GTCN_3727 | 47881 |
| ATCN_1280 | 33823 | ATCN_3983 | 47882 |
| CTCN_2128 | 33824 | TTCN_5745 | 47883 |
| CTCN_2129 | 33825 | TTCN_5746 | 47884 |
| ATCN_1281 | 33826 | ATCN_3984 | 47885 |
| ATCN_1282 | 33827 | CTCN_6971 | 47886 |
| TTCN_1782 | 33828 | CTCN_6972 | 47887 |
| GTCN_1178 | 33829 | ATCN_3985 | 47888 |
| CTCN_2130 | 33830 | GTCN_3728 | 47889 |
| ATCN_1283 | 33831 | CTCN_6973 | 47890 |
| CTCN_2131 | 33832 | TTCN_5747 | 47891 |
| CTCN_2132 | 33833 | TTCN_5748 | 47892 |
| CTCN_2133 | 33834 | GTCN_3729 | 47893 |
| ATCN_1284 | 33835 | CTCN_6974 | 47894 |
| ATCN_1285 | 33836 | CTCN_6975 | 47895 |
| TTCN_1783 | 33837 | ATCN_3986 | 47896 |
| CTCN_2134 | 33838 | TTCN_5749 | 47897 |
| CTCN_2135 | 33839 | CTCN_6976 | 47898 |
| CTCN_2136 | 33840 | CTCN_6977 | 47899 |
| CTCN_2137 | 33841 | TTCN_5750 | 47900 |
| ATCN_1286 | 33842 | TTCN_5751 | 47901 |
| ATCN_1287 | 33843 | CTCN_6978 | 47902 |
| CTCN_2138 | 33844 | TTCN_5752 | 47903 |
| CTCN_2139 | 33845 | TTCN_5753 | 47904 |
| CTCN_2140 | 33846 | GTCN_3730 | 47905 |
| GTCN_1179 | 33847 | CTCN_6979 | 47906 |
| CTCN_2141 | 33848 | TTCN_5754 | 47907 |
| TTCN_1784 | 33849 | GTCN_3731 | 47908 |
| CTCN_2142 | 33850 | GTCN_3732 | 47909 |
| CTCN_2143 | 33851 | TTCN_5755 | 47910 |
| CTCN_2144 | 33852 | TTCN_5756 | 47911 |
| ATCN_1288 | 33853 | TTCN_5757 | 47912 |
| GTCN_1180 | 33854 | ATCN_3987 | 47913 |
| CTCN_2145 | 33855 | ATCN_3988 | 47914 |
| CTCN_2146 | 33856 | TTCN_5758 | 47915 |
| CTCN_2147 | 33857 | CTCN_6980 | 47916 |

| | | | |
|---|---|---|---|
| TTCN_1785 | 33858 | TTCN_5759 | 47917 |
| ATCN_1289 | 33859 | TTCN_5760 | 47918 |
| TTCN_1786 | 33860 | TTCN_5761 | 47919 |
| TTCN_1787 | 33861 | CTCN_6981 | 47920 |
| TTCN_1788 | 33862 | CTCN_6982 | 47921 |
| CTCN_2148 | 33863 | TTCN_5762 | 47922 |
| GTCN_1181 | 33864 | GTCN_3733 | 47923 |
| CTCN_2149 | 33865 | ATCN_3989 | 47924 |
| GTCN_1182 | 33866 | CTCN_6983 | 47925 |
| TTCN_1789 | 33867 | TTCN_5763 | 47926 |
| CTCN_2150 | 33868 | TTCN_5764 | 47927 |
| TTCN_1790 | 33869 | CTCN_6984 | 47928 |
| CTCN_2151 | 33870 | ATCN_3990 | 47929 |
| CTCN_2152 | 33871 | TTCN_5765 | 47930 |
| CTCN_2153 | 33872 | TTCN_5766 | 47931 |
| ATCN_1290 | 33873 | ATCN_3991 | 47932 |
| ATCN_1291 | 33874 | TTCN_5767 | 47933 |
| CTCN_2154 | 33875 | ATCN_3992 | 47934 |
| CTCN_2155 | 33876 | CTCN_6985 | 47935 |
| TTCN_1791 | 33877 | TTCN_5768 | 47936 |
| CTCN_2156 | 33878 | GTCN_3734 | 47937 |
| TTCN_1792 | 33879 | ATCN_3993 | 47938 |
| ATCN_1292 | 33880 | TTCN_5769 | 47939 |
| TTCN_1793 | 33881 | TTCN_5770 | 47940 |
| GTCN_1183 | 33882 | GTCN_3735 | 47941 |
| CTCN_2157 | 33883 | CTCN_6986 | 47942 |
| CTCN_2158 | 33884 | ATCN_3994 | 47943 |
| ATCN_1293 | 33885 | ATCN_3995 | 47944 |
| ATCN_1294 | 33886 | CTCN_6987 | 47945 |
| TTCN_1794 | 33887 | ATCN_3996 | 47946 |
| ATCN_1295 | 33888 | GTCN_3736 | 47947 |
| TTCN_1795 | 33889 | TTCN_5771 | 47948 |
| TTCN_1796 | 33890 | TTCN_5772 | 47949 |
| TTCN_1797 | 33891 | GTCN_3737 | 47950 |
| ATCN_1296 | 33892 | TTCN_5773 | 47951 |
| TTCN_1798 | 33893 | TTCN_5774 | 47952 |
| TTCN_1799 | 33894 | CTCN_6988 | 47953 |
| GTCN_1184 | 33895 | GTCN_3738 | 47954 |
| TTCN_1800 | 33896 | ATCN_3997 | 47955 |
| CTCN_2159 | 33897 | ATCN_3998 | 47956 |
| GTCN_1185 | 33898 | CTCN_6989 | 47957 |
| CTCN_2160 | 33899 | TTCN_5775 | 47958 |
| CTCN_2161 | 33900 | ATCN_3999 | 47959 |

FIG. 37 (continued)

| | | | |
|---|---|---|---|
| ATCN_1297 | 33901 | ATCN_4000 | 47960 |
| ATCN_1298 | 33902 | TTCN_5776 | 47961 |
| ATCN_1299 | 33903 | TTCN_5777 | 47962 |
| TTCN_1801 | 33904 | TTCN_5778 | 47963 |
| TTCN_1802 | 33905 | ATCN_4001 | 47964 |
| TTCN_1803 | 33906 | TTCN_5779 | 47965 |
| ATCN_1300 | 33907 | ATCN_4002 | 47966 |
| ATCN_1301 | 33908 | CTCN_6990 | 47967 |
| GTCN_1186 | 33909 | CTCN_6991 | 47968 |
| CTCN_2162 | 33910 | TTCN_5780 | 47969 |
| ATCN_1302 | 33911 | ATCN_4003 | 47970 |
| CTCN_2163 | 33912 | GTCN_3739 | 47971 |
| CTCN_2164 | 33913 | TTCN_5781 | 47972 |
| CTCN_2165 | 33914 | TTCN_5782 | 47973 |
| CTCN_2166 | 33915 | CTCN_6992 | 47974 |
| TTCN_1804 | 33916 | TTCN_5783 | 47975 |
| GTCN_1187 | 33917 | GTCN_3740 | 47976 |
| CTCN_2167 | 33918 | CTCN_6993 | 47977 |
| TTCN_1805 | 33919 | TTCN_5784 | 47978 |
| ATCN_1303 | 33920 | TTCN_5785 | 47979 |
| TTCN_1806 | 33921 | CTCN_6994 | 47980 |
| GTCN_1188 | 33922 | ATCN_4004 | 47981 |
| CTCN_2168 | 33923 | CTCN_6995 | 47982 |
| TTCN_1807 | 33924 | TTCN_5786 | 47983 |
| TTCN_1808 | 33925 | TTCN_5787 | 47984 |
| GTCN_1189 | 33926 | ATCN_4005 | 47985 |
| GTCN_1190 | 33927 | TTCN_5788 | 47986 |
| ATCN_1304 | 33928 | CTCN_6996 | 47987 |
| TTCN_1809 | 33929 | TTCN_5789 | 47988 |
| ATCN_1305 | 33930 | TTCN_5790 | 47989 |
| TTCN_1810 | 33931 | ATCN_4006 | 47990 |
| TTCN_1811 | 33932 | ATCN_4007 | 47991 |
| CTCN_2169 | 33933 | ATCN_4008 | 47992 |
| CTCN_2170 | 33934 | CTCN_6997 | 47993 |
| TTCN_1812 | 33935 | ATCN_4009 | 47994 |
| ATCN_1306 | 33936 | ATCN_4010 | 47995 |
| ATCN_1307 | 33937 | GTCN_3741 | 47996 |
| ATCN_1308 | 33938 | GTCN_3742 | 47997 |
| TTCN_1813 | 33939 | TTCN_5791 | 47998 |
| CTCN_2171 | 33940 | CTCN_6998 | 47999 |
| CTCN_2172 | 33941 | TTCN_5792 | 48000 |
| GTCN_1191 | 33942 | CTCN_6999 | 48001 |
| TTCN_1814 | 33943 | ATCN_4011 | 48002 |

| | | | |
|---|---|---|---|
| ATCN_1309 | 33944 | CTCN_7000 | 48003 |
| TTCN_1815 | 33945 | GTCN_3743 | 48004 |
| ATCN_1310 | 33946 | ATCN_4012 | 48005 |
| GTCN_1192 | 33947 | TTCN_5793 | 48006 |
| TTCN_1816 | 33948 | GTCN_3744 | 48007 |
| CTCN_2173 | 33949 | TTCN_5794 | 48008 |
| TTCN_1817 | 33950 | ATCN_4013 | 48009 |
| GTCN_1193 | 33951 | GTCN_3745 | 48010 |
| TTCN_1818 | 33952 | TTCN_5795 | 48011 |
| ATCN_1311 | 33953 | ATCN_4014 | 48012 |
| TTCN_1819 | 33954 | ATCN_4015 | 48013 |
| ATCN_1312 | 33955 | TTCN_5796 | 48014 |
| TTCN_1820 | 33956 | TTCN_5797 | 48015 |
| TTCN_1821 | 33957 | CTCN_7001 | 48016 |
| CTCN_2174 | 33958 | TTCN_5798 | 48017 |
| TTCN_1822 | 33959 | ATCN_4016 | 48018 |
| GTCN_1194 | 33960 | TTCN_5799 | 48019 |
| CTCN_2175 | 33961 | CTCN_7002 | 48020 |
| TTCN_1823 | 33962 | TTCN_5800 | 48021 |
| TTCN_1824 | 33963 | TTCN_5801 | 48022 |
| TTCN_1825 | 33964 | GTCN_3746 | 48023 |
| CTCN_2176 | 33965 | TTCN_5802 | 48024 |
| TTCN_1826 | 33966 | ATCN_4017 | 48025 |
| ATCN_1313 | 33967 | ATCN_4018 | 48026 |
| CTCN_2177 | 33968 | ATCN_4019 | 48027 |
| ATCN_1314 | 33969 | ATCN_4020 | 48028 |
| TTCN_1827 | 33970 | ATCN_4021 | 48029 |
| CTCN_2178 | 33971 | TTCN_5803 | 48030 |
| CTCN_2179 | 33972 | TTCN_5804 | 48031 |
| TTCN_1828 | 33973 | ATCN_4022 | 48032 |
| TTCN_1829 | 33974 | ATCN_4023 | 48033 |
| TTCN_1830 | 33975 | TTCN_5805 | 48034 |
| ATCN_1315 | 33976 | TTCN_5806 | 48035 |
| ATCN_1316 | 33977 | GTCN_3747 | 48036 |
| CTCN_2180 | 33978 | CTCN_7003 | 48037 |
| CTCN_2181 | 33979 | ATCN_4024 | 48038 |
| CTCN_2182 | 33980 | CTCN_7004 | 48039 |
| ATCN_1317 | 33981 | TTCN_5807 | 48040 |
| TTCN_1831 | 33982 | TTCN_5808 | 48041 |
| GTCN_1195 | 33983 | CTCN_7005 | 48042 |
| CTCN_2183 | 33984 | GTCN_3748 | 48043 |
| ATCN_1318 | 33985 | ATCN_4025 | 48044 |
| GTCN_1196 | 33986 | CTCN_7006 | 48045 |

FIG. 37 (continued)

| | | | |
|---|---|---|---|
| ATCN_1319 | 33987 | CTCN_7007 | 48046 |
| ATCN_1320 | 33988 | GTCN_3749 | 48047 |
| TTCN_1832 | 33989 | CTCN_7008 | 48048 |
| CTCN_2184 | 33990 | CTCN_7009 | 48049 |
| CTCN_2185 | 33991 | CTCN_7010 | 48050 |
| TTCN_1833 | 33992 | CTCN_7011 | 48051 |
| TTCN_1834 | 33993 | TTCN_5809 | 48052 |
| ATCN_1321 | 33994 | CTCN_7012 | 48053 |
| TTCN_1835 | 33995 | TTCN_5810 | 48054 |
| ATCN_1322 | 33996 | TTCN_5811 | 48055 |
| TTCN_1836 | 33997 | TTCN_5812 | 48056 |
| TTCN_1837 | 33998 | CTCN_7013 | 48057 |
| TTCN_1838 | 33999 | CTCN_7014 | 48058 |
| ATCN_1323 | 34000 | TTCN_5813 | 48059 |
| TTCN_1839 | 34001 | TTCN_5814 | 48060 |
| ATCN_1324 | 34002 | CTCN_7015 | 48061 |
| ATCN_1325 | 34003 | CTCN_7016 | 48062 |
| TTCN_1840 | 34004 | TTCN_5815 | 48063 |
| TTCN_1841 | 34005 | CTCN_7017 | 48064 |
| ATCN_1326 | 34006 | ATCN_4026 | 48065 |
| GTCN_1197 | 34007 | GTCN_3750 | 48066 |
| CTCN_2186 | 34008 | ATCN_4027 | 48067 |
| ATCN_1327 | 34009 | TTCN_5816 | 48068 |
| ATCN_1328 | 34010 | TTCN_5817 | 48069 |
| CTCN_2187 | 34011 | GTCN_3751 | 48070 |
| CTCN_2188 | 34012 | GTCN_3752 | 48071 |
| TTCN_1842 | 34013 | ATCN_4028 | 48072 |
| CTCN_2189 | 34014 | ATCN_4029 | 48073 |
| CTCN_2190 | 34015 | ATCN_4030 | 48074 |
| TTCN_1843 | 34016 | ATCN_4031 | 48075 |
| ATCN_1329 | 34017 | CTCN_7018 | 48076 |
| CTCN_2191 | 34018 | GTCN_3753 | 48077 |
| TTCN_1844 | 34019 | CTCN_7019 | 48078 |
| ATCN_1330 | 34020 | GTCN_3754 | 48079 |
| TTCN_1845 | 34021 | ATCN_4032 | 48080 |
| CTCN_2192 | 34022 | ATCN_4033 | 48081 |
| CTCN_2193 | 34023 | CTCN_7020 | 48082 |
| GTCN_1198 | 34024 | CTCN_7021 | 48083 |
| TTCN_1846 | 34025 | CTCN_7022 | 48084 |
| CTCN_2194 | 34026 | TTCN_5818 | 48085 |
| TTCN_1847 | 34027 | GTCN_3755 | 48086 |
| TTCN_1848 | 34028 | CTCN_7023 | 48087 |
| TTCN_1849 | 34029 | TTCN_5819 | 48088 |

| | | | |
|---|---|---|---|
| TTCN_1850 | 34030 | ATCN_4034 | 48089 |
| ATCN_1331 | 34031 | ATCN_4035 | 48090 |
| ATCN_1332 | 34032 | GTCN_3756 | 48091 |
| ATCN_1333 | 34033 | TTCN_5820 | 48092 |
| ATCN_1334 | 34034 | GTCN_3757 | 48093 |
| TTCN_1851 | 34035 | CTCN_7024 | 48094 |
| GTCN_1199 | 34036 | ATCN_4036 | 48095 |
| GTCN_1200 | 34037 | ATCN_4037 | 48096 |
| GTCN_1201 | 34038 | TTCN_5821 | 48097 |
| CTCN_2195 | 34039 | CTCN_7025 | 48098 |
| CTCN_2196 | 34040 | ATCN_4038 | 48099 |
| CTCN_2197 | 34041 | CTCN_7026 | 48100 |
| TTCN_1852 | 34042 | TTCN_5822 | 48101 |
| TTCN_1853 | 34043 | TTCN_5823 | 48102 |
| CTCN_2198 | 34044 | TTCN_5824 | 48103 |
| GTCN_1202 | 34045 | TTCN_5825 | 48104 |
| CTCN_2199 | 34046 | GTCN_3758 | 48105 |
| TTCN_1854 | 34047 | TTCN_5826 | 48106 |
| GTCN_1203 | 34048 | TTCN_5827 | 48107 |
| ATCN_1335 | 34049 | TTCN_5828 | 48108 |
| ATCN_1336 | 34050 | CTCN_7027 | 48109 |
| TTCN_1855 | 34051 | GTCN_3759 | 48110 |
| ATCN_1337 | 34052 | CTCN_7028 | 48111 |
| GTCN_1204 | 34053 | CTCN_7029 | 48112 |
| ATCN_1338 | 34054 | GTCN_3760 | 48113 |
| GTCN_1205 | 34055 | CTCN_7030 | 48114 |
| ATCN_1339 | 34056 | ATCN_4039 | 48115 |
| ATCN_1340 | 34057 | TTCN_5829 | 48116 |
| GTCN_1206 | 34058 | CTCN_7031 | 48117 |
| CTCN_2200 | 34059 | CTCN_7032 | 48118 |
| TTCN_1856 | 34060 | GTCN_3761 | 48119 |
| ATCN_1341 | 34061 | TTCN_5830 | 48120 |
| ATCN_1342 | 34062 | TTCN_5831 | 48121 |
| ATCN_1343 | 34063 | TTCN_5832 | 48122 |
| ATCN_1344 | 34064 | ATCN_4040 | 48123 |
| CTCN_2201 | 34065 | CTCN_7033 | 48124 |
| ATCN_1345 | 34066 | CTCN_7034 | 48125 |
| TTCN_1857 | 34067 | TTCN_5833 | 48126 |
| ATCN_1346 | 34068 | CTCN_7035 | 48127 |
| TTCN_1858 | 34069 | ATCN_4041 | 48128 |
| GTCN_1207 | 34070 | TTCN_5834 | 48129 |
| TTCN_1859 | 34071 | GTCN_3762 | 48130 |
| GTCN_1208 | 34072 | CTCN_7036 | 48131 |

FIG. 37 (continued)

| | | | |
|---|---|---|---|
| TTCN_1860 | 34073 | TTCN_5835 | 48132 |
| CTCN_2202 | 34074 | CTCN_7037 | 48133 |
| ATCN_1347 | 34075 | TTCN_5836 | 48134 |
| TTCN_1861 | 34076 | ATCN_4042 | 48135 |
| TTCN_1862 | 34077 | GTCN_3763 | 48136 |
| CTCN_2203 | 34078 | CTCN_7038 | 48137 |
| ATCN_1348 | 34079 | CTCN_7039 | 48138 |
| TTCN_1863 | 34080 | CTCN_7040 | 48139 |
| ATCN_1349 | 34081 | TTCN_5837 | 48140 |
| ATCN_1350 | 34082 | CTCN_7041 | 48141 |
| CTCN_2204 | 34083 | GTCN_3764 | 48142 |
| TTCN_1864 | 34084 | TTCN_5838 | 48143 |
| ATCN_1351 | 34085 | ATCN_4043 | 48144 |
| TTCN_1865 | 34086 | TTCN_5839 | 48145 |
| TTCN_1866 | 34087 | ATCN_4044 | 48146 |
| GTCN_1209 | 34088 | TTCN_5840 | 48147 |
| TTCN_1867 | 34089 | CTCN_7042 | 48148 |
| TTCN_1868 | 34090 | CTCN_7043 | 48149 |
| TTCN_1869 | 34091 | TTCN_5841 | 48150 |
| GTCN_1210 | 34092 | CTCN_7044 | 48151 |
| ATCN_1352 | 34093 | CTCN_7045 | 48152 |
| ATCN_1353 | 34094 | GTCN_3765 | 48153 |
| TTCN_1870 | 34095 | GTCN_3766 | 48154 |
| TTCN_1871 | 34096 | TTCN_5842 | 48155 |
| TTCN_1872 | 34097 | CTCN_7046 | 48156 |
| TTCN_1873 | 34098 | CTCN_7047 | 48157 |
| CTCN_2205 | 34099 | CTCN_7048 | 48158 |
| ATCN_1354 | 34100 | GTCN_3767 | 48159 |
| ATCN_1355 | 34101 | CTCN_7049 | 48160 |
| TTCN_1874 | 34102 | GTCN_3768 | 48161 |
| TTCN_1875 | 34103 | CTCN_7050 | 48162 |
| ATCN_1356 | 34104 | GTCN_3769 | 48163 |
| ATCN_1357 | 34105 | GTCN_3770 | 48164 |
| TTCN_1876 | 34106 | CTCN_7051 | 48165 |
| CTCN_2206 | 34107 | CTCN_7052 | 48166 |
| ATCN_1358 | 34108 | ATCN_4045 | 48167 |
| TTCN_1877 | 34109 | GTCN_3771 | 48168 |
| TTCN_1878 | 34110 | TTCN_5843 | 48169 |
| TTCN_1879 | 34111 | GTCN_3772 | 48170 |
| TTCN_1880 | 34112 | TTCN_5844 | 48171 |
| TTCN_1881 | 34113 | ATCN_4046 | 48172 |
| TTCN_1882 | 34114 | ATCN_4047 | 48173 |
| GTCN_1211 | 34115 | TTCN_5845 | 48174 |

| | | | |
|---|---|---|---|
| ATCN_1359 | 34116 | TTCN_5846 | 48175 |
| ATCN_1360 | 34117 | ATCN_4048 | 48176 |
| TTCN_1883 | 34118 | CTCN_7053 | 48177 |
| ATCN_1361 | 34119 | TTCN_5847 | 48178 |
| TTCN_1884 | 34120 | GTCN_3773 | 48179 |
| TTCN_1885 | 34121 | TTCN_5848 | 48180 |
| CTCN_2207 | 34122 | ATCN_4049 | 48181 |
| TTCN_1886 | 34123 | CTCN_7054 | 48182 |
| ATCN_1362 | 34124 | TTCN_5849 | 48183 |
| TTCN_1887 | 34125 | GTCN_3774 | 48184 |
| TTCN_1888 | 34126 | ATCN_4050 | 48185 |
| TTCN_1889 | 34127 | TTCN_5850 | 48186 |
| TTCN_1890 | 34128 | CTCN_7055 | 48187 |
| CTCN_2208 | 34129 | TTCN_5851 | 48188 |
| GTCN_1212 | 34130 | CTCN_7056 | 48189 |
| TTCN_1891 | 34131 | ATCN_4051 | 48190 |
| TTCN_1892 | 34132 | ATCN_4052 | 48191 |
| TTCN_1893 | 34133 | TTCN_5852 | 48192 |
| ATCN_1363 | 34134 | ATCN_4053 | 48193 |
| CTCN_2209 | 34135 | CTCN_7057 | 48194 |
| TTCN_1894 | 34136 | TTCN_5853 | 48195 |
| ATCN_1364 | 34137 | TTCN_5854 | 48196 |
| CTCN_2210 | 34138 | GTCN_3775 | 48197 |
| GTCN_1213 | 34139 | ATCN_4054 | 48198 |
| GTCN_1214 | 34140 | CTCN_7058 | 48199 |
| TTCN_1895 | 34141 | CTCN_7059 | 48200 |
| GTCN_1215 | 34142 | CTCN_7060 | 48201 |
| ATCN_1365 | 34143 | GTCN_3776 | 48202 |
| GTCN_1216 | 34144 | ATCN_4055 | 48203 |
| TTCN_1896 | 34145 | ATCN_4056 | 48204 |
| TTCN_1897 | 34146 | GTCN_3777 | 48205 |
| TTCN_1898 | 34147 | ATCN_4057 | 48206 |
| TTCN_1899 | 34148 | ATCN_4058 | 48207 |
| GTCN_1217 | 34149 | GTCN_3778 | 48208 |
| TTCN_1900 | 34150 | GTCN_3779 | 48209 |
| CTCN_2211 | 34151 | TTCN_5855 | 48210 |
| ATCN_1366 | 34152 | CTCN_7061 | 48211 |
| CTCN_2212 | 34153 | CTCN_7062 | 48212 |
| ATCN_1367 | 34154 | GTCN_3780 | 48213 |
| ATCN_1368 | 34155 | ATCN_4059 | 48214 |
| TTCN_1901 | 34156 | CTCN_7063 | 48215 |
| GTCN_1218 | 34157 | TTCN_5856 | 48216 |
| GTCN_1219 | 34158 | CTCN_7064 | 48217 |

FIG. 37 (continued)

| | | | |
|---|---|---|---|
| ATCN_1369 | 34159 | GTCN_3781 | 48218 |
| TTCN_1902 | 34160 | TTCN_5857 | 48219 |
| ATCN_1370 | 34161 | ATCN_4060 | 48220 |
| CTCN_2213 | 34162 | ATCN_4061 | 48221 |
| CTCN_2214 | 34163 | ATCN_4062 | 48222 |
| CTCN_2215 | 34164 | GTCN_3782 | 48223 |
| TTCN_1903 | 34165 | GTCN_3783 | 48224 |
| ATCN_1371 | 34166 | CTCN_7065 | 48225 |
| ATCN_1372 | 34167 | GTCN_3784 | 48226 |
| CTCN_2216 | 34168 | ATCN_4063 | 48227 |
| ATCN_1373 | 34169 | ATCN_4064 | 48228 |
| TTCN_1904 | 34170 | TTCN_5858 | 48229 |
| ATCN_1374 | 34171 | TTCN_5859 | 48230 |
| ATCN_1375 | 34172 | CTCN_7066 | 48231 |
| GTCN_1220 | 34173 | GTCN_3785 | 48232 |
| TTCN_1905 | 34174 | TTCN_5860 | 48233 |
| CTCN_2217 | 34175 | GTCN_3786 | 48234 |
| ATCN_1376 | 34176 | TTCN_5861 | 48235 |
| ATCN_1377 | 34177 | TTCN_5862 | 48236 |
| GTCN_1221 | 34178 | TTCN_5863 | 48237 |
| TTCN_1906 | 34179 | CTCN_7067 | 48238 |
| ATCN_1378 | 34180 | CTCN_7068 | 48239 |
| ATCN_1379 | 34181 | CTCN_7069 | 48240 |
| ATCN_1380 | 34182 | ATCN_4065 | 48241 |
| CTCN_2218 | 34183 | ATCN_4066 | 48242 |
| TTCN_1907 | 34184 | TTCN_5864 | 48243 |
| ATCN_1381 | 34185 | ATCN_4067 | 48244 |
| GTCN_1222 | 34186 | TTCN_5865 | 48245 |
| TTCN_1908 | 34187 | GTCN_3787 | 48246 |
| CTCN_2219 | 34188 | TTCN_5866 | 48247 |
| TTCN_1909 | 34189 | CTCN_7070 | 48248 |
| TTCN_1910 | 34190 | GTCN_3788 | 48249 |
| TTCN_1911 | 34191 | CTCN_7071 | 48250 |
| GTCN_1223 | 34192 | GTCN_3789 | 48251 |
| CTCN_2220 | 34193 | ATCN_4068 | 48252 |
| ATCN_1382 | 34194 | TTCN_5867 | 48253 |
| CTCN_2221 | 34195 | TTCN_5868 | 48254 |
| GTCN_1224 | 34196 | CTCN_7072 | 48255 |
| CTCN_2222 | 34197 | CTCN_7073 | 48256 |
| GTCN_1225 | 34198 | ATCN_4069 | 48257 |
| CTCN_2223 | 34199 | CTCN_7074 | 48258 |
| ATCN_1383 | 34200 | GTCN_3790 | 48259 |
| CTCN_2224 | 34201 | TTCN_5869 | 48260 |
| CTCN_2225 | 34202 | TTCN_5870 | 48261 |
| TTCN_1912 | 34203 | TTCN_5871 | 48262 |
| TTCN_1913 | 34204 | ATCN_4070 | 48263 |
| TTCN_1914 | 34205 | CTCN_7075 | 48264 |
| CTCN_2226 | 34206 | TTCN_5872 | 48265 |
| CTCN_2227 | 34207 | GTCN_3791 | 48266 |
| CTCN_2228 | 34208 | CTCN_7076 | 48267 |
| CTCN_2229 | 34209 | TTCN_5873 | 48268 |
| ATCN_1384 | 34210 | CTCN_7077 | 48269 |
| GTCN_1226 | 34211 | CTCN_7078 | 48270 |
| CTCN_2230 | 34212 | GTCN_3792 | 48271 |
| ATCN_1385 | 34213 | GTCN_3793 | 48272 |
| TTCN_1915 | 34214 | CTCN_7079 | 48273 |
| GTCN_1227 | 34215 | TTCN_5874 | 48274 |
| TTCN_1916 | 34216 | TTCN_5875 | 48275 |
| TTCN_1917 | 34217 | ATCN_4071 | 48276 |
| CTCN_2231 | 34218 | TTCN_5876 | 48277 |
| GTCN_1228 | 34219 | TTCN_5877 | 48278 |
| CTCN_2232 | 34220 | ATCN_4072 | 48279 |
| ATCN_1386 | 34221 | ATCN_4073 | 48280 |
| ATCN_1387 | 34222 | ATCN_4074 | 48281 |
| CTCN_2233 | 34223 | GTCN_3794 | 48282 |
| ATCN_1388 | 34224 | TTCN_5878 | 48283 |
| CTCN_2234 | 34225 | TTCN_5879 | 48284 |
| GTCN_1229 | 34226 | CTCN_7080 | 48285 |
| TTCN_1918 | 34227 | TTCN_5880 | 48286 |
| GTCN_1230 | 34228 | GTCN_3795 | 48287 |
| ATCN_1389 | 34229 | TTCN_5881 | 48288 |
| CTCN_2235 | 34230 | CTCN_7081 | 48289 |
| ATCN_1390 | 34231 | GTCN_3796 | 48290 |
| TTCN_1919 | 34232 | TTCN_5882 | 48291 |
| ATCN_1391 | 34233 | GTCN_3797 | 48292 |
| TTCN_1920 | 34234 | ATCN_4075 | 48293 |
| TTCN_1921 | 34235 | CTCN_7082 | 48294 |
| GTCN_1231 | 34236 | TTCN_5883 | 48295 |
| TTCN_1922 | 34237 | CTCN_7083 | 48296 |
| ATCN_1392 | 34238 | GTCN_3798 | 48297 |
| ATCN_1393 | 34239 | TTCN_5884 | 48298 |
| CTCN_2236 | 34240 | CTCN_7084 | 48299 |
| CTCN_2237 | 34241 | ATCN_4076 | 48300 |
| ATCN_1394 | 34242 | TTCN_5885 | 48301 |
| TTCN_1923 | 34243 | GTCN_3799 | 48302 |
| TTCN_1924 | 34244 | GTCN_3800 | 48303 |

FIG. 37 (continued)

| | | | |
|---|---|---|---|
| CTCN_2238 | 34245 | ATCN_4077 | 48304 |
| CTCN_2239 | 34246 | ATCN_4078 | 48305 |
| GTCN_1232 | 34247 | TTCN_5886 | 48306 |
| GTCN_1233 | 34248 | TTCN_5887 | 48307 |
| TTCN_1925 | 34249 | CTCN_7085 | 48308 |
| GTCN_1234 | 34250 | CTCN_7086 | 48309 |
| TTCN_1926 | 34251 | TTCN_5888 | 48310 |
| ATCN_1395 | 34252 | ATCN_4079 | 48311 |
| GTCN_1235 | 34253 | TTCN_5889 | 48312 |
| TTCN_1927 | 34254 | TTCN_5890 | 48313 |
| CTCN_2240 | 34255 | GTCN_3801 | 48314 |
| TTCN_1928 | 34256 | GTCN_3802 | 48315 |
| CTCN_2241 | 34257 | CTCN_7087 | 48316 |
| TTCN_1929 | 34258 | TTCN_5891 | 48317 |
| CTCN_2242 | 34259 | TTCN_5892 | 48318 |
| GTCN_1236 | 34260 | TTCN_5893 | 48319 |
| ATCN_1396 | 34261 | ATCN_4080 | 48320 |
| TTCN_1930 | 34262 | ATCN_4081 | 48321 |
| TTCN_1931 | 34263 | TTCN_5894 | 48322 |
| TTCN_1932 | 34264 | TTCN_5895 | 48323 |
| ATCN_1397 | 34265 | GTCN_3803 | 48324 |
| CTCN_2243 | 34266 | ATCN_4082 | 48325 |
| ATCN_1398 | 34267 | CTCN_7088 | 48326 |
| TTCN_1933 | 34268 | TTCN_5896 | 48327 |
| CTCN_2244 | 34269 | CTCN_7089 | 48328 |
| ATCN_1399 | 34270 | GTCN_3804 | 48329 |
| CTCN_2245 | 34271 | CTCN_7090 | 48330 |
| GTCN_1237 | 34272 | ATCN_4083 | 48331 |
| GTCN_1238 | 34273 | TTCN_5897 | 48332 |
| CTCN_2246 | 34274 | CTCN_7091 | 48333 |
| ATCN_1400 | 34275 | TTCN_5898 | 48334 |
| CTCN_2247 | 34276 | ATCN_4084 | 48335 |
| CTCN_2248 | 34277 | CTCN_7092 | 48336 |
| CTCN_2249 | 34278 | GTCN_3805 | 48337 |
| CTCN_2250 | 34279 | CTCN_7093 | 48338 |
| CTCN_2251 | 34280 | CTCN_7094 | 48339 |
| CTCN_2252 | 34281 | TTCN_5899 | 48340 |
| CTCN_2253 | 34282 | GTCN_3806 | 48341 |
| TTCN_1934 | 34283 | GTCN_3807 | 48342 |
| GTCN_1239 | 34284 | TTCN_5900 | 48343 |
| TTCN_1935 | 34285 | TTCN_5901 | 48344 |
| GTCN_1240 | 34286 | TTCN_5902 | 48345 |
| ATCN_1401 | 34287 | TTCN_5903 | 48346 |

| | | | |
|---|---|---|---|
| TTCN_1936 | 34288 | ATCN_4085 | 48347 |
| TTCN_1937 | 34289 | GTCN_3808 | 48348 |
| GTCN_1241 | 34290 | ATCN_4086 | 48349 |
| CTCN_2254 | 34291 | GTCN_3809 | 48350 |
| TTCN_1938 | 34292 | CTCN_7095 | 48351 |
| TTCN_1939 | 34293 | ATCN_4087 | 48352 |
| TTCN_1940 | 34294 | TTCN_5904 | 48353 |
| TTCN_1941 | 34295 | TTCN_5905 | 48354 |
| TTCN_1942 | 34296 | ATCN_4088 | 48355 |
| CTCN_2255 | 34297 | GTCN_3810 | 48356 |
| TTCN_1943 | 34298 | TTCN_5906 | 48357 |
| GTCN_1242 | 34299 | CTCN_7096 | 48358 |
| CTCN_2256 | 34300 | GTCN_3811 | 48359 |
| TTCN_1944 | 34301 | ATCN_4089 | 48360 |
| ATCN_1402 | 34302 | CTCN_7097 | 48361 |
| GTCN_1243 | 34303 | ATCN_4090 | 48362 |
| CTCN_2257 | 34304 | GTCN_3812 | 48363 |
| CTCN_2258 | 34305 | TTCN_5907 | 48364 |
| TTCN_1945 | 34306 | GTCN_3813 | 48365 |
| ATCN_1403 | 34307 | CTCN_7098 | 48366 |
| TTCN_1946 | 34308 | ATCN_4091 | 48367 |
| CTCN_2259 | 34309 | TTCN_5908 | 48368 |
| CTCN_2260 | 34310 | GTCN_3814 | 48369 |
| ATCN_1404 | 34311 | GTCN_3815 | 48370 |
| ATCN_1405 | 34312 | TTCN_5909 | 48371 |
| CTCN_2261 | 34313 | ATCN_4092 | 48372 |
| GTCN_1244 | 34314 | CTCN_7099 | 48373 |
| TTCN_1947 | 34315 | GTCN_3816 | 48374 |
| TTCN_1948 | 34316 | CTCN_7100 | 48375 |
| ATCN_1406 | 34317 | ATCN_4093 | 48376 |
| GTCN_1245 | 34318 | TTCN_5910 | 48377 |
| CTCN_2262 | 34319 | TTCN_5911 | 48378 |
| TTCN_1949 | 34320 | GTCN_3817 | 48379 |
| CTCN_2263 | 34321 | CTCN_7101 | 48380 |
| CTCN_2264 | 34322 | ATCN_4094 | 48381 |
| ATCN_1407 | 34323 | ATCN_4095 | 48382 |
| ATCN_1408 | 34324 | TTCN_5912 | 48383 |
| CTCN_2265 | 34325 | TTCN_5913 | 48384 |
| GTCN_1246 | 34326 | TTCN_5914 | 48385 |
| TTCN_1950 | 34327 | CTCN_7102 | 48386 |
| TTCN_1951 | 34328 | GTCN_3818 | 48387 |
| GTCN_1247 | 34329 | ATCN_4096 | 48388 |
| TTCN_1952 | 34330 | TTCN_5915 | 48389 |

FIG. 37 (continued)

| | | | |
|---|---|---|---|
| CTCN_2266 | 34331 | TTCN_5916 | 48390 |
| TTCN_1953 | 34332 | ATCN_4097 | 48391 |
| GTCN_1248 | 34333 | CTCN_7103 | 48392 |
| TTCN_1954 | 34334 | CTCN_7104 | 48393 |
| ATCN_1409 | 34335 | TTCN_5917 | 48394 |
| TTCN_1955 | 34336 | CTCN_7105 | 48395 |
| ATCN_1410 | 34337 | TTCN_5918 | 48396 |
| GTCN_1249 | 34338 | TTCN_5919 | 48397 |
| TTCN_1956 | 34339 | TTCN_5920 | 48398 |
| ATCN_1411 | 34340 | TTCN_5921 | 48399 |
| CTCN_2267 | 34341 | CTCN_7106 | 48400 |
| ATCN_1412 | 34342 | TTCN_5922 | 48401 |
| GTCN_1250 | 34343 | CTCN_7107 | 48402 |
| TTCN_1957 | 34344 | ATCN_4098 | 48403 |
| GTCN_1251 | 34345 | TTCN_5923 | 48404 |
| CTCN_2268 | 34346 | TTCN_5924 | 48405 |
| GTCN_1252 | 34347 | ATCN_4099 | 48406 |
| CTCN_2269 | 34348 | TTCN_5925 | 48407 |
| TTCN_1958 | 34349 | ATCN_4100 | 48408 |
| ATCN_1413 | 34350 | GTCN_3819 | 48409 |
| TTCN_1959 | 34351 | TTCN_5926 | 48410 |
| CTCN_2270 | 34352 | TTCN_5927 | 48411 |
| CTCN_2271 | 34353 | GTCN_3820 | 48412 |
| CTCN_2272 | 34354 | CTCN_7108 | 48413 |
| GTCN_1253 | 34355 | TTCN_5928 | 48414 |
| CTCN_2273 | 34356 | GTCN_3821 | 48415 |
| ATCN_1414 | 34357 | CTCN_7109 | 48416 |
| CTCN_2274 | 34358 | ATCN_4101 | 48417 |
| CTCN_2275 | 34359 | TTCN_5929 | 48418 |
| ATCN_1415 | 34360 | GTCN_3822 | 48419 |
| ATCN_1416 | 34361 | CTCN_7110 | 48420 |
| ATCN_1417 | 34362 | TTCN_5930 | 48421 |
| ATCN_1418 | 34363 | ATCN_4102 | 48422 |
| TTCN_1960 | 34364 | ATCN_4103 | 48423 |
| ATCN_1419 | 34365 | CTCN_7111 | 48424 |
| ATCN_1420 | 34366 | CTCN_7112 | 48425 |
| GTCN_1254 | 34367 | CTCN_7113 | 48426 |
| CTCN_2276 | 34368 | TTCN_5931 | 48427 |
| ATCN_1421 | 34369 | ATCN_4104 | 48428 |
| CTCN_2277 | 34370 | CTCN_7114 | 48429 |
| ATCN_1422 | 34371 | TTCN_5932 | 48430 |
| CTCN_2278 | 34372 | TTCN_5933 | 48431 |
| ATCN_1423 | 34373 | TTCN_5934 | 48432 |

| | | | |
|---|---|---|---|
| CTCN_2279 | 34374 | TTCN_5935 | 48433 |
| GTCN_1255 | 34375 | CTCN_7115 | 48434 |
| CTCN_2280 | 34376 | CTCN_7116 | 48435 |
| ATCN_1424 | 34377 | CTCN_7117 | 48436 |
| CTCN_2281 | 34378 | CTCN_7118 | 48437 |
| GTCN_1256 | 34379 | GTCN_3823 | 48438 |
| CTCN_2282 | 34380 | CTCN_7119 | 48439 |
| CTCN_2283 | 34381 | ATCN_4105 | 48440 |
| ATCN_1425 | 34382 | TTCN_5936 | 48441 |
| ATCN_1426 | 34383 | GTCN_3824 | 48442 |
| CTCN_2284 | 34384 | TTCN_5937 | 48443 |
| TTCN_1961 | 34385 | CTCN_7120 | 48444 |
| TTCN_1962 | 34386 | TTCN_5938 | 48445 |
| GTCN_1257 | 34387 | CTCN_7121 | 48446 |
| TTCN_1963 | 34388 | CTCN_7122 | 48447 |
| CTCN_2285 | 34389 | TTCN_5939 | 48448 |
| CTCN_2286 | 34390 | TTCN_5940 | 48449 |
| GTCN_1258 | 34391 | GTCN_3825 | 48450 |
| GTCN_1259 | 34392 | CTCN_7123 | 48451 |
| CTCN_2287 | 34393 | ATCN_4106 | 48452 |
| ATCN_1427 | 34394 | TTCN_5941 | 48453 |
| CTCN_2288 | 34395 | ATCN_4107 | 48454 |
| GTCN_1260 | 34396 | CTCN_7124 | 48455 |
| GTCN_1261 | 34397 | ATCN_4108 | 48456 |
| TTCN_1964 | 34398 | ATCN_4109 | 48457 |
| CTCN_2289 | 34399 | GTCN_3826 | 48458 |
| ATCN_1428 | 34400 | ATCN_4110 | 48459 |
| CTCN_2290 | 34401 | ATCN_4111 | 48460 |
| CTCN_2291 | 34402 | CTCN_7125 | 48461 |
| TTCN_1965 | 34403 | TTCN_5942 | 48462 |
| CTCN_2292 | 34404 | GTCN_3827 | 48463 |
| CTCN_2293 | 34405 | TTCN_5943 | 48464 |
| ATCN_1429 | 34406 | ATCN_4112 | 48465 |
| ATCN_1430 | 34407 | ATCN_4113 | 48466 |
| CTCN_2294 | 34408 | TTCN_5944 | 48467 |
| GTCN_1262 | 34409 | TTCN_5945 | 48468 |
| GTCN_1263 | 34410 | GTCN_3828 | 48469 |
| GTCN_1264 | 34411 | CTCN_7126 | 48470 |
| CTCN_2295 | 34412 | TTCN_5946 | 48471 |
| ATCN_1431 | 34413 | TTCN_5947 | 48472 |
| ATCN_1432 | 34414 | ATCN_4114 | 48473 |
| GTCN_1265 | 34415 | TTCN_5948 | 48474 |
| TTCN_1966 | 34416 | TTCN_5949 | 48475 |

FIG. 37 (continued)

| | | | |
|---|---|---|---|
| ATCN_1433 | 34417 | CTCN_7127 | 48476 |
| CTCN_2296 | 34418 | ATCN_4115 | 48477 |
| CTCN_2297 | 34419 | CTCN_7128 | 48478 |
| TTCN_1967 | 34420 | GTCN_3829 | 48479 |
| ATCN_1434 | 34421 | CTCN_7129 | 48480 |
| TTCN_1968 | 34422 | ATCN_4116 | 48481 |
| GTCN_1266 | 34423 | ATCN_4117 | 48482 |
| GTCN_1267 | 34424 | CTCN_7130 | 48483 |
| CTCN_2298 | 34425 | CTCN_7131 | 48484 |
| CTCN_2299 | 34426 | TTCN_5950 | 48485 |
| GTCN_1268 | 34427 | CTCN_7132 | 48486 |
| TTCN_1969 | 34428 | TTCN_5951 | 48487 |
| CTCN_2300 | 34429 | ATCN_4118 | 48488 |
| ATCN_1435 | 34430 | ATCN_4119 | 48489 |
| CTCN_2301 | 34431 | ATCN_4120 | 48490 |
| TTCN_1970 | 34432 | TTCN_5952 | 48491 |
| TTCN_1971 | 34433 | CTCN_7133 | 48492 |
| CTCN_2302 | 34434 | ATCN_4121 | 48493 |
| GTCN_1269 | 34435 | CTCN_7134 | 48494 |
| CTCN_2303 | 34436 | CTCN_7135 | 48495 |
| TTCN_1972 | 34437 | GTCN_3830 | 48496 |
| ATCN_1436 | 34438 | ATCN_4122 | 48497 |
| CTCN_2304 | 34439 | ATCN_4123 | 48498 |
| GTCN_1270 | 34440 | CTCN_7136 | 48499 |
| TTCN_1973 | 34441 | GTCN_3831 | 48500 |
| ATCN_1437 | 34442 | CTCN_7137 | 48501 |
| ATCN_1438 | 34443 | ATCN_4124 | 48502 |
| ATCN_1439 | 34444 | CTCN_7138 | 48503 |
| TTCN_1974 | 34445 | GTCN_3832 | 48504 |
| ATCN_1440 | 34446 | ATCN_4125 | 48505 |
| TTCN_1975 | 34447 | TTCN_5953 | 48506 |
| CTCN_2305 | 34448 | GTCN_3833 | 48507 |
| TTCN_1976 | 34449 | ATCN_4126 | 48508 |
| ATCN_1441 | 34450 | TTCN_5954 | 48509 |
| TTCN_1977 | 34451 | CTCN_7139 | 48510 |
| TTCN_1978 | 34452 | ATCN_4127 | 48511 |
| CTCN_2306 | 34453 | CTCN_7140 | 48512 |
| TTCN_1979 | 34454 | TTCN_5955 | 48513 |
| CTCN_2307 | 34455 | CTCN_7141 | 48514 |
| GTCN_1271 | 34456 | CTCN_7142 | 48515 |
| TTCN_1980 | 34457 | ATCN_4128 | 48516 |
| TTCN_1981 | 34458 | CTCN_7143 | 48517 |
| ATCN_1442 | 34459 | GTCN_3834 | 48518 |

| | | | |
|---|---|---|---|
| CTCN_2308 | 34460 | CTCN_7144 | 48519 |
| CTCN_2309 | 34461 | GTCN_3835 | 48520 |
| ATCN_1443 | 34462 | ATCN_4129 | 48521 |
| TTCN_1982 | 34463 | TTCN_5956 | 48522 |
| GTCN_1272 | 34464 | ATCN_4130 | 48523 |
| CTCN_2310 | 34465 | CTCN_7145 | 48524 |
| TTCN_1983 | 34466 | CTCN_7146 | 48525 |
| TTCN_1984 | 34467 | ATCN_4131 | 48526 |
| ATCN_1444 | 34468 | CTCN_7147 | 48527 |
| GTCN_1273 | 34469 | CTCN_7148 | 48528 |
| CTCN_2311 | 34470 | TTCN_5957 | 48529 |
| CTCN_2312 | 34471 | CTCN_7149 | 48530 |
| TTCN_1985 | 34472 | CTCN_7150 | 48531 |
| CTCN_2313 | 34473 | GTCN_3836 | 48532 |
| CTCN_2314 | 34474 | CTCN_7151 | 48533 |
| ATCN_1445 | 34475 | TTCN_5958 | 48534 |
| CTCN_2315 | 34476 | ATCN_4132 | 48535 |
| GTCN_1274 | 34477 | CTCN_7152 | 48536 |
| TTCN_1986 | 34478 | TTCN_5959 | 48537 |
| CTCN_2316 | 34479 | TTCN_5960 | 48538 |
| GTCN_1275 | 34480 | CTCN_7153 | 48539 |
| CTCN_2317 | 34481 | GTCN_3837 | 48540 |
| CTCN_2318 | 34482 | TTCN_5961 | 48541 |
| CTCN_2319 | 34483 | GTCN_3838 | 48542 |
| TTCN_1987 | 34484 | CTCN_7154 | 48543 |
| CTCN_2320 | 34485 | ATCN_4133 | 48544 |
| CTCN_2321 | 34486 | ATCN_4134 | 48545 |
| CTCN_2322 | 34487 | GTCN_3839 | 48546 |
| ATCN_1446 | 34488 | ATCN_4135 | 48547 |
| CTCN_2323 | 34489 | TTCN_5962 | 48548 |
| CTCN_2324 | 34490 | CTCN_7155 | 48549 |
| TTCN_1988 | 34491 | TTCN_5963 | 48550 |
| ATCN_1447 | 34492 | ATCN_4136 | 48551 |
| ATCN_1448 | 34493 | TTCN_5964 | 48552 |
| CTCN_2325 | 34494 | TTCN_5965 | 48553 |
| GTCN_1276 | 34495 | ATCN_4137 | 48554 |
| CTCN_2326 | 34496 | GTCN_3840 | 48555 |
| TTCN_1989 | 34497 | ATCN_4138 | 48556 |
| CTCN_2327 | 34498 | TTCN_5966 | 48557 |
| GTCN_1277 | 34499 | ATCN_4139 | 48558 |
| ATCN_1449 | 34500 | TTCN_5967 | 48559 |
| CTCN_2328 | 34501 | TTCN_5968 | 48560 |
| CTCN_2329 | 34502 | CTCN_7156 | 48561 |

FIG. 37 (continued)

| | | | |
|---|---|---|---|
| CTCN_2330 | 34503 | CTCN_7157 | 48562 |
| CTCN_2331 | 34504 | CTCN_7158 | 48563 |
| GTCN_1278 | 34505 | CTCN_7159 | 48564 |
| ATCN_1450 | 34506 | GTCN_3841 | 48565 |
| ATCN_1451 | 34507 | TTCN_5969 | 48566 |
| CTCN_2332 | 34508 | TTCN_5970 | 48567 |
| TTCN_1990 | 34509 | GTCN_3842 | 48568 |
| GTCN_1279 | 34510 | GTCN_3843 | 48569 |
| GTCN_1280 | 34511 | CTCN_7160 | 48570 |
| GTCN_1281 | 34512 | ATCN_4140 | 48571 |
| CTCN_2333 | 34513 | GTCN_3844 | 48572 |
| ATCN_1452 | 34514 | CTCN_7161 | 48573 |
| TTCN_1991 | 34515 | TTCN_5971 | 48574 |
| CTCN_2334 | 34516 | CTCN_7162 | 48575 |
| CTCN_2335 | 34517 | ATCN_4141 | 48576 |
| CTCN_2336 | 34518 | ATCN_4142 | 48577 |
| TTCN_1992 | 34519 | CTCN_7163 | 48578 |
| TTCN_1993 | 34520 | ATCN_4143 | 48579 |
| GTCN_1282 | 34521 | ATCN_4144 | 48580 |
| TTCN_1994 | 34522 | ATCN_4145 | 48581 |
| GTCN_1283 | 34523 | CTCN_7164 | 48582 |
| CTCN_2337 | 34524 | CTCN_7165 | 48583 |
| TTCN_1995 | 34525 | CTCN_7166 | 48584 |
| ATCN_1453 | 34526 | CTCN_7167 | 48585 |
| GTCN_1284 | 34527 | CTCN_7168 | 48586 |
| CTCN_2338 | 34528 | CTCN_7169 | 48587 |
| CTCN_2339 | 34529 | TTCN_5972 | 48588 |
| TTCN_1996 | 34530 | GTCN_3845 | 48589 |
| CTCN_2340 | 34531 | CTCN_7170 | 48590 |
| GTCN_1285 | 34532 | CTCN_7171 | 48591 |
| CTCN_2341 | 34533 | TTCN_5973 | 48592 |
| CTCN_2342 | 34534 | CTCN_7172 | 48593 |
| TTCN_1997 | 34535 | CTCN_7173 | 48594 |
| TTCN_1998 | 34536 | CTCN_7174 | 48595 |
| CTCN_2343 | 34537 | CTCN_7175 | 48596 |
| TTCN_1999 | 34538 | CTCN_7176 | 48597 |
| TTCN_2000 | 34539 | CTCN_7177 | 48598 |
| ATCN_1454 | 34540 | GTCN_3846 | 48599 |
| TTCN_2001 | 34541 | ATCN_4146 | 48600 |
| CTCN_2344 | 34542 | CTCN_7178 | 48601 |
| CTCN_2345 | 34543 | CTCN_7179 | 48602 |
| GTCN_1286 | 34544 | CTCN_7180 | 48603 |
| ATCN_1455 | 34545 | CTCN_7181 | 48604 |

| | | | |
|---|---|---|---|
| ATCN_1456 | 34546 | CTCN_7182 | 48605 |
| GTCN_1287 | 34547 | ATCN_4147 | 48606 |
| ATCN_1457 | 34548 | GTCN_3847 | 48607 |
| ATCN_1458 | 34549 | CTCN_7183 | 48608 |
| CTCN_2346 | 34550 | TTCN_5974 | 48609 |
| TTCN_2002 | 34551 | GTCN_3848 | 48610 |
| GTCN_1288 | 34552 | ATCN_4148 | 48611 |
| GTCN_1289 | 34553 | ATCN_4149 | 48612 |
| TTCN_2003 | 34554 | ATCN_4150 | 48613 |
| ATCN_1459 | 34555 | ATCN_4151 | 48614 |
| ATCN_1460 | 34556 | CTCN_7184 | 48615 |
| ATCN_1461 | 34557 | CTCN_7185 | 48616 |
| CTCN_2347 | 34558 | GTCN_3849 | 48617 |
| GTCN_1290 | 34559 | ATCN_4152 | 48618 |
| CTCN_2348 | 34560 | TTCN_5975 | 48619 |
| CTCN_2349 | 34561 | CTCN_7186 | 48620 |
| TTCN_2004 | 34562 | CTCN_7187 | 48621 |
| CTCN_2350 | 34563 | TTCN_5976 | 48622 |
| ATCN_1462 | 34564 | TTCN_5977 | 48623 |
| CTCN_2351 | 34565 | GTCN_3850 | 48624 |
| ATCN_1463 | 34566 | GTCN_3851 | 48625 |
| ATCN_1464 | 34567 | TTCN_5978 | 48626 |
| CTCN_2352 | 34568 | CTCN_7188 | 48627 |
| ATCN_1465 | 34569 | TTCN_5979 | 48628 |
| ATCN_1466 | 34570 | CTCN_7189 | 48629 |
| TTCN_2005 | 34571 | GTCN_3852 | 48630 |
| GTCN_1291 | 34572 | CTCN_7190 | 48631 |
| GTCN_1292 | 34573 | CTCN_7191 | 48632 |
| CTCN_2353 | 34574 | CTCN_7192 | 48633 |
| GTCN_1293 | 34575 | TTCN_5980 | 48634 |
| ATCN_1467 | 34576 | ATCN_4153 | 48635 |
| GTCN_1294 | 34577 | TTCN_5981 | 48636 |
| CTCN_2354 | 34578 | GTCN_3853 | 48637 |
| CTCN_2355 | 34579 | ATCN_4154 | 48638 |
| CTCN_2356 | 34580 | TTCN_5982 | 48639 |
| CTCN_2357 | 34581 | TTCN_5983 | 48640 |
| TTCN_2006 | 34582 | TTCN_5984 | 48641 |
| TTCN_2007 | 34583 | ATCN_4155 | 48642 |
| TTCN_2008 | 34584 | TTCN_5985 | 48643 |
| CTCN_2358 | 34585 | CTCN_7193 | 48644 |
| CTCN_2359 | 34586 | TTCN_5986 | 48645 |
| CTCN_2360 | 34587 | TTCN_5987 | 48646 |
| ATCN_1468 | 34588 | TTCN_5988 | 48647 |

FIG. 37 (continued)

| | | | |
|---|---|---|---|
| ATCN_1469 | 34589 | ATCN_4156 | 48648 |
| CTCN_2361 | 34590 | TTCN_5989 | 48649 |
| GTCN_1295 | 34591 | GTCN_3854 | 48650 |
| CTCN_2362 | 34592 | TTCN_5990 | 48651 |
| GTCN_1296 | 34593 | GTCN_3855 | 48652 |
| CTCN_2363 | 34594 | TTCN_5991 | 48653 |
| ATCN_1470 | 34595 | GTCN_3856 | 48654 |
| CTCN_2364 | 34596 | GTCN_3857 | 48655 |
| CTCN_2365 | 34597 | TTCN_5992 | 48656 |
| TTCN_2009 | 34598 | ATCN_4157 | 48657 |
| CTCN_2366 | 34599 | TTCN_5993 | 48658 |
| TTCN_2010 | 34600 | TTCN_5994 | 48659 |
| CTCN_2367 | 34601 | ATCN_4158 | 48660 |
| CTCN_2368 | 34602 | CTCN_7194 | 48661 |
| CTCN_2369 | 34603 | CTCN_7195 | 48662 |
| TTCN_2011 | 34604 | CTCN_7196 | 48663 |
| TTCN_2012 | 34605 | CTCN_7197 | 48664 |
| CTCN_2370 | 34606 | CTCN_7198 | 48665 |
| GTCN_1297 | 34607 | TTCN_5995 | 48666 |
| GTCN_1298 | 34608 | GTCN_3858 | 48667 |
| CTCN_2371 | 34609 | TTCN_5996 | 48668 |
| GTCN_1299 | 34610 | ATCN_4159 | 48669 |
| TTCN_2013 | 34611 | GTCN_3859 | 48670 |
| TTCN_2014 | 34612 | ATCN_4160 | 48671 |
| GTCN_1300 | 34613 | ATCN_4161 | 48672 |
| CTCN_2372 | 34614 | ATCN_4162 | 48673 |
| CTCN_2373 | 34615 | TTCN_5997 | 48674 |
| CTCN_2374 | 34616 | CTCN_7199 | 48675 |
| CTCN_2375 | 34617 | CTCN_7200 | 48676 |
| TTCN_2015 | 34618 | CTCN_7201 | 48677 |
| TTCN_2016 | 34619 | GTCN_3860 | 48678 |
| CTCN_2376 | 34620 | CTCN_7202 | 48679 |
| CTCN_2377 | 34621 | GTCN_3861 | 48680 |
| TTCN_2017 | 34622 | TTCN_5998 | 48681 |
| GTCN_1301 | 34623 | CTCN_7203 | 48682 |
| GTCN_1302 | 34624 | CTCN_7204 | 48683 |
| TTCN_2018 | 34625 | CTCN_7205 | 48684 |
| CTCN_2378 | 34626 | TTCN_5999 | 48685 |
| GTCN_1303 | 34627 | TTCN_6000 | 48686 |
| CTCN_2379 | 34628 | TTCN_6001 | 48687 |
| CTCN_2380 | 34629 | CTCN_7206 | 48688 |
| GTCN_1304 | 34630 | TTCN_6002 | 48689 |
| CTCN_2381 | 34631 | TTCN_6003 | 48690 |

| | | | |
|---|---|---|---|
| GTCN_1305 | 34632 | TTCN_6004 | 48691 |
| CTCN_2382 | 34633 | CTCN_7207 | 48692 |
| TTCN_2019 | 34634 | CTCN_7208 | 48693 |
| CTCN_2383 | 34635 | TTCN_6005 | 48694 |
| CTCN_2384 | 34636 | GTCN_3862 | 48695 |
| CTCN_2385 | 34637 | CTCN_7209 | 48696 |
| TTCN_2020 | 34638 | ATCN_4163 | 48697 |
| TTCN_2021 | 34639 | GTCN_3863 | 48698 |
| CTCN_2386 | 34640 | TTCN_6006 | 48699 |
| ATCN_1471 | 34641 | TTCN_6007 | 48700 |
| CTCN_2387 | 34642 | GTCN_3864 | 48701 |
| TTCN_2022 | 34643 | ATCN_4164 | 48702 |
| CTCN_2388 | 34644 | GTCN_3865 | 48703 |
| TTCN_2023 | 34645 | GTCN_3866 | 48704 |
| CTCN_2389 | 34646 | GTCN_3867 | 48705 |
| TTCN_2024 | 34647 | CTCN_7210 | 48706 |
| TTCN_2025 | 34648 | TTCN_6008 | 48707 |
| TTCN_2026 | 34649 | ATCN_4165 | 48708 |
| CTCN_2390 | 34650 | TTCN_6009 | 48709 |
| CTCN_2391 | 34651 | TTCN_6010 | 48710 |
| CTCN_2392 | 34652 | ATCN_4166 | 48711 |
| TTCN_2027 | 34653 | GTCN_3868 | 48712 |
| CTCN_2393 | 34654 | ATCN_4167 | 48713 |
| CTCN_2394 | 34655 | TTCN_6011 | 48714 |
| TTCN_2028 | 34656 | TTCN_6012 | 48715 |
| TTCN_2029 | 34657 | TTCN_6013 | 48716 |
| CTCN_2395 | 34658 | CTCN_7211 | 48717 |
| CTCN_2396 | 34659 | TTCN_6014 | 48718 |
| CTCN_2397 | 34660 | GTCN_3869 | 48719 |
| CTCN_2398 | 34661 | GTCN_3870 | 48720 |
| TTCN_2030 | 34662 | TTCN_6015 | 48721 |
| TTCN_2031 | 34663 | TTCN_6016 | 48722 |
| CTCN_2399 | 34664 | TTCN_6017 | 48723 |
| ATCN_1472 | 34665 | TTCN_6018 | 48724 |
| ATCN_1473 | 34666 | TTCN_6019 | 48725 |
| CTCN_2400 | 34667 | TTCN_6020 | 48726 |
| TTCN_2032 | 34668 | CTCN_7212 | 48727 |
| GTCN_1306 | 34669 | TTCN_6021 | 48728 |
| GTCN_1307 | 34670 | ATCN_4168 | 48729 |
| CTCN_2401 | 34671 | ATCN_4169 | 48730 |
| TTCN_2033 | 34672 | CTCN_7213 | 48731 |
| CTCN_2402 | 34673 | ATCN_4170 | 48732 |
| ATCN_1474 | 34674 | CTCN_7214 | 48733 |

FIG. 37 (continued)

| | | | | | | | |
|---|---|---|---|---|---|---|---|
| CTCN_2403 | 34675 | TTCN_6022 | 48734 | TTCN_2040 | 34718 | TTCN_6034 | 48777 |
| CTCN_2404 | 34676 | TTCN_6023 | 48735 | GTCN_1318 | 34719 | CTCN_7225 | 48778 |
| GTCN_1308 | 34677 | ATCN_4171 | 48736 | TTCN_2041 | 34720 | TTCN_6035 | 48779 |
| CTCN_2405 | 34678 | CTCN_7215 | 48737 | ATCN_1482 | 34721 | ATCN_4183 | 48780 |
| TTCN_2034 | 34679 | ATCN_4172 | 48738 | CTCN_2423 | 34722 | CTCN_7226 | 48781 |
| GTCN_1309 | 34680 | ATCN_4173 | 48739 | TTCN_2042 | 34723 | TTCN_6036 | 48782 |
| CTCN_2406 | 34681 | ATCN_4174 | 48740 | TTCN_2043 | 34724 | TTCN_6037 | 48783 |
| TTCN_2035 | 34682 | ATCN_4175 | 48741 | GTCN_1319 | 34725 | CTCN_7227 | 48784 |
| GTCN_1310 | 34683 | TTCN_6024 | 48742 | CTCN_2424 | 34726 | TTCN_6038 | 48785 |
| TTCN_2036 | 34684 | GTCN_3871 | 48743 | CTCN_2425 | 34727 | TTCN_6039 | 48786 |
| TTCN_2037 | 34685 | ATCN_4176 | 48744 | TTCN_2044 | 34728 | TTCN_6040 | 48787 |
| CTCN_2407 | 34686 | GTCN_3872 | 48745 | ATCN_1483 | 34729 | CTCN_7228 | 48788 |
| GTCN_1311 | 34687 | GTCN_3873 | 48746 | GTCN_1320 | 34730 | TTCN_6041 | 48789 |
| GTCN_1312 | 34688 | TTCN_6025 | 48747 | ATCN_1484 | 34731 | ATCN_4184 | 48790 |
| TTCN_2038 | 34689 | TTCN_6026 | 48748 | TTCN_2045 | 34732 | TTCN_6042 | 48791 |
| CTCN_2408 | 34690 | CTCN_7216 | 48749 | ATCN_1485 | 34733 | ATCN_4185 | 48792 |
| CTCN_2409 | 34691 | GTCN_3874 | 48750 | TTCN_2046 | 34734 | TTCN_6043 | 48793 |
| GTCN_1313 | 34692 | ATCN_4177 | 48751 | CTCN_2426 | 34735 | GTCN_3880 | 48794 |
| ATCN_1475 | 34693 | CTCN_7217 | 48752 | TTCN_2047 | 34736 | ATCN_4186 | 48795 |
| ATCN_1476 | 34694 | CTCN_7218 | 48753 | CTCN_2427 | 34737 | CTCN_7229 | 48796 |
| CTCN_2410 | 34695 | TTCN_6027 | 48754 | GTCN_1321 | 34738 | GTCN_3881 | 48797 |
| CTCN_2411 | 34696 | GTCN_3875 | 48755 | CTCN_2428 | 34739 | GTCN_3882 | 48798 |
| ATCN_1477 | 34697 | GTCN_3876 | 48756 | ATCN_1486 | 34740 | TTCN_6044 | 48799 |
| ATCN_1478 | 34698 | CTCN_7219 | 48757 | ATCN_1487 | 34741 | TTCN_6045 | 48800 |
| CTCN_2412 | 34699 | CTCN_7220 | 48758 | ATCN_1488 | 34742 | CTCN_7230 | 48801 |
| CTCN_2413 | 34700 | TTCN_6028 | 48759 | TTCN_2048 | 34743 | TTCN_6046 | 48802 |
| CTCN_2414 | 34701 | GTCN_3877 | 48760 | TTCN_2049 | 34744 | ATCN_4187 | 48803 |
| GTCN_1314 | 34702 | GTCN_3878 | 48761 | GTCN_1322 | 34745 | TTCN_6047 | 48804 |
| CTCN_2415 | 34703 | CTCN_7221 | 48762 | CTCN_2429 | 34746 | ATCN_4188 | 48805 |
| ATCN_1479 | 34704 | GTCN_3879 | 48763 | GTCN_1323 | 34747 | TTCN_6048 | 48806 |
| CTCN_2416 | 34705 | ATCN_4178 | 48764 | GTCN_1324 | 34748 | ATCN_4189 | 48807 |
| GTCN_1315 | 34706 | ATCN_4179 | 48765 | TTCN_2050 | 34749 | ATCN_4190 | 48808 |
| CTCN_2417 | 34707 | TTCN_6029 | 48766 | TTCN_2051 | 34750 | CTCN_7231 | 48809 |
| GTCN_1316 | 34708 | ATCN_4180 | 48767 | GTCN_1325 | 34751 | CTCN_7232 | 48810 |
| TTCN_2039 | 34709 | CTCN_7222 | 48768 | ATCN_1489 | 34752 | TTCN_6049 | 48811 |
| CTCN_2418 | 34710 | TTCN_6030 | 48769 | TTCN_2052 | 34753 | GTCN_3883 | 48812 |
| CTCN_2419 | 34711 | CTCN_7223 | 48770 | GTCN_1326 | 34754 | TTCN_6050 | 48813 |
| ATCN_1480 | 34712 | TTCN_6031 | 48771 | GTCN_1327 | 34755 | GTCN_3884 | 48814 |
| ATCN_1481 | 34713 | ATCN_4181 | 48772 | ATCN_1490 | 34756 | GTCN_3885 | 48815 |
| CTCN_2420 | 34714 | TTCN_6032 | 48773 | ATCN_1491 | 34757 | TTCN_6051 | 48816 |
| CTCN_2421 | 34715 | TTCN_6033 | 48774 | TTCN_2053 | 34758 | ATCN_4191 | 48817 |
| CTCN_2422 | 34716 | ATCN_4182 | 48775 | TTCN_2054 | 34759 | TTCN_6052 | 48818 |
| GTCN_1317 | 34717 | CTCN_7224 | 48776 | ATCN_1492 | 34760 | GTCN_3886 | 48819 |

FIG. 37 (continued)

| | | | |
|---|---|---|---|
| ATCN_1493 | 34761 | ATCN_4192 | 48820 |
| TTCN_2055 | 34762 | TTCN_6053 | 48821 |
| GTCN_1328 | 34763 | ATCN_4193 | 48822 |
| TTCN_2056 | 34764 | TTCN_6054 | 48823 |
| TTCN_2057 | 34765 | GTCN_3887 | 48824 |
| TTCN_2058 | 34766 | GTCN_3888 | 48825 |
| GTCN_1329 | 34767 | CTCN_7233 | 48826 |
| TTCN_2059 | 34768 | TTCN_6055 | 48827 |
| CTCN_2430 | 34769 | CTCN_7234 | 48828 |
| TTCN_2060 | 34770 | TTCN_6056 | 48829 |
| ATCN_1494 | 34771 | GTCN_3889 | 48830 |
| GTCN_1330 | 34772 | GTCN_3890 | 48831 |
| GTCN_1331 | 34773 | CTCN_7235 | 48832 |
| CTCN_2431 | 34774 | GTCN_3891 | 48833 |
| CTCN_2432 | 34775 | ATCN_4194 | 48834 |
| TTCN_2061 | 34776 | CTCN_7236 | 48835 |
| CTCN_2433 | 34777 | GTCN_3892 | 48836 |
| TTCN_2062 | 34778 | GTCN_3893 | 48837 |
| CTCN_2434 | 34779 | ATCN_4195 | 48838 |
| GTCN_1332 | 34780 | CTCN_7237 | 48839 |
| ATCN_1495 | 34781 | CTCN_7238 | 48840 |
| TTCN_2063 | 34782 | TTCN_6057 | 48841 |
| CTCN_2435 | 34783 | ATCN_4196 | 48842 |
| TTCN_2064 | 34784 | TTCN_6058 | 48843 |
| CTCN_2436 | 34785 | GTCN_3894 | 48844 |
| GTCN_1333 | 34786 | CTCN_7239 | 48845 |
| GTCN_1334 | 34787 | TTCN_6059 | 48846 |
| ATCN_1496 | 34788 | TTCN_6060 | 48847 |
| ATCN_1497 | 34789 | TTCN_6061 | 48848 |
| CTCN_2437 | 34790 | TTCN_6062 | 48849 |
| TTCN_2065 | 34791 | TTCN_6063 | 48850 |
| TTCN_2066 | 34792 | CTCN_7240 | 48851 |
| TTCN_2067 | 34793 | ATCN_4197 | 48852 |
| CTCN_2438 | 34794 | ATCN_4198 | 48853 |
| CTCN_2439 | 34795 | CTCN_7241 | 48854 |
| CTCN_2440 | 34796 | TTCN_6064 | 48855 |
| CTCN_2441 | 34797 | TTCN_6065 | 48856 |
| TTCN_2068 | 34798 | CTCN_7242 | 48857 |
| GTCN_1335 | 34799 | CTCN_7243 | 48858 |
| TTCN_2069 | 34800 | ATCN_4199 | 48859 |
| CTCN_2442 | 34801 | CTCN_7244 | 48860 |
| CTCN_2443 | 34802 | TTCN_6066 | 48861 |
| TTCN_2070 | 34803 | CTCN_7245 | 48862 |

| | | | |
|---|---|---|---|
| CTCN_2444 | 34804 | CTCN_7246 | 48863 |
| CTCN_2445 | 34805 | ATCN_4200 | 48864 |
| TTCN_2071 | 34806 | ATCN_4201 | 48865 |
| CTCN_2446 | 34807 | TTCN_6067 | 48866 |
| TTCN_2072 | 34808 | ATCN_4202 | 48867 |
| CTCN_2447 | 34809 | ATCN_4203 | 48868 |
| CTCN_2448 | 34810 | CTCN_7247 | 48869 |
| CTCN_2449 | 34811 | ATCN_4204 | 48870 |
| TTCN_2073 | 34812 | TTCN_6068 | 48871 |
| ATCN_1498 | 34813 | GTCN_3895 | 48872 |
| ATCN_1499 | 34814 | ATCN_4205 | 48873 |
| GTCN_1336 | 34815 | ATCN_4206 | 48874 |
| CTCN_2450 | 34816 | TTCN_6069 | 48875 |
| TTCN_2074 | 34817 | TTCN_6070 | 48876 |
| TTCN_2075 | 34818 | TTCN_6071 | 48877 |
| CTCN_2451 | 34819 | ATCN_4207 | 48878 |
| GTCN_1337 | 34820 | GTCN_3896 | 48879 |
| TTCN_2076 | 34821 | TTCN_6072 | 48880 |
| CTCN_2452 | 34822 | CTCN_7248 | 48881 |
| CTCN_2453 | 34823 | TTCN_6073 | 48882 |
| CTCN_2454 | 34824 | ATCN_4208 | 48883 |
| TTCN_2077 | 34825 | TTCN_6074 | 48884 |
| TTCN_2078 | 34826 | CTCN_7249 | 48885 |
| CTCN_2455 | 34827 | GTCN_3897 | 48886 |
| TTCN_2079 | 34828 | TTCN_6075 | 48887 |
| CTCN_2456 | 34829 | TTCN_6076 | 48888 |
| TTCN_2080 | 34830 | TTCN_6077 | 48889 |
| CTCN_2457 | 34831 | GTCN_3898 | 48890 |
| GTCN_1338 | 34832 | CTCN_7250 | 48891 |
| GTCN_1339 | 34833 | ATCN_4209 | 48892 |
| CTCN_2458 | 34834 | CTCN_7251 | 48893 |
| CTCN_2459 | 34835 | CTCN_7252 | 48894 |
| CTCN_2460 | 34836 | ATCN_4210 | 48895 |
| TTCN_2081 | 34837 | ATCN_4211 | 48896 |
| TTCN_2082 | 34838 | CTCN_7253 | 48897 |
| CTCN_2461 | 34839 | CTCN_7254 | 48898 |
| GTCN_1340 | 34840 | TTCN_6078 | 48899 |
| CTCN_2462 | 34841 | CTCN_7255 | 48900 |
| TTCN_2083 | 34842 | GTCN_3899 | 48901 |
| GTCN_1341 | 34843 | ATCN_4212 | 48902 |
| TTCN_2084 | 34844 | CTCN_7256 | 48903 |
| ATCN_1500 | 34845 | TTCN_6079 | 48904 |
| TTCN_2085 | 34846 | TTCN_6080 | 48905 |

FIG. 37 (continued)

| | | | |
|---|---|---|---|
| TTCN_2086 | 34847 | TTCN_6081 | 48906 |
| TTCN_2087 | 34848 | ATCN_4213 | 48907 |
| ATCN_1501 | 34849 | TTCN_6082 | 48908 |
| ATCN_1502 | 34850 | GTCN_3900 | 48909 |
| GTCN_1342 | 34851 | TTCN_6083 | 48910 |
| CTCN_2463 | 34852 | TTCN_6084 | 48911 |
| CTCN_2464 | 34853 | CTCN_7257 | 48912 |
| CTCN_2465 | 34854 | ATCN_4214 | 48913 |
| CTCN_2466 | 34855 | TTCN_6085 | 48914 |
| GTCN_1343 | 34856 | CTCN_7258 | 48915 |
| CTCN_2467 | 34857 | ATCN_4215 | 48916 |
| CTCN_2468 | 34858 | TTCN_6086 | 48917 |
| CTCN_2469 | 34859 | TTCN_6087 | 48918 |
| CTCN_2470 | 34860 | GTCN_3901 | 48919 |
| TTCN_2088 | 34861 | ATCN_4216 | 48920 |
| ATCN_1503 | 34862 | GTCN_3902 | 48921 |
| GTCN_1344 | 34863 | TTCN_6088 | 48922 |
| TTCN_2089 | 34864 | ATCN_4217 | 48923 |
| CTCN_2471 | 34865 | ATCN_4218 | 48924 |
| ATCN_1504 | 34866 | TTCN_6089 | 48925 |
| CTCN_2472 | 34867 | TTCN_6090 | 48926 |
| CTCN_2473 | 34868 | ATCN_4219 | 48927 |
| CTCN_2474 | 34869 | TTCN_6091 | 48928 |
| ATCN_1505 | 34870 | CTCN_7259 | 48929 |
| CTCN_2475 | 34871 | ATCN_4220 | 48930 |
| GTCN_1345 | 34872 | ATCN_4221 | 48931 |
| TTCN_2090 | 34873 | CTCN_7260 | 48932 |
| ATCN_1506 | 34874 | CTCN_7261 | 48933 |
| CTCN_2476 | 34875 | CTCN_7262 | 48934 |
| CTCN_2477 | 34876 | CTCN_7263 | 48935 |
| TTCN_2091 | 34877 | GTCN_3903 | 48936 |
| GTCN_1346 | 34878 | GTCN_3904 | 48937 |
| CTCN_2478 | 34879 | TTCN_6092 | 48938 |
| GTCN_1347 | 34880 | TTCN_6093 | 48939 |
| CTCN_2479 | 34881 | TTCN_6094 | 48940 |
| TTCN_2092 | 34882 | TTCN_6095 | 48941 |
| TTCN_2093 | 34883 | ATCN_4222 | 48942 |
| CTCN_2480 | 34884 | TTCN_6096 | 48943 |
| CTCN_2481 | 34885 | TTCN_6097 | 48944 |
| TTCN_2094 | 34886 | GTCN_3905 | 48945 |
| CTCN_2482 | 34887 | CTCN_7264 | 48946 |
| TTCN_2095 | 34888 | TTCN_6098 | 48947 |
| GTCN_1348 | 34889 | TTCN_6099 | 48948 |

| | | | |
|---|---|---|---|
| CTCN_2483 | 34890 | ATCN_4223 | 48949 |
| TTCN_2096 | 34891 | ATCN_4224 | 48950 |
| TTCN_2097 | 34892 | ATCN_4225 | 48951 |
| TTCN_2098 | 34893 | ATCN_4226 | 48952 |
| ATCN_1507 | 34894 | GTCN_3906 | 48953 |
| TTCN_2099 | 34895 | TTCN_6100 | 48954 |
| GTCN_1349 | 34896 | ATCN_4227 | 48955 |
| TTCN_2100 | 34897 | TTCN_6101 | 48956 |
| CTCN_2484 | 34898 | CTCN_7265 | 48957 |
| CTCN_2485 | 34899 | TTCN_6102 | 48958 |
| CTCN_2486 | 34900 | CTCN_7266 | 48959 |
| CTCN_2487 | 34901 | CTCN_7267 | 48960 |
| CTCN_2488 | 34902 | TTCN_6103 | 48961 |
| CTCN_2489 | 34903 | GTCN_3907 | 48962 |
| ATCN_1508 | 34904 | TTCN_6104 | 48963 |
| ATCN_1509 | 34905 | TTCN_6105 | 48964 |
| TTCN_2101 | 34906 | TTCN_6106 | 48965 |
| ATCN_1510 | 34907 | CTCN_7268 | 48966 |
| CTCN_2490 | 34908 | CTCN_7269 | 48967 |
| GTCN_1350 | 34909 | ATCN_4228 | 48968 |
| CTCN_2491 | 34910 | CTCN_7270 | 48969 |
| ATCN_1511 | 34911 | ATCN_4229 | 48970 |
| CTCN_2492 | 34912 | GTCN_3908 | 48971 |
| CTCN_2493 | 34913 | ATCN_4230 | 48972 |
| ATCN_1512 | 34914 | TTCN_6107 | 48973 |
| ATCN_1513 | 34915 | TTCN_6108 | 48974 |
| CTCN_2494 | 34916 | GTCN_3909 | 48975 |
| CTCN_2495 | 34917 | TTCN_6109 | 48976 |
| TTCN_2102 | 34918 | ATCN_4231 | 48977 |
| ATCN_1514 | 34919 | GTCN_3910 | 48978 |
| CTCN_2496 | 34920 | ATCN_4232 | 48979 |
| TTCN_2103 | 34921 | CTCN_7271 | 48980 |
| TTCN_2104 | 34922 | CTCN_7272 | 48981 |
| CTCN_2497 | 34923 | TTCN_6110 | 48982 |
| CTCN_2498 | 34924 | CTCN_7273 | 48983 |
| CTCN_2499 | 34925 | CTCN_7274 | 48984 |
| ATCN_1515 | 34926 | GTCN_3911 | 48985 |
| CTCN_2500 | 34927 | TTCN_6111 | 48986 |
| GTCN_1351 | 34928 | GTCN_3912 | 48987 |
| TTCN_2105 | 34929 | ATCN_4233 | 48988 |
| CTCN_2501 | 34930 | CTCN_7275 | 48989 |
| GTCN_1352 | 34931 | ATCN_4234 | 48990 |
| TTCN_2106 | 34932 | ATCN_4235 | 48991 |

FIG. 37 (continued)

| | | | |
|---|---|---|---|
| CTCN_2502 | 34933 | ATCN_4236 | 48992 |
| GTCN_1353 | 34934 | CTCN_7276 | 48993 |
| ATCN_1516 | 34935 | CTCN_7277 | 48994 |
| ATCN_1517 | 34936 | TTCN_6112 | 48995 |
| ATCN_1518 | 34937 | TTCN_6113 | 48996 |
| ATCN_1519 | 34938 | GTCN_3913 | 48997 |
| CTCN_2503 | 34939 | ATCN_4237 | 48998 |
| CTCN_2504 | 34940 | TTCN_6114 | 48999 |
| TTCN_2107 | 34941 | CTCN_7278 | 49000 |
| ATCN_1520 | 34942 | GTCN_3914 | 49001 |
| GTCN_1354 | 34943 | CTCN_7279 | 49002 |
| CTCN_2505 | 34944 | TTCN_6115 | 49003 |
| TTCN_2108 | 34945 | ATCN_4238 | 49004 |
| CTCN_2506 | 34946 | ATCN_4239 | 49005 |
| GTCN_1355 | 34947 | ATCN_4240 | 49006 |
| ATCN_1521 | 34948 | GTCN_3915 | 49007 |
| ATCN_1522 | 34949 | GTCN_3916 | 49008 |
| ATCN_1523 | 34950 | GTCN_3917 | 49009 |
| ATCN_1524 | 34951 | CTCN_7280 | 49010 |
| GTCN_1356 | 34952 | TTCN_6116 | 49011 |
| CTCN_2507 | 34953 | CTCN_7281 | 49012 |
| TTCN_2109 | 34954 | ATCN_4241 | 49013 |
| TTCN_2110 | 34955 | TTCN_6117 | 49014 |
| ATCN_1525 | 34956 | CTCN_7282 | 49015 |
| ATCN_1526 | 34957 | GTCN_3918 | 49016 |
| ATCN_1527 | 34958 | TTCN_6118 | 49017 |
| CTCN_2508 | 34959 | CTCN_7283 | 49018 |
| ATCN_1528 | 34960 | CTCN_7284 | 49019 |
| ATCN_1529 | 34961 | TTCN_6119 | 49020 |
| TTCN_2111 | 34962 | ATCN_4242 | 49021 |
| ATCN_1530 | 34963 | ATCN_4243 | 49022 |
| TTCN_2112 | 34964 | ATCN_4244 | 49023 |
| TTCN_2113 | 34965 | TTCN_6120 | 49024 |
| CTCN_2509 | 34966 | TTCN_6121 | 49025 |
| CTCN_2510 | 34967 | ATCN_4245 | 49026 |
| CTCN_2511 | 34968 | TTCN_6122 | 49027 |
| TTCN_2114 | 34969 | GTCN_3919 | 49028 |
| ATCN_1531 | 34970 | TTCN_6123 | 49029 |
| CTCN_2512 | 34971 | ATCN_4246 | 49030 |
| GTCN_1357 | 34972 | TTCN_6124 | 49031 |
| GTCN_1358 | 34973 | TTCN_6125 | 49032 |
| CTCN_2513 | 34974 | TTCN_6126 | 49033 |
| CTCN_2514 | 34975 | TTCN_6127 | 49034 |

| | | | |
|---|---|---|---|
| CTCN_2515 | 34976 | TTCN_6128 | 49035 |
| GTCN_1359 | 34977 | TTCN_6129 | 49036 |
| GTCN_1360 | 34978 | CTCN_7285 | 49037 |
| CTCN_2516 | 34979 | TTCN_6130 | 49038 |
| CTCN_2517 | 34980 | ATCN_4247 | 49039 |
| GTCN_1361 | 34981 | GTCN_3920 | 49040 |
| TTCN_2115 | 34982 | CTCN_7286 | 49041 |
| TTCN_2116 | 34983 | GTCN_3921 | 49042 |
| CTCN_2518 | 34984 | CTCN_7287 | 49043 |
| TTCN_2117 | 34985 | CTCN_7288 | 49044 |
| ATCN_1532 | 34986 | ATCN_4248 | 49045 |
| GTCN_1362 | 34987 | CTCN_7289 | 49046 |
| TTCN_2118 | 34988 | ATCN_4249 | 49047 |
| TTCN_2119 | 34989 | TTCN_6131 | 49048 |
| ATCN_1533 | 34990 | TTCN_6132 | 49049 |
| ATCN_1534 | 34991 | TTCN_6133 | 49050 |
| TTCN_2120 | 34992 | GTCN_3922 | 49051 |
| TTCN_2121 | 34993 | TTCN_6134 | 49052 |
| GTCN_1363 | 34994 | CTCN_7290 | 49053 |
| TTCN_2122 | 34995 | CTCN_7291 | 49054 |
| ATCN_1535 | 34996 | GTCN_3923 | 49055 |
| TTCN_2123 | 34997 | TTCN_6135 | 49056 |
| TTCN_2124 | 34998 | TTCN_6136 | 49057 |
| CTCN_2519 | 34999 | CTCN_7292 | 49058 |
| ATCN_1536 | 35000 | GTCN_3924 | 49059 |
| CTCN_2520 | 35001 | CTCN_7293 | 49060 |
| TTCN_2125 | 35002 | CTCN_7294 | 49061 |
| CTCN_2521 | 35003 | TTCN_6137 | 49062 |
| CTCN_2522 | 35004 | TTCN_6138 | 49063 |
| ATCN_1537 | 35005 | ATCN_4250 | 49064 |
| TTCN_2126 | 35006 | CTCN_7295 | 49065 |
| TTCN_2127 | 35007 | ATCN_4251 | 49066 |
| CTCN_2523 | 35008 | TTCN_6139 | 49067 |
| GTCN_1364 | 35009 | TTCN_6140 | 49068 |
| CTCN_2524 | 35010 | TTCN_6141 | 49069 |
| GTCN_1365 | 35011 | CTCN_7296 | 49070 |
| GTCN_1366 | 35012 | TTCN_6142 | 49071 |
| CTCN_2525 | 35013 | GTCN_3925 | 49072 |
| TTCN_2128 | 35014 | ATCN_4252 | 49073 |
| CTCN_2526 | 35015 | ATCN_4253 | 49074 |
| CTCN_2527 | 35016 | GTCN_3926 | 49075 |
| TTCN_2129 | 35017 | TTCN_6143 | 49076 |
| GTCN_1367 | 35018 | TTCN_6144 | 49077 |

FIG. 37 (continued)

| | | | |
|---|---|---|---|
| GTCN_1368 | 35019 | TTCN_6145 | 49078 |
| GTCN_1369 | 35020 | ATCN_4254 | 49079 |
| ATCN_1538 | 35021 | ATCN_4255 | 49080 |
| TTCN_2130 | 35022 | TTCN_6146 | 49081 |
| ATCN_1539 | 35023 | TTCN_6147 | 49082 |
| ATCN_1540 | 35024 | ATCN_4256 | 49083 |
| CTCN_2528 | 35025 | GTCN_3927 | 49084 |
| TTCN_2131 | 35026 | GTCN_3928 | 49085 |
| CTCN_2529 | 35027 | TTCN_6148 | 49086 |
| ATCN_1541 | 35028 | GTCN_3929 | 49087 |
| ATCN_1542 | 35029 | CTCN_7297 | 49088 |
| ATCN_1543 | 35030 | GTCN_3930 | 49089 |
| TTCN_2132 | 35031 | GTCN_3931 | 49090 |
| TTCN_2133 | 35032 | GTCN_3932 | 49091 |
| CTCN_2530 | 35033 | TTCN_6149 | 49092 |
| GTCN_1370 | 35034 | TTCN_6150 | 49093 |
| GTCN_1371 | 35035 | TTCN_6151 | 49094 |
| CTCN_2531 | 35036 | ATCN_4257 | 49095 |
| ATCN_1544 | 35037 | ATCN_4258 | 49096 |
| ATCN_1545 | 35038 | ATCN_4259 | 49097 |
| TTCN_2134 | 35039 | TTCN_6152 | 49098 |
| TTCN_2135 | 35040 | CTCN_7298 | 49099 |
| CTCN_2532 | 35041 | CTCN_7299 | 49100 |
| GTCN_1372 | 35042 | TTCN_6153 | 49101 |
| GTCN_1373 | 35043 | CTCN_7300 | 49102 |
| GTCN_1374 | 35044 | GTCN_3933 | 49103 |
| CTCN_2533 | 35045 | GTCN_3934 | 49104 |
| TTCN_2136 | 35046 | GTCN_3935 | 49105 |
| ATCN_1546 | 35047 | TTCN_6154 | 49106 |
| CTCN_2534 | 35048 | CTCN_7301 | 49107 |
| TTCN_2137 | 35049 | GTCN_3936 | 49108 |
| TTCN_2138 | 35050 | CTCN_7302 | 49109 |
| ATCN_1547 | 35051 | CTCN_7303 | 49110 |
| CTCN_2535 | 35052 | GTCN_3937 | 49111 |
| TTCN_2139 | 35053 | TTCN_6155 | 49112 |
| CTCN_2536 | 35054 | CTCN_7304 | 49113 |
| ATCN_1548 | 35055 | CTCN_7305 | 49114 |
| TTCN_2140 | 35056 | TTCN_6156 | 49115 |
| ATCN_1549 | 35057 | TTCN_6157 | 49116 |
| CTCN_2537 | 35058 | TTCN_6158 | 49117 |
| CTCN_2538 | 35059 | GTCN_3938 | 49118 |
| CTCN_2539 | 35060 | GTCN_3939 | 49119 |
| CTCN_2540 | 35061 | CTCN_7306 | 49120 |

| | | | |
|---|---|---|---|
| ATCN_1550 | 35062 | TTCN_6159 | 49121 |
| TTCN_2141 | 35063 | ATCN_4260 | 49122 |
| TTCN_2142 | 35064 | ATCN_4261 | 49123 |
| GTCN_1375 | 35065 | GTCN_3940 | 49124 |
| ATCN_1551 | 35066 | CTCN_7307 | 49125 |
| GTCN_1376 | 35067 | TTCN_6160 | 49126 |
| CTCN_2541 | 35068 | ATCN_4262 | 49127 |
| CTCN_2542 | 35069 | TTCN_6161 | 49128 |
| GTCN_1377 | 35070 | CTCN_7308 | 49129 |
| CTCN_2543 | 35071 | ATCN_4263 | 49130 |
| TTCN_2143 | 35072 | TTCN_6162 | 49131 |
| TTCN_2144 | 35073 | ATCN_4264 | 49132 |
| TTCN_2145 | 35074 | TTCN_6163 | 49133 |
| TTCN_2146 | 35075 | CTCN_7309 | 49134 |
| ATCN_1552 | 35076 | GTCN_3941 | 49135 |
| CTCN_2544 | 35077 | CTCN_7310 | 49136 |
| TTCN_2147 | 35078 | GTCN_3942 | 49137 |
| GTCN_1378 | 35079 | CTCN_7311 | 49138 |
| GTCN_1379 | 35080 | GTCN_3943 | 49139 |
| ATCN_1553 | 35081 | TTCN_6164 | 49140 |
| GTCN_1380 | 35082 | CTCN_7312 | 49141 |
| CTCN_2545 | 35083 | TTCN_6165 | 49142 |
| CTCN_2546 | 35084 | TTCN_6166 | 49143 |
| TTCN_2148 | 35085 | GTCN_3944 | 49144 |
| ATCN_1554 | 35086 | TTCN_6167 | 49145 |
| CTCN_2547 | 35087 | CTCN_7313 | 49146 |
| CTCN_2548 | 35088 | ATCN_4265 | 49147 |
| TTCN_2149 | 35089 | TTCN_6168 | 49148 |
| GTCN_1381 | 35090 | CTCN_7314 | 49149 |
| CTCN_2549 | 35091 | GTCN_3945 | 49150 |
| GTCN_1382 | 35092 | TTCN_6169 | 49151 |
| CTCN_2550 | 35093 | CTCN_7315 | 49152 |
| GTCN_1383 | 35094 | GTCN_3946 | 49153 |
| TTCN_2150 | 35095 | CTCN_7316 | 49154 |
| TTCN_2151 | 35096 | ATCN_4266 | 49155 |
| CTCN_2551 | 35097 | TTCN_6170 | 49156 |
| GTCN_1384 | 35098 | GTCN_3947 | 49157 |
| CTCN_2552 | 35099 | TTCN_6171 | 49158 |
| TTCN_2152 | 35100 | TTCN_6172 | 49159 |
| CTCN_2553 | 35101 | TTCN_6173 | 49160 |
| TTCN_2153 | 35102 | TTCN_6174 | 49161 |
| ATCN_1555 | 35103 | ATCN_4267 | 49162 |
| CTCN_2554 | 35104 | TTCN_6175 | 49163 |

FIG. 37 (continued)

| | | | |
|---|---|---|---|
| ATCN_1556 | 35105 | CTCN_7317 | 49164 |
| ATCN_1557 | 35106 | CTCN_7318 | 49165 |
| TTCN_2154 | 35107 | GTCN_3948 | 49166 |
| CTCN_2555 | 35108 | GTCN_3949 | 49167 |
| GTCN_1385 | 35109 | CTCN_7319 | 49168 |
| ATCN_1558 | 35110 | GTCN_3950 | 49169 |
| ATCN_1559 | 35111 | ATCN_4268 | 49170 |
| CTCN_2556 | 35112 | CTCN_7320 | 49171 |
| GTCN_1386 | 35113 | GTCN_3951 | 49172 |
| TTCN_2155 | 35114 | CTCN_7321 | 49173 |
| CTCN_2557 | 35115 | TTCN_6176 | 49174 |
| CTCN_2558 | 35116 | CTCN_7322 | 49175 |
| TTCN_2156 | 35117 | TTCN_6177 | 49176 |
| TTCN_2157 | 35118 | TTCN_6178 | 49177 |
| GTCN_1387 | 35119 | TTCN_6179 | 49178 |
| CTCN_2559 | 35120 | TTCN_6180 | 49179 |
| CTCN_2560 | 35121 | ATCN_4269 | 49180 |
| GTCN_1388 | 35122 | TTCN_6181 | 49181 |
| CTCN_2561 | 35123 | ATCN_4270 | 49182 |
| TTCN_2158 | 35124 | CTCN_7323 | 49183 |
| ATCN_1560 | 35125 | TTCN_6182 | 49184 |
| GTCN_1389 | 35126 | ATCN_4271 | 49185 |
| CTCN_2562 | 35127 | GTCN_3952 | 49186 |
| GTCN_1390 | 35128 | ATCN_4272 | 49187 |
| TTCN_2159 | 35129 | ATCN_4273 | 49188 |
| CTCN_2563 | 35130 | CTCN_7324 | 49189 |
| TTCN_2160 | 35131 | TTCN_6183 | 49190 |
| CTCN_2564 | 35132 | ATCN_4274 | 49191 |
| CTCN_2565 | 35133 | TTCN_6184 | 49192 |
| GTCN_1391 | 35134 | GTCN_3953 | 49193 |
| ATCN_1561 | 35135 | TTCN_6185 | 49194 |
| TTCN_2161 | 35136 | TTCN_6186 | 49195 |
| CTCN_2566 | 35137 | GTCN_3954 | 49196 |
| GTCN_1392 | 35138 | ATCN_4275 | 49197 |
| CTCN_2567 | 35139 | CTCN_7325 | 49198 |
| TTCN_2162 | 35140 | GTCN_3955 | 49199 |
| ATCN_1562 | 35141 | CTCN_7326 | 49200 |
| TTCN_2163 | 35142 | TTCN_6187 | 49201 |
| GTCN_1393 | 35143 | CTCN_7327 | 49202 |
| CTCN_2568 | 35144 | TTCN_6188 | 49203 |
| GTCN_1394 | 35145 | TTCN_6189 | 49204 |
| CTCN_2569 | 35146 | CTCN_7328 | 49205 |
| TTCN_2164 | 35147 | TTCN_6190 | 49206 |

| | | | |
|---|---|---|---|
| TTCN_2165 | 35148 | GTCN_3956 | 49207 |
| GTCN_1395 | 35149 | ATCN_4276 | 49208 |
| TTCN_2166 | 35150 | TTCN_6191 | 49209 |
| CTCN_2570 | 35151 | TTCN_6192 | 49210 |
| CTCN_2571 | 35152 | CTCN_7329 | 49211 |
| TTCN_2167 | 35153 | ATCN_4277 | 49212 |
| GTCN_1396 | 35154 | ATCN_4278 | 49213 |
| ATCN_1563 | 35155 | TTCN_6193 | 49214 |
| TTCN_2168 | 35156 | TTCN_6194 | 49215 |
| CTCN_2572 | 35157 | CTCN_7330 | 49216 |
| TTCN_2169 | 35158 | GTCN_3957 | 49217 |
| ATCN_1564 | 35159 | CTCN_7331 | 49218 |
| ATCN_1565 | 35160 | ATCN_4279 | 49219 |
| CTCN_2573 | 35161 | CTCN_7332 | 49220 |
| TTCN_2170 | 35162 | TTCN_6195 | 49221 |
| CTCN_2574 | 35163 | GTCN_3958 | 49222 |
| TTCN_2171 | 35164 | CTCN_7333 | 49223 |
| TTCN_2172 | 35165 | CTCN_7334 | 49224 |
| ATCN_1566 | 35166 | ATCN_4280 | 49225 |
| ATCN_1567 | 35167 | TTCN_6196 | 49226 |
| CTCN_2575 | 35168 | CTCN_7335 | 49227 |
| TTCN_2173 | 35169 | CTCN_7336 | 49228 |
| CTCN_2576 | 35170 | TTCN_6197 | 49229 |
| GTCN_1397 | 35171 | ATCN_4281 | 49230 |
| CTCN_2577 | 35172 | ATCN_4282 | 49231 |
| CTCN_2578 | 35173 | TTCN_6198 | 49232 |
| CTCN_2579 | 35174 | CTCN_7337 | 49233 |
| CTCN_2580 | 35175 | TTCN_6199 | 49234 |
| CTCN_2581 | 35176 | ATCN_4283 | 49235 |
| CTCN_2582 | 35177 | CTCN_7338 | 49236 |
| CTCN_2583 | 35178 | CTCN_7339 | 49237 |
| TTCN_2174 | 35179 | TTCN_6200 | 49238 |
| TTCN_2175 | 35180 | GTCN_3959 | 49239 |
| TTCN_2176 | 35181 | TTCN_6201 | 49240 |
| CTCN_2584 | 35182 | GTCN_3960 | 49241 |
| TTCN_2177 | 35183 | CTCN_7340 | 49242 |
| TTCN_2178 | 35184 | ATCN_4284 | 49243 |
| ATCN_1568 | 35185 | ATCN_4285 | 49244 |
| CTCN_2585 | 35186 | ATCN_4286 | 49245 |
| GTCN_1398 | 35187 | TTCN_6202 | 49246 |
| CTCN_2586 | 35188 | GTCN_3961 | 49247 |
| CTCN_2587 | 35189 | GTCN_3962 | 49248 |
| CTCN_2588 | 35190 | GTCN_3963 | 49249 |

FIG. 37 (continued)

| | | | |
|---|---|---|---|
| ATCN_1569 | 35191 | TTCN_6203 | 49250 |
| CTCN_2589 | 35192 | CTCN_7341 | 49251 |
| TTCN_2179 | 35193 | ATCN_4287 | 49252 |
| GTCN_1399 | 35194 | TTCN_6204 | 49253 |
| CTCN_2590 | 35195 | TTCN_6205 | 49254 |
| TTCN_2180 | 35196 | CTCN_7342 | 49255 |
| ATCN_1570 | 35197 | ATCN_4288 | 49256 |
| GTCN_1400 | 35198 | ATCN_4289 | 49257 |
| TTCN_2181 | 35199 | CTCN_7343 | 49258 |
| CTCN_2591 | 35200 | ATCN_4290 | 49259 |
| CTCN_2592 | 35201 | TTCN_6206 | 49260 |
| TTCN_2182 | 35202 | ATCN_4291 | 49261 |
| TTCN_2183 | 35203 | ATCN_4292 | 49262 |
| CTCN_2593 | 35204 | GTCN_3964 | 49263 |
| GTCN_1401 | 35205 | CTCN_7344 | 49264 |
| TTCN_2184 | 35206 | CTCN_7345 | 49265 |
| TTCN_2185 | 35207 | TTCN_6207 | 49266 |
| TTCN_2186 | 35208 | TTCN_6208 | 49267 |
| TTCN_2187 | 35209 | GTCN_3965 | 49268 |
| TTCN_2188 | 35210 | ATCN_4293 | 49269 |
| CTCN_2594 | 35211 | CTCN_7346 | 49270 |
| GTCN_1402 | 35212 | ATCN_4294 | 49271 |
| TTCN_2189 | 35213 | TTCN_6209 | 49272 |
| TTCN_2190 | 35214 | GTCN_3966 | 49273 |
| CTCN_2595 | 35215 | CTCN_7347 | 49274 |
| GTCN_1403 | 35216 | CTCN_7348 | 49275 |
| CTCN_2596 | 35217 | CTCN_7349 | 49276 |
| TTCN_2191 | 35218 | CTCN_7350 | 49277 |
| TTCN_2192 | 35219 | CTCN_7351 | 49278 |
| GTCN_1404 | 35220 | TTCN_6210 | 49279 |
| TTCN_2193 | 35221 | CTCN_7352 | 49280 |
| ATCN_1571 | 35222 | CTCN_7353 | 49281 |
| CTCN_2597 | 35223 | TTCN_6211 | 49282 |
| TTCN_2194 | 35224 | TTCN_6212 | 49283 |
| ATCN_1572 | 35225 | TTCN_6213 | 49284 |
| ATCN_1573 | 35226 | TTCN_6214 | 49285 |
| TTCN_2195 | 35227 | GTCN_3967 | 49286 |
| ATCN_1574 | 35228 | TTCN_6215 | 49287 |
| TTCN_2196 | 35229 | ATCN_4295 | 49288 |
| ATCN_1575 | 35230 | CTCN_7354 | 49289 |
| TTCN_2197 | 35231 | GTCN_3968 | 49290 |
| CTCN_2598 | 35232 | CTCN_7355 | 49291 |
| GTCN_1405 | 35233 | TTCN_6216 | 49292 |

| | | | |
|---|---|---|---|
| GTCN_1406 | 35234 | TTCN_6217 | 49293 |
| GTCN_1407 | 35235 | GTCN_3969 | 49294 |
| TTCN_2198 | 35236 | CTCN_7356 | 49295 |
| ATCN_1576 | 35237 | TTCN_6218 | 49296 |
| ATCN_1577 | 35238 | CTCN_7357 | 49297 |
| CTCN_2599 | 35239 | GTCN_3970 | 49298 |
| CTCN_2600 | 35240 | GTCN_3971 | 49299 |
| CTCN_2601 | 35241 | TTCN_6219 | 49300 |
| CTCN_2602 | 35242 | CTCN_7358 | 49301 |
| ATCN_1578 | 35243 | CTCN_7359 | 49302 |
| TTCN_2199 | 35244 | CTCN_7360 | 49303 |
| TTCN_2200 | 35245 | ATCN_4296 | 49304 |
| CTCN_2603 | 35246 | ATCN_4297 | 49305 |
| CTCN_2604 | 35247 | ATCN_4298 | 49306 |
| CTCN_2605 | 35248 | GTCN_3972 | 49307 |
| CTCN_2606 | 35249 | GTCN_3973 | 49308 |
| ATCN_1579 | 35250 | CTCN_7361 | 49309 |
| CTCN_2607 | 35251 | GTCN_3974 | 49310 |
| CTCN_2608 | 35252 | GTCN_3975 | 49311 |
| GTCN_1408 | 35253 | CTCN_7362 | 49312 |
| TTCN_2201 | 35254 | CTCN_7363 | 49313 |
| ATCN_1580 | 35255 | TTCN_6220 | 49314 |
| GTCN_1409 | 35256 | CTCN_7364 | 49315 |
| CTCN_2609 | 35257 | GTCN_3976 | 49316 |
| CTCN_2610 | 35258 | ATCN_4299 | 49317 |
| GTCN_1410 | 35259 | GTCN_3977 | 49318 |
| CTCN_2611 | 35260 | CTCN_7365 | 49319 |
| ATCN_1581 | 35261 | TTCN_6221 | 49320 |
| ATCN_1582 | 35262 | CTCN_7366 | 49321 |
| CTCN_2612 | 35263 | TTCN_6222 | 49322 |
| TTCN_2202 | 35264 | ATCN_4300 | 49323 |
| ATCN_1583 | 35265 | ATCN_4301 | 49324 |
| CTCN_2613 | 35266 | CTCN_7367 | 49325 |
| CTCN_2614 | 35267 | CTCN_7368 | 49326 |
| CTCN_2615 | 35268 | GTCN_3978 | 49327 |
| GTCN_1411 | 35269 | CTCN_7369 | 49328 |
| ATCN_1584 | 35270 | TTCN_6223 | 49329 |
| TTCN_2203 | 35271 | TTCN_6224 | 49330 |
| CTCN_2616 | 35272 | TTCN_6225 | 49331 |
| ATCN_1585 | 35273 | CTCN_7370 | 49332 |
| ATCN_1586 | 35274 | CTCN_7371 | 49333 |
| GTCN_1412 | 35275 | TTCN_6226 | 49334 |
| CTCN_2617 | 35276 | CTCN_7372 | 49335 |

FIG. 37 (continued)

| | | | |
|---|---|---|---|
| GTCN_1413 | 35277 | TTCN_6227 | 49336 |
| ATCN_1587 | 35278 | TTCN_6228 | 49337 |
| ATCN_1588 | 35279 | CTCN_7373 | 49338 |
| TTCN_2204 | 35280 | TTCN_6229 | 49339 |
| CTCN_2618 | 35281 | CTCN_7374 | 49340 |
| ATCN_1589 | 35282 | GTCN_3979 | 49341 |
| TTCN_2205 | 35283 | GTCN_3980 | 49342 |
| GTCN_1414 | 35284 | CTCN_7375 | 49343 |
| TTCN_2206 | 35285 | CTCN_7376 | 49344 |
| TTCN_2207 | 35286 | ATCN_4302 | 49345 |
| ATCN_1590 | 35287 | CTCN_7377 | 49346 |
| ATCN_1591 | 35288 | GTCN_3981 | 49347 |
| GTCN_1415 | 35289 | GTCN_3982 | 49348 |
| TTCN_2208 | 35290 | CTCN_7378 | 49349 |
| CTCN_2619 | 35291 | ATCN_4303 | 49350 |
| CTCN_2620 | 35292 | CTCN_7379 | 49351 |
| GTCN_1416 | 35293 | CTCN_7380 | 49352 |
| CTCN_2621 | 35294 | CTCN_7381 | 49353 |
| ATCN_1592 | 35295 | CTCN_7382 | 49354 |
| TTCN_2209 | 35296 | GTCN_3983 | 49355 |
| CTCN_2622 | 35297 | CTCN_7383 | 49356 |
| ATCN_1593 | 35298 | TTCN_6230 | 49357 |
| CTCN_2623 | 35299 | ATCN_4304 | 49358 |
| TTCN_2210 | 35300 | TTCN_6231 | 49359 |
| ATCN_1594 | 35301 | CTCN_7384 | 49360 |
| ATCN_1595 | 35302 | GTCN_3984 | 49361 |
| CTCN_2624 | 35303 | ATCN_4305 | 49362 |
| TTCN_2211 | 35304 | ATCN_4306 | 49363 |
| CTCN_2625 | 35305 | CTCN_7385 | 49364 |
| CTCN_2626 | 35306 | GTCN_3985 | 49365 |
| TTCN_2212 | 35307 | CTCN_7386 | 49366 |
| CTCN_2627 | 35308 | CTCN_7387 | 49367 |
| TTCN_2213 | 35309 | GTCN_3986 | 49368 |
| TTCN_2214 | 35310 | TTCN_6232 | 49369 |
| TTCN_2215 | 35311 | TTCN_6233 | 49370 |
| CTCN_2628 | 35312 | CTCN_7388 | 49371 |
| TTCN_2216 | 35313 | CTCN_7389 | 49372 |
| ATCN_1596 | 35314 | CTCN_7390 | 49373 |
| TTCN_2217 | 35315 | CTCN_7391 | 49374 |
| GTCN_1417 | 35316 | CTCN_7392 | 49375 |
| CTCN_2629 | 35317 | GTCN_3987 | 49376 |
| ATCN_1597 | 35318 | CTCN_7393 | 49377 |
| CTCN_2630 | 35319 | CTCN_7394 | 49378 |

| | | | |
|---|---|---|---|
| TTCN_2218 | 35320 | CTCN_7395 | 49379 |
| CTCN_2631 | 35321 | CTCN_7396 | 49380 |
| ATCN_1598 | 35322 | TTCN_6234 | 49381 |
| TTCN_2219 | 35323 | TTCN_6235 | 49382 |
| TTCN_2220 | 35324 | GTCN_3988 | 49383 |
| GTCN_1418 | 35325 | CTCN_7397 | 49384 |
| CTCN_2632 | 35326 | CTCN_7398 | 49385 |
| TTCN_2221 | 35327 | TTCN_6236 | 49386 |
| ATCN_1599 | 35328 | GTCN_3989 | 49387 |
| TTCN_2222 | 35329 | GTCN_3990 | 49388 |
| ATCN_1600 | 35330 | TTCN_6237 | 49389 |
| TTCN_2223 | 35331 | CTCN_7399 | 49390 |
| CTCN_2633 | 35332 | CTCN_7400 | 49391 |
| ATCN_1601 | 35333 | ATCN_4307 | 49392 |
| ATCN_1602 | 35334 | GTCN_3991 | 49393 |
| TTCN_2224 | 35335 | CTCN_7401 | 49394 |
| ATCN_1603 | 35336 | CTCN_7402 | 49395 |
| CTCN_2634 | 35337 | TTCN_6238 | 49396 |
| TTCN_2225 | 35338 | GTCN_3992 | 49397 |
| TTCN_2226 | 35339 | GTCN_3993 | 49398 |
| TTCN_2227 | 35340 | GTCN_3994 | 49399 |
| GTCN_1419 | 35341 | CTCN_7403 | 49400 |
| TTCN_2228 | 35342 | TTCN_6239 | 49401 |
| ATCN_1604 | 35343 | TTCN_6240 | 49402 |
| TTCN_2229 | 35344 | CTCN_7404 | 49403 |
| CTCN_2635 | 35345 | TTCN_6241 | 49404 |
| GTCN_1420 | 35346 | GTCN_3995 | 49405 |
| GTCN_1421 | 35347 | GTCN_3996 | 49406 |
| CTCN_2636 | 35348 | ATCN_4308 | 49407 |
| GTCN_1422 | 35349 | TTCN_6242 | 49408 |
| CTCN_2637 | 35350 | TTCN_6243 | 49409 |
| ATCN_1605 | 35351 | TTCN_6244 | 49410 |
| CTCN_2638 | 35352 | GTCN_3997 | 49411 |
| CTCN_2639 | 35353 | TTCN_6245 | 49412 |
| ATCN_1606 | 35354 | CTCN_7405 | 49413 |
| CTCN_2640 | 35355 | GTCN_3998 | 49414 |
| CTCN_2641 | 35356 | ATCN_4309 | 49415 |
| GTCN_1423 | 35357 | GTCN_3999 | 49416 |
| ATCN_1607 | 35358 | TTCN_6246 | 49417 |
| CTCN_2642 | 35359 | ATCN_4310 | 49418 |
| ATCN_1608 | 35360 | TTCN_6247 | 49419 |
| CTCN_2643 | 35361 | CTCN_7406 | 49420 |
| CTCN_2644 | 35362 | GTCN_4000 | 49421 |

FIG. 37 (continued)

| | | | |
|---|---|---|---|
| GTCN_1424 | 35363 | GTCN_4001 | 49422 |
| CTCN_2645 | 35364 | GTCN_4002 | 49423 |
| ATCN_1609 | 35365 | TTCN_6248 | 49424 |
| CTCN_2646 | 35366 | ATCN_4311 | 49425 |
| GTCN_1425 | 35367 | TTCN_6249 | 49426 |
| CTCN_2647 | 35368 | GTCN_4003 | 49427 |
| TTCN_2230 | 35369 | GTCN_4004 | 49428 |
| GTCN_1426 | 35370 | ATCN_4312 | 49429 |
| CTCN_2648 | 35371 | TTCN_6250 | 49430 |
| TTCN_2231 | 35372 | TTCN_6251 | 49431 |
| CTCN_2649 | 35373 | CTCN_7407 | 49432 |
| GTCN_1427 | 35374 | GTCN_4005 | 49433 |
| CTCN_2650 | 35375 | TTCN_6252 | 49434 |
| CTCN_2651 | 35376 | ATCN_4313 | 49435 |
| ATCN_1610 | 35377 | ATCN_4314 | 49436 |
| GTCN_1428 | 35378 | CTCN_7408 | 49437 |
| TTCN_2232 | 35379 | GTCN_4006 | 49438 |
| CTCN_2652 | 35380 | TTCN_6253 | 49439 |
| GTCN_1429 | 35381 | GTCN_4007 | 49440 |
| TTCN_2233 | 35382 | CTCN_7409 | 49441 |
| GTCN_1430 | 35383 | GTCN_4008 | 49442 |
| ATCN_1611 | 35384 | CTCN_7410 | 49443 |
| ATCN_1612 | 35385 | GTCN_4009 | 49444 |
| GTCN_1431 | 35386 | TTCN_6254 | 49445 |
| ATCN_1613 | 35387 | TTCN_6255 | 49446 |
| ATCN_1614 | 35388 | ATCN_4315 | 49447 |
| ATCN_1615 | 35389 | CTCN_7411 | 49448 |
| ATCN_1616 | 35390 | CTCN_7412 | 49449 |
| CTCN_2653 | 35391 | CTCN_7413 | 49450 |
| CTCN_2654 | 35392 | GTCN_4010 | 49451 |
| ATCN_1617 | 35393 | CTCN_7414 | 49452 |
| ATCN_1618 | 35394 | ATCN_4316 | 49453 |
| TTCN_2234 | 35395 | CTCN_7415 | 49454 |
| TTCN_2235 | 35396 | GTCN_4011 | 49455 |
| TTCN_2236 | 35397 | CTCN_7416 | 49456 |
| TTCN_2237 | 35398 | CTCN_7417 | 49457 |
| ATCN_1619 | 35399 | TTCN_6256 | 49458 |
| TTCN_2238 | 35400 | TTCN_6257 | 49459 |
| TTCN_2239 | 35401 | TTCN_6258 | 49460 |
| CTCN_2655 | 35402 | GTCN_4012 | 49461 |
| CTCN_2656 | 35403 | TTCN_6259 | 49462 |
| ATCN_1620 | 35404 | ATCN_4317 | 49463 |
| GTCN_1432 | 35405 | TTCN_6260 | 49464 |

| | | | |
|---|---|---|---|
| CTCN_2657 | 35406 | CTCN_7418 | 49465 |
| TTCN_2240 | 35407 | CTCN_7419 | 49466 |
| CTCN_2658 | 35408 | GTCN_4013 | 49467 |
| CTCN_2659 | 35409 | TTCN_6261 | 49468 |
| CTCN_2660 | 35410 | CTCN_7420 | 49469 |
| CTCN_2661 | 35411 | GTCN_4014 | 49470 |
| CTCN_2662 | 35412 | ATCN_4318 | 49471 |
| TTCN_2241 | 35413 | ATCN_4319 | 49472 |
| TTCN_2242 | 35414 | TTCN_6262 | 49473 |
| TTCN_2243 | 35415 | ATCN_4320 | 49474 |
| GTCN_1433 | 35416 | CTCN_7421 | 49475 |
| CTCN_2663 | 35417 | CTCN_7422 | 49476 |
| TTCN_2244 | 35418 | GTCN_4015 | 49477 |
| ATCN_1621 | 35419 | CTCN_7423 | 49478 |
| CTCN_2664 | 35420 | GTCN_4016 | 49479 |
| GTCN_1434 | 35421 | GTCN_4017 | 49480 |
| GTCN_1435 | 35422 | CTCN_7424 | 49481 |
| TTCN_2245 | 35423 | GTCN_4018 | 49482 |
| TTCN_2246 | 35424 | GTCN_4019 | 49483 |
| TTCN_2247 | 35425 | GTCN_4020 | 49484 |
| TTCN_2248 | 35426 | CTCN_7425 | 49485 |
| GTCN_1436 | 35427 | TTCN_6263 | 49486 |
| CTCN_2665 | 35428 | TTCN_6264 | 49487 |
| ATCN_1622 | 35429 | ATCN_4321 | 49488 |
| CTCN_2666 | 35430 | TTCN_6265 | 49489 |
| CTCN_2667 | 35431 | CTCN_7426 | 49490 |
| GTCN_1437 | 35432 | TTCN_6266 | 49491 |
| GTCN_1438 | 35433 | CTCN_7427 | 49492 |
| ATCN_1623 | 35434 | ATCN_4322 | 49493 |
| TTCN_2249 | 35435 | TTCN_6267 | 49494 |
| TTCN_2250 | 35436 | TTCN_6268 | 49495 |
| GTCN_1439 | 35437 | CTCN_7428 | 49496 |
| CTCN_2668 | 35438 | TTCN_6269 | 49497 |
| CTCN_2669 | 35439 | CTCN_7429 | 49498 |
| GTCN_1440 | 35440 | GTCN_4021 | 49499 |
| TTCN_2251 | 35441 | TTCN_6270 | 49500 |
| ATCN_1624 | 35442 | CTCN_7430 | 49501 |
| ATCN_1625 | 35443 | GTCN_4022 | 49502 |
| GTCN_1441 | 35444 | GTCN_4023 | 49503 |
| TTCN_2252 | 35445 | CTCN_7431 | 49504 |
| CTCN_2670 | 35446 | CTCN_7432 | 49505 |
| CTCN_2671 | 35447 | TTCN_6271 | 49506 |
| GTCN_1442 | 35448 | CTCN_7433 | 49507 |

FIG. 37 (continued)

| | | | |
|---|---|---|---|
| GTCN_1443 | 35449 | ATCN_4323 | 49508 |
| GTCN_1444 | 35450 | CTCN_7434 | 49509 |
| CTCN_2672 | 35451 | GTCN_4024 | 49510 |
| CTCN_2673 | 35452 | ATCN_4324 | 49511 |
| CTCN_2674 | 35453 | CTCN_7435 | 49512 |
| TTCN_2253 | 35454 | GTCN_4025 | 49513 |
| GTCN_1445 | 35455 | CTCN_7436 | 49514 |
| GTCN_1446 | 35456 | CTCN_7437 | 49515 |
| GTCN_1447 | 35457 | TTCN_6272 | 49516 |
| CTCN_2675 | 35458 | TTCN_6273 | 49517 |
| TTCN_2254 | 35459 | TTCN_6274 | 49518 |
| ATCN_1626 | 35460 | CTCN_7438 | 49519 |
| CTCN_2676 | 35461 | ATCN_4325 | 49520 |
| ATCN_1627 | 35462 | TTCN_6275 | 49521 |
| CTCN_2677 | 35463 | CTCN_7439 | 49522 |
| CTCN_2678 | 35464 | TTCN_6276 | 49523 |
| ATCN_1628 | 35465 | CTCN_7440 | 49524 |
| TTCN_2255 | 35466 | TTCN_6277 | 49525 |
| CTCN_2679 | 35467 | ATCN_4326 | 49526 |
| GTCN_1448 | 35468 | TTCN_6278 | 49527 |
| CTCN_2680 | 35469 | GTCN_4026 | 49528 |
| CTCN_2681 | 35470 | CTCN_7441 | 49529 |
| TTCN_2256 | 35471 | TTCN_6279 | 49530 |
| CTCN_2682 | 35472 | ATCN_4327 | 49531 |
| ATCN_1629 | 35473 | ATCN_4328 | 49532 |
| ATCN_1630 | 35474 | CTCN_7442 | 49533 |
| CTCN_2683 | 35475 | TTCN_6280 | 49534 |
| CTCN_2684 | 35476 | TTCN_6281 | 49535 |
| CTCN_2685 | 35477 | GTCN_4027 | 49536 |
| CTCN_2686 | 35478 | ATCN_4329 | 49537 |
| TTCN_2257 | 35479 | TTCN_6282 | 49538 |
| TTCN_2258 | 35480 | CTCN_7443 | 49539 |
| CTCN_2687 | 35481 | TTCN_6283 | 49540 |
| CTCN_2688 | 35482 | ATCN_4330 | 49541 |
| CTCN_2689 | 35483 | ATCN_4331 | 49542 |
| ATCN_1631 | 35484 | TTCN_6284 | 49543 |
| ATCN_1632 | 35485 | CTCN_7444 | 49544 |
| TTCN_2259 | 35486 | GTCN_4028 | 49545 |
| CTCN_2690 | 35487 | GTCN_4029 | 49546 |
| GTCN_1449 | 35488 | GTCN_4030 | 49547 |
| TTCN_2260 | 35489 | CTCN_7445 | 49548 |
| TTCN_2261 | 35490 | TTCN_6285 | 49549 |
| TTCN_2262 | 35491 | GTCN_4031 | 49550 |

| | | | |
|---|---|---|---|
| TTCN_2263 | 35492 | TTCN_6286 | 49551 |
| GTCN_1450 | 35493 | GTCN_4032 | 49552 |
| CTCN_2691 | 35494 | CTCN_7446 | 49553 |
| ATCN_1633 | 35495 | TTCN_6287 | 49554 |
| ATCN_1634 | 35496 | ATCN_4332 | 49555 |
| CTCN_2692 | 35497 | CTCN_7447 | 49556 |
| GTCN_1451 | 35498 | GTCN_4033 | 49557 |
| CTCN_2693 | 35499 | GTCN_4034 | 49558 |
| CTCN_2694 | 35500 | CTCN_7448 | 49559 |
| ATCN_1635 | 35501 | CTCN_7449 | 49560 |
| CTCN_2695 | 35502 | GTCN_4035 | 49561 |
| CTCN_2696 | 35503 | CTCN_7450 | 49562 |
| GTCN_1452 | 35504 | TTCN_6288 | 49563 |
| CTCN_2697 | 35505 | CTCN_7451 | 49564 |
| TTCN_2264 | 35506 | ATCN_4333 | 49565 |
| ATCN_1636 | 35507 | CTCN_7452 | 49566 |
| TTCN_2265 | 35508 | CTCN_7453 | 49567 |
| CTCN_2698 | 35509 | GTCN_4036 | 49568 |
| CTCN_2699 | 35510 | ATCN_4334 | 49569 |
| TTCN_2266 | 35511 | ATCN_4335 | 49570 |
| TTCN_2267 | 35512 | TTCN_6289 | 49571 |
| TTCN_2268 | 35513 | TTCN_6290 | 49572 |
| CTCN_2700 | 35514 | TTCN_6291 | 49573 |
| CTCN_2701 | 35515 | CTCN_7454 | 49574 |
| CTCN_2702 | 35516 | ATCN_4336 | 49575 |
| TTCN_2269 | 35517 | TTCN_6292 | 49576 |
| CTCN_2703 | 35518 | GTCN_4037 | 49577 |
| CTCN_2704 | 35519 | TTCN_6293 | 49578 |
| GTCN_1453 | 35520 | TTCN_6294 | 49579 |
| TTCN_2270 | 35521 | CTCN_7455 | 49580 |
| CTCN_2705 | 35522 | ATCN_4337 | 49581 |
| CTCN_2706 | 35523 | TTCN_6295 | 49582 |
| GTCN_1454 | 35524 | TTCN_6296 | 49583 |
| ATCN_1637 | 35525 | GTCN_4038 | 49584 |
| CTCN_2707 | 35526 | GTCN_4039 | 49585 |
| CTCN_2708 | 35527 | CTCN_7456 | 49586 |
| CTCN_2709 | 35528 | GTCN_4040 | 49587 |
| ATCN_1638 | 35529 | CTCN_7457 | 49588 |
| CTCN_2710 | 35530 | GTCN_4041 | 49589 |
| TTCN_2271 | 35531 | TTCN_6297 | 49590 |
| ATCN_1639 | 35532 | TTCN_6298 | 49591 |
| CTCN_2711 | 35533 | GTCN_4042 | 49592 |
| CTCN_2712 | 35534 | ATCN_4338 | 49593 |

FIG. 37 (continued)

| | | | |
|---|---|---|---|
| CTCN_2713 | 35535 | ATCN_4339 | 49594 |
| ATCN_1640 | 35536 | TTCN_6299 | 49595 |
| GTCN_1455 | 35537 | TTCN_6300 | 49596 |
| CTCN_2714 | 35538 | GTCN_4043 | 49597 |
| CTCN_2715 | 35539 | TTCN_6301 | 49598 |
| TTCN_2272 | 35540 | CTCN_7458 | 49599 |
| ATCN_1641 | 35541 | TTCN_6302 | 49600 |
| CTCN_2716 | 35542 | TTCN_6303 | 49601 |
| ATCN_1642 | 35543 | GTCN_4044 | 49602 |
| GTCN_1456 | 35544 | GTCN_4045 | 49603 |
| GTCN_1457 | 35545 | TTCN_6304 | 49604 |
| ATCN_1643 | 35546 | TTCN_6305 | 49605 |
| GTCN_1458 | 35547 | CTCN_7459 | 49606 |
| CTCN_2717 | 35548 | TTCN_6306 | 49607 |
| CTCN_2718 | 35549 | TTCN_6307 | 49608 |
| CTCN_2719 | 35550 | ATCN_4340 | 49609 |
| GTCN_1459 | 35551 | TTCN_6308 | 49610 |
| GTCN_1460 | 35552 | TTCN_6309 | 49611 |
| GTCN_1461 | 35553 | CTCN_7460 | 49612 |
| TTCN_2273 | 35554 | ATCN_4341 | 49613 |
| GTCN_1462 | 35555 | ATCN_4342 | 49614 |
| GTCN_1463 | 35556 | TTCN_6310 | 49615 |
| TTCN_2274 | 35557 | GTCN_4046 | 49616 |
| GTCN_1464 | 35558 | TTCN_6311 | 49617 |
| CTCN_2720 | 35559 | GTCN_4047 | 49618 |
| CTCN_2721 | 35560 | ATCN_4343 | 49619 |
| GTCN_1465 | 35561 | GTCN_4048 | 49620 |
| TTCN_2275 | 35562 | CTCN_7461 | 49621 |
| ATCN_1644 | 35563 | CTCN_7462 | 49622 |
| ATCN_1645 | 35564 | GTCN_4049 | 49623 |
| CTCN_2722 | 35565 | CTCN_7463 | 49624 |
| TTCN_2276 | 35566 | CTCN_7464 | 49625 |
| TTCN_2277 | 35567 | TTCN_6312 | 49626 |
| TTCN_2278 | 35568 | CTCN_7465 | 49627 |
| CTCN_2723 | 35569 | ATCN_4344 | 49628 |
| TTCN_2279 | 35570 | GTCN_4050 | 49629 |
| ATCN_1646 | 35571 | CTCN_7466 | 49630 |
| GTCN_1466 | 35572 | TTCN_6313 | 49631 |
| CTCN_2724 | 35573 | CTCN_7467 | 49632 |
| CTCN_2725 | 35574 | TTCN_6314 | 49633 |
| ATCN_1647 | 35575 | CTCN_7468 | 49634 |
| GTCN_1467 | 35576 | CTCN_7469 | 49635 |
| TTCN_2280 | 35577 | TTCN_6315 | 49636 |

| | | | |
|---|---|---|---|
| TTCN_2281 | 35578 | GTCN_4051 | 49637 |
| ATCN_1648 | 35579 | GTCN_4052 | 49638 |
| GTCN_1468 | 35580 | GTCN_4053 | 49639 |
| CTCN_2726 | 35581 | CTCN_7470 | 49640 |
| ATCN_1649 | 35582 | GTCN_4054 | 49641 |
| GTCN_1469 | 35583 | CTCN_7471 | 49642 |
| ATCN_1650 | 35584 | GTCN_4055 | 49643 |
| TTCN_2282 | 35585 | TTCN_6316 | 49644 |
| GTCN_1470 | 35586 | TTCN_6317 | 49645 |
| CTCN_2727 | 35587 | TTCN_6318 | 49646 |
| CTCN_2728 | 35588 | CTCN_7472 | 49647 |
| TTCN_2283 | 35589 | CTCN_7473 | 49648 |
| GTCN_1471 | 35590 | GTCN_4056 | 49649 |
| GTCN_1472 | 35591 | CTCN_7474 | 49650 |
| CTCN_2729 | 35592 | GTCN_4057 | 49651 |
| GTCN_1473 | 35593 | CTCN_7475 | 49652 |
| CTCN_2730 | 35594 | ATCN_4345 | 49653 |
| GTCN_1474 | 35595 | GTCN_4058 | 49654 |
| CTCN_2731 | 35596 | CTCN_7476 | 49655 |
| CTCN_2732 | 35597 | CTCN_7477 | 49656 |
| CTCN_2733 | 35598 | ATCN_4346 | 49657 |
| GTCN_1475 | 35599 | GTCN_4059 | 49658 |
| ATCN_1651 | 35600 | ATCN_4347 | 49659 |
| CTCN_2734 | 35601 | CTCN_7478 | 49660 |
| GTCN_1476 | 35602 | CTCN_7479 | 49661 |
| TTCN_2284 | 35603 | CTCN_7480 | 49662 |
| TTCN_2285 | 35604 | GTCN_4060 | 49663 |
| TTCN_2286 | 35605 | GTCN_4061 | 49664 |
| TTCN_2287 | 35606 | CTCN_7481 | 49665 |
| TTCN_2288 | 35607 | CTCN_7482 | 49666 |
| CTCN_2735 | 35608 | TTCN_6319 | 49667 |
| GTCN_1477 | 35609 | GTCN_4062 | 49668 |
| CTCN_2736 | 35610 | ATCN_4348 | 49669 |
| GTCN_1478 | 35611 | CTCN_7483 | 49670 |
| CTCN_2737 | 35612 | TTCN_6320 | 49671 |
| CTCN_2738 | 35613 | TTCN_6321 | 49672 |
| GTCN_1479 | 35614 | TTCN_6322 | 49673 |
| CTCN_2739 | 35615 | ATCN_4349 | 49674 |
| ATCN_1652 | 35616 | CTCN_7484 | 49675 |
| CTCN_2740 | 35617 | TTCN_6323 | 49676 |
| CTCN_2741 | 35618 | TTCN_6324 | 49677 |
| CTCN_2742 | 35619 | TTCN_6325 | 49678 |
| TTCN_2289 | 35620 | CTCN_7485 | 49679 |

FIG. 37 (continued)

| | | | |
|---|---|---|---|
| ATCN_1653 | 35621 | CTCN_7486 | 49680 |
| TTCN_2290 | 35622 | TTCN_6326 | 49681 |
| CTCN_2743 | 35623 | TTCN_6327 | 49682 |
| ATCN_1654 | 35624 | TTCN_6328 | 49683 |
| CTCN_2744 | 35625 | TTCN_6329 | 49684 |
| GTCN_1480 | 35626 | TTCN_6330 | 49685 |
| CTCN_2745 | 35627 | TTCN_6331 | 49686 |
| CTCN_2746 | 35628 | TTCN_6332 | 49687 |
| ATCN_1655 | 35629 | TTCN_6333 | 49688 |
| CTCN_2747 | 35630 | TTCN_6334 | 49689 |
| TTCN_2291 | 35631 | TTCN_6335 | 49690 |
| ATCN_1656 | 35632 | ATCN_4350 | 49691 |
| GTCN_1481 | 35633 | TTCN_6336 | 49692 |
| TTCN_2292 | 35634 | CTCN_7487 | 49693 |
| CTCN_2748 | 35635 | ATCN_4351 | 49694 |
| GTCN_1482 | 35636 | GTCN_4063 | 49695 |
| CTCN_2749 | 35637 | GTCN_4064 | 49696 |
| ATCN_1657 | 35638 | CTCN_7488 | 49697 |
| ATCN_1658 | 35639 | CTCN_7489 | 49698 |
| CTCN_2750 | 35640 | ATCN_4352 | 49699 |
| CTCN_2751 | 35641 | ATCN_4353 | 49700 |
| GTCN_1483 | 35642 | CTCN_7490 | 49701 |
| ATCN_1659 | 35643 | CTCN_7491 | 49702 |
| CTCN_2752 | 35644 | CTCN_7492 | 49703 |
| GTCN_1484 | 35645 | GTCN_4065 | 49704 |
| TTCN_2293 | 35646 | ATCN_4354 | 49705 |
| TTCN_2294 | 35647 | ATCN_4355 | 49706 |
| TTCN_2295 | 35648 | GTCN_4066 | 49707 |
| GTCN_1485 | 35649 | GTCN_4067 | 49708 |
| TTCN_2296 | 35650 | GTCN_4068 | 49709 |
| ATCN_1660 | 35651 | CTCN_7493 | 49710 |
| TTCN_2297 | 35652 | CTCN_7494 | 49711 |
| GTCN_1486 | 35653 | CTCN_7495 | 49712 |
| CTCN_2753 | 35654 | ATCN_4356 | 49713 |
| TTCN_2298 | 35655 | CTCN_7496 | 49714 |
| GTCN_1487 | 35656 | CTCN_7497 | 49715 |
| TTCN_2299 | 35657 | ATCN_4357 | 49716 |
| CTCN_2754 | 35658 | CTCN_7498 | 49717 |
| CTCN_2755 | 35659 | TTCN_6337 | 49718 |
| GTCN_1488 | 35660 | TTCN_6338 | 49719 |
| TTCN_2300 | 35661 | CTCN_7499 | 49720 |
| TTCN_2301 | 35662 | CTCN_7500 | 49721 |
| TTCN_2302 | 35663 | TTCN_6339 | 49722 |

| | | | |
|---|---|---|---|
| TTCN_2303 | 35664 | CTCN_7501 | 49723 |
| ATCN_1661 | 35665 | ATCN_4358 | 49724 |
| TTCN_2304 | 35666 | TTCN_6340 | 49725 |
| ATCN_1662 | 35667 | CTCN_7502 | 49726 |
| ATCN_1663 | 35668 | TTCN_6341 | 49727 |
| CTCN_2756 | 35669 | ATCN_4359 | 49728 |
| TTCN_2305 | 35670 | ATCN_4360 | 49729 |
| TTCN_2306 | 35671 | ATCN_4361 | 49730 |
| CTCN_2757 | 35672 | ATCN_4362 | 49731 |
| GTCN_1489 | 35673 | TTCN_6342 | 49732 |
| CTCN_2758 | 35674 | ATCN_4363 | 49733 |
| CTCN_2759 | 35675 | TTCN_6343 | 49734 |
| TTCN_2307 | 35676 | TTCN_6344 | 49735 |
| CTCN_2760 | 35677 | CTCN_7503 | 49736 |
| GTCN_1490 | 35678 | ATCN_4364 | 49737 |
| TTCN_2308 | 35679 | TTCN_6345 | 49738 |
| GTCN_1491 | 35680 | ATCN_4365 | 49739 |
| CTCN_2761 | 35681 | TTCN_6346 | 49740 |
| TTCN_2309 | 35682 | CTCN_7504 | 49741 |
| CTCN_2762 | 35683 | GTCN_4069 | 49742 |
| GTCN_1492 | 35684 | GTCN_4070 | 49743 |
| TTCN_2310 | 35685 | CTCN_7505 | 49744 |
| TTCN_2311 | 35686 | CTCN_7506 | 49745 |
| TTCN_2312 | 35687 | GTCN_4071 | 49746 |
| TTCN_2313 | 35688 | CTCN_7507 | 49747 |
| ATCN_1664 | 35689 | TTCN_6347 | 49748 |
| TTCN_2314 | 35690 | TTCN_6348 | 49749 |
| GTCN_1493 | 35691 | TTCN_6349 | 49750 |
| CTCN_2763 | 35692 | ATCN_4366 | 49751 |
| ATCN_1665 | 35693 | GTCN_4072 | 49752 |
| TTCN_2315 | 35694 | TTCN_6350 | 49753 |
| TTCN_2316 | 35695 | CTCN_7508 | 49754 |
| TTCN_2317 | 35696 | TTCN_6351 | 49755 |
| CTCN_2764 | 35697 | TTCN_6352 | 49756 |
| CTCN_2765 | 35698 | GTCN_4073 | 49757 |
| ATCN_1666 | 35699 | TTCN_6353 | 49758 |
| ATCN_1667 | 35700 | GTCN_4074 | 49759 |
| CTCN_2766 | 35701 | TTCN_6354 | 49760 |
| CTCN_2767 | 35702 | TTCN_6355 | 49761 |
| CTCN_2768 | 35703 | ATCN_4367 | 49762 |
| TTCN_2318 | 35704 | TTCN_6356 | 49763 |
| ATCN_1668 | 35705 | CTCN_7509 | 49764 |
| ATCN_1669 | 35706 | GTCN_4075 | 49765 |

FIG. 37 (continued)

| | | | |
|---|---|---|---|
| CTCN_2769 | 35707 | TTCN_6357 | 49766 |
| CTCN_2770 | 35708 | CTCN_7510 | 49767 |
| CTCN_2771 | 35709 | GTCN_4076 | 49768 |
| CTCN_2772 | 35710 | TTCN_6358 | 49769 |
| ATCN_1670 | 35711 | CTCN_7511 | 49770 |
| ATCN_1671 | 35712 | GTCN_4077 | 49771 |
| CTCN_2773 | 35713 | TTCN_6359 | 49772 |
| TTCN_2319 | 35714 | GTCN_4078 | 49773 |
| CTCN_2774 | 35715 | GTCN_4079 | 49774 |
| CTCN_2775 | 35716 | CTCN_7512 | 49775 |
| GTCN_1494 | 35717 | ATCN_4368 | 49776 |
| ATCN_1672 | 35718 | GTCN_4080 | 49777 |
| ATCN_1673 | 35719 | TTCN_6360 | 49778 |
| TTCN_2320 | 35720 | CTCN_7513 | 49779 |
| ATCN_1674 | 35721 | ATCN_4369 | 49780 |
| CTCN_2776 | 35722 | CTCN_7514 | 49781 |
| TTCN_2321 | 35723 | CTCN_7515 | 49782 |
| TTCN_2322 | 35724 | TTCN_6361 | 49783 |
| CTCN_2777 | 35725 | CTCN_7516 | 49784 |
| CTCN_2778 | 35726 | ATCN_4370 | 49785 |
| CTCN_2779 | 35727 | TTCN_6362 | 49786 |
| ATCN_1675 | 35728 | TTCN_6363 | 49787 |
| GTCN_1495 | 35729 | CTCN_7517 | 49788 |
| TTCN_2323 | 35730 | CTCN_7518 | 49789 |
| CTCN_2780 | 35731 | CTCN_7519 | 49790 |
| GTCN_1496 | 35732 | CTCN_7520 | 49791 |
| CTCN_2781 | 35733 | ATCN_4371 | 49792 |
| GTCN_1497 | 35734 | ATCN_4372 | 49793 |
| CTCN_2782 | 35735 | CTCN_7521 | 49794 |
| TTCN_2324 | 35736 | TTCN_6364 | 49795 |
| TTCN_2325 | 35737 | GTCN_4081 | 49796 |
| TTCN_2326 | 35738 | ATCN_4373 | 49797 |
| TTCN_2327 | 35739 | CTCN_7522 | 49798 |
| GTCN_1498 | 35740 | ATCN_4374 | 49799 |
| ATCN_1676 | 35741 | CTCN_7523 | 49800 |
| CTCN_2783 | 35742 | CTCN_7524 | 49801 |
| CTCN_2784 | 35743 | CTCN_7525 | 49802 |
| CTCN_2785 | 35744 | CTCN_7526 | 49803 |
| CTCN_2786 | 35745 | GTCN_4082 | 49804 |
| TTCN_2328 | 35746 | CTCN_7527 | 49805 |
| ATCN_1677 | 35747 | GTCN_4083 | 49806 |
| TTCN_2329 | 35748 | CTCN_7528 | 49807 |
| TTCN_2330 | 35749 | CTCN_7529 | 49808 |

| | | | |
|---|---|---|---|
| CTCN_2787 | 35750 | GTCN_4084 | 49809 |
| CTCN_2788 | 35751 | GTCN_4085 | 49810 |
| CTCN_2789 | 35752 | CTCN_7530 | 49811 |
| ATCN_1678 | 35753 | TTCN_6365 | 49812 |
| ATCN_1679 | 35754 | TTCN_6366 | 49813 |
| CTCN_2790 | 35755 | GTCN_4086 | 49814 |
| CTCN_2791 | 35756 | CTCN_7531 | 49815 |
| TTCN_2331 | 35757 | TTCN_6367 | 49816 |
| CTCN_2792 | 35758 | CTCN_7532 | 49817 |
| GTCN_1499 | 35759 | GTCN_4087 | 49818 |
| GTCN_1500 | 35760 | GTCN_4088 | 49819 |
| GTCN_1501 | 35761 | CTCN_7533 | 49820 |
| CTCN_2793 | 35762 | CTCN_7534 | 49821 |
| CTCN_2794 | 35763 | CTCN_7535 | 49822 |
| TTCN_2332 | 35764 | CTCN_7536 | 49823 |
| ATCN_1680 | 35765 | ATCN_4375 | 49824 |
| CTCN_2795 | 35766 | TTCN_6368 | 49825 |
| TTCN_2333 | 35767 | CTCN_7537 | 49826 |
| CTCN_2796 | 35768 | GTCN_4089 | 49827 |
| TTCN_2334 | 35769 | TTCN_6369 | 49828 |
| ATCN_1681 | 35770 | TTCN_6370 | 49829 |
| TTCN_2335 | 35771 | CTCN_7538 | 49830 |
| GTCN_1502 | 35772 | TTCN_6371 | 49831 |
| TTCN_2336 | 35773 | CTCN_7539 | 49832 |
| CTCN_2797 | 35774 | CTCN_7540 | 49833 |
| TTCN_2337 | 35775 | CTCN_7541 | 49834 |
| CTCN_2798 | 35776 | TTCN_6372 | 49835 |
| ATCN_1682 | 35777 | CTCN_7542 | 49836 |
| ATCN_1683 | 35778 | GTCN_4090 | 49837 |
| ATCN_1684 | 35779 | ATCN_4376 | 49838 |
| GTCN_1503 | 35780 | ATCN_4377 | 49839 |
| TTCN_2338 | 35781 | TTCN_6373 | 49840 |
| CTCN_2799 | 35782 | CTCN_7543 | 49841 |
| CTCN_2800 | 35783 | CTCN_7544 | 49842 |
| CTCN_2801 | 35784 | GTCN_4091 | 49843 |
| CTCN_2802 | 35785 | CTCN_7545 | 49844 |
| TTCN_2339 | 35786 | CTCN_7546 | 49845 |
| CTCN_2803 | 35787 | CTCN_7547 | 49846 |
| ATCN_1685 | 35788 | CTCN_7548 | 49847 |
| ATCN_1686 | 35789 | CTCN_7549 | 49848 |
| TTCN_2340 | 35790 | TTCN_6374 | 49849 |
| CTCN_2804 | 35791 | TTCN_6375 | 49850 |
| GTCN_1504 | 35792 | ATCN_4378 | 49851 |

FIG. 37 (continued)

| | | | |
|---|---|---|---|
| TTCN_2341 | 35793 | ATCN_4379 | 49852 |
| CTCN_2805 | 35794 | CTCN_7550 | 49853 |
| GTCN_1505 | 35795 | GTCN_4092 | 49854 |
| TTCN_2342 | 35796 | CTCN_7551 | 49855 |
| CTCN_2806 | 35797 | CTCN_7552 | 49856 |
| ATCN_1687 | 35798 | ATCN_4380 | 49857 |
| CTCN_2807 | 35799 | CTCN_7553 | 49858 |
| ATCN_1688 | 35800 | CTCN_7554 | 49859 |
| CTCN_2808 | 35801 | ATCN_4381 | 49860 |
| GTCN_1506 | 35802 | ATCN_4382 | 49861 |
| TTCN_2343 | 35803 | CTCN_7555 | 49862 |
| GTCN_1507 | 35804 | ATCN_4383 | 49863 |
| TTCN_2344 | 35805 | ATCN_4384 | 49864 |
| CTCN_2809 | 35806 | CTCN_7556 | 49865 |
| CTCN_2810 | 35807 | GTCN_4093 | 49866 |
| GTCN_1508 | 35808 | TTCN_6376 | 49867 |
| ATCN_1689 | 35809 | GTCN_4094 | 49868 |
| GTCN_1509 | 35810 | CTCN_7557 | 49869 |
| ATCN_1690 | 35811 | TTCN_6377 | 49870 |
| GTCN_1510 | 35812 | GTCN_4095 | 49871 |
| CTCN_2811 | 35813 | CTCN_7558 | 49872 |
| GTCN_1511 | 35814 | GTCN_4096 | 49873 |
| GTCN_1512 | 35815 | TTCN_6378 | 49874 |
| ATCN_1691 | 35816 | ATCN_4385 | 49875 |
| TTCN_2345 | 35817 | TTCN_6379 | 49876 |
| GTCN_1513 | 35818 | CTCN_7559 | 49877 |
| ATCN_1692 | 35819 | TTCN_6380 | 49878 |
| ATCN_1693 | 35820 | CTCN_7560 | 49879 |
| CTCN_2812 | 35821 | CTCN_7561 | 49880 |
| CTCN_2813 | 35822 | GTCN_4097 | 49881 |
| TTCN_2346 | 35823 | CTCN_7562 | 49882 |
| TTCN_2347 | 35824 | ATCN_4386 | 49883 |
| CTCN_2814 | 35825 | CTCN_7563 | 49884 |
| CTCN_2815 | 35826 | TTCN_6381 | 49885 |
| CTCN_2816 | 35827 | TTCN_6382 | 49886 |
| CTCN_2817 | 35828 | CTCN_7564 | 49887 |
| ATCN_1694 | 35829 | GTCN_4098 | 49888 |
| TTCN_2348 | 35830 | GTCN_4099 | 49889 |
| GTCN_1514 | 35831 | GTCN_4100 | 49890 |
| CTCN_2818 | 35832 | TTCN_6383 | 49891 |
| CTCN_2819 | 35833 | GTCN_4101 | 49892 |
| CTCN_2820 | 35834 | ATCN_4387 | 49893 |
| GTCN_1515 | 35835 | CTCN_7565 | 49894 |

| | | | |
|---|---|---|---|
| CTCN_2821 | 35836 | GTCN_4102 | 49895 |
| ATCN_1695 | 35837 | TTCN_6384 | 49896 |
| CTCN_2822 | 35838 | CTCN_7566 | 49897 |
| ATCN_1696 | 35839 | GTCN_4103 | 49898 |
| ATCN_1697 | 35840 | GTCN_4104 | 49899 |
| TTCN_2349 | 35841 | TTCN_6385 | 49900 |
| ATCN_1698 | 35842 | CTCN_7567 | 49901 |
| TTCN_2350 | 35843 | GTCN_4105 | 49902 |
| ATCN_1699 | 35844 | TTCN_6386 | 49903 |
| ATCN_1700 | 35845 | CTCN_7568 | 49904 |
| ATCN_1701 | 35846 | GTCN_4106 | 49905 |
| TTCN_2351 | 35847 | GTCN_4107 | 49906 |
| TTCN_2352 | 35848 | ATCN_4388 | 49907 |
| GTCN_1516 | 35849 | CTCN_7569 | 49908 |
| GTCN_1517 | 35850 | GTCN_4108 | 49909 |
| TTCN_2353 | 35851 | CTCN_7570 | 49910 |
| TTCN_2354 | 35852 | CTCN_7571 | 49911 |
| GTCN_1518 | 35853 | GTCN_4109 | 49912 |
| TTCN_2355 | 35854 | TTCN_6387 | 49913 |
| TTCN_2356 | 35855 | TTCN_6388 | 49914 |
| GTCN_1519 | 35856 | TTCN_6389 | 49915 |
| TTCN_2357 | 35857 | GTCN_4110 | 49916 |
| TTCN_2358 | 35858 | CTCN_7572 | 49917 |
| GTCN_1520 | 35859 | ATCN_4389 | 49918 |
| TTCN_2359 | 35860 | TTCN_6390 | 49919 |
| TTCN_2360 | 35861 | TTCN_6391 | 49920 |
| TTCN_2361 | 35862 | ATCN_4390 | 49921 |
| CTCN_2823 | 35863 | TTCN_6392 | 49922 |
| CTCN_2824 | 35864 | TTCN_6393 | 49923 |
| CTCN_2825 | 35865 | TTCN_6394 | 49924 |
| CTCN_2826 | 35866 | GTCN_4111 | 49925 |
| TTCN_2362 | 35867 | CTCN_7573 | 49926 |
| TTCN_2363 | 35868 | CTCN_7574 | 49927 |
| TTCN_2364 | 35869 | TTCN_6395 | 49928 |
| ATCN_1702 | 35870 | ATCN_4391 | 49929 |
| GTCN_1521 | 35871 | ATCN_4392 | 49930 |
| CTCN_2827 | 35872 | CTCN_7575 | 49931 |
| CTCN_2828 | 35873 | CTCN_7576 | 49932 |
| ATCN_1703 | 35874 | TTCN_6396 | 49933 |
| ATCN_1704 | 35875 | CTCN_7577 | 49934 |
| ATCN_1705 | 35876 | TTCN_6397 | 49935 |
| CTCN_2829 | 35877 | CTCN_7578 | 49936 |
| TTCN_2365 | 35878 | TTCN_6398 | 49937 |

FIG. 37 (continued)

| | | | |
|---|---|---|---|
| CTCN_2830 | 35879 | CTCN_7579 | 49938 |
| GTCN_1522 | 35880 | ATCN_4393 | 49939 |
| ATCN_1706 | 35881 | ATCN_4394 | 49940 |
| CTCN_2831 | 35882 | GTCN_4112 | 49941 |
| ATCN_1707 | 35883 | TTCN_6399 | 49942 |
| CTCN_2832 | 35884 | CTCN_7580 | 49943 |
| TTCN_2366 | 35885 | CTCN_7581 | 49944 |
| CTCN_2833 | 35886 | CTCN_7582 | 49945 |
| ATCN_1708 | 35887 | GTCN_4113 | 49946 |
| TTCN_2367 | 35888 | ATCN_4395 | 49947 |
| ATCN_1709 | 35889 | ATCN_4396 | 49948 |
| TTCN_2368 | 35890 | ATCN_4397 | 49949 |
| CTCN_2834 | 35891 | ATCN_4398 | 49950 |
| CTCN_2835 | 35892 | ATCN_4399 | 49951 |
| CTCN_2836 | 35893 | TTCN_6400 | 49952 |
| GTCN_1523 | 35894 | CTCN_7583 | 49953 |
| CTCN_2837 | 35895 | ATCN_4400 | 49954 |
| CTCN_2838 | 35896 | ATCN_4401 | 49955 |
| ATCN_1710 | 35897 | CTCN_7584 | 49956 |
| TTCN_2369 | 35898 | CTCN_7585 | 49957 |
| CTCN_2839 | 35899 | CTCN_7586 | 49958 |
| GTCN_1524 | 35900 | GTCN_4114 | 49959 |
| GTCN_1525 | 35901 | GTCN_4115 | 49960 |
| CTCN_2840 | 35902 | CTCN_7587 | 49961 |
| TTCN_2370 | 35903 | CTCN_7588 | 49962 |
| ATCN_1711 | 35904 | GTCN_4116 | 49963 |
| GTCN_1526 | 35905 | CTCN_7589 | 49964 |
| CTCN_2841 | 35906 | ATCN_4402 | 49965 |
| GTCN_1527 | 35907 | CTCN_7590 | 49966 |
| TTCN_2371 | 35908 | CTCN_7591 | 49967 |
| ATCN_1712 | 35909 | CTCN_7592 | 49968 |
| CTCN_2842 | 35910 | CTCN_7593 | 49969 |
| TTCN_2372 | 35911 | GTCN_4117 | 49970 |
| TTCN_2373 | 35912 | CTCN_7594 | 49971 |
| TTCN_2374 | 35913 | CTCN_7595 | 49972 |
| ATCN_1713 | 35914 | TTCN_6401 | 49973 |
| CTCN_2843 | 35915 | GTCN_4118 | 49974 |
| ATCN_1714 | 35916 | ATCN_4403 | 49975 |
| TTCN_2375 | 35917 | CTCN_7596 | 49976 |
| CTCN_2844 | 35918 | CTCN_7597 | 49977 |
| GTCN_1528 | 35919 | GTCN_4119 | 49978 |
| GTCN_1529 | 35920 | CTCN_7598 | 49979 |
| TTCN_2376 | 35921 | ATCN_4404 | 49980 |

| | | | |
|---|---|---|---|
| ATCN_1715 | 35922 | GTCN_4120 | 49981 |
| TTCN_2377 | 35923 | CTCN_7599 | 49982 |
| CTCN_2845 | 35924 | TTCN_6402 | 49983 |
| GTCN_1530 | 35925 | CTCN_7600 | 49984 |
| TTCN_2378 | 35926 | CTCN_7601 | 49985 |
| TTCN_2379 | 35927 | CTCN_7602 | 49986 |
| CTCN_2846 | 35928 | ATCN_4405 | 49987 |
| CTCN_2847 | 35929 | CTCN_7603 | 49988 |
| GTCN_1531 | 35930 | CTCN_7604 | 49989 |
| TTCN_2380 | 35931 | CTCN_7605 | 49990 |
| GTCN_1532 | 35932 | ATCN_4406 | 49991 |
| GTCN_1533 | 35933 | ATCN_4407 | 49992 |
| CTCN_2848 | 35934 | ATCN_4408 | 49993 |
| TTCN_2381 | 35935 | CTCN_7606 | 49994 |
| ATCN_1716 | 35936 | TTCN_6403 | 49995 |
| TTCN_2382 | 35937 | CTCN_7607 | 49996 |
| TTCN_2383 | 35938 | GTCN_4121 | 49997 |
| TTCN_2384 | 35939 | GTCN_4122 | 49998 |
| GTCN_1534 | 35940 | CTCN_7608 | 49999 |
| GTCN_1535 | 35941 | GTCN_4123 | 50000 |
| TTCN_2385 | 35942 | CTCN_7609 | 50001 |
| GTCN_1536 | 35943 | TTCN_6404 | 50002 |
| CTCN_2849 | 35944 | CTCN_7610 | 50003 |
| CTCN_2850 | 35945 | TTCN_6405 | 50004 |
| CTCN_2851 | 35946 | ATCN_4409 | 50005 |
| GTCN_1537 | 35947 | ATCN_4410 | 50006 |
| TTCN_2386 | 35948 | CTCN_7611 | 50007 |
| CTCN_2852 | 35949 | CTCN_7612 | 50008 |
| CTCN_2853 | 35950 | TTCN_6406 | 50009 |
| CTCN_2854 | 35951 | TTCN_6407 | 50010 |
| CTCN_2855 | 35952 | ATCN_4411 | 50011 |
| GTCN_1538 | 35953 | CTCN_7613 | 50012 |
| GTCN_1539 | 35954 | CTCN_7614 | 50013 |
| CTCN_2856 | 35955 | TTCN_6408 | 50014 |
| GTCN_1540 | 35956 | ATCN_4412 | 50015 |
| CTCN_2857 | 35957 | TTCN_6409 | 50016 |
| CTCN_2858 | 35958 | CTCN_7615 | 50017 |
| CTCN_2859 | 35959 | TTCN_6410 | 50018 |
| TTCN_2387 | 35960 | ATCN_4413 | 50019 |
| TTCN_2388 | 35961 | ATCN_4414 | 50020 |
| CTCN_2860 | 35962 | TTCN_6411 | 50021 |
| GTCN_1541 | 35963 | TTCN_6412 | 50022 |
| CTCN_2861 | 35964 | TTCN_6413 | 50023 |

FIG. 37 (continued)

| | | | |
|---|---|---|---|
| CTCN_2862 | 35965 | CTCN_7616 | 50024 |
| CTCN_2863 | 35966 | CTCN_7617 | 50025 |
| CTCN_2864 | 35967 | CTCN_7618 | 50026 |
| CTCN_2865 | 35968 | CTCN_7619 | 50027 |
| ATCN_1717 | 35969 | TTCN_6414 | 50028 |
| CTCN_2866 | 35970 | CTCN_7620 | 50029 |
| TTCN_2389 | 35971 | CTCN_7621 | 50030 |
| GTCN_1542 | 35972 | TTCN_6415 | 50031 |
| GTCN_1543 | 35973 | CTCN_7622 | 50032 |
| TTCN_2390 | 35974 | TTCN_6416 | 50033 |
| ATCN_1718 | 35975 | ATCN_4415 | 50034 |
| TTCN_2391 | 35976 | CTCN_7623 | 50035 |
| CTCN_2867 | 35977 | CTCN_7624 | 50036 |
| GTCN_1544 | 35978 | TTCN_6417 | 50037 |
| CTCN_2868 | 35979 | TTCN_6418 | 50038 |
| TTCN_2392 | 35980 | GTCN_4124 | 50039 |
| TTCN_2393 | 35981 | CTCN_7625 | 50040 |
| TTCN_2394 | 35982 | TTCN_6419 | 50041 |
| TTCN_2395 | 35983 | ATCN_4416 | 50042 |
| GTCN_1545 | 35984 | TTCN_6420 | 50043 |
| TTCN_2396 | 35985 | CTCN_7626 | 50044 |
| CTCN_2869 | 35986 | TTCN_6421 | 50045 |
| CTCN_2870 | 35987 | GTCN_4125 | 50046 |
| GTCN_1546 | 35988 | ATCN_4417 | 50047 |
| TTCN_2397 | 35989 | ATCN_4418 | 50048 |
| CTCN_2871 | 35990 | TTCN_6422 | 50049 |
| GTCN_1547 | 35991 | TTCN_6423 | 50050 |
| TTCN_2398 | 35992 | ATCN_4419 | 50051 |
| TTCN_2399 | 35993 | GTCN_4126 | 50052 |
| ATCN_1719 | 35994 | CTCN_7627 | 50053 |
| CTCN_2872 | 35995 | CTCN_7628 | 50054 |
| GTCN_1548 | 35996 | GTCN_4127 | 50055 |
| GTCN_1549 | 35997 | GTCN_4128 | 50056 |
| TTCN_2400 | 35998 | ATCN_4420 | 50057 |
| TTCN_2401 | 35999 | TTCN_6424 | 50058 |
| CTCN_2873 | 36000 | GTCN_4129 | 50059 |
| CTCN_2874 | 36001 | CTCN_7629 | 50060 |
| CTCN_2875 | 36002 | CTCN_7630 | 50061 |
| CTCN_2876 | 36003 | ATCN_4421 | 50062 |
| ATCN_1720 | 36004 | CTCN_7631 | 50063 |
| ATCN_1721 | 36005 | TTCN_6425 | 50064 |
| TTCN_2402 | 36006 | TTCN_6426 | 50065 |
| CTCN_2877 | 36007 | GTCN_4130 | 50066 |

| | | | |
|---|---|---|---|
| GTCN_1550 | 36008 | ATCN_4422 | 50067 |
| CTCN_2878 | 36009 | TTCN_6427 | 50068 |
| TTCN_2403 | 36010 | TTCN_6428 | 50069 |
| TTCN_2404 | 36011 | TTCN_6429 | 50070 |
| CTCN_2879 | 36012 | CTCN_7632 | 50071 |
| GTCN_1551 | 36013 | CTCN_7633 | 50072 |
| ATCN_1722 | 36014 | TTCN_6430 | 50073 |
| GTCN_1552 | 36015 | ATCN_4423 | 50074 |
| GTCN_1553 | 36016 | TTCN_6431 | 50075 |
| TTCN_2405 | 36017 | GTCN_4131 | 50076 |
| CTCN_2880 | 36018 | ATCN_4424 | 50077 |
| CTCN_2881 | 36019 | CTCN_7634 | 50078 |
| TTCN_2406 | 36020 | TTCN_6432 | 50079 |
| GTCN_1554 | 36021 | ATCN_4425 | 50080 |
| CTCN_2882 | 36022 | ATCN_4426 | 50081 |
| CTCN_2883 | 36023 | TTCN_6433 | 50082 |
| CTCN_2884 | 36024 | TTCN_6434 | 50083 |
| TTCN_2407 | 36025 | ATCN_4427 | 50084 |
| ATCN_1723 | 36026 | CTCN_7635 | 50085 |
| CTCN_2885 | 36027 | TTCN_6435 | 50086 |
| TTCN_2408 | 36028 | CTCN_7636 | 50087 |
| TTCN_2409 | 36029 | CTCN_7637 | 50088 |
| TTCN_2410 | 36030 | CTCN_7638 | 50089 |
| TTCN_2411 | 36031 | TTCN_6436 | 50090 |
| GTCN_1555 | 36032 | CTCN_7639 | 50091 |
| CTCN_2886 | 36033 | CTCN_7640 | 50092 |
| GTCN_1556 | 36034 | TTCN_6437 | 50093 |
| CTCN_2887 | 36035 | TTCN_6438 | 50094 |
| CTCN_2888 | 36036 | CTCN_7641 | 50095 |
| GTCN_1557 | 36037 | CTCN_7642 | 50096 |
| TTCN_2412 | 36038 | CTCN_7643 | 50097 |
| ATCN_1724 | 36039 | ATCN_4428 | 50098 |
| GTCN_1558 | 36040 | GTCN_4132 | 50099 |
| CTCN_2889 | 36041 | ATCN_4429 | 50100 |
| TTCN_2413 | 36042 | ATCN_4430 | 50101 |
| GTCN_1559 | 36043 | CTCN_7644 | 50102 |
| CTCN_2890 | 36044 | ATCN_4431 | 50103 |
| GTCN_1560 | 36045 | ATCN_4432 | 50104 |
| TTCN_2414 | 36046 | GTCN_4133 | 50105 |
| ATCN_1725 | 36047 | CTCN_7645 | 50106 |
| TTCN_2415 | 36048 | GTCN_4134 | 50107 |
| CTCN_2891 | 36049 | ATCN_4433 | 50108 |
| ATCN_1726 | 36050 | ATCN_4434 | 50109 |

FIG. 37 (continued)

| | | | |
|---|---|---|---|
| TTCN_2416 | 36051 | GTCN_4135 | 50110 |
| CTCN_2892 | 36052 | TTCN_6439 | 50111 |
| TTCN_2417 | 36053 | CTCN_7646 | 50112 |
| CTCN_2893 | 36054 | GTCN_4136 | 50113 |
| ATCN_1727 | 36055 | CTCN_7647 | 50114 |
| CTCN_2894 | 36056 | TTCN_6440 | 50115 |
| CTCN_2895 | 36057 | TTCN_6441 | 50116 |
| TTCN_2418 | 36058 | GTCN_4137 | 50117 |
| CTCN_2896 | 36059 | TTCN_6442 | 50118 |
| CTCN_2897 | 36060 | TTCN_6443 | 50119 |
| ATCN_1728 | 36061 | TTCN_6444 | 50120 |
| CTCN_2898 | 36062 | CTCN_7648 | 50121 |
| CTCN_2899 | 36063 | TTCN_6445 | 50122 |
| CTCN_2900 | 36064 | CTCN_7649 | 50123 |
| TTCN_2419 | 36065 | TTCN_6446 | 50124 |
| GTCN_1561 | 36066 | CTCN_7650 | 50125 |
| CTCN_2901 | 36067 | ATCN_4435 | 50126 |
| CTCN_2902 | 36068 | GTCN_4138 | 50127 |
| CTCN_2903 | 36069 | TTCN_6447 | 50128 |
| TTCN_2420 | 36070 | GTCN_4139 | 50129 |
| CTCN_2904 | 36071 | CTCN_7651 | 50130 |
| GTCN_1562 | 36072 | CTCN_7652 | 50131 |
| GTCN_1563 | 36073 | TTCN_6448 | 50132 |
| CTCN_2905 | 36074 | GTCN_4140 | 50133 |
| CTCN_2906 | 36075 | TTCN_6449 | 50134 |
| GTCN_1564 | 36076 | CTCN_7653 | 50135 |
| ATCN_1729 | 36077 | TTCN_6450 | 50136 |
| ATCN_1730 | 36078 | CTCN_7654 | 50137 |
| CTCN_2907 | 36079 | ATCN_4436 | 50138 |
| CTCN_2908 | 36080 | CTCN_7655 | 50139 |
| CTCN_2909 | 36081 | TTCN_6451 | 50140 |
| GTCN_1565 | 36082 | CTCN_7656 | 50141 |
| CTCN_2910 | 36083 | TTCN_6452 | 50142 |
| CTCN_2911 | 36084 | CTCN_7657 | 50143 |
| TTCN_2421 | 36085 | GTCN_4141 | 50144 |
| CTCN_2912 | 36086 | GTCN_4142 | 50145 |
| TTCN_2422 | 36087 | TTCN_6453 | 50146 |
| GTCN_1566 | 36088 | ATCN_4437 | 50147 |
| CTCN_2913 | 36089 | TTCN_6454 | 50148 |
| GTCN_1567 | 36090 | GTCN_4143 | 50149 |
| CTCN_2914 | 36091 | TTCN_6455 | 50150 |
| ATCN_1731 | 36092 | TTCN_6456 | 50151 |
| ATCN_1732 | 36093 | GTCN_4144 | 50152 |
| TTCN_2423 | 36094 | CTCN_7658 | 50153 |
| ATCN_1733 | 36095 | GTCN_4145 | 50154 |
| CTCN_2915 | 36096 | TTCN_6457 | 50155 |
| CTCN_2916 | 36097 | CTCN_7659 | 50156 |
| CTCN_2917 | 36098 | CTCN_7660 | 50157 |
| TTCN_2424 | 36099 | TTCN_6458 | 50158 |
| TTCN_2425 | 36100 | TTCN_6459 | 50159 |
| TTCN_2426 | 36101 | TTCN_6460 | 50160 |
| TTCN_2427 | 36102 | TTCN_6461 | 50161 |
| TTCN_2428 | 36103 | GTCN_4146 | 50162 |
| CTCN_2918 | 36104 | CTCN_7661 | 50163 |
| CTCN_2919 | 36105 | CTCN_7662 | 50164 |
| ATCN_1734 | 36106 | TTCN_6462 | 50165 |
| GTCN_1568 | 36107 | CTCN_7663 | 50166 |
| GTCN_1569 | 36108 | ATCN_4438 | 50167 |
| CTCN_2920 | 36109 | CTCN_7664 | 50168 |
| GTCN_1570 | 36110 | CTCN_7665 | 50169 |
| CTCN_2921 | 36111 | TTCN_6463 | 50170 |
| CTCN_2922 | 36112 | CTCN_7666 | 50171 |
| CTCN_2923 | 36113 | TTCN_6464 | 50172 |
| CTCN_2924 | 36114 | TTCN_6465 | 50173 |
| CTCN_2925 | 36115 | CTCN_7667 | 50174 |
| TTCN_2429 | 36116 | GTCN_4147 | 50175 |
| GTCN_1571 | 36117 | GTCN_4148 | 50176 |
| GTCN_1572 | 36118 | TTCN_6466 | 50177 |
| CTCN_2926 | 36119 | CTCN_7668 | 50178 |
| CTCN_2927 | 36120 | ATCN_4439 | 50179 |
| GTCN_1573 | 36121 | CTCN_7669 | 50180 |
| CTCN_2928 | 36122 | CTCN_7670 | 50181 |
| TTCN_2430 | 36123 | GTCN_4149 | 50182 |
| ATCN_1735 | 36124 | ATCN_4440 | 50183 |
| CTCN_2929 | 36125 | ATCN_4441 | 50184 |
| CTCN_2930 | 36126 | CTCN_7671 | 50185 |
| CTCN_2931 | 36127 | ATCN_4442 | 50186 |
| GTCN_1574 | 36128 | CTCN_7672 | 50187 |
| GTCN_1575 | 36129 | ATCN_4443 | 50188 |
| CTCN_2932 | 36130 | GTCN_4150 | 50189 |
| GTCN_1576 | 36131 | CTCN_7673 | 50190 |
| GTCN_1577 | 36132 | CTCN_7674 | 50191 |
| CTCN_2933 | 36133 | CTCN_7675 | 50192 |
| ATCN_1736 | 36134 | GTCN_4151 | 50193 |
| ATCN_1737 | 36135 | TTCN_6467 | 50194 |
| TTCN_2431 | 36136 | ATCN_4444 | 50195 |

FIG. 37 (continued)

| | | | |
|---|---|---|---|
| TTCN_2432 | 36137 | TTCN_6468 | 50196 |
| CTCN_2934 | 36138 | CTCN_7676 | 50197 |
| TTCN_2433 | 36139 | CTCN_7677 | 50198 |
| ATCN_1738 | 36140 | ATCN_4445 | 50199 |
| GTCN_1578 | 36141 | TTCN_6469 | 50200 |
| CTCN_2935 | 36142 | TTCN_6470 | 50201 |
| TTCN_2434 | 36143 | CTCN_7678 | 50202 |
| CTCN_2936 | 36144 | GTCN_4152 | 50203 |
| TTCN_2435 | 36145 | CTCN_7679 | 50204 |
| CTCN_2937 | 36146 | CTCN_7680 | 50205 |
| CTCN_2938 | 36147 | ATCN_4446 | 50206 |
| CTCN_2939 | 36148 | CTCN_7681 | 50207 |
| TTCN_2436 | 36149 | TTCN_6471 | 50208 |
| TTCN_2437 | 36150 | TTCN_6472 | 50209 |
| CTCN_2940 | 36151 | ATCN_4447 | 50210 |
| TTCN_2438 | 36152 | TTCN_6473 | 50211 |
| CTCN_2941 | 36153 | TTCN_6474 | 50212 |
| GTCN_1579 | 36154 | ATCN_4448 | 50213 |
| CTCN_2942 | 36155 | ATCN_4449 | 50214 |
| CTCN_2943 | 36156 | TTCN_6475 | 50215 |
| GTCN_1580 | 36157 | ATCN_4450 | 50216 |
| CTCN_2944 | 36158 | ATCN_4451 | 50217 |
| GTCN_1581 | 36159 | ATCN_4452 | 50218 |
| CTCN_2945 | 36160 | GTCN_4153 | 50219 |
| ATCN_1739 | 36161 | ATCN_4453 | 50220 |
| ATCN_1740 | 36162 | ATCN_4454 | 50221 |
| CTCN_2946 | 36163 | CTCN_7682 | 50222 |
| TTCN_2439 | 36164 | TTCN_6476 | 50223 |
| GTCN_1582 | 36165 | CTCN_7683 | 50224 |
| GTCN_1583 | 36166 | ATCN_4455 | 50225 |
| TTCN_2440 | 36167 | TTCN_6477 | 50226 |
| CTCN_2947 | 36168 | GTCN_4154 | 50227 |
| TTCN_2441 | 36169 | GTCN_4155 | 50228 |
| TTCN_2442 | 36170 | GTCN_4156 | 50229 |
| GTCN_1584 | 36171 | ATCN_4456 | 50230 |
| TTCN_2443 | 36172 | TTCN_6478 | 50231 |
| ATCN_1741 | 36173 | TTCN_6479 | 50232 |
| CTCN_2948 | 36174 | TTCN_6480 | 50233 |
| CTCN_2949 | 36175 | GTCN_4157 | 50234 |
| TTCN_2444 | 36176 | TTCN_6481 | 50235 |
| ATCN_1742 | 36177 | TTCN_6482 | 50236 |
| CTCN_2950 | 36178 | TTCN_6483 | 50237 |
| CTCN_2951 | 36179 | TTCN_6484 | 50238 |

| | | | |
|---|---|---|---|
| CTCN_2952 | 36180 | TTCN_6485 | 50239 |
| CTCN_2953 | 36181 | TTCN_6486 | 50240 |
| CTCN_2954 | 36182 | CTCN_7684 | 50241 |
| CTCN_2955 | 36183 | GTCN_4158 | 50242 |
| ATCN_1743 | 36184 | GTCN_4159 | 50243 |
| ATCN_1744 | 36185 | ATCN_4457 | 50244 |
| GTCN_1585 | 36186 | ATCN_4458 | 50245 |
| CTCN_2956 | 36187 | ATCN_4459 | 50246 |
| CTCN_2957 | 36188 | CTCN_7685 | 50247 |
| CTCN_2958 | 36189 | CTCN_7686 | 50248 |
| TTCN_2445 | 36190 | CTCN_7687 | 50249 |
| ATCN_1745 | 36191 | GTCN_4160 | 50250 |
| TTCN_2446 | 36192 | CTCN_7688 | 50251 |
| CTCN_2959 | 36193 | CTCN_7689 | 50252 |
| CTCN_2960 | 36194 | CTCN_7690 | 50253 |
| ATCN_1746 | 36195 | CTCN_7691 | 50254 |
| ATCN_1747 | 36196 | ATCN_4460 | 50255 |
| GTCN_1586 | 36197 | ATCN_4461 | 50256 |
| TTCN_2447 | 36198 | CTCN_7692 | 50257 |
| ATCN_1748 | 36199 | TTCN_6487 | 50258 |
| ATCN_1749 | 36200 | TTCN_6488 | 50259 |
| CTCN_2961 | 36201 | ATCN_4462 | 50260 |
| ATCN_1750 | 36202 | CTCN_7693 | 50261 |
| ATCN_1751 | 36203 | TTCN_6489 | 50262 |
| CTCN_2962 | 36204 | ATCN_4463 | 50263 |
| CTCN_2963 | 36205 | GTCN_4161 | 50264 |
| TTCN_2448 | 36206 | CTCN_7694 | 50265 |
| CTCN_2964 | 36207 | ATCN_4464 | 50266 |
| CTCN_2965 | 36208 | GTCN_4162 | 50267 |
| CTCN_2966 | 36209 | ATCN_4465 | 50268 |
| GTCN_1587 | 36210 | GTCN_4163 | 50269 |
| CTCN_2967 | 36211 | CTCN_7695 | 50270 |
| CTCN_2968 | 36212 | ATCN_4466 | 50271 |
| CTCN_2969 | 36213 | ATCN_4467 | 50272 |
| CTCN_2970 | 36214 | ATCN_4468 | 50273 |
| TTCN_2449 | 36215 | GTCN_4164 | 50274 |
| TTCN_2450 | 36216 | TTCN_6490 | 50275 |
| CTCN_2971 | 36217 | ATCN_4469 | 50276 |
| CTCN_2972 | 36218 | CTCN_7696 | 50277 |
| ATCN_1752 | 36219 | TTCN_6491 | 50278 |
| ATCN_1753 | 36220 | ATCN_4470 | 50279 |
| ATCN_1754 | 36221 | CTCN_7697 | 50280 |
| CTCN_2973 | 36222 | GTCN_4165 | 50281 |

FIG. 37 (continued)

| | | | |
|---|---|---|---|
| GTCN_1588 | 36223 | TTCN_6492 | 50282 |
| TTCN_2451 | 36224 | CTCN_7698 | 50283 |
| TTCN_2452 | 36225 | CTCN_7699 | 50284 |
| ATCN_1755 | 36226 | CTCN_7700 | 50285 |
| CTCN_2974 | 36227 | CTCN_7701 | 50286 |
| GTCN_1589 | 36228 | CTCN_7702 | 50287 |
| TTCN_2453 | 36229 | ATCN_4471 | 50288 |
| CTCN_2975 | 36230 | TTCN_6493 | 50289 |
| GTCN_1590 | 36231 | TTCN_6494 | 50290 |
| CTCN_2976 | 36232 | GTCN_4166 | 50291 |
| CTCN_2977 | 36233 | TTCN_6495 | 50292 |
| GTCN_1591 | 36234 | GTCN_4167 | 50293 |
| CTCN_2978 | 36235 | ATCN_4472 | 50294 |
| CTCN_2979 | 36236 | CTCN_7703 | 50295 |
| CTCN_2980 | 36237 | CTCN_7704 | 50296 |
| CTCN_2981 | 36238 | CTCN_7705 | 50297 |
| TTCN_2454 | 36239 | CTCN_7706 | 50298 |
| TTCN_2455 | 36240 | CTCN_7707 | 50299 |
| CTCN_2982 | 36241 | GTCN_4168 | 50300 |
| CTCN_2983 | 36242 | TTCN_6496 | 50301 |
| CTCN_2984 | 36243 | ATCN_4473 | 50302 |
| GTCN_1592 | 36244 | GTCN_4169 | 50303 |
| TTCN_2456 | 36245 | TTCN_6497 | 50304 |
| GTCN_1593 | 36246 | CTCN_7708 | 50305 |
| TTCN_2457 | 36247 | GTCN_4170 | 50306 |
| TTCN_2458 | 36248 | CTCN_7709 | 50307 |
| CTCN_2985 | 36249 | CTCN_7710 | 50308 |
| CTCN_2986 | 36250 | CTCN_7711 | 50309 |
| CTCN_2987 | 36251 | ATCN_4474 | 50310 |
| TTCN_2459 | 36252 | CTCN_7712 | 50311 |
| TTCN_2460 | 36253 | GTCN_4171 | 50312 |
| CTCN_2988 | 36254 | TTCN_6498 | 50313 |
| CTCN_2989 | 36255 | CTCN_7713 | 50314 |
| CTCN_2990 | 36256 | ATCN_4475 | 50315 |
| ATCN_1756 | 36257 | ATCN_4476 | 50316 |
| TTCN_2461 | 36258 | TTCN_6499 | 50317 |
| TTCN_2462 | 36259 | TTCN_6500 | 50318 |
| TTCN_2463 | 36260 | ATCN_4477 | 50319 |
| CTCN_2991 | 36261 | TTCN_6501 | 50320 |
| CTCN_2992 | 36262 | CTCN_7714 | 50321 |
| TTCN_2464 | 36263 | CTCN_7715 | 50322 |
| CTCN_2993 | 36264 | CTCN_7716 | 50323 |
| CTCN_2994 | 36265 | GTCN_4172 | 50324 |

| | | | |
|---|---|---|---|
| TTCN_2465 | 36266 | CTCN_7717 | 50325 |
| GTCN_1594 | 36267 | GTCN_4173 | 50326 |
| CTCN_2995 | 36268 | CTCN_7718 | 50327 |
| ATCN_1757 | 36269 | CTCN_7719 | 50328 |
| ATCN_1758 | 36270 | GTCN_4174 | 50329 |
| CTCN_2996 | 36271 | CTCN_7720 | 50330 |
| ATCN_1759 | 36272 | TTCN_6502 | 50331 |
| GTCN_1595 | 36273 | GTCN_4175 | 50332 |
| GTCN_1596 | 36274 | CTCN_7721 | 50333 |
| CTCN_2997 | 36275 | CTCN_7722 | 50334 |
| ATCN_1760 | 36276 | GTCN_4176 | 50335 |
| CTCN_2998 | 36277 | CTCN_7723 | 50336 |
| CTCN_2999 | 36278 | CTCN_7724 | 50337 |
| CTCN_3000 | 36279 | CTCN_7725 | 50338 |
| GTCN_1597 | 36280 | TTCN_6503 | 50339 |
| CTCN_3001 | 36281 | TTCN_6504 | 50340 |
| ATCN_1761 | 36282 | CTCN_7726 | 50341 |
| GTCN_1598 | 36283 | GTCN_4177 | 50342 |
| CTCN_3002 | 36284 | GTCN_4178 | 50343 |
| TTCN_2466 | 36285 | TTCN_6505 | 50344 |
| ATCN_1762 | 36286 | CTCN_7727 | 50345 |
| CTCN_3003 | 36287 | GTCN_4179 | 50346 |
| TTCN_2467 | 36288 | GTCN_4180 | 50347 |
| ATCN_1763 | 36289 | ATCN_4478 | 50348 |
| ATCN_1764 | 36290 | TTCN_6506 | 50349 |
| ATCN_1765 | 36291 | ATCN_4479 | 50350 |
| ATCN_1766 | 36292 | GTCN_4181 | 50351 |
| TTCN_2468 | 36293 | CTCN_7728 | 50352 |
| ATCN_1767 | 36294 | CTCN_7729 | 50353 |
| TTCN_2469 | 36295 | TTCN_6507 | 50354 |
| CTCN_3004 | 36296 | CTCN_7730 | 50355 |
| CTCN_3005 | 36297 | TTCN_6508 | 50356 |
| CTCN_3006 | 36298 | CTCN_7731 | 50357 |
| ATCN_1768 | 36299 | CTCN_7732 | 50358 |
| ATCN_1769 | 36300 | CTCN_7733 | 50359 |
| ATCN_1770 | 36301 | TTCN_6509 | 50360 |
| ATCN_1771 | 36302 | CTCN_7734 | 50361 |
| GTCN_1599 | 36303 | CTCN_7735 | 50362 |
| CTCN_3007 | 36304 | CTCN_7736 | 50363 |
| TTCN_2470 | 36305 | GTCN_4182 | 50364 |
| GTCN_1600 | 36306 | TTCN_6510 | 50365 |
| CTCN_3008 | 36307 | CTCN_7737 | 50366 |
| GTCN_1601 | 36308 | TTCN_6511 | 50367 |

FIG. 37 (continued)

| | | | |
|---|---|---|---|
| CTCN_3009 | 36309 | GTCN_4183 | 50368 |
| GTCN_1602 | 36310 | CTCN_7738 | 50369 |
| CTCN_3010 | 36311 | GTCN_4184 | 50370 |
| ATCN_1772 | 36312 | TTCN_6512 | 50371 |
| GTCN_1603 | 36313 | GTCN_4185 | 50372 |
| CTCN_3011 | 36314 | CTCN_7739 | 50373 |
| ATCN_1773 | 36315 | TTCN_6513 | 50374 |
| CTCN_3012 | 36316 | TTCN_6514 | 50375 |
| CTCN_3013 | 36317 | GTCN_4186 | 50376 |
| CTCN_3014 | 36318 | ATCN_4480 | 50377 |
| CTCN_3015 | 36319 | CTCN_7740 | 50378 |
| CTCN_3016 | 36320 | GTCN_4187 | 50379 |
| ATCN_1774 | 36321 | CTCN_7741 | 50380 |
| TTCN_2471 | 36322 | ATCN_4481 | 50381 |
| CTCN_3017 | 36323 | ATCN_4482 | 50382 |
| CTCN_3018 | 36324 | ATCN_4483 | 50383 |
| GTCN_1604 | 36325 | ATCN_4484 | 50384 |
| ATCN_1775 | 36326 | ATCN_4485 | 50385 |
| TTCN_2472 | 36327 | TTCN_6515 | 50386 |
| GTCN_1605 | 36328 | GTCN_4188 | 50387 |
| CTCN_3019 | 36329 | TTCN_6516 | 50388 |
| CTCN_3020 | 36330 | TTCN_6517 | 50389 |
| ATCN_1776 | 36331 | TTCN_6518 | 50390 |
| TTCN_2473 | 36332 | ATCN_4486 | 50391 |
| CTCN_3021 | 36333 | TTCN_6519 | 50392 |
| GTCN_1606 | 36334 | TTCN_6520 | 50393 |
| GTCN_1607 | 36335 | CTCN_7742 | 50394 |
| CTCN_3022 | 36336 | CTCN_7743 | 50395 |
| CTCN_3023 | 36337 | CTCN_7744 | 50396 |
| TTCN_2474 | 36338 | CTCN_7745 | 50397 |
| ATCN_1777 | 36339 | GTCN_4189 | 50398 |
| GTCN_1608 | 36340 | CTCN_7746 | 50399 |
| GTCN_1609 | 36341 | TTCN_6521 | 50400 |
| ATCN_1778 | 36342 | CTCN_7747 | 50401 |
| TTCN_2475 | 36343 | CTCN_7748 | 50402 |
| GTCN_1610 | 36344 | CTCN_7749 | 50403 |
| GTCN_1611 | 36345 | CTCN_7750 | 50404 |
| CTCN_3024 | 36346 | GTCN_4190 | 50405 |
| ATCN_1779 | 36347 | TTCN_6522 | 50406 |
| CTCN_3025 | 36348 | CTCN_7751 | 50407 |
| TTCN_2476 | 36349 | CTCN_7752 | 50408 |
| CTCN_3026 | 36350 | TTCN_6523 | 50409 |
| TTCN_2477 | 36351 | TTCN_6524 | 50410 |

| | | | |
|---|---|---|---|
| ATCN_1780 | 36352 | GTCN_4191 | 50411 |
| TTCN_2478 | 36353 | GTCN_4192 | 50412 |
| TTCN_2479 | 36354 | GTCN_4193 | 50413 |
| CTCN_3027 | 36355 | ATCN_4487 | 50414 |
| ATCN_1781 | 36356 | CTCN_7753 | 50415 |
| TTCN_2480 | 36357 | ATCN_4488 | 50416 |
| ATCN_1782 | 36358 | ATCN_4489 | 50417 |
| TTCN_2481 | 36359 | ATCN_4490 | 50418 |
| CTCN_3028 | 36360 | TTCN_6525 | 50419 |
| CTCN_3029 | 36361 | ATCN_4491 | 50420 |
| TTCN_2482 | 36362 | TTCN_6526 | 50421 |
| TTCN_2483 | 36363 | CTCN_7754 | 50422 |
| GTCN_1612 | 36364 | GTCN_4194 | 50423 |
| CTCN_3030 | 36365 | ATCN_4492 | 50424 |
| ATCN_1783 | 36366 | TTCN_6527 | 50425 |
| CTCN_3031 | 36367 | CTCN_7755 | 50426 |
| GTCN_1613 | 36368 | CTCN_7756 | 50427 |
| GTCN_1614 | 36369 | TTCN_6528 | 50428 |
| GTCN_1615 | 36370 | CTCN_7757 | 50429 |
| TTCN_2484 | 36371 | CTCN_7758 | 50430 |
| CTCN_3032 | 36372 | ATCN_4493 | 50431 |
| CTCN_3033 | 36373 | TTCN_6529 | 50432 |
| CTCN_3034 | 36374 | GTCN_4195 | 50433 |
| TTCN_2485 | 36375 | GTCN_4196 | 50434 |
| ATCN_1784 | 36376 | CTCN_7759 | 50435 |
| ATCN_1785 | 36377 | CTCN_7760 | 50436 |
| CTCN_3035 | 36378 | GTCN_4197 | 50437 |
| CTCN_3036 | 36379 | CTCN_7761 | 50438 |
| ATCN_1786 | 36380 | GTCN_4198 | 50439 |
| ATCN_1787 | 36381 | GTCN_4199 | 50440 |
| GTCN_1616 | 36382 | CTCN_7762 | 50441 |
| ATCN_1788 | 36383 | TTCN_6530 | 50442 |
| TTCN_2486 | 36384 | TTCN_6531 | 50443 |
| TTCN_2487 | 36385 | CTCN_7763 | 50444 |
| TTCN_2488 | 36386 | CTCN_7764 | 50445 |
| TTCN_2489 | 36387 | CTCN_7765 | 50446 |
| TTCN_2490 | 36388 | CTCN_7766 | 50447 |
| ATCN_1789 | 36389 | GTCN_4200 | 50448 |
| ATCN_1790 | 36390 | CTCN_7767 | 50449 |
| ATCN_1791 | 36391 | ATCN_4494 | 50450 |
| TTCN_2491 | 36392 | ATCN_4495 | 50451 |
| ATCN_1792 | 36393 | TTCN_6532 | 50452 |
| ATCN_1793 | 36394 | CTCN_7768 | 50453 |

FIG. 37 (continued)

| | | | | | | | |
|---|---|---|---|---|---|---|---|
| CTCN_3037 | 36395 | CTCN_7769 | 50454 | CTCN_3064 | 36438 | CTCN_7784 | 50497 |
| CTCN_3038 | 36396 | ATCN_4496 | 50455 | TTCN_2499 | 36439 | GTCN_4208 | 50498 |
| CTCN_3039 | 36397 | ATCN_4497 | 50456 | ATCN_1799 | 36440 | TTCN_6544 | 50499 |
| TTCN_2492 | 36398 | TTCN_6533 | 50457 | CTCN_3065 | 36441 | TTCN_6545 | 50500 |
| ATCN_1794 | 36399 | GTCN_4201 | 50458 | TTCN_2500 | 36442 | GTCN_4209 | 50501 |
| CTCN_3040 | 36400 | TTCN_6534 | 50459 | GTCN_1621 | 36443 | CTCN_7785 | 50502 |
| CTCN_3041 | 36401 | TTCN_6535 | 50460 | GTCN_1622 | 36444 | CTCN_7786 | 50503 |
| ATCN_1795 | 36402 | CTCN_7770 | 50461 | GTCN_1623 | 36445 | TTCN_6546 | 50504 |
| CTCN_3042 | 36403 | TTCN_6536 | 50462 | GTCN_1624 | 36446 | CTCN_7787 | 50505 |
| CTCN_3043 | 36404 | TTCN_6537 | 50463 | TTCN_2501 | 36447 | GTCN_4210 | 50506 |
| TTCN_2493 | 36405 | GTCN_4202 | 50464 | TTCN_2502 | 36448 | CTCN_7788 | 50507 |
| GTCN_1617 | 36406 | CTCN_7771 | 50465 | ATCN_1800 | 36449 | CTCN_7789 | 50508 |
| CTCN_3044 | 36407 | CTCN_7772 | 50466 | TTCN_2503 | 36450 | ATCN_4506 | 50509 |
| TTCN_2494 | 36408 | TTCN_6538 | 50467 | CTCN_3066 | 36451 | ATCN_4507 | 50510 |
| CTCN_3045 | 36409 | GTCN_4203 | 50468 | TTCN_2504 | 36452 | TTCN_6547 | 50511 |
| ATCN_1796 | 36410 | TTCN_6539 | 50469 | GTCN_1625 | 36453 | ATCN_4508 | 50512 |
| CTCN_3046 | 36411 | TTCN_6540 | 50470 | ATCN_1801 | 36454 | CTCN_7790 | 50513 |
| CTCN_3047 | 36412 | ATCN_4498 | 50471 | TTCN_2505 | 36455 | CTCN_7791 | 50514 |
| CTCN_3048 | 36413 | GTCN_4204 | 50472 | ATCN_1802 | 36456 | TTCN_6548 | 50515 |
| CTCN_3049 | 36414 | ATCN_4499 | 50473 | TTCN_2506 | 36457 | TTCN_6549 | 50516 |
| TTCN_2495 | 36415 | ATCN_4500 | 50474 | TTCN_2507 | 36458 | CTCN_7792 | 50517 |
| ATCN_1797 | 36416 | GTCN_4205 | 50475 | ATCN_1803 | 36459 | CTCN_7793 | 50518 |
| TTCN_2496 | 36417 | ATCN_4501 | 50476 | TTCN_2508 | 36460 | ATCN_4509 | 50519 |
| CTCN_3050 | 36418 | CTCN_7773 | 50477 | GTCN_1626 | 36461 | ATCN_4510 | 50520 |
| CTCN_3051 | 36419 | GTCN_4206 | 50478 | ATCN_1804 | 36462 | GTCN_4211 | 50521 |
| CTCN_3052 | 36420 | TTCN_6541 | 50479 | GTCN_1627 | 36463 | ATCN_4511 | 50522 |
| CTCN_3053 | 36421 | ATCN_4502 | 50480 | GTCN_1628 | 36464 | ATCN_4512 | 50523 |
| CTCN_3054 | 36422 | ATCN_4503 | 50481 | CTCN_3067 | 36465 | CTCN_7794 | 50524 |
| CTCN_3055 | 36423 | GTCN_4207 | 50482 | ATCN_1805 | 36466 | GTCN_4212 | 50525 |
| CTCN_3056 | 36424 | TTCN_6542 | 50483 | TTCN_2509 | 36467 | CTCN_7795 | 50526 |
| CTCN_3057 | 36425 | TTCN_6543 | 50484 | ATCN_1806 | 36468 | CTCN_7796 | 50527 |
| ATCN_1798 | 36426 | ATCN_4504 | 50485 | GTCN_1629 | 36469 | GTCN_4213 | 50528 |
| CTCN_3058 | 36427 | CTCN_7774 | 50486 | ATCN_1807 | 36470 | GTCN_4214 | 50529 |
| GTCN_1618 | 36428 | CTCN_7775 | 50487 | TTCN_2510 | 36471 | CTCN_7797 | 50530 |
| GTCN_1619 | 36429 | CTCN_7776 | 50488 | TTCN_2511 | 36472 | CTCN_7798 | 50531 |
| CTCN_3059 | 36430 | CTCN_7777 | 50489 | CTCN_3068 | 36473 | CTCN_7799 | 50532 |
| TTCN_2497 | 36431 | CTCN_7778 | 50490 | ATCN_1808 | 36474 | TTCN_6550 | 50533 |
| CTCN_3060 | 36432 | CTCN_7779 | 50491 | TTCN_2512 | 36475 | CTCN_7800 | 50534 |
| CTCN_3061 | 36433 | ATCN_4505 | 50492 | TTCN_2513 | 36476 | CTCN_7801 | 50535 |
| CTCN_3062 | 36434 | CTCN_7780 | 50493 | ATCN_1809 | 36477 | TTCN_6551 | 50536 |
| TTCN_2498 | 36435 | CTCN_7781 | 50494 | TTCN_2514 | 36478 | CTCN_7802 | 50537 |
| GTCN_1620 | 36436 | CTCN_7782 | 50495 | TTCN_2515 | 36479 | CTCN_7803 | 50538 |
| CTCN_3063 | 36437 | CTCN_7783 | 50496 | TTCN_2516 | 36480 | ATCN_4513 | 50539 |

FIG. 37 (continued)

| | | | |
|---|---|---|---|
| ATCN_1810 | 36481 | GTCN_4215 | 50540 |
| TTCN_2517 | 36482 | TTCN_6552 | 50541 |
| TTCN_2518 | 36483 | TTCN_6553 | 50542 |
| TTCN_2519 | 36484 | CTCN_7804 | 50543 |
| CTCN_3069 | 36485 | CTCN_7805 | 50544 |
| ATCN_1811 | 36486 | CTCN_7806 | 50545 |
| ATCN_1812 | 36487 | GTCN_4216 | 50546 |
| CTCN_3070 | 36488 | TTCN_6554 | 50547 |
| TTCN_2520 | 36489 | TTCN_6555 | 50548 |
| TTCN_2521 | 36490 | GTCN_4217 | 50549 |
| ATCN_1813 | 36491 | TTCN_6556 | 50550 |
| CTCN_3071 | 36492 | GTCN_4218 | 50551 |
| TTCN_2522 | 36493 | CTCN_7807 | 50552 |
| CTCN_3072 | 36494 | GTCN_4219 | 50553 |
| CTCN_3073 | 36495 | CTCN_7808 | 50554 |
| TTCN_2523 | 36496 | ATCN_4514 | 50555 |
| CTCN_3074 | 36497 | TTCN_6557 | 50556 |
| CTCN_3075 | 36498 | TTCN_6558 | 50557 |
| TTCN_2524 | 36499 | CTCN_7809 | 50558 |
| GTCN_1630 | 36500 | GTCN_4220 | 50559 |
| CTCN_3076 | 36501 | GTCN_4221 | 50560 |
| CTCN_3077 | 36502 | CTCN_7810 | 50561 |
| GTCN_1631 | 36503 | ATCN_4515 | 50562 |
| TTCN_2525 | 36504 | TTCN_6559 | 50563 |
| ATCN_1814 | 36505 | TTCN_6560 | 50564 |
| GTCN_1632 | 36506 | CTCN_7811 | 50565 |
| TTCN_2526 | 36507 | TTCN_6561 | 50566 |
| TTCN_2527 | 36508 | CTCN_7812 | 50567 |
| GTCN_1633 | 36509 | GTCN_4222 | 50568 |
| TTCN_2528 | 36510 | CTCN_7813 | 50569 |
| TTCN_2529 | 36511 | TTCN_6562 | 50570 |
| ATCN_1815 | 36512 | GTCN_4223 | 50571 |
| GTCN_1634 | 36513 | GTCN_4224 | 50572 |
| TTCN_2530 | 36514 | CTCN_7814 | 50573 |
| TTCN_2531 | 36515 | TTCN_6563 | 50574 |
| TTCN_2532 | 36516 | TTCN_6564 | 50575 |
| TTCN_2533 | 36517 | CTCN_7815 | 50576 |
| ATCN_1816 | 36518 | TTCN_6565 | 50577 |
| ATCN_1817 | 36519 | CTCN_7816 | 50578 |
| TTCN_2534 | 36520 | CTCN_7817 | 50579 |
| ATCN_1818 | 36521 | GTCN_4225 | 50580 |
| TTCN_2535 | 36522 | ATCN_4516 | 50581 |
| ATCN_1819 | 36523 | CTCN_7818 | 50582 |

| | | | |
|---|---|---|---|
| GTCN_1635 | 36524 | ATCN_4517 | 50583 |
| TTCN_2536 | 36525 | CTCN_7819 | 50584 |
| CTCN_3078 | 36526 | GTCN_4226 | 50585 |
| GTCN_1636 | 36527 | GTCN_4227 | 50586 |
| TTCN_2537 | 36528 | CTCN_7820 | 50587 |
| ATCN_1820 | 36529 | TTCN_6566 | 50588 |
| GTCN_1637 | 36530 | CTCN_7821 | 50589 |
| ATCN_1821 | 36531 | CTCN_7822 | 50590 |
| GTCN_1638 | 36532 | TTCN_6567 | 50591 |
| GTCN_1639 | 36533 | GTCN_4228 | 50592 |
| CTCN_3079 | 36534 | CTCN_7823 | 50593 |
| TTCN_2538 | 36535 | TTCN_6568 | 50594 |
| CTCN_3080 | 36536 | TTCN_6569 | 50595 |
| TTCN_2539 | 36537 | CTCN_7824 | 50596 |
| TTCN_2540 | 36538 | TTCN_6570 | 50597 |
| ATCN_1822 | 36539 | TTCN_6571 | 50598 |
| GTCN_1640 | 36540 | ATCN_4518 | 50599 |
| TTCN_2541 | 36541 | TTCN_6572 | 50600 |
| TTCN_2542 | 36542 | TTCN_6573 | 50601 |
| TTCN_2543 | 36543 | GTCN_4229 | 50602 |
| ATCN_1823 | 36544 | TTCN_6574 | 50603 |
| GTCN_1641 | 36545 | CTCN_7825 | 50604 |
| GTCN_1642 | 36546 | GTCN_4230 | 50605 |
| ATCN_1824 | 36547 | GTCN_4231 | 50606 |
| TTCN_2544 | 36548 | GTCN_4232 | 50607 |
| GTCN_1643 | 36549 | CTCN_7826 | 50608 |
| TTCN_2545 | 36550 | ATCN_4519 | 50609 |
| TTCN_2546 | 36551 | ATCN_4520 | 50610 |
| ATCN_1825 | 36552 | GTCN_4233 | 50611 |
| CTCN_3081 | 36553 | ATCN_4521 | 50612 |
| CTCN_3082 | 36554 | ATCN_4522 | 50613 |
| TTCN_2547 | 36555 | ATCN_4523 | 50614 |
| GTCN_1644 | 36556 | TTCN_6575 | 50615 |
| TTCN_2548 | 36557 | GTCN_4234 | 50616 |
| ATCN_1826 | 36558 | GTCN_4235 | 50617 |
| CTCN_3083 | 36559 | CTCN_7827 | 50618 |
| GTCN_1645 | 36560 | CTCN_7828 | 50619 |
| GTCN_1646 | 36561 | ATCN_4524 | 50620 |
| GTCN_1647 | 36562 | ATCN_4525 | 50621 |
| CTCN_3084 | 36563 | GTCN_4236 | 50622 |
| TTCN_2549 | 36564 | CTCN_7829 | 50623 |
| GTCN_1648 | 36565 | GTCN_4237 | 50624 |
| TTCN_2550 | 36566 | CTCN_7830 | 50625 |

FIG. 37 (continued)

| | | | |
|---|---|---|---|
| TTCN_2551 | 36567 | TTCN_6576 | 50626 |
| TTCN_2552 | 36568 | TTCN_6577 | 50627 |
| ATCN_1827 | 36569 | TTCN_6578 | 50628 |
| TTCN_2553 | 36570 | ATCN_4526 | 50629 |
| TTCN_2554 | 36571 | GTCN_4238 | 50630 |
| CTCN_3085 | 36572 | CTCN_7831 | 50631 |
| TTCN_2555 | 36573 | GTCN_4239 | 50632 |
| ATCN_1828 | 36574 | TTCN_6579 | 50633 |
| CTCN_3086 | 36575 | TTCN_6580 | 50634 |
| GTCN_1649 | 36576 | CTCN_7832 | 50635 |
| ATCN_1829 | 36577 | TTCN_6581 | 50636 |
| ATCN_1830 | 36578 | GTCN_4240 | 50637 |
| CTCN_3087 | 36579 | GTCN_4241 | 50638 |
| GTCN_1650 | 36580 | TTCN_6582 | 50639 |
| CTCN_3088 | 36581 | GTCN_4242 | 50640 |
| TTCN_2556 | 36582 | CTCN_7833 | 50641 |
| GTCN_1651 | 36583 | CTCN_7834 | 50642 |
| CTCN_3089 | 36584 | CTCN_7835 | 50643 |
| GTCN_1652 | 36585 | ATCN_4527 | 50644 |
| TTCN_2557 | 36586 | ATCN_4528 | 50645 |
| TTCN_2558 | 36587 | ATCN_4529 | 50646 |
| ATCN_1831 | 36588 | ATCN_4530 | 50647 |
| TTCN_2559 | 36589 | CTCN_7836 | 50648 |
| CTCN_3090 | 36590 | CTCN_7837 | 50649 |
| CTCN_3091 | 36591 | CTCN_7838 | 50650 |
| CTCN_3092 | 36592 | ATCN_4531 | 50651 |
| ATCN_1832 | 36593 | TTCN_6583 | 50652 |
| ATCN_1833 | 36594 | TTCN_6584 | 50653 |
| ATCN_1834 | 36595 | GTCN_4243 | 50654 |
| ATCN_1835 | 36596 | TTCN_6585 | 50655 |
| CTCN_3093 | 36597 | GTCN_4244 | 50656 |
| TTCN_2560 | 36598 | CTCN_7839 | 50657 |
| CTCN_3094 | 36599 | GTCN_4245 | 50658 |
| GTCN_1653 | 36600 | TTCN_6586 | 50659 |
| TTCN_2561 | 36601 | ATCN_4532 | 50660 |
| GTCN_1654 | 36602 | ATCN_4533 | 50661 |
| CTCN_3095 | 36603 | TTCN_6587 | 50662 |
| CTCN_3096 | 36604 | ATCN_4534 | 50663 |
| ATCN_1836 | 36605 | GTCN_4246 | 50664 |
| CTCN_3097 | 36606 | CTCN_7840 | 50665 |
| CTCN_3098 | 36607 | GTCN_4247 | 50666 |
| CTCN_3099 | 36608 | TTCN_6588 | 50667 |
| TTCN_2562 | 36609 | ATCN_4535 | 50668 |

| | | | |
|---|---|---|---|
| ATCN_1837 | 36610 | ATCN_4536 | 50669 |
| TTCN_2563 | 36611 | CTCN_7841 | 50670 |
| CTCN_3100 | 36612 | ATCN_4537 | 50671 |
| CTCN_3101 | 36613 | GTCN_4248 | 50672 |
| ATCN_1838 | 36614 | CTCN_7842 | 50673 |
| CTCN_3102 | 36615 | CTCN_7843 | 50674 |
| CTCN_3103 | 36616 | TTCN_6589 | 50675 |
| ATCN_1839 | 36617 | TTCN_6590 | 50676 |
| ATCN_1840 | 36618 | CTCN_7844 | 50677 |
| CTCN_3104 | 36619 | GTCN_4249 | 50678 |
| CTCN_3105 | 36620 | TTCN_6591 | 50679 |
| TTCN_2564 | 36621 | CTCN_7845 | 50680 |
| CTCN_3106 | 36622 | TTCN_6592 | 50681 |
| GTCN_1655 | 36623 | ATCN_4538 | 50682 |
| CTCN_3107 | 36624 | TTCN_6593 | 50683 |
| TTCN_2565 | 36625 | GTCN_4250 | 50684 |
| TTCN_2566 | 36626 | TTCN_6594 | 50685 |
| ATCN_1841 | 36627 | GTCN_4251 | 50686 |
| TTCN_2567 | 36628 | TTCN_6595 | 50687 |
| GTCN_1656 | 36629 | GTCN_4252 | 50688 |
| CTCN_3108 | 36630 | CTCN_7846 | 50689 |
| TTCN_2568 | 36631 | TTCN_6596 | 50690 |
| TTCN_2569 | 36632 | TTCN_6597 | 50691 |
| ATCN_1842 | 36633 | TTCN_6598 | 50692 |
| CTCN_3109 | 36634 | CTCN_7847 | 50693 |
| GTCN_1657 | 36635 | ATCN_4539 | 50694 |
| TTCN_2570 | 36636 | CTCN_7848 | 50695 |
| TTCN_2571 | 36637 | CTCN_7849 | 50696 |
| CTCN_3110 | 36638 | ATCN_4540 | 50697 |
| CTCN_3111 | 36639 | ATCN_4541 | 50698 |
| ATCN_1843 | 36640 | CTCN_7850 | 50699 |
| GTCN_1658 | 36641 | GTCN_4253 | 50700 |
| CTCN_3112 | 36642 | CTCN_7851 | 50701 |
| GTCN_1659 | 36643 | TTCN_6599 | 50702 |
| ATCN_1844 | 36644 | GTCN_4254 | 50703 |
| ATCN_1845 | 36645 | GTCN_4255 | 50704 |
| CTCN_3113 | 36646 | TTCN_6600 | 50705 |
| GTCN_1660 | 36647 | ATCN_4542 | 50706 |
| CTCN_3114 | 36648 | CTCN_7852 | 50707 |
| TTCN_2572 | 36649 | ATCN_4543 | 50708 |
| ATCN_1846 | 36650 | CTCN_7853 | 50709 |
| GTCN_1661 | 36651 | CTCN_7854 | 50710 |
| CTCN_3115 | 36652 | CTCN_7855 | 50711 |

FIG. 37 (continued)

| | | | | | | | |
|---|---|---|---|---|---|---|---|
| CTCN_3116 | 36653 | TTCN_6601 | 50712 | TTCN_2583 | 36696 | CTCN_7880 | 50755 |
| GTCN_1662 | 36654 | ATCN_4544 | 50713 | CTCN_3129 | 36697 | CTCN_7881 | 50756 |
| CTCN_3117 | 36655 | TTCN_6602 | 50714 | ATCN_1854 | 36698 | CTCN_7882 | 50757 |
| ATCN_1847 | 36656 | CTCN_7856 | 50715 | GTCN_1675 | 36699 | CTCN_7883 | 50758 |
| GTCN_1663 | 36657 | ATCN_4545 | 50716 | CTCN_3130 | 36700 | CTCN_7884 | 50759 |
| GTCN_1664 | 36658 | CTCN_7857 | 50717 | CTCN_3131 | 36701 | CTCN_7885 | 50760 |
| CTCN_3118 | 36659 | TTCN_6603 | 50718 | ATCN_1855 | 36702 | CTCN_7886 | 50761 |
| GTCN_1665 | 36660 | CTCN_7858 | 50719 | ATCN_1856 | 36703 | CTCN_7887 | 50762 |
| ATCN_1848 | 36661 | ATCN_4546 | 50720 | TTCN_2584 | 36704 | CTCN_7888 | 50763 |
| ATCN_1849 | 36662 | ATCN_4547 | 50721 | CTCN_3132 | 36705 | CTCN_7889 | 50764 |
| CTCN_3119 | 36663 | TTCN_6604 | 50722 | ATCN_1857 | 36706 | CTCN_7890 | 50765 |
| ATCN_1850 | 36664 | TTCN_6605 | 50723 | TTCN_2585 | 36707 | CTCN_7891 | 50766 |
| CTCN_3120 | 36665 | CTCN_7859 | 50724 | CTCN_3133 | 36708 | CTCN_7892 | 50767 |
| GTCN_1666 | 36666 | GTCN_4256 | 50725 | GTCN_1676 | 36709 | CTCN_7893 | 50768 |
| TTCN_2573 | 36667 | CTCN_7860 | 50726 | GTCN_1677 | 36710 | CTCN_7894 | 50769 |
| TTCN_2574 | 36668 | CTCN_7861 | 50727 | CTCN_3134 | 36711 | CTCN_7895 | 50770 |
| TTCN_2575 | 36669 | GTCN_4257 | 50728 | ATCN_1858 | 36712 | CTCN_7896 | 50771 |
| GTCN_1667 | 36670 | CTCN_7862 | 50729 | GTCN_1678 | 36713 | TTCN_6614 | 50772 |
| CTCN_3121 | 36671 | CTCN_7863 | 50730 | CTCN_3135 | 36714 | TTCN_6615 | 50773 |
| TTCN_2576 | 36672 | CTCN_7864 | 50731 | TTCN_2586 | 36715 | TTCN_6616 | 50774 |
| GTCN_1668 | 36673 | CTCN_7865 | 50732 | ATCN_1859 | 36716 | TTCN_6617 | 50775 |
| GTCN_1669 | 36674 | CTCN_7866 | 50733 | TTCN_2587 | 36717 | CTCN_7897 | 50776 |
| CTCN_3122 | 36675 | CTCN_7867 | 50734 | TTCN_2588 | 36718 | TTCN_6618 | 50777 |
| TTCN_2577 | 36676 | CTCN_7868 | 50735 | CTCN_3136 | 36719 | TTCN_6619 | 50778 |
| CTCN_3123 | 36677 | TTCN_6606 | 50736 | ATCN_1860 | 36720 | TTCN_6620 | 50779 |
| ATCN_1851 | 36678 | TTCN_6607 | 50737 | GTCN_1679 | 36721 | TTCN_6621 | 50780 |
| CTCN_3124 | 36679 | TTCN_6608 | 50738 | GTCN_1680 | 36722 | CTCN_7898 | 50781 |
| GTCN_1670 | 36680 | TTCN_6609 | 50739 | ATCN_1861 | 36723 | TTCN_6622 | 50782 |
| GTCN_1671 | 36681 | TTCN_6610 | 50740 | TTCN_2589 | 36724 | TTCN_6623 | 50783 |
| TTCN_2578 | 36682 | TTCN_6611 | 50741 | GTCN_1681 | 36725 | TTCN_6624 | 50784 |
| TTCN_2579 | 36683 | TTCN_6612 | 50742 | CTCN_3137 | 36726 | TTCN_6625 | 50785 |
| CTCN_3125 | 36684 | TTCN_6613 | 50743 | CTCN_3138 | 36727 | TTCN_6626 | 50786 |
| ATCN_1852 | 36685 | CTCN_7869 | 50744 | TTCN_2590 | 36728 | TTCN_6627 | 50787 |
| TTCN_2580 | 36686 | CTCN_7870 | 50745 | TTCN_2591 | 36729 | TTCN_6628 | 50788 |
| GTCN_1672 | 36687 | CTCN_7871 | 50746 | GTCN_1682 | 36730 | TTCN_6629 | 50789 |
| GTCN_1673 | 36688 | CTCN_7872 | 50747 | CTCN_3139 | 36731 | TTCN_6630 | 50790 |
| TTCN_2581 | 36689 | CTCN_7873 | 50748 | GTCN_1683 | 36732 | TTCN_6631 | 50791 |
| GTCN_1674 | 36690 | CTCN_7874 | 50749 | ATCN_1862 | 36733 | TTCN_6632 | 50792 |
| CTCN_3126 | 36691 | CTCN_7875 | 50750 | GTCN_1684 | 36734 | TTCN_6633 | 50793 |
| CTCN_3127 | 36692 | CTCN_7876 | 50751 | TTCN_2592 | 36735 | GTCN_4258 | 50794 |
| CTCN_3128 | 36693 | CTCN_7877 | 50752 | CTCN_3140 | 36736 | CTCN_7899 | 50795 |
| ATCN_1853 | 36694 | CTCN_7878 | 50753 | ATCN_1863 | 36737 | ATCN_4548 | 50796 |
| TTCN_2582 | 36695 | CTCN_7879 | 50754 | CTCN_3141 | 36738 | TTCN_6634 | 50797 |

FIG. 37 (continued)

| | | | |
|---|---|---|---|
| ATCN_1864 | 36739 | GTCN_4259 | 50798 |
| CTCN_3142 | 36740 | TTCN_6635 | 50799 |
| GTCN_1685 | 36741 | TTCN_6636 | 50800 |
| TTCN_2593 | 36742 | TTCN_6637 | 50801 |
| CTCN_3143 | 36743 | TTCN_6638 | 50802 |
| TTCN_2594 | 36744 | TTCN_6639 | 50803 |
| TTCN_2595 | 36745 | CTCN_7900 | 50804 |
| TTCN_2596 | 36746 | ATCN_4549 | 50805 |
| TTCN_2597 | 36747 | CTCN_7901 | 50806 |
| TTCN_2598 | 36748 | ATCN_4550 | 50807 |
| TTCN_2599 | 36749 | CTCN_7902 | 50808 |
| CTCN_3144 | 36750 | CTCN_7903 | 50809 |
| CTCN_3145 | 36751 | ATCN_4551 | 50810 |
| GTCN_1686 | 36752 | TTCN_6640 | 50811 |
| CTCN_3146 | 36753 | CTCN_7904 | 50812 |
| GTCN_1687 | 36754 | GTCN_4260 | 50813 |
| ATCN_1865 | 36755 | CTCN_7905 | 50814 |
| CTCN_3147 | 36756 | GTCN_4261 | 50815 |
| CTCN_3148 | 36757 | ATCN_4552 | 50816 |
| GTCN_1688 | 36758 | GTCN_4262 | 50817 |
| TTCN_2600 | 36759 | GTCN_4263 | 50818 |
| GTCN_1689 | 36760 | CTCN_7906 | 50819 |
| TTCN_2601 | 36761 | ATCN_4553 | 50820 |
| ATCN_1866 | 36762 | TTCN_6641 | 50821 |
| CTCN_3149 | 36763 | CTCN_7907 | 50822 |
| ATCN_1867 | 36764 | TTCN_6642 | 50823 |
| CTCN_3150 | 36765 | TTCN_6643 | 50824 |
| GTCN_1690 | 36766 | CTCN_7908 | 50825 |
| CTCN_3151 | 36767 | TTCN_6644 | 50826 |
| CTCN_3152 | 36768 | TTCN_6645 | 50827 |
| ATCN_1868 | 36769 | ATCN_4554 | 50828 |
| TTCN_2602 | 36770 | ATCN_4555 | 50829 |
| CTCN_3153 | 36771 | CTCN_7909 | 50830 |
| GTCN_1691 | 36772 | ATCN_4556 | 50831 |
| ATCN_1869 | 36773 | TTCN_6646 | 50832 |
| ATCN_1870 | 36774 | CTCN_7910 | 50833 |
| TTCN_2603 | 36775 | TTCN_6647 | 50834 |
| ATCN_1871 | 36776 | CTCN_7911 | 50835 |
| ATCN_1872 | 36777 | GTCN_4264 | 50836 |
| GTCN_1692 | 36778 | TTCN_6648 | 50837 |
| CTCN_3154 | 36779 | TTCN_6649 | 50838 |
| CTCN_3155 | 36780 | CTCN_7912 | 50839 |
| TTCN_2604 | 36781 | CTCN_7913 | 50840 |

| | | | |
|---|---|---|---|
| GTCN_1693 | 36782 | CTCN_7914 | 50841 |
| ATCN_1873 | 36783 | CTCN_7915 | 50842 |
| ATCN_1874 | 36784 | TTCN_6650 | 50843 |
| GTCN_1694 | 36785 | GTCN_4265 | 50844 |
| ATCN_1875 | 36786 | GTCN_4266 | 50845 |
| GTCN_1695 | 36787 | ATCN_4557 | 50846 |
| CTCN_3156 | 36788 | TTCN_6651 | 50847 |
| TTCN_2605 | 36789 | TTCN_6652 | 50848 |
| GTCN_1696 | 36790 | CTCN_7916 | 50849 |
| CTCN_3157 | 36791 | CTCN_7917 | 50850 |
| GTCN_1697 | 36792 | CTCN_7918 | 50851 |
| TTCN_2606 | 36793 | TTCN_6653 | 50852 |
| TTCN_2607 | 36794 | TTCN_6654 | 50853 |
| CTCN_3158 | 36795 | CTCN_7919 | 50854 |
| CTCN_3159 | 36796 | CTCN_7920 | 50855 |
| TTCN_2608 | 36797 | GTCN_4267 | 50856 |
| ATCN_1876 | 36798 | GTCN_4268 | 50857 |
| TTCN_2609 | 36799 | ATCN_4558 | 50858 |
| TTCN_2610 | 36800 | GTCN_4269 | 50859 |
| CTCN_3160 | 36801 | CTCN_7921 | 50860 |
| TTCN_2611 | 36802 | GTCN_4270 | 50861 |
| CTCN_3161 | 36803 | TTCN_6655 | 50862 |
| TTCN_2612 | 36804 | CTCN_7922 | 50863 |
| CTCN_3162 | 36805 | TTCN_6656 | 50864 |
| TTCN_2613 | 36806 | ATCN_4559 | 50865 |
| ATCN_1877 | 36807 | TTCN_6657 | 50866 |
| TTCN_2614 | 36808 | TTCN_6658 | 50867 |
| TTCN_2615 | 36809 | CTCN_7923 | 50868 |
| ATCN_1878 | 36810 | CTCN_7924 | 50869 |
| CTCN_3163 | 36811 | GTCN_4271 | 50870 |
| GTCN_1698 | 36812 | TTCN_6659 | 50871 |
| CTCN_3164 | 36813 | TTCN_6660 | 50872 |
| CTCN_3165 | 36814 | GTCN_4272 | 50873 |
| ATCN_1879 | 36815 | GTCN_4273 | 50874 |
| TTCN_2616 | 36816 | TTCN_6661 | 50875 |
| CTCN_3166 | 36817 | CTCN_7925 | 50876 |
| TTCN_2617 | 36818 | CTCN_7926 | 50877 |
| TTCN_2618 | 36819 | CTCN_7927 | 50878 |
| TTCN_2619 | 36820 | GTCN_4274 | 50879 |
| TTCN_2620 | 36821 | ATCN_4560 | 50880 |
| TTCN_2621 | 36822 | CTCN_7928 | 50881 |
| ATCN_1880 | 36823 | GTCN_4275 | 50882 |
| TTCN_2622 | 36824 | GTCN_4276 | 50883 |

FIG. 37 (continued)

| | | | |
|---|---|---|---|
| CTCN_3167 | 36825 | TTCN_6662 | 50884 |
| GTCN_1699 | 36826 | CTCN_7929 | 50885 |
| GTCN_1700 | 36827 | CTCN_7930 | 50886 |
| CTCN_3168 | 36828 | CTCN_7931 | 50887 |
| CTCN_3169 | 36829 | CTCN_7932 | 50888 |
| CTCN_3170 | 36830 | GTCN_4277 | 50889 |
| GTCN_1701 | 36831 | CTCN_7933 | 50890 |
| CTCN_3171 | 36832 | CTCN_7934 | 50891 |
| CTCN_3172 | 36833 | CTCN_7935 | 50892 |
| CTCN_3173 | 36834 | ATCN_4561 | 50893 |
| CTCN_3174 | 36835 | TTCN_6663 | 50894 |
| CTCN_3175 | 36836 | GTCN_4278 | 50895 |
| ATCN_1881 | 36837 | TTCN_6664 | 50896 |
| CTCN_3176 | 36838 | TTCN_6665 | 50897 |
| CTCN_3177 | 36839 | CTCN_7936 | 50898 |
| CTCN_3178 | 36840 | TTCN_6666 | 50899 |
| CTCN_3179 | 36841 | TTCN_6667 | 50900 |
| GTCN_1702 | 36842 | TTCN_6668 | 50901 |
| CTCN_3180 | 36843 | CTCN_7937 | 50902 |
| ATCN_1882 | 36844 | GTCN_4279 | 50903 |
| TTCN_2623 | 36845 | ATCN_4562 | 50904 |
| TTCN_2624 | 36846 | GTCN_4280 | 50905 |
| CTCN_3181 | 36847 | ATCN_4563 | 50906 |
| ATCN_1883 | 36848 | CTCN_7938 | 50907 |
| TTCN_2625 | 36849 | CTCN_7939 | 50908 |
| GTCN_1703 | 36850 | CTCN_7940 | 50909 |
| CTCN_3182 | 36851 | CTCN_7941 | 50910 |
| CTCN_3183 | 36852 | TTCN_6669 | 50911 |
| CTCN_3184 | 36853 | TTCN_6670 | 50912 |
| GTCN_1704 | 36854 | GTCN_4281 | 50913 |
| ATCN_1884 | 36855 | CTCN_7942 | 50914 |
| CTCN_3185 | 36856 | ATCN_4564 | 50915 |
| CTCN_3186 | 36857 | CTCN_7943 | 50916 |
| CTCN_3187 | 36858 | CTCN_7944 | 50917 |
| CTCN_3188 | 36859 | ATCN_4565 | 50918 |
| ATCN_1885 | 36860 | ATCN_4566 | 50919 |
| ATCN_1886 | 36861 | CTCN_7945 | 50920 |
| ATCN_1887 | 36862 | GTCN_4282 | 50921 |
| CTCN_3189 | 36863 | CTCN_7946 | 50922 |
| GTCN_1705 | 36864 | TTCN_6671 | 50923 |
| CTCN_3190 | 36865 | CTCN_7947 | 50924 |
| ATCN_1888 | 36866 | GTCN_4283 | 50925 |
| TTCN_2626 | 36867 | TTCN_6672 | 50926 |

| | | | |
|---|---|---|---|
| ATCN_1889 | 36868 | ATCN_4567 | 50927 |
| CTCN_3191 | 36869 | GTCN_4284 | 50928 |
| CTCN_3192 | 36870 | CTCN_7948 | 50929 |
| TTCN_2627 | 36871 | ATCN_4568 | 50930 |
| ATCN_1890 | 36872 | CTCN_7949 | 50931 |
| TTCN_2628 | 36873 | CTCN_7950 | 50932 |
| CTCN_3193 | 36874 | CTCN_7951 | 50933 |
| TTCN_2629 | 36875 | TTCN_6673 | 50934 |
| CTCN_3194 | 36876 | ATCN_4569 | 50935 |
| TTCN_2630 | 36877 | TTCN_6674 | 50936 |
| GTCN_1706 | 36878 | CTCN_7952 | 50937 |
| CTCN_3195 | 36879 | CTCN_7953 | 50938 |
| GTCN_1707 | 36880 | CTCN_7954 | 50939 |
| CTCN_3196 | 36881 | CTCN_7955 | 50940 |
| TTCN_2631 | 36882 | CTCN_7956 | 50941 |
| GTCN_1708 | 36883 | TTCN_6675 | 50942 |
| CTCN_3197 | 36884 | CTCN_7957 | 50943 |
| TTCN_2632 | 36885 | GTCN_4285 | 50944 |
| GTCN_1709 | 36886 | CTCN_7958 | 50945 |
| GTCN_1710 | 36887 | CTCN_7959 | 50946 |
| TTCN_2633 | 36888 | ATCN_4570 | 50947 |
| ATCN_1891 | 36889 | TTCN_6676 | 50948 |
| CTCN_3198 | 36890 | ATCN_4571 | 50949 |
| CTCN_3199 | 36891 | TTCN_6677 | 50950 |
| GTCN_1711 | 36892 | TTCN_6678 | 50951 |
| ATCN_1892 | 36893 | TTCN_6679 | 50952 |
| CTCN_3200 | 36894 | TTCN_6680 | 50953 |
| ATCN_1893 | 36895 | TTCN_6681 | 50954 |
| GTCN_1712 | 36896 | TTCN_6682 | 50955 |
| CTCN_3201 | 36897 | TTCN_6683 | 50956 |
| ATCN_1894 | 36898 | ATCN_4572 | 50957 |
| ATCN_1895 | 36899 | CTCN_7960 | 50958 |
| GTCN_1713 | 36900 | TTCN_6684 | 50959 |
| TTCN_2634 | 36901 | ATCN_4573 | 50960 |
| CTCN_3202 | 36902 | GTCN_4286 | 50961 |
| CTCN_3203 | 36903 | CTCN_7961 | 50962 |
| CTCN_3204 | 36904 | CTCN_7962 | 50963 |
| CTCN_3205 | 36905 | ATCN_4574 | 50964 |
| GTCN_1714 | 36906 | ATCN_4575 | 50965 |
| ATCN_1896 | 36907 | ATCN_4576 | 50966 |
| ATCN_1897 | 36908 | TTCN_6685 | 50967 |
| GTCN_1715 | 36909 | TTCN_6686 | 50968 |
| TTCN_2635 | 36910 | GTCN_4287 | 50969 |

FIG. 37 (continued)

| | | | |
|---|---|---|---|
| ATCN_1898 | 36911 | TTCN_6687 | 50970 |
| GTCN_1716 | 36912 | ATCN_4577 | 50971 |
| ATCN_1899 | 36913 | CTCN_7963 | 50972 |
| TTCN_2636 | 36914 | TTCN_6688 | 50973 |
| ATCN_1900 | 36915 | CTCN_7964 | 50974 |
| CTCN_3206 | 36916 | CTCN_7965 | 50975 |
| CTCN_3207 | 36917 | CTCN_7966 | 50976 |
| GTCN_1717 | 36918 | TTCN_6689 | 50977 |
| TTCN_2637 | 36919 | CTCN_7967 | 50978 |
| ATCN_1901 | 36920 | TTCN_6690 | 50979 |
| CTCN_3208 | 36921 | ATCN_4578 | 50980 |
| ATCN_1902 | 36922 | CTCN_7968 | 50981 |
| CTCN_3209 | 36923 | ATCN_4579 | 50982 |
| GTCN_1718 | 36924 | GTCN_4288 | 50983 |
| CTCN_3210 | 36925 | CTCN_7969 | 50984 |
| CTCN_3211 | 36926 | ATCN_4580 | 50985 |
| GTCN_1719 | 36927 | GTCN_4289 | 50986 |
| TTCN_2638 | 36928 | TTCN_6691 | 50987 |
| CTCN_3212 | 36929 | CTCN_7970 | 50988 |
| ATCN_1903 | 36930 | TTCN_6692 | 50989 |
| GTCN_1720 | 36931 | TTCN_6693 | 50990 |
| CTCN_3213 | 36932 | TTCN_6694 | 50991 |
| GTCN_1721 | 36933 | GTCN_4290 | 50992 |
| TTCN_2639 | 36934 | CTCN_7971 | 50993 |
| GTCN_1722 | 36935 | CTCN_7972 | 50994 |
| CTCN_3214 | 36936 | ATCN_4581 | 50995 |
| CTCN_3215 | 36937 | CTCN_7973 | 50996 |
| GTCN_1723 | 36938 | CTCN_7974 | 50997 |
| ATCN_1904 | 36939 | CTCN_7975 | 50998 |
| ATCN_1905 | 36940 | TTCN_6695 | 50999 |
| ATCN_1906 | 36941 | TTCN_6696 | 51000 |
| ATCN_1907 | 36942 | GTCN_4291 | 51001 |
| TTCN_2640 | 36943 | ATCN_4582 | 51002 |
| CTCN_3216 | 36944 | ATCN_4583 | 51003 |
| TTCN_2641 | 36945 | TTCN_6697 | 51004 |
| CTCN_3217 | 36946 | CTCN_7976 | 51005 |
| CTCN_3218 | 36947 | TTCN_6698 | 51006 |
| GTCN_1724 | 36948 | TTCN_6699 | 51007 |
| CTCN_3219 | 36949 | CTCN_7977 | 51008 |
| GTCN_1725 | 36950 | TTCN_6700 | 51009 |
| CTCN_3220 | 36951 | TTCN_6701 | 51010 |
| CTCN_3221 | 36952 | TTCN_6702 | 51011 |
| CTCN_3222 | 36953 | GTCN_4292 | 51012 |
| TTCN_2642 | 36954 | GTCN_4293 | 51013 |
| TTCN_2643 | 36955 | GTCN_4294 | 51014 |
| GTCN_1726 | 36956 | CTCN_7978 | 51015 |
| CTCN_3223 | 36957 | CTCN_7979 | 51016 |
| CTCN_3224 | 36958 | CTCN_7980 | 51017 |
| GTCN_1727 | 36959 | TTCN_6703 | 51018 |
| TTCN_2644 | 36960 | CTCN_7981 | 51019 |
| CTCN_3225 | 36961 | CTCN_7982 | 51020 |
| GTCN_1728 | 36962 | TTCN_6704 | 51021 |
| CTCN_3226 | 36963 | ATCN_4584 | 51022 |
| CTCN_3227 | 36964 | CTCN_7983 | 51023 |
| CTCN_3228 | 36965 | TTCN_6705 | 51024 |
| GTCN_1729 | 36966 | CTCN_7984 | 51025 |
| CTCN_3229 | 36967 | TTCN_6706 | 51026 |
| TTCN_2645 | 36968 | GTCN_4295 | 51027 |
| CTCN_3230 | 36969 | CTCN_7985 | 51028 |
| ATCN_1908 | 36970 | TTCN_6707 | 51029 |
| ATCN_1909 | 36971 | ATCN_4585 | 51030 |
| CTCN_3231 | 36972 | CTCN_7986 | 51031 |
| CTCN_3232 | 36973 | GTCN_4296 | 51032 |
| CTCN_3233 | 36974 | ATCN_4586 | 51033 |
| TTCN_2646 | 36975 | TTCN_6708 | 51034 |
| TTCN_2647 | 36976 | GTCN_4297 | 51035 |
| CTCN_3234 | 36977 | TTCN_6709 | 51036 |
| ATCN_1910 | 36978 | CTCN_7987 | 51037 |
| CTCN_3235 | 36979 | ATCN_4587 | 51038 |
| CTCN_3236 | 36980 | ATCN_4588 | 51039 |
| ATCN_1911 | 36981 | CTCN_7988 | 51040 |
| CTCN_3237 | 36982 | ATCN_4589 | 51041 |
| GTCN_1730 | 36983 | CTCN_7989 | 51042 |
| TTCN_2648 | 36984 | TTCN_6710 | 51043 |
| ATCN_1912 | 36985 | CTCN_7990 | 51044 |
| CTCN_3238 | 36986 | GTCN_4298 | 51045 |
| TTCN_2649 | 36987 | GTCN_4299 | 51046 |
| GTCN_1731 | 36988 | CTCN_7991 | 51047 |
| CTCN_3239 | 36989 | GTCN_4300 | 51048 |
| ATCN_1913 | 36990 | TTCN_6711 | 51049 |
| ATCN_1914 | 36991 | CTCN_7992 | 51050 |
| GTCN_1732 | 36992 | CTCN_7993 | 51051 |
| CTCN_3240 | 36993 | ATCN_4590 | 51052 |
| CTCN_3241 | 36994 | ATCN_4591 | 51053 |
| TTCN_2650 | 36995 | CTCN_7994 | 51054 |
| TTCN_2651 | 36996 | CTCN_7995 | 51055 |

FIG. 37 (continued)

| | | | |
|---|---|---|---|
| ATCN_1915 | 36997 | ATCN_4592 | 51056 |
| CTCN_3242 | 36998 | CTCN_7996 | 51057 |
| CTCN_3243 | 36999 | ATCN_4593 | 51058 |
| CTCN_3244 | 37000 | ATCN_4594 | 51059 |
| CTCN_3245 | 37001 | CTCN_7997 | 51060 |
| TTCN_2652 | 37002 | ATCN_4595 | 51061 |
| ATCN_1916 | 37003 | CTCN_7998 | 51062 |
| CTCN_3246 | 37004 | ATCN_4596 | 51063 |
| TTCN_2653 | 37005 | ATCN_4597 | 51064 |
| TTCN_2654 | 37006 | GTCN_4301 | 51065 |
| TTCN_2655 | 37007 | CTCN_7999 | 51066 |
| TTCN_2656 | 37008 | TTCN_6712 | 51067 |
| ATCN_1917 | 37009 | TTCN_6713 | 51068 |
| GTCN_1733 | 37010 | ATCN_4598 | 51069 |
| ATCN_1918 | 37011 | CTCN_8000 | 51070 |
| ATCN_1919 | 37012 | CTCN_8001 | 51071 |
| TTCN_2657 | 37013 | GTCN_4302 | 51072 |
| CTCN_3247 | 37014 | TTCN_6714 | 51073 |
| TTCN_2658 | 37015 | CTCN_8002 | 51074 |
| CTCN_3248 | 37016 | GTCN_4303 | 51075 |
| TTCN_2659 | 37017 | ATCN_4599 | 51076 |
| GTCN_1734 | 37018 | TTCN_6715 | 51077 |
| TTCN_2660 | 37019 | CTCN_8003 | 51078 |
| TTCN_2661 | 37020 | TTCN_6716 | 51079 |
| TTCN_2662 | 37021 | TTCN_6717 | 51080 |
| ATCN_1920 | 37022 | GTCN_4304 | 51081 |
| TTCN_2663 | 37023 | CTCN_8004 | 51082 |
| CTCN_3249 | 37024 | GTCN_4305 | 51083 |
| ATCN_1921 | 37025 | CTCN_8005 | 51084 |
| CTCN_3250 | 37026 | CTCN_8006 | 51085 |
| GTCN_1735 | 37027 | ATCN_4600 | 51086 |
| CTCN_3251 | 37028 | TTCN_6718 | 51087 |
| CTCN_3252 | 37029 | ATCN_4601 | 51088 |
| GTCN_1736 | 37030 | ATCN_4602 | 51089 |
| CTCN_3253 | 37031 | CTCN_8007 | 51090 |
| TTCN_2664 | 37032 | TTCN_6719 | 51091 |
| CTCN_3254 | 37033 | GTCN_4306 | 51092 |
| ATCN_1922 | 37034 | TTCN_6720 | 51093 |
| GTCN_1737 | 37035 | CTCN_8008 | 51094 |
| CTCN_3255 | 37036 | TTCN_6721 | 51095 |
| CTCN_3256 | 37037 | ATCN_4603 | 51096 |
| GTCN_1738 | 37038 | CTCN_8009 | 51097 |
| CTCN_3257 | 37039 | CTCN_8010 | 51098 |

| | | | |
|---|---|---|---|
| ATCN_1923 | 37040 | CTCN_8011 | 51099 |
| ATCN_1924 | 37041 | CTCN_8012 | 51100 |
| CTCN_3258 | 37042 | TTCN_6722 | 51101 |
| CTCN_3259 | 37043 | GTCN_4307 | 51102 |
| TTCN_2665 | 37044 | CTCN_8013 | 51103 |
| CTCN_3260 | 37045 | CTCN_8014 | 51104 |
| GTCN_1739 | 37046 | CTCN_8015 | 51105 |
| TTCN_2666 | 37047 | CTCN_8016 | 51106 |
| TTCN_2667 | 37048 | ATCN_4604 | 51107 |
| ATCN_1925 | 37049 | CTCN_8017 | 51108 |
| ATCN_1926 | 37050 | ATCN_4605 | 51109 |
| TTCN_2668 | 37051 | CTCN_8018 | 51110 |
| ATCN_1927 | 37052 | ATCN_4606 | 51111 |
| ATCN_1928 | 37053 | ATCN_4607 | 51112 |
| ATCN_1929 | 37054 | ATCN_4608 | 51113 |
| TTCN_2669 | 37055 | GTCN_4308 | 51114 |
| ATCN_1930 | 37056 | ATCN_4609 | 51115 |
| GTCN_1740 | 37057 | GTCN_4309 | 51116 |
| TTCN_2670 | 37058 | CTCN_8019 | 51117 |
| CTCN_3261 | 37059 | ATCN_4610 | 51118 |
| CTCN_3262 | 37060 | CTCN_8020 | 51119 |
| TTCN_2671 | 37061 | CTCN_8021 | 51120 |
| GTCN_1741 | 37062 | GTCN_4310 | 51121 |
| ATCN_1931 | 37063 | GTCN_4311 | 51122 |
| GTCN_1742 | 37064 | CTCN_8022 | 51123 |
| GTCN_1743 | 37065 | TTCN_6723 | 51124 |
| CTCN_3263 | 37066 | GTCN_4312 | 51125 |
| CTCN_3264 | 37067 | GTCN_4313 | 51126 |
| CTCN_3265 | 37068 | TTCN_6724 | 51127 |
| GTCN_1744 | 37069 | GTCN_4314 | 51128 |
| ATCN_1932 | 37070 | CTCN_8023 | 51129 |
| CTCN_3266 | 37071 | ATCN_4611 | 51130 |
| ATCN_1933 | 37072 | GTCN_4315 | 51131 |
| TTCN_2672 | 37073 | ATCN_4612 | 51132 |
| CTCN_3267 | 37074 | TTCN_6725 | 51133 |
| CTCN_3268 | 37075 | ATCN_4613 | 51134 |
| TTCN_2673 | 37076 | CTCN_8024 | 51135 |
| TTCN_2674 | 37077 | CTCN_8025 | 51136 |
| TTCN_2675 | 37078 | GTCN_4316 | 51137 |
| ATCN_1934 | 37079 | TTCN_6726 | 51138 |
| GTCN_1745 | 37080 | GTCN_4317 | 51139 |
| CTCN_3269 | 37081 | CTCN_8026 | 51140 |
| TTCN_2676 | 37082 | ATCN_4614 | 51141 |

FIG. 37 (continued)

| | | | |
|---|---|---|---|
| ATCN_1935 | 37083 | CTCN_8027 | 51142 |
| ATCN_1936 | 37084 | CTCN_8028 | 51143 |
| ATCN_1937 | 37085 | CTCN_8029 | 51144 |
| ATCN_1938 | 37086 | CTCN_8030 | 51145 |
| TTCN_2677 | 37087 | ATCN_4615 | 51146 |
| ATCN_1939 | 37088 | ATCN_4616 | 51147 |
| GTCN_1746 | 37089 | ATCN_4617 | 51148 |
| TTCN_2678 | 37090 | CTCN_8031 | 51149 |
| CTCN_3270 | 37091 | CTCN_8032 | 51150 |
| CTCN_3271 | 37092 | CTCN_8033 | 51151 |
| ATCN_1940 | 37093 | GTCN_4318 | 51152 |
| ATCN_1941 | 37094 | CTCN_8034 | 51153 |
| TTCN_2679 | 37095 | CTCN_8035 | 51154 |
| TTCN_2680 | 37096 | CTCN_8036 | 51155 |
| ATCN_1942 | 37097 | ATCN_4618 | 51156 |
| GTCN_1747 | 37098 | TTCN_6727 | 51157 |
| ATCN_1943 | 37099 | CTCN_8037 | 51158 |
| GTCN_1748 | 37100 | ATCN_4619 | 51159 |
| CTCN_3272 | 37101 | CTCN_8038 | 51160 |
| ATCN_1944 | 37102 | CTCN_8039 | 51161 |
| CTCN_3273 | 37103 | CTCN_8040 | 51162 |
| GTCN_1749 | 37104 | CTCN_8041 | 51163 |
| GTCN_1750 | 37105 | GTCN_4319 | 51164 |
| GTCN_1751 | 37106 | ATCN_4620 | 51165 |
| GTCN_1752 | 37107 | GTCN_4320 | 51166 |
| ATCN_1945 | 37108 | CTCN_8042 | 51167 |
| TTCN_2681 | 37109 | GTCN_4321 | 51168 |
| GTCN_1753 | 37110 | CTCN_8043 | 51169 |
| CTCN_3274 | 37111 | TTCN_6728 | 51170 |
| CTCN_3275 | 37112 | CTCN_8044 | 51171 |
| CTCN_3276 | 37113 | GTCN_4322 | 51172 |
| CTCN_3277 | 37114 | GTCN_4323 | 51173 |
| GTCN_1754 | 37115 | CTCN_8045 | 51174 |
| TTCN_2682 | 37116 | TTCN_6729 | 51175 |
| ATCN_1946 | 37117 | ATCN_4621 | 51176 |
| TTCN_2683 | 37118 | TTCN_6730 | 51177 |
| CTCN_3278 | 37119 | GTCN_4324 | 51178 |
| GTCN_1755 | 37120 | GTCN_4325 | 51179 |
| CTCN_3279 | 37121 | TTCN_6731 | 51180 |
| CTCN_3280 | 37122 | CTCN_8046 | 51181 |
| CTCN_3281 | 37123 | TTCN_6732 | 51182 |
| ATCN_1947 | 37124 | TTCN_6733 | 51183 |
| ATCN_1948 | 37125 | CTCN_8047 | 51184 |

| | | | |
|---|---|---|---|
| GTCN_1756 | 37126 | TTCN_6734 | 51185 |
| CTCN_3282 | 37127 | CTCN_8048 | 51186 |
| GTCN_1757 | 37128 | CTCN_8049 | 51187 |
| CTCN_3283 | 37129 | GTCN_4326 | 51188 |
| TTCN_2684 | 37130 | GTCN_4327 | 51189 |
| CTCN_3284 | 37131 | TTCN_6735 | 51190 |
| CTCN_3285 | 37132 | TTCN_6736 | 51191 |
| GTCN_1758 | 37133 | TTCN_6737 | 51192 |
| TTCN_2685 | 37134 | GTCN_4328 | 51193 |
| CTCN_3286 | 37135 | TTCN_6738 | 51194 |
| TTCN_2686 | 37136 | TTCN_6739 | 51195 |
| ATCN_1949 | 37137 | ATCN_4622 | 51196 |
| CTCN_3287 | 37138 | ATCN_4623 | 51197 |
| TTCN_2687 | 37139 | TTCN_6740 | 51198 |
| CTCN_3288 | 37140 | CTCN_8050 | 51199 |
| CTCN_3289 | 37141 | TTCN_6741 | 51200 |
| ATCN_1950 | 37142 | TTCN_6742 | 51201 |
| TTCN_2688 | 37143 | ATCN_4624 | 51202 |
| CTCN_3290 | 37144 | GTCN_4329 | 51203 |
| ATCN_1951 | 37145 | ATCN_4625 | 51204 |
| CTCN_3291 | 37146 | TTCN_6743 | 51205 |
| GTCN_1759 | 37147 | CTCN_8051 | 51206 |
| CTCN_3292 | 37148 | CTCN_8052 | 51207 |
| TTCN_2689 | 37149 | TTCN_6744 | 51208 |
| CTCN_3293 | 37150 | TTCN_6745 | 51209 |
| CTCN_3294 | 37151 | CTCN_8053 | 51210 |
| TTCN_2690 | 37152 | CTCN_8054 | 51211 |
| GTCN_1760 | 37153 | CTCN_8055 | 51212 |
| GTCN_1761 | 37154 | CTCN_8056 | 51213 |
| ATCN_1952 | 37155 | ATCN_4626 | 51214 |
| TTCN_2691 | 37156 | GTCN_4330 | 51215 |
| TTCN_2692 | 37157 | CTCN_8057 | 51216 |
| TTCN_2693 | 37158 | GTCN_4331 | 51217 |
| GTCN_1762 | 37159 | GTCN_4332 | 51218 |
| CTCN_3295 | 37160 | GTCN_4333 | 51219 |
| CTCN_3296 | 37161 | GTCN_4334 | 51220 |
| TTCN_2694 | 37162 | GTCN_4335 | 51221 |
| TTCN_2695 | 37163 | CTCN_8058 | 51222 |
| CTCN_3297 | 37164 | GTCN_4336 | 51223 |
| TTCN_2696 | 37165 | ATCN_4627 | 51224 |
| GTCN_1763 | 37166 | ATCN_4628 | 51225 |
| CTCN_3298 | 37167 | ATCN_4629 | 51226 |
| TTCN_2697 | 37168 | CTCN_8059 | 51227 |

FIG. 37 (continued)

| | | | |
|---|---|---|---|
| ATCN_1953 | 37169 | GTCN_4337 | 51228 |
| TTCN_2698 | 37170 | ATCN_4630 | 51229 |
| ATCN_1954 | 37171 | CTCN_8060 | 51230 |
| CTCN_3299 | 37172 | CTCN_8061 | 51231 |
| GTCN_1764 | 37173 | CTCN_8062 | 51232 |
| CTCN_3300 | 37174 | GTCN_4338 | 51233 |
| TTCN_2699 | 37175 | CTCN_8063 | 51234 |
| CTCN_3301 | 37176 | CTCN_8064 | 51235 |
| CTCN_3302 | 37177 | GTCN_4339 | 51236 |
| TTCN_2700 | 37178 | GTCN_4340 | 51237 |
| CTCN_3303 | 37179 | CTCN_8065 | 51238 |
| CTCN_3304 | 37180 | GTCN_4341 | 51239 |
| CTCN_3305 | 37181 | ATCN_4631 | 51240 |
| CTCN_3306 | 37182 | GTCN_4342 | 51241 |
| ATCN_1955 | 37183 | ATCN_4632 | 51242 |
| ATCN_1956 | 37184 | ATCN_4633 | 51243 |
| CTCN_3307 | 37185 | TTCN_6746 | 51244 |
| TTCN_2701 | 37186 | TTCN_6747 | 51245 |
| CTCN_3308 | 37187 | CTCN_8066 | 51246 |
| GTCN_1765 | 37188 | CTCN_8067 | 51247 |
| CTCN_3309 | 37189 | ATCN_4634 | 51248 |
| TTCN_2702 | 37190 | ATCN_4635 | 51249 |
| CTCN_3310 | 37191 | ATCN_4636 | 51250 |
| GTCN_1766 | 37192 | CTCN_8068 | 51251 |
| TTCN_2703 | 37193 | CTCN_8069 | 51252 |
| TTCN_2704 | 37194 | ATCN_4637 | 51253 |
| CTCN_3311 | 37195 | TTCN_6748 | 51254 |
| CTCN_3312 | 37196 | GTCN_4343 | 51255 |
| CTCN_3313 | 37197 | ATCN_4638 | 51256 |
| TTCN_2705 | 37198 | ATCN_4639 | 51257 |
| TTCN_2706 | 37199 | TTCN_6749 | 51258 |
| GTCN_1767 | 37200 | TTCN_6750 | 51259 |
| CTCN_3314 | 37201 | CTCN_8070 | 51260 |
| TTCN_2707 | 37202 | TTCN_6751 | 51261 |
| TTCN_2708 | 37203 | TTCN_6752 | 51262 |
| TTCN_2709 | 37204 | CTCN_8071 | 51263 |
| CTCN_3315 | 37205 | ATCN_4640 | 51264 |
| GTCN_1768 | 37206 | TTCN_6753 | 51265 |
| CTCN_3316 | 37207 | CTCN_8072 | 51266 |
| GTCN_1769 | 37208 | TTCN_6754 | 51267 |
| CTCN_3317 | 37209 | TTCN_6755 | 51268 |
| GTCN_1770 | 37210 | CTCN_8073 | 51269 |
| CTCN_3318 | 37211 | TTCN_6756 | 51270 |

| | | | |
|---|---|---|---|
| GTCN_1771 | 37212 | CTCN_8074 | 51271 |
| CTCN_3319 | 37213 | GTCN_4344 | 51272 |
| CTCN_3320 | 37214 | TTCN_6757 | 51273 |
| ATCN_1957 | 37215 | TTCN_6758 | 51274 |
| ATCN_1958 | 37216 | CTCN_8075 | 51275 |
| CTCN_3321 | 37217 | GTCN_4345 | 51276 |
| CTCN_3322 | 37218 | TTCN_6759 | 51277 |
| CTCN_3323 | 37219 | CTCN_8076 | 51278 |
| CTCN_3324 | 37220 | CTCN_8077 | 51279 |
| TTCN_2710 | 37221 | GTCN_4346 | 51280 |
| TTCN_2711 | 37222 | GTCN_4347 | 51281 |
| CTCN_3325 | 37223 | GTCN_4348 | 51282 |
| CTCN_3326 | 37224 | GTCN_4349 | 51283 |
| ATCN_1959 | 37225 | CTCN_8078 | 51284 |
| CTCN_3327 | 37226 | CTCN_8079 | 51285 |
| CTCN_3328 | 37227 | CTCN_8080 | 51286 |
| GTCN_1772 | 37228 | CTCN_8081 | 51287 |
| TTCN_2712 | 37229 | GTCN_4350 | 51288 |
| GTCN_1773 | 37230 | CTCN_8082 | 51289 |
| GTCN_1774 | 37231 | CTCN_8083 | 51290 |
| TTCN_2713 | 37232 | CTCN_8084 | 51291 |
| CTCN_3329 | 37233 | GTCN_4351 | 51292 |
| GTCN_1775 | 37234 | ATCN_4641 | 51293 |
| CTCN_3330 | 37235 | CTCN_8085 | 51294 |
| ATCN_1960 | 37236 | CTCN_8086 | 51295 |
| CTCN_3331 | 37237 | ATCN_4642 | 51296 |
| CTCN_3332 | 37238 | ATCN_4643 | 51297 |
| CTCN_3333 | 37239 | CTCN_8087 | 51298 |
| ATCN_1961 | 37240 | TTCN_6760 | 51299 |
| CTCN_3334 | 37241 | ATCN_4644 | 51300 |
| CTCN_3335 | 37242 | CTCN_8088 | 51301 |
| TTCN_2714 | 37243 | GTCN_4352 | 51302 |
| CTCN_3336 | 37244 | CTCN_8089 | 51303 |
| CTCN_3337 | 37245 | CTCN_8090 | 51304 |
| ATCN_1962 | 37246 | GTCN_4353 | 51305 |
| TTCN_2715 | 37247 | CTCN_8091 | 51306 |
| CTCN_3338 | 37248 | GTCN_4354 | 51307 |
| CTCN_3339 | 37249 | CTCN_8092 | 51308 |
| CTCN_3340 | 37250 | TTCN_6761 | 51309 |
| TTCN_2716 | 37251 | CTCN_8093 | 51310 |
| TTCN_2717 | 37252 | CTCN_8094 | 51311 |
| CTCN_3341 | 37253 | CTCN_8095 | 51312 |
| TTCN_2718 | 37254 | GTCN_4355 | 51313 |

FIG. 37 (continued)

| | | | |
|---|---|---|---|
| CTCN_3342 | 37255 | CTCN_8096 | 51314 |
| GTCN_1776 | 37256 | CTCN_8097 | 51315 |
| CTCN_3343 | 37257 | CTCN_8098 | 51316 |
| ATCN_1963 | 37258 | CTCN_8099 | 51317 |
| GTCN_1777 | 37259 | CTCN_8100 | 51318 |
| CTCN_3344 | 37260 | TTCN_6762 | 51319 |
| CTCN_3345 | 37261 | GTCN_4356 | 51320 |
| TTCN_2719 | 37262 | TTCN_6763 | 51321 |
| TTCN_2720 | 37263 | ATCN_4645 | 51322 |
| ATCN_1964 | 37264 | GTCN_4357 | 51323 |
| TTCN_2721 | 37265 | TTCN_6764 | 51324 |
| GTCN_1778 | 37266 | GTCN_4358 | 51325 |
| ATCN_1965 | 37267 | CTCN_8101 | 51326 |
| CTCN_3346 | 37268 | CTCN_8102 | 51327 |
| GTCN_1779 | 37269 | GTCN_4359 | 51328 |
| ATCN_1966 | 37270 | CTCN_8103 | 51329 |
| CTCN_3347 | 37271 | CTCN_8104 | 51330 |
| CTCN_3348 | 37272 | CTCN_8105 | 51331 |
| TTCN_2722 | 37273 | ATCN_4646 | 51332 |
| TTCN_2723 | 37274 | CTCN_8106 | 51333 |
| ATCN_1967 | 37275 | TTCN_6765 | 51334 |
| GTCN_1780 | 37276 | TTCN_6766 | 51335 |
| CTCN_3349 | 37277 | GTCN_4360 | 51336 |
| TTCN_2724 | 37278 | CTCN_8107 | 51337 |
| ATCN_1968 | 37279 | GTCN_4361 | 51338 |
| CTCN_3350 | 37280 | CTCN_8108 | 51339 |
| GTCN_1781 | 37281 | CTCN_8109 | 51340 |
| CTCN_3351 | 37282 | TTCN_6767 | 51341 |
| CTCN_3352 | 37283 | CTCN_8110 | 51342 |
| CTCN_3353 | 37284 | TTCN_6768 | 51343 |
| TTCN_2725 | 37285 | CTCN_8111 | 51344 |
| GTCN_1782 | 37286 | CTCN_8112 | 51345 |
| ATCN_1969 | 37287 | TTCN_6769 | 51346 |
| CTCN_3354 | 37288 | TTCN_6770 | 51347 |
| TTCN_2726 | 37289 | GTCN_4362 | 51348 |
| TTCN_2727 | 37290 | TTCN_6771 | 51349 |
| CTCN_3355 | 37291 | ATCN_4647 | 51350 |
| GTCN_1783 | 37292 | CTCN_8113 | 51351 |
| GTCN_1784 | 37293 | TTCN_6772 | 51352 |
| TTCN_2728 | 37294 | TTCN_6773 | 51353 |
| CTCN_3356 | 37295 | CTCN_8114 | 51354 |
| CTCN_3357 | 37296 | TTCN_6774 | 51355 |
| ATCN_1970 | 37297 | GTCN_4363 | 51356 |

| | | | |
|---|---|---|---|
| CTCN_3358 | 37298 | GTCN_4364 | 51357 |
| ATCN_1971 | 37299 | GTCN_4365 | 51358 |
| ATCN_1972 | 37300 | TTCN_6775 | 51359 |
| TTCN_2729 | 37301 | TTCN_6776 | 51360 |
| CTCN_3359 | 37302 | CTCN_8115 | 51361 |
| CTCN_3360 | 37303 | GTCN_4366 | 51362 |
| TTCN_2730 | 37304 | TTCN_6777 | 51363 |
| ATCN_1973 | 37305 | TTCN_6778 | 51364 |
| ATCN_1974 | 37306 | CTCN_8116 | 51365 |
| TTCN_2731 | 37307 | CTCN_8117 | 51366 |
| TTCN_2732 | 37308 | TTCN_6779 | 51367 |
| TTCN_2733 | 37309 | GTCN_4367 | 51368 |
| CTCN_3361 | 37310 | ATCN_4648 | 51369 |
| ATCN_1975 | 37311 | CTCN_8118 | 51370 |
| CTCN_3362 | 37312 | ATCN_4649 | 51371 |
| CTCN_3363 | 37313 | ATCN_4650 | 51372 |
| TTCN_2734 | 37314 | GTCN_4368 | 51373 |
| ATCN_1976 | 37315 | GTCN_4369 | 51374 |
| CTCN_3364 | 37316 | CTCN_8119 | 51375 |
| CTCN_3365 | 37317 | CTCN_8120 | 51376 |
| ATCN_1977 | 37318 | CTCN_8121 | 51377 |
| TTCN_2735 | 37319 | CTCN_8122 | 51378 |
| TTCN_2736 | 37320 | TTCN_6780 | 51379 |
| TTCN_2737 | 37321 | TTCN_6781 | 51380 |
| CTCN_3366 | 37322 | TTCN_6782 | 51381 |
| ATCN_1978 | 37323 | CTCN_8123 | 51382 |
| ATCN_1979 | 37324 | GTCN_4370 | 51383 |
| ATCN_1980 | 37325 | GTCN_4371 | 51384 |
| TTCN_2738 | 37326 | CTCN_8124 | 51385 |
| ATCN_1981 | 37327 | CTCN_8125 | 51386 |
| GTCN_1785 | 37328 | CTCN_8126 | 51387 |
| CTCN_3367 | 37329 | TTCN_6783 | 51388 |
| TTCN_2739 | 37330 | ATCN_4651 | 51389 |
| GTCN_1786 | 37331 | ATCN_4652 | 51390 |
| ATCN_1982 | 37332 | ATCN_4653 | 51391 |
| TTCN_2740 | 37333 | ATCN_4654 | 51392 |
| CTCN_3368 | 37334 | TTCN_6784 | 51393 |
| CTCN_3369 | 37335 | CTCN_8127 | 51394 |
| CTCN_3370 | 37336 | CTCN_8128 | 51395 |
| CTCN_3371 | 37337 | CTCN_8129 | 51396 |
| CTCN_3372 | 37338 | ATCN_4655 | 51397 |
| TTCN_2741 | 37339 | TTCN_6785 | 51398 |
| TTCN_2742 | 37340 | GTCN_4372 | 51399 |

FIG. 37 (continued)

| | | | |
|---|---|---|---|
| GTCN_1787 | 37341 | ATCN_4656 | 51400 |
| GTCN_1788 | 37342 | ATCN_4657 | 51401 |
| TTCN_2743 | 37343 | CTCN_8130 | 51402 |
| ATCN_1983 | 37344 | TTCN_6786 | 51403 |
| TTCN_2744 | 37345 | ATCN_4658 | 51404 |
| ATCN_1984 | 37346 | CTCN_8131 | 51405 |
| TTCN_2745 | 37347 | CTCN_8132 | 51406 |
| GTCN_1789 | 37348 | GTCN_4373 | 51407 |
| ATCN_1985 | 37349 | CTCN_8133 | 51408 |
| ATCN_1986 | 37350 | GTCN_4374 | 51409 |
| ATCN_1987 | 37351 | CTCN_8134 | 51410 |
| TTCN_2746 | 37352 | CTCN_8135 | 51411 |
| TTCN_2747 | 37353 | TTCN_6787 | 51412 |
| CTCN_3373 | 37354 | GTCN_4375 | 51413 |
| CTCN_3374 | 37355 | TTCN_6788 | 51414 |
| ATCN_1988 | 37356 | GTCN_4376 | 51415 |
| TTCN_2748 | 37357 | ATCN_4659 | 51416 |
| TTCN_2749 | 37358 | GTCN_4377 | 51417 |
| TTCN_2750 | 37359 | ATCN_4660 | 51418 |
| CTCN_3375 | 37360 | TTCN_6789 | 51419 |
| GTCN_1790 | 37361 | ATCN_4661 | 51420 |
| TTCN_2751 | 37362 | CTCN_8136 | 51421 |
| GTCN_1791 | 37363 | ATCN_4662 | 51422 |
| GTCN_1792 | 37364 | CTCN_8137 | 51423 |
| CTCN_3376 | 37365 | GTCN_4378 | 51424 |
| CTCN_3377 | 37366 | TTCN_6790 | 51425 |
| CTCN_3378 | 37367 | CTCN_8138 | 51426 |
| CTCN_3379 | 37368 | TTCN_6791 | 51427 |
| TTCN_2752 | 37369 | TTCN_6792 | 51428 |
| GTCN_1793 | 37370 | CTCN_8139 | 51429 |
| TTCN_2753 | 37371 | CTCN_8140 | 51430 |
| CTCN_3380 | 37372 | ATCN_4663 | 51431 |
| TTCN_2754 | 37373 | ATCN_4664 | 51432 |
| CTCN_3381 | 37374 | ATCN_4665 | 51433 |
| CTCN_3382 | 37375 | CTCN_8141 | 51434 |
| GTCN_1794 | 37376 | GTCN_4379 | 51435 |
| CTCN_3383 | 37377 | ATCN_4666 | 51436 |
| ATCN_1989 | 37378 | ATCN_4667 | 51437 |
| TTCN_2755 | 37379 | GTCN_4380 | 51438 |
| ATCN_1990 | 37380 | GTCN_4381 | 51439 |
| CTCN_3384 | 37381 | TTCN_6793 | 51440 |
| ATCN_1991 | 37382 | TTCN_6794 | 51441 |
| CTCN_3385 | 37383 | TTCN_6795 | 51442 |

| | | | |
|---|---|---|---|
| CTCN_3386 | 37384 | CTCN_8142 | 51443 |
| GTCN_1795 | 37385 | TTCN_6796 | 51444 |
| CTCN_3387 | 37386 | GTCN_4382 | 51445 |
| TTCN_2756 | 37387 | CTCN_8143 | 51446 |
| ATCN_1992 | 37388 | GTCN_4383 | 51447 |
| TTCN_2757 | 37389 | CTCN_8144 | 51448 |
| TTCN_2758 | 37390 | TTCN_6797 | 51449 |
| ATCN_1993 | 37391 | TTCN_6798 | 51450 |
| GTCN_1796 | 37392 | ATCN_4668 | 51451 |
| CTCN_3388 | 37393 | ATCN_4669 | 51452 |
| GTCN_1797 | 37394 | GTCN_4384 | 51453 |
| GTCN_1798 | 37395 | TTCN_6799 | 51454 |
| GTCN_1799 | 37396 | CTCN_8145 | 51455 |
| TTCN_2759 | 37397 | TTCN_6800 | 51456 |
| TTCN_2760 | 37398 | CTCN_8146 | 51457 |
| TTCN_2761 | 37399 | TTCN_6801 | 51458 |
| ATCN_1994 | 37400 | TTCN_6802 | 51459 |
| ATCN_1995 | 37401 | GTCN_4385 | 51460 |
| TTCN_2762 | 37402 | GTCN_4386 | 51461 |
| CTCN_3389 | 37403 | CTCN_8147 | 51462 |
| CTCN_3390 | 37404 | GTCN_4387 | 51463 |
| TTCN_2763 | 37405 | CTCN_8148 | 51464 |
| CTCN_3391 | 37406 | CTCN_8149 | 51465 |
| CTCN_3392 | 37407 | CTCN_8150 | 51466 |
| CTCN_3393 | 37408 | CTCN_8151 | 51467 |
| TTCN_2764 | 37409 | CTCN_8152 | 51468 |
| CTCN_3394 | 37410 | CTCN_8153 | 51469 |
| CTCN_3395 | 37411 | CTCN_8154 | 51470 |
| ATCN_1996 | 37412 | TTCN_6803 | 51471 |
| GTCN_1800 | 37413 | CTCN_8155 | 51472 |
| CTCN_3396 | 37414 | TTCN_6804 | 51473 |
| CTCN_3397 | 37415 | GTCN_4388 | 51474 |
| CTCN_3398 | 37416 | CTCN_8156 | 51475 |
| TTCN_2765 | 37417 | GTCN_4389 | 51476 |
| CTCN_3399 | 37418 | GTCN_4390 | 51477 |
| CTCN_3400 | 37419 | CTCN_8157 | 51478 |
| CTCN_3401 | 37420 | TTCN_6805 | 51479 |
| CTCN_3402 | 37421 | CTCN_8158 | 51480 |
| ATCN_1997 | 37422 | GTCN_4391 | 51481 |
| ATCN_1998 | 37423 | CTCN_8159 | 51482 |
| ATCN_1999 | 37424 | ATCN_4670 | 51483 |
| ATCN_2000 | 37425 | CTCN_8160 | 51484 |
| TTCN_2766 | 37426 | TTCN_6806 | 51485 |

FIG. 37 (continued)

| | | | | | | | |
|---|---|---|---|---|---|---|---|
| CTCN_3403 | 37427 | CTCN_8161 | 51486 | ATCN_2012 | 37470 | CTCN_8178 | 51529 |
| ATCN_2001 | 37428 | GTCN_4392 | 51487 | CTCN_3413 | 37471 | CTCN_8179 | 51530 |
| CTCN_3404 | 37429 | CTCN_8162 | 51488 | GTCN_1809 | 37472 | CTCN_8180 | 51531 |
| CTCN_3405 | 37430 | TTCN_6807 | 51489 | CTCN_3414 | 37473 | ATCN_4682 | 51532 |
| TTCN_2767 | 37431 | TTCN_6808 | 51490 | GTCN_1810 | 37474 | ATCN_4683 | 51533 |
| GTCN_1801 | 37432 | ATCN_4671 | 51491 | TTCN_2781 | 37475 | CTCN_8181 | 51534 |
| TTCN_2768 | 37433 | TTCN_6809 | 51492 | CTCN_3415 | 37476 | CTCN_8182 | 51535 |
| TTCN_2769 | 37434 | TTCN_6810 | 51493 | CTCN_3416 | 37477 | ATCN_4684 | 51536 |
| TTCN_2770 | 37435 | ATCN_4672 | 51494 | TTCN_2782 | 37478 | CTCN_8183 | 51537 |
| ATCN_2002 | 37436 | TTCN_6811 | 51495 | ATCN_2013 | 37479 | CTCN_8184 | 51538 |
| GTCN_1802 | 37437 | GTCN_4393 | 51496 | TTCN_2783 | 37480 | CTCN_8185 | 51539 |
| TTCN_2771 | 37438 | CTCN_8163 | 51497 | CTCN_3417 | 37481 | CTCN_8186 | 51540 |
| CTCN_3406 | 37439 | CTCN_8164 | 51498 | CTCN_3418 | 37482 | ATCN_4685 | 51541 |
| ATCN_2003 | 37440 | ATCN_4673 | 51499 | CTCN_3419 | 37483 | ATCN_4686 | 51542 |
| CTCN_3407 | 37441 | ATCN_4674 | 51500 | ATCN_2014 | 37484 | CTCN_8187 | 51543 |
| TTCN_2772 | 37442 | CTCN_8165 | 51501 | TTCN_2784 | 37485 | CTCN_8188 | 51544 |
| GTCN_1803 | 37443 | CTCN_8166 | 51502 | CTCN_3420 | 37486 | CTCN_8189 | 51545 |
| ATCN_2004 | 37444 | CTCN_8167 | 51503 | GTCN_1811 | 37487 | GTCN_4395 | 51546 |
| TTCN_2773 | 37445 | ATCN_4675 | 51504 | ATCN_2015 | 37488 | GTCN_4396 | 51547 |
| ATCN_2005 | 37446 | TTCN_6812 | 51505 | TTCN_2785 | 37489 | GTCN_4397 | 51548 |
| ATCN_2006 | 37447 | TTCN_6813 | 51506 | GTCN_1812 | 37490 | ATCN_4687 | 51549 |
| GTCN_1804 | 37448 | CTCN_8168 | 51507 | CTCN_3421 | 37491 | CTCN_8190 | 51550 |
| CTCN_3408 | 37449 | GTCN_4394 | 51508 | CTCN_3422 | 37492 | GTCN_4398 | 51551 |
| TTCN_2774 | 37450 | TTCN_6814 | 51509 | GTCN_1813 | 37493 | ATCN_4688 | 51552 |
| CTCN_3409 | 37451 | ATCN_4676 | 51510 | CTCN_3423 | 37494 | CTCN_8191 | 51553 |
| GTCN_1805 | 37452 | CTCN_8169 | 51511 | ATCN_2016 | 37495 | CTCN_8192 | 51554 |
| TTCN_2775 | 37453 | CTCN_8170 | 51512 | ATCN_2017 | 37496 | CTCN_8193 | 51555 |
| TTCN_2776 | 37454 | CTCN_8171 | 51513 | CTCN_3424 | 37497 | TTCN_6819 | 51556 |
| GTCN_1806 | 37455 | CTCN_8172 | 51514 | CTCN_3425 | 37498 | ATCN_4689 | 51557 |
| CTCN_3410 | 37456 | ATCN_4677 | 51515 | ATCN_2018 | 37499 | ATCN_4690 | 51558 |
| TTCN_2777 | 37457 | ATCN_4678 | 51516 | TTCN_2786 | 37500 | CTCN_8194 | 51559 |
| GTCN_1807 | 37458 | CTCN_8173 | 51517 | TTCN_2787 | 37501 | CTCN_8195 | 51560 |
| TTCN_2778 | 37459 | TTCN_6815 | 51518 | CTCN_3426 | 37502 | TTCN_6820 | 51561 |
| TTCN_2779 | 37460 | ATCN_4679 | 51519 | TTCN_2788 | 37503 | CTCN_8196 | 51562 |
| CTCN_3411 | 37461 | TTCN_6816 | 51520 | TTCN_2789 | 37504 | ATCN_4691 | 51563 |
| TTCN_2780 | 37462 | ATCN_4680 | 51521 | ATCN_2019 | 37505 | CTCN_8197 | 51564 |
| ATCN_2007 | 37463 | CTCN_8174 | 51522 | TTCN_2790 | 37506 | GTCN_4399 | 51565 |
| ATCN_2008 | 37464 | CTCN_8175 | 51523 | CTCN_3427 | 37507 | TTCN_6821 | 51566 |
| ATCN_2009 | 37465 | CTCN_8176 | 51524 | CTCN_3428 | 37508 | GTCN_4400 | 51567 |
| GTCN_1808 | 37466 | TTCN_6817 | 51525 | GTCN_1814 | 37509 | GTCN_4401 | 51568 |
| ATCN_2010 | 37467 | CTCN_8177 | 51526 | GTCN_1815 | 37510 | CTCN_8198 | 51569 |
| CTCN_3412 | 37468 | TTCN_6818 | 51527 | ATCN_2020 | 37511 | TTCN_6822 | 51570 |
| ATCN_2011 | 37469 | ATCN_4681 | 51528 | TTCN_2791 | 37512 | ATCN_4692 | 51571 |

FIG. 37 (continued)

| | | | |
|---|---|---|---|
| TTCN_2792 | 37513 | TTCN_6823 | 51572 |
| ATCN_2021 | 37514 | TTCN_6824 | 51573 |
| CTCN_3429 | 37515 | CTCN_8199 | 51574 |
| GTCN_1816 | 37516 | TTCN_6825 | 51575 |
| GTCN_1817 | 37517 | TTCN_6826 | 51576 |
| TTCN_2793 | 37518 | TTCN_6827 | 51577 |
| CTCN_3430 | 37519 | TTCN_6828 | 51578 |
| TTCN_2794 | 37520 | ATCN_4693 | 51579 |
| CTCN_3431 | 37521 | CTCN_8200 | 51580 |
| CTCN_3432 | 37522 | TTCN_6829 | 51581 |
| CTCN_3433 | 37523 | CTCN_8201 | 51582 |
| CTCN_3434 | 37524 | TTCN_6830 | 51583 |
| TTCN_2795 | 37525 | TTCN_6831 | 51584 |
| CTCN_3435 | 37526 | TTCN_6832 | 51585 |
| TTCN_2796 | 37527 | TTCN_6833 | 51586 |
| CTCN_3436 | 37528 | ATCN_4694 | 51587 |
| ATCN_2022 | 37529 | TTCN_6834 | 51588 |
| CTCN_3437 | 37530 | CTCN_8202 | 51589 |
| ATCN_2023 | 37531 | ATCN_4695 | 51590 |
| CTCN_3438 | 37532 | TTCN_6835 | 51591 |
| TTCN_2797 | 37533 | CTCN_8203 | 51592 |
| GTCN_1818 | 37534 | GTCN_4402 | 51593 |
| CTCN_3439 | 37535 | GTCN_4403 | 51594 |
| ATCN_2024 | 37536 | TTCN_6836 | 51595 |
| ATCN_2025 | 37537 | ATCN_4696 | 51596 |
| ATCN_2026 | 37538 | TTCN_6837 | 51597 |
| CTCN_3440 | 37539 | TTCN_6838 | 51598 |
| TTCN_2798 | 37540 | TTCN_6839 | 51599 |
| TTCN_2799 | 37541 | CTCN_8204 | 51600 |
| GTCN_1819 | 37542 | CTCN_8205 | 51601 |
| TTCN_2800 | 37543 | CTCN_8206 | 51602 |
| TTCN_2801 | 37544 | TTCN_6840 | 51603 |
| TTCN_2802 | 37545 | CTCN_8207 | 51604 |
| TTCN_2803 | 37546 | GTCN_4404 | 51605 |
| CTCN_3441 | 37547 | GTCN_4405 | 51606 |
| TTCN_2804 | 37548 | GTCN_4406 | 51607 |
| TTCN_2805 | 37549 | CTCN_8208 | 51608 |
| GTCN_1820 | 37550 | TTCN_6841 | 51609 |
| CTCN_3442 | 37551 | CTCN_8209 | 51610 |
| GTCN_1821 | 37552 | GTCN_4407 | 51611 |
| ATCN_2027 | 37553 | TTCN_6842 | 51612 |
| ATCN_2028 | 37554 | TTCN_6843 | 51613 |
| CTCN_3443 | 37555 | CTCN_8210 | 51614 |

| | | | |
|---|---|---|---|
| GTCN_1822 | 37556 | GTCN_4408 | 51615 |
| TTCN_2806 | 37557 | TTCN_6844 | 51616 |
| CTCN_3444 | 37558 | ATCN_4697 | 51617 |
| ATCN_2029 | 37559 | GTCN_4409 | 51618 |
| CTCN_3445 | 37560 | ATCN_4698 | 51619 |
| GTCN_1823 | 37561 | CTCN_8211 | 51620 |
| ATCN_2030 | 37562 | GTCN_4410 | 51621 |
| TTCN_2807 | 37563 | GTCN_4411 | 51622 |
| CTCN_3446 | 37564 | CTCN_8212 | 51623 |
| GTCN_1824 | 37565 | CTCN_8213 | 51624 |
| GTCN_1825 | 37566 | GTCN_4412 | 51625 |
| CTCN_3447 | 37567 | CTCN_8214 | 51626 |
| ATCN_2031 | 37568 | GTCN_4413 | 51627 |
| CTCN_3448 | 37569 | ATCN_4699 | 51628 |
| ATCN_2032 | 37570 | ATCN_4700 | 51629 |
| CTCN_3449 | 37571 | GTCN_4414 | 51630 |
| TTCN_2808 | 37572 | CTCN_8215 | 51631 |
| GTCN_1826 | 37573 | TTCN_6845 | 51632 |
| CTCN_3450 | 37574 | CTCN_8216 | 51633 |
| CTCN_3451 | 37575 | CTCN_8217 | 51634 |
| ATCN_2033 | 37576 | ATCN_4701 | 51635 |
| CTCN_3452 | 37577 | CTCN_8218 | 51636 |
| CTCN_3453 | 37578 | CTCN_8219 | 51637 |
| CTCN_3454 | 37579 | ATCN_4702 | 51638 |
| CTCN_3455 | 37580 | ATCN_4703 | 51639 |
| TTCN_2809 | 37581 | CTCN_8220 | 51640 |
| ATCN_2034 | 37582 | GTCN_4415 | 51641 |
| ATCN_2035 | 37583 | CTCN_8221 | 51642 |
| CTCN_3456 | 37584 | TTCN_6846 | 51643 |
| ATCN_2036 | 37585 | GTCN_4416 | 51644 |
| TTCN_2810 | 37586 | GTCN_4417 | 51645 |
| GTCN_1827 | 37587 | TTCN_6847 | 51646 |
| CTCN_3457 | 37588 | GTCN_4418 | 51647 |
| CTCN_3458 | 37589 | CTCN_8222 | 51648 |
| GTCN_1828 | 37590 | ATCN_4704 | 51649 |
| CTCN_3459 | 37591 | TTCN_6848 | 51650 |
| ATCN_2037 | 37592 | CTCN_8223 | 51651 |
| CTCN_3460 | 37593 | CTCN_8224 | 51652 |
| GTCN_1829 | 37594 | CTCN_8225 | 51653 |
| CTCN_3461 | 37595 | CTCN_8226 | 51654 |
| TTCN_2811 | 37596 | TTCN_6849 | 51655 |
| TTCN_2812 | 37597 | ATCN_4705 | 51656 |
| ATCN_2038 | 37598 | TTCN_6850 | 51657 |

FIG. 37 (continued)

| | | | |
|---|---|---|---|
| CTCN_3462 | 37599 | CTCN_8227 | 51658 |
| TTCN_2813 | 37600 | TTCN_6851 | 51659 |
| TTCN_2814 | 37601 | CTCN_8228 | 51660 |
| TTCN_2815 | 37602 | CTCN_8229 | 51661 |
| GTCN_1830 | 37603 | ATCN_4706 | 51662 |
| GTCN_1831 | 37604 | ATCN_4707 | 51663 |
| TTCN_2816 | 37605 | CTCN_8230 | 51664 |
| TTCN_2817 | 37606 | GTCN_4419 | 51665 |
| CTCN_3463 | 37607 | CTCN_8231 | 51666 |
| TTCN_2818 | 37608 | GTCN_4420 | 51667 |
| GTCN_1832 | 37609 | CTCN_8232 | 51668 |
| CTCN_3464 | 37610 | ATCN_4708 | 51669 |
| TTCN_2819 | 37611 | CTCN_8233 | 51670 |
| TTCN_2820 | 37612 | CTCN_8234 | 51671 |
| TTCN_2821 | 37613 | GTCN_4421 | 51672 |
| TTCN_2822 | 37614 | CTCN_8235 | 51673 |
| GTCN_1833 | 37615 | ATCN_4709 | 51674 |
| GTCN_1834 | 37616 | TTCN_6852 | 51675 |
| CTCN_3465 | 37617 | CTCN_8236 | 51676 |
| CTCN_3466 | 37618 | CTCN_8237 | 51677 |
| TTCN_2823 | 37619 | GTCN_4422 | 51678 |
| ATCN_2039 | 37620 | GTCN_4423 | 51679 |
| ATCN_2040 | 37621 | TTCN_6853 | 51680 |
| CTCN_3467 | 37622 | ATCN_4710 | 51681 |
| TTCN_2824 | 37623 | ATCN_4711 | 51682 |
| TTCN_2825 | 37624 | CTCN_8238 | 51683 |
| TTCN_2826 | 37625 | ATCN_4712 | 51684 |
| TTCN_2827 | 37626 | TTCN_6854 | 51685 |
| ATCN_2041 | 37627 | GTCN_4424 | 51686 |
| GTCN_1835 | 37628 | TTCN_6855 | 51687 |
| CTCN_3468 | 37629 | CTCN_8239 | 51688 |
| GTCN_1836 | 37630 | CTCN_8240 | 51689 |
| CTCN_3469 | 37631 | ATCN_4713 | 51690 |
| ATCN_2042 | 37632 | GTCN_4425 | 51691 |
| CTCN_3470 | 37633 | GTCN_4426 | 51692 |
| TTCN_2828 | 37634 | ATCN_4714 | 51693 |
| ATCN_2043 | 37635 | GTCN_4427 | 51694 |
| TTCN_2829 | 37636 | CTCN_8241 | 51695 |
| CTCN_3471 | 37637 | CTCN_8242 | 51696 |
| CTCN_3472 | 37638 | GTCN_4428 | 51697 |
| TTCN_2830 | 37639 | CTCN_8243 | 51698 |
| GTCN_1837 | 37640 | TTCN_6856 | 51699 |
| CTCN_3473 | 37641 | TTCN_6857 | 51700 |

| | | | |
|---|---|---|---|
| CTCN_3474 | 37642 | TTCN_6858 | 51701 |
| ATCN_2044 | 37643 | TTCN_6859 | 51702 |
| TTCN_2831 | 37644 | TTCN_6860 | 51703 |
| TTCN_2832 | 37645 | ATCN_4715 | 51704 |
| TTCN_2833 | 37646 | TTCN_6861 | 51705 |
| CTCN_3475 | 37647 | GTCN_4429 | 51706 |
| TTCN_2834 | 37648 | CTCN_8244 | 51707 |
| CTCN_3476 | 37649 | TTCN_6862 | 51708 |
| GTCN_1838 | 37650 | CTCN_8245 | 51709 |
| GTCN_1839 | 37651 | TTCN_6863 | 51710 |
| ATCN_2045 | 37652 | ATCN_4716 | 51711 |
| CTCN_3477 | 37653 | TTCN_6864 | 51712 |
| TTCN_2835 | 37654 | CTCN_8246 | 51713 |
| CTCN_3478 | 37655 | GTCN_4430 | 51714 |
| CTCN_3479 | 37656 | TTCN_6865 | 51715 |
| ATCN_2046 | 37657 | CTCN_8247 | 51716 |
| GTCN_1840 | 37658 | ATCN_4717 | 51717 |
| CTCN_3480 | 37659 | TTCN_6866 | 51718 |
| CTCN_3481 | 37660 | TTCN_6867 | 51719 |
| CTCN_3482 | 37661 | GTCN_4431 | 51720 |
| GTCN_1841 | 37662 | TTCN_6868 | 51721 |
| CTCN_3483 | 37663 | TTCN_6869 | 51722 |
| ATCN_2047 | 37664 | TTCN_6870 | 51723 |
| ATCN_2048 | 37665 | CTCN_8248 | 51724 |
| ATCN_2049 | 37666 | GTCN_4432 | 51725 |
| GTCN_1842 | 37667 | CTCN_8249 | 51726 |
| CTCN_3484 | 37668 | CTCN_8250 | 51727 |
| CTCN_3485 | 37669 | TTCN_6871 | 51728 |
| GTCN_1843 | 37670 | CTCN_8251 | 51729 |
| GTCN_1844 | 37671 | GTCN_4433 | 51730 |
| ATCN_2050 | 37672 | TTCN_6872 | 51731 |
| ATCN_2051 | 37673 | ATCN_4718 | 51732 |
| TTCN_2836 | 37674 | CTCN_8252 | 51733 |
| TTCN_2837 | 37675 | TTCN_6873 | 51734 |
| GTCN_1845 | 37676 | CTCN_8253 | 51735 |
| TTCN_2838 | 37677 | GTCN_4434 | 51736 |
| CTCN_3486 | 37678 | ATCN_4719 | 51737 |
| CTCN_3487 | 37679 | CTCN_8254 | 51738 |
| GTCN_1846 | 37680 | GTCN_4435 | 51739 |
| CTCN_3488 | 37681 | CTCN_8255 | 51740 |
| CTCN_3489 | 37682 | CTCN_8256 | 51741 |
| TTCN_2839 | 37683 | TTCN_6874 | 51742 |
| GTCN_1847 | 37684 | TTCN_6875 | 51743 |

FIG. 37 (continued)

| | | | |
|---|---|---|---|
| CTCN_3490 | 37685 | CTCN_8257 | 51744 |
| GTCN_1848 | 37686 | GTCN_4436 | 51745 |
| GTCN_1849 | 37687 | TTCN_6876 | 51746 |
| GTCN_1850 | 37688 | GTCN_4437 | 51747 |
| TTCN_2840 | 37689 | GTCN_4438 | 51748 |
| GTCN_1851 | 37690 | CTCN_8258 | 51749 |
| CTCN_3491 | 37691 | CTCN_8259 | 51750 |
| GTCN_1852 | 37692 | CTCN_8260 | 51751 |
| GTCN_1853 | 37693 | TTCN_6877 | 51752 |
| ATCN_2052 | 37694 | CTCN_8261 | 51753 |
| CTCN_3492 | 37695 | GTCN_4439 | 51754 |
| TTCN_2841 | 37696 | CTCN_8262 | 51755 |
| TTCN_2842 | 37697 | ATCN_4720 | 51756 |
| CTCN_3493 | 37698 | ATCN_4721 | 51757 |
| GTCN_1854 | 37699 | ATCN_4722 | 51758 |
| TTCN_2843 | 37700 | TTCN_6878 | 51759 |
| GTCN_1855 | 37701 | ATCN_4723 | 51760 |
| GTCN_1856 | 37702 | TTCN_6879 | 51761 |
| CTCN_3494 | 37703 | ATCN_4724 | 51762 |
| TTCN_2844 | 37704 | CTCN_8263 | 51763 |
| CTCN_3495 | 37705 | CTCN_8264 | 51764 |
| ATCN_2053 | 37706 | CTCN_8265 | 51765 |
| TTCN_2845 | 37707 | TTCN_6880 | 51766 |
| ATCN_2054 | 37708 | GTCN_4440 | 51767 |
| TTCN_2846 | 37709 | CTCN_8266 | 51768 |
| ATCN_2055 | 37710 | ATCN_4725 | 51769 |
| TTCN_2847 | 37711 | GTCN_4441 | 51770 |
| ATCN_2056 | 37712 | TTCN_6881 | 51771 |
| ATCN_2057 | 37713 | CTCN_8267 | 51772 |
| GTCN_1857 | 37714 | ATCN_4726 | 51773 |
| GTCN_1858 | 37715 | TTCN_6882 | 51774 |
| CTCN_3496 | 37716 | TTCN_6883 | 51775 |
| TTCN_2848 | 37717 | CTCN_8268 | 51776 |
| CTCN_3497 | 37718 | ATCN_4727 | 51777 |
| ATCN_2058 | 37719 | CTCN_8269 | 51778 |
| ATCN_2059 | 37720 | TTCN_6884 | 51779 |
| GTCN_1859 | 37721 | ATCN_4728 | 51780 |
| CTCN_3498 | 37722 | TTCN_6885 | 51781 |
| CTCN_3499 | 37723 | CTCN_8270 | 51782 |
| GTCN_1860 | 37724 | CTCN_8271 | 51783 |
| CTCN_3500 | 37725 | TTCN_6886 | 51784 |
| ATCN_2060 | 37726 | ATCN_4729 | 51785 |
| ATCN_2061 | 37727 | ATCN_4730 | 51786 |

| | | | |
|---|---|---|---|
| CTCN_3501 | 37728 | CTCN_8272 | 51787 |
| CTCN_3502 | 37729 | TTCN_6887 | 51788 |
| CTCN_3503 | 37730 | TTCN_6888 | 51789 |
| ATCN_2062 | 37731 | TTCN_6889 | 51790 |
| TTCN_2849 | 37732 | ATCN_4731 | 51791 |
| CTCN_3504 | 37733 | ATCN_4732 | 51792 |
| TTCN_2850 | 37734 | TTCN_6890 | 51793 |
| CTCN_3505 | 37735 | ATCN_4733 | 51794 |
| ATCN_2063 | 37736 | TTCN_6891 | 51795 |
| CTCN_3506 | 37737 | TTCN_6892 | 51796 |
| GTCN_1861 | 37738 | GTCN_4442 | 51797 |
| TTCN_2851 | 37739 | TTCN_6893 | 51798 |
| CTCN_3507 | 37740 | GTCN_4443 | 51799 |
| CTCN_3508 | 37741 | ATCN_4734 | 51800 |
| CTCN_3509 | 37742 | ATCN_4735 | 51801 |
| CTCN_3510 | 37743 | TTCN_6894 | 51802 |
| TTCN_2852 | 37744 | ATCN_4736 | 51803 |
| ATCN_2064 | 37745 | GTCN_4444 | 51804 |
| GTCN_1862 | 37746 | TTCN_6895 | 51805 |
| GTCN_1863 | 37747 | CTCN_8273 | 51806 |
| CTCN_3511 | 37748 | TTCN_6896 | 51807 |
| CTCN_3512 | 37749 | TTCN_6897 | 51808 |
| CTCN_3513 | 37750 | CTCN_8274 | 51809 |
| ATCN_2065 | 37751 | CTCN_8275 | 51810 |
| CTCN_3514 | 37752 | ATCN_4737 | 51811 |
| ATCN_2066 | 37753 | CTCN_8276 | 51812 |
| CTCN_3515 | 37754 | ATCN_4738 | 51813 |
| CTCN_3516 | 37755 | ATCN_4739 | 51814 |
| TTCN_2853 | 37756 | CTCN_8277 | 51815 |
| ATCN_2067 | 37757 | GTCN_4445 | 51816 |
| TTCN_2854 | 37758 | ATCN_4740 | 51817 |
| TTCN_2855 | 37759 | ATCN_4741 | 51818 |
| TTCN_2856 | 37760 | CTCN_8278 | 51819 |
| CTCN_3517 | 37761 | TTCN_6898 | 51820 |
| GTCN_1864 | 37762 | CTCN_8279 | 51821 |
| ATCN_2068 | 37763 | TTCN_6899 | 51822 |
| ATCN_2069 | 37764 | GTCN_4446 | 51823 |
| CTCN_3518 | 37765 | ATCN_4742 | 51824 |
| TTCN_2857 | 37766 | TTCN_6900 | 51825 |
| CTCN_3519 | 37767 | CTCN_8280 | 51826 |
| GTCN_1865 | 37768 | GTCN_4447 | 51827 |
| TTCN_2858 | 37769 | CTCN_8281 | 51828 |
| GTCN_1866 | 37770 | CTCN_8282 | 51829 |

FIG. 37 (continued)

| | | | |
|---|---|---|---|
| TTCN_2859 | 37771 | GTCN_4448 | 51830 |
| ATCN_2070 | 37772 | ATCN_4743 | 51831 |
| ATCN_2071 | 37773 | CTCN_8283 | 51832 |
| TTCN_2860 | 37774 | CTCN_8284 | 51833 |
| CTCN_3520 | 37775 | CTCN_8285 | 51834 |
| GTCN_1867 | 37776 | CTCN_8286 | 51835 |
| ATCN_2072 | 37777 | TTCN_6901 | 51836 |
| GTCN_1868 | 37778 | ATCN_4744 | 51837 |
| CTCN_3521 | 37779 | TTCN_6902 | 51838 |
| CTCN_3522 | 37780 | CTCN_8287 | 51839 |
| CTCN_3523 | 37781 | CTCN_8288 | 51840 |
| TTCN_2861 | 37782 | CTCN_8289 | 51841 |
| ATCN_2073 | 37783 | ATCN_4745 | 51842 |
| TTCN_2862 | 37784 | CTCN_8290 | 51843 |
| TTCN_2863 | 37785 | CTCN_8291 | 51844 |
| GTCN_1869 | 37786 | GTCN_4449 | 51845 |
| CTCN_3524 | 37787 | CTCN_8292 | 51846 |
| CTCN_3525 | 37788 | CTCN_8293 | 51847 |
| ATCN_2074 | 37789 | CTCN_8294 | 51848 |
| CTCN_3526 | 37790 | TTCN_6903 | 51849 |
| ATCN_2075 | 37791 | TTCN_6904 | 51850 |
| ATCN_2076 | 37792 | TTCN_6905 | 51851 |
| CTCN_3527 | 37793 | TTCN_6906 | 51852 |
| GTCN_1870 | 37794 | CTCN_8295 | 51853 |
| CTCN_3528 | 37795 | TTCN_6907 | 51854 |
| TTCN_2864 | 37796 | TTCN_6908 | 51855 |
| TTCN_2865 | 37797 | TTCN_6909 | 51856 |
| GTCN_1871 | 37798 | ATCN_4746 | 51857 |
| TTCN_2866 | 37799 | CTCN_8296 | 51858 |
| ATCN_2077 | 37800 | ATCN_4747 | 51859 |
| CTCN_3529 | 37801 | GTCN_4450 | 51860 |
| TTCN_2867 | 37802 | ATCN_4748 | 51861 |
| CTCN_3530 | 37803 | TTCN_6910 | 51862 |
| TTCN_2868 | 37804 | TTCN_6911 | 51863 |
| TTCN_2869 | 37805 | TTCN_6912 | 51864 |
| ATCN_2078 | 37806 | CTCN_8297 | 51865 |
| CTCN_3531 | 37807 | TTCN_6913 | 51866 |
| CTCN_3532 | 37808 | CTCN_8298 | 51867 |
| CTCN_3533 | 37809 | GTCN_4451 | 51868 |
| ATCN_2079 | 37810 | ATCN_4749 | 51869 |
| CTCN_3534 | 37811 | CTCN_8299 | 51870 |
| GTCN_1872 | 37812 | GTCN_4452 | 51871 |
| CTCN_3535 | 37813 | TTCN_6914 | 51872 |

| | | | |
|---|---|---|---|
| CTCN_3536 | 37814 | TTCN_6915 | 51873 |
| GTCN_1873 | 37815 | GTCN_4453 | 51874 |
| CTCN_3537 | 37816 | GTCN_4454 | 51875 |
| GTCN_1874 | 37817 | GTCN_4455 | 51876 |
| CTCN_3538 | 37818 | ATCN_4750 | 51877 |
| TTCN_2870 | 37819 | TTCN_6916 | 51878 |
| TTCN_2871 | 37820 | CTCN_8300 | 51879 |
| CTCN_3539 | 37821 | CTCN_8301 | 51880 |
| GTCN_1875 | 37822 | CTCN_8302 | 51881 |
| CTCN_3540 | 37823 | TTCN_6917 | 51882 |
| TTCN_2872 | 37824 | GTCN_4456 | 51883 |
| CTCN_3541 | 37825 | ATCN_4751 | 51884 |
| TTCN_2873 | 37826 | TTCN_6918 | 51885 |
| CTCN_3542 | 37827 | CTCN_8303 | 51886 |
| CTCN_3543 | 37828 | TTCN_6919 | 51887 |
| CTCN_3544 | 37829 | TTCN_6920 | 51888 |
| TTCN_2874 | 37830 | TTCN_6921 | 51889 |
| TTCN_2875 | 37831 | CTCN_8304 | 51890 |
| CTCN_3545 | 37832 | CTCN_8305 | 51891 |
| TTCN_2876 | 37833 | TTCN_6922 | 51892 |
| TTCN_2877 | 37834 | CTCN_8306 | 51893 |
| CTCN_3546 | 37835 | TTCN_6923 | 51894 |
| CTCN_3547 | 37836 | TTCN_6924 | 51895 |
| CTCN_3548 | 37837 | TTCN_6925 | 51896 |
| GTCN_1876 | 37838 | CTCN_8307 | 51897 |
| TTCN_2878 | 37839 | TTCN_6926 | 51898 |
| TTCN_2879 | 37840 | CTCN_8308 | 51899 |
| CTCN_3549 | 37841 | TTCN_6927 | 51900 |
| CTCN_3550 | 37842 | TTCN_6928 | 51901 |
| CTCN_3551 | 37843 | TTCN_6929 | 51902 |
| CTCN_3552 | 37844 | TTCN_6930 | 51903 |
| CTCN_3553 | 37845 | GTCN_4457 | 51904 |
| TTCN_2880 | 37846 | TTCN_6931 | 51905 |
| CTCN_3554 | 37847 | CTCN_8309 | 51906 |
| CTCN_3555 | 37848 | ATCN_4752 | 51907 |
| TTCN_2881 | 37849 | ATCN_4753 | 51908 |
| TTCN_2882 | 37850 | ATCN_4754 | 51909 |
| TTCN_2883 | 37851 | TTCN_6932 | 51910 |
| ATCN_2080 | 37852 | CTCN_8310 | 51911 |
| GTCN_1877 | 37853 | ATCN_4755 | 51912 |
| TTCN_2884 | 37854 | TTCN_6933 | 51913 |
| ATCN_2081 | 37855 | CTCN_8311 | 51914 |
| GTCN_1878 | 37856 | CTCN_8312 | 51915 |

FIG. 37 (continued)

| | | | |
|---|---|---|---|
| GTCN_1879 | 37857 | CTCN_8313 | 51916 |
| ATCN_2082 | 37858 | ATCN_4756 | 51917 |
| TTCN_2885 | 37859 | ATCN_4757 | 51918 |
| GTCN_1880 | 37860 | CTCN_8314 | 51919 |
| GTCN_1881 | 37861 | CTCN_8315 | 51920 |
| TTCN_2886 | 37862 | GTCN_4458 | 51921 |
| GTCN_1882 | 37863 | GTCN_4459 | 51922 |
| ATCN_2083 | 37864 | GTCN_4460 | 51923 |
| TTCN_2887 | 37865 | CTCN_8316 | 51924 |
| CTCN_3556 | 37866 | CTCN_8317 | 51925 |
| ATCN_2084 | 37867 | CTCN_8318 | 51926 |
| TTCN_2888 | 37868 | GTCN_4461 | 51927 |
| CTCN_3557 | 37869 | CTCN_8319 | 51928 |
| ATCN_2085 | 37870 | TTCN_6934 | 51929 |
| CTCN_3558 | 37871 | TTCN_6935 | 51930 |
| ATCN_2086 | 37872 | CTCN_8320 | 51931 |
| ATCN_2087 | 37873 | CTCN_8321 | 51932 |
| CTCN_3559 | 37874 | TTCN_6936 | 51933 |
| GTCN_1883 | 37875 | CTCN_8322 | 51934 |
| CTCN_3560 | 37876 | CTCN_8323 | 51935 |
| TTCN_2889 | 37877 | GTCN_4462 | 51936 |
| GTCN_1884 | 37878 | GTCN_4463 | 51937 |
| TTCN_2890 | 37879 | GTCN_4464 | 51938 |
| GTCN_1885 | 37880 | CTCN_8324 | 51939 |
| CTCN_3561 | 37881 | GTCN_4465 | 51940 |
| ATCN_2088 | 37882 | CTCN_8325 | 51941 |
| CTCN_3562 | 37883 | TTCN_6937 | 51942 |
| CTCN_3563 | 37884 | CTCN_8326 | 51943 |
| GTCN_1886 | 37885 | TTCN_6938 | 51944 |
| CTCN_3564 | 37886 | CTCN_8327 | 51945 |
| TTCN_2891 | 37887 | CTCN_8328 | 51946 |
| ATCN_2089 | 37888 | TTCN_6939 | 51947 |
| TTCN_2892 | 37889 | CTCN_8329 | 51948 |
| CTCN_3565 | 37890 | TTCN_6940 | 51949 |
| CTCN_3566 | 37891 | TTCN_6941 | 51950 |
| CTCN_3567 | 37892 | TTCN_6942 | 51951 |
| ATCN_2090 | 37893 | TTCN_6943 | 51952 |
| TTCN_2893 | 37894 | TTCN_6944 | 51953 |
| CTCN_3568 | 37895 | TTCN_6945 | 51954 |
| CTCN_3569 | 37896 | CTCN_8330 | 51955 |
| GTCN_1887 | 37897 | TTCN_6946 | 51956 |
| CTCN_3570 | 37898 | GTCN_4466 | 51957 |
| TTCN_2894 | 37899 | TTCN_6947 | 51958 |

| | | | |
|---|---|---|---|
| TTCN_2895 | 37900 | TTCN_6948 | 51959 |
| ATCN_2091 | 37901 | TTCN_6949 | 51960 |
| ATCN_2092 | 37902 | CTCN_8331 | 51961 |
| TTCN_2896 | 37903 | GTCN_4467 | 51962 |
| GTCN_1888 | 37904 | TTCN_6950 | 51963 |
| ATCN_2093 | 37905 | ATCN_4758 | 51964 |
| ATCN_2094 | 37906 | TTCN_6951 | 51965 |
| ATCN_2095 | 37907 | CTCN_8332 | 51966 |
| ATCN_2096 | 37908 | CTCN_8333 | 51967 |
| GTCN_1889 | 37909 | GTCN_4468 | 51968 |
| ATCN_2097 | 37910 | TTCN_6952 | 51969 |
| GTCN_1890 | 37911 | CTCN_8334 | 51970 |
| GTCN_1891 | 37912 | CTCN_8335 | 51971 |
| CTCN_3571 | 37913 | CTCN_8336 | 51972 |
| TTCN_2897 | 37914 | CTCN_8337 | 51973 |
| CTCN_3572 | 37915 | CTCN_8338 | 51974 |
| GTCN_1892 | 37916 | CTCN_8339 | 51975 |
| CTCN_3573 | 37917 | GTCN_4469 | 51976 |
| CTCN_3574 | 37918 | GTCN_4470 | 51977 |
| ATCN_2098 | 37919 | GTCN_4471 | 51978 |
| CTCN_3575 | 37920 | CTCN_8340 | 51979 |
| CTCN_3576 | 37921 | CTCN_8341 | 51980 |
| ATCN_2099 | 37922 | CTCN_8342 | 51981 |
| GTCN_1893 | 37923 | GTCN_4472 | 51982 |
| GTCN_1894 | 37924 | GTCN_4473 | 51983 |
| ATCN_2100 | 37925 | CTCN_8343 | 51984 |
| ATCN_2101 | 37926 | CTCN_8344 | 51985 |
| TTCN_2898 | 37927 | TTCN_6953 | 51986 |
| CTCN_3577 | 37928 | CTCN_8345 | 51987 |
| CTCN_3578 | 37929 | TTCN_6954 | 51988 |
| TTCN_2899 | 37930 | GTCN_4474 | 51989 |
| TTCN_2900 | 37931 | CTCN_8346 | 51990 |
| CTCN_3579 | 37932 | TTCN_6955 | 51991 |
| CTCN_3580 | 37933 | TTCN_6956 | 51992 |
| CTCN_3581 | 37934 | CTCN_8347 | 51993 |
| CTCN_3582 | 37935 | GTCN_4475 | 51994 |
| CTCN_3583 | 37936 | GTCN_4476 | 51995 |
| GTCN_1895 | 37937 | TTCN_6957 | 51996 |
| TTCN_2901 | 37938 | GTCN_4477 | 51997 |
| TTCN_2902 | 37939 | CTCN_8348 | 51998 |
| CTCN_3584 | 37940 | TTCN_6958 | 51999 |
| TTCN_2903 | 37941 | CTCN_8349 | 52000 |
| CTCN_3585 | 37942 | GTCN_4478 | 52001 |

FIG. 37 (continued)

| | | | |
|---|---|---|---|
| CTCN_3586 | 37943 | TTCN_6959 | 52002 |
| TTCN_2904 | 37944 | GTCN_4479 | 52003 |
| TTCN_2905 | 37945 | CTCN_8350 | 52004 |
| CTCN_3587 | 37946 | TTCN_6960 | 52005 |
| ATCN_2102 | 37947 | GTCN_4480 | 52006 |
| TTCN_2906 | 37948 | CTCN_8351 | 52007 |
| TTCN_2907 | 37949 | CTCN_8352 | 52008 |
| TTCN_2908 | 37950 | TTCN_6961 | 52009 |
| TTCN_2909 | 37951 | TTCN_6962 | 52010 |
| GTCN_1896 | 37952 | TTCN_6963 | 52011 |
| TTCN_2910 | 37953 | GTCN_4481 | 52012 |
| ATCN_2103 | 37954 | CTCN_8353 | 52013 |
| ATCN_2104 | 37955 | GTCN_4482 | 52014 |
| CTCN_3588 | 37956 | CTCN_8354 | 52015 |
| CTCN_3589 | 37957 | CTCN_8355 | 52016 |
| ATCN_2105 | 37958 | GTCN_4483 | 52017 |
| CTCN_3590 | 37959 | GTCN_4484 | 52018 |
| TTCN_2911 | 37960 | TTCN_6964 | 52019 |
| TTCN_2912 | 37961 | CTCN_8356 | 52020 |
| CTCN_3591 | 37962 | ATCN_4759 | 52021 |
| ATCN_2106 | 37963 | ATCN_4760 | 52022 |
| ATCN_2107 | 37964 | CTCN_8357 | 52023 |
| CTCN_3592 | 37965 | GTCN_4485 | 52024 |
| TTCN_2913 | 37966 | CTCN_8358 | 52025 |
| GTCN_1897 | 37967 | TTCN_6965 | 52026 |
| TTCN_2914 | 37968 | CTCN_8359 | 52027 |
| CTCN_3593 | 37969 | TTCN_6966 | 52028 |
| GTCN_1898 | 37970 | CTCN_8360 | 52029 |
| CTCN_3594 | 37971 | CTCN_8361 | 52030 |
| TTCN_2915 | 37972 | CTCN_8362 | 52031 |
| TTCN_2916 | 37973 | GTCN_4486 | 52032 |
| ATCN_2108 | 37974 | TTCN_6967 | 52033 |
| CTCN_3595 | 37975 | CTCN_8363 | 52034 |
| GTCN_1899 | 37976 | ATCN_4761 | 52035 |
| TTCN_2917 | 37977 | GTCN_4487 | 52036 |
| CTCN_3596 | 37978 | CTCN_8364 | 52037 |
| ATCN_2109 | 37979 | GTCN_4488 | 52038 |
| TTCN_2918 | 37980 | CTCN_8365 | 52039 |
| TTCN_2919 | 37981 | TTCN_6968 | 52040 |
| ATCN_2110 | 37982 | CTCN_8366 | 52041 |
| CTCN_3597 | 37983 | CTCN_8367 | 52042 |
| CTCN_3598 | 37984 | TTCN_6969 | 52043 |
| CTCN_3599 | 37985 | ATCN_4762 | 52044 |

| | | | |
|---|---|---|---|
| GTCN_1900 | 37986 | CTCN_8368 | 52045 |
| ATCN_2111 | 37987 | CTCN_8369 | 52046 |
| ATCN_2112 | 37988 | CTCN_8370 | 52047 |
| CTCN_3600 | 37989 | CTCN_8371 | 52048 |
| GTCN_1901 | 37990 | GTCN_4489 | 52049 |
| CTCN_3601 | 37991 | GTCN_4490 | 52050 |
| CTCN_3602 | 37992 | GTCN_4491 | 52051 |
| TTCN_2920 | 37993 | ATCN_4763 | 52052 |
| TTCN_2921 | 37994 | TTCN_6970 | 52053 |
| GTCN_1902 | 37995 | CTCN_8372 | 52054 |
| CTCN_3603 | 37996 | CTCN_8373 | 52055 |
| ATCN_2113 | 37997 | CTCN_8374 | 52056 |
| CTCN_3604 | 37998 | GTCN_4492 | 52057 |
| CTCN_3605 | 37999 | CTCN_8375 | 52058 |
| CTCN_3606 | 38000 | CTCN_8376 | 52059 |
| TTCN_2922 | 38001 | CTCN_8377 | 52060 |
| TTCN_2923 | 38002 | TTCN_6971 | 52061 |
| TTCN_2924 | 38003 | CTCN_8378 | 52062 |
| CTCN_3607 | 38004 | CTCN_8379 | 52063 |
| GTCN_1903 | 38005 | GTCN_4493 | 52064 |
| CTCN_3608 | 38006 | CTCN_8380 | 52065 |
| ATCN_2114 | 38007 | CTCN_8381 | 52066 |
| CTCN_3609 | 38008 | ATCN_4764 | 52067 |
| GTCN_1904 | 38009 | ATCN_4765 | 52068 |
| CTCN_3610 | 38010 | CTCN_8382 | 52069 |
| GTCN_1905 | 38011 | CTCN_8383 | 52070 |
| CTCN_3611 | 38012 | CTCN_8384 | 52071 |
| GTCN_1906 | 38013 | TTCN_6972 | 52072 |
| CTCN_3612 | 38014 | CTCN_8385 | 52073 |
| TTCN_2925 | 38015 | CTCN_8386 | 52074 |
| TTCN_2926 | 38016 | TTCN_6973 | 52075 |
| TTCN_2927 | 38017 | GTCN_4494 | 52076 |
| CTCN_3613 | 38018 | CTCN_8387 | 52077 |
| CTCN_3614 | 38019 | GTCN_4495 | 52078 |
| CTCN_3615 | 38020 | GTCN_4496 | 52079 |
| GTCN_1907 | 38021 | CTCN_8388 | 52080 |
| ATCN_2115 | 38022 | GTCN_4497 | 52081 |
| CTCN_3616 | 38023 | ATCN_4766 | 52082 |
| ATCN_2116 | 38024 | TTCN_6974 | 52083 |
| GTCN_1908 | 38025 | CTCN_8389 | 52084 |
| TTCN_2928 | 38026 | CTCN_8390 | 52085 |
| ATCN_2117 | 38027 | CTCN_8391 | 52086 |
| TTCN_2929 | 38028 | ATCN_4767 | 52087 |

FIG. 37 (continued)

| | | | |
|---|---|---|---|
| CTCN_3617 | 38029 | ATCN_4768 | 52088 |
| GTCN_1909 | 38030 | TTCN_6975 | 52089 |
| ATCN_2118 | 38031 | CTCN_8392 | 52090 |
| TTCN_2930 | 38032 | CTCN_8393 | 52091 |
| TTCN_2931 | 38033 | CTCN_8394 | 52092 |
| TTCN_2932 | 38034 | CTCN_8395 | 52093 |
| ATCN_2119 | 38035 | CTCN_8396 | 52094 |
| CTCN_3618 | 38036 | CTCN_8397 | 52095 |
| CTCN_3619 | 38037 | CTCN_8398 | 52096 |
| TTCN_2933 | 38038 | CTCN_8399 | 52097 |
| TTCN_2934 | 38039 | CTCN_8400 | 52098 |
| CTCN_3620 | 38040 | GTCN_4498 | 52099 |
| ATCN_2120 | 38041 | GTCN_4499 | 52100 |
| GTCN_1910 | 38042 | CTCN_8401 | 52101 |
| TTCN_2935 | 38043 | ATCN_4769 | 52102 |
| CTCN_3621 | 38044 | TTCN_6976 | 52103 |
| ATCN_2121 | 38045 | CTCN_8402 | 52104 |
| TTCN_2936 | 38046 | ATCN_4770 | 52105 |
| CTCN_3622 | 38047 | CTCN_8403 | 52106 |
| GTCN_1911 | 38048 | CTCN_8404 | 52107 |
| CTCN_3623 | 38049 | GTCN_4500 | 52108 |
| CTCN_3624 | 38050 | CTCN_8405 | 52109 |
| ATCN_2122 | 38051 | ATCN_4771 | 52110 |
| TTCN_2937 | 38052 | ATCN_4772 | 52111 |
| CTCN_3625 | 38053 | CTCN_8406 | 52112 |
| CTCN_3626 | 38054 | CTCN_8407 | 52113 |
| GTCN_1912 | 38055 | GTCN_4501 | 52114 |
| CTCN_3627 | 38056 | CTCN_8408 | 52115 |
| ATCN_2123 | 38057 | TTCN_6977 | 52116 |
| GTCN_1913 | 38058 | CTCN_8409 | 52117 |
| TTCN_2938 | 38059 | GTCN_4502 | 52118 |
| TTCN_2939 | 38060 | TTCN_6978 | 52119 |
| ATCN_2124 | 38061 | GTCN_4503 | 52120 |
| GTCN_1914 | 38062 | CTCN_8410 | 52121 |
| GTCN_1915 | 38063 | ATCN_4773 | 52122 |
| TTCN_2940 | 38064 | CTCN_8411 | 52123 |
| TTCN_2941 | 38065 | CTCN_8412 | 52124 |
| TTCN_2942 | 38066 | CTCN_8413 | 52125 |
| ATCN_2125 | 38067 | CTCN_8414 | 52126 |
| TTCN_2943 | 38068 | TTCN_6979 | 52127 |
| ATCN_2126 | 38069 | ATCN_4774 | 52128 |
| TTCN_2944 | 38070 | TTCN_6980 | 52129 |
| CTCN_3628 | 38071 | CTCN_8415 | 52130 |

| | | | |
|---|---|---|---|
| TTCN_2945 | 38072 | ATCN_4775 | 52131 |
| ATCN_2127 | 38073 | CTCN_8416 | 52132 |
| ATCN_2128 | 38074 | CTCN_8417 | 52133 |
| ATCN_2129 | 38075 | CTCN_8418 | 52134 |
| TTCN_2946 | 38076 | CTCN_8419 | 52135 |
| ATCN_2130 | 38077 | GTCN_4504 | 52136 |
| TTCN_2947 | 38078 | GTCN_4505 | 52137 |
| TTCN_2948 | 38079 | GTCN_4506 | 52138 |
| TTCN_2949 | 38080 | ATCN_4776 | 52139 |
| ATCN_2131 | 38081 | TTCN_6981 | 52140 |
| ATCN_2132 | 38082 | TTCN_6982 | 52141 |
| TTCN_2950 | 38083 | CTCN_8420 | 52142 |
| TTCN_2951 | 38084 | CTCN_8421 | 52143 |
| ATCN_2133 | 38085 | GTCN_4507 | 52144 |
| TTCN_2952 | 38086 | GTCN_4508 | 52145 |
| TTCN_2953 | 38087 | CTCN_8422 | 52146 |
| ATCN_2134 | 38088 | ATCN_4777 | 52147 |
| ATCN_2135 | 38089 | CTCN_8423 | 52148 |
| GTCN_1916 | 38090 | TTCN_6983 | 52149 |
| ATCN_2136 | 38091 | TTCN_6984 | 52150 |
| CTCN_3629 | 38092 | TTCN_6985 | 52151 |
| ATCN_2137 | 38093 | GTCN_4509 | 52152 |
| ATCN_2138 | 38094 | CTCN_8424 | 52153 |
| ATCN_2139 | 38095 | CTCN_8425 | 52154 |
| TTCN_2954 | 38096 | TTCN_6986 | 52155 |
| TTCN_2955 | 38097 | CTCN_8426 | 52156 |
| ATCN_2140 | 38098 | CTCN_8427 | 52157 |
| CTCN_3630 | 38099 | ATCN_4778 | 52158 |
| TTCN_2956 | 38100 | ATCN_4779 | 52159 |
| ATCN_2141 | 38101 | GTCN_4510 | 52160 |
| TTCN_2957 | 38102 | ATCN_4780 | 52161 |
| ATCN_2142 | 38103 | CTCN_8428 | 52162 |
| CTCN_3631 | 38104 | GTCN_4511 | 52163 |
| GTCN_1917 | 38105 | TTCN_6987 | 52164 |
| CTCN_3632 | 38106 | GTCN_4512 | 52165 |
| TTCN_2958 | 38107 | GTCN_4513 | 52166 |
| TTCN_2959 | 38108 | TTCN_6988 | 52167 |
| CTCN_3633 | 38109 | ATCN_4781 | 52168 |
| TTCN_2960 | 38110 | TTCN_6989 | 52169 |
| CTCN_3634 | 38111 | CTCN_8429 | 52170 |
| CTCN_3635 | 38112 | TTCN_6990 | 52171 |
| GTCN_1918 | 38113 | CTCN_8430 | 52172 |
| CTCN_3636 | 38114 | CTCN_8431 | 52173 |

FIG. 37 (continued)

| | | | |
|---|---|---|---|
| GTCN_1919 | 38115 | TTCN_6991 | 52174 |
| CTCN_3637 | 38116 | ATCN_4782 | 52175 |
| GTCN_1920 | 38117 | GTCN_4514 | 52176 |
| TTCN_2961 | 38118 | TTCN_6992 | 52177 |
| GTCN_1921 | 38119 | ATCN_4783 | 52178 |
| GTCN_1922 | 38120 | TTCN_6993 | 52179 |
| GTCN_1923 | 38121 | TTCN_6994 | 52180 |
| TTCN_2962 | 38122 | CTCN_8432 | 52181 |
| ATCN_2143 | 38123 | GTCN_4515 | 52182 |
| TTCN_2963 | 38124 | TTCN_6995 | 52183 |
| GTCN_1924 | 38125 | TTCN_6996 | 52184 |
| TTCN_2964 | 38126 | CTCN_8433 | 52185 |
| ATCN_2144 | 38127 | ATCN_4784 | 52186 |
| TTCN_2965 | 38128 | ATCN_4785 | 52187 |
| CTCN_3638 | 38129 | GTCN_4516 | 52188 |
| CTCN_3639 | 38130 | CTCN_8434 | 52189 |
| CTCN_3640 | 38131 | CTCN_8435 | 52190 |
| CTCN_3641 | 38132 | ATCN_4786 | 52191 |
| TTCN_2966 | 38133 | ATCN_4787 | 52192 |
| CTCN_3642 | 38134 | GTCN_4517 | 52193 |
| CTCN_3643 | 38135 | TTCN_6997 | 52194 |
| ATCN_2145 | 38136 | GTCN_4518 | 52195 |
| TTCN_2967 | 38137 | GTCN_4519 | 52196 |
| ATCN_2146 | 38138 | ATCN_4788 | 52197 |
| CTCN_3644 | 38139 | ATCN_4789 | 52198 |
| CTCN_3645 | 38140 | TTCN_6998 | 52199 |
| CTCN_3646 | 38141 | CTCN_8436 | 52200 |
| CTCN_3647 | 38142 | ATCN_4790 | 52201 |
| GTCN_1925 | 38143 | TTCN_6999 | 52202 |
| GTCN_1926 | 38144 | GTCN_4520 | 52203 |
| CTCN_3648 | 38145 | TTCN_7000 | 52204 |
| GTCN_1927 | 38146 | CTCN_8437 | 52205 |
| CTCN_3649 | 38147 | CTCN_8438 | 52206 |
| CTCN_3650 | 38148 | CTCN_8439 | 52207 |
| CTCN_3651 | 38149 | CTCN_8440 | 52208 |
| ATCN_2147 | 38150 | ATCN_4791 | 52209 |
| ATCN_2148 | 38151 | CTCN_8441 | 52210 |
| TTCN_2968 | 38152 | TTCN_7001 | 52211 |
| ATCN_2149 | 38153 | CTCN_8442 | 52212 |
| TTCN_2969 | 38154 | ATCN_4792 | 52213 |
| TTCN_2970 | 38155 | TTCN_7002 | 52214 |
| TTCN_2971 | 38156 | TTCN_7003 | 52215 |
| CTCN_3652 | 38157 | CTCN_8443 | 52216 |

| | | | |
|---|---|---|---|
| ATCN_2150 | 38158 | TTCN_7004 | 52217 |
| TTCN_2972 | 38159 | GTCN_4521 | 52218 |
| CTCN_3653 | 38160 | TTCN_7005 | 52219 |
| TTCN_2973 | 38161 | GTCN_4522 | 52220 |
| CTCN_3654 | 38162 | ATCN_4793 | 52221 |
| TTCN_2974 | 38163 | GTCN_4523 | 52222 |
| TTCN_2975 | 38164 | ATCN_4794 | 52223 |
| CTCN_3655 | 38165 | GTCN_4524 | 52224 |
| CTCN_3656 | 38166 | CTCN_8444 | 52225 |
| CTCN_3657 | 38167 | TTCN_7006 | 52226 |
| CTCN_3658 | 38168 | CTCN_8445 | 52227 |
| CTCN_3659 | 38169 | GTCN_4525 | 52228 |
| TTCN_2976 | 38170 | TTCN_7007 | 52229 |
| CTCN_3660 | 38171 | ATCN_4795 | 52230 |
| TTCN_2977 | 38172 | TTCN_7008 | 52231 |
| CTCN_3661 | 38173 | GTCN_4526 | 52232 |
| CTCN_3662 | 38174 | CTCN_8446 | 52233 |
| CTCN_3663 | 38175 | TTCN_7009 | 52234 |
| ATCN_2151 | 38176 | TTCN_7010 | 52235 |
| CTCN_3664 | 38177 | GTCN_4527 | 52236 |
| CTCN_3665 | 38178 | ATCN_4796 | 52237 |
| GTCN_1928 | 38179 | TTCN_7011 | 52238 |
| TTCN_2978 | 38180 | ATCN_4797 | 52239 |
| CTCN_3666 | 38181 | GTCN_4528 | 52240 |
| TTCN_2979 | 38182 | CTCN_8447 | 52241 |
| CTCN_3667 | 38183 | TTCN_7012 | 52242 |
| GTCN_1929 | 38184 | ATCN_4798 | 52243 |
| CTCN_3668 | 38185 | ATCN_4799 | 52244 |
| GTCN_1930 | 38186 | TTCN_7013 | 52245 |
| TTCN_2980 | 38187 | TTCN_7014 | 52246 |
| CTCN_3669 | 38188 | TTCN_7015 | 52247 |
| CTCN_3670 | 38189 | CTCN_8448 | 52248 |
| CTCN_3671 | 38190 | TTCN_7016 | 52249 |
| TTCN_2981 | 38191 | CTCN_8449 | 52250 |
| CTCN_3672 | 38192 | ATCN_4800 | 52251 |
| TTCN_2982 | 38193 | CTCN_8450 | 52252 |
| ATCN_2152 | 38194 | CTCN_8451 | 52253 |
| GTCN_1931 | 38195 | TTCN_7017 | 52254 |
| CTCN_3673 | 38196 | TTCN_7018 | 52255 |
| TTCN_2983 | 38197 | CTCN_8452 | 52256 |
| GTCN_1932 | 38198 | TTCN_7019 | 52257 |
| ATCN_2153 | 38199 | ATCN_4801 | 52258 |
| GTCN_1933 | 38200 | ATCN_4802 | 52259 |

FIG. 37 (continued)

| | | | | | | | |
|---|---|---|---|---|---|---|---|
| CTCN_3674 | 38201 | CTCN_8453 | 52260 | TTCN_2993 | 38244 | TTCN_7034 | 52303 |
| TTCN_2984 | 38202 | CTCN_8454 | 52261 | TTCN_2994 | 38245 | CTCN_8464 | 52304 |
| TTCN_2985 | 38203 | CTCN_8455 | 52262 | ATCN_2161 | 38246 | TTCN_7035 | 52305 |
| CTCN_3675 | 38204 | ATCN_4803 | 52263 | GTCN_1941 | 38247 | ATCN_4811 | 52306 |
| ATCN_2154 | 38205 | ATCN_4804 | 52264 | TTCN_2995 | 38248 | TTCN_7036 | 52307 |
| CTCN_3676 | 38206 | CTCN_8456 | 52265 | CTCN_3694 | 38249 | GTCN_4539 | 52308 |
| CTCN_3677 | 38207 | GTCN_4529 | 52266 | TTCN_2996 | 38250 | TTCN_7037 | 52309 |
| CTCN_3678 | 38208 | TTCN_7020 | 52267 | GTCN_1942 | 38251 | CTCN_8465 | 52310 |
| CTCN_3679 | 38209 | TTCN_7021 | 52268 | GTCN_1943 | 38252 | CTCN_8466 | 52311 |
| CTCN_3680 | 38210 | TTCN_7022 | 52269 | ATCN_2162 | 38253 | ATCN_4812 | 52312 |
| CTCN_3681 | 38211 | ATCN_4805 | 52270 | GTCN_1944 | 38254 | TTCN_7038 | 52313 |
| GTCN_1934 | 38212 | CTCN_8457 | 52271 | TTCN_2997 | 38255 | TTCN_7039 | 52314 |
| CTCN_3682 | 38213 | CTCN_8458 | 52272 | GTCN_1945 | 38256 | ATCN_4813 | 52315 |
| TTCN_2986 | 38214 | TTCN_7023 | 52273 | TTCN_2998 | 38257 | GTCN_4540 | 52316 |
| ATCN_2155 | 38215 | GTCN_4530 | 52274 | ATCN_2163 | 38258 | CTCN_8467 | 52317 |
| CTCN_3683 | 38216 | CTCN_8459 | 52275 | TTCN_2999 | 38259 | ATCN_4814 | 52318 |
| CTCN_3684 | 38217 | GTCN_4531 | 52276 | CTCN_3695 | 38260 | CTCN_8468 | 52319 |
| GTCN_1935 | 38218 | CTCN_8460 | 52277 | GTCN_1946 | 38261 | CTCN_8469 | 52320 |
| ATCN_2156 | 38219 | TTCN_7024 | 52278 | CTCN_3696 | 38262 | CTCN_8470 | 52321 |
| TTCN_2987 | 38220 | TTCN_7025 | 52279 | ATCN_2164 | 38263 | TTCN_7040 | 52322 |
| TTCN_2988 | 38221 | TTCN_7026 | 52280 | CTCN_3697 | 38264 | ATCN_4815 | 52323 |
| GTCN_1936 | 38222 | GTCN_4532 | 52281 | TTCN_3000 | 38265 | ATCN_4816 | 52324 |
| CTCN_3685 | 38223 | CTCN_8461 | 52282 | CTCN_3698 | 38266 | TTCN_7041 | 52325 |
| GTCN_1937 | 38224 | ATCN_4806 | 52283 | TTCN_3001 | 38267 | CTCN_8471 | 52326 |
| GTCN_1938 | 38225 | CTCN_8462 | 52284 | GTCN_1947 | 38268 | TTCN_7042 | 52327 |
| CTCN_3686 | 38226 | GTCN_4533 | 52285 | ATCN_2165 | 38269 | TTCN_7043 | 52328 |
| GTCN_1939 | 38227 | TTCN_7027 | 52286 | CTCN_3699 | 38270 | ATCN_4817 | 52329 |
| GTCN_1940 | 38228 | ATCN_4807 | 52287 | TTCN_3002 | 38271 | TTCN_7044 | 52330 |
| CTCN_3687 | 38229 | ATCN_4808 | 52288 | GTCN_1948 | 38272 | TTCN_7045 | 52331 |
| CTCN_3688 | 38230 | CTCN_8463 | 52289 | ATCN_2166 | 38273 | GTCN_4541 | 52332 |
| ATCN_2157 | 38231 | TTCN_7028 | 52290 | TTCN_3003 | 38274 | CTCN_8472 | 52333 |
| ATCN_2158 | 38232 | TTCN_7029 | 52291 | ATCN_2167 | 38275 | GTCN_4542 | 52334 |
| ATCN_2159 | 38233 | GTCN_4534 | 52292 | CTCN_3700 | 38276 | CTCN_8473 | 52335 |
| ATCN_2160 | 38234 | TTCN_7030 | 52293 | GTCN_1949 | 38277 | ATCN_4818 | 52336 |
| CTCN_3689 | 38235 | TTCN_7031 | 52294 | GTCN_1950 | 38278 | ATCN_4819 | 52337 |
| CTCN_3690 | 38236 | GTCN_4535 | 52295 | CTCN_3701 | 38279 | TTCN_7046 | 52338 |
| CTCN_3691 | 38237 | GTCN_4536 | 52296 | TTCN_3004 | 38280 | ATCN_4820 | 52339 |
| CTCN_3692 | 38238 | ATCN_4809 | 52297 | ATCN_2168 | 38281 | TTCN_7047 | 52340 |
| TTCN_2989 | 38239 | ATCN_4810 | 52298 | ATCN_2169 | 38282 | CTCN_8474 | 52341 |
| CTCN_3693 | 38240 | TTCN_7032 | 52299 | CTCN_3702 | 38283 | GTCN_4543 | 52342 |
| TTCN_2990 | 38241 | GTCN_4537 | 52300 | CTCN_3703 | 38284 | ATCN_4821 | 52343 |
| TTCN_2991 | 38242 | TTCN_7033 | 52301 | TTCN_3005 | 38285 | CTCN_8475 | 52344 |
| TTCN_2992 | 38243 | GTCN_4538 | 52302 | CTCN_3704 | 38286 | GTCN_4544 | 52345 |

FIG. 37 (continued)

| | | | | | | | |
|---|---|---|---|---|---|---|---|
| GTCN_1951 | 38287 | TTCN_7048 | 52346 | CTCN_3720 | 38330 | CTCN_8499 | 52389 |
| CTCN_3705 | 38288 | CTCN_8476 | 52347 | CTCN_3721 | 38331 | CTCN_8500 | 52390 |
| TTCN_3006 | 38289 | GTCN_4545 | 52348 | CTCN_3722 | 38332 | CTCN_8501 | 52391 |
| CTCN_3706 | 38290 | GTCN_4546 | 52349 | TTCN_3021 | 38333 | CTCN_8502 | 52392 |
| CTCN_3707 | 38291 | TTCN_7049 | 52350 | GTCN_1956 | 38334 | CTCN_8503 | 52393 |
| CTCN_3708 | 38292 | CTCN_8477 | 52351 | CTCN_3723 | 38335 | CTCN_8504 | 52394 |
| ATCN_2170 | 38293 | GTCN_4547 | 52352 | ATCN_2178 | 38336 | GTCN_4555 | 52395 |
| CTCN_3709 | 38294 | CTCN_8478 | 52353 | ATCN_2179 | 38337 | CTCN_8505 | 52396 |
| TTCN_3007 | 38295 | CTCN_8479 | 52354 | ATCN_2180 | 38338 | TTCN_7054 | 52397 |
| TTCN_3008 | 38296 | CTCN_8480 | 52355 | TTCN_3022 | 38339 | CTCN_8506 | 52398 |
| GTCN_1952 | 38297 | TTCN_7050 | 52356 | TTCN_3023 | 38340 | GTCN_4556 | 52399 |
| TTCN_3009 | 38298 | CTCN_8481 | 52357 | GTCN_1957 | 38341 | CTCN_8507 | 52400 |
| ATCN_2171 | 38299 | ATCN_4822 | 52358 | TTCN_3024 | 38342 | GTCN_4557 | 52401 |
| CTCN_3710 | 38300 | CTCN_8482 | 52359 | CTCN_3724 | 38343 | CTCN_8508 | 52402 |
| ATCN_2172 | 38301 | GTCN_4548 | 52360 | TTCN_3025 | 38344 | TTCN_7055 | 52403 |
| CTCN_3711 | 38302 | CTCN_8483 | 52361 | GTCN_1958 | 38345 | CTCN_8509 | 52404 |
| CTCN_3712 | 38303 | CTCN_8484 | 52362 | CTCN_3725 | 38346 | CTCN_8510 | 52405 |
| TTCN_3010 | 38304 | CTCN_8485 | 52363 | TTCN_3026 | 38347 | GTCN_4558 | 52406 |
| TTCN_3011 | 38305 | CTCN_8486 | 52364 | GTCN_1959 | 38348 | TTCN_7056 | 52407 |
| TTCN_3012 | 38306 | ATCN_4823 | 52365 | TTCN_3027 | 38349 | ATCN_4826 | 52408 |
| CTCN_3713 | 38307 | ATCN_4824 | 52366 | ATCN_2181 | 38350 | ATCN_4827 | 52409 |
| TTCN_3013 | 38308 | CTCN_8487 | 52367 | CTCN_3726 | 38351 | GTCN_4559 | 52410 |
| GTCN_1953 | 38309 | CTCN_8488 | 52368 | TTCN_3028 | 38352 | CTCN_8511 | 52411 |
| ATCN_2173 | 38310 | TTCN_7051 | 52369 | TTCN_3029 | 38353 | TTCN_7057 | 52412 |
| TTCN_3014 | 38311 | CTCN_8489 | 52370 | CTCN_3727 | 38354 | GTCN_4560 | 52413 |
| TTCN_3015 | 38312 | GTCN_4549 | 52371 | TTCN_3030 | 38355 | CTCN_8512 | 52414 |
| TTCN_3016 | 38313 | ATCN_4825 | 52372 | GTCN_1960 | 38356 | CTCN_8513 | 52415 |
| CTCN_3714 | 38314 | CTCN_8490 | 52373 | GTCN_1961 | 38357 | ATCN_4828 | 52416 |
| CTCN_3715 | 38315 | CTCN_8491 | 52374 | CTCN_3728 | 38358 | CTCN_8514 | 52417 |
| CTCN_3716 | 38316 | GTCN_4550 | 52375 | CTCN_3729 | 38359 | ATCN_4829 | 52418 |
| ATCN_2174 | 38317 | GTCN_4551 | 52376 | CTCN_3730 | 38360 | ATCN_4830 | 52419 |
| CTCN_3717 | 38318 | GTCN_4552 | 52377 | CTCN_3731 | 38361 | CTCN_8515 | 52420 |
| CTCN_3718 | 38319 | CTCN_8492 | 52378 | CTCN_3732 | 38362 | TTCN_7058 | 52421 |
| GTCN_1954 | 38320 | CTCN_8493 | 52379 | GTCN_1962 | 38363 | CTCN_8516 | 52422 |
| ATCN_2175 | 38321 | CTCN_8494 | 52380 | ATCN_2182 | 38364 | CTCN_8517 | 52423 |
| ATCN_2176 | 38322 | CTCN_8495 | 52381 | CTCN_3733 | 38365 | GTCN_4561 | 52424 |
| TTCN_3017 | 38323 | GTCN_4553 | 52382 | TTCN_3031 | 38366 | GTCN_4562 | 52425 |
| ATCN_2177 | 38324 | TTCN_7052 | 52383 | ATCN_2183 | 38367 | GTCN_4563 | 52426 |
| TTCN_3018 | 38325 | CTCN_8496 | 52384 | CTCN_3734 | 38368 | CTCN_8518 | 52427 |
| TTCN_3019 | 38326 | CTCN_8497 | 52385 | TTCN_3032 | 38369 | ATCN_4831 | 52428 |
| GTCN_1955 | 38327 | CTCN_8498 | 52386 | CTCN_3735 | 38370 | CTCN_8519 | 52429 |
| CTCN_3719 | 38328 | TTCN_7053 | 52387 | ATCN_2184 | 38371 | CTCN_8520 | 52430 |
| TTCN_3020 | 38329 | GTCN_4554 | 52388 | CTCN_3736 | 38372 | CTCN_8521 | 52431 |

FIG. 37 (continued)

| | | | |
|---|---|---|---|
| CTCN_3737 | 38373 | CTCN_8522 | 52432 |
| TTCN_3033 | 38374 | TTCN_7059 | 52433 |
| TTCN_3034 | 38375 | ATCN_4832 | 52434 |
| TTCN_3035 | 38376 | TTCN_7060 | 52435 |
| CTCN_3738 | 38377 | CTCN_8523 | 52436 |
| ATCN_2185 | 38378 | CTCN_8524 | 52437 |
| TTCN_3036 | 38379 | CTCN_8525 | 52438 |
| CTCN_3739 | 38380 | CTCN_8526 | 52439 |
| GTCN_1963 | 38381 | ATCN_4833 | 52440 |
| TTCN_3037 | 38382 | CTCN_8527 | 52441 |
| TTCN_3038 | 38383 | CTCN_8528 | 52442 |
| CTCN_3740 | 38384 | CTCN_8529 | 52443 |
| TTCN_3039 | 38385 | ATCN_4834 | 52444 |
| GTCN_1964 | 38386 | CTCN_8530 | 52445 |
| TTCN_3040 | 38387 | GTCN_4564 | 52446 |
| TTCN_3041 | 38388 | CTCN_8531 | 52447 |
| TTCN_3042 | 38389 | CTCN_8532 | 52448 |
| TTCN_3043 | 38390 | GTCN_4565 | 52449 |
| TTCN_3044 | 38391 | GTCN_4566 | 52450 |
| ATCN_2186 | 38392 | ATCN_4835 | 52451 |
| ATCN_2187 | 38393 | TTCN_7061 | 52452 |
| TTCN_3045 | 38394 | GTCN_4567 | 52453 |
| CTCN_3741 | 38395 | TTCN_7062 | 52454 |
| TTCN_3046 | 38396 | CTCN_8533 | 52455 |
| ATCN_2188 | 38397 | GTCN_4568 | 52456 |
| TTCN_3047 | 38398 | CTCN_8534 | 52457 |
| TTCN_3048 | 38399 | CTCN_8535 | 52458 |
| CTCN_3742 | 38400 | GTCN_4569 | 52459 |
| GTCN_1965 | 38401 | TTCN_7063 | 52460 |
| TTCN_3049 | 38402 | GTCN_4570 | 52461 |
| TTCN_3050 | 38403 | GTCN_4571 | 52462 |
| TTCN_3051 | 38404 | ATCN_4836 | 52463 |
| TTCN_3052 | 38405 | CTCN_8536 | 52464 |
| CTCN_3743 | 38406 | CTCN_8537 | 52465 |
| CTCN_3744 | 38407 | CTCN_8538 | 52466 |
| GTCN_1966 | 38408 | CTCN_8539 | 52467 |
| TTCN_3053 | 38409 | CTCN_8540 | 52468 |
| TTCN_3054 | 38410 | CTCN_8541 | 52469 |
| TTCN_3055 | 38411 | TTCN_7064 | 52470 |
| ATCN_2189 | 38412 | TTCN_7065 | 52471 |
| TTCN_3056 | 38413 | ATCN_4837 | 52472 |
| TTCN_3057 | 38414 | GTCN_4572 | 52473 |
| ATCN_2190 | 38415 | GTCN_4573 | 52474 |

| | | | |
|---|---|---|---|
| CTCN_3745 | 38416 | CTCN_8542 | 52475 |
| GTCN_1967 | 38417 | CTCN_8543 | 52476 |
| TTCN_3058 | 38418 | CTCN_8544 | 52477 |
| TTCN_3059 | 38419 | CTCN_8545 | 52478 |
| CTCN_3746 | 38420 | TTCN_7066 | 52479 |
| CTCN_3747 | 38421 | CTCN_8546 | 52480 |
| GTCN_1968 | 38422 | TTCN_7067 | 52481 |
| ATCN_2191 | 38423 | TTCN_7068 | 52482 |
| GTCN_1969 | 38424 | TTCN_7069 | 52483 |
| ATCN_2192 | 38425 | TTCN_7070 | 52484 |
| TTCN_3060 | 38426 | GTCN_4574 | 52485 |
| CTCN_3748 | 38427 | TTCN_7071 | 52486 |
| ATCN_2193 | 38428 | CTCN_8547 | 52487 |
| CTCN_3749 | 38429 | CTCN_8548 | 52488 |
| TTCN_3061 | 38430 | CTCN_8549 | 52489 |
| GTCN_1970 | 38431 | CTCN_8550 | 52490 |
| CTCN_3750 | 38432 | ATCN_4838 | 52491 |
| GTCN_1971 | 38433 | ATCN_4839 | 52492 |
| GTCN_1972 | 38434 | CTCN_8551 | 52493 |
| CTCN_3751 | 38435 | GTCN_4575 | 52494 |
| TTCN_3062 | 38436 | ATCN_4840 | 52495 |
| TTCN_3063 | 38437 | GTCN_4576 | 52496 |
| CTCN_3752 | 38438 | TTCN_7072 | 52497 |
| CTCN_3753 | 38439 | ATCN_4841 | 52498 |
| TTCN_3064 | 38440 | GTCN_4577 | 52499 |
| GTCN_1973 | 38441 | ATCN_4842 | 52500 |
| ATCN_2194 | 38442 | GTCN_4578 | 52501 |
| CTCN_3754 | 38443 | CTCN_8552 | 52502 |
| TTCN_3065 | 38444 | CTCN_8553 | 52503 |
| CTCN_3755 | 38445 | GTCN_4579 | 52504 |
| GTCN_1974 | 38446 | TTCN_7073 | 52505 |
| CTCN_3756 | 38447 | CTCN_8554 | 52506 |
| CTCN_3757 | 38448 | CTCN_8555 | 52507 |
| CTCN_3758 | 38449 | CTCN_8556 | 52508 |
| GTCN_1975 | 38450 | ATCN_4843 | 52509 |
| ATCN_2195 | 38451 | CTCN_8557 | 52510 |
| CTCN_3759 | 38452 | GTCN_4580 | 52511 |
| CTCN_3760 | 38453 | TTCN_7074 | 52512 |
| TTCN_3066 | 38454 | TTCN_7075 | 52513 |
| ATCN_2196 | 38455 | TTCN_7076 | 52514 |
| GTCN_1976 | 38456 | CTCN_8558 | 52515 |
| CTCN_3761 | 38457 | CTCN_8559 | 52516 |
| CTCN_3762 | 38458 | ATCN_4844 | 52517 |

FIG. 37 (continued)

| | | | |
|---|---|---|---|
| TTCN_3067 | 38459 | CTCN_8560 | 52518 |
| CTCN_3763 | 38460 | CTCN_8561 | 52519 |
| TTCN_3068 | 38461 | ATCN_4845 | 52520 |
| CTCN_3764 | 38462 | ATCN_4846 | 52521 |
| GTCN_1977 | 38463 | ATCN_4847 | 52522 |
| CTCN_3765 | 38464 | GTCN_4581 | 52523 |
| GTCN_1978 | 38465 | TTCN_7077 | 52524 |
| ATCN_2197 | 38466 | CTCN_8562 | 52525 |
| ATCN_2198 | 38467 | CTCN_8563 | 52526 |
| TTCN_3069 | 38468 | CTCN_8564 | 52527 |
| ATCN_2199 | 38469 | TTCN_7078 | 52528 |
| TTCN_3070 | 38470 | CTCN_8565 | 52529 |
| ATCN_2200 | 38471 | TTCN_7079 | 52530 |
| TTCN_3071 | 38472 | GTCN_4582 | 52531 |
| GTCN_1979 | 38473 | GTCN_4583 | 52532 |
| CTCN_3766 | 38474 | CTCN_8566 | 52533 |
| CTCN_3767 | 38475 | ATCN_4848 | 52534 |
| CTCN_3768 | 38476 | TTCN_7080 | 52535 |
| ATCN_2201 | 38477 | ATCN_4849 | 52536 |
| CTCN_3769 | 38478 | ATCN_4850 | 52537 |
| CTCN_3770 | 38479 | ATCN_4851 | 52538 |
| TTCN_3072 | 38480 | CTCN_8567 | 52539 |
| GTCN_1980 | 38481 | CTCN_8568 | 52540 |
| TTCN_3073 | 38482 | CTCN_8569 | 52541 |
| GTCN_1981 | 38483 | ATCN_4852 | 52542 |
| TTCN_3074 | 38484 | CTCN_8570 | 52543 |
| GTCN_1982 | 38485 | ATCN_4853 | 52544 |
| CTCN_3771 | 38486 | ATCN_4854 | 52545 |
| CTCN_3772 | 38487 | TTCN_7081 | 52546 |
| GTCN_1983 | 38488 | CTCN_8571 | 52547 |
| TTCN_3075 | 38489 | TTCN_7082 | 52548 |
| CTCN_3773 | 38490 | TTCN_7083 | 52549 |
| CTCN_3774 | 38491 | TTCN_7084 | 52550 |
| TTCN_3076 | 38492 | GTCN_4584 | 52551 |
| TTCN_3077 | 38493 | ATCN_4855 | 52552 |
| TTCN_3078 | 38494 | TTCN_7085 | 52553 |
| TTCN_3079 | 38495 | GTCN_4585 | 52554 |
| ATCN_2202 | 38496 | ATCN_4856 | 52555 |
| TTCN_3080 | 38497 | TTCN_7086 | 52556 |
| GTCN_1984 | 38498 | CTCN_8572 | 52557 |
| TTCN_3081 | 38499 | TTCN_7087 | 52558 |
| CTCN_3775 | 38500 | TTCN_7088 | 52559 |
| ATCN_2203 | 38501 | TTCN_7089 | 52560 |

| | | | |
|---|---|---|---|
| ATCN_2204 | 38502 | GTCN_4586 | 52561 |
| ATCN_2205 | 38503 | TTCN_7090 | 52562 |
| ATCN_2206 | 38504 | TTCN_7091 | 52563 |
| GTCN_1985 | 38505 | CTCN_8573 | 52564 |
| TTCN_3082 | 38506 | GTCN_4587 | 52565 |
| TTCN_3083 | 38507 | ATCN_4857 | 52566 |
| TTCN_3084 | 38508 | CTCN_8574 | 52567 |
| CTCN_3776 | 38509 | TTCN_7092 | 52568 |
| TTCN_3085 | 38510 | CTCN_8575 | 52569 |
| ATCN_2207 | 38511 | ATCN_4858 | 52570 |
| ATCN_2208 | 38512 | ATCN_4859 | 52571 |
| ATCN_2209 | 38513 | CTCN_8576 | 52572 |
| ATCN_2210 | 38514 | CTCN_8577 | 52573 |
| ATCN_2211 | 38515 | GTCN_4588 | 52574 |
| ATCN_2212 | 38516 | GTCN_4589 | 52575 |
| TTCN_3086 | 38517 | GTCN_4590 | 52576 |
| TTCN_3087 | 38518 | TTCN_7093 | 52577 |
| ATCN_2213 | 38519 | GTCN_4591 | 52578 |
| TTCN_3088 | 38520 | TTCN_7094 | 52579 |
| ATCN_2214 | 38521 | CTCN_8578 | 52580 |
| TTCN_3089 | 38522 | CTCN_8579 | 52581 |
| TTCN_3090 | 38523 | GTCN_4592 | 52582 |
| CTCN_3777 | 38524 | TTCN_7095 | 52583 |
| CTCN_3778 | 38525 | CTCN_8580 | 52584 |
| TTCN_3091 | 38526 | CTCN_8581 | 52585 |
| TTCN_3092 | 38527 | TTCN_7096 | 52586 |
| CTCN_3779 | 38528 | CTCN_8582 | 52587 |
| ATCN_2215 | 38529 | CTCN_8583 | 52588 |
| GTCN_1986 | 38530 | ATCN_4860 | 52589 |
| TTCN_3093 | 38531 | GTCN_4593 | 52590 |
| TTCN_3094 | 38532 | ATCN_4861 | 52591 |
| TTCN_3095 | 38533 | ATCN_4862 | 52592 |
| GTCN_1987 | 38534 | CTCN_8584 | 52593 |
| ATCN_2216 | 38535 | GTCN_4594 | 52594 |
| CTCN_3780 | 38536 | CTCN_8585 | 52595 |
| CTCN_3781 | 38537 | ATCN_4863 | 52596 |
| TTCN_3096 | 38538 | CTCN_8586 | 52597 |
| CTCN_3782 | 38539 | CTCN_8587 | 52598 |
| TTCN_3097 | 38540 | CTCN_8588 | 52599 |
| TTCN_3098 | 38541 | ATCN_4864 | 52600 |
| CTCN_3783 | 38542 | ATCN_4865 | 52601 |
| CTCN_3784 | 38543 | CTCN_8589 | 52602 |
| GTCN_1988 | 38544 | GTCN_4595 | 52603 |

FIG. 37 (continued)

| | | | |
|---|---|---|---|
| TTCN_3099 | 38545 | TTCN_7097 | 52604 |
| ATCN_2217 | 38546 | GTCN_4596 | 52605 |
| TTCN_3100 | 38547 | CTCN_8590 | 52606 |
| CTCN_3785 | 38548 | ATCN_4866 | 52607 |
| TTCN_3101 | 38549 | ATCN_4867 | 52608 |
| CTCN_3786 | 38550 | TTCN_7098 | 52609 |
| GTCN_1989 | 38551 | CTCN_8591 | 52610 |
| CTCN_3787 | 38552 | CTCN_8592 | 52611 |
| CTCN_3788 | 38553 | TTCN_7099 | 52612 |
| ATCN_2218 | 38554 | CTCN_8593 | 52613 |
| TTCN_3102 | 38555 | GTCN_4597 | 52614 |
| TTCN_3103 | 38556 | ATCN_4868 | 52615 |
| ATCN_2219 | 38557 | CTCN_8594 | 52616 |
| ATCN_2220 | 38558 | GTCN_4598 | 52617 |
| TTCN_3104 | 38559 | CTCN_8595 | 52618 |
| CTCN_3789 | 38560 | GTCN_4599 | 52619 |
| TTCN_3105 | 38561 | GTCN_4600 | 52620 |
| TTCN_3106 | 38562 | CTCN_8596 | 52621 |
| ATCN_2221 | 38563 | TTCN_7100 | 52622 |
| TTCN_3107 | 38564 | CTCN_8597 | 52623 |
| TTCN_3108 | 38565 | ATCN_4869 | 52624 |
| CTCN_3790 | 38566 | TTCN_7101 | 52625 |
| GTCN_1990 | 38567 | CTCN_8598 | 52626 |
| TTCN_3109 | 38568 | ATCN_4870 | 52627 |
| GTCN_1991 | 38569 | CTCN_8599 | 52628 |
| TTCN_3110 | 38570 | GTCN_4601 | 52629 |
| CTCN_3791 | 38571 | ATCN_4871 | 52630 |
| CTCN_3792 | 38572 | TTCN_7102 | 52631 |
| CTCN_3793 | 38573 | ATCN_4872 | 52632 |
| ATCN_2222 | 38574 | ATCN_4873 | 52633 |
| CTCN_3794 | 38575 | TTCN_7103 | 52634 |
| ATCN_2223 | 38576 | TTCN_7104 | 52635 |
| TTCN_3111 | 38577 | CTCN_8600 | 52636 |
| CTCN_3795 | 38578 | GTCN_4602 | 52637 |
| ATCN_2224 | 38579 | GTCN_4603 | 52638 |
| ATCN_2225 | 38580 | CTCN_8601 | 52639 |
| ATCN_2226 | 38581 | TTCN_7105 | 52640 |
| TTCN_3112 | 38582 | GTCN_4604 | 52641 |
| TTCN_3113 | 38583 | GTCN_4605 | 52642 |
| ATCN_2227 | 38584 | CTCN_8602 | 52643 |
| ATCN_2228 | 38585 | GTCN_4606 | 52644 |
| CTCN_3796 | 38586 | TTCN_7106 | 52645 |
| TTCN_3114 | 38587 | CTCN_8603 | 52646 |

| | | | |
|---|---|---|---|
| CTCN_3797 | 38588 | ATCN_4874 | 52647 |
| ATCN_2229 | 38589 | ATCN_4875 | 52648 |
| TTCN_3115 | 38590 | TTCN_7107 | 52649 |
| CTCN_3798 | 38591 | ATCN_4876 | 52650 |
| TTCN_3116 | 38592 | CTCN_8604 | 52651 |
| TTCN_3117 | 38593 | GTCN_4607 | 52652 |
| CTCN_3799 | 38594 | CTCN_8605 | 52653 |
| ATCN_2230 | 38595 | GTCN_4608 | 52654 |
| CTCN_3800 | 38596 | ATCN_4877 | 52655 |
| TTCN_3118 | 38597 | ATCN_4878 | 52656 |
| CTCN_3801 | 38598 | GTCN_4609 | 52657 |
| TTCN_3119 | 38599 | GTCN_4610 | 52658 |
| ATCN_2231 | 38600 | ATCN_4879 | 52659 |
| TTCN_3120 | 38601 | GTCN_4611 | 52660 |
| ATCN_2232 | 38602 | TTCN_7108 | 52661 |
| CTCN_3802 | 38603 | GTCN_4612 | 52662 |
| ATCN_2233 | 38604 | TTCN_7109 | 52663 |
| ATCN_2234 | 38605 | ATCN_4880 | 52664 |
| ATCN_2235 | 38606 | TTCN_7110 | 52665 |
| CTCN_3803 | 38607 | CTCN_8606 | 52666 |
| GTCN_1992 | 38608 | CTCN_8607 | 52667 |
| TTCN_3121 | 38609 | TTCN_7111 | 52668 |
| TTCN_3122 | 38610 | ATCN_4881 | 52669 |
| ATCN_2236 | 38611 | TTCN_7112 | 52670 |
| ATCN_2237 | 38612 | GTCN_4613 | 52671 |
| TTCN_3123 | 38613 | CTCN_8608 | 52672 |
| TTCN_3124 | 38614 | GTCN_4614 | 52673 |
| TTCN_3125 | 38615 | CTCN_8609 | 52674 |
| TTCN_3126 | 38616 | CTCN_8610 | 52675 |
| CTCN_3804 | 38617 | ATCN_4882 | 52676 |
| GTCN_1993 | 38618 | ATCN_4883 | 52677 |
| CTCN_3805 | 38619 | TTCN_7113 | 52678 |
| TTCN_3127 | 38620 | ATCN_4884 | 52679 |
| TTCN_3128 | 38621 | CTCN_8611 | 52680 |
| GTCN_1994 | 38622 | CTCN_8612 | 52681 |
| ATCN_2238 | 38623 | CTCN_8613 | 52682 |
| GTCN_1995 | 38624 | GTCN_4615 | 52683 |
| TTCN_3129 | 38625 | GTCN_4616 | 52684 |
| GTCN_1996 | 38626 | CTCN_8614 | 52685 |
| TTCN_3130 | 38627 | GTCN_4617 | 52686 |
| GTCN_1997 | 38628 | TTCN_7114 | 52687 |
| GTCN_1998 | 38629 | GTCN_4618 | 52688 |
| TTCN_3131 | 38630 | TTCN_7115 | 52689 |

FIG. 37 (continued)

| | | | |
|---|---|---|---|
| GTCN_1999 | 38631 | ATCN_4885 | 52690 |
| CTCN_3806 | 38632 | ATCN_4886 | 52691 |
| CTCN_3807 | 38633 | GTCN_4619 | 52692 |
| CTCN_3808 | 38634 | TTCN_7116 | 52693 |
| GTCN_2000 | 38635 | TTCN_7117 | 52694 |
| TTCN_3132 | 38636 | TTCN_7118 | 52695 |
| CTCN_3809 | 38637 | TTCN_7119 | 52696 |
| GTCN_2001 | 38638 | CTCN_8615 | 52697 |
| CTCN_3810 | 38639 | CTCN_8616 | 52698 |
| TTCN_3133 | 38640 | GTCN_4620 | 52699 |
| TTCN_3134 | 38641 | GTCN_4621 | 52700 |
| GTCN_2002 | 38642 | CTCN_8617 | 52701 |
| GTCN_2003 | 38643 | GTCN_4622 | 52702 |
| TTCN_3135 | 38644 | CTCN_8618 | 52703 |
| ATCN_2239 | 38645 | GTCN_4623 | 52704 |
| GTCN_2004 | 38646 | TTCN_7120 | 52705 |
| GTCN_2005 | 38647 | ATCN_4887 | 52706 |
| CTCN_3811 | 38648 | GTCN_4624 | 52707 |
| CTCN_3812 | 38649 | ATCN_4888 | 52708 |
| CTCN_3813 | 38650 | GTCN_4625 | 52709 |
| GTCN_2006 | 38651 | CTCN_8619 | 52710 |
| CTCN_3814 | 38652 | ATCN_4889 | 52711 |
| TTCN_3136 | 38653 | CTCN_8620 | 52712 |
| ATCN_2240 | 38654 | CTCN_8621 | 52713 |
| CTCN_3815 | 38655 | ATCN_4890 | 52714 |
| GTCN_2007 | 38656 | ATCN_4891 | 52715 |
| CTCN_3816 | 38657 | CTCN_8622 | 52716 |
| TTCN_3137 | 38658 | GTCN_4626 | 52717 |
| CTCN_3817 | 38659 | CTCN_8623 | 52718 |
| CTCN_3818 | 38660 | CTCN_8624 | 52719 |
| GTCN_2008 | 38661 | GTCN_4627 | 52720 |
| ATCN_2241 | 38662 | TTCN_7121 | 52721 |
| TTCN_3138 | 38663 | GTCN_4628 | 52722 |
| ATCN_2242 | 38664 | GTCN_4629 | 52723 |
| ATCN_2243 | 38665 | CTCN_8625 | 52724 |
| CTCN_3819 | 38666 | CTCN_8626 | 52725 |
| CTCN_3820 | 38667 | GTCN_4630 | 52726 |
| CTCN_3821 | 38668 | CTCN_8627 | 52727 |
| ATCN_2244 | 38669 | TTCN_7122 | 52728 |
| TTCN_3139 | 38670 | ATCN_4892 | 52729 |
| TTCN_3140 | 38671 | CTCN_8628 | 52730 |
| GTCN_2009 | 38672 | GTCN_4631 | 52731 |
| TTCN_3141 | 38673 | CTCN_8629 | 52732 |

| | | | |
|---|---|---|---|
| GTCN_2010 | 38674 | CTCN_8630 | 52733 |
| CTCN_3822 | 38675 | ATCN_4893 | 52734 |
| CTCN_3823 | 38676 | ATCN_4894 | 52735 |
| CTCN_3824 | 38677 | CTCN_8631 | 52736 |
| ATCN_2245 | 38678 | CTCN_8632 | 52737 |
| ATCN_2246 | 38679 | GTCN_4632 | 52738 |
| CTCN_3825 | 38680 | CTCN_8633 | 52739 |
| GTCN_2011 | 38681 | CTCN_8634 | 52740 |
| TTCN_3142 | 38682 | GTCN_4633 | 52741 |
| GTCN_2012 | 38683 | CTCN_8635 | 52742 |
| CTCN_3826 | 38684 | TTCN_7123 | 52743 |
| GTCN_2013 | 38685 | ATCN_4895 | 52744 |
| TTCN_3143 | 38686 | ATCN_4896 | 52745 |
| CTCN_3827 | 38687 | CTCN_8636 | 52746 |
| GTCN_2014 | 38688 | GTCN_4634 | 52747 |
| GTCN_2015 | 38689 | GTCN_4635 | 52748 |
| CTCN_3828 | 38690 | TTCN_7124 | 52749 |
| CTCN_3829 | 38691 | ATCN_4897 | 52750 |
| ATCN_2247 | 38692 | CTCN_8637 | 52751 |
| ATCN_2248 | 38693 | GTCN_4636 | 52752 |
| TTCN_3144 | 38694 | TTCN_7125 | 52753 |
| ATCN_2249 | 38695 | ATCN_4898 | 52754 |
| CTCN_3830 | 38696 | ATCN_4899 | 52755 |
| TTCN_3145 | 38697 | CTCN_8638 | 52756 |
| CTCN_3831 | 38698 | CTCN_8639 | 52757 |
| CTCN_3832 | 38699 | CTCN_8640 | 52758 |
| CTCN_3833 | 38700 | TTCN_7126 | 52759 |
| CTCN_3834 | 38701 | TTCN_7127 | 52760 |
| GTCN_2016 | 38702 | CTCN_8641 | 52761 |
| TTCN_3146 | 38703 | GTCN_4637 | 52762 |
| TTCN_3147 | 38704 | GTCN_4638 | 52763 |
| CTCN_3835 | 38705 | GTCN_4639 | 52764 |
| CTCN_3836 | 38706 | CTCN_8642 | 52765 |
| TTCN_3148 | 38707 | ATCN_4900 | 52766 |
| CTCN_3837 | 38708 | CTCN_8643 | 52767 |
| GTCN_2017 | 38709 | CTCN_8644 | 52768 |
| CTCN_3838 | 38710 | CTCN_8645 | 52769 |
| ATCN_2250 | 38711 | ATCN_4901 | 52770 |
| TTCN_3149 | 38712 | ATCN_4902 | 52771 |
| TTCN_3150 | 38713 | CTCN_8646 | 52772 |
| TTCN_3151 | 38714 | TTCN_7128 | 52773 |
| TTCN_3152 | 38715 | CTCN_8647 | 52774 |
| GTCN_2018 | 38716 | GTCN_4640 | 52775 |

FIG. 37 (continued)

| | | | |
|---|---|---|---|
| CTCN_3839 | 38717 | TTCN_7129 | 52776 |
| TTCN_3153 | 38718 | ATCN_4903 | 52777 |
| ATCN_2251 | 38719 | CTCN_8648 | 52778 |
| TTCN_3154 | 38720 | CTCN_8649 | 52779 |
| GTCN_2019 | 38721 | CTCN_8650 | 52780 |
| CTCN_3840 | 38722 | CTCN_8651 | 52781 |
| TTCN_3155 | 38723 | CTCN_8652 | 52782 |
| TTCN_3156 | 38724 | CTCN_8653 | 52783 |
| TTCN_3157 | 38725 | TTCN_7130 | 52784 |
| CTCN_3841 | 38726 | TTCN_7131 | 52785 |
| GTCN_2020 | 38727 | CTCN_8654 | 52786 |
| ATCN_2252 | 38728 | GTCN_4641 | 52787 |
| TTCN_3158 | 38729 | GTCN_4642 | 52788 |
| ATCN_2253 | 38730 | CTCN_8655 | 52789 |
| CTCN_3842 | 38731 | ATCN_4904 | 52790 |
| TTCN_3159 | 38732 | CTCN_8656 | 52791 |
| CTCN_3843 | 38733 | GTCN_4643 | 52792 |
| GTCN_2021 | 38734 | CTCN_8657 | 52793 |
| TTCN_3160 | 38735 | GTCN_4644 | 52794 |
| CTCN_3844 | 38736 | CTCN_8658 | 52795 |
| ATCN_2254 | 38737 | CTCN_8659 | 52796 |
| GTCN_2022 | 38738 | ATCN_4905 | 52797 |
| CTCN_3845 | 38739 | TTCN_7132 | 52798 |
| CTCN_3846 | 38740 | ATCN_4906 | 52799 |
| CTCN_3847 | 38741 | TTCN_7133 | 52800 |
| GTCN_2023 | 38742 | CTCN_8660 | 52801 |
| GTCN_2024 | 38743 | TTCN_7134 | 52802 |
| GTCN_2025 | 38744 | TTCN_7135 | 52803 |
| TTCN_3161 | 38745 | CTCN_8661 | 52804 |
| CTCN_3848 | 38746 | CTCN_8662 | 52805 |
| GTCN_2026 | 38747 | CTCN_8663 | 52806 |
| TTCN_3162 | 38748 | CTCN_8664 | 52807 |
| ATCN_2255 | 38749 | CTCN_8665 | 52808 |
| CTCN_3849 | 38750 | ATCN_4907 | 52809 |
| ATCN_2256 | 38751 | CTCN_8666 | 52810 |
| ATCN_2257 | 38752 | CTCN_8667 | 52811 |
| TTCN_3163 | 38753 | CTCN_8668 | 52812 |
| TTCN_3164 | 38754 | ATCN_4908 | 52813 |
| ATCN_2258 | 38755 | CTCN_8669 | 52814 |
| CTCN_3850 | 38756 | CTCN_8670 | 52815 |
| GTCN_2027 | 38757 | GTCN_4645 | 52816 |
| GTCN_2028 | 38758 | ATCN_4909 | 52817 |
| GTCN_2029 | 38759 | CTCN_8671 | 52818 |

| | | | |
|---|---|---|---|
| ATCN_2259 | 38760 | TTCN_7136 | 52819 |
| TTCN_3165 | 38761 | GTCN_4646 | 52820 |
| TTCN_3166 | 38762 | GTCN_4647 | 52821 |
| TTCN_3167 | 38763 | CTCN_8672 | 52822 |
| ATCN_2260 | 38764 | TTCN_7137 | 52823 |
| CTCN_3851 | 38765 | GTCN_4648 | 52824 |
| ATCN_2261 | 38766 | CTCN_8673 | 52825 |
| TTCN_3168 | 38767 | CTCN_8674 | 52826 |
| TTCN_3169 | 38768 | CTCN_8675 | 52827 |
| TTCN_3170 | 38769 | GTCN_4649 | 52828 |
| CTCN_3852 | 38770 | TTCN_7138 | 52829 |
| ATCN_2262 | 38771 | CTCN_8676 | 52830 |
| CTCN_3853 | 38772 | TTCN_7139 | 52831 |
| GTCN_2030 | 38773 | CTCN_8677 | 52832 |
| ATCN_2263 | 38774 | TTCN_7140 | 52833 |
| ATCN_2264 | 38775 | TTCN_7141 | 52834 |
| CTCN_3854 | 38776 | CTCN_8678 | 52835 |
| GTCN_2031 | 38777 | CTCN_8679 | 52836 |
| CTCN_3855 | 38778 | TTCN_7142 | 52837 |
| ATCN_2265 | 38779 | TTCN_7143 | 52838 |
| TTCN_3171 | 38780 | CTCN_8680 | 52839 |
| GTCN_2032 | 38781 | TTCN_7144 | 52840 |
| CTCN_3856 | 38782 | TTCN_7145 | 52841 |
| ATCN_2266 | 38783 | CTCN_8681 | 52842 |
| CTCN_3857 | 38784 | TTCN_7146 | 52843 |
| CTCN_3858 | 38785 | CTCN_8682 | 52844 |
| CTCN_3859 | 38786 | CTCN_8683 | 52845 |
| CTCN_3860 | 38787 | TTCN_7147 | 52846 |
| TTCN_3172 | 38788 | TTCN_7148 | 52847 |
| ATCN_2267 | 38789 | TTCN_7149 | 52848 |
| TTCN_3173 | 38790 | GTCN_4650 | 52849 |
| CTCN_3861 | 38791 | GTCN_4651 | 52850 |
| CTCN_3862 | 38792 | CTCN_8684 | 52851 |
| CTCN_3863 | 38793 | CTCN_8685 | 52852 |
| ATCN_2268 | 38794 | GTCN_4652 | 52853 |
| ATCN_2269 | 38795 | CTCN_8686 | 52854 |
| CTCN_3864 | 38796 | CTCN_8687 | 52855 |
| CTCN_3865 | 38797 | CTCN_8688 | 52856 |
| GTCN_2033 | 38798 | GTCN_4653 | 52857 |
| CTCN_3866 | 38799 | GTCN_4654 | 52858 |
| GTCN_2034 | 38800 | CTCN_8689 | 52859 |
| CTCN_3867 | 38801 | CTCN_8690 | 52860 |
| TTCN_3174 | 38802 | CTCN_8691 | 52861 |

FIG. 37 (continued)

| | | | |
|---|---|---|---|
| TTCN_3175 | 38803 | CTCN_8692 | 52862 |
| TTCN_3176 | 38804 | CTCN_8693 | 52863 |
| ATCN_2270 | 38805 | GTCN_4655 | 52864 |
| CTCN_3868 | 38806 | GTCN_4656 | 52865 |
| CTCN_3869 | 38807 | CTCN_8694 | 52866 |
| CTCN_3870 | 38808 | ATCN_4910 | 52867 |
| TTCN_3177 | 38809 | ATCN_4911 | 52868 |
| GTCN_2035 | 38810 | TTCN_7150 | 52869 |
| CTCN_3871 | 38811 | TTCN_7151 | 52870 |
| CTCN_3872 | 38812 | CTCN_8695 | 52871 |
| ATCN_2271 | 38813 | CTCN_8696 | 52872 |
| GTCN_2036 | 38814 | CTCN_8697 | 52873 |
| GTCN_2037 | 38815 | CTCN_8698 | 52874 |
| TTCN_3178 | 38816 | GTCN_4657 | 52875 |
| GTCN_2038 | 38817 | TTCN_7152 | 52876 |
| TTCN_3179 | 38818 | CTCN_8699 | 52877 |
| CTCN_3873 | 38819 | GTCN_4658 | 52878 |
| CTCN_3874 | 38820 | GTCN_4659 | 52879 |
| TTCN_3180 | 38821 | TTCN_7153 | 52880 |
| GTCN_2039 | 38822 | CTCN_8700 | 52881 |
| TTCN_3181 | 38823 | GTCN_4660 | 52882 |
| TTCN_3182 | 38824 | CTCN_8701 | 52883 |
| TTCN_3183 | 38825 | CTCN_8702 | 52884 |
| TTCN_3184 | 38826 | GTCN_4661 | 52885 |
| CTCN_3875 | 38827 | TTCN_7154 | 52886 |
| GTCN_2040 | 38828 | ATCN_4912 | 52887 |
| CTCN_3876 | 38829 | TTCN_7155 | 52888 |
| GTCN_2041 | 38830 | GTCN_4662 | 52889 |
| TTCN_3185 | 38831 | ATCN_4913 | 52890 |
| CTCN_3877 | 38832 | ATCN_4914 | 52891 |
| CTCN_3878 | 38833 | CTCN_8703 | 52892 |
| CTCN_3879 | 38834 | TTCN_7156 | 52893 |
| GTCN_2042 | 38835 | CTCN_8704 | 52894 |
| GTCN_2043 | 38836 | GTCN_4663 | 52895 |
| ATCN_2272 | 38837 | GTCN_4664 | 52896 |
| TTCN_3186 | 38838 | ATCN_4915 | 52897 |
| TTCN_3187 | 38839 | TTCN_7157 | 52898 |
| TTCN_3188 | 38840 | GTCN_4665 | 52899 |
| TTCN_3189 | 38841 | TTCN_7158 | 52900 |
| TTCN_3190 | 38842 | TTCN_7159 | 52901 |
| TTCN_3191 | 38843 | CTCN_8705 | 52902 |
| TTCN_3192 | 38844 | CTCN_8706 | 52903 |
| TTCN_3193 | 38845 | TTCN_7160 | 52904 |

| | | | |
|---|---|---|---|
| ATCN_2273 | 38846 | TTCN_7161 | 52905 |
| TTCN_3194 | 38847 | GTCN_4666 | 52906 |
| ATCN_2274 | 38848 | GTCN_4667 | 52907 |
| TTCN_3195 | 38849 | CTCN_8707 | 52908 |
| TTCN_3196 | 38850 | CTCN_8708 | 52909 |
| CTCN_3880 | 38851 | ATCN_4916 | 52910 |
| ATCN_2275 | 38852 | GTCN_4668 | 52911 |
| ATCN_2276 | 38853 | GTCN_4669 | 52912 |
| CTCN_3881 | 38854 | GTCN_4670 | 52913 |
| ATCN_2277 | 38855 | CTCN_8709 | 52914 |
| ATCN_2278 | 38856 | ATCN_4917 | 52915 |
| CTCN_3882 | 38857 | ATCN_4918 | 52916 |
| GTCN_2044 | 38858 | CTCN_8710 | 52917 |
| CTCN_3883 | 38859 | CTCN_8711 | 52918 |
| CTCN_3884 | 38860 | CTCN_8712 | 52919 |
| GTCN_2045 | 38861 | GTCN_4671 | 52920 |
| TTCN_3197 | 38862 | CTCN_8713 | 52921 |
| ATCN_2279 | 38863 | CTCN_8714 | 52922 |
| CTCN_3885 | 38864 | GTCN_4672 | 52923 |
| TTCN_3198 | 38865 | ATCN_4919 | 52924 |
| ATCN_2280 | 38866 | ATCN_4920 | 52925 |
| CTCN_3886 | 38867 | TTCN_7162 | 52926 |
| CTCN_3887 | 38868 | GTCN_4673 | 52927 |
| TTCN_3199 | 38869 | CTCN_8715 | 52928 |
| ATCN_2281 | 38870 | CTCN_8716 | 52929 |
| TTCN_3200 | 38871 | TTCN_7163 | 52930 |
| TTCN_3201 | 38872 | TTCN_7164 | 52931 |
| CTCN_3888 | 38873 | ATCN_4921 | 52932 |
| CTCN_3889 | 38874 | CTCN_8717 | 52933 |
| ATCN_2282 | 38875 | ATCN_4922 | 52934 |
| CTCN_3890 | 38876 | CTCN_8718 | 52935 |
| CTCN_3891 | 38877 | CTCN_8719 | 52936 |
| GTCN_2046 | 38878 | CTCN_8720 | 52937 |
| CTCN_3892 | 38879 | CTCN_8721 | 52938 |
| TTCN_3202 | 38880 | CTCN_8722 | 52939 |
| TTCN_3203 | 38881 | GTCN_4674 | 52940 |
| ATCN_2283 | 38882 | CTCN_8723 | 52941 |
| TTCN_3204 | 38883 | CTCN_8724 | 52942 |
| TTCN_3205 | 38884 | CTCN_8725 | 52943 |
| TTCN_3206 | 38885 | TTCN_7165 | 52944 |
| GTCN_2047 | 38886 | TTCN_7166 | 52945 |
| ATCN_2284 | 38887 | CTCN_8726 | 52946 |
| TTCN_3207 | 38888 | CTCN_8727 | 52947 |

FIG. 37 (continued)

| | | | |
|---|---|---|---|
| TTCN_3208 | 38889 | GTCN_4675 | 52948 |
| ATCN_2285 | 38890 | TTCN_7167 | 52949 |
| ATCN_2286 | 38891 | CTCN_8728 | 52950 |
| ATCN_2287 | 38892 | CTCN_8729 | 52951 |
| CTCN_3893 | 38893 | TTCN_7168 | 52952 |
| TTCN_3209 | 38894 | CTCN_8730 | 52953 |
| ATCN_2288 | 38895 | TTCN_7169 | 52954 |
| GTCN_2048 | 38896 | ATCN_4923 | 52955 |
| ATCN_2289 | 38897 | CTCN_8731 | 52956 |
| CTCN_3894 | 38898 | CTCN_8732 | 52957 |
| ATCN_2290 | 38899 | TTCN_7170 | 52958 |
| ATCN_2291 | 38900 | TTCN_7171 | 52959 |
| TTCN_3210 | 38901 | ATCN_4924 | 52960 |
| TTCN_3211 | 38902 | TTCN_7172 | 52961 |
| TTCN_3212 | 38903 | TTCN_7173 | 52962 |
| ATCN_2292 | 38904 | ATCN_4925 | 52963 |
| CTCN_3895 | 38905 | TTCN_7174 | 52964 |
| CTCN_3896 | 38906 | CTCN_8733 | 52965 |
| TTCN_3213 | 38907 | CTCN_8734 | 52966 |
| ATCN_2293 | 38908 | TTCN_7175 | 52967 |
| TTCN_3214 | 38909 | GTCN_4676 | 52968 |
| TTCN_3215 | 38910 | CTCN_8735 | 52969 |
| ATCN_2294 | 38911 | CTCN_8736 | 52970 |
| TTCN_3216 | 38912 | TTCN_7176 | 52971 |
| GTCN_2049 | 38913 | GTCN_4677 | 52972 |
| GTCN_2050 | 38914 | CTCN_8737 | 52973 |
| ATCN_2295 | 38915 | TTCN_7177 | 52974 |
| CTCN_3897 | 38916 | ATCN_4926 | 52975 |
| ATCN_2296 | 38917 | TTCN_7178 | 52976 |
| CTCN_3898 | 38918 | GTCN_4678 | 52977 |
| CTCN_3899 | 38919 | TTCN_7179 | 52978 |
| ATCN_2297 | 38920 | TTCN_7180 | 52979 |
| TTCN_3217 | 38921 | ATCN_4927 | 52980 |
| CTCN_3900 | 38922 | GTCN_4679 | 52981 |
| TTCN_3218 | 38923 | ATCN_4928 | 52982 |
| TTCN_3219 | 38924 | GTCN_4680 | 52983 |
| ATCN_2298 | 38925 | GTCN_4681 | 52984 |
| CTCN_3901 | 38926 | TTCN_7181 | 52985 |
| ATCN_2299 | 38927 | ATCN_4929 | 52986 |
| ATCN_2300 | 38928 | CTCN_8738 | 52987 |
| TTCN_3220 | 38929 | TTCN_7182 | 52988 |
| CTCN_3902 | 38930 | TTCN_7183 | 52989 |
| TTCN_3221 | 38931 | TTCN_7184 | 52990 |

| | | | |
|---|---|---|---|
| TTCN_3222 | 38932 | CTCN_8739 | 52991 |
| TTCN_3223 | 38933 | CTCN_8740 | 52992 |
| TTCN_3224 | 38934 | ATCN_4930 | 52993 |
| CTCN_3903 | 38935 | CTCN_8741 | 52994 |
| GTCN_2051 | 38936 | ATCN_4931 | 52995 |
| GTCN_2052 | 38937 | ATCN_4932 | 52996 |
| CTCN_3904 | 38938 | TTCN_7185 | 52997 |
| CTCN_3905 | 38939 | GTCN_4682 | 52998 |
| TTCN_3225 | 38940 | CTCN_8742 | 52999 |
| CTCN_3906 | 38941 | TTCN_7186 | 53000 |
| ATCN_2301 | 38942 | CTCN_8743 | 53001 |
| TTCN_3226 | 38943 | CTCN_8744 | 53002 |
| CTCN_3907 | 38944 | TTCN_7187 | 53003 |
| TTCN_3227 | 38945 | ATCN_4933 | 53004 |
| CTCN_3908 | 38946 | TTCN_7188 | 53005 |
| CTCN_3909 | 38947 | TTCN_7189 | 53006 |
| CTCN_3910 | 38948 | GTCN_4683 | 53007 |
| TTCN_3228 | 38949 | ATCN_4934 | 53008 |
| GTCN_2053 | 38950 | CTCN_8745 | 53009 |
| GTCN_2054 | 38951 | CTCN_8746 | 53010 |
| TTCN_3229 | 38952 | TTCN_7190 | 53011 |
| CTCN_3911 | 38953 | TTCN_7191 | 53012 |
| GTCN_2055 | 38954 | TTCN_7192 | 53013 |
| CTCN_3912 | 38955 | ATCN_4935 | 53014 |
| TTCN_3230 | 38956 | CTCN_8747 | 53015 |
| GTCN_2056 | 38957 | CTCN_8748 | 53016 |
| ATCN_2302 | 38958 | CTCN_8749 | 53017 |
| CTCN_3913 | 38959 | TTCN_7193 | 53018 |
| CTCN_3914 | 38960 | GTCN_4684 | 53019 |
| ATCN_2303 | 38961 | CTCN_8750 | 53020 |
| ATCN_2304 | 38962 | GTCN_4685 | 53021 |
| TTCN_3231 | 38963 | TTCN_7194 | 53022 |
| CTCN_3915 | 38964 | CTCN_8751 | 53023 |
| TTCN_3232 | 38965 | TTCN_7195 | 53024 |
| CTCN_3916 | 38966 | TTCN_7196 | 53025 |
| CTCN_3917 | 38967 | ATCN_4936 | 53026 |
| TTCN_3233 | 38968 | CTCN_8752 | 53027 |
| GTCN_2057 | 38969 | CTCN_8753 | 53028 |
| TTCN_3234 | 38970 | ATCN_4937 | 53029 |
| TTCN_3235 | 38971 | GTCN_4686 | 53030 |
| TTCN_3236 | 38972 | TTCN_7197 | 53031 |
| ATCN_2305 | 38973 | CTCN_8754 | 53032 |
| CTCN_3918 | 38974 | TTCN_7198 | 53033 |

FIG. 37 (continued)

| | | | |
|---|---|---|---|
| ATCN_2306 | 38975 | TTCN_7199 | 53034 |
| TTCN_3237 | 38976 | CTCN_8755 | 53035 |
| CTCN_3919 | 38977 | CTCN_8756 | 53036 |
| ATCN_2307 | 38978 | TTCN_7200 | 53037 |
| TTCN_3238 | 38979 | ATCN_4938 | 53038 |
| CTCN_3920 | 38980 | CTCN_8757 | 53039 |
| GTCN_2058 | 38981 | GTCN_4687 | 53040 |
| ATCN_2308 | 38982 | ATCN_4939 | 53041 |
| ATCN_2309 | 38983 | TTCN_7201 | 53042 |
| TTCN_3239 | 38984 | GTCN_4688 | 53043 |
| CTCN_3921 | 38985 | CTCN_8758 | 53044 |
| CTCN_3922 | 38986 | TTCN_7202 | 53045 |
| CTCN_3923 | 38987 | CTCN_8759 | 53046 |
| GTCN_2059 | 38988 | TTCN_7203 | 53047 |
| CTCN_3924 | 38989 | CTCN_8760 | 53048 |
| GTCN_2060 | 38990 | GTCN_4689 | 53049 |
| CTCN_3925 | 38991 | CTCN_8761 | 53050 |
| CTCN_3926 | 38992 | TTCN_7204 | 53051 |
| GTCN_2061 | 38993 | CTCN_8762 | 53052 |
| TTCN_3240 | 38994 | CTCN_8763 | 53053 |
| CTCN_3927 | 38995 | CTCN_8764 | 53054 |
| ATCN_2310 | 38996 | CTCN_8765 | 53055 |
| TTCN_3241 | 38997 | TTCN_7205 | 53056 |
| TTCN_3242 | 38998 | CTCN_8766 | 53057 |
| TTCN_3243 | 38999 | CTCN_8767 | 53058 |
| CTCN_3928 | 39000 | CTCN_8768 | 53059 |
| CTCN_3929 | 39001 | TTCN_7206 | 53060 |
| CTCN_3930 | 39002 | ATCN_4940 | 53061 |
| GTCN_2062 | 39003 | GTCN_4690 | 53062 |
| CTCN_3931 | 39004 | GTCN_4691 | 53063 |
| CTCN_3932 | 39005 | CTCN_8769 | 53064 |
| CTCN_3933 | 39006 | CTCN_8770 | 53065 |
| CTCN_3934 | 39007 | CTCN_8771 | 53066 |
| GTCN_2063 | 39008 | GTCN_4692 | 53067 |
| CTCN_3935 | 39009 | CTCN_8772 | 53068 |
| CTCN_3936 | 39010 | CTCN_8773 | 53069 |
| GTCN_2064 | 39011 | TTCN_7207 | 53070 |
| GTCN_2065 | 39012 | TTCN_7208 | 53071 |
| CTCN_3937 | 39013 | ATCN_4941 | 53072 |
| ATCN_2311 | 39014 | CTCN_8774 | 53073 |
| ATCN_2312 | 39015 | CTCN_8775 | 53074 |
| CTCN_3938 | 39016 | TTCN_7209 | 53075 |
| TTCN_3244 | 39017 | CTCN_8776 | 53076 |

| | | | |
|---|---|---|---|
| ATCN_2313 | 39018 | GTCN_4693 | 53077 |
| GTCN_2066 | 39019 | CTCN_8777 | 53078 |
| TTCN_3245 | 39020 | GTCN_4694 | 53079 |
| CTCN_3939 | 39021 | CTCN_8778 | 53080 |
| GTCN_2067 | 39022 | CTCN_8779 | 53081 |
| CTCN_3940 | 39023 | GTCN_4695 | 53082 |
| CTCN_3941 | 39024 | CTCN_8780 | 53083 |
| GTCN_2068 | 39025 | CTCN_8781 | 53084 |
| ATCN_2314 | 39026 | GTCN_4696 | 53085 |
| CTCN_3942 | 39027 | CTCN_8782 | 53086 |
| CTCN_3943 | 39028 | GTCN_4697 | 53087 |
| ATCN_2315 | 39029 | CTCN_8783 | 53088 |
| TTCN_3246 | 39030 | CTCN_8784 | 53089 |
| CTCN_3944 | 39031 | CTCN_8785 | 53090 |
| GTCN_2069 | 39032 | ATCN_4942 | 53091 |
| CTCN_3945 | 39033 | CTCN_8786 | 53092 |
| TTCN_3247 | 39034 | GTCN_4698 | 53093 |
| CTCN_3946 | 39035 | CTCN_8787 | 53094 |
| CTCN_3947 | 39036 | TTCN_7210 | 53095 |
| GTCN_2070 | 39037 | GTCN_4699 | 53096 |
| GTCN_2071 | 39038 | GTCN_4700 | 53097 |
| CTCN_3948 | 39039 | CTCN_8788 | 53098 |
| GTCN_2072 | 39040 | CTCN_8789 | 53099 |
| CTCN_3949 | 39041 | TTCN_7211 | 53100 |
| GTCN_2073 | 39042 | TTCN_7212 | 53101 |
| CTCN_3950 | 39043 | GTCN_4701 | 53102 |
| TTCN_3248 | 39044 | CTCN_8790 | 53103 |
| CTCN_3951 | 39045 | CTCN_8791 | 53104 |
| CTCN_3952 | 39046 | TTCN_7213 | 53105 |
| ATCN_2316 | 39047 | CTCN_8792 | 53106 |
| CTCN_3953 | 39048 | GTCN_4702 | 53107 |
| TTCN_3249 | 39049 | CTCN_8793 | 53108 |
| GTCN_2074 | 39050 | ATCN_4943 | 53109 |
| ATCN_2317 | 39051 | TTCN_7214 | 53110 |
| TTCN_3250 | 39052 | GTCN_4703 | 53111 |
| CTCN_3954 | 39053 | ATCN_4944 | 53112 |
| CTCN_3955 | 39054 | ATCN_4945 | 53113 |
| CTCN_3956 | 39055 | ATCN_4946 | 53114 |
| TTCN_3251 | 39056 | GTCN_4704 | 53115 |
| CTCN_3957 | 39057 | TTCN_7215 | 53116 |
| CTCN_3958 | 39058 | TTCN_7216 | 53117 |
| CTCN_3959 | 39059 | CTCN_8794 | 53118 |
| ATCN_2318 | 39060 | CTCN_8795 | 53119 |

FIG. 37 (continued)

| | | | |
|---|---|---|---|
| CTCN_3960 | 39061 | ATCN_4947 | 53120 |
| GTCN_2075 | 39062 | TTCN_7217 | 53121 |
| GTCN_2076 | 39063 | GTCN_4705 | 53122 |
| GTCN_2077 | 39064 | ATCN_4948 | 53123 |
| TTCN_3252 | 39065 | ATCN_4949 | 53124 |
| GTCN_2078 | 39066 | TTCN_7218 | 53125 |
| CTCN_3961 | 39067 | CTCN_8796 | 53126 |
| CTCN_3962 | 39068 | GTCN_4706 | 53127 |
| CTCN_3963 | 39069 | CTCN_8797 | 53128 |
| ATCN_2319 | 39070 | TTCN_7219 | 53129 |
| GTCN_2079 | 39071 | GTCN_4707 | 53130 |
| CTCN_3964 | 39072 | GTCN_4708 | 53131 |
| CTCN_3965 | 39073 | CTCN_8798 | 53132 |
| ATCN_2320 | 39074 | TTCN_7220 | 53133 |
| GTCN_2080 | 39075 | TTCN_7221 | 53134 |
| CTCN_3966 | 39076 | TTCN_7222 | 53135 |
| ATCN_2321 | 39077 | TTCN_7223 | 53136 |
| CTCN_3967 | 39078 | TTCN_7224 | 53137 |
| TTCN_3253 | 39079 | TTCN_7225 | 53138 |
| CTCN_3968 | 39080 | ATCN_4950 | 53139 |
| TTCN_3254 | 39081 | ATCN_4951 | 53140 |
| TTCN_3255 | 39082 | ATCN_4952 | 53141 |
| ATCN_2322 | 39083 | CTCN_8799 | 53142 |
| CTCN_3969 | 39084 | CTCN_8800 | 53143 |
| ATCN_2323 | 39085 | CTCN_8801 | 53144 |
| CTCN_3970 | 39086 | GTCN_4709 | 53145 |
| TTCN_3256 | 39087 | CTCN_8802 | 53146 |
| ATCN_2324 | 39088 | CTCN_8803 | 53147 |
| CTCN_3971 | 39089 | TTCN_7226 | 53148 |
| CTCN_3972 | 39090 | CTCN_8804 | 53149 |
| TTCN_3257 | 39091 | CTCN_8805 | 53150 |
| TTCN_3258 | 39092 | GTCN_4710 | 53151 |
| TTCN_3259 | 39093 | TTCN_7227 | 53152 |
| ATCN_2325 | 39094 | TTCN_7228 | 53153 |
| CTCN_3973 | 39095 | CTCN_8806 | 53154 |
| TTCN_3260 | 39096 | GTCN_4711 | 53155 |
| CTCN_3974 | 39097 | CTCN_8807 | 53156 |
| TTCN_3261 | 39098 | ATCN_4953 | 53157 |
| CTCN_3975 | 39099 | CTCN_8808 | 53158 |
| CTCN_3976 | 39100 | ATCN_4954 | 53159 |
| TTCN_3262 | 39101 | GTCN_4712 | 53160 |
| TTCN_3263 | 39102 | TTCN_7229 | 53161 |
| ATCN_2326 | 39103 | GTCN_4713 | 53162 |

| | | | |
|---|---|---|---|
| GTCN_2081 | 39104 | TTCN_7230 | 53163 |
| TTCN_3264 | 39105 | TTCN_7231 | 53164 |
| CTCN_3977 | 39106 | ATCN_4955 | 53165 |
| TTCN_3265 | 39107 | GTCN_4714 | 53166 |
| GTCN_2082 | 39108 | CTCN_8809 | 53167 |
| GTCN_2083 | 39109 | TTCN_7232 | 53168 |
| ATCN_2327 | 39110 | CTCN_8810 | 53169 |
| TTCN_3266 | 39111 | GTCN_4715 | 53170 |
| ATCN_2328 | 39112 | TTCN_7233 | 53171 |
| ATCN_2329 | 39113 | CTCN_8811 | 53172 |
| ATCN_2330 | 39114 | TTCN_7234 | 53173 |
| CTCN_3978 | 39115 | GTCN_4716 | 53174 |
| GTCN_2084 | 39116 | ATCN_4956 | 53175 |
| CTCN_3979 | 39117 | ATCN_4957 | 53176 |
| TTCN_3267 | 39118 | TTCN_7235 | 53177 |
| CTCN_3980 | 39119 | CTCN_8812 | 53178 |
| TTCN_3268 | 39120 | GTCN_4717 | 53179 |
| CTCN_3981 | 39121 | GTCN_4718 | 53180 |
| CTCN_3982 | 39122 | CTCN_8813 | 53181 |
| TTCN_3269 | 39123 | CTCN_8814 | 53182 |
| ATCN_2331 | 39124 | CTCN_8815 | 53183 |
| CTCN_3983 | 39125 | GTCN_4719 | 53184 |
| CTCN_3984 | 39126 | TTCN_7236 | 53185 |
| GTCN_2085 | 39127 | CTCN_8816 | 53186 |
| ATCN_2332 | 39128 | GTCN_4720 | 53187 |
| GTCN_2086 | 39129 | CTCN_8817 | 53188 |
| ATCN_2333 | 39130 | CTCN_8818 | 53189 |
| CTCN_3985 | 39131 | TTCN_7237 | 53190 |
| CTCN_3986 | 39132 | TTCN_7238 | 53191 |
| CTCN_3987 | 39133 | ATCN_4958 | 53192 |
| ATCN_2334 | 39134 | CTCN_8819 | 53193 |
| CTCN_3988 | 39135 | TTCN_7239 | 53194 |
| CTCN_3989 | 39136 | ATCN_4959 | 53195 |
| TTCN_3270 | 39137 | CTCN_8820 | 53196 |
| GTCN_2087 | 39138 | CTCN_8821 | 53197 |
| CTCN_3990 | 39139 | CTCN_8822 | 53198 |
| TTCN_3271 | 39140 | ATCN_4960 | 53199 |
| ATCN_2335 | 39141 | GTCN_4721 | 53200 |
| CTCN_3991 | 39142 | CTCN_8823 | 53201 |
| CTCN_3992 | 39143 | TTCN_7240 | 53202 |
| GTCN_2088 | 39144 | TTCN_7241 | 53203 |
| CTCN_3993 | 39145 | GTCN_4722 | 53204 |
| CTCN_3994 | 39146 | TTCN_7242 | 53205 |

FIG. 37 (continued)

| | | | |
|---|---|---|---|
| CTCN_3995 | 39147 | CTCN_8824 | 53206 |
| GTCN_2089 | 39148 | TTCN_7243 | 53207 |
| CTCN_3996 | 39149 | CTCN_8825 | 53208 |
| GTCN_2090 | 39150 | TTCN_7244 | 53209 |
| CTCN_3997 | 39151 | TTCN_7245 | 53210 |
| ATCN_2336 | 39152 | CTCN_8826 | 53211 |
| CTCN_3998 | 39153 | TTCN_7246 | 53212 |
| CTCN_3999 | 39154 | TTCN_7247 | 53213 |
| TTCN_3272 | 39155 | ATCN_4961 | 53214 |
| CTCN_4000 | 39156 | GTCN_4723 | 53215 |
| ATCN_2337 | 39157 | TTCN_7248 | 53216 |
| ATCN_2338 | 39158 | CTCN_8827 | 53217 |
| CTCN_4001 | 39159 | ATCN_4962 | 53218 |
| CTCN_4002 | 39160 | TTCN_7249 | 53219 |
| TTCN_3273 | 39161 | TTCN_7250 | 53220 |
| CTCN_4003 | 39162 | CTCN_8828 | 53221 |
| GTCN_2091 | 39163 | GTCN_4724 | 53222 |
| TTCN_3274 | 39164 | TTCN_7251 | 53223 |
| ATCN_2339 | 39165 | ATCN_4963 | 53224 |
| TTCN_3275 | 39166 | ATCN_4964 | 53225 |
| CTCN_4004 | 39167 | CTCN_8829 | 53226 |
| CTCN_4005 | 39168 | GTCN_4725 | 53227 |
| ATCN_2340 | 39169 | TTCN_7252 | 53228 |
| TTCN_3276 | 39170 | TTCN_7253 | 53229 |
| CTCN_4006 | 39171 | ATCN_4965 | 53230 |
| GTCN_2092 | 39172 | CTCN_8830 | 53231 |
| GTCN_2093 | 39173 | CTCN_8831 | 53232 |
| CTCN_4007 | 39174 | CTCN_8832 | 53233 |
| TTCN_3277 | 39175 | TTCN_7254 | 53234 |
| TTCN_3278 | 39176 | CTCN_8833 | 53235 |
| TTCN_3279 | 39177 | CTCN_8834 | 53236 |
| GTCN_2094 | 39178 | CTCN_8835 | 53237 |
| TTCN_3280 | 39179 | CTCN_8836 | 53238 |
| ATCN_2341 | 39180 | CTCN_8837 | 53239 |
| CTCN_4008 | 39181 | TTCN_7255 | 53240 |
| GTCN_2095 | 39182 | CTCN_8838 | 53241 |
| ATCN_2342 | 39183 | CTCN_8839 | 53242 |
| TTCN_3281 | 39184 | CTCN_8840 | 53243 |
| TTCN_3282 | 39185 | GTCN_4726 | 53244 |
| GTCN_2096 | 39186 | CTCN_8841 | 53245 |
| CTCN_4009 | 39187 | GTCN_4727 | 53246 |
| CTCN_4010 | 39188 | CTCN_8842 | 53247 |
| CTCN_4011 | 39189 | GTCN_4728 | 53248 |

| | | | |
|---|---|---|---|
| CTCN_4012 | 39190 | CTCN_8843 | 53249 |
| ATCN_2343 | 39191 | CTCN_8844 | 53250 |
| TTCN_3283 | 39192 | CTCN_8845 | 53251 |
| ATCN_2344 | 39193 | CTCN_8846 | 53252 |
| TTCN_3284 | 39194 | GTCN_4729 | 53253 |
| CTCN_4013 | 39195 | CTCN_8847 | 53254 |
| ATCN_2345 | 39196 | CTCN_8848 | 53255 |
| GTCN_2097 | 39197 | CTCN_8849 | 53256 |
| TTCN_3285 | 39198 | CTCN_8850 | 53257 |
| ATCN_2346 | 39199 | GTCN_4730 | 53258 |
| GTCN_2098 | 39200 | CTCN_8851 | 53259 |
| GTCN_2099 | 39201 | CTCN_8852 | 53260 |
| CTCN_4014 | 39202 | CTCN_8853 | 53261 |
| GTCN_2100 | 39203 | CTCN_8854 | 53262 |
| GTCN_2101 | 39204 | CTCN_8855 | 53263 |
| CTCN_4015 | 39205 | CTCN_8856 | 53264 |
| TTCN_3286 | 39206 | GTCN_4731 | 53265 |
| GTCN_2102 | 39207 | TTCN_7256 | 53266 |
| ATCN_2347 | 39208 | TTCN_7257 | 53267 |
| CTCN_4016 | 39209 | CTCN_8857 | 53268 |
| GTCN_2103 | 39210 | TTCN_7258 | 53269 |
| CTCN_4017 | 39211 | CTCN_8858 | 53270 |
| ATCN_2348 | 39212 | TTCN_7259 | 53271 |
| TTCN_3287 | 39213 | CTCN_8859 | 53272 |
| CTCN_4018 | 39214 | GTCN_4732 | 53273 |
| GTCN_2104 | 39215 | CTCN_8860 | 53274 |
| CTCN_4019 | 39216 | CTCN_8861 | 53275 |
| ATCN_2349 | 39217 | ATCN_4966 | 53276 |
| TTCN_3288 | 39218 | CTCN_8862 | 53277 |
| GTCN_2105 | 39219 | GTCN_4733 | 53278 |
| TTCN_3289 | 39220 | GTCN_4734 | 53279 |
| ATCN_2350 | 39221 | GTCN_4735 | 53280 |
| CTCN_4020 | 39222 | CTCN_8863 | 53281 |
| TTCN_3290 | 39223 | GTCN_4736 | 53282 |
| CTCN_4021 | 39224 | GTCN_4737 | 53283 |
| TTCN_3291 | 39225 | ATCN_4967 | 53284 |
| TTCN_3292 | 39226 | CTCN_8864 | 53285 |
| ATCN_2351 | 39227 | TTCN_7260 | 53286 |
| ATCN_2352 | 39228 | GTCN_4738 | 53287 |
| TTCN_3293 | 39229 | GTCN_4739 | 53288 |
| CTCN_4022 | 39230 | CTCN_8865 | 53289 |
| GTCN_2106 | 39231 | CTCN_8866 | 53290 |
| TTCN_3294 | 39232 | ATCN_4968 | 53291 |

FIG. 37 (continued)

| | | | |
|---|---|---|---|
| CTCN_4023 | 39233 | CTCN_8867 | 53292 |
| TTCN_3295 | 39234 | CTCN_8868 | 53293 |
| CTCN_4024 | 39235 | TTCN_7261 | 53294 |
| TTCN_3296 | 39236 | CTCN_8869 | 53295 |
| ATCN_2353 | 39237 | GTCN_4740 | 53296 |
| TTCN_3297 | 39238 | CTCN_8870 | 53297 |
| TTCN_3298 | 39239 | CTCN_8871 | 53298 |
| CTCN_4025 | 39240 | CTCN_8872 | 53299 |
| ATCN_2354 | 39241 | CTCN_8873 | 53300 |
| CTCN_4026 | 39242 | GTCN_4741 | 53301 |
| CTCN_4027 | 39243 | CTCN_8874 | 53302 |
| CTCN_4028 | 39244 | GTCN_4742 | 53303 |
| TTCN_3299 | 39245 | TTCN_7262 | 53304 |
| TTCN_3300 | 39246 | TTCN_7263 | 53305 |
| CTCN_4029 | 39247 | ATCN_4969 | 53306 |
| GTCN_2107 | 39248 | GTCN_4743 | 53307 |
| TTCN_3301 | 39249 | GTCN_4744 | 53308 |
| ATCN_2355 | 39250 | CTCN_8875 | 53309 |
| TTCN_3302 | 39251 | CTCN_8876 | 53310 |
| TTCN_3303 | 39252 | CTCN_8877 | 53311 |
| TTCN_3304 | 39253 | TTCN_7264 | 53312 |
| CTCN_4030 | 39254 | CTCN_8878 | 53313 |
| CTCN_4031 | 39255 | TTCN_7265 | 53314 |
| TTCN_3305 | 39256 | CTCN_8879 | 53315 |
| CTCN_4032 | 39257 | CTCN_8880 | 53316 |
| CTCN_4033 | 39258 | CTCN_8881 | 53317 |
| GTCN_2108 | 39259 | CTCN_8882 | 53318 |
| TTCN_3306 | 39260 | CTCN_8883 | 53319 |
| CTCN_4034 | 39261 | ATCN_4970 | 53320 |
| CTCN_4035 | 39262 | TTCN_7266 | 53321 |
| CTCN_4036 | 39263 | ATCN_4971 | 53322 |
| GTCN_2109 | 39264 | CTCN_8884 | 53323 |
| TTCN_3307 | 39265 | CTCN_8885 | 53324 |
| TTCN_3308 | 39266 | CTCN_8886 | 53325 |
| ATCN_2356 | 39267 | CTCN_8887 | 53326 |
| TTCN_3309 | 39268 | CTCN_8888 | 53327 |
| CTCN_4037 | 39269 | ATCN_4972 | 53328 |
| CTCN_4038 | 39270 | TTCN_7267 | 53329 |
| CTCN_4039 | 39271 | CTCN_8889 | 53330 |
| CTCN_4040 | 39272 | CTCN_8890 | 53331 |
| CTCN_4041 | 39273 | CTCN_8891 | 53332 |
| ATCN_2357 | 39274 | ATCN_4973 | 53333 |
| TTCN_3310 | 39275 | CTCN_8892 | 53334 |

| | | | |
|---|---|---|---|
| GTCN_2110 | 39276 | GTCN_4745 | 53335 |
| CTCN_4042 | 39277 | GTCN_4746 | 53336 |
| ATCN_2358 | 39278 | TTCN_7268 | 53337 |
| CTCN_4043 | 39279 | GTCN_4747 | 53338 |
| GTCN_2111 | 39280 | CTCN_8893 | 53339 |
| CTCN_4044 | 39281 | ATCN_4974 | 53340 |
| TTCN_3311 | 39282 | ATCN_4975 | 53341 |
| CTCN_4045 | 39283 | CTCN_8894 | 53342 |
| ATCN_2359 | 39284 | ATCN_4976 | 53343 |
| GTCN_2112 | 39285 | CTCN_8895 | 53344 |
| TTCN_3312 | 39286 | ATCN_4977 | 53345 |
| GTCN_2113 | 39287 | ATCN_4978 | 53346 |
| CTCN_4046 | 39288 | CTCN_8896 | 53347 |
| CTCN_4047 | 39289 | CTCN_8897 | 53348 |
| GTCN_2114 | 39290 | CTCN_8898 | 53349 |
| GTCN_2115 | 39291 | CTCN_8899 | 53350 |
| CTCN_4048 | 39292 | CTCN_8900 | 53351 |
| CTCN_4049 | 39293 | GTCN_4748 | 53352 |
| TTCN_3313 | 39294 | CTCN_8901 | 53353 |
| ATCN_2360 | 39295 | CTCN_8902 | 53354 |
| ATCN_2361 | 39296 | CTCN_8903 | 53355 |
| CTCN_4050 | 39297 | CTCN_8904 | 53356 |
| TTCN_3314 | 39298 | TTCN_7269 | 53357 |
| TTCN_3315 | 39299 | ATCN_4979 | 53358 |
| GTCN_2116 | 39300 | TTCN_7270 | 53359 |
| CTCN_4051 | 39301 | CTCN_8905 | 53360 |
| ATCN_2362 | 39302 | GTCN_4749 | 53361 |
| ATCN_2363 | 39303 | CTCN_8906 | 53362 |
| GTCN_2117 | 39304 | ATCN_4980 | 53363 |
| GTCN_2118 | 39305 | ATCN_4981 | 53364 |
| GTCN_2119 | 39306 | CTCN_8907 | 53365 |
| GTCN_2120 | 39307 | GTCN_4750 | 53366 |
| GTCN_2121 | 39308 | CTCN_8908 | 53367 |
| CTCN_4052 | 39309 | GTCN_4751 | 53368 |
| GTCN_2122 | 39310 | ATCN_4982 | 53369 |
| CTCN_4053 | 39311 | GTCN_4752 | 53370 |
| CTCN_4054 | 39312 | CTCN_8909 | 53371 |
| CTCN_4055 | 39313 | ATCN_4983 | 53372 |
| TTCN_3316 | 39314 | TTCN_7271 | 53373 |
| GTCN_2123 | 39315 | TTCN_7272 | 53374 |
| CTCN_4056 | 39316 | CTCN_8910 | 53375 |
| TTCN_3317 | 39317 | GTCN_4753 | 53376 |
| ATCN_2364 | 39318 | CTCN_8911 | 53377 |

FIG. 37 (continued)

| | | | |
|---|---|---|---|
| ATCN_2365 | 39319 | TTCN_7273 | 53378 |
| ATCN_2366 | 39320 | TTCN_7274 | 53379 |
| ATCN_2367 | 39321 | CTCN_8912 | 53380 |
| TTCN_3318 | 39322 | CTCN_8913 | 53381 |
| TTCN_3319 | 39323 | TTCN_7275 | 53382 |
| GTCN_2124 | 39324 | TTCN_7276 | 53383 |
| GTCN_2125 | 39325 | GTCN_4754 | 53384 |
| ATCN_2368 | 39326 | TTCN_7277 | 53385 |
| ATCN_2369 | 39327 | GTCN_4755 | 53386 |
| TTCN_3320 | 39328 | CTCN_8914 | 53387 |
| TTCN_3321 | 39329 | CTCN_8915 | 53388 |
| ATCN_2370 | 39330 | CTCN_8916 | 53389 |
| ATCN_2371 | 39331 | ATCN_4984 | 53390 |
| ATCN_2372 | 39332 | CTCN_8917 | 53391 |
| CTCN_4057 | 39333 | CTCN_8918 | 53392 |
| ATCN_2373 | 39334 | CTCN_8919 | 53393 |
| CTCN_4058 | 39335 | TTCN_7278 | 53394 |
| GTCN_2126 | 39336 | TTCN_7279 | 53395 |
| CTCN_4059 | 39337 | ATCN_4985 | 53396 |
| CTCN_4060 | 39338 | TTCN_7280 | 53397 |
| CTCN_4061 | 39339 | GTCN_4756 | 53398 |
| ATCN_2374 | 39340 | CTCN_8920 | 53399 |
| ATCN_2375 | 39341 | CTCN_8921 | 53400 |
| CTCN_4062 | 39342 | CTCN_8922 | 53401 |
| ATCN_2376 | 39343 | CTCN_8923 | 53402 |
| ATCN_2377 | 39344 | ATCN_4986 | 53403 |
| CTCN_4063 | 39345 | TTCN_7281 | 53404 |
| TTCN_3322 | 39346 | ATCN_4987 | 53405 |
| ATCN_2378 | 39347 | CTCN_8924 | 53406 |
| TTCN_3323 | 39348 | GTCN_4757 | 53407 |
| CTCN_4064 | 39349 | TTCN_7282 | 53408 |
| CTCN_4065 | 39350 | ATCN_4988 | 53409 |
| CTCN_4066 | 39351 | TTCN_7283 | 53410 |
| CTCN_4067 | 39352 | CTCN_8925 | 53411 |
| TTCN_3324 | 39353 | CTCN_8926 | 53412 |
| GTCN_2127 | 39354 | TTCN_7284 | 53413 |
| TTCN_3325 | 39355 | TTCN_7285 | 53414 |
| CTCN_4068 | 39356 | ATCN_4989 | 53415 |
| GTCN_2128 | 39357 | GTCN_4758 | 53416 |
| GTCN_2129 | 39358 | CTCN_8927 | 53417 |
| CTCN_4069 | 39359 | GTCN_4759 | 53418 |
| TTCN_3326 | 39360 | TTCN_7286 | 53419 |
| CTCN_4070 | 39361 | CTCN_8928 | 53420 |

| | | | |
|---|---|---|---|
| ATCN_2379 | 39362 | GTCN_4760 | 53421 |
| ATCN_2380 | 39363 | ATCN_4990 | 53422 |
| CTCN_4071 | 39364 | CTCN_8929 | 53423 |
| ATCN_2381 | 39365 | CTCN_8930 | 53424 |
| ATCN_2382 | 39366 | CTCN_8931 | 53425 |
| CTCN_4072 | 39367 | GTCN_4761 | 53426 |
| GTCN_2130 | 39368 | TTCN_7287 | 53427 |
| CTCN_4073 | 39369 | TTCN_7288 | 53428 |
| ATCN_2383 | 39370 | GTCN_4762 | 53429 |
| CTCN_4074 | 39371 | CTCN_8932 | 53430 |
| ATCN_2384 | 39372 | TTCN_7289 | 53431 |
| ATCN_2385 | 39373 | CTCN_8933 | 53432 |
| TTCN_3327 | 39374 | CTCN_8934 | 53433 |
| CTCN_4075 | 39375 | CTCN_8935 | 53434 |
| TTCN_3328 | 39376 | CTCN_8936 | 53435 |
| TTCN_3329 | 39377 | CTCN_8937 | 53436 |
| GTCN_2131 | 39378 | GTCN_4763 | 53437 |
| CTCN_4076 | 39379 | TTCN_7290 | 53438 |
| ATCN_2386 | 39380 | GTCN_4764 | 53439 |
| CTCN_4077 | 39381 | CTCN_8938 | 53440 |
| ATCN_2387 | 39382 | GTCN_4765 | 53441 |
| CTCN_4078 | 39383 | CTCN_8939 | 53442 |
| ATCN_2388 | 39384 | CTCN_8940 | 53443 |
| TTCN_3330 | 39385 | CTCN_8941 | 53444 |
| CTCN_4079 | 39386 | ATCN_4991 | 53445 |
| TTCN_3331 | 39387 | ATCN_4992 | 53446 |
| GTCN_2132 | 39388 | CTCN_8942 | 53447 |
| CTCN_4080 | 39389 | GTCN_4766 | 53448 |
| CTCN_4081 | 39390 | ATCN_4993 | 53449 |
| GTCN_2133 | 39391 | CTCN_8943 | 53450 |
| CTCN_4082 | 39392 | CTCN_8944 | 53451 |
| ATCN_2389 | 39393 | CTCN_8945 | 53452 |
| TTCN_3332 | 39394 | TTCN_7291 | 53453 |
| CTCN_4083 | 39395 | GTCN_4767 | 53454 |
| ATCN_2390 | 39396 | TTCN_7292 | 53455 |
| CTCN_4084 | 39397 | TTCN_7293 | 53456 |
| CTCN_4085 | 39398 | CTCN_8946 | 53457 |
| GTCN_2134 | 39399 | TTCN_7294 | 53458 |
| GTCN_2135 | 39400 | CTCN_8947 | 53459 |
| CTCN_4086 | 39401 | TTCN_7295 | 53460 |
| CTCN_4087 | 39402 | TTCN_7296 | 53461 |
| GTCN_2136 | 39403 | GTCN_4768 | 53462 |
| CTCN_4088 | 39404 | CTCN_8948 | 53463 |

FIG. 37 (continued)

| | | | |
|---|---|---|---|
| TTCN_3333 | 39405 | TTCN_7297 | 53464 |
| CTCN_4089 | 39406 | GTCN_4769 | 53465 |
| ATCN_2391 | 39407 | CTCN_8949 | 53466 |
| ATCN_2392 | 39408 | TTCN_7298 | 53467 |
| ATCN_2393 | 39409 | CTCN_8950 | 53468 |
| CTCN_4090 | 39410 | GTCN_4770 | 53469 |
| CTCN_4091 | 39411 | CTCN_8951 | 53470 |
| CTCN_4092 | 39412 | CTCN_8952 | 53471 |
| ATCN_2394 | 39413 | GTCN_4771 | 53472 |
| TTCN_3334 | 39414 | CTCN_8953 | 53473 |
| ATCN_2395 | 39415 | TTCN_7299 | 53474 |
| TTCN_3335 | 39416 | ATCN_4994 | 53475 |
| CTCN_4093 | 39417 | CTCN_8954 | 53476 |
| TTCN_3336 | 39418 | ATCN_4995 | 53477 |
| GTCN_2137 | 39419 | TTCN_7300 | 53478 |
| TTCN_3337 | 39420 | TTCN_7301 | 53479 |
| TTCN_3338 | 39421 | TTCN_7302 | 53480 |
| CTCN_4094 | 39422 | TTCN_7303 | 53481 |
| CTCN_4095 | 39423 | TTCN_7304 | 53482 |
| TTCN_3339 | 39424 | GTCN_4772 | 53483 |
| TTCN_3340 | 39425 | TTCN_7305 | 53484 |
| TTCN_3341 | 39426 | CTCN_8955 | 53485 |
| TTCN_3342 | 39427 | GTCN_4773 | 53486 |
| TTCN_3343 | 39428 | TTCN_7306 | 53487 |
| ATCN_2396 | 39429 | CTCN_8956 | 53488 |
| ATCN_2397 | 39430 | GTCN_4774 | 53489 |
| TTCN_3344 | 39431 | TTCN_7307 | 53490 |
| TTCN_3345 | 39432 | CTCN_8957 | 53491 |
| CTCN_4096 | 39433 | TTCN_7308 | 53492 |
| CTCN_4097 | 39434 | TTCN_7309 | 53493 |
| CTCN_4098 | 39435 | GTCN_4775 | 53494 |
| TTCN_3346 | 39436 | ATCN_4996 | 53495 |
| TTCN_3347 | 39437 | CTCN_8958 | 53496 |
| GTCN_2138 | 39438 | ATCN_4997 | 53497 |
| CTCN_4099 | 39439 | CTCN_8959 | 53498 |
| CTCN_4100 | 39440 | CTCN_8960 | 53499 |
| TTCN_3348 | 39441 | TTCN_7310 | 53500 |
| TTCN_3349 | 39442 | GTCN_4776 | 53501 |
| CTCN_4101 | 39443 | CTCN_8961 | 53502 |
| TTCN_3350 | 39444 | TTCN_7311 | 53503 |
| ATCN_2398 | 39445 | TTCN_7312 | 53504 |
| TTCN_3351 | 39446 | TTCN_7313 | 53505 |
| CTCN_4102 | 39447 | TTCN_7314 | 53506 |

| | | | |
|---|---|---|---|
| CTCN_4103 | 39448 | ATCN_4998 | 53507 |
| ATCN_2399 | 39449 | ATCN_4999 | 53508 |
| TTCN_3352 | 39450 | TTCN_7315 | 53509 |
| CTCN_4104 | 39451 | CTCN_8962 | 53510 |
| TTCN_3353 | 39452 | TTCN_7316 | 53511 |
| ATCN_2400 | 39453 | TTCN_7317 | 53512 |
| CTCN_4105 | 39454 | TTCN_7318 | 53513 |
| ATCN_2401 | 39455 | CTCN_8963 | 53514 |
| CTCN_4106 | 39456 | ATCN_5000 | 53515 |
| TTCN_3354 | 39457 | CTCN_8964 | 53516 |
| TTCN_3355 | 39458 | GTCN_4777 | 53517 |
| TTCN_3356 | 39459 | CTCN_8965 | 53518 |
| CTCN_4107 | 39460 | ATCN_5001 | 53519 |
| TTCN_3357 | 39461 | TTCN_7319 | 53520 |
| CTCN_4108 | 39462 | TTCN_7320 | 53521 |
| CTCN_4109 | 39463 | TTCN_7321 | 53522 |
| GTCN_2139 | 39464 | TTCN_7322 | 53523 |
| ATCN_2402 | 39465 | TTCN_7323 | 53524 |
| ATCN_2403 | 39466 | CTCN_8966 | 53525 |
| CTCN_4110 | 39467 | TTCN_7324 | 53526 |
| ATCN_2404 | 39468 | GTCN_4778 | 53527 |
| ATCN_2405 | 39469 | GTCN_4779 | 53528 |
| TTCN_3358 | 39470 | TTCN_7325 | 53529 |
| ATCN_2406 | 39471 | TTCN_7326 | 53530 |
| CTCN_4111 | 39472 | GTCN_4780 | 53531 |
| CTCN_4112 | 39473 | TTCN_7327 | 53532 |
| ATCN_2407 | 39474 | CTCN_8967 | 53533 |
| CTCN_4113 | 39475 | GTCN_4781 | 53534 |
| TTCN_3359 | 39476 | CTCN_8968 | 53535 |
| CTCN_4114 | 39477 | TTCN_7328 | 53536 |
| TTCN_3360 | 39478 | TTCN_7329 | 53537 |
| ATCN_2408 | 39479 | TTCN_7330 | 53538 |
| TTCN_3361 | 39480 | CTCN_8969 | 53539 |
| GTCN_2140 | 39481 | TTCN_7331 | 53540 |
| CTCN_4115 | 39482 | TTCN_7332 | 53541 |
| GTCN_2141 | 39483 | CTCN_8970 | 53542 |
| CTCN_4116 | 39484 | CTCN_8971 | 53543 |
| CTCN_4117 | 39485 | TTCN_7333 | 53544 |
| CTCN_4118 | 39486 | ATCN_5002 | 53545 |
| GTCN_2142 | 39487 | CTCN_8972 | 53546 |
| CTCN_4119 | 39488 | ATCN_5003 | 53547 |
| CTCN_4120 | 39489 | TTCN_7334 | 53548 |
| CTCN_4121 | 39490 | CTCN_8973 | 53549 |

FIG. 37 (continued)

| | | | |
|---|---|---|---|
| ATCN_2409 | 39491 | GTCN_4782 | 53550 |
| ATCN_2410 | 39492 | CTCN_8974 | 53551 |
| TTCN_3362 | 39493 | TTCN_7335 | 53552 |
| TTCN_3363 | 39494 | TTCN_7336 | 53553 |
| CTCN_4122 | 39495 | CTCN_8975 | 53554 |
| TTCN_3364 | 39496 | CTCN_8976 | 53555 |
| TTCN_3365 | 39497 | ATCN_5004 | 53556 |
| CTCN_4123 | 39498 | TTCN_7337 | 53557 |
| TTCN_3366 | 39499 | GTCN_4783 | 53558 |
| ATCN_2411 | 39500 | CTCN_8977 | 53559 |
| ATCN_2412 | 39501 | TTCN_7338 | 53560 |
| CTCN_4124 | 39502 | CTCN_8978 | 53561 |
| ATCN_2413 | 39503 | CTCN_8979 | 53562 |
| ATCN_2414 | 39504 | CTCN_8980 | 53563 |
| CTCN_4125 | 39505 | CTCN_8981 | 53564 |
| GTCN_2143 | 39506 | TTCN_7339 | 53565 |
| CTCN_4126 | 39507 | TTCN_7340 | 53566 |
| TTCN_3367 | 39508 | ATCN_5005 | 53567 |
| CTCN_4127 | 39509 | ATCN_5006 | 53568 |
| GTCN_2144 | 39510 | ATCN_5007 | 53569 |
| TTCN_3368 | 39511 | CTCN_8982 | 53570 |
| GTCN_2145 | 39512 | CTCN_8983 | 53571 |
| CTCN_4128 | 39513 | GTCN_4784 | 53572 |
| GTCN_2146 | 39514 | TTCN_7341 | 53573 |
| ATCN_2415 | 39515 | CTCN_8984 | 53574 |
| CTCN_4129 | 39516 | GTCN_4785 | 53575 |
| CTCN_4130 | 39517 | GTCN_4786 | 53576 |
| TTCN_3369 | 39518 | CTCN_8985 | 53577 |
| ATCN_2416 | 39519 | GTCN_4787 | 53578 |
| CTCN_4131 | 39520 | ATCN_5008 | 53579 |
| CTCN_4132 | 39521 | ATCN_5009 | 53580 |
| CTCN_4133 | 39522 | ATCN_5010 | 53581 |
| CTCN_4134 | 39523 | CTCN_8986 | 53582 |
| ATCN_2417 | 39524 | CTCN_8987 | 53583 |
| CTCN_4135 | 39525 | GTCN_4788 | 53584 |
| ATCN_2418 | 39526 | TTCN_7342 | 53585 |
| ATCN_2419 | 39527 | CTCN_8988 | 53586 |
| ATCN_2420 | 39528 | ATCN_5011 | 53587 |
| CTCN_4136 | 39529 | ATCN_5012 | 53588 |
| CTCN_4137 | 39530 | CTCN_8989 | 53589 |
| CTCN_4138 | 39531 | CTCN_8990 | 53590 |
| TTCN_3370 | 39532 | GTCN_4789 | 53591 |
| GTCN_2147 | 39533 | CTCN_8991 | 53592 |

| | | | |
|---|---|---|---|
| CTCN_4139 | 39534 | GTCN_4790 | 53593 |
| GTCN_2148 | 39535 | GTCN_4791 | 53594 |
| CTCN_4140 | 39536 | CTCN_8992 | 53595 |
| CTCN_4141 | 39537 | GTCN_4792 | 53596 |
| GTCN_2149 | 39538 | TTCN_7343 | 53597 |
| ATCN_2421 | 39539 | CTCN_8993 | 53598 |
| CTCN_4142 | 39540 | CTCN_8994 | 53599 |
| TTCN_3371 | 39541 | ATCN_5013 | 53600 |
| TTCN_3372 | 39542 | ATCN_5014 | 53601 |
| TTCN_3373 | 39543 | CTCN_8995 | 53602 |
| CTCN_4143 | 39544 | CTCN_8996 | 53603 |
| TTCN_3374 | 39545 | ATCN_5015 | 53604 |
| TTCN_3375 | 39546 | CTCN_8997 | 53605 |
| CTCN_4144 | 39547 | TTCN_7344 | 53606 |
| GTCN_2150 | 39548 | TTCN_7345 | 53607 |
| TTCN_3376 | 39549 | TTCN_7346 | 53608 |
| TTCN_3377 | 39550 | TTCN_7347 | 53609 |
| ATCN_2422 | 39551 | TTCN_7348 | 53610 |
| TTCN_3378 | 39552 | TTCN_7349 | 53611 |
| GTCN_2151 | 39553 | TTCN_7350 | 53612 |
| ATCN_2423 | 39554 | CTCN_8998 | 53613 |
| CTCN_4145 | 39555 | CTCN_8999 | 53614 |
| ATCN_2424 | 39556 | TTCN_7351 | 53615 |
| CTCN_4146 | 39557 | TTCN_7352 | 53616 |
| TTCN_3379 | 39558 | ATCN_5016 | 53617 |
| ATCN_2425 | 39559 | TTCN_7353 | 53618 |
| CTCN_4147 | 39560 | TTCN_7354 | 53619 |
| CTCN_4148 | 39561 | CTCN_9000 | 53620 |
| CTCN_4149 | 39562 | ATCN_5017 | 53621 |
| GTCN_2152 | 39563 | GTCN_4793 | 53622 |
| CTCN_4150 | 39564 | TTCN_7355 | 53623 |
| TTCN_3380 | 39565 | CTCN_9001 | 53624 |
| ATCN_2426 | 39566 | CTCN_9002 | 53625 |
| CTCN_4151 | 39567 | CTCN_9003 | 53626 |
| TTCN_3381 | 39568 | TTCN_7356 | 53627 |
| GTCN_2153 | 39569 | CTCN_9004 | 53628 |
| CTCN_4152 | 39570 | TTCN_7357 | 53629 |
| CTCN_4153 | 39571 | GTCN_4794 | 53630 |
| CTCN_4154 | 39572 | TTCN_7358 | 53631 |
| CTCN_4155 | 39573 | GTCN_4795 | 53632 |
| ATCN_2427 | 39574 | TTCN_7359 | 53633 |
| CTCN_4156 | 39575 | TTCN_7360 | 53634 |
| CTCN_4157 | 39576 | TTCN_7361 | 53635 |

FIG. 37 (continued)

| | | | | | | | |
|---|---|---|---|---|---|---|---|
| TTCN_3382 | 39577 | TTCN_7362 | 53636 | CTCN_4174 | 39620 | CTCN_9023 | 53679 |
| GTCN_2154 | 39578 | GTCN_4796 | 53637 | ATCN_2440 | 39621 | CTCN_9024 | 53680 |
| ATCN_2428 | 39579 | GTCN_4797 | 53638 | ATCN_2441 | 39622 | GTCN_4805 | 53681 |
| GTCN_2155 | 39580 | ATCN_5018 | 53639 | CTCN_4175 | 39623 | ATCN_5025 | 53682 |
| CTCN_4158 | 39581 | TTCN_7363 | 53640 | CTCN_4176 | 39624 | TTCN_7371 | 53683 |
| GTCN_2156 | 39582 | TTCN_7364 | 53641 | CTCN_4177 | 39625 | ATCN_5026 | 53684 |
| ATCN_2429 | 39583 | TTCN_7365 | 53642 | CTCN_4178 | 39626 | CTCN_9025 | 53685 |
| CTCN_4159 | 39584 | CTCN_9005 | 53643 | CTCN_4179 | 39627 | TTCN_7372 | 53686 |
| ATCN_2430 | 39585 | GTCN_4798 | 53644 | TTCN_3386 | 39628 | GTCN_4806 | 53687 |
| ATCN_2431 | 39586 | CTCN_9006 | 53645 | GTCN_2165 | 39629 | ATCN_5027 | 53688 |
| GTCN_2157 | 39587 | CTCN_9007 | 53646 | TTCN_3387 | 39630 | ATCN_5028 | 53689 |
| GTCN_2158 | 39588 | GTCN_4799 | 53647 | CTCN_4180 | 39631 | CTCN_9026 | 53690 |
| GTCN_2159 | 39589 | CTCN_9008 | 53648 | CTCN_4181 | 39632 | CTCN_9027 | 53691 |
| CTCN_4160 | 39590 | ATCN_5019 | 53649 | CTCN_4182 | 39633 | GTCN_4807 | 53692 |
| CTCN_4161 | 39591 | ATCN_5020 | 53650 | CTCN_4183 | 39634 | ATCN_5029 | 53693 |
| GTCN_2160 | 39592 | CTCN_9009 | 53651 | GTCN_2166 | 39635 | GTCN_4808 | 53694 |
| CTCN_4162 | 39593 | CTCN_9010 | 53652 | CTCN_4184 | 39636 | TTCN_7373 | 53695 |
| ATCN_2432 | 39594 | CTCN_9011 | 53653 | ATCN_2442 | 39637 | GTCN_4809 | 53696 |
| ATCN_2433 | 39595 | CTCN_9012 | 53654 | GTCN_2167 | 39638 | CTCN_9028 | 53697 |
| CTCN_4163 | 39596 | TTCN_7366 | 53655 | CTCN_4185 | 39639 | GTCN_4810 | 53698 |
| CTCN_4164 | 39597 | ATCN_5021 | 53656 | CTCN_4186 | 39640 | ATCN_5030 | 53699 |
| CTCN_4165 | 39598 | TTCN_7367 | 53657 | TTCN_3388 | 39641 | TTCN_7374 | 53700 |
| CTCN_4166 | 39599 | CTCN_9013 | 53658 | GTCN_2168 | 39642 | TTCN_7375 | 53701 |
| ATCN_2434 | 39600 | CTCN_9014 | 53659 | GTCN_2169 | 39643 | ATCN_5031 | 53702 |
| ATCN_2435 | 39601 | GTCN_4800 | 53660 | TTCN_3389 | 39644 | ATCN_5032 | 53703 |
| TTCN_3383 | 39602 | GTCN_4801 | 53661 | CTCN_4187 | 39645 | GTCN_4811 | 53704 |
| GTCN_2161 | 39603 | TTCN_7368 | 53662 | GTCN_2170 | 39646 | TTCN_7376 | 53705 |
| GTCN_2162 | 39604 | CTCN_9015 | 53663 | TTCN_3390 | 39647 | CTCN_9029 | 53706 |
| CTCN_4167 | 39605 | GTCN_4802 | 53664 | GTCN_2171 | 39648 | ATCN_5033 | 53707 |
| TTCN_3384 | 39606 | ATCN_5022 | 53665 | ATCN_2443 | 39649 | TTCN_7377 | 53708 |
| ATCN_2436 | 39607 | CTCN_9016 | 53666 | ATCN_2444 | 39650 | ATCN_5034 | 53709 |
| ATCN_2437 | 39608 | TTCN_7369 | 53667 | ATCN_2445 | 39651 | ATCN_5035 | 53710 |
| CTCN_4168 | 39609 | CTCN_9017 | 53668 | CTCN_4188 | 39652 | GTCN_4812 | 53711 |
| CTCN_4169 | 39610 | GTCN_4803 | 53669 | TTCN_3391 | 39653 | TTCN_7378 | 53712 |
| GTCN_2163 | 39611 | CTCN_9018 | 53670 | CTCN_4189 | 39654 | CTCN_9030 | 53713 |
| CTCN_4170 | 39612 | ATCN_5023 | 53671 | CTCN_4190 | 39655 | ATCN_5036 | 53714 |
| CTCN_4171 | 39613 | ATCN_5024 | 53672 | ATCN_2446 | 39656 | TTCN_7379 | 53715 |
| TTCN_3385 | 39614 | CTCN_9019 | 53673 | CTCN_4191 | 39657 | CTCN_9031 | 53716 |
| CTCN_4172 | 39615 | CTCN_9020 | 53674 | TTCN_3392 | 39658 | GTCN_4813 | 53717 |
| GTCN_2164 | 39616 | CTCN_9021 | 53675 | ATCN_2447 | 39659 | CTCN_9032 | 53718 |
| CTCN_4173 | 39617 | TTCN_7370 | 53676 | TTCN_3393 | 39660 | ATCN_5037 | 53719 |
| ATCN_2438 | 39618 | CTCN_9022 | 53677 | CTCN_4192 | 39661 | ATCN_5038 | 53720 |
| ATCN_2439 | 39619 | GTCN_4804 | 53678 | GTCN_2172 | 39662 | TTCN_7380 | 53721 |

FIG. 37 (continued)

| | | | |
|---|---|---|---|
| GTCN_2173 | 39663 | GTCN_4814 | 53722 |
| TTCN_3394 | 39664 | CTCN_9033 | 53723 |
| CTCN_4193 | 39665 | GTCN_4815 | 53724 |
| ATCN_2448 | 39666 | TTCN_7381 | 53725 |
| GTCN_2174 | 39667 | TTCN_7382 | 53726 |
| TTCN_3395 | 39668 | ATCN_5039 | 53727 |
| CTCN_4194 | 39669 | TTCN_7383 | 53728 |
| CTCN_4195 | 39670 | CTCN_9034 | 53729 |
| TTCN_3396 | 39671 | TTCN_7384 | 53730 |
| ATCN_2449 | 39672 | TTCN_7385 | 53731 |
| TTCN_3397 | 39673 | TTCN_7386 | 53732 |
| GTCN_2175 | 39674 | TTCN_7387 | 53733 |
| CTCN_4196 | 39675 | GTCN_4816 | 53734 |
| CTCN_4197 | 39676 | ATCN_5040 | 53735 |
| CTCN_4198 | 39677 | GTCN_4817 | 53736 |
| TTCN_3398 | 39678 | TTCN_7388 | 53737 |
| TTCN_3399 | 39679 | TTCN_7389 | 53738 |
| TTCN_3400 | 39680 | GTCN_4818 | 53739 |
| CTCN_4199 | 39681 | ATCN_5041 | 53740 |
| CTCN_4200 | 39682 | GTCN_4819 | 53741 |
| CTCN_4201 | 39683 | CTCN_9035 | 53742 |
| CTCN_4202 | 39684 | CTCN_9036 | 53743 |
| CTCN_4203 | 39685 | CTCN_9037 | 53744 |
| GTCN_2176 | 39686 | GTCN_4820 | 53745 |
| CTCN_4204 | 39687 | TTCN_7390 | 53746 |
| CTCN_4205 | 39688 | ATCN_5042 | 53747 |
| GTCN_2177 | 39689 | GTCN_4821 | 53748 |
| CTCN_4206 | 39690 | CTCN_9038 | 53749 |
| GTCN_2178 | 39691 | ATCN_5043 | 53750 |
| TTCN_3401 | 39692 | ATCN_5044 | 53751 |
| CTCN_4207 | 39693 | TTCN_7391 | 53752 |
| CTCN_4208 | 39694 | TTCN_7392 | 53753 |
| ATCN_2450 | 39695 | GTCN_4822 | 53754 |
| CTCN_4209 | 39696 | CTCN_9039 | 53755 |
| CTCN_4210 | 39697 | TTCN_7393 | 53756 |
| CTCN_4211 | 39698 | CTCN_9040 | 53757 |
| ATCN_2451 | 39699 | CTCN_9041 | 53758 |
| GTCN_2179 | 39700 | GTCN_4823 | 53759 |
| CTCN_4212 | 39701 | CTCN_9042 | 53760 |
| GTCN_2180 | 39702 | ATCN_5045 | 53761 |
| CTCN_4213 | 39703 | ATCN_5046 | 53762 |
| GTCN_2181 | 39704 | CTCN_9043 | 53763 |
| CTCN_4214 | 39705 | TTCN_7394 | 53764 |

| | | | |
|---|---|---|---|
| CTCN_4215 | 39706 | GTCN_4824 | 53765 |
| GTCN_2182 | 39707 | GTCN_4825 | 53766 |
| TTCN_3402 | 39708 | GTCN_4826 | 53767 |
| TTCN_3403 | 39709 | CTCN_9044 | 53768 |
| CTCN_4216 | 39710 | ATCN_5047 | 53769 |
| GTCN_2183 | 39711 | CTCN_9045 | 53770 |
| CTCN_4217 | 39712 | CTCN_9046 | 53771 |
| CTCN_4218 | 39713 | TTCN_7395 | 53772 |
| CTCN_4219 | 39714 | CTCN_9047 | 53773 |
| CTCN_4220 | 39715 | TTCN_7396 | 53774 |
| CTCN_4221 | 39716 | ATCN_5048 | 53775 |
| GTCN_2184 | 39717 | CTCN_9048 | 53776 |
| CTCN_4222 | 39718 | TTCN_7397 | 53777 |
| CTCN_4223 | 39719 | CTCN_9049 | 53778 |
| GTCN_2185 | 39720 | CTCN_9050 | 53779 |
| CTCN_4224 | 39721 | TTCN_7398 | 53780 |
| GTCN_2186 | 39722 | CTCN_9051 | 53781 |
| CTCN_4225 | 39723 | ATCN_5049 | 53782 |
| GTCN_2187 | 39724 | ATCN_5050 | 53783 |
| CTCN_4226 | 39725 | CTCN_9052 | 53784 |
| CTCN_4227 | 39726 | TTCN_7399 | 53785 |
| GTCN_2188 | 39727 | GTCN_4827 | 53786 |
| ATCN_2452 | 39728 | GTCN_4828 | 53787 |
| CTCN_4228 | 39729 | CTCN_9053 | 53788 |
| GTCN_2189 | 39730 | GTCN_4829 | 53789 |
| TTCN_3404 | 39731 | CTCN_9054 | 53790 |
| ATCN_2453 | 39732 | GTCN_4830 | 53791 |
| GTCN_2190 | 39733 | CTCN_9055 | 53792 |
| CTCN_4229 | 39734 | TTCN_7400 | 53793 |
| GTCN_2191 | 39735 | CTCN_9056 | 53794 |
| ATCN_2454 | 39736 | ATCN_5051 | 53795 |
| GTCN_2192 | 39737 | GTCN_4831 | 53796 |
| CTCN_4230 | 39738 | CTCN_9057 | 53797 |
| GTCN_2193 | 39739 | ATCN_5052 | 53798 |
| CTCN_4231 | 39740 | TTCN_7401 | 53799 |
| TTCN_3405 | 39741 | GTCN_4832 | 53800 |
| TTCN_3406 | 39742 | TTCN_7402 | 53801 |
| CTCN_4232 | 39743 | TTCN_7403 | 53802 |
| TTCN_3407 | 39744 | GTCN_4833 | 53803 |
| CTCN_4233 | 39745 | TTCN_7404 | 53804 |
| CTCN_4234 | 39746 | ATCN_5053 | 53805 |
| TTCN_3408 | 39747 | GTCN_4834 | 53806 |
| ATCN_2455 | 39748 | CTCN_9058 | 53807 |

FIG. 37 (continued)

| | | | | | | | |
|---|---|---|---|---|---|---|---|
| GTCN_2194 | 39749 | TTCN_7405 | 53808 | CTCN_4257 | 39792 | TTCN_7420 | 53851 |
| CTCN_4235 | 39750 | GTCN_4835 | 53809 | ATCN_2460 | 39793 | GTCN_4844 | 53852 |
| CTCN_4236 | 39751 | TTCN_7406 | 53810 | CTCN_4258 | 39794 | TTCN_7421 | 53853 |
| GTCN_2195 | 39752 | GTCN_4836 | 53811 | CTCN_4259 | 39795 | TTCN_7422 | 53854 |
| TTCN_3409 | 39753 | CTCN_9059 | 53812 | GTCN_2201 | 39796 | TTCN_7423 | 53855 |
| TTCN_3410 | 39754 | ATCN_5054 | 53813 | CTCN_4260 | 39797 | CTCN_9072 | 53856 |
| CTCN_4237 | 39755 | CTCN_9060 | 53814 | GTCN_2202 | 39798 | TTCN_7424 | 53857 |
| GTCN_2196 | 39756 | CTCN_9061 | 53815 | TTCN_3419 | 39799 | CTCN_9073 | 53858 |
| CTCN_4238 | 39757 | GTCN_4837 | 53816 | CTCN_4261 | 39800 | ATCN_5060 | 53859 |
| TTCN_3411 | 39758 | CTCN_9062 | 53817 | TTCN_3420 | 39801 | TTCN_7425 | 53860 |
| ATCN_2456 | 39759 | TTCN_7407 | 53818 | CTCN_4262 | 39802 | CTCN_9074 | 53861 |
| ATCN_2457 | 39760 | CTCN_9063 | 53819 | GTCN_2203 | 39803 | TTCN_7426 | 53862 |
| TTCN_3412 | 39761 | TTCN_7408 | 53820 | ATCN_2461 | 39804 | TTCN_7427 | 53863 |
| CTCN_4239 | 39762 | GTCN_4838 | 53821 | GTCN_2204 | 39805 | TTCN_7428 | 53864 |
| CTCN_4240 | 39763 | GTCN_4839 | 53822 | CTCN_4263 | 39806 | CTCN_9075 | 53865 |
| CTCN_4241 | 39764 | CTCN_9064 | 53823 | GTCN_2205 | 39807 | GTCN_4845 | 53866 |
| ATCN_2458 | 39765 | TTCN_7409 | 53824 | CTCN_4264 | 39808 | GTCN_4846 | 53867 |
| CTCN_4242 | 39766 | TTCN_7410 | 53825 | CTCN_4265 | 39809 | TTCN_7429 | 53868 |
| GTCN_2197 | 39767 | CTCN_9065 | 53826 | TTCN_3421 | 39810 | ATCN_5061 | 53869 |
| TTCN_3413 | 39768 | CTCN_9066 | 53827 | ATCN_2462 | 39811 | TTCN_7430 | 53870 |
| TTCN_3414 | 39769 | TTCN_7411 | 53828 | TTCN_3422 | 39812 | CTCN_9076 | 53871 |
| CTCN_4243 | 39770 | TTCN_7412 | 53829 | CTCN_4266 | 39813 | CTCN_9077 | 53872 |
| TTCN_3415 | 39771 | TTCN_7413 | 53830 | CTCN_4267 | 39814 | TTCN_7431 | 53873 |
| GTCN_2198 | 39772 | TTCN_7414 | 53831 | ATCN_2463 | 39815 | TTCN_7432 | 53874 |
| CTCN_4244 | 39773 | CTCN_9067 | 53832 | CTCN_4268 | 39816 | GTCN_4847 | 53875 |
| CTCN_4245 | 39774 | TTCN_7415 | 53833 | ATCN_2464 | 39817 | TTCN_7433 | 53876 |
| CTCN_4246 | 39775 | CTCN_9068 | 53834 | CTCN_4269 | 39818 | CTCN_9078 | 53877 |
| CTCN_4247 | 39776 | GTCN_4840 | 53835 | CTCN_4270 | 39819 | TTCN_7434 | 53878 |
| TTCN_3416 | 39777 | ATCN_5055 | 53836 | CTCN_4271 | 39820 | CTCN_9079 | 53879 |
| CTCN_4248 | 39778 | ATCN_5056 | 53837 | CTCN_4272 | 39821 | CTCN_9080 | 53880 |
| CTCN_4249 | 39779 | TTCN_7416 | 53838 | CTCN_4273 | 39822 | TTCN_7435 | 53881 |
| CTCN_4250 | 39780 | GTCN_4841 | 53839 | CTCN_4274 | 39823 | TTCN_7436 | 53882 |
| CTCN_4251 | 39781 | CTCN_9069 | 53840 | TTCN_3423 | 39824 | GTCN_4848 | 53883 |
| TTCN_3417 | 39782 | TTCN_7417 | 53841 | CTCN_4275 | 39825 | TTCN_7437 | 53884 |
| CTCN_4252 | 39783 | ATCN_5057 | 53842 | GTCN_2206 | 39826 | TTCN_7438 | 53885 |
| CTCN_4253 | 39784 | ATCN_5058 | 53843 | TTCN_3424 | 39827 | TTCN_7439 | 53886 |
| ATCN_2459 | 39785 | ATCN_5059 | 53844 | GTCN_2207 | 39828 | GTCN_4849 | 53887 |
| CTCN_4254 | 39786 | GTCN_4842 | 53845 | GTCN_2208 | 39829 | ATCN_5062 | 53888 |
| GTCN_2199 | 39787 | CTCN_9070 | 53846 | TTCN_3425 | 39830 | ATCN_5063 | 53889 |
| TTCN_3418 | 39788 | CTCN_9071 | 53847 | ATCN_2465 | 39831 | ATCN_5064 | 53890 |
| CTCN_4255 | 39789 | TTCN_7418 | 53848 | CTCN_4276 | 39832 | ATCN_5065 | 53891 |
| GTCN_2200 | 39790 | GTCN_4843 | 53849 | GTCN_2209 | 39833 | TTCN_7440 | 53892 |
| CTCN_4256 | 39791 | TTCN_7419 | 53850 | GTCN_2210 | 39834 | CTCN_9081 | 53893 |

FIG. 37 (continued)

| | | | |
|---|---|---|---|
| CTCN_4277 | 39835 | TTCN_7441 | 53894 |
| TTCN_3426 | 39836 | GTCN_4850 | 53895 |
| TTCN_3427 | 39837 | TTCN_7442 | 53896 |
| CTCN_4278 | 39838 | TTCN_7443 | 53897 |
| TTCN_3428 | 39839 | GTCN_4851 | 53898 |
| CTCN_4279 | 39840 | GTCN_4852 | 53899 |
| CTCN_4280 | 39841 | ATCN_5066 | 53900 |
| GTCN_2211 | 39842 | TTCN_7444 | 53901 |
| CTCN_4281 | 39843 | CTCN_9082 | 53902 |
| CTCN_4282 | 39844 | TTCN_7445 | 53903 |
| CTCN_4283 | 39845 | GTCN_4853 | 53904 |
| TTCN_3429 | 39846 | ATCN_5067 | 53905 |
| CTCN_4284 | 39847 | TTCN_7446 | 53906 |
| CTCN_4285 | 39848 | CTCN_9083 | 53907 |
| CTCN_4286 | 39849 | TTCN_7447 | 53908 |
| TTCN_3430 | 39850 | CTCN_9084 | 53909 |
| CTCN_4287 | 39851 | ATCN_5068 | 53910 |
| TTCN_3431 | 39852 | CTCN_9085 | 53911 |
| GTCN_2212 | 39853 | GTCN_4854 | 53912 |
| ATCN_2466 | 39854 | ATCN_5069 | 53913 |
| TTCN_3432 | 39855 | GTCN_4855 | 53914 |
| CTCN_4288 | 39856 | GTCN_4856 | 53915 |
| TTCN_3433 | 39857 | GTCN_4857 | 53916 |
| TTCN_3434 | 39858 | TTCN_7448 | 53917 |
| ATCN_2467 | 39859 | GTCN_4858 | 53918 |
| ATCN_2468 | 39860 | GTCN_4859 | 53919 |
| ATCN_2469 | 39861 | TTCN_7449 | 53920 |
| ATCN_2470 | 39862 | GTCN_4860 | 53921 |
| ATCN_2471 | 39863 | TTCN_7450 | 53922 |
| TTCN_3435 | 39864 | CTCN_9086 | 53923 |
| GTCN_2213 | 39865 | GTCN_4861 | 53924 |
| CTCN_4289 | 39866 | TTCN_7451 | 53925 |
| GTCN_2214 | 39867 | ATCN_5070 | 53926 |
| ATCN_2472 | 39868 | TTCN_7452 | 53927 |
| TTCN_3436 | 39869 | TTCN_7453 | 53928 |
| TTCN_3437 | 39870 | TTCN_7454 | 53929 |
| TTCN_3438 | 39871 | TTCN_7455 | 53930 |
| GTCN_2215 | 39872 | ATCN_5071 | 53931 |
| GTCN_2216 | 39873 | ATCN_5072 | 53932 |
| ATCN_2473 | 39874 | ATCN_5073 | 53933 |
| CTCN_4290 | 39875 | CTCN_9087 | 53934 |
| TTCN_3439 | 39876 | CTCN_9088 | 53935 |
| ATCN_2474 | 39877 | CTCN_9089 | 53936 |

| | | | |
|---|---|---|---|
| CTCN_4291 | 39878 | ATCN_5074 | 53937 |
| ATCN_2475 | 39879 | ATCN_5075 | 53938 |
| TTCN_3440 | 39880 | GTCN_4862 | 53939 |
| TTCN_3441 | 39881 | TTCN_7456 | 53940 |
| GTCN_2217 | 39882 | TTCN_7457 | 53941 |
| CTCN_4292 | 39883 | ATCN_5076 | 53942 |
| TTCN_3442 | 39884 | ATCN_5077 | 53943 |
| TTCN_3443 | 39885 | ATCN_5078 | 53944 |
| TTCN_3444 | 39886 | CTCN_9090 | 53945 |
| TTCN_3445 | 39887 | GTCN_4863 | 53946 |
| CTCN_4293 | 39888 | CTCN_9091 | 53947 |
| CTCN_4294 | 39889 | TTCN_7458 | 53948 |
| TTCN_3446 | 39890 | GTCN_4864 | 53949 |
| TTCN_3447 | 39891 | GTCN_4865 | 53950 |
| ATCN_2476 | 39892 | ATCN_5079 | 53951 |
| CTCN_4295 | 39893 | GTCN_4866 | 53952 |
| GTCN_2218 | 39894 | ATCN_5080 | 53953 |
| TTCN_3448 | 39895 | CTCN_9092 | 53954 |
| TTCN_3449 | 39896 | ATCN_5081 | 53955 |
| TTCN_3450 | 39897 | GTCN_4867 | 53956 |
| CTCN_4296 | 39898 | GTCN_4868 | 53957 |
| CTCN_4297 | 39899 | GTCN_4869 | 53958 |
| TTCN_3451 | 39900 | GTCN_4870 | 53959 |
| TTCN_3452 | 39901 | TTCN_7459 | 53960 |
| CTCN_4298 | 39902 | GTCN_4871 | 53961 |
| GTCN_2219 | 39903 | CTCN_9093 | 53962 |
| TTCN_3453 | 39904 | TTCN_7460 | 53963 |
| CTCN_4299 | 39905 | GTCN_4872 | 53964 |
| TTCN_3454 | 39906 | TTCN_7461 | 53965 |
| GTCN_2220 | 39907 | TTCN_7462 | 53966 |
| GTCN_2221 | 39908 | TTCN_7463 | 53967 |
| GTCN_2222 | 39909 | CTCN_9094 | 53968 |
| CTCN_4300 | 39910 | TTCN_7464 | 53969 |
| CTCN_4301 | 39911 | CTCN_9095 | 53970 |
| CTCN_4302 | 39912 | GTCN_4873 | 53971 |
| CTCN_4303 | 39913 | CTCN_9096 | 53972 |
| GTCN_2223 | 39914 | CTCN_9097 | 53973 |
| CTCN_4304 | 39915 | CTCN_9098 | 53974 |
| GTCN_2224 | 39916 | TTCN_7465 | 53975 |
| CTCN_4305 | 39917 | ATCN_5082 | 53976 |
| GTCN_2225 | 39918 | GTCN_4874 | 53977 |
| TTCN_3455 | 39919 | CTCN_9099 | 53978 |
| CTCN_4306 | 39920 | TTCN_7466 | 53979 |

FIG. 37 (continued)

| | | | | | | | |
|---|---|---|---|---|---|---|---|
| CTCN_4307 | 39921 | CTCN_9100 | 53980 | TTCN_3468 | 39964 | ATCN_5092 | 54023 |
| TTCN_3456 | 39922 | CTCN_9101 | 53981 | ATCN_2480 | 39965 | TTCN_7478 | 54024 |
| TTCN_3457 | 39923 | GTCN_4875 | 53982 | GTCN_2235 | 39966 | CTCN_9114 | 54025 |
| ATCN_2477 | 39924 | CTCN_9102 | 53983 | CTCN_4326 | 39967 | ATCN_5093 | 54026 |
| CTCN_4308 | 39925 | GTCN_4876 | 53984 | TTCN_3469 | 39968 | CTCN_9115 | 54027 |
| TTCN_3458 | 39926 | ATCN_5083 | 53985 | CTCN_4327 | 39969 | CTCN_9116 | 54028 |
| GTCN_2226 | 39927 | TTCN_7467 | 53986 | CTCN_4328 | 39970 | CTCN_9117 | 54029 |
| TTCN_3459 | 39928 | TTCN_7468 | 53987 | TTCN_3470 | 39971 | ATCN_5094 | 54030 |
| ATCN_2478 | 39929 | ATCN_5084 | 53988 | CTCN_4329 | 39972 | ATCN_5095 | 54031 |
| TTCN_3460 | 39930 | TTCN_7469 | 53989 | ATCN_2481 | 39973 | CTCN_9118 | 54032 |
| GTCN_2227 | 39931 | CTCN_9103 | 53990 | TTCN_3471 | 39974 | GTCN_4884 | 54033 |
| TTCN_3461 | 39932 | CTCN_9104 | 53991 | GTCN_2236 | 39975 | CTCN_9119 | 54034 |
| GTCN_2228 | 39933 | GTCN_4877 | 53992 | CTCN_4330 | 39976 | TTCN_7479 | 54035 |
| CTCN_4309 | 39934 | CTCN_9105 | 53993 | GTCN_2237 | 39977 | CTCN_9120 | 54036 |
| CTCN_4310 | 39935 | ATCN_5085 | 53994 | GTCN_2238 | 39978 | GTCN_4885 | 54037 |
| CTCN_4311 | 39936 | GTCN_4878 | 53995 | GTCN_2239 | 39979 | CTCN_9121 | 54038 |
| CTCN_4312 | 39937 | TTCN_7470 | 53996 | CTCN_4331 | 39980 | TTCN_7480 | 54039 |
| CTCN_4313 | 39938 | GTCN_4879 | 53997 | GTCN_2240 | 39981 | TTCN_7481 | 54040 |
| CTCN_4314 | 39939 | CTCN_9106 | 53998 | TTCN_3472 | 39982 | CTCN_9122 | 54041 |
| ATCN_2479 | 39940 | ATCN_5086 | 53999 | GTCN_2241 | 39983 | TTCN_7482 | 54042 |
| CTCN_4315 | 39941 | TTCN_7471 | 54000 | ATCN_2482 | 39984 | GTCN_4886 | 54043 |
| TTCN_3462 | 39942 | TTCN_7472 | 54001 | TTCN_3473 | 39985 | CTCN_9123 | 54044 |
| CTCN_4316 | 39943 | TTCN_7473 | 54002 | GTCN_2242 | 39986 | CTCN_9124 | 54045 |
| GTCN_2229 | 39944 | TTCN_7474 | 54003 | TTCN_3474 | 39987 | GTCN_4887 | 54046 |
| GTCN_2230 | 39945 | ATCN_5087 | 54004 | TTCN_3475 | 39988 | TTCN_7483 | 54047 |
| TTCN_3463 | 39946 | CTCN_9107 | 54005 | TTCN_3476 | 39989 | GTCN_4888 | 54048 |
| CTCN_4317 | 39947 | CTCN_9108 | 54006 | TTCN_3477 | 39990 | CTCN_9125 | 54049 |
| GTCN_2231 | 39948 | ATCN_5088 | 54007 | ATCN_2483 | 39991 | GTCN_4889 | 54050 |
| TTCN_3464 | 39949 | ATCN_5089 | 54008 | CTCN_4332 | 39992 | TTCN_7484 | 54051 |
| GTCN_2232 | 39950 | GTCN_4880 | 54009 | CTCN_4333 | 39993 | ATCN_5096 | 54052 |
| CTCN_4318 | 39951 | CTCN_9109 | 54010 | GTCN_2243 | 39994 | TTCN_7485 | 54053 |
| GTCN_2233 | 39952 | TTCN_7475 | 54011 | ATCN_2484 | 39995 | TTCN_7486 | 54054 |
| CTCN_4319 | 39953 | GTCN_4881 | 54012 | ATCN_2485 | 39996 | CTCN_9126 | 54055 |
| TTCN_3465 | 39954 | TTCN_7476 | 54013 | CTCN_4334 | 39997 | ATCN_5097 | 54056 |
| CTCN_4320 | 39955 | ATCN_5090 | 54014 | CTCN_4335 | 39998 | TTCN_7487 | 54057 |
| GTCN_2234 | 39956 | CTCN_9110 | 54015 | TTCN_3478 | 39999 | GTCN_4890 | 54058 |
| CTCN_4321 | 39957 | ATCN_5091 | 54016 | TTCN_3479 | 40000 | TTCN_7488 | 54059 |
| CTCN_4322 | 39958 | GTCN_4882 | 54017 | ATCN_2486 | 40001 | ATCN_5098 | 54060 |
| CTCN_4323 | 39959 | GTCN_4883 | 54018 | GTCN_2244 | 40002 | TTCN_7489 | 54061 |
| CTCN_4324 | 39960 | CTCN_9111 | 54019 | CTCN_4336 | 40003 | CTCN_9127 | 54062 |
| CTCN_4325 | 39961 | CTCN_9112 | 54020 | ATCN_2487 | 40004 | TTCN_7490 | 54063 |
| TTCN_3466 | 39962 | CTCN_9113 | 54021 | ATCN_2488 | 40005 | GTCN_4891 | 54064 |
| TTCN_3467 | 39963 | TTCN_7477 | 54022 | TTCN_3480 | 40006 | GTCN_4892 | 54065 |

FIG. 37 (continued)

| | | | |
|---|---|---|---|
| GTCN_2245 | 40007 | TTCN_7491 | 54066 |
| GTCN_2246 | 40008 | CTCN_9128 | 54067 |
| CTCN_4337 | 40009 | TTCN_7492 | 54068 |
| GTCN_2247 | 40010 | CTCN_9129 | 54069 |
| TTCN_3481 | 40011 | CTCN_9130 | 54070 |
| ATCN_2489 | 40012 | ATCN_5099 | 54071 |
| ATCN_2490 | 40013 | GTCN_4893 | 54072 |
| TTCN_3482 | 40014 | CTCN_9131 | 54073 |
| TTCN_3483 | 40015 | GTCN_4894 | 54074 |
| CTCN_4338 | 40016 | TTCN_7493 | 54075 |
| CTCN_4339 | 40017 | ATCN_5100 | 54076 |
| CTCN_4340 | 40018 | GTCN_4895 | 54077 |
| ATCN_2491 | 40019 | GTCN_4896 | 54078 |
| ATCN_2492 | 40020 | TTCN_7494 | 54079 |
| CTCN_4341 | 40021 | TTCN_7495 | 54080 |
| CTCN_4342 | 40022 | CTCN_9132 | 54081 |
| CTCN_4343 | 40023 | TTCN_7496 | 54082 |
| ATCN_2493 | 40024 | CTCN_9133 | 54083 |
| GTCN_2248 | 40025 | TTCN_7497 | 54084 |
| ATCN_2494 | 40026 | TTCN_7498 | 54085 |
| ATCN_2495 | 40027 | GTCN_4897 | 54086 |
| ATCN_2496 | 40028 | CTCN_9134 | 54087 |
| GTCN_2249 | 40029 | TTCN_7499 | 54088 |
| ATCN_2497 | 40030 | CTCN_9135 | 54089 |
| ATCN_2498 | 40031 | CTCN_9136 | 54090 |
| GTCN_2250 | 40032 | ATCN_5101 | 54091 |
| TTCN_3484 | 40033 | ATCN_5102 | 54092 |
| CTCN_4344 | 40034 | TTCN_7500 | 54093 |
| CTCN_4345 | 40035 | CTCN_9137 | 54094 |
| ATCN_2499 | 40036 | TTCN_7501 | 54095 |
| CTCN_4346 | 40037 | TTCN_7502 | 54096 |
| CTCN_4347 | 40038 | ATCN_5103 | 54097 |
| CTCN_4348 | 40039 | GTCN_4898 | 54098 |
| GTCN_2251 | 40040 | TTCN_7503 | 54099 |
| GTCN_2252 | 40041 | TTCN_7504 | 54100 |
| CTCN_4349 | 40042 | ATCN_5104 | 54101 |
| GTCN_2253 | 40043 | ATCN_5105 | 54102 |
| ATCN_2500 | 40044 | CTCN_9138 | 54103 |
| ATCN_2501 | 40045 | TTCN_7505 | 54104 |
| CTCN_4350 | 40046 | ATCN_5106 | 54105 |
| GTCN_2254 | 40047 | GTCN_4899 | 54106 |
| TTCN_3485 | 40048 | GTCN_4900 | 54107 |
| ATCN_2502 | 40049 | CTCN_9139 | 54108 |

| | | | |
|---|---|---|---|
| TTCN_3486 | 40050 | CTCN_9140 | 54109 |
| ATCN_2503 | 40051 | TTCN_7506 | 54110 |
| GTCN_2255 | 40052 | GTCN_4901 | 54111 |
| CTCN_4351 | 40053 | GTCN_4902 | 54112 |
| GTCN_2256 | 40054 | TTCN_7507 | 54113 |
| CTCN_4352 | 40055 | ATCN_5107 | 54114 |
| TTCN_3487 | 40056 | TTCN_7508 | 54115 |
| CTCN_4353 | 40057 | TTCN_7509 | 54116 |
| CTCN_4354 | 40058 | TTCN_7510 | 54117 |
| GTCN_2257 | 40059 | GTCN_4903 | 54118 |
| CTCN_4355 | 40060 | TTCN_7511 | 54119 |
| TTCN_3488 | 40061 | GTCN_4904 | 54120 |
| TTCN_3489 | 40062 | CTCN_9141 | 54121 |
| CTCN_4356 | 40063 | ATCN_5108 | 54122 |
| TTCN_3490 | 40064 | CTCN_9142 | 54123 |
| GTCN_2258 | 40065 | TTCN_7512 | 54124 |
| CTCN_4357 | 40066 | CTCN_9143 | 54125 |
| CTCN_4358 | 40067 | GTCN_4905 | 54126 |
| TTCN_3491 | 40068 | ATCN_5109 | 54127 |
| GTCN_2259 | 40069 | TTCN_7513 | 54128 |
| TTCN_3492 | 40070 | GTCN_4906 | 54129 |
| CTCN_4359 | 40071 | CTCN_9144 | 54130 |
| ATCN_2504 | 40072 | TTCN_7514 | 54131 |
| GTCN_2260 | 40073 | CTCN_9145 | 54132 |
| GTCN_2261 | 40074 | ATCN_5110 | 54133 |
| TTCN_3493 | 40075 | TTCN_7515 | 54134 |
| TTCN_3494 | 40076 | CTCN_9146 | 54135 |
| CTCN_4360 | 40077 | TTCN_7516 | 54136 |
| ATCN_2505 | 40078 | GTCN_4907 | 54137 |
| ATCN_2506 | 40079 | TTCN_7517 | 54138 |
| ATCN_2507 | 40080 | ATCN_5111 | 54139 |
| CTCN_4361 | 40081 | CTCN_9147 | 54140 |
| TTCN_3495 | 40082 | ATCN_5112 | 54141 |
| ATCN_2508 | 40083 | TTCN_7518 | 54142 |
| TTCN_3496 | 40084 | ATCN_5113 | 54143 |
| CTCN_4362 | 40085 | CTCN_9148 | 54144 |
| TTCN_3497 | 40086 | ATCN_5114 | 54145 |
| TTCN_3498 | 40087 | GTCN_4908 | 54146 |
| TTCN_3499 | 40088 | ATCN_5115 | 54147 |
| GTCN_2262 | 40089 | ATCN_5116 | 54148 |
| CTCN_4363 | 40090 | GTCN_4909 | 54149 |
| TTCN_3500 | 40091 | ATCN_5117 | 54150 |
| CTCN_4364 | 40092 | TTCN_7519 | 54151 |

FIG. 37 (continued)

| | | | |
|---|---|---|---|
| ATCN_2509 | 40093 | CTCN_9149 | 54152 |
| TTCN_3501 | 40094 | TTCN_7520 | 54153 |
| GTCN_2263 | 40095 | ATCN_5118 | 54154 |
| GTCN_2264 | 40096 | GTCN_4910 | 54155 |
| TTCN_3502 | 40097 | ATCN_5119 | 54156 |
| ATCN_2510 | 40098 | CTCN_9150 | 54157 |
| CTCN_4365 | 40099 | GTCN_4911 | 54158 |
| TTCN_3503 | 40100 | TTCN_7521 | 54159 |
| CTCN_4366 | 40101 | GTCN_4912 | 54160 |
| CTCN_4367 | 40102 | ATCN_5120 | 54161 |
| TTCN_3504 | 40103 | TTCN_7522 | 54162 |
| GTCN_2265 | 40104 | TTCN_7523 | 54163 |
| CTCN_4368 | 40105 | GTCN_4913 | 54164 |
| GTCN_2266 | 40106 | CTCN_9151 | 54165 |
| CTCN_4369 | 40107 | ATCN_5121 | 54166 |
| CTCN_4370 | 40108 | ATCN_5122 | 54167 |
| GTCN_2267 | 40109 | TTCN_7524 | 54168 |
| GTCN_2268 | 40110 | CTCN_9152 | 54169 |
| ATCN_2511 | 40111 | GTCN_4914 | 54170 |
| CTCN_4371 | 40112 | ATCN_5123 | 54171 |
| CTCN_4372 | 40113 | CTCN_9153 | 54172 |
| CTCN_4373 | 40114 | CTCN_9154 | 54173 |
| CTCN_4374 | 40115 | ATCN_5124 | 54174 |
| GTCN_2269 | 40116 | CTCN_9155 | 54175 |
| GTCN_2270 | 40117 | GTCN_4915 | 54176 |
| TTCN_3505 | 40118 | ATCN_5125 | 54177 |
| CTCN_4375 | 40119 | CTCN_9156 | 54178 |
| CTCN_4376 | 40120 | ATCN_5126 | 54179 |
| ATCN_2512 | 40121 | CTCN_9157 | 54180 |
| ATCN_2513 | 40122 | GTCN_4916 | 54181 |
| TTCN_3506 | 40123 | ATCN_5127 | 54182 |
| TTCN_3507 | 40124 | CTCN_9158 | 54183 |
| CTCN_4377 | 40125 | TTCN_7525 | 54184 |
| ATCN_2514 | 40126 | GTCN_4917 | 54185 |
| TTCN_3508 | 40127 | CTCN_9159 | 54186 |
| CTCN_4378 | 40128 | CTCN_9160 | 54187 |
| CTCN_4379 | 40129 | TTCN_7526 | 54188 |
| CTCN_4380 | 40130 | TTCN_7527 | 54189 |
| CTCN_4381 | 40131 | CTCN_9161 | 54190 |
| CTCN_4382 | 40132 | CTCN_9162 | 54191 |
| TTCN_3509 | 40133 | CTCN_9163 | 54192 |
| TTCN_3510 | 40134 | ATCN_5128 | 54193 |
| TTCN_3511 | 40135 | TTCN_7528 | 54194 |

| | | | |
|---|---|---|---|
| TTCN_3512 | 40136 | GTCN_4918 | 54195 |
| ATCN_2515 | 40137 | ATCN_5129 | 54196 |
| ATCN_2516 | 40138 | ATCN_5130 | 54197 |
| TTCN_3513 | 40139 | GTCN_4919 | 54198 |
| GTCN_2271 | 40140 | CTCN_9164 | 54199 |
| TTCN_3514 | 40141 | ATCN_5131 | 54200 |
| CTCN_4383 | 40142 | TTCN_7529 | 54201 |
| ATCN_2517 | 40143 | TTCN_7530 | 54202 |
| GTCN_2272 | 40144 | TTCN_7531 | 54203 |
| CTCN_4384 | 40145 | TTCN_7532 | 54204 |
| GTCN_2273 | 40146 | CTCN_9165 | 54205 |
| TTCN_3515 | 40147 | TTCN_7533 | 54206 |
| CTCN_4385 | 40148 | CTCN_9166 | 54207 |
| TTCN_3516 | 40149 | TTCN_7534 | 54208 |
| GTCN_2274 | 40150 | CTCN_9167 | 54209 |
| CTCN_4386 | 40151 | CTCN_9168 | 54210 |
| TTCN_3517 | 40152 | GTCN_4920 | 54211 |
| ATCN_2518 | 40153 | TTCN_7535 | 54212 |
| CTCN_4387 | 40154 | CTCN_9169 | 54213 |
| CTCN_4388 | 40155 | TTCN_7536 | 54214 |
| TTCN_3518 | 40156 | CTCN_9170 | 54215 |
| ATCN_2519 | 40157 | GTCN_4921 | 54216 |
| TTCN_3519 | 40158 | TTCN_7537 | 54217 |
| TTCN_3520 | 40159 | TTCN_7538 | 54218 |
| TTCN_3521 | 40160 | ATCN_5132 | 54219 |
| CTCN_4389 | 40161 | CTCN_9171 | 54220 |
| ATCN_2520 | 40162 | TTCN_7539 | 54221 |
| ATCN_2521 | 40163 | ATCN_5133 | 54222 |
| TTCN_3522 | 40164 | TTCN_7540 | 54223 |
| GTCN_2275 | 40165 | CTCN_9172 | 54224 |
| ATCN_2522 | 40166 | CTCN_9173 | 54225 |
| TTCN_3523 | 40167 | TTCN_7541 | 54226 |
| TTCN_3524 | 40168 | CTCN_9174 | 54227 |
| GTCN_2276 | 40169 | GTCN_4922 | 54228 |
| ATCN_2523 | 40170 | GTCN_4923 | 54229 |
| TTCN_3525 | 40171 | CTCN_9175 | 54230 |
| GTCN_2277 | 40172 | GTCN_4924 | 54231 |
| GTCN_2278 | 40173 | CTCN_9176 | 54232 |
| CTCN_4390 | 40174 | ATCN_5134 | 54233 |
| GTCN_2279 | 40175 | ATCN_5135 | 54234 |
| TTCN_3526 | 40176 | TTCN_7542 | 54235 |
| CTCN_4391 | 40177 | TTCN_7543 | 54236 |
| GTCN_2280 | 40178 | GTCN_4925 | 54237 |

FIG. 37 (continued)

| | | | |
|---|---|---|---|
| CTCN_4392 | 40179 | GTCN_4926 | 54238 |
| CTCN_4393 | 40180 | CTCN_9177 | 54239 |
| GTCN_2281 | 40181 | TTCN_7544 | 54240 |
| GTCN_2282 | 40182 | GTCN_4927 | 54241 |
| GTCN_2283 | 40183 | CTCN_9178 | 54242 |
| CTCN_4394 | 40184 | CTCN_9179 | 54243 |
| CTCN_4395 | 40185 | CTCN_9180 | 54244 |
| TTCN_3527 | 40186 | TTCN_7545 | 54245 |
| ATCN_2524 | 40187 | ATCN_5136 | 54246 |
| ATCN_2525 | 40188 | TTCN_7546 | 54247 |
| GTCN_2284 | 40189 | CTCN_9181 | 54248 |
| TTCN_3528 | 40190 | CTCN_9182 | 54249 |
| TTCN_3529 | 40191 | CTCN_9183 | 54250 |
| TTCN_3530 | 40192 | CTCN_9184 | 54251 |
| TTCN_3531 | 40193 | ATCN_5137 | 54252 |
| TTCN_3532 | 40194 | ATCN_5138 | 54253 |
| TTCN_3533 | 40195 | TTCN_7547 | 54254 |
| TTCN_3534 | 40196 | CTCN_9185 | 54255 |
| CTCN_4396 | 40197 | GTCN_4928 | 54256 |
| CTCN_4397 | 40198 | CTCN_9186 | 54257 |
| TTCN_3535 | 40199 | CTCN_9187 | 54258 |
| TTCN_3536 | 40200 | GTCN_4929 | 54259 |
| TTCN_3537 | 40201 | CTCN_9188 | 54260 |
| TTCN_3538 | 40202 | GTCN_4930 | 54261 |
| TTCN_3539 | 40203 | CTCN_9189 | 54262 |
| TTCN_3540 | 40204 | CTCN_9190 | 54263 |
| TTCN_3541 | 40205 | TTCN_7548 | 54264 |
| TTCN_3542 | 40206 | CTCN_9191 | 54265 |
| CTCN_4398 | 40207 | GTCN_4931 | 54266 |
| CTCN_4399 | 40208 | GTCN_4932 | 54267 |
| TTCN_3543 | 40209 | TTCN_7549 | 54268 |
| TTCN_3544 | 40210 | ATCN_5139 | 54269 |
| CTCN_4400 | 40211 | GTCN_4933 | 54270 |
| TTCN_3545 | 40212 | CTCN_9192 | 54271 |
| TTCN_3546 | 40213 | TTCN_7550 | 54272 |
| TTCN_3547 | 40214 | TTCN_7551 | 54273 |
| TTCN_3548 | 40215 | CTCN_9193 | 54274 |
| TTCN_3549 | 40216 | CTCN_9194 | 54275 |
| TTCN_3550 | 40217 | GTCN_4934 | 54276 |
| TTCN_3551 | 40218 | ATCN_5140 | 54277 |
| CTCN_4401 | 40219 | GTCN_4935 | 54278 |
| CTCN_4402 | 40220 | CTCN_9195 | 54279 |
| CTCN_4403 | 40221 | GTCN_4936 | 54280 |

| | | | |
|---|---|---|---|
| TTCN_3552 | 40222 | ATCN_5141 | 54281 |
| TTCN_3553 | 40223 | ATCN_5142 | 54282 |
| TTCN_3554 | 40224 | CTCN_9196 | 54283 |
| CTCN_4404 | 40225 | GTCN_4937 | 54284 |
| CTCN_4405 | 40226 | ATCN_5143 | 54285 |
| TTCN_3555 | 40227 | ATCN_5144 | 54286 |
| TTCN_3556 | 40228 | ATCN_5145 | 54287 |
| TTCN_3557 | 40229 | CTCN_9197 | 54288 |
| TTCN_3558 | 40230 | TTCN_7552 | 54289 |
| TTCN_3559 | 40231 | GTCN_4938 | 54290 |
| TTCN_3560 | 40232 | TTCN_7553 | 54291 |
| CTCN_4406 | 40233 | CTCN_9198 | 54292 |
| CTCN_4407 | 40234 | CTCN_9199 | 54293 |
| TTCN_3561 | 40235 | GTCN_4939 | 54294 |
| TTCN_3562 | 40236 | CTCN_9200 | 54295 |
| TTCN_3563 | 40237 | GTCN_4940 | 54296 |
| TTCN_3564 | 40238 | ATCN_5146 | 54297 |
| CTCN_4408 | 40239 | ATCN_5147 | 54298 |
| CTCN_4409 | 40240 | ATCN_5148 | 54299 |
| CTCN_4410 | 40241 | TTCN_7554 | 54300 |
| CTCN_4411 | 40242 | CTCN_9201 | 54301 |
| CTCN_4412 | 40243 | ATCN_5149 | 54302 |
| CTCN_4413 | 40244 | CTCN_9202 | 54303 |
| TTCN_3565 | 40245 | GTCN_4941 | 54304 |
| TTCN_3566 | 40246 | CTCN_9203 | 54305 |
| CTCN_4414 | 40247 | TTCN_7555 | 54306 |
| CTCN_4415 | 40248 | TTCN_7556 | 54307 |
| ATCN_2526 | 40249 | TTCN_7557 | 54308 |
| CTCN_4416 | 40250 | CTCN_9204 | 54309 |
| CTCN_4417 | 40251 | GTCN_4942 | 54310 |
| CTCN_4418 | 40252 | CTCN_9205 | 54311 |
| TTCN_3567 | 40253 | CTCN_9206 | 54312 |
| TTCN_3568 | 40254 | GTCN_4943 | 54313 |
| TTCN_3569 | 40255 | GTCN_4944 | 54314 |
| TTCN_3570 | 40256 | TTCN_7558 | 54315 |
| TTCN_3571 | 40257 | CTCN_9207 | 54316 |
| TTCN_3572 | 40258 | CTCN_9208 | 54317 |
| TTCN_3573 | 40259 | CTCN_9209 | 54318 |
| TTCN_3574 | 40260 | TTCN_7559 | 54319 |
| TTCN_3575 | 40261 | TTCN_7560 | 54320 |
| CTCN_4419 | 40262 | TTCN_7561 | 54321 |
| CTCN_4420 | 40263 | ATCN_5150 | 54322 |
| TTCN_3576 | 40264 | TTCN_7562 | 54323 |

FIG. 37 (continued)

| | | | |
|---|---|---|---|
| CTCN_4421 | 40265 | CTCN_9210 | 54324 |
| TTCN_3577 | 40266 | TTCN_7563 | 54325 |
| TTCN_3578 | 40267 | CTCN_9211 | 54326 |
| TTCN_3579 | 40268 | CTCN_9212 | 54327 |
| TTCN_3580 | 40269 | GTCN_4945 | 54328 |
| CTCN_4422 | 40270 | GTCN_4946 | 54329 |
| TTCN_3581 | 40271 | ATCN_5151 | 54330 |
| TTCN_3582 | 40272 | ATCN_5152 | 54331 |
| CTCN_4423 | 40273 | ATCN_5153 | 54332 |
| TTCN_3583 | 40274 | ATCN_5154 | 54333 |
| TTCN_3584 | 40275 | TTCN_7564 | 54334 |
| CTCN_4424 | 40276 | ATCN_5155 | 54335 |
| TTCN_3585 | 40277 | CTCN_9213 | 54336 |
| TTCN_3586 | 40278 | ATCN_5156 | 54337 |
| CTCN_4425 | 40279 | CTCN_9214 | 54338 |
| TTCN_3587 | 40280 | ATCN_5157 | 54339 |
| TTCN_3588 | 40281 | ATCN_5158 | 54340 |
| TTCN_3589 | 40282 | CTCN_9215 | 54341 |
| TTCN_3590 | 40283 | GTCN_4947 | 54342 |
| TTCN_3591 | 40284 | CTCN_9216 | 54343 |
| TTCN_3592 | 40285 | TTCN_7565 | 54344 |
| TTCN_3593 | 40286 | GTCN_4948 | 54345 |
| TTCN_3594 | 40287 | GTCN_4949 | 54346 |
| TTCN_3595 | 40288 | CTCN_9217 | 54347 |
| TTCN_3596 | 40289 | GTCN_4950 | 54348 |
| CTCN_4426 | 40290 | CTCN_9218 | 54349 |
| CTCN_4427 | 40291 | CTCN_9219 | 54350 |
| GTCN_2285 | 40292 | CTCN_9220 | 54351 |
| CTCN_4428 | 40293 | CTCN_9221 | 54352 |
| GTCN_2286 | 40294 | GTCN_4951 | 54353 |
| CTCN_4429 | 40295 | TTCN_7566 | 54354 |
| CTCN_4430 | 40296 | CTCN_9222 | 54355 |
| TTCN_3597 | 40297 | CTCN_9223 | 54356 |
| ATCN_2527 | 40298 | CTCN_9224 | 54357 |
| CTCN_4431 | 40299 | CTCN_9225 | 54358 |
| CTCN_4432 | 40300 | ATCN_5159 | 54359 |
| CTCN_4433 | 40301 | CTCN_9226 | 54360 |
| CTCN_4434 | 40302 | GTCN_4952 | 54361 |
| ATCN_2528 | 40303 | TTCN_7567 | 54362 |
| ATCN_2529 | 40304 | CTCN_9227 | 54363 |
| CTCN_4435 | 40305 | GTCN_4953 | 54364 |
| CTCN_4436 | 40306 | CTCN_9228 | 54365 |
| CTCN_4437 | 40307 | ATCN_5160 | 54366 |

| | | | |
|---|---|---|---|
| GTCN_2287 | 40308 | CTCN_9229 | 54367 |
| GTCN_2288 | 40309 | TTCN_7568 | 54368 |
| CTCN_4438 | 40310 | CTCN_9230 | 54369 |
| GTCN_2289 | 40311 | TTCN_7569 | 54370 |
| ATCN_2530 | 40312 | CTCN_9231 | 54371 |
| TTCN_3598 | 40313 | GTCN_4954 | 54372 |
| GTCN_2290 | 40314 | ATCN_5161 | 54373 |
| GTCN_2291 | 40315 | TTCN_7570 | 54374 |
| CTCN_4439 | 40316 | ATCN_5162 | 54375 |
| CTCN_4440 | 40317 | TTCN_7571 | 54376 |
| CTCN_4441 | 40318 | CTCN_9232 | 54377 |
| CTCN_4442 | 40319 | GTCN_4955 | 54378 |
| ATCN_2531 | 40320 | ATCN_5163 | 54379 |
| CTCN_4443 | 40321 | GTCN_4956 | 54380 |
| CTCN_4444 | 40322 | CTCN_9233 | 54381 |
| CTCN_4445 | 40323 | CTCN_9234 | 54382 |
| ATCN_2532 | 40324 | CTCN_9235 | 54383 |
| CTCN_4446 | 40325 | CTCN_9236 | 54384 |
| CTCN_4447 | 40326 | ATCN_5164 | 54385 |
| TTCN_3599 | 40327 | GTCN_4957 | 54386 |
| CTCN_4448 | 40328 | CTCN_9237 | 54387 |
| TTCN_3600 | 40329 | CTCN_9238 | 54388 |
| ATCN_2533 | 40330 | TTCN_7572 | 54389 |
| CTCN_4449 | 40331 | GTCN_4958 | 54390 |
| ATCN_2534 | 40332 | TTCN_7573 | 54391 |
| CTCN_4450 | 40333 | TTCN_7574 | 54392 |
| CTCN_4451 | 40334 | TTCN_7575 | 54393 |
| CTCN_4452 | 40335 | TTCN_7576 | 54394 |
| GTCN_2292 | 40336 | ATCN_5165 | 54395 |
| ATCN_2535 | 40337 | TTCN_7577 | 54396 |
| ATCN_2536 | 40338 | CTCN_9239 | 54397 |
| CTCN_4453 | 40339 | TTCN_7578 | 54398 |
| CTCN_4454 | 40340 | GTCN_4959 | 54399 |
| TTCN_3601 | 40341 | CTCN_9240 | 54400 |
| CTCN_4455 | 40342 | ATCN_5166 | 54401 |
| GTCN_2293 | 40343 | ATCN_5167 | 54402 |
| ATCN_2537 | 40344 | ATCN_5168 | 54403 |
| GTCN_2294 | 40345 | CTCN_9241 | 54404 |
| GTCN_2295 | 40346 | CTCN_9242 | 54405 |
| GTCN_2296 | 40347 | GTCN_4960 | 54406 |
| CTCN_4456 | 40348 | TTCN_7579 | 54407 |
| TTCN_3602 | 40349 | CTCN_9243 | 54408 |
| TTCN_3603 | 40350 | TTCN_7580 | 54409 |

FIG. 37 (continued)

| | | | |
|---|---|---|---|
| TTCN_3604 | 40351 | GTCN_4961 | 54410 |
| TTCN_3605 | 40352 | CTCN_9244 | 54411 |
| GTCN_2297 | 40353 | CTCN_9245 | 54412 |
| ATCN_2538 | 40354 | CTCN_9246 | 54413 |
| ATCN_2539 | 40355 | CTCN_9247 | 54414 |
| ATCN_2540 | 40356 | CTCN_9248 | 54415 |
| ATCN_2541 | 40357 | GTCN_4962 | 54416 |
| TTCN_3606 | 40358 | GTCN_4963 | 54417 |
| CTCN_4457 | 40359 | CTCN_9249 | 54418 |
| TTCN_3607 | 40360 | GTCN_4964 | 54419 |
| CTCN_4458 | 40361 | CTCN_9250 | 54420 |
| ATCN_2542 | 40362 | GTCN_4965 | 54421 |
| GTCN_2298 | 40363 | CTCN_9251 | 54422 |
| CTCN_4459 | 40364 | GTCN_4966 | 54423 |
| GTCN_2299 | 40365 | CTCN_9252 | 54424 |
| TTCN_3608 | 40366 | TTCN_7581 | 54425 |
| ATCN_2543 | 40367 | CTCN_9253 | 54426 |
| ATCN_2544 | 40368 | CTCN_9254 | 54427 |
| CTCN_4460 | 40369 | GTCN_4967 | 54428 |
| ATCN_2545 | 40370 | GTCN_4968 | 54429 |
| CTCN_4461 | 40371 | TTCN_7582 | 54430 |
| CTCN_4462 | 40372 | GTCN_4969 | 54431 |
| CTCN_4463 | 40373 | CTCN_9255 | 54432 |
| TTCN_3609 | 40374 | GTCN_4970 | 54433 |
| TTCN_3610 | 40375 | CTCN_9256 | 54434 |
| CTCN_4464 | 40376 | GTCN_4971 | 54435 |
| CTCN_4465 | 40377 | CTCN_9257 | 54436 |
| CTCN_4466 | 40378 | GTCN_4972 | 54437 |
| ATCN_2546 | 40379 | TTCN_7583 | 54438 |
| CTCN_4467 | 40380 | ATCN_5169 | 54439 |
| GTCN_2300 | 40381 | CTCN_9258 | 54440 |
| GTCN_2301 | 40382 | TTCN_7584 | 54441 |
| TTCN_3611 | 40383 | GTCN_4973 | 54442 |
| CTCN_4468 | 40384 | GTCN_4974 | 54443 |
| CTCN_4469 | 40385 | TTCN_7585 | 54444 |
| ATCN_2547 | 40386 | CTCN_9259 | 54445 |
| TTCN_3612 | 40387 | CTCN_9260 | 54446 |
| CTCN_4470 | 40388 | GTCN_4975 | 54447 |
| CTCN_4471 | 40389 | CTCN_9261 | 54448 |
| CTCN_4472 | 40390 | TTCN_7586 | 54449 |
| ATCN_2548 | 40391 | ATCN_5170 | 54450 |
| TTCN_3613 | 40392 | GTCN_4976 | 54451 |
| ATCN_2549 | 40393 | CTCN_9262 | 54452 |

| | | | |
|---|---|---|---|
| CTCN_4473 | 40394 | CTCN_9263 | 54453 |
| ATCN_2550 | 40395 | CTCN_9264 | 54454 |
| CTCN_4474 | 40396 | TTCN_7587 | 54455 |
| CTCN_4475 | 40397 | CTCN_9265 | 54456 |
| TTCN_3614 | 40398 | CTCN_9266 | 54457 |
| GTCN_2302 | 40399 | TTCN_7588 | 54458 |
| GTCN_2303 | 40400 | TTCN_7589 | 54459 |
| GTCN_2304 | 40401 | ATCN_5171 | 54460 |
| ATCN_2551 | 40402 | TTCN_7590 | 54461 |
| ATCN_2552 | 40403 | ATCN_5172 | 54462 |
| TTCN_3615 | 40404 | CTCN_9267 | 54463 |
| ATCN_2553 | 40405 | ATCN_5173 | 54464 |
| CTCN_4476 | 40406 | TTCN_7591 | 54465 |
| CTCN_4477 | 40407 | TTCN_7592 | 54466 |
| GTCN_2305 | 40408 | TTCN_7593 | 54467 |
| CTCN_4478 | 40409 | CTCN_9268 | 54468 |
| CTCN_4479 | 40410 | GTCN_4977 | 54469 |
| GTCN_2306 | 40411 | TTCN_7594 | 54470 |
| GTCN_2307 | 40412 | CTCN_9269 | 54471 |
| GTCN_2308 | 40413 | CTCN_9270 | 54472 |
| ATCN_2554 | 40414 | CTCN_9271 | 54473 |
| CTCN_4480 | 40415 | GTCN_4978 | 54474 |
| CTCN_4481 | 40416 | CTCN_9272 | 54475 |
| ATCN_2555 | 40417 | ATCN_5174 | 54476 |
| ATCN_2556 | 40418 | TTCN_7595 | 54477 |
| CTCN_4482 | 40419 | TTCN_7596 | 54478 |
| TTCN_3616 | 40420 | CTCN_9273 | 54479 |
| GTCN_2309 | 40421 | TTCN_7597 | 54480 |
| CTCN_4483 | 40422 | ATCN_5175 | 54481 |
| TTCN_3617 | 40423 | CTCN_9274 | 54482 |
| CTCN_4484 | 40424 | CTCN_9275 | 54483 |
| GTCN_2310 | 40425 | CTCN_9276 | 54484 |
| GTCN_2311 | 40426 | CTCN_9277 | 54485 |
| CTCN_4485 | 40427 | ATCN_5176 | 54486 |
| ATCN_2557 | 40428 | TTCN_7598 | 54487 |
| TTCN_3618 | 40429 | CTCN_9278 | 54488 |
| TTCN_3619 | 40430 | CTCN_9279 | 54489 |
| GTCN_2312 | 40431 | CTCN_9280 | 54490 |
| TTCN_3620 | 40432 | ATCN_5177 | 54491 |
| CTCN_4486 | 40433 | CTCN_9281 | 54492 |
| TTCN_3621 | 40434 | GTCN_4979 | 54493 |
| TTCN_3622 | 40435 | GTCN_4980 | 54494 |
| TTCN_3623 | 40436 | GTCN_4981 | 54495 |

FIG. 37 (continued)

| | | | |
|---|---|---|---|
| TTCN_3624 | 40437 | CTCN_9282 | 54496 |
| ATCN_2558 | 40438 | CTCN_9283 | 54497 |
| ATCN_2559 | 40439 | TTCN_7599 | 54498 |
| TTCN_3625 | 40440 | ATCN_5178 | 54499 |
| CTCN_4487 | 40441 | ATCN_5179 | 54500 |
| TTCN_3626 | 40442 | TTCN_7600 | 54501 |
| TTCN_3627 | 40443 | TTCN_7601 | 54502 |
| CTCN_4488 | 40444 | ATCN_5180 | 54503 |
| ATCN_2560 | 40445 | TTCN_7602 | 54504 |
| ATCN_2561 | 40446 | GTCN_4982 | 54505 |
| CTCN_4489 | 40447 | TTCN_7603 | 54506 |
| GTCN_2313 | 40448 | ATCN_5181 | 54507 |
| TTCN_3628 | 40449 | TTCN_7604 | 54508 |
| CTCN_4490 | 40450 | ATCN_5182 | 54509 |
| CTCN_4491 | 40451 | GTCN_4983 | 54510 |
| TTCN_3629 | 40452 | CTCN_9284 | 54511 |
| CTCN_4492 | 40453 | TTCN_7605 | 54512 |
| TTCN_3630 | 40454 | ATCN_5183 | 54513 |
| TTCN_3631 | 40455 | TTCN_7606 | 54514 |
| TTCN_3632 | 40456 | TTCN_7607 | 54515 |
| TTCN_3633 | 40457 | GTCN_4984 | 54516 |
| TTCN_3634 | 40458 | CTCN_9285 | 54517 |
| GTCN_2314 | 40459 | GTCN_4985 | 54518 |
| TTCN_3635 | 40460 | ATCN_5184 | 54519 |
| TTCN_3636 | 40461 | TTCN_7608 | 54520 |
| CTCN_4493 | 40462 | TTCN_7609 | 54521 |
| TTCN_3637 | 40463 | ATCN_5185 | 54522 |
| GTCN_2315 | 40464 | ATCN_5186 | 54523 |
| CTCN_4494 | 40465 | GTCN_4986 | 54524 |
| ATCN_2562 | 40466 | TTCN_7610 | 54525 |
| GTCN_2316 | 40467 | ATCN_5187 | 54526 |
| GTCN_2317 | 40468 | CTCN_9286 | 54527 |
| ATCN_2563 | 40469 | ATCN_5188 | 54528 |
| TTCN_3638 | 40470 | GTCN_4987 | 54529 |
| CTCN_4495 | 40471 | TTCN_7611 | 54530 |
| GTCN_2318 | 40472 | TTCN_7612 | 54531 |
| TTCN_3639 | 40473 | CTCN_9287 | 54532 |
| CTCN_4496 | 40474 | TTCN_7613 | 54533 |
| GTCN_2319 | 40475 | TTCN_7614 | 54534 |
| TTCN_3640 | 40476 | GTCN_4988 | 54535 |
| TTCN_3641 | 40477 | CTCN_9288 | 54536 |
| GTCN_2320 | 40478 | CTCN_9289 | 54537 |
| CTCN_4497 | 40479 | CTCN_9290 | 54538 |

| | | | |
|---|---|---|---|
| TTCN_3642 | 40480 | TTCN_7615 | 54539 |
| ATCN_2564 | 40481 | ATCN_5189 | 54540 |
| CTCN_4498 | 40482 | TTCN_7616 | 54541 |
| CTCN_4499 | 40483 | CTCN_9291 | 54542 |
| CTCN_4500 | 40484 | CTCN_9292 | 54543 |
| CTCN_4501 | 40485 | CTCN_9293 | 54544 |
| CTCN_4502 | 40486 | ATCN_5190 | 54545 |
| TTCN_3643 | 40487 | ATCN_5191 | 54546 |
| CTCN_4503 | 40488 | GTCN_4989 | 54547 |
| TTCN_3644 | 40489 | GTCN_4990 | 54548 |
| CTCN_4504 | 40490 | CTCN_9294 | 54549 |
| TTCN_3645 | 40491 | ATCN_5192 | 54550 |
| CTCN_4505 | 40492 | TTCN_7617 | 54551 |
| CTCN_4506 | 40493 | ATCN_5193 | 54552 |
| TTCN_3646 | 40494 | ATCN_5194 | 54553 |
| TTCN_3647 | 40495 | TTCN_7618 | 54554 |
| CTCN_4507 | 40496 | GTCN_4991 | 54555 |
| ATCN_2565 | 40497 | CTCN_9295 | 54556 |
| ATCN_2566 | 40498 | CTCN_9296 | 54557 |
| CTCN_4508 | 40499 | CTCN_9297 | 54558 |
| TTCN_3648 | 40500 | CTCN_9298 | 54559 |
| CTCN_4509 | 40501 | CTCN_9299 | 54560 |
| CTCN_4510 | 40502 | TTCN_7619 | 54561 |
| GTCN_2321 | 40503 | GTCN_4992 | 54562 |
| CTCN_4511 | 40504 | TTCN_7620 | 54563 |
| CTCN_4512 | 40505 | TTCN_7621 | 54564 |
| TTCN_3649 | 40506 | TTCN_7622 | 54565 |
| TTCN_3650 | 40507 | ATCN_5195 | 54566 |
| TTCN_3651 | 40508 | TTCN_7623 | 54567 |
| TTCN_3652 | 40509 | TTCN_7624 | 54568 |
| TTCN_3653 | 40510 | CTCN_9300 | 54569 |
| TTCN_3654 | 40511 | CTCN_9301 | 54570 |
| TTCN_3655 | 40512 | CTCN_9302 | 54571 |
| TTCN_3656 | 40513 | GTCN_4993 | 54572 |
| TTCN_3657 | 40514 | GTCN_4994 | 54573 |
| CTCN_4513 | 40515 | CTCN_9303 | 54574 |
| TTCN_3658 | 40516 | TTCN_7625 | 54575 |
| TTCN_3659 | 40517 | CTCN_9304 | 54576 |
| TTCN_3660 | 40518 | GTCN_4995 | 54577 |
| TTCN_3661 | 40519 | CTCN_9305 | 54578 |
| TTCN_3662 | 40520 | ATCN_5196 | 54579 |
| TTCN_3663 | 40521 | ATCN_5197 | 54580 |
| TTCN_3664 | 40522 | GTCN_4996 | 54581 |

FIG. 37 (continued)

| | | | |
|---|---|---|---|
| TTCN_3665 | 40523 | CTCN_9306 | 54582 |
| TTCN_3666 | 40524 | GTCN_4997 | 54583 |
| TTCN_3667 | 40525 | CTCN_9307 | 54584 |
| CTCN_4514 | 40526 | TTCN_7626 | 54585 |
| CTCN_4515 | 40527 | GTCN_4998 | 54586 |
| GTCN_2322 | 40528 | TTCN_7627 | 54587 |
| CTCN_4516 | 40529 | ATCN_5198 | 54588 |
| CTCN_4517 | 40530 | ATCN_5199 | 54589 |
| GTCN_2323 | 40531 | ATCN_5200 | 54590 |
| CTCN_4518 | 40532 | GTCN_4999 | 54591 |
| ATCN_2567 | 40533 | ATCN_5201 | 54592 |
| CTCN_4519 | 40534 | GTCN_5000 | 54593 |
| GTCN_2324 | 40535 | TTCN_7628 | 54594 |
| CTCN_4520 | 40536 | TTCN_7629 | 54595 |
| CTCN_4521 | 40537 | TTCN_7630 | 54596 |
| CTCN_4522 | 40538 | TTCN_7631 | 54597 |
| CTCN_4523 | 40539 | GTCN_5001 | 54598 |
| GTCN_2325 | 40540 | ATCN_5202 | 54599 |
| ATCN_2568 | 40541 | CTCN_9308 | 54600 |
| TTCN_3668 | 40542 | TTCN_7632 | 54601 |
| CTCN_4524 | 40543 | CTCN_9309 | 54602 |
| CTCN_4525 | 40544 | TTCN_7633 | 54603 |
| CTCN_4526 | 40545 | ATCN_5203 | 54604 |
| CTCN_4527 | 40546 | CTCN_9310 | 54605 |
| GTCN_2326 | 40547 | ATCN_5204 | 54606 |
| GTCN_2327 | 40548 | TTCN_7634 | 54607 |
| ATCN_2569 | 40549 | CTCN_9311 | 54608 |
| CTCN_4528 | 40550 | GTCN_5002 | 54609 |
| GTCN_2328 | 40551 | TTCN_7635 | 54610 |
| TTCN_3669 | 40552 | GTCN_5003 | 54611 |
| ATCN_2570 | 40553 | ATCN_5205 | 54612 |
| GTCN_2329 | 40554 | TTCN_7636 | 54613 |
| CTCN_4529 | 40555 | TTCN_7637 | 54614 |
| ATCN_2571 | 40556 | TTCN_7638 | 54615 |
| TTCN_3670 | 40557 | TTCN_7639 | 54616 |
| GTCN_2330 | 40558 | TTCN_7640 | 54617 |
| CTCN_4530 | 40559 | CTCN_9312 | 54618 |
| ATCN_2572 | 40560 | TTCN_7641 | 54619 |
| ATCN_2573 | 40561 | ATCN_5206 | 54620 |
| CTCN_4531 | 40562 | TTCN_7642 | 54621 |
| CTCN_4532 | 40563 | TTCN_7643 | 54622 |
| ATCN_2574 | 40564 | ATCN_5207 | 54623 |
| CTCN_4533 | 40565 | TTCN_7644 | 54624 |

| | | | |
|---|---|---|---|
| CTCN_4534 | 40566 | GTCN_5004 | 54625 |
| CTCN_4535 | 40567 | CTCN_9313 | 54626 |
| GTCN_2331 | 40568 | TTCN_7645 | 54627 |
| TTCN_3671 | 40569 | CTCN_9314 | 54628 |
| GTCN_2332 | 40570 | GTCN_5005 | 54629 |
| CTCN_4536 | 40571 | ATCN_5208 | 54630 |
| CTCN_4537 | 40572 | TTCN_7646 | 54631 |
| ATCN_2575 | 40573 | CTCN_9315 | 54632 |
| CTCN_4538 | 40574 | CTCN_9316 | 54633 |
| CTCN_4539 | 40575 | ATCN_5209 | 54634 |
| ATCN_2576 | 40576 | GTCN_5006 | 54635 |
| ATCN_2577 | 40577 | GTCN_5007 | 54636 |
| CTCN_4540 | 40578 | GTCN_5008 | 54637 |
| CTCN_4541 | 40579 | CTCN_9317 | 54638 |
| GTCN_2333 | 40580 | GTCN_5009 | 54639 |
| TTCN_3672 | 40581 | CTCN_9318 | 54640 |
| ATCN_2578 | 40582 | GTCN_5010 | 54641 |
| CTCN_4542 | 40583 | GTCN_5011 | 54642 |
| GTCN_2334 | 40584 | GTCN_5012 | 54643 |
| CTCN_4543 | 40585 | CTCN_9319 | 54644 |
| CTCN_4544 | 40586 | GTCN_5013 | 54645 |
| CTCN_4545 | 40587 | GTCN_5014 | 54646 |
| TTCN_3673 | 40588 | GTCN_5015 | 54647 |
| ATCN_2579 | 40589 | ATCN_5210 | 54648 |
| TTCN_3674 | 40590 | TTCN_7647 | 54649 |
| CTCN_4546 | 40591 | ATCN_5211 | 54650 |
| CTCN_4547 | 40592 | CTCN_9320 | 54651 |
| CTCN_4548 | 40593 | CTCN_9321 | 54652 |
| CTCN_4549 | 40594 | ATCN_5212 | 54653 |
| ATCN_2580 | 40595 | CTCN_9322 | 54654 |
| ATCN_2581 | 40596 | TTCN_7648 | 54655 |
| GTCN_2335 | 40597 | TTCN_7649 | 54656 |
| ATCN_2582 | 40598 | TTCN_7650 | 54657 |
| GTCN_2336 | 40599 | ATCN_5213 | 54658 |
| CTCN_4550 | 40600 | ATCN_5214 | 54659 |
| CTCN_4551 | 40601 | CTCN_9323 | 54660 |
| GTCN_2337 | 40602 | TTCN_7651 | 54661 |
| ATCN_2583 | 40603 | CTCN_9324 | 54662 |
| CTCN_4552 | 40604 | GTCN_5016 | 54663 |
| TTCN_3675 | 40605 | TTCN_7652 | 54664 |
| CTCN_4553 | 40606 | TTCN_7653 | 54665 |
| TTCN_3676 | 40607 | TTCN_7654 | 54666 |
| CTCN_4554 | 40608 | CTCN_9325 | 54667 |

FIG. 37 (continued)

| | | | |
|---|---|---|---|
| CTCN_4555 | 40609 | CTCN_9326 | 54668 |
| ATCN_2584 | 40610 | CTCN_9327 | 54669 |
| CTCN_4556 | 40611 | GTCN_5017 | 54670 |
| TTCN_3677 | 40612 | CTCN_9328 | 54671 |
| ATCN_2585 | 40613 | ATCN_5215 | 54672 |
| TTCN_3678 | 40614 | CTCN_9329 | 54673 |
| GTCN_2338 | 40615 | GTCN_5018 | 54674 |
| CTCN_4557 | 40616 | TTCN_7655 | 54675 |
| GTCN_2339 | 40617 | CTCN_9330 | 54676 |
| ATCN_2586 | 40618 | GTCN_5019 | 54677 |
| TTCN_3679 | 40619 | TTCN_7656 | 54678 |
| ATCN_2587 | 40620 | GTCN_5020 | 54679 |
| TTCN_3680 | 40621 | ATCN_5216 | 54680 |
| ATCN_2588 | 40622 | GTCN_5021 | 54681 |
| ATCN_2589 | 40623 | TTCN_7657 | 54682 |
| GTCN_2340 | 40624 | CTCN_9331 | 54683 |
| ATCN_2590 | 40625 | TTCN_7658 | 54684 |
| TTCN_3681 | 40626 | CTCN_9332 | 54685 |
| TTCN_3682 | 40627 | CTCN_9333 | 54686 |
| GTCN_2341 | 40628 | TTCN_7659 | 54687 |
| TTCN_3683 | 40629 | TTCN_7660 | 54688 |
| ATCN_2591 | 40630 | GTCN_5022 | 54689 |
| TTCN_3684 | 40631 | ATCN_5217 | 54690 |
| GTCN_2342 | 40632 | ATCN_5218 | 54691 |
| TTCN_3685 | 40633 | ATCN_5219 | 54692 |
| CTCN_4558 | 40634 | GTCN_5023 | 54693 |
| GTCN_2343 | 40635 | GTCN_5024 | 54694 |
| TTCN_3686 | 40636 | CTCN_9334 | 54695 |
| ATCN_2592 | 40637 | TTCN_7661 | 54696 |
| TTCN_3687 | 40638 | GTCN_5025 | 54697 |
| ATCN_2593 | 40639 | CTCN_9335 | 54698 |
| TTCN_3688 | 40640 | GTCN_5026 | 54699 |
| CTCN_4559 | 40641 | CTCN_9336 | 54700 |
| CTCN_4560 | 40642 | ATCN_5220 | 54701 |
| ATCN_2594 | 40643 | ATCN_5221 | 54702 |
| ATCN_2595 | 40644 | ATCN_5222 | 54703 |
| GTCN_2344 | 40645 | TTCN_7662 | 54704 |
| TTCN_3689 | 40646 | CTCN_9337 | 54705 |
| ATCN_2596 | 40647 | CTCN_9338 | 54706 |
| CTCN_4561 | 40648 | CTCN_9339 | 54707 |
| ATCN_2597 | 40649 | GTCN_5027 | 54708 |
| ATCN_2598 | 40650 | CTCN_9340 | 54709 |
| CTCN_4562 | 40651 | GTCN_5028 | 54710 |

| | | | |
|---|---|---|---|
| GTCN_2345 | 40652 | ATCN_5223 | 54711 |
| CTCN_4563 | 40653 | ATCN_5224 | 54712 |
| ATCN_2599 | 40654 | CTCN_9341 | 54713 |
| ATCN_2600 | 40655 | GTCN_5029 | 54714 |
| CTCN_4564 | 40656 | TTCN_7663 | 54715 |
| TTCN_3690 | 40657 | ATCN_5225 | 54716 |
| CTCN_4565 | 40658 | CTCN_9342 | 54717 |
| GTCN_2346 | 40659 | CTCN_9343 | 54718 |
| TTCN_3691 | 40660 | ATCN_5226 | 54719 |
| ATCN_2601 | 40661 | CTCN_9344 | 54720 |
| TTCN_3692 | 40662 | ATCN_5227 | 54721 |
| CTCN_4566 | 40663 | CTCN_9345 | 54722 |
| CTCN_4567 | 40664 | CTCN_9346 | 54723 |
| TTCN_3693 | 40665 | TTCN_7664 | 54724 |
| TTCN_3694 | 40666 | TTCN_7665 | 54725 |
| TTCN_3695 | 40667 | ATCN_5228 | 54726 |
| TTCN_3696 | 40668 | TTCN_7666 | 54727 |
| TTCN_3697 | 40669 | TTCN_7667 | 54728 |
| CTCN_4568 | 40670 | TTCN_7668 | 54729 |
| GTCN_2347 | 40671 | CTCN_9347 | 54730 |
| ATCN_2602 | 40672 | GTCN_5030 | 54731 |
| ATCN_2603 | 40673 | CTCN_9348 | 54732 |
| CTCN_4569 | 40674 | CTCN_9349 | 54733 |
| TTCN_3698 | 40675 | ATCN_5229 | 54734 |
| TTCN_3699 | 40676 | CTCN_9350 | 54735 |
| ATCN_2604 | 40677 | TTCN_7669 | 54736 |
| ATCN_2605 | 40678 | GTCN_5031 | 54737 |
| TTCN_3700 | 40679 | CTCN_9351 | 54738 |
| TTCN_3701 | 40680 | TTCN_7670 | 54739 |
| TTCN_3702 | 40681 | TTCN_7671 | 54740 |
| GTCN_2348 | 40682 | TTCN_7672 | 54741 |
| TTCN_3703 | 40683 | TTCN_7673 | 54742 |
| GTCN_2349 | 40684 | CTCN_9352 | 54743 |
| CTCN_4570 | 40685 | TTCN_7674 | 54744 |
| TTCN_3704 | 40686 | TTCN_7675 | 54745 |
| TTCN_3705 | 40687 | TTCN_7676 | 54746 |
| GTCN_2350 | 40688 | GTCN_5032 | 54747 |
| TTCN_3706 | 40689 | TTCN_7677 | 54748 |
| CTCN_4571 | 40690 | ATCN_5230 | 54749 |
| ATCN_2606 | 40691 | CTCN_9353 | 54750 |
| TTCN_3707 | 40692 | TTCN_7678 | 54751 |
| GTCN_2351 | 40693 | GTCN_5033 | 54752 |
| CTCN_4572 | 40694 | CTCN_9354 | 54753 |

FIG. 37 (continued)

| | | | |
|---|---|---|---|
| ATCN_2607 | 40695 | CTCN_9355 | 54754 |
| ATCN_2608 | 40696 | TTCN_7679 | 54755 |
| GTCN_2352 | 40697 | TTCN_7680 | 54756 |
| CTCN_4573 | 40698 | ATCN_5231 | 54757 |
| ATCN_2609 | 40699 | CTCN_9356 | 54758 |
| ATCN_2610 | 40700 | CTCN_9357 | 54759 |
| CTCN_4574 | 40701 | ATCN_5232 | 54760 |
| TTCN_3708 | 40702 | CTCN_9358 | 54761 |
| CTCN_4575 | 40703 | ATCN_5233 | 54762 |
| ATCN_2611 | 40704 | CTCN_9359 | 54763 |
| CTCN_4576 | 40705 | ATCN_5234 | 54764 |
| CTCN_4577 | 40706 | CTCN_9360 | 54765 |
| CTCN_4578 | 40707 | GTCN_5034 | 54766 |
| GTCN_2353 | 40708 | GTCN_5035 | 54767 |
| CTCN_4579 | 40709 | GTCN_5036 | 54768 |
| CTCN_4580 | 40710 | CTCN_9361 | 54769 |
| CTCN_4581 | 40711 | GTCN_5037 | 54770 |
| ATCN_2612 | 40712 | CTCN_9362 | 54771 |
| ATCN_2613 | 40713 | CTCN_9363 | 54772 |
| CTCN_4582 | 40714 | ATCN_5235 | 54773 |
| TTCN_3709 | 40715 | ATCN_5236 | 54774 |
| CTCN_4583 | 40716 | GTCN_5038 | 54775 |
| TTCN_3710 | 40717 | ATCN_5237 | 54776 |
| GTCN_2354 | 40718 | ATCN_5238 | 54777 |
| GTCN_2355 | 40719 | ATCN_5239 | 54778 |
| GTCN_2356 | 40720 | GTCN_5039 | 54779 |
| TTCN_3711 | 40721 | CTCN_9364 | 54780 |
| GTCN_2357 | 40722 | GTCN_5040 | 54781 |
| TTCN_3712 | 40723 | CTCN_9365 | 54782 |
| CTCN_4584 | 40724 | TTCN_7681 | 54783 |
| TTCN_3713 | 40725 | GTCN_5041 | 54784 |
| ATCN_2614 | 40726 | CTCN_9366 | 54785 |
| ATCN_2615 | 40727 | TTCN_7682 | 54786 |
| TTCN_3714 | 40728 | CTCN_9367 | 54787 |
| CTCN_4585 | 40729 | TTCN_7683 | 54788 |
| TTCN_3715 | 40730 | TTCN_7684 | 54789 |
| CTCN_4586 | 40731 | GTCN_5042 | 54790 |
| CTCN_4587 | 40732 | ATCN_5240 | 54791 |
| GTCN_2358 | 40733 | CTCN_9368 | 54792 |
| CTCN_4588 | 40734 | GTCN_5043 | 54793 |
| ATCN_2616 | 40735 | CTCN_9369 | 54794 |
| CTCN_4589 | 40736 | TTCN_7685 | 54795 |
| CTCN_4590 | 40737 | CTCN_9370 | 54796 |

| | | | |
|---|---|---|---|
| TTCN_3716 | 40738 | CTCN_9371 | 54797 |
| TTCN_3717 | 40739 | CTCN_9372 | 54798 |
| TTCN_3718 | 40740 | CTCN_9373 | 54799 |
| CTCN_4591 | 40741 | TTCN_7686 | 54800 |
| GTCN_2359 | 40742 | GTCN_5044 | 54801 |
| GTCN_2360 | 40743 | TTCN_7687 | 54802 |
| CTCN_4592 | 40744 | CTCN_9374 | 54803 |
| CTCN_4593 | 40745 | CTCN_9375 | 54804 |
| CTCN_4594 | 40746 | CTCN_9376 | 54805 |
| ATCN_2617 | 40747 | ATCN_5241 | 54806 |
| ATCN_2618 | 40748 | CTCN_9377 | 54807 |
| CTCN_4595 | 40749 | GTCN_5045 | 54808 |
| ATCN_2619 | 40750 | CTCN_9378 | 54809 |
| CTCN_4596 | 40751 | TTCN_7688 | 54810 |
| CTCN_4597 | 40752 | CTCN_9379 | 54811 |
| CTCN_4598 | 40753 | GTCN_5046 | 54812 |
| ATCN_2620 | 40754 | CTCN_9380 | 54813 |
| TTCN_3719 | 40755 | CTCN_9381 | 54814 |
| CTCN_4599 | 40756 | CTCN_9382 | 54815 |
| CTCN_4600 | 40757 | CTCN_9383 | 54816 |
| TTCN_3720 | 40758 | TTCN_7689 | 54817 |
| CTCN_4601 | 40759 | ATCN_5242 | 54818 |
| GTCN_2361 | 40760 | TTCN_7690 | 54819 |
| GTCN_2362 | 40761 | CTCN_9384 | 54820 |
| CTCN_4602 | 40762 | CTCN_9385 | 54821 |
| GTCN_2363 | 40763 | CTCN_9386 | 54822 |
| CTCN_4603 | 40764 | GTCN_5047 | 54823 |
| GTCN_2364 | 40765 | TTCN_7691 | 54824 |
| CTCN_4604 | 40766 | TTCN_7692 | 54825 |
| GTCN_2365 | 40767 | CTCN_9387 | 54826 |
| TTCN_3721 | 40768 | GTCN_5048 | 54827 |
| CTCN_4605 | 40769 | CTCN_9388 | 54828 |
| CTCN_4606 | 40770 | TTCN_7693 | 54829 |
| GTCN_2366 | 40771 | ATCN_5243 | 54830 |
| CTCN_4607 | 40772 | ATCN_5244 | 54831 |
| CTCN_4608 | 40773 | ATCN_5245 | 54832 |
| TTCN_3722 | 40774 | CTCN_9389 | 54833 |
| GTCN_2367 | 40775 | ATCN_5246 | 54834 |
| CTCN_4609 | 40776 | CTCN_9390 | 54835 |
| TTCN_3723 | 40777 | GTCN_5049 | 54836 |
| CTCN_4610 | 40778 | CTCN_9391 | 54837 |
| CTCN_4611 | 40779 | ATCN_5247 | 54838 |
| TTCN_3724 | 40780 | ATCN_5248 | 54839 |

FIG. 37 (continued)

| | | | |
|---|---|---|---|
| ATCN_2621 | 40781 | CTCN_9392 | 54840 |
| TTCN_3725 | 40782 | ATCN_5249 | 54841 |
| ATCN_2622 | 40783 | CTCN_9393 | 54842 |
| GTCN_2368 | 40784 | GTCN_5050 | 54843 |
| TTCN_3726 | 40785 | TTCN_7694 | 54844 |
| GTCN_2369 | 40786 | TTCN_7695 | 54845 |
| CTCN_4612 | 40787 | TTCN_7696 | 54846 |
| TTCN_3727 | 40788 | TTCN_7697 | 54847 |
| TTCN_3728 | 40789 | CTCN_9394 | 54848 |
| CTCN_4613 | 40790 | TTCN_7698 | 54849 |
| CTCN_4614 | 40791 | TTCN_7699 | 54850 |
| CTCN_4615 | 40792 | ATCN_5250 | 54851 |
| GTCN_2370 | 40793 | ATCN_5251 | 54852 |
| GTCN_2371 | 40794 | TTCN_7700 | 54853 |
| GTCN_2372 | 40795 | ATCN_5252 | 54854 |
| TTCN_3729 | 40796 | TTCN_7701 | 54855 |
| GTCN_2373 | 40797 | TTCN_7702 | 54856 |
| CTCN_4616 | 40798 | ATCN_5253 | 54857 |
| TTCN_3730 | 40799 | TTCN_7703 | 54858 |
| CTCN_4617 | 40800 | ATCN_5254 | 54859 |
| GTCN_2374 | 40801 | CTCN_9395 | 54860 |
| GTCN_2375 | 40802 | TTCN_7704 | 54861 |
| CTCN_4618 | 40803 | CTCN_9396 | 54862 |
| GTCN_2376 | 40804 | CTCN_9397 | 54863 |
| CTCN_4619 | 40805 | GTCN_5051 | 54864 |
| CTCN_4620 | 40806 | TTCN_7705 | 54865 |
| GTCN_2377 | 40807 | CTCN_9398 | 54866 |
| CTCN_4621 | 40808 | GTCN_5052 | 54867 |
| TTCN_3731 | 40809 | GTCN_5053 | 54868 |
| ATCN_2623 | 40810 | CTCN_9399 | 54869 |
| ATCN_2624 | 40811 | CTCN_9400 | 54870 |
| CTCN_4622 | 40812 | TTCN_7706 | 54871 |
| TTCN_3732 | 40813 | TTCN_7707 | 54872 |
| CTCN_4623 | 40814 | CTCN_9401 | 54873 |
| ATCN_2625 | 40815 | GTCN_5054 | 54874 |
| CTCN_4624 | 40816 | CTCN_9402 | 54875 |
| CTCN_4625 | 40817 | GTCN_5055 | 54876 |
| GTCN_2378 | 40818 | ATCN_5255 | 54877 |
| CTCN_4626 | 40819 | TTCN_7708 | 54878 |
| GTCN_2379 | 40820 | ATCN_5256 | 54879 |
| TTCN_3733 | 40821 | GTCN_5056 | 54880 |
| CTCN_4627 | 40822 | CTCN_9403 | 54881 |
| CTCN_4628 | 40823 | TTCN_7709 | 54882 |

| | | | |
|---|---|---|---|
| ATCN_2626 | 40824 | ATCN_5257 | 54883 |
| ATCN_2627 | 40825 | CTCN_9404 | 54884 |
| ATCN_2628 | 40826 | TTCN_7710 | 54885 |
| CTCN_4629 | 40827 | TTCN_7711 | 54886 |
| CTCN_4630 | 40828 | CTCN_9405 | 54887 |
| TTCN_3734 | 40829 | ATCN_5258 | 54888 |
| TTCN_3735 | 40830 | CTCN_9406 | 54889 |
| CTCN_4631 | 40831 | CTCN_9407 | 54890 |
| GTCN_2380 | 40832 | ATCN_5259 | 54891 |
| CTCN_4632 | 40833 | ATCN_5260 | 54892 |
| CTCN_4633 | 40834 | CTCN_9408 | 54893 |
| CTCN_4634 | 40835 | TTCN_7712 | 54894 |
| CTCN_4635 | 40836 | GTCN_5057 | 54895 |
| GTCN_2381 | 40837 | CTCN_9409 | 54896 |
| CTCN_4636 | 40838 | GTCN_5058 | 54897 |
| GTCN_2382 | 40839 | GTCN_5059 | 54898 |
| ATCN_2629 | 40840 | ATCN_5261 | 54899 |
| TTCN_3736 | 40841 | ATCN_5262 | 54900 |
| TTCN_3737 | 40842 | GTCN_5060 | 54901 |
| CTCN_4637 | 40843 | TTCN_7713 | 54902 |
| GTCN_2383 | 40844 | TTCN_7714 | 54903 |
| TTCN_3738 | 40845 | TTCN_7715 | 54904 |
| CTCN_4638 | 40846 | ATCN_5263 | 54905 |
| CTCN_4639 | 40847 | TTCN_7716 | 54906 |
| TTCN_3739 | 40848 | GTCN_5061 | 54907 |
| ATCN_2630 | 40849 | GTCN_5062 | 54908 |
| CTCN_4640 | 40850 | TTCN_7717 | 54909 |
| CTCN_4641 | 40851 | CTCN_9410 | 54910 |
| ATCN_2631 | 40852 | ATCN_5264 | 54911 |
| CTCN_4642 | 40853 | CTCN_9411 | 54912 |
| ATCN_2632 | 40854 | CTCN_9412 | 54913 |
| GTCN_2384 | 40855 | ATCN_5265 | 54914 |
| ATCN_2633 | 40856 | CTCN_9413 | 54915 |
| ATCN_2634 | 40857 | GTCN_5063 | 54916 |
| TTCN_3740 | 40858 | CTCN_9414 | 54917 |
| ATCN_2635 | 40859 | GTCN_5064 | 54918 |
| GTCN_2385 | 40860 | CTCN_9415 | 54919 |
| ATCN_2636 | 40861 | GTCN_5065 | 54920 |
| ATCN_2637 | 40862 | ATCN_5266 | 54921 |
| TTCN_3741 | 40863 | TTCN_7718 | 54922 |
| GTCN_2386 | 40864 | GTCN_5066 | 54923 |
| TTCN_3742 | 40865 | TTCN_7719 | 54924 |
| CTCN_4643 | 40866 | CTCN_9416 | 54925 |

FIG. 37 (continued)

| | | | |
|---|---|---|---|
| TTCN_3743 | 40867 | CTCN_9417 | 54926 |
| CTCN_4644 | 40868 | TTCN_7720 | 54927 |
| CTCN_4645 | 40869 | TTCN_7721 | 54928 |
| CTCN_4646 | 40870 | CTCN_9418 | 54929 |
| CTCN_4647 | 40871 | CTCN_9419 | 54930 |
| TTCN_3744 | 40872 | CTCN_9420 | 54931 |
| CTCN_4648 | 40873 | CTCN_9421 | 54932 |
| ATCN_2638 | 40874 | ATCN_5267 | 54933 |
| CTCN_4649 | 40875 | CTCN_9422 | 54934 |
| GTCN_2387 | 40876 | CTCN_9423 | 54935 |
| CTCN_4650 | 40877 | CTCN_9424 | 54936 |
| TTCN_3745 | 40878 | GTCN_5067 | 54937 |
| CTCN_4651 | 40879 | CTCN_9425 | 54938 |
| TTCN_3746 | 40880 | ATCN_5268 | 54939 |
| TTCN_3747 | 40881 | CTCN_9426 | 54940 |
| ATCN_2639 | 40882 | ATCN_5269 | 54941 |
| TTCN_3748 | 40883 | CTCN_9427 | 54942 |
| GTCN_2388 | 40884 | GTCN_5068 | 54943 |
| ATCN_2640 | 40885 | CTCN_9428 | 54944 |
| CTCN_4652 | 40886 | GTCN_5069 | 54945 |
| GTCN_2389 | 40887 | GTCN_5070 | 54946 |
| CTCN_4653 | 40888 | TTCN_7722 | 54947 |
| CTCN_4654 | 40889 | TTCN_7723 | 54948 |
| ATCN_2641 | 40890 | GTCN_5071 | 54949 |
| TTCN_3749 | 40891 | CTCN_9429 | 54950 |
| GTCN_2390 | 40892 | ATCN_5270 | 54951 |
| CTCN_4655 | 40893 | ATCN_5271 | 54952 |
| GTCN_2391 | 40894 | CTCN_9430 | 54953 |
| TTCN_3750 | 40895 | GTCN_5072 | 54954 |
| CTCN_4656 | 40896 | CTCN_9431 | 54955 |
| TTCN_3751 | 40897 | GTCN_5073 | 54956 |
| CTCN_4657 | 40898 | ATCN_5272 | 54957 |
| TTCN_3752 | 40899 | GTCN_5074 | 54958 |
| CTCN_4658 | 40900 | CTCN_9432 | 54959 |
| CTCN_4659 | 40901 | CTCN_9433 | 54960 |
| CTCN_4660 | 40902 | TTCN_7724 | 54961 |
| ATCN_2642 | 40903 | ATCN_5273 | 54962 |
| TTCN_3753 | 40904 | ATCN_5274 | 54963 |
| GTCN_2392 | 40905 | ATCN_5275 | 54964 |
| ATCN_2643 | 40906 | ATCN_5276 | 54965 |
| GTCN_2393 | 40907 | ATCN_5277 | 54966 |
| ATCN_2644 | 40908 | TTCN_7725 | 54967 |
| ATCN_2645 | 40909 | CTCN_9434 | 54968 |

| | | | |
|---|---|---|---|
| ATCN_2646 | 40910 | TTCN_7726 | 54969 |
| TTCN_3754 | 40911 | GTCN_5075 | 54970 |
| ATCN_2647 | 40912 | CTCN_9435 | 54971 |
| CTCN_4661 | 40913 | ATCN_5278 | 54972 |
| CTCN_4662 | 40914 | CTCN_9436 | 54973 |
| TTCN_3755 | 40915 | GTCN_5076 | 54974 |
| ATCN_2648 | 40916 | ATCN_5279 | 54975 |
| ATCN_2649 | 40917 | ATCN_5280 | 54976 |
| GTCN_2394 | 40918 | CTCN_9437 | 54977 |
| CTCN_4663 | 40919 | TTCN_7727 | 54978 |
| GTCN_2395 | 40920 | ATCN_5281 | 54979 |
| CTCN_4664 | 40921 | CTCN_9438 | 54980 |
| CTCN_4665 | 40922 | GTCN_5077 | 54981 |
| CTCN_4666 | 40923 | ATCN_5282 | 54982 |
| TTCN_3756 | 40924 | TTCN_7728 | 54983 |
| TTCN_3757 | 40925 | GTCN_5078 | 54984 |
| GTCN_2396 | 40926 | ATCN_5283 | 54985 |
| TTCN_3758 | 40927 | ATCN_5284 | 54986 |
| CTCN_4667 | 40928 | CTCN_9439 | 54987 |
| CTCN_4668 | 40929 | CTCN_9440 | 54988 |
| CTCN_4669 | 40930 | CTCN_9441 | 54989 |
| TTCN_3759 | 40931 | CTCN_9442 | 54990 |
| TTCN_3760 | 40932 | TTCN_7729 | 54991 |
| ATCN_2650 | 40933 | ATCN_5285 | 54992 |
| GTCN_2397 | 40934 | TTCN_7730 | 54993 |
| GTCN_2398 | 40935 | CTCN_9443 | 54994 |
| TTCN_3761 | 40936 | GTCN_5079 | 54995 |
| GTCN_2399 | 40937 | CTCN_9444 | 54996 |
| CTCN_4670 | 40938 | ATCN_5286 | 54997 |
| GTCN_2400 | 40939 | CTCN_9445 | 54998 |
| TTCN_3762 | 40940 | CTCN_9446 | 54999 |
| ATCN_2651 | 40941 | ATCN_5287 | 55000 |
| ATCN_2652 | 40942 | ATCN_5288 | 55001 |
| CTCN_4671 | 40943 | CTCN_9447 | 55002 |
| TTCN_3763 | 40944 | CTCN_9448 | 55003 |
| CTCN_4672 | 40945 | GTCN_5080 | 55004 |
| CTCN_4673 | 40946 | TTCN_7731 | 55005 |
| TTCN_3764 | 40947 | GTCN_5081 | 55006 |
| ATCN_2653 | 40948 | CTCN_9449 | 55007 |
| CTCN_4674 | 40949 | CTCN_9450 | 55008 |
| CTCN_4675 | 40950 | TTCN_7732 | 55009 |
| CTCN_4676 | 40951 | TTCN_7733 | 55010 |
| TTCN_3765 | 40952 | ATCN_5289 | 55011 |

FIG. 37 (continued)

| | | | |
|---|---|---|---|
| ATCN_2654 | 40953 | GTCN_5082 | 55012 |
| GTCN_2401 | 40954 | GTCN_5083 | 55013 |
| ATCN_2655 | 40955 | GTCN_5084 | 55014 |
| TTCN_3766 | 40956 | GTCN_5085 | 55015 |
| ATCN_2656 | 40957 | ATCN_5290 | 55016 |
| TTCN_3767 | 40958 | TTCN_7734 | 55017 |
| CTCN_4677 | 40959 | TTCN_7735 | 55018 |
| TTCN_3768 | 40960 | TTCN_7736 | 55019 |
| TTCN_3769 | 40961 | GTCN_5086 | 55020 |
| ATCN_2657 | 40962 | TTCN_7737 | 55021 |
| TTCN_3770 | 40963 | TTCN_7738 | 55022 |
| ATCN_2658 | 40964 | TTCN_7739 | 55023 |
| TTCN_3771 | 40965 | GTCN_5087 | 55024 |
| TTCN_3772 | 40966 | TTCN_7740 | 55025 |
| ATCN_2659 | 40967 | CTCN_9451 | 55026 |
| TTCN_3773 | 40968 | ATCN_5291 | 55027 |
| ATCN_2660 | 40969 | TTCN_7741 | 55028 |
| TTCN_3774 | 40970 | TTCN_7742 | 55029 |
| GTCN_2402 | 40971 | GTCN_5088 | 55030 |
| TTCN_3775 | 40972 | CTCN_9452 | 55031 |
| CTCN_4678 | 40973 | CTCN_9453 | 55032 |
| CTCN_4679 | 40974 | CTCN_9454 | 55033 |
| ATCN_2661 | 40975 | ATCN_5292 | 55034 |
| CTCN_4680 | 40976 | TTCN_7743 | 55035 |
| CTCN_4681 | 40977 | CTCN_9455 | 55036 |
| ATCN_2662 | 40978 | TTCN_7744 | 55037 |
| TTCN_3776 | 40979 | CTCN_9456 | 55038 |
| ATCN_2663 | 40980 | ATCN_5293 | 55039 |
| CTCN_4682 | 40981 | CTCN_9457 | 55040 |
| GTCN_2403 | 40982 | TTCN_7745 | 55041 |
| TTCN_3777 | 40983 | TTCN_7746 | 55042 |
| CTCN_4683 | 40984 | TTCN_7747 | 55043 |
| GTCN_2404 | 40985 | TTCN_7748 | 55044 |
| ATCN_2664 | 40986 | TTCN_7749 | 55045 |
| GTCN_2405 | 40987 | TTCN_7750 | 55046 |
| CTCN_4684 | 40988 | ATCN_5294 | 55047 |
| TTCN_3778 | 40989 | TTCN_7751 | 55048 |
| ATCN_2665 | 40990 | TTCN_7752 | 55049 |
| TTCN_3779 | 40991 | CTCN_9458 | 55050 |
| CTCN_4685 | 40992 | GTCN_5089 | 55051 |
| CTCN_4686 | 40993 | CTCN_9459 | 55052 |
| GTCN_2406 | 40994 | CTCN_9460 | 55053 |
| TTCN_3780 | 40995 | ATCN_5295 | 55054 |

| | | | |
|---|---|---|---|
| GTCN_2407 | 40996 | TTCN_7753 | 55055 |
| TTCN_3781 | 40997 | CTCN_9461 | 55056 |
| GTCN_2408 | 40998 | ATCN_5296 | 55057 |
| TTCN_3782 | 40999 | CTCN_9462 | 55058 |
| TTCN_3783 | 41000 | CTCN_9463 | 55059 |
| CTCN_4687 | 41001 | CTCN_9464 | 55060 |
| CTCN_4688 | 41002 | CTCN_9465 | 55061 |
| ATCN_2666 | 41003 | CTCN_9466 | 55062 |
| ATCN_2667 | 41004 | CTCN_9467 | 55063 |
| ATCN_2668 | 41005 | CTCN_9468 | 55064 |
| ATCN_2669 | 41006 | GTCN_5090 | 55065 |
| ATCN_2670 | 41007 | TTCN_7754 | 55066 |
| TTCN_3784 | 41008 | CTCN_9469 | 55067 |
| CTCN_4689 | 41009 | GTCN_5091 | 55068 |
| TTCN_3785 | 41010 | CTCN_9470 | 55069 |
| CTCN_4690 | 41011 | ATCN_5297 | 55070 |
| ATCN_2671 | 41012 | TTCN_7755 | 55071 |
| ATCN_2672 | 41013 | ATCN_5298 | 55072 |
| ATCN_2673 | 41014 | TTCN_7756 | 55073 |
| CTCN_4691 | 41015 | CTCN_9471 | 55074 |
| ATCN_2674 | 41016 | ATCN_5299 | 55075 |
| ATCN_2675 | 41017 | CTCN_9472 | 55076 |
| ATCN_2676 | 41018 | TTCN_7757 | 55077 |
| TTCN_3786 | 41019 | CTCN_9473 | 55078 |
| TTCN_3787 | 41020 | TTCN_7758 | 55079 |
| GTCN_2409 | 41021 | TTCN_7759 | 55080 |
| GTCN_2410 | 41022 | TTCN_7760 | 55081 |
| CTCN_4692 | 41023 | CTCN_9474 | 55082 |
| CTCN_4693 | 41024 | TTCN_7761 | 55083 |
| GTCN_2411 | 41025 | CTCN_9475 | 55084 |
| CTCN_4694 | 41026 | CTCN_9476 | 55085 |
| ATCN_2677 | 41027 | CTCN_9477 | 55086 |
| CTCN_4695 | 41028 | TTCN_7762 | 55087 |
| CTCN_4696 | 41029 | ATCN_5300 | 55088 |
| ATCN_2678 | 41030 | CTCN_9478 | 55089 |
| CTCN_4697 | 41031 | ATCN_5301 | 55090 |
| CTCN_4698 | 41032 | TTCN_7763 | 55091 |
| ATCN_2679 | 41033 | TTCN_7764 | 55092 |
| CTCN_4699 | 41034 | CTCN_9479 | 55093 |
| ATCN_2680 | 41035 | GTCN_5092 | 55094 |
| CTCN_4700 | 41036 | TTCN_7765 | 55095 |
| TTCN_3788 | 41037 | ATCN_5302 | 55096 |
| CTCN_4701 | 41038 | TTCN_7766 | 55097 |

FIG. 37 (continued)

| | | | |
|---|---|---|---|
| GTCN_2412 | 41039 | TTCN_7767 | 55098 |
| GTCN_2413 | 41040 | CTCN_9480 | 55099 |
| CTCN_4702 | 41041 | ATCN_5303 | 55100 |
| GTCN_2414 | 41042 | CTCN_9481 | 55101 |
| TTCN_3789 | 41043 | ATCN_5304 | 55102 |
| GTCN_2415 | 41044 | CTCN_9482 | 55103 |
| TTCN_3790 | 41045 | GTCN_5093 | 55104 |
| TTCN_3791 | 41046 | CTCN_9483 | 55105 |
| CTCN_4703 | 41047 | CTCN_9484 | 55106 |
| CTCN_4704 | 41048 | GTCN_5094 | 55107 |
| ATCN_2681 | 41049 | GTCN_5095 | 55108 |
| CTCN_4705 | 41050 | CTCN_9485 | 55109 |
| CTCN_4706 | 41051 | ATCN_5305 | 55110 |
| CTCN_4707 | 41052 | ATCN_5306 | 55111 |
| ATCN_2682 | 41053 | CTCN_9486 | 55112 |
| CTCN_4708 | 41054 | CTCN_9487 | 55113 |
| GTCN_2416 | 41055 | CTCN_9488 | 55114 |
| TTCN_3792 | 41056 | ATCN_5307 | 55115 |
| ATCN_2683 | 41057 | TTCN_7768 | 55116 |
| GTCN_2417 | 41058 | TTCN_7769 | 55117 |
| CTCN_4709 | 41059 | CTCN_9489 | 55118 |
| GTCN_2418 | 41060 | CTCN_9490 | 55119 |
| CTCN_4710 | 41061 | CTCN_9491 | 55120 |
| CTCN_4711 | 41062 | ATCN_5308 | 55121 |
| CTCN_4712 | 41063 | CTCN_9492 | 55122 |
| ATCN_2684 | 41064 | ATCN_5309 | 55123 |
| ATCN_2685 | 41065 | CTCN_9493 | 55124 |
| TTCN_3793 | 41066 | TTCN_7770 | 55125 |
| CTCN_4713 | 41067 | GTCN_5096 | 55126 |
| TTCN_3794 | 41068 | TTCN_7771 | 55127 |
| TTCN_3795 | 41069 | CTCN_9494 | 55128 |
| CTCN_4714 | 41070 | GTCN_5097 | 55129 |
| CTCN_4715 | 41071 | TTCN_7772 | 55130 |
| CTCN_4716 | 41072 | ATCN_5310 | 55131 |
| TTCN_3796 | 41073 | ATCN_5311 | 55132 |
| CTCN_4717 | 41074 | CTCN_9495 | 55133 |
| GTCN_2419 | 41075 | CTCN_9496 | 55134 |
| TTCN_3797 | 41076 | ATCN_5312 | 55135 |
| GTCN_2420 | 41077 | TTCN_7773 | 55136 |
| TTCN_3798 | 41078 | TTCN_7774 | 55137 |
| CTCN_4718 | 41079 | CTCN_9497 | 55138 |
| GTCN_2421 | 41080 | ATCN_5313 | 55139 |
| CTCN_4719 | 41081 | TTCN_7775 | 55140 |

| | | | |
|---|---|---|---|
| ATCN_2686 | 41082 | CTCN_9498 | 55141 |
| ATCN_2687 | 41083 | TTCN_7776 | 55142 |
| CTCN_4720 | 41084 | TTCN_7777 | 55143 |
| CTCN_4721 | 41085 | ATCN_5314 | 55144 |
| ATCN_2688 | 41086 | TTCN_7778 | 55145 |
| CTCN_4722 | 41087 | GTCN_5098 | 55146 |
| TTCN_3799 | 41088 | ATCN_5315 | 55147 |
| ATCN_2689 | 41089 | ATCN_5316 | 55148 |
| TTCN_3800 | 41090 | CTCN_9499 | 55149 |
| CTCN_4723 | 41091 | ATCN_5317 | 55150 |
| ATCN_2690 | 41092 | CTCN_9500 | 55151 |
| ATCN_2691 | 41093 | CTCN_9501 | 55152 |
| ATCN_2692 | 41094 | ATCN_5318 | 55153 |
| TTCN_3801 | 41095 | TTCN_7779 | 55154 |
| CTCN_4724 | 41096 | TTCN_7780 | 55155 |
| CTCN_4725 | 41097 | GTCN_5099 | 55156 |
| GTCN_2422 | 41098 | TTCN_7781 | 55157 |
| ATCN_2693 | 41099 | GTCN_5100 | 55158 |
| TTCN_3802 | 41100 | GTCN_5101 | 55159 |
| TTCN_3803 | 41101 | TTCN_7782 | 55160 |
| GTCN_2423 | 41102 | TTCN_7783 | 55161 |
| GTCN_2424 | 41103 | ATCN_5319 | 55162 |
| TTCN_3804 | 41104 | TTCN_7784 | 55163 |
| CTCN_4726 | 41105 | GTCN_5102 | 55164 |
| TTCN_3805 | 41106 | TTCN_7785 | 55165 |
| GTCN_2425 | 41107 | CTCN_9502 | 55166 |
| ATCN_2694 | 41108 | CTCN_9503 | 55167 |
| TTCN_3806 | 41109 | GTCN_5103 | 55168 |
| TTCN_3807 | 41110 | CTCN_9504 | 55169 |
| CTCN_4727 | 41111 | GTCN_5104 | 55170 |
| GTCN_2426 | 41112 | CTCN_9505 | 55171 |
| TTCN_3808 | 41113 | CTCN_9506 | 55172 |
| GTCN_2427 | 41114 | TTCN_7786 | 55173 |
| CTCN_4728 | 41115 | CTCN_9507 | 55174 |
| TTCN_3809 | 41116 | CTCN_9508 | 55175 |
| CTCN_4729 | 41117 | ATCN_5320 | 55176 |
| CTCN_4730 | 41118 | ATCN_5321 | 55177 |
| ATCN_2695 | 41119 | CTCN_9509 | 55178 |
| CTCN_4731 | 41120 | CTCN_9510 | 55179 |
| GTCN_2428 | 41121 | CTCN_9511 | 55180 |
| CTCN_4732 | 41122 | TTCN_7787 | 55181 |
| TTCN_3810 | 41123 | ATCN_5322 | 55182 |
| TTCN_3811 | 41124 | TTCN_7788 | 55183 |

FIG. 37 (continued)

| | | | |
|---|---|---|---|
| ATCN_2696 | 41125 | TTCN_7789 | 55184 |
| TTCN_3812 | 41126 | CTCN_9512 | 55185 |
| TTCN_3813 | 41127 | GTCN_5105 | 55186 |
| CTCN_4733 | 41128 | CTCN_9513 | 55187 |
| TTCN_3814 | 41129 | ATCN_5323 | 55188 |
| CTCN_4734 | 41130 | ATCN_5324 | 55189 |
| ATCN_2697 | 41131 | CTCN_9514 | 55190 |
| GTCN_2429 | 41132 | CTCN_9515 | 55191 |
| GTCN_2430 | 41133 | CTCN_9516 | 55192 |
| CTCN_4735 | 41134 | ATCN_5325 | 55193 |
| CTCN_4736 | 41135 | GTCN_5106 | 55194 |
| CTCN_4737 | 41136 | TTCN_7790 | 55195 |
| CTCN_4738 | 41137 | CTCN_9517 | 55196 |
| ATCN_2698 | 41138 | ATCN_5326 | 55197 |
| CTCN_4739 | 41139 | GTCN_5107 | 55198 |
| CTCN_4740 | 41140 | ATCN_5327 | 55199 |
| ATCN_2699 | 41141 | TTCN_7791 | 55200 |
| CTCN_4741 | 41142 | GTCN_5108 | 55201 |
| GTCN_2431 | 41143 | TTCN_7792 | 55202 |
| ATCN_2700 | 41144 | CTCN_9518 | 55203 |
| CTCN_4742 | 41145 | ATCN_5328 | 55204 |
| CTCN_4743 | 41146 | TTCN_7793 | 55205 |
| CTCN_4744 | 41147 | TTCN_7794 | 55206 |
| GTCN_2432 | 41148 | TTCN_7795 | 55207 |
| GTCN_2433 | 41149 | GTCN_5109 | 55208 |
| GTCN_2434 | 41150 | TTCN_7796 | 55209 |
| TTCN_3815 | 41151 | CTCN_9519 | 55210 |
| GTCN_2435 | 41152 | ATCN_5329 | 55211 |
| TTCN_3816 | 41153 | ATCN_5330 | 55212 |
| CTCN_4745 | 41154 | GTCN_5110 | 55213 |
| CTCN_4746 | 41155 | TTCN_7797 | 55214 |
| CTCN_4747 | 41156 | CTCN_9520 | 55215 |
| GTCN_2436 | 41157 | CTCN_9521 | 55216 |
| CTCN_4748 | 41158 | GTCN_5111 | 55217 |
| GTCN_2437 | 41159 | CTCN_9522 | 55218 |
| CTCN_4749 | 41160 | GTCN_5112 | 55219 |
| CTCN_4750 | 41161 | CTCN_9523 | 55220 |
| CTCN_4751 | 41162 | TTCN_7798 | 55221 |
| GTCN_2438 | 41163 | TTCN_7799 | 55222 |
| GTCN_2439 | 41164 | GTCN_5113 | 55223 |
| GTCN_2440 | 41165 | CTCN_9524 | 55224 |
| TTCN_3817 | 41166 | CTCN_9525 | 55225 |
| ATCN_2701 | 41167 | CTCN_9526 | 55226 |

| | | | |
|---|---|---|---|
| GTCN_2441 | 41168 | TTCN_7800 | 55227 |
| CTCN_4752 | 41169 | ATCN_5331 | 55228 |
| CTCN_4753 | 41170 | TTCN_7801 | 55229 |
| TTCN_3818 | 41171 | CTCN_9527 | 55230 |
| CTCN_4754 | 41172 | CTCN_9528 | 55231 |
| ATCN_2702 | 41173 | CTCN_9529 | 55232 |
| CTCN_4755 | 41174 | ATCN_5332 | 55233 |
| CTCN_4756 | 41175 | CTCN_9530 | 55234 |
| ATCN_2703 | 41176 | CTCN_9531 | 55235 |
| GTCN_2442 | 41177 | CTCN_9532 | 55236 |
| CTCN_4757 | 41178 | GTCN_5114 | 55237 |
| CTCN_4758 | 41179 | TTCN_7802 | 55238 |
| TTCN_3819 | 41180 | GTCN_5115 | 55239 |
| ATCN_2704 | 41181 | CTCN_9533 | 55240 |
| GTCN_2443 | 41182 | TTCN_7803 | 55241 |
| CTCN_4759 | 41183 | CTCN_9534 | 55242 |
| GTCN_2444 | 41184 | GTCN_5116 | 55243 |
| TTCN_3820 | 41185 | CTCN_9535 | 55244 |
| ATCN_2705 | 41186 | ATCN_5333 | 55245 |
| TTCN_3821 | 41187 | ATCN_5334 | 55246 |
| ATCN_2706 | 41188 | CTCN_9536 | 55247 |
| GTCN_2445 | 41189 | CTCN_9537 | 55248 |
| TTCN_3822 | 41190 | CTCN_9538 | 55249 |
| TTCN_3823 | 41191 | TTCN_7804 | 55250 |
| CTCN_4760 | 41192 | TTCN_7805 | 55251 |
| CTCN_4761 | 41193 | ATCN_5335 | 55252 |
| GTCN_2446 | 41194 | ATCN_5336 | 55253 |
| TTCN_3824 | 41195 | TTCN_7806 | 55254 |
| TTCN_3825 | 41196 | CTCN_9539 | 55255 |
| TTCN_3826 | 41197 | TTCN_7807 | 55256 |
| TTCN_3827 | 41198 | GTCN_5117 | 55257 |
| TTCN_3828 | 41199 | ATCN_5337 | 55258 |
| ATCN_2707 | 41200 | CTCN_9540 | 55259 |
| GTCN_2447 | 41201 | CTCN_9541 | 55260 |
| GTCN_2448 | 41202 | ATCN_5338 | 55261 |
| TTCN_3829 | 41203 | GTCN_5118 | 55262 |
| CTCN_4762 | 41204 | CTCN_9542 | 55263 |
| TTCN_3830 | 41205 | GTCN_5119 | 55264 |
| ATCN_2708 | 41206 | CTCN_9543 | 55265 |
| GTCN_2449 | 41207 | GTCN_5120 | 55266 |
| TTCN_3831 | 41208 | ATCN_5339 | 55267 |
| TTCN_3832 | 41209 | CTCN_9544 | 55268 |
| TTCN_3833 | 41210 | CTCN_9545 | 55269 |

FIG. 37 (continued)

| | | | |
|---|---|---|---|
| TTCN_3834 | 41211 | ATCN_5340 | 55270 |
| GTCN_2450 | 41212 | TTCN_7808 | 55271 |
| GTCN_2451 | 41213 | CTCN_9546 | 55272 |
| GTCN_2452 | 41214 | GTCN_5121 | 55273 |
| TTCN_3835 | 41215 | TTCN_7809 | 55274 |
| TTCN_3836 | 41216 | CTCN_9547 | 55275 |
| CTCN_4763 | 41217 | TTCN_7810 | 55276 |
| CTCN_4764 | 41218 | CTCN_9548 | 55277 |
| GTCN_2453 | 41219 | CTCN_9549 | 55278 |
| TTCN_3837 | 41220 | CTCN_9550 | 55279 |
| ATCN_2709 | 41221 | ATCN_5341 | 55280 |
| GTCN_2454 | 41222 | ATCN_5342 | 55281 |
| CTCN_4765 | 41223 | GTCN_5122 | 55282 |
| CTCN_4766 | 41224 | ATCN_5343 | 55283 |
| GTCN_2455 | 41225 | ATCN_5344 | 55284 |
| CTCN_4767 | 41226 | GTCN_5123 | 55285 |
| GTCN_2456 | 41227 | GTCN_5124 | 55286 |
| CTCN_4768 | 41228 | TTCN_7811 | 55287 |
| GTCN_2457 | 41229 | GTCN_5125 | 55288 |
| ATCN_2710 | 41230 | CTCN_9551 | 55289 |
| CTCN_4769 | 41231 | TTCN_7812 | 55290 |
| CTCN_4770 | 41232 | CTCN_9552 | 55291 |
| TTCN_3838 | 41233 | GTCN_5126 | 55292 |
| CTCN_4771 | 41234 | CTCN_9553 | 55293 |
| GTCN_2458 | 41235 | TTCN_7813 | 55294 |
| CTCN_4772 | 41236 | ATCN_5345 | 55295 |
| CTCN_4773 | 41237 | GTCN_5127 | 55296 |
| TTCN_3839 | 41238 | TTCN_7814 | 55297 |
| CTCN_4774 | 41239 | TTCN_7815 | 55298 |
| CTCN_4775 | 41240 | GTCN_5128 | 55299 |
| CTCN_4776 | 41241 | TTCN_7816 | 55300 |
| TTCN_3840 | 41242 | TTCN_7817 | 55301 |
| CTCN_4777 | 41243 | ATCN_5346 | 55302 |
| CTCN_4778 | 41244 | TTCN_7818 | 55303 |
| TTCN_3841 | 41245 | CTCN_9554 | 55304 |
| CTCN_4779 | 41246 | TTCN_7819 | 55305 |
| GTCN_2459 | 41247 | CTCN_9555 | 55306 |
| CTCN_4780 | 41248 | CTCN_9556 | 55307 |
| GTCN_2460 | 41249 | TTCN_7820 | 55308 |
| ATCN_2711 | 41250 | CTCN_9557 | 55309 |
| TTCN_3842 | 41251 | GTCN_5129 | 55310 |
| TTCN_3843 | 41252 | TTCN_7821 | 55311 |
| ATCN_2712 | 41253 | CTCN_9558 | 55312 |

| | | | |
|---|---|---|---|
| GTCN_2461 | 41254 | TTCN_7822 | 55313 |
| TTCN_3844 | 41255 | CTCN_9559 | 55314 |
| CTCN_4781 | 41256 | TTCN_7823 | 55315 |
| ATCN_2713 | 41257 | TTCN_7824 | 55316 |
| CTCN_4782 | 41258 | ATCN_5347 | 55317 |
| GTCN_2462 | 41259 | CTCN_9560 | 55318 |
| CTCN_4783 | 41260 | GTCN_5130 | 55319 |
| CTCN_4784 | 41261 | ATCN_5348 | 55320 |
| GTCN_2463 | 41262 | GTCN_5131 | 55321 |
| CTCN_4785 | 41263 | CTCN_9561 | 55322 |
| TTCN_3845 | 41264 | GTCN_5132 | 55323 |
| ATCN_2714 | 41265 | TTCN_7825 | 55324 |
| ATCN_2715 | 41266 | CTCN_9562 | 55325 |
| CTCN_4786 | 41267 | CTCN_9563 | 55326 |
| CTCN_4787 | 41268 | TTCN_7826 | 55327 |
| TTCN_3846 | 41269 | TTCN_7827 | 55328 |
| TTCN_3847 | 41270 | TTCN_7828 | 55329 |
| TTCN_3848 | 41271 | GTCN_5133 | 55330 |
| CTCN_4788 | 41272 | CTCN_9564 | 55331 |
| CTCN_4789 | 41273 | TTCN_7829 | 55332 |
| CTCN_4790 | 41274 | TTCN_7830 | 55333 |
| ATCN_2716 | 41275 | TTCN_7831 | 55334 |
| GTCN_2464 | 41276 | GTCN_5134 | 55335 |
| CTCN_4791 | 41277 | CTCN_9565 | 55336 |
| GTCN_2465 | 41278 | TTCN_7832 | 55337 |
| TTCN_3849 | 41279 | TTCN_7833 | 55338 |
| GTCN_2466 | 41280 | ATCN_5349 | 55339 |
| CTCN_4792 | 41281 | TTCN_7834 | 55340 |
| CTCN_4793 | 41282 | TTCN_7835 | 55341 |
| ATCN_2717 | 41283 | TTCN_7836 | 55342 |
| ATCN_2718 | 41284 | TTCN_7837 | 55343 |
| CTCN_4794 | 41285 | TTCN_7838 | 55344 |
| ATCN_2719 | 41286 | ATCN_5350 | 55345 |
| ATCN_2720 | 41287 | GTCN_5135 | 55346 |
| CTCN_4795 | 41288 | CTCN_9566 | 55347 |
| CTCN_4796 | 41289 | ATCN_5351 | 55348 |
| CTCN_4797 | 41290 | TTCN_7839 | 55349 |
| ATCN_2721 | 41291 | CTCN_9567 | 55350 |
| CTCN_4798 | 41292 | TTCN_7840 | 55351 |
| CTCN_4799 | 41293 | CTCN_9568 | 55352 |
| ATCN_2722 | 41294 | ATCN_5352 | 55353 |
| GTCN_2467 | 41295 | ATCN_5353 | 55354 |
| CTCN_4800 | 41296 | CTCN_9569 | 55355 |

FIG. 37 (continued)

| | | | |
|---|---|---|---|
| ATCN_2723 | 41297 | TTCN_7841 | 55356 |
| CTCN_4801 | 41298 | CTCN_9570 | 55357 |
| CTCN_4802 | 41299 | CTCN_9571 | 55358 |
| GTCN_2468 | 41300 | GTCN_5136 | 55359 |
| GTCN_2469 | 41301 | GTCN_5137 | 55360 |
| TTCN_3850 | 41302 | CTCN_9572 | 55361 |
| TTCN_3851 | 41303 | ATCN_5354 | 55362 |
| CTCN_4803 | 41304 | CTCN_9573 | 55363 |
| CTCN_4804 | 41305 | GTCN_5138 | 55364 |
| TTCN_3852 | 41306 | GTCN_5139 | 55365 |
| GTCN_2470 | 41307 | CTCN_9574 | 55366 |
| CTCN_4805 | 41308 | CTCN_9575 | 55367 |
| CTCN_4806 | 41309 | ATCN_5355 | 55368 |
| TTCN_3853 | 41310 | ATCN_5356 | 55369 |
| TTCN_3854 | 41311 | CTCN_9576 | 55370 |
| ATCN_2724 | 41312 | ATCN_5357 | 55371 |
| ATCN_2725 | 41313 | CTCN_9577 | 55372 |
| TTCN_3855 | 41314 | ATCN_5358 | 55373 |
| TTCN_3856 | 41315 | TTCN_7842 | 55374 |
| CTCN_4807 | 41316 | ATCN_5359 | 55375 |
| TTCN_3857 | 41317 | ATCN_5360 | 55376 |
| TTCN_3858 | 41318 | ATCN_5361 | 55377 |
| ATCN_2726 | 41319 | CTCN_9578 | 55378 |
| GTCN_2471 | 41320 | ATCN_5362 | 55379 |
| TTCN_3859 | 41321 | CTCN_9579 | 55380 |
| CTCN_4808 | 41322 | CTCN_9580 | 55381 |
| ATCN_2727 | 41323 | TTCN_7843 | 55382 |
| TTCN_3860 | 41324 | ATCN_5363 | 55383 |
| GTCN_2472 | 41325 | CTCN_9581 | 55384 |
| ATCN_2728 | 41326 | GTCN_5140 | 55385 |
| GTCN_2473 | 41327 | CTCN_9582 | 55386 |
| TTCN_3861 | 41328 | TTCN_7844 | 55387 |
| CTCN_4809 | 41329 | CTCN_9583 | 55388 |
| TTCN_3862 | 41330 | GTCN_5141 | 55389 |
| TTCN_3863 | 41331 | TTCN_7845 | 55390 |
| ATCN_2729 | 41332 | ATCN_5364 | 55391 |
| TTCN_3864 | 41333 | CTCN_9584 | 55392 |
| TTCN_3865 | 41334 | ATCN_5365 | 55393 |
| TTCN_3866 | 41335 | GTCN_5142 | 55394 |
| CTCN_4810 | 41336 | CTCN_9585 | 55395 |
| GTCN_2474 | 41337 | CTCN_9586 | 55396 |
| TTCN_3867 | 41338 | CTCN_9587 | 55397 |
| CTCN_4811 | 41339 | TTCN_7846 | 55398 |

| | | | |
|---|---|---|---|
| ATCN_2730 | 41340 | TTCN_7847 | 55399 |
| ATCN_2731 | 41341 | CTCN_9588 | 55400 |
| TTCN_3868 | 41342 | CTCN_9589 | 55401 |
| TTCN_3869 | 41343 | CTCN_9590 | 55402 |
| TTCN_3870 | 41344 | CTCN_9591 | 55403 |
| CTCN_4812 | 41345 | ATCN_5366 | 55404 |
| TTCN_3871 | 41346 | ATCN_5367 | 55405 |
| GTCN_2475 | 41347 | CTCN_9592 | 55406 |
| CTCN_4813 | 41348 | CTCN_9593 | 55407 |
| TTCN_3872 | 41349 | GTCN_5143 | 55408 |
| TTCN_3873 | 41350 | GTCN_5144 | 55409 |
| TTCN_3874 | 41351 | CTCN_9594 | 55410 |
| TTCN_3875 | 41352 | TTCN_7848 | 55411 |
| GTCN_2476 | 41353 | TTCN_7849 | 55412 |
| TTCN_3876 | 41354 | CTCN_9595 | 55413 |
| TTCN_3877 | 41355 | CTCN_9596 | 55414 |
| CTCN_4814 | 41356 | TTCN_7850 | 55415 |
| GTCN_2477 | 41357 | ATCN_5368 | 55416 |
| CTCN_4815 | 41358 | CTCN_9597 | 55417 |
| TTCN_3878 | 41359 | CTCN_9598 | 55418 |
| CTCN_4816 | 41360 | CTCN_9599 | 55419 |
| GTCN_2478 | 41361 | CTCN_9600 | 55420 |
| TTCN_3879 | 41362 | TTCN_7851 | 55421 |
| ATCN_2732 | 41363 | CTCN_9601 | 55422 |
| ATCN_2733 | 41364 | TTCN_7852 | 55423 |
| ATCN_2734 | 41365 | CTCN_9602 | 55424 |
| CTCN_4817 | 41366 | TTCN_7853 | 55425 |
| GTCN_2479 | 41367 | TTCN_7854 | 55426 |
| CTCN_4818 | 41368 | TTCN_7855 | 55427 |
| TTCN_3880 | 41369 | GTCN_5145 | 55428 |
| TTCN_3881 | 41370 | ATCN_5369 | 55429 |
| TTCN_3882 | 41371 | TTCN_7856 | 55430 |
| TTCN_3883 | 41372 | GTCN_5146 | 55431 |
| GTCN_2480 | 41373 | GTCN_5147 | 55432 |
| ATCN_2735 | 41374 | ATCN_5370 | 55433 |
| ATCN_2736 | 41375 | CTCN_9603 | 55434 |
| ATCN_2737 | 41376 | ATCN_5371 | 55435 |
| TTCN_3884 | 41377 | TTCN_7857 | 55436 |
| TTCN_3885 | 41378 | CTCN_9604 | 55437 |
| TTCN_3886 | 41379 | CTCN_9605 | 55438 |
| TTCN_3887 | 41380 | GTCN_5148 | 55439 |
| CTCN_4819 | 41381 | GTCN_5149 | 55440 |
| GTCN_2481 | 41382 | TTCN_7858 | 55441 |

FIG. 37 (continued)

| | | | |
|---|---|---|---|
| GTCN_2482 | 41383 | GTCN_5150 | 55442 |
| CTCN_4820 | 41384 | CTCN_9606 | 55443 |
| ATCN_2738 | 41385 | CTCN_9607 | 55444 |
| ATCN_2739 | 41386 | TTCN_7859 | 55445 |
| CTCN_4821 | 41387 | CTCN_9608 | 55446 |
| CTCN_4822 | 41388 | CTCN_9609 | 55447 |
| CTCN_4823 | 41389 | CTCN_9610 | 55448 |
| TTCN_3888 | 41390 | CTCN_9611 | 55449 |
| ATCN_2740 | 41391 | ATCN_5372 | 55450 |
| TTCN_3889 | 41392 | ATCN_5373 | 55451 |
| CTCN_4824 | 41393 | ATCN_5374 | 55452 |
| CTCN_4825 | 41394 | CTCN_9612 | 55453 |
| CTCN_4826 | 41395 | GTCN_5151 | 55454 |
| ATCN_2741 | 41396 | TTCN_7860 | 55455 |
| ATCN_2742 | 41397 | TTCN_7861 | 55456 |
| TTCN_3890 | 41398 | TTCN_7862 | 55457 |
| CTCN_4827 | 41399 | TTCN_7863 | 55458 |
| GTCN_2483 | 41400 | ATCN_5375 | 55459 |
| TTCN_3891 | 41401 | GTCN_5152 | 55460 |
| GTCN_2484 | 41402 | GTCN_5153 | 55461 |
| GTCN_2485 | 41403 | GTCN_5154 | 55462 |
| TTCN_3892 | 41404 | GTCN_5155 | 55463 |
| ATCN_2743 | 41405 | TTCN_7864 | 55464 |
| ATCN_2744 | 41406 | TTCN_7865 | 55465 |
| ATCN_2745 | 41407 | TTCN_7866 | 55466 |
| CTCN_4828 | 41408 | ATCN_5376 | 55467 |
| TTCN_3893 | 41409 | GTCN_5156 | 55468 |
| ATCN_2746 | 41410 | ATCN_5377 | 55469 |
| CTCN_4829 | 41411 | TTCN_7867 | 55470 |
| ATCN_2747 | 41412 | GTCN_5157 | 55471 |
| TTCN_3894 | 41413 | GTCN_5158 | 55472 |
| ATCN_2748 | 41414 | TTCN_7868 | 55473 |
| TTCN_3895 | 41415 | TTCN_7869 | 55474 |
| TTCN_3896 | 41416 | ATCN_5378 | 55475 |
| ATCN_2749 | 41417 | GTCN_5159 | 55476 |
| ATCN_2750 | 41418 | ATCN_5379 | 55477 |
| ATCN_2751 | 41419 | ATCN_5380 | 55478 |
| GTCN_2486 | 41420 | ATCN_5381 | 55479 |
| CTCN_4830 | 41421 | GTCN_5160 | 55480 |
| GTCN_2487 | 41422 | GTCN_5161 | 55481 |
| GTCN_2488 | 41423 | TTCN_7870 | 55482 |
| ATCN_2752 | 41424 | CTCN_9613 | 55483 |
| ATCN_2753 | 41425 | ATCN_5382 | 55484 |

| | | | |
|---|---|---|---|
| ATCN_2754 | 41426 | TTCN_7871 | 55485 |
| CTCN_4831 | 41427 | GTCN_5162 | 55486 |
| ATCN_2755 | 41428 | TTCN_7872 | 55487 |
| TTCN_3897 | 41429 | TTCN_7873 | 55488 |
| GTCN_2489 | 41430 | GTCN_5163 | 55489 |
| GTCN_2490 | 41431 | CTCN_9614 | 55490 |
| ATCN_2756 | 41432 | CTCN_9615 | 55491 |
| ATCN_2757 | 41433 | TTCN_7874 | 55492 |
| TTCN_3898 | 41434 | ATCN_5383 | 55493 |
| GTCN_2491 | 41435 | ATCN_5384 | 55494 |
| ATCN_2758 | 41436 | ATCN_5385 | 55495 |
| CTCN_4832 | 41437 | TTCN_7875 | 55496 |
| CTCN_4833 | 41438 | CTCN_9616 | 55497 |
| CTCN_4834 | 41439 | CTCN_9617 | 55498 |
| TTCN_3899 | 41440 | TTCN_7876 | 55499 |
| GTCN_2492 | 41441 | ATCN_5386 | 55500 |
| CTCN_4835 | 41442 | GTCN_5164 | 55501 |
| TTCN_3900 | 41443 | ATCN_5387 | 55502 |
| CTCN_4836 | 41444 | CTCN_9618 | 55503 |
| ATCN_2759 | 41445 | GTCN_5165 | 55504 |
| ATCN_2760 | 41446 | CTCN_9619 | 55505 |
| TTCN_3901 | 41447 | ATCN_5388 | 55506 |
| GTCN_2493 | 41448 | ATCN_5389 | 55507 |
| ATCN_2761 | 41449 | ATCN_5390 | 55508 |
| CTCN_4837 | 41450 | GTCN_5166 | 55509 |
| ATCN_2762 | 41451 | ATCN_5391 | 55510 |
| TTCN_3902 | 41452 | ATCN_5392 | 55511 |
| ATCN_2763 | 41453 | CTCN_9620 | 55512 |
| TTCN_3903 | 41454 | TTCN_7877 | 55513 |
| TTCN_3904 | 41455 | GTCN_5167 | 55514 |
| CTCN_4838 | 41456 | CTCN_9621 | 55515 |
| GTCN_2494 | 41457 | GTCN_5168 | 55516 |
| CTCN_4839 | 41458 | CTCN_9622 | 55517 |
| TTCN_3905 | 41459 | GTCN_5169 | 55518 |
| CTCN_4840 | 41460 | CTCN_9623 | 55519 |
| CTCN_4841 | 41461 | CTCN_9624 | 55520 |
| GTCN_2495 | 41462 | CTCN_9625 | 55521 |
| CTCN_4842 | 41463 | ATCN_5393 | 55522 |
| TTCN_3906 | 41464 | CTCN_9626 | 55523 |
| CTCN_4843 | 41465 | CTCN_9627 | 55524 |
| CTCN_4844 | 41466 | CTCN_9628 | 55525 |
| CTCN_4845 | 41467 | TTCN_7878 | 55526 |
| TTCN_3907 | 41468 | TTCN_7879 | 55527 |

FIG. 37 (continued)

| | | | |
|---|---|---|---|
| TTCN_3908 | 41469 | GTCN_5170 | 55528 |
| CTCN_4846 | 41470 | CTCN_9629 | 55529 |
| CTCN_4847 | 41471 | CTCN_9630 | 55530 |
| CTCN_4848 | 41472 | CTCN_9631 | 55531 |
| CTCN_4849 | 41473 | CTCN_9632 | 55532 |
| CTCN_4850 | 41474 | ATCN_5394 | 55533 |
| ATCN_2764 | 41475 | CTCN_9633 | 55534 |
| CTCN_4851 | 41476 | ATCN_5395 | 55535 |
| GTCN_2496 | 41477 | CTCN_9634 | 55536 |
| TTCN_3909 | 41478 | TTCN_7880 | 55537 |
| CTCN_4852 | 41479 | GTCN_5171 | 55538 |
| GTCN_2497 | 41480 | CTCN_9635 | 55539 |
| GTCN_2498 | 41481 | TTCN_7881 | 55540 |
| CTCN_4853 | 41482 | CTCN_9636 | 55541 |
| CTCN_4854 | 41483 | GTCN_5172 | 55542 |
| GTCN_2499 | 41484 | CTCN_9637 | 55543 |
| ATCN_2765 | 41485 | ATCN_5396 | 55544 |
| ATCN_2766 | 41486 | ATCN_5397 | 55545 |
| CTCN_4855 | 41487 | CTCN_9638 | 55546 |
| CTCN_4856 | 41488 | CTCN_9639 | 55547 |
| ATCN_2767 | 41489 | TTCN_7882 | 55548 |
| CTCN_4857 | 41490 | ATCN_5398 | 55549 |
| CTCN_4858 | 41491 | TTCN_7883 | 55550 |
| TTCN_3910 | 41492 | GTCN_5173 | 55551 |
| CTCN_4859 | 41493 | TTCN_7884 | 55552 |
| TTCN_3911 | 41494 | GTCN_5174 | 55553 |
| ATCN_2768 | 41495 | ATCN_5399 | 55554 |
| GTCN_2500 | 41496 | TTCN_7885 | 55555 |
| TTCN_3912 | 41497 | CTCN_9640 | 55556 |
| ATCN_2769 | 41498 | GTCN_5175 | 55557 |
| GTCN_2501 | 41499 | TTCN_7886 | 55558 |
| GTCN_2502 | 41500 | CTCN_9641 | 55559 |
| CTCN_4860 | 41501 | ATCN_5400 | 55560 |
| TTCN_3913 | 41502 | CTCN_9642 | 55561 |
| ATCN_2770 | 41503 | CTCN_9643 | 55562 |
| GTCN_2503 | 41504 | CTCN_9644 | 55563 |
| CTCN_4861 | 41505 | ATCN_5401 | 55564 |
| ATCN_2771 | 41506 | TTCN_7887 | 55565 |
| TTCN_3914 | 41507 | CTCN_9645 | 55566 |
| TTCN_3915 | 41508 | GTCN_5176 | 55567 |
| TTCN_3916 | 41509 | GTCN_5177 | 55568 |
| CTCN_4862 | 41510 | CTCN_9646 | 55569 |
| GTCN_2504 | 41511 | CTCN_9647 | 55570 |
| GTCN_2505 | 41512 | GTCN_5178 | 55571 |
| TTCN_3917 | 41513 | CTCN_9648 | 55572 |

232782404 v1

COMPOSITIONS AND METHODS FOR USE IN IMMUNOTHERAPY

CROSS REFERENCE TO RELATED APPLICATIONS

This application is a U.S. National Stage Application, filed under 35 U.S.C. § 371, of International Application No. PCT/US2020/050008, filed Sep. 9, 2020, which claims priority to U.S. provisional patent application Nos. 62/897,947, filed on Sep. 9, 2019, and 63/075,041 filed on Sep. 4, 2020, the contents of each of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SCRB 016 02US SeqList ST25.txt, date recorded: Mar. 8, 2022, file size 12.0 megabytes).

BACKGROUND

Many approved therapeutics, for example cancer therapeutics, are cytotoxic drugs that kill normal cells as well as diseased cells. The therapeutic benefit of these cytotoxic drugs depends on diseased cells being more sensitive than normal cells, thereby allowing clinical responses to be achieved using doses that do not result in unacceptable side effects. However, essentially all of these non-specific drugs result in some if not severe damage to normal tissues, which often limits treatment suitability.

Genome engineering can offer a different approach to cytotoxic drugs in that it permits the creation of immune cells programmed to specifically bind and kill diseased cells, for example cancer cells. The advent of the chimeric antigen receptor T cell (CAR-T) technology has led to new modalities of therapeutic benefit in certain types of cancers. By engineering cells comprising CAR to reduce a mismatch in the HLA protein, reduce or eliminate the wild-type T cell receptor or other component of the modified cell, in comparison to those of the recipient subject, it reduces or eliminates the potential for host vs. graft disease (GVHD) by eliminating host T cell receptor recognition of and response to mismatched (e.g., allogeneic) graft tissue (see, e.g., Takahiro Kamiya, T. et al. A novel method to generate T-cell receptor-deficient chimeric antigen receptor T cells. Blood Advances 2:517 (2018)). This approach, therefore, could be used to generate immune cells with an improved therapeutic index for immuno-oncologic applications in a subject with a disease such as cancer, autoimmune disease and transplant rejection.

As CRISPR/Cas systems have been adapted for genome editing in eukaryotic cells, the two technologies have the potential to permit the engineering of immune cells that have potent cytotoxicity versus the targeted cells, yet permit the reduction or elimination of cell markers that contribute to triggering unwanted recipient immune responses to transplants of such cells, especially in the case of allogeneic transplants of these cells. Accordingly, there exists a need for modified cells and methods to modify such cells into engineered CAR-T cells that exhibit these properties for use in immunotherapy treatment, for example allogeneic-based immunotherapy treatments.

SUMMARY

In some aspects, the present disclosure provides compositions of CasX:guide nucleic acid systems (CasX:gNA system) and methods used to modify target nucleic acid sequences of cell genes encoding one or more proteins involved in antigen processing, antigen presentation, antigen recognition, and/or antigen response. In the foregoing, the proteins are selected from the group consisting of beta-2-microglobulin (B2M), T cell receptor alpha chain constant region (TRAC, or TCRA), class II major histocompatibility complex transactivator (CIITA), T cell receptor beta constant 1 (TRBC1, or TCRB), T cell receptor beta constant 2 (TRBC2), programmed cell death 1 (PD-1), cytokine inducible SH2 (CISH), T cell immunoreceptor with Ig and ITIM domains (TIGIT), adenosine A2a receptor (ADORA2A), killer cell lectin like receptor C1 (NKG2A), cytotoxic T-lymphocyte-associated protein 4 (CTLA-4), lymphocyte activating 3 (LAG-3), T-cell immunoglobulin and mucin domain 3 (TIM-3), 2B4 (CD244), human leukocyte antigen A (HLA-A), human leukocyte antigen B (HLA-B), TGFβ Receptor 2 (TGFβRII), cluster of differentiation 247 (CD247), CD3d molecule (CD3D), CD3e molecule (CD3E), CD3g molecule (CD3G), CD52 molecule (CD52), human leukocyte antigen C (HLA-C), deoxycytidine kinase (dCK), or FKBP prolyl isomerase 1A (FKBP1A). The CasX:gNA systems can comprise a reference CasX protein, a CasX variant protein with improved properties relative to the reference CasX, a guide nucleic acid (gNA) that is a reference sequence or a gNA variant with improved properties relative to the reference sequence, as well as donor template nucleic acids that can be inserted into the break sites of the target nucleic acid sequences in cells introduced by the CasX nucleases to modify the target nucleic acid sequences. Embodiments of these components are described herein, below. In some aspects, the present disclosure provides gene editing pairs of CasX and gNA as of any of the embodiments described herein complexed as a ribonuclear protein complex (RNP). In some embodiments, the present disclosure provides methods to modify the genes of cells encoding the proteins involved in antigen processing, antigen presentation, antigen recognition, and/or antigen response in which the gene are knocked-down or knocked out from expression of such proteins.

The cells modified by the CasX:gNA systems are useful for, among other things, immunotherapy applications; e.g. preparation and use of immune cells with reduced potential for graft-versus-host disease (GVHD), and that are also modified to express one or more chimeric antigen receptor (CAR) for use in the treatment of cancer or an autoimmune disease in a subject. Such cells also are also engineered to reduce host vs. graft complications. In other embodiments, the CasX-gNA systems are used to knock-in nucleic acids into the cells that encode CAR and/or an engineered T cell receptor (TCR), the CAR and/or the TCR comprising binding domains specific for tumor cell antigens, including those listed herein, below. Such binding domains can be in the form of a linear antibody, a single domain antibody (sdAb) such as a VHH, or a single-chain variable fragment (scFv). The cells that can be used for the preparation of the modified cells include progenitor cells, hematopoietic stem cells, pluripotent stem cells, or immune cells selected from the group consisting of T cells, TREG cells, NK cells, B cells, macrophages, or dendritic cells.

In some aspects, the present disclosure provides polynucleotides and vectors encoding or comprising the CasX proteins, gNAs, the gene editing pairs, or comprising the donor template nucleic acids described herein. In some embodiments, the vectors are viral vectors such as an Adeno-Associated Viral (AAV) vector or a lentiviral vector. In other embodiments, the vectors are non-viral particles such as virus-like particles (VLP) or nanoparticles.

In some aspects, the disclosure provides methods of modifying a target nucleic acid sequence of in a population of cells, comprising introducing into each cell of the population: a) the CasX:gNA system of any of the embodiments disclosed herein; or b) the nucleic acid of any of the embodiments disclosed herein; or c) the vector of any of the embodiments disclosed herein; d) the VLP of any of the embodiments disclosed herein; or e) combinations of two or more of (a)-(d)), above, wherein the target nucleic acid sequence of the cells is modified by the CasX protein (e.g., a single- or double-stranded break, or an insertion, deletion, substitution, duplication, or inversion of one or more nucleotides in the target nucleic acid sequence).

In some aspects, the present disclosure provides populations of cells modified by the ex vivo methods of modification of the target nucleic acid by the CasX:gNA systems, vectors, or VLPs (or combinations thereof) of any of the embodiments described herein, wherein the expression of MHC Class I molecules or T cell receptors or the proteins involved in antigen processing, antigen presentation, antigen recognition, and/or antigen response have been reduced or eliminated in the modified cells. In some embodiments, the present disclosure provides populations of cells modified by the ex vivo methods of modification of the target nucleic acid by the CasX:gNA systems, vectors, or VLPs (or combinations thereof) of any of the embodiments described herein, wherein the modified cells express a detectable level of the CAR and/or TCR of any of the embodiments described herein.

In some aspects, the present disclosure provides methods of providing an anti-tumor immunity in a subject, the method comprising administering to the subject a therapeutically effective amount of the modified cells of any of the embodiments described herein.

In some aspects, the present disclosure provides methods of treating a subject having a disease associated with expression of a tumor antigen, the method comprising administering to the subject a therapeutically effective amount of the modified cells of any one of embodiments described herein.

In another aspect, provided herein are compositions of immune cells modified by CasX and gNA gene editing pairs and, optionally, donor templates and/or polynucleotides encoding CAR and/or TCR for use as a medicament for the treatment of a subject having a disease associated with expression of a tumor antigen. In the foregoing, the CasX can be a CasX variant of any of the embodiments described herein (e.g., the sequences of Table 4) and the gNA can be a gNA variant of any of the embodiments described herein (e.g., the sequences of Table 2). In other embodiments, the disclosure provides compositions cells modified by vectors comprising or encoding the gene editing pairs of CasX and gNA, donor templates and/or polynucleotides encoding CAR for use as a medicament for the treatment of a subject having a disease associated with expression of a tumor antigen.

In some aspects, the present disclosure provides kits comprising the CasX:gNA systems, the vectors, or the VLP described herein, and further comprising an excipient and a container.

In another aspect, provided herein are CasX:gNA systems, compositions comprising CasX:gNA systems, vectors comprising or encoding CasX:gNA systems, VLP comprising CasX:gNA systems, or populations of cells edited using the CasX:gNA systems, for use as a medicament for the treatment of a disease or disorder.

In another aspect, provided herein are CasX:gNA systems, composition comprising g CasX:gNA systems, or vectors comprising or encoding CasX:gNA systems, VLP comprising CasX:gNA systems, populations of cells edited using the CasX:gNA systems, for use in a method of treatment of a disease or disorder.

INCORPORATION BY REFERENCE

All publications, patents, and patent applications mentioned in this specification are herein incorporated by reference to the same extent as if each individual publication, patent, or patent application was specifically and individually indicated to be incorporated by reference. The contents of PCT/US2020/036505, filed on Jun. 5, 2020, which discloses CasX variants and gNA variants, are hereby incorporated by reference in their entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows the improvement in editing efficiency of a CasX sgRNA variant of SEQ ID NO:5 versus the reference of SEQ ID NO:4 across 10 targets. When averaged across 10 targets, the editing efficiency of sgRNA SEQ ID NO:5 improved 176% compared to SEQ ID NO:4.

FIG. 35 shows Table 3A, a table of gNA targeting sequences (spacers) targeting the B2Mgene (SEQ ID NOs: 725-2100 and 2281-7085).

FIG. 36 shows Table 3B, a table of gNA targeting sequences (spacers) targeting the TRAC gene (SEQ ID NOs: 7086-27454).

FIG. 37 shows Table 3C, a table of gNA targeting sequences (spacers) targeting the CIITA gene (SEQ ID NOs: 27455-55572).

DETAILED DESCRIPTION

Figure 1:
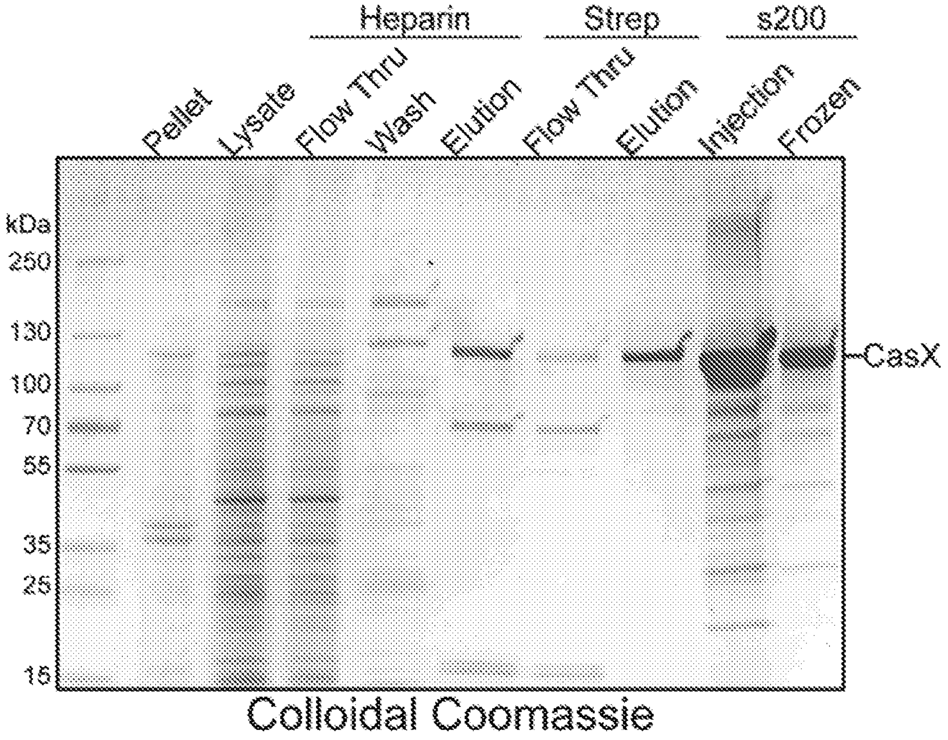
FIG. 1 shows an SDS-PAGE gel of StX2 purification fractions visualized by colloidal Coomassie staining, as described in Example 1.

While exemplary embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the invention.

Definitions

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

"Hybridizable" or "complementary" are used interchangeably to mean that a nucleic acid (e.g., RNA, DNA) comprises a sequence of nucleotides that enables it to non-covalently bind, i.e., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. It is understood that the sequence of a polynucleotide need not be 100% complementary to that of its target nucleic acid sequence to be specifically hybridizable; it can have at least about 70%, at least about 80%, or at least about 90%, or at least about 95% sequence identity and still hybridize to the target nucleic acid sequence. Moreover, a polynucleotide may hybridize over one or more segments such that intervening or adjacent segments are not involved in the hybridization event (e.g., a loop structure or hairpin structure, a 'bulge', and the like).

A "gene," for the purposes of the present disclosure, includes a DNA region encoding a gene product (e.g., a protein, RNA), as well as all DNA regions which regulate the production of the gene product, whether or not such regulatory sequences are adjacent to coding and/or transcribed sequences. Accordingly, a gene may include regulatory element sequences including, but not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Coding sequences encode a gene product upon transcription or transcription and translation; the coding sequences of the disclosure may comprise fragments and need not contain a full-length open reading frame. A gene can include both the strand that is transcribed, e.g. the strand containing the coding sequence, as well as the complementary strand.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

The term "regulatory element" is used interchangeably herein with the term "regulatory sequence," and is intended to include promoters, enhancers, and other expression regulatory elements (e.g. transcription termination signals, such as polyadenylation signals and poly-U sequences). Exemplary regulatory elements include a transcription promoter such as, but not limited to, CMV, CMV+intron A, SV40, RSV, HIV-Ltr, elongation factor 1 alpha (EF1$\alpha$), MMLV-ltr, internal ribosome entry site (IRES) or P2A peptide to permit translation of multiple genes from a single transcript, metallothionein, a transcription enhancer element, a transcription termination signal, polyadenylation sequences, sequences for optimization of initiation of translation, and translation termination sequences. It will be understood that the choice of the appropriate regulatory element will depend on the encoded component to be expressed (e.g., protein or RNA) or whether the nucleic acid comprises multiple components that require different polymerases or are not intended to be expressed as a fusion protein.

The term "promoter" refers to a DNA sequence that contains an RNA polymerase binding site, transcription start site, TATA box, and/or B recognition element and assists or promotes the transcription and expression of an associated transcribable polynucleotide sequence and/or gene (or transgene). A promoter can be synthetically produced or can be derived from a known or naturally occurring promoter sequence or another promoter sequence. A promoter can be proximal or distal to the gene to be transcribed. A promoter can also include a chimeric promoter comprising a combination of two or more heterologous sequences to confer certain properties. A promoter of the present disclosure can include variants of promoter sequences that are similar in composition, but not identical to, other promoter sequence(s) known or provided herein. A promoter can be classified according to criteria relating to the pattern of expression of an associated coding or transcribable sequence or gene operably linked to the promoter, such as constitutive, developmental, tissue-specific, inducible, etc.

The term "enhancer" refers to regulatory DNA sequences that, when bound by specific proteins called transcription factors, regulate the expression of an associated gene. Enhancers may be located in the intron of the gene, or 5' or 3' of the coding sequence of the gene. Enhancers may be proximal to the gene (i.e., within a few tens or hundreds of base pairs (bp) of the promoter), or may be located distal to the gene (i.e., thousands of bp, hundreds of thousands of bp, or even millions of bp away from the promoter). A single gene may be regulated by more than one enhancer, all of which are envisaged as within the scope of the instant disclosure.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "enhancers" and "promoters", above).

The term "recombinant polynucleotide" or "recombinant nucleic acid" refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

As used herein, the term "contacting" means establishing a physical connection between two or more entities. For example, contacting a target nucleic acid sequence with a guide nucleic acid means that the target nucleic acid sequence and the guide nucleic acid are made to share a physical connection; e.g., can hybridize if the sequences share sequence similarity.

"Dissociation constant", or "$K_d$", are used interchangeably and mean the affinity between a ligand "L" and a protein "P"; i.e., how tightly a ligand binds to a particular protein. It can be calculated using the formula $K_d$=[L][P]/[LP], where [P], [L] and [LP] represent molar concentrations of the protein, ligand and complex, respectively.

The term "knock-out" refers to the elimination of a gene or the expression of a gene. For example, a gene can be knocked out by either a deletion or an addition of a nucleotide sequence that leads to a disruption of the reading frame. As another example, a gene may be knocked out by replacing a part of the gene with an irrelevant sequence. The term "knock-down" as used herein refers to reduction in the expression of a gene or its gene product(s). As a result of a gene knock-down, the protein activity or function may be attenuated or the protein levels may be reduced or eliminated.

As used herein, "homology-directed repair" (HDR) refers to the form of DNA repair that takes place during repair of double-strand breaks in cells. This process requires nucleotide sequence homology, and uses a donor template to repair or knock-out a target DNA, and leads to the transfer of genetic information from the donor to the target. Homology-directed repair can result in an alteration of the sequence of the target sequence by insertion, deletion, or mutation if the donor template differs from the target DNA sequence and part or all of the sequence of the donor template is incorporated into the target DNA.

As used herein, "non-homologous end joining" (NHEJ) refers to the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

As used herein "micro-homology mediated end joining" (MMEJ) refers to a mutagenic DSB repair mechanism, which always associates with deletions flanking the break sites without the need for a homologous template (in contrast to homology-directed repair, which requires a homologous sequence to guide repair). MMEJ often results in the loss (deletion) of nucleotide sequence near the site of the double-strand break.

A polynucleotide or polypeptide has a certain percent "sequence similarity" or "sequence identity" to another polynucleotide or polypeptide, meaning that, when aligned, that percentage of bases or amino acids are the same, and in the same relative position, when comparing the two sequences. Sequence similarity (sometimes referred to as percent similarity, percent identity, or homology) can be determined in a number of different manners. To determine sequence similarity, sequences can be aligned using the methods and computer programs that are known in the art, including BLAST, available over the world wide web at ncbi.nlm.nih.gov/BLAST. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence.

A "vector" or "expression vector" is a replicon, such as plasmid, phage, virus, or cosmid, to which another DNA segment, i.e., an "insert", may be attached so as to bring about the replication or expression of the attached segment in a cell.

The term "naturally-occurring" or "unmodified" or "wild type" as used herein as applied to a nucleic acid, a polypeptide, a cell, or an organism, refers to a nucleic acid, polypeptide, cell, or organism that is found in nature.

As used herein, a "mutation" refers to an insertion, deletion, substitution, duplication, or inversion of one or more amino acids or nucleotides as compared to a reference amino acid sequence or to a reference nucleotide sequence.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

A "host cell," as used herein, denotes a eukaryotic cell, a prokaryotic cell, or a cell from a multicellular organism (e.g., in a cell line), which eukaryotic or prokaryotic cells are used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

The term "Chimeric Antigen Receptor" or a "CAR" comprises at least two domains, which when expressed in a cell, provides the cell with specificity for a target antigen, or a target cell bearing a target antigen, typically a diseased cell bearing a specific disease-related antigen. In some embodiments, a CAR comprises at least an extracellular antigen binding domain (e.g., a scFv with binding specificity to the protein involved in a disease (e.g. cancer), a transmembrane domain and a cytoplasmic signaling domain (also referred to herein as "an intracellular signaling domain") comprising a functional signaling domain derived from one or more stimulatory and/or costimulatory molecules as provided below. In some aspects, the set of polypeptides are contiguous with each other. The portion of the CAR of the disclosure comprising antigen binding domain thereof may exist in a variety of forms where the antigen binding domain is expressed as part of a contiguous polypeptide chain including, for example, a single domain antibody fragment (sdAb), a single chain antibody (scFv), a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426), and may further comprise hinge regions, for example of an immunoglobulin molecule, and spacers, that provide flexibility to the receptor. The hinge, spacer, and transmembrane domains connect the scFv to the activation domains and anchor the CAR in the T-cell membrane. In some embodiments, the CAR composition of the disclosure comprises an antigen binding domain. In a further embodiments, the CAR comprises an antibody fragment that comprises a scFv. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof.

The term "T cell receptor (TCR)" refers to a protein complex found on the surface of T cells that is responsible for recognizing peptide antigens bound to major histocompatibility complex (MHC) molecules. The TCR is composed of multiple subunits, including a TCR alpha and TCR beta chain (encoded by TRAC, or TCRA, and TBRC1, or TCRB, respectively) and within these chains are complementary determining regions (CDRs) which determine the antigen to which the TCR will bind. Additional subunits include CD-epsilon (CD3E), CD3-delta (CD3D), CD3-gamma (CD3G) and CD3-zeta (CD3Z). The extracellular domains of the TCR alpha and TCR beta subunits form the antigen binding site of the native TCR. The CDRs of the extracellular domains of the TCR are the antigen binding sections and a diverse recognition capability leads to efficient protection against foreign antigens or disease cells and the generation of optimal immune responses. Once the TCR is properly engaged with the antigen, conformational changes in the associated CD3 chains are induced that initiates, with other factors, the signaling process and T cell activation.

As used herein, an "engineered TCR" refers to a TCR which has been engineered to include an antigen binding domain with specificity for a target antigen, or a target cell bearing a target antigen, typically a diseased cell bearing a specific disease-related antigen. For example, an engineered TCR may include an antigen binding domain fused to either the TCR alpha or TCR beta subunits of the TCR, or a combination of thereof. Any antigen binding domain, including, for example, a single domain antibody fragment (sdAb), a single chain antibody (scFv), a humanized antibody or bispecific antibody may be used with the engineered TCRs described herein. In addition to the subunit or subunits fused to the antigen binding domain, engineered TCRs may also include wild type subunits that are encoded by the genome of the cell. For example, an engineered TCR may include an antigen binding domain fused to either the TCR alpha or TCR beta subunits of the TCR, as well as wild type CD3-delta, CD3-gamma, CD3-epsilon and CD3-zeta subunits.

"Signaling domain" refers to the functional portion of a protein that acts by transmitting information within the cell to regulate cellular activity via defined signaling pathways by generating second messengers or functioning as effectors by responding to such messengers.

An "intracellular signaling domain" refers to an intracellular portion of a molecule and, as used herein, is a component of the CAR. Examples of T cell-derived signaling domains are derived from polypeptides selected from the group consisting of CD247 molecule (CD3-zeta, or CD3Z), CD27 molecule (CD27), CD28 molecule (CD28), TNF receptor superfamily member 9 (4-1BB, or 41BB), inducible T cell costimulator (ICOS), TNF receptor superfamily member 4 (OX40), or a combination thereof. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines. An intracellular signaling domain can comprise a signaling motif which is known as an immunoreceptor tyrosine-based activation motif or ITAM. Examples of ITAM containing primary cytoplasmic signaling sequences include, but are not limited to, those derived from CD3zeta, Fc fragment of IgE receptor Ig (common FcR gamma, or FCER1G), Fc fragment of IgG receptor IIa (Fc gamma RIIa, or FCGR2A), Fc receptor gamma RIIB, CD3g molecule (CD3 gamma, or CD3G), CD3d molecule (CD3 delta, or CD3D), CD3e molecule (CD3 epsilon, or CD3E), CD79a, CD79b, DAP10, and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, or non-human primate, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In some embodiments, the cytoplasmic domain of zeta comprises residues 52 through 164 of GenBank Acc. No. BAG36664.1 or the equivalent residues from a non-human species that are functional orthologs thereof.

"Protein involved in antigen processing, antigen presentation, antigen recognition, and/or antigen response" as used herein, refers to extracellular, transmembrane and intracellular proteins or glycoproteins involved in antigen processing, presentation, recognition, and/or response. In some cases, the protein or glycoprotein is expressed on the surface of cells and can conveniently serve as a marker of a specific cell type. For example, T cell and B cell surface proteins identify their lineage and stage in the differentiation process. In some cases, protein involved in antigen processing, antigen presentation, antigen recognition, and/or antigen response is a receptor that has binding affinity for a ligand.

A "tumor antigen" is expressed on the surface of a cancer cell, either entirely or as a fragment (e.g., an MHC peptide), and which is useful for the preferential targeting of an immune cell to the cancer cell. In some embodiments, a tumor antigen is a marker expressed by both normal cells and cancer cells, e.g., CD19 on B cells. In some embodiments, a tumor antigen is a cell surface molecule that is overexpressed in a cancer cell in comparison to a normal cell.

The term "antibody," as used herein, encompasses various antibody structures, including but not limited to monoclonal antibodies, polyclonal antibodies, multispecific antibodies (e.g., bispecific antibodies), nanobodies, single domain antibodies such as VHH antibodies, and antibody fragments so long as they exhibit the desired antigen-binding activity or immunological activity. Antibodies represent a large family of molecules that include several types of molecules, such as IgD, IgG, IgA, IgM and IgE.

A "humanized" antibody refers to a antibody comprising amino acid residues from non-human complementarity-determining regions (CDRs) and amino acid residues from human framework regions (FRs). Typically, a humanized antibody will comprise substantially all of the variable domains in which all or substantially all of the CDRs correspond to those of a non-human antibody (which may include amino acid substitutions), and all or substantially all of the FRs correspond to those of a human antibody.

The term "monoclonal antibody" as used herein refers to an antibody obtained from a population of substantially homogeneous antibodies wherein the population are identical and/or bind the same epitope. Thus, the modifier "monoclonal" indicates the character of the antibody as being obtained from a substantially homogeneous population of antibodies, and is not to be construed as requiring production of the antibody by any particular method.

An "antigen binding domain" as used herein refers to immunologically active portions of a molecule that contains an antigen-binding site which specifically binds ("immunoreacts with") an antigen. An antigen binding domain "specifically binds to" or is "specific for" an antigen if it binds with greater affinity or avidity than it binds to other reference antigens including polypeptides or other substances. Examples of proteins that comprise antigen binding domains include but are not limited to Fv, Fab, Fab', Fab'-SH, F(ab')2, diabodies, linear antibodies (see, U.S. Pat. No. 5,641,870), a single domain antibody, a single domain camelid antibody, single-chain fragment variable (scFv) antibody molecules, or any polypeptide chain-containing molecular structure that has a specific shape which fits to and recognizes and binds to an epitope.

"scFv" or "single chain fragment variable" are used interchangeably herein to refer to an antibody fragment format comprising variable regions of heavy ("VH") and light ("VL") chains or two copies of a VH or VL chain of an antibody, which are joined together by a short flexible peptide linker which enables the scFv to form the desired structure for antigen binding. The scFv is a fusion protein of the variable regions of the heavy (VH) and light chains (VL) of immunoglobulins each comprising complementarity-determining regions (CDRs), which can be in either order; VH-VL or VL-VH and are usually joined by linkers.

The term "4-1BB" refers to a member of the TNF-R superfamily having an amino acid sequence provided as GenBank Acc. No. AAA62478.2, or the equivalent residues from a non-human species; and a "4-1BB costimulatory domain" is defined as amino acid residues 214-255 of GenBank Acc. No. AAA62478.2, or the equivalent residues from a non-human species.

"Immune effector cell" refers to a cell that is involved in an immune response, e.g., in the promotion of an immune effector response. Examples of immune effector cells include T cells, such as helper T cells and cytotoxic T cells, gamma-delta T cells, tumor infiltrating lymphocytes, NK cells, B cells, monocytes, macrophages, or dendritic cells.

"Immune effector function" or "immune effector response," refers to function or response, e.g., of an immune effector cell, that enhances or promotes an immune attack of a target cell. In the context of the present disclosure, an immune effector function or response refers a property of a T or NK cell that promotes killing or the inhibition of growth or proliferation of a target cell.

As used herein, "treatment" or "treating," are used interchangeably herein and refer to an approach for obtaining beneficial or desired results, including but not limited to a therapeutic benefit and/or a prophylactic benefit. By therapeutic benefit is meant eradication or amelioration of the underlying disorder or disease being treated. A therapeutic benefit can also be achieved with the eradication or amelioration of one or more of the symptoms or an improvement in one or more clinical parameters associated with the underlying disease such that an improvement is observed in the subject, notwithstanding that the subject may still be afflicted with the underlying disorder.

The terms "therapeutically effective amount" and "therapeutically effective dose", as used herein, refer to an amount of a drug or a biologic, alone or as a part of a composition, that is capable of having any detectable, beneficial effect on any symptom, aspect, measured parameter or characteristics of a disease state or condition when administered in one or repeated doses to a subject such as a human or an experimental animal. Such effect need not be absolute to be beneficial.

As used herein, "administering" is meant a method of giving a dosage of a compound (e.g., a composition of the disclosure) or a composition (e.g., a pharmaceutical composition) to a subject.

A "subject" is a mammal. Mammals include, but are not limited to, domesticated animals, non-human primates, humans, rabbits, mice, rats and other rodents.

I. General Methods

The practice of the present disclosure employs, unless otherwise indicated, conventional techniques of immunology, biochemistry, chemistry, molecular biology, microbiology, cell biology, genomics and recombinant DNA, which can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Where a range of values is provided, it is understood that endpoints are included, and that each intervening value, to the tenth of the unit of the lower limit unless the context clearly dictates otherwise, between the upper and lower limit of that range and any other stated or intervening value in that stated range, is encompassed. The upper and lower limits of these smaller ranges may independently be included in the smaller ranges, and are also encompassed, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art to which this invention belongs. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise.

It will be appreciated that certain features of the invention, which are, for clarity, described in the context of separate embodiments, may also be provided in combination in a single embodiment. In other cases, various features of the invention, which are, for brevity, described in the context of a single embodiment, may also be provided separately or in any suitable sub-combination. It is intended that all combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

II. Systems for Genetic Editing of Proteins involved in Antigen Processing, Presentation, Recognition, and/or Response In a first aspect, the present disclosure provides systems comprising a CRISPR nuclease and one or more guide nucleic acids (gNA) that have utility in genome editing of eukaryotic cells. In some embodiments, the CRISPR nuclease is selected from the group consisting of Cas9, Cas12a, Cas12b, Cas12c, Cas12d (CasY), CasX, Cas13a, Cas13b, Cas13c, Cas13d, CasX, CasY, Cas14, Cpfl, C2cl, Csn2, and Cas Phi. In some embodiments, the CRISPR nuclease is a is a Type V CRISPR nuclease. In some embodiments, the present disclosure provides CasX:gNA systems comprising a CasX protein and one or more guide nucleic acids (gNA) that are specifically designed to modify a target nucleic acid sequence of one or more cell genes encoding proteins involved in antigen processing, antigen presentation, antigen recognition, and/or antigen response. A gNA and a CasX protein of the disclosure can form a complex and bind via non-covalent interactions, referred to herein as a ribonucleoprotein (RNP) complex. The use of a pre-complexed CasX:gNA confers advantages in the delivery of the system components to a cell or target nucleic acid sequence for editing of the target nucleic acid sequence. In the RNP, the gNA can provide target specificity to the complex by including a targeting sequence (or "spacer") having a nucleotide sequence that is complementary to a sequence of the target nucleic acid sequence while the CasX protein of the pre-complexed CasX:gNA provides the site-specific activity that is guided to a target site (e.g., stabilized at a target site)

within a target nucleic acid sequence (e.g., a B2M or TRAC gene to be modified) by virtue of its association with the guide NA. The CasX protein of the complex provides the site-specific activities of the complex such as cleavage or nicking of the target sequence by the CasX protein and/or an activity provided by the fusion partner in the case of a chimeric CasX protein. Additionally, the present disclosure provides methods useful for modifying the target nucleic acid sequence of a populations of cells to introduce or regulate the expression of the one or more proteins involved in antigen processing, presentation, recognition and/or response using the CasX:gNA systems. Such modified populations of cells in which a protein involved in antigen processing, antigen presentation, antigen recognition, and/or antigen response have been down-regulated or eliminated are useful for immunotherapies. The CasX:gNA systems of the disclosure comprise one or more of a CasX protein, one or more guide nucleic acids (gNA) and, optionally, one or more donor template nucleic acids comprising a nucleic acid encoding a modification of a protein involved in antigen processing, antigen presentation, antigen recognition, and/or antigen response wherein the nucleic acid comprises a deletion, insertion, or mutation of one or more nucleotides in comparison to a genomic nucleic acid sequence encoding the protein or its regulatory element to knock-down/knock-out gene function. In some embodiments, the donor polynucleotide comprises at least about 10, at least about 50, at least about 100, or at least about 200, or at least about 300, or at least about 400, or at least about 500, or at least about 600, or at least about 700, or at least about 800, or at least about 900, or at least about 1000, or at least about 10,000, or at least about 15,000 nucleotides of all or a portion of a target nucleic acid sequence of a cell gene to be modified. In other embodiments, the donor polynucleotide comprises at least about 10 to about 10,000 nucleotides, or at least about 100 to about 8000 nucleotides, or at least about 400 to about 6000 nucleotides, or at least about 600 to about 4000 nucleotides, or at least about 1000 to about 2000 nucleotides of a cell gene to be modified. In some embodiments, the donor template is a single stranded DNA template or a single stranded RNA template. In other embodiments, the donor template is a double stranded DNA template.

In other embodiments, the present disclosure provides polynucleic acids encoding a chimeric antigen receptor (CAR) with binding specificity for a disease antigen, optionally a tumor cell antigen, which can be introduced into the cells to be modified, such that the modified cell is able to express the CAR in the modified cell. In other embodiments, the present disclosure provides polynucleic acids encoding an engineered T cell receptor (TCR) with binding specificity for a disease antigen, optionally a tumor cell antigen, which can be introduced into the cells to be modified, such that the modified cell is able to express the TCR in the modified cell.

The CasX:gNA systems have utility in the treatment of a subject having certain diseases or conditions, including, cancer, autoimmune diseases, and transplant rejection. Each of the components of the CasX:gNA systems and their use in the editing of the target nucleic acids in cells to modify one or more proteins involved in antigen processing, antigen presentation, antigen recognition, and/or antigen response, as well as the use of polynucleic acids encoding CAR and engineered TCR subunit or subunits, is described herein. The CasX:gNA systems and polynucleic acids described herein have utility in the creation of modified populations of cells that efficiently kill target cells associated with diseases such cancer, autoimmune diseases, and transplant rejection. Further, the modified populations of cells can be used to confer immunity in a subject having such diseases.

III. Guide Nucleic Acids of the Systems for Genetic Editing

In another aspect, the disclosure relates to a guide nucleic acid (gNA) comprising a targeting sequence complementary to a target nucleic acid sequence in the target strand of a gene encoding a protein involved in antigen processing, antigen presentation, antigen recognition, and/or antigen response, wherein the gNA is capable of forming a complex with a CRISPR protein that is specific to a protospacer adjacent motif (PAM) sequence comprising a TC motif in the complementary non-target strand, and wherein the PAM sequence is located 1 nucleotide 5' of the sequence in the non-target strand that is complementary to the target nucleic acid sequence in the target strand.

In some embodiments, present disclosure relates to guide nucleic acids (gNA) utilized in the CasX:gNA systems that have utility in genome editing of eukaryotic cells. The present disclosure provides specifically-designed guide nucleic acids ("gNAs") wherein the targeting sequence (or spacer, described more fully, below) of the gNA is complementary to (and are therefore able to hybridize with) target nucleic acid sequences when used as a component of the gene editing CasX:gNA systems. It is envisioned that in some embodiments, multiple gNAs are delivered in the CasX:gNA system for the modification of a target nucleic acid sequence. For example, when a knock-down/knock-out of a protein-encoding gene is desired, a pair of gNAs can be used in order to bind and cleave at two different sites within the gene.

The present disclosure provides specifically-designed guide nucleic acids ("gNAs") with targeting sequences that are complementary to (and are therefore able to hybridize with) the target nucleic acid as a component of the gene editing CasX:gNA systems. As described more fully, below, representative, but non-limiting examples of targeting sequences to the target nucleic acid sequence of a cell gene encoding a protein involved in antigen processing, antigen presentation, antigen recognition, and/or antigen response are presented in Tables 3A, 3B, and 3C (Tables 3A, 3B, and 3C are provided as FIGS. 35-37). It is envisioned that in some embodiments, multiple gNAs are delivered in the CasX:gNA system for the modification of the target nucleic acid sequence(s). For example, when a knock-down/knock-out of a protein-encoding gene is desired, a pair of gNAs with targeting sequences to different or overlapping regions of the target nucleic acid sequence can be used in order to bind and the CasX to cleave at two different or overlapping sites within or proximal to the gene, which is then edited by non-homologous end joining (NHEJ), homology-directed repair (HDR, which can include, for example, insertion of a donor template to replace all or a portion of the intron), homology-independent targeted integration (HITI), micro-homology mediated end joining (MMEJ), single strand annealing (SSA) or base excision repair (BER).

a. Reference gNA and gNA Variants

In some embodiments, a gNA of the present disclosure comprises a sequence of a naturally-occurring gNA (a "reference gNA"). In other cases, a reference gNA of the disclosure may be subjected to one or more mutagenesis methods, such as the mutagenesis methods described herein, which may include Deep Mutational Evolution (DME), deep mutational scanning (DMS), error prone PCR, cassette mutagenesis, random mutagenesis, staggered extension PCR, gene shuffling, or domain swapping, in order to generate one or more gNA variants with enhanced or varied properties relative to the reference gNA. gNA variants also include variants comprising one or more exogenous sequences, for example fused to either the 5' or 3' end, or inserted internally. The activity of reference gNAs may be used as a benchmark against which the activity of gNA variants are compared, thereby measuring improvements in function or other characteristics of the gNA variants. In other embodiments, a reference gNA may be subjected to one or more deliberate, targeted mutations in order to produce a gNA variant, for example a rationally designed variant. As used herein, the terms gNA, gRNA, and gDNA cover naturally-occurring molecules, as well as sequence variants. Thus, in some embodiments, the gNA is a deoxyribonucleic acid molecule ("gDNA"); in some embodiments, the gNA is a ribonucleic acid molecule ("gRNA"), and in other embodiments, the gNA is a chimera, and comprises both DNA and RNA.

The targeting sequence of a gNA is capable of binding to a target nucleic acid sequence, including a coding sequence, a complement of a coding sequence, a non-coding sequence, and to regulatory elements. The gNA scaffold (or "protein-binding sequence") interacts with (e.g., binds to) a CasX protein, forming an RNP (described more fully, below). In some embodiments, the targeting sequence and scaffold each include complementary stretches of nucleotides that hybridize to one another to form a double stranded duplex (dsRNA duplex for a dgRNA). Site-specific binding and/or cleavage of a target nucleic acid sequence (e.g., genomic DNA) by the CasX protein can occur at one or more locations (e.g., a sequence of a target nucleic acid) determined by base-pairing complementarity between the targeting sequence of the gNA and the target nucleic acid sequence. Thus, for example, the gNA of the disclosure have sequences complementarity to and therefore can hybridize to a protein involved in antigen processing, antigen presentation, antigen recognition, and/or antigen response gene and/or its regulatory sequence in a nucleic acid in a eukaryotic cell, e.g., a eukaryotic nucleic acid (e.g., a eukaryotic chromosome, chromosomal sequence, a eukaryotic RNA, etc.) that is adjacent to a sequence complementary to a TC PAM motif or a PAM sequence, such as ATC, CTC, GTC, or TTC.

In the context of nucleic acids, cleavage refers to the breakage of the covalent backbone of a nucleic acid molecule; either DNA or RNA. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends.

In some embodiments, the disclosure provides gene editing pairs of a CasX and a gNA of any of the embodiments described herein that are capable of being bound together prior to their use for gene editing and, thus, are "pre-complexed" as a ribonuclear protein complex (RNP). The use of a pre-complexed RNP confers advantages in the delivery of the system components to a cell or target nucleic acid sequence for editing of the target nucleic acid sequence. The CasX protein of the RNP provides the site-specific activity that is guided to a target site (e.g., stabilized at a target site) within a target nucleic acid sequence by virtue of its association with the guide RNA comprising a targeting sequence capable of hybridizing to the target nucleic acid sequence.

In some embodiments, wherein the gNA is a gRNA, the term "targeter" or "targeter RNA" is used herein to refer to a crRNA-like molecule (crRNA: "CRISPR RNA") of a CasX dual guide RNA (and therefore of a CasX single guide RNA when the "activator" and the "targeter" are linked together, e.g., by intervening nucleotides). Thus, for example, a CasX guide RNA (dgRNA or sgRNA) comprises a guide sequence and a duplex-forming segment of a crRNA, which can also be referred to as a crRNA repeat. Because the sequence of a guide sequence hybridizes with a sequence of a target nucleic acid sequence, a targeter can be modified by a user to hybridize with a specific target nucleic acid sequence, so long as the location of the PAM sequence is considered. Thus, in some cases, the sequence of a targeter may be a non-naturally occurring sequence. In other cases, the sequence of a targeter may be a naturally-occurring sequence, derived from the gene to be edited. In the case of a dual guide RNA, the targeter and the activator each have a duplex-forming segment, where the duplex forming segment of the targeter and the duplex-forming segment of the activator have complementarity with one another and hybridize to one another to form a double stranded duplex (dsRNA duplex for a gRNA). In some embodiments, a targeter comprises both the guide sequence of the guide RNA and a stretch of nucleotides that forms one half of the dsRNA duplex of the protein-binding segment of the gRNA. A corresponding tracrRNA-like molecule (activator) also comprises a duplex-forming stretch of nucleotides that forms the other half of the dsRNA duplex of the protein-binding segment of the CasX guide RNA. Thus, a targeter and an activator, as a corresponding pair, hybridize to form a CasX dual guide NA, referred to herein as a "dual guide NA", a "dual-molecule gNA", a "dgNA", a "double-molecule guide NA", or a "two-molecule guide NA".

In some embodiments, the activator and targeter of the reference gNA are covalently linked to one another and comprise a single molecule, referred to herein as a "single-molecule gNA," "one-molecule guide NA," "single guide NA", "single guide RNA", a "single-molecule guide RNA," a "one-molecule guide RNA", a "single guide DNA", a "single-molecule DNA", or a "one-molecule guide DNA", ("sgNA", "sgRNA", or a "sgDNA"). In some embodiments, the sgNA includes an "activator" or a "targeter" and thus can be an "activator-RNA" and a "targeter-RNA," respectively.

Collectively, the gNAs of the disclosure comprise four distinct regions, or domains: the RNA triplex, the scaffold stem, the extended stem, and the targeting sequence that, in the embodiments of the disclosure are specific for a target nucleic acid. The RNA triplex, the scaffold stem, and the extended stem, together, are referred to as the "scaffold" of the gNA. In some embodiments, the targeting sequence is on the 3' end of the gNA.

b. RNA Triplex

In some embodiments of the guide NAs provided herein (including reference sgNAs), there is a RNA-triplex, and the RNA triplex comprises the sequence of a UUU--nX(~4-15)--UUU stem loop (SEQ ID NO: 19) that ends with an AAAG after 2 intervening stem loops (the scaffold stem loop and the extended stem loop), forming a pseudoknot that may also extend past the triplex into a duplex pseudoknot. The UU-UUU-AAA sequence of the triplex forms as a nexus between the spacer, scaffold stem, and extended stem. In exemplary reference CasX sgNAs, the UUU-loop-UUU region is coded for first, then the scaffold stem loop, and then the extended stem loop, which is linked by the tetraloop, and then an AAAG closes off the triplex before becoming the spacer.

c. Scaffold Stem Loop

In some embodiments of sgNAs of the disclosure, the triplex region is followed by the scaffold stem loop. The scaffold stem loop is a region of the gNA that is bound by CasX protein (such as a reference or CasX variant protein). In some embodiments, the scaffold stem loop is a fairly short and stable stem loop. In some cases, the scaffold stem loop does not tolerate many changes, and requires some form of an RNA bubble. In some embodiments, the scaffold stem is necessary for CasX sgNA function. While it is perhaps analogous to the nexus stem of Cas9 as being a critical stem loop, the scaffold stem of a CasX sgNA, in some embodiments, has a necessary bulge (RNA bubble) that is different from many other stem loops found in CRISPR/Cas systems. In some embodiments, the presence of this bulge is conserved across sgNA that interact with different CasX proteins. An exemplary sequence of a scaffold stem loop sequence of a gNA comprises the sequence CCAGCGAC-UAUGUCGUAUGG (SEQ ID NO: 20. In other embodiments, the disclosure provides gNA variants wherein the scaffold stem loop is replaced with an RNA stem loop sequence from a heterologous RNA source with proximal 5' and 3' ends, such as, but not limited to stem loop sequences selected from MS2, Q β, U1 hairpin II, Uvsx, or PP7 stem loops. In some cases, the heterologous RNA stem loop of the gNA is capable of binding a protein, an RNA structure, a DNA sequence, or a small molecule.

d. Extended Stem Loop

In some embodiments of the CasX sgNAs of the disclosure, the scaffold stem loop is followed by the extended stem loop. In some embodiments, the extended stem comprises a synthetic tracr and crRNA fusion that is largely unbound by the CasX protein. In some embodiments, the extended stem loop can be highly malleable. In some embodiments, a single guide gRNA is made with a GAAA tetraloop linker or a GAGAAA linker between the tracr and crRNA in the extended stem loop. In some cases, the targeter and activator of a CasX sgNA are linked to one another by intervening nucleotides and the linker can have a length of from 3 to 20 nucleotides. In some embodiments of the CasX sgNAs of the disclosure, the extended stem is a large 32-bp loop that sits outside of the CasX protein in the ribonucleoprotein complex. An exemplary sequence of an extended stem loop sequence of a sgNA comprises the sequence GCGC-UUAUUUAUCG-GAGAGAAAUCCGAUAAAUAAGAAGC (SEQ ID NO: 21). In some embodiments, the extended stem loop comprises a GAGAAA spacer sequence. In some embodiments, the disclosure provides gNA variants wherein the extended stem loop is replaced with an RNA stem loop sequence from a heterologous RNA source with proximal 5' and 3' ends, such as, but not limited to stem loop sequences selected from MS2, QP, U1 hairpin II, Uvsx, or PP7 stem loops. In such cases, the heterologous RNA stem loop increases the stability of the gNA. In other embodiments, the disclosure provides gNA variants having an extended stem loop region comprising at least 10, at least 100, at least 500, at least 1000, or at least 10,000 nucleotides.

e. Targeting Sequence

In some embodiments of the gNAs of the disclosure, the extended stem loop is followed by a region that forms part of the triplex, and then the targeting sequence (or "spacer"). The targeting sequence targets the CasX ribonucleoprotein holo complex to a specific region of the target nucleic acid sequence of the gene to be modified. Thus, for example, gNA targeting sequences of the disclosure have sequences complementarity to, and therefore can hybridize to, a portion of the B2M gene in a nucleic acid in a eukaryotic cell (e.g., a eukaryotic chromosome, chromosomal sequence, a eukaryotic RNA, etc.) as a component of the RNP when any one of the PAM sequences TTC, ATC, GTC, or CTC is located 1 nucleotide 5' to the non-target strand sequence complementary to the target sequence. The targeting sequence of a gNA can be modified so that the gNA can target a desired sequence of any desired target nucleic acid sequence, so long as the PAM sequence location is taken into consideration. In some embodiments, the gNA scaffold is 5' of the targeting sequence, with the targeting sequence on the 3' end of the gNA. In some embodiments, the PAM sequence recognized by the RNP is TC. In other embodiments, the PAM sequence recognized by the RNP is NTC.

In some embodiments, the targeting sequence of the gNA is specific for, and is capable of hybridizing with, a portion of a gene encoding a protein involved in antigen processing, antigen presentation, antigen recognition, and/or antigen response, including, but not limited to beta-2-microglobulin (B2M), T cell receptor alpha chain constant region (TRAC), class II major histocompatibility complex transactivator (CIITA), T cell receptor beta constant 1 (TRBC1), T cell receptor beta constant 2 (TRBC2), human leukocyte antigen A (HLA-A), human leukocyte antigen B (HLA-B), TGFβ Receptor 2 (TGFβRII), programmed cell death 1 (PD-1), cytokine inducible SH2 (CISH), lymphocyte activating 3 (LAG-3), T cell immunoreceptor with Ig and ITIM domains (TIGIT), adenosine A2a receptor (ADORA2A), killer cell lectin like receptor C1 (NKG2A), cytotoxic T-lymphocyte-associated protein 4 (CTLA-4), T-cell immunoglobulin and mucin domain 3 (TIM-3), and 2B4 (CD244). In one particular embodiment, the gene is B2M. The B2M gene encodes a serum protein found in association with the major histocompatibility complex (MHC) class I heavy chain on the surface of nearly all nucleated cells. In another particular embodiment, the gene is TRAC. The TRAC gene encodes the C-terminal constant region, linked to one of 70 variable regions of the T cell alpha receptor. Following similar synthesis of the beta chain, the alpha and beta chains pair to yield the alpha-beta T-cell receptor heterodimer. In another particular embodiment, the gene is CITTA. The CIITA gene provides instructions for making a protein that primarily helps control the activity (transcription) of genes of the major histocompatibility complex (MHC) class II. In the foregoing, the genomic targets are those in which the encoding gene of the target is intended to be knocked out or knocked down such that the protein (e.g., a cell marker or intracellular protein) is not expressed or is expressed at a lower level in a cell. In some embodiments, the targeting sequence of a gNA is specific for an exon of the gene. In other embodiments, the targeting sequence of a gNA is specific for an intron of the gene. In other embodiments, the targeting sequence of a gNA is specific for a regulatory element of the gene. In other embodiments, the targeting sequence of a gNA is specific for a junction of the exon, intron, and/or regulatory element of the gene. In other embodiments, the targeting sequence of a gNA is specific for an intergenic region. In those cases where the targeting sequence is specific for a regulatory element, such regulatory elements include, but are not limited to promoter regions, enhancer regions, intergenic regions, 5' untranslated regions (5' UTR), 3' untranslated regions (3' UTR), conserved elements, and regions comprising cis-regulatory elements. The promoter region is intended to encompass nucleotides within 5 kb of the initiation point of the encoding sequence or, in the case of gene enhancer elements or conserved elements, can be thousands of bp, hundreds of thousands of bp, or even millions of bp away from the encoding sequence of the gene of the target nucleic acid. In the foregoing, the targets are those in which the encoding gene of the target is intended to be knocked out or knocked down such that the targeted protein is not expressed or is expressed at a lower level in a cell.

In some embodiments, the targeting sequence of the gNA has between 14 and 35 consecutive nucleotides. In some embodiments, the targeting sequence has 14, 15, 16, 18, 18, 19, 20, 21, 22, 23 24, 25, 26, 27, 28, 29, 30, 31, 32, 33, 34 or 35 consecutive nucleotides. In some embodiments, the targeting sequence consists of 20 consecutive nucleotides. In some embodiments, the targeting sequence consists of 19 consecutive nucleotides. In some embodiments, the targeting sequence consists of 18 consecutive nucleotides. In some embodiments, the targeting sequence consists of 17 consecutive nucleotides. In some embodiments, the targeting sequence consists of 16 consecutive nucleotides. In some embodiments, the targeting sequence consists of 15 consecutive nucleotides. In some embodiments, the targeting sequence has 14, 15, 16, 17, 18, 19, 20, 21, 22, 23, 24, 25, 26, 27, 28, 29, 30, 31, 32, 33, 34 or 35 consecutive nucleotides and the targeting sequence can comprise 0 to 5, 0 to 4, 0 to 3, or 0 to 2 mismatches relative to the target nucleic acid sequence and retain sufficient binding specificity such that the RNP comprising the gNA comprising the targeting sequence can form a complementary bond with respect to the target nucleic acid.

Representative, but non-limiting examples of targeting sequences for inclusion in the gNA of the disclosure are presented in Tables 3A, 3B, and 3C (included as FIGS. 35-37), representing targeting sequences for B2M, TRAC, and CIITA, respectively.

Exemplary targeting sequences (spacer sequences) of the gNA embodiments utilized with the CasX:gNA system for editing of the B2M gene are provided in Table 3A (SEQ ID NOs: 725-2100 and 2281-7085). In one embodiment, the targeting sequence of the B2M gNA comprises a sequence having at least about 65%, at least about 75%, at least about 85%, or at least about 95% identity to a sequence selected from the group consisting of sequences set forth in Table 3A. In another embodiment, the targeting sequence of the gNA consists of a sequence selected from the group consisting of sequences set forth in Table 3A. In the foregoing embodiments, thymine (T) nucleotides can be substituted for one or more or all of the uracil (U) nucleotides in any of the targeting sequences such that the gNA can be a gDNA or a gRNA, or a chimera of RNA and DNA. In some embodiments, a targeting sequence of Table 3A has at least 1, 2, 3, 4, 5, or 6 or more thymine nucleotides substituted for thymine nucleotides. In other embodiments, a gNA, gRNA, or gDNA of the disclosure comprises 1, 2, 3 or more targeting sequences of Table 3A, or targeting sequences that are at least 50% identical, at least 55% identical, at least 60% identical, at least 65% identical, at least 70% identical, at least 75% identical, at least 80% identical, at least 85% identical, at least 90% identical, at least 95% identical to one or more sequences of Table 3A.

Exemplary targeting sequences (spacer sequences) of the gNA embodiments utilized with the CasX:gNA system for editing of the TRAC gene are provided in Table 3B. In one embodiment, the targeting sequence of the TRAC gNA comprises a sequence having at least about 65%, at least about 75%, at least about 85%, or at least about 95% identity to a sequence selected from the group consisting of sequences set forth in Table 3B. In another embodiment, the targeting sequence of the gNA consists of a sequence selected from the group consisting of sequences set forth in Table 3B. In the foregoing embodiments, thymine (T) nucleotides can be substituted for one or more or all of the uracil (U) nucleotides in any of the targeting sequences such that the gNA can be a gDNA or a gRNA, or a chimera of RNA and DNA. In some embodiments, a targeting sequence of Table 3B has at least 1, 2, 3, 4, 5, or 6 or more thymine nucleotides substituted for uracil nucleotides. In other embodiments, a gNA, gRNA, or gDNA of the disclosure comprises 1, 2, 3 or more targeting sequences of Table 3B, or targeting sequences that are at least 50% identical, at least 55% identical, at least 60% identical, at least 65% identical, at least 70% identical, at least 75% identical, at least 80% identical, at least 85% identical, at least 90% identical, at least 95% identical to one or more sequences of Table 3B.

Exemplary targeting sequences (spacer sequences) of the gNA embodiments utilized with the CasX:gNA system for editing of the CIITA gene are provided in Table 3C. In one embodiment, the targeting sequence of the TRAC gNA comprises a sequence having at least about 65%, at least about 75%, at least about 85%, or at least about 95% identity to a sequence selected from the group consisting of sequences set forth in Table 3C. In another embodiment, the targeting sequence of the gNA consists of a sequence selected from the group consisting of sequences set forth in Table 3C. In the foregoing embodiments, thymine (T) nucleotides can be substituted for one or more or all of the uracil (U) nucleotides in any of the targeting sequences such that the gNA can be a gDNA or a gRNA, or a chimera of RNA and DNA. In some embodiments, a targeting sequence of Table 3C has at least 1, 2, 3, 4, 5, or 6 or more thymine nucleotides substituted for uracil nucleotides. In other embodiments, a gNA, gRNA, or gDNA of the disclosure comprises 1, 2, 3 or more targeting sequences of Table 3C, or targeting sequences that are at least 50% identical, at least 55% identical, at least 60% identical, at least 65% identical, at least 70% identical, at least 75% identical, at least 80% identical, at least 85% identical, at least 90% identical, at least 95% identical to one or more sequences of Table 3C.

In some embodiments, the CasX:gNA system comprises a first gNA and further comprises a second (and optionally a third, fourth, fifth, or more) gNA, wherein the second gNA or additional gNA has a targeting sequence complementary to a different or overlapping portion of the target nucleic acid sequence compared to the targeting sequence of the first gNA such that multiple points in the target nucleic acid are targeted, and, for example, multiple breaks are introduced in the target nucleic acid by the CasX. It will be understood that in such cases, the second or additional gNA is complexed with an additional copy of the CasX protein. By selection of the targeting sequences of the gNA, defined regions of the target nucleic acid sequence bracketing a particular location within the target nucleic acid can be modified or edited using the CasX:gNA systems described herein, including facilitating the insertion of a donor template.

f. gNA Scaffolds

In some embodiments, a CasX reference gRNA comprises a sequence isolated or derived from Deltaproteobacter. In some embodiments, the sequence is a CasX tracrRNA sequence. Exemplary CasX reference tracrRNA sequences isolated or derived from Deltaproteobacter may include: ACAUCUGGCGCGUUUAUUCCAUUACUUUG-GAGCCAGUCCCAGCGACUAUGUCG UAUGGACGAAGCGCUUAUUUAUCGGAGA (SEQ ID NO: 22) and ACAUCUGGCGCGUUUAUUCCAUUAC-UUUGGAGCCAGUCCCAGCGACUAUGUCG UAUGGACGAAGCGCUUAUUUAUCGG (SEQ ID NO:

23). Exemplary crRNA sequences isolated or derived from Deltaproteobacter may comprise a sequence of CCGAUA-AGUAAAACGCAUCAAAG (SEQ ID NO: 24). In some embodiments, a CasX reference gNA comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence isolated or derived from Deltaproteobacter.

In some embodiments, a CasX reference guide RNA comprises a sequence isolated or derived from Planctomycetes. In some embodiments, the sequence is a CasX tracrRNA sequence. Exemplary CasX reference tracrRNA sequences isolated or derived from Planctomycetes may include: UACUGGCGCUUUUAUCUCAUUAC-UUUGAGAGCCAUCACCAGCGACUAUGUCGU AUGGGUAAAGCGCUUAUUUAUCGGAGA (SEQ ID NO: 25) and UACUGGCGCUUUUAUCUCAUUAC-UUUGAGAGCCAUCACCAGCGACUA UGU-CGUAUGGGUAAAGCGCUUAUUUAUCGG (SEQ ID NO: 26). Exemplary crRNA sequences isolated or derived from Planctomycetes may comprise a sequence of UCUCCGAUAAAUAAGAAGCAUCAAAG (SEQ ID NO: 27). In some embodiments, a CasX reference gNA comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence isolated or derived from Planctomycetes.

In some embodiments, a CasX reference gNA comprises a sequence isolated or derived from Candidatus Sungbacteria. In some embodiments, the sequence is a CasX tracrRNA sequence. Exemplary CasX reference tracrRNA sequences isolated or derived from Candidatus Sungbacteria may comprise sequences of: GUUUACACACUCCCUCU-CAUAGGGU (SEQ ID NO: 28), GUUUACACACUCC-CUCUCAUGAGGU (SEQ ID NO: 29), UUUUACAUACCCCCUCUCAUGGGAU (SEQ ID NO: 30) and GUUUACACACUCCCUCUCAUGGGGG (SEQ ID NO: 31). In some embodiments, a CasX reference guide RNA comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence isolated or derived from Candidatus Sungbacteria.

Table 1 provides the sequences of reference gRNAs tracr and scaffold sequences. In some embodiments, the disclosure provides gNA sequences wherein the gNA has a scaffold comprising a sequence having at least one nucleotide modification relative to a reference gNA sequence having a sequence of any one of SEQ ID NOS:4-16 of Table 1. It will be understood that in those embodiments wherein a vector comprises a DNA encoding sequence for a gNA, or where a gNA is a gDNA or a chimera of RNA and DNA, that thymine (T) bases can be substituted for the uracil (U) bases of any of the gNA sequence embodiments described herein.

TABLE 1

Reference gRNA sequences

| SEQ ID NO. | Nucleotide Sequence |
|---|---|
| 4 | ACAUCUGGCGCGUUUAUUCCAUUACUUUGGAGCCAGUCCCAGCG ACUAUGUCGUAUGGACGAAGCGCUUAUUUAUCGGAGAGAAACCG AUAAGUAAAACGCAUCAAAG |
| 5 | UACUGGCGCUUUUAUCUCAUUACUUUGAGAGCCAUCACCAGCGA CUAUGUCGUAUGGGUAAAGCGCUUAUUUAUCGGAGAGAAAUCCG AUAAAUAAGAAGCAUCAAAG |
| 6 | ACAUCUGGCGCGUUUAUUCCAUUACUUUGGAGCCAGUCCCAGCG ACUAUGUCGUAUGGACGAAGCGCUUAUUUAUCGGAGA |
| 7 | ACAUCUGGCGCGUUUAUUCCAUUACUUUGGAGCCAGUCCCAGCG ACUAUGUCGUAUGGACGAAGCGCUUAUUUAUCGG |
| 8 | UACUGGCGCUUUUAUCUCAUUACUUUGAGAGCCAUCACCAGCGA CUAUGUCGUAUGGGUAAAGCGCUUAUUUAUCGGAGA |
| 9 | UACUGGCGCUUUUAUCUCAUUACUUUGAGAGCCAUCACCAGCGA CUAUGUCGUAUGGGUAAAGCGCUUAUUUAUCGG |
| 10 | GUUUACACACUCCCUCUCAUAGGGU |
| 11 | GUUUACACACUCCCUCUCAUGAGGU |
| 12 | UUUUACAUACCCCCUCUCAUGGGAU |
| 13 | GUUUACACACUCCCUCUCAUGGGGG |
| 14 | CCAGCGACUAUGUCGUAUGG |
| 15 | GCGCUUAUUUAUCGGAGAGAAAUCCGAUAAAUAAGAAGC |
| 16 | GGCGCUUUUAUCUCAUUACUUUGAGAGCCAUCACCAGCGACUAU GUCGUAUGGGUAAAGCGCUUAUUUAUCGGA |

g. gNA Variants

In another aspect, the disclosure relates to guide nucleic acid variants (referred to herein alternatively as "gNA variant" or "gRNA variant"), which comprise one or more modifications relative to a reference gRNA scaffold. As used herein, "scaffold" refers to all parts to the gNA necessary for gNA function with the exception of the spacer sequence.

In some embodiments, a gNA variant comprises one or more nucleotide substitutions, insertions, deletions, or swapped or replaced regions relative to a reference gRNA sequence of the disclosure. In some embodiments, a mutation can occur in any region of a reference gRNA to produce a gNA variant. In some embodiments, the scaffold of the gNA variant sequence has at least 20%, at least 30%, at least 40%, at least 50%, at least 60%, or at least 70%, at least 80%, at least 85%, at least about 90%, at least about 95%, at least about 96%, at least about 97%, at least about 98%, or at least about 99% identity to the sequence of SEQ ID NO:4 or SEQ ID NO:5.

In some embodiments, a gNA variant comprises one or more nucleotide changes within one or more regions of the reference gRNA that improve a characteristic of the reference gRNA. Exemplary regions include the RNA triplex, the pseudoknot, the scaffold stem loop, and the extended stem loop. In some cases, the variant scaffold stem further comprises a bubble. In other cases, the variant scaffold further comprises a triplex loop region. In still other cases, the variant scaffold further comprises a 5' unstructured region. In one embodiment, the gNA variant scaffold comprises a scaffold stem loop having at least 60% sequence identity to SEQ ID NO:14. In another embodiment, the gNA variant comprises a scaffold stem loop having the sequence of CCAGCGACUAUGUCGUAGUGG (SEQ ID NO: 32). In another embodiment, the disclosure provides a gNA scaffold comprising, relative to SEQ ID NO:5, a C18G substitution, a G55 insertion, a U1 deletion, and a modified extended stem loop in which the original 6 nt loop and 13 most-loop-proximal base pairs (32 nucleotides total) are replaced by a Uvsx hairpin (4 nt loop and 5 loop-proximal base pairs; 14 nucleotides total) and the loop-distal base of the extended stem was converted to a fully base-paired stem contiguous with the new Uvsx hairpin by deletion of the A99 and substitution of G64U. In the foregoing embodiment, the gNA scaffold comprises the sequence (SEQ ID NO: 33)
ACUGGCGCUUUUAUCUGAUUACUUUGAGAGCCAUCACCAGCGACUAUGUC

GUAGUGGGUAAAGCUCCCUCUUCGGAGGGAGCAUCAAAG.

All gNA variants that have one or more improved functions or characteristics, or add one or more new functions when the variant gNA is compared to a reference gRNA described herein, are envisaged as within the scope of the disclosure. A representative example of such a gNA variant is guide 174 (SEQ ID NO:2238), the design of which is described in the Examples. In some embodiments, the gNA variant adds a new function to the RNP comprising the gNA variant. In some embodiments, the gNA variant has an improved characteristic selected from: improved stability; improved solubility; improved transcription of the gNA; improved resistance to nuclease activity; increased folding rate of the gNA; decreased side product formation during folding; increased productive folding; improved binding affinity to a CasX protein; improved binding affinity to a target DNA when complexed with a CasX protein; improved gene editing when complexed with a CasX protein; improved specificity of editing when complexed with a CasX protein; and improved ability to utilize a greater spectrum of one or more PAM sequences, including ATC, CTC, GTC, or TTC, in the editing of target DNA when complexed with a CasX protein, or any combination thereof. In some cases, the one or more of the improved characteristics of the gNA variant is at least about 1.1 to about 100,000-fold improved relative to the reference gNA of SEQ ID NO:4 or SEQ ID NO:5. In other cases, the one or more improved characteristics of the gNA variant is at least about 1.1, at least about 10, at least about 100, at least about 1000, at least about 10,000, at least about 100,000-fold or more improved relative to the reference gNA of SEQ ID NO:4 or SEQ ID NO:5. In other cases, the one or more of the improved characteristics of the gNA variant is about 1.1 to 100,00-fold, about 1.1 to 10,00-fold, about 1.1 to 1,000-fold, about 1.1 to 500-fold, about 1.1 to 100-fold, about 1.1 to 50-fold, about 1.1 to 20-fold, about 10 to 100,00-fold, about 10 to 10,00-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100,00-fold, about 100 to 10,00-fold, about 100 to 1,000-fold, about 100 to 500-fold, about 500 to 100,00-fold, about 500 to 10,00-fold, about 500 to 1,000-fold, about 500 to 750-fold, about 1,000 to 100,00-fold, about 10,000 to 100,00-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to the reference gNA of SEQ ID NO:4 or SEQ ID NO:5. In other cases, the one or more improved characteristics of the gNA variant is about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475-fold, or 500-fold improved relative to the reference gNA of SEQ ID NO:4 or SEQ ID NO:5.

In some embodiments, a gNA variant can be created by subjecting a reference gRNA to a one or more mutagenesis methods, such as the mutagenesis methods described herein, below, which may include Deep Mutational Evolution (DME), deep mutational scanning (DMS), error prone PCR, cassette mutagenesis, random mutagenesis, staggered extension PCR, gene shuffling, or domain swapping, in order to generate the gNA variants of the disclosure. The activity of reference gRNAs may be used as a benchmark against which the activity of gNA variants are compared, thereby measuring improvements in function of gNA variants. In other embodiments, a reference gRNA may be subjected to one or more deliberate, targeted mutations, substitutions, or domain swaps in order to produce a gNA variant, for example a rationally designed variant. Exemplary gRNA variants produced by such methods are described in the Examples and representative sequences of gNA scaffolds are presented in Table 2.

In some embodiments, the gNA variant comprises one or more modifications compared to a reference guide nucleic acid scaffold sequence, wherein the one or more modification is selected from: at least one nucleotide substitution in a region of the gNA variant; at least one nucleotide deletion in a region of the gNA variant; at least one nucleotide insertion in a region of the gNA variant; a substitution of all or a portion of a region of the gNA variant; a deletion of all or a portion of a region of the gNA variant; or any combination of the foregoing. In some cases, the modification is a substitution of 1 to 15 consecutive or non-consecutive nucleotides in the gNA variant in one or more regions. In other cases, the modification is a deletion of 1 to 10 consecutive or non-consecutive nucleotides in the gNA variant in one or more regions. In other cases, the modification is an insertion of 1 to 10 consecutive or non-consecutive nucleotides in the gNA variant in one or more regions. In other cases, the modification is a substitution of the scaffold stem loop or the extended stem loop with an RNA stem loop sequence from a heterologous RNA source with proximal 5' and 3' ends. In some cases, a gNA variant of the disclosure comprises two or more modifications in one region. In other cases, a gNA variant of the disclosure comprises modifications in two or more regions. In other cases, a gNA variant comprises any combination of the foregoing modifications described in this paragraph.

In some embodiments, a 5' G is added to a gNA variant sequence for expression in vivo, as transcription from a U6 promoter is more efficient and more consistent with regard to the start site when the +1 nucleotide is a G. In other embodiments, two 5' Gs are added to a gNA variant sequence for in vitro transcription to increase production efficiency, as T7 polymerase strongly prefers a G in the +1 position and a purine in the +2 position. In some cases, the 5' G bases are added to the reference scaffolds of Table 1. In other cases, the 5' G bases are added to the variant scaffolds of Table 2.

Table 2 provides exemplary gNA variant scaffold sequences. In Table 2, (−) indicates a deletion at the specified position(s) relative to the reference sequence of SEQ ID NO:5, (+) indicates an insertion of the specified base(s) at the position indicated relative to SEQ ID NO:5, (:) indicates the range of bases at the specified start:stop coordinates of a deletion or substitution relative to SEQ ID NO:5, and multiple insertions, deletions or substitutions are separated by commas; e.g., A14C, U17G. In some embodiments, the gNA variant scaffold comprises any one of the sequences listed in Table 2, SEQ ID NOS:2101-2280, or a sequence having at least about 50%, at least about 60%, at least about 70%, at least about 80%, at least about 90%, at least about 95%, at least about 95%, at least about 96%, at least about 97%, at least about 98%, at least about 99% sequence identity thereto. It will be understood that in those embodiments wherein a vector comprises a DNA encoding sequence for a gNA, or where a gNA is a gDNA or a chimera of RNA and DNA, that thymine (T) bases can be substituted for the uracil (U) bases of any of the gNA sequence embodiments described herein.

TABLE 2

Exemplary gNA Scaffold Sequences

| SEQ ID NO: | NAME or Modification | NUCLEOTIDE SEQUENCE |
|---|---|---|
| 2101 | phage replication stable | UACUGGCGCUUUUAUCUCAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2102 | Kissing loop_b1 | UACUGGCGCUUUUAUCUCAUUACUUUGAGAGCCAUCACCAGCGACUAUGUCGUAUGGGUAAAGCGCUGCUCGACGCGUCCUCGAGCAGAAGCAUCAAAG |
| 2103 | Kissing loop_a | UACUGGCGCUUUUAUCUCAUUACUUUGAGAGCCAUCACCAGCGACUAUGUCGUAUGGGUAAAGCGCUGCUCGCUCCGUUCGAGCAGAAGCAUCAAAG |
| 2104 | 32: uvsX hairpin | GUACUGGCGCUUUUAUCUCAUUACUUUGAGAGCCAUCACCAGCGACUAUGUCGUAUGGGUAAAGCGCCCUCUUCGGAGGGAAGCAUCAAAG |
| 2105 | PP7 | UACUGGCGCUUUUAUCUCAUUACUUUGAGAGCCAUCACCAGCGACUAUGUCGUAUGGGUAAAGCGCAGGAGUUUCUAUGGAAACCCUGAAGCAUCAAAG |
| 2106 | 64: trip mut, extended stem truncation | GUACUGGCGCCUUUAUCUCAUUACUUUGAGAGCCAUCACCAGCGACUAUGUCGUAUGGGUAAAGCGCUUACGGACUUCGGUCCGUAAGAAGCAUCAAAG |
| 2107 | hyperstable tetraloop | UACUGGCGCUUUUAUCUCAUUACUUUGAGAGCCAUCACCAGCGACUAUGUCGUAUGGGUAAAGCGCUGCGCUUGCGCAGAAGCAUCAAAG |
| 2108 | C18G | UACUGGCGCUUUUAUCUGAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2109 | U17G | UACUGGCGCUUUUAUCGCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2110 | CUUCGG loop | UACUGGCGCUUUUAUCUCAUUACUUUGAGAGCCAUCACCAGCGACUAUGUCGUAUGGGUAAAGCGCUUAUUUAUCGGAGACUUCGGUCCGAUAAAUAAGAAGCAUCAAAG |
| 2111 | MS2 | UACUGGCGCUUUUAUCUCAUUACUUUGAGAGCCAUCACCAGCGACUAUGUCGUAUGGGUAAAGCGCACAUGAGGAUUACCCAUGUGAAGCAUCAAAG |
| 2112 | −1, A2G, −78, G77U | GCUGGCGCUUUUAUCUCAUUACUUUGAGAGCCAUCACCAGCGACUAUGUCGUAUGGGUAAAGCGCUUAUUUAUCGUGAGAAAUCCGAUAAAUAAGAAGCAUCAAAG |

TABLE 2-continued

| Exemplary qNA Scaffold Sequences | | |
|---|---|---|
| SEQ ID NO: | NAME or Modification | NUCLEOTIDE SEQUENCE |
| 2113 | QB | UACUGGCGCUUUUAUCUCAUUACUUUGAGAGCCAUCACCAGCGACUAUGUCGUAUGGGUAAAGCGCUGCAUGUCUAAGACAGCAGAAGCAUCAAAG |
| 2114 | 45, 44 hairpin | UACUGGCGCUUUUAUCUCAUUACUUUGAGAGCCAUCACCAGCGACUAUGUCGUAUGGGUAAAGCGCAGGGCUUCGGCCGAAGCAUCAAAG |
| 2115 | U1A | UACUGGCGCUUUUAUCUCAUUACUUUGAGAGCCAUCACCAGCGACUAUGUCGUAUGGGUAAAGCGCAAUCCAUUGCACUCCGGAUUGAAGCAUCAAAG |
| 2116 | A14C, U17G | UACUGGCGCUUUUCUCGCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2117 | CUUCGG loop modified | UACUGGCGCUUUUAUCUCAUUACUUUGAGAGCCAUCACCAGCGACUAUGUCGUAUGGGUAAAGCGCUUAUUUAUCGGACUUCGGUCCGAUAAAUAAGAAGCAUCAAAG |
| 2118 | Kissing loop_b2 | UACUGGCGCUUUUAUCUCAUUACUUUGAGAGCCAUCACCAGCGACUAUGUCGUAUGGGUAAAGCGCUGCUCGUUUGCGGCUACGAGCAGAAGCAUCAAAG |
| 2119 | -76:78, -83:87 | UACUGGCGCUUUUAUCUCAUUACUUUGAGAGCCAUCACCAGCGACUAUGUCGUAUGGGUAAAGCGCUUAUUUAUCGAGAGAUAAAUAAGAAGCAUCAAAG |
| 2120 | -4 | UACGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2121 | extended stem truncation | UACUGGCGCCUUUUAUCUCAUUACUUUGAGAGCCAUCACCAGCGACUAUGUCGUAUGGGUAAAGCGCUUACGGACUUCGGUCCGUAAGAAGCAUCAAAG |
| 2122 | C55 | UACUGGCGCUUUUAUCUCAUUACUUUGAGAGCCAUCACCAGCGACUAUGUCGUAUCGGUAAAGCGCUUAUUUAUCGGAGAGAAAUCCGAUAAAUAAGAAGCAUCAAAG |
| 2123 | trip mut | UACUGGCGCCUUUAUCUCAUUACUUUGAGAGCCAUCACCAGCGACUAUGUCGUAUGGGUAAAGCGCUUAUUUAUCGGACUUCGGUCCGAUAAAUAAGAAGCAUCAAAG |
| 2124 | -76:78 | UACUGGCGCUUUUAUCUCAUUACUUUGAGAGCCAUCACCAGCGACUAUGUCGUAUGGGUAAAGCGCUUAUUUAUCGAGAAAUCCGAUAAAUAAGAAGCAUCAAAG |
| 2125 | -1:5 | GCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2126 | -83:87 | UACUGGCGCUUUUAUCUCAUUACUUUGAGAGCCAUCACCAGCGACUAUGUCGUAUGGGUAAAGCGCUUAUUUAUCGGAGAGAGAUAAAUAAGAAGCAUCAAAG |
| 2127 | =+G28, A82U, -84, | UACUGGCGCUUUUAUCUCAUUACUUUGGAGAGCCAUCACCAGCGACUAUGUCGUAUGGGUAAAGCGCUUAUUUAUCGGAGAGUAUCCGAUAAAUAAGAAGCAUCAAAG |
| 2128 | =+51U | UACUGGCGCUUUUAUCUCAUUACUUUGAGAGCCAUCACCAGCGACUAUGUUCGUAUGGGUAAAGCGCUUAUUUAUCGGAGAGAAAUCCGAUAAAUAAGAAGCAUCAAAG |
| 2129 | -1:4, +G5A, +G86, | AGCGCUUUUAUCUCAUUACUUUGAGAGCCAUCACCAGCGACUAUGUCGUAUGGGUAAAGCGCUUAUUUAUCGGAGAGAAAUGCCGAUAAAUAAGAAGCAUCAAAG |
| 2130 | =+A94 | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAAUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2131 | =+G72 | UACUGGCGCUUUUAUCUCAUUACUUUGAGAGCCAUCACCAGCGACUAUGUCGUAUGGGUAAAGCGCUUAUUGUAUCGGAGAGAAAUCCGAUAAAUAAGAAGCAUCAAAG |
| 2132 | shorten front, CUUCGG loop modified, extend extended | GCGCUUUUAUCUCAUUACUUUGAGAGCCAUCACCAGCGACUAUGUCGUAUGGGUAAAGCGCUUAUUUAUCGGACUUCGGUCCGAUAAAUAAGCGCAUCAAAG |
| 2133 | A14C | UACUGGCGCUUUUCUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2134 | -1:3, +G3 | GUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2135 | =+C45, +U46 | UACUGGCGCUUUUAUCUCAUUACUUUGAGAGCCAUCACCAGCGACCUUAUGUCGUAUGGGUAAAGCGCUUAUUUAUCGGAGAGAAAUCCGAUAAAUAAGAAGCAUCAAAG |
| 2136 | CUUCGG loop modified, fun start | GAUGGCGCUUUUAUCUCAUUACUUUGAGAGCCAUCACCAGCGACUAUGUCGUAUGGGUAAAGCGCUUAUUUAUCGGACUUCGGUCCGAUAAAUAAGAAGCAUCAAAG |
| 2137 | -93:94 | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAAGAAGCAUCAAAG |
| 2138 | =+U45 | UACUGGCGCUUUUAUCUCAUUACUUUGAGAGCCAUCACCAGCGAUCUAUGUCGUAUGGGUAAAGCGCUUAUUUAUCGGAGAGAAAUCCGAUAAAUAAGAAGCAUCAAAG |
| 2139 | -69, -94 | UACUGGCGCUUUUAUCUCAUUACUUUGAGAGCCAUCACCAGCGACUAUGUCGUAUGGGUAAAGGCUUAUUUAUCGGAGAGAAAUCCGAUAAAAAGAAGCAUCAAAG |
| 2140 | -94 | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAAAGAAGCAUCAAAG |
| 2141 | modified CUUCGG, minus U in 1st triplex | UACUGGCGCUUUAUCUCAUUACUUUGAGAGCCAUCACCAGCGACUAUGUCGUAUGGGUAAAGCGCUUAUUUAUCGGACUUCGGUCCGAUAAAUAAGAAGCAUCAAAG |
| 2142 | -1:4, +C4, A14C, U17G, +G72, -76:78, -83:87 | CGGCGCUUUUCUCGCAUUACUUUGAGAGCCAUCACCAGCGACUAUGUCGUAUGGGUAAAGCGCUUAUUGUAUCGAGAGAUAAAUAAGAAGCAUCAAAG |
| 2143 | U1C, -73 | CACUGGCGCUUUUAUCUCAUUACUUUGAGAGCCAUCACCAGCGACUAUGUCGUAUGGGUAAAGCGCUUAUUUUCGGAGAGAAAUCCGAUAAAUAAGAAGCAUCAAAG |
| 2144 | Scaffold uuCG, stem uuCG. Stem swap, t shorten | UACUGGCGCUUUAUCUCAUUACUUUGAGAGCCAUCACCAGCGACUUCGGUCGUAUGGGUAAAGCGCUUAUGUAUCGGCUUCGGCCGAUACAUAAGAAGCAUCAAAG |
| 2145 | Scaffold uuCG, stem uuCG. Stem swap | UACUGGCGCUUUUAUCUCAUUACUUUGAGAGCCAUCACCAGCGACUUCGGUCGUAUGGGUAAAGCGCUUAUGUAUCGGCUUCGGCCGAUACAUAAGAAGCAUCAAAG |
| 2146 | =+G60 | UACUGGCGCUUUUAUCUCAUUACUUUGAGAGCCAUCACCAGCGACUAUGUCGUAUGGGUGAAAGCGCUUAUUUAUCGGAGAGAAAUCCGAUAAAUAAGAAGCAUCAAAG |

TABLE 2-continued

| Exemplary gNA Scaffold Sequences | | |
|---|---|---|
| SEQ ID NO: | NAME or Modification | NUCLEOTIDE SEQUENCE |
| 2147 | no stem Scaffold uuCG | UACUGGCGCUUUUAUCUCAUUACUUUGAGAGCCAUCACCAGCGACUU CGGUCGUAUGGGUAAAG |
| 2148 | no stem Scaffold uuCG, fun start | GAUGGGCUUUUAUCUCAUUACUUUGAGAGCCAUCACCAGCGACUUCG GUCGUAUGGGUAAAG |
| 2149 | Scaffold uuCG, stem uuCG, fun start | GAUGGGCUUUUAUCUCAUUACUUUGAGAGCCAUCACCAGCGACUUCG GUCGUAUGGGUAAAGCGCUUAUUUAUCGGCUUCGGCCGAUAAAUAAG AAGCAUCAAAG |
| 2150 | Pseudoknots | UACUGGCGCUUUUAUCUCAUUACUUUGAGAGCCAUCACCAGCGACUA UGUCGUAUGGGUAAAGCGCUACACUGGGAUCGCUGAAUUAGAGAUCG GCGUCCUUUCAUUCUAUAUACUUUGGAGUUUUAAAAUGUCUCUAAGU ACAGAAGCAUCAAAG |
| 2151 | Scaffold uuCG, stem uuCG | GGCGCUUUUAUCUCAUUACUUUGAGAGCCAUCACCAGCGACUUCGGU CGUAUGGGUAAAGCGCUUAUUUAUCGGCUUCGGCCGAUAAAUAAGAA GCAUCAAAG |
| 2152 | Scaffold uuCG, stem uuCG, no start | GCUGGCGCUUUUAUCUCAUUACUUUGAGAGCCAUCACCAGCGACUUC GGUCGUAUGGGUAAAGCGCUUAUUUAUCGGCUUCGGCCGAUAAAUAA GAAGCAUCAAAG |
| 2153 | Scaffold uuCG | UACUGGCGCUUUUAUCUCAUUACUUUGAGAGCCAUCACCAGCGACUU CGGUCGUAUGGGUAAAGCGCUUAUUUAUCGGAGAGAAAUCCGAUAAA UAAGAAGCAUCAAAG |
| 2154 | =+GCUC36 | UACUGGCGCUUUUAUCUCAUUACUUUGAGAGCCAUGCUCCACCAGCG ACUAUGUCGUAUGGGUAAAGCGCUUAUUUAUCGGAGAGAAAUCCGAU AAAUAAGAAGCAUCAAAG |
| 2155 | G quadriplex telomere basket + ends | UACUGGCGCUUUUAUCUCAUUACUUUGAGAGCCAUCACCAGCGACUA UGUCGUAUGGGUAAAGCGGGGUUAGGGUUAGGGUUAGGGAAGCAUCA AAG |
| 2156 | G quadriplex M3q | UACUGGCGCUUUUAUCUCAUUACUUUGAGAGCCAUCACCAGCGACUA UGUCGUAUGGGUAAAGCGGAGGGAGGGAGGGAGAGGGAAAGCAUCAA AG |
| 2157 | G quadriplex telomere basket no ends | UACUGGCGCUUUUAUCUCAUUACUUUGAGAGCCAUCACCAGCGACUA UGUCGUAUGGGUAAAGCGUUGGGUUAGGGUUAGGGUUAGGGAAAAGC AUCAAAG |
| 2158 | 45, 44 hairpin (old version) | UACUGGCGCUUUUAUCUCAUUACUUUGAGAGCCAUCACCAGCGACUA UGUCGUAUGGGUAAAGCGC--------AGGGCUUCGGCCG------- --GAAGCAUCAAAG |
| 2159 | Sarcin-ricin loop | UACUGGCGCUUUUAUCUCAUUACUUUGAGAGCCAUCACCAGCGACUA UGUCGUAUGGGUAAAGCGCCUGCUCAGUACGAGAGGAACCGCAGGAA GCAUCAAAG |
| 2160 | uvsX, C18G | UACUGGCGCUUUUAUCUGAUUACUUUGAGAGCCAUCACCAGCGACUA UGUCGUAUGGGUAAAGCGCCCUCUUCGGAGGGAAGCAUCAAAG |
| 2161 | truncated stem loop, C18G, trip mut (U10C) | UACUGGCGCCUUUAUCUGAUUACUUUGAGAGCCAUCACCAGCGACUA UGUCGUAUGGGUAAAGCGCUUACGGACUUCGGUCCGUAAGAAGCAUC AAAG |
| 2162 | short phage rep, C18G | UACUGGCGCUUUUAUCUGAUUACUUUGAGAGCCAUCACCAGCGACUA UGUCGUAUGGGUAAAGCGCGGACGACCUCUCGGUCGUCCGAAGCAUC AAAG |
| 2163 | phage rep loop, C18G | UACUGGCGCUUUUAUCUGAUUACUUUGAGAGCCAUCACCAGCGACUA UGUCGUAUGGGUAAAGCGCAGGUGGGACGACCUCUCGGUCGUCCUAU CUGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2164 | =+G18, stacked onto 64 | UACUGGCGCCUUUAUCUGCAUUACUUUGAGAGCCAUCACCAGCGACUAUGUCGUAUGGGUAAAGCGCUUACGGACUUCGGUCCGUAAGAAGCAUCAAAG |
| 2165 | truncated stem loop, C18G, -1 A2G | GCUGGCGCUUUUAUCUGAUUACUUUGAGAGCCAUCACCAGCGACUAUGUCGUAUGGGUAAAGCGCUUACGGACUUCGGUCCGUAAGAAGCAUCAAAG |
| 2166 | phage rep loop, C18G, trip mut (U10C) | UACUGGCGCCUUUAUCUGAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2167 | short phage rep, C18G, trip mut (U10C) | UACUGGCGCCUUUAUCUGAUUACUUUGAGAGCCAUCACCAGCGACUAUGUCGUAUGGGUAAAGCGCGGACGACCUCUCGGUCGUCCGAAGCAUCAAAG |
| 2168 | uvsX, trip mut (U10C) | UACUGGCGCCUUUAUCUCAUUACUUUGAGAGCCAUCACCAGCGACUAUGUCGUAUGGGUAAAGCGCCCUCUUCGGAGGGAAGCAUCAAAG |
| 2169 | truncated stem loop | UACUGGCGCUUUUAUCUCAUUACUUUGAGAGCCAUCACCAGCGACUAUGUCGUAUGGGUAAAGCGCUUACGGACUUCGGUCCGUAAGAAGCAUCAAAG |
| 2170 | =+A17, stacked onto 64 | UACUGGCGCCUUUAUCAUCAUUACUUUGAGAGCCAUCACCAGCGACUAUGUCGUAUGGGUAAAGCGCUUACGGACUUCGGUCCGUAAGAAGCAUCAAAG |
| 2171 | 3' HDV genomic ribozyme | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGGGCCGGCAUGGUCCCAGCCUCCUCGCUGGCGCCGGCUGGGCAACAUUCCGAGGGGACCGUCCCCUCGGUAAUGGCGAAUGGGACCC |
| 2172 | phage rep loop, trip mut (U10C) | UACUGGCGCCUUUAUCUCAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2173 | -79:80 | UACUGGCGCUUUUAUCUCAUUACUUUGAGAGCCAUCACCAGCGACUAUGUCGUAUGGGUAAAGCGCUUAUUUAUCGGAGAAAUCCGAUAAAUAAGAAGCAUCAAAG |
| 2174 | short phage rep, trip mut (U10C) | UACUGGCGCCUUUAUCUCAUUACUUUGAGAGCCAUCACCAGCGACUAUGUCGUAUGGGUAAAGCGCGGACGACCUCUCGGUCGUCCGAAGCAUCAAAG |
| 2175 | extra truncated stem loop | UACUGGCGCUUUUAUCUCAUUACUUUGAGAGCCAUCACCAGCGACUAUGUCGUAUGGGUAAAGCGCCGGACUUCGGUCCGGAAGCAUCAAAG |
| 2176 | U17G, C18G | UACUGGCGCUUUUAUCGGAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2177 | short phage rep | UACUGGCGCUUUUAUCUCAUUACUUUGAGAGCCAUCACCAGCGACUAUGUCGUAUGGGUAAAGCGCGGACGACCUCUCGGUCGUCCGAAGCAUCAAAG |
| 2178 | uvsX, C18G, -1 A2G | GCUGGCGCUUUUAUCUGAUUACUUUGAGAGCCAUCACCAGCGACUAUGUCGUAUGGGUAAAGCGCCCUCUUCGGAGGGAAGCAUCAAAG |
| 2179 | uvsX, C18G, trip mut (U10C), -1 A2G, HDV -99 G65U | GCUGGCGCCUUUAUCUGAUUACUUUGAGAGCCAUCACCAGCGACUAUGUCGUAUGGGUAAAGCUCCCUCUUCGGAGGGAGCAUCAAAG |
| 2180 | 3' HDV antigenomic ribozyme | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGGGGUCGGCAUGGCAUCUCCACCUCCUCGCGGUCCGACCUGGGCAUCCGAAGGAGGACGCACGUCCACUCGGAUGGCUAAGGGAGAGCCA |

TABLE 2-continued

| SEQ ID NO: | NAME or Modification | NUCLEOTIDE SEQUENCE |
|---|---|---|
| Exemplary gNA Scaffold Sequences | | |
| 2181 | uvsX, C18G, trip mut (U10C), -1 A2G, HDV AA(98:99)C | GCUGGCGCCUUUAUCUGAUUACUUUGAGAGCCAUCACCAGCGACUAUGUCGUAUGGGUAAAGCGCCCUCUUCGGAGGGCGCAUCAAAG |
| 2182 | 3' HDV ribozyme (Lior Nissim, Timothy Lu) | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGUUUUGGCCGGCAUGGUCCCAGCCUCCUCGCUGGCGCCGGCUGGGCAACAUGCUUCGGCAUGGCGAAUGGGACCCCGGG |
| 2183 | TAC(1:3)GA, stacked onto 64 | GAUGGCGCCUUUAUCUCAUUACUUUGAGAGCCAUCACCAGCGACUAUGUCGUAUGGGUAAAGCGCUUACGGACUUCGGUCCGUAAGAAGCAUCAAAG |
| 2184 | uvsX, -1 A2G | GCUGGCGCUUUUAUCUCAUUACUUUGAGAGCCAUCACCAGCGACUAUGUCGUAUGGGUAAAGCGCCCUCUUCGGAGGGAAGCAUCAAAG |
| 2185 | truncated stem loop, C18G, trip mut (U10C), -1 A2G, HDV -99 G65U | GCUGGCGCCUUUAUCUGAUUACUUUGAGAGCCAUCACCAGCGACUAUGUCGUAUGGGUAAAGCUCUUACGGACUUCGGUCCGUAAGAGCAUCAAAG |
| 2186 | short phage rep, C18G, trip mut (U10C), -1 A2G, HDV -99 G65U | GCUGGCGCCUUUAUCUGAUUACUUUGAGAGCCAUCACCAGCGACUAUGUCGUAUGGGUAAAGCUCGGACGACCUCUCGGUCGUCCGAGCAUCAAAG |
| 2187 | 3' sTRSV WT viral Hammerhead ribozyme | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGCCUGUCACCGGAUGUGCUUUCCGGUCUGAUGAGUCCGUGAGGACGAAACAGG |
| 2188 | short phage rep, C18G, -1 A2G | GCUGGCGCUUUUAUCUGAUUACUUUGAGAGCCAUCACCAGCGACUAUGUCGUAUGGGUAAAGCGCGGACGACCUCUCGGUCGUCCGAAGCAUCAAAG |
| 2189 | short phage rep, C18G, trip mut (U10C), -1 A2G, 3' genomic HDV | GCUGGCGCCUUUAUCUGAUUACUUUGAGAGCCAUCACCAGCGACUAUGUCGUAUGGGUAAAGCGCGGACGACCUCUCGGUCGUCCGAAGCAUCAAAG |
| 2190 | phage rep loop, C18G, trip mut (U10C), -1 A2G, HDV -99 G65U | GCUGGCGCCUUUAUCUGAUUACUUUGAGAGCCAUCACCAGCGACUAUGUCGUAUGGGUAAAGCUCAGGUGGGACGACCUCUCGGUCGUCCUAUCUGAGCAUCAAAG |
| 2191 | 3' HDV ribozyme (Owen Ryan, Jamie Cate) | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGGAUGGCCGGCAUGGUCCCAGCCUCCUCGCUGGCGCCGGCUGGGCAACACCUUCGGGUGGCGAAUGGGAC |
| 2192 | phage rep loop, C18G, -1 A2G | GCUGGCGCUUUUAUCUGAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2193 | 0.14 | UACUGGCGCUUUUAUCUCAUUACUUUGAGAGCCAUCACCAGCGACUAUGUCGUACUGGGUAAAGCGCUUAUUUAUCGGAGAGAAAUCCGAUAAAUAAGAAGCAUCAAAG |
| 2194 | -78, G77U | UACUGGCGCUUUUAUCUCAUUACUUUGAGAGCCAUCACCAGCGACUAUGUCGUAUGGGUAAAGCGCUUAUUUAUCGUGAGAAAUCCGAUAAAUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2195 | | GUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2196 | short phage rep, -1 A2G | GCUGGCGCUUUUAUCUCAUUACUUUGAGAGCCAUCACCAGCGACUAUGUCGUAUGGGUAAAGCGCGGACGACCUCUCGGUCGUCCGAAGCAUCAAAG |
| 2197 | truncated stem loop, C18G, trip mut (U10C), -1 A2G | GCUGGCGCCUUUAUCUGAUUACUUUGAGAGCCAUCACCAGCGACUAUGUCGUAUGGGUAAAGCGCUUACGGACUUCGGUCCGUAAGAAGCAUCAAAG |
| 2198 | -1, A2G | GCUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2199 | truncated stem loop, trip mut (U10C), -1 A2G | GCUGGCGCCUUUAUCUCAUUACUUUGAGAGCCAUCACCAGCGACUAUGUCGUAUGGGUAAAGCGCUUACGGACUUCGGUCCGUAAGAAGCAUCAAAG |
| 2200 | uvsX, C18G, trip mut (U10C), -1 A2G | GCUGGCGCCUUUAUCUGAUUACUUUGAGAGCCAUCACCAGCGACUAUGUCGUAUGGGUAAAGCGCCCUCUUCGGAGGGAAGCAUCAAAG |
| 2201 | phage rep loop, -1 A2G | GCUGGCGCUUUUAUCUCAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2202 | phage rep loop, trip mut (U10C), -1 A2G | GCUGGCGCCUUUAUCUCAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2203 | phage rep loop, C18G, trip mut (U10C), -1 A2G | GCUGGCGCCUUUAUCUGAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2204 | truncated stem loop, C18G | UACUGGCGCUUUUAUCUGAUUACUUUGAGAGCCAUCACCAGCGACUAUGUCGUAUGGGUAAAGCGCUUACGGACUUCGGUCCGUAAGAAGCAUCAAAG |
| 2205 | uvsX, trip mut (U10C), -1 A2G | GCUGGCGCCUUUAUCUCAUUACUUUGAGAGCCAUCACCAGCGACUAUGUCGUAUGGGUAAAGCGCCCUCUUCGGAGGGAAGCAUCAAAG |
| 2206 | truncated stem loop, -1 A2G | GCUGGCGCUUUUAUCUCAUUACUUUGAGAGCCAUCACCAGCGACUAUGUCGUAUGGGUAAAGCGCUUACGGACUUCGGUCCGUAAGAAGCAUCAAAG |
| 2207 | short phage rep, trip mut (U10C), -1 A2G | GCUGGCGCCUUUAUCUCAUUACUUUGAGAGCCAUCACCAGCGACUAUGUCGUAUGGGUAAAGCGCGGACGACCUCUCGGUCGUCCGAAGCAUCAAAG |
| 2208 | 5' HDV ribozyme (Owen Ryan, Jamie Cate) | GAUGGCCGGCAUGGUCCCAGCCUCCUCGCUGGCGCCGGCUGGGCAACACCUUCGGGUGGCGAAUGGGACUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2209 | 5' HDV genomic ribozyme | GGCCGGCAUGGUCCCAGCCUCCUCGCUGGCGCCGGCUGGGCAACAUUCCGAGGGGACCGUCCCCUCGGUAAUGGCGAAUGGGACCCUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2210 | truncated stem loop, C18G, trip mut (U10C), -1 A2G, HDV AA(98:99)C | GCUGGCGCCUUUAUCUGAUUACUUUGAGAGCCAUCACCAGCGACUAUGUCGUAUGGGUAAAGCGCUUACGGACUUCGGUCCGUAAGCGCAUCAAAG |
| 2211 | 5' env25 pistol ribozyme (with an added CUUCGG loop) | CGUGGUUAGGGCCACGUUAAAUAGUUGCUUAAGCCCUAAGCGUUGAUCUUCGGAUCAGGUGCAAUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2212 | 5' HDV antigenomic ribozyme | GGGUCGGCAUGGCAUCUCCACCUCCUCGCGGUCCGACCUGGGCAUCCGAAGGAGGACGCACGUCCACUCGGAUGGCUAAGGGAGAGCCAUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2213 | 3' Hammerhead ribozyme (Lior Nissim, Timothy Lu) guide scaffold scar | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGCCAGUACUGAUGAGUCCGUGAGGACGAAACGAGUAAGCUCGUCUACUGGCGCUUUUAUCUCAU |
| 2214 | =+A27, stacked onto 64 | UACUGGCGCCUUUAUCUCAUUACUUUAGAGAGCCAUCACCAGCGACUAUGUCGUAUGGGUAAAGCGCUUACGGACUUCGGUCCGUAAGAAGCAUCAAAG |
| 2215 | 5' Hammerhead ribozyme (Lior Nissim, Timothy Lu) smaller scar | CGACUACUGAUGAGUCCGUGAGGACGAAACGAGUAAGCUCGUCUAGUCGUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2216 | phage rep loop, C18G, trip mut (U10C), -1 A2G, HDV AA(98:99)C | GCUGGCGCCUUUAUCUGAUUACUUUGAGAGCCAUCACCAGCGACUAUGUCGUAUGGGUAAAGCGCAGGUGGGACGACCUCUCGGUCGUCCUAUCUGCGCAUCAAAG |
| 2217 | -27, stacked onto 64 | UACUGGCGCCUUUAUCUCAUUACUUUAGAGCCAUCACCAGCGACUAUGUCGUAUGGGUAAAGCGCUUACGGACUUCGGUCCGUAAGAAGCAUCAAAG |
| 2218 | 3' Hatchet | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGCAUUCCUCAGAAAAUGACAAACCUGUGGGGCGUAAGUAGAUCUUCGGAUCUAUGAUCGUGCAGACGUUAAAAUCAGGU |
| 2219 | 3' Hammerhead ribozyme (Lior Nissim, Timothy Lu) | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGCGACUACUGAUGAGUCCGUGAGGACGAAACGAGUAAGCUCGUCUAGUCGCGUGUAGCGAAGCA |
| 2220 | 5' Hatchet | CAUUCCUCAGAAAAUGACAAACCUGUGGGGCGUAAGUAGAUCUUCGGAUCUAUGAUCGUGCAGACGUUAAAAUCAGGUUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2221 | 5' HDV ribozyme (Lior Nissim, Timothy Lu) | UUUUGGCCGGCAUGGUCCCAGCCUCCUCGCUGGCGCCGGCUGGGCAACAUGCUUCGGCAUGGCGAAUGGGACCCCGGGUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |

TABLE 2-continued

| SEQ ID NO: | NAME or Modification | NUCLEOTIDE SEQUENCE |
|---|---|---|
| | Exemplary gNA Scaffold Sequences | |
| 2222 | 5' Hammerhead ribozyme (Lior Nissim, Timothy Lu) | CGACUACUGAUGAGUCCGUGAGGACGAAACGAGUAAGCUCGUCUAGU CGCGUGUAGCGAAGCAUACUGGCGCUUUUAUCUCAUUACUUUGAGAG CCAUCACCAGCGACUAUGUCGUAUGGGUAAAGCGCUUAUUUAUCGGA GAGAAAUCCGAUAAAUAAGAAGCAUCAAAG |
| 2223 | 3' HH15 Minimal Hammerhead ribozyme | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGGGGAGCCCCGCUGAUGAGGUCGGGGAGACCGAA AGGGACUUCGGUCCCUACGGGGCUCCC |
| 2224 | 5' RBMX recruiting motif | CCACCCCCACCACCACCCCCACCCCCACCACCACCCUACUGGCGCUU UUAUCUCAUUACUUUGAGAGCCAUCACCAGCGACUAUGUCGUAUGGG UAAAGCGCUUAUUUAUCGGAGAGAAAUCCGAUAAAUAAGAAGCAUCA AAG |
| 2225 | 3' Hammerhead ribozyme (Lior Nissim, Timothy Lu) smaller scar | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGCGACUACUGAUGAGUCCGUGAGGACGAAACGAG UAAGCUCGUCUAGUCG |
| 2226 | 3' env25 pistol ribozyme (with an added CUUCGG loop) | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGCGUGGUUAGGGCCACGUUAAAUAGUUGCUUAAG CCCUAAGCGUUGAUCUUCGGAUCAGGUGCAA |
| 2227 | 3' Env-9 Twister | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGGGCAAUAAAGCGGUUACAAGCCCGCAAAAAUAG CAGAGUAAUGUCGCGAUAGCGCGGCAUUAAUGCAGCUUUAUUG |
| 2228 | =+AUUAUC UCAUUACU 25 | UACUGGCGCUUUUAUCUCAUUACUAUUAUCUCAUUACUUUGAGAGCC AUCACCAGCGACUAUGUCGUAUGGGUAAAGCGCUUAUUUAUCGGAGA GAAAUCCGAUAAAUAAGAAGCAUCAAAG |
| 2229 | 5' Env-9 Twister | GGCAAUAAAGCGGUUACAAGCCCGCAAAAAUAGCAGAGUAAUGUCGC GAUAGCGCGGCAUUAAUGCAGCUUUAUUGUACUGGCGCUUUUAUCUC AUUACUUUGAGAGCCAUCACCAGCGACUAUGUCGUAUGGGUAAAGCG CUUAUUUAUCGGAGAGAAAUCCGAUAAAUAAGAAGCAUCAAAG |
| 2230 | 3' Twisted Sister 1 | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGACCCGCAAGGCCGACGGCAUCCGCCGCCGCUGG UGCAAGUCCAGCCGCCCCUUCGGGGGCGGGCGCUCAUGGGUAAC |
| 2231 | no stem | UACUGGCGCUUUUAUCUCAUUACUUUGAGAGCCAUCACCAGCGACUA UGUCGUAUGGGUAAAG |
| 2232 | 5' HH15 Minimal Hammerhead ribozyme | GGGAGCCCCGCUGAUGAGGUCGGGGAGACCGAAAGGGACUUCGGUCC CUACGGGGCUCCCUACUGGCGCUUUUAUCUCAUUACUUUGAGAGCCA UCACCAGCGACUAUGUCGUAUGGGUAAAGCGCUUAUUUAUCGGAGAG AAAUCCGAUAAAUAAGAAGCAUCAAAG |
| 2233 | 5' Hammerhead ribozyme (Lior Nissim, Timothy Lu) guide scaffold scar | CCAGUACUGAUGAGUCCGUGAGGACGAAACGAGUAAGCUCGUCUACU GGCGCUUUUAUCUCAUUACUGGCGCUUUUAUCUCAUUACUUUGAGAG CCAUCACCAGCGACUAUGUCGUAUGGGUAAAGCGCUUAUUUAUCGGA GAGAAAUCCGAUAAAUAAGAAGCAUCAAAG |
| 2234 | 5' Twisted Sister 1 | ACCCGCAAGGCCGACGGCAUCCGCCGCCGCUGGUGCAAGUCCAGCCG CCCCUUCGGGGGCGGGCGCUCAUGGGUAACUACUGGCGCUUUUAUCU CAUUACUUUGAGAGCCAUCACCAGCGACUAUGUCGUAUGGGUAAAGC GCUUAUUUAUCGGAGAGAAAUCCGAUAAAUAAGAAGCAUCAAAG |
| 2235 | 5' sTRSV WT viral Hammerhead ribozyme | CCUGUCACCGGAUGUGCUUUCCGGUCUGAUGAGUCCGUGAGGACGAA ACAGGUACUGGCGCUUUUAUCUCAUUACUUUGAGAGCCAUCACCAGC GACUAUGUCGUAUGGGUAAAGCGCUUAUUUAUCGGAGAGAAAUCCGA UAAAUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2236 | 148: =+G55, stacked onto 64 | GUACUGGCGCCUUUAUCUCAUUACUUUGAGAGCCAUCACCAGCGACUAUGUCGUAGUGGGUAAAGCGCUUACGGACUUCGGUCCGUAAGAAGCAUCAAAG |
| 2237 | 158: 103 + 148(+G55) -99, G65U | GUACUGGCGCUUUUAUCUGAUUACUUUGAGAGCCAUCACCAGCGACUAUGUCGUAGUGGGUAAAGCUCCCUCUUCGGAGGGAGCAUCAAAG |
| 2238 | 174: Uvsx Extended stem with [A99] G65U), C18G, G55, [GU-1] | ACUGGCGCUUUUAUCUGAUUACUUUGAGAGCCAUCACCAGCGACUAUGUCGUAGUGGGUAAAGCUCCCUCUUCGGAGGGAGCAUCAAAG |
| 2239 | 175: extended stem truncation, U10C, [GU-1] | ACUGGCGCCUUUAUCUCAUUACUUUGAGAGCCAUCACCAGCGACUAUGUCGUAUGGGUAAAGCGCUUACGGACUUCGGUCCGUAAGAAGCAUCAAAG |
| 2240 | 176: 174 with A1G substitution for T7 transcription | GCUGGCGCUUUUAUCUGAUUACUUUGAGAGCCAUCACCAGCGACUAUGUCGUAGUGGGUAAAGCUCCCUCUUCGGAGGGAGCAUCAAAG |
| 2241 | 177: 174 with bubble (+G55) removed | ACUGGCGCUUUUAUCUGAUUACUUUGAGAGCCAUCACCAGCGACUAUGUCGUAUGGGUAAAGCUCCCUCUUCGGAGGGAGCAUCAAAG |
| 2242 | 181: stem 42 (truncated stem loop); U10C, C18G, [GU-1] (95 + [GU-1]) | ACUGGCGCCUUUAUCUGAUUACUUUGAGAGCCAUCACCAGCGACUAUGUCGUAUGGGUAAAGCGCUUACGGACUUCGGUCCGUAAGAAGCAUCAAAG |
| 2243 | 182: stem 42 (truncated stem loop); C18G, [GU-1] | ACUGGCGCUUUUAUCUGAUUACUUUGAGAGCCAUCACCAGCGACUAUGUCGUAUGGGUAAAGCGCUUACGGACUUCGGUCCGUAAGAAGCAUCAAAG |
| 2244 | 183: stem 42 (truncated stem loop); C18G, G55, [GU-1] | ACUGGCGCUUUUAUCUGAUUACUUUGAGAGCCAUCACCAGCGACUAUGUCGUAGUGGGUAAAGCGCUUACGGACUUCGGUCCGUAAGAAGCAUCAAAG |
| 2245 | 184: stem 48 (uvsx, -99 g65t); C18G, T55, [GU-1] | ACUGGCGCUUUUAUCUGAUUACUUUGAGAGCCAUCACCAGCGACUAUGUCGUAUUGGGUAAAGCUCCCUCUUCGGAGGGAGCAUCAAAG |
| 2246 | 185: stem 42 (truncated stem loop); C18G, U55, [GU-1] | ACUGGCGCUUUUAUCUGAUUACUUUGAGAGCCAUCACCAGCGACUAUGUCGUAUUGGGUAAAGCGCUUACGGACUUCGGUCCGUAAGAAGCAUCAAAG |
| 2247 | 186: stem 42 (truncated stem loop); U10C, A17, [GU-1] | ACUGGCGCCUUUAUCAUCAUUACUUUGAGAGCCAUCACCAGCGACUAUGUCGUAUGGGUAAAGCGCUUACGGACUUCGGUCCGUAAGAAGCAUCAAAG |
| 2248 | 187: stem 46 (uvsx); C18G, G55, [GU-1] | ACUGGCGCUUUUAUCUGAUUACUUUGAGAGCCAUCACCAGCGACUAUGUCGUAGUGGGUAAAGCGCCCUCUUCGGAGGGAAGCAUCAAAG |

TABLE 2-continued

| Exemplary gNA Scaffold Sequences | | |
|---|---|---|
| SEQ ID NO: | NAME or Modification | NUCLEOTIDE SEQUENCE |
| 2249 | 188: stem 50 (ms2 U15C, -99, g65t); C18G, G55, [GU-1] | ACUGGCGCUUUUAUCUGAUUACUUUGAGAGCCAUCACCAGCGACUAUGUCGUAGUGGGUAAAGCUCACAUGAGGAUCACCCAUGUGAGCAUCAAAG |
| 2250 | 189: 174 + G8A; U15C; U35A | ACUGGCACUUUUACCUGAUUACUUUGAGAGCCAACACCAGCGACUAUGUCGUAGUGGGUAAAGCUCCCUCUUCGGAGGGAGCAUCAAAG |
| 2251 | 190: 174 + G8A | ACUGGCACUUUUAUCUGAUUACUUUGAGAGCCAUCACCAGCGACUAUGUCGUAGUGGGUAAAGCUCCCUCUUCGGAGGGAGCAUCAAAG |
| 2252 | 191: 174 + G8C | ACUGGCCCUUUUAUCUGAUUACUUUGAGAGCCAUCACCAGCGACUAUGUCGUAGUGGGUAAAGCUCCCUCUUCGGAGGGAGCAUCAAAG |
| 2253 | 192: 174 + U15C | ACUGGCGCUUUUACCUGAUUACUUUGAGAGCCAUCACCAGCGACUAUGUCGUAGUGGGUAAAGCUCCCUCUUCGGAGGGAGCAUCAAAG |
| 2254 | 193, 174 + U35A | ACUGGCGCUUUUAUCUGAUUACUUUGAGAGCCAACACCAGCGACUAUGUCGUAGUGGGUAAAGCUCCCUCUUCGGAGGGAGCAUCAAAG |
| 2255 | 195:175 + C18G + G8A; U15C; U35A | ACUGGCACCUUUACCUGAUUACUUUGAGAGCCAACACCAGGGACUAUGUCGUAUGGGUAAAGCGCUUACGGACUUCGGUCCGUAAGAAGCAUCAAAG |
| 2256 | 196: 175 + C18G + G8A | ACUGGCACCUUUAUCUGAUUACUUUGAGAGCCAUCACCAGCGACUAUGUCGUAUGGGUAAAGCGCUUACGGACUUCGGUCCGUAAGAAGCAUCAAAG |
| 2257 | 197: 175 + C18G + G8C | ACUGGCCCCUUUAUCUGAUUACUUUGAGAGCCAUCACCAGCGACUAUGUCGUAUGGGUAAAGCGCUUACGGACUUCGGUCCGUAAGAAGCAUCAAAG |
| 2258 | 198: 175 + C18G + U35A | ACUGGCGCCUUUAUCUGAUUACUUUGAGAGCCAACACCAGCGACUAUGUCGUAUGGGUAAAGCGCUUACGGACUUCGGUCCGUAAGAAGCAUCAAAG |
| 2259 | 199: 174 + A2G (test G transcription at start; ccGCT . . .) | GCUGGCGCUUUUAUCUGAUUACUUUGAGAGCCAUCACCAGCGACUAUGUCGUAGUGGGUAAAGCUCCCUCUUCGGAGGGAGCAUCAAAG |
| 2260 | 200: 174 + G1 (ccGACU . . .) | GACUGGCGCUUUUAUCUGAUUACUUUGAGAGCCAUCACCAGCGACUAUGUCGUAGUGGGUAAAGCUCCCUCUUCGGAGGGAGCAUCAAAG |
| 2261 | 201: 174 + U10C; G28 | ACUGGCGCCUUUAUCUGAUUACUUUGGAGAGCCAUCACCAGCGACUAUGUCGUAGUGGGUAAAGCUCCCUCUUCGGAGGGAGCAUCAAAG |
| 2262 | 202: 174 + U10A; A28U | ACUGGCGCAUUUAUCUGAUUACUUUGUGAGCCAUCACCAGCGACUAUGUCGUAGUGGGUAAAGCUCCCUCUUCGGAGGGAGCAUCAAAG |
| 2263 | 203: 174 + U10C | ACUGGCGCCUUUAUCUGAUUACUUUGAGAGCCAUCACCAGCGACUAUGUCGUAGUGGGUAAAGCUCCCUCUUCGGAGGGAGCAUCAAAG |
| 2264 | 204: 174 + G28 | ACUGGCGCUUUUAUCUGAUUACUUUGGAGAGCCAUCACCAGCGACUAUGUCGUAGUGGGUAAAGCUCCCUCUUCGGAGGGAGCAUCAAAG |
| 2265 | 205: 174 + U10A | ACUGGCGCAUUUAUCUGAUUACUUUGAGAGCCAUCACCAGCGACUAUGUCGUAGUGGGUAAAGCUCCCUCUUCGGAGGGAGCAUCAAAG |
| 2266 | 206, 174 + A28U | ACUGGCGCUUUUAUCUGAUUACUUUGUGAGCCAUCACCAGCGACUAUGUCGUAGUGGGUAAAGCUCCCUCUUCGGAGGGAGCAUCAAAG |
| 2267 | 207: 174 + U15 | ACUGGCGCUUUUAUUCUGAUUACUUUGAGAGCCAUCACCAGCGACUAUGUCGUAGUGGGUAAAGCUCCCUCUUCGGAGGGAGCAUCAAAG |
| 2268 | 208: 174 + [U4] | ACGGCGCUUUUAUCUGAUUACUUUGAGAGCCAUCACCAGCGACUAUGUCGUAGUGGGUAAAGCUCCCUCUUCGGAGGGAGCAUCAAAG |

TABLE 2-continued

Exemplary gNA Scaffold Sequences

| SEQ ID NO: | NAME or Modification | NUCLEOTIDE SEQUENCE |
|---|---|---|
| 2269 | 209: 174 + C16A | ACUGGCGCUUUUAUAUGAUUACUUUGAGAGCCAUCACCAGCGACUAU GUCGUAGUGGGUAAAGCUCCCUCUUCGGAGGGAGCAUCAAAG |
| 2270 | 210: 174 + U17 | ACUGGCGCUUUUAUCUUGAUUACUUUGAGAGCCAUCACCAGCGACUA UGUCGUAGUGGGUAAAGCUCCCUCUUCGGAGGGAGCAUCAAAG |
| 2271 | 211: 174 + U35G (compare with 174 + U35A above) | ACUGGCGCUUUUAUCUGAUUACUUUGAGAGCCAGCACCAGCGACUAU GUCGUAGUGGGUAAAGCUCCCUCUUCGGAGGGAGCAUCAAAG |
| 2272 | 212: 174 + U11G, A105G (A86G), U26C | ACUGGCGCUGUUAUCUGAUUACUUCGAGAGCCAUCACCAGCGACUAU GUCGUAGUGGGUAAAGCUCCCUCUUCGGAGGGAGCAUCGAAG |
| 2273 | 213: 174 + U11C, A105G (A86G), U26C | ACUGGCGCUCUUAUCUGAUUACUUCGAGAGCCAUCACCAGCGACUAU GUCGUAGUGGGUAAAGCUCCCUCUUCGGAGGGAGCAUCGAAG |
| 2274 | 214: 174 + U12G; A106G (A87G), U25C | ACUGGCGCUUGUAUCUGAUUACUCUGAGAGCCAUCACCAGCGACUAU GUCGUAGUGGGUAAAGCUCCCUCUUCGGAGGGAGCAUCAGAG |
| 2275 | 215: 174 + U12C; A106G (A87G), U25C | ACUGGCGCUUCUAUCUGAUUACUCUGAGAGCCAUCACCAGCGACUAU GUCGUAGUGGGUAAAGCUCCCUCUUCGGAGGGAGCAUCAGAG |
| 2276 | 216: 174_tx_11.G, 87.G, 22.C | ACUGGCGCUUUGAUCUGAUUACCUUGAGAGCCAUCACCAGCGACUAU GUCGUAGUGGGUAAAGCUCCCUCUUCGGAGGGAGCAUCAAGG |
| 2277 | 217: 174_tx_11.C, 87.G, 22.C | ACUGGCGCUUUCAUCUGAUUACCUUGAGAGCCAUCACCAGCGACUAU GUCGUAGUGGGUAAAGCUCCCUCUUCGGAGGGAGCAUCAAGG |
| 2278 | 218: 174 + U11G | ACUGGCGCUGUUAUCUGAUUACUUUGAGAGCCAUCACCAGCGACUAU GUCGUAGUGGGUAAAGCUCCCUCUUCGGAGGGAGCAUCAAAG |
| 2279 | 219: 174+ A105G (A86G) | ACUGGCGCUUUUAUCUGAUUACUUUGAGAGCCAUCACCAGCGACUAU GUCGUAGUGGGUAAAGCUCCCUCUUCGGAGGGAGCAUCGAAG |
| 2280 | 220: 174 + U26C | ACUGGCGCUUUUAUCUGAUUACUUCGAGAGCCAUCACCAGCGACUAU GUCGUAGUGGGUAAAGCUCCCUCUUCGGAGGGAGCAUCAAAG |

In some embodiments, the gNA variant comprises a tracrRNA stem loop comprising the sequence -UUU-N4-25-UUU- (SEQ ID NO: 34). For example, the gNA variant comprises a scaffold stem loop or a replacement thereof, flanked by two triplet U motifs that contribute to the triplex region. In some embodiments, the scaffold stem loop or replacement thereof comprises at least 4 nucleotides, at least 5 nucleotides, at least 6 nucleotides, at least 7 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, or at least 25 nucleotides.

In some embodiments, the gNA variant comprises a crRNA sequence with -AAAG- in a location 5' to the spacer region. In some embodiments, the -AAAG- sequence is immediately 5' to the spacer region.

In some embodiments, the at least one nucleotide modification to a reference gNA to produce a gNA variant comprises at least one nucleotide deletion in the CasX variant gNA relative to the reference gRNA. In some embodiments, a gNA variant comprises a deletion of 1, 2, 3, 4, 5, 6, 7, 8, 9, 10, 11, 12, 13, 14, 15, 16, 17, 18, 19 or 20 consecutive or non-consecutive nucleotides relative to a reference gNA. In some embodiments, the at least one deletion comprises a deletion of 1, 2, 3, 4, 5, 6, 7, 8, 9, 10, 11, 12, 13, 14, 15, 16, 17, 18, 19 or 20 or more consecutive nucleotides relative to a reference gNA. In some embodiments, the gNA variant comprises 2, 3, 4, 5, 6, 7, 8, 9, 10, 11, 12, 13, 14, 15, 16, 17, 18, 19 or 20 or more nucleotide deletions relative to the reference gNA, and the deletions are not in consecutive nucleotides. In those embodiments where there are two or more non-consecutive deletions in the gNA variant relative to the reference gRNA, any length of deletions, and any combination of lengths of deletions, as described herein, are contemplated as within the scope of the disclosure. For example, in some embodiments, a gNA variant may comprise a first deletion of one nucleotide, and a second deletion of two nucleotides and the two deletions are not consecutive. In some embodiments, a gNA variant comprises at least two deletions in different regions of the reference gRNA. In some embodiments, a gNA variant comprises at least two deletions in the same region of the reference gRNA. For example, the regions may be the extended stem loop, scaffold stem loop, scaffold stem bubble, triplex loop, pseudoknot, triplex, or a 5' end of the gNA variant. The deletion of any nucleotide in a reference gRNA is contemplated as within the scope of the disclosure.

In some embodiments, the at least one nucleotide modification of a reference gRNA to generate a gNA variant comprises at least one nucleotide insertion. In some embodiments, a gNA variant comprises an insertion of 1, 2, 3, 4, 5, 6, 7, 8, 9 or 10 consecutive or non-consecutive nucleotides relative to a reference gRNA. In some embodiments, the at least one nucleotide insertion comprises an insertion of 1, 2, 3, 4, 5, 6, 7, 8, 9, 10, 11, 12, 13, 14, 15, 16, 17, 18, 19 or 20 or more consecutive nucleotides relative to a reference gRNA. In some embodiments, the gNA variant comprises 2 or more insertions relative to the reference gRNA, and the insertions are not consecutive. In those embodiments where there are two or more non-consecutive insertions in the gNA variant relative to the reference gRNA, any length of insertions, and any combination of lengths of insertions, as described herein, are contemplated as within the scope of the disclosure. For example, in some embodiments, a gNA variant may comprise a first insertion of one nucleotide, and a second insertion of two nucleotides and the two insertions are not consecutive. In some embodiments, a gNA variant comprises at least two insertions in different regions of the reference gRNA. In some embodiments, a gNA variant comprises at least two insertions in the same region of the reference gRNA. For example, the regions may be the extended stem loop, scaffold stem loop, scaffold stem bubble, triplex loop, pseudoknot, triplex, or a 5' end of the gNA variant. Any insertion of A, G, C, U (or T, in the corresponding DNA) or combinations thereof at any location in the reference gRNA is contemplated as within the scope of the disclosure.

In some embodiments, the at least one nucleotide modification of a reference gRNA to generate a gNA variant comprises at least one nucleic acid substitution. In some embodiments, a gNA variant comprises 1, 2, 3, 4, 5, 6, 7, 8, 9, 10, 11, 12, 13, 14, 15, 16, 17, 18, 19 or 20 or more consecutive or non-consecutive substituted nucleotides relative to a reference gRNA. In some embodiments, a gNA variant comprises 1-4 nucleotide substitutions relative to a reference gRNA. In some embodiments, the at least one substitution comprises a substitution of 1, 2, 3, 4, 5, 6, 7, 8, 9, 10, 11, 12, 13, 14, 15, 16, 17, 18, 19 or 20 or more consecutive nucleotides relative to a reference gRNA. In some embodiments, the gNA variant comprises 2 or more substitutions relative to the reference gRNA, and the substitutions are not consecutive. In those embodiments where there are two or more non-consecutive substitutions in the gNA variant relative to the reference gRNA, any length of substituted nucleotides, and any combination of lengths of substituted nucleotides, as described herein, are contemplated as within the scope of the disclosure. For example, in some embodiments, a gNA variant may comprise a first substitution of one nucleotide, and a second substitution of two nucleotides and the two substitutions are not consecutive. In some embodiments, a gNA variant comprises at least two substitutions in different regions of the reference gRNA. In some embodiments, a gNA variant comprises at least two substitutions in the same region of the reference gRNA. For example, the regions may be the triplex, the extended stem loop, scaffold stem loop, scaffold stem bubble, triplex loop, pseudoknot, triplex, or a 5' end of the gNA variant. Any substitution of A, G, C, U (or T, in the corresponding DNA) or combinations thereof at any location in the reference gRNA is contemplated as within the scope of the disclosure.

Any of the substitutions, insertions and deletions described herein can be combined to generate a gNA variant of the disclosure. For example, a gNA variant can comprise at least one substitution and at least one deletion relative to a reference gRNA, at least one substitution and at least one insertion relative to a reference gRNA, at least one insertion and at least one deletion relative to a reference gRNA, or at least one substitution, one insertion and one deletion relative to a reference gRNA.

In some embodiments, the gNA variant comprises a scaffold region at least 20% identical, at least 30% identical, at least 40% identical, at least 50% identical, at least 60% identical, at least 65% identical, at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to any one of SEQ ID NOS:4-16. In some embodiments, the gNA variant comprises a scaffold region at least 60% homologous (or identical) to any one of SEQ ID NOS:4-16.

In some embodiments, the gNA variant comprises a tracr stem loop at least 60% identical, at least 65% identical, at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to SEQ ID NO:14. In some embodiments, the gNA variant comprises a tracr stem loop at least 60% homologous (or identical) to SEQ ID NO:14.

In some embodiments, the gNA variant comprises an extended stem loop at least 60% identical, at least 65% identical, at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to SEQ ID NO:15. In some embodiments, the gNA variant comprises an extended stem loop at least 60% homologous (or identical) to SEQ ID NO:15.

In some embodiments, the gNA variant comprises an exogenous extended stem loop, with such differences from a reference gNA described as follows. In some embodiments, an exogenous extended stem loop has little or no identity to the reference stem loop regions disclosed herein (e.g., SEQ ID NO:15). In some embodiments, an exogenous stem loop is at least 10 bp, at least 20 bp, at least 30 bp, at least 40 bp, at least 50 bp, at least 60 bp, at least 70 bp, at least 80 bp, at least 90 bp, at least 100 bp, at least 200 bp, at least 300 bp, at least 400 bp, at least 500 bp, at least 600 bp, at least 700 bp, at least 800 bp, at least 900 bp, at least 1,000 bp, at least 2,000 bp, at least 3,000 bp, at least 4,000 bp, at least 5,000 bp, at least 6,000 bp, at least 7,000 bp, at least 8,000 bp, at least 9,000 bp, at least 10,000 bp, at least 12,000 bp, at least 15,000 bp or at least 20,000 bp. In some embodiments, the gNA variant comprises an extended stem loop region comprising at least 10, at least 100, at least 500, at least 1000, or at least 10,000 nucleotides. In some embodiments, the heterologous stem loop increases the stability of the gNA. In some embodiments, the heterologous RNA stem loop is capable of binding a protein, an RNA structure, a DNA sequence, or a small molecule. In some embodiments, an exogenous stem loop region comprises an RNA stem loop or hairpin, for example a thermostable RNA such as MS2 (ACAUGAGGAUUACCCAUGU (SEQ ID NO: 35)), QP (UGCAUGUCUAAGACAGCA (SEQ ID NO: 36)), U1 hairpin II (AAUCCAUUGCACUCCGGAUU (SEQ ID NO: 37)), Uvsx (CCUCUUCGGAGG (SEQ ID NO: 38)), PP7 (AGGAGUUUCUAUGGAAACCCU (SEQ ID NO: 39)), Phage replication loop (AGGUGGGACGAC-CUCUCGGUCGUCCUAUCU (SEQ ID NO: 40)), Kissing loop_a (UGCUCGCUCCGUUCGAGCA (SEQ ID NO: 41)), Kissing loop_b1 (UGCUCGACGCGUCCUCGAGCA (SEQ ID NO: 42)), Kissing loop_b2 (UG-CUCGUUUGCGGCUACGAGCA (SEQ ID NO: 43)), G quadriplex M3q (AGGGAGGGAGGGAGAGG (SEQ ID NO: 44)), G quadriplex telomere basket (GGUUAGG-GUUAGGGUUAGG (SEQ ID NO: 45)), Sarcin-ricin loop (CUGCUCAGUACGAGAGGAACCGCAG (SEQ ID NO: 46)) or Pseudoknots (UACACUGGGAUCGCUGAAUUA-GAGAUCGGCGUCCUUUCAUUCUAUAUACUUU GGAGUUUUAAAAUGUCUCUAAGUACA (SEQ ID NO: 47)). In some embodiments, an exogenous stem loop comprises an RNA scaffold. As used herein, an "RNA scaffold" refers to a multi-dimensional RNA structure capable of interacting with and organizing or localizing one or more proteins. In some embodiments, the RNA scaffold is synthetic or non-naturally occurring. In some embodiments, an exogenous stem loop comprises a long non-coding RNA (lncRNA). As used herein, a lncRNA refers to a non-coding RNA that is longer than approximately 200 bp in length. In some embodiments, the 5' and 3' ends of the exogenous stem loop are base paired, i.e., interact to form a region of duplex RNA. In some embodiments, the 5' and 3' ends of the exogenous stem loop are base paired, and one or more regions between the 5' and 3' ends of the exogenous stem loop are not base paired. In some embodiments, the at least one nucleotide modification comprises: (a) substitution of 1 to 15 consecutive or non-consecutive nucleotides in the gNA variant in one or more regions; (b) a deletion of 1 to 10 consecutive or non-consecutive nucleotides in the gNA variant in one or more regions; (c) an insertion of 1 to 10 consecutive or non-consecutive nucleotides in the gNA variant in one or more regions; (d) a substitution of the scaffold stem loop or the extended stem loop with an RNA stem loop sequence from a heterologous RNA source with proximal 5' and 3' ends; or any combination of (a)-(d).

In some embodiments, the gNA variant comprises a scaffold stem loop having at least 60% identity to SEQ ID NO:14. In some embodiments, the gNA variant comprises a scaffold stem loop having at least 60% identity, at least 70% identity, at least 80% identity, at least 90% identity, at least 95% identity, at least 98% identity or at least 99% identity to SEQ ID NO:14. In some embodiments, the gNA variant comprises a scaffold stem loop comprising SEQ ID NO:14.

In some embodiments, the gNA variant comprises a scaffold stem loop sequence of CCAGCGACUAUGU-CGUAGUGG (SEQ ID NO: 32). In some embodiments, the gNA variant comprises a scaffold stem loop sequence of CCAGCGACUAUGUCGUAGUGG (SEQ ID NO: 32) with at least 1, 2, 3, 4, or 5 mismatches thereto.

In some embodiments, the gNA variant comprises an extended stem loop region comprising less than 32 nucleotides, less than 31 nucleotides, less than 30 nucleotides, less than 29 nucleotides, less than 28 nucleotides, less than 27 nucleotides, less than 26 nucleotides, less than 25 nucleotides, less than 24 nucleotides, less than 23 nucleotides, less than 22 nucleotides, less than 21 nucleotides, or less than 20 nucleotides. In some embodiments, the gNA variant comprises an extended stem loop region comprising less than 32 nucleotides. In some embodiments, the gNA variant further comprises a thermostable stem loop.

In some embodiments, a sgRNA variant comprises a sequence of SEQ ID NO:2104, SEQ ID NO:2106, SEQ ID NO:2163, SEQ ID NO:2107, SEQ ID NO:2164, SEQ ID NO:2165, SEQ ID NO:2166, SEQ ID NO:2103, SEQ ID NO:2167, SEQ ID NO:2105, SEQ ID NO:2108, SEQ ID NO:2112, SEQ ID NO:2160, SEQ ID NO:2170, SEQ ID NO:2114, SEQ ID NO:2171, SEQ ID NO:2112, SEQ ID NO:2173, SEQ ID NO:2102, SEQ ID NO:2174, SEQ ID NO:2175, SEQ ID NO:2109, SEQ ID NO:2176, SEQ ID NO:2238, SEQ ID NO:2239, SEQ ID NO:2240, SEQ ID NO:2241, SEQ ID NO:2274, or SEQ ID NO:2275.

In some embodiments, the gNA variant comprises the sequence of any one of SEQ ID NOS:2236, 2237, 2238, 2241, 2244, 2248, 2249, or 2259-2280, or having at least about 80%, at least about 90%, at least about 95%, at least about 96%, at least about 97%, at least about 98%, at least about 99% identity thereto. In some embodiments, the gNA variant comprises one or more additional changes to a sequence of any one of SEQ ID NOs: 2201-2280. In some embodiments, the gNA variant comprises the sequence of any one of SEQ ID NOS:2236, 2237, 2238, 2241, 2244, 2248, 2249, or 2259-2280.

In some embodiments, a sgRNA variant comprises one or more additional changes to a sequence of SEQ ID NO:2104, SEQ ID NO:2163, SEQ ID NO:2107, SEQ ID NO:2164, SEQ ID NO:2165, SEQ ID NO:2166, SEQ ID NO:2103, SEQ ID NO:2167, SEQ ID NO:2105, SEQ ID NO:2108, SEQ ID NO:2112, SEQ ID NO:2160, SEQ ID NO:2170, SEQ ID NO:2114, SEQ ID NO:2171, SEQ ID NO:2112, SEQ ID NO:2173, SEQ ID NO:2102, SEQ ID NO:2174, SEQ ID NO:2175, SEQ ID NO:2109, SEQ ID NO:2176, SEQ ID NO:2238, SEQ ID NO:2239, SEQ ID NO:2240, SEQ ID NO:2241, SEQ ID NO:2274, or SEQ ID NO:2275.

In some embodiments of the gNA variants of the disclosure, the gNA variant comprises at least one modification, wherein the at least one modification compared to the reference guide scaffold of SEQ ID NO:5 is selected from one or more of: (a) a C18G substitution in the triplex loop; (b) a G55 insertion in the stem bubble; (c) a U1 deletion; (d) a modification of the extended stem loop wherein (i) a 6 nt loop and 13 loop-proximal base pairs are replaced by a Uvsx hairpin; and (ii) a deletion of A99 and a substitution of G65U that results in a loop-distal base that is fully base-paired. In such embodiments, the gNA variant comprises the sequence of any one of SEQ ID NOS:2236, 2237, 2238, 2241, 2244, 2248, 2249, or 2259-2280.

In some embodiments, the scaffold of the gNA variant comprises the sequence of any one of SEQ ID NOS:2201-

2280 of Table 2. In some embodiments, the scaffold of the gNA consists or consists essentially of the sequence of any one of SEQ ID NOS:2201-2280. In some embodiments, the scaffold of the gNA variant sequence is at least about 60% identical, at least about 65% identical, at least about 70% identical, at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical or at least about 99% identical to any one of SEQ ID NOS:2201 to 2280.

In the embodiments of the gNA variants, the gNA further comprises a spacer (or targeting sequence) region, described more fully, supra, which comprises at least 14 to about 35 nucleotides wherein the spacer is designed with a sequence that is complementary to a target DNA. In some embodiments, the gNA variant comprises a targeting sequence of at least 10 to 30 nucleotides complementary to a target DNA. In some embodiments, the targeting sequence has 14, 15, 16, 17, 18, 19, 20, 21, 22, 23, 24, 25, 26, 27, 28, 29, 30, 31, 32, 33, 34 or 35 nucleotides. In some embodiments, the gNA variant comprises a targeting sequence having 20 nucleotides. In some embodiments, the targeting sequence has 25 nucleotides. In some embodiments, the targeting sequence has 24 nucleotides. In some embodiments, the targeting sequence has 23 nucleotides. In some embodiments, the targeting sequence has 22 nucleotides. In some embodiments, the targeting sequence has 21 nucleotides. In some embodiments, the targeting sequence has 20 nucleotides. In some embodiments, the targeting sequence has 19 nucleotides. In some embodiments, the targeting sequence has 18 nucleotides. In some embodiments, the targeting sequence has 17 nucleotides. In some embodiments, the targeting sequence has 16 nucleotides. In some embodiments, the targeting sequence has 15 nucleotides. In some embodiments, the targeting sequence has 14 nucleotides. In some embodiments, the disclosure provides targeting sequences for inclusion in the gNA variants of the disclosure comprising a sequence that is at least 50% identical, at least 55% identical, at least 60% identical, at least 65% identical, at least 70% identical, at least 75% identical, at least 80% identical, at least 85% identical, at least 90% identical, at least 95% identical, or 100% identical to a sequence in Tables 3A, 3B, or 3C. In some embodiments, the targeting sequence of the gNA variant comprises a sequence a sequence of Tables 3A, 3B, or 3C with a single nucleotide removed from the 3' end of the sequence. In other embodiments, the targeting sequence of the gNA variant comprises a sequence a sequence of Tables 3A, 3B, or 3C with two nucleotides removed from the 3' end of the sequence. In other embodiments, the targeting sequence of the gNA variant comprises a sequence a sequence of Tables 3A, 3B, or 3C with three nucleotides removed from the 3' end of the sequence. In other embodiments, the targeting sequence of the gNA variant comprises a sequence a sequence of Tables 3A, 3B, or 3C with four nucleotides removed from the 3' end of the sequence. In other embodiments, the targeting sequence of the gNA variant comprises a sequence a sequence of Table 3 with five nucleotides removed from the 3' end of the sequence.

Table 3A. gNA Targeting Sequences for B2M

Table 3A is provided in FIG. 35, and is referred to as Table 3A throughout.

Table 3B. gNA Targeting Sequences for TRAC

Table 3B is provided in FIG. 36, and is referred to as Table 3B throughout.

Table 3C: gNA Targeting Sequences for CIITA

Table 3C is provided in FIG. 37, and is referred to as Table 3C throughout.

In Tables 3A, 3B and 3C the left column indicates the PAM sequence, the right column indicates the SEQ ID NO of the corresponding spacer sequence (sometimes referred to herein as a targeting sequence).

In some embodiments, the scaffold of the gNA variant is part of an RNP with a reference CasX protein comprising SEQ ID NO:1, SEQ ID NO:2, or SEQ ID NO:3. In other embodiments, the scaffold of the gNA variant is part of an RNP with a CasX variant protein comprising any one of the sequences of Tables 4, 7, 8, 9, or 11 or a sequence having at least about 50%, at least about 60%, at least about 70%, at least about 80%, at least about 85%, at least about 90%, at least about 91%, at least about 92%, at least about 93%, at least about 94%, at least about 95%, at least about 96%, at least about 97%, at least about 98%, or at least about 99% identity thereto. In the foregoing embodiments, the gNA further comprises a spacer sequence.

In some embodiments, the scaffold of the gNA variant is a variant comprising one or more additional changes to a sequence of a reference gRNA that comprises SEQ ID NO:4 or SEQ ID NO:5. In those embodiments where the scaffold of the reference gRNA is derived from SEQ ID NO:4 or SEQ ID NO:5, the one or more improved or added characteristics of the gNA variant are improved compared to the same characteristic in SEQ ID NO:4 or SEQ ID NO:5.

h. Complex Formation with CasX Protein

In some embodiments, a gNA variant has an improved ability to form a complex with a CasX protein (such as a reference CasX or a CasX variant protein) when compared to a reference gRNA. In some embodiments, a gNA variant has an improved affinity for a CasX protein (such as a reference or variant protein) when compared to a reference gRNA, thereby improving its ability to form a ribonucleoprotein (RNP) complex with the CasX protein, as described in the Examples. Improving ribonucleoprotein complex formation may, in some embodiments, improve the efficiency with which functional RNPs are assembled. In some embodiments, greater than 90%, greater than 93%, greater than 95%, greater than 96%, greater than 97%, greater than 98% or greater than 99% of RNPs comprising a gNA variant and its spacer are competent for gene editing of a target nucleic acid.

Exemplary nucleotide changes that can improve the ability of gNA variants to form a complex with CasX protein may, in some embodiments, include replacing the scaffold stem with a thermostable stem loop. Without wishing to be bound by any theory, replacing the scaffold stem with a thermostable stem loop could increase the overall binding stability of the gNA variant with the CasX protein. Alternatively, or in addition, removing a large section of the stem loop could change the gNA variant folding kinetics and make a functional folded gNA easier and quicker to structurally-assemble, for example by lessening the degree to which the gNA variant can get "tangled" in itself. In some embodiments, choice of scaffold stem loop sequence could change with different spacers that are utilized for the gNA. In some embodiments, scaffold sequence can be tailored to the spacer and therefore the target sequence. Biochemical assays can be used to evaluate the binding affinity of CasX protein for the gNA variant to form the RNP, including the assays of the Examples. For example, a person of ordinary skill can measure changes in the amount of a fluorescently tagged gNA that is bound to an immobilized CasX protein, as a response to increasing concentrations of an additional unlabeled "cold competitor" gNA. Alternatively, or in addition, fluorescence signal can be monitored to or seeing how it changes as different amounts of fluorescently labeled gNA are flowed over immobilized CasX protein. Alternatively, the ability to form an RNP can be assessed using in vitro cleavage assays against a defined target nucleic acid sequence.

i. gNA Stability

In some embodiments, a gNA variant has improved stability when compared to a reference gRNA. Increased stability and efficient folding may, in some embodiments, increase the extent to which a gNA variant persists inside a target cell, which may thereby increase the chance of forming a functional RNP capable of carrying out CasX functions such as gene editing. Increased stability of gNA variants may also, in some embodiments, allow for a similar outcome with a lower amount of gNA delivered to a cell, which may in turn reduce the chance of off-target effects during gene editing.

In another aspect, the disclosure provides gNA in which the scaffold stem loop and/or the extended stem loop is replaced with a hairpin loop or a thermostable RNA stem loop in which the resulting gNA has increased stability and, depending on the choice of loop, can interact with certain cellular proteins or RNA. In some embodiments, the replacement RNA loop is selected from MS2, QP, U1 hairpin II, Uvsx, PP7, Phage replication loop, Kissing loop_a, Kissing loop_b1, Kissing loop_b2, G quadriplex M3q, G quadriplex telomere basket, Sarcin-ricin loop and Pseudoknots. Sequences of gNA variants including such components are provided in Table 2B.

Guide RNA stability can be assessed in a variety of ways, including for example in vitro by assembling the guide, incubating for varying periods of time in a solution that mimics the intracellular environment, and then measuring functional activity via the in vitro cleavage assays described herein. Alternatively, or in addition, gNAs can be harvested from cells at varying time points after initial transfection/transduction of the gNA to determine how long gNA variants persist relative to reference gRNAs.

j. Solubility

In some embodiments, a gNA variant has improved solubility when compared to a reference gRNA. In some embodiments, a gNA variant has improved solubility of the CasX protein:gNA RNP when compared to a reference gRNA. In some embodiments, solubility of the CasX protein:gNA RNP is improved by the addition of a ribozyme sequence to a 5' or 3' end of the gNA variant, for example the 5' or 3' of a reference sgRNA. Some ribozymes, such as the M1 ribozyme, can increase solubility of proteins through RNA mediated protein folding.

Increased solubility of CasX RNPs comprising a gNA variant as described herein can be evaluated through a variety of means known to one of skill in the art, such as by taking densitometry readings on a gel of the soluble fraction of lysed *E. coli* in which the CasX and gNA variants are expressed.

k. Resistance to Nuclease Activity

In some embodiments, a gNA variant has improved resistance to nuclease activity compared to a reference gRNA. Without wishing to be bound by any theory, increased resistance to nucleases, such as nucleases found in cells, may for example increase the persistence of a variant gNA in an intracellular environment, thereby improving gene editing.

Many nucleases are processive, and degrade RNA in a 3' to 5' fashion. Therefore, in some embodiments the addition of a nuclease resistant secondary structure to one or both termini of the gNA, or nucleotide changes that change the secondary structure of a sgNA, can produce gNA variants with increased resistance to nuclease activity. Resistance to nuclease activity may be evaluated through a variety of methods known to one of skill in the art. For example, in vitro methods of measuring resistance to nuclease activity may include for example contacting reference gNA and variants with one or more exemplary RNA nucleases and measuring degradation. Alternatively, or in addition, measuring persistence of a gNA variant in a cellular environment using the methods described herein can indicate the degree to which the gNA variant is nuclease resistant.

l. Binding Affinity to a Target DNA

In some embodiments, a gNA variant has improved affinity for the target DNA relative to a reference gRNA. In certain embodiments, a ribonucleoprotein complex comprising a gNA variant has improved affinity for the target DNA, relative to the affinity of an RNP comprising a reference gRNA. In some embodiments, the improved affinity of the RNP for the target DNA comprises improved affinity for the target sequence, improved affinity for the PAM sequence, improved ability of the RNP to search DNA for the target sequence, or any combinations thereof. In some embodiments, the improved affinity for the target DNA is the result of increased overall DNA binding affinity.

Without wishing to be bound by theory, it is possible that nucleotide changes in the gNA variant that affect the function of the OBD in the CasX protein may increase the affinity of CasX variant protein binding to the protospacer adjacent motif (PAM), as well as the ability to bind or utilize an increased spectrum of PAM sequences other than the canonical TTC PAM recognized by the reference CasX protein of SEQ ID NO:2, including PAM sequences selected from the group consisting of TTC, ATC, GTC, and CTC, thereby increasing the affinity and diversity of the CasX variant protein for target DNA sequences resulting in a substantial increase in the target nucleic acid sequences that can be edited and/or bound, compared to a reference CasX. As described more fully, below, increasing the sequences of the target nucleic acid that can be edited, compared to a reference CasX, refers to both the PAM and the protospacer sequence and their directionality according to the orientation of the non-target strand. This does not imply that the PAM sequence of the non-target strand, rather than the target strand, is determinative of cleavage or mechanistically involved in target recognition. For example, when reference is to a TTC PAM, it may in fact be the complementary GAA sequence that is required for target cleavage, or it may be some combination of nucleotides from both strands. In the case of the CasX proteins disclosed herein, the PAM is located 5' of the protospacer with at least a single nucleotide separating the PAM from the first nucleotide of the protospacer. Alternatively, or in addition, changes in the gNA that affect function of the helical I and/or helical II domains that increase the affinity of the CasX variant protein for the target DNA strand can increase the affinity of the CasX RNP comprising the variant gNA for target DNA.

m. Adding or Changing gNA Function

In some embodiments, gNA variants can comprise larger structural changes that change the topology of the gNA variant with respect to the reference gRNA, thereby allowing for different gNA functionality. For example, in some embodiments a gNA variant has swapped an endogenous stem loop of the reference gRNA scaffold with a previously identified stable RNA structure or a stem loop that can interact with a protein or RNA binding partner to recruit additional moieties to the CasX or to recruit CasX to a specific location, such as the inside of a viral capsid, that has the binding partner to the said RNA structure. In other scenarios the RNAs may be recruited to each other, as in Kissing loops, such that two CasX proteins can be co-localized for more effective gene editing at the target DNA sequence. Such RNA structures may include MS2, QP, U1 hairpin II, Uvsx, PP7, Phage replication loop, Kissing loop_a, Kissing loop_b1, Kissing loop_b2, G quadriplex M3q, G quadriplex telomere basket, Sarcin-ricin loop, or a Pseudoknot.

In some embodiments, a gNA variant comprises a terminal fusion partner. Exemplary terminal fusions may include fusion of the gRNA to a self-cleaving ribozyme or protein binding motif. As used herein, a "ribozyme" refers to an RNA or segment thereof with one or more catalytic activities similar to a protein enzyme. Exemplary ribozyme catalytic activities may include, for example, cleavage and/or ligation of RNA, cleavage and/or ligation of DNA, or peptide bond formation. In some embodiments, such fusions could either improve scaffold folding or recruit DNA repair machinery. For example, a gRNA may in some embodiments be fused to a hepatitis delta virus (HDV) antigenomic ribozyme, HDV genomic ribozyme, hatchet ribozyme (from metagenomic data), env25 pistol ribozyme (representative from Aliistipes putredinis), HH15 Minimal Hammerhead ribozyme, tobacco ringspot virus (TRSV) ribozyme, WT viral Hammerhead ribozyme (and rational variants), or Twisted Sister 1 or RBMX recruiting motif. Hammerhead ribozymes are RNA motifs that catalyze reversible cleavage and ligation reactions at a specific site within an RNA molecule. Hammerhead ribozymes include type I, type II and type III hammerhead ribozymes. The HDV, pistol, and hatchet ribozymes have self-cleaving activities. gNA variants comprising one or more ribozymes may allow for expanded gNA function as compared to a gRNA reference. For example, gNAs comprising self-cleaving ribozymes can, in some embodiments, be transcribed and processed into mature gNAs as part of polycistronic transcripts. Such fusions may occur at either the 5' or the 3' end of the gNA. In some embodiments, a gNA variant comprises a fusion at both the 5' and the 3' end, wherein each fusion is independently as described herein. In some embodiments, a gNA variant comprises a phage replication loop or a tetraloop. In some embodiments, a gNA comprises a hairpin loop that is capable of binding a protein. For example, in some embodiments the hairpin loop is an MS2, Qβ, U1 hairpin II, Uvsx, or PP7 hairpin loop.

In some embodiments, a gNA variant comprises one or more RNA aptamers. As used herein, an "RNA aptamer" refers to an RNA molecule that binds a target with high affinity and high specificity.

In some embodiments, a gNA variant comprises one or more riboswitches. As used herein, a "riboswitch" refers to an RNA molecule that changes state upon binding a small molecule.

In some embodiments, the gNA variant further comprises one or more protein binding motifs. Adding protein binding motifs to a reference gRNA or gNA variant of the disclosure may, in some embodiments, allow a CasX RNP to associate with additional proteins, which can, for example, add the functionality of those proteins to the CasX RNP.

n. Chemically Modified gNA

In some embodiments, the disclosure relates to chemically-modified gNA. In some embodiments, the present disclosure provides a chemically-modified gNA that has guide RNA functionality and has reduced susceptibility to cleavage by a nuclease. A gNA that comprises any nucleotide other than the four canonical ribonucleotides A, C, G, and U, or a deoxynucleotide, is a chemically modified gNA. In some cases, a chemically-modified gNA comprises any backbone or internucleotide linkage other than a natural phosphodiester internucleotide linkage. In certain embodiments, the retained functionality includes the ability of the modified gNA to bind to a CasX of any of the embodiments described herein. In certain embodiments, the retained functionality includes the ability of the modified gNA to bind to a target nucleic acid sequence. In certain embodiments, the retained functionality includes targeting a CasX protein or the ability of a pre-complexed CasX protein-gNA to bind to a target nucleic acid sequence. In certain embodiments, the retained functionality includes the ability to nick a target polynucleotide by a CasX-gNA. In certain embodiments, the retained functionality includes the ability to cleave a target nucleic acid sequence by a CasX-gNA. In certain embodiments, the retained functionality is any other known function of a gNA in a CasX system with a CasX protein of the embodiments of the disclosure.

In some embodiments, the disclosure provides a chemically-modified gNA in which a nucleotide sugar modification is incorporated into the gNA selected from the group consisting of 2'-O—$C_{14}$alkyl such as 2'-O-methyl (2'-OMe), 2'-deoxy (2'-H), 2'-O $C_{1-3}$ alkyl-O—$C_{1-3}$alkyl such as 2'-methoxyethyl ("2'-MOE"), 2'-fluoro ("2'-F"), 2'-amino ("2'-$NH_2$"), 2'-arabinosyl ("2'-arabino") nucleotide, 2'-F-arabinosyl ("2'-F-arabino") nucleotide, 2'-locked nucleic acid ("LNA") nucleotide, 2'-unlocked nucleic acid ("ULNA") nucleotide, a sugar in L form ("L-sugar"), and 4'-thioribosyl nucleotide. In other embodiments, an internucleotide linkage modification incorporated into the guide RNA is selected from the group consisting of: phosphorothioate "P(S)" (P(S)), phosphonocarboxylate ($P(CH_2)$ nCOOR) such as phosphonoacetate "PACE" ($P(CH_2COO—)$), thiophosphonocarboxylate ($(S)P(CH_2)_n$ COOR) such as thiophosphonoacetate "thioPACE" ($(S)P(CH_2)_nCOO^-)$), alkylphosphonate ($P(C_{1-3}$alkyl) such as methylphosphonate $P(CH_3)$, boranophosphonate ($P(BH_3)$), and phosphorodithioate ($P(S)_2$).

In certain embodiments, the disclosure provides a chemically-modified gNA in which a nucleobase ("base") modification is incorporated into the gNA selected from the group consisting of: 2-thiouracil ("2-thioU"), 2-thiocytosine ("2-thioC"), 4-thiouracil ("4-thioU"), 6-thioguanine ("6-thioG"), 2-aminoadenine ("2-aminoA"), 2-aminopurine, pseudouracil, hypoxanthine, 7-deazaguanine, 7-deaza-8-azaguanine, 7-deazaadenine, 7-deaza-8-azaadenine, 5-methylcytosine ("5-methylC"), 5-methyluracil ("5-methylU"), 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil ("5-allylU"), 5-allylcytosine ("5-allylC"), 5-aminoallyluracil ("5-aminoallylU"), 5-aminoallyl-cytosine ("5-aminoallylC"), an abasic nucleotide, Z base, P base, Unstructured Nucleic Acid ("UNA"), isoguanine ("isoG"), isocytosine ("isoC"), 5-methyl-2-pyrimidine, x(A,G,C,T) and y(A,G,C,T).

In other embodiments, the disclosure provides a chemically-modified gNA in which one or more isotopic modifications are introduced on the nucleotide sugar, the nucleobase, the phosphodiester linkage and/or the nucleotide phosphates, including nucleotides comprising one or more $^{15}N$, $^{13}C$, $^{14}C$, deuterium, $^{3}H$, $^{32}P$, $^{125}I$, $^{131}I$ atoms or other atoms or elements used as tracers.

In some embodiments, an "end" modification incorporated into the gNA is selected from the group consisting of: PEG (polyethyleneglycol), hydrocarbon linkers (including: heteroatom (O,S,N)-substituted hydrocarbon spacers; halo-substituted hydrocarbon spacers; keto-, carboxyl-, amido-, thionyl-, carbamoyl-, thionocarbamaoyl-containing hydrocarbon spacers), spermine linkers, dyes including fluorescent dyes (for example fluoresceins, rhodamines, cyanines) attached to linkers such as for example 6-fluorescein-hexyl, quenchers (for example dabcyl, BHQ) and other labels (for example biotin, digoxigenin, acridine, streptavidin, avidin, peptides and/or proteins). In some embodiments, an "end" modification comprises a conjugation (or ligation) of the gNA to another molecule comprising an oligonucleotide of deoxynucleotides and/or ribonucleotides, a peptide, a protein, a sugar, an oligosaccharide, a steroid, a lipid, a folic acid, a vitamin and/or other molecule. In certain embodiments, the disclosure provides a chemically-modified gNA in which an "end" modification (described above) is located internally in the gNA sequence via a linker such as, for example, a 2-(4-butylamidofluorescein)propane-1,3-diol bis (phosphodiester) linker, which is incorporated as a phosphodiester linkage and can be incorporated anywhere between two nucleotides in the gNA.

In some embodiments, the disclosure provides a chemically-modified gNA having an end modification comprising a terminal functional group such as an amine, a thiol (or sulfhydryl), a hydroxyl, a carboxyl, carbonyl, thionyl, thiocarbonyl, a carbamoyl, a thiocarbamoyl, a phoshoryl, an alkene, an alkyne, an halogen or a functional group-terminated linker that can be subsequently conjugated to a desired moiety selected from the group consisting of a fluorescent dye, a non-fluorescent label, a tag (for $^{14}C$, example biotin, avidin, streptavidin, or moiety containing an isotopic label such as $^{15}N$, $^{13}C$, deuterium, $^{3}H$, $^{32}P$, $^{125}I$ and the like), an oligonucleotide (comprising deoxynucleotides and/or ribonucleotides, including an aptamer), an amino acid, a peptide, a protein, a sugar, an oligosaccharide, a steroid, a lipid, a folic acid, and a vitamin. The conjugation employs standard chemistry well-known in the art, including but not limited to coupling via N-hydroxysuccinimide, isothiocyanate, DCC (or DCI), and/or any other standard method as described in "Bioconjugate Techniques" by Greg T. Hermanson, Publisher Eslsevier Science, $3^{rd}$ ed. (2013), the contents of which are incorporated herein by reference in its entirety.

IV. Proteins for Modifying a Target Nucleic Acid

The present disclosure provides systems comprising a CRISPR nuclease that have utility in genome editing of eukaryotic cells. In some embodiments, the CRISPR nuclease is selected from the group consisting of Cas9, Cas12a, Cas12b, Cas12c, Cas12d (CasY), CasX, Cas13a, Cas13b, Cas13c, Cas13d, CasX, CasY, Cas14, Cpfl, C2cl, Csn2, and Cas Phi. In some embodiments, the CRISPR nuclease is a is a Type V CRISPR nuclease. In some embodiments, the present disclosure provides systems comprising a CasX protein and one or more guide nucleic acids (gNA) that are specifically designed to modify a target nucleic acid sequence in eukaryotic cells.

The term "CasX protein", as used herein, refers to a family of proteins, and encompasses all naturally occurring CasX proteins, proteins that share at least 50% identity to naturally occurring CasX proteins, as well as CasX variants possessing one or more improved characteristics relative to a naturally-occurring reference CasX protein. CasX proteins belong to CRISPR-Cas Type V proteins. Exemplary improved characteristics of the CasX variant embodiments include, but are not limited to improved folding of the variant, improved binding affinity to the gNA, improved binding affinity to the target nucleic acid, improved ability to utilize a greater spectrum of PAM sequences in the editing and/or binding of target DNA, improved unwinding of the target DNA, increased editing activity, improved editing efficiency, improved editing specificity, increased percentage of a eukaryotic genome that can be efficiently edited, increased activity of the nuclease, increased target strand loading for double strand cleavage, decreased target strand loading for single strand nicking, decreased off-target cleavage, improved binding of the non-target strand of DNA, improved protein stability, improved protein:gNA (RNP) complex stability, improved protein solubility, improved protein:gNA (RNP) complex solubility, improved protein yield, improved protein expression, and improved fusion characteristics, as described more fully, below. In the foregoing embodiments, the one or more of the improved characteristics of an RNP of the CasX variant and the gNA variant is at least about 1.1 to about 100,000-fold improved relative to an RNP of the reference CasX protein of SEQ ID NO:1, SEQ ID NO:2, or SEQ ID NO:3 and the gNA of Table 1, when assayed in a comparable fashion. In other cases, the one or more improved characteristics of an RNP of the CasX variant and the gNA variant is at least about 1.1, at least about 10, at least about 100, at least about 1000, at least about 10,000, at least about 100,000-fold or more improved relative to an RNP of the reference CasX protein of SEQ ID NO:1, SEQ ID NO:2, or SEQ ID NO:3 and the gNA of Table 1. In other cases, the one or more of the improved characteristics of an RNP of the CasX variant and the gNA variant is about 1.1 to 100,00-fold, about 1.1 to 10,00-fold, about 1.1 to 1,000-fold, about 1.1 to 500-fold, about 1.1 to 100-fold, about 1.1 to 50-fold, about 1.1 to 20-fold, about 10 to 100,00-fold, about 10 to 10,00-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100,00-fold, about 100 to 10,00-fold, about 100 to 1,000-fold, about 100 to 500-fold, about 500 to 100,00-fold, about 500 to 10,00-fold, about 500 to 1,000-fold, about 500 to 750-fold, about 1,000 to 100,00-fold, about 10,000 to 100,00-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to an RNP of the reference CasX protein of SEQ ID NO:1, SEQ ID NO:2, or SEQ ID NO:3 and the gNA of Table 1, when assayed in a comparable fashion. In other cases, the one or more improved characteristics of an RNP of the CasX variant and the gNA variant is about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475-fold, or 500-fold improved relative to an RNP of the reference CasX protein of SEQ ID NO:1, SEQ ID NO:2, or SEQ ID NO:3 and the gNA of Table 1, when assayed in a comparable fashion.

The term “CasX variant” is inclusive of variants that are fusion proteins; i.e., the CasX is “fused to” a heterologous sequence. This includes CasX variants comprising CasX variant sequences and N-terminal, C-terminal, or internal fusions of the CasX to a heterologous protein or domain thereof.

CasX proteins of the disclosure comprise at least one of the following domains: a non-target strand binding (NTSB) domain, a target strand loading (TSL) domain, a helical I domain, a helical II domain, an oligonucleotide binding domain (OBD), and a RuvC DNA cleavage domain (the last of which may be modified or deleted in a catalytically dead CasX variant), described more fully, below. Additionally, the CasX variant proteins of the disclosure have an enhanced ability to efficiently edit and/or bind target DNA, when complexed with a gNA as an RNP, utilizing PAM sequences selected from TTC, ATC, GTC, or CTC, compared to an RNP of a reference CasX protein and reference gNA. In some embodiments, the PAM sequence comprises a TC motif. In the foregoing, the PAM sequence is located at least 1 nucleotide 5' to the non-target strand of the protospacer having identity with the targeting sequence of the gNA in a assay system compared to the editing efficiency and/or binding of an RNP comprising a reference CasX protein and reference gNA in a comparable assay system. In one embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is TTC. In another embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is ATC. In another embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is CTC. In another embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is GTC. In the foregoing embodiments, the increased editing efficiency and/or binding affinity for the one or more PAM sequences is at least 1.5-fold greater compared to the editing efficiency and/or binding affinity of an RNP of any one of the CasX proteins of SEQ ID NOS:1-3 and the gNA of Table 1 for the PAM sequences.

In some cases, the CasX protein is a naturally-occurring protein (e.g., naturally occurs in and is isolated from prokaryotic cells). In other embodiments, the CasX protein is not a naturally-occurring protein (e.g., the CasX protein is a CasX variant protein, a chimeric protein, and the like). A naturally-occurring CasX protein (referred to herein as a “reference CasX protein”) functions as an endonuclease that catalyzes a double strand break at a specific sequence in a targeted double-stranded DNA (dsDNA). The sequence specificity is provided by the targeting sequence of the associated gNA to which it is complexed, which hybridizes to a target sequence within the target nucleic acid.

In some embodiments, a CasX protein can bind and/or modify (e.g., cleave, nick, methylate, demethylate, etc.) a target nucleic acid and/or a polypeptide associated with target nucleic acid (e.g., methylation or acetylation of a histone tail). In some embodiments, the CasX protein is catalytically dead (dCasX) but retains the ability to bind a target nucleic acid. An exemplary catalytically dead CasX protein comprises one or more mutations in the active site of the RuvC domain of the CasX protein. In some embodiments, a catalytically dead CasX protein comprises substitutions at residues 672, 769 and/or 935 of SEQ ID NO:1. In one embodiment, a catalytically dead CasX protein comprises substitutions of D672A, E769A and/or D935A in a reference CasX protein of SEQ ID NO:1. In other embodiments, a catalytically dead CasX protein comprises substitutions at amino acids 659, 756 and/or 922 in a reference CasX protein of SEQ ID NO:2. In some embodiments, a catalytically dead CasX protein comprises D659A, E756A and/or D922A substitutions in a reference CasX protein of SEQ ID NO:2. In further embodiments, a catalytically dead CasX protein comprises deletions of all or part of the RuvC domain of the CasX protein. It will be understood that the same foregoing substitutions can similarly be introduced into the CasX variants of the disclosure, resulting in a dCasX variant. In one embodiment, all or a portion of the RuvC domain is deleted from the CasX variant, resulting in a dCasX variant. Catalytically inactive dCasX variant proteins can, in some embodiments, be used for base editing or epigenetic modifications. With a higher affinity for DNA, in some embodiments, catalytically inactive dCasX variant proteins can, relative to catalytically active CasX, find their target nucleic acid faster, remain bound to target nucleic acid for longer periods of time, bind target nucleic acid in a more stable fashion, or a combination thereof, thereby improving these functions of the catalytically dead CasX variant protein compared to a CasX variant that retains its cleavage capability.

a. Non-Target Strand Binding Domain

The reference CasX proteins of the disclosure comprise a non-target strand binding domain (NTSBD). The NTSBD is a domain not previously found in any Cas proteins; for example this domain is not present in Cas proteins such as Cas9, Cas12a/Cpf1, Cas13, Cas14, CASCADE, CSM, or CSY. Without being bound to theory or mechanism, a NTSBD in a CasX allows for binding to the non-target DNA strand and may aid in unwinding of the non-target and target strands. The NTSBD is presumed to be responsible for the unwinding, or the capture, of a non-target DNA strand in the unwound state. The NTSBD is in direct contact with the non-target strand in CryoEM model structures derived to date and may contain a non-canonical zinc finger domain. The NTSBD may also play a role in stabilizing DNA during unwinding, guide RNA invasion and R-loop formation. In some embodiments, an exemplary NTSBD comprises amino acids 101-191 of SEQ ID NO:1 or amino acids 103-192 of SEQ ID NO:2. In some embodiments, the NTSBD of a reference CasX protein comprises a four-stranded beta sheet.

b. Target Strand Loading Domain

The reference CasX proteins of the disclosure comprise a Target Strand Loading (TSL) domain. The TSL domain is a domain not found in certain Cas proteins such as Cas9, CASCADE, CSM, or CSY. Without wishing to be bound by theory or mechanism, it is thought that the TSL domain is responsible for aiding the loading of the target DNA strand into the RuvC active site of a CasX protein. In some embodiments, the TSL acts to place or capture the target-strand in a folded state that places the scissile phosphate of the target strand DNA backbone in the RuvC active site. The TSL comprises a cys4 (CXXC, CXXC zinc finger/ribbon domain (SEQ ID NO: 48) that is separated by the bulk of the TSL. In some embodiments, an exemplary TSL comprises amino acids 825-934 of SEQ ID NO:1 or amino acids 813-921 of SEQ ID NO:2.

c. Helical I Domain

The reference CasX proteins of the disclosure comprise a helical I domain. Certain Cas proteins other than CasX have domains that may be named in a similar way. However, in some embodiments, the helical I domain of a CasX protein comprises one or more unique structural features, or comprises a unique sequence, or a combination thereof, compared to non-CasX proteins. For example, in some embodiments, the helical I domain of a CasX protein comprises one or more unique secondary structures compared to domains in other Cas proteins that may have a similar name. For example, in some embodiments the helical I domain in a CasX protein comprises one or more alpha helices of unique structure and sequence in arrangement, number and length compared to other CRISPR proteins. In certain embodiments, the helical I domain is responsible for interacting with the bound DNA and spacer of the guide RNA. Without wishing to be bound by theory, it is thought that in some cases the helical I domain may contribute to binding of the protospacer adjacent motif (PAM). In some embodiments, an exemplary helical I domain comprises amino acids 57-100 and 192-332 of SEQ ID NO:1, or amino acids 59-102 and 193-333 of SEQ ID NO:2. In some embodiments, the helical I domain of a reference CasX protein comprises one or more alpha helices.

d. Helical II Domain

The reference CasX proteins of the disclosure comprise a helical II domain. Certain Cas proteins other than CasX have domains that may be named in a similar way. However, in some embodiments, the helical II domain of a CasX protein comprises one or more unique structural features, or a unique sequence, or a combination thereof, compared to domains in other Cas proteins that may have a similar name. For example, in some embodiments, the helical II domain comprises one or more unique structural alpha helical bundles that align along the target DNA:guide RNA channel. In some embodiments, in a CasX comprising a helical II domain, the target strand and guide RNA interact with helical II (and the helical I domain, in some embodiments) to allow RuvC domain access to the target DNA. The helical II domain is responsible for binding to the guide RNA scaffold stem loop as well as the bound DNA. In some embodiments, an exemplary helical II domain comprises amino acids 333-509 of SEQ ID NO:1, or amino acids 334-501 of SEQ ID NO:2.

e. Oligonucleotide Binding Domain

The reference CasX proteins of the disclosure comprise an Oligonucleotide Binding Domain (OBD). Certain Cas proteins other than CasX have domains that may be named in a similar way. However, in some embodiments, the OBD comprises one or more unique functional features, or comprises a sequence unique to a CasX protein, or a combination thereof. For example, in some embodiments the bridged helix (BH), helical I domain, helical II domain, and Oligonucleotide Binding Domain (OBD) together are responsible for binding of a CasX protein to the guide RNA. Thus, for example, in some embodiments the OBD is unique to a CasX protein in that it interacts functionally with a helical I domain, or a helical II domain, or both, each of which may be unique to a CasX protein as described herein. Specifically, in CasX the OBD largely binds the RNA triplex of the guide RNA scaffold. The OBD may also be responsible for binding to the protospacer adjacent motif (PAM). An exemplary OBD domain comprises amino acids 1-56 and 510-660 of SEQ ID NO:1, or amino acids 1-58 and 502-647 of SEQ ID NO:2.

f. RuvC DNA Cleavage Domain

The reference CasX proteins of the disclosure comprise a RuvC domain, that includes 2 partial RuvC domains (RuvC-I and RuvC-II). The RuvC domain is the ancestral domain of all type 12 CRISPR proteins. The RuvC domain originates from a TNPB (transposase B) like transposase. Similar to other RuvC domains, the CasX RuvC domain has a DED catalytic triad that is responsible for coordinating a magnesium (Mg) ion and cleaving DNA. In some embodiments, the RuvC has a DED motif active site that is responsible for cleaving both strands of DNA (one by one, most likely the non-target strand first at 11-14 nucleotides (nt) into the targeted sequence and then the target strand next at 2-4 nucleotides after the target sequence). Specifically in CasX, the RuvC domain is unique in that it is also responsible for binding the guide RNA scaffold stem loop that is critical for CasX function. An exemplary RuvC domain comprises amino acids 661-824 and 935-986 of SEQ ID NO:1, or amino acids 648-812 and 922-978 of SEQ ID NO:2.

g. Reference CasX Proteins

The disclosure provides reference CasX proteins. In some embodiments, a reference CasX protein is a naturally-occurring protein. For example, reference CasX proteins can be isolated from naturally occurring prokaryotes, such as Deltaproteobacteria, Planctomycetes, or Candidatus Sungbacteria species. A reference CasX protein (sometimes referred to herein as a reference CasX protein) is a type II CRISPR/Cas endonuclease belonging to the CasX (sometimes referred to as Cas12e) family of proteins that is capable of interacting with a guide NA to form a ribonucleoprotein (RNP) complex. In some embodiments, the RNP complex comprising the reference CasX protein can be targeted to a particular site in a target nucleic acid via base pairing between the targeting sequence (or spacer) of the gNA and a target sequence in the target nucleic acid. In some embodiments, the RNP comprising the reference CasX protein is capable of cleaving target DNA. In some embodiments, the RNP comprising the reference CasX protein is capable of nicking target DNA. In some embodiments, the RNP comprising the reference CasX protein is capable of editing target DNA, for example in those embodiments where the reference CasX protein is capable of cleaving or nicking DNA, followed by non-homologous end joining (NHEJ), homology-directed repair (HDR), homology-independent targeted integration (HITI), micro-homology mediated end joining (MMEJ), single strand annealing (SSA) or base excision repair (BER). In some embodiments, the RNP comprising the CasX protein is a catalytically dead (is catalytically inactive or has substantially no cleavage activity) CasX protein (dCasX), but retains the ability to bind the target DNA, described more fully, supra.

In some cases, a reference CasX protein is isolated or derived from Deltaproteobacteria. In some embodiments, a CasX protein comprises a sequence at least 50% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence of:

(SEQ ID NO: 1)

1 MEKRINKIRK KLSADNATKP VSRSGPMKTL LVRVMTDDLK KRLEKRRKKP EVMPQVISNN

61 AANNLRMLLD DYTKMKEAIL QVYWQEFKDD HVGLMCKFAQ PASKKIDQNK LKPEMDEKGN

121 LTTAGFACSQ CGQPLFVYKL EQVSEKGKAY TNYFGRCNVA EHEKLILLAQ LKPEKDSDEA

181 VTYSLGKFGQ RALDFYSIHV TKESTHPVKP LAQIAGNRYA SGPVGKALSD ACMGTIASFL

241 SKYQDIIIEH QKVVKGNQKR LESLRELAGK ENLEYPSVTL PPQPHTKEGV DAYNEVIARV

301 RMWVNLNLWQ KLKLSRDDAK PLLRLKGFPS FPVVERRENE VDWWNTINEV KKLIDAKRDM

361 GRVFWSGVTA EKRNTILEGY NYLPNENDHK KREGSLENPK KPAKRQFGDL LLYLEKKYAG

421 DWGKVFDEAW ERIDKKIAGL TSHIEREEAR NAEDAQSKAV LTDWLRAKAS FVLERLKEMD

481 EKEFYACEIQ LQKWYGDLRG NPFAVEAENR VVDISGESIG SDGHSIQYRN LLAWKYLENG

541 KREFYLLMNY GKKGRIRFTD GTDIKKSGKW QGLLYGGGKA KVIDLTFDPD DEQLIILPLA

601 FGTRQGREFI WNDLLSLETG LIKLANGRVI EKTIYNKKIG RDEPALFVAL TFERREVVDP

661 SNIKPVNLIG VDRGENIPAV IALTDPEGCP LPEFKDSSGG PTDILRIGEG YKEKQRAIQA

721 AKEVEQRRAG GYSRKFASKS RNLADDMVRN SARDLFYHAV THDAVLVFEN LSRGFGRQGK

781 RTFMTERQYT KMEDWLTAKL AYEGLTSKTY LSKTLAQYTS KTCSNCGFTI TTADYDGMLV

841 RLKKTSDGWA TTLNNKELKA EGQITYYNRY KRQTVEKELS AELDRLSEES GNNDISKWTK

901 GRRDEALFLL KKRFSHRPVQ EQFVCLDCGH EVHADEQAAL NIARSWLFLN SNSTEFKSYK

961 SGKQPFVGAW QAFYKRRLKE VWKPNA.

In some cases, a reference CasX protein is isolated or derived from Planctomycetes. In some embodiments, a CasX protein comprises a sequence at least 50% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence of:

(SEQ ID NO: 2)

1 MQEIKRINKI RRRLVKDSNT KKAGKTGPMK TLLVRVMTPD LRERLENLRK KPENIPQPIS

61 NTSRANLNKL LTDYTEMKKA ILHVYWEEFQ KDPVGLMSRV AQPAPKNIDQ RKLIPVKDGN

121 ERLTSSGEAC SQCCQPLYVY KLEQVNDKGK PHTNYFGRCN VSEHERLILL SPHKPEANDE

181 LVTYSLGKFG QRALDFYSIH VTRESNHPVK PLEQIGGNSC ASGPVGKALS DACMGAVASF

241 LTKYQDIILE HQKVIKKNEK RLANLKDIAS ANGLAEPKIT LPPQPHTKEG IEAYNNVVAQ

301 IVIWVNLNLW QKLKIGRDEA KPLQRLKGFP SFPLVERQAN EVDWWDMVCN VKKLINEKKE

361 DGKVFWQNLA GYKRQEALLP YLSSEEDRKK GKKFARYQFG DLLLHLEKKH GEDWGKVYDE

421 AWERIDKKVE GLSKHIKLEE ERRSEDAQSK AALTDWLRAK ASFVIEGLKE ADKDEFCRCE

481 LKLQKWYGDL RGKPFAIEAE NSILDISGES KQYNCAFIWQ KDGVKKLNLY LIINYFKGGK

541 LRFKKIKPEA FEANRFYTVI NKKSGEIVPM EVNFNFDDPN LIILPLAFGK RQGREFIWND

601 LLSLETGSLK LANGRVIEKT LYNRRTRQDE PALEVALTEE RREVLDSSNI KPMNLIGIDR

661 GENIPAVIAL TDPEGCPLSR FKDSLGNPTH ILRIGESYKE KQRTIQAAKE VEQRRAGGYS

-continued

```
721 RKYASKAKNL ADDMVRNTAR DLLYYAVTQD AMLIFENLSR GFGRQGKRTF MAERQYTRME
781 DWLTAKLAYE GLPSKTYLSK TLAQYTSKTC SNCGFTITSA DYDRVLEKLK KTATGWMTTI
841 NGKELKVEGQ ITYYNRYKRQ NVVKDLSVEL DRLSEESVNN DISSWTKGRS GEALSLLKKR
901 FSHRPVQEKF VCLNCGFETH ADEQAALNIA RSWLFLRSQE YKKYQTNKTT GNTDKRAFVE
961 TWQSFYRKKL KEVWKPAV.
```

In some embodiments, the CasX protein comprises the sequence of SEQ ID NO:2, or at least 60% similarity thereto. In some embodiments, the CasX protein comprises the sequence of SEQ ID NO:2, or at least 80% similarity thereto. In some embodiments, the CasX protein comprises the sequence of SEQ ID NO:2, or at least 90% similarity thereto. In some embodiments, the CasX protein comprises the sequence of SEQ ID NO:2, or at least 95% similarity thereto. In some embodiments, the CasX protein consists of the sequence of SEQ ID NO:2. In some embodiments, the CasX protein comprises or consists of a sequence that has at least 1, at least 2, at least 3, at least 4, at least 5, at least 6, at least 7, at least 8, at least 9, at least 10, at least 20, at least 30, at least 40 or at least 50 mutations relative to the sequence of SEQ ID NO:2. These mutations can be insertions, deletions, amino acid substitutions, or any combinations thereof.

In some cases, a reference CasX protein is isolated or derived from Candidatus Sungbacteria. In some embodiments, a CasX protein comprises a sequence at least 50% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence of

```
                                                          (SEQ ID NO: 3)
  1 MDNANKPSTK SLVNTTRISD HFGVTPGQVT RVFSFGIIPT KRQYAIIERW FAAVEAARER
 61 LYGMLYAHFQ ENPPAYLKEK FSYETFFKGR PVLNGLRDID PTIMTSAVFT ALRHKAEGAM
121 AAFHTNHRRL FEEARKKMRE YAECLKANEA LLRGAADIDW DKIVNALRTR LNTCLAPEYD
181 AVIADFGALC AFRALIAETN ALKGAYNHAL NQMLPALVKV DEPEEAEESP RLRFFNGRIN
241 DLPKFPVAER ETPPDTETII RQLEDMARVI PDTAEILGYI HRIRHKAARR KPGSAVPLPQ
301 RVALYCAIRM ERNPEEDPST VAGHFLGEID RVCEKRRQGL VRTPFDSQIR ARYMDIISER
361 ATLAHPDRWT EIQFLRSNAA SRRVRAETIS APFEGFSWTS NRTNPAPQYG MALAKDANAP
421 ADAPELCIGL SPSSAAFSVR EKGGDLIYMR PTGGRRGKDN PGKEITWVPG SFDEYPASGV
481 ALKLRLYFGR SQARRMLTNK TWGLLSDNPR VFAANAELVG KKRNPQDRWK LFFHMVISGP
541 PPVEYLDFSS DVRSRARTVI GINRGEVNPL AYAVVSVEDG QVLEEGLLGK KEYIDQLIET
601 RRRISEYQSR EQTPPRDLRQ RVRHLQDTVL GSARAKIHSL IAFWKGILAI ERLDDQFHGR
661 EQKIIPKKTY LANKTGFMNA LSFSGAVRVD KKGNPWGGMI EIYPGGISRT CTQCGTVWLA
721 RRPKNPGHRD AMVVIPDIVD DAAATGFDNV DCDAGTVDYG ELFTLSREWV RLTPRYSRVM
781 RGTLGDLERA IRQGDDRKSR QMLELALEPQ PQWGQFFCHR CGFNGQSDVL AATNLARRAI
841 SLIRRLPDTD TPPTP.
```

In some embodiments, the CasX protein comprises the sequence of SEQ ID NO:3, or at least 60% similarity thereto. In some embodiments, the CasX protein comprises the sequence of SEQ ID NO:3, or at least 80% similarity thereto. In some embodiments, the CasX protein comprises the sequence of SEQ ID NO:3, or at least 90% similarity thereto. In some embodiments, the CasX protein comprises the sequence of SEQ ID NO:3, or at least 95% similarity thereto. In some embodiments, the CasX protein consists of the sequence of SEQ ID NO:3. In some embodiments, the CasX protein comprises or consists of a sequence that has at least 1, at least 2, at least 3, at least 4, at least 5, at least 6, at least 7, at least 8, at least 9, at least 10, at least 20, at least 30, at least 40 or at least 50 mutations relative to the sequence of SEQ ID NO:3. These mutations can be insertions, deletions, amino acid substitutions, or any combinations thereof.

h. CasX Variant Proteins

The present disclosure provides variants of a reference CasX protein (interchangeably referred to herein as "CasX variant" or "CasX variant protein"), wherein the CasX variants comprise at least one modification in at least one domain of the reference CasX protein, including the sequences of SEQ ID NOS:1-3. In some embodiments, the CasX variant exhibits at least one improved characteristic compared to the reference CasX protein. All variants that improve one or more functions or characteristics of the CasX variant protein when compared to a reference CasX protein described herein are envisaged as being within the scope of the disclosure. In some embodiments, the modification is a mutation in one or more amino acids of the reference CasX. In other embodiments, the modification is a substitution of one or more domains of the reference CasX with one or more domains from a different CasX. In some embodiments, insertion includes the insertion of a part or all of a domain from a different CasX protein. Mutations can occur in any one or more domains of the reference CasX protein, and may include, for example, deletion of part or all of one or more domains, or one or more amino acid substitutions, deletions, or insertions in any domain of the reference CasX protein. The domains of CasX proteins include the non-target strand binding (NTSB) domain, the target strand loading (TSL) domain, the helical I domain, the helical II domain, the oligonucleotide binding domain (OBD), and the RuvC DNA cleavage domain. Any change in amino acid sequence of a reference CasX protein that leads to an improved characteristic of the CasX protein is considered a CasX variant protein of the disclosure. For example, CasX variants can comprise one or more amino acid substitutions, insertions, deletions, or swapped domains, or any combinations thereof, relative to a reference CasX protein sequence.

In some embodiments, the CasX variant protein comprises at least one modification in at least each of two domains of the reference CasX protein, including the sequences of SEQ ID NOS:1-3. In some embodiments, the CasX variant protein comprises at least one modification in at least 2 domains, in at least 3 domains, at least 4 domains or at least 5 domains of the reference CasX protein. In some embodiments, the CasX variant protein comprises two or more modifications in at least one domain of the reference CasX protein. In some embodiments, the CasX variant protein comprises at least two modifications in at least one domain of the reference CasX protein, at least three modifications in at least one domain of the reference CasX protein or at least four modifications in at least one domain of the reference CasX protein. In some embodiments, wherein the CasX variant comprises two or more modifications compared to a reference CasX protein, each modification is made in a domain independently selected from the group consisting of a NTSBD, TSLD, Helical I domain, Helical II domain, OBD, and RuvC DNA cleavage domain.

In some embodiments, the at least one modification of the CasX variant protein comprises a deletion of at least a portion of one domain of the reference CasX protein, including the sequences of SEQ ID NOS:1-3. In some embodiments, the deletion is in the NTSBD, TSLD, Helical I domain, Helical II domain, OBD, or RuvC DNA cleavage domain.

Suitable mutagenesis methods for generating CasX variant proteins of the disclosure may include, for example, Deep Mutational Evolution (DME), deep mutational scanning (DMS), error prone PCR, cassette mutagenesis, random mutagenesis, staggered extension PCR, gene shuffling, or domain swapping. In some embodiments, the CasX variants are designed, for example by selecting one or more desired mutations in a reference CasX. In certain embodiments, the activity of a reference CasX protein is used as a benchmark against which the activity of one or more CasX variants are compared, thereby measuring improvements in function of the CasX variants. Exemplary improvements of CasX variants include, but are not limited to, improved folding of the variant, improved binding affinity to the gNA, improved binding affinity to the target DNA, altered binding affinity to one or more PAM sequences, improved unwinding of the target DNA, increased activity, improved editing efficiency, improved editing specificity, increased activity of the nuclease, increased target strand loading for double strand cleavage, decreased target strand loading for single strand nicking, decreased off-target cleavage, improved binding of the non-target strand of DNA, improved protein stability, improved protein:gNA complex stability, improved protein solubility, improved protein:gNA complex solubility, improved protein yield, improved protein expression, and improved fusion characteristics, as described more fully, below.

In some embodiments of the CasX variants described herein, the at least one modification comprises: (a) a substitution of 1 to 100 consecutive or non-consecutive amino acids in the CasX variant compared to a reference CasX of SEQ ID NO:1, SEQ ID NO:2, or SEQ ID NO:3; (b) a deletion of 1 to 100 consecutive or non-consecutive amino acids in the CasX variant compared to a reference CasX; (c) an insertion of 1 to 100 consecutive or non-consecutive amino acids in the CasX compared to a reference CasX; or (d) any combination of (a)-(c). In some embodiments, the at least one modification comprises: (a) a substitution of 5-10 consecutive or non-consecutive amino acids in the CasX variant compared to a reference CasX of SEQ ID NO:1, SEQ ID NO:2, or SEQ ID NO:3; (b) a deletion of 1-5 consecutive or non-consecutive amino acids in the CasX variant compared to a reference CasX; (c) an insertion of 1-5 consecutive or non-consecutive amino acids in the CasX compared to a reference CasX; or (d) any combination of (a)-(c).

In some embodiments, the CasX variant protein comprises or consists of a sequence that has at least 1, at least 2, at least 3, at least 4, at least 5, at least 6, at least 7, at least 8, at least 9, at least 10, at least 20, at least 30, at least 40 or at least 50 mutations relative to the sequence of SEQ ID NO:1, SEQ ID NO:2, or SEQ ID NO:3. These mutations can be insertions, deletions, amino acid substitutions, or any combinations thereof.

In some embodiments, the CasX variant protein comprises at least one amino acid substitution in at least one domain of a reference CasX protein. In some embodiments, the CasX variant protein comprises at least about 1-4 amino acid substitutions, 1-10 amino acid substitutions, 1-20 amino acid substitutions, 1-30 amino acid substitutions, 1-40 amino acid substitutions, 1-50 amino acid substitutions, 1-60 amino acid substitutions, 1-70 amino acid substitutions, 1-80 amino acid substitutions, 1-90 amino acid substitutions, 1-100 amino acid substitutions, 2-10 amino acid substitutions, 2-20 amino acid substitutions, 2-30 amino acid substitutions, 3-10 amino acid substitutions, 3-20 amino acid substitutions, 3-30 amino acid substitutions, 4-10 amino acid substitutions, 4-20 amino acid substitutions, 3-300 amino acid substitutions, 5-10 amino acid substitutions, 5-20 amino acid substitutions, 5-30 amino acid substitutions, 10-50 amino acid substitutions, or 20-50 amino acid substitutions, relative to a reference CasX protein. In some embodiments, the CasX variant protein comprises at least about 100 amino acid substitutions relative to a reference CasX protein. In some embodiments, the CasX variant protein comprises 1, 2, 3, 4, 5, 6, 7, 8, 9 or 10 amino acid substitutions relative to a reference CasX protein. In some embodiments, the CasX variant protein comprises 1, 2, 3, 4, 5, 6, 7, 8, 9 or 10 amino acid substitutions in a single domain relative to the reference CasX protein. In some embodiments, the amino acid substitutions are conservative substitutions. In other embodiments, the substitutions are non-conservative; e.g., a polar amino acid is substituted for a non-polar amino acid, or vice versa.

In some embodiments, a CasX variant protein comprises 1 amino acid substitution, 2-3 consecutive amino acid substitutions, 2-4 consecutive amino acid substitutions, 2-5 consecutive amino acid substitutions, 2-6 consecutive amino acid substitutions, 2-7 consecutive amino acid substitutions, 2-8 consecutive amino acid substitutions, 2-9 consecutive amino acid substitutions, 2-10 consecutive amino acid substitutions, 2-20 consecutive amino acid substitutions, 2-30 consecutive amino acid substitutions, 2-40 consecutive amino acid substitutions, 2-50 consecutive amino acid substitutions, 2-60 consecutive amino acid substitutions, 2-70 consecutive amino acid substitutions, 2-80 consecutive amino acid substitutions, 2-90 consecutive amino acid substitutions, 2-100 consecutive amino acid substitutions, 3-10 consecutive amino acid substitutions, 3-20 consecutive amino acid substitutions, 3-30 consecutive amino acid substitutions, 4-10 consecutive amino acid substitutions, 4-20 consecutive amino acid substitutions, 3-300 consecutive amino acid substitutions, 5-10 consecutive amino acid substitutions, 5-20 consecutive amino acid substitutions, 5-30 consecutive amino acid substitutions, 10-50 consecutive amino acid substitutions or 20-50 consecutive amino acid substitutions relative to a reference CasX protein. In some embodiments, a CasX variant protein comprises 2, 3, 4, 5, 6, 7, 8, 9, 10, 11, 12, 13, 14, 15, 16, 17, 18, 19 or 20 consecutive amino acid substitutions. In some embodiments, a CasX variant protein comprises a substitution of at least about 100 consecutive amino acids. As used herein "consecutive amino acids" refer to amino acids that are contiguous in the primary sequence of a polypeptide.

In some embodiments, a CasX variant protein comprises two or more substitutions relative to a reference CasX protein, and the two or more substitutions are not in consecutive amino acids of the reference CasX sequence. For example, a first substitution may be in a first domain of the reference CasX protein, and a second substitution may be in a second domain of the reference CasX protein. In some embodiments, a CasX variant protein comprises 2, 3, 4, 5, 6, 7, 8, 9, 10, 11, 12, 13, 14, 15, 16, 17, 18, 19 or 20 non-consecutive substitutions relative to a reference CasX protein. In some embodiments, a CasX variant protein comprises at least 20 non-consecutive substitutions relative to a reference CasX protein. Each non-consecutive substitution may be of any length of amino acids described herein, e.g., 1-4 amino acids, 1-10 amino acids, and the like. In some embodiments, the two or more substitutions relative to the reference CasX protein are not the same length, for example one substitution is one amino acid and a second substitution is three amino acids. In some embodiments, the two or more substitutions relative to the reference CasX protein are the same length, for example both substitutions are two consecutive amino acids in length.

Any amino acid can be substituted for any other amino acid in the substitutions described herein. The substitution can be a conservative substitution (e.g., a basic amino acid is substituted for another basic amino acid). The substitution can be a non-conservative substitution (e.g., a basic amino acid is substituted for an acidic amino acid or vice versa). For example, a proline in a reference CasX protein can be substituted for any of arginine, histidine, lysine, aspartic acid, glutamic acid, serine, threonine, asparagine, glutamine, cysteine, glycine, alanine, isoleucine, leucine, methionine, phenylalanine, tryptophan, tyrosine or valine to generate a CasX variant protein of the disclosure.

In some embodiments, a CasX variant protein comprises at least one amino acid deletion relative to a reference CasX protein. In some embodiments, a CasX variant protein comprises a deletion of 1-4 amino acids, 1-10 amino acids, 1-20 amino acids, 1-30 amino acids, 1-40 amino acids, 1-50 amino acids, 1-60 amino acids, 1-70 amino acids, 1-80 amino acids, 1-90 amino acids, 1-100 amino acids, 2-10 amino acids, 2-20 amino acids, 2-30 amino acids, 3-10 amino acids, 3-20 amino acids, 3-30 amino acids, 4-10 amino acids, 4-20 amino acids, 3-300 amino acids, 5-10 amino acids, 5-20 amino acids, 5-30 amino acids, 10-50 amino acids or 20-50 amino acids relative to a reference CasX protein. In some embodiments, a CasX protein comprises a deletion of at least about 100 consecutive amino acids relative to a reference CasX protein. In some embodiments, a CasX variant protein comprises a deletion of at least 1, 2, 3, 4, 5, 6, 7, 8, 9, 10, 20, 30, 40, 50 or 100 consecutive amino acids relative to a reference CasX protein. In some embodiments, a CasX variant protein comprises a deletion of 1, 2, 3, 4, 5, 6, 7, 8, 9 or 10 consecutive amino acids.

In some embodiments, a CasX variant protein comprises two or more deletions relative to a reference CasX protein, and the two or more deletions are not consecutive amino acids. For example, a first deletion may be in a first domain of the reference CasX protein, and a second deletion may be in a second domain of the reference CasX protein. In some embodiments, a CasX variant protein comprises 2, 3, 4, 5, 6, 7, 8, 9, 10, 11, 12, 13, 14, 15, 16, 17, 18, 19 or 20 non-consecutive deletions relative to a reference CasX protein. In some embodiments, a CasX variant protein comprises at least 20 non-consecutive deletions relative to a reference CasX protein. Each non-consecutive deletion may be of any length of amino acids described herein, e.g., 1-4 amino acids, 1-10 amino acids, and the like.

In some embodiments, the CasX variant protein comprises at least one amino acid insertion relative to the sequence of SEQ ID NOS:1, 2, or 3. In some embodiments, a CasX variant protein comprises an insertion of 1 amino acid, an insertion of 2-3 consecutive amino acids, 2-4 consecutive amino acids, 2-5 consecutive amino acids, 2-6 consecutive amino acids, 2-7 consecutive amino acids, 2-8 consecutive amino acids, 2-9 consecutive amino acids, 2-10 consecutive amino acids, 2-20 consecutive amino acids, 2-30 consecutive amino acids, 2-40 consecutive amino acids, 2-50 consecutive amino acids, 2-60 consecutive amino acids, 2-70 consecutive amino acids, 2-80 consecutive amino acids, 2-90 consecutive amino acids, 2-100 consecutive amino acids, 3-10 consecutive amino acids, 3-20 consecutive amino acids, 3-30 consecutive amino acids, 4-10 consecutive amino acids, 4-20 consecutive amino acids, 3-300 consecutive amino acids, 5-10 consecutive amino acids, 5-20 consecutive amino acids, 5-30 consecutive amino acids, 10-50 consecutive amino acids or 20-50 consecutive amino acids relative to a reference CasX protein. In some embodiments, the CasX variant protein comprises an insertion of 2, 3, 4, 5, 6, 7, 8, 9, 10, 11, 12, 13, 14, 15, 16, 17, 18, 19 or 20 consecutive amino acids. In some embodiments, a CasX variant protein comprises an insertion of at least about 100 consecutive amino acids.

In some embodiments, a CasX variant protein comprises two or more insertions relative to a reference CasX protein, and the two or more insertions are not consecutive amino acids of the sequence. For example, a first insertion may be in a first domain of the reference CasX protein, and a second insertion may be in a second domain of the reference CasX protein. In some embodiments, a CasX variant protein comprises 2, 3, 4, 5, 6, 7, 8, 9, 10, 11, 12, 13, 14, 15, 16, 17, 18, 19 or 20 non-consecutive insertions relative to a reference CasX protein. In some embodiments, a CasX variant protein comprises at least 10 to about 20 or more non-consecutive insertions relative to a reference CasX protein. Each non-consecutive insertion may be of any length of amino acids described herein, e.g., 1-4 amino acids, 1-10 amino acids, and the like.

Any amino acid, or combination of amino acids, can be inserted in the insertions described herein. For example, a proline, arginine, histidine, lysine, aspartic acid, glutamic acid, serine, threonine, asparagine, glutamine, cysteine, glycine, alanine, isoleucine, leucine, methionine, phenylalanine, tryptophan, tyrosine or valine or any combination thereof can be inserted into a reference CasX protein of the disclosure to generate a CasX variant protein.

Any permutation of the substitution, insertion and deletion embodiments described herein can be combined to generate a CasX variant protein of the disclosure. For example, a CasX variant protein can comprise at least one substitution and at least one deletion relative to a reference CasX protein sequence, at least one substitution and at least one insertion relative to a reference CasX protein sequence, at least one insertion and at least one deletion relative to a reference CasX protein sequence, or at least one substitution, one insertion and one deletion relative to a reference CasX protein sequence.

In some embodiments, the CasX variant protein has at least about 60% sequence similarity, at least 70% similarity, at least 80% similarity, at least 85% similarity, at least 86% similarity, at least 87% similarity, at least 88% similarity, at least 89% similarity, at least 90% similarity, at least 91% similarity, at least 92% similarity, at least 93% similarity, at least 94% similarity, at least 95% similarity, at least 96% similarity, at least 97% similarity, at least 98% similarity, at least 99% similarity, at least 99.5% similarity, at least 99.6% similarity, at least 99.7% similarity, at least 99.8% similarity or at least 99.9% similarity to one of SEQ ID NO:1, SEQ ID NO:2, or SEQ ID NO:3.

In some embodiments, the CasX variant protein has at least about 60% sequence similarity to SEQ ID NO:2 or a portion thereof. In some embodiments, the CasX variant protein comprises a substitution of Y789T of SEQ ID NO:2, a deletion of P793 of SEQ ID NO:2, a substitution of Y789D of SEQ ID NO:2, a substitution of T72S of SEQ ID NO:2, a substitution of I546V of SEQ ID NO:2, a substitution of E552A of SEQ ID NO:2, a substitution of A636D of SEQ ID NO:2, a substitution of F536S of SEQ ID NO:2, a substitution of A708K of SEQ ID NO:2, a substitution of Y797L of SEQ ID NO:2, a substitution of L792G SEQ ID NO:2, a substitution of A739V of SEQ ID NO:2, a substitution of G791M of SEQ ID NO:2, an insertion of A at position 661 of SEQ ID NO:2, a substitution of A788W of SEQ ID NO:2, a substitution of K390R of SEQ ID NO:2, a substitution of A751S of SEQ ID NO:2, a substitution of E385A of SEQ ID NO:2, an insertion of P at position 696 of SEQ ID NO:2, an insertion of M at position 773 of SEQ ID NO:2, a substitution of G695H of SEQ ID NO:2, an insertion of AS at position 793 of SEQ ID NO:2, an insertion of AS at position 795 of SEQ ID NO:2, a substitution of C477R of SEQ ID NO:2, a substitution of C477K of SEQ ID NO:2, a substitution of C479A of SEQ ID NO:2, a substitution of C479L of SEQ ID NO:2, a substitution of I55F of SEQ ID NO:2, a substitution of K210R of SEQ ID NO:2, a substitution of C233S of SEQ ID NO:2, a substitution of D231N of SEQ ID NO:2, a substitution of Q338E of SEQ ID NO:2, a substitution of Q338R of SEQ ID NO:2, a substitution of L379R of SEQ ID NO:2, a substitution of K390R of SEQ ID NO:2, a substitution of L481Q of SEQ ID NO:2, a substitution of F495S of SEQ ID NO:2, a substitution of D600N of SEQ ID NO:2, a substitution of T886K of SEQ ID NO:2, a substitution of A739V of SEQ ID NO:2, a substitution of K460N of SEQ ID NO:2, a substitution of I199F of SEQ ID NO:2, a substitution of G492P of SEQ ID NO:2, a substitution of T153I of SEQ ID NO:2, a substitution of R591I of SEQ ID NO:2, an insertion of AS at position 795 of SEQ ID NO:2, an insertion of AS at position 796 of SEQ ID NO:2, an insertion of L at position 889 of SEQ ID NO:2, a substitution of E121D of SEQ ID NO:2, a substitution of S270W of SEQ ID NO:2, a substitution of E712Q of SEQ ID NO:2, a substitution of K942Q of SEQ ID NO:2, a substitution of E552K of SEQ ID NO:2, a substitution of K25Q of SEQ ID NO:2, a substitution of N47D of SEQ ID NO:2, an insertion of T at position 696 of SEQ ID NO:2, a substitution of L685I of SEQ ID NO:2, a substitution of N880D of SEQ ID NO:2, a substitution of Q102R of SEQ ID NO:2, a substitution of M734K of SEQ ID NO:2, a substitution of A724S of SEQ ID NO:2, a substitution of T704K of SEQ ID NO:2, a substitution of P224K of SEQ ID NO:2, a substitution of K25R of SEQ ID NO:2, a substitution of M29E of SEQ ID NO:2, a substitution of H152D of SEQ ID NO:2, a substitution of S219R of SEQ ID NO:2, a substitution of E475K of SEQ ID NO:2, a substitution of G226R of SEQ ID NO:2, a substitution of A377K of SEQ ID NO:2, a substitution of E480K of SEQ ID NO:2, a substitution of K416E of SEQ ID NO:2, a substitution of H164R of SEQ ID NO:2, a substitution of K767R of SEQ ID NO:2, a substitution of I7F of SEQ ID NO:2, a substitution of M29R of SEQ ID NO:2, a substitution of H435R of SEQ ID NO:2, a substitution of E385Q of SEQ ID NO:2, a substitution of E385K of SEQ ID NO:2, a substitution of I279F of SEQ ID NO:2, a substitution of D489S of SEQ ID NO:2, a substitution of D732N of SEQ ID NO:2, a substitution of A739T of SEQ ID NO:2, a substitution of W885R of SEQ ID NO:2, a substitution of E53K of SEQ ID NO:2, a substitution of A238T of SEQ ID NO:2, a substitution of P283Q of SEQ ID NO:2, a substitution of E292K of SEQ ID NO:2, a substitution of Q628E of SEQ ID NO:2, a substitution of R388Q of SEQ ID NO:2, a substitution of G791M of SEQ ID NO:2, a substitution of L792K of SEQ ID NO:2, a substitution of L792E of SEQ ID NO:2, a substitution of M779N of SEQ ID NO:2, a substitution of G27D of SEQ ID NO:2, a substitution of K955R of SEQ ID NO:2, a substitution of S867R of SEQ ID NO:2, a substitution of R693I of SEQ ID NO:2, a substitution of F189Y of SEQ ID NO:2, a substitution of V635M of SEQ ID NO:2, a substitution of F399L of SEQ ID NO:2, a substitution of E498K of SEQ ID NO:2, a substitution of E386R of SEQ ID NO:2, a substitution of V254G of SEQ ID NO:2, a substitution of P793S of SEQ ID NO:2, a substitution of K188E of SEQ ID NO:2, a substitution of QT945KI of SEQ ID NO:2, a substitution of T620P of SEQ ID NO:2, a substitution of T946P of SEQ ID NO:2, a substitution of TT949PP of SEQ ID NO:2, a substitution of N952T of SEQ ID NO:2, a substitution of K682E of SEQ ID NO:2, a substitution of K975R of SEQ ID NO:2, a substitution of L212P of SEQ ID NO:2, a substitution of E292R of SEQ ID NO:2, a substitution of I303K of SEQ ID NO:2, a substitution of C349E of SEQ ID NO:2, a substitution of E385P of SEQ ID NO:2, a substitution of E386N of SEQ ID NO:2, a substitution of D387K of SEQ ID NO:2, a substitution of L404K of SEQ ID NO:2, a substitution of E466H of SEQ ID NO:2, a substitution of C477Q of SEQ ID NO:2, a substitution of C477H of SEQ ID NO:2, a substitution of C479A of SEQ ID NO:2, a substitution of D659H of SEQ ID NO:2, a substitution of T806V of SEQ ID NO:2, a substitution of K808S of SEQ ID NO:2, an insertion of AS at position 797 of SEQ ID NO:2, a substitution of V959M of SEQ ID NO:2, a substitution of K975Q of SEQ ID NO:2, a substitution of W974G of SEQ ID NO:2, a substitution of A708Q of SEQ ID NO:2, a substitution of V711K of SEQ ID NO:2, a substitution of D733T of SEQ ID NO:2, a substitution of L742W of SEQ ID NO:2, a substitution of V747K of SEQ ID NO:2, a substitution of F755M of SEQ ID NO:2, a substitution of M771A of SEQ ID NO:2, a substitution of M771Q of SEQ ID NO:2, a substitution of W782Q of SEQ ID NO:2, a substitution of G791F, of SEQ ID NO:2 a substitution of L792D of SEQ ID NO:2, a substitution of L792K of SEQ ID NO:2, a substitution of P793Q of SEQ ID NO:2, a substitution of P793G of SEQ ID NO:2, a substitution of Q804A of SEQ ID NO:2, a substitution of Y966N of SEQ ID NO:2, a substitution of Y723N of SEQ ID NO:2, a substitution of Y857R of SEQ ID NO:2, a substitution of S890R of SEQ ID NO:2, a substitution of S932M of SEQ ID NO:2, a substitution of L897M of SEQ ID NO:2, a substitution of R624G of SEQ ID NO:2, a substitution of S603G of SEQ ID NO:2, a substitution of N737S of SEQ ID NO:2, a substitution of L307K of SEQ ID NO:2, a substitution of I658V of SEQ ID NO:2, an insertion of PT at position 688 of SEQ ID NO:2, an insertion of SA at position 794 of SEQ ID NO:2, a substitution of S877R of SEQ ID NO:2, a substitution of N580T of SEQ ID NO:2, a substitution of V335G of SEQ ID NO:2, a substitution of T620S of SEQ ID NO:2, a substitution of W345G of SEQ ID NO:2, a substitution of T280S of SEQ ID NO:2, a substitution of L406P of SEQ ID NO:2, a substitution of A612D of SEQ ID NO:2, a substitution of A751S of SEQ ID NO:2, a substitution of E386R of SEQ ID NO:2, a substitution of V351M of SEQ ID NO: 2, a substitution of K210N of SEQ ID NO:2, a substitution of D40A of SEQ ID NO:2, a substitution of E773G of SEQ ID NO:2, a substitution of H207L of SEQ ID NO:2, a substitution of T62A SEQ ID NO:2, a substitution of T287P of SEQ ID NO:2, a substitution of T832A of SEQ ID NO:2, a substitution of A893S of SEQ ID NO:2, an insertion of V at position 14 of SEQ ID NO:2, an insertion of AG at position 13 of SEQ ID NO:2, a substitution of R11V of SEQ ID NO:2, a substitution of R12N of SEQ ID NO: 2, a substitution of R13H of SEQ ID NO:2, an insertion of Y at position 13 of SEQ ID NO:2, a substitution of R12L of SEQ ID NO:2, an insertion of Q at position 13 of SEQ ID NO:2, an substitution of V15S of SEQ ID NO:2, an insertion of D at position 17 of SEQ ID NO:2 or a combination thereof.

In some embodiments, the CasX variant comprises at least one modification in the NTSB domain.

In some embodiments, the CasX variant comprises at least one modification in the TSL domain. In some embodiments, the at least one modification in the TSL domain comprises an amino acid substitution of one or more of amino acids Y857, S890, or S932 of SEQ ID NO:2.

In some embodiments, the CasX variant comprises at least one modification in the helical I domain. In some embodiments, the at least one modification in the helical I domain comprises an amino acid substitution of one or more of amino acids S219, L249, E259, Q252, E292, L307, or D318 of SEQ ID NO:2.

In some embodiments, the CasX variant comprises at least one modification in the helical II domain. In some embodiments, the at least one modification in the helical II domain comprises an amino acid substitution of one or more of amino acids D361, L379, E385, E386, D387, F399, L404, R458, C477, or D489 of SEQ ID NO:2.

In some embodiments, the CasX variant comprises at least one modification in the OBD domain. In some embodiments, the at least one modification in the OBD comprises an amino acid substitution of one or more of amino acids F536, E552, T620, or 1658 of SEQ ID NO:2.

In some embodiments, the CasX variant comprises at least one modification in the RuvC DNA cleavage domain. In some embodiments, the at least one modification in the RuvC DNA cleavage domain comprises an amino acid substitution of one or more of amino acids K682, G695, A708, V711, D732, A739, D733, L742, V747, F755, M771, M779, W782, A788, G791, L792, P793, Y797, M799, Q804, S819, or Y857 or a deletion of amino acid P793 of SEQ ID NO:2.

In some embodiments, the CasX variant comprises at least one modification compared to the reference CasX sequence of SEQ ID NO:2 is selected from one or more of: (a) an amino acid substitution of L379R; (b) an amino acid substitution of A708K; (c) an amino acid substitution of T620P; (d) an amino acid substitution of E385P; (e) an amino acid substitution of Y857R; (f) an amino acid substitution of I658V; (g) an amino acid substitution of F399L; (h) an amino acid substitution of Q252K; (i) an amino acid substitution of L404K; and (j) an amino acid deletion of P793.

In some embodiments, a CasX variant protein comprises at least two amino acid changes to a reference CasX protein amino acid sequence. The at least two amino acid changes can be substitutions, insertions, or deletions of a reference CasX protein amino acid sequence, or any combination thereof. The substitutions, insertions or deletions can be any substitution, insertion or deletion in the sequence of a reference CasX protein described herein. In some embodiments, the changes are contiguous, non-contiguous, or a combination of contiguous and non-contiguous amino acid changes to a reference CasX protein sequence. In some embodiments, the reference CasX protein is SEQ ID NO:2. In some embodiments, a CasX variant protein comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 40, at least 45, at least 50, at least 55, at least 60, at least 65, at least 70, at least 75, at least 80, at least 85, at least 90, at least 95 or at least 100 amino acid changes to a reference CasX protein sequence. In some embodiments, a CasX variant protein comprises 1-50, 3-40, 5-30, 5-20, 5-15, 5-10, 10-50, 10-40, 10-30, 10-20, 15-50, 15-40, 15-30, 2-25, 2-24, 2-22, 2-23, 2-22, 2-21, 2-20, 2-19, 2-18, 2-17, 2-16, 2-15, 2-14, 2-12, 2-11, 2-10, 2-9, 2-8, 2-7, 2-6, 2-5, 2-4, 2-3, 3-25, 3-24, 3-22, 3-23, 3-22, 3-21, 3-20, 3-19, 3-18, 3-17, 3-16, 3-15, 3-14, 3-12, 3-11, 3-10, 3-9, 3-8, 3-7, 3-6, 3-5, 3-4,4-25, 4-24, 4-22, 4-23, 4-22, 4-21, 4-20, 4-19, 4-18, 4-17, 4-16, 4-15, 4-14, 4-12, 4-11, 4-10, 4-9, 4-8, 4-7, 4-6, 4-5, 5-25, 5-24, 5-22, 5-23, 5-22, 5-21, 5-20, 5-19, 5-18, 5-17, 5-16, 5-15, 5-14, 5-12, 5-11, 5-10, 5-9, 5-8, 5-7 or 5-6 amino acid changes to a reference CasX protein sequence. In some embodiments, a CasX variant protein comprises 15-20 changes to a reference CasX protein sequence. In some embodiments, a CasX variant protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid changes to a reference CasX protein sequence. In some embodiments, the at least two amino acid changes to the sequence of a reference CasX variant protein are selected from the group consisting of: a substitution of Y789T of SEQ ID NO:2, a deletion of P793 of SEQ ID NO:2, a substitution of Y789D of SEQ ID NO:2, a substitution of T72S of SEQ ID NO:2, a substitution of I546V of SEQ ID NO:2, a substitution of E552A of SEQ ID NO:2, a substitution of A636D of SEQ ID NO:2, a substitution of F536S of SEQ ID NO:2, a substitution of A708K of SEQ ID NO:2, a substitution of Y797L of SEQ ID NO:2, a substitution of L792G SEQ ID NO:2, a substitution of A739V of SEQ ID NO:2, a substitution of G791M of SEQ ID NO:2, an insertion of A at position 661 of SEQ ID NO:2, a substitution of A788W of SEQ ID NO:2, a substitution of K390R of SEQ ID NO:2, a substitution of A751S of SEQ ID NO:2, a substitution of E385A of SEQ ID NO:2, an insertion of P at position 696 of SEQ ID NO:2, an insertion of M at position 773 of SEQ ID NO:2, a substitution of G695H of SEQ ID NO:2, an insertion of AS at position 793 of SEQ ID NO:2, an insertion of AS at position 795 of SEQ ID NO:2, a substitution of C477R of SEQ ID NO:2, a substitution of C477K of SEQ ID NO:2, a substitution of C479A of SEQ ID NO:2, a substitution of C479L of SEQ ID NO:2, a substitution of I55F of SEQ ID NO:2, a substitution of K210R of SEQ ID NO:2, a substitution of C233S of SEQ ID NO:2, a substitution of D231N of SEQ ID NO:2, a substitution of Q338E of SEQ ID NO:2, a substitution of Q338R of SEQ ID NO:2, a substitution of L379R of SEQ ID NO:2, a substitution of K390R of SEQ ID NO:2, a substitution of L481Q of SEQ ID NO:2, a substitution of F495S of SEQ ID NO:2, a substitution of D600N of SEQ ID NO:2, a substitution of T886K of SEQ ID NO:2, a substitution of A739V of SEQ ID NO:2, a substitution of K460N of SEQ ID NO:2, a substitution of I199F of SEQ ID NO:2, a substitution of G492P of SEQ ID NO:2, a substitution of T153I of SEQ ID NO:2, a substitution of R591I of SEQ ID NO:2, an insertion of AS at position 795 of SEQ ID NO:2, an insertion of AS at position 796 of SEQ ID NO:2, an insertion of L at position 889 of SEQ ID NO:2, a substitution of E121D of SEQ ID NO:2, a substitution of S270W of SEQ ID NO:2, a substitution of E712Q of SEQ ID NO:2, a substitution of K942Q of SEQ ID NO:2, a substitution of E552K of SEQ ID NO:2, a substitution of K25Q of SEQ ID NO:2, a substitution of N47D of SEQ ID NO:2, an insertion of T at position 696 of SEQ ID NO:2, a substitution of L685I of SEQ ID NO:2, a substitution of N880D of SEQ ID NO:2, a substitution of Q102R of SEQ ID NO:2, a substitution of M734K of SEQ ID NO:2, a substitution of A724S of SEQ ID NO:2, a substitution of T704K of SEQ ID NO:2, a substitution of P224K of SEQ ID NO:2, a substitution of K25R of SEQ ID NO:2, a substitution of M29E of SEQ ID NO:2, a substitution of H152D of SEQ ID NO:2, a substitution of S219R of SEQ ID NO:2, a substitution of E475K of SEQ ID NO:2, a substitution of G226R of SEQ ID NO:2, a substitution of A377K of SEQ ID NO:2, a substitution of E480K of SEQ ID NO:2, a substitution of K416E of SEQ ID NO:2, a substitution of H164R of SEQ ID NO:2, a substitution of K767R of SEQ ID NO:2, a substitution of I7F of SEQ ID NO:2, a substitution of M29R of SEQ ID NO:2, a substitution of H435R of SEQ ID NO:2, a substitution of E385Q of SEQ ID NO:2, a substitution of E385K of SEQ ID NO:2, a substitution of I279F of SEQ ID NO:2, a substitution of D489S of SEQ ID NO:2, a substitution of D732N of SEQ ID NO:2, a substitution of A739T of SEQ ID NO:2, a substitution of W885R of SEQ ID NO:2, a substitution of E53K of SEQ ID NO:2, a substitution of A238T of SEQ ID NO:2, a substitution of P283Q of SEQ ID NO:2, a substitution of E292K of SEQ ID NO:2, a substitution of Q628E of SEQ ID NO:2, a substitution of R388Q of SEQ ID NO:2, a substitution of G791M of SEQ ID NO:2, a substitution of L792K of SEQ ID NO:2, a substitution of L792E of SEQ ID NO:2, a substitution of M779N of SEQ ID NO:2, a substitution of G27D of SEQ ID NO:2, a substitution of K955R of SEQ ID NO:2, a substitution of S867R of SEQ ID NO:2, a substitution of R693I of SEQ ID NO:2, a substitution of F189Y of SEQ ID NO:2, a substitution of V635M of SEQ ID NO:2, a substitution of F399L of SEQ ID NO:2, a substitution of E498K of SEQ ID NO:2, a substitution of E386R of SEQ ID NO:2, a substitution of V254G of SEQ ID NO:2, a substitution of P793S of SEQ ID NO:2, a substitution of K188E of SEQ ID NO:2, a substitution of QT945KI of SEQ ID NO:2, a substitution of T620P of SEQ ID NO:2, a substitution of T946P of SEQ ID NO:2, a substitution of TT949PP of SEQ ID NO:2, a substitution of N952T of SEQ ID NO:2, a substitution of K682E of SEQ ID NO:2, a substitution of K975R of SEQ ID NO:2, a substitution of L212P of SEQ ID NO:2, a substitution of E292R of SEQ ID NO:2, a substitution of I303K of SEQ ID NO:2, a substitution of C349E of SEQ ID NO:2, a substitution of E385P of SEQ ID NO:2, a substitution of E386N of SEQ ID NO:2, a substitution of D387K of SEQ ID NO:2, a substitution of L404K of SEQ ID NO:2, a substitution of E466H of SEQ ID NO:2, a substitution of C477Q of SEQ ID NO:2, a substitution of C477H of SEQ ID NO:2, a substitution of C479A of SEQ ID NO:2, a substitution of D659H of SEQ ID NO:2, a substitution of T806V of SEQ ID NO:2, a substitution of K808S of SEQ ID NO:2, an insertion of AS at position 797 of SEQ ID NO:2, a substitution of V959M of SEQ ID NO:2, a substitution of K975Q of SEQ ID NO:2, a substitution of W974G of SEQ ID NO:2, a substitution of A708Q of SEQ ID NO:2, a substitution of V711K of SEQ ID NO:2, a substitution of D733T of SEQ ID NO:2, a substitution of L742W of SEQ ID NO:2, a substitution of V747K of SEQ ID NO:2, a substitution of F755M of SEQ ID NO:2, a substitution of M771A of SEQ ID NO:2, a substitution of M771Q of SEQ ID NO:2, a substitution of W782Q of SEQ ID NO:2, a substitution of G791F, of SEQ ID NO:2 a substitution of L792D of SEQ ID NO:2, a substitution of L792K of SEQ ID NO:2, a substitution of P793Q of SEQ ID NO:2, a substitution of P793G of SEQ ID NO:2, a substitution of Q804A of SEQ ID NO:2, a substitution of Y966N of SEQ ID NO:2, a substitution of Y723N of SEQ ID NO:2, a substitution of Y857R of SEQ ID NO:2, a substitution of S890R of SEQ ID NO:2, a substitution of S932M of SEQ ID NO:2, a substitution of L897M of SEQ ID NO:2, a substitution of R624G of SEQ ID NO:2, a substitution of S603G of SEQ ID NO:2, a substitution of N737S of SEQ ID NO:2, a substitution of L307K of SEQ ID NO:2, a substitution of I658V of SEQ ID NO:2, an insertion of PT at position 688 of SEQ ID NO:2, an insertion of SA at position 794 of SEQ ID NO:2, a substitution of S877R of SEQ ID NO:2, a substitution of N580T of SEQ ID NO:2, a substitution of V335G of SEQ ID NO:2, a substitution of T620S of SEQ ID NO:2, a substitution of W345G of SEQ ID NO:2, a substitution of T280S of SEQ ID NO:2, a substitution of L406P of SEQ ID NO:2, a substitution of A612D of SEQ ID NO:2, a substitution of A751S of SEQ ID NO:2, a substitution of E386R of SEQ ID NO:2, a substitution of V351M of SEQ ID NO:2, a substitution of K210N of SEQ ID NO:2, a substitution of D40A of SEQ ID NO:2, a substitution of E773G of SEQ ID NO:2, a substitution of H207L of SEQ ID NO:2, a substitution of T62A SEQ ID NO:2, a substitution of T287P of SEQ ID NO:2, a substitution of T832A of SEQ ID NO:2, a substitution of A893S of SEQ ID NO:2, an insertion of V at position 14 of SEQ ID NO:2, an insertion of AG at position 13 of SEQ ID NO:2, a substitution of R11V of SEQ ID NO:2, a substitution of R12N of SEQ ID NO: 2, a substitution of R13H of SEQ ID NO:2, an insertion of Y at position 13 of SEQ ID NO:2, a substitution of R12L of SEQ ID NO:2, an insertion of Q at position 13 of SEQ ID NO:2, an substitution of V15S of SEQ ID NO:2 and an insertion of D at position 17 of SEQ ID NO:2. In some embodiments, the at least two amino acid changes to a reference CasX protein are selected from the amino acid changes disclosed in the sequences of Table 4. In some embodiments, a CasX variant comprises any combination of the foregoing embodiments of this paragraph.

In some embodiments, a CasX variant protein comprises more than one substitution, insertion and/or deletion of a reference CasX protein amino acid sequence. In some embodiments, the reference CasX protein comprises or consists essentially of SEQ ID NO:2. In some embodiments, a CasX variant protein comprises a substitution of S794R and a substitution of Y797L of SEQ ID NO:2. In some embodiments, a CasX variant protein comprises a substitution of K416E and a substitution of A708K of SEQ ID NO:2. In some embodiments, a CasX variant protein comprises a substitution of A708K and a deletion of P793 of SEQ ID NO:2. In some embodiments, a CasX variant protein comprises a deletion of P793 and an insertion of AS at position 795 SEQ ID NO:2. In some embodiments, a CasX variant protein comprises a substitution of Q367K and a substitution of 1425S of SEQ ID NO:2. In some embodiments, a CasX variant protein comprises a substitution of A708K, a deletion of P position 793 and a substitution A793V of SEQ ID NO:2. In some embodiments, a CasX variant protein comprises a substitution of Q338R and a substitution of A339E of SEQ ID NO:2. In some embodiments, a CasX variant protein comprises a substitution of Q338R and a substitution of A339K of SEQ ID NO:2. In some embodiments, a CasX variant protein comprises a substitution of S507G and a substitution of G508R of SEQ ID NO:2. In some embodiments, a CasX variant protein comprises a substitution of L379R, a substitution of A708K and a deletion of P at position 793 of SEQ ID NO:2. In some embodiments, a CasX variant protein comprises a substitution of C477K, a substitution of A708K and a deletion of P at position 793 of SEQ ID NO:2. In some embodiments, a CasX variant protein comprises a substitution of L379R, a substitution of C477K, a substitution of A708K and a deletion of P at position of 793 of SEQ ID NO:2. In some embodiments, a CasX variant protein comprises a substitution of L379R, a substitution of A708K, a deletion of P at position 793 and a substitution A739V of SEQ ID NO:2. In some embodiments, a CasX variant protein comprises a substitution of C477K, a substitution of A708K, a deletion of P at position 793 and a substitution of A739V of SEQ ID NO:2. In some embodiments, a CasX variant protein comprises a substitution of L379R, a substitution of C477K, a substitution of A708K, a deletion of P at position 793 and a substitution of A739V of SEQ ID NO:2. In some embodiments, a CasX variant protein comprises a substitution of L379R, a substitution of A708K, a deletion of P at position 793 and a substitution of M779N of SEQ ID NO:2. In some embodiments, a CasX variant protein comprises a substitution of L379R, a substitution of A708K, a deletion of P at position 793 and a substitution of M771N of SEQ ID NO:2. In some embodiments, a CasX variant protein comprises a substitution of L379R, a substitution of 708K, a deletion of P at position 793 and a substitution of D489S of SEQ ID NO:2. In some embodiments, a CasX variant protein comprises a substitution of L379R, a substitution of A708K, a deletion of P at position 793 and a substitution of A739T of SEQ ID NO:2. In some embodiments, a CasX variant protein comprises a substitution of L379R, a substitution of A708K, a deletion of P at position 793 and a substitution of D732N of SEQ ID NO:2. In some embodiments, a CasX variant protein comprises a substitution of L379R, a substitution of A708K, a deletion of P at position 793 and a substitution of G791M of SEQ ID NO:2. In some embodiments, a CasX variant protein comprises a substitution of L379R, a substitution of 708K, a deletion of P at position 793 and a substitution of Y797L of SEQ ID NO:2. In some embodiments, a CasX variant protein comprises a substitution of L379R, a substitution of C477K, a substitution of A708K, a deletion of P at position 793 and a substitution of M779N of SEQ ID NO:2. In some embodiments, a CasX variant protein comprises a substitution of L379R, a substitution of C477K, a substitution of A708K, a deletion of P at position 793 and a substitution of M771N of SEQ ID NO:2. In some embodiments, a CasX variant protein comprises a substitution of L379R, a substitution of C477K, a substitution of A708K, a deletion of P at position 793 and a substitution of D489S of SEQ ID NO:2. In some embodiments, a CasX variant protein comprises a substitution of L379R, a substitution of C477K, a substitution of A708K, a deletion of P at position 793 and a substitution of A739T of SEQ ID NO:2. In some embodiments, a CasX variant protein comprises a substitution of L379R, a substitution of C477K, a substitution of A708K, a deletion of P at position 793 and a substitution of D732N of SEQ ID NO:2. In some embodiments, a CasX variant protein comprises a substitution of L379R, a substitution of C477K, a substitution of A708K, a deletion of P at position 793 and a substitution of G791M of SEQ ID NO:2. In some embodiments, a CasX variant protein comprises a substitution of L379R, a substitution of C477K, a substitution of A708K, a deletion of P at position 793 and a substitution of Y797L of SEQ ID NO:2. In some embodiments, a CasX variant protein comprises a substitution of L379R, a substitution of C477K, a substitution of A708K, a deletion of P at position 793 and a substitution of T620P of SEQ ID NO:2. In some embodiments, a CasX variant protein comprises a substitution of A708K, a deletion of P at position 793 and a substitution of E386S of SEQ ID NO:2. In some embodiments, a CasX variant protein comprises a substitution of E386R, a substitution of F399L and a deletion of P at position 793 of SEQ ID NO:2. In some embodiments, a CasX variant protein comprises a substitution of R581I and A739V of SEQ ID NO:2. In some embodiments, a CasX variant comprises any combination of the foregoing embodiments of this paragraph.

In some embodiments, a CasX variant protein comprises more than one substitution, insertion and/or deletion of a reference CasX protein amino acid sequence. In some embodiments, a CasX variant protein comprises a substitution of A708K, a deletion of P at position 793 and a substitution of A739V of SEQ ID NO:2. In some embodiments, a CasX variant protein comprises a substitution of L379R, a substitution of A708K and a deletion of P at position 793 of SEQ ID NO:2. In some embodiments, a CasX variant protein comprises a substitution of C477K, a substitution of A708K and a deletion of P at position 793 of SEQ ID NO:2. In some embodiments, a CasX variant protein comprises a substitution of L379R, a substitution of C477K, a substitution of A708K and a deletion of P at position 793 of SEQ ID NO:2. In some embodiments, a CasX variant protein comprises a substitution of L379R, a substitution of A708K, a deletion of P at position 793 and a substitution of A739V of SEQ ID NO:2. In some embodiments, a CasX variant protein comprises a substitution of C477K, a substitution of A708K, a deletion of P at position 793 and a substitution of A739 of SEQ ID NO:2. In some embodiments, a CasX variant protein comprises a substitution of L379R, a substitution of C477K, a substitution of A708K, a deletion of P at position 793 and a substitution of A739V of SEQ ID NO:2. In some embodiments, a CasX variant protein comprises a substitution of L379R, a substitution of C477K, a substitution of A708K, a deletion of P at position 793 and a substitution of T620P of SEQ ID NO:2. In some embodiments, a CasX variant protein comprises a substitution of M771A of SEQ ID NO:2. In some embodiments, a CasX variant protein comprises a substitution of L379R, a substitution of A708K, a deletion of P at position 793 and a substitution of D732N of SEQ ID NO:2. In some embodiments, a CasX variant comprises any combination of the foregoing embodiments of this paragraph.

In some embodiments, a CasX variant protein comprises a substitution of W782Q of SEQ ID NO:2. In some embodiments, a CasX variant protein comprises a substitution of M771Q of SEQ ID NO:2. In some embodiments, a CasX variant protein comprises a substitution of R458I and a substitution of A739V of SEQ ID NO:2. In some embodiments, a CasX variant protein comprises a substitution of L379R, a substitution of A708K, a deletion of P at position 793 and a substitution of M77iN of SEQ ID NO:2. In some embodiments, a CasX variant protein comprises a substitution of L379R, a substitution of A708K, a deletion of P at position 793 and a substitution of A739T of SEQ ID NO:2. In some embodiments, a CasX variant protein comprises a substitution of L379R, a substitution of C477K, a substitution of A708K, a deletion of P at position 793 and a substitution of D489S of SEQ ID NO:2. In some embodiments, a CasX variant protein comprises a substitution of L379R, a substitution of C477K, a substitution of A708K, a deletion of P at position 793 and a substitution of D732N of SEQ ID NO:2. In some embodiments, a CasX variant protein comprises a substitution of V711K of SEQ ID NO:2. In some embodiments, a CasX variant protein comprises a substitution of L379R, a substitution of C477K, a substitution of A708K, a deletion of P at position 793 and a substitution of Y797L of SEQ ID NO:2. In some embodiments, a CasX variant protein comprises a substitution of L379R, a substitution of A708K and a deletion of P at position 793 of SEQ ID NO:2. In some embodiments, a CasX variant protein comprises a substitution of L379R, a substitution of C477K, a substitution of A708K, a deletion of P at position 793 and a substitution of M771N of SEQ ID NO:2. In some embodiments, a CasX variant protein comprises a substitution of A708K, a substitution of P at position 793 and a substitution of E386S of SEQ ID NO:2. In some embodiments, a CasX variant protein comprises a substitution of L379R, a substitution of C477K, a substitution of A708K and a deletion of P at position 793 of SEQ ID NO:2. In some embodiments, a CasX variant protein comprises a substitution of L792D of SEQ ID NO:2. In some embodiments, a CasX variant protein comprises a substitution of G791F of SEQ ID NO:2. In some embodiments, a CasX variant protein comprises a substitution of A708K, a deletion of P at position 793 and a substitution of A739V of SEQ ID NO:2. In some embodiments, a CasX variant protein comprises a substitution of L379R, a substitution of A708K, a deletion of P at position 793 and a substitution of A739V of SEQ ID NO:2. In some embodiments, a CasX variant protein comprises a substitution of C477K, a substitution of A708K and a substitution of P at position 793 of SEQ ID NO:2. In some embodiments, a CasX variant protein comprises a substitution of L249I and a substitution of M771N of SEQ ID NO:2. In some embodiments, a CasX variant protein comprises a substitution of V747K of SEQ ID NO:2. In some embodiments, a CasX variant protein comprises a substitution of L379R, a substitution of C477, a substitution of A708K, a deletion of P at position 793 and a substitution of M779N of SEQ ID NO:2. In some embodiments, a CasX variant protein comprises a substitution of F755M. In some embodiments, a CasX variant comprises any combination of the foregoing embodiments of this paragraph.

In some embodiments, a CasX variant protein comprises at least one modification compared to the reference CasX sequence of SEQ ID NO:2, wherein the at least one modification is selected from one or more of: an amino acid substitution of L379R; an amino acid substitution of A708K; an amino acid substitution of T620P; an amino acid substitution of E385P; an amino acid substitution of Y857R; an amino acid substitution of I658V; an amino acid substitution of F399L; an amino acid substitution of Q252K; and an amino acid deletion of [P793]. In some embodiments, a CasX variant protein comprises at least one modification compared to the reference CasX sequence of SEQ ID NO:2, wherein the at least one modification is selected from one or more of: an amino acid substitution of L379R; an amino acid substitution of A708K; an amino acid substitution of T620P; an amino acid substitution of E385P; an amino acid substitution of Y857R; an amino acid substitution of I658V; an amino acid substitution of F399L; an amino acid substitution of Q252K; an amino acid substitution of L404K; and an amino acid deletion of [P793]. In other embodiments, a CasX variant protein comprises any combination of the foregoing substitutions or deletions compared to the reference CasX sequence of SEQ ID NO:2. In other embodiments, the CasX variant protein can, in addition to the foregoing substitutions or deletions, further comprise a substitution of an NTSB and/or a helical 1b domain from the reference CasX of SEQ ID NO:1.

In some embodiments, the CasX variant protein comprises between 400 and 2000 amino acids, between 500 and 1500 amino acids, between 700 and 1200 amino acids, between 800 and 1100 amino acids, or between 900 and 1000 amino acids.

In some embodiments, the CasX variant protein comprises one or more modifications in a region of non-contiguous residues that form a channel in which gNA:target DNA complexing occurs. In some embodiments, the CasX variant protein comprises one or more modifications comprising a region of non-contiguous residues that form an interface which binds with the gNA. For example, in some embodiments of a reference CasX protein, the helical I, helical II and OBD domains all contact or are in proximity to the gNA:target DNA complex, and one or more modifications to non-contiguous residues within any of these domains may improve function of the CasX variant protein.

In some embodiments, the CasX variant protein comprises one or more modifications in a region of non-contiguous residues that form a channel which binds with the non-target strand DNA. For example, a CasX variant protein can comprise one or more modifications to non-contiguous residues of the NTSBD. In some embodiments, the CasX variant protein comprises one or more modifications in a region of non-contiguous residues that form an interface which binds with the PAM. For example, a CasX variant protein can comprise one or more modifications to non-contiguous residues of the helical I domain or OBD. In some embodiments, the CasX variant protein comprises one or more modifications comprising a region of non-contiguous surface-exposed residues. As used herein, "surface-exposed residues" refers to amino acids on the surface of the CasX protein, or amino acids in which at least a portion of the amino acid, such as the backbone or a part of the side chain is on the surface of the protein. Surface exposed residues of cellular proteins such as CasX, which are exposed to an aqueous intracellular environment, are frequently selected from positively charged hydrophilic amino acids, for example arginine, asparagine, aspartate, glutamine, glutamate, histidine, lysine, serine, and threonine. Thus, for example, in some embodiments of the variants provided herein, a region of surface exposed residues comprises one or more insertions, deletions, or substitutions compared to a reference CasX protein. In some embodiments, one or more positively charged residues are substituted for one or more other positively charged residues, or negatively charged residues, or uncharged residues, or any combinations thereof. In some embodiments, one or more amino acids residues for substitution are near bound nucleic acid, for example residues in the RuvC domain or helical I domain that contact target DNA, or residues in the OBD or helical II domain that bind the gNA, can be substituted for one or more positively charged or polar amino acids.

In some embodiments, the CasX variant protein comprises one or more modifications in a region of non-contiguous residues that form a core through hydrophobic packing in a domain of the reference CasX protein. Without wishing to be bound by any theory, regions that form cores through hydrophobic packing are rich in hydrophobic amino acids such as valine, isoleucine, leucine, methionine, phenylalanine, tryptophan, and cysteine. For example, in some reference CasX proteins, RuvC domains comprise a hydrophobic pocket adjacent to the active site. In some embodiments, between 2 to 15 residues of the region are charged, polar, or base-stacking. Charged amino acids (sometimes referred to herein as residues) may include, for example, arginine, lysine, aspartic acid, and glutamic acid, and the side chains of these amino acids may form salt bridges provided a bridge partner is also present. Polar amino acids may include, for example, glutamine, asparagine, histidine, serine, threonine, tyrosine, and cysteine. Polar amino acids can, in some embodiments, form hydrogen bonds as proton donors or acceptors, depending on the identity of their side chains. As used herein, "base-stacking" includes the interaction of aromatic side chains of an amino acid residue (such as tryptophan, tyrosine, phenylalanine, or histidine) with stacked nucleotide bases in a nucleic acid. Any modification to a region of non-contiguous amino acids that are in close spatial proximity to form a functional part of the CasX variant protein is envisaged as within the scope of the disclosure.

i. CasX Variant Proteins with Domains from Multiple Source Proteins

In certain embodiments, the disclosure provides a chimeric CasX protein comprising protein domains from two or more different CasX proteins, such as two or more reference CasX proteins, or two or more CasX variant protein sequences as described herein. As used herein, a "chimeric CasX protein" refers to a CasX containing at least two domains isolated or derived from different sources, such as two naturally occurring proteins, which may, in some embodiments, be isolated from different species. For example, in some embodiments, a chimeric CasX protein comprises a first domain from a first CasX protein and a second domain from a second, different CasX protein. In some embodiments, the first domain can be selected from the group consisting of the NTSB, TSL, Helical I, Helical II, OBD and RuvC domains. In some embodiments, the second domain is selected from the group consisting of the NTSB, TSL, Helical I, Helical II, OBD and RuvC domains with the second domain being different from the foregoing first domain. For example, a chimeric CasX protein may comprise an NTSB, TSL, Helical I, Helical II, OBD domains from a CasX protein of SEQ ID NO:2, and a RuvC domain from a CasX protein of SEQ ID NO:1, or vice versa. As a further example, a chimeric CasX protein may comprise an NTSB, TSL, Helical II, OBD and RuvC domain from CasX protein of SEQ ID NO:2, and a Helical I domain from a CasX protein of SEQ ID NO:1, or vice versa. Thus, in certain embodiments, a chimeric CasX protein may comprise an NTSB, TSL, Helical II, OBD and RuvC domain from a first CasX protein, and a Helical I domain from a second CasX protein. In some embodiments of the chimeric CasX proteins, the domains of the first CasX protein are derived from the sequences of SEQ ID NO:1, SEQ ID NO:2 or SEQ ID NO:3, and the domains of the second CasX protein are derived from the sequences of SEQ ID NO:1, SEQ ID NO:2 or SEQ ID NO:3, and the first and second CasX proteins are not the same. In some embodiments, domains of the first CasX protein comprise sequences derived from SEQ ID NO:1 and domains of the second CasX protein comprise sequences derived from SEQ ID NO:2. In some embodiments, domains of the first CasX protein comprise sequences derived from SEQ ID NO:1 and domains of the second CasX protein comprise sequences derived from SEQ ID NO:3. In some embodiments, domains of the first CasX protein comprise sequences derived from SEQ ID NO:2 and domains of the second CasX protein comprise sequences derived from SEQ ID NO:3. In some embodiments, the CasX variant is selected of group consisting of CasX variants 387, 388, 389, 390, 395, 485, 486, 487, 488, 489, 490, and 491, the sequences of which are set forth in Table 4.

In some embodiments, a CasX variant protein comprises at least one chimeric domain comprising a first part from a first CasX protein and a second part from a second, different CasX protein. As used herein, a "chimeric domain" refers to a domain containing at least two parts isolated or derived from different sources, such as two naturally occurring proteins or portions of domains from two reference CasX proteins. The at least one chimeric domain can be any of the NTSB, TSL, helical I, helical II, OBD or RuvC domains as described herein. In some embodiments, the first portion of a CasX domain comprises a sequence of SEQ ID NO:1 and the second portion of a CasX domain comprises a sequence of SEQ ID NO:2. In some embodiments, the first portion of the CasX domain comprises a sequence of SEQ ID NO:1 and the second portion of the CasX domain comprises a sequence of SEQ ID NO:3. In some embodiments, the first portion of the CasX domain comprises a sequence of SEQ ID NO:2 and the second portion of the CasX domain comprises a sequence of SEQ ID NO:3. In some embodiments, the at least one chimeric domain comprises a chimeric RuvC domain. As an example of the foregoing, the chimeric RuvC domain comprises amino acids 661 to 824 of SEQ ID NO:1 and amino acids 922 to 978 of SEQ ID NO:2. As an alternative example of the foregoing, a chimeric RuvC domain comprises amino acids 648 to 812 of SEQ ID NO:2 and amino acids 935 to 986 of SEQ ID NO:1. In some embodiments, a CasX protein comprises a first domain from a first CasX protein and a second domain from a second CasX protein, and at least one chimeric domain comprising at least two parts isolated from different CasX proteins using the approach of the embodiments described in this paragraph. In the foregoing embodiments, the chimeric CasX proteins having domains or portions of domains derived from SEQ ID NOS:1, 2 and 3, can further comprise amino acid insertions, deletions, or substitutions of any of the embodiments disclosed herein.

In some embodiments, a CasX variant protein comprises a sequence set forth in Tables 4, 7, 8, 9, or 11. In some embodiments, a CasX variant protein consists of a sequence set forth in Table 4. In other embodiments, a CasX variant protein comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical to a sequence set forth in Tables 4, 7, 8, 9, or 11. In other embodiments, a CasX variant protein comprises a sequence set forth in Table 4, and further comprises one or more NLS disclosed herein at or near either the N-terminus, the C-terminus, or both. It will be understood that in some cases, the N-terminal methionine of the CasX variants of the Tables is removed from the expressed CasX variant during post-translational modification.

TABLE 4

CasX Variant Sequences

| Description* | Amino Acid Sequence |
|---|---|
| TSL, Helical I, Helical II, OBD and RuvC domains from SEQ ID NO: 2 and an NTSB domain from SEQ ID NO: 1 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPASKKIDQNKLKPEMDEKGNLTTAGFACSQCGQPLFVYKLEQVSEK GKAYTNYFGRCNVAEHEKLILLAQLKPEKDSDEAVTYSLGKFGQRALDF YSIHVTRESNHPVKPLEQIGGNSCASGPVGKALSDACMGAVASFLTKYQ DIILEHQKVIKKNEKRLANLKDIASANGLAFPKITLPPQPHTKEGIEAYNNV VAQIVIWVNLNLWQKLKIGRDEAKPLQRLKGFPSFPLVERQANEVDWW DMVCNVKKLINEKKEDGKVFWQNLAGYKRQEALRPYLSSEEDRKKGKK FARYQFGDLLLHLEKKHGEDWGKVYDEAWERIDKKVEGLSKHIKLEEER RSEDAQSKAALTDWLRAKASFVIEGLKEADKDEFCRCELKLQKWYGDL RGKPFAIEAENSILDISGFSKQYNCAFIWQKDGVKKLNLYLIINYFKGGKL RFKKIKPEAFEANRFYTVINKKSGEIVPMEVNFNFDDPNLIILPLAFGKRQ GREFIWNDLLSLETGSLKLANGRVIEKTLYNRRTRQDEPALFVALTFERR EVLDSSNIKPMNLIGIDRGENIPAVIALTDPEGCPLSRFKDSLGNPTHILRI GESYKEKQRTIQAKKEVEQRRAGGYSRKYASKAKNLADDMVRNTARDL LYYAVTQDAMLIFENLSRGFGRQGKRTFMAERQYTRMEDWLTAKLAYE GLSKTYLSKTLAQYTSKTCSNCGFTITSADYDRVLEKLKKTATGWMTTIN GKELKVEGQITYYNRYKRQNVVKDLSVELDRLSEESVNNDISSWTKGRS GEALSLLKKRFSHRPVQEKFVCLNCGFETHADEQAALNIARSWLFLRSQ EYKKYQTNKTTGNTDKRAFVETWQSFYRKKLKEVWKPAV (SEQ ID NO: 49) |
| NTSB, Helical I, Helical II, OBD and RuvC domains from SEQ ID NO: 2 and a TSL domain from SEQ ID NO: 1. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITTADYDGMLVRLKKTSDGWATTLNNK ELKAEGQITYYNRYKRQTVEKELSAELDRLSEESGNNDISKWTKGRRDE ALFLLKKRFSHRPVQEQFVCLDCGHEVHADEQAALNIARSWLFLRSQEY KKYQTNKTTGNTDKRAFVETWQSFYRKKLKEVWKPAV (SEQ ID NO: 50) |

TABLE 4-continued

CasX Variant Sequences

| Description* | Amino Acid Sequence |
|---|---|
| TSL, Helical I, Helical II, OBD and RuvC domains from SEQ ID NO: 1 and an NTSB domain from SEQ ID NO: 2 | MEKRINKIRKKLSADNATKPVSRSGPMKTLLVRVMTDDLKKRLEKRRKK PEVMPQVISNNAANNLRMLLDDYTKMKEAILQVYWQEFKDDHVGLMCK FAQPAPKNIDQRKLIPVKDGNERLTSSGFACSQCCQPLYVYKLEQVNDK GKPHTNYFGRCNVSEHERLILLSPHKPEANDELVTYSLGKFGQRALDFY SIHVTKESTHPVKPLAQIAGNRYASGPVGKALSDACMGTIASFLSKYQDII IEHQKVVKGNQKRLESLRELAGKENLEYPSVTLPPQPHTKEGVDAYNEV IARVRMWVNLNLWQKLKLSRDDAKPLLRLKGFPSFPVVERRENEVDWW NTINEVKKLIDAKRDMGRVFWSGVTAEKRNTILEGYNYLPNENDHKKRE GSLENPKKPAKRQFGDLLLYLEKKYAGDWGKVFDEAWERIDKKIAGLTS HIEREEARNAEDAQSKAVLTDWLRAKASFVLERLKEMDEKEFYACEIQL QKWYGDLRGNPFAVEAENRWVDISGFSIGSDGHSIQYRNLLAWKYLEN GKREFYLLMNYGKKGRIRFTDGTDIKKSGKWQGLLYGGGKAKVIDLTFD PDDEQLIILPLAFGTRQGREFIWNDLLSLETGLIKLANGRVIEKTIYNKKIG RDEPALFVALTFERREWDPSNIKPVNLIGVDRGENIPAVIALTDPEGCPL PEFKDSSGGPTDILRIGEGYKEKQRAIQAAKEVEQRRAGGYSRKFASKS RNLADDMVRNSARDLFYHAVTHDAVLVFENLSRGFGRQGKRTFMTER QYTKMEDWLTAKLAYEGLTSKTYLSKTLAQYTSKTCSNCGFTITTADYD GMLVRLKKTSDGWATTLNNKELKAEGQITYYNRYKRQTVEKELSAELDR LSEESGNNDISKWTKGRRDEALFLLKKRFSHRPVQEQFVCLDCGHEVH ADEQAALNIARSWLFLNSNSTEFKSYKSGKQPFVGAWQAFYKRRLKEV WKPNA (SEQ ID NO: 51) |
| NTSB, Helical I, Helical II, OBD and RuvC domains from SEQ ID NO: 1 and an TSL domain from SEQ ID NO: 2. | MEKRINKIRKKLSADNATKPVSRSGPMKTLLVRVMTDDLKKRLEKRRKK PEVMPQVISNNAANNLRMLLDDYTKMKEAILQVYWQEFKDDHVGLMCK FAQPASKKIDQNKLKPEMDEKGNLTTAGFACSQCGQPLFVYKLEQVSE KGKAYTNYFGRCNVAEHEKLILLAQLKPEKDSDEAVTYSLGKFGQRALD FYSIHVTKESTHPVKPLAQIAGNRYASGPVGKALSDACMGTIASFLSKYQ DIIIEHQKVVKGNQKRLESLRELAGKENLEYPSVTLPPQPHTKEGVDAYN EVIARVRMWVNLNLWQKLKLSRDDAKPLLRLKGFPSFPWVERRENEVD WWNTINEVKKLIDAKRDMGRVFWSGVTAEKRNTILEGYNYLPNENDHK KREGSLENPKKPAKRQFGDLLLYLEKKYAGDWGKVFDEAWERIDKKIAG LTSHIEREEARNAEDAQSKAVLTDWLRAKASFVLERLKEMDEKEFYACEI QLQKWYGDLRGNPFAVEAENRVVDISGFSIGSDGHSIQYRNLLAWKYLE NGKREFYLLMNYGKKGRIRFTDGTDIKKSGKWQGLLYGGGKAKVIDLTF DPDDEQLIILPLAFGTRQGREFIWNDLLSLETGLIKLANGRVIEKTIYNKKI GRDEPALFVALTFERREVVDPSNIKPVNLIGVDRGENIPAVIALTDPEGCP LPEFKDSSGGPTDILRIGEGYKEKQRAIQAAKEVEQRRAGGYSRKFASK SRNLADDMVRNSARDLFYHAVTHDAVLVFENLSRGFGRQGKRTFMTER QYTKMEDWLTAKLAYEGLTSKTYLSKTLAQYTSKTCSNCGFTITSADYD RVLEKLKKTATGWMTTINGKELKVEGQITYYNRYKRQNVVKDLSVELDR LSEESVNNDISSWTKGRSGEALSLLKKRFSHRPVQEKFVCLNCGFETHA DEQAALNIARSWLFLNSNSTEFKSYKSGKQPFVGAWQAFYKRRLKEVW KPNA (SEQ ID NO: 52) |
| NTSB, TSL, Helical I, Helical II and OBD domains SEQ ID NO: 2 and an exogenous RuvC domain or a portion thereof from a second CasX protein. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPVNLIGVDRGENIPAVIALTDPEGCPLPEFKDSSGGPTDILRIGE GYKEKQRAIQAAKEVEQRRAGGYSRKFASKSRNLADDMVRNSARDLFY HAVTHDAVLVFENLSRGFGRQGKRTFMTERQYTKMEDWLTAKLAYEGL TSKTYLSKTLAQYTSKTCSNCGFTITSADYDRVLEKLKKTATGWMTTING KELKVEGQITYYNRYKRQNVVKDLSVELDRLSEESVNNDISSWTKGRSG EALSLLKKRFSHRPVQEKFVCLNCGFETHA (SEQ ID NO: 53) |
| | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE |

TABLE 4-continued

CasX Variant Sequences

| Description* | Amino Acid Sequence |
|---|---|
| | FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHA (SEQ ID NO: 54) |
| NTSB, TSL, Helical II, OBD and RuvC domains from SEQ ID NO: 2 and a Helical I domain from SEQ ID NO: 1 | MQEIKRINKIRRRLVKDSNTKKAGKTGPMKTLLVRVMTPDLRERLENLRK<br>KPENIPQPISNNAANNLRMLLDDYTKMKEAILQVYWQEFKDDHVGLMCK<br>FAQPAPKNIDQRKLIPVKDGNERLTSSGFACSQCCQPLYVYKLEQVNDK<br>GKPHTNYFGRCNVSEHERLILLSPHKPEANDELVTYSLGKFGQRALDFY<br>SIHVTKESTHPVKPLAQIAGNRYASGPVGKALSDACMGTIASFLSKYQDII<br>IEHQKVVKGNQKRLESLRELAGKENLEYPSVTLPPQPHTKEGVDAYNEV<br>IARVRMWVNLNLWQKLKLSRDDAKPLLRLKGFPSFPLVERQANEVDWW<br>DMVCNVKKLINEKKEDGKVFWQNLAGYKRQEALRPYLSSEEDRKKGKK<br>FARYQFGDLLLHLEKKHGEDWGKVYDEAWERIDKKVEGLSKHIKLEEER<br>RSEDAQSKAALTDWLRAKASFVIEGLKEADKDEFCRCELKLQKWYGDL<br>RGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQ<br>GREFIWNDLLSLETGSLKLANGRVIEKTLYNRRTRQDEPALFVALTFERR<br>EVLDSSNIKPMNLIGIDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRYKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 55) |
| NTSB, TSL, Helical I, OBD and RuvC domains from SEQ ID NO: 2 and a Helical II domain from SEQ ID NO: 1 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPVVERRENEVDWWNTI<br>NEVKKLIDAKRDMGRVFWSGVTAEKRNTILEGYNYLPNENDHKKREGSL<br>ENPKKPAKRQFGDLLLYLEKKYAGDWGKVFDEAWERIDKKIAGLTSHIE<br>REEARNAEDAQSKAVLTDWLRAKASFVLERLKEMDEKEFYACEIQLQK<br>WYGDLRGNPFAVEAENSILDISGFSKQYNCAFIWQKDGVKKLNLYLIINY<br>FKGGKLRFKKIKPEAFEANRFYTVINKKSGEIVPMEVNFNFDDPNLIILPLA<br>FGKRQGREFIWNDLLSLETGSLKLANGRVIEKTLYNRRTRQDEPALFVAL<br>TFERREVLDSSNIKPMNLIGIDRGENIPAVIALTDPEGCPLSRFKDSLGNP<br>THILRIGESYKEKQRTIQAKKEVEQRRAGGYSRKYASKAKNLADDMVRN<br>TARDLLYYAVTQDAMLIFENLSRGFGRQGKRTFMAERQYTRMEDWLTA<br>KLAYEGLSKTYLSKTLAQYTSKTCSNCGFTITSADYDRVLEKLKKTATGW<br>MTTINGKELKVEGQITYYNRYKRQNVVKDLSVELDRLSEESVNNDISSW<br>TKGRSGEALSLLKKRFSHRPVQEKFVCLNCGFETHADEQAALNIARSWL<br>FLRSQEYKKYQTNKTTGNTDKRAFVETWQSFYRKKLKEVWKPAV<br>(SEQ ID NO: 56) |
| NTSB, TSL, Helical I, Helical II and RuvC domains from a first CasX protein and an exogenous OBD or a part thereof from a second CasX protein | MISNTSRANLNKLLTDYTEMKKAILHVYWEEFQKDPVGLMSRVAQPAPK<br>NIDQRKLIPVKDGNERLTSSGFACSQCCQPLYVYKLEQVNDKGKPHTNY<br>FGRCNVSEHERLILLSPHKPEANDELVTYSLGKFGQRALDFYSIHVTRES<br>NHPVKPLEQIGGNSCASGPVGKALSDACMGAVASFLTKYQDIILEHQKVI<br>KKNEKRLANLKDIASANGLAFPKITLPPQPHTKEGIEAYNNVVAQIVIWVN<br>LNLWQKLKIGRDEAKPLQRLKGFPSFPLVERQANEVDWWDMVCNVKKL<br>INEKKEDGKVFWQNLAGYKRQEALRPYLSSEEDRKKGKKFARYQFGDL<br>LLHLEKKHGEDWGKVYDEAWERIDKKVEGLSKHIKLEEERRSEDAQSKA<br>ALTDWLRAKASFVIEGLKEADKDEFCRCELKLQKWYGDLRGKPFAIEAE<br>NRVVDISGFSIGSDGHSIQYRNLLAWKYLENGKREFYLLMNYGKKGRIR<br>FTDGTDIKKSGKWQGLLYGGGKAKVIDLTFDPDDEQLIILPLAFGTRQGR<br>EFIWNDLLSLETGLIKLANGRVIEKTIYNKKIGRDEPALFVALTFERREVVD<br>PSNIKPMNLIGIDRGENIPAVIALTDPEGCPLSRFKDSLGNPTHILRIGESY<br>KEKQRTIQAKKEVEQRRAGGYSRKYASKAKNLADDMVRNTARDLLYYA<br>VTQDAMLIFENLSRGFGRQGKRTFMAERQYTRMEDWLTAKLAYEGLSK<br>TYLSKTLAQYTSKTCSNCGFTITSADYDRVLEKLKKTATGWMTTINGKEL<br>KVEGQITYYNRYKRQNVVKDLSVELDRLSEESVNNDISSWTKGRSGEAL<br>SLLKKRFSHRPVQEKFVCLNCGFETHADEQAALNIARSWLFLRSQEYKK<br>YQTNKTTGNTDKRAFVETWQSFYRKKLKEVWKPAV<br>(SEQ ID NO: 57) |
| | MEKRINKIRKKLSADNATKPVSRSGPMKTLLVRVMTDDLKKRLEKRRKK<br>PEVMPQVISNTSRANLNKLLTDYTEMKKAILHVYWEEFQKDPVGLMSRV<br>AQPAPKNIDQRKLIPVKDGNERLTSSGFACSQCCQPLYVYKLEQVNDKG |

TABLE 4-continued

CasX Variant Sequences

| Description* | Amino Acid Sequence |
|---|---|
| | KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 58) |
| | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENRWDISGFSIGSDGHSIQYRNLLAWKYLENGKREFYLLMNY GKKGRIRFTDGTDIKKSGKWQGLLYGGGKAKVIDLTFDPDDEQLIILPLAF GTRQGREFIWNDLLSLETGLIKLANGRVIEKTIYNKKIGRDEPALFVALTF ERREVVDPSNIKPMNLIGIDRGENIPAVIALTDPEGCPLSRFKDSLGNPTH ILRIGESYKEKQRTIQAKKEVEQRRAGGYSRKYASKAKNLADDMVRNTA RDLLYYAVTQDAMLIFENLSRGFGRQGKRTFMAERQYTRMEDWLTAKL AYEGLSKTYLSKTLAQYTSKTCSNCGFTITSADYDRVLEKLKKTATGWM TTINGKELKVEGQITYYNRYKRQNVVKDLSVELDRLSEESVNNDISSWTK GRSGEALSLLKKRFSHRPVQEKFVCLNCGFETHADEQAALNIARSWLFL RSQEYKKYQTNKTTGNTDKRAFVETWQSFYRKKLKEVWKPAV (SEQ ID NO: 59) |
| substitution of L379R, a substitution of C477K, a substitution of A708K, a deletion of P at position 793 and a substitution of T620P of SEQ ID NO: 2 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFKRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKPLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 60) |
| substitution of M771A of SEQ ID NO: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALLPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL |

TABLE 4-continued

| CasX Variant Sequences | |
|---|---|
| Description* | Amino Acid Sequence |
| | DSSNIKPMNLIGIDRGENIPAVIALTDPEGCPLSRFKDSLGNPTHILRIGES<br>YKEKQRTIQAAKEVEQRRAGGYSRKYASKAKNLADDMVRNTARDLLYY<br>AVTQDAMLIFENLSRGFGRQGKRTFAAERQYTRMEDWLTAKLAYEGLP<br>SKTYLSKTLAQYTSKTCSNCGFTITSADYDRVLEKLKKTATGWMTTINGK<br>ELKVEGQITYYNRYKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPA<br>(SEQ ID NO: 61) |
| substitution of L379R, a substitution of A708K, a deletion of P at position 793 and a substitution of D732N of SEQ ID NO: 2. | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLANDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 62) |
| substitution of W782Q of SEQ ID NO: 2. | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALLPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAAKEVEQRRAGGYSRKYASKAKNLADDMVRNTARDLLYY<br>AVTQDAMLIFENLSRGFGRQGKRTFMAERQYTRMEDQLTAKLAYEGLP<br>SKTYLSKTLAQYTSKTCSNCGFTITSADYDRVLEKLKKTATGWMTTINGK<br>ELKVEGQITYYNRYKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 63) |
| substitution of M771Q of SEQID NO: 2 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALLPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAAKEVEQRRAGGYSRKYASKAKNLADDMVRNTARDLLYY<br>AVTQDAMLIFENLSRGFGRQGKRTFQAERQYTRMEDWLTAKLAYEGLP<br>SKTYLSKTLAQYTSKTCSNCGFTITSADYDRVLEKLKKTATGWMTTINGK<br>ELKVEGQITYYNRYKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 64) |

TABLE 4-continued

CasX Variant Sequences

| Description* | Amino Acid Sequence |
|---|---|
| substitution of R458I and a substitution of A739V of SEQ ID NO: 2. | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALLPYLSSEEDRKKGKKFA<br>RYQFGDLLLHLEKKHGEDWGKVYDEAWERIDKKVEGLSKHIKLEEERRS<br>EDAQSKAALTDWLIAKASFVIEGLKEADKDEFCRCELKLQKWYGDLRGK<br>PFAIEAENSILDISGFSKQYNCAFIWQKDGVKKLNLYLIINYFKGGKLRFKK<br>IKPEAFEANRFYTVINKKSGEIVPMEVNFNFDDPNLIILPLAFGKRQGREFI<br>WNDLLSLETGSLKLANGRVIEKTLYNRRTRQDEPALFVALTFERREVLDS<br>SNIKPMNLIGIDRGENIPAVIALTDPEGCPLSRFKDSLGNPTHILRIGESYK<br>EKQRTIQAAKEVEQRRAGGYSRKYASKAKNLADDMVRNTVRDLLYYAV<br>TQDAMLIFENLSRGFGRQGKRTFMAERQYTRMEDWLTAKLAYEGLPSK<br>TYLSKTLAQYTSKTCSNCGFTITSADYDRVLEKLKKTATGWMTTINGKEL<br>KVEGQITYYNRYKRQNVVKDLSVELDRLSEESVNNDISSWTKGRSGEAL<br>SLLKKRFSHRPVQEKFVCLNCGFETHADEQAALNIARSWLFLRSQEYKK<br>YQTNKTTGNTDKRAFVETWQSFYRKKLKEVWKPAV<br>(SEQ ID NO: 65) |
| L379R, a substitution of A708K, a deletion of P at position 793 and a substitution of M771N of SEQ ID NO: 2 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFNAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 66) |
| substitution of L379R, a substitution of A708K, a deletion of P at position 793 and a substitution of A739T of SEQ ID NO: 2 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTTRDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 67) |
| substitution of L379R, a substitution of C477K, a substitution of A708K, a deletion of P at position 793 and a | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS |

TABLE 4-continued

CasX Variant Sequences

| Description* | Amino Acid Sequence |
|---|---|
| substitution of D489S of SEQ ID NO: 2. | EDAQSKAALTDWLRAKASFVIEGLKEADKDEFKRCELKLQKWYGSLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 68) |
| substitution of L379R, a substitution of C477K, a substitution of A708K, a deletion of P at position 793 and a substitution of D732N of SEQ ID NO: 2. | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFKRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLANDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 69) |
| substitution of V711K of SEQ ID NO: 2. | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALLPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAAKEKEQRRAGGYSRKYASKAKNLADDMVRNTARDLLYY<br>AVTQDAMLIFENLSRGFGRQGKRTFMAERQYTRMEDWLTAKLAYEGLP<br>SKTYLSKTLAQYTSKTCSNCGFTITSADYDRVLEKLKKTATGWMTTINGK<br>ELKVEGQITYYNRYKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 70) |
| substitution of L379R, a substitution of C477K, a substitution of A708K, a deletion of P at position 793 and a substitution of Y797L of SEQ ID NO: 2. | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFKRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTLLSKTLAQYTSKTCSNCGFTITSADYDRVLEKLKKTATGWMTTINGKE |

TABLE 4-continued

| CasX Variant Sequences | |
|---|---|
| Description* | Amino Acid Sequence |
| | LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 71) |
| 119: substitution of L379R, a substitution of A708K and a deletion of P at position 793 of SEQ ID NO: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 72) |
| substitution of L379R, a substitution of C477K, a substitution of A708K, a deletion of P at position 793 and a substitution of M771N of SEQ ID NO: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFKRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFNAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 73) |
| substitution of A708K, a deletion of P at position 793 and a substitution of E386S of SEQ ID NO: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALLPYLSSESDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 74) |
| substitution of L379R, a substitution of C477K, a substitution | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII |

TABLE 4-continued

CasX Variant Sequences

| Description* | Amino Acid Sequence |
|---|---|
| of A708K and a deletion of P at position 793 of SEQ ID NO: 2. | LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFKRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 75) |
| substitution of L792D of SEQ ID NO: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALLPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAAKEVEQRRAGGYSRKYASKAKNLADDMVRNTARDLLYY AVTQDAMLIFENLSRGFGRQGKRTFMAERQYTRMEDWLTAKLAYEGDP SKTYLSKTLAQYTSKTCSNCGFTITSADYDRVLEKLKKTATGWMTTINGK ELKVEGQITYYNRYKRQNVVKDLSVELDRLSEESVNNDISSWTKGRSGE ALSLLKKRFSHRPVQEKFVCLNCGFETHADEQAALNIARSWLFLRSQEY KKYQTNKTTGNTDKRAFVETWQSFYRKKLKEVWKPAV (SEQ ID NO: 76) |
| substitution of G791F of SEQ ID NO: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALLPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAAKEVEQRRAGGYSRKYASKAKNLADDMVRNTARDLLYY AVTQDAMLIFENLSRGFGRQGKRTFMAERQYTRMEDWLTAKLAYEFLP SKTYLSKTLAQYTSKTCSNCGFTITSADYDRVLEKLKKTATGWMTTINGK ELKVEGQITYYNRYKRQNVVKDLSVELDRLSEESVNNDISSWTKGRSGE ALSLLKKRFSHRPVQEKFVCLNCGFETHADEQAALNIARSWLFLRSQEY KKYQTNKTTGNTDKRAFVETWQSFYRKKLKEVWKPAV (SEQ ID NO: 77) |
| substitution of A708K, a deletion of P at position 793 and a substitution of A739V of SEQ ID NO: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALLPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTVRDLLYY |

TABLE 4-continued

CasX Variant Sequences

| Description* | Amino Acid Sequence |
|---|---|
| | AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 78) |
| substitution of L379R, a substitution of A708K, a deletion of P at position 793 and a substitution of A739V of SEQ ID NO: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTVRDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 79) |
| substitution of C477K, a substitution of A708K and a deletion of P at position 793 of SEQ IDN O: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALLPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFKRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 80) |
| substitution of L249I and a substitution of M771N of SEQ ID NO: 2. | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDIII EHQKVIKKNEKRLANLKDIASANGLAFPKITLPPQPHTKEGIEAYNNVVAQ IVIWVNLNLWQKLKIGRDEAKPLQRLKGFPSFPLVERQANEVDWWDMV CNVKKLINEKKEDGKVFWQNLAGYKRQEALLPYLSSEEDRKKGKKFAR YQFGDLLLHLEKKHGEDWGKVYDEAWERIDKKVEGLSKHIKLEEERRSE DAQSKAALTDWLRAKASFVIEGLKEADKDEFCRCELKLQKWYGDLRGK PFAIEAENSILDISGFSKQYNCAFIWQKDGVKKLNLYLIINYFKGGKLRFKK IKPEAFEANRFYTVINKKSGEIVPMEVNFNFDDPNLIILPLAFGKRQGREFI WNDLLSLETGSLKLANGRVIEKTLYNRRTRQDEPALFVALTFERREVLDS SNIKPMNLIGIDRGENIPAVIALTDPEGCPLSRFKDSLGNPTHILRIGESYK EKQRTIQAAKEVEQRRAGGYSRKYASKAKNLADDMVRNTARDLLYYAV TQDAMLIFENLSRGFGRQGKRTFNAERQYTRMEDWLTAKLAYEGLPSK TYLSKTLAQYTSKTCSNCGFTITSADYDRVLEKLKKTATGWMTTINGKEL KVEGQITYYNRYKRQNVVKDLSVELDRLSEESVNNDISSWTKGRSGEAL SLLKKRFSHRPVQEKFVCLNCGFETHADEQAALNIARSWLFLRSQEYKK YQTNKTTGNTDKRAFVETWQSFYRKKLKEVWKPAV (SEQ ID NO: 81) |
| substitution of V747K of SEQ ID | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG |

TABLE 4-continued

CasX Variant Sequences

| Description* | Amino Acid Sequence |
|---|---|
| NO: 2. | KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALLPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAAKEVEQRRAGGYSRKYASKAKNLADDMVRNTARDLLYY<br>AKTQDAMLIFENLSRGFGRQGKRTFMAERQYTRMEDWLTAKLAYEGLP<br>SKTYLSKTLAQYTSKTCSNCGFTITSADYDRVLEKLKKTATGWMTTINGK<br>ELKVEGQITYYNRYKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 82) |
| substitution of L379R, a substitution of C477K, a substitution of A708K, a deletion of P at position 793 and a substitution of M779N of SEQ ID NO: 2. | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFKRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRNEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 83) |
| L379R, F755M | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALLPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAAKEVEQRRAGGYSRKYASKAKNLADDMVRNTARDLLYY<br>AVTQDAMLIMENLSRGFGRQGKRTFMAERQYTRMEDWLTAKLAYEGLP<br>SKTYLSKTLAQYTSKTCSNCGFTITSADYDRVLEKLKKTATGWMTTINGK<br>ELKVEGQITYYNRYKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 84) |
| 429: L379R, A708K, P793_, Y857R | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL |

TABLE 4-continued

| CasX Variant Sequences | |
|---|---|
| Description* | Amino Acid Sequence |
| | DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRRKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 85) |
| 430:<br>L379R,<br>A708K,<br>P793_,<br>Y857R,<br>I658V | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTYLSKTLAQYTSKTCSNCGFTITSADYDRVLEKLKKTATGWMTTINGK<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 86) |
| 431:<br>L379R,<br>A708K,<br>P793_,<br>Y857R,<br>I658V,<br>E386N | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSENDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTYLSKTLAQYTSKTCSNCGFTITSADYDRVLEKLKKTATGWMTTINGK<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 87) |
| 432:<br>L379R,<br>A708K,<br>P793_,<br>Y857R,<br>I658V,<br>L404K | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLKHLEKKHGEDWGKVYDEAWERIDKKVEGLSKHIKLEEERR<br>SEDAQSKAALTDWLRAKASFVIEGLKEADKDEFCRCELKLQKWYGDLR<br>GKPFAIEAENSILDISGFSKQYNCAFIWQKDGVKKLNLYLIINYFKGGKLR<br>FKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERRE<br>VLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRRKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 88) |

TABLE 4-continued

CasX Variant Sequences

| Description* | Amino Acid Sequence |
|---|---|
| 433: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQVRALDFY |
| Y857R, | SIHVTRESNHPVKPLEQIGGNSCASGPVGKALSDACMGAVASFLTKYQD |
| I658V, | IILEHQKVIKKNEKRLANLKDIASANGLAFPKITLPPQPHTKEGIEAYNNVV |
| V192 | AQIVIWVNLNLWQKLKIGRDEAKPLQRLKGFPSFPLVERQANEVDWWD |
| | MVCNVKKLINEKKEDGKVFWQNLAGYKRQEALRPYLSSEEDRKKGKKF |
| | ARYQFGDLLLHLEKKHGEDWGKVYDEAWERIDKKVEGLSKHIKLEEERR |
| | SEDAQSKAALTDWLRAKASFVIEGLKEADKDEFCRCELKLQKWYGDLR |
| | GKPFAIEAENSILDISGFSKQYNCAFIWQKDGVKKLNLYLIINYFKGGKLR |
| | FKKIKPEAFEANRFYTVINKKSGEIVPMEVNFNFDDPNLIILPLAFGKRQG |
| | REFIWNDLLSLETGSLKLANGRVIEKTLYNRRTRQDEPALFVALTFERRE |
| | VLDSSNIKPMNLIGVDRGENIPAVIALTDPEGCPLSRFKDSLGNPTHILRI |
| | GESYKEKQRTIQAKKEVEQRRAGGYSRKYASKAKNLADDMVRNTARDL |
| | LYYAVTQDAMLIFENLSRGFGRQGKRTFMAERQYTRMEDWLTAKLAYE |
| | GLSKTYLSKTLAQYTSKTCSNCGFTITSADYDRVLEKLKKTATGWMTTIN |
| | GKELKVEGQITYYNRRKRQNVVKDLSVELDRLSEESVNNDISSWTKGRS |
| | GEALSLLKKRFSHRPVQEKFVCLNCGFETHADEQAALNIARSWLFLRSQ |
| | EYKKYQTNKTTGNTDKRAFVETWQSFYRKKLKEVWKPAV |
| | (SEQ ID NO: 89) |
| 434: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| Y857R, | HVTRESNHPVKPLEQIGGNSCASGPVGKALSDACMGAVASFLTKYQDII |
| I658V, | LEHQKVIKKNEKRLANLKDIASANGLAFPKITLPPQPHTKEGIEAYNNVVA |
| L404K, | QIVIWVNLNLWQKLKIGRDEAKPLQRLKGFPSFPLVERQANEVDWWDM |
| E386N | VCNVKKLINEKKEDGKVFWQNLAGYKRQEALRPYLSSENDRKKGKKFA |
| | RYQFGDLLKHLEKKHGEDWGKVYDEAWERIDKKVEGLSKHIKLEEERR |
| | SEDAQSKAALTDWLRAKASFVIEGLKEADKDEFCRCELKLQKWYGDLR |
| | GKPFAIEAENSILDISGFSKQYNCAFIWQKDGVKKLNLYLIINYFKGGKLR |
| | FKKIKPEAFEANRFYTVINKKSGEIVPMEVNFNFDDPNLIILPLAFGKRQG |
| | REFIWNDLLSLETGSLKLANGRVIEKTLYNRRTRQDEPALFVALTFERRE |
| | VLDSSNIKPMNLIGVDRGENIPAVIALTDPEGCPLSRFKDSLGNPTHILRI |
| | GESYKEKQRTIQAKKEVEQRRAGGYSRKYASKAKNLADDMVRNTARDL |
| | LYYAVTQDAMLIFENLSRGFGRQGKRTFMAERQYTRMEDWLTAKLAYE |
| | GLSKTYLSKTLAQYTSKTCSNCGFTITSADYDRVLEKLKKTATGWMTTIN |
| | GKELKVEGQITYYNRRKRQNVVKDLSVELDRLSEESVNNDISSWTKGRS |
| | GEALSLLKKRFSHRPVQEKFVCLNCGFETHADEQAALNIARSWLFLRSQ |
| | EYKKYQTNKTTGNTDKRAFVETWQSFYRKKLKEVWKPAV |
| | (SEQ ID NO: 90) |
| 435: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| Y857R, | HVTRESNHPVKPLEQIGGNSCASGPVGKALSDACMGAVASFLTKYQDII |
| I658V, | LEHQKVIKKNEKRLANLKDIASANGLAFPKITLPPQPHTKEGIEAYNNVVA |
| F399L | QIVIWVNLNLWQKLKIGRDEAKPLQRLKGFPSFPLVERQANEVDWWDM |
| | VCNVKKLINEKKEDGKVFWQNLAGYKRQEALRPYLSSEEDRKKGKKFA |
| | RYQLGDLLLHLEKKHGEDWGKVYDEAWERIDKKVEGLSKHIKLEEERRS |
| | EDAQSKAALTDWLRAKASFVIEGLKEADKDEFCRCELKLQKWYGDLRG |
| | KPFAIEAENSILDISGFSKQYNCAFIWQKDGVKKLNLYLIINYFKGGKLRFK |
| | KIKPEAFEANRFYTVINKKSGEIVPMEVNFNFDDPNLIILPLAFGKRQGRE |
| | FIWNDLLSLETGSLKLANGRVIEKTLYNRRTRQDEPALFVALTFERREVL |
| | DSSNIKPMNLIGVDRGENIPAVIALTDPEGCPLSRFKDSLGNPTHILRIGE |
| | SYKEKQRTIQAKKEVEQRRAGGYSRKYASKAKNLADDMVRNTARDLLY |
| | YAVTQDAMLIFENLSRGFGRQGKRTFMAERQYTRMEDWLTAKLAYEGL |
| | SKTYLSKTLAQYTSKTCSNCGFTITSADYDRVLEKLKKTATGWMTTINGK |
| | ELKVEGQITYYNRRKRQNVVKDLSVELDRLSEESVNNDISSWTKGRSGE |
| | ALSLLKKRFSHRPVQEKFVCLNCGFETHADEQAALNIARSWLFLRSQEY |
| | KKYQTNKTTGNTDKRAFVETWQSFYRKKLKEVWKPAV |
| | (SEQ ID NO: 91) |
| 436: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| Y857R, | HVTRESNHPVKPLEQIGGNSCASGPVGKALSDACMGAVASFLTKYQDII |
| I658V, | LEHQKVIKKNEKRLANLKDIASANGLAFPKITLPPQPHTKEGIEAYNNVVA |
| F399L, | QIVIWVNLNLWQKLKIGRDEAKPLQRLKGFPSFPLVERQANEVDWWDM |
| E386N | VCNVKKLINEKKEDGKVFWQNLAGYKRQEALRPYLSSENDRKKGKKFA |
| | RYQLGDLLLHLEKKHGEDWGKVYDEAWERIDKKVEGLSKHIKLEEERRS |

TABLE 4-continued

CasX Variant Sequences

| Description* | Amino Acid Sequence |
|---|---|
| | EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTYLSKTLAQYTSKTCSNCGFTITSADYDRVLEKLKKTATGWMTTINGK<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 92) |
| 437:<br>L379R,<br>A708K,<br>P793_,<br>Y857R,<br>I658V,<br>F399L,<br>C477S | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQLGDLLLHLEKKHGEDWGKVYDEAWERIDKKVEGLSKHIKLEEERRS<br>EDAQSKAALTDWLRAKASFVIEGLKEADKDEFSRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTYLSKTLAQYTSKTCSNCGFTITSADYDRVLEKLKKTATGWMTTINGK<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 93) |
| 438:<br>L379R,<br>A708K,<br>P793_,<br>Y857R,<br>I658V,<br>F399L,<br>L404K | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQLGDLLKHLEKKHGEDWGKVYDEAWERIDKKVEGLSKHIKLEEERR<br>SEDAQSKAALTDWLRAKASFVIEGLKEADKDEFCRCELKLQKWYGDLR<br>GKPFAIEAENSILDISGFSKQYNCAFIWQKDGVKKLNLYLIINYFKGGKLR<br>FKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERRE<br>VLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRRKRQNNNKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 94) |
| 439:<br>L379R,<br>A708K,<br>P793_,<br>Y857R,<br>I658V,<br>F399L,<br>E386N,<br>C477S,<br>L404K | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSENDRKKGKKFA<br>RYQLGDLLKHLEKKHGEDWGKVYDEAWERIDKKVEGLSKHIKLEEERR<br>SEDAQSKAALTDWLRAKASFVIEGLKEADKDEFSRCELKLQKWYGDLR<br>GKPFAIEAENSILDISGFSKQYNCAFIWQKDGVKKLNLYLIINYFKGGKLR<br>FKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERRE<br>VLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN |

TABLE 4-continued

| CasX Variant Sequences | |
|---|---|
| Description* | Amino Acid Sequence |
| | GKELKVEGQITYYNRRKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 95) |
| 440:<br>L379R,<br>A708K,<br>P793_,<br>Y857R,<br>I658V,<br>F399L,<br>Y797L | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQLGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTLLSKTLAQYTSKTCSNCGFTITSADYDRVLEKLKKTATGWMTTINGK<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 96) |
| 441:<br>L379R,<br>A708K,<br>P793_,<br>Y857R,<br>I658V,<br>F399L,<br>Y797L,<br>E386N | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSENDRKKGKKFA<br>RYQLGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTLLSKTLAQYTSKTCSNCGFTITSADYDRVLEKLKKTATGWMTTINKG<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 97) |
| 442:<br>L379R,<br>A708K,<br>P793_,<br>Y857R,<br>I658V,<br>F399L,<br>Y797L,<br>E386N,<br>C477S,<br>L404K | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSENDRKKGKKFA<br>RYQLGDLLKHLEKKHGEDWGKVYDEAWERIDKKVEGLSKHIKLEEERR<br>SEDAQSKAALTDWLRAKASFVIEGLKEADKDEFSRCELKLQKWYGDLR<br>GKPFAIEAENSILDISGFSKQYNCAFIWQKDGVKKLNLYLIINYFKGGKLR<br>FKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERRE<br>VLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTLLSKTLAQYTSKTCSNCGFTITSADYDRVLEKLKKTATGWMTTIN<br>GKELKVEGQITYYNRRKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 98) |
| 443:<br>L379R,<br>A708K,<br>P793_,<br>Y857R, | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII |

TABLE 4-continued

| CasX Variant Sequences | |
|---|---|
| Description* | Amino Acid Sequence |
| I658V,<br>Y797L | LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTLLSKTLAQYTSKTCSNCGFTITSADYDRVLEKLKKTATGWMTTINGK<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 99) |
| 444:<br>L379R,<br>A708K,<br>P793_,<br>Y857R,<br>I658V,<br>Y797L,<br>L404K | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLKHLEKKHGEDWGKVYDEAWERIDKKVEGLSKHIKLEEERR<br>SEDAQSKAALTDWLRAKASFVIEGLKEADKDEFCRCELKLQKWYGDLR<br>GKPFAIEAENSILDISGFSKQYNCAFIWQKDGVKKLNLYLIINYFKGGKLR<br>FKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERRE<br>VLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTLLSKTLAQYTSKTCSNCGFTITSADYDRVLEKLKKTATGWMTTIN<br>GKELKVEGQITYYNRRKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 100) |
| 445:<br>L379R,<br>A708K,<br>P793_,<br>Y857R,<br>I658V,<br>Y797L,<br>E386N | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSENDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTLLSKTLAQYTSKTCSNCGFTITSADYDRVLEKLKKTATGWMTTINGK<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 101) |
| 446:<br>L379R,<br>A708K,<br>P793_,<br>Y857R,<br>I658V,<br>Y797L,<br>E386N,<br>C477S,<br>L404K | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSENDRKKGKKFA<br>RYQFGDLLKHLEKKHGEDWGKVYDEAWERIDKKVEGLSKHIKLEEERR<br>SEDAQSKAALTDWLRAKASFVIEGLKEADKDEFSRCELKLQKWYGDLR<br>GKPFAIEAENSILDISGFSKQYNCAFIWQKDGVKKLNLYLIINYFKGGKLR<br>FKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERRE<br>VLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL |

TABLE 4-continued

CasX Variant Sequences

| Description* | Amino Acid Sequence |
|---|---|
| | LYYAVTQDAMLIFENLSRGFGRQGKRTFMAERQYTRMEDWLTAKLAYE GLSKTLLSKTLAQYTSKTCSNCGFTITSADYDRVLEKLKKTATGWMTTIN GKELKVEGQITYYNRRKRQNVVKDLSVELDRLSEESVNNDISSWTKGRS GEALSLLKKRFSHRPVQEKFVCLNCGFETHADEQAALNIARSWLFLRSQ EYKKYQTNKTTGNTDKRAFVETWQSFYRKKLKEVWKPAV (SEQ ID NO: 102) |
| 447: L379R, A708K, P793_, Y857R, E386N | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSENDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRRKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 103) |
| 448: L379R, A708K, P793_ Y857R, E386N, L404K | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSENDRKKGKKFA RYQFGDLLKHLEKKHGEDWGKVYDEAWERIDKKVEGLSKHIKLEEERR SEDAQSKAALTDWLRAKASFVIEGLKEADKDEFCRCELKLQKWYGDLR GKPFAIEAENSILDISGFSKQYNCAFIWQKDGVKKLNLYLIINYFKGGKLR FKKIKPEAFEANRFYTVINKKSGEIVPMEVNFNFDDPNLIILPLAFGKRQG REFIWNDLLSLETGSLKLANGRVIEKTLYNRRTRQDEPALFVALTFERRE VLDSSNIKPMNLIGIDRGENIPAVIALTDPEGCPLSRFKDSLGNPTHILRIG ESYKEKQRTIQAKKEVEQRRAGGYSRKYASKAKNLADDMVRNTARDLL YYAVTQDAMLIFENLSRGFGRQGKRTFMAERQYTRMEDWLTAKLAYEG LSKTYLSKTLAQYTSKTCSNCGFTITSADYDRVLEKLKKTATGWMTTING KELKVEGQITYYNRRKRQNVVKDLSVELDRLSEESVNNDISSWTKGRSG EALSLLKKRFSHRPVQEKFVCLNCGFETHADEQAALNIARSWLFLRSQE YKKYQTNKTTGNTDKRAFVETWQSFYRKKLKEVWKPAV (SEQ ID NO: 104) |
| 449: L379R, A708K, P793_, D732N, E385P, Y857R | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSPEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLANDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRRKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 105) |
| 450: L379R, A708K, | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG |

TABLE 4-continued

| CasX Variant Sequences | |
|---|---|
| Description* | Amino Acid Sequence |
| P793_, | KPHTNYFGRCNVSEHERLILLSPHKPEANDELVTYSLGKFGQRALDFYSI |
| D732N, | HVTRESNHPVKPLEQIGGNSCASGPVGKALSDACMGAVASFLTKYQDII |
| E385P | LEHQKVIKKNEKRLANLKDIASANGLAFPKITLPPQPHTKEGIEAYNNVVA |
| Y857R, | QIVIWVNLNLWQKLKIGRDEAKPLQRLKGFPSFPLVERQANEVDWWDM |
| I658V | VCNVKKLINEKKEDGKVFWQNLAGYKRQEALRPYLSSPEDRKKGKKFA |
| | RYQFGDLLLHLEKKHGEDWGKVYDEAWERIDKKVEGLSKHIKLEEERRS |
| | EDAQSKAALTDWLRAKASFVIEGLKEADKDEFCRCELKLQKWYGDLRG |
| | KPFAIEAENSILDISGFSKQYNCAFIWQKDGVKKLNLYLIINYFKGGKLRFK |
| | KIKPEAFEANRFYTVINKKSGEIVPMEVNFNFDDPNLIILPLAFGKRQGRE |
| | FIWNDLLSLETGSLKLANGRVIEKTLYNRRTRQDEPALFVALTFERREVL |
| | DSSNIKPMNLIGVDRGENIPAVIALTDPEGCPLSRFKDSLGNPTHILRIGE |
| | SYKEKQRTIQAKKEVEQRRAGGYSRKYASKAKNLANDMVRNTARDLLY |
| | YAVTQDAMLIFENLSRGFGRQGKRTFMAERQYTRMEDWLTAKLAYEGL |
| | SKTYLSKTLAQYTSKTCSNCGFTITSADYDRVLEKLKKTATGWMTTINGK |
| | ELKVEGQITYYNRRKRQNVVKDLSVELDRLSEESVNNDISSWTKGRSGE |
| | ALSLLKKRFSHRPVQEKFVCLNCGFETHADEQAALNIARSWLFLRSQEY |
| | KKYQTNKTTGNTDKRAFVETWQSFYRKKLKEVWKPAV |
| | (SEQ ID NO: 106) |
| 451: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| D732N, | HVTRESNHPVKPLEQIGGNSCASGPVGKALSDACMGAVASFLTKYQDII |
| E385P, | LEHQKVIKKNEKRLANLKDIASANGLAFPKITLPPQPHTKEGIEAYNNVVA |
| Y857R, | QIVIWVNLNLWQKLKIGRDEAKPLQRLKGFPSFPLVERQANEVDWWDM |
| I658V, | VCNVKKLINEKKEDGKVFWQNLAGYKRQEALRPYLSSPEDRKKGKKFA |
| F399L | RYQLGDLLLHLEKKHGEDWGKVYDEAWERIDKKVEGLSKHIKLEEERRS |
| | EDAQSKAALTDWLRAKASFVIEGLKEADKDEFCRCELKLQKWYGDLRG |
| | KPFAIEAENSILDISGFSKQYNCAFIWQKDGVKKLNLYLIINYFKGGKLRFK |
| | KIKPEAFEANRFYTVINKKSGEIVPMEVNFNFDDPNLIILPLAFGKRQGRE |
| | FIWNDLLSLETGSLKLANGRVIEKTLYNRRTRQDEPALFVALTFERREVL |
| | DSSNIKPMNLIGVDRGENIPAVIALTDPEGCPLSRFKDSLGNPTHILRIGE |
| | SYKEKQRTIQAKKEVEQRRAGGYSRKYASKAKNLANDMVRNTARDLLY |
| | YAVTQDAMLIFENLSRGFGRQGKRTFMAERQYTRMEDWLTAKLAYEGL |
| | SKTYLSKTLAQYTSKTCSNCGFTITSADYDRVLEKLKKTATGWMTTINGK |
| | ELKVEGQITYYNRRKRQNVVKDLSVELDRLSEESVNNDISSWTKGRSGE |
| | ALSLLKKRFSHRPVQEKFVCLNCGFETHADEQAALNIARSWLFLRSQEY |
| | KKYQTNKTTGNTDKRAFVETWQSFYRKKLKEVWKPAV |
| | (SEQ ID NO: 107) |
| 452: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| D732N, | HVTRESNHPVKPLEQIGGNSCASGPVGKALSDACMGAVASFLTKYQDII |
| E385P, | LEHQKVIKKNEKRLANLKDIASANGLAFPKITLPPQPHTKEGIEAYNNVVA |
| Y857R, | QIVIWVNLNLWQKLKIGRDEAKPLQRLKGFPSFPLVERQANEVDWWDM |
| I658V, | VCNVKKLINEKKEDGKVFWQNLAGYKRQEALRPYLSSPNDRKKGKKFA |
| E386N | RYQFGDLLLHLEKKHGEDWGKVYDEAWERIDKKVEGLSKHIKLEEERRS |
| | EDAQSKAALTDWLRAKASFVIEGLKEADKDEFCRCELKLQKWYGDLRG |
| | KPFAIEAENSILDISGFSKQYNCAFIWQKDGVKKLNLYLIINYFKGGKLRFK |
| | KIKPEAFEANRFYTVINKKSGEIVPMEVNFNFDDPNLIILPLAFGKRQGRE |
| | FIWNDLLSLETGSLKLANGRVIEKTLYNRRTRQDEPALFVALTFERREVL |
| | DSSNIKPMNLIGVDRGENIPAVIALTDPEGCPLSRFKDSLGNPTHILRIGE |
| | SYKEKQRTIQAKKEVEQRRAGGYSRKYASKAKNLANDMVRNTARDLLY |
| | YAVTQDAMLIFENLSRGFGRQGKRTFMAERQYTRMEDWLTAKLAYEGL |
| | SKTYLSKTLAQYTSKTCSNCGFTITSADYDRVLEKLKKTATGWMTTINGK |
| | ELKVEGQITYYNRRKRQNVVKDLSVELDRLSEESVNNDISSWTKGRSGE |
| | ALSLLKKRFSHRPVQEKFVCLNCGFETHADEQAALNIARSWLFLRSQEY |
| | KKYQTNKTTGNTDKRAFVETWQSFYRKKLKEVWKPAV |
| | (SEQ ID NO: 108) |
| 453: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| D732N, | HVTRESNHPVKPLEQIGGNSCASGPVGKALSDACMGAVASFLTKYQDII |
| E385P, | LEHQKVIKKNEKRLANLKDIASANGLAFPKITLPPQPHTKEGIEAYNNVVA |
| Y857R, | QIVIWVNLNLWQKLKIGRDEAKPLQRLKGFPSFPLVERQANEVDWWDM |
| I658V, | VCNVKKLINEKKEDGKVFWQNLAGYKRQEALRPYLSSPEDRKKGKKFA |
| L404K | RYQFGDLLKHLEKKHGEDWGKVYDEAWERIDKKVEGLSKHIKLEEERR |
| | SEDAQSKAALTDWLRAKASFVIEGLKEADKDEFCRCELKLQKWYGDLR |
| | GKPFAIEAENSILDISGFSKQYNCAFIWQKDGVKKLNLYLIINYFKGGKLR |
| | FKKIKPEAFEANRFYTVINKKSGEIVPMEVNFNFDDPNLIILPLAFGKRQG |
| | REFIWNDLLSLETGSLKLANGRVIEKTLYNRRTRQDEPALFVALTFERRE |

TABLE 4-continued

| CasX Variant Sequences | |
|---|---|
| Description* | Amino Acid Sequence |
| | VLDSSNIKPMNLIGVDRGENIPAVIALTDPEGCPLSRFKDSLGNPTHILRI<br>GESYKEKQRTIQAKKEVEQRRAGGYSRKYASKAKNLANDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRRKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 109) |
| 454:<br>L379R,<br>A708K,<br>P793_,<br>T620P,<br>E385P,<br>Y857R,<br>Q252K | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHKKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSPEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKPLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRRKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 110) |
| 455:<br>L379R,<br>A708K,<br>P793_,<br>T620P,<br>E385P,<br>Y857R,<br>I658V,<br>Q252K | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHKKVIKKNEKRLANLKDIASANGLAFPKITLPPQPHTKEGIEAYNNVVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSPEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKPLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTYLSKTLAQYTSKTCSNCGFTITSADYDRVLEKLKKTATGWMTTINGK<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 111) |
| 456:<br>L379R,<br>A708K,<br>P793_,<br>T620P,<br>E385P,<br>Y857R,<br>I658V,<br>E386N,<br>Q252K | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHKKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSPNDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKPLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTYLSKTLAQYTSKTCSNCGFTITSADYDRVLEKLKKTATGWMTTINGK<br>ELKVEGQITYYNRRKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 112) |

TABLE 4-continued

CasX Variant Sequences

| Description* | Amino Acid Sequence |
|---|---|
| 457: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| T620P, | HVTRESNHPVKPLEQIGGNSCASGPVGKALSDACMGAVASFLTKYQDII |
| E385P, | LEHKKVIKKNEKRLANLKDIASANGLAFPKITLPPQPHTKEGIEAYNNVVA |
| Y857R, | QIVIWVNLNLWQKLKIGRDEAKPLQRLKGFPSFPLVERQANEVDWWDM |
| I658V, | VCNVKKLINEKKEDGKVFWQNLAGYKRQEALRPYLSSPEDRKKGKKFA |
| F399L, | RYQLGDLLLHLEKKHGEDWGKVYDEAWERIDKKVEGLSKHIKLEEERRS |
| Q252K | EDAQSKAALTDWLRAKASFVIEGLKEADKDEFCRCELKLQKWYGDLRG |
| | KPFAIEAENSILDISGFSKQYNCAFIWQKDGVKKLNLYLIINYFKGGKLRFK |
| | KIKPEAFEANRFYTVINKKSGEIVPMEVNFNFDDPNLIILPLAFGKRQGRE |
| | FIWNDLLSLETGSLKLANGRVIEKPLYNRRTRQDEPALFVALTFERREVL |
| | DSSNIKPMNLIGVDRGENIPAVIALTDPEGCPLSRFKDSLGNPTHILRIGE |
| | SYKEKQRTIQAKKEVEQRRAGGYSRKYASKAKNLADDMVRNTARDLLY |
| | YAVTQDAMLIFENLSRGFGRQGKRTFMAERQYTRMEDWLTAKLAYEGL |
| | SKTYLSKTLAQYTSKTCSNCGFTITSADYDRVLEKLKKTATGWMTTINGK |
| | ELKVEGQITYYNRRKRQNVVKDLSVELDRLSEESVNNDISSWTKGRSGE |
| | ALSLLKKRFSHRPVQEKFVCLNCGFETHADEQAALNIARSWLFLRSQEY |
| | KKYQTNKTTGNTDKRAFVETWQSFYRKKLKEVWKPAV |
| | (SEQ ID NO: 113) |
| 458: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| T620P, | HVTRESNHPVKPLEQIGGNSCASGPVGKALSDACMGAVASFLTKYQDII |
| E385P, | LEHKKVIKKNEKRLANLKDIASANGLAFPKITLPPQPHTKEGIEAYNNVVVA |
| Y857R, | QIVIWVNLNLWQKLKIGRDEAKPLQRLKGFPSFPLVERQANEVDWWDM |
| I658V, | VCNVKKLINEKKEDGKVFWQNLAGYKRQEALRPYLSSPEDRKKGKKFA |
| L404K, | RYQFGDLLKHLEKKHGEDWGKVYDEAWERIDKKVEGLSKHIKLEEERR |
| Q252K | SEDAQSKAALTDWLRAKASFVIEGLKEADKDEFCRCELKLQKWYGDLR |
| | GKPFAIEAENSILDISGFSKQYNCAFIWQKDGVKKLNLYLIINYFKGGKLR |
| | FKKIKPEAFEANRFYTVINKKSGEIVPMEVNFNFDDPNLIILPLAFGKRQG |
| | REFIWNDLLSLETGSLKLANGRVIEKPLYNRRTRQDEPALFVALTFERRE |
| | VLDSSNIKPMNLIGVDRGENIPAVIALTDPEGCPLSRFKDSLGNPTHILRI |
| | GESYKEKQRTIQAKKEVEQRRAGGYSRKYASKAKNLADDMVRNTARDL |
| | LYYAVTQDAMLIFENLSRGFGRQGKRTFMAERQYTRMEDWLTAKLAYE |
| | GLSKTYLSKTLAQYTSKTCSNCGFTITSADYDRVLEKLKKTATGWMTTIN |
| | GKELKVEGQITYYNRRKRQNVVKDLSVELDRLSEESVNNDISSWTKGRS |
| | GEALSLLKKRFSHRPVQEKFVCLNCGFETHADEQAALNIARSWLFLRSQ |
| | EYKKYQTNKTTGNTDKRAFVETWQSFYRKKLKEVWKPAV |
| | (SEQ ID NO: 114) |
| 459: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| T620P, | HVTRESNHPVKPLEQIGGNSCASGPVGKALSDACMGAVASFLTKYQDII |
| Y857R, | LEHQKVIKKNEKRLANLKDIASANGLAFPKITLPPQPHTKEGIEAYNNVVA |
| I658V, | QIVIWVNLNLWQKLKIGRDEAKPLQRLKGFPSFPLVERQANEVDWWDM |
| E386N | VCNVKKLINEKKEDGKVFWQNLAGYKRQEALRPYLSSENDRKKGKKFA |
| | RYQFGDLLLHLEKKHGEDWGKVYDEAWERIDKKVEGLSKHIKLEEERRS |
| | EDAQSKAALTDWLRAKASFVIEGLKEADKDEFCRCELKLQKWYGDLRG |
| | KPFAIEAENSILDISGFSKQYNCAFIWQKDGVKKLNLYLIINYFKGGKLRFK |
| | KIKPEAFEANRFYTVINKKSGEIVPMEVNFNFDDPNLIILPLAFGKRQGRE |
| | FIWNDLLSLETGSLKLANGRVIEKPLYNRRTRQDEPALFVALTFERREVL |
| | DSSNIKPMNLIGVDRGENIPAVIALTDPEGCPLSRFKDSLGNPTHILRIGE |
| | SYKEKQRTIQAKKEVEQRRAGGYSRKYASKAKNLADDMVRNTARDLLY |
| | YAVTQDAMLIFENLSRGFGRQGKRTFMAERQYTRMEDWLTAKLAYEGL |
| | SKTYLSKTLAQYTSKTCSNCGFTITSADYDRVLEKLKKTATGWMTTINGK |
| | ELKVEGQITYYNRRKRQNVVKDLSVELDRLSEESVNNDISSWTKGRSGE |
| | ALSLLKKRFSHRPVQEKFVCLNCGFETHADEQAALNIARSWLFLRSQEY |
| | KKYQTNKTTGNTDKRAFVETWQSFYRKKLKEVWKPAV |
| | (SEQ ID NO: 115) |
| 460: | MQEIKRINKIRRRLVKDSNTKKAGKTGPMKTLLVRVMTPDLRERLENLRK |
| L379R, | KPENIPQPISNTSRANLNKLLTDYTEMKKAILHVYWEEFQKDPVGLMSRV |
| A708K, | AQPAPKNIDQRKLIPVKDGNERLTSSGFACSQCCQPLYVYKLEQVNDKG |
| P793_, | KPHTNYFGRCNVSEHERLILLSPHKPEANDELVTYSLGKFGQRALDFYSI |
| T620P, | HVTRESNHPVKPLEQIGGNSCASGPVGKALSDACMGAVASFLTKYQDII |
| E385P, | LEHKKVIKKNEKRLANLKDIASANGLAFPKITLPPQPHTKEGIEAYNNVVA |
| Q252K | QIVIWVNLNLWQKLKIGRDEAKPLQRLKGFPSFPLVERQANEVDWWDM |
| | VCNVKKLINEKKEDGKVFWQNLAGYKRQEALRPYLSSPEDRKKGKKFA |
| | RYQFGDLLLHLEKKHGEDWGKVYDEAWERIDKKVEGLSKHIKLEEERRS |

TABLE 4-continued

CasX Variant Sequences

| Description* | Amino Acid Sequence |
|---|---|
| | EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKPLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 116) |
| 278 | QEIKRINKIRRRLVKDSNTKKAGKTGPMKTLLVRVMTPDLRERLENLRKK<br>PENIPQPISNTSRANLNKLLTDYTEMKKAILHVYWEEFQKDPVGLMSRVA<br>QPAPKNIDQRKLIPVKDGNERLTSSGFACSQCCQPLYVYKLEQVNDKGK<br>PHTNYFGRCNVSEHERLILLSPHKPEANDELVTYSLGKFGQRALDFYSIH<br>VTRESNHPVKPLEQIGGNSCASGPVGKALSDACMGAVASFLTKYQDIIL<br>EHQKVIKKNEKRLANLKDIASANGLAFPKITLPPQPHTKEGIEAYNNVVAQ<br>IVIWVNLNLWQKLKIGRDEAKPLQRLKGFPSFPLVERQANEVDWWDMV<br>CNVKKLINEKKEDGKVFWQNLAGYKRQEALRPYLSSEEDRKKGKKFAR<br>YQFGDLLLHLEKKHGEDWGKVYDEAWERIDKKVEGLSKHIKLEEERRSE<br>DAQSKAALTDWLRAKASFVIEGLKEADKDEFCRCELKLQKWYGDLRGK<br>PFAIEAENSILDISGFSKQYNCAFIWQKDGVKKLNLYLIINYFKGGKLRFKK<br>IKPEAFEANRFYTVINKKSGEIVPMEVNFNFDDPNLIILPLAFGKRQGREFI<br>WNDLLSLETGSLKLANGRVIEKTLYNRRTRQDEPALFVALTFERREVLDS<br>SNIKPMNLIGIDRGENIPAVIALTDPEGCPLSRFKDSLGNPTHILRIGESYK<br>EKQRTIQAKKEVEQRRAGGYSRKYASKAKNLADDMVRNTARDLLYYAV<br>TQDAMLIFENLSRGFGRQGKRTFMAERQYTRMEDWLTAKLAYEGLSKT<br>YLSKTLAQYTSKTCSNCGFTITSADYDRVLEKLKKTATGWMTTINGKELK<br>VEGQITYYNRYKRQNVVKDLSVELDRLSEESVNNDISSWTKGRSGEALS<br>LLKKRFSHRPVQEKFVCLNCGFETHADEQAALNIARSWLFLRSQEYKKY<br>QTNKTTGNTDKRAFVETWQSFYRKKLKEVWKPAV<br>(SEQ ID NO: 117) |
| 279 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 118) |
| 280 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE |

TABLE 4-continued

CasX Variant Sequences

| Description* | Amino Acid Sequence |
|---|---|
| | LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 119) |
| 285 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 120) |
| 286 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 121) |
| 287 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 122) |
| 288 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTMSSGFACSQCCQPLYVYKLEQVNDK GKPHTNYFGRCNVSEHERLILLSPHKPEANDELVTYSLGKFGQRALDFY SIHVTRESNHPVKPLEQIGGNSCASGPVGKALSDACMGAVASFLTKYQD |

TABLE 4-continued

CasX Variant Sequences

| Description* | Amino Acid Sequence |
|---|---|
| | IILEHQKVIKKNEKRLANLKDIASANGLAFPKITLPPQPHTKEGIEAYNNVV<br>AQIVIWVNLNLWQKLKIGRDEAKPLQRLKGFPSFPLVERQANEVDWWD<br>MVCNVKKLINEKKEDGKVFWQNLAGYKRQEALRPYLSSEEDRKKGKKF<br>ARYQFGDLLLHLEKKHGEDWGKVYDEAWERIDKKVEGLSKHIKLEEERR<br>SEDAQSKAALTDWLRAKASFVIEGLKEADKDEFCRCELKLQKWYGDLR<br>GKPFAIEAENSILDISGFSKQYNCAFIWQKDGVKKLNLYLIINYFKGGKLR<br>FKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERRE<br>VLDSSNIKPMNLIGIDRGENIPAVIALTDPEGCPLSRFKDSLGNPTHILRIG<br>ESYKEKQRTIQAKKEVEQRRAGGYSRKYASKAKNLADDMVRNTARDLL<br>YYAVTQDAMLIFENLSRGFGRQGKRTFMAERQYTRMEDWLTAKLAYEG<br>LSKTYLSKTLAQYTSKTCSNCGFTITSADYDRVLEKLKKTATGWMTTING<br>KELKVEGQITYYNRYKRQNVVKDLSVELDRLSEESVNNDISSWTKGRSG<br>EALSLLKKRFSHRPVQEKFVCLNCGFETHADEQAALNIARSWLFLRSQE<br>YKKYQTNKTTGNTDKRAFVETWQSFYRKKLKEVWKPAV<br>(SEQ ID NO: 123) |
| 290 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 124) |
| 291 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY<br>AVTQDAMLIFENLSRGFGRQGKRTFMAERQYTRMEDWLTAKLAYEGLS<br>KTYLSKTLAQYTSKTCSNCGFTITSADYDRVLEKLKKTATGWMTTINGKE<br>LKVEGQITYYNRYKRQNVVKDLSVELDRLSEESVNNDISSWTKGRSGEA<br>LSLLKKRFSHRPVQEKFVCLNCGFETHADEQAALNIARSWLFLRSQEYK<br>KYQTNKTTGNTDKRAFVETWQSFYRKKLKEVWKPAV<br>(SEQ ID NO: 125) |
| 293 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALRPYLSSEEDRKKGKKFA<br>RYQFGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYY |

TABLE 4-continued

CasX Variant Sequences

| Description* | Amino Acid Sequence |
|---|---|
| | AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 126) |
| 300 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 127) |
| 492 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 128) |
| 493 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 129) |
| 387: NTSB swap from SEQ ID | QEIKRINKIRRRLVKDSNTKKAGKTGPMKTLLVRVMTPDLRERLENLRKK PENIPQPISNTSRANLNKLLTDYTEMKKAILHVYWEEFQKDPVGLMSRVA QPASKKIDQNKLKPEMDEKGNLTTAGFACSQCGQPLFVYKLEQVSEKG |

TABLE 4-continued

CasX Variant Sequences

| Description* | Amino Acid Sequence |
|---|---|
| NO: 1 | KAYTNYFGRCNVAEHEKLILLAQLKPEKDSDEAVTYSLGKFGQRALDFY SIHVTRESNHPVKPLEQIGGNSCASGPVGKALSDACMGAVASFLTKYQD IILEHQKVIKKNEKRLANLKDIASANGLAFPKITLPPQPHTKEGIEAYNNVV AQIVIWVNLNLWQKLKIGRDEAKPLQRLKGFPSFPLVERQANEVDWWD MVCNVKKLINEKKEDGKVFWQNLAGYKRQEALRPYLSSEEDRKKGKKF ARYQFGDLLLHLEKKHGEDWGKVYDEAWERIDKKVEGLSKHIKLEEERR SEDAQSKAALTDWLRAKASFVIEGLKEADKDEFCRCELKLQKWYGDLR GKPFAIEAENSILDISGFSKQYNCAFIWQKDGVKKLNLYLIINYFKGGKLR FKKIKPEAFEANRFYTVINKKSGEIVPMEVNFNFDDPNLIILPLAFGKRQG REFIWNDLLSLETGSLKLANGRVIEKTLYNRRTRQDEPALFVALTFERRE VLDSSNIKPMNLIGIDRGENIPAVIALTDPEGCPLSRFKDSLGNPTHILRIG ESYKEKQRTIQAKKEVEQRRAGGYSRKYASKAKNLADDMVRNTARDLL YYAVTQDAMLIFENLSRGFGRQGKRTFMAERQYTRMEDWLTAKLAYEG LSKTYLSKTLAQYTSKTCSNCGFTITSADYDRVLEKLKKTATGWMTTING KELKVEGQITYYNRYKRQNVVKDLSVELDRLSEESVNNDISSWTKGRSG EALSLLKKRFSHRPVQEKFVCLNCGFETHADEQAALNIARSWLFLRSQE YKKYQTNKTTGNTDKRAFVETWQSFYRKKLKEVWKPAV (SEQ ID NO: 130) |
| 395: Helical 1B swap from SEQ ID NO: 1 | QEIKRINKIRRRLVKDSNTKKAGKTGPMKTLLVRVMTPDLRERLENLRKK PENIPQPISNTSRANLNKLLTDYTEMKKAILHVYWEEFQKDPVGLMSRVA QPAPKNIDQRKLIPVKDGNERLTSSGFACSQCCQPLYVYKLEQVNDKGK PHTNYFGRCNVSEHERLILLSPHKPEANDELVTYSLGKFGQRALDFYSIH VTKESTHPVKPLAQIAGNRYASGPVGKALSDACMGTIASFLSKYQDIIIEH QKVVKGNQKRLESLRELAGKENLEYPSVTLPPQPHTKEGVDAYNEVIAR VRMWVNLNLWQKLKLSRDDAKPLLRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLRSQEYK KYQTNKTTGNTDKRAFVETWQSFYRKKLKEVWKPAV (SEQ ID NO: 131) |
| 485: Helical 1B swap from SEQ ID NO: 1 | QEIKRINKIRRRLVKDSNTKKAGKTGPMKTLLVRVMTPDLRERLENLRKK PENIPQPISNTSRANLNKLLTDYTEMKKAILHVYWEEFQKDPVGLMSRVA QPAPKNIDQRKLIPVKDGNERLTSSGFACSQCCQPLYVYKLEQVNDKGK PHTNYFGRCNVSEHERLILLSPHKPEANDELVTYSLGKFGQRALDFYSIH VTKESTHPVKPLAQIAGNRYASGPVGKALSDACMGTIASFLSKYQDIIIEH QKVVKGNQKRLESLRELAGKENLEYPSVTLPPQPHTKEGVDAYNEVIAR VRMWVNLNLWQKLKLSRDDAKPLLRLKGFPSFPLVERQANEVDWWDM VCNVKKLINEKKEDGKVFWQNLAGYKRQEALRPYLSSEEDRKKGKKFA RYQLGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGVDRGENIPAVIALTDPEGCPLSRFKDSLGNPTHILRIGE SYKEKQRTIQAKKEVEQRRAGGYSRKYASKAKNLADDMVRNTARDLLY YAVTQDAMLIFENLSRGFGRQGKRTFMAERQYTRMEDWLTAKLAYEGL SKTYLSKTLAQYTSKTCSNCGFTITSADYDRVLEKLKKTATGWMTTINGK ELKVEGQITYYNRRKRQNVVKDLSVELDRLSEESVNNDISSWTKGRSGE ALSLLKKRFSHRPVQEKFVCLNCGFETHADEQAALNIARSWLFLRSQEY KKYQTNKTTGNTDKRAFVETWQSFYRKKLKEVWKPAV (SEQ ID NO: 132) |
| 486: Helical 1B swap from SEQ ID NO: 1 | QEIKRINKIRRRLVKDSNTKKAGKTGPMKTLLVRVMTPDLRERLENLRKK PENIPQPISNTSRANLNKLLTDYTEMKKAILHVYWEEFQKDPVGLMSRVA QPAPKNIDQRKLIPVKDGNERLTSSGFACSQCCQPLYVYKLEQVNDKGK PHTNYFGRCNVSEHERLILLSPHKPEANDELVTYSLGKFGQRALDFYSIH VTKESTHPVKPLAQIAGNRYASGPVGKALSDACMGTIASFLSKYQDIIIEH QKVVKGNQKRLESLRELAGKENLEYPSVTLPPQPHTKEGVDAYNEVIAR VRMWVNLNLWQKLKLSRDDAKPLLRLKGFPSFPLVERQANEVDWWDM VCNVKKLINEKKEDGKVFWQNLAGYKRQEALRPYLSSEEDRKKGKKFA RYQLGDLLKHLEKKHGEDWGKVYDEAWERIDKKVEGLSKHIKLEEERR SEDAQSKAALTDWLRAKASFVIEGLKEADKDEFCRCELKLQKWYGDLR GKPFAIEAENSILDISGFSKQYNCAFIWQKDGVKKLNLYLIINYFKGGKLR FKKIKPEAFEANRFYTVINKKSGEIVPMEVNFNFDDPNLIILPLAFGKRQG REFIWNDLLSLETGSLKLANGRVIEKTLYNRRTRQDEPALFVALTFERRE |

TABLE 4-continued

CasX Variant Sequences

| Description* | Amino Acid Sequence |
|---|---|
| | VLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRRKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 133) |
| 487:<br>Helical 1B<br>swap from<br>SEQ ID<br>NO: 1 | QEIKRINKIRRRLVKDSNTKKAGKTGPMKTLLVRVMTPDLRERLENLRKK<br>PENIPQPISNTSRANLNKLLTDYTEMKKAILHVYWEEFQKDPVGLMSRVA<br>QPAPKNIDQRKLIPVKDGNERLTSSGFACSQCCQPLYVYKLEQVNDKGK<br>PHTNYFGRCNVSEHERLILLSPHKPEANDELVTYSLGKFGQRALDFYSIH<br>VTKESTHPVKPLAQIAGNRYASGPVGKALSDACMGTIASFLSKYQDIIIEH<br>QKVVKGNQKRLESLRELAGKENLEYPSVTLPPQPHTKEGVDAYNEVIAR<br>VRMWVNLNLWQKLKLSRDDAKPLLRLKGFPSFPLVERQANEVDWWDM<br>VCNVKKLINEKKEDGKVFWQNLAGYKRQEALRPYLSSEEDRKKGKKFA<br>RYQLGDLLLHLEKKHGEDWGKVYDEAWERIDKKVEGLSKHIKLEEERRS<br>EDAQSKAALTDWLRAKASFVIEGLKEADKDEFCRCELKLQKWYGDLRG<br>KPFAIEAENSILDISGFSKQYNCAFIWQKDGVKKLNLYLIINYFKGGKLRFK<br>KIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVL<br>DSSNIKPMNLIGVDRGENIPAVIALTDPEGCPLSRFKDSLGNPTHILRIGE<br>SYKEKQRTIQAKKEVEQRRAGGYSRKYASKAKNLADDMVRNTARDLLY<br>YAVTQDAMLIFENLSRGFGRQGKRTFMAERQYTRMEDWLTAKLAYEGL<br>SKTYLSKTLAQYTSKTCSNCGFTITSADYDRVLEKLKKTATGWMTTINGK<br>ELKVEGQITYYNRYKRQNVVKDLSVELDRLSEESVNNDISSWTKGRSGE<br>ALSLLKKRFSHRPVQEKFVCLNCGFETHADEQAALNIARSWLFLRSQEY<br>KKYQTNKTTGNTDKRAFVETWQSFYRKKLKEVWKPAV<br>(SEQ ID NO: 134) |
| 488:<br>NTSB and<br>Helical 1B<br>swap from<br>SEQ ID<br>NO: 1 | QEIKRINKIRRRLVKDSNTKKAGKTGPMKTLLVRVMTPDLRERLENLRKK<br>PENIPQPISNTSRANLNKLLTDYTEMKKAILHVYWEEFQKDPVGLMSRVA<br>QPASKKIDQNKLKPEMDEKGNLTTAGFACSQCGQPLFVYKLEQVSEKG<br>KAYTNYFGRCNVAEHEKLILLAQLKPEKDSDEAVTYSLGKFGQRALDFY<br>SIHVTKESTHPVKPLAQIAGNRYASGPVGKALSDACMGTIASFLSKYQDII<br>IEHQKWKGNQKRLESLRELAGKENLEYPSVTLPPQPHTKEGVDAYNEV<br>IARVRMWVNLNLWQKLKLSRDDAKPLLRLKGFPSFPLVERQANEVDWW<br>DMVCNVKKLINEKKEDGKVFWQNLAGYKRQEALRPYLSSEEDRKKGKK<br>FARYQFGDLLLHLEKKHGEDWGKVYDEAWERIDKKVEGLSKHIKLEEER<br>RSEDAQSKAALTDWLRAKASFVIEGLKEADKDEFCRCELKLQKWYGDL<br>RGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQ<br>GREFIWNDLLSLETGSLKLANGRVIEKTLYNRRTRQDEPALFVALTFERR<br>EVLDSSNIKPMNLIGIDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRYKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 135) |
| 489:<br>NTSB and<br>Helical 1B<br>swap from<br>SEQ ID<br>NO: 1 | QEIKRINKIRRRLVKDSNTKKAGKTGPMKTLLVRVMTPDLRERLENLRKK<br>PENIPQPISNTSRANLNKLLTDYTEMKKAILHVYWEEFQKDPVGLMSRVA<br>QPASKKIDQNKLKPEMDEKGNLTTAGFACSQCGQPLFVYKLEQVSEKG<br>KAYTNYFGRCNVAEHEKLILLAQLKPEKDSDEAVTYSLGKFGQRALDFY<br>SIHVTKESTHPVKPLAQIAGNRYASGPVGKALSDACMGTIASFLSKYQDII<br>IEHQKVVVKGNQKRLESLRELAGKENLEYPSVTLPPQPHTKEGVDAYNEV<br>IARVRMWVNLNLWQKLKLSRDDAKPLLRLKGFPSFPLVERQANEVDWW<br>DMVCNVKKLINEKKEDGKVFWQNLAGYKRQEALRPYLSSEEDRKKGKK<br>FARYQLGDLLLHLEKKHGEDWGKVYDEAWERIDKKVEGLSKHIKLEEER<br>RSEDAQSKAALTDWLRAKASFVIEGLKEADKDEFCRCELKLQKWYGDL<br>RGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQ<br>GREFIWNDLLSLETGSLKLANGRVIEKTLYNRRTRQDEPALFVALTFERR<br>EVLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRRKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 136) |

TABLE 4-continued

| CasX Variant Sequences | |
|---|---|
| Description* | Amino Acid Sequence |
| 490:<br>NTSB and<br>Helical 1B<br>swap from<br>SEQ ID<br>NO: 1 | QEIKRINKIRRRLVKDSNTKKAGKTGPMKTLLVRVMTPDLRERLENLRKK<br>PENIPQPISNTSRANLNKLLTDYTEMKKAILHVYWEEFQKDPVGLMSRVA<br>QPASKKIDQNKLKPEMDEKGNLTTAGFACSQCGQPLFVYKLEQVSEKG<br>KAYTNYFGRCNVAEHEKLILLAQLKPEKDSDEAVTYSLGKFGQRALDFY<br>SIHVTKESTHPVKPLAQIAGNRYASGPVGKALSDACMGTIASFLSKYQDII<br>IEHQKVVKGNQKRLESLRELAGKENLEYPSVTLPPQPHTKEGVDAYNEV<br>IARVRMWVNLNLWQKLKLSRDDAKPLLRLKGFPSFPLVERQANEVDWW<br>DMVCNVKKLINEKKEDGKVFWQNLAGYKRQEALRPYLSSEEDRKKGKK<br>FARYQLGDLLKHLEKKHGEDWGKVYDEAWERIDKKVEGLSKHIKLEEER<br>RSEDAQSKAALTDWLRAKASFVIEGLKEADKDEFCRCELKLQKWYGDL<br>RGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQ<br>GREFIWNDLLSLETGSLKLANGRVIEKTLYNRRTRQDEPALFVALTFERR<br>EVLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRRKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 137) |
| 491:<br>NTSB and<br>Helical 1B<br>swap from<br>SEQ ID<br>NO: 1 | QEIKRINKIRRRLVKDSNTKKAGKTGPMKTLLVRVMTPDLRERLENLRKK<br>PENIPQPISNTSRANLNKLLTDYTEMKKAILHVYWEEFQKDPVGLMSRVA<br>QPASKKIDQNKLKPEMDEKGNLTTAGFACSQCGQPLFVYKLEQVSEKG<br>KAYTNYFGRCNVAEHEKLILLAQLKPEKDSDEAVTYSLGKFGQRALDFY<br>SIHVTKESTHPVKPLAQIAGNRYASGPVGKALSDACMGTIASFLSKYQDII<br>IEHQKWKGNQKRLESLRELAGKENLEYPSVTLPPQPHTKEGVDAYNEV<br>IARVRMWVNLNLWQKLKLSRDDAKPLLRLKGFPSFPLVERQANEVDWW<br>DMVCNVKKLINEKKEDGKVFWQNLAGYKRQEALRPYLSSEEDRKKGKK<br>FARYQLGDLLLHLEKKHGEDWGKVYDEAWERIDKKVEGLSKHIKLEEER<br>RSEDAQSKAALTDWLRAKASFVIEGLKEADKDEFCRCELKLQKWYGDL<br>RGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQ<br>GREFIWNDLLSLETGSLKLANGRVIEKTLYNRRTRQDEPALFVALTFERR<br>EVLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRYKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 138) |
| 494:<br>NTSB swap<br>from SEQ ID<br>NO: 1 | QEIKRINKIRRRLVKDSNTKKAGKTGPMKTLLVRVMTPDLRERLENLRKK<br>PENIPQPISNTSRANLNKLLTDYTEMKKAILHVYWEEFQKDPVGLMSRVA<br>QPASKKIDQNKLKPEMDEKGNLTTAGFACSQCGQPLFVYKLEQVSEKG<br>KAYTNYFGRCNVAEHEKLILLAQLKPEKDSDEAVTYSLGKFGQRALDFY<br>SIHVTRESNHPVKPLEQIGGNSCASGPVGKALSDACMGAVASFLTKYQD<br>IILEHQKVIKKNEKRLANLKDIASANGLAFPKITLPPQPHTKEGIEAYNNVV<br>AQIVIWVNLNLWQKLKIGRDEAKPLQRLKGFPSFPLVERQANEVDWWD<br>MVCNVKKLINEKKEDGKVFWQNLAGYKRQEALRPYLSSEEDRKKGKKF<br>ARYQLGDLLLHLEKKHGEDWGKVYDEAWERIDKKVEGLSKHIKLEEERR<br>SEDAQSKAALTDWLRAKASFVIEGLKEADKDEFCRCELKLQKWYGDLR<br>GKPFAIEAENSILDISGFSKQYNCAFIWQKDGVKKLNLYLIINYFKGGKLR<br>FKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERRE<br>VLDSSNIKPMNLIGVDRGENIPAVIALTDPEGCPLSRFKDSLGNPTHILRI<br>GESYKEKQRTIQAKKEVEQRRAGGYSRKYASKAKNLADDMVRNTARDL<br>LYYAVTQDAMLIFENLSRGFGRQGKRTFMAERQYTRMEDWLTAKLAYE<br>GLSKTYLSKTLAQYTSKTCSNCGFTITSADYDRVLEKLKKTATGWMTTIN<br>GKELKVEGQITYYNRYKRQNVVKDLSVELDRLSEESVNNDISSWTKGRS<br>GEALSLLKKRFSHRPVQEKFVCLNCGFETHADEQAALNIARSWLFLRSQ<br>EYKKYQTNKTTGNTDKRAFVETWQSFYRKKLKEVWKPAV<br>(SEQ ID NO: 139) |
| 328: S867G | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDII<br>LEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDM<br>VCNVKKLINEKKEDGKVFWQNLAGYKRQEALLPYLSSEEDRKKGKKFA<br>RYQFGDLLLHLEKKHGEDWGKVYDEAWERIDKKVEGLSKHIKLEEERRS |

TABLE 4-continued

CasX Variant Sequences

| Description* | Amino Acid Sequence |
|---|---|
| | EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAAKEVEQRRAGGYSRKYASKAKNLADDMVRNTARDLLYY AVTQDAMLIFENLSRGFGRQGKRTFMAERQYTRMEDWLTAKLAYEGLP SKTYLSKTLAQYTSKTCSNCGFTITSADYDRVLEKLKKTATGWMTTINGK ELKVEGQITYYNRYKRQNVVKDLGVELDRLSEESVNNDISSWTKGRSGE ALSLLKKRFSHRPVQEKFVCLNCGFETHADEQAALNIARSWLFLRSQEY KKYQTNKTTGNTDKRAFVETWQSFYRKKLKEVWKPAV (SEQ ID NO: 140) |
| 388: L379R + A708K + [P793] + X1 Helical2 swap | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVVA QIVIWVNLNLWQKLKIGRDEAKPLQRLKGFPSFPVVERRENEVDWWNTI NEVKKLIDAKRDMGRVFWSGVTAEKRNTILEGYNYLPNENDHKKREGSL ENPKKPAKRQFGDLLLYLEKKYAGDWGKVFDEAWERIDKKIAGLTSHIE REEARNAEDAQSKAVLTDWLRAKASFVLERLKEMDEKEFYACEIQLQK WYGDLRGNPFAVEAENSILDISGFSKQYNCAFIWQKDGVKKLNLYLIINY FKGGKLRFKKIKPEAFEANRFYTVINKKSGEIVPMEVNFNFDDPNLIILPLA FGKRQGREFIWNDLLSLETGSLKLANGRVIEKTLYNRRTRQDEPALFVAL TFERREVLDSSNIKPMNLIGIDRGENIPAVIALTDPEGCPLSRFKDSLGNP THILRIGESYKEKQRTIQAKKEVEQRRAGGYSRKYASKAKNLADDMVRN TARDLLYYAVTQDAMLIFENLSRGFGRQGKRTFMAERQYTRMEDWLTA KLAYEGLSKTYLSKTLAQYTSKTCSNCGFTITSADYDRVLEKLKKTATGW MTTINGKELKVEGQITYYNRYKRQNVVKDLSVELDRLSEESVNNDISSW TKGRSGEALSLLKKRFSHRPVQEKFVCLNCGFETHADEQAALNIARSWL FLRSQEYKKYQTNKTTGNTDKRAFVETWQSFYRKKLKEVWKPAV (SEQ ID NO: 141) |
| 389: L379R + A708K + [P793] + X1 RuvC1 swap | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPVNLIGVDRGENIPAVIALTDPEGCPLPEFKDSSGGPTDILRIGE GYKEKQRAIQAAKEVEQRRAGGYSRKFASKSRNLADDMVRNSARDLFY HAVTHDAVLVFENLSRGFGRQGKRTFMTERQYTKMEDWLTAKLAYEGL TSKTYLSKTLAQYTSKTCSNCGFTITSADYDRVLEKLKKTATGWMTTING KELKVEGQITYYNRYKRQNVVKDLSVELDRLSEESVNNDISSWTKGRSG EALSLLKKRFSHRPVQEKFVCLNCGFETHADEQAALNIARSWLFLRSQE YKKYQTNKTTGNTDKRAFVETWQSFYRKKLKEVWKPAV (SEQ ID NO: 142) |
| 390: L379R + A708K + [P793] + X1 RuvC2 swap | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDII LEHQKVIKKNEKRLANLKDIASANGLAFPKITLPPQPHTKEGIEAYNNVVA QIVIWVNLNLWQKLKIGRDEAKPLQRLKGFPSFPLVERQANEVDWWDM VCNVKKLINEKKEDGKVFWQNLAGYKRQEALRPYLSSEEDRKKGKKFA RYQFGDLLLHLEKKHGEDWGKVYDEAWERIDKKVEGLSKHIKLEEERRS EDAQSKAALTDWLRAKASFVIEGLKEADKDEFCRCELKLQKWYGDLRG KPFAIEAENSILDISGFSKQYNCAFIWQKDGVKKLNLYLIINYFKGGKLRFK KIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVL DSSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYY AVTQDAMLIFENLSRGFGRQGKRTFMAERQYTRMEDWLTAKLAYEGLS |

TABLE 4-continued

| CasX Variant Sequences | |
|---|---|
| Description* | Amino Acid Sequence |
| | KTYLSKTLAQYTSKTCSNCGFTITSADYDRVLEKLKKTATGWMTTINGKE LKVEGQITYYNRYKRQNVVKDLSVELDRLSEESVNNDISSWTKGRSGEA LSLLKKRFSHRPVQEKFVCLNCGFETHADEQAALNIARSWLFLNSNSTE FKSYKSGKQPFVGAWQAFYKRRLKEVWKPNA (SEQ ID NO: 143) |

In some embodiments, the CasX variant protein comprises a sequence selected from the group consisting of SEQ ID NOs: 49-143, 438, 440, 442, 444, 446, 448-460, 472, 474, 478, 480, 482, 484, 486, 488, 490, 612 and 613. In some embodiments, the CasX variant protein comprises a sequence selected from the group consisting of SEQ ID NOs: 49-143, 438, 440, 442, 444, 446, 448-460, 472, 474, 478, 480, 482, 484, 486, 488, 490, 612 and 613, or a sequence having at least about 50%, at least about 60%, at least about 70%, at least about 80%, at least about 90%, or at least about 95%, or at least about 95%, or at least about 96%, or at least about 97%, or at least about 98%, or at least about 99% sequence identity thereto. In some embodiments, the CasX variant protein comprises a sequence selected from the group consisting of SEQ ID NOs: 49-143, or a sequence having at least about 50%, at least about 60%, at least about 70%, at least about 80%, at least about 90%, or at least about 95%, or at least about 95%, or at least about 96%, or at least about 97%, or at least about 98%, or at least about 99% sequence identity thereto. In some embodiments, the CasX variant protein comprises a sequence selected from the group consisting of SEQ ID NOs: 49-143.

In some embodiments, the CasX variant protein has one or more improved characteristic of the CasX protein when compared to a reference CasX protein, for example a reference protein of SEQ ID NO:1, SEQ ID NO:2 or SEQ ID NO:3. In some embodiments, the at least one improved characteristic of the CasX variant is at least about 1.1 to about 100,000-fold improved relative to the reference protein. In some embodiments, the at least one improved characteristic of the CasX variant is at least about 1.1 to about 10,000-fold improved, at least about 1.1 to about 1,000-fold improved, at least about 1.1 to about 500-fold improved, at least about 1.1 to about 400-fold improved, at least about 1.1 to about 300-fold improved, at least about 1.1 to about 200-fold improved, at least about 1.1 to about 100-fold improved, at least about 1.1 to about 50-fold improved, at least about 1.1 to about 40-fold improved, at least about 1.1 to about 30-fold improved, at least about 1.1 to about 20-fold improved, at least about 1.1 to about 10-fold improved, at least about 1.1 to about 9-fold improved, at least about 1.1 to about 8-fold improved, at least about 1.1 to about 7-fold improved, at least about 1.1 to about 6-fold improved, at least about 1.1 to about 5-fold improved, at least about 1.1 to about 4-fold improved, at least about 1.1 to about 3-fold improved, at least about 1.1 to about 2-fold improved, at least about 1.1 to about 1.5-fold improved, at least about 1.5 to about 3-fold improved, at least about 1.5 to about 4-fold improved, at least about 1.5 to about 5-fold improved, at least about 1.5 to about 10-fold improved, at least about 5 to about 10-fold improved, at least about 10 to about 20-fold improved, at least 10 to about 30-fold improved, at least 10 to about 50-fold improved or at least 10 to about 100-fold improved than the reference CasX protein. In some embodiments, the at least one improved characteristic of the CasX variant is at least about 10 to about 1000-fold improved relative to the reference CasX protein.

In some embodiments, the one or more improved characteristics of the CasX variant protein is at least about 5, at least about 10, at least about 20, at least about 30, at least about 40, at least about 50, at least about 60, at least about 70, at least about 80, at least about 90, at least about 100, at least about 250, at least about 500, or at least about 1000, at least about 5,000, at least about 10,000, or at least about 100,000-fold improved relative to a reference CasX protein. In some embodiments, an improved characteristics of the CasX variant protein is at least about 1.1, at least about 1.2, at least about 1.3, at least about 1.4, at least about 1.5, at least about 1.6, at least about 1.7, at least about 1.8, at least about 1.9, at least about 2, at least about 2.1, at least about 2.2, at least about 2.3, at least about 2.4, at least about 2.5, at least about 2.6, at least about 2.7, at least about 2.8, at least about 2.9, at least about 3, at least about 3.5, at least about 4, at least about 4.5, at least about 5, at least about 5.5, at least about 6, at least about 6.5, at least about 7.0, at least about 7.5, at least about 8, at least about 8.5, at least about 9, at least about 9.5, at least about 10, at least about 11, at least about 12, at least about 13, at least about 14, at least about 15, at least about 20, at least about 30, at least about 40, at least about 50, at least about 60, at least about 70, at least about 80, at least about 90 at least about 100, at least about 500, at least about 1,000, at least about 10,000, or at least about 100,000-fold improved relative to a reference CasX protein. In other cases, the one or more improved characteristics of the CasX variant is about 1.1 to 100,00-fold, about 1.1 to 10,00-fold, about 1.1 to 1,000-fold, about 1.1 to 500-fold, about 1.1 to 100-fold, about 1.1 to 50-fold, about 1.1 to 20-fold, about 10 to 100,00-fold, about 10 to 10,00-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100,00-fold, about 100 to 10,00-fold, about 100 to 1,000-fold, about 100 to 500-fold, about 500 to 100,00-fold, about 500 to 10,00-fold, about 500 to 1,000-fold, about 500 to 750-fold, about 1,000 to 100,00-fold, about 10,000 to 100,00-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to the reference CasX of SEQ ID NO:1, SEQ ID NO:2 or SEQ ID NO:3. In other cases, the one or more improved characteristics of the CasX variant is about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475-fold, or 500-fold or more improved relative to the reference CasX of SEQ ID NO:1, SEQ ID NO:2 or SEQ ID NO:3. Exemplary characteristics that can be improved in CasX variant proteins relative to the same characteristics in reference CasX proteins include, but are not limited to, improved folding of the variant, improved binding affinity to the gNA, improved binding affinity to the target DNA, improved ability to utilize a greater spectrum of PAM sequences in the editing and/or binding of target DNA, improved unwinding of the target DNA, increased editing activity, improved editing efficiency, improved editing specificity, increased activity of the nuclease, increased target strand loading for double strand cleavage, decreased target strand loading for single strand nicking, decreased off-target cleavage, improved binding of the non-target strand of DNA, improved protein stability, improved CasX: gNA RNA complex stability, improved protein solubility, improved CasX:gNA RNP complex solubility, improved ability to form cleavage-competent RNP with a gNA, improved protein yield, improved protein expression, and improved fusion characteristics. In some embodiments, the variant comprises at least one improved characteristic. In other embodiments, the variant comprises at least two improved characteristics. In further embodiments, the variant comprises at least three improved characteristics. In some embodiments, the variant comprises at least four improved characteristics. In still further embodiments, the variant comprises at least five, at least six, at least seven, at least eight, at least nine, at least ten, at least eleven, at least twelve, at least thirteen, or more improved characteristics.

Exemplary improved characteristic include, as one example, improved editing efficiency. In some embodiments, an RNP comprising the CasX protein and a gNA of the disclosure, at a concentration of 20 pM or less, is capable of cleaving a double stranded DNA target with an efficiency of at least 80%. In some embodiments, the RNP at a concentration of 20 pM or less, is capable of cleaving a double stranded DNA target with an efficiency of at least 40%, at least 50%, at least 60%, at least 70%, at least 80%, at least 85%, at least 90% or at least 95%. In some embodiments, the RNP at a concentration of 50 pM or less, 40 pM or less, 30 pM or less, 20 pM or less, 10 pM or less, or 5 pM or less, is capable of cleaving a double stranded DNA target with an efficiency of at least 40%, at least 50%, at least 60%, at least 70%, at least 80%, at least 85%, at least 90% or at least 95%.

These improved characteristics are described in more detail below.

j. Protein Stability

In some embodiments, the disclosure provides a CasX variant protein with improved stability relative to a reference CasX protein. In some embodiments, improved stability of the CasX variant protein results in expression of a higher steady state of protein, which improves editing efficiency. In some embodiments, improved stability of the CasX variant protein results in a larger fraction of CasX protein that remains folded in a functional conformation and improves editing efficiency or improves purifiability for manufacturing purposes. As used herein, a "functional conformation" refers to a CasX protein that is in a conformation where the protein is capable of binding a gNA and target DNA. In embodiments wherein the CasX variant does not carry one or more mutations rendering it catalytically dead, the CasX variant is capable of cleaving, nicking, or otherwise modifying the target DNA. For example, a functional CasX variant can, in some embodiments, be used for gene-editing, and a functional conformation refers to an "editing-competent" conformation. In some exemplary embodiments, including those embodiments where the CasX variant protein results in a larger fraction of CasX protein that remains folded in a functional conformation, a lower concentration of CasX variant is needed for applications such as gene editing compared to a reference CasX protein. Thus, in some embodiments, the CasX variant with improved stability has improved efficiency compared to a reference CasX in one or more gene editing contexts.

In some embodiments, the disclosure provides a CasX variant protein having improved thermostability relative to a reference CasX protein. In some embodiments, the CasX variant protein has improved thermostability of the CasX variant protein at a particular temperature range. Without wishing to be bound by any theory, some reference CasX proteins natively function in organisms with niches in groundwater and sediment; thus, some reference CasX proteins may have evolved to exhibit optimal function at lower or higher temperatures that may be desirable for certain applications. For example, one application of CasX variant proteins is gene editing of mammalian cells, which is typically carried out at about 37° C. In some embodiments, a CasX variant protein as described herein has improved thermostability compared to a reference CasX protein at a temperature of at least 16° C., at least 18° C., at least 20° C., at least 22° C., at least 24° C., at least 26° C., at least 28° C., at least 30° C., at least 32° C., at least 34° C., at least 35° C., at least 36° C., at least 37° C., at least 38° C., at least 39° C., at least 40° C., at least 41° C., at least 42° C., at least 44° C., at least 46° C., at least 48° C., at least 50° C., at least 52° C., or greater. In some embodiments, a CasX variant protein has improved thermostability and functionality compared to a reference CasX protein that results in improved gene editing functionality, such as mammalian gene editing applications, which may include human gene editing applications.

In some embodiments, the disclosure provides a CasX variant protein having improved stability of the CasX variant protein:gNA complex relative to the reference CasX protein:gNA complex such that the RNP remains in a functional form. Stability improvements can include increased thermostability, resistance to proteolytic degradation, enhanced pharmacokinetic properties, stability across a range of pH conditions, salt conditions, and tonicity. Improved stability of the complex may, in some embodiments, lead to improved editing efficiency. In some embodiments, the RNP of the CasX variant and gNA variant has at least a 5%, at least a 10%, at least a 15%, or at least a 20%, or at least a 5-20% higher percentage of cleavage-competent RNP compared to an RNP of the reference CasX of SEQ ID NOS: 1-3 and the gNA of any one of SEQ ID NOS:4-16 of Table 1.

In some embodiments, the disclosure provides a CasX variant protein having improved thermostability of the CasX variant protein:gNA complex relative to the reference CasX protein:gNA complex. In some embodiments, a CasX variant protein has improved thermostability relative to a reference CasX protein. In some embodiments, the CasX variant protein:gNA complex has improved thermostability relative to a complex comprising a reference CasX protein at temperatures of at least 16° C., at least 18° C., at least 20° C., at least 22° C., at least 24° C., at least 26° C., at least 28° C., at least 30° C., at least 32° C., at least 34° C., at least 35° C., at least 36° C., at least 37° C., at least 38° C., at least 39° C., at least 40° C., at least 41° C., at least 42° C., at least 44° C., at least 46° C., at least 48° C., at least 50° C., at least 52° C., or greater. In some embodiments, a CasX variant protein has improved thermostability of the CasX variant protein:gNA complex compared to a reference CasX protein:gNA complex, which results in improved function for gene editing applications, such as mammalian gene editing applications, which may include human gene editing applications.

In some embodiments, the improved stability and/or thermostability of the CasX variant protein comprises faster folding kinetics of the CasX variant protein relative to a reference CasX protein, slower unfolding kinetics of the CasX variant protein relative to a reference CasX protein, a larger free energy release upon folding of the CasX variant protein relative to a reference CasX protein, a higher temperature at which 50% of the CasX variant protein is unfolded (Tm) relative to a reference CasX protein, or any combination thereof. These characteristics may be improved by a wide range of values; for example, at least 1.1, at least 1.5, at least 10, at least 50, at least 100, at least 500, at least 1,000, at least 5,000, or at least a 10,000-fold improved, as compared to a reference CasX protein. In some embodiments, improved thermostability of the CasX variant protein comprises a higher Tm of the CasX variant protein relative to a reference CasX protein. In some embodiments, the Tm of the CasX variant protein is between about 20° C. to about 30° C., between about 30° C. to about 40° C., between about 40° C. to about 50° C., between about 50° C. to about 60° C., between about 60° C. to about 70° C., between about 70° C. to about 80° C., between about 80° C. to about 90° C. or between about 90° C. to about 100° C. Thermal stability is determined by measuring the "melting temperature" (Tm), which is defined as the temperature at which half of the molecules are denatured. Methods of measuring characteristics of protein stability such as Tm and the free energy of unfolding are known to persons of ordinary skill in the art, and can be measured using standard biochemical techniques in vitro. For example, Tm may be measured using Differential Scanning Calorimetry, a thermo-analytical technique in which the difference in the amount of heat required to increase the temperature of a sample and a reference is measured as a function of temperature (Chen et al (2003) Pharm Res 20:1952-60; Ghirlando et al (1999) Immunol Lett 68:47-52). Alternatively, or in addition, CasX variant protein Tm may be measured using commercially available methods such as the ThermoFisher Protein Thermal Shift system. Alternatively, or in addition, circular dichroism may be used to measure the kinetics of folding and unfolding, as well as the Tm (Murray et al. (2002) J. Chromatogr Sci 40:343-9). Circular dichroism (CD) relies on the unequal absorption of left-handed and right-handed circularly polarized light by asymmetric molecules such as proteins. Certain structures of proteins, for example alpha-helices and beta-sheets, have characteristic CD spectra. Accordingly, in some embodiments, CD may be used to determine the secondary structure of a CasX variant protein.

In some embodiments, improved stability and/or thermostability of the CasX variant protein comprises improved folding kinetics of the CasX variant protein relative to a reference CasX protein. In some embodiments, folding kinetics of the CasX variant protein are improved relative to a reference CasX protein by at least about 5, at least about 10, at least about 50, at least about 100, at least about 500, at least about 1,000, at least about 2,000, at least about 3,000, at least about 4,000, at least about 5,000, or at least about a 10,000-fold improvement. In some embodiments, folding kinetics of the CasX variant protein are improved relative to a reference CasX protein by at least about 1 kJ/mol, at least about 5 kJ/mol, at least about 10 kJ/mol, at least about 20 kJ/mol, at least about 30 kJ/mol, at least about 40 kJ/mol, at least about 50 kJ/mol, at least about 60 kJ/mol, at least about 70 kJ/mol, at least about 80 kJ/mol, at least about 90 kJ/mol, at least about 100 kJ/mol, at least about 150 kJ/mol, at least about 200 kJ/mol, at least about 250 kJ/mol, at least about 300 kJ/mol, at least about 350 kJ/mol, at least about 400 kJ/mol, at least about 450 kJ/mol, or at least about 500 kJ/mol.

Exemplary amino acid changes that can increase the stability of a CasX variant protein relative to a reference CasX protein may include, but are not limited to, amino acid changes that increase the number of hydrogen bonds within the CasX variant protein, increase the number of disulfide bridges within the CasX variant protein, increase the number of salt bridges within the CasX variant protein, strengthen interactions between parts of the CasX variant protein, increase the buried hydrophobic surface area of the CasX variant protein, or any combinations thereof.

k. Protein Yield

In some embodiments, the disclosure provides a CasX variant protein having improved yield during expression and purification relative to a reference CasX protein. In some embodiments, the yield of CasX variant proteins purified from bacterial or eukaryotic host cells is improved relative to a reference CasX protein. In some embodiments, the bacterial host cells are *Escherichia coli* cells. In some embodiments, the eukaryotic cells are yeast, plant (e.g. tobacco), insect (e.g. *Spodoptera frugiperda* sf9 cells), mouse, rat, hamster, guinea pig, monkey, or human cells. In some embodiments, the eukaryotic host cells are mammalian cells, including, but not limited to human embryonic kidney 293 (HEK293) cells, baby hamster kidney (BHK) cells, NS0 cells, SP2/0 cells, YO myeloma cells, P3X63 mouse myeloma cells, PER cells, PER.C6 cells, hybridoma cells, NIH3T3 cells, COS, HeLa, or chinese hamster ovary (CHO) cells.

In some embodiments, improved yield of the CasX variant protein is achieved through codon optimization. Cells use 64 different codons, 61 of which encode the 20 standard amino acids, while another 3 function as stop codons. In some cases, a single amino acid is encoded by more than one codon. Different organisms exhibit bias towards use of different codons for the same naturally occurring amino acid. Therefore, the choice of codons in a protein, and matching codon choice to the organism in which the protein will be expressed, can, in some cases, significantly affect protein translation and therefore protein expression levels. In some embodiments, the CasX variant protein is encoded by a nucleic acid that has been codon optimized. In some embodiments, the nucleic acid encoding the CasX variant protein has been codon optimized for expression in a bacterial cell, a yeast cell, an insect cell, a plant cell, or a mammalian cell. In some embodiments, the mammal cell is a mouse, a rat, a hamster, a guinea pig, a monkey, or a human. In some embodiments, the CasX variant protein is encoded by a nucleic acid that has been codon optimized for expression in a human cell. In some embodiments, the CasX variant protein is encoded by a nucleic acid from which nucleotide sequences that reduce translation rates in prokaryotes and eukaryotes have been removed. For example, runs of greater than three thymine residues in a row can reduce translation rates in certain organisms or internal polyadenylation signals can reduce translation.

In some embodiments, improvements in solubility and stability, as described herein, result in improved yield of the CasX variant protein relative to a reference CasX protein.

Improved protein yield during expression and purification can be evaluated by methods known in the art. For example, the amount of CasX variant protein can be determined by running the protein on an SDS-page gel, and comparing the CasX variant protein to a either a control whose amount or concentration is known in advance to determine an absolute level of protein. Alternatively, or in addition, a purified CasX variant protein can be run on an SDS-page gel next to a reference CasX protein undergoing the same purification process to determine relative improvements in CasX variant protein yield. Alternatively, or in addition, levels of protein can be measured using immunohistochemical methods such as Western blot or ELISA with an antibody to CasX, or by HPLC. For proteins in solution, concentration can be determined by measuring of the protein's intrinsic UV absorbance, or by methods which use protein-dependent color changes such as the Lowry assay, the Smith copper/bicinchoninic assay or the Bradford dye assay. Such methods can be used to calculate the total protein (such as, for example, total soluble protein) yield obtained by expression under certain conditions. This can be compared, for example, to the protein yield of a reference CasX protein under similar expression conditions.

l. Protein Solubility

In some embodiments, a CasX variant protein has improved solubility relative to a reference CasX protein. In some embodiments, a CasX variant protein has improved solubility of the CasX:gNA ribonucleoprotein complex variant relative to a ribonucleoprotein complex comprising a reference CasX protein.

In some embodiments, an improvement in protein solubility leads to higher yield of protein from protein purification techniques such as purification from *E. coli*. Improved solubility of CasX variant proteins may, in some embodiments, enable more efficient activity in cells, as a more soluble protein may be less likely to aggregate in cells. Protein aggregates can in certain embodiments be toxic or burdensome on cells, and, without wishing to be bound by any theory, increased solubility of a CasX variant protein may ameliorate this result of protein aggregation. Further, improved solubility of CasX variant proteins may allow for enhanced formulations permitting the delivery of a higher effective dose of functional protein, for example in a desired gene editing application. In some embodiments, improved solubility of a CasX variant protein relative to a reference CasX protein results in improved yield of the CasX variant protein during purification of at least about 5, at least about 10, at least about 20, at least about 30, at least about 40, at least about 50, at least about 60, at least about 70, at least about 80, at least about 90, at least about 100, at least about 250, at least about 500, or at least about 1000-fold greater yield. In some embodiments, improved solubility of a CasX variant protein relative to a reference CasX protein improves activity of the CasX variant protein in cells by at least about 1.1, at least about 1.2, at least about 1.3, at least about 1.4, at least about 1.5, at least about 1.6, at least about 1.7, at least about 1.8, at least about 1.9, at least about 2, at least about 2.1, at least about 2.2, at least about 2.3, at least about 2.4, at least about 2.5, at least about 2.6, at least about 2.7, at least about 2.8, at least about 2.9, at least about 3, at least about 3.5, at least about 4, at least about 4.5, at least about 5, at least about 5.5, at least about 6, at least about 6.5, at least about 7.0, at least about 7.5, at least about 8, at least about 8.5, at least about 9, at least about 9.5, at least about 10, at least about 11, at least about 12, at least about 13, at least about 14, or at least about 15-fold greater activity.

Methods of measuring CasX protein solubility, and improvements thereof in CasX variant proteins, will be readily apparent to the person of ordinary skill in the art. For example, CasX variant protein solubility can in some embodiments be measured by taking densitometry readings on a gel of the soluble fraction of lysed *E. coli*. Alternatively, or addition, improvements in CasX variant protein solubility can be measured by measuring the maintenance of soluble protein product through the course of a full protein purification. For example, soluble protein product can be measured at one or more steps of gel affinity purification, tag cleavage, cation exchange purification, running the protein on a sizing column. In some embodiments, the densitometry of every band of protein on a gel is read after each step in the purification process. CasX variant proteins with improved solubility may, in some embodiments, maintain a higher concentration at one or more steps in the protein purification process when compared to the reference CasX protein, while an insoluble protein variant may be lost at one or more steps due to buffer exchanges, filtration steps, interactions with a purification column, and the like.

In some embodiments, improving the solubility of CasX variant proteins results in a higher yield in terms of mg/L of protein during protein purification when compared to a reference CasX protein.

In some embodiments, improving the solubility of CasX variant proteins enables a greater amount of editing events compared to a less soluble protein when assessed in editing assays such as the EGFP disruption assays described herein.

m. Protein Affinity for the gNA

In some embodiments, a CasX variant protein has improved affinity for the gNA relative to a reference CasX protein, leading to the formation of the ribonucleoprotein complex. Increased affinity of the CasX variant protein for the gNA may, for example, result in a lower $K_d$ for the generation of a RNP complex, which can, in some cases, result in a more stable ribonucleoprotein complex formation. In some embodiments, increased affinity of the CasX variant protein for the gNA results in increased stability of the ribonucleoprotein complex when delivered to human cells. This increased stability can affect the function and utility of the complex in the cells of a subject, as well as result in improved pharmacokinetic properties in blood, when delivered to a subject. In some embodiments, increased affinity of the CasX variant protein, and the resulting increased stability of the ribonucleoprotein complex, allows for a lower dose of the CasX variant protein to be delivered to the subject or cells while still having the desired activity, for example in vivo or in vitro gene editing.

In some embodiments, a higher affinity (tighter binding) of a CasX variant protein to a gNA allows for a greater amount of editing events when both the CasX variant protein and the gNA remain in an RNP complex. Increased editing events can be assessed using editing assays such as the EGFP disruption assay described herein.

In some embodiments, the $K_d$ of a CasX variant protein for a gNA is increased relative to a reference CasX protein by a factor of at least about 1.1, at least about 1.2, at least about 1.3, at least about 1.4, at least about 1.5, at least about 1.6, at least about 1.7, at least about 1.8, at least about 1.9, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100. In some embodiments, the CasX variant has about 1.1 to about 10-fold increased binding affinity to the gNA compared to the reference CasX protein of SEQ ID NO:2.

Without wishing to be bound by theory, in some embodiments amino acid changes in the Helical I domain can increase the binding affinity of the CasX variant protein with the gNA targeting sequence, while changes in the Helical II domain can increase the binding affinity of the CasX variant protein with the gNA scaffold stem loop, and changes in the oligonucleotide binding domain (OBD) increase the binding affinity of the CasX variant protein with the gRNA triplex.

Methods of measuring CasX protein binding affinity for a gNA include in vitro methods using purified CasX protein and gNA. The binding affinity for reference CasX and variant proteins can be measured by fluorescence polarization if the gNA or CasX protein is tagged with a fluorophore. Alternatively, or in addition, binding affinity can be measured by biolayer interferometry, electrophoretic mobility shift assays (EMSAs), or filter binding. Additional standard techniques to quantify absolute affinities of RNA binding proteins such as the reference CasX and variant proteins of the disclosure for specific gNAs such as reference gNAs and variants thereof include, but are not limited to, isothermal calorimetry (ITC), and surface plasmon resonance (SPR), as well as the methods of the Examples.

n. Affinity for Target DNA

In some embodiments, a CasX variant protein has improved binding affinity for a target nucleic acid relative to the affinity of a reference CasX protein for a target nucleic acid. In some embodiments, the improved affinity for the target nucleic acid comprises improved affinity for the target nucleic acid sequence, improved affinity for the PAM sequence, an improved ability to search DNA for the target nucleic acid sequence, or any combinations thereof. Without wishing to be bound by theory, it is thought that CRISPR/Cas system proteins such as CasX may find their target nucleic acid sequences by one-dimension diffusion along a DNA molecule. The process is thought to include (1) binding of the ribonucleoprotein to the DNA molecule followed by (2) stalling at the target nucleic acid sequence, either of which may be, in some embodiments, affected by improved affinity of CasX proteins for a target nucleic acid sequence, thereby improving function of the CasX variant protein compared to a reference CasX protein.

In some embodiments, a CasX variant protein with improved target nucleic acid affinity has increased overall affinity for DNA. In some embodiments, a CasX variant protein with improved target nucleic acid affinity has increased affinity for specific PAM sequences other than the canonical TTC PAM recognized by the reference CasX protein of SEQ ID NO:2, including binding affinity for PAM sequences selected from the group consisting of TTC, ATC, GTC, and CTC. Without wishing to be bound by theory, it is possible that these protein variants will interact more strongly with DNA overall and will have an increased ability to access and edit sequences within the target DNA due to the ability to bind additional PAM sequences beyond those of wild-type Cas X, thereby allowing for a more efficient search process of the CasX protein for the target sequence. A higher overall affinity for DNA also, in some embodiments, can increase the frequency at which a CasX protein can effectively start and finish a binding and unwinding step, thereby facilitating target strand invasion and R-loop formation, and ultimately the cleavage of a target nucleic acid sequence.

Without wishing to be bound by theory, it is possible that amino acid changes in the NTSBD that increase the efficiency of unwinding, or capture, of a non-target DNA strand in the unwound state, can increase the affinity of CasX variant proteins for target DNA. Alternatively, or in addition, amino acid changes in the NTSBD that increase the ability of the NTSBD to stabilize DNA during unwinding can increase the affinity of CasX variant proteins for target DNA. Alternatively, or in addition, amino acid changes in the OBD may increase the affinity of CasX variant protein binding to the protospacer adjacent motif (PAM), thereby increasing affinity of the CasX variant protein for target nucleic acid. Alternatively, or in addition, amino acid changes in the Helical I and/or II, RuvC and TSL domains that increase the affinity of the CasX variant protein for the target nucleic acid strand can increase the affinity of the CasX variant protein for target nucleic acid.

In some embodiments, the CasX variant protein has increased binding affinity to the target nucleic acid sequence compared to the reference protein of SEQ ID NO:1, SEQ ID NO:2, or SEQ ID NO:3. In some embodiments, affinity of a CasX variant protein of the disclosure for a target nucleic acid molecule is increased relative to a reference CasX protein by a factor of at least about 1.1, at least about 1.2, at least about 1.3, at least about 1.4, at least about 1.5, at least about 1.6, at least about 1.7, at least about 1.8, at least about 1.9, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100.

In some embodiments, a CasX variant protein has improved binding affinity for the non-target strand of the target nucleic acid. As used herein, the term "non-target strand" refers to the strand of the DNA target nucleic acid sequence that does not form Watson and Crick base pairs with the targeting sequence in the gNA, and is complementary to the target strand.

Methods of measuring CasX protein (such as reference or variant) affinity for a target nucleic acid molecule may include electrophoretic mobility shift assays (EMSAs), filter binding, isothermal calorimetry (ITC), and surface plasmon resonance (SPR), fluorescence polarization and biolayer interferometry (BLI). Further methods of measuring CasX protein affinity for a target include in vitro biochemical assays that measure DNA cleavage events over time.

CasX variant proteins with higher affinity for their target nucleic acid may, in some embodiments, cleave the target nucleic acid sequence more rapidly than a reference CasX protein that does not have increased affinity for the target nucleic acid.

In some embodiments, the CasX variant protein is catalytically dead (dCasX). In some embodiments, the disclosure provides RNP comprising a catalytically-dead CasX protein that retains the ability to bind target DNA. An exemplary catalytically-dead CasX variant protein comprises one or more mutations in the active site of the RuvC domain of the CasX protein. In some embodiments, a catalytically-dead CasX variant protein comprises substitutions at residues 672, 769 and/or 935 of SEQ ID NO:1. In some embodiments, a catalytically-dead CasX variant protein comprises substitutions of D672A, E769A and/or D935A in the reference CasX protein of SEQ ID NO:1. In some embodiments, a catalytically-dead CasX protein comprises substitutions at amino acids 659, 765 and/or 922 of SEQ ID NO:2. In some embodiments, a catalytically-dead CasX protein comprises D659A, E756A and/or D922A substitutions in a reference CasX protein of SEQ ID NO:2. In further embodiments, a catalytically-dead CasX variant protein comprises deletions of all or part of the RuvC domain of the reference CasX protein.

In some embodiments, improved affinity for DNA of a CasX variant protein also improves the function of catalytically inactive versions of the CasX variant protein. In some embodiments, the catalytically inactive version of the CasX variant protein comprises one or mutations in the DED motif in the RuvC. Catalytically dead CasX variant proteins can, in some embodiments, be used for base editing or epigenetic modifications. With a higher affinity for DNA, in some embodiments, catalytically dead CasX variant proteins can, relative to catalytically active CasX, find their target DNA faster, remain bound to target DNA for longer periods of time, bind target DNA in a more stable fashion, or a combination thereof, thereby improving the function of the catalytically dead CasX variant protein.

o. Improved Specificity for a Target Site

In some embodiments, a CasX variant protein has improved specificity for a target DNA sequence relative to a reference CasX protein. As used herein, "specificity," sometimes referred to as "target specificity," refers to the degree to which a CRISPR/Cas system ribonucleoprotein complex cleaves off-target sequences that are similar, but not identical to the target DNA sequence; e.g., a CasX variant RNP with a higher degree of specificity would exhibit reduced off-target cleavage of sequences relative to a reference CasX protein. The specificity, and the reduction of potentially deleterious off-target effects, of CRISPR/Cas system proteins can be vitally important in order to achieve an acceptable therapeutic index for use in mammalian subjects.

In some embodiments, a CasX variant protein has improved specificity for a target site within the target sequence that is complementary to the targeting sequence of the gNA.

Without wishing to be bound by theory, it is possible that amino acid changes in the Helical I and II domains that increase the specificity of the CasX variant protein for the target DNA strand can increase the specificity of the CasX variant protein for the target DNA overall. In some embodiments, amino acid changes that increase specificity of CasX variant proteins for target DNA may also result in decreased affinity of CasX variant proteins for DNA.

Methods of testing CasX protein (such as variant or reference) target specificity may include guide and Circularization for In vitro Reporting of Cleavage Effects by Sequencing (CIRCLE-seq), or similar methods. In brief, in CIRCLE-seq techniques, genomic DNA is sheared and circularized by ligation of stem-loop adapters, which are nicked in the stem-loop regions to expose 4 nucleotide palindromic overhangs. This is followed by intramolecular ligation and degradation of remaining linear DNA. Circular DNA molecules containing a CasX cleavage site are subsequently linearized with CasX, and adapter adapters are ligated to the exposed ends followed by high-throughput sequencing to generate paired end reads that contain information about the off-target site. Additional assays that can be used to detect off-target events, and therefore CasX protein specificity include assays used to detect and quantify indels (insertions and deletions) formed at those selected off-target sites such as mismatch-detection nuclease assays and next generation sequencing (NGS). Exemplary mismatch-detection assays include nuclease assays, in which genomic DNA from cells treated with CasX and sgNA is PCR amplified, denatured and rehybridized to form hetero-duplex DNA, containing one wild type strand and one strand with an indel. Mismatches are recognized and cleaved by mismatch detection nucleases, such as Surveyor nuclease or T7 endonuclease I.

p. Unwinding of DNA

In some embodiments, a CasX variant protein has improved ability of unwinding DNA relative to a reference CasX protein. In some embodiments, a CasX variant protein has enhanced DNA unwinding characteristics. Poor dsDNA unwinding has been shown previously to impair or prevent the ability of CRISPR/Cas system proteins anaCas9 or Cas14s to cleave DNA. Therefore, without wishing to be bound by any theory, it is likely that increased DNA cleavage activity by some CasX variant proteins is due at least in part to an increased ability to find and unwind the dsDNA at a target site.

Without wishing to be bound by theory, it is thought that amino acid changes in the NTSB domain may produce CasX variant proteins with increased DNA unwinding characteristics. Alternatively, or in addition, amino acid changes in the OBD or the helical domain regions that interact with the PAM may also produce CasX variant proteins with increased DNA unwinding characteristics.

Methods of measuring the ability of CasX proteins (such as variant or reference) to unwind DNA include, but are not limited to, in vitro assays that observe increased on rates of dsDNA targets in fluorescence polarization or biolayer interferometry.

q. Catalytic Activity

The ribonucleoprotein complex of the CasX:gNA systems disclosed herein comprise a reference CasX protein or variant thereof that bind to a target nucleic acid sequence and cleaves the target nucleic acid sequence. In some embodiments, a CasX variant protein has improved catalytic activity relative to a reference CasX protein. Without wishing to be bound by theory, it is thought that in some cases cleavage of the target strand can be a limiting factor for Cas12-like molecules in creating a dsDNA break. In some embodiments, CasX variant proteins improve bending of the target strand of DNA and cleavage of this strand, resulting in an improvement in the overall efficiency of dsDNA cleavage by the CasX ribonucleoprotein complex.

In some embodiments, a CasX variant protein has increased nuclease activity compared to a reference CasX protein. Variants with increased nuclease activity can be generated, for example, through amino acid changes in the RuvC nuclease domain. In one embodiment, the CasX variant comprises a nuclease domain having nickase activity. In the foregoing embodiment, the CasX nickase of a CasX:gNA system generates a single-stranded break within 10-18 nucleotides 3' of a PAM site in the non-target strand. In another embodiment, the CasX variant comprises a nuclease domain having double-stranded cleavage activity. In the foregoing embodiment, the CasX of the CasX:gNA system generates a double-stranded break within 18-26 nucleotides 5' of a PAM site on the target strand and 10-18 nucleotides 3' on the non-target strand. Nuclease activity can be assayed by a variety of methods, including those of the Examples. In one embodiment, a CasX variant has a Kcleave constant that is at least 2-fold, or at least 3-fold, or at least 4-fold, or at least 5-fold, or at least 6-fold, or at least 7-fold, or at least 8-fold, or at least 9-fold, or at least 10-fold greater compared to a reference wild-type CasX.

In some embodiments, a CasX variant protein has increased target strand loading for double strand cleavage.

Variants with increased target strand loading activity can be generated, for example, through amino acid changes in the TLS domain.

Without wishing to be bound by theory, amino acid changes in the TSL domain may result in CasX variant proteins with improved catalytic activity. Alternatively, or in addition, amino acid changes around the binding channel for the RNA:DNA duplex may also improve catalytic activity of the CasX variant protein.

In some embodiments, a CasX variant protein has increased collateral cleavage activity compared to a reference CasX protein. As used herein, "collateral cleavage activity" refers to additional, non-targeted cleavage of nucleic acids following recognition and cleavage of a target nucleic acid sequence. In some embodiments, a CasX variant protein has decreased collateral cleavage activity compared to a reference CasX protein.

In some embodiments, for example those embodiments encompassing applications where target DNA cleavage is not a desired outcome, improving the catalytic activity of a CasX variant protein comprises altering, reducing, or abolishing the catalytic activity of the CasX variant protein. In some embodiments, a ribonucleoprotein complex comprising a CasX variant protein binds to a target DNA and does not cleave the target DNA.

In some embodiments, the CasX ribonucleoprotein complex comprising a CasX variant protein binds a target DNA but generates a single stranded nick in the target DNA. In some embodiments, particularly those embodiments wherein the CasX protein is a nickase, a CasX variant protein has decreased target strand loading for single strand nicking. Variants with decreased target strand loading may be generated, for example, through amino acid changes in the TSL domain.

Exemplary methods for characterizing the catalytic activity of CasX proteins may include, but are not limited to, in vitro cleavage assays. In some embodiments, electrophoresis of DNA products on agarose gels can interrogate the kinetics of strand cleavage.

r. Affinity for Target DNA and RNA

In some embodiments, a ribonucleoprotein complex comprising a reference CasX protein or variant thereof binds to a target DNA and cleaves the target DNA. In some embodiments, variants of a reference CasX protein increase the specificity of the CasX variant protein for a target RNA, and increase the activity of the CasX variant protein with respect to a target RNA when compared to the reference CasX protein. For example, CasX variant proteins can display increased binding affinity for target RNAs, or increased cleavage of target RNAs, when compared to reference CasX proteins. In some embodiments, a ribonucleoprotein complex comprising a CasX variant protein binds to a target RNA and/or cleaves the target RNA. In one embodiment, a CasX variant has at least about two-fold to about 10-fold increased binding affinity to the target nucleic acid sequence compared to the reference protein of SEQ ID NO:1, SEQ ID NO:2, or SEQ ID NO:3.

s. Combinations of Mutations

In some embodiments, the present disclosure provides variants that are a combination of mutations from separate CasX variant proteins. In some embodiments, any variant to any domain described herein can be combined with other variants described herein. In some embodiments, any variant within any domain described herein can be combined with other variants described herein, in the same domain. Combinations of different amino acid changes may in some embodiments produce new optimized variants whose function is further improved by the combination of amino acid changes. In some embodiments, the effect of combining amino acid changes on CasX protein function is linear. As used herein, a combination that is linear refers to a combination whose effect on function is equal to the sum of the effects of each individual amino acid change when assayed in isolation. In some embodiments, the effect of combining amino acid changes on CasX protein function is synergistic. As used herein, a combination of variants that is synergistic refers to a combination whose effect on function is greater than the sum of the effects of each individual amino acid change when assayed in isolation. In some embodiments, combining amino acid changes produces CasX variant proteins in which more than one function of the CasX protein has been improved relative to the reference CasX protein.

t. CasX Fusion Proteins

In some embodiments, the disclosure provides CasX proteins comprising a heterologous protein fused to the CasX. In some cases, the CasX is a reference CasX protein. In other cases, the CasX is a CasX variant of any of the embodiments described herein.

In some embodiments, the CasX variant protein is fused to one or more proteins or domains thereof that has a different activity of interest (i.e., is part of a fusion protein). For example, in some embodiments, the CasX variant protein is fused to a protein (or domain thereof) that inhibits transcription, modifies a target nucleic acid sequence, or modifies a polypeptide associated with a nucleic acid (e.g., histone modification).

In some embodiments, a heterologous polypeptide (or heterologous amino acid such as a cysteine residue or a non-natural amino acid) can be inserted at one or more positions within a CasX protein to generate a CasX fusion protein. In other embodiments, a cysteine residue can be inserted at one or more positions within a CasX protein followed by conjugation of a heterologous polypeptide described below. In some alternative embodiments, a heterologous polypeptide or heterologous amino acid can be added at the N- or C-terminus of the reference or CasX variant protein. In other embodiments, a heterologous polypeptide or heterologous amino acid can be inserted internally within the sequence of the CasX protein.

In some embodiments, the reference CasX or variant fusion protein retains RNA-guided sequence specific target nucleic acid binding and cleavage activity. In some cases, the reference CasX or variant fusion protein has (retains) 50% or more of the activity (e.g., cleavage and/or binding activity) of the corresponding reference CasX or variant protein that does not have the insertion of the heterologous protein. In some cases, the reference CasX or variant fusion protein retains at least about 60%, or at least about 70% or more, at least about 80%, or at least about 90%, or at least about 92%, or at least about 95%, or at least about 98%, or at least about 100% of the activity (e.g., cleavage and/or binding activity) of the corresponding CasX protein that does not have the insertion of the heterologous protein.

In some cases, the reference CasX or variant fusion polypeptide retains (has) target nucleic acid binding activity relative to the activity of the CasX protein without the inserted heterologous amino acid or heterologous polypeptide. For example, in some cases, the reference CasX or variant fusion polypeptide has (retains) 50% or more of the binding activity of the corresponding CasX protein (the CasX protein that does not have the insertion). For example, in some cases, the reference CasX or variant fusion polypeptide has (retains) 60% or more (70% or more, 80% or more, 90% or more, 92% or more, 95% or more, 98% or more, or 100%) of the binding activity of the corresponding parent CasX protein (the CasX protein that does not have the insertion).

In some cases, the reference CasX or variant fusion polypeptide retains (has) target nucleic acid binding and/or cleavage activity relative to the activity of the parent CasX protein without the inserted heterologous amino acid or heterologous polypeptide. For example, in some cases, the reference CasX or variant fusion polypeptide has (retains) 50% or more of the binding and/or cleavage activity of the corresponding parent CasX protein (the CasX protein that does not have the insertion). For example, in some cases, the reference CasX or variant fusion polypeptide has (retains) 60% or more (70% or more, 80% or more, 90% or more, 92% or more, 95% or more, 98% or more, or 100%) of the binding and/or cleavage activity of the corresponding CasX parent polypeptide (the CasX protein that does not have the insertion). Methods of measuring cleaving and/or binding activity of a CasX protein and/or a CasX fusion polypeptide will be known to one of ordinary skill in the art and any convenient method can be used.

A variety of heterologous polypeptides are suitable for inclusion in a reference CasX or CasX variant fusion protein of the disclosure. In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a fusion partner has enzymatic activity that modifies a target nucleic acid sequence (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a fusion partner has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used as a fusion partner to increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET domain containing 1A, histone lysine methyltransferase (SET1A), SET domain containing 1B, histone lysine methyltransferase (SET1B), lysine methyltransferase 2A (MLL1 to 5, ASCL1 (ASH1) achaete-scute family bHLH transcription factor 1 (ASH1), SET and MYND domain containing 2 (SYMD2), nuclear receptor binding SET domain protein 1 (NSD1), and the like; histone lysine demethylases such as lysine demethylase 3A (JHDM2a)/Lysine-specific demethylase 3B (JHDM2b), lysine demethylase 6A (UTX), lysine demethylase 6B (JMJD3), and the like; histone acetyltransferases such as lysine acetyltransferase 2A (GCN5), lysine acetyltransferase 2B (PCAF), CREB binding protein (CBP), E1A binding protein p300 (p300), TATA-box binding protein associated factor 1 (TAF1), lysine acetyltransferase 5 (TIP60/PLIP), lysine acetyltransferase 6A (MOZ/MYST3), lysine acetyltransferase 6B (MORF/MYST4), SRC proto-oncogene, non-receptor tyrosine kinase (SRC1), nuclear receptor coactivator 3 (ACTR), MYB binding protein 1a (P160), clock circadian regulator (CLOCK), and the like; and DNA demethylases such as Ten-Eleven Translocation (TET) dioxygenase 1 (TET1CD), tet methylcytosine dioxygenase 1 (TET1), demeter (DME), demeter-like 1 (DML1), demeter-like 2 (DML2), protein ROS1 (ROS1), and the like.

Examples of proteins (or fragments thereof) that can be used as a fusion partner to decrease transcription include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as PR/SET domain containing protein (Pr-SET7/8), lysine methyltransferase 5B (SUV4-20H1), PR/SET domain 2 (RIZ1), and the like; histone lysine demethylases such as lysine demethylase 4A (JMJD2A/JHDM3A), lysine demethylase 4B (JMJD2B), lysine demethylase 4C (JMJD2C/GASC1), lysine demethylase 4D (JMJD2D), lysine demethylase 5A (JARID1A/RBP2), lysine demethylase 5B (JARID1B/PLU-1), lysine demethylase 5C (JARID 1C/SMCX), lysine demethylase 5D (JARID1D/SMCY), and the like; histone lysine deacetylases such as histone deacetylase 1 (HDAC1), HDAC2, HDAC3, HDAC8, HDAC4, HDAC5, HDAC7, HDAC9, sirtuin 1 (SIRT1), SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), methyltransferase 1 (MET1), S-adenosyl-L-methionine-dependent methyltransferases superfamily protein (DRM3) (plants), DNA cytosine methyltransferase MET2a (ZMET2), chromomethylase 1 (CMT1), chromomethylase 2 (CMT2) (plants), and the like; and periphery recruitment elements such as Lamin A, Lamin B, and the like.

In some cases the fusion partner has enzymatic activity that modifies the target nucleic acid sequence (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., Hhal DNA m5c-methyltransferase (M.Hhal), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET 1 CD), TET1, DME, DML1, DML2, ROS1, and the like), DNA repair activity, DNA damage activity, deamination activity such as that provided by a deaminase (e.g., a cytosine deaminase enzyme, e.g., an APOBEC protein such as rat APOBECl), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, a reference CasX or Cas X variant protein of the present disclosure is fused to a polypeptide selected from: a domain for increasing transcription (e.g., a VP16 domain, a VP64 domain), a domain for decreasing transcription (e.g., a KRAB domain, e.g., from the Kox1 protein), a core catalytic domain of a histone acetyltransferase (e.g., histone acetyltransferase p300), a protein/domain that provides a detectable signal (e.g., a fluorescent protein such as GFP), a nuclease domain (e.g., a FokI nuclease), and a base editor (e.g., cytidine deaminase such as APOBEC1).

In some cases, the fusion partner has enzymatic activity that modifies a protein associated with the target nucleic acid sequence (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB 1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HB01/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDACS, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of suitable fusion partners are (i) a dihydrofolate reductase (DHFR) destabilization domain to generate a chemically controllable subject RNA-guided polypeptide or a conditionally active RNA-guided polypeptide, and (ii) a chloroplast transit peptide.

Suitable chloroplast transit peptides include, but are not limited to:

(SEQ ID NO: 144)
MASMISSSAVTTVSRASRGQSAAMAPFGGLKSMTGFPVRKVNTDITSITS
NGGRVKCMQVWPPIGKKKFETLSYLPPLTRDSRA;

(SEQ ID NO: 145)
MASMISSSAVTTVSRASRGQSAAMAPFGGLKSMTGFPVRKVNTDITSITS
NGGRVKS;

(SEQ ID NO: 146)
MASSMLSSATMVASPAQATMVAPFNGLKSSAAFPATRKANNDITSITSNG
GRVNCMQV WPPIEKKKFETLSYLPDLTDSGGRVNC;

(SEQ ID NO: 147)
MAQVSRICNGVQNPSLISNLSKSSQRKSPLSVSLKTQQHPRAYPISSSWG
LKKSGMTLIG SELRPLKVMSSVSTAC;

(SEQ ID NO: 148)
MAQVSRICNGVWNPSLISNLSKSSQRKSPLSVSLKTQQHPRAYPISSSWG
LKKSGMTLIG SELRPLKVMSSVSTAC;

(SEQ ID NO: 149)
MAQINNMAQGIQTLNPNSNFHKPQVPKSSSFLVFGSKKLKNSANSMLVLK
KDSIFMQLF CSFRISASVATAC;

(SEQ ID NO: 150)
MAALVTSQLATSGTVLSVTDRFRRPGFQGLRPRNPADAALGMRTVGASAA
PKQSRKPH RFDRRCLSMVV;

(SEQ ID NO: 151)
MAALTTSQLATSATGFGIADRSAPSSLLRHGFQGLKPRSPAGGDATSLSV
TTSARATPKQ QRSVQRGSRRFPSVVVC;

(SEQ ID NO: 152)
MASSVLSSAAVATRSNVAQANMVAPFTGLKSAASFPVSRKQNLDITSIAS
NGGRVQC;

(SEQ ID NO: 153)
MESLAATSVFAPSRVAVPAARALVRAGTVVPTRRTSSTSGTSGVKCSAAV
TPQASPVISRSAAAA;
and (SEQ ID NO: 154)
MGAAATSMQSLKFSNRLVPPSRRLSPVPNNVTCNNLPKSAAPVRTVKCCA
SSWNSTINGAAATTNGASAASS.

In some cases, a reference CasX or variant polypeptide of the present disclosure can include an endosomal escape peptide. In some cases, an endosomal escape polypeptide comprises the amino acid sequence GLFX-ALLXLLXSLWXLLLXA (SEQ ID NO: 155), wherein each X is independently selected from lysine, histidine, and arginine. In some cases, an endosomal escape polypeptide comprises the amino acid sequence GLF-HALLHLLHSLWHLLLHA (SEQ ID NO: 156), or HIHHHHHHHHII (SEQ ID NO: 157).

Non-limiting examples of fusion partners for use when targeting ssRNA target nucleic acid sequences include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

A fusion partner can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP SI, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI Dl and terminal uridylate transferase); proteins and protein domains responsible for RNA localization (for example from EVIP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as a fusion partner have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP Al binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP Al can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived post mitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cc-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pill/Abyl, etc.).

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a subject RNA-guided polypeptide or a conditionally active RNA-guided polypeptide and/or subject CasX fusion polypeptide does not include a NLS so that the protein is not targeted to the nucleus (which can be advantageous, e.g., when the target nucleic acid sequence is an RNA that is present in the cytosol). In some embodiments, a fusion partner can provide a tag (i.e., the heterologous polypeptide is a detectable label) for ease of tracking and/or purification (e.g., a fluorescent protein, e.g., green fluorescent protein (GFP), yellow fluorescent protein (YFP), red fluorescent protein (RFP), cyan fluorescent protein (CFP), mCherry, tdTomato, and the like; a histidine tag, e.g., a 6×His tag; a hemagglutinin (HA) tag; a FLAG tag; a Myc tag; and the like).

In some cases a reference or CasX variant polypeptide includes (is fused to) a nuclear localization signal (NLS) (e.g., in some cases 2 or more, 3 or more, 4 or more, or 5 or more 6 or more, 7 or more, 8 or more NLSs). Thus, in some cases, a reference or CasX variant polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus. In some cases a reference or CasX variant polypeptide includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a reference or CasX variant polypeptide includes (is fused to) between 2 and 5 NLSs (e.g., 2-4, or 2-3 NLSs).

Non-limiting examples of NLSs include sequences derived from: the NLS of the SV40 virus large T-antigen, having the amino acid sequence PKKKRKV (SEQ ID NO: 158); the NLS from nucleoplasmin (e.g., the nucleoplasmin bipartite NLS with the sequence KRPAATKKAGQAKKKK (SEQ ID NO: 159); the c-myc NLS having the amino acid sequence PAAKRVKLD (SEQ ID NO: 160) or RQRRNELKRSP (SEQ ID NO: 161); the hRNPAl M9 NLS having the sequence NQSSNFGPMKGGNFGGRSSGPYGGGGQYFAKPRNQGGY (SEQ ID NO: 162); the sequence RMRIZFKNKGKDTAELRRRRVEVSVELRKAKKDEQILKRRNV (SEQ ID NO: 163) of the IBB domain from importin-alpha; the sequences VSRKRPRP (SEQ ID NO: 164) and PPKKARED (SEQ ID NO: 165) of the myoma T protein; the sequence PQPKKKPL (SEQ ID NO: 166) of human p53; the sequence SALIKKKKKMAP (SEQ ID NO: 167) of mouse c-abl IV; the sequences DRLRR (SEQ ID NO: 168) and PKQKKRK (SEQ ID NO: 169) of the influenza virus NS1; the sequence RKLKKKIKKL (SEQ ID NO: 170) of the Hepatitis virus delta antigen; the sequence REKKKFLKRR (SEQ ID NO: 171) of the mouse Mxl protein; the sequence KRKGDEVDGVDEVAKKKSKK (SEQ ID NO: 172) of the human poly(ADP-ribose) polymerase; the sequence RKCLQAGMNLEARKTKK (SEQ ID NO: 173) of the steroid hormone receptors (human) glucocorticoid; the sequence PRPRKIPR (SEQ ID NO: 174) of Borna disease virus P protein (BDV-P1); the sequence PPRKKRTVV (SEQ ID NO: 175) of hepatitis C virus nonstructural protein (HCV-NS5A); the sequence NLSKKKKRKREK (SEQ ID NO: 176) of LEF1; the sequence RRPSRPFRKP (SEQ ID NO: 177) of ORF57 simirae; the sequence KRPRSPSS (SEQ ID NO: 178) of EBV LANA; the sequence KRGINDRNFWRGENERKTR (SEQ ID NO: 179) of Influenza A protein; the sequence PRPPKMARYDN (SEQ ID NO: 180) of human RNA helicase A (RHA); the sequence KRSFSKAF (SEQ ID NO: 181) of nucleolar RNA helicase II; the sequence KLKIKRPVK (SEQ ID NO: 182) of TUS-protein; the sequence PKKKRKVPPPPAAKRVKLD (SEQ ID NO: 183) associated with importin-alpha; the sequence PKTRRRPRRSQRKRPPT (SEQ ID NO: 184) from the Rex protein in HTLV-1; the sequence MSRRRKANPTKLSENAKKLAKEVEN (SEQ ID NO: 185) from the EGL-13 protein of *Caenorhabditis elegans*; and the sequences KTRRRPRRSQRKRPPT (SEQ ID NO: 186), RRKKRRPRRKKRR (SEQ ID NO: 187), PKKKSRKPKKKSRK (SEQ ID NO: 188), HKKKHPDASVNFSEFSK (SEQ ID NO: 189), QRPGPYDRPQRPGPYDRP (SEQ ID NO: 190), LSPSLSPLLSPSLSPL (SEQ ID NO: 191), RGKGGKGLGKGGAKRHRK (SEQ ID NO: 192), PKRGRGRPKRGRGR (SEQ ID NO: 193), PKKKRKVPPPPAAKRVKLD (SEQ ID NO: 183) and PKKKRKVPPPPKKKRKV (SEQ ID NO: 194). In general, NLS (or multiple NLSs) are of sufficient strength to drive accumulation of a reference or CasX variant fusion protein in the nucleus of a eukaryotic cell. Detection of accumulation in the nucleus may be performed by any suitable technique. For example, a detectable marker may be fused to a reference or CasX variant fusion protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined.

In some cases, a reference or CasX variant fusion protein includes a "Protein Transduction Domain" or PTD (also known as a CPP-cell penetrating peptide), which refers to a protein, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from an extracellular space to an intracellular space, or from the cytosol to within an organelle. In some embodiments, a PTD is covalently linked to the amino terminus of a reference or CasX variant fusion protein. In some embodiments, a PTD is covalently linked to the carboxyl terminus of a reference or CasX variant fusion protein. In some cases, the PTD is inserted internally in the sequence of a reference or CasX variant fusion protein at a suitable insertion site. In some cases, a reference or CasX variant fusion protein includes (is conjugated to, is fused to) one or more PTDs (e.g., two or more, three or more, four or more PTDs). In some cases, a PTD includes one or more nuclear localization signals (NLS). Examples of PTDs include but are not limited to peptide transduction domain of HIV TAT comprising YGRKKRRQRRR (SEQ ID NO: 195), RKKRRQRR (SEQ ID NO: 196); YARAAARQARA (SEQ ID NO: 197); THRLPRRRRRR (SEQ ID NO: 198); and GGRRARRRRRR (SEQ ID NO: 199); a polyarginine sequence comprising a number of arginines sufficient to direct entry into a cell (e.g., 3, 4, 5, 6, 7, 8, 9, 10, or 10-50 arginines (SEQ ID NO: 200)); a VP22 domain (Zender et al. (2002) Cancer Gene Ther. 9(6):489-96); an *Drosophila* Antennapedia protein transduction domain (Noguchi et al. (2003) Diabetes 52(7): 1732-1737); a truncated human calcitonin peptide (Trehin et al. (2004) Pharm. Research 21:1248-1256); polylysine (Wender et al. (2000) Proc. Natl. Acad. Sci. USA 97: 13003-13008); RRQRRTSKLMKR (SEQ ID NO: 201); Transportan GWTLNSAGYLLGKINLKALAALAKKIL (SEQ ID NO: 202); KALAWEAKLAKALAKALAKHLAKALAKALKCEA (SEQ ID NO: 203); and RQIKIWFQNRRMKWKK (SEQ ID NO: 204). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

In some embodiments, a reference or CasX variant fusion protein can include a CasX protein that is linked to an internally inserted heterologous amino acid or heterologous polypeptide (a heterologous amino acid sequence) via a linker polypeptide (e.g., one or more linker polypeptides). In some embodiments, a reference or CasX variant fusion protein can be linked at the C-terminal and/or N-terminal end to a heterologous polypeptide (fusion partner) via a linker polypeptide (e.g., one or more linker polypeptides) The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers are generally produced by using synthetic, linker-encoding oligonucleotides to couple the proteins. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use. Example linker polypeptides include glycine polymers (G)n, glycine-serine polymer (including, for example, (GS)n, GSGGSn (SEQ ID NO: 205), GGSGGSn (SEQ ID NO: 206), and GGGSn (SEQ ID NO: 207), where n is an integer of at least one), glycine-alanine polymers, alanine-serine polymers, glycine-proline polymers, proline polymers and proline-alanine polymers. Example linkers can comprise amino acid sequences including, but not limited to, GGSG (SEQ ID NO: 208), GGSGG (SEQ ID NO: 209), GSGSG (SEQ ID NO: 210), GSGGG (SEQ ID NO: 211), GGGSG (SEQ ID NO: 212), GSSSG (SEQ ID NO: 213), GPGP (SEQ ID NO: 214), GGP, PPP, PPAPPA (SEQ ID NO: 215), PPPGPPP (SEQ ID NO: 216) and the like. The ordinarily skilled artisan will recognize that design of a peptide conjugated to any elements described above can include linkers that are all or partially flexible, such that the linker can include a flexible linker as well as one or more portions that confer less flexible structure.

V. CasX:gNA Systems and Methods for Modification of Nucleic Acids Encoding for Proteins Involved in Antigen Processing, Presentation, Recognition and/or Response and their Regulatory Regions The CasX proteins, guide nucleic acids, and variants thereof provided herein are useful for various applications, including as therapeutics, diagnostics, and for research. To effect the methods of the disclosure for gene editing, provided herein are programmable CasX:gNA systems. The programmable nature of the CasX:gNA system provided herein allows for the precise targeting to achieve the desired effect (nicking, cleaving, repairing, etc.) at one or more regions of predetermined interest in the target nucleic acid sequence of the gene encoding the protein of interest. In some embodiments, the CasX:gNA systems provided herein comprise a CasX variant of Table 4, 7, 8, 9, or 11 or a variant having at least 50%, at least 60%, at least 70%, at least 80%, or at least 90%, or at least 95%, or at least 99% sequence identity to a sequence of Table 4, and a gNA (e.g., a gNA comprising a scaffold variant of Table 2, or a variant having at least 50%, at least 60%, at least 70%, at least 80%, or at least 90%, or at least 95%, or at least 99% sequence identity to a sequence of Table 2) or one or more polynucleotides encoding a CasX variant protein and a gNA, wherein the targeting sequence of the gNA is complementary to, and therefore is capable of hybridizing with a target nucleic acid sequence encoding the target protein, its regulatory element, or both, or a sequence complementary thereto. In other cases, the CasX:gNA system can comprise a reference CasX or a reference gNA. In some cases, the CasX:gNA system further comprises a donor template nucleic acid.

A variety of strategies and methods can be employed to modify a target nucleic acid sequence encoding a cell surface marker protein, a transmembrane protein, or intracellular or extracellular protein and/or to introduce a protein involved in antigen processing, antigen presentation, antigen recognition, and/or antigen response into a cell using the CasX:gNA systems provided herein. As used herein "modifying" includes but is not limited to cleaving, nicking, editing, deleting, knocking in, knocking out, repairing/correcting, and the like. The term "knock-out" refers to the elimination of a gene or the expression of a gene. For example, a gene can be knocked out by either a deletion or an addition of a nucleotide sequence that leads to a disruption of the reading frame. As another example, a gene may be knocked-out by replacing a part of the gene with an irrelevant sequence or one or more substituted bases. The term "knock-down" as used herein refers to reduction in the expression of a gene or its gene product(s). As a result of a gene knock-down, the protein activity or function may be attenuated or the protein levels may be reduced or eliminated. In such embodiments, gNAs having targeting sequences specific for a portion of the gene encoding the protein involved in antigen processing, antigen presentation, antigen recognition, and/or antigen response or its regulatory element, or the complement of the sequence, may be utilized. Depending on the CasX protein and gNA utilized, the event may be a cleavage event, allowing for knock-down/knock-out of expression. In some embodiments gene expression for the protein may be disrupted or eliminated by introducing random insertions or deletions (indels), for example by utilizing the imprecise non-homologous DNA end joining (NHEJ) repair pathway. In such embodiments, the targeted region of the protein involved in antigen processing, antigen presentation, antigen recognition, and/or antigen response includes coding sequences (exons) of the gene, wherein inserting or deleting nucleotides can generate a frame shift mutation. This approach can also be used in other non-coding regions such as introns, or regulatory elements to disturb expression of the target gene.

In some embodiments, the method of the disclosure provides CasX protein and one or more gNA that generate site-specific double strand breaks (DSBs) or single strand breaks (SSBs) (e.g., when the CasX protein is a nickase that can cleave only one strand of a target nucleic acid) within double-stranded DNA (dsDNA) target nucleic acids, which can then be repaired either by non-homologous end joining (NHEJ), homology-directed repair (HDR), homology-independent targeted integration (HITI), micro-homology mediated end joining (MMEJ), single strand annealing (SSA) or base excision repair (BER), resulting in modification of the target nucleic acid sequence. In some embodiments, it may be desirable to utilize one or a pair (or 3 or 4) of gNAs, each having a targeting sequence specific for a different region of the protein involved in antigen processing, antigen presentation, antigen recognition, and/or antigen response allele, followed by introduction of a donor template comprising a polynucleotide sequence that will be inserted at the break site.

In one embodiment, the disclosure provides for a method of modifying a target nucleic acid sequence of a gene in a population of cells, wherein the gene encodes a protein involved in antigen processing, antigen presentation, antigen recognition, and/or antigen response, comprising introducing into each cell of the population: a) the CasX:gNA system of any one of the embodiments described herein; b) a nucleic acid that encodes the CasX:gNA system of any one of the embodiments described herein; c) a vector comprising the nucleic acid of (b), above; d) a VLP comprising the CasX:gNA system of any one of the embodiments described herein; or e) combinations of two or more of (a) to (d), wherein the target nucleic acid sequence of the cells is modified by the CasX protein. In one embodiment, the CasX:gNA system is introduced into the cells as an RNP. In some embodiments of the method, the cells are selected from the group consisting of rodent cells, mouse cells, rat cells, and non-human primate cells. In other embodiments of the method, the cells are human cells. In other embodiments of the method, the cells are selected from the group consisting of progenitor cells, hematopoietic stem cells, and pluripotent stem cells. In other embodiments of the method, the cells are induced pluripotent stem cells. In other embodiments of the method, the cells are immune cells selected from the group consisting of T cells, tumor infiltrating lymphocytes, NK cells, B cells, monocytes, macrophages, or dendritic cells. In a particular embodiment, the T cells are selected from the group consisting of CD4+ T cells, CD8+ T cells, gamma-delta T cells, or a combination thereof. Where a T cell is the cell to be modified, mixtures of CD4+ and CD8+ T cells are often selected in the engineering of CAR-T cells, likely because the CD4 T cells provide growth factors and other signals to maintain function and survival of the infused CTLs (Barrett, D M, et al. Chimeric antigen receptor (CAR) and T cell receptor (TCR) Modified T cells Enter Main Street and Wall Street. J Immunol. 195(3): 755-761(2015)). In some embodiments, the cell is autologous with respect to a subject to be administered said cell. In other embodiments of the method, the cell is allogeneic with respect to a subject to be administered said cell.

In some embodiments of the method of modifying a target nucleic acid sequence of a gene in a population of cells, the modifying comprises introducing one or more single-stranded breaks in the target nucleic acid sequence of the cells of the population. In other embodiments of the method, the modifying comprises introducing one or more double-stranded breaks in the target nucleic acid sequence of the cells of the population. In other embodiments of the method, the modifying comprises introducing an insertion, deletion, substitution, duplication, or inversion of one or more nucleotides in the target nucleic acid sequence of the cells of the population, resulting in a knock-down or knock-out of the gene in the cells of the population encoding one or more of the proteins involved in antigen processing, antigen presentation, antigen recognition, and/or antigen response. In some embodiments, the targeted protein is selected from beta-2-microglobulin (B2M), T cell receptor alpha chain constant region (TRAC), ICP47 polypeptide, class II major histocompatibility complex transactivator (CIITA), T cell receptor beta constant 1 (TRBC1), T cell receptor beta constant 2 (TRBC2), human leukocyte antigen A (HLA-A), human leukocyte antigen B (HLA-B), TGFβ Receptor 2 (TGFβRII), programmed cell death 1 (PD-1), cytokine inducible SH2 (CISH), lymphocyte activating 3 (LAG-3), T cell immunoreceptor with Ig and ITIM domains (TIGIT), adenosine A2a receptor (ADORA2A), killer cell lectin like receptor C1 (NKG2A), cytotoxic T-lymphocyte-associated protein 4 (CTLA-4), T-cell immunoglobulin and mucin domain 3 (TIM-3), and 2B4 (CD244). In one exemplary embodiment, the cell surface marker protein is B2M and the targeting sequence of the gNA comprises a sequence selected from the sequences of Table 3A. In another exemplary embodiment, the cell surface marker protein is TRAC and the targeting sequence of the gNA comprises a sequence selected from the sequences of Table 3B. In another exemplary embodiment, the intracellular protein is CIITA and the targeting sequence of the gNA comprises a sequence selected from the sequences of Table 3C. In another embodiment of the method, the genes to be modified are at least two of the proteins selected from the group consisting of B2M, TRAC, and CIITA. In one embodiment of the foregoing, the cells of the population have been modified such that expression of the one or more proteins is reduced by at least about 50%, at least about 60%, at least about 70%, at least about 80%, at least about 90%, or at least about 95% in comparison to a cell that has not been modified. In another embodiment of the foregoing, the cells of the population have been modified such that at least about 50%, at least about 60%, at least about 70%, at least about 80%, at least about 90%, or at least about 95% of the cells do not express a detectable level of the one or more proteins in comparison to a cell that has not been modified. In another embodiment of the method, the cells have been modified such that at least 70%, at least 75%, at least 80%, at least 85%, at least 90%, or at least 95% of the modified cells do not express a detectable level of MHC Class I molecules. In another embodiment of the method, the cells have been modified such that at least 70%, at least 75%, at least 80%, at least 85%, at least 90%, or at least 95% of the modified cells do not express a detectable level of wild-type T cell receptor.

In some embodiments, the method comprises insertion of the donor template into the break site(s) of the target nucleic acid sequence of the cells of the population. Depending on whether the system is used to knock-down/knock-out or to knock-in a protein involved in antigen processing, antigen presentation, antigen recognition, and/or antigen response, the donor template can be a short single-stranded or double-stranded oligonucleotide, or a long single-stranded or double-stranded oligonucleotide encoding the gene for the protein involved in antigen processing, antigen presentation, antigen recognition, and/or antigen response. For knock-down/knock-outs, the donor template sequence is typically not identical to the genomic sequence that it replaces and may contain one or more single base changes, insertions, deletions, inversions or rearrangements with respect to the genomic sequence, provided that there is sufficient homology with the target sequence to support homology-directed repair, which can result in a frame-shift or other mutation such that the target protein is not expressed or is expressed at a lower level. In certain embodiments, for knock-down/knock-out modifications, the donor template sequence will have at least about 60%, 70%, 80%, 90%, 95%, 98%, 99%, or 99.9% sequence identity to the target genomic sequence with which recombination is desired. In some embodiments, the donor template sequence comprises a non-homologous sequence flanked by two regions of homology ("homologous arms"), such that homology-directed repair between the target DNA region and the two flanking sequences results in insertion of the non-homologous sequence at the target region. The upstream and downstream sequences share sequence similarity with either side of the site of integration in the target DNA, facilitating insertion of the sequence. In some embodiments, the homologous region of a donor template sequence will have at least 50% sequence identity to the target genomic sequence with which recombination is desired. The donor template sequence may comprise certain sequence differences as compared to the genomic sequence, e.g., restriction sites, nucleotide polymorphisms, selectable markers (e.g., drug resistance genes, fluorescent proteins, enzymes etc.), etc., which may be used to assess for successful insertion of the donor nucleic acid at the cleavage site or in some cases may be used for other purposes (e.g., to signify expression at the targeted genomic locus). Alternatively, these sequence differences may include flanking recombination sequences such as FLPs, loxP sequences, or the like, that can be activated at a later time for removal of the marker sequence. In some embodiments, the donor template comprises at least about 10, at least about 50, at least about 100, or at least about 200, or at least about 300, or at least about 400, or at least about 500, or at least about 600, or at least about 700, or at least about 800, or at least about 900, or at least about 1000, or at least about 10,000, or at least 15,000 nucleotides of a target gene. In other embodiments the donor template comprises at least about 20 to about 10,000 nucleotides, or at least about 200 to about 8000 nucleotides, or at least about 400 to about 6000 nucleotides, or at least about 600 to about 4000 nucleotides, or at least about 1000 to about 2000 nucleotides of a target gene. In other embodiments, the disclosure provides a method to alter a target sequence of a cell using a CasX:gNA system and a donor template comprising a deletion, insertion, or mutation of 20 or fewer nucleotides, 10 or fewer nucleotides, 5 or fewer nucleotides, 4 or fewer nucleotides, 3 or fewer nucleotides, 2 nucleotides, or a single nucleotide in an encoding nucleic acid of the gene wherein the insertion of the donor template results in a cell wherein the expression of the target protein is reduced by at least about 50%, at least about 60%, at least about 70%, at least about 80%, or at least about 90%, or at least about 95% in comparison to a cell that has not been modified. In some embodiments, the donor template comprises a single stranded DNA sequence. In other embodiments, the donor template comprises a single stranded RNA template. In other embodiments, the donor template comprises a double stranded DNA sequence.

In other cases, an exogenous donor template is inserted between the ends generated by CasX cleavage by homology-independent targeted integration (HITI) mechanisms. The exogenous sequence inserted by HITI can be any length, for example, a relatively short sequence of between 1 and 50 nucleotides in length, or a longer sequence of about 50-1000 nucleotides in length. The lack of homology can be, for example, having no more than 20-50% sequence identity and/or lacking in specific hybridization at low stringency. In other cases, the lack of homology can further include a criterion of having no more than 5, 6, 7, 8, or 9 bp identity. The donor template insertion can be mediated by homology-directed repair (HDR) or homology-independent targeted integration (HITI). In some cases, the insertion of the donor template results in a knock-down or knock-out of the gene in the cells of the population encoding the one or more proteins involved in antigen processing, antigen presentation, antigen recognition, and/or antigen response. In some cases, the cells of the population have been modified such that expression of the one or more proteins is reduced by at least about 50%, at least about 60%, at least about 70%, at least about 80%, at least about 90%, or at least about 95% in comparison to a cell that has not been modified. In other cases, the cells of the population have been modified such that the cells do not express a detectable level of the one or more proteins. In a particular embodiment, the one or more proteins are selected from the group consisting of B2M, TRAC, and CIITA. In one embodiment, the method is conducted ex vivo on the population of cells. In another embodiment, the method is conducted in vivo in a subject.

In some embodiments of the method of modifying a target nucleic acid sequence of a gene in a population of cells, the modifying further comprises insertion of a polynucleotide encoding a chimeric antigen receptor (CAR), described more fully below, resulting in expression of a detectable level of the CAR in the modified cells of the population. Exemplary CARs, and methods for engineering and introducing such receptors into cells, include those described, for example, in international patent application publication numbers WO2013126726, WO2012129514, WO2014031687, WO2013166321, WO2013071154, WO2013123061 U.S. patent application publication numbers US2002131960, US2013287748, US20130149337, US 20190136230, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, incorporated by reference herein. The polynucleotide can be introduced into the cells to be modified by a vector as described herein, or as a plasmid using conventional methods known in the art; e.g. electroporation or microinjection.

In some embodiments of the method of modifying a target nucleic acid sequence of a gene in a population of cells, the modifying further comprises insertion of a polynucleotide encoding a fusion protein comprising a subunit of a TCR linked to an antigen binding domain capable of re-targeting the TCR (referred to here as an engineered T cell receptor, or engineered TCR) to a desired protein involved in antigen processing, antigen presentation, antigen recognition, and/or antigen response. The engineering of the T cell results in expression of a detectable level of the engineered TCR in the modified cells of the population, resulting in cells with a TCR for a second defined specificity that have utility in the treatment of a disease, like cancer or autoimmune diseases. The one or more subunits of the TCR may comprise any of TCR alpha, TCR beta, CD3-delta, CD3-epsilon, CD-gamma or CD3-zeta. Thus, the engineered TCR comprises a fusion protein comprising at least a portion of a TCR extracellular domain or transmembrane domain, and an antigen binding domain wherein the TCR subunit and the antigen binding domain are operatively linked. In some embodiments, the engineered TCR comprises a fusion protein comprising at least a portion of a TCR extracellular domain or transmembrane domain, a TCR intracellular domain comprising a stimulatory domain, and an antigen binding domain wherein the TCR subunit and the antigen domain are operatively linked. Besides the ability of the modified population of T cells expressing a CAR or a second TCR to recognize and destroy respective target cells in vitro/ex vivo, the modified population of cells have utility in the treatment of subjects having a disease such as cancer or an autoimmune disease.

In some embodiments, the CAR or engineered TCR has an antigen binding domain having specific binding affinity for a disease antigen, optionally a tumor cell antigen. In the foregoing, the tumor cell antigen can be selected from the group consisting of cluster of differentiation 19 (CD19), cluster of differentiation 3 (CD3), CD3d molecule (CD3D), CD3g molecule (CD3G), CD3e molecule (CD3E), CD247 molecule (CD247, or CD3Z), CD8a molecule (CD8), CD7 molecule (CD7), membrane metalloendopeptidase (CD10), membrane spanning 4-domains A1 (CD20), CD22 molecule (CD22), TNF receptor superfamily member 8 (CD30), C-type lectin domain family 12 member A (CLL1), CD33 molecule (CD33), CD34 molecule (CD34), CD38 molecule (CD38), integrin subunit alpha 2b (CD41), CD44 molecule (Indian blood group) (CD44), CD47 molecule (CD47), integrin alpha 6 (CD49f), neural cell adhesion molecule 1 (CD56), CD70 molecule (CD70), CD74 molecule (CD74), CD99 molecule (Xg blood group) (CD99), interleukin 3 receptor subunit alpha (CD123), prominin 1 (CD133), syndecan 1 (CD138), carbonix anhydrase IX (CAIX), CC chemokine receptor 4 (CCR4), ADAM metallopeptidase domain 12 (ADAM12), adhesion G protein-coupled receptor E2 (ADGRE2), alkaline phosphatase placental-like 2 (ALPPL2), alpha 4 Integrin, angiopoietin-2 (ANG2), B-cell maturation antigen (BCMA), CD44V6, carcinoembryonic antigen (CEA), CEAC, CEA cell adhesion molecule 5 (CEACAM5), Claudin 6 (CLDN6), CLDN18, C-type lectin domain family 12 member A (CLEC12A), mesenchymal-epithelial transition factor (cMET), cytotoxic T-lymphocyte-associated protein 4 (CTLA4), epidermal growth factor receptor 1 (EGF1R), epidermal growth factor receptor variant III (EGFRvIII), epithelial glycoprotein 2 (EGP-2), epithelial cell adhesion molecule (EGP-40 or EpCAM), EPH receptor A2 (EphA2), ectonucleotide pyrophosphatase/phosphodiesterase 3 (ENPP3), erb-b2 receptor tyrosine kinase 2 (ERBB2), erb-b2 receptor tyrosine kinase 3 (ERBB3), erb-b2 receptor tyrosine kinase 4 (ERBB4), folate binding protein (FBP), fetal nicotinic acetylcholine receptor (AChR), folate receptor alpha (Fralpha or FOLR1), G protein-coupled receptor 143 (GPR143), glutamate metabotropic receptor 8 (GRM8), glypican-3 (GPC3), ganglioside GD2, ganglioside GD3, human epidermal growth factor receptor 1 (HER1), human epidermal growth factor receptor 2 (HER2), human epidermal growth factor receptor 3 (HER3), Integrin B7, intercellular cell-adhesion molecule-1 (ICAM-1), human telomerase reverse transcriptase (hTERT), Interleukin-13 receptor $\alpha 2$ (IL-13R-a2), K-light chain, Kinase insert domain receptor (KDR), Lewis-Y (LeY), chondromodulin-1 (LECT1), L1 cell adhesion molecule (LiCAM), Lysophosphatidic acid receptor 3 (LPAR3), melanoma-associated antigen 1 (MAGE-A1), mesothelin (MSLN), mucin 1 (MUC1), mucin 16, cell surface associated (MUC16), melanoma-associated antigen 3 (MAGEA3), tumor protein p53 (p53), Melanoma Antigen Recognized by T cells 1 (MART1), glycoprotein 100 (GP100), Proteinase3 (PR1), ephrin-A receptor 2 (EphA2), Natural killer group 2D ligand (NKG2D ligand), New York esophageal squamous cell carcinoma 1 (NY-ESO-1), oncofetal antigen (h5T4), prostate-specific membrane antigen (PSMA), programmed death ligand 1 (PDL-1), receptor tyrosine kinase-like orphan receptor 1 (ROR1), trophoblast glycoprotein (TPBG), tumor-associated glycoprotein 72 (TAG-72), tumor-associated calcium signal transducer 2 (TROP-2), tyrosinase, survivin, vascular endothelial growth factor receptor 2 (VEGF-R2), Wilms tumor-1 (WT-1), leukocyte immunoglobulin-like receptor B2 (LILRB2), Preferentially Expressed Antigen In Melanoma (PRAME), T cell receptor beta constant 1 (TRBC1), TRBC2, and (T-cell immunoglobulin mucin-3) TIM-3. In one embodiment, the CAR or engineered TCR comprises an antigen binding domain selected from the group consisting of linear antibody, single domain antibody (sdAb), and single-chain variable fragment (scFv). In another embodiment, the CAR further comprises at least one intracellular signaling domain, wherein the at least one intracellular signaling domain comprises one or more intracellular signaling domains isolated or derived from CD247 molecule (CD3-zeta), CD27 molecule (CD27), CD28 molecule (CD28), TNF receptor superfamily member 9 (4-1BB), inducible T cell costimulator (ICOS), or TNF receptor superfamily member 4 (OX40). In another embodiment, the CAR further comprises an extracellular hinge domain or spacer. In one embodiment, the extracellular hinge domain is an immunoglobulin like domain, wherein the hinge domain is isolated or derived from IgG1, IgG2, or IgG4. In another embodiment, the hinge domain is isolated or derived from CD8a molecule (CD8) or CD28. In another embodiment, the CAR further comprises a transmembrane domain. The transmembrane domain can be isolated or derived from the group consisting of CD3-zeta, CD4, CD8, and CD28.

In some embodiments, the antigen binding domain of the CAR or engineered TCR is selected from the group consisting of linear antibody, single domain antibody (sdAb), and single-chain variable fragment (scFv). In a particular embodiment, the antigen binding domain is an scFv. In some embodiments, the scFv comprises a heavy chain variable domain (VH) and a light chain variable domain (VL) with specific binding affinity to the tumor cell antigen or target cell marker. Typically, the VH comprises a CDR-H1 region, a CDR-H2 region, a CDR-H3 region with interspersed framework regions (FR) connecting each CDR, and the VL comprises a CDR-L1 region, a CDR-L2 region, and a CDR-L3 region with its interspersed FR. In some embodiments, antigen binding domain exhibits an affinity with an equilibrium binding constant for a tumor cell antigen of between or between about $10^{-5}$ and $10^{-12}$ M and all individual values and ranges therein; such binding affinity being "specific". In other embodiments, the scFv comprises heavy chain complementarity determining regions (CDRs) and light chain CDRs identical to a reference antibody. In some cases, the reference antibody is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins in which residues from a CDR of the recipient antibody are replaced by residues from a CDR of a non-human species, such as mouse, rat, or rabbit having the desired specificity, affinity, and capacity. In some instances, Fv framework region (FR) residues are replaced by corresponding non-human residues. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. In some embodiments of the method, the reference antibody utilized to provide the antigen binding domain of the CAR comprises VH and VL and/or heavy chain and light chain CDRs selected from the group consisting of the sequences set forth in Table 5. It will be understood that the VH and VL sequences of Table 5 comprise a CDR-H1 region, a CDR-H2 region, a CDR-H3 region, a CDR-L1 region, a CDR-L2 region, and a CDR-H3 region (indicated by the underlined sequences of Table 5), and that the antigen binding domains of the CAR and/or engineered TCR embodiments can be constructed with these CDRs utilizing alternative framework regions than those of the corresponding VH and VL, yet still retain specific binding affinity to the target cell marker. In some cases, the CDRs or the VL and VH can have one or more amino acid substitutions, deletions, or insertions so long as specific binding affinity to the target cell marker is retained. In the foregoing embodiments, a nucleic acid encoding the CDRs or the VH and VL of the scFv as a component of the encoded CAR or TCR is utilized to modify the population of cells.

TABLE 5

Reference Antibody Sequences

| Trade Name | Antibody Name | Target Cell Marker | VH Sequence | VL Sequence |
|---|---|---|---|---|
| | huOKT3 | CD3 | QVQLVQSGGGVVQPGR<br>SLRLSCKAS**GYTFTRYT**<br>**MH**WVRQAPGKGLEWIG<br>**YINPSRGYTNYNQKVKD**<br>RFTISRDNSKNTAFLQM<br>DSLRPEDTGVYFCAR**YY**<br>**DDHYCLDY**WGQGTPVT<br>VSS<br>(SEQ ID NO: 217) | DIQMTQSPSSLSASVG<br>DRVTITC**SASSSVSYM**<br>**N**WYQQTPGKAPKRWI<br>Y**DTSKLAS**GVPSRFSG<br>SGSGTDYTFTISSLQPE<br>DIATYYC**QQWSSNPFT**<br>FGQGTKLQITR<br>(SEQ ID NO: 218) |
| | huUCHT 1 | CD3 | EVQLVESGGGLVQPGG<br>SLRLSCAAS**GYSFTGYT**<br>**MN**WVRQAPGKGLEWVA<br>**LINPYKGVST**YNQKFKD<br>RFTISVDKSKNTAYLQMN<br>SLRAEDTAVYYCAR**SGY**<br>**YGDSDWYFDV**WGQGTL<br>VTVSS<br>(SEQ ID NO: 219) | DIQMTQSPSSLSASVG<br>DRVTITC**RASQDIRNYL**<br>**N**WYQQKPGKAPKLLIY<br>**YTSRLES**GVPSRFSGS<br>GSGTDYTLTISSLQPED<br>FATYYC**QQGNTLPWT**F<br>GQGTKVEIK<br>(SEQ ID NO: 220) |
| | hu12F6 | CD3 | QVQLVQSGGGVVQPGR<br>SLRLSCKAS**GYTFTSYT**<br>**MH**WVRQAPGKGLEWIG<br>**YINPSSGYTKYNQKFKD**<br>RFTISADKSKSTAFLQMD<br>SLRPEDTGVYFCAR**WQ**<br>**DYDVYFDY**WGQGTPVT<br>VSS<br>(SEQ ID NO: 221) | DIQMTQSPSSLSASVG<br>DRVTMTC**RASSSVSY**<br>**MH**WYQQTPGKAPKPW<br>IY**ATSNLAS**GVPSRFS<br>GSGSGTDYTLTISSLQP<br>EDIATYYC**QQWSSNPP**<br>TFGQGTKLQITR<br>(SEQ ID NO: 222) |
| | mOKT3 | CD3 | QVQLQQSGAELARPGAS<br>VKMSCKAS**GYTFTRYTM**<br>**YI**WVKQRPGQGLEWIG**H**<br>**NPSRGYTNYNQKFKD**KA<br>TLTTDKSSSTAYMQLSSL<br>TSEDSAVYYCAR**YYDDH**<br>**YCLDY**WGQGTTLTVSS<br>(SEQ ID NO: 223) | QIVLTQSPAIMSASPGE<br>KVTMTC**SASSSVSYMN**<br>WYQQKSGTSPKRWIY<br>**DTSKLAS**GVPAHFRGS<br>GSGTSYSLTISGMEAE<br>DAATYYC**QQWSSNPF**<br>**T**FGSGTKLEINR<br>(SEQ ID NO: 224) |
| | blinatu-momab | CD3 | DIKLQQSGAELARPGAS<br>VKMSCKTS**GYTFTRYTM**<br>**H**WVKQRPGQGLEWIG**YI**<br>**NPSRGYTNYNQKFKD**KA<br>TLTTDKSSSTAYMQLSSL<br>TSEDSAVYYCAR**YYDDH**<br>**YCLDY**WGQGTTLTVSS<br>(SEQ ID NO: 225) | DIQLTQSPAIMSASPGE<br>KVTMTC**RASSSVSYMN**<br>WYQQKSGTSPKRWIY<br>**DTSKVAS**GVPYRFSGS<br>GSGTSYSLTISSMEAE<br>DAATYYC**QQWSSNPL**<br>**T**FGAGTKLELK<br>(SEQ ID NO: 226) |
| | Solito-mab | CD3 | DVQLVQSGAEVKKPGAS<br>VKVSCKAS**GYTFTRYTM**<br>**H**WVRQAPGQGLEWIG**YI**<br>**NPSRGYTNYADSVKG**RF<br>TITTDKSTSTAYMELSSL<br>RSEDTATYYCAR**YYDDH**<br>**YCLDY**WGQGTTVTVSS<br>(SEQ ID NO: 227) | DIVLTQSPATLSLSPGE<br>RATLSC**RASQSVSYMN**<br>WYQQKPGKAPKRWIY<br>**DTSKVAS** GVPARFSGS<br>GSGTDYSLTINSLEAED<br>AATYYC**QQWSSNPLT**F<br>GGGTKVEIK<br>(SEQ ID NO: 228) |
| | | CD3 | EVQLVESGGGLVQPGG<br>SLKLSCAASGFTFNKYA<br>MNWVRQAPGKGLEWVA<br>RIRSKYNNYATYYADSVK<br>DRFTISRDDSKNTAYLQ<br>MNNLKTEDTAVYYCVRH<br>GNFGNSYISYWAYWGQ<br>GTLVTVSS<br>(SEQ ID NO: 229) | QTVVTQEPSLTVSPGG<br>TVTLTCGSSTGAVTSG<br>YYPNWVQQKPGQAPR<br>GLIGGTKFLAPGTPARF<br>SGSLLGGKAALTLSGV<br>QPEDEAEYYCALWYSN<br>RWVFGGGTKLTVL<br>(SEQ ID NO: 230) |
| | | CD3 | EVQLVESGGGLVQPGG<br>SLRLSCAASGFTFNTYA<br>MNWVRQAPGKGLEWVG<br>RIRSKYNNYATYYADSVK | QAVVTQEPSLTVSPGG<br>TVTLTCGSSTGAVTTS<br>NYANWVQQKPGQAPR<br>GLIGGTNKRAPGVPAR |

TABLE 5-continued

Reference Antibody Sequences

| Trade Name | Antibody Name | Target Cell Marker | VH Sequence | VL Sequence |
|---|---|---|---|---|
| | | | GRFTISRDDSKNTLYLQ<br>MNSLRAEDTAVYYCVRH<br>GNFGNSYVSWFAYWGQ<br>GTLVTVSS<br>(SEQ ID NO: 231) | FSGSLLGGKAALTLSG<br>AQPEDEAEYYCALWYS<br>NLWVFGGGTKLTVL<br>(SEQ ID NO: 232) |
| | | CD3 | EVQLLESGGGLVQPGGS<br>LKLSCAASGFTFNTYAM<br>NWVRQAPGKGLEWVAR<br>IRSKYNNYATYYADSVKD<br>RFTISRDDSKNTAYLQM<br>NNLKTEDTAVYYCVRHG<br>NFGNSYVSWFAYWGQG<br>TLVTVSS<br>(SEQ ID NO: 233) | ELVVTQEPSLTVSPGG<br>TVTLTCRSSTGAVTTS<br>NYANWVQQKPGQAPR<br>GLIGGTNKRAPGTPAR<br>FSGSLLGGKAALTLSG<br>VQPEDEAEYYCALWYS<br>NLWVFGGGTKLTVL<br>(SEQ ID NO: 234) |
| | | CD3 | EVKLLESGGGLVQPKGS<br>LKLSCAASGFTFNTYAM<br>NWVRQAPGKGLEWVAR<br>IRSKYNNYATYYADSVKD<br>RFTISRDDSQSILYLQMN<br>NLKTEDTAMYYCVRHGN<br>FGNSYVSWFAYWGQGT<br>LVTVSS<br>(SEQ ID NO: 235) | QAVVTQESALTTSPGE<br>TVTLTCRSSTGAVTTS<br>NYANWVQEKPDHLFT<br>GLIGGTNKRAPGVPAR<br>FSGSLIGDKAALTITGA<br>QTEDEAIYFCALWYSN<br>LWVFGGGTKLTVL<br>(SEQ ID NO: 236) |
| Tysabri ™ | natali-<br>zumab | Alpha 4<br>Integrin | QVQLVQSGAEVKKPGAS<br>VKVSCKASGFNIK**DTYIH**<br>WVRQAPGQRLEWMG**RI**<br>**DPANGYTKYDPKFQG**R<br>VTITADTSASTAYMELSS<br>LRSEDTAVYYCAR**EGYY**<br>**GNYGVYAMDY**WGQGTL<br>VTVSS<br>(SEQ ID NO: 237) | DIQMTQSPSSLSASVG<br>DRVTITC**KTSQDINKYM**<br>**A**WYQQTPGKAPRLLIH<br>**YTSALQ**PGIPSRFSGS<br>GSGRDYTFTISSLQPE<br>DIATYYC**LQYDNLWT**F<br>GQGTKVEIK<br>(SEQ ID NO: 238) |
| REGN<br>910 | nesva-<br>cumab | Ang2 | EVQLVESGGGLVQPGG<br>SLRLSCAASG**GFTFSSYDI**<br>**H**WVRQATGKGLEWVSAI<br>**GPAGDTYYPGSV**KGRFT<br>ISRENAKNSLYLQMNSLR<br>AGDTAVYYCAR**GLITFG**<br>**GLIAPFD**YWGQGTLVTV<br>SS<br>(SEQ ID NO: 239) | EIVLTQSPGTLSLSPGE<br>RATLSCRA**SQSVSSTY**<br>**LA**WYQQKPGQAPRLLI<br>Y**GASSRAT**GIPDRFSG<br>SGSGTDFTLTISRLEPE<br>DFAVYYC**QHYDNSQ**TF<br>GQGTKVEIK<br>(SEQ ID NO: 240) |
| hMFE2<br>3 | | CEA | QVKLEQSGAEVVKPGAS<br>VKLSCKAS**GFNIKDS**YM<br>HWLRQGPGQRLEWIGW<br>**IDPENGD**TEYAPKFQGK<br>ATFTTDTSANTAYLGLSS<br>LRPEDTAVYYCNEG**TPT**<br>**GPYYFD**YWGQGTLVTVS<br>S<br>(SEQ ID NO: 241) | ENVLTQSPSSMSASVG<br>DRVNIACSA**SSSVS**YM<br>HWFQQKPGKSPKLWIY<br>STSN**LAS**GVPSRFSGS<br>GSGTDYSLTISSMQPE<br>DAATYYCQQ**RSSYYPL**T<br>FGGGTKLEIK<br>(SEQ ID NO: 242) |
| M5A<br>(human-<br>ized<br>T84.66) | | CEA | EVQLVESGGGLVQPGG<br>SLRLSCAASGFNIK**DTYM**<br>**H**WVRQAPGKGLEVVVA**R**<br>**IDPANGNSKYADSVKG**R<br>FTISADTSKNTAYLQMNS<br>LRAEDTAVYYCAP**FGYY**<br>**VSDYAMAY**WGQGTLVT<br>VSS<br>(SEQ ID NO: 243) | DIQLTQSPSSLSASVGD<br>RVTITC**RAGESVDIFGV**<br>**GFLH**WYQQKPGKAPK<br>LLIY**RASNLES**GVPSRF<br>SGSGSRTDFTLTISSLQ<br>PEDFATYYC**QQTNEDP**<br>**YT**FGQGTKVEIK<br>(SEQ ID NO: 244) |
| M5B<br>(human-<br>ized<br>T84.66) | | CEA | EVQLVESGGGLVQPGG<br>SLRLSCAASGFNIK**DTYM**<br>HWVRQAPGKGLEVVVA**R**<br>**IDPANGNSKYVPKFQG**R<br>ATISADTSKNTAYLQMNS | DIQLTQSPSSLSASVGD<br>RVTITC**RAGESVDIFGV**<br>**GFLH**WYQQKPGKAPK<br>LLIY**RASNLES**GVPSRF<br>SGSGSRTDFTLTISSLQ |

TABLE 5-continued

| Reference Antibody Sequences | | | | |
|---|---|---|---|---|
| Trade Name | Antibody Name | Target Cell Marker | VH Sequence | VL Sequence |
| | | | LRAEDTAVYYCAP**FGYYVSDYAMAY**WGQGTLVTVSS (SEQ ID NO: 245) | PEDFATYYC**QQTNEDPYT**FGQGTKVEIK (SEQ ID NO: 246) |
| CEA-Cide | Labetu-zumab (MN-14) | CEACAM 5 | EVQLVESGGGVVQPGRSLRLSCSASGFDFT**TYWMS**WVRQAPGKGLEWIG**EIHPDSSTINYAPSLKD**RFTISRDNAKNTLFLQMDSLRPEDTGVYFCAS**LYFGFPWFAY**WGQGTPVTVSS (SEQ ID NO: 247) | DIQLTQSPSSLSASVGDRVTITC**KASQDVGTSVA**WYQQKPGKAPKLLIY**WTSTRHT**GVPSRFSGSGSGTDFTFTISSLQPEDIATYYC**QQYSLYRS**FGQGTKVEIK (SEQ ID NO: 248) |
| CEA-Scan | arcitu-momab | CEACAM 5 | EVKLVESGGGLVQPGGSLRLSCATS**GFTFTDYYMN**WVRQPPGKALEWLG**FIGNKANGYTTEYSAS**VKGRFTISRDKSQSILYLQMNTLRAEDSA**TYYCTRDR**GLRFYFDYWGQGTTLTVSS (SEQ ID NO: 249) | QTVLSQSPAILSASPGEKVTMTC**RASSSVTYIHW**YQQKPGSSPKSWIYA**TSNLASG**VPARFSGSGSGTSYSLTISRVEAEDAATYYC**QHWSSKPPT**FGGGTKLEIKR (SEQ ID NO: 250) |
| MT110 | | CEACAM 5 | EVQLVESGGGLVQPGRSLRLSCAASGFTVS**SYWMH**WVRQAPGKGLEVVVG**FIRNKANGGTTEYAASVKG**RFTISRDDSKNTLYLQMNSLRAEDTAVYYCAR**DRGLRFYFDY**WGQGTTVTVSS (SEQ ID NO: 251) | QAVLTQPASLSASPGASASLTC**TLRRGINVGAYSIY**WYQQKPGSPPQYLLR**YKSDSDKQQGS**GVSSRFSASKDASANAGILLISGLQSEDEADYYC**MIWHSGASAV**FGGGTKLTVL (SEQ ID NO: 252) |
| MT103 | blinatu-momab | CD19 | QVQLQQSGAELVRPGSSVKISCKASGYAFS**SYWMN**WVKQRPGQGLEWIG**QIWPGDGDTNYNGKFKG**KATLTADESSSTAYMQLSSLASEDSAVYFCAR**RETTTVGRYYYAMDY**WGQGTTVTVSS (SEQ ID NO: 253) | DIQLTQSPASLAVSLGQRATISC**KASQSVDYDGDSY**LNWYQQIPGQPPKLLI**YDASNLVS**GIPPRFSGSGSGTDFTLNIHPVEKVDAATYHC**QQSTEDPWT**FGGGTKLEIK (SEQ ID NO: 254) |
| Arzerra | ofatu-mumab | CD20 | EVQLVESGGGLVQPGRSLRLSCAASGFTFN**DYAMH**WVRQAPGKGLEWVS**TISWNSGSIGYADSVKG**RFTISRDNAKKSLYLQMNSLRAEDTALYYCAK**DIQYGNYYYGMDV**WGQGTTVTVSS (SEQ ID NO: 255) | EIVLTQSPATLSLSPGERATLSC**RASQSVSSYLA**WYQQKPGQAPRLLIY**DASNRAT**GIPARFSGSGSGTDFTLTISSLEPEDFAVYYC**QQRSNWPIT**FGQGTRLEIK (SEQ ID NO: 256) |
| Bexxar ™ | tositu-momab | CD20 | QAYLQQSGAELVRPGASVKMSCKASGYTFT**SYNMH**WVKQTPRQGLEWIG**AIYPGNGDTSYNQKFKG**KATLTVDKSSSTAYMQLSSLTSEDSAVYFCAR**VVYYSNSYWYFDV**WGTGTTVTVSG (SEQ ID NO: 257) | QIVLSQSPAILSASPGEKVTMTC**RASSSVSYMH**WYQQKPGSSPKPWIY**APSNLAS**GVPARFSGSGSGTSYSLTISRVEAEDAATYYC**QQWSFNPPT**FGAGTKLELK (SEQ ID NO: 258) |
| GAZYVA | Obinutu-zumab | CD20 | QVQLVQSGAEVKKPGSSVKVSCKASGYAFS**YSWIN**WVRQAPGQGLEWMG**RIFPGDGDTDYNGKFKG**RVTITADKSTSTAYMELSSLRSEDTAVYYCAR**NVFDGYWLVY**WGQGTLVTVSS (SEQ ID NO: 259) | DIVMTQTPLSLPVTPGEPASISC**RSSKSLLHSNGITYLY**WYLQKPGQSPQLLIY**QMSNLVS**GVPDRFSGSGSGTDFTLKISRVEAEDVGVYYC**AQNLELPYT**FGGGTKVEIK (SEQ ID NO: 260) |

TABLE 5-continued

Reference Antibody Sequences

| Trade Name | Antibody Name | Target Cell Marker | VH Sequence | VL Sequence |
|---|---|---|---|---|
| | Ocrelizumab/ 2H7 v16 | CD20 | EVQLVESGGGLVQPGGSLRLSCAAS**GYTFTSYN**MHWVRQAPGKGLEWVGA**IYPGNGDT**SYNQKFKGRFTISVDKSKNTLYLQMNSLRAEDTAVYYCAR**VVYYSNSYWYFDV**WGQGTLVTVSS (SEQ ID NO: 261) | DIQMTQSPSSLSASVGDRVTITC**RASSSVSYMH**WYQQKPGKAPKPLIY**APSNLAS**GVPSRFSGSGSGTDFTLTISSLQPEDFATYYC**QQWSFNPPT**FGQGTKVEIK (SEQ ID NO: 262) |
| Rituxan ™ | rituximab | CD20 | QVQLQQPGAELVKPGASVKMSCKAS**GYTFTSYN**MHWVKQTPGRGLEWIGAI**YPGNGDT**SYNQKFKGKATLTADKSSSTAYMQLSSLTSEDSAVYYC**ARSTYYGGDWYFNV**WGAGTTVTVSA (SEQ ID NO: 263) | QIVLSQSPAILSASPGEKVTMTCRAS**SSVSY**IHWFQQKPGSSPKPWIY**ATS**NLASGVPVRFSGSGSGTSYSLTISRVEAEDAATYYC**QQWTSNPPT**FGGGTKLEIK (SEQ ID NO: 264) |
| Zevalin ™ | ibritumomab tieuxetan | CD20 | QAYLQQSGAELVRPGASVKMSCKAS**GYTFTSYN**MHWVKQTPRQGLEWIG**AIYPGNGDTSYNQKF**KGKATLTVDKSSSTAYMQLSSLTSEDSAVYFCAR**VVYYSNSYWYFDV**WGTGTTVTVSA (SEQ ID NO: 265) | QIVLSQSPAILSASPGEKVTMTC**RASSSVSYMH**WYQQKPGSSPKPWIY**APSNLAS**GVPARFSGSGSGTSYSLTISRVEAEDAATYYC**QQWSFNPPT**FGAGTKLELK (SEQ ID NO: 266) |
| Mylotarg | Gemtuzumab (hP67.6) | CD33 | QLVQSGAEVKKPGSSVKVSCKAS**GYTITDSNIH**WVRQAPGQSLEWIG**YIYPYNGGTDYNQKFKN**RATLTVDNPTNTAYMELSSLRSEDTDFYYCVN**GNPWLAY**WGQGTLVTVSS (SEQ ID NO: 267) | DIQLTQSPSTLSASVGDRVTITC**RASESLDNYGIRFLT**WFQQKPGKAPKLLMY**AASNQGS**GVPSRFSGSGSGTEFTLTISSLQPDDFATYYC**QQTKEVPWS**FGQGTKVEVK (SEQ ID NO: 268) |
| Daratumumab | | CD38 | EVQLLESGGGLVQPGGSLRLSCAVS**GFTFNSFA**MSWVRQAPGKGLEWVSA**ISGSGGGT**YYADSVKGRFTISRDNSKNTLYLQMNSLRAEDTAVYFC**AKDKILWFGEPVFDY**WGQGTLVTVSS (SEQ ID NO: 269) | EIVLTQSPATLSLSPGERATLSCRAS**QSVSSY**LAWYQQKPGQAPRLLIY**DAS**NRATGIPARFSGSGSGTDFTLTISSLEPEDFAVYYC**QQRSNWPPT**FGQGTKVEIK (SEQ ID NO: 270) |
| | 1F6 | CD70 | QIQLVQSGPEVKKPGETVKISCKAS**GYTFTNYGMN**WVKQAPGKGLKVVMG**WINTYTGEPTYADAFKG**RFAFSLETSASTAYLQINNLKNEDTATYFCAR**DYGDYGMDY**WGQGTSVTVSS (SEQ ID NO: 271) | DIVLTQSPASLAVSLGQRATISC**RASKSVSTSGYSFMH**WYQQKPGQPPKLLIY**LASNLES**GVPARFSGSGSGTDFTLNIHPVEEEDAATYYC**QHSREVPWT**FGGGTKLEIK (SEQ ID NO: 272) |
| | 2F2 | CD70 | QVQLQQSGTELMTPGASVTMSCKTS**GYTFSTYWIE**WVKQRPGHGLEWIG**EI**I**LGPSGYTDYNEKFKA**KATFTADTSSNTAYMQLSSLASEDSAVYYCAR**WDRLYAMDY**WGGGTSVTVSS (SEQ ID NO: 273) | DIVLTQSPASLTVSLGQKTTISC**RASKSVSTSGYSFMH**WYQLKPGQSPKLLIY**LASDLPS**GVPARFSGSGSGTDFTLKIHPVEEEDAATYYC**QHSREIDYT**FGGGTKLEIT (SEQ ID NO: 274) |
| | 2H5 | CD70 | QVQLVESGGGVVQPGRSLRLSCAASGFTFS**SYIMH**WVRQAPGKGLEWVA**VISYDGRNKYYADSVKG**R | EIVLTQSPATLSLSPGERATLSC**RASQSVSSYLA**WYQQKPGQAPRLLI**YDASNRA**TGIPARFSGS |

TABLE 5-continued

| Reference Antibody Sequences | | | | |
|---|---|---|---|---|
| Trade Name | Antibody Name | Target Cell Marker | VH Sequence | VL Sequence |
| | | | FTISRDNSKNTLYLQMNS<br>LRAED<br>TAVYYCAR**DTDGYDFDY**<br>WGQGTLVTVSS<br>(SEQ ID NO: 275) | GSGTDFTLTISSLEPED<br>FAVYYC**QQ**<br>**RTNWPLT**FGGGTKVEI<br>K<br>(SEQ ID NO: 276) |
| | 10B4 | CD70 | QIQLVESGGGVVQPGRS<br>LRLSCAASGFTFG**YYAM**<br>**H**WVRQAPGKGLEWVA**VI**<br>**SYDGSIKYYADSVKG**RF<br>TISRDNSKNTLYLQMNSL<br>RAED<br>TAVYYCAR**EGPYSNYLD**<br>**Y**WGQGTLVTVSS<br>(SEQ ID NO: 277) | AIQLTQSPSSLSASVGD<br>RVTITC**RASQGISSALA**<br>WYQQKPGKAPKFLIY**D**<br>**ASSLES**GVPSRFSGSG<br>SGTDFTLTISSLQPEDF<br>ATYYC**QQ**<br>**FNSYPFT**FGPGTKVDIK<br>(SEQ ID NO: 278) |
| | 8B5 | CD70 | QVQLVESGGGVVQPGR<br>SLRLSCATSGFTFS**DYG**<br>**MH**WVRQAPGKGLEWVA<br>**VIWYDGSNKYYADSVKG**<br>RFTISRDNSKKTLSLQMN<br>SLRAED<br>TAVYYCAR**DSIMVRGDY**<br>WGQGTLVTVSS<br>(SEQ ID NO: 279) | DIQMTQSPSSLSASVG<br>DRVTITC**RASQGISSW**<br>**LA**WYQQKPEKAPKSLI<br>Y**AASSLQS**GVPSRFSG<br>SGSGTDFTLTISSLQPE<br>DFATYYC**QQ**<br>**YNSYPLT**FGGGTKVEIK<br>(SEQ ID NO: 280) |
| | 18E7 | CD70 | QVQLVESGGGVVQPGR<br>SLRLSCAASGFTFS**DHG**<br>**MH**WVRQAPGKGLEWVA<br>**VIWYDGSNKYYADSVKG**<br>RFTISRDNSKNTLYLQMN<br>SLRAED<br>TAVYYCAR**DSIMVRGDY**<br>WGQGTLVTVSS<br>(SEQ ID NO: 281) | DIQMTQSPSSLSASVG<br>DRVTITC**RASQGISSW**<br>**LA**WYQQKPEKAPKSLI<br>Y**AASSLQS**GVPSRFSG<br>SGSGTDFTLTISSLQPE<br>DFATYYC**QQ**<br>**YNSYPLT**FGGGTKVEIK<br>(SEQ ID NO: 282) |
| | 69A7 | CD70 | QVQLQESGPGLVKPSET<br>LSLTCTVSGGSVS**SDYY**<br>**YWS**WIRQPPGKGLEWL<br>G**YIYYSGSTNYNPSLKS**<br>RVTISVDTSKNQFSLKLR<br>SVTTA<br>DTAVYYCAR**GDGDYGG**<br>**NCF**DYWGQGTLVTVSS<br>(SEQ ID NO: 283) | EIVLTQSPATLSLSPGE<br>RATLSC**RASQSVSSYL**<br>**A**WYQQKPGQAPRLLIF<br>**DASNRAT**GIPARFSGS<br>GSGTDFTLTISSLEPED<br>FAVYYC**QQ**<br>**RSNWPLT**FGGGTKVEI<br>K<br>(SEQ ID NO: 284) |
| CE-355621 | | cMET | QVQLVQSGAEVKKPGAS<br>VKVSCKASGYTFT**SYGF**<br>**S**WVRQAPGQGLEWMG<br>**WISASNGNTYYAQKLQG**<br>RVTMTTDTSTSTAYMEL<br>RSLRSDDTAVYYCAR**VY**<br>**ADYADY**WGQGTLVTVS<br>S<br>(SEQ ID NO: 285) | DIQMTQSPSSVSASVG<br>DRVTITC**RASQGINTW**<br>**LA**WYQQKPGKAPKLLI<br>Y**AASSLKS**GVPSRFSG<br>SGSGTDFTLTISSLQPE<br>DFATYYC**QQANSFPLT**<br>FGGGTKVEIK<br>(SEQ ID NO: 286) |
| LY2875358 | emibetuzumab | cMET | QVQLVQSGAEVKKPGAS<br>VKVSCKAS**GYTFTDYY**M<br>HWVRQAPGQGLEWMG<br>R**VNPNRRGTT**YNQKFEG<br>RVTMTTDTSTSTAYMEL<br>RSLRSDDTAVYYC**ARAN**<br>**WLDY**WGQGTTVTVSS<br>(SEQ ID NO: 287) | DIQMTQSPSSLSASVG<br>DRVTITCSVS**SSVSSIY**<br>LHWYQQKPGKAPKLLI<br>Y**STS**NLASGVPSRFSG<br>SGSGTDFTLTISSLQPE<br>DFATYYC**QVYSGYPLT**<br>FGGGTKVEIK<br>(SEQ ID NO: 288) |
| MetMAb | onartuzumab | cMET | EVQLVESGGGLVQPGG<br>SLRLSCAASGYTFT**SYW**<br>**LH**WVRQAPGKGLEWVG<br>**MIDPSNSDTRFNPNFKD**<br>RFTISADTSKNTAYLQMN<br>SLRAEDTAVYYC**ATYRS**<br>**YVTPLDY**WGQGTLVTVS<br>S<br>(SEQ ID NO: 289) | DIQMTQSPSSLSASVG<br>DRVTITC**KSSQSLLYTS**<br>**SQKNYLA**WYQQKPGK<br>APKLLIY**WASTRES**GV<br>PSRFSGSGSGTDFTLTI<br>SSLQPEDFATYYC**QQY**<br>**YAYPWT**FGQGTKVEIK<br>(SEQ ID NO: 290) |

TABLE 5-continued

Reference Antibody Sequences

| Trade Name | Antibody Name | Target Cell Marker | VH Sequence | VL Sequence |
|---|---|---|---|---|
| | tremeli-mumab (CP-675206, or 11.2.1) | CTLA4 | QVQLVESGGGVVQPGR SLRLSCAAS**GFTFSSYG** **MH**WVRQAPGKGLEWVA **VIWYDGSNKYYADSV**KG RFTISRDNSKNTLYLQMN SLRAEDTAVYYCAR**DPR** **GATLYYYYYGMDV**WGQ GTTVTVSS (SEQ ID NO: 291) | DIQMTQSPSSLSASVG DRVTITC**RASQSINSYL** **D**WYQQKPGKAPKLLIY **AASSLQS**GVPSRFSGS GSGTDFTLTISSLQPED FATYYC**QQYYSTPFT**F GPGTKVEIK (SEQ ID NO: 292) |
| Yervoy | Ipili-mumab 10D1 | CTLA4 | QVQLVESGGGVVQPGR SLRLSCAASGFTFS**SYT** **MH**WVRQAPGKGLEWVT **FISYDGNNKYYADSVKG** RFTISRDNSKNTLYLQMN SLRAEDTAIYYCAR**TGW** **LGPFDY**WGQGTLVTVSS (SEQ ID NO: 293) | EIVLTQSPGTLSLSPGE RATLSC**RASQSVGSSY** **LA**WYQQKPGQAPRLLI Y**GAFSRAT**GIPDRFSG SGSGTDFTLTISRLEPE DFAVYYC**QQYGSSPW** **T**FGQGTKVEIK (SEQ ID NO: 294) |
| AGS16 F | H16-7.8 | ENPP3 | QVQLQESGPGLVKPSQT LSLTCTVSGGSIS**SGGYY** WSWIRQHPGKGLEWIG**II** **YYSGSTYYNPSLKS**RVTI SVDTSKNQFSLKLNSVT AADTAVFYCAR**VAIVTTI** **PGGMDV**WGQGTTVTVS S (SEQ ID NO: 295) | EIVLTQSPDFQSVTPKE KVTITC**RASQSIGISLH** WYQQKPDQSPKLLIK**Y** **ASQSFS**GVPSRFSGSG SGTDFTLTINSLEAEDA ATYYC**HQSRSFPWT**FG QGTKVEIK (SEQ ID NO: 296) |
| MT110 | solit-omab | EpCAM | EVQLLEQSGAELVRPGT SVKISCKASGYAFT**NYW** **LG**WVKQRPGHGLEWIG **DIFPGSGNIHYNEKFKG**K ATLTADKSSSTAYMQLS SLTFEDSAVYFCAR**LRN** **WDEPMDY**WGQGTTVTV SS (SEQ ID NO: 297) | ELVMTQSPSSLTVTAG EKVTMSC**KSSQSLLNS** **GNQKNYLT**WYQQKPG QPPKLLIY**WASTRES**G VPDRFTGSGSGTDFTL TISSVQAEDLAVYYC**Q** **NDYSYPLT**FGAGTKLEI K (SEQ ID NO: 298) |
| MT201 | Adecatu-mumab | EpCAM | EVQLLESGGGVVQPGRS LRLSCAASGFTFS**SYGM** **H**WVRQAPGKGLEWVA**VI** **SYDGSNKYYADSVKG**R FTISRDNSKNTLYLQMNS LRAEDTAVYYCAK**DMG** **WGSGWRPYYYYGMDV** WGQGTTVTVSS (SEQ ID NO: 299) | ELQMTQSPSSLSASVG DRVTITC**RTSQSISSYL** **N**WYQQKPGQPPKLLIY **WASTRES**GVPDRFSG SGSGTDFTLTISSLQPE DSATYYC**QQSYDIPYT** FGQGTKLEIK (SEQ ID NO: 300) |
| Panore x | Edrecol-omab Mab CO17-1A | EpCAM | QVQLQQSGAELVRPGTS VKVSCKAS**GYAFTNYL**IE WVKQRPGQGLEWIGV**IN** **PGSGGT**NYNEKFKGKAT LTADKSSSTAYMQLSSLT SDDSAVYFC**ARDGPWF** **AY**WGQGTLVTVSA (SEQ ID NO: 301) | NIVMTQSPKSMSMSVG ERVTLTCKAS**ENVVTY** VSWYQQKPEQSPKLLI Y**GAS**NRYTGVPDRFTG SGSATDFTLTISSVQAE DLADYHC**GQGYSYPYT** FGGGTKLEIK (SEQ ID NO: 302) |
| | tucotu-zumab | EpCAM | QIQLVQSGPELKKPGET VKISCKAS**GYTFTNYGM** **N**WVRQAPGKGLKVVMG **WINTYTGEPTYAD**DFKG RFVFSLETSASTAFLQLN NLRSEDTATYFCVRFI**SK** **GDY**YWGQGTSVTVSS (SEQ ID NO: 303) | QILLTQSPAIMSASPGE KVTMTC**SASSSVS**YML WYQQKPGSSPKPWIF **DTSNLAS**GFPARFSGS GSGTSYSLIISSMEAED AATYYC**HQRSGYPYT**F GGGTKLEIK (SEQ ID NO: 304) |
| UBS-54 | | EpCAM | VQLQQSDAELVKPGASV KISCKAS**GYTFTDHAIH**W VKQNPEQGLEWIG**YFSP** | DIVMTQSPDSLAVSLG ERATINC**KSSQSVLYS** **SNNKNYLA**WYQQKPG |

TABLE 5-continued

| Reference Antibody Sequences | | | | |
|---|---|---|---|---|
| Trade Name | Antibody Name | Target Cell Marker | VH Sequence | VL Sequence |
| | | | **GNDDFKYNE**RFKGKATL<br>TADKSSSTAYVQLNSLTS<br>EDSAVYFCTR**SLNMAY**<br>WGQGTSVTVSS<br>(SEQ ID NO: 305) | QPPKLLIY**WASTRES**G<br>VPDRFSGSGSGTDFTL<br>TISSLQAEDVAVYYC**Q**<br>**QYYSYPLT**FGGGTKVK<br>ES<br>(SEQ ID NO: 306) |
| 3622W 94 | 323/A3 | EpCAM | EVQLVQSGPEVKKPGAS<br>VKVSCKAS**GYTFTNYGM**<br>**N**WVRQAPGQGLEWMG<br>**WINTYTGEPTYGE**DFKG<br>RFAFSLDTSASTAYMELS<br>SLRSEDTAVYFCARFG**N**<br>**YVDY**WGQGSLVTVSS<br>(SEQ ID NO: 307) | DIVMTQSPLSLPVTPGE<br>PASISC**RSSINKKGSNG**<br>**ITY**LYWYLQKPGQSPQ<br>LLIYQMSNLASGVPDRF<br>**SGSGS**GTDFTLKISRVE<br>AEDVGVYYC**AQNLEIP**<br>**RT**FGQGTKVEIK<br>(SEQ ID NO: 308) |
| 4D5M OCBv2 | | EpCAM | EVQLVQSGPGLVQPGG<br>SVRISCAASGYTFT**NYG**<br>**MN**WVKQAPGKGLEWM<br>G**WINTYTGESTYADSFK**<br>**G**RFTFSLDTSASAAYLQI<br>NSLRAEDTAVYYCAR**FAI**<br>**KGD**YWGQGTLLTVSS<br>(SEQ ID NO: 309) | DIQMTQSPSSLSASVG<br>DRVTITC**RSTKSLLHSN**<br>**GITYLY**WYQQKPGKAP<br>KLLIY**QMSNLAS**GVPS<br>RFSSSGSGTDFTLTISS<br>LQPEDFATYYC**AQNLEI**<br>**PRT**FGQGTKVEIK<br>(SEQ ID NO: 310) |
| 4D5M OCB | | EpCAM | EVQLVQSGPGLVQPGG<br>SVRISCAASGYTFT**NYG**<br>**MN**WVKQAPGKGLEWM<br>G**WINTYTGESTYADSFK**<br>**G**RFTFSLDTSASAAYLQI<br>NSLRAEDTAVYYCAR**FAI**<br>**KGDY**WGQGTLLTVSS<br>(SEQ ID NO: 311) | DIQMTQSPSSLSASVG<br>DRVTITC**RSTKSLLHSN**<br>**GITYLY**WYQQKPGKAP<br>KLLIY**QMSNLAS**GVPS<br>RFSSSGSGTDFTLTISS<br>LQPEDFATYYC**AQNLEI**<br>**PRT**FGQGTKVELK<br>(SEQ ID NO: 312) |
| MEDI-547 | 1C1 | EphA2 | EVQLLESGGGLVQPGGS<br>LRLSCAASGFTFS**HYMM**<br>**A**WVRQAPGKGLEWVS**R**<br>**IGPSGGPTHYADSVKG**R<br>FTISRDNSKNTLYLQMNS<br>LRAEDTAVYYCAGYDSG<br>**YDYVAVAGPAEYFQH**W<br>GQGTLVTVSS<br>(SEQ ID NO: 313) | DIQMTQSPSSLSASVG<br>DRVTITCR**RASQSISTWL**<br>**A**WYQQKPGKAPKLLIY<br>**KASNLHT**GVPSRFSGS<br>GSGTEFSLTISGLQPDD<br>FATYYC**QQYNSYSRT**F<br>GQGTKVEIK<br>(SEQ ID NO: 314) |
| MORA b-003 | farletu-zumab | FOLR1 | EVQLVESGGGVVQPGR<br>SLRLSCSAS**GFTFSGYG**<br>LSWVRQAPGKGLEWVA<br>M**ISSGGSYT**YYADSVKG<br>RFAISRDNAKNTLFLQMD<br>SLRPEDTGVYFC**ARHGD**<br>**DPAWF**AYWGQGTPVTV<br>SS<br>(SEQ ID NO: 315) | DIQLTQSPSSLSASVGD<br>RVTITCSVS**SSISSNN**L<br>HWYQQKPGKAPKPWI<br>Y**GTS**NLASGVPSRFSG<br>SGSGTDYTFTISSLQPE<br>DIATYYC**QQWSSYPYM**<br>**YT**FGQGTKVEIK<br>(SEQ ID NO: 316) |
| M9346 A | huMOV1 9 (vLCv1.0 0) | FOLR1 | QVQLVQSGAEVVKPGAS<br>VKISCKASGYTFT**GYFM**<br>**N**WVKQSPGQSLEWIG**RI**<br>**HPYDGDTFYNQKFQG**K<br>ATLTVDKSSNTAHMELLS<br>LTSEDFAVYYCTR**YDGS**<br>**RAMDY**WGQGTTVTVSS<br>(SEQ ID NO: 317) | DIVLTQSPLSLAVSLGQ<br>PAIISC**KASQSVSFAGT**<br>**SLMH**WYHQKPGQQPR<br>LLIY**RASNLEA**GVPDRF<br>SGSGSKTDFTLNISPVE<br>AEDAATYYC**QQSREYP**<br>**YT**FGGGTKLEIK<br>(SEQ ID NO: 318) |
| M9346 A | huMOV1 9 (vLCv1.6 0) | FOLR1 | QVQLVQSGAEVVKPGAS<br>VKISCKASGYTFT**GYFM**<br>**N**WVKQSPGQSLEWIG**RI**<br>**HPYDGDTFYNQKFQG**K<br>ATLTVDKSSNTAHMELLS<br>LTSEDFAVYYCTR**YDGS**<br>**RAMD**WGQGTTVTVSS<br>(SEQ ID NO: 319) | DIVLTQSPLSLAVSLGQ<br>PAIISC**KASQSVSFAGT**<br>**SLMH**WYHQKPGQQPR<br>LLIY**RASNLEA**GVPDRF<br>SGSGSKTDFTLTISPVE<br>AEDAATYYC**QQSREYP**<br>**YT**FGGGTKLEIK<br>(SEQ ID NO: 320) |

TABLE 5-continued

Reference Antibody Sequences

| Trade Name | Antibody Name | Target Cell Marker | VH Sequence | VL Sequence |
|---|---|---|---|---|
| 26B3.F2 | | FOLR1 | GPELVKPGASVKISCKASDYSFT**GYFMN**WVMQSHGKSLEWIG**RIFPYNGDTFYNQKFKG**RATLTVDKSSSTAHMELRSLASEDSAVYFCAR**GTHYFDY**WGQGTTLTVSS (SEQ ID NO: 321) | PASLSASVGETVTITC**RTSENIFSYLA**WYQQKQGISPQLLVY**NAKTLAE**GVPSRFSGSGSGTQFSLKINSLQPEDFGSYYC**QHHYAFPWT**FGGGSKLEIK (SEQ ID NO: 322) |
| RG7686 | GC33 | GPC3 | QVQLVQSGAEVKKPGASVKVSCKASGYTFT**DYEMH**WVRQAPGQGLEWMG**ALDPKTGDTAYSQKFKG**RVTLTADKSTSTAYMELSSLTSEDTAVYYCTR**FYSYTY**WGQGTLVTVSS (SEQ ID NO: 323) | DVVMTQSPLSLPVTPGEPASISC**RSSQSLVHSNGNTYLH**WYLQKPGQSPQLLIY**KVSNRFS**GVPDRFSGSGSGTDFTLKISRVEAEDVGVYYC**SQNTHVPPT**FGQGTKLEIK (SEQ ID NO: 324) |
| | 4A6 | GPC3 | EVQLVQSGAEVKKPGESLKISCKGSGYSFT**SYWIA**WVRQMPGKGLEWMG**IIFPGDSDTRYSPSFQG**QVTISADRSIRTAYLQWSSLKASDTALYYCAR**TREGYFDY**WGQGTLVTVSS (SEQ ID NO: 325) | EIVLTQSPGTLSLSPGERATLSC**RACQSVSSSYLA**WYQQKPGQAPRLLIY**GASSRAT**GIPDRFSGSGSGTDFTLTISRLEPEDFAVYYC**QQYGSSPT**FGGGTKVEIK (SEQ ID NO: 326) |
| | 11E7 | GPC3 | EVQLVQSGAEVKKPGESLKISCKGSGYSFT**NYWIA**WVRQMPGKGLEWMG**IIYPGDSDTRYSPSFQG**QVTISADKSIRTAYLQWSSLKASDTAMYYCAR**TREGYFDY**WGQGTLVTVSS (SEQ ID NO: 327) | EIVLTQSPGTLSLSPGERATLSC**RASQSVSSSYLA**WYQQKPGQAPRLLIY**GASSRAT**GIPDRFSGSGSGTDFTLTISRLEPEDFAVYYC**QQYGSSPT**FGGGTKVEIK (SEQ ID NO: 328) |
| | 16D10 | GPC3 | EVQLVQSGADVTKPGESLKISCKVSGYRFT**NYWIG**WMRQMSGKGLEWMG**IIYPGDSDTRYSPSFQG**HVTISADKSINTAYLRWSSLKASDTAIYYCAR**TREGFFDY**WGQGTPVTVSS (SEQ ID NO: 329) | EILLTQSPGTLSLSPGERATLSC**RASQSVSSSYLA**WYQQKPGQAPRLLIY**GASSRAT**GIPDRFSGSGSGTDFTLTISRLEPEDFAVYYC**QQYGSSPT**FGQGTKVEIK (SEQ ID NO: 330) |
| AMG-595 | | EGFR | QVQLVESGGGVVQSGRSLRLSCAAS**GFTFRNYGMH**WVRQAPGKGLEW**VAVIWYDGSDKYYADSVRG**RFTISRDNSKNTLYLQMNSLRAEDTAVYYCARDGY**DILTGNPRDFDY**WGQGTLVTVSS (SEQ ID NO: 331) | DTVMTQTPLSSHVTLGQPASISC**RSSQSLVHSDGNTYLS**WLQQRPGQPPRLLIY**RISRRFS**GVPDRFSGSGAGTDFTLEISRVEAEDVGVYYC**MQSTHVPRT**FGQGTKVEIK (SEQ ID NO: 332) |
| Erubitux ™ | cetuximab | EGFR | QVQLKQSGPGLVQPSQSLSITCTVS**GFSLTNYG**VHWVRQSPGKGLEWLGV**IWSGGNT**DYNTPFTSRLSINKDNSKSQVFFKMNSLQSNDTAIYYC**ARALTYYDYEFAY**WGQGTLVTVSA (SEQ ID NO: 333) | DILLTQSPVILSVSPGERVSFSCRAS**QSIGTN**IHWYQQRTNGSPRLLIK**YAS**ESISGIPSRFSGSGSGTDFTLSINSVESEDIADYYC**QQNNNWPTT**FGAGTKLELK (SEQ ID NO: 334) |
| GA201 | Imgatuzumab | EGFR | QVQLVQSGAEVKKPGSSVKVSCKASGFTFT**DYKIH**WVRQAPGQGLEWMG**YFNPNSGYSTYAQKFQG**RVTITADKSTSTAYMELSS | DIQMTQSPSSLSASVGDRVTITC**RASQGINNYLN**WYQQKPGKAPKRLIY**NTNNLQT**GVPSRFSGSGSGTEFTLTISSLQPED |

TABLE 5-continued

Reference Antibody Sequences

| Trade Name | Antibody Name | Target Cell Marker | VH Sequence | VL Sequence |
|---|---|---|---|---|
| | | | LRSEDTAVYYCAR**LSPGGYYVMDA**WGQGTTVTVSS (SEQ ID NO: 335) | FATYYC**LQHNSFPT**FGQGTKLEIK (SEQ ID NO: 336) |
| Humax | zalutu-mumab | EGFR | QVQLVESGGGVVQPGRSLRLSCAASGFTFS**TYGMH**WVRQAPGKGLEWVA**VIWDDGSYKYYGDSVKG**RFTISRDNSKNTLYLQMNSLRAEDTAVYYCAR**DGITMVRGVMKDYFDY**WGQGTLVTVSS (SEQ ID NO: 337) | AIQLTQSPSSLSASVGDRVTITC**RASQDISSALV**WYQQKPGKAPKLLIY**DASSLES**GVPSRFSGSESGTDFTLTISSLQPEDFATYYC**QQFNSYPLT**FGGGTKVEIK (SEQ ID NO: 338) |
| IMC-11F8 | necitu-mumab | EGFR | QVQLQESGPGLVKPSQTLSLTCTVSGGSIS**SGDYYWS**WIRQPPGKGLEWIG**YIYYSGSTDYNPSLKS**RVTMSVDTSKNQFSLKVNSVTAADTAVYYCAR**VSIFGVGTFDY**WGQGTLVTVSS (SEQ ID NO: 339) | EIVMTQSPATLSLSPGERATLSC**RASQSVSSYLA**WYQQKPGQAPRLLIY**DASNRAT**GIPARFSGSGSGTDFTLTISSLEPEDFAVYYC**HQYGSTPLT**FGGGTKAEIK (SEQ ID NO: 340) |
| MM-151 | P1X | EGFR | QVQLVQSGAEVKKPGSSVKVSCKASGGTFS**SYAIS**WVRQAPGQGLEWMG**SIIPIFGTVNYAQKFQG**RVTITADESTSTAYMELSSLRSEDTAVYYCAR**DPSVNLYWYFDL**WGRGTLVTVSS (SEQ ID NO: 341) | DIQMTQSPSTLSASVGDRVTITC**RASQSISSWWA**WYQQKPGKAPKLLIY**DASSLES**GVPSRFSGSGSGTEFTLTISSLQPDDFATYYC**QQYHAHPTT**FGGGTKVEIK (SEQ ID NO: 342) |
| MM-151 | P2X | EGFR | QVQLVQSGAEVKKPGSSVKVSCKASGGTFG**SYAIS**WVRQAPGQGLEWMG**SIIPIFGAANPAQKSQG**RVTITADESTSTAYMELSSLRSEDTAVYYCAK**MGRGKVAFDI**WGQGTMVTVSS (SEQ ID NO: 343) | DIVMTQSPDSLAVSLGERATINC**KSSQSVLYSPNNKNYLA**WYQQKPGQPPKLLIY**WASTRES**GVPDRFSGSGSGTDFTLTISSLQAEDVAVYYC**QQYYGSPIT**FGGGTKVEIK (SEQ ID NO: 344) |
| MM-151 | P3X | EGFR | QVQLVQSGAEVKKPGASVKVSCKASGYAFT**SYGIN**WVRQAPGQGLEWMG**WISAYNGNTYYAQKLRG**RVTMTTDTSTSTAYMELRSLRSDDTAVYYCAR**DLGGYGSGSVPFDP**WGQGTLVTVSS (SEQ ID NO: 345) | EIVMTQSPATLSVSPGERATLSC**RASQSVSSNLA**WYQQKPGQAPRLLIY**GASTRAT**GIPARFSGSGSGTEFTLTISSLQSEDFAVYYC**QDYRTWPRRV**FGGGTKVEIK (SEQ ID NO: 346) |
| TheraCIM | nimotu-zumab | EGFR | QVQLQQSGAEVKKPGSSVKVSCKASGYTFT**NYYIY**WVRQAPGQGLEWIG**GINPTSGGSNFNEKFKT**RVTITADESSTTAYMELSSLRSEDTAFYFCTR**QGLWFDSDRGFDF**WGQGTTVTVSS (SEQ ID NO: 347) | DIQMTQSPSSLSASVGDRVTITC**RSSQNIVHSNGNTYLD**WYQQTPGKAPKLLIY**KVSNRFS**GVPSRFSGSGSGTDFTFTISSLQPEDIATYYC**FQYSHVPWT**FGQGTKLQIT (SEQ ID NO: 348) |
| Vecti-bix ™ | panitu-mimab | EGFR | QVQLQESGPGLVKPSETLSLTCTVS**GGSVSSGDYY**WTWIRQSPGKGLEWIGH**IYYSGNT**NYNPSLKSRLTISIDTSKTQFSLKLSSVTAADTAIYYC**VRDRVTGAFDI**WGQGTMVTVSS (SEQ ID NO: 349) | DIQMTQSPSSLSASVGDRVTITCQAS**QDISNY**LNWYQQKPGKAPKLLIY**DAS**NLETGVPSRFSGSGSGTDFTFTISSLQPEDIATYFC**QHFDHLPLA**FGGGTKVEIK (SEQ ID NO: 350) |

TABLE 5-continued

Reference Antibody Sequences

| Trade Name | Antibody Name | Target Cell Marker | VH Sequence | VL Sequence |
| --- | --- | --- | --- | --- |
| 07D06 | | EGFR | QIQLVQSGPELKKPGETVKISCKAS**GYTFTEYP**IHWVKQAPGKGFKVVMGM**IYTDIGKP**TYAEEFKGRFAFSLETSASTAYLQINNLKNEDTATYFC**VRDRYDSLFDY**WGQGTTLTVSS (SEQ ID NO: 351) | DVVMTQTPLSLPVSLGDQASISCRSS**QSLVHSNGNTY**LHWYLQKPGQSPKLLIY**KVSNR**FSGVPDRFSGSGSGTDFTLKISRVEAEDLGVYFC**SQSTHVPWT**FGGGTKLEIK (SEQ ID NO: 352) |
| 12D03 | | EGFR | EMQLVESGGGFVKPGGSLKLSCAASGFAFS**HYDMS**WVRQTPKQRLEWVA**YIASGGDITYYADTVKG**RFTISRDNAQNTLYLQMSSLKSEDTAMFYCSR**SSYGNNGDALDF**WGQGTSVTVSS (SEQ ID NO: 353) | DVVMTQTPLSLPVSLGDQASISC**RSSQSLVHSNGNTYLH**WYLQKPGQSPKLLIY**KVSNRFS**GVPDRFSGSGSGTDFTLKISRVEAEDLGVYFC**SQSTHVLT**FGSGTKLEIK (SEQ ID NO: 354) |
| | C1 | HER2 | QVQLVESGGGLVQPGGSLRLSCAASGFTFS**SYAMG**WVRQAPGKGLEWVS**SISGSSRYIYYADSVKG**RFTISRDNSKNTLYLQMNSLRAEDTAVYYCAK**MDASGSYFNE**WGQGTLVTVSS (SEQ ID NO: 355) | QSPSFLSAFVGDRITITC**RASPGIRNYLA**WYQQKPGKAPKLLIY**AASTLQS**GVPSRFSGSGSGTDFTLTISSLQPEDFATYYC**QQYNSYPLS**FGGGTKVEIK (SEQ ID NO: 356) |
| Erbicin | | HER2 | QVQLLQSAAEVKKPGESLKISCKGSGYSFT**SYWIG**WVRQMPGKGLEWMG**IIYPGDSDTRYSPSFQG**QVTISADKSISTAYLQWSSLKASDTAVYYCAR**WRDSPL**WGQGTLVTVSS (SEQ ID NO: 357) | QAVVTQEPSFSVSPGGTVTLTC**GLSSGSVSTSYYPS**WYQQTPGQAPRTLIY**STNTRSS**GVPDRFSGSILGNKAALTITGAQADDESDYYC**VLYMGSGQYV**FGGGTKLTVL (SEQ ID NO: 358) |
| Hercep-tin | trastu-zumab | HER2 | EVQLVESGGGLVQPGGSLRLSCAAS**GFNIKDTY**IHWVRQAPGKGLEWVAR**IYPTNGYT**RYADSVKGRFTISADTSKNTAYLQMNSLRAEDTAVYYC**SRWGGDGFYAMDY**WGQGTLVTVSS (SEQ ID NO: 359) | DIQMTQSPSSLSASVGDRVTITCRAS**QDVNTA**VAWYQQKPGKAPKLLIY**SAS**FLYSGVPSRFSGSRSGTDFTLTISSLQPEDFATYYC**QQHYTTPPT**FGQGTKVEIK (SEQ ID NO: 360) |
| MAGH 22 | margetu-ximab | HER2 | QVQLQQSGPELVKPGASLKLSCTAS**GFNIKDTY**IHWVKQRPEQGLEWIGR**IYPTNGYT**RYDPKFQDKATITADTSSNTAYLQVSRLTSEDTAVYYC**SRWGGDGFYAMDY**WGQGASVTVSS (SEQ ID NO: 361) | DIVMTQSHKFMSTSVGDRVSITCKAS**QDVNTA**VAWYQQKPGHSPKLLIY**SAS**FRYTGVPDRFTGSRSGTDFTFTISSVQAEDLAVYYC**QQHYTTPPT**FGGGTKVEIK (SEQ ID NO: 362) |
| MM-302 | F5 | HER2 | QVQLVESGGGLVQPGGSLRLSCAASGFTFR**SYAMS**WVRQAPGKGLEWVS**AISGRGDNTYYADSVKG**RFTISRDNSKNTLYLQMNSLRAEDTAVYYC**AKMTSNAFAFDY**WGQGTLVTVSS (SEQ ID NO: 363) | QSVLTQPPSVSGAPGQRVTISC**TGSSSNIGAGYGVH**WYQQLPGTAPKLLIY**GNTNRPS**GVPDRFSGFKSGTSASLAITGLQAEDEADYYC**QFYDSSLSGWV**FGGGTKLTVL (SEQ ID NO: 364) |
| Perjeta | pertu-zumab | HER2 | EVQLVESGGGLVQPGGSLRLSCAAS**GFTFTDYT**MDWVRQAPGKGLEWVAD**VNPNSGGS**IYNQRFKGRFTLSVDRSKNTLYLQMNSLRAEDTAVYYC**ARNL** | DIQMTQSPSSLSASVGDRVTITCKASQ**DVSIG**VAWYQQKPGKAPKLLIY**SAS**YRYTGVPSRFSGSGSGTDFTLTISSLQPEDFATYYC**QQYYIYPYT**FG |

TABLE 5-continued

Reference Antibody Sequences

| Trade Name | Antibody Name | Target Cell Marker | VH Sequence | VL Sequence |
|---|---|---|---|---|
| | | | **GPSFYFDY**WGQGTLVTVSS (SEQ ID NO: 365) | QGTKVEIK (SEQ ID NO: 366) |
| MM-121/SAR256212 | | HER3 | EVQLLESGGGLVQPGGSLRLSCAASGFTFS**HYVMA**WVRQAPGKGLEWVS**SISSSGGWTLYADSVKG**RFTISRDNSKNTLYLQMNSLRAEDTAVYYCTR**GLKMATIFDY**WGQGTLVTVSS (SEQ ID NO: 367) | QSALTQPASVSGSPGQSITISC**TGTSSDVGSYNVVS**WYQQHPGKAPKLIIY**EVSQRPS**GVSNRFSGSKSGNTASLTISGLQTEDEADYYC**CSYAGSSIFVI**FGGGTKVTVL (SEQ ID NO: 368) |
| MEHD 7945A | Duligo-tumab | EGFR/HER3 | EVQLVESGGGLVQPGGSLRLSCAASGFTL**GDWIH**WVRQAPGKGLEWVG**EISAAGGYTDYADSVKG**RFTISADTSKNTAYLQMNSLRAEDTAVYYCAR**ESRVSFEAAMDY**WGQGTLVTVSS (SEQ ID NO: 369) | DIQMTQSPSSLSASVGDRVTITC**RASQNIATDVA**WYQQKPGKAPKLLIY**SASFLYS**GVPSRFSGSGSGTDFTLTISSLQPEDFATYYC**QQSEPEPYT**FGQGTKVEIK (SEQ ID NO: 370) |
| MM-111 | | HER2/3 | QVQLQESGGGLVKPGGSLRLSCAASGFTFS**SYWMS**WVRQAPGKGLEWVA**NINRDGSASYYVDSVKG**RFTISRDDAKNSLYLQMNSLRAEDTAVYYCAR**DRGVGYFDL**WGRGTLVTVSS (SEQ ID NO: 371) | QSALTQPASVSGSPGQSITISC**TGTSSDVGGYNFVS**WYQQHPGKAPKLMIY**DVSDRPS**GVSDRFSGSKSGNTASLIISGLQADDEADYYC**SSYGSSSTHVI**FGGGTKVTVL (SEQ ID NO: 372) |
| MM-111 | | HER2/3 | QVQLVQSGAEVKKPGESLKISCKGSGYSFT**SYWIA**WVRQMPGKGLEYMG**LIYPGDSDTKYSPSFQG**QVTISVDKSVSTAYLQWSSLKPSDSAVYFCAR**HDVGYCTDRTCAKWPEWLGV**WGQGTLVTVSS (SEQ ID NO: 373) | QSVLTQPPSVSAAPGQKVTISC**SGSSSNIGNNYVS**WYQQLPGTAPKLLIY**DHTNRPA**GVPDRFSGSKSGTSASLAISGFRSEDEADYYC**ASWDYTLSGWV**FGGGTKLTVL (SEQ ID NO: 374) |
| | Hu3S193 | Lewis-Y | EVQLVESGGGVVQPGRSLRLSCSTSGFTFS**DYYMY**WVRQAPGKGLEWVA**YMSNVGAITDYPDTVKG**RFTISRDNSKNTLFLQMDSLRPEDTGVYFCAR**GTRDGSWFAY**WGQGTPVTVSS (SEQ ID NO: 375) | DIQMTQSPSSLSASVGDRVTITC**RSSQRIVHSNGNTYLE**WYQQTPGKAPKLLIY**KVSNRFS**GVPSRFSGSGSGTDFTFTISSLQPEDIATYYC**FQGSHVPFT**FGQGTKLQIT (SEQ ID NO: 376) |
| BAY 94-9343 | anetu-mab ravtan-sine | Meso-thelin | QVELVQSGAEVKKPGESLKISCKGS**GYSFTSYW**IGWVRQAPGKGLEWMGI**IDPGDSRT**RYSPSFQGQVTISADKSISTAYLQWSSLKASDTAMYYC**ARGQLYGGTYMDG**WGQGTLVTVSS (SEQ ID NO: 377) | DIALTQPASVSGSPGQSITISCTGT**SSDIGGYNS**VSWYQQHPGKAPKLMIY**GVN**NRPSGVSNRFSGSKSGNTASLTISGLQAEDEADYYC**SSYDIESATPV**FGGGTKLTVL (SEQ ID NO: 378) |
| | SS1 | Meso-thelin | QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGQGTTVTVSS (SEQ ID NO: 379) | DIELTQSPAIMSASPGEKVTMTCSASSSVSYMHWYQQKSGTSPKRWIYDTSKLASGVPGRFSGSGSGNSYSLTISSVEAEDDATYYCQQWSGYPLTFGAGTKLEIK (SEQ ID NO: 380) |
| | | Meso-thelin | QVYLVESGGGVVQPGRSLRLSCAASGITFS**IYGMH**WVRQAPGKGLEWVA**VI** | EIVLTQSPATLSLSPGERATLSC**RASQSVSSYLA**WYQQKPGQAPRLLIY |

TABLE 5-continued

Reference Antibody Sequences

| Trade Name | Antibody Name | Target Cell Marker | VH Sequence | VL Sequence |
| --- | --- | --- | --- | --- |
| | | | **WYDGSHEYYADSVKG**RFTISRDNSKNTLYLLMNSLRAEDTAVYYCARDG**DGDYYDSGSPLDY**WGQGTLVTVSS (SEQ ID NO: 381) | **DASNRAT**GIPARFSGSGSGTDFTLTISSLEPEDFAVYYC**QQRSNWPLT**FGGGTKVEIK (SEQ ID NO: 382) |
| | | Mesothelin | QVHLVESGGGVVQPGRSLRLSCVASGITF**RIYGM**HWVRQAPGKGLEWVA**VLWYDGSHEYYADSVKG**RFTISRDNSKNTLYLQMNSLRAEDTAIYYCAR**DGDYYDSGSPLDY**WGQGTLVTVSS (SEQ ID NO: 383) | EIVLTQSPATLSLSPGERATLSC**RASQSVSSYLA**WYQQKPGQAPRLLIY**DASNRAT**GIPARFSGSGSGTDFTLTISSLEPEDFAVYYC**QQRSNWPLT**FGGGTKVEIK (SEQ ID NO: 384) |
| | | Mesothelin | EVHLVESGGGLVQPGGSLRLSCAASGFTFS**RYWMS**WVRQAQGKGLEWVA**SIKQAGSEKTYVDSVKG**RFTISRDNAKNSLSLQMNSLRAEDTAVYYCAR**EGAYYYDSASYYPYYYYYSMDV**WGQGTTVTVSS (SEQ ID NO: 385) | EIVLTQSPGTLSLSPGERATLSC**RASQSVSSSYLA**WYQQKPGQAPRLLIY**GASSRAT**GIPDRFSGSGSGTDFTLTISRLEPEDFAVYYC**QQYGSSQYT**FGQGTKLEIK (SEQ ID NO: 386) |
| MORAb-009 | amatuximab | Mesothelin | QVQLQQSGPELEKPGASVKISCKASGYSFT**GYTMN**WVKQSHGKSLEWIG**LITPYNGASSYNQKFRG**KATLTVDKSSSTAYMDLLSLTSEDSAVYFCAR**GGYDGRGFDY**WGSGTPVTVSS (SEQ ID NO: 387) | DIELTQSPAIMSASPGEKVTMTC**SASSSVSYMH**WYQQKSGTSPKRWIY**DTSKLAS**GVPGRFSGSGSGNSYSLTISSVEAEDDATYYC**QQWSKHPLT**FGSGTKVEIK (SEQ ID NO: 388) |
| hPAM4 | | MUC-1 | EVQLQESGPELVKPGASVKMSCKASGYTFP**SYVLH**WVKQKPGQGLEWIG**YINPYNDGTQYNEKFKG**KATLTSDKSSSTAYMELSRLTSEDSAVYYCAR**GFGGSYGFAY**WGQGTLITVSA (SEQ ID NO: 389) | DIVMTQSPAIMSASPGEKVTMTC**SASSSVSSSYLY**WYQQKPGSSPKLWIY**STSNLAS**GVPARFSGSGSGTSYSLTISSMEAEDAASYFC**HQWNRYPYT**FGGGTKLEIK (SEQ ID NO: 390) |
| hPAM4-Cide | clivatuzumab | MUC1 | QVQLQQSGAEVKKFGASVKVSCEASGYTFP**SYVLH**WVKQAPGQGLEWIG**YINPYNDGTQTNKKFKG**KATLTRDTSINTAYMELSRLRSDDTAVYYCAR**GFGGSYGFAY**NGQGTLVTVSS (SEQ ID NO: 391) | DIQLTQSPSSLSASVGDRVTMTC**SASSSVSSSYLY**WYQQKPGKAPKLWIY**STSNLAS**GVPARFSGSGSGTDFTLTISSLQPEDSASYFC**HQWNRYPYT**FGGGTRLEIK (SEQ ID NO: 392) |
| SAR566658 | huDS6v1.01 | MUC1 | QAQLQVSGAEVVKPGASVKMSCKASGYTFT**SYNMH**WVKQTPGQGLEWIG**YIYPGNGATNYNQKFQG**KATLTADTSSSTAYMQISSLTSEDSAVYFCAR**GDSVPFAY**WGQGTLVTVSA (SEQ ID NO: 393) | EIVLTQSPATMSASPGERVTITC**SAHSSVSFMH**WFQQKPGTSPKLWIY**STSSLAS**GVPARFGGSGSGTSYSLTISSMEAEDAATYYC**QQRSSFPLT**FGAGTKLELK (SEQ ID NO: 394) |
| Theragyn | Pemtumomab muHMFG1 | MUC1 | QVQLQQSGAELMKPGASVKISCKATGYTFS**AYWIE**WVKQRPGHGLEWIG**EILPGSNNSRYNEKFKG**KATFTADTSSNTAYMQLSSLTSEDSAVYYCSR**SYDFAWFAY**WGQGTPVTVSA (SEQ ID NO: 395) | DIVMSQSPSSLAVSVGEKVTMSC**KSSQSLLYSSNQKIYLA**WYQQKPGQSPKWYW**ASTRES**GVPDRFTGGGSGTDFTLTISSVKAEDLAVYYC**QQYYRYPRT**FGGGTKLEIK (SEQ ID NO: 396) |

TABLE 5-continued

Reference Antibody Sequences

| Trade Name | Antibody Name | Target Cell Marker | VH Sequence | VL Sequence |
|---|---|---|---|---|
| Therex | Sontu-zumab huHMFG 1 AS1402 R1150 | MUC1 | QVQLVQSGAEVKKPGASVKVSCKASGYTFSAYWIEWVRQAPGKGLEWVGEILPGSNNSRYNEKFKGRVTVTRDTSTNTAYMELSSLRSEDTAVYYCARSYDFAWFAYWGQGTLVTVSS (SEQ ID NO: 397) | DIQMTQSPSSLSASVGDRVTITCKSSQSLLYSSNQKIYLAWYQQKPGKAPKLLIYWASTRESGVPSRFSGSGSGTDFTFTISSLQPEDIATYYCQQYYRYPRTFGQGTKVEIK (SEQ ID NO: 398) |
| MDX-1105 or BMS-936559 | PD-L1 | | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS (SEQ ID NO: 399) | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK (SEQ ID NO: 400) |
| MEDI-4736 | durval-umab | PD-L1 | EVQLVESGGGLVQPGGSLRLSCAASGFTFSRYWMSWVRQAPGKGLEWVANIKQDGSEKYYVDSVKGRFTISRDNAKNSLYLQMNSLRAEDTAVYYCAREGGWFGELAFDYWGQGTLVTVSS (SEQ ID NO: 401) | EIVLTQSPGTLSLSPGERATLSCRASQRVSSSYLAWYQQKPGQAPRLLIYDASSRATGIPDRFSGSGSGTDFTLTISRLEPEDFAVYYCQQYGSLPWTFGQGTKVEIK (SEQ ID NO: 402) |
| MPDL 3280A | atezoli-zumab | PD-L1 | EVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGFDYWGQGTLVTVSS (SEQ ID NO: 403) | DIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIK (SEQ ID NO: 404) |
| MSB00 10718C | avelu-mab | PD-L1 | EVQLLESGGGLVQPGGSLRLSCAASGFTFSSYIMMWVRQAPGKGLEWVSSIYPSGGITFYADTVKGRFTISRDNSKNTLYLQMNSLRAEDTAVYYCARIKLGTVTTVDYWGQGTLVTVSS (SEQ ID NO: 405) | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTRVFGTGTKVTVL (SEQ ID NO: 406) |
| MLN5 91 | | PSMA | EVQLVQSGPEVKKPGATVKISCKTSGYTFTEYTIHWVKQAPGKGLEWIGNINPNNGGTTYNQKFEDKATLTVDKSTDTAYMELSSLRSEDTAVYYCAAGWNFDYWGQGTLLTVSS (SEQ ID NO: 407) | DIQMTQSPSSLSTSVGDRVTLTCKASQDVGTAVDWYQQKPGPSPKLLIYWASTRHTGIPSRFSGSGSGTDFTLTISSLQPEDFADYYCQQYNSYPLTFGPGTKVDIK (SEQ ID NO: 408) |
| MT112 | pasotux-izumab | PSMA | QVQLVESGGGLVKPGESLRLSCAASGFTFSDYYMYWVRQAPGKGLEWVAIISDGGYYTYYSDIIKGRFTISRDNAKNSLYLQMNSLKAEDTAVYYCARGFPLLRHGAMDYWGQGTLVTVSS (SEQ ID NO: 409) | DIQMTQSPSSLSASVGDRVTITCKASQNVDTNVAWYQQKPGQAPKSLIYSASYRYSDVPSRFSGSASGTDFTLTISSVQSEDFATYYCQQYDSYPYTFGGGTKLEIK (SEQ ID NO: 410) |
| | | ROR1 | QEQLVESGGRLVTPGGSLTLSCKASGFDFSAYYMSWVRQAPGKGLEWIATIYPSSGKTYYATWVNGR | ELVLTQSPSVSAALGSPAKITCTLSSAHKTDTIDWYQQLQGEAPRYLMQVQSDGSYTKRPGVP |

TABLE 5-continued

Reference Antibody Sequences

| Trade Name | Antibody Name | Target Cell Marker | VH Sequence | VL Sequence |
|---|---|---|---|---|
| | | | FTISSDNAQNTVDLQMN<br>SLTAAD<br>RATYFCARDSYADDGAL<br>FNIWGPGTLVTISS<br>(SEQ ID NO: 411) | DRFSGSSSGADRYLIIP<br>SVQADDEADY<br>YC**GADYIGGYV**FGGGT<br>QLTVTG<br>(SEQ ID NO: 412) |
| | | ROR1 | EVKLVESGGGLVKPGGS<br>LKLSCAASGFTFS**SYAM**<br>**S**WVRQIPEKRLEVVVA**SI**<br>**SRGGTTYYPDSVKG**RFT<br>ISRDNVRNILYLQMSSLR<br>SEDT<br>AMYYCGR**YDYDGYYAM**<br>**DY**WGQGTSVTVSS<br>(SEQ ID NO: 413) | DIKMTQSPSSMYASLG<br>ERVTITC**KASPDINSYL**<br>**S**WFQQKPGKSPKTLIY<br>**RANRLVD**GVPSRFSG<br>GGSGQDYSLTINSLEY<br>EDMGIYYC**LQ**<br>**YDEFPYT**FGGGTKLEM<br>K<br>(SEQ ID NO: 414) |
| | | ROR1 | QSLEESGGRLVTPGTPL<br>TLTCTVSGIDLN**SHWMS**<br>EVRQAPGKGLEWIG**IIA**<br>**ASGSTYYANWAKG**RFTI<br>SKTSTTVDLRIASPTTED<br>TATY<br>FCAR**DYGDYRLVTFN**W<br>GPGTLVTVSS<br>(SEQ ID NO: 415) | ELVMTQTPSSVSAAVG<br>GTVTINC**QASQSIGSYL**<br>**A**WYQQKPGQPPKLLIY<br>**YASNLAS**GVPSRFSGS<br>GSGTEYTLTISGVQRE<br>DAATYYC**LG**<br>**SLSNSDNV**FGGGTELE<br>IL<br>(SEQ ID NO: 416) |
| | | ROR1 | QSVKESEGDLVTPAGNL<br>TLTCTASGSDIN**DYPIS**W<br>VRQAPGKGLEWIG**FINS**<br>**GGSTWYASWVKG**RFTIS<br>RTSTTVDLKMTSLTTDDT<br>ATY<br>FCAR**GYSTYYCDFNI**WG<br>PGTLVTISS<br>(SEQ ID NO: 417) | ELVMTQTPSSTSGAVG<br>GTVTINC**QASQSIDSNL**<br>**A**WFQQKPGQPPTLLIY<br>**RASNLAS**GVPSRFSGS<br>RSGTEYTLTISGVQRE<br>DAATYYC**LG**<br>**GVGNVSYRTS**FGGGT<br>EVVVK<br>(SEQ ID NO: 418) |
| CC49 (Human-ized) | | TAG-72 | QVQLVQSGAEVVKPGAS<br>VKISCKASGYTFT**DHAIH**<br>WVKQNPGQRLEWIG**YF**<br>**SPGNDDFKYNERFKG**KA<br>TLTADTSASTAYVELSSL<br>RSEDTAVYFCTR**SLNMA**<br>**Y**WGQGTLVTVSS<br>(SEQ ID NO: 419) | DIVMSQSPDSLAVSLG<br>ERVTLNCKSS**QSLLYS**<br>**GNQKNYLA**WYQQKPG<br>QSPKLLIY**WASARES**G<br>VPDRFSGSGSGTDFTL<br>TISSVQAEDVAVYYC**Q**<br>**QYYSYPLT**FGAGTKLE<br>LK<br>(SEQ ID NO: 420) |
| | Murine A1 | TPBG/ 5T4 | QIQLVQSGPELKKPGETVK<br>ISCKAS**GYTFTNFGMN**WVK<br>QGPGEGLKWMG**WINTNTGE**<br>P**PRYAEEFKG**RXAFSLETTA<br>STAYLQINNLKNEDTATYF<br>CAR**DWDGAYFFDY**WGQGTT<br>LTVSS<br>(SEQ ID NO: 421) | S IVMTQTPKFLLVSAGDR<br>VTITC**KASQSVSNDVA**WY<br>QQKPGQSPKLLIN**FATNR**<br>**YT**GVPNRFTGSGYGTDFT<br>FTISTVQAEDLALYFC**QQ**<br>**DYSSPWT**FGGGTKLEIK<br>(SEQ ID NO: 422) |
| | Murine A2 | TPBG/ 5T4 | QVQLQQSRPELVKPGASVK<br>MSCKAS**GYTFTDYVIS**WVK<br>QRTGQGLEWIG**EIYPGSNS**<br>**IYYNEKFKG**RATLTA<br>DKSSSTAYMQLSSLTSEDS<br>AVYFCAM**GGNYGFDY**WGQG<br>TTLTVSS<br>(SEQ ID NO: 423) | SVIMSRGQIVLTQSPAIM<br>SASLGERVTLTC**TASSSV**<br>**NSNYLH**WYQQKPGSSPKL<br>WIY**STSNLAS**GVPARFSG<br>SGSGTSYSLTISSMEAED<br>AATYYC**HQYHRSPLT**FGA<br>GTKLELK<br>(SEQ ID NO: 424) |
| | Murine A3 | TPBG/ 5T4 | EVQLVESGGGLVQPKGSLK<br>LSCAAS**GFTFNTYAMN**WVR<br>QAPGKGLEWVA**RIRSKSNN**<br>**YATYYADSVKD**RFTISRDD<br>SQSMLYLQMNNLKTEDTAM<br>YXCVR**QWDYDVRAMNY**WGQ<br>GTSVTVSS<br>(SEQ ID NO: 425) | DIVMTQSHIFMSTSVGDR<br>VSITC**KASQDVDTAVA**WY<br>QQKPGQSPKLLIY**WASTR**<br>**LT**GVPDRFTGSGSGTDFT<br>LTISNVQSEDLADYFC**QQ**<br>**YSSYPYT**FGGGTKLEIK<br>(SEQ ID NO: 426) |

TABLE 5-continued

Reference Antibody Sequences

| Trade Name | Antibody Name | Target Cell Marker | VH Sequence | VL Sequence |
|---|---|---|---|---|
| IMMU-132 | hRS-7 | TROP-2 | QVQLQQSGSELKKPGASVKVSCKASGYTFTNYGMNWVKQAPGQGLKWMGWINTYTGEPTYTDDFKGRFAFSLDTSVSTAYLQISSLKADDTAVYFCARGGFGSSYWYFDVWGQGSLVTVSS (SEQ ID NO: 427) | DIQLTQSPSSLSASVGDRVSITCKASQDVSIAVAWYQQKPGKAPKLLIYSASYRYTGVPDRFSGSGSGTDFTLTISSLQPEDFAVYYCQQHYITPLTFGAGTKVEIK (SEQ ID NO:428) |
| IMC-18F1 | icrucu-mab | VEGFR1 | QAQVVESGGGVVQSGRSLRLSCAASGFAFSSYGMHWVRQAPGKGLEWVAVIWYDGSNKYYADSVRGRFTISRDNSENTLYLQMNSLRAEDTAVYYCARDHYGSGVHHYFYYGLDVWGQGTTVTVSS (SEQ ID NO: 429) | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGGGTKVEIK (SEQ ID NO: 430) |
| Cyramza | ramucir-umab | VEGFR2 | EVQLVQSGGGLVKPGGSLRLSCAASGFTFSSYSMNWVRQAPGKGLEWVSSISSSSSYIYYADSVKGRFTISRDNAKNSLYLQMNSLRAEDTAVYYCARVTDAFDIWGQGTMVTVSSA (SEQ ID NO: 431) | DIQMTQSPSSVSASIGDRVTITCRASQGIDNWLGWYQQKPGKAPKLLIYDASNLDTGVPSRFSGSGSGTYFTLTISSLQAEDFAVYFCQQAKAFPPTFGGGTKVDIK (SEQ ID NO: 432) |
| g165D FM-PEG | alacizum abpegol | VEGFR2 | EVQLVESGGGLVQPGGSLRLSCAASGFTFSSYGMSWVRQAPGKGLEWVATITSGGSYTYYVDSVKGRFTISRDNAKNTLYLQMNSLRAEDTAVYYCVRIGEDALDYWGQGTLVTVSS (SEQ ID NO: 433) | DIQMTQSPSSLSASVGDRVTITCRASQDIAGSLNWLQQKPGKAIKRLIYATSSLDSGVPKRFSGSRSGSDYTLTISSLQPEDFATYYCLQYGSFPPTFGQGTKVEIK (SEQ ID NO: 434) |
| Imclon e6.64 | | VEGFR2 | KVQLQQSGTELVKPGASVKVSCKASGYIFTEYIIHWVKQRSGQGLEWIGWLYPESNIIKYNEKFKDKATLTADKSSSTVYMELSRLTSEDSAVYFCTRHDGTNFDYWGQGTTLTVSSA (SEQ ID NO: 435) | DIVLTQSPASLAVSLGQRATISCRASESVDSYGNSFMHWYQQKPGQPPKLLIYRASNLESGIPARFSGSGSRTDFTLTINPVEADDVATYYCQQSNEDPLTFGAGTKLELK (SEQ ID NO: 436) |

*underlined sequences, if present, are CDRs within the VL and VH

In some embodiments, the CAR and/or engineered TCR of the disclosure comprises an antigen binding domain comprising a VH and a VL, and the VH and VL are selected from the group consisting of SEQ ID NO: 217 and SEQ ID NO: 218, SEQ ID NO: 219 and SEQ ID NO: 220, SEQ ID NO: 221 and SEQ ID NO: 222, SEQ ID NO: 223 and SEQ ID NO: 224, SEQ ID NO: 225 and SEQ ID NO: 226, SEQ ID NO: 227 and SEQ ID NO: 228, SEQ ID NO: 229 and SEQ ID NO: 230, SEQ ID NO: 231 and SEQ ID NO: 232, SEQ ID NO: 233 and SEQ ID NO: 234, SEQ ID NO: 235 and SEQ ID NO: 236, SEQ ID NO: 237 and SEQ ID NO: 238, SEQ ID NO: 239 and SEQ ID NO: 240, SEQ ID NO: 241 and SEQ ID NO: 242, SEQ ID NO: 243 and SEQ ID NO: 244, SEQ ID NO: 245 and SEQ ID NO: 246, SEQ ID NO: 247 and SEQ ID NO: 248, SEQ ID NO: 249 and SEQ ID NO: 250, SEQ ID NO: 251 and SEQ ID NO: 252, SEQ ID NO: 253 and SEQ ID NO: 254, SEQ ID NO: 255 and SEQ ID NO: 256, SEQ ID NO: 257 and SEQ ID NO: 258, SEQ ID NO: 259 and SEQ ID NO: 260, SEQ ID NO: 261 and SEQ ID NO: 262, SEQ ID NO: 263 and SEQ ID NO: 264, SEQ ID NO: 265 and SEQ ID NO: 266, SEQ ID NO: 267 and SEQ ID NO: 268, SEQ ID NO: 269 and SEQ ID NO: 270, SEQ ID NO: 271 and SEQ ID NO: 272, SEQ ID NO: 273 and SEQ ID NO: 274, SEQ ID NO: 275 and SEQ ID NO: 276, SEQ ID NO: 277 and SEQ ID NO: 278, SEQ ID NO: 279 and SEQ ID NO: 280, SEQ ID NO: 281 and SEQ ID NO: 282, SEQ ID NO: 283 and SEQ ID NO: 284, SEQ ID NO: 285 and SEQ ID NO: 286, SEQ ID NO: 287 and SEQ ID NO: 288, SEQ ID NO: 289 and SEQ ID NO: 290, SEQ ID NO: 291 and SEQ ID NO: 292, SEQ ID NO: 293 and SEQ ID NO: 294, SEQ ID NO: 295 and SEQ ID NO: 296, SEQ ID NO: 297 and SEQ ID NO: 298, SEQ ID NO: 299 and SEQ ID NO: 300, SEQ ID NO: 301 and SEQ ID NO: 302, SEQ ID NO: 303 and SEQ ID NO: 304, SEQ ID NO: 305 and SEQ ID NO: 306, SEQ ID NO: 307 and SEQ ID NO: 308, SEQ ID NO: 309 and SEQ ID NO: 310, SEQ ID NO: 311 and SEQ ID NO: 312, SEQ ID NO: 313 and SEQ ID NO: 314, SEQ ID NO: 315 and SEQ ID NO:

316, SEQ ID NO: 317 and SEQ ID NO: 318, SEQ ID NO: 319 and SEQ ID NO: 320, SEQ ID NO: 321 and SEQ ID NO: 322, SEQ ID NO: 323 and SEQ ID NO: 324, SEQ ID NO: 325 and SEQ ID NO: 326, SEQ ID NO: 327 and SEQ ID NO: 328, SEQ ID NO: 329 and SEQ ID NO: 330, SEQ ID NO: 331 and SEQ ID NO: 332, SEQ ID NO: 333 and SEQ ID NO: 334, SEQ ID NO: 335 and SEQ ID NO: 336, SEQ ID NO: 337 and SEQ ID NO: 338, SEQ ID NO: 339 and SEQ ID NO: 340, SEQ ID NO: 341 and SEQ ID NO: 342, SEQ ID NO: 343 and SEQ ID NO: 344, SEQ ID NO: 345 and SEQ ID NO: 346, SEQ ID NO: 347 and SEQ ID NO: 348, SEQ ID NO: 349 and SEQ ID NO: 350, SEQ ID NO: 351 and SEQ ID NO: 352, SEQ ID NO: 353 and SEQ ID NO: 354, SEQ ID NO: 355 and SEQ ID NO: 356, SEQ ID NO: 357 and SEQ ID NO: 358, SEQ ID NO: 359 and SEQ ID NO: 360, SEQ ID NO: 361 and SEQ ID NO: 362, SEQ ID NO: 363 and SEQ ID NO: 364, SEQ ID NO: 365 and SEQ ID NO: 366, SEQ ID NO: 367 and SEQ ID NO: 368, SEQ ID NO: 369 and SEQ ID NO: 370, SEQ ID NO: 371 and SEQ ID NO: 372, SEQ ID NO: 373 and SEQ ID NO: 374, SEQ ID NO: 375 and SEQ ID NO: 376, SEQ ID NO: 377 and SEQ ID NO: 378, SEQ ID NO: 379 and SEQ ID NO: 380, SEQ ID NO: 381 and SEQ ID NO: 382, SEQ ID NO: 383 and SEQ ID NO: 384, SEQ ID NO: 385 and SEQ ID NO: 386, SEQ ID NO: 387 and SEQ ID NO: 388, SEQ ID NO: 389 and SEQ ID NO: 390, SEQ ID NO: 391 and SEQ ID NO: 392, SEQ ID NO: 393 and SEQ ID NO: 394, SEQ ID NO: 395 and SEQ ID NO: 396, SEQ ID NO: 397 and SEQ ID NO: 398, SEQ ID NO: 399 and SEQ ID NO: 400, SEQ ID NO: 401 and SEQ ID NO: 402, SEQ ID NO: 403 and SEQ ID NO: 404, SEQ ID NO: 405 and SEQ ID NO: 406, SEQ ID NO: 407 and SEQ ID NO: 408, SEQ ID NO: 409 and SEQ ID NO: 410, SEQ ID NO: 411 and SEQ ID NO: 412, SEQ ID NO: 413 and SEQ ID NO: 414, SEQ ID NO: 415 and SEQ ID NO: 416, SEQ ID NO: 417 and SEQ ID NO: 418, SEQ ID NO: 419 and SEQ ID NO: 420, SEQ ID NO: 421 and SEQ ID NO:422, SEQ ID NO: 423 and SEQ ID NO: 424, SEQ ID NO: 425 and SEQ ID NO: 426, SEQ ID NO: 427 and SEQ ID NO: 418, SEQ ID NO: 419 and SEQ ID NO: 430, SEQ ID NO: 431 and SEQ ID NO: 432. SEQ ID NO: 433 and SEQ ID NO: 434, SEQ ID NO: 435 and SEQ ID NO: 436, or sequences having at least 90%, at least 95% or at least 99% identity thereto.

In some embodiments, the cells of the population have been modified such that at least 70%, at least 75%, at least 80%, at least 85%, at least 90%, or at least 95% of the modified cells express a detectable level of the chimeric antigen receptor (CAR) or engineered TCR. In one embodiment, the method of modifying a target nucleic acid sequence of a gene in a population of cells is conducted ex vivo on the population of cells. In another embodiment, the method is conducted in vivo in a subject, wherein the subject is selected from the group consisting of a rodent, a mouse, a rat, a non-human primate, and a human.

Thus, the CasX:gNA systems and methods described herein can be used, in combination with conventional molecular biology methods, to modify populations of cells (examples of which are described more fully, below) to produce a cell having an allogeneic CAR- or TCR-engineered T cell function that, for example, reduces or eliminates undesirable immunogenicity (such as a host versus graft response or a graft versus host response), and enhances survival, proliferation and/or efficacy by altering the gene of a component of the major histocompatibility complex, e.g., an HLA protein, e.g., HLA-A, HLA-B, HLA-C or B2M (encoded by the B2M gene), or a protein that regulates expression of one or more components of the major histocompatibility complex, eliminates proteins that are a part of the T-cell receptor, such as TRAC, represses expression of transcriptional coactivators that regulates y-interferon-activated transcription of Major Histocompatibility Complex (MHC) class I and II genes, such as CIITA, or allows the modified cells to escape the immunosuppressive effects of a factor, such as TGFβ. By reducing a mismatch in the HLA protein, reducing or eliminating the wild-type T cell receptor or other component of the modified cell in comparison to those of the recipient subject, it reduces or eliminates the potential for host vs. graft disease (GVHD) by eliminating host T cell receptor recognition of and response to mismatched (e.g., allogeneic) graft tissue (see, e.g., Takahiro Kamiya, T. et al. A novel method to generate T-cell receptor-deficient chimeric antigen receptor T cells. Blood Advances 2:517 (2018)). This approach, therefore, could be used to generate immune cells with an improved therapeutic index for immuno-oncologic applications in a subject with a disease such as cancer, autoimmune diseases and transplant rejection.

VI. Polynucleotides and Vectors

In another aspect, the present disclosure relates to polynucleotides of the CasX:gNA systems encoding the CasX proteins and the polynucleotides of the gNAs (e.g., the gDNAs and gRNAs) of any of the embodiments described herein. In a further aspect, the disclosure provides donor template polynucleotides for use in modifying the target proteins in the modified cells. In yet a further aspect, the disclosure relates to vectors comprising polynucleotides encoding the CasX proteins and the gNAs described herein, as well as the donor templates and polynucleotides encoding the CAR of the embodiments. In yet a further aspect, the disclosure relates to vectors comprising polynucleotides encoding fusion proteins of the engineered TCR of the embodiments.

In some embodiments, the disclosure provides polynucleotide sequences encoding the reference CasX of SEQ ID NOS:1-3. In other embodiments, the disclosure provides polynucleotide sequences encoding the CasX variants of any of the embodiments described herein. In some embodiments, the disclosure provides an isolated polynucleotide sequence encoding a CasX variant polypeptide sequence set forth in Table 4, or a sequence having at least about 50%, at least about 60%, at least about 70%, at least about 80%, at least about 90%, at least about 95%, at least about 96%, at least about 97%, at least about 98%, or at least about 99% sequence identity thereto. In some embodiments, the disclosure provides an isolated polynucleotide sequence encoding a gNA sequence of any of the embodiments described herein. In some embodiments, the polynucleotide encodes a gNA scaffold sequence set forth in Table 1 or Table 2, or a sequence having at least about 50%, at least about 60%, at least about 70%, at least about 80%, at least about 90%, at least about 95%, at least about 96%, at least about 97%, at least about 98%, at least about 99% sequence identity thereto. In some embodiments, the polynucleotide encodes a gNA scaffold sequence selected from the group consisting of SEQ ID NOS:2101-2280, or a sequence having at least about 50%, at least about 60%, at least about 70%, at least about 80%, at least about 90%, at least about 95%, at least about 96%, at least about 97%, at least about 98%, at least about 99% sequence identity thereto. In other embodiments, the disclosure provides targeting sequence polynucleotides of Tables 3A 3B, or 3C, or a sequences having at least about 65%, at least about 75%, at least about 85%, or at least about 95% identity thereto, as well as DNA encoding the targeting sequences. In some embodiments, the polynucleotide encoding the scaffold sequence further comprises the sequence encoding the targeting sequence such that a gNA capable of binding the CasX and the target sequence can be expressed as a sgNA or dgNA. In other embodiments, the disclosure provides an isolated polynucleotide sequence encoding a gNA sequence that hybridizes with the target gene encoding a protein involved in antigen processing, antigen presentation, antigen recognition, and/or antigen response. In some cases, the polynucleotide sequence encodes a gNA sequence that hybridizes with a target gene exon. In other cases, the polynucleotide sequence encodes a gNA sequence that hybridizes with a target gene intron. In other cases, the polynucleotide sequence encodes a gNA sequence that hybridizes with a target gene intron-exon junction. In other cases, the polynucleotide sequence encodes a gNA sequence that hybridizes with an intergenic region of the target gene. In other cases, the polynucleotide sequence encodes a gNA sequence that hybridizes with a regulatory element of the target gene. In some cases, the cell surface marker regulatory element is 5' of the gene. In other cases, the regulatory element is 3' of the cell surface marker gene. In other cases, the regulatory element comprises the 5' UTR of the target gene. In still other cases, the regulatory element comprises the 3'UTR of the target gene.

In other embodiments, the disclosure provides donor template nucleic acids wherein the donor template comprises a nucleotide sequence having homology but not complete identity to a target sequence of the target nucleic acid for which gene editing is intended. For knock-down/knock-outs, the donor template sequence is typically not identical to the genomic sequence that it replaces and may contain one or more single base changes, insertions, deletions, inversions or rearrangements with respect to the genomic sequence, provided that there is sufficient homology with the target sequence to support homology-directed repair, or the donor template has homologous arms, whereupon insertion can result in a frame-shift or other mutation such that the target protein is not expressed or is expressed at a lower level. In certain embodiments, for knock-down/knock-out modifications, the donor template sequence will have at least about 60%, 70%, 80%, 90%, 95%, 98%, 99%, or 99.9% sequence identity to the target genomic sequence with which recombination is desired. In some embodiments, the target sequence has a sequence that hybridizes with the protein target gene and is inserted at the break sites introduced by the CasX, effecting a modification of the gene sequence. In some cases, the target sequence has a sequence that hybridizes with a target gene exon. In other cases, the target sequence has a sequence that hybridizes with a target gene intron. In other cases, the target sequence has a sequence that hybridizes with a target gene intron-exon junction. In other cases, the target sequence has a sequence that hybridizes with an intergenic region of the target gene. In still other cases, the target sequence has a sequence that hybridizes with a regulatory element of the target gene. In the foregoing embodiments, the donor template can range in size from 10-15,000 nucleotides, 50-10,000 nucleotides, or 100-1000 nucleotides. In some embodiments, the donor template is a single-stranded DNA template. In other embodiments, the donor template is a single stranded RNA template. In other embodiments, the donor template is a double-stranded DNA template.

In other embodiments, the disclosure provides polynucleotides encoding a chimeric antigen receptor (CAR), engineered TCR, or one or more subunits of an engineered TCR with a binding domain specific for a disease antigen, optionally a tumor cell antigen, that is to be introduced into the target cells of the population for expression of the CAR or engineered TCR. In the foregoing, the tumor cell antigen is selected from the group consisting of Cluster of Differentiation 19 (CD19), CD3, CD8, CD7, CD10, CD20, CD22, CD30, CLL1, CD33, CD34, CD38, CD41, CD44, CD47, CD49f, CD56, CD70, CD74, CD99, CD123, CD133, CD138, carbonix anhydrase IX (CAIX), CC chemokine receptor 4 (CCR4), ADAM metallopeptidase domain 12 (ADAM12), adhesion G protein-coupled receptor E2 (ADGRE2), alkaline phosphatase placental-like 2 (ALPPL2), alpha 4 Integrin, angiopoietin-2 (ANG2), B-cell maturation antigen (BCMA), CD44V6, carcinoembryonic antigen (CEA), CEAC, CEACAM5, Claudin 6 (CLDN6), CLDN18, C-type lectin domain family 12 member A (CLEC12A), mesenchymal-epithelial transition factor (cMET), cytotoxic T-lymphocyte-associated protein 4 (CTLA4), epidermal growth factor receptor 1 (EGF1R), EGFR-VIII, epithelial glycoprotein 2 (EGP-2), EGP-40, EphA2, ENPP3, epithelial cell adhesion molecule (Ep-CAM), erb-B2,3,4, folate binding protein (FBP), fetal acetylcholine receptor, folate receptor-a, folate receptor 1 (FOLR1), G protein-coupled receptor 143 (GPR143), glutamate metabotropic receptor 8 (GRM8), glypican-3 (GPC3), ganglioside GD2, ganglioside GD3, human epidermal growth factor receptor 1 (HER1), human epidermal growth factor receptor 2 (HER2), HER3, Integrin B7, intercellular cell-adhesion molecule-1 (ICAM-1), human telomerase reverse transcriptase (hTERT), Interleukin-13 receptor a2 (IL-13R-a2), K-light chain, Kinase insert domain receptor (KDR), Lewis-Y (LeY), chondromodulin-1 (LECT1), L1 cell adhesion molecule, Lysophosphatidic acid receptor 3 (LPAR3), melanoma-associated antigen 1 (MAGE-A1), mesothelin, mucin 1 (MUC1), MUC16, melanoma-associated antigen 3 (MAGEA3), tumor protein p53 (p53), Melanoma Antigen Recognized by T cells 1 (MART1), glycoprotein 100 (GP100), Proteinase3 (PR1), ephrin-A receptor 2 (EphA2), Natural killer group 2D ligand (NKG2D ligand), New York esophageal squamous cell carcinoma 1 (NY-ESO-1), oncofetal antigen (h5T4), prostate-specific membrane antigen (PSMA), programmed death ligand 1 (PDL-1), receptor tyrosine kinase-like orphan receptor 1 (ROR1), trophoblast glycoprotein (TPBG), tumor-associated glycoprotein 72 (TAG-72), tumor-associated calcium signal transducer 2 (TROP-2), tyrosinase, survivin, vascular endothelial growth factor receptor 2 (VEGF-R2), Wilms tumor-1 (WT-1), leukocyte immunoglobulin-like receptor B2 (LILRB2), Preferentially Expressed Antigen In Melanoma (PRAME), T cell receptor beta constant 1 (TRBC1), TRBC2, and (T-cell immunoglobulin mucin-3) TIM-3. In some embodiments, the CAR or engineered TCR comprises an antigen binding domain selected from the group consisting of linear antibody, single domain antibody (sdAb), and single-chain variable fragment (scFv). In a particular embodiment, the antigen binding domain is a scFv. Exemplary CDR and VL and VH sequences suitable for use in the scFv of the embodiments are described herein, including the sequences of Table 5. In one embodiment, the VH, VL, and/or the CDRs of the scFv have one or more amino acid modifications relative to the sequences of Table 5, wherein the scFv retains binding affinity to the tumor antigen, and wherein the modification is selected from the group consisting of a substitution, deletion, and insertion.

In those embodiments comprising a CAR, the CAR can further comprise one or more intracellular signaling domains, wherein the at least one intracellular signaling domain comprises at least one intracellular signaling domain isolated or derived from CD247 molecule (CD3-zeta), CD27 molecule (CD27), CD28 molecule (CD28), TNF receptor superfamily member 9 (4-11B), inducible T cell costimulator (ICOS), or TNF receptor superfamily member 4 (OX40). In another embodiment, the at least one intracellular signaling domain comprises: a) a CD3-zeta intracellular signaling domain; b) a CD3-zeta intracellular signaling domain and a 4-1BB or CD28 intracellular signaling domain; c) a CD-zeta intracellular signaling domain, a 4-1BB intracellular signaling domain, and a CD28 intracellular signaling domain; or d) a CD-zeta intracellular signaling domain, a CD28 intracellular signaling domain, a 4-1BB intracellular signaling domain, and a CD27 or OX40 intracellular signaling domain. In another embodiment, the CAR further comprises an extracellular hinge domain, wherein the hinge domain is an immunoglobulin like domain or wherein the hinge domain is isolated or derived from IgG1, IgG2, or IgG4, or wherein the hinge domain is isolated or derived from CD8a molecule (CD8) or CD28. In another embodiment, the CAR further comprises a transmembrane domain, wherein the transmembrane domain is isolated or derived from the group consisting of CD3-zeta, CD4, CD8, and CD28.

In those embodiments comprising an engineered T cell receptor (TCR), the TCR can further comprise one or more subunits selected from the group consisting of TCR alpha, TCR beta, CD3-delta, CD3-epsilon, CD-gamma or CD3-zeta. In some embodiments, the TCR further comprises an intracellular domain comprising a stimulatory domain from an intracellular signaling domain, wherein the antigen binding domain of the TCR is operably linked to the one or more subunits.

In some embodiments, the disclosure further provides polynucleotides encoding inducible expression cassettes coding for immune stimulatory cytokines selected from the group consisting of IL-7, IL-12, IL-15, and IL-18, wherein the polynucleotides are to be introduced into the modified target cells of the population expressing CAR, wherein expression of the cytokines render the modified cells resistant to the immunosuppressive tumor environment when administered to a subject. The polynucleotides encoding the CAR with the foregoing components can be introduced into the cells by several conventional methods, described below.

In some embodiments, the disclosure relates to methods to produce polynucleotide sequences encoding the reference CasX, the CasX variants, or the gNA of any of the embodiments described herein, including variants thereof, or sequences complementary to the target sequences, as well as methods to express the proteins expressed or RNA transcribed by the polynucleotide sequences. In general, the methods include producing a polynucleotide sequence coding for the reference CasX, the CasX variants, or the gNA of any of the embodiments described herein and incorporating the encoding gene into an expression vector appropriate for a host cell. For production of the encoded reference CasX, the CasX variants, or the gNA of any of the embodiments described herein, the method includes transforming an appropriate host cell with an expression vector comprising the encoding polynucleotide, and culturing the host cell under conditions causing or permitting the resulting reference CasX, the CasX variants, or the gNA of any of the embodiments described herein to be expressed or transcribed in the transformed host cell, thereby producing the reference CasX, the CasX variants, or the gNA, which is recovered by methods described herein or by standard purification methods known in the art. Standard recombinant techniques in molecular biology are used to make the polynucleotides and expression vectors of the present disclosure.

In accordance with the disclosure, polynucleotide sequences that encode the reference CasX, the CasX variants, the gNA, the CAR or the expression cassettes for the immune stimulatory cytokines of any of the embodiments described herein are used to generate recombinant DNA molecules that direct the expression in appropriate host cells. Several cloning strategies are suitable for performing the present disclosure, many of which are used to generate a construct that comprises a gene coding for a composition of the present disclosure, or its complement. In some embodiments, the cloning strategy is used to create a gene that encodes a construct that comprises nucleotides encoding the reference CasX, the CasX variants, or the gNA that is used to transform a host cell for expression of the composition.

In one approach, a construct is first prepared containing the DNA sequence encoding a reference CasX, a CasX variant, or a gNA. Exemplary methods for the preparation of such constructs are described in the Examples. The construct is then used to create an expression vector suitable for transforming a host cell, such as a prokaryotic or eukaryotic host cell for the expression and recovery of the polypeptide construct. Where desired, the host cell is an *E. coli*. In other embodiments, the host cell is selected from BHK cells, HEK293 cells, HEK293T cells, NS0 cells, SP2/0 cells, YO myeloma cells, P3X63 mouse myeloma cells, PER cells, PER.C6 cells, hybridoma cells, NIH3T3 cells, COS, HeLa, CHO, or yeast cells. Exemplary methods for the creation of expression vectors, the transformation of host cells and the expression and recovery of reference CasX, the CasX variants, or the gNA are described in the Examples.

The gene or genes encoding for the reference CasX, the CasX variants, the gNA constructs, the CAR, the one or more fusion polypeptides comprising a TCR subunit, or the immune stimulatory cytokines can be made in one or more steps, either fully synthetically or by synthesis combined with enzymatic processes, such as restriction enzyme-mediated cloning, PCR and overlap extension, including methods more fully described in the Examples. The methods disclosed herein can be used, for example, to ligate sequences of polynucleotides encoding the various components (e.g., CasX and gNA) genes of a desired sequence. Genes encoding polypeptide compositions are assembled from oligonucleotides using standard techniques of gene synthesis.

In some embodiments, the nucleotide sequence encoding a CasX protein, CAR, engineered TCR, or one or more subunits of the engineered TCR is codon optimized. This type of optimization can entail a mutation of an encoding nucleotide sequence to mimic the codon preferences of the intended host organism or cell while encoding the same CasX protein, CAR or TCR. Thus, the codons can be changed, but the encoded protein remains unchanged. For example, if the intended target cell of the CasX protein was a human cell, a human codon-optimized CasX-encoding nucleotide sequence could be used. As another non-limiting example, if the intended host cell were a mouse cell, then a mouse codon-optimized CasX-encoding nucleotide sequence could be generated. As another non-limiting example, if the intended host cell were a plant cell, then a plant codon-optimized CasX protein variant-encoding nucleotide sequence could be generated. As another non-limiting example, if the intended host cell were an insect cell, then an insect codon-optimized CasX protein-encoding nucleotide sequence could be generated. The gene design can be performed using algorithms that optimize codon usage and amino acid composition appropriate for the host cell utilized in the production of the reference CasX, the CasX variants, or the gNA. In one method of the disclosure, a library of polynucleotides encoding the components of the constructs is created and then assembled, as described above. The resulting genes are then assembled and the resulting genes used to transform a host cell and produce and recover the reference CasX, the CasX variants, or the gNA compositions for evaluation of its properties, as described herein.

In some embodiments, a nucleotide sequence encoding a gNA is operably linked to a control element, e.g., a transcriptional control element, such as a promoter. In some embodiments, a nucleotide sequence encoding a CasX protein is operably linked to a control element, e.g., a transcriptional control element, such as a promoter. In some embodiments, a nucleotide sequence encoding a CAR is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., neurons, spinal motor neurons, oligodendrocytes, or glial cells.

Non-limiting examples of eukaryotic promoters (promoters functional in a eukaryotic cell) include EF1alpha, EF1alpha core promoter, those from cytomegalovirus (CMV) immediate early, herpes simplex virus (HSV) thymidine kinase, early and late SV40, long terminal repeats (LTRs) from retrovirus, and mouse metallothionein-I. Further non-limiting examples of eukaryotic promoters include the CMV promoter full-length promoter, the minimal CMV promoter, the chicken β-actin promoter, the hPGK promoter, the HSV TK promoter, the Mini-TK promoter, the human synapsin I promoter which confers neuron-specific expression, the Mecp2 promoter for selective expression in neurons, the minimal IL-2 promoter, the Rous sarcoma virus enhancer/promoter (single), the spleen focus-forming virus long terminal repeat (LTR) promoter, the SV40 promoter, the SV40 enhancer and early promoter, the TBG promoter: promoter from the human thyroxine-binding globulin gene (Liver specific), the PGK promoter, the human ubiquitin C promoter, the UCOE promoter (Promoter of HNRPA2B1-CBX3), the Histone H2 promoter, the Histone H3 promoter, the Ulal small nuclear RNA promoter (226 nt), the U1b2 small nuclear RNA promoter (246 nt) 26, the TTR minimal enhancer/promoter, the b-kinesin promoter, the human eIF4A1 promoter, the ROSA26 promoter and the glyceraldehyde 3-phosphate dehydrogenase (GAPDH) promoter.

Selection of the appropriate vector and promoter is well within the level of ordinary skill in the art, as it related to controlling expression, e.g., for modifying a protein involved in antigen processing, antigen presentation, antigen recognition, and/or antigen response and/or its regulatory element. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the CasX protein, thus resulting in a chimeric CasX protein that are used for purification or detection.

In some embodiments, a nucleotide sequence encoding each of a gNA variant or a CasX protein, a CAR, or an expression cassette for the immune stimulatory cytokines is operably linked to an inducible promoter, a constitutively active promoter, a spatially restricted promoter (i.e., transcriptional control element, enhancer, tissue specific promoter, cell type specific promoter, etc.), or a temporally restricted promoter. In other embodiments, individual nucleotide sequences encoding the gNA, the CasX, the CAR, or an expression cassette for the immune stimulatory cytokines are linked to one of the foregoing categories of promoters, which are then introduced into the cells to be modified by conventional methods, described below.

In certain embodiments, suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human HI promoter (HI), a POL1 promoter, a 7SK promoter, tRNA promoters and the like.

In some embodiments, one or more nucleotide sequences encoding a CasX and gNA and, optionally, comprising a donor template or a polynucleic acid encoding a CAR, are each operably linked to (under the control of) a promoter operable in a eukaryotic cell. Examples of inducible promoters may include, but are not limited to, T7 RNA polymerase promoter, T3 RNA polymerase promoter, isopropyl-beta-D-thiogalactopyranoside (IPTG)-regulated promoter, lactose induced promoter, heat shock promoter, tetracycline-regulated promoter, steroid-regulated promoter, metal-regulated promoter, estrogen receptor-regulated promoter, etc. Inducible promoters can therefore, in some embodiments, be regulated by molecules including, but not limited to, doxycycline; estrogen and/or an estrogen analog; IPTG; etc.

In certain embodiments, inducible promoters suitable for use may include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR, etc.), tetracycline regulated promoters, (e.g., promoter systems including Tet Activators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Recombinant expression vectors of the disclosure can also comprise elements that facilitate robust expression of CasX proteins, the gNAs, and the CAR of the disclosure. For example, recombinant expression vectors can include one or more of a polyadenylation signal (PolyA), an intronic sequence or a post-transcriptional regulatory element such as a woodchuck hepatitis post-transcriptional regulatory element (WPRE). Exemplary polyA sequences include hGH poly(A) signal (short), HSV TK poly(A) signal, synthetic polyadenylation signals, SV40 poly(A) signal, β-globin poly (A) signal and the like. A person of ordinary skill in the art will be able to select suitable elements to include in the recombinant expression vectors described herein.

The polynucleotides encoding the reference CasX, the CasX variants, the gNA sequences, and the CAR, engineered TCR, or one or more subunits of the engineered TCR can then be individually cloned into one or more expression vectors. In some embodiments, the present disclosure provides vectors comprising the polynucleotides selected from the group consisting of a retroviral vector, a lentiviral vector, an adenoviral vector, an adeno-associated viral (AAV) vector, a virus-like particle (VLP), a herpes simplex virus (HSV) vector, a plasmid, a minicircle, a nanoplasmid, a DNA vector, and an RNA vector. In some embodiments, the vector is a recombinant expression vector that comprises a nucleotide sequence encoding a CasX protein. In other embodiments, the disclosure provides a recombinant expression vector comprising a nucleotide sequence encoding a CasX protein and a nucleotide sequence encoding a gNA. In some cases, the nucleotide sequence encoding the CasX protein variant and/or the nucleotide sequence encoding the gNA are operably linked to a promoter that is operable in a cell type of choice. In other embodiments, the nucleotide sequence encoding the CasX protein variant and the nucleotide sequence encoding the gNA are provided in separate vectors operably linked to a promoter. In other embodiments, the vector can comprise a donor template or a polynucleotide encoding one or more CAR, engineered TCR, one or more engineered TCR subunits, or a separate vector can be utilized to introduce the donor template or the one or more CAR or engineered TCR subunits into the target cell to be modified.

In some embodiments, provided herein are one or more recombinant expression vectors comprising one or more of: (i) a nucleotide sequence of a donor template nucleic acid where the donor template comprises a nucleotide sequence having homology to a target sequence of a target nucleic acid (e.g., a target genome); (ii) a nucleotide sequence that encodes a gNA that hybridizes to a target sequence of the locus of the targeted genome (e.g., configured as a single or dual guide RNA) operably linked to a promoter that is operable in a target cell such as a eukaryotic cell; (iii) a nucleotide sequence encoding a CasX protein operably linked to a promoter that is operable in a target cell such as a eukaryotic cell; (iv) a nucleotide sequence encoding a CAR operably linked to a promoter that is operable in a target cell such as a eukaryotic cell; and (v) a nucleotide sequence encoding an expression cassette for the immune stimulatory cytokines operably linked to a promoter that is operable in a target cell such as a eukaryotic cell. In some embodiments, the sequences encoding the donor template, the gNA, the CasX protein, the CAR, the engineered TCR or one or more subunits thereof, and the expression cassette are in different recombinant expression vectors, and in other embodiments one or more polynucleotide sequences (for the donor template, CasX, gNA, the CAR, the engineered TCR or one or more subunits thereof, and the expression cassette) are in the same recombinant expression vector. In other cases, the CasX and gNA are delivered to the target cell as an RNP (e.g., by electroporation or chemical means) and the donor template and/or the polynucleotide encoding the CAR, or engineered TCR or one or more subunits thereof, and the expression cassette are delivered by a vector.

The polynucleotide sequence(s) are inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan. Such techniques are well known in the art and well described in the scientific and patent literature. Various vectors are publicly available. The vector may, for example, be in the form of a plasmid, cosmid, viral particle, or phage that may conveniently be subjected to recombinant DNA procedures, and the choice of vector will often depend on the host cell into which it is to be introduced. Thus, the vector may be an autonomously replicating vector, i.e., a vector, which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated. Once introduced into a suitable host cell, expression of the protein involved in antigen processing, antigen presentation, antigen recognition, and/or antigen response can be determined using any nucleic acid or protein assay known in the art. For example, the presence of transcribed mRNA of reference CasX or the CasX variants can be detected and/or quantified by conventional hybridization assays (e.g., Northern blot analysis), amplification procedures (e.g. RT-PCR), SAGE (U.S. Pat. No. 5,695,937), and array-based technologies (see e.g., U.S. Pat. Nos. 5,405,783, 5,412,087 and 5,445,934), using probes complementary to any region of the polynucleotide.

The disclosure provides for the use of plasmid expression vectors containing replication and control sequences that are compatible with and recognized by the host cell and are operably linked to the gene encoding the polypeptide for controlled expression of the polypeptide or transcription of the RNA. Such vector sequences are well known for a variety of bacteria, yeast, and viruses. Useful expression vectors that can be used include, for example, segments of chromosomal, non-chromosomal and synthetic DNA sequences. "Expression vector" refers to a DNA construct containing a DNA sequence that is operably linked to a suitable control sequence capable of effecting the expression of the DNA encoding the polypeptide in a suitable host. The requirements are that the vectors are replicable and viable in the host cell of choice. Low- or high-copy number vectors may be used as desired. The control sequences of the vector include a promoter to effect transcription, an optional operator sequence to control such transcription, a sequence encoding suitable mRNA ribosome binding sites, and sequences that control termination of transcription and translation. The promoter may be any DNA sequence, which shows transcriptional activity in the host cell of choice and may be derived from genes encoding proteins either homologous or heterologous to the host cell.

The polynucleotides and recombinant expression vectors can be delivered to the target host cells by a variety of methods. Such methods include, but are not limited to, viral infection, transfection, lipofection, electroporation, calcium phosphate precipitation, polyethyleneimine (PEI)-mediated transfection, DEAE-dextran mediated transfection, microinjection, liposome-mediated transfection, particle gun technology, nucleofection, direct addition by cell penetrating CasX proteins that are fused to or recruit donor DNA, cell squeezing, calcium phosphate precipitation, direct microinjection, nanoparticle-mediated nucleic acid delivery, and using the commercially available TransMessenger® reagents from Qiagen, Stemfect™ RNA Transfection Kit from Stemgent, and TransIT®-mRNA Transfection Kit from Mirus Bio LLC, Lonza nucleofection, Maxagen electroporation and the like.

A recombinant expression vector sequence can be packaged into a virus or virus-like particle (also referred to herein as a "VLP" or "virion") for subsequent infection and transformation of a cell, ex vivo, in vitro or in vivo. Such VLP or virions will typically include proteins that encapsidate or package the vector genome. Suitable expression vectors may include viral expression vectors based on vaccinia virus; poliovirus; adenovirus; a retroviral vector (e.g., Murine Leukemia Virus), spleen necrosis virus, and vectors derived from retroviruses such as Rous Sarcoma Virus, Harvey Sarcoma Virus, avian leukosis virus, retrovirus, a lentivirus, human immunodeficiency virus, myeloproliferative sarcoma virus, and mammary tumor virus; and the like. In some embodiments, a recombinant expression vector of the present disclosure is a recombinant adeno-associated virus (AAV) vector. In a particular embodiment, a recombinant expression vector of the present disclosure is a recombinant retrovirus vector. In another particular embodiment, a recombinant expression vector of the present disclosure is a recombinant lentivirus vector.

AAV is a small (20 nm), nonpathogenic virus that is useful in treating human diseases in situations that employ a viral vector for delivery to a cell such as a eukaryotic cell, either in vivo or ex vivo for cells to be prepared for administration to a subject. A construct is generated, for example, encoding any of the CasX proteins and gNA embodiments as described herein, and optionally a donor template or a polynucleotide encoding a CAR, and can be flanked with AAV inverted terminal repeat (ITR) sequences, thereby enabling packaging of the AAV vector into an AAV viral particle.

An "AAV" vector may refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are many known serotypes of primate AAVs. In some embodiments, the AAV vector is selected from AAV1, AAV2, AAV3, AAV4, AAV5, AAV6, AAV7, AAV8, AAV9, AAV 10, AAV-Rh74 (Rhesus macaque-derived AAV), and AAVRh10, and modified capsids of these serotypes. For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped recombinant AAV (rAAV) are produced using standard techniques described in the art. As used herein, for example, rAAV1 may be used to refer an AAV having both capsid proteins and 5'-3' ITRs from the same serotype or it may refer to an AAV having capsid proteins from serotype 1 and 5'-3' ITRs from a different AAV serotype, e.g., AAV serotype 2. For each example illustrated herein the description of the vector design and production describes the serotype of the capsid and 5'-3' ITR sequences.

An "AAV virus" or "AAV viral particle" refers to a viral particle composed of at least one AAV capsid protein (preferably by all of the capsid proteins of a wild-type AAV) and an encapsidated polynucleotide. If the particle additionally comprises a heterologous polynucleotide (i.e., a polynucleotide other than a wild-type AAV genome to be delivered to a mammalian cell), it is typically referred to as "rAAV". An exemplary heterologous polynucleotide is a polynucleotide comprising a CasX protein and/or sgNA and, optionally, a donor template of any of the embodiments described herein.

By "adeno-associated virus inverted terminal repeats" or "AAV ITRs" is meant the art recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, for example Kotin, R. M. (1994) Human Gene Therapy 5:793-801; Berns, K. I. "Parvoviridae and their Replication" in Fundamental Virology, $2^{nd}$ Edition, (B. N. Fields and D. M. Knipe, eds.). As used herein, an AAV ITR need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV6, AAV7, AAV8, AAV9, AAV10, AAV-Rh74, and AAVRh10, and modified capsids of these serotypes. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Use of AAV serotypes for integration of heterologous sequences into a host cell is known in the art (see, e.g., WO2018195555A1 and US20180258424A1, incorporated by reference herein.)

By "AAV rep coding region" is meant the region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome.

By "AAV cap coding region" is meant the region of the AAV genome which encodes the capsid proteins VP1, VP2, and VP3, or functional homologues thereof. These Cap expression products supply the packaging functions which are collectively required for packaging the viral genome.

In some embodiments, AAV capsids utilized for delivery of the CasX, gNA, and, optionally, donor template nucleotides or polynucleotides encoding the CAR and/or the expression cassette for the cytokines, to a host cell can be derived from any of several AAV serotypes, including without limitation, AAV1, AAV2, AAV3, AAV4, AAV5, AAV6, AAV7, AAV8, AAV9, AAV10, AAV-Rh74 (Rhesus macaque-derived AAV), and AAVRh10, and the AAV ITRs are derived from AAV serotype 2.

In order to produce rAAV viral particles, an AAV expression vector is introduced into a suitable host cell using known techniques, such as by transfection. Packaging cells are typically used to form virus particles; such cells include HEK293 or HEK293T cells (and other cells known in the art), which package adenovirus. A number of transfection techniques are generally known in the art; see, e.g., Sambrook et al. (1989) Molecular Cloning, a laboratory manual, Cold Spring Harbor Laboratories, New York. Particularly suitable transfection methods include calcium phosphate co-precipitation, direct microinjection into cultured cells, electroporation, liposome mediated gene transfer, lipid-mediated transduction, and nucleic acid delivery using high-velocity microprojectiles.

In some embodiments, host cells transfected with the above-described AAV expression vectors are rendered capable of providing AAV helper functions in order to replicate and encapsidate the nucleotide sequences flanked by the AAV ITRs to produce rAAV viral particles. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs (open reading frames), encoding the rep and cap coding regions, or functional homologues thereof. Accessory functions can be introduced into and then expressed in host cells using methods known to those of skill in the art. Commonly, accessory functions are provided by infection of the host cells with an unrelated helper virus. In some embodiments, accessory functions are provided using an accessory function vector. Depending on the host/vector system utilized, any of a number of suitable transcription and translation control elements, including constitutive and inducible promoters, transcription enhancer elements, transcription terminators, etc., may be used in the expression vector.

In other embodiments, suitable vectors may include virus-like particles (VLP). Virus-like particles (VLPs) are particles that closely resemble viruses, but do not contain viral genetic material and are therefore non-infectious. In some embodiments, VLPs comprise a polynucleotide encoding a transgene of interest, for example any of the CasX protein and/or a gNA embodiments, and, optionally, donor template polynucleotides or polynucleotides encoding CAR, described herein, packaged with one or more viral structural proteins.

In other embodiments, the disclosure provides VLPs produced in vitro that comprise a CasX:gNA RNP complex and, optionally, a donor template or polynucleotides encoding CAR, engineered TCR, or fusion polypeptides comprising subunits of the engineered TCR. Combinations of structural proteins from different viruses can be used to create VLPs, including components from virus families including Parvoviridae (e.g., adeno-associated virus), Retroviridae (e.g., HIV), Flaviviridae (e.g., Hepatitis C virus), Paramyxoviridae (e.g., Nipah) and bacteriophages (e.g., QP, AP205). In some embodiments, the disclosure provides VLP systems designed using components of retrovirus, including lentiviruses such as HIV, in which individual plasmids comprising polynucleotides encoding the various components are introduced into a packaging cell that, in turn, produce the VLP. In some embodiments, the disclosure provides VLP comprising one or more components of a gag polyprotein selected from the group of matrix protein (MA), nucleocapsid protein (NC), capsid protein (CA), p1-p6 protein, and a protease cleavage site wherein the resulting VLP particle encapsidates a CasX:gNA RNP, and wherein the VLP particle further comprises targeting glycoproteins on the surface that provides tropism to the target cell, wherein upon administration and entry into the target cell, the RNP molecule is free to be transported into the nucleus of the cell. In other embodiments, the disclosure provides VLP comprising one or more components of a gag polyprotein selected from the group of matrix protein (MA), nucleocapsid protein (NC), capsid protein (CA), p1-p6 protein, one or more components of a pol polyprotein, a protease cleavage site, wherein the resulting VLP particle encapsidates a CasX:gNA RNP, and wherein the VLP particle further comprises targeting glycoproteins on the surface that provides tropism to the target cell, wherein upon administration and entry into the target cell, the RNP molecule is free to be transported into the nucleus of the cell. The foregoing offers advantages over other vectors in the art in that viral transduction to dividing and non-dividing cells is efficient and that the VLP delivers potent and short-lived RNP that escape a subject's immune surveillance mechanisms that would otherwise detect a foreign protein. In some embodiments, a system to make VLP in a host cell comprises polynucleotides encoding one or more components selected from i) a gag polyprotein or portions thereof; ii) a CasX protein of any of the embodiments described herein; iii) a protease cleavage site; iv) a protease; v) a guide RNA of any of the embodiments described herein; vi) a pol polyprotein or portions thereof, vii) a pseudotyping glycoprotein or antibody fragment that provides for binding and fusion of the VLP to a target cell; and viii) a CAR or engineered TCR. The envelope protein or glycoprotein can be derived from any enveloped viruses known in the art to confer tropism to VLP, including but not limited to the group consisting of Argentine hemorrhagic fever virus, Australian bat virus, *Autographa californica* multiple nucleopolyhedrovirus, Avian leukosis virus, baboon endogenous virus, Bolivian hemorrhagic fever virus, Boma disease virus, Breda virus, Bunyamwera virus, Chandipura virus, Chikungunya virus, Crimean-Congo hemorrhagic fever virus, Dengue fever virus, Duvenhage virus, Eastern equine encephalitis virus, Ebola hemorrhagic fever virus, Ebola Zaire virus, enteric adenovirus, Ephemerovirus, Epstein-Bar virus (EBV), European bat virus 1, European bat virus 2, Fug Synthetic gP Fusion, Gibbon ape leukemia virus, Hantavirus, Hendra virus, hepatitis A virus, hepatitis B virus, hepatitis C virus, hepatitis D virus, hepatitis E virus, hepatitis G Virus (GB virus C), herpes simplex virus type 1, herpes simplex virus type 2, human cytomegalovirus (HHV5), human foamy virus, human herpesvirus (HHV), human Herpesvirus 7, human herpesvirus type 6, human herpesvirus type 8, human immunodeficiency virus 1 (HIV-1), human metapneumovirus, human T-lymphotro pic virus 1, influenza A, influenza B, influenza C virus, Japanese encephalitis virus, Kaposi's sarcoma-associated herpesvirus (HHV8), Kaysanur Forest disease virus, La Crosse virus, Lagos bat virus, Lassa fever virus, lymphocytic choriomeningitis virus (LCMV), Machupo virus, Marburg hemorrhagic fever virus, measles virus, Middle eastern respiratory syndrome-related coronavirus, Mokola virus, Moloney murine leukemia virus, monkey pox, mouse mammary tumor virus, mumps virus, murine gammaherpesvirus, Newcastle disease virus, Nipah virus, Nipah virus, Norwalk virus, Omsk hemorrhagic fever virus, papilloma virus, parvovirus, pseudorabies virus, Quaranfil virus, rabies virus, RD 114 Endogenous Feline Retrovirus, respiratory syncytial virus (RSV), Rift Valley fever virus, Ross River virus, rRotavirus, Rous sarcoma virus, rubella virus, Sabia-associated hemorrhagic fever virus, SARS-associated coronavirus (SARS-CoV), Sendai virus, Tacaribe virus, Thogotovirus, tick-borne encephalitis causing virus, varicella zoster virus (HHV3), varicella zoster virus (HHV3), variola major virus, variola minor virus, Venezuelan equine encephalitis virus, Venezuelan hemorrhagic fever virus, vesicular stomatitis virus (VSV), VSV-G, Vesiculovirus, West Nile virus, western equine encephalitis virus, and Zika Virus. In some embodiments, the packaging cell used for the production of VLP is selected from the group consisting of HEK293 cells, *Lenti*-X 293T cells, BHK cells, HepG2 cells, Saos-2 cells, HuH7 cells, NS0 cells, SP2/0 cells, YO myeloma cells, A549 cells, P3X63 mouse myeloma cells, PER cells, PER.C6 cells, hybridoma cells, VERO cells, NIH3T3 cells, COS cells, WI38 cells, MRC5 cells, A549 cells, HeLa cells, CHO cells, or HT1080 cells.

VII. Cells

In some embodiments, the present disclosure provides a population of cells that has been modified to knock-down or knock out one or more proteins of the cell involved in antigen processing, antigen presentation, antigen recognition, and/or antigen response. In other embodiments, the present disclosure provides a population of cells that has been modified to knock in one or more chimeric antigen receptor (CAR) or fusion polypeptides comprising subunits of an engineered TCR with binding affinity for a disease antigen. In still other embodiments, the present disclosure provides a population of cells that has been modified to knock in one or more T cell-derived signaling chain polypeptides. In some embodiments, the population of cells comprises all of the foregoing modifications; e.g., the knock-down/knock-out of the one or more proteins of the cell involved in antigen processing, antigen presentation, antigen recognition, and/or antigen response, the knock in of the one or more chimeric antigen receptor (CAR) or fusion polypeptides of an engineered TCR specific for a disease antigen. Such modified cells altered in this manner are useful for immunotherapy applications, for example for ex vivo preparation of cells bearing a CAR, for use in a subject in need thereof.

In some embodiments, the disclosure provides a population of cells comprising a CasX:gNA system comprising a CasX protein and one or more gNA, wherein the gNA comprises a targeting sequence complementary to a target nucleic acid sequence of a gene encoding a protein involved in antigen processing, antigen presentation, antigen recognition, and/or antigen response, wherein the CasX and gNA are designed to modify the gene encoding the protein. In one embodiment of the foregoing, the CasX:gNA system is designed to knock-down/knock-out genes encoding the one or more proteins involved in antigen processing, antigen presentation, antigen recognition, and/or antigen response, resulting in the modified population of cells. In another embodiment of the foregoing, the CasX:gNA system is designed to knock-down/knock-out genes encoding the MHC Class I molecules, resulting in the modified population of cells. In some embodiments, the protein is an immune cell surface marker. In other embodiments, the protein is an intracellular protein. In some embodiments, the CasX and one or more gNA are introduced into the population of cells complexed as an RNP, such that the RNP can then modify the target gene. In other cases, the CasX and the one or more gNA are introduced into the population of cells as encoding polynucleotides using a vector.

In other embodiments, the populations of cells have been modified by either contacting the cell with a CasX protein, one or more gNA comprising a targeting sequence, and a donor template wherein the donor template is inserted into or replaces all or a portion of the target nucleic acid sequence of a cell gene encoding a protein involved in antigen processing, antigen presentation, antigen recognition, and/or antigen response. In the foregoing embodiment, the donor template comprises at least a portion of a target gene, wherein the target gene portion is selected from an exon, an intron, an intron-exon junction, or a regulatory element and the modification of the cell results in a mutation of the wild-type sequence and the knocking-down or knocking-out of the target gene. In some cases, the donor template is a single-stranded DNA template or a single stranded RNA template. In other cases, the donor template is a double-stranded DNA template. In some cases, the cell is contacted with a CasX and a gNA wherein the gNA is a guide RNA (gRNA). In other cases, the cell is contacted with a CasX and a gNA wherein the gNA is a guide DNA (gDNA). In other cases, the cell is contacted with a CasX and a gNA wherein the gNA is a chimera comprising DNA and RNA.

As described herein, in embodiments of any of the combinations, each of said gNA molecules (a combination of the scaffold and targeting sequence, which can be configured as a sgRNA or a dgRNA) can be provided as an RNP complexed with a CasX molecule described herein. An RNP can be introduced into a cell to be modified via any suitable method, including via electroporation, injection, nucleofection, delivery via liposomes, delivery by nanoparticles, or using a protein transduction domain (PTD) conjugated to one or more components of the CasX:gNA. Additional methods of modification of the cells using the CasX:gNA system components include viral infection, transfection, conjugation, protoplast fusion, particle gun technology, calcium phosphate precipitation, direct microinjection, and the like. The choice of method is generally dependent on the type of cell being transformed and the circumstances under which the transformation is taking place; e.g., in vitro, ex vivo, or in vivo. A general discussion of these methods can be found in Ausubel, et al, Short Protocols in Molecular Biology, 3rd ed., Wiley & Sons, 1995.

In exemplary embodiments, the protein involved in antigen processing, antigen presentation, antigen recognition, and/or antigen response is selected from beta-2-microglobulin (B2M), T cell receptor alpha chain constant region (TRAC), class II major histocompatibility complex transactivator (CIITA), ICP47, T cell receptor beta constant 1 (TRBC1), T cell receptor beta constant 2 (TRBC2), human leukocyte antigen A (HLA-A), human leukocyte antigen B (HLA-B), PD-1, CTLA-4, LAG-3, TIM-3, 2B4, TIGIT, CISH, ADORA2A, NKG2A, or TGFβ Receptor 2 (TGFβRII). In other embodiments, the protein is selected from cluster of differentiation 247 (CD247), CD3D, CD3E, CD3G, CD52, human leukocyte antigen C (HLA-C), deoxycytidine kinase (dCK), or FKBP1A. In still other embodiments, the protein to be modified in the cell is selected from one of i) beta-2-microglobulin (B2M), T cell receptor alpha chain constant region (TRAC), class II major histocompatibility complex transactivator (CIITA), ICP47, T cell receptor beta constant 1 (TRBC1), T cell receptor beta constant 2 (TRBC2), TIGIT, CISH ADORA2A, NKG2A, PD-1, CTLA-4, LAG-3, TIM-3, 2B4, human leukocyte antigen A (HLA-A), human leukocyte antigen B (HLA-B), or TGFβ Receptor 2 (TGFβRII) and another selected from one of ii) cluster of differentiation 247 (CD247), CD3D, CD3E, CD3G, CD52, human leukocyte antigen C (HLA-C), deoxycytidine kinase (dCK), or FKBP1A.

In some embodiments, the population of cells includes one or more cells that have reduced or eliminated expression of a component of the T-cell receptor (TCR). In some embodiments, the T-cell receptor is a native T-cell receptor. In some embodiments, the reduced or eliminated expression of a component of the T-cell receptor (TCR) includes reduced or eliminated expression of TRAC. In other embodiments, the reduced or eliminated expression of a component of the T-cell receptor (TCR) includes reduced or eliminated expression of TRBC1. In still other embodiments, the reduced or eliminated expression of a component of the T-cell receptor (TCR) includes reduced or eliminated expression of TRBC2. In still other embodiments, the reduced or eliminated expression of a component of the T-cell receptor (TCR) includes reduced or eliminated expression of CD3G. In yet other embodiments, the reduced or eliminated expression of a component of the T-cell receptor (TCR) includes reduced or eliminated expression of CD3D. In other embodiments, the reduced or eliminated expression of a component of the T-cell receptor (TCR) includes reduced or eliminated expression of CD3E. In some cases, the reduced or eliminated expression of said component of the TCR is the result of introduction of one or more, e.g., one or two, e.g., one gNA molecules described herein specific to the component of the TCR into the cell. For example, the method employing the CasX:gNA system can introduce into the cell an indel, e.g., a frameshift mutation, e.g., as described herein, at or near the target sequence of a targeting domain of a gNA molecule to the TCR. In other cases, the reduced or eliminated expression of said component of the TCR is the result of introduction of the CasX, one or more gNA, and a donor template comprising one or more mutations in comparison to the TCR to be knock-down or knocked-out. In some embodiments, the population of cells includes at least about 50%, e.g., at least about 60%, e.g., at least about 70%, e.g., at least about 80%, e.g., at least about 90% or more cells (as described herein) which exhibit reduced or eliminated expression of a component of the TCR; e.g., TRAC. In embodiments, said reduced or eliminated expression of a component of the TCR is as measured by flow cytometry or other methods know in the art. In other embodiments, at least 70%, at least 75%, at least 80%, at least 85%, at least 90%, or at least 95% of the modified cells do not express a detectable level of wild-type T cell receptor.

In some embodiments, (including either alternatively, or in addition to, the reduced or eliminated expression of a component of the TCR) the cell or the population of cells includes one or more cells that have reduced or eliminated expression of beta-2 microglobulin (B2M). In embodiments, said reduced or eliminated expression of said B2M is the result of introduction of one or more, e.g., one or two, e.g., one gNA molecule described herein targeted to the gene encoding B2M into said cell. In the foregoing embodiment, the targeting sequence of the gNA comprises a sequence selected from the group consisting of sequences set forth in Table 3A, Table 13, and Table 16, or a sequence having at least about 65%, at least about 75%, at least about 85%, or at least about 95% identity thereto. In some embodiments, the modified cell includes an indel, e.g., a frameshift mutation, as described herein, at or near the target sequence of a targeting domain of a gNA molecule to said B2M. In some embodiments, the population of cells includes at least about 50%, e.g., at least about 60%, e.g., at least about 70%, e.g., at least about 80%, e.g., at least about 90% or more cells (as described herein) which exhibit reduced or eliminated expression of B2M. In embodiments, said reduced or eliminated expression of B2M is as measured by flow cytometry or other methods know in the art.

In certain embodiments, (including either alternatively, or in addition to, the reduced or eliminated expression of a component of the TCR and/or B2M) the cell or population of cells includes one or more cells that have reduced or eliminated expression of CIITA. In the foregoing embodiment, the targeting sequence of the gNA comprises a sequence selected from the group consisting of sequences set forth in Table 3C, or a sequence having at least about 65%, at least about 75%, at least about 85%, or at least about 95% identity thereto. In some embodiments, said reduced or eliminated expression of said CIITA is the result of introduction of one or more, e.g., one or two, e.g., one gNA molecule targeted to the gene encoding said CIITA described herein into said cell. In the foregoing, the targeting sequence of the gNA comprises a sequence selected from the group consisting of sequences set forth in Table 3C, or a sequence having at least about 65%, at least about 75%, at least about 85%, or at least about 95% identity thereto. In embodiments, the cell includes an indel, e.g., a frameshift mutation, e.g., as described herein, at or near the target sequence of a targeting domain of a gNA molecule to said CIITA. In embodiments, the population of cells includes at least about 50%, e.g., at least about 60%, e.g., at least about 70%, e.g., at least about 80%, e.g., at least about 90% or more cells (as described herein) which exhibit reduced or eliminated expression of CIITA. In embodiments, said reduced or eliminated expression of CIITA is as measured by flow cytometry or other methods know in the art.

In other embodiments, the disclosure provides populations of cells wherein the cells have been modified such that at least about 50%, at least about 60%, at least about 70%, at least about 80%, at least about 90%, or at least about 95% of the cells do not express a detectable level of at least two of the proteins selected from the group consisting of B2M, TRAC, and CIITA. In still other embodiments, the disclosure provides populations of cells wherein the cells have been modified such that at least about 50%, at least about 60%, at least about 70%, at least about 80%, at least about 90%, or at least about 95% of the cells do not express a detectable level of the proteins B2M, TRAC, and CIITA. In other embodiments, the disclosure provides a population of cells, wherein the cells have been modified such that at least 70%, at least 75%, at least 80%, at least 85%, at least 90%, or at least 95% of the modified cells do not express a detectable level of MHC Class I molecules or a wild-type T-cell receptor. In other embodiments, the disclosure provides populations of cells modified to produce CAR and are further modified such that at least about 50%, at least about 60%, at least about 70%, at least about 80%, at least about 90%, or at least about 95% of the cells comprise an inducible expression cassette coding for one or more immune stimulatory cytokines selected from the group consisting of IL-7, IL-12, IL-15, and IL-18.

In some embodiments, the present disclosure provides populations of cells modified to: i) have reduced or eliminated expression of MHC Class I molecules and/or a wild-type T-cell receptor, and ii) express CAR or engineered TCR. Such cells are capable of specifically binding a tumor antigen of a cell that is a ligand of the CAR or engineered TCR, whereupon such binding, the modified cells are capable of a response selected from: i) becoming activated; ii) inducing proliferation of the modified cell; iii) cytokine secretion by the modified cell; or iv) inducing cytotoxicity of the cell bearing said tumor antigen. For example, a population of cells may have reduced or eliminated expression of wild type TRAC and TRBC1, and express fusion polypeptides comprising the TRAC and/or TRBC1 transmembrane and intracellular domain fused to an antigen binding domain. Activation includes a clonal expansion and differentiation, expression of cytokines, including IFN-γ, TNF-α, or IL-2. The production of cytokines and assessment of cytotoxicity can be determined by standard assays such as ELISA, $^{51}$CR release, flow-cytometry, and other such assays known in the art.

In exemplary embodiments in which it is intended to reduce or eliminate expression in the cell or population of cells of both a component of the T cell receptor, e.g., TRAC, (including embodiments when expression or function of an additional target, e.g., more than one additional target, is also reduced or eliminated), the gNA targeting sequence molecule which targets TRAC is selected from a sequence of Table 3B. For example, the cell exhibits reduced or eliminated expression of a component of the TCR (e.g., TRAC, TRBC1, TRBC2, CD3E, CD3G, and/or CD3D), and reduced or eliminated expression of a target of an immunosuppressant or immune checkpoint protein, e.g., FKBP1A, or proteins selected from the group consisting of PD-1, CISH, CTLA-4, LAG-3, TIM-3, 2B4, TIGIT, ADORA2A, NKG2A, cluster of differentiation 247 (CD247), CD3D, CD3E, CD3G, CD52, human leukocyte antigen C (HLA-C), and deoxycytidine kinase (dCK). As described herein, in embodiments of any of the combinations, each of said gNA molecules (a combination of the scaffold and targeting sequence, which can be configured as, for example, a sgRNA or a dgRNA) can be provided as an RNP with a CasX molecule described herein for the modification of the population of the cells. In other embodiments of any of the combinations, each of said gNA molecules (a combination of the scaffold and targeting sequence, which can be configured as, for example, a sgRNA or a dgRNA) and the CasX can be provided as encoded polynucleotides within a vector for the modification of the population of the cells.

In some embodiments, the population of cells are animal cells, for example, derived from a rodent, rat, mouse, rabbit or dog cell. In some embodiments, the cell is a human cell. In some embodiments, the cell is a non-human primate cell; e.g., a cynomolgus monkey cell. In some embodiments, the cell is a progenitor cell, a hematopoietic stem cell, or a pluripotent stem cell. In one embodiment, the cell is an induced pluripotent stem cell. In some embodiments, the cell is an immune cell. In some embodiments, the cell is an immune effector cell (e.g., a population of cells including one or more immune effector cells), for example, a T cell, NK cell, B cell, a macrophage, or a dendritic cells. T cells include, but are not limited to, regulatory T cells (TREG), gamma-delta T cells, helper T cells and cytotoxic T cells. In some embodiments, the cell is a T cell selected from the group consisting of CD4+ T cells, CD8+ T cells, or a combination thereof. In some embodiments, the population of cells are autologous or allogeneic (genetically mismatched) with respect to a subject to be administered said population of cells.

In some embodiments, the disclosure provides a cell or population of cells that are a CAR or engineered TCR-expressing, and that have been modified to reduce or eliminate one or more proteins involved with antigen processing, presentation, recognition, or response, as described above. In some embodiments, a CAR or engineered TCR cell, as described herein, is modified and/or altered by the methods described herein, ex vivo, by the introduction of a polynucleotide encoding the CAR or engineered TCR, or a vector comprising the polynucleotide. In other embodiments, CAR or engineered TCR cell, as described herein, is modified and/or altered by the methods described herein, in vivo utilizing the CasX:gNA molecules and/or compositions (e.g., compositions comprising CasX, more than one gNA molecule and, optionally, a donor template, as well as a polynucleotide encoding the CAR) that are introduced into a cell as described herein. In the embodiments, the cell has been, is, or will be, modified to express a chimeric antigen receptor (CAR) or engineered TCR, as described herein (for example, the cell includes, or will include, a polynucleotide sequence encoding a CAR, or a fusion protein comprising a subunit of the engineered TCR). In embodiments, the CAR or engineered TCR has specific binding affinity for antigen selected from Cluster of Differentiation 19 (CD19), CD3, CD8, CD7, CD10, CD20, CD22, CD30, CLL1, CD33, CD34, CD38, CD41, CD44, CD47, CD49f, CD56, CD70, CD74, CD99, CD123, CD133, CD138, carbonix anhydrase IX (CAIX), CC chemokine receptor 4 (CCR4), ADAM metallopeptidase domain 12 (ADAM12), adhesion G protein-coupled receptor E2 (ADGRE2), alkaline phosphatase placental-like 2 (ALPPL2), alpha 4 Integrin, angiopoietin-2 (ANG2), B-cell maturation antigen (BCMA), CD44V6, carcinoembryonic antigen (CEA), CEAC, CEACAM5, Claudin 6 (CLDN6), CLDN18, C-type lectin domain family 12 member A (CLEC12A), mesenchymal-epithelial transition factor (cMET), cytotoxic T-lymphocyte-associated protein 4 (CTLA4), epidermal growth factor receptor 1 (EGF1R), EGFR-VIII, epithelial glycoprotein 2 (EGP-2), EGP-40, EphA2, ENPP3, epithelial cell adhesion molecule (EpCAM), erb-B2,3,4, folate binding protein (FBP), fetal acetylcholine receptor, folate receptor-a, folate receptor 1 (FOLR1), G protein-coupled receptor 143 (GPR143), glutamate metabotropic receptor 8 (GRM8), glypican-3 (GPC3), ganglioside GD2, ganglioside GD3, human epidermal growth factor receptor 1 (HER1), human epidermal growth factor receptor 2 (HER2), HER3, Integrin B7, intercellular cell-adhesion molecule-1 (ICAM-1), human telomerase reverse transcriptase (hTERT), Interleukin-13 receptor a2 (IL-13R-a2), K-light chain, Kinase insert domain receptor (KDR), Lewis-Y (LeY), chondromodulin-1 (LECT1), L1 cell adhesion molecule, Lysophosphatidic acid receptor 3 (LPAR3), melanoma-associated antigen 1 (MAGE-A1), mesothelin, mucin 1 (MUC1), MUC16, melanoma-associated antigen 3 (MAGEA3), tumor protein p53 (p53), Melanoma Antigen Recognized by T cells 1 (MARTl), glycoprotein 100 (GP100), Proteinase3 (PR1), ephrin-A receptor 2 (EphA2), Natural killer group 2D ligand (NKG2D ligand), New York esophageal squamous cell carcinoma 1 (NY-ESO-1), oncofetal antigen (h5T4), prostate-specific membrane antigen (PSMA), programmed death ligand 1 (PDL-1), receptor tyrosine kinase-like orphan receptor 1 (ROR1), trophoblast glycoprotein (TPBG), tumor-associated glycoprotein 72 (TAG-72), tumor-associated calcium signal transducer 2 (TROP-2), tyrosinase, survivin, vascular endothelial growth factor receptor 2 (VEGF-R2), Wilms tumor-1 (WT-1), leukocyte immunoglobulin-like receptor B2 (LILRB2), Preferentially Expressed Antigen In Melanoma (PRAME), T cell receptor beta constant 1 (TRBC1), TRBC2, and (T-cell immunoglobulin mucin-3) TIM-3. In the foregoing, the CAR or engineered TCR comprises an antigen binding domain selected from single domain antibody, linear antibody, or single-chain variable fragment (scFv), which can be derived from a reference antibody; e.g., an antibody of Table 5 (having the VL, VH, and/or the CDR sequences of Table 5). In some embodiments, the antigen binding domain exhibits an affinity with an equilibrium binding constant for the target antigen of between or between about $10^{-5}$ and $10^{-12}$ M and all individual values and ranges therein (e.g., $10^{-5}$ M, $10^{-6}$ M, $10^{-7}$ M, $10^{-8}$M, $10^{-9}$M, $10^{-10}$M, $10^{-11}$M, or $10^{-2}$ M); such binding affinity being “specific”. In some embodiments, the CAR or engineered TCR includes an antigen binding domain, a transmembrane domain derived from a polypeptide selected from the group consisting of CD3-zeta, CD4, CD8, and CD28, and an intracellular signaling domain, which can be linked by spacer sequences. In some embodiments, the encoded CAR further comprises one or more T cell-derived signaling chain polypeptides, including, but not limited to of CD3-zeta, CD27, CD28, 4-1BB (41BB), ICOS, or OX40, linked to the CAR antigen binding domain either directly, or by domain hinge and/or a spacer. The hinge domain can be an immunoglobulin-like hinge, or a hinge domain isolated or derived from CD8a molecule (CD8) or CD28. The hinge, spacer, and transmembrane domains connect the antigen binding domain to the activation domains and anchor the CAR in the T-cell membrane. In other embodiments, the CAR or engineered TCR-expressing cell described herein can further comprise a second CAR or engineered TCR, e.g., a second CAR that includes a different antigen binding domain, e.g., to the same target or a different target (e.g., a target other than a cancer associated antigen described herein or a different cancer associated antigen described herein, supra). In some embodiments, the second CAR or engineered includes an antigen binding domain to a target expressed on the same cancer cell type as the cancer associated antigen. In some embodiments, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory T cell-derived signaling domain, e.g., CD27, CD28, 4-1BB (41BB), ICOS, or OX40, onto the first CAR, and the primary signaling domain, e.g., CD3 zeta, on the second CAR can limit the CAR activity to cells where both targets are expressed. In some embodiments, the CAR expressing cell comprises a first disease (e.g. cancer) associated antigen CAR that includes an antigen binding domain that binds a target antigen described herein, a transmembrane domain and a costimulatory domain and a second CAR that targets a different target antigen (e.g., an antigen expressed on that same cell type as the first target antigen) and includes an antigen binding domain, a transmembrane domain and a primary signaling domain. In other embodiments, the CAR expressing cell comprises a first CAR that includes an antigen binding domain that binds a target antigen described herein, a transmembrane domain and a primary signaling domain and a second CAR that targets an antigen other than the first target antigen (e.g., an antigen expressed on the same cancer cell type as the first target antigen) and includes an antigen binding domain to the antigen, a transmembrane domain and a costimulatory signaling domain.

In another embodiment, the present disclosure provides populations of CAR or engineered TCR-expressing cells modified with inducible expression cassettes coding for expression of immune stimulatory cytokines such as IL-7, IL-12, IL-15, and/or IL-18, wherein the cytokines improve CAR or engineered TCR cell expansion and persistence while rendering them resistant to the immunosuppressive tumor environment when administered to a subject. In some embodiments, the disclosure provides a population of cells, wherein at least 70%, at least 75%, at least 80%, at least 85%, at least 90%, or at least 95% of the modified cells of the population express a detectable level of the CAR or engineered TCR.

In embodiments, a population of CAR or engineered TCR-expressing cells of the invention in which expression or function of one or more proteins has been reduced or eliminated by the methods described herein, maintains the ability to become activated and to proliferate in response to stimulation, for example, binding of the CAR or engineered TCR to its target antigen. In embodiments, the proliferation occurs ex vivo such that the population of cells can be expanded. In one embodiment, the population of CAR or engineered TCR-expressing cells is expanded by in vitro culture in an appropriate medium under appropriate growth conditions. In other embodiments, the proliferation occurs in vivo. In embodiments, the proliferation occurs both ex vivo and in vivo. In the embodiments, the level of proliferation is substantially the same as the level of proliferation exhibited by the same cell type (e.g., a CAR-expressing cell of the same type) but which has not had expression or function of one or more proteins reduced or eliminated.

The method provides that immune cells; e.g., T cells, TREG cells, gamma-delta T cells, NK cells, B cells, macrophages, or dendritic cells, can be obtained from a unit of blood collected from a subject using any number of techniques known to the skilled artisan. In one exemplary aspect, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the T cells are CD4+ T cells, CD8+ T cells, or a combination thereof. The cells collected by apheresis may be washed to remove the plasma fraction and, optionally, to place the cells in an appropriate buffer or media for subsequent processing steps. In some embodiments, T cells are isolated from peripheral blood lymphocytes by lysing the red blood cells and depleting the monocytes, for example, by centrifugation through a PERCOLL™ gradient or by counterflow centrifugal elutriation. The method may include the steps of i) introducing the CasX:gNA system components for the editing of the target nucleic acids; ii) introducing a nucleic acid encoding a CAR and/or one or more fusion polypeptides of an engineered TCR of the embodiments to the cells; iii) i) expansion of the cells, and iv) cryopreservation of the cells for subsequent administration to the subject. The procedure for ex vivo expansion of hematopoietic stem and progenitor cells is described in U.S. Pat. No. 5,199,942, incorporated herein by reference, can be applied to the cells of the present invention.

Among the sub-types and subpopulations of T cells and/or of CD4+ and/or of CD8+ T cells are naïve T cells, effector T cells, memory T cells and sub-types thereof, such as stem cell memory T, central memory T, effector memory T, or terminally differentiated effector memory T cells, tumor-infiltrating lymphocytes, immature T cells, mature T cells, helper T cells, cytotoxic T cells, mucosa-associated invariant T cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

The methods described herein can include selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells. In some embodiments, the method provides that T regulatory cells, e.g., CD25+ T cells, are removed from the population using an anti-CD25 antibody, or fragment thereof, or a CD25-binding ligand, IL-2. In other embodiments, the anti-CD25 antibody is conjugated to a substrate, e.g., a bead, or is otherwise coated on a substrate over which the population of cells is added and washed to effect the separation.

In other embodiments, T cells are isolated from peripheral blood lymphocytes by lysing the red blood cells and depleting the monocytes, for example, by centrifugation through a PERCOLL™ gradient or by counterflow centrifugal elutriation. The cells typically are primary cells, such as those isolated directly from a subject and/or isolated from a subject and frozen.

The methods described herein can further include removing cells from the population which express a disease antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR described herein. In some embodiments, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., a bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

T cells for stimulation can also be frozen after a washing step, and the freeze and subsequent thaw step provides a more uniform product by removing granulocytes and to some extent monocytes in the cell population. After the washing step that removes plasma and platelets, the cells may be suspended in a suitable freezing solution. In certain cases, cryopreserved cells are thawed and washed and allowed to rest for one hour at room temperature prior to activation using the methods of the present disclosure.

In other embodiments, the cells of the disclosure (e.g., the immune cells of the disclosure and/or the CAR-expressing cells of the invention) are induced pluripotent stem cells ("iPSCs") or embryonic stem cells (ESCs), or are T cells generated from (e.g., differentiated from) said iPSC and/or ESC. iPSCs can be generated, for example, by methods known in the art, from peripheral blood T lymphocytes, e.g., peripheral blood T lymphocytes isolated from a healthy volunteer. As well, such cells may be differentiated into T cells by methods known in the art (see e.g., Themeli M. et al., Nat. Biotechnol. 31:928 (2013); doi:10.1038/nbt.2678; and WO2014/165707, the contents of each of which are incorporated herein by reference in their entirety).

In some embodiments, the disclosure provides a population of modified cells for use in methods to provide anti-tumor immunity in a subject (immunotherapy) having a disease associated with cancer or a tumor. In some embodiments, the method comprising administering to the subject a therapeutically effective amount of a population of any of the modified cell embodiments described herein.

In some embodiments, the dose of total cells and/or dose of individual sub-populations of cells is within a range of between at or about $10^4$ and at or about $10^9$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight.

In some embodiments, the administration of the effective amount of the modified cells results in an improvement in a clinical parameter or endpoint associated with the disease in the subject, wherein the clinical parameter or endpoint is selected from one or any combination of the group consisting of tumor shrinkage as a complete, partial or incomplete response; time-to-progression, time to treatment failure, biomarker response; progression-free survival; disease free-survival; time to recurrence; time to metastasis; time of overall survival; improvement of quality of life; and improvement of symptoms.

In some embodiments, the disclosure provides a method of preparing cells for immunotherapy in a subject comprising modifying immune effector cells by reducing or eliminating expression of one or more proteins involved in antigen processing, antigen presentation, antigen recognition, and/or antigen response. In some embodiments, the one or more proteins involved in antigen processing, antigen presentation, antigen recognition, and/or antigen response are selected from beta-2-microglobulin (B2M), T cell receptor alpha chain constant region (TRAC), ICP47 polypeptide, class II major histocompatibility complex transactivator (CIITA), T cell receptor beta constant 1 (TRBC1), T cell receptor beta constant 2 (TRBC2), PD-1, CTLA-4, LAG-3, TIM-3, 2B4, CISH, ADORA2A, TIGIT, NKG2A, human leukocyte antigen A (HLA-A), human leukocyte antigen B (HLA-B), TGFβ Receptor 2 (TGFβRII), cluster of differentiation 247 (CD247), CD3D, CD3E, CD3G, CD52, human leukocyte antigen C (HLA-C), deoxycytidine kinase (dCK), or FKBP1A. In some embodiments, the method comprises contacting the target nucleic acid sequence of the immune effector cell with a CasX:gNA system comprising a CasX protein and a guide nucleic acid (gNA), wherein the gNA comprises a targeting sequence (a) complementary to a target nucleic acid sequence for a gene or a portion of a gene encoding the protein, a regulatory element for the gene, or both, or (b) is complementary to a complement of a target nucleic acid sequence of genes encoding the one or more proteins. In some embodiments, the cell has been modified such that expression of the one or more proteins is reduced by at least about 50%, at least about 60%, at least about 70%, at least about 80%, or at least about 90%, or at least about 95% in comparison to a cell that has not been modified. In other embodiments of the method, the cell has been modified such that the cell does not express a detectable level of the one or more proteins. In an exemplary embodiment of the method, the proteins to be knocked-down or knocked-out are selected from B2M, TRAC, or CIITA. In other embodiments of the method, the cell has been modified such that at least 70%, at least 75%, at least 80%, at least 85%, at least 90%, or at least 95% of the modified cells do not express a detectable level of MHC Class I molecules. In other embodiments of the method, the cell has been modified such that at least 70%, at least 75%, at least 80%, at least 85%, at least 90%, or at least 95% of the modified cells do not express a detectable level of wild-type T cell receptor.

In some embodiments, the disclosure provides a method of preparing cells for immunotherapy in a subject that, in addition to modifying immune effector cells by reducing or eliminating expression of a protein involved in antigen processing, antigen presentation, antigen recognition, and/or antigen response, further comprises modifying the cells by introducing a nucleic acid that encodes a chimeric antigen receptor (CAR) specific for a tumor cell antigen. In some embodiments, the tumor cell antigen ligand of the CAR is selected from Cluster of Differentiation 19 (CD19), CD3, CD8, CD7, CD10, CD20, CD22, CD30, CLL1, CD33, CD34, CD38, CD41, CD44, CD47, CD49f, CD56, CD70, CD74, CD99, CD123, CD133, CD138, carbonix anhydrase IX (CAIX), CC chemokine receptor 4 (CCR4), ADAM metallopeptidase domain 12 (ADAM12), adhesion G protein-coupled receptor E2 (ADGRE2), alkaline phosphatase placental-like 2 (ALPPL2), alpha 4 Integrin, angiopoietin-2 (ANG2), B-cell maturation antigen (BCMA), CD44V6, carcinoembryonic antigen (CEA), CEAC, CEACAM5, Claudin 6 (CLDN6), CLDN18, C-type lectin domain family 12 member A (CLEC12A), mesenchymal-epithelial transition factor (cMET), cytotoxic T-lymphocyte-associated protein 4 (CTLA4), epidermal growth factor receptor 1 (EGF1R), EGFR-VIII, epithelial glycoprotein 2 (EGP-2), EGP-40, EphA2, ENPP3, epithelial cell adhesion molecule (EpCAM), erb-B2,3,4, folate binding protein (FBP), fetal acetylcholine receptor, folate receptor-a, folate receptor 1 (FOLR1), G protein-coupled receptor 143 (GPR143), glutamate metabotropic receptor 8 (GRM8), glypican-3 (GPC3), ganglioside GD2, ganglioside GD3, human epidermal growth factor receptor 1 (HER1), human epidermal growth factor receptor 2 (HER2), HER3, Integrin B7, intercellular cell-adhesion molecule-1 (ICAM-1), human telomerase reverse transcriptase (hTERT), Interleukin-13 receptor a2 (IL-13R-a2), K-light chain, Kinase insert domain receptor (KDR), Lewis-Y (LeY), chondromodulin-1 (LECT1), L1 cell adhesion molecule, Lysophosphatidic acid receptor 3 (LPAR3), melanoma-associated antigen 1 (MAGE-A1), mesothelin, mucin 1 (MUC1), MUC16, melanoma-associated antigen 3 (MAGE-A3), tumor protein p53 (p53), Melanoma Antigen Recognized by T cells 1 (MART1), glycoprotein 100 (GP100), Proteinase3 (PR1), ephrin-A receptor 2 (EphA2), Natural killer group 2D ligand (NKG2D ligand), New York esophageal squamous cell carcinoma 1 (NY-ESO-1), oncofetal antigen (h5T4), prostate-specific membrane antigen (PSMA), programmed death ligand 1 (PDL-1), receptor tyrosine kinase-like orphan receptor 1 (ROR1), trophoblast glycoprotein (TPBG), tumor-associated glycoprotein 72 (TAG-72), tumor-associated calcium signal transducer 2 (TROP-2), tyrosinase, survivin, vascular endothelial growth factor receptor 2 (VEGF-R2), Wilms tumor-1 (WT-1), leukocyte immunoglobulin-like receptor B2 (LILRB2), Preferentially Expressed Antigen In Melanoma (PRAME), T cell receptor beta constant 1 (TRBC1), TRBC2, and (T-cell immunoglobulin mucin-3) TIM-3. In some embodiments, the CAR comprises an antigen binding domain selected from linear antibody, single domain antibody (sdAb), or single-chain variable fragment (scFv). In some embodiments, the antigen binding domain is an scFv derived from a reference antibody with specific binding affinity to a tumor cell antigen. In some embodiments, the scFv comprises VH and VL and/or heavy chain and light chain CDRs selected from the group consisting of the sequences set forth in Table 5. In the foregoing embodiment, the VH, VL, and/or the CDRs can have one or more amino acid substitutions wherein the scFv retains specific binding affinity to the tumor antigen.

In other embodiments of the method of preparing cells for immunotherapy in a subject, the nucleic acid encoding the CAR further comprises a nucleic acid encoding at least one intracellular signaling domain, wherein the at least one intracellular signaling domain comprises at least one intracellular signaling domain isolated or derived from CD247 molecule (CD3-zeta), CD27 molecule (CD27), CD28 molecule (CD28), TNF receptor superfamily member 9 (4-1BB), inducible T cell costimulator (ICOS), or TNF receptor superfamily member 4 (OX40). In one embodiment, the at least one intracellular signaling domain comprises: a) a CD3-zeta intracellular signaling domain; b) a CD3-zeta intracellular signaling domain and a 4-1BB or CD28 intracellular signaling domain; c) a CD-zeta intracellular signaling domain, a 4-1BB intracellular signaling domain, and a CD28 intracellular signaling domain; or d) a CD-zeta intracellular signaling domain, a CD28 intracellular signaling domain, a 4-1BB intracellular signaling domain, and a CD27 or OX40 intracellular signaling domain. In other embodiments, the CAR further comprises an extracellular hinge domain, wherein the hinge domain is an immunoglobulin like domain, or wherein the hinge domain is isolated or derived from IgG1, IgG2, or IgG4, or wherein the hinge domain is isolated or derived from CD8a molecule (CD8) or CD28. In some embodiments, the CAR further comprises a transmembrane domain, wherein the transmembrane domain is isolated or derived from the group consisting of CD3-zeta, CD4, CD8, and CD28. In the foregoing, the components of the CAR are operably linked with appropriate linkers to form a single chimeric fusion polypeptide.

In some embodiments, the TCR comprises one or more subunits selected from the group consisting of TCR alpha, TCR beta, CD3-delta, CD3-epsilon, CD-gamma or CD3-zeta, operably linked to the antigen binding domain arranged such that the extracellular antigen binding domain and the subunit form a single chimeric fusion polypeptide. In some embodiments, the single chimeric fusion polypeptide comprises a linker between the TCR subunit and the antigen binding domain.

In some embodiments, the TCR comprises one or more subunits selected from the group consisting of TCR alpha, TCR beta, CD3-delta, CD3-epsilon, CD-gamma or CD3-zeta, operably linked to the antigen binding domain and one or more intracellular domains comprising an intracellular signaling domain arranged such that the extracellular antigen binding domain, the intracellular signaling domain (and appropriate linkers) form a single chimeric fusion polypeptide. The one or more intracellular signaling domains can be isolated or derived from the group consisting of CD247 molecule (CD3-zeta), CD27 molecule (CD27), CD28 molecule (CD28), TNF receptor superfamily member 9 (4-1BB), inducible T cell costimulator (ICOS), or TNF receptor superfamily member 4 (OX40).

In some embodiments, the method further comprises introducing into the immune cells a polynucleic acid encoding an inducible expression cassette coding for an immune stimulatory cytokine selected from the group consisting of IL-7, IL-12, IL-15, and IL-18. In other embodiments, the method further comprises expanding the population of cells by in vitro culture in an appropriate medium and under appropriate conditions, for subsequent administration to a subject in need thereof.

In some embodiments of a method of preparing cells for immunotherapy in a subject, the method further comprises introducing into the immune cells a polynucleic acid encoding a TCR comprising one or more subunits selected from the group consisting of TCR alpha, TCR beta, CD3-delta, CD3-epsilon, CD-gamma or CD3-zeta. In some embodiment, the TCR further comprises an intracellular domain comprising a stimulatory domain from an intracellular signaling domain. In some embodiments, the antigen binding domain of the TCR is operably linked to the one ore more subunits. In some cases, the antigen binding domain of the TCR is an scFv comprising variable heavy (VH) and variable light (VL) and/or heavy chain and light chain CDRs selected from the group consisting of the sequences set forth in Table 5.

VIII. Therapeutic Methods

In another aspect, the present disclosure relates to methods of treating a subject having a disease associated with expression of a tumor antigen or having an autoimmune disease. In some embodiments, the present disclosure provides methods of immunotherapy for treating a disease in a subject in need thereof. In some embodiments of the disclosure, the methods of treatment can prevent, treat and/or ameliorate a disease of a subject by the administration to the subject of a therapeutically effective amount of the cells or populations of cells modified by CasX:gNA system composition(s) and the polynucleic acids of the embodiments described herein. In some embodiments, the method of treatment comprises the administration to the subject of a cell or a population of cells modified by a CasX:gNA composition and, optionally, a donor template, wherein one or more genes encoding one or more proteins involved in antigen processing, antigen presentation, antigen recognition, and/or antigen response are modified. In some cases, the cell or a population of cells have been also been modified to express a CAR or engineered TCR of any of the embodiments described herein. In one embodiment, the disease is a cancer. In another embodiment, the disease is an autoimmune disease. Unlike antibody therapies, the modified cells of the embodiments are able to replicate in vivo, resulting in long-term persistence that can lead to sustained control of the underlying disease. In various aspects, the modified cells administered to the subject, or their progeny, persist in the subject for at least one month, two month, three months, four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the modified cells to the subject. By the methods of treatment, the administration of the modified cells results in the killing of the cells causing or related to the underlying disease, such as a tumor cell.

In one embodiment, the disclosure provides a method of treating a subject having a disease associated with expression of a tumor antigen, comprising administering a population of cells wherein the cells have been modified such that expression of one or more proteins involved in antigen processing, antigen presentation, antigen recognition, and/or antigen response is reduced by at least about 50%, at least about 60%, at least about 70%, at least about 80%, at least about 90%, or at least about 95% in comparison to a cell that has not been modified, or wherein the cell does not express a detectable level of the protein. In one embodiment the protein is selected from the group consisting of beta-2-microglobulin (B2M), T cell receptor alpha chain constant region (TRAC), class II major histocompatibility complex transactivator (CIITA), ICP47 polypeptide, T cell receptor beta constant 1 (TRBC1), T cell receptor beta constant 2 (TRBC2), programmed cell death-1 receptor (PD-1), cytotoxic T-lymphocyte-associated protein 4 (CTLA-4), lymphocyte-activation gene 3 (LAG-3), T-cell immunoglobulin and mucin domain 3 (TIM-3), 2B4 (CD244), CISH, ADORA2A, TIGIT, NGK2A, human leukocyte antigen A (HLA-A), human leukocyte antigen B (HLA-B), and TGFβ Receptor 2 (TGFβRII). In another embodiment, the protein is selected from the group consisting of cluster of differentiation 247 (CD247), CD3D, CD3E, CD3G, CD52, human leukocyte antigen C (HLA-C), deoxycytidine kinase (dCK), and FKBP1A. In a particular embodiment, the protein is selected from the group consisting of B2M, TRAC, and CIITA. In some embodiments, the cell to be modified is selected from the group consisting of a rodent cell, a mouse cell, a rat cell, a non-human primate cell, or a human cell. In some embodiments, the cell to be modified is selected from the group consisting of a progenitor cell, a hematopoietic stem cell, and a pluripotent stem call. In one case, the cell is an induced pluripotent stem cell. In some embodiments, the cell to be modified is an immune cell selected from a T cell, Treg cell, NK cell, B cell, macrophage, or dendritic cell.

In the case where the immune cell is a T cell, the T cell can be a CD4+ T cell, a CD8+ T cell, gamma-delta T cells, or a combination thereof. In a particular embodiment, the cells to be modified are autologous with respect to a subject to be administered the cell. In another embodiment, the cells to be modified are allogeneic with respect to a subject to be administered the cell. The methods to modify the cells for administration to a subject have been described herein, but, briefly, the modifying comprises contacting the cells with: a) CasX:gNA system comprising a CasX protein and gNA of any of the embodiments described herein; b) a nucleic acid encoding the CasX protein and gNA; c) a vector comprising the nucleic acid of b); or d) any of a) to c), wherein expression of the one or more proteins (of those listed, above) is reduced or the cell does not express a detectable level of the one or more proteins. In the case of the foregoing target proteins, the method of treatment comprises knocking-down or knocking out expression of the one or more target protein. In the foregoing method of treatment embodiments, the cells can also be modified such that at least 70%, at least 75%, at least 80%, at least 85%, at least 90%, or at least 95% of the modified cells express a detectable level of the chimeric antigen receptor (CAR) or engineered TCR specific for a tumor cell antigen. In the foregoing, the CAR or engineered TCR can be specific for a tumor cell antigen selected from the group consisting of Cluster of Differentiation 19 (CD19), CD3, CD8, CD7, CD10, CD20, CD22, CD30, CLL1, CD33, CD34, CD38, CD41, CD44, CD47, CD49f, CD56, CD70, CD74, CD99, CD123, CD133, CD138, carbonix anhydrase IX (CAIX), CC chemokine receptor 4 (CCR4), ADAM metallopeptidase domain 12 (ADAM12), adhesion G protein-coupled receptor E2 (ADGRE2), alkaline phosphatase placental-like 2 (ALPPL2), alpha 4 Integrin, angiopoietin-2 (ANG2), B-cell maturation antigen (BCMA), CD44V6, carcinoembryonic antigen (CEA), CEAC, CEACAM5, Claudin 6 (CLDN6), CLDN18, C-type lectin domain family 12 member A (CLEC12A), mesenchymal-epithelial transition factor (cMET), cytotoxic T-lymphocyte-associated protein 4 (CTLA4), epidermal growth factor receptor 1 (EGF1R), EGFR-VIII, epithelial glycoprotein 2 (EGP-2), EGP-40, EphA2, ENPP3, epithelial cell adhesion molecule (EpCAM), erb-B2,3,4, folate binding protein (FBP), fetal acetylcholine receptor, folate receptor-a, folate receptor 1 (FOLR1), G protein-coupled receptor 143 (GPR143), glutamate metabotropic receptor 8 (GRM8), glypican-3 (GPC3), ganglioside GD2, ganglioside GD3, human epidermal growth factor receptor 1 (HER1), human epidermal growth factor receptor 2 (HER2), HER3, Integrin B7, intercellular cell-adhesion molecule-1 (ICAM-1), human telomerase reverse transcriptase (hTERT), Interleukin-13 receptor a2 (IL-13R-a2), K-light chain, Kinase insert domain receptor (KDR), Lewis-Y (LeY), chondromodulin-1 (LECT1), L1 cell adhesion molecule, Lysophosphatidic acid receptor 3 (LPAR3), melanoma-associated antigen 1 (MAGE-A1), mesothelin, mucin 1 (MUC1), MUC16, melanoma-associated antigen 3 (MAGEA3), tumor protein p53 (p53), Melanoma Antigen Recognized by T cells 1 (MARTl), glycoprotein 100 (GP100), Proteinase3 (PR1), ephrin-A receptor 2 (EphA2), Natural killer group 2D ligand (NKG2D ligand), New York esophageal squamous cell carcinoma 1 (NY-ESO-1), oncofetal antigen (h5T4), prostate-specific membrane antigen (PSMA), programmed death ligand 1 (PDL-1), receptor tyrosine kinase-like orphan receptor 1 (ROR1), trophoblast glycoprotein (TPBG), tumor-associated glycoprotein 72 (TAG-72), tumor-associated calcium signal transducer 2 (TROP-2), tyrosinase, survivin, vascular endothelial growth factor receptor 2 (VEGF-R2), Wilms tumor-1 (WT-1), leukocyte immunoglobulin-like receptor B2 (LILRB2), Preferentially Expressed Antigen In Melanoma (PRAME), T cell receptor beta constant 1 (TRBC1), TRBC2, and (T-cell immunoglobulin mucin-3) TIM-3. In some embodiments of the method of treatment, the CAR or engineered TCR comprises an antigen binding domain selected from the group consisting of linear antibody, single domain antibody (sdAb), and single-chain variable fragment (scFv). In some cases, the CAR further comprises one or more polypeptides selected from the group consisting of CD3zeta, CD27, CD28, 4-1BB (41BB), ICOS, and OX40. The one or more of CD3-zeta, CD27, CD28, 4-1BB (41BB), ICOS, or OX40 can be linked to the CAR antigen binding domain by an immunoglobulin-like domain hinge and/or a spacer sequence, and further comprises a transmembrane domain derived from a polypeptide selected from the group consisting of CD3-zeta, CD4, CD8, and CD28. In other cases, the cells are further modified by introducing into the immune cell a polynucleic acid encoding an inducible expression cassette coding for an immune stimulatory cytokine selected from the group consisting of IL-7, IL-12, IL-15, and IL-18.

In some embodiments of the method of treating a subject having a disease associated with expression of a tumor antigen, the administering to the subject of a therapeutically effective amount of the modified population of cells of any one of the embodiments described herein can produce a beneficial effect in helping to treat (e.g., cure or reduce the severity) or prevent (e.g., reduce the likelihood of recurrence) of a cancer or a tumor or result in an improvement in a clinical parameter or endpoint associated with the disease in the subject, wherein the clinical parameter or endpoint is selected from one or any combination of the group consisting of tumor shrinkage as a complete, partial or incomplete response; time-to-progression, time to treatment failure, biomarker response; progression-free survival; disease free-survival; time to recurrence; time to metastasis; time of overall survival; improvement of quality of life; and improvement of symptoms.

In the foregoing embodiment, the disease associated with expression of a tumor antigen is a cancer. In some embodiments, the cancer comprises a solid tumor or a liquid tumor. In some embodiments, the cancer is selected from colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), acute myeloid leukemia (AML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, Hodgkin's lymphoma, plasmablastic lymphoma, plasmacytoid dendritic cell neoplasm, Waldenstrom macroglobulinemia, or pre-leukemia, combinations of said cancers, or metastatic lesions of said cancers. In the method, upon binding of the CAR or engineered TCR-bearing modified cell to the tumor antigen of a cell bearing a ligand of the CAR or engineered TCR, the administered cells are capable of: i) becoming activated; ii) inducing proliferation of the modified cell; iii) cytokine secretion by the modified cell; or iv) inducing cytotoxicity of the cell bearing said tumor antigen. In other embodiments of the method of treating a subject having a disease associated with expression of a tumor antigen, the method further comprises administering a chemotherapeutic agent. Non-limiting examples of chemotherapeutic agents include immunosuppressive agents, such as cyclosporin, azathioprine, methotrexate, mycophenolate, and FK506, or other immunoablative agents such as alemtuzumab, anti-CD3 antibodies or other anti-tumor antibody therapies, cytoxin, fludarabine, cyclosporin, FK506, rapamycin, mycophenolic acid, steroids, FR901228, and cytokines.

In some embodiments, the disclosure provides a method of treating a subject having an autoimmune disease. In some embodiments, the subject having an autoimmune disease is administered an effective amount of a population of allogeneic immune cells (e.g., Treg cells) modified to reduce the expression of one or more proteins involved in antigen processing, presentation, recognition, and/or response.

In another embodiment, the invention provides a method of treatment of a subject having disease associated with expression of a tumor antigen, the method comprising administering to the subject a plurality of cells modified to express a detectable level of the chimeric antigen receptor (CAR) or engineered TCR, and that have a reduced or undetectable level of MHC Class I molecules and/or wild-type T-cell receptor according to a treatment regimen comprising one or more consecutive doses using a therapeutically effective dose of the cells. In one embodiment of the treatment regimen, the therapeutically effective dose of the cells is administered as a single dose. In another embodiment of the treatment regimen, the therapeutically effective dose of the cells is administered to the subject as two or more doses over a period of at least two weeks, or at least one month, or at least two months, or at least three months, or at least four months, or at least five months, or at least six months, or once a year, or every 2 or 3 years. In some embodiments, the dose of total cells and/or dose of individual sub-populations of cells is within a range of between at or about $10^4$ and at or about $10^9$ cells/kilograms (kg) body weight per dose, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight per dose. For example, in some embodiments, the cells are administered at, or within a certain range of error of, between at or about $10^4$ and at or about $10^9$ cells/kilograms (kg) body weight per dose, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight per dose.

In another embodiment, the invention provides a method of treatment of a subject having disease associated with expression of a tumor antigen, the method comprising administering to the subject a plurality of cells modified to express a CAR or engineered TCR of any of the embodiments described herein, and further modified such that expression of one or more proteins involved in antigen processing, antigen presentation, antigen recognition, and/or antigen response are reduced by at least about 50%, at least about 60%, at least about 70%, at least about 80%, at least about 90%, or at least about 95% in comparison to a cell that has not been modified, wherein the administration is according to a treatment regimen comprising one or more consecutive doses using a therapeutically effective dose of the cells. In one embodiment of the treatment regimen, the therapeutically effective dose of the cells is administered as a single dose. In another embodiment of the treatment regimen, the therapeutically effective dose of the cells is administered to the subject as two or more doses over a period of at least two weeks, or at least one month, or at least two months, or at least three months, or at least four months, or at least five months, or at least six months, or on an annual basis or every 2 or 3 years. In some embodiments, the treatment regimen results in the improvement of a clinical parameter or endpoint associated with the disease in the subject, wherein the clinical parameter or endpoint is selected from one or any combination of the group consisting of tumor shrinkage as a complete, partial or incomplete response; time-to-progression, time to treatment failure, biomarker response; progression-free survival; disease free-survival; time to recurrence; time to metastasis; time of overall survival; improvement of quality of life; and improvement of symptoms. In the foregoing embodiments of the treatment regimen, the one or more proteins are selected from the group consisting of beta-2-microglobulin (B2M), T cell receptor alpha chain constant region (TRAC), class II major histocompatibility complex transactivator (CIITA), ICP47 polypeptide, T cell receptor beta constant 1 (TRBC1), T cell receptor beta constant 2 (TRBC2), PD-1, CTLA-4, LAG-3, TIM-3, 2B4, CISH, ADORA2A, TIGIT, NKG2A, human leukocyte antigen A (HLA-A), human leukocyte antigen B (HLA-B), and TGFβ Receptor 2 (TGFβRII). In another embodiment, the cells are further modified to reduce expression of one or more proteins selected from the group consisting of cluster of differentiation 247 (CD247), CD3D, CD3E, CD3G, CD52, human leukocyte antigen C (HLA-C), deoxycytidine kinase (dCK), and FKBP1A.

The cells can be administered by any suitable means, for example, by bolus infusion, by injection, e.g., intraparenchymal, intravenous, intra-arterial, intracerebroventricular, intracisternal, intrathecal, intracranial, intra-lumbar, intraperitoneal, or by subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration.

In some embodiments, provided herein are compositions of immune cells modified by CasX and gNA gene editing pairs and, optionally, donor templates and/or polynucleotides encoding CAR, engineered TCR, or fusion polypeptides comprising subunits thereof for use as a medicament for the treatment of a subject having a disease associated with expression of a tumor antigen. In the foregoing, the CasX can be a CasX variant of any of the embodiments described herein (e.g., the sequences of Table 4) and the gNA can be a gNA variant of any of the embodiments described herein (e.g., the sequences of Table 2). In other embodiments, the disclosure provides compositions cells modified by vectors comprising or encoding the gene editing pairs of CasX and gNA, donor templates and/or polynucleotides encoding CAR for use as a medicament for the treatment of a subject having a disease associated with expression of a tumor antigen.

IX. Kits and Articles of Manufacture

In another aspect, provided herein are kits comprising the compositions of the embodiments described herein. In some embodiments, the kit comprises a CasX protein and one or a plurality of gNA of any of the embodiments of the disclosure comprising a targeting sequence complementary to a cell gene encoding a protein involved in antigen processing, antigen presentation, antigen recognition, and/or antigen response, an excipient and a suitable container (for example a tube, vial or plate). In other embodiments, the kit comprises a nucleic acid encoding a CasX protein and one or a plurality of gNA of any of the embodiments of the disclosure comprising a targeting sequence complementary to a cell gene encoding a protein involved in antigen processing, antigen presentation, antigen recognition, and/or antigen response, a nucleic acid encoding a CAR, or engineered TCR, an excipient and a suitable container. In other embodiments, the kit comprises a vector comprising a nucleic acid encoding a CasX protein and one or a plurality of gNA of any of the embodiments of the disclosure comprising a targeting sequence complementary to a cell gene encoding a protein involved in antigen processing, antigen presentation, antigen recognition, and/or antigen response, a nucleic acid encoding a CAR or engineered TCR, an excipient and a suitable container. In still other embodiments, the kit comprises a VLP comprising a CasX protein and one or a plurality of gNA of any of the embodiments of the disclosure comprising a targeting sequence complementary to a cell gene encoding a protein involved in antigen processing, antigen presentation, antigen recognition, and/or antigen response, a nucleic acid encoding a CAR, an excipient and a suitable container.

In some embodiments, the kit further comprises a buffer, a nuclease inhibitor, a protease inhibitor, a liposome, a therapeutic agent, a label, a label visualization reagent, or any combination of the foregoing. In some embodiments, the kit further comprises a pharmaceutically acceptable carrier, diluent or excipient.

In some embodiments, the kit comprises appropriate control compositions for gene modifying applications, and instructions for use.

The present description sets forth numerous exemplary configurations, methods, parameters, and the like. It should be recognized, however, that such description is not intended as a limitation on the scope of the present disclosure, but is instead provided as a description of exemplary embodiments.

Examples of Non-Limiting Embodiments of the Disclosure

Embodiments of the present subject matter described above may be beneficial alone or in combination, with one or more other embodiments. Without limiting the foregoing description, certain non-limiting aspects of the disclosure, numbered 1-234 are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiment explicitly provided below:

Embodiment Set No. 1

1. A CasX:gNA system comprising a CasX polypeptide and a guide nucleic acid (gNA), wherein the gNA comprises a targeting sequence (a) complementary to a nucleic acid sequence encoding a protein involved in antigen processing, antigen presentation, antigen recognition, and/or antigen response and/or its regulatory region; or (b) complementary to a complement of a nucleic acid sequence encoding a protein involved in antigen processing, antigen presentation, antigen recognition, and/or antigen response or its regulatory region.
2. The CasX:gNA system of 1, wherein the protein is an immune cell surface marker.
3. The CasX:gNA system of 1, wherein the protein is an intracellular protein.
4. The CasX:gNA system of any one of 1-3, wherein the protein is selected from the group consisting of beta-2-microglobulin (B2M), T cell receptor alpha chain constant region (TRAC), class II major histocompatibility complex transactivator (CIITA), T cell receptor beta constant 1 (TRBC1), T cell receptor beta constant 2 (TRBC2), human leukocyte antigen A (HLA-A), and human leukocyte antigen B (HLA-B).
5. The CasX:gNA system of 4, further comprising a gNA comprising a targeting sequence (a) complementary to a nucleic acid sequence encoding a protein selected from the group consisting of cluster of differentiation 247 (CD247), CD3D, CD3E, CD3G, CD52, human leukocyte antigen C (HLA-C), deoxycytidine kinase (dCK), and FKBP1A; or (b) is complementary to a complement of a nucleic acid sequence encoding a protein selected from the group consisting of cluster of differentiation 247 (CD247), CD3D, CD3E, CD3G, CD52, human leukocyte antigen C (HLA-C), deoxycytidine kinase (dCK), and FKBP1A.
6. The CasX:gNA system of any one of 1-5, wherein the gNA is a guide RNA (gRNA).
7. The CasX:gNA system of any one of 1-5, wherein the gNA is a guide DNA (gDNA).
8. The CasX:gNA system of any one of 1-5, wherein the gNA is a chimera comprising DNA and RNA.
9. The CasX:gNA system of 4, wherein the protein is B2M.
10. The CasX:gNA system of 9, wherein the targeting sequence of the gNA comprises a sequence having at least about 65%, at least about 75%, at least about 85%, or at least about 95% identity to a sequence selected from the group consisting of sequences set forth in Table 3A.
11. The CasX:gNA system of 4 wherein the protein is TRAC.
12. The CasX:gNA system of 11, wherein the targeting sequence of the gNA comprises a sequence having at least about 65%, at least about 75%, at least about 85%, or at least about 95% identity to a sequence selected from the group consisting of sequences set forth in Table 3B.

13. The CasX:gNA system of 4, wherein the protein is CIITA.
14. The CasX:gNA system of any one of 1-13, wherein the gNA has a scaffold comprising a sequence having at least about 50%, at least about 60%, at least about 70%, at least about 80%, at least about 90%, at least about 95%, or 100% sequence identity to a sequence of Table 2.
15. The CasX:gNA system of any one of 1-14, wherein the targeting sequence consists of 14, 15, 16, 17, 18, 19, 20, 21, 22, 23, 24, 25, 26, 27, 28, 29, or 30 consecutive nucleotides.
16. The composition of any one of 1-15, wherein the CasX polypeptide comprises any one of SEQ ID NOS: 1-3 or a sequence of Table 4, or a sequence having at least about 50%, at least about 60%, at least about 70%, at least about 80%, at least about 90%, or at least about 95% sequence identity thereto.
17. The CasX:gNA system of any one of 1-16, wherein the CasX polypeptide and the gNA are associated together in a ribonuclear protein complex (RNP).
18. The CasX:gNA system of any one of 1-17, further comprising a donor template nucleic acid.
19. The CasX:gNA system of 18, wherein the donor template comprises a nucleic acid encoding i) a chimeric antigen receptor (CAR) specific for a disease antigen, optionally a tumor cell antigen; and/or ii) the protein of 4.
20. The CasX:gNA system of 19, wherein the tumor cell antigen is selected from the group consisting of CD47, CD19, CD20, CD22, CD33, CD123, CD138, FLT3, BCMA, EGFR, and mesothelin.
21. The CasX:gNA system of 19 or 20, wherein the CAR comprises an antigen binding domain selected from the group consisting of linear antibody, single domain antibody (sdAb), and single-chain variable fragment (scFv).
22. The CasX:gNA system of 19, wherein the CAR further comprises one or more polypeptides selected from the group consisting of CD3zeta, CD27, CD28, 4-1BB (41BB), ICOS, and OX40.
23. The CasX:gNA system of 22, wherein the one or more of CD3zeta, CD27, CD28, 4-1BB (41BB), ICOS, or OX40 are linked to the CAR antigen binding domain by an immunoglobulin-like domain hinge and, optionally, a spacer sequence.
24. The CasX:gNA system of any one of 18-23, wherein the donor template comprises a nucleic acid for a gene or a portion of a gene encoding the protein of 4 or a regulatory region for the gene, wherein the nucleic acid comprises a deletion, insertion, or mutation of one or more nucleotides in comparison to a genomic nucleic acid sequence encoding the protein or its regulatory region.
25. A nucleic acid comprising a sequence that encodes the CasX:gNA system of any one of 1-17.
26. A vector comprising the nucleic acid of 25.
27. A vector comprising a donor template, wherein the donor template comprises a nucleic acid encoding i) a chimeric antigen receptor (CAR) specific for a disease antigen, optionally a tumor cell antigen; and/or ii) a gene or a portion of a gene encoding a protein selected from the group consisting of beta-2-microglobulin (B2M), T cell receptor alpha chain constant region (TRAC), class II major histocompatibility complex transactivator (CIITA), T cell receptor beta constant 1 (TRBC1), T cell receptor beta constant 2 (TRBC2), human leukocyte antigen A (HLA-A), and human leukocyte antigen B (HLA-B) or iii) a regulatory region for the gene of ii).
28. The vector of 27, wherein the tumor cell antigen is selected from the group consisting of CD47, CD19, CD20, CD22, CD33, CD123, CD138, FLT3, BCMA, EGFR, and mesothelin.
29. The vector of 27 or 28, wherein the CAR comprises an antigen binding domain selected from the group consisting of linear antibody, single domain antibody (sdAb), and single-chain variable fragment (scFv).
30. The vector of 29, wherein the CAR further comprises one or more polypeptides selected from the group consisting of CD3zeta, CD27, CD28, 4-1BB (41BB), ICOS, and OX40 linked to the antigen binding domain.
31. The vector of 30, wherein the one or more of CD3zeta, CD27, CD28, 4-1BB (41BB), ICOS, or OX40 are linked to the CAR antigen binding domain by an immunoglobulin-like domain hinge and, optionally, a linker sequence.
32. The vector of any one of 27-31, further comprising the nucleic acid of 25.
33. The vector of any one of 26-32, wherein the vector is selected from the group consisting of a lentiviral vector, an adenoviral vector, an adeno-associated viral (AAV) vector, a herpes simplex virus (HSV) vector, a plasmid, a minicircle, a nanoplasmid, and an RNA vector.
34. A method of altering a target sequence of a cell, comprising contacting said cell with: a) CasX:gNA system of any one of 1-24; b) the nucleic acid of 25; c) the vector as in any one of 26-33; or d) any of a) to c), above.
35. The method of 34, wherein the cell has been engineered such that expression of the protein is reduced by at least about 50%, at least about 60%, at least about 70%, at least about 80%, at least about 90%, or at least about 95% in comparison to a cell that has not been engineered.
36. The method of 34 or 35, wherein the cell has been engineered such that the cell does not express a detectable level of the protein.
37. The method of 35 or 36, wherein the protein is selected from the group consisting of B2M, TRAC, and CIITA.
38. A population of cells engineered by the method of 34 or 35, wherein the cells have been engineered such that at least 70%, at least 75%, at least 80%, at least 85%, at least 90%, or at least 95% of the engineered cells do not express a detectable level of MHC Class I molecules.
39. A population of cells engineered by the method of 34 or 35, wherein the cell has been engineered such that at least 70%, at least 75%, at least 80%, at least 85%, at least 90%, or at least 95% of the engineered cells do not express a detectable level of wild-type T cell receptor.
40. The population of cells of 38 or 39, wherein the cell has been engineered such that at least 70%, at least 75%, at least 80%, at least 85%, at least 90%, or at least 95% of the engineered cells express a detectable level of the chimeric antigen receptor (CAR).
41. The population of cells of any one of 38-40, wherein the cell is a non-primate mammalian cell, a non-human primate cell, or a human cell.
42. The population of cells of any one of 38-41, wherein the cell is selected from the group consisting of a progenitor cell, a hematopoietic stem cell, and a pluripotent stem call.

43. The population of cells of 42, wherein the cell is an induced pluripotent stem cell.
44. The population of cells of any one of 38-41, wherein the cell is an immune cell.
45. The population of cells of 44, wherein the immune cell is a T cell, TREG cell, NK cell, B cell, macrophage, or dendritic cell.
46. The population of cells of 45, wherein the immune cell is a T cell, wherein the T cell is a CD4+ T cell, a CD8+ T cell, or a combination thereof.
47. The population of cells of any one of 38-46, wherein the cells are autologous with respect to a patient to be administered the cell.
48. The population of cells of any one of 38-46, wherein the cells are allogeneic with respect to a patient to be administered the cell.
49. A population of cells, comprising the CasX:gNA system of any one of 1-24.
50. The population of cells of 49, wherein the cells have been engineered to i) express a chimeric antigen receptor (CAR) specific for a disease antigen, optionally a tumor cell antigen; and/or ii) disrupt expression of the protein of 4.
51. The population of cells of 50, wherein at least 70%, at least 75%, at least 80%, at least 85%, at least 90%, or at least 95% of the engineered cells express a detectable level of the CAR.
52. The population of cells of 50 or 51, wherein the cell has been engineered such that expression of the protein is reduced by at least about 50%, at least about 60%, at least about 70%, at least about 80%, at least about 90%, or at least about 95% in comparison to a cell that has not been engineered.
53. The population of cells of any one of 49-52, wherein the cells are autologous with respect to a patient to be administered the cell.
54. The population of cell of any one of 49-52, wherein the cells are allogeneic with respect to a patient to be administered the cell.
55. The population of cells of any one of 49-54, wherein at least 75%, at least 80%, at least 85%, at least 90%, or at least 95% of the engineered cells do not express a detectable level of MHC Class I molecules.
56. The population of cells of any one of 49-55, wherein at least 75%, at least 80%, at least 85%, at least 90%, or at least 95% of the engineered cells do not express a detectable level of wild-type T cell receptor.
57. A method of providing an anti-tumor immunity in a subject, the method comprising administering to the subject an effective amount of the cells of any one of 49-56.
58. A method of treating a subject having a disease associated with expression of a tumor antigen or having an autoimmune disease, the method comprising administering to the subject an effective amount of the cell of any one of 49-56.
59. The method of 58, wherein the disease associated with expression of a tumor antigen is a cancer selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), acute myeloid leukemia (AML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, Hodgkin's lymphoma, plasmablastic lymphoma, plasmacytoid dendritic cell neoplasm, Waldenstrom macroglobulinemia, pre-leukemia, combinations of said cancers, and metastatic lesions of said cancers.
60. The method of any one of 57-59, wherein the method further comprises administering a chemotherapeutic agent.
61. A method of preparing cells for immunotherapy comprising modifying immune cells by reducing or eliminating expression of i) a protein involved in antigen processing, antigen presentation, antigen recognition, and/or antigen response or ii) the regulatory region of the protein.
62. The method of 61, comprising contacting a nucleic acid of the immune cell with a CasX:gNA system comprising a CasX polypeptide and a guide nucleic acid (gNA), wherein the gNA comprises a targeting sequence (a) complementary to the nucleic acid sequence for a gene or a portion of a gene encoding the protein or a regulatory region for the gene, or (b) is complementary to a complement of a nucleic acid sequence encoding the protein or its regulatory region.
63. The method of 61, wherein the protein is selected from the group consisting of beta-2-microglobulin (B2M), T cell receptor alpha chain constant region (TRAC), class II major histocompatibility complex transactivator (CIITA), T cell receptor beta constant 1 (TRBC1), T cell receptor beta constant 2 (TRBC2), human leukocyte antigen A (HLA-A), and human leukocyte antigen B (HLA-B).
64. The method of 63, further comprising a gNA comprising a targeting sequence (a) complementary to a nucleic acid sequence encoding a protein selected from the group consisting of cluster of differentiation 247 (CD247), CD3D, CD3E, CD3G, CD52, human leukocyte antigen C (HLA-C), deoxycytidine kinase (dCK), and FKBP1A; or (b) is complementary to a complement of a nucleic acid sequence encoding a protein selected from the group consisting of cluster of differentiation 247 (CD247), CD3D, CD3E, CD3G, CD52, human leukocyte antigen C (HLA-C), deoxycytidine kinase (dCK), and FKBP1A.

65. The method of any one of 61-64, wherein the cell has been engineered such that expression of the protein is reduced by at least about 50%, at least about 60%, at least about 70%, at least about 80%, at least about 90%, or at least about 95% in comparison to a cell that has not been engineered.

66. The method of any one of 61-65, wherein the cell has been engineered such that the cell does not express a detectable level of the protein.

67. The method of 65 or 66, wherein the protein is selected from the group consisting of B2M, TRAC, and CIITA.

68. The method of any one of 61-67, wherein the cells have been engineered such that at least 70%, at least 75%, at least 80%, at least 85%, at least 90%, or at least 95% of the engineered cells do not express a detectable level of MHC Class I molecules.

69. The method of 61-68, wherein the cells have been engineered such that at least 70%, at least 75%, at least 80%, at least 85%, at least 90%, or at least 95% of the engineered cells do not express a detectable level of wild-type T cell receptor.

70. The method of any one of 61-69, further comprising contacting the nucleic acid of the immune cell with a donor template nucleic acid wherein the donor template comprises a nucleic acid encoding a chimeric antigen receptor (CAR) specific for a tumor cell antigen.

71. The method of 70, wherein the tumor cell antigen is selected from the group consisting of CD47, CD19, CD20, CD22, CD33, CD123, CD138, FLT3, BCMA, EGFR, and mesothelin.

72. The method of 70 or 71, wherein the CAR comprises an antigen binding domain selected from the group consisting of linear antibody, single domain antibody (sdAb), and single-chain variable fragment (scFv).

73. The method of 72, wherein the CAR comprises one or more polypeptides selected from the group consisting of CD3zeta, CD27, CD28, 4-1BB (41BB), ICOS, and OX40.

74. The method of 73, wherein the one or more of CD3zeta, CD27, CD28, 4-1BB (41BB), ICOS, or OX40 are linked to the CAR antigen binding domain by an immunoglobulin-like domain hinge and, optionally, a spacer sequence.

75. The method of any one of 61-74, further comprising expanding a population of said cells.

76. A method of treating a subject in need thereof comprising administering cells prepared by the method of any one of 61-75.

77. A method of treating a subject in need thereof comprising administering cells prepared by the method of any one of 61-75 in combination with an immunosuppressive agent.

78. The method of 76 or 77, wherein the cells are autologous to the subject.

79. The method of 76 or 77, wherein the cells are allogeneic to the subject.

80. The method of any one of 76-79, wherein the subject has a disease associated with expression of a tumor antigen, wherein said administration treats said disease associated with expression of a tumor antigen.

81. The method of 80, wherein the disease associated with expression of a tumor antigen is a cancer selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), acute myeloid leukemia (AML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, Hodgkin's lymphoma, plasmablastic lymphoma, plasmacytoid dendritic cell neoplasm, Waldenstrom macroglobulinemia, pre-leukemia, combinations of said cancers, and metastatic lesions of said cancers.

EXAMPLES

Example 1: Creation, Expression and Purification of CasX Stx2

1. Growth and Expression

An expression construct for CasX Stx2 (also referred to herein as CasX2), derived from Planctomycetes (having the CasX amino acid sequence of SEQ ID NO: 2 and encoded by the sequence of the Table 6, below), was constructed from gene fragments (Twist Biosciences) that were codon optimized for *E. coli*. The assembled construct contains a TEV-cleavable, C-terminal, TwinStrep tag and was cloned into a pBR322-derivative plasmid backbone containing an ampicillin resistance gene. The expression construct was transformed into chemically competent BL21* (DE3) *E. coli* and a starter culture was grown overnight in LB broth supplemented with carbenicillin at 37° C., 200 RPM, in UltraYield Flasks (Thomson Instrument Company). The following day, this culture was used to seed expression cultures at a 1:100 ratio (starter culture:expression culture). Expression cultures were Terrific Broth (Novagen) supplemented with carbenicillin and grown in UltraYield flasks at 37° C., 200 RPM. Once the cultures reached an optical density (OD) of 2, they were chilled to 16° C. and IPTG (isopropyl β-D-1-thiogalactopyranoside) was added to a final concentration of 1 mM, from a 1 M stock. The cultures were induced at 16° C., 200 RPM for 20 hours before being harvested by centrifugation at 4,000×g for 15 minutes, 4° C.

The cell paste was weighed and resuspended in lysis buffer (50 mM HEPES-NaOH, 250 mM NaCl, 5 mM $MgCl_2$, 1 mM TCEP, 1 mM benzamidine-HCL, 1 mM PMSF, 0.5% CHAPS, 10% glycerol, pH 8) at a ratio of 5 mL of lysis buffer per gram of cell paste. Once resuspended, the sample was frozen at −80° C. until purification.

TABLE 6

DNA sequence of CasX Stx2 construct

| Construct | DNA Sequence |
| --- | --- |
| SV40 NLS-CasX-SV40 NLS-TEV cleavage site - TwinStrep tag | (SEQ ID NO: 437) |

2. Purification

Frozen samples were thawed overnight at 4° C. with magnetic stirring. The viscosity of the resulting lysate was reduced by sonication and lysis was completed by homogenization in three passes at 17 k PSI using an Emulsiflex C3 (Avestin). Lysate was clarified by centrifugation at 50,000× g, 4° C., for 30 minutes and the supernatant was collected. The clarified supernatant was applied to a Heparin 6 Fast Flow column (GE Life Sciences) by gravity flow. The column was washed with 5 CV of Heparin Buffer A (50 mM HEPES-NaOH, 250 mM NaCl, 5 mM $MgCl_2$, 1 mM TCEP, 10% glycerol, pH 8), then with 5 CV of Heparin Buffer B (Buffer A with the NaCl concentration adjusted to 500 mM). Protein was eluted with 5 CV of Heparin Buffer C (Buffer A with the NaCl concentration adjusted to 1 M), collected in fractions. Fractions were assayed for protein by Bradford Assay and protein-containing fractions were pooled. The pooled heparin eluate was applied to a Strep-Tactin XT Superflow column (IBA Life Sciences) by gravity flow. The column was washed with 5 CV of Strep Buffer (50 mM HEPES-NaOH, 500 mM NaCl, 5 mM $MgCl_2$, 1 mM TCEP, 10% glycerol, pH 8). Protein was eluted from the column using 5 CV of Strep Buffer with 50 mM D-Biotin added and collected in fractions. CasX-containing fractions were pooled, concentrated at 4° C. using a 30 kDa cut-off spin concentrator, and purified by size exclusion chromatography on a Superdex 200 pg column (GE Life Sciences). The column was equilibrated with SEC Buffer (25 mM sodium phosphate, 300 mM NaCl, 1 mM TCEP, 10% glycerol, pH 7.25) operated by an AKTA Pure FPLC system (GE Life Sciences). CasX-containing fractions that eluted at the appropriate molecular weight were pooled, concentrated at 4° C. using a 30 kDa cut-off spin concentrator, aliquoted, and snap-frozen in liquid nitrogen before being stored at −80° C.

3. Results

Figure 2:
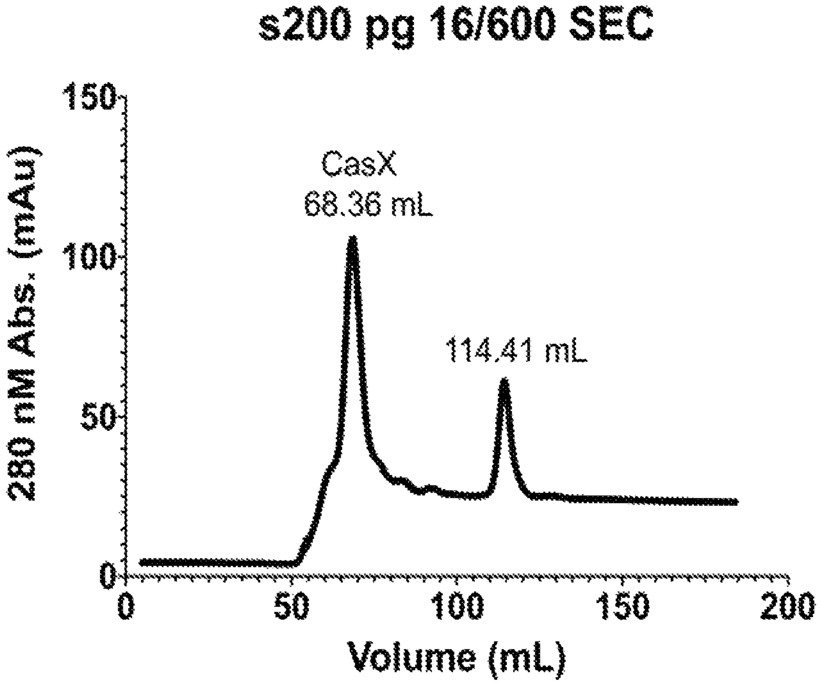
FIG. 2 shows the chromatogram from a size exclusion chromatography assay of the StX2, using of Superdex 200 16/600 pg Gel Filtration, as described in Example 1.
Figure 3:
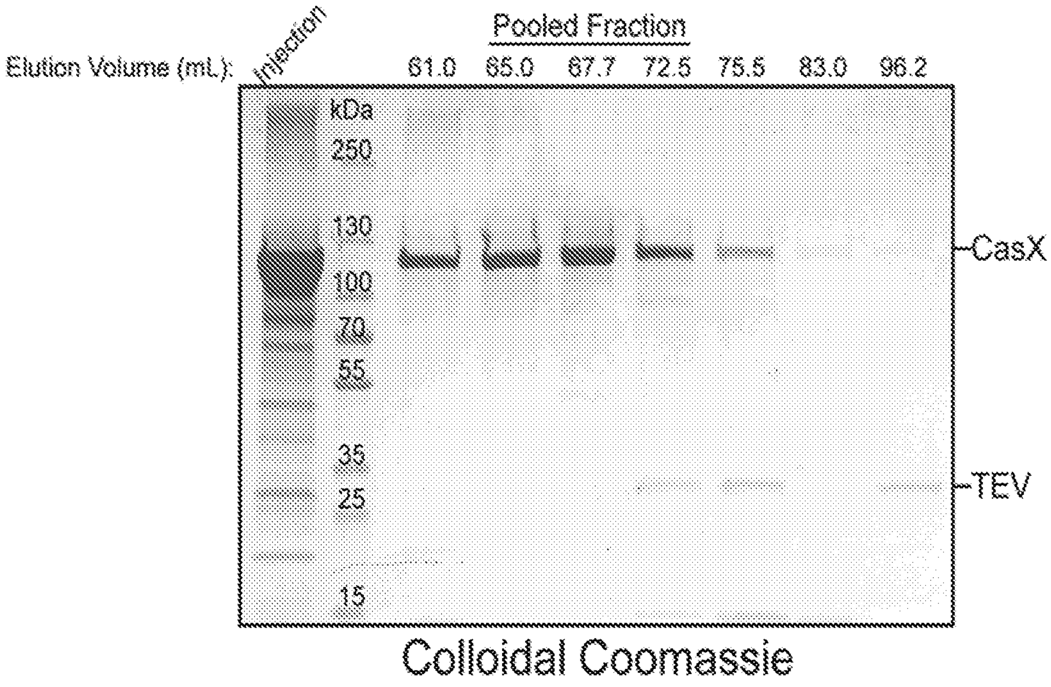
FIG. 3 shows an SDS-PAGE gel of StX2 purification fractions visualized by colloidal Coomassie staining, as described in Example 1.

Samples from throughout the purification were resolved by SDS-PAGE and visualized by colloidal Coomassie staining, as shown in FIG. 1 and FIG. 3. In FIG. 1, the lanes, from left to right, are: molecular weight standards, Pellet: insoluble portion following cell lysis, Lysate: soluble portion following cell lysis, Flow Thru: protein that did not bind the Heparin column, Wash: protein that eluted from the column in wash buffer, Elution: protein eluted from the heparin column with elution buffer, Flow Thru: Protein that did not bind the StrepTactinXT column, Elution: protein eluted from the StrepTactin XT column with elution buffer, Injection: concentrated protein injected onto the s200 gel filtration column, Frozen: pooled fractions from the s200 elution that have been concentrated and frozen. In FIG. 3, the lanes from right to left, are the injection (sample of protein injected onto the gel filtration column) molecular weight markers, lanes 3-9 are samples from the indicated elution volumes. Results from the gel filtration are shown in FIG. 2. The 68.36 mL peak corresponds to the apparent molecular weight of CasX and contained the majority of CasX protein. The average yield was 0.75 mg of purified CasX protein per liter of culture, with 75% purity, as evaluated by colloidal Coomassie staining.

Example 2: CasX Construct 119, 438 and 457

Figure 4:
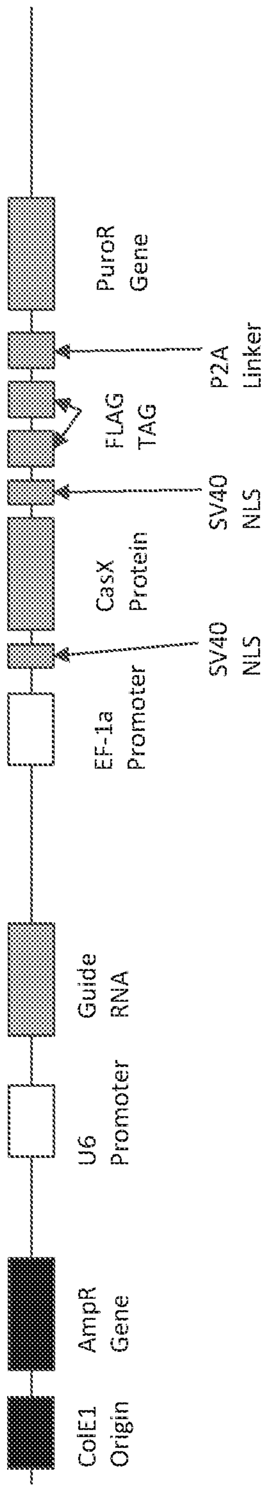
FIG. 4 is a schematic showing the organization of the components in the pSTX34 plasmid used to assemble the CasX constructs, as described in Example 2.
Figure 6:
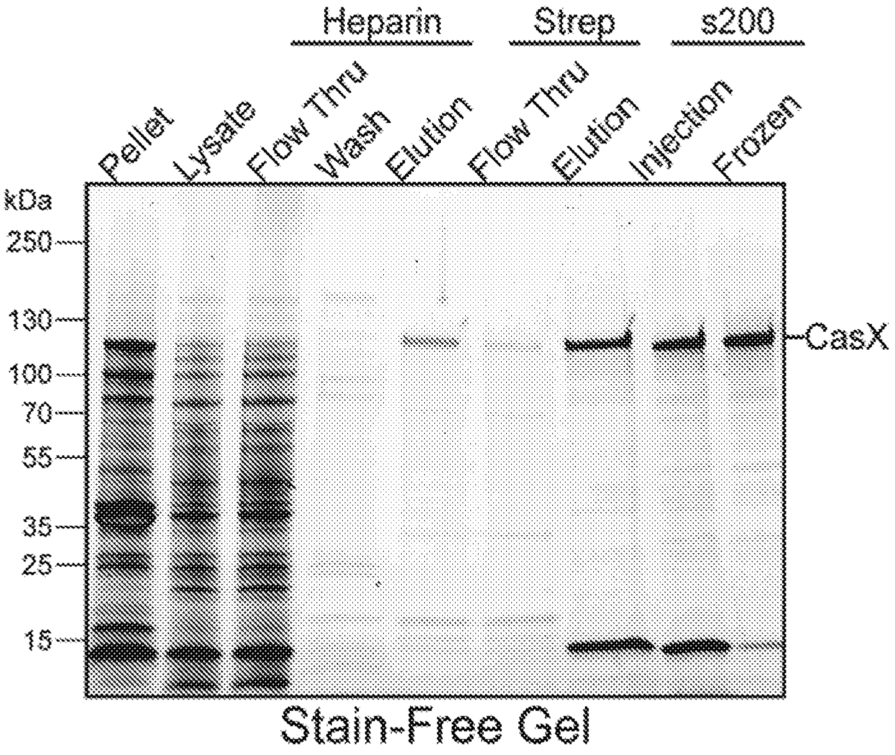
FIG. 6 shows an SDS-PAGE gel of purification samples, visualized on a Bio-Rad Stain-Free™ gel, as described in Example 2.
Figure 7:
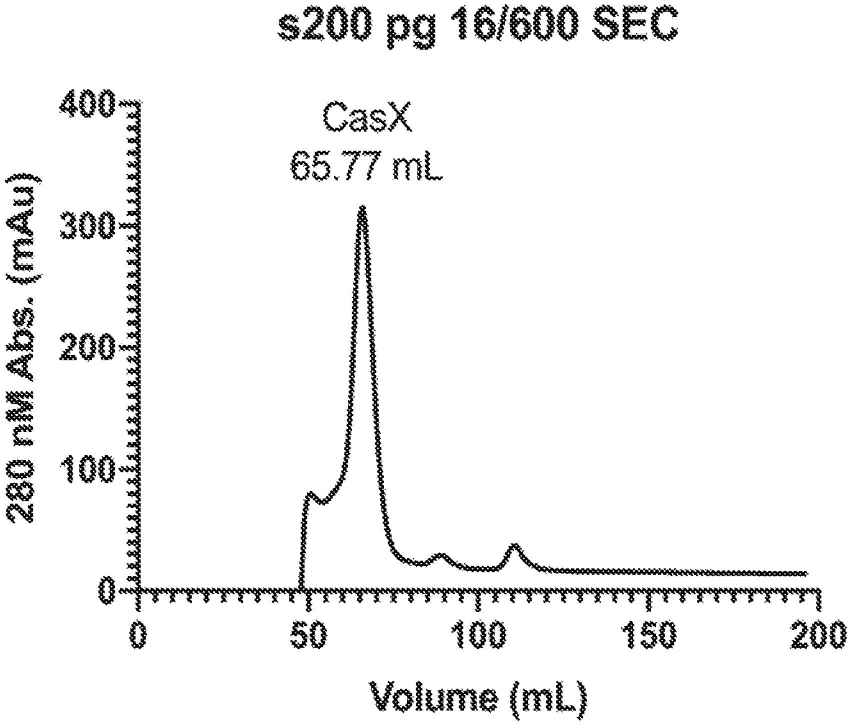
FIG. 7 shows the chromatogram of Superdex 200 16/600 pg Gel Filtration, as described in Example 2.
Figure 8:
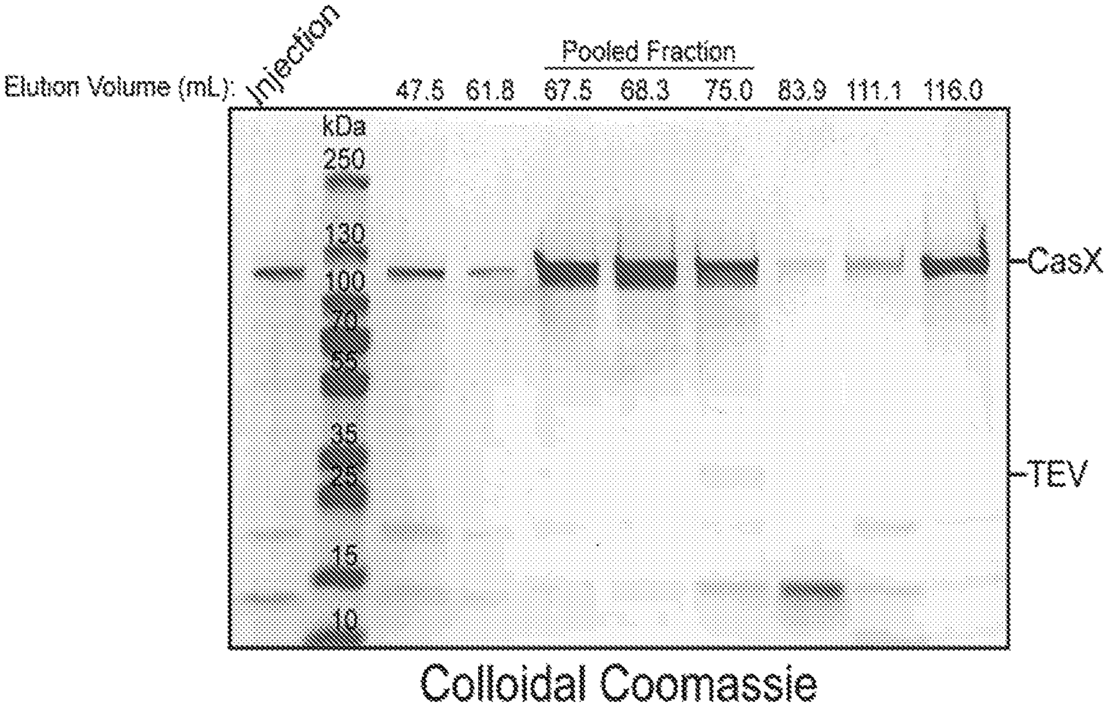
FIG. 8 shows an SDS-PAGE gel of gel filtration samples, stained with colloidal Coomassie, as described in Example 2.

In order to generate the CasX 119, 438, and 457 constructs (sequences in Table 7), the codon-optimized CasX 37 construct (based on the CasX Stx2 construct of Example 1, encoding Planctomycetes CasX SEQ ID NO: 2, with a A708K substitution and a [P793] deletion with fused NLS, and linked guide and non-targeting sequences) was cloned into a mammalian expression plasmid (pStX; see FIG. 4) using standard cloning methods. To build CasX 119, the CasX 37 construct DNA was PCR amplified in two reactions using Q5 DNA polymerase (New England BioLabs Cat #M0491L) according to the manufacturer's protocol, using primers oIC539 and oIC88 as well as oIC87 and oIC540 respectively (see FIG. 5). To build CasX 457, the CasX 365 construct DNA was PCR amplified in four reactions using Q5 DNA polymerase (New England BioLabs Cat #M0491L) according to the manufacturer's protocol, using primers oIC539 and oIC212, oIC211 and oIC376, oIC375 and oIC551, and oIC550 and oIC540 respectively. To build CasX 438, the CasX 119 construct DNA was PCR amplified in four reactions using Q5 DNA polymerase (New England BioLabs Cat #M0491L) according to the manufacturer's protocol, using primers oIC539 and oIC689, oIC688 and oIC376, oIC375 and oIC551, and oIC550 and oIC540 respectively. The resulting PCR amplification products were then purified using Zymoclean DNA clean and concentrator (Zymo Research Cat #4014) according to the manufacturer's protocol. The pStX backbone was digested using XbaI and SpeI in order to remove the 2931 base pair fragment of DNA between the two sites in plasmid pStx34. The digested backbone fragment was purified by gel extraction from a 1% agarose gel (Gold Bio Cat #A-201-500) using Zymoclean Gel DNA Recovery Kit (Zymo Research Cat #D4002) according to the manufacturer's protocol. The three fragments were then pieced together using Gibson assembly (New England BioLabs Cat #E2621S) following the manufacturer's protocol. Assembled products in the pStx34 were transformed into chemically-competent or electro-competent Turbo Competent *E. coli* bacterial cells, plated on LB-Agar plates (LB: Teknova Cat #L9315, Agar: Quartzy Cat #214510) containing carbenicillin. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct assembly. pStX34 includes an EF-1α promoter for the protein as well as a selection marker for both puromycin and carbenicillin. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C2984I), plated on LB-Agar plates (LB: Teknova Cat #L9315, Agar: Quartzy Cat #214510) containing carbenicillin. Individual colonies were picked and miniprepped using Qiagen Qiaprep spin Miniprep Kit (Qiagen Cat #27104) and following the manufacturer's protocol. The resultant plasmids were sequenced using Sanger sequencing to ensure correct ligation. SaCas9 and SpyCas9 control plasmids were prepared similarly to pStX plasmids described above, with the protein and guide regions of pStX exchanged for the respective protein and guide. Targeting sequences for SaCas9 and SpyCas9 were either obtained from the literature or were rationally designed according to established methods. The expression and recovery of the CasX 119 and 457 proteins was performed using the general methodologies of Example 1 (however the DNA sequences were codon optimized for expression in *E. coli*). The results of analytical assays for CasX 119 are shown in FIGS. 6-8. The average yield of the CasX 119 was 1.56 mg of purified CasX protein per liter of culture at 75% purity, as evaluated by colloidal Coomassie staining. FIG. 6 shows an SDS-PAGE gel of purification samples, visualized on a Bio-Rad Stain-Free™ gel, as described. The lanes, from left to right, are: Pellet: insoluble portion following cell lysis, Lysate: soluble portion following cell lysis, Flow Thru: protein that did not bind the Heparin column, Wash: protein that eluted from the column in wash buffer, Elution: protein eluted from the heparin column with elution buffer, Flow Thru: Protein that did not bind the StrepTactinXT column, Elution: protein eluted from the StrepTactin XT column with elution buffer, Injection: concentrated protein injected onto the s200 gel filtration column, Frozen: pooled fractions from the s200 elution that have been concentrated and frozen.

FIG. 7 shows the chromatogram of Superdex 200 16/600 pg Gel Filtration, as described. Gel filtration run of CasX variant 119 protein plotted as 280 nm absorbance against elution volume. The 65.77 mL peak corresponds to the apparent molecular weight of CasX variant 119 and contained the majority of CasX variant 119 protein. FIG. 8 shows an SDS-PAGE gel of gel filtration samples, stained with colloidal Coomassie, as described. Samples from the indicated fractions were resolved by SDS-PAGE and stained with colloidal Coomassie. From right to left, Injection: sample of protein injected onto the gel filtration column, molecular weight markers, lanes 3-10: samples from the indicated elution volumes.

TABLE 7

TABLE 7-continued

Sequences of CasX 119, 438 and 457

| Construct | DNA Sequence | Amino Acid Sequence |
|---|---|---|
| CasX 119 | (SEQ ID NO: 438) | QEIKRINKIRRRLVKDSNTKKAGKTGPMK<br>TLLVRVMTPDLRERLENLRKKPENIPQPI<br>SNTSRANLNKLLTDYTEMKKAILHVYWEE<br>FQKDPVGLMSRVAQPAPKNIDQRKLIPVK<br>DGNERLTSSGFACSQCCQPLYVYKLEQVN<br>DKGKPHTNYFGRCNVSEHERLILLSPHKP<br>EANDELVTYSLGKFGQRALDFYSIHVTRE<br>SNHPVKPLEQIGGNSCASGPVGKALSDAC<br>MGAVASFLTKYQDIILEHQKVIKKNEKRL<br>ANLKDIASANGLAFPKITLPPQPHTKEGI<br>EAYNNVVAQIVIWVNLNLWQKLKIGRDEA<br>KPLQRLKGFPSFPLVERQANEVDWWDMVC<br>NVKKLINEKKEDGKVFWQNLAGYKRQEAL<br>RPYLSSEEDRKKGKKFARYQFGDLLLHLE<br>KKHGEDWGKVYDEAWERIDKKVEGLSKHI<br>KLEEERRSEDAQSKAALTDWLRAKASFVI<br>EGLKEADKDEFCRCELKLQKWYGDLRGKP<br>FAIEAENSILDISGFSKQYNCAFIWQKDG<br>VKKLNLYLIINYFKGGKLRFKKIKPEAFE<br>ANRFYTVINKKSGEIVPMEVNFNFDDPNL<br>IILPLAFGKRQGREFIWNDLLSLETGSLK<br>LANGRVIEKTLYNRRTRQDEPALFVALTF<br>ERREVLDSSNIKPMNLIGIDRGENIPAVI<br>ALTDPEGCPLSRFKDSLGNPTHILRIGES<br>YKEKQRTIQAKKEVEQRRAGGYSRKYASK<br>AKNLADDMVRNTARDLLYYAVTQDAMLIF<br>ENLSRGFGRQGKRTFMAERQYTRMEDWLT<br>AKLAYEGLSKTYLSKTLAQYTSKTCSNCG<br>FTITSADYDRVLEKLKKTATGWMTTINGK<br>ELKVEGQITYYNRYKRQNVVKDLSVELDR<br>LSEESVNNDISSWTKGRSGEALSLLKKRF<br>SHRPVQEKFVCLNCGFETHADEQAALNIA<br>RSWLFLRSQEYKKYQTNKTTGNTDKRAFV<br>ETWQSFYRKKLKEVWKPAV<br>(SEQ ID NO: 439) |
| CasX 457 | (SEQ ID NO: 440) | QEIKRINKIRRRLVKDSNTKKAGKTGPMK<br>TLLVRVMTPDLRERLENLRKKPENIPQPI<br>SNTSRANLNKLLTDYTEMKKAILHVYWEE<br>FQKDPVGLMSRVAQPAPKNIDQRKLIPVK<br>DGNERLTSSGFACSQCCQPLYVYKLEQVN<br>DKGKPHTNYFGRCNVSEHERLILLSPHKP<br>EANDELVTYSLGKFGQRALDFYSIHVTRE<br>SNHPVKPLEQIGGNSCASGPVGKALSDAC<br>MGAVASFLTKYQDIILEHKKVIKKNEKRL<br>ANLKDIASANGLAFPKITLPPQPHTKEGI<br>EAYNNVVAQIVIWVNLNLWQKLKIGRDEA<br>KPLQRLKGFPSFPLVERQANEVDWWDMVC<br>NVKKLINEKKEDGKVFWQNLAGYKRQEAL<br>RPYLSSPEDRKKGKKFARYQLGDLLLHLE<br>KKHGEDWGKVYDEAWERIDKKVEGLSKHI<br>KLEEERRSEDAQSKAALTDWLRAKASFVI<br>EGLKEADKDEFCRCELKLQKWYGDLRGKP<br>FAIEAENSILDISGFSKQYNCAFIWQKDG<br>VKKLNLYLIINYFKGGKLRFKKIKPEAFE<br>ANRFYTVINKKSGEIVPMEVNFNFDDPNL<br>IILPLAFGKRQGREFIWNDLLSLETGSLK<br>LANGRVIEKPLYNRRTRQDEPALFVALTF<br>ERREVLDSSNIKPMNLIGVDRGENIPAVI<br>ALTDPEGCPLSRFKDSLGNPTHILRIGES<br>YKEKQRTIQAKKEVEQRRAGGYSRKYASK<br>AKNLADDMVRNTARDLLYYAVTQDAMLIF<br>ENLSRGFGRQGKRTFMAERQYTRMEDWLT<br>AKLAYEGLSKTYLSKTLAQYTSKTCSNCG<br>FTITSADYDRVLEKLKKTATGWMTTINGK<br>ELKVEGQITYYNRRKRQNVVKDLSVELDR<br>LSEESVNNDISSWTKGRSGEALSLLKKRF<br>SHRPVQEKFVCLNCGFETHADEQAALNIA<br>RSWLFLRSQEYKKYQTNKTTGNTDKRAFV<br>ETWQSFYRKKLKEVWKPAV<br>(SEQ ID NO: 441) |
| CasX 438 | (SEQ ID NO: 442) | QEIKRINKIRRRLVKDSNTKKAGKTGPMK<br>TLLVRVMTPDLRERLENLRKKPENIPQPI<br>SNTSRANLNKLLTDYTEMKKAILHVYWEE<br>FQKDPVGLMSRVAQPAPKNIDQRKLIPVK<br>DGNERLTSSGFACSQCCQPLYVYKLEQVN<br>DKGKPHTNYFGRCNVSEHERLILLSPHKP<br>EANDELVTYSLGKFGQRALDFYSIHVTRE<br>SNHPVKPLEQIGGNSCASGPVGKALSDAC<br>MGAVASFLTKYQDIILEHQKVIKKNEKRL<br>ANLKDIASANGLAFPKITLPPQPHTKEGI<br>EAYNNVVAQIVIWVNLNLWQKLKIGRDEA<br>KPLQRLKGFPSFPLVERQANEVDWWDMVC<br>NVKKLINEKKEDGKVFWQNLAGYKRQEAL<br>RPYLSSEEDRKKGKKFARYQLGDLLKHLE<br>KKHGEDWGKVYDEAWERIDKKVEGLSKHI<br>KLEEERRSEDAQSKAALTDWLRAKASFVI<br>EGLKEADKDEFCRCELKLQKWYGDLRGKP<br>FAIEAENSILDISGFSKQYNCAFIWQKDG<br>VKKLNLYLIINYFKGGKLRFKKIKPEAFE |

TABLE 7-continued

| Sequences of CasX 119, 438 and 457 | | |
|---|---|---|
| Construct | DNA Sequence | Amino Acid Sequence |
| | | ANRFYTVINKKSGEIVPMEVNFNFDDPNL IILPLAFGKRQGREFIWNDLLSLETGSLK LANGRVIEKTLYNRRTRQDEPALFVALTF ERREVLDSSNIKPMNLIGVDRGENIPAVI ALTDPEGCPLSRFKDSLGNPTHILRIGES YKEKQRTIQAKKEVEQRRAGGYSRKYASK AKNLADDMVRNTARDLLYYAVTQDAMLIF ENLSRGFGRQGKRTFMAERQYTRMEDWLT AKLAYEGLSKTYLSKTLAQYTSKTCSNCG FTITSADYDRVLEKLKKTATGWMTTINGK ELKVEGQITYYNRRKRQNVVKDLSVELDR LSEESVNNDISSWTKGRSGEALSLLKKRF SHRPVQEKFVCLNCGFETHADEQAALNIA RSWLFLRSQEYKKYQTNKTTGNTDKRAFV ETWQSFYRKKLKEVWKPAV (SEQ ID NO: 443) |

Example 3: CasX Construct 488 and 491

In order to generate the CasX 488 construct (sequences in Table 8), the codon-optimized CasX 119 construct (based on the CasX Stx2 construct of Example 1, encoding Planctomycetes CasX SEQ ID NO: 2, with a A708K substitution, a L379R substitution, and a [P793] deletion with fused NLS, and linked guide and non-targeting sequences) was cloned into a mammalian expression plasmid (pStX; see FIG. 4) using standard cloning methods. Construct CasX 1 (based on the CasX Stx1 construct of Example 1, encoding CasX SEQ ID NO: 1) was cloned into a destination vector using standard cloning methods. To build CasX 488, the CasX 119 construct DNA was PCR amplified using Q5 DNA polymerase (New England BioLabs Cat #M0491L) according to the manufacturer's protocol, using primers oIC765 and oIC762 (see FIG. 5). The CasX 1 construct was PCR amplified using Q5 DNA polymerase (New England BioLabs Cat #M0491L) according to the manufacturer's protocol, using primers oIC766 and oIC784. The PCR products were purified by gel extraction from a 1% agarose gel (Gold Bio Cat #A-201-500) using Zymoclean Gel DNA Recovery Kit (Zymo Research Cat #D4002) according to the manufacturer's protocol. The two fragments were then pieced together using Gibson assembly (New England BioLabs Cat #E2621S) following the manufacturer's protocol. Assembled products in pStx1 were transformed into chemically-competent Turbo Competent *E. coli* bacterial cells, plated on LB-Agar plates (LB: Teknova Cat #L9315, Agar: Quartzy Cat #214510) containing kanamycin. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct assembly. The correct clones were then subcloned into the mammalian expression vector pStx34 using restriction enzyme cloning. The pStx34 backbone and the CasX 488 clone in pStx1 were digested with XbaI and BamHI respectively. The digested backbone and insert fragments were purified by gel extraction from a 1% agarose gel (Gold Bio Cat #A-201-500) using Zymoclean Gel DNA Recovery Kit (Zymo Research Cat #D4002) according to the manufacturer's protocol. The clean backbone and insert were then ligated together using T4 Ligase (New England Biolabs Cat #M0202L) according to the manufacturer's protocol. The ligated product was transformed into chemically-competent Turbo Competent *E. coli* bacterial cells, plated on LB-Agar plates (LB: Teknova Cat #L9315, Agar: Quartzy Cat #214510) containing carbenicillin. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct assembly.

Figure 5:
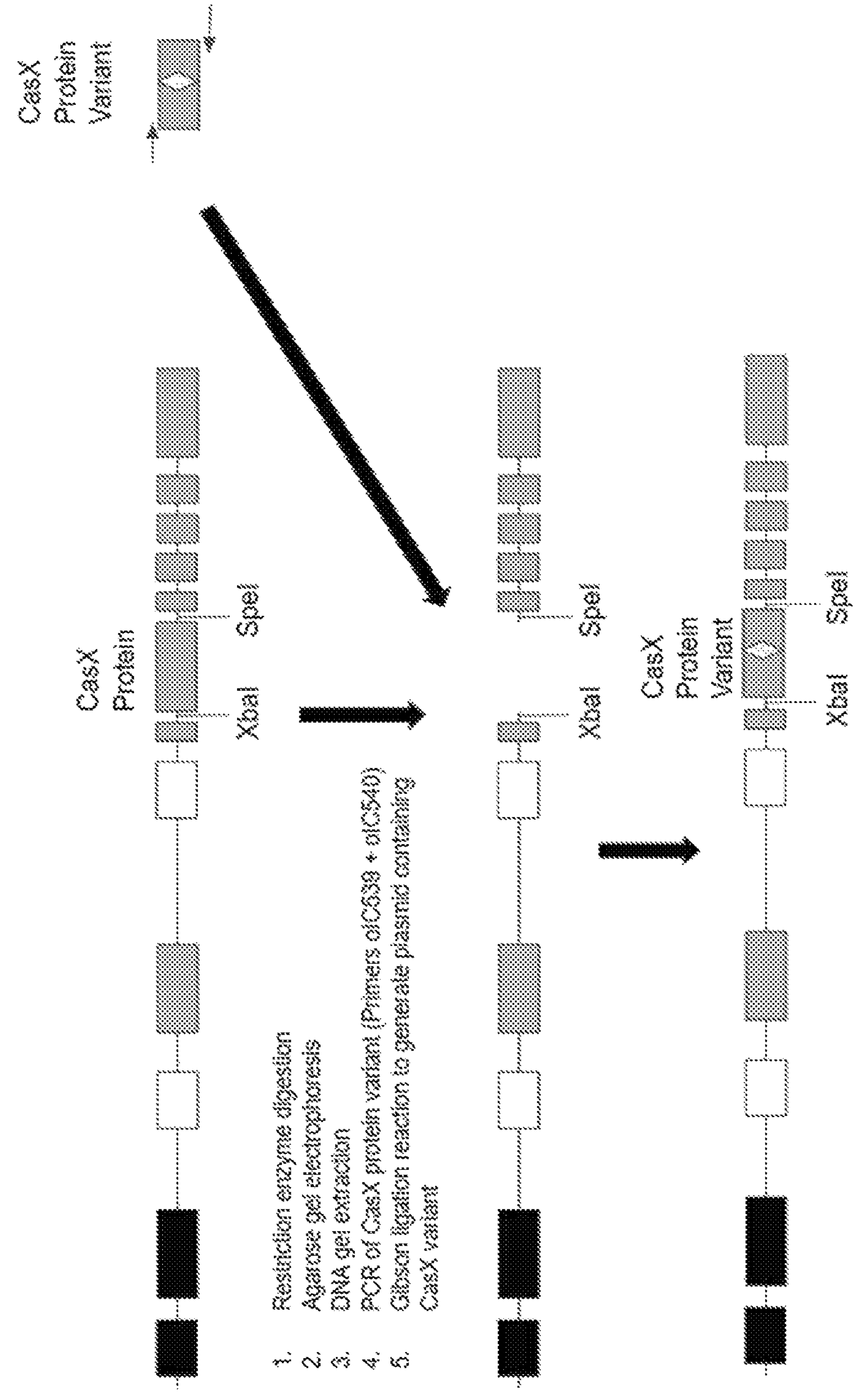
FIG. 5 is a schematic showing the steps of generating the CasX 119 variant, as described in Example 2.

In order to generate CasX 491 (sequences in Table 8), the CasX 484 construct DNA was PCR amplified using Q5 DNA polymerase (New England BioLabs Cat #M0491L) according to the manufacturer's protocol, using primers oIC765 and oIC762 (see FIG. 5). The CasX 1 construct was PCR amplified using Q5 DNA polymerase (New England BioLabs Cat #M0491L) according to the manufacturer's protocol, using primers oIC766 and oIC784. The PCR products were purified by gel extraction from a 1% agarose gel (Gold Bio Cat #A-201-500) using Zymoclean Gel DNA Recovery Kit (Zymo Research Cat #D4002) according to the manufacturer's protocol. The two fragments were then pieced together using Gibson assembly (New England BioLabs Cat #E2621S) following the manufacturer's protocol. Assembled products in pStx1 were transformed into chemically-competent Turbo Competent *E. coli* bacterial cells, plated on LB-Agar plates (LB: Teknova Cat #L9315, Agar: Quartzy Cat #214510) containing kanamycin. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct assembly. The correct clones were then subcloned into the mammalian expression vector pStx34 using restriction enzyme cloning. The pStx34 backbone and the CasX 491 clone in pStx1 were digested with XbaI and BamHI respectively. The digested backbone and insert fragments were purified by gel extraction from a 1% agarose gel (Gold Bio Cat #A-201-500) using Zymoclean Gel DNA Recovery Kit (Zymo Research Cat #D4002) according to the manufacturer's protocol. The clean backbone and insert were then ligated together using T4 Ligase (New England Biolabs Cat #M0202L) according to the manufacturer's protocol. The ligated product was transformed into chemically-competent Turbo Competent *E. coli* bacterial cells, plated on LB-Agar plates (LB: Teknova Cat #L9315, Agar: Quartzy Cat #214510) containing carbenicillin. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct assembly. pStX34 includes an EF-1α promoter for the protein as well as a selection marker for both puromycin and carbenicillin. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C2984I), plated on LB-Agar plates (LB: Teknova Cat #L9315, Agar: Quartzy Cat #214510) containing carbenicillin. Individual colonies were picked and miniprepped using Qiagen Qiaprep spin Miniprep Kit (Qiagen Cat #27104) and following the manufacturer's protocol. The resultant plasmids were sequenced using Sanger sequencing to ensure correct ligation. SaCas9 and SpyCas9 control plasmids were prepared similarly to pStX plasmids described above, with the protein and guide regions of pStX exchanged for the respective protein and guide. Targeting sequences for SaCas9 and SpyCas9 were either obtained from the literature or were rationally designed according to established methods. The expression and recovery of the CasX constructs was performed using the general methodologies of Example 1 and Example 2, with similar results obtained.

TABLE 8

Sequences of CasX 488 and 491

| Construct | DNA Sequence | Amino Acid Sequence |
|---|---|---|
| CasX 488 | (SEQ ID NO: 444) | QEIKRINKIRRRLVKDSNTKKAGKTGPMK<br>TLLVRVMTPDLRERLENLRKKPENIPQPI<br>SNTSRANLNKLLTDYTEMKKAILHVYWEE<br>FQKDPVGLMSRVAQPASKKIDQNKLKPEM<br>DEKGNLTTAGFACSQCGQPLFVYKLEQVS<br>EKGKAYTNYFGRCNVAEHEKLILLAQLKP<br>EKDSDEAVTYSLGKFGQRALDFYSIHVTK<br>ESTHPVKPLAQIAGNRYASGPVGKALSDA<br>CMGTIASFLSKYQDIIIEHQKVVKGNQKR<br>LESLRELAGKENLEYPSVTLPPQPHTKEG<br>VDAYNEVIARVRMWVNLNLWQKLKLSRDD<br>AKPLLRLKGFPSFPLVERQANEVDWWDMV<br>CNVKKLINEKKEDGKVFWQNLAGYKRQEA<br>LRPYLSSEEDRKKGKKFARYQFGDLLLHL<br>EKKHGEDWGKVYDEAWERIDKKVEGLSKH<br>IKLEEERRSEDAQSKAALTDWLRAKASFV<br>IEGLKEADKDEFCRCELKLQKWYGDLRGK<br>PFAIEAENSILDISGFSKQYNCAFIWQKD<br>GVKKLNLYLIINYFKGGKLRFKKIKPEAF<br>EANRFYTVINKKSGEIVPMEVNFNFDDPN<br>LIILPLAFGKRQGREFIWNDLLSLETGSL<br>KLANGRVIEKTLYNRRTRQDEPALFVALT<br>FERREVLDSSNIKPMNLIGIDRGENIPAV<br>IALTDPEGCPLSRFKDSLGNPTHILRIGE<br>SYKEKQRTIQAKKEVEQRRAGGYSRKYAS<br>KAKNLADDMVRNTARDLLYYAVTQDAMLI<br>FENLSRGFGRQGKRTFMAERQYTRMEDWL<br>TAKLAYEGLSKTYLSKTLAQYTSKTCSNC<br>GFTITSADYDRVLEKLKKTATGWMTTING<br>KELKVEGQITYYNRYKRQNVVKDLSVELD<br>RLSEESVNNDISSWTKGRSGEALSLLKKR<br>FSHRPVQEKFVCLNCGFETHADEQAALNI<br>ARSWLFLRSQEYKKYQTNKTTGNTDKRAF<br>VETWQSFYRKKLKEVWKPAV<br>(SEQ ID NO: 445) |
| CasX 491 | (SEQ ID NO: 446) | QEIKRINKIRRRLVKDSNTKKAGKTGPMK<br>TLLVRVMTPDLRERLENLRKKPENIPQPI<br>SNTSRANLNKLLTDYTEMKKAILHVYWEE<br>FQKDPVGLMSRVAQPASKKIDQNKLKPEM<br>DEKGNLTTAGFACSQCGQPLFVYKLEQVS<br>EKGKAYTNYFGRCNVAEHEKLILLAQLKP<br>EKDSDEAVTYSLGKFGQRALDFYSIHVTK<br>ESTHPVKPLAQIAGNRYASGPVGKALSDA<br>CMGTIASFLSKYQDIIIEHQKVVKGNQKR<br>LESLRELAGKENLEYPSVTLPPQPHTKEG<br>VDAYNEVIARVRMWVNLNLWQKLKLSRDD<br>AKPLLRLKGFPSFPLVERQANEVDWWDMV<br>CNVKKLINEKKEDGKVFWQNLAGYKRQEA<br>LRPYLSSEEDRKKGKKFARYQLGDLLLHL<br>EKKHGEDWGKVYDEAWERIDKKVEGLSKH<br>IKLEEERRSEDAQSKAALTDWLRAKASFV<br>IEGLKEADKDEFCRCELKLQKWYGDLRGK<br>PFAIEAENSILDISGFSKQYNCAFIWQKD<br>GVKKLNLYLIINYFKGGKLRFKKIKPEAF<br>EANRFYTVINKKSGEIVPMEVNFNFDDPN<br>LIILPLAFGKRQGREFIWNDLLSLETGSL<br>KLANGRVIEKTLYNRRTRQDEPALFVALT<br>FERREVLDSSNIKPMNLIGVDRGENIPAV<br>IALTDPEGCPLSRFKDSLGNPTHILRIGE<br>SYKEKQRTIQAKKEVEQRRAGGYSRKYAS |

TABLE 8-continued

Sequences of CasX 488 and 491

| Construct | DNA Sequence | Amino Acid Sequence |
|---|---|---|
| | | KAKNLADDMVRNTARDLLYYAVTQDAMLI<br>FENLSRGFGRQGKRTFMAERQYTRMEDWL<br>TAKLAYEGLSKTYLSKTLAQYTSKTCSNC<br>GFTITSADYDRVLEKLKKTATGWMTTING<br>KELKVEGQITYYNRYKRQNVVKDLSVELD<br>RLSEESVNNDISSWTKGRSGEALSLLKKR<br>FSHRPVQEKFVCLNCGFETHADEQAALNI<br>ARSWLFLRSQEYKKYQTNKTTGNTDKRAF<br>VETWQSFYRKKLKEVWKPAV<br>(SEQ ID NO: 447) |

Example 4: Design and Generation of CasX Constructs 278-280, 285-288, 290, 291, 293, 300, 492, and 493

In order to generate the CasX 278-280, 285-288, 290, 291, 293, 300, 492, and 493 constructs (sequences in Table 9), the N- and C-termini of the codon-optimized CasX 119 construct (based on the CasX Stx37 construct of Example 2, encoding Planctomycetes CasX SEQ ID NO:2, with a A708K substitution and a [P793] deletion with fused NLS, and linked guide and non-targeting sequences) in a mammalian expression vector were manipulated to delete or add NLS sequences (sequences in Table 10). Constructs 278, 279, and 280 were manipulations of the N- and C-termini using only an SV40 NLS sequence. Construct 280 had no NLS on the N-terminus and added two SV40 NLS' on the C-terminus with a triple proline linker in between the two SV40 NLS sequences. Constructs 278, 279, and 280 were made by amplifying pStx34.119.174.NT with Q5 DNA polymerase (New England BioLabs Cat #M0491L) according to the manufacturer's protocol, using primers oIC527 and oIC528, oIC730 and oIC522, and oIC730 and oIC530 for the first fragments each and using oIC529 and oIC520, oIC519 and oIC731, and oIC529 and oIC731 to create the second fragments each. These fragments were purified by gel extraction from a 1% agarose gel (Gold Bio Cat #A-201-500) using Zymoclean Gel DNA Recovery Kit (Zymo Research Cat #D4002) according to the manufacturer's protocol. The respective fragments were cloned together using Gibson assembly (New England BioLabs Cat #E2621S) following the manufacturer's protocol. Assembled products in the pStx34 were transformed into chemically-competent Turbo Competent *E. coli* bacterial cells, plated on LB-Agar plates (LB: Teknova Cat #L9315, Agar: Quartzy Cat #214510) containing carbenicillin and incubated at 37° C. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct assembly. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically- or electrocompetent cells such as NEB Turbo competent *E. coli* (NEB Cat #C2984I), plated on LB-Agar plates (LB: Teknova Cat #L9315, Agar: Quartzy Cat #214510) containing carbenicillin and incubated at 37° C. Individual colonies were picked and miniprepped using Qiagen Qiaprep spin Miniprep Kit (Qiagen Cat #27104) and following the manufacturer's protocol. The resultant plasmids were sequenced using Sanger sequencing to ensure correct ligation.

In order to generate constructs 285-288, 290, 291, 293, and 300, a nested PCR method was used for cloning. The backbone vector and PCR template used was construct pStx34 279.119.174.NT, having the CasX 119, guide 174, and non-targeting spacer (see Examples 8 and 9 and Tables therein for sequences). Construct 278 has the configuration SV40NLS-CasX119. Construct 279 has the configuration CasX119-SV40NLS. Construct 280 has the configuration CasX119-SV40NLS-PPP linker-SV40NLS. Construct 285 has the configuration CasX119-SV40NLS-PPP linker-SynthNLS3. Construct 286 has the configuration CasX119-SV40NLS-PPP linker-SynthNLS4. Construct 287 has the configuration CasX119-SV40NLS-PPP linker-SynthNLS5. Construct 288 has the configuration CasX119-SV40NLS-PPP linker-SynthNLS6. Constrict 290 has the configuration CasX119-SV40NLS-PPP linker-EGL-13 NLS. Construct 291 has the configuration CasX119-SV40NLS-PPP linker-c-Myc NLS. Construct 293 has the configuration CasX119-SV40NLS-PPP linker-Nucleolar RNA Helicase II NLS. Construct 300 has the configuration CasX119-SV40NLS-PPP linker-Influenza A protein NLS. Construct 492 has the configuration SV40NLS-CasX119-SV40NLS-PPP linker-SV40NLS. Construct 493 has the configuration SV40NLS-CasX119-SV40NLS-PPP linker-c-Myc NLS. Each variant had a set of three PCRs; two of which were nested, were purified by gel extraction, digested, and then ligated into the digested and purified backbone. Assembled products in the pStx34 were transformed into chemically-competent Turbo Competent *E. coli* bacterial cells, plated on LB-Agar plates (LB: Teknova Cat #L9315, Agar: Quartzy Cat #214510) containing carbenicillin and incubated at 37° C. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct assembly. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into the resulting pStX individually or in bulk by Golden Gate assembly using T4 DNA Ligase (New England BioLabs Cat #M0202L) and an appropriate restriction enzyme for the plasmid. Golden Gate products were transformed into chemically- or electro-competent cells such as NEB Turbo competent *E. coli* (NEB Cat #C2984I), plated on LB-Agar plates (LB: Teknova Cat #L9315, Agar: Quartzy Cat #214510) containing carbenicillin and incubated at 37° C. Individual colonies were picked and miniprepped using Qiagen Qiaprep spin Miniprep Kit (Qiagen Cat #27104) and following the manufacturer's protocol. The resultant plasmids were sequenced using Sanger sequencing to ensure correct ligation.

In order to generate constructs 492 and 493, constructs 280 and 291 were digested using XbaI and BamHI (NEB #R0145S and NEB #R3136S) according to the manufacturer's protocol. Next, they were purified by gel extraction from a 1% agarose gel (Gold Bio Cat #A-201-500) using Zymoclean Gel DNA Recovery Kit (Zymo Research Cat #D4002) according to the manufacturer's protocol. Finally, they were ligated using T4 DNA ligase (NEB #M0202S) according to the manufacturer's protocol into the digested and purified pStx34.119.174.NT using XbaI and BamHI and Zymoclean Gel DNA Recovery Kit. Assembled products in the pStx34 were transformed into chemically-competent Turbo Competent *E. coli* bacterial cells, plated on LB-Agar plates (LB: Teknova Cat #L9315, Agar: Quartzy Cat #214510) containing carbenicillin and incubated at 37° C. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct assembly. Sequences encoding the targeting spacer sequences that target the gene of interest were designed based on CasX PAM locations. Targeting sequence DNA was ordered as single-stranded DNA (ssDNA) oligos (Integrated DNA Technologies) consisting of the targeting spacer sequence and the reverse complement of this sequence. These two oligos were annealed together and cloned into each pStX individually or in bulk by Golden Gate assembly using T4 DNA Ligase (New England BioLabs Cat #M0202L) and an appropriate restriction enzyme for the respective plasmids. Golden Gate products were transformed into chemically- or electro-competent cells such as NEB Turbo competent *E. coli* (NEB Cat #C2984I), plated on LB-Agar plates (LB: Teknova Cat #L9315, Agar: Quartzy Cat #214510) containing carbenicillin and incubated at 37° C. Individual colonies were picked and miniprepped using Qiagen Qiaprep spin Miniprep Kit (Qiagen Cat #27104) and following the manufacturer's protocol. The resultant plasmids were sequenced using Sanger sequencing to ensure correct ligation. The plasmids were used to produce and recover CasX protein utilizing the general methodologies of Examples 1 and 2.

TABLE 9

CasX 278-280, 285-288, 290, 291, 293, 300, 492, and 493 sequences

| Construct | Amino Acid Sequence |
|---|---|
| 278 | MAPKKKRKVSRQEIKRINKIRRRLVKDSNTKKAGKTGPMKTLLVRVMTP DLRERLENLRKKPENIPQPISNTSRANLNKLLTDYTEMKKAILHVYWEEF QKDPVGLMSRVAQPAPKNIDQRKLIPVKDGNERLTSSGFACSQCCQPLY VYKLEQVNDKGKPHTNYFGRCNVSEHERLILLSPHKPEANDELVTYSLG KFGQRALDFYSIHVTRESNHPVKPLEQIGGNSCASGPVGKALSDACMGA VASFLTKYQDIILEHQKVIKKNEKRLANLKDIASANGLAFPKITLPPQPHTK EGIEAYNNVVAQIVIWVNLNLWQKLKIGRDEAKPLQRLKGFPSFPLVERQ ANEVDWWDMVCNVKKLINEKKEDGKVFWQNLAGYKRQEALRPYLSSE EDRKKGKKFARYQFGDLLLHLEKKHGEDWGKVYDEAWERIDKKVEGLS KHIKLEEERRSEDAQSKAALTDWLRAKASFVIEGLKEADKDEFCRCELKL |

TABLE 9-continued

CasX 278-280, 285-288, 290, 291, 293, 300, 492, and 493 sequences

| Construct | Amino Acid Sequence |
|---|---|
| | QKWYGDLRGKPFAIEAENSILDISGFSKQYNCAFIWQKDGVKKLNLYLIIN<br>YFKGGKLRFKKIKPEAFEANRFYTVINKKSGEIVPMEVNFNFDDPNLIILPL<br>AFGKRQGREFIWNDLLSLETGSLKLANGRVIEKTLYNRRTRQDEPALFVA<br>LTFERREVLDSSNIKPMNLIGIDRGENIPAVIALTDPEGCPLSRFKDSLGN<br>PTHILRIGESYKEKQRTIQAKKEVEQRRAGGYSRKYASKAKNLADDMVR<br>NTARDLLYYAVTQDAMLIFENLSRGFGRQGKRTFMAERQYTRMEDWLT<br>AKLAYEGLSKTYLSKTLAQYTSKTCSNCGFTITSADYDRVLEKLKKTATG<br>WMTTINGKELKVEGQITYYNRYKRQNVVKDLSVELDRLSEESVNNDISS<br>WTKGRSGEALSLLKKRFSHRPVQEKFVCLNCGFETHADEQAALNIARS<br>WLFLRSQEYKKYQTNKTTGNTDKRAFVETWQSFYRKKLKEVWKPAV<br>(SEQ ID NO: 448) |
| 279 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDIIL<br>EHQKVIKKNEKRLANLKDIASANGLAFPKITLPPQPHTKEGIEAYNNVVAQI<br>VIWVNLNLWQKLKIGRDEAKPLQRLKGFPSFPLVERQANEVDWWDMVC<br>NVKKLINEKKEDGKVFWQNLAGYKRQEALRPYLSSEEDRKKGKKFARYQ<br>FGDLLLHLEKKHGEDWGKVYDEAWERIDKKVEGLSKHIKLEEERRSEDA<br>QSKAALTDWLRAKASFVIEGLKEADKDEFCRCELKLQKWYGDLRGKPFA<br>IEAENSILDISGFSKQYNCAFIWQKDGVKKLNLYLIINYFKGGKLRFKKIKP<br>EAFEANRFYTVINKKSGEIVPMEVNFNFDDPNLIILPLAFGKRQGREFIWN<br>DLLSLETGSLKLANGRVIEKTLYNRRTRQDEPALFVALTFERREVLDSSNI<br>KPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDA<br>MLIFENLSRGFGRQGKRTFMAERQYTRMEDWLTAKLAYEGLSKTYLSKT<br>LAQYTSKTCSNCGFTITSADYDRVLEKLKKTATGWMTTINGKELKVEGQI<br>TYYNRYKRQNVVKDLSVELDRLSEESVNNDISSWTKGRSGEALSLLKKR<br>FSHRPVQEKFVCLNCGFETHADEQAALNIARSWLFLRSQEYKKYQTNKT<br>TGNTDKRAFVETWQSFYRKKLKEVWKPAVTSPKKKRKV<br>(SEQ ID NO: 449) |
| 280 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDIIL<br>EHQKVIKKNEKRLANLKDIASANGLAFPKITLPPQPHTKEGIEAYNNVVAQI<br>VIWVNLNLWQKLKIGRDEAKPLQRLKGFPSFPLVERQANEVDWWDMVC<br>NVKKLINEKKEDGKVFWQNLAGYKRQEALRPYLSSEEDRKKGKKFARYQ<br>FGDLLLHLEKKHGEDWGKVYDEAWERIDKKVEGLSKHIKLEEERRSEDA<br>QSKAALTDWLRAKASFVIEGLKEADKDEFCRCELKLQKWYGDLRGKPFA<br>IEAENSILDISGFSKQYNCAFIWQKDGVKKLNLYLIINYFKGGKLRFKKIKP<br>EAFEANRFYTVINKKSGEIVPMEVNFNFDDPNLIILPLAFGKRQGREFIWN<br>DLLSLETGSLKLANGRVIEKTLYNRRTRQDEPALFVALTFERREVLDSSNI<br>KPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDA<br>MLIFENLSRGFGRQGKRTFMAERQYTRMEDWLTAKLAYEGLSKTYLSKT<br>LAQYTSKTCSNCGFTITSADYDRVLEKLKKTATGWMTTINGKELKVEGQI<br>TYYNRYKRQNVVKDLSVELDRLSEESVNNDISSWTKGRSGEALSLLKKR<br>FSHRPVQEKFVCLNCGFETHADEQAALNIARSWLFLRSQEYKKYQTNKT<br>TGNTDKRAFVETWQSFYRKKLKEVWKPAVTSPKKKRKVPPPPKKKRKV<br>(SEQ ID NO: 450) |
| 285 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDIIL<br>EHQKVIKKNEKRLANLKDIASANGLAFPKITLPPQPHTKEGIEAYNNVVAQI<br>VIWVNLNLWQKLKIGRDEAKPLQRLKGFPSFPLVERQANEVDWWDMVC<br>NVKKLINEKKEDGKVFWQNLAGYKRQEALRPYLSSEEDRKKGKKFARYQ<br>FGDLLLHLEKKHGEDWGKVYDEAWERIDKKVEGLSKHIKLEEERRSEDA<br>QSKAALTDWLRAKASFVIEGLKEADKDEFCRCELKLQKWYGDLRGKPFA<br>IEAENSILDISGFSKQYNCAFIWQKDGVKKLNLYLIINYFKGGKLRFKKIKP<br>EAFEANRFYTVINKKSGEIVPMEVNFNFDDPNLIILPLAFGKRQGREFIWN<br>DLLSLETGSLKLANGRVIEKTLYNRRTRQDEPALFVALTFERREVLDSSNI<br>KPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDA<br>MLIFENLSRGFGRQGKRTFMAERQYTRMEDWLTAKLAYEGLSKTYLSKT<br>LAQYTSKTCSNCGFTITSADYDRVLEKLKKTATGWMTTINGKELKVEGQI<br>TYYNRYKRQNVVKDLSVELDRLSEESVNNDISSWTKGRSGEALSLLKKR<br>FSHRPVQEKFVCLNCGFETHADEQAALNIARSWLFLRSQEYKKYQTNKT |

TABLE 9-continued

| CasX 278-280, 285-288, 290, 291, 293, 300, 492, and 493 sequences | |
|---|---|
| Construct | Amino Acid Sequence |
| | TGNTDKRAFVETWQSFYRKKLKEVWKPAVTSPKKKRKVPPPHKKKHPD<br>ASVNFSEFSK<br>(SEQ ID NO: 451) |
| 286 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDIIL<br>EHQKVIKKNEKRLANLKDIASANGLAFPKITLPPQPHTKEGIEAYNNVVAQI<br>VIWVNLNLWQKLKIGRDEAKPLQRLKGFPSFPLVERQANEVDWWDMVC<br>NVKKLINEKKEDGKVFWQNLAGYKRQEALRPYLSSEEDRKKGKKFARYQ<br>FGDLLLHLEKKHGEDWGKVYDEAWERIDKKVEGLSKHIKLEEERRSEDA<br>QSKAALTDWLRAKASFVIEGLKEADKDEFCRCELKLQKWYGDLRGKPFA<br>IEAENSILDISGFSKQYNCAFIWQKDGVKKLNLYLIINYFKGGKLRFKKIKP<br>EAFEANRFYTVINKKSGEIVPMEVNFNFDDPNLIILPLAFGKRQGREFIWN<br>DLLSLETGSLKLANGRVIEKTLYNRRTRQDEPALFVALTFERREVLDSSNI<br>KPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDA<br>MLIFENLSRGFGRQGKRTFMAERQYTRMEDWLTAKLAYEGLSKTYLSKT<br>LAQYTSKTCSNCGFTITSADYDRVLEKLKKTATGWMTTINGKELKVEGQI<br>TYYNRYKRQNVVKDLSVELDRLSEESVNNDISSWTKGRSGEALSLLKKR<br>FSHRPVQEKFVCLNCGFETHADEQAALNIARSWLFLRSQEYKKYQTNKT<br>TGNTDKRAFVETWQSFYRKKLKEVWKPAVTSPKKKRKVPPPQRPGPYD<br>RPQRPGPYDRP<br>(SEQ ID NO: 452) |
| 287 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKG<br>KPHTNYFGRCNVSEHERLILLSPHKPEANDELVTYSLGKFGQRALDFYSI<br>HVTRESNHPVKPLEQIGGNSCASGPVGKALSDACMGAVASFLTKYQDIIL<br>EHQKVIKKNEKRLANLKDIASANGLAFPKITLPPQPHTKEGIEAYNNVVAQI<br>VIWVNLNLWQKLKIGRDEAKPLQRLKGFPSFPLVERQANEVDWWDMVC<br>NVKKLINEKKEDGKVFWQNLAGYKRQEALRPYLSSEEDRKKGKKFARYQ<br>FGDLLLHLEKKHGEDWGKVYDEAWERIDKKVEGLSKHIKLEEERRSEDA<br>QSKAALTDWLRAKASFVIEGLKEADKDEFCRCELKLQKWYGDLRGKPFA<br>IEAENSILDISGFSKQYNCAFIWQKDGVKKLNLYLIINYFKGGKLRFKKIKP<br>EAFEANRFYTVINKKSGEIVPMEVNFNFDDPNLIILPLAFGKRQGREFIWN<br>DLLSLETGSLKLANGRVIEKTLYNRRTRQDEPALFVALTFERREVLDSSNI<br>KPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDA<br>MLIFENLSRGFGRQGKRTFMAERQYTRMEDWLTAKLAYEGLSKTYLSKT<br>LAQYTSKTCSNCGFTITSADYDRVLEKLKKTATGWMTTINGKELKVEGQI<br>TYYNRYKRQNVVKDLSVELDRLSEESVNNDISSWTKGRSGEALSLLKKR<br>FSHRPVQEKFVCLNCGFETHADEQAALNIARSWLFLRSQEYKKYQTNKT<br>TGNTDKRAFVETWQSFYRKKLKEVWKPAVTSPKKKRKVPPPLSPSLSPL<br>LSPSLSPL<br>(SEQ ID NO: 453) |
| 288 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTMSSGFACSQCCQPLYVYKLEQVNDK<br>GKPHTNYFGRCNVSEHERLILLSPHKPEANDELVTYSLGKFGQRALDFY<br>SIHVTRESNHPVKPLEQIGGNSCASGPVGKALSDACMGAVASFLTKYQDI<br>ILEHQKVIKKNEKRLANLKDIASANGLAFPKITLPPQPHTKEGIEAYNNVVA<br>QIVIWVNLNLWQKLKIGRDEAKPLQRLKGFPSFPLVERQANEVDWWDMV<br>CNVKKLINEKKEDGKVFWQNLAGYKRQEALRPYLSSEEDRKKGKKFARY<br>QFGDLLLHLEKKHGEDWGKVYDEAWERIDKKVEGLSKHIKLEEERRSED<br>AQSKAALTDWLRAKASFVIEGLKEADKDEFCRCELKLQKWYGDLRGKPF<br>AIEAENSILDISGFSKQYNCAFIWQKDGVKKLNLYLIINYFKGGKLRFKKIK<br>PEAFEANRFYTVINKKSGEIVPMEVNFNFDDPNLIILPLAFGKRQGREFIW<br>NDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKE<br>KQRTIQAKKEVEQRRAGGYSRKYASKAKNLADDMVRNTARDLLYYAVT<br>QDAMLIFENLSRGFGRQGKRTFMAERQYTRMEDWLTAKLAYEGLSKTY<br>LSKTLAQYTSKTCSNCGFTITSADYDRVLEKLKKTATGWMTTINGKELKV<br>EGQITYYNRYKRQNVVKDLSVELDRLSEESVNNDISSWTKGRSGEALSL<br>LKKRFSHRPVQEKFVCLNCGFETHADEQAALNIARSWLFLRSQEYKKYQ<br>TNKTTGNTDKRAFVETWQSFYRKKLKEVWKPAVTSPKKKRKVPPPRGK<br>GGKGLGKGGAKRHRK<br>(SEQ ID NO: 454) |

TABLE 9-continued

| CasX 278-280, 285-288, 290, 291, 293, 300, 492, and 493 sequences | |
|---|---|
| Construct | Amino Acid Sequence |
| 290 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDIIL EHQKVIKKNEKRLANLKDIASANGLAFPKITLPPQPHTKEGIEAYNNVVAQI VIWVNLNLWQKLKIGRDEAKPLQRLKGFPSFPLVERQANEVDWWDMVC NVKKLINEKKEDGKVFWQNLAGYKRQEALRPYLSSEEDRKKGKKFARYQ FGDLLLHLEKKHGEDWGKVYDEAWERIDKKVEGLSKHIKLEEERRSEDA QSKAALTDWLRAKASFVIEGLKEADKDEFCRCELKLQKWYGDLRGKPFA IEAENSILDISGFSKQYNCAFIWQKDGVKKLNLYLIINYFKGGKLRFKKIKP EAFEANRFYTVINKKSGEIVPMEVNFNFDDPNLIILPLAFGKRQGREFIWN DLLSLETGSLKLANGRVIEKTLYNRRTRQDEPALFVALTFERREVLDSSNI KPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDA MLIFENLSRGFGRQGKRTFMAERQYTRMEDWLTAKLAYEGLSKTYLSKT LAQYTSKTCSNCGFTITSADYDRVLEKLKKTATGWMTTINGKELKVEGQI TYYNRYKRQNVVKDLSVELDRLSEESVNNDISSWTKGRSGEALSLLKKR FSHRPVQEKFVCLNCGFETHADEQAALNIARSWLFLRSQEYKKYQTNKT TGNTDKRAFVETWQSFYRKKLKEVWKPAVTSPKKKRKVPPPSRRRKAN PTKLSENAKKLAKEVEN (SEQ ID NO: 455) |
| 291 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDIIL EHQKVIKKNEKRLANLKDIASANGLAFPKITLPPQPHTKEGIEAYNNVVAQI VIWVNLNLWQKLKIGRDEAKPLQRLKGFPSFPLVERQANEVDWWDMVC NVKKLINEKKEDGKVFWQNLAGYKRQEALRPYLSSEEDRKKGKKFARYQ FGDLLLHLEKKHGEDWGKVYDEAWERIDKKVEGLSKHIKLEEERRSEDA QSKAALTDWLRAKASFVIEGLKEADKDEFCRCELKLQKWYGDLRGKPFA IEAENSILDISGFSKQYNCAFIWQKDGVKKLNLYLIINYFKGGKLRFKKIKP EAFEANRFYTVINKKSGEIVPMEVNFNFDDPNLIILPLAFGKRQGREFIWN DLLSLETGSLKLANGRVIEKTLYNRRTRQDEPALFVALTFERREVLDSSNI KPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDA MLIFENLSRGFGRQGKRTFMAERQYTRMEDWLTAKLAYEGLSKTYLSKT LAQYTSKTCSNCGFTITSADYDRVLEKLKKTATGWMTTINGKELKVEGQI TYYNRYKRQNVVKDLSVELDRLSEESVNNDISSWTKGRSGEALSLLKKR FSHRPVQEKFVCLNCGFETHADEQAALNIARSWLFLRSQEYKKYQTNKT TGNTDKRAFVETWQSFYRKKLKEVWKPAVTSPKKKRKVPPPPAAKRVK LD (SEQ ID NO: 456) |
| 293 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDIIL EHQKVIKKNEKRLANLKDIASANGLAFPKITLPPQPHTKEGIEAYNNVVAQI VIWVNLNLWQKLKIGRDEAKPLQRLKGFPSFPLVERQANEVDWWDMVC NVKKLINEKKEDGKVFWQNLAGYKRQEALRPYLSSEEDRKKGKKFARYQ FGDLLLHLEKKHGEDWGKVYDEAWERIDKKVEGLSKHIKLEEERRSEDA QSKAALTDWLRAKASFVIEGLKEADKDEFCRCELKLQKWYGDLRGKPFA IEAENSILDISGFSKQYNCAFIWQKDGVKKLNLYLIINYFKGGKLRFKKIKP EAFEANRFYTVINKKSGEIVPMEVNFNFDDPNLIILPLAFGKRQGREFIWN DLLSLETGSLKLANGRVIEKTLYNRRTRQDEPALFVALTFERREVLDSSNI KPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDA MLIFENLSRGFGRQGKRTFMAERQYTRMEDWLTAKLAYEGLSKTYLSKT LAQYTSKTCSNCGFTITSADYDRVLEKLKKTATGWMTTINGKELKVEGQI TYYNRYKRQNVVKDLSVELDRLSEESVNNDISSWTKGRSGEALSLLKKR FSHRPVQEKFVCLNCGFETHADEQAALNIARSWLFLRSQEYKKYQTNKT TGNTDKRAFVETWQSFYRKKLKEVWKPAVTSPKKKRKVPPPKRSFSKA F (SEQ ID NO: 457) |
| 300 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKG KPHTNYFGRCNVSEHERLILLSPHKPEANDELVTYSLGKFGQRALDFYSI HVTRESNHPVKPLEQIGGNSCASGPVGKALSDACMGAVASFLTKYQDIIL |

TABLE 9-continued

CasX 278-280, 285-288, 290, 291, 293, 300, 492, and 493 sequences

| Construct | Amino Acid Sequence |
|---|---|
| | EHQKVIKKNEKRLANLKDIASANGLAFPKITLPPQPHTKEGIEAYNNVVAQI VIWVNLNLWQKLKIGRDEAKPLQRLKGFPSFPLVERQANEVDWWDMVC NVKKLINEKKEDGKVFWQNLAGYKRQEALRPYLSSEEDRKKGKKFARYQ FGDLLLHLEKKHGEDWGKVYDEAWERIDKKVEGLSKHIKLEEERRSEDA QSKAALTDWLRAKASFVIEGLKEADKDEFCRCELKLQKWYGDLRGKPFA IEAENSILDISGFSKQYNCAFIWQKDGVKKLNLYLIINYFKGGKLRFKKIKP EAFEANRFYTVINKKSGEIVPMEVNFNFDDPNLIILPLAFGKRQGREFIWN DLLSLETGSLKLANGRVIEKTLYNRRTRQDEPALFVALTFERREVLDSSNI KPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDA MLIFENLSRGFGRQGKRTFMAERQYTRMEDWLTAKLAYEGLSKTYLSKT LAQYTSKTCSNCGFTITSADYDRVLEKLKKTATGWMTTINGKELKVEGQI TYYNRYKRQNVVKDLSVELDRLSEESVNNDISSWTKGRSGEALSLLKKR FSHRPVQEKFVCLNCGFETHADEQAALNIARSWLFLRSQEYKKYQTNKT TGNTDKRAFVETWQSFYRKKLKEVWKPAVTSPKKKRKVPPPKRGINDR NFWRGENERKTR (SEQ ID NO: 458) |
| 492 | MAPKKKRKVSRMQEIKRINKIRRRLVKDSNTKKAGKTGPMKTLLVRVMTP DLRERLENLRKKPENIPQPISNTSRANLNKLLTDYTEMKKAILHVYWEEFQ KDPVGLMSRVAQPAPKNIDQRKLIPVKDGNERLTSSGFACSQCCQPLYV YKLEQVNDKGKPHTNYFGRCNVSEHERLILLSPHKPEANDELVTYSLGKF GQRALDFYSIHVTRESNHPVKPLEQIGGNSCASGPVGKALSDACMGAVA SFLTKYQDIILEHQKVIKKNEKRLANLKDIASANGLAFPKITLPPQPHTKEGI EAYNNVVAQIVIWVNLNLWQKLKIGRDEAKPLQRLKGFPSFPLVERQANE VDWWDMVCNVKKLINEKKEDGKVFWQNLAGYKRQEALRPYLSSEEDRK KGKKFARYQFGDLLLHLEKKHGEDWGKVYDEAWERIDKKVEGLSKHIKL EEERRSEDAQSKAALTDWLRAKASFVIEGLKEADKDEFCRCELKLQKWY GDLRGKPFAIEAENSILDISGFSKQYNCAFIWQKDGVKKLNLYLIINYFKG GKLRFKKIKPEAFEANRFYTVINKKSGEIVPMEVNFNFDDPNLIILPLAFGK RQGREFIWNDLLSLETGSLKLANGRVIEKTLYNRRTRQDEPALFVALTFE RREVLDSSNIKPMNLIGIDRGENIPAVIALTDPEGCPLSRFKDSLGNPTHIL RIGESYKEKQRTIQAKKEVEQRRAGGYSRKYASKAKNLADDMVRNTARD LLYYAVTQDAMLIFENLSRGFGRQGKRTFMAERQYTRMEDWLTAKLAYE GLSKTYLSKTLAQYTSKTCSNCGFTITSADYDRVLEKLKKTATGWMTTIN GKELKVEGQITYYNRYKRQNVVKDLSVELDRLSEESVNNDISSWTKGRS GEALSLLKKRFSHRPVQEKFVCLNCGFETHADEQAALNIARSWLFLRSQ EYKKYQTNKTTGNTDKRAFVETWQSFYRKKLKEVWKPAVTSPKKKRKV PPPPKKKRKV (SEQ ID NO: 459) |
| 493 | MAPKKKRKVSRMQEIKRINKIRRRLVKDSNTKKAGKTGPMKTLLVRVMTP DLRERLENLRKKPENIPQPISNTSRANLNKLLTDYTEMKKAILHVYWEEFQ KDPVGLMSRVAQPAPKNIDQRKLIPVKDGNERLTSSGFACSQCCQPLYV YKLEQVNDKGKPHTNYFGRCNVSEHERLILLSPHKPEANDELVTYSLGKF GQRALDFYSIHVTRESNHPVKPLEQIGGNSCASGPVGKALSDACMGAVA SFLTKYQDIILEHQKVIKKNEKRLANLKDIASANGLAFPKITLPPQPHTKEGI EAYNNVVAQIVIWVNLNLWQKLKIGRDEAKPLQRLKGFPSFPLVERQANE VDWWDMVCNVKKLINEKKEDGKVFWQNLAGYKRQEALRPYLSSEEDRK KGKKFARYQFGDLLLHLEKKHGEDWGKVYDEAWERIDKKVEGLSKHIKL EEERRSEDAQSKAALTDWLRAKASFVIEGLKEADKDEFCRCELKLQKWY GDLRGKPFAIEAENSILDISGFSKQYNCAFIWQKDGVKKLNLYLIINYFKG GKLRFKKIKPEAFEANRFYTVINKKSGEIVPMEVNFNFDDPNLIILPLAFGK RQGREFIWNDLLSLETGSLKLANGRVIEKTLYNRRTRQDEPALFVALTFE RREVLDSSNIKPMNLIGIDRGENIPAVIALTDPEGCPLSRFKDSLGNPTHIL RIGESYKEKQRTIQAKKEVEQRRAGGYSRKYASKAKNLADDMVRNTARD LLYYAVTQDAMLIFENLSRGFGRQGKRTFMAERQYTRMEDWLTAKLAYE GLSKTYLSKTLAQYTSKTCSNCGFTITSADYDRVLEKLKKTATGWMTTIN GKELKVEGQITYYNRYKRQNVVKDLSVELDRLSEESVNNDISSWTKGRS GEALSLLKKRFSHRPVQEKFVCLNCGFETHADEQAALNIARSWLFLRSQ EYKKYQTNKTTGNTDKRAFVETWQSFYRKKLKEVWKPAVTSPKKKRKV PPPPAAKRVKLD (SEQ ID NO: 460) |

TABLE 10

Nuclear localization sequence list

| CasX | NLS | DNA Sequence | Amino Acid Sequence |
|---|---|---|---|
| 278, 279, 280, 492, 493 | SV40 | CCAAAGAAGAAGCGGAAGGTC (SEQ ID NO: 461) | PKKKRKV (SEQ ID NO: 158) |
| 285 | SynthNLS3 | CACAAGAAGAAACATCCAGACGCATCAGTCAACTTTAGCAGTTCAGTAAA (SEQ ID NO: 462) | HKKKHPDASVNFGSEFSK (SEQ ID NO: 189) |
| 286 | SynthNLS4 | CAGCGCCCTGGGCCTTACGATAGGCCGCAAAGACCCGGACCGTATGATCGCCCT (SEQ ID NO: 463) | QRPGPYDRPQRPGPYDRP (SEQ ID NO: 190) |
| 287 | SynthNLS5 | CTCAGCCCGAGTCTTAGTCCACTGCTTTCCCCGTCCCTGCTCCACTG (SEQ ID NO: 464) | LSPSLSPLLSPSTLSPL (SEQ ID NO: 191) |
| 288 | SynthNLS6 | CGGGGCAAGGGTGGCAAGGGGCTTGGCAAGGGGGGGGCAAAGAGGCACAGGAAG (SEQ ID NO: 465) | RGKGGKGLGKGGAKRHRK (SEQ ID NO: 192) |
| 290 | EGL-13 | AGCCGCCGCAGAAAAGCCAATCCTACAAAACTGTCAGAAAATGCGAAAAAACTTGCTAAGGAGGTGGAAAAC (SEQ ID NO: 466) | SRRRKANPTKLSENAKKLAKEVEN (SEQ ID NO: 470) |
| 291 | c-Myc | CCTGCCGCAAAGCGAGTGAAATTGGAC (SEQ ID NO: 467) | PAAKRVKLD (SEQ ID NO: 160) |
| 293 | Nucleolar RNA Helicase II | AAGCGGTCCTTCAGTAAGGCCTTT (SEQ ID NO: 468) | KRSFSKAF (SEQ ID NO: 181) |
| 300 | Influenza A protein | AAACGGGGAATAAACGACCGGAACTTCTGGCGCGGGGAAAACGAGCGCAAAACCCGA (SEQ ID NO: 469) | KRGINDRNFWRGENERKTR (SEQ ID NO: 179) |

Example 5: Design and Generation of CasX Constructs 387, 395, 485-491, and 494

In order to generate CasX 395, CasX 485, CasX 486, CasX 487, the codon optimized CasX 119 (based on the CasX 37 construct of Example 2, encoding Planctomycetes CasX SEQ ID NO: 2, with a A708K substitution and a [P793] deletion with fused NLS, and linked guide and non-targeting sequences), CasX 435, CasX 438, and CasX 484 (each based on CasX 119 construct of Example 2 encoding Planctomycetes CasX SEQ ID NO: 2, with a L379R substitution, a A708K substitution, and a [P793] deletion with fused NLS, and linked guide and non-targeting sequences) were cloned respectively into a 4 kb staging vector comprising a KanR marker, colE1 ori, and CasX with fused NLS (pStx1) using standard cloning methods. Gibson primers were designed to amplify the CasX SEQ ID NO: 1 Helical I domain from amino acid 192-331 in its own vector to replace this corresponding region (aa 193-332) on CasX 119, CasX 435, CasX 438, and CasX 484 in pStx1 respectively. The Helical I domain from CasX SEQ ID NO: 1 was amplified with primers oIC768 and oIC784 using Q5 DNA polymerase (New England BioLabs Cat #M0491L) according to the manufacturer's protocol. The destination vector containing the desired CasX variant was amplified with primers oIC765 and oIC764 using Q5 DNA polymerase (New England BioLabs Cat #M0491L) according to the manufacturer's protocol. The two fragments were purified by gel extraction from a 1% agarose gel (Gold Bio Cat #A-201-500) using Zymoclean Gel DNA Recovery Kit (Zymo Research Cat #D4002) according to the manufacturer's protocol. The insert and backbone fragments were then pieced together using Gibson assembly (New England BioLabs Cat #E2621S) following the manufacturer's protocol. Assembled products in the pStx1 staging vector were transformed into chemically-competent Turbo Competent *E. coli* bacterial cells, plated on LB-Agar plates (LB: Teknova Cat #L9315, Agar: Quartzy Cat #214510) containing kanamycin and incubated at 37° C. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct assembly. Correct clones were then cut and pasted into a mammalian expression plasmid (see FIG. 5) using standard cloning methods. The resultant plasmids were sequenced using Sanger sequencing to ensure correct assembly. Sequences encoding the targeting spacer sequences that target the gene of interest were designed based on CasX PAM locations. Targeting spacer sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C2984I), plated on LB-Agar plates (LB: Teknova Cat #L9315, Agar: Quartzy Cat #214510) containing carbenicillin and incubated at 37° C. Individual colonies were picked and miniprepped using Qiagen Qiaprep spin Miniprep Kit (Qiagen Cat #27104) following the manufacturer's protocol. The resultant plasmids were sequenced using Sanger sequencing to ensure correct ligation.

In order to generate CasX 488, CasX 489, CasX 490, and CasX 491 (sequences in Table 11), the codon optimized CasX 119 (based on the CasX 37 construct of Example 2, encoding Planctomycetes CasX SEQ ID NO: 2, with a A708K substitution and a [P793] deletion with fused NLS, and linked guide and non-targeting sequences), CasX 435, CasX 438, and CasX 484 (each based on CasX119 construct of Example 2 encoding Planctomycetes CasX SEQ ID NO: 2, with a L379R substitution, a A708K substitution, and a [P793] deletion with fused NLS, and linked guide and non-targeting sequences) were cloned respectively into a 4 kb staging vector that was made up of a KanR marker, colE1 ori, and STX with fused NLS (pStx1) using standard cloning methods. Gibson primers were designed to amplify the CasX Stx1 NTSB domain from amino acid 101-191 and Helical I domain from amino acid 192-331 in its own vector to replace this similar region (aa 103-332) on CasX 119, CasX 435, CasX 438, and CasX 484 in pStx1 respectively. The NTSB and Helical I domain from CasX SEQ ID NO: 1 were amplified with primers oIC766 and oIC784 using Q5 DNA polymerase (New England BioLabs Cat #M0491L) according to the manufacturer's protocol. The destination vector containing the desired CasX variant was amplified with primers oIC762 and oIC765 using Q5 DNA polymerase (New England BioLabs Cat #M0491L) according to the manufacturer's protocol. The two fragments were purified by gel extraction from a 1% agarose gel (Gold Bio Cat #A-201-500) using Zymoclean Gel DNA Recovery Kit (Zymo Research Cat #D4002) according to the manufacturer's protocol. The insert and backbone fragments were then pieced together using Gibson assembly (New England BioLabs Cat #E2621S) following the manufacturer's protocol. Assembled products in the pStx1 staging vector were transformed into chemically-competent Turbo Competent *E. coli* bacterial cells, plated on LB-Agar plates (LB: Teknova Cat #L9315, Agar: Quartzy Cat #214510) containing kanamycin and incubated at 37° C. Individual colonies were picked and minipreped using Qiagen Qiaprep spin Miniprep Kit (Qiagen Cat #27104) following the manufacturer's protocol. The resultant plasmids were sequenced using Sanger sequencing to ensure correct assembly. Correct clones were then cut and pasted into a mammalian expression plasmid (see FIG. 5) using standard cloning methods. The resultant plasmids were sequenced using Sanger sequencing to ensure correct assembly. Sequences encoding the targeting spacer sequences that target the gene of interest were designed based on CasX PAM locations. Targeting spacer sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C2984I), plated on LB-Agar plates (LB: Teknova Cat #L9315, Agar: Quartzy Cat #214510) containing carbenicillin and incubated at 37° C. Individual colonies were picked and minipreped using Qiagen Qiaprep spin Miniprep Kit (Qiagen Cat #27104) and following the manufacturer's protocol. The resultant plasmids were sequenced using Sanger sequencing to ensure correct ligation.

In order to generate CasX 387 and CasX 494 (sequences in Table 11), the codon optimized CasX 119 (based on the CasX 37 construct of Example 2, encoding Planctomycetes CasX SEQ ID NO:2, with a A708K substitution and a [P793] deletion with fused NLS, and linked guide and non-targeting sequences) and CasX 484 (based on CasX119 construct of Example 2 encoding Planctomycetes CasX SEQ ID NO: 2, with a L379R substitution, a A708K substitution, and a [P793] deletion with fused NLS, and linked guide and non-targeting sequences) were cloned respectively into a 4 kb staging vector that was made up of a KanR marker, colE1 ori, and STX with fused NLS (pStx1) using standard cloning methods. Gibson primers were designed to amplify the CasX Stx1 NTSB domain from amino acid 101-191 in its own vector to replace this similar region (aa 103-192) on CasX 119 and CasX 484 in pStx1 respectively. The NTSB domain from CasX Stx1 was amplified with primers oIC766 and oIC767 using Q5 DNA polymerase (New England BioLabs Cat #M0491L) according to the manufacturer's protocol. The destination vector containing the desired CasX variant was amplified with primers oIC763 and oIC762 using Q5 DNA polymerase (New England BioLabs Cat #M0491L) according to the manufacturer's protocol. The two fragments were purified by gel extraction from a 1% agarose gel (Gold Bio Cat #A-201-500) using Zymoclean Gel DNA Recovery Kit (Zymo Research Cat #D4002) according to the manufacturer's protocol. The insert and backbone fragments were then pieced together using Gibson assembly (New England BioLabs Cat #E2621S) following the manufacturer's protocol. Assembled products in the pStx1 staging vector were transformed into chemically-competent Turbo Competent *E. coli* bacterial cells, plated on LB-Agar plates (LB: Teknova Cat #L9315, Agar: Quartzy Cat #214510) containing kanamycin and incubated at 37° C. Individual colonies were picked and minipreped using Qiagen Qiaprep spin Miniprep Kit (Qiagen Cat #27104) following the manufacturer's protocol. The resultant plasmids were sequenced using Sanger sequencing to ensure correct assembly. Correct clones were then cut and pasted into a mammalian expression plasmid (see FIG. 5) using standard cloning methods. The resultant plasmids were sequenced using Sanger sequencing to ensure correct assembly. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C2984I), plated on LB-Agar plates (LB: Teknova Cat #L9315, Agar: Quartzy Cat #214510) containing carbenicillin and incubated at 37° C. Individual colonies were picked and minipreped using Qiagen Qiaprep spin Miniprep Kit (Qiagen Cat #27104) and following the manufacturer's protocol. The resultant plasmids were sequenced using Sanger sequencing to ensure correct ligation. Sequences of the resulting constructs are listed in Table 11.

TABLE 11

Sequences of CasX 395 and 485-491

| Construct | DNA Sequence | Amino Acid Sequence |
|---|---|---|
| CasX 387 | (SEQ ID NO: 471) | MAPKKKRKVSRQEIKRINKIRRRLVKDSNTKKAGKTGPMKTL LVRVMTPDLRERLENLRKKPENIPQPISNTSRANLNKLLTDY TEMKKAILHVYWEEFQKDPVGLMSRVAQPASKKIDQNKLKP EMDEKGNLTTAGFACSQCGQPLFVYKLEQVSEKGKAYTNY FGRCNVAEHEKLILLAQLKPEKDSDEAVTYSLGKFGQRALD FYSIHVTRESNHPVKPLEQIGGNSCASGPVGKALSDACMGA VASFLTKYQDIILEHQKVIKKNEKRLANLKDIASANGLAFPKIT LPPQPHTKEGIEAYNNVVAQIVIWVNLNLWQKLKIGRDEAKP LQRLKGFPSFPLVERQANEVDWWDMVCNVKKLINEKKEDG KVFWQNLAGYKRQEALRPYLSSEEDRKKGKKFARYQFGDL LLHLEKKHGEDWGKVYDEAWERIDKKVEGLSKHIKLEEERR |

TABLE 11-continued

| Sequences of CasX 395 and 485-491 | | |
|---|---|---|
| Construct | DNA Sequence | Amino Acid Sequence |
| | | SEDAQSKAALTDWLRAKASFVIEGLKEADKDEFCRCELKLQ<br>KWYGDLRGKPFAIEAENSILDISGFSKQYNCAFIWQKDGVKK<br>LNLYLIINYFKGGKLRFKKIKPEAFEANRFYTVINKKSGEIVPM<br>EVNFNFDDPNLIILPLAFGKRQGREFIWNDLLSLETGSLKLAN<br>GRVIEKTLYNRRTRQDEPALFVALTFERREVLDSSNIKPMNLI<br>GIDRGENIPAVIALTDPEGCPLSRFKDSLGNPTHILRIGESYK<br>EKQRTIQAKKEVEQRRAGGYSRKYASKAKNLADDMVRNTA<br>RDLLYYAVTQDAMLIFENLSRGFGRQGKRTFMAERQYTRM<br>EDWLTAKLAYEGLSKTYLSKTLAQYTSKTCSNCGFTITSADY<br>DRVLEKLKKTATGWMTTINGKELKVEGQITYYNRYKRQNVV<br>KDLSVELDRLSEESVNNDISSWTKGRSGEALSLLKKRFSHR<br>PVQEKFVCLNCGFETHADEQAALNIARSWLFLRSQEYKKYQ<br>TNKTTGNTDKRAFVETWQSFYRKKLKEVWKPAVTSPKKKR<br>KV (SEQ ID NO: 472) |
| CasX 395 | (SEQ ID NO: 473) | MAPKKKRKVSRQEIKRINKIRRRLVKDSNTKKAGKTGPMKTL<br>LVRVMTPDLRERLENLRKKPENIPQPISNTSRANLNKLLTDY<br>TEMKKAILHVYWEEFQKDPVGLMSRVAQPAPKNIDQRKLIP<br>VKDGNERLTSSGFACSQCCQPLYVYKLEQVNDKGKPHTNY<br>FGRCNVSEHERLILLSPHKPEANDELVTYSLGKFGQRALDF<br>YSIHVTKESTHPVKPLAQIAGNRYASGPVGKALSDACMGTIA<br>SFLSKYQDIIIEHQKWKGNQKRLESLRELAGKENLEYPSVTL<br>PPQPHTKEGVDAYNEVIARVRMWVNLNLWQKLKLSRDDAK<br>PLLRLKGFPSFPLVERQANEVDWWDMVCNVKKLINEKKED<br>GKVFWQNLAGYKRQEALRPYLSSEEDRKKGKKFARYQFGD<br>LLLHLEKKHGEDWGKVYDEAWERIDKKVEGLSKHIKLEEER<br>RSEDAQSKAALTDWLRAKASFVIEGLKEADKDEFCRCELKL<br>QKWYGDLRGKPFAIEAENSILDISGFSKQYNCAFIWQKDGV<br>KKLNLYLIINYFKGGKLRFKKIKPEAFEANRFYTVINKKSGEIV<br>PMEVNFNFDDPNLIILPLAFGKRQGREFIWNDLLSLETGSLK<br>LANGRVIEKTLYNRRTRQDEPALFVALTFERREVLDSSNIKP<br>MNLIGIDRGENIPAVIALTDPEGCPLSRFKDSLGNPTHILRIGE<br>SYKEKQRTIQAKKEVEQRRAGGYSRKYASKAKNLADDMVR<br>NTARDLLYYAVTQDAMLIFENLSRGFGRQGKRTFMAERQYT<br>RMEDWLTAKLAYEGLSKTYLSKTLAQYTSKTCSNCGFTITSA<br>DYDRVLEKLKKTATGWMTTINGKELKVEGQITYYNRYKRQN<br>VVKDLSVELDRLSEESVNNDISSWTKGRSGEALSLLKKRFS<br>HRPVQEKFVCLNCGFETHADEQAALNIARSWLFLRSQEYKK<br>YQTNKTTGNTDKRAFVETWQSFYRKKLKEVWKPAVTSPKK<br>KRKVTSPKKKRKV (SEQ ID NO: 474) |
| CasX 485 | (SEQ ID NO: 475) | MAPKKKRKVSRQEIKRINKIRRRLVKDSNTKKAGKTGPMKTL<br>LVRVMTPDLRERLENLRKKPENIPQPISNTSRANLNKLLTDY<br>TEMKKAILHVYWEEFQKDPVGLMSRVAQPAPKNIDQRKLIP<br>VKDGNERLTSSGFACSQCCQPLYVYKLEQVNDKGKPHTNY<br>FGRCNVSEHERLILLSPHKPEANDELVTYSLGKFGQRALDF<br>YSIHVTKESTHPVKPLAQIAGNRYASGPVGKALSDACMGTIA<br>SFLSKYQDIIIEHQKWKGNQKRLESLRELAGKENLEYPSVTL<br>PPQPHTKEGVDAYNEVIARVRMWWNLNLWQKLKLSRDDAK<br>PLLRLKGFPSFPLVERQANEVDWWDMVCNVKKLINEKKED<br>GKVFWQNLAGYKRQEALRPYLSSEEDRKKGKKFARYQLGD<br>LLLHLEKKHGEDWGKVYDEAWERIDKKVEGLSKHIKLEEER<br>RSEDAQSKAALTDWLRAKASFVIEGLKEADKDEFCRCELKL<br>QKWYGDLRGKPFAIEAENSILDISGFSKQYNCAFIWQKDGV<br>KKLNLYLIINYFKGGKLRFKKIKPEAFEANRFYTVINKKSGEIV<br>PMEVNFNFDDPNLIILPLAFGKRQGREFIWNDLLSLETGSLK<br>LANGRVIEKTLYNRRTRQDEPALFVALTFERREVLDSSNIKP<br>MNLIGVDRGENIPAVIALTDPEGCPLSRFKDSLGNPTHILRIG<br>ESYKEKQRTIQAKKEVEQRRAGGYSRKYASKAKNLADDMV<br>RNTARDLLYYAVTQDAMLIFENLSRGFGRQGKRTFMAERQ<br>YTRMEDWLTAKLAYEGLSKTYLSKTLAQYTSKTCSNCGFTIT<br>SADYDRVLEKLKKTATGWMTTINGKELKVEGQITYYNRRKR<br>QNWKDLSVELDRLSEESVNNDISSWTKGRSGEALSLLKKR<br>FSHRPVQEKFVCLNCGFETHADEQAALNIARSWLFLRSQEY<br>KKYQTNKTTGNTDKRAFVETWQSFYRKKLKEVWKPAVTSP<br>KKKRKV (SEQ ID NO: 476) |
| CasX 486 | (SEQ ID NO: 477) | MAPKKKRKVSRQEIKRINKIRRRLVKDSNTKKAGKTGPMKTL<br>LVRVMTPDLRERLENLRKKPENIPQPISNTSRANLNKLLTDY<br>TEMKKAILHVYWEEFQKDPVGLMSRVAQPAPKNIDQRKLIP<br>VKDGNERLTSSGFACSQCCQPLYVYKLEQVNDKGKPHTNY<br>FGRCNVSEHERLILLSPHKPEANDELVTYSLGKFGQRALDF<br>YSIHVTKESTHPVKPLAQIAGNRYASGPVGKALSDACMGTIA<br>SFLSKYQDIIIEHQKWKGNQKRLESLRELAGKENLEYPSVTL<br>PPQPHTKEGVDAYNEVIARVRMWNLNLWQKLKLSRDDAK |

TABLE 11-continued

Sequences of CasX 395 and 485-491

| Construct | DNA Sequence | Amino Acid Sequence |
|---|---|---|
| | | PLLRLKGFPSFPLVERQANEVDWWDMVCNVKKLINEKKED<br>GKVFWQNLAGYKRQEALRPYLSSEEDRKKGKKFARYQLGD<br>LLKHLEKKHGEDWGKVYDEAWERIDKKVEGLSKHIKLEEER<br>RSEDAQSKAALTDWLRAKASFVIEGLKEADKDEFCRCELKL<br>QKWYGDLRGKPFAIEAENSILDISGFSKQYNCAFIWQKDGV<br>KKLNLYLIINYFKGGKLRFKKIKPEAFEANRFYTVINKKSGEIV<br>PMEVNFNFDDPNLIILPLAFGKRQGREFIWNDLLSLETGSLK<br>LANGRVIEKTLYNRRTRQDEPALFVALTFERREVLDSSNIKP<br>MNLIGVDRGENIPAVIALTDPEGCPLSRFKDSLGNPTHILRIG<br>ESYKEKQRTIQAKKEVEQRRAGGYSRKYASKAKNLADDMV<br>RNTARDLLYYAVTQDAMLIFENLSRGFGRQGKRTFMAERQ<br>YTRMEDWLTAKLAYEGLSKTYLSKTLAQYTSKTCSNCGFTIT<br>SADYDRVLEKLKKTATGWMTTINGKELKVEGQITYYNRRKR<br>QNWKDLSVELDRLSEESVNNDISSWTKGRSGEALSLLKKR<br>FSHRPVQEKFVCLNCGFETHADEQAALNIARSWLFLRSQEY<br>KKYQTNKTTGNTDKRAFVETWQSFYRKKLKEVWKPAVTSP<br>KKKRKV (SEQ ID NO: 478) |
| CasX 487 | (SEQ ID NO: 479) | MAPKKKRKVSRQEIKRINKIRRRLVKDSNTKKAGKTGPMKTL<br>LVRVMTPDLRERLENLRKKPENIPQPISNTSRANLNKLLTDY<br>TEMKKAILHVYWEEFQKDPVGLMSRVAQPAPKNIDQRKLIP<br>VKDGNERLTSSGFACSQCCQPLYVYKLEQVNDKGKPHTNY<br>FGRCNVSEHERLILLSPHKPEANDELVTYSLGKFGQRALDF<br>YSIHVTKESTHPVKPLAQIAGNRYASGPVGKALSDACMGTIA<br>SFLSKYQDIIIEHQKWKGNQKRLESLRELAGKENLEYPSVTL<br>PPQPHTKEGVDAYNEVIARVRMWNLNLWQKLKLSRDDAK<br>PLLRLKGFPSFPLVERQANEVDWWDMVCNVKKLINEKKED<br>GKVFWQNLAGYKRQEALRPYLSSEEDRKKGKKFARYQLGD<br>LLLHLEKKHGEDWGKVYDEAWERIDKKVEGLSKHIKLEEER<br>RSEDAQSKAALTDWLRAKASFVIEGLKEADKDEFCRCELKL<br>QKWYGDLRGKPFAIEAENSILDISGFSKQYNCAFIWQKDGV<br>KKLNLYLIINYFKGGKLRFKKIKPEAFEANRFYTVINKKSGEIV<br>PMEVNFNFDDPNLIILPLAFGKRQGREFIWNDLLSLETGSLK<br>LANGRVIEKTLYNRRTRQDEPALFVALTFERREVLDSSNIKP<br>MNLIGVDRGENIPAVIALTDPEGCPLSRFKDSLGNPTHILRIG<br>ESYKEKQRTIQAKKEVEQRRAGGYSRKYASKAKNLADDMV<br>RNTARDLLYYAVTQDAMLIFENLSRGFGRQGKRTFMAERQ<br>YTRMEDWLTAKLAYEGLSKTYLSKTLAQYTSKTCSNCGFTIT<br>SADYDRVLEKLKKTATGWMTTINGKELKVEGQITYYNRYKR<br>QNWKDLSVELDRLSEESVNNDISSWTKGRSGEALSLLKKR<br>FSHRPVQEKFVCLNCGFETHADEQAALNIARSWLFLRSQEY<br>KKYQTNKTTGNTDKRAFVETWQSFYRKKLKEVWKPAVTSP<br>KKKRKV (SEQ ID NO: 480) |
| CasX 488 | (SEQ ID NO: 481) | MAPKKKRKVSRQEIKRINKIRRRLVKDSNTKKAGKTGPMKTL<br>LVRVMTPDLRERLENLRKKPENIPQPISNTSRANLNKLLTDY<br>TEMKKAILHVYWEEFQKDPVGLMSRVAQPASKKIDQNKLKP<br>EMDEKGNLTTAGFACSQCGQPLFVYKLEQVSEKGKAYTNY<br>FGRCNVAEHEKLILLAQLKPEKDSDEAVTYSLGKFGQRALD<br>FYSIHVTKESTHPVKPLAQIAGNRYASGPVGKALSDACMGTI<br>ASFLSKYQDIIIEHQKVVKGNQKRLESLRELAGKENLEYPSV<br>TLPPQPHTKEGVDAYNEVIARVRMWVNLNLWQKLKLSRDD<br>AKPLLRLKGFPSFPLVERQANEVDWWDMVCNVKKLINEKKE<br>DGKVFWQNLAGYKRQEALRPYLSSEEDRKKGKKFARYQFG<br>DLLLHLEKKHGEDWGKVYDEAWERIDKKVEGLSKHIKLEEE<br>RRSEDAQSKAALTDWLRAKASFVIEGLKEADKDEFCRCELK<br>LQKWYGDLRGKPFAIEAENSILDISGFSKQYNCAFIWQKDGV<br>KKLNLYLIINYFKGGKLRFKKIKPEAFEANRFYTVINKKSGEIV<br>PMEVNFNFDDPNLIILPLAFGKRQGREFIWNDLLSLETGSLK<br>LANGRVIEKTLYNRRTRQDEPALFVALTFERREVLDSSNIKP<br>MNLIGIDRGENIPAVIALTDPEGCPLSRFKDSLGNPTHILRIGE<br>SYKEKQRTIQAKKEVEQRRAGGYSRKYASKAKNLADDMVR<br>NTARDLLYYAVTQDAMLIFENLSRGFGRQGKRTFMAERQYT<br>RMEDWLTAKLAYEGLSKTYLSKTLAQYTSKTCSNCGFTITSA<br>DYDRVLEKLKKTATGWMTTINGKELKVEGQITYYNRYKRQN<br>VVKDLSVELDRLSEESVNNDISSWTKGRSGEALSLLKKRFS<br>HRPVQEKFVCLNCGFETHADEQAALNIARSWLFLRSQEYKK<br>YQTNKTTGNTDKRAFVETWQSFYRKKLKEVWKPAVTSPKK<br>KRKV (SEQ ID NO: 482) |
| CasX 489 | (SEQ ID NO: 483) | MAPKKKRKVSRQEIKRINKIRRRLVKDSNTKKAGKTGPMKTL<br>LVRVMTPDLRERLENLRKKPENIPQPISNTSRANLNKLLTDY<br>TEMKKAILHVYWEEFQKDPVGLMSRVAQPASKKIDQNKLKP<br>EMDEKGNLTTAGFACSQCGQPLFVYKLEQVSEKGKAYTNY<br>FGRCNVAEHEKLILLAQLKPEKDSDEAVTYSLGKFGQRALD |

TABLE 11-continued

| Sequences of CasX 395 and 485-491 | | |
|---|---|---|
| Construct | DNA Sequence | Amino Acid Sequence |
| | | FYSIHVTKESTHPVKPLAQIAGNRYASGPVGKALSDACMGTI ASFLSKYQDIIIEHQKVVKGNQKRLESLRELAGKENLEYPSV TLPPQPHTKEGVDAYNEVIARVRMWVNLNLWQKLKLSRDD AKPLLRLKGFPSFPLVERQANEVDWWDMVCNVKKLINEKKE DGKVFWQNLAGYKRQEALRPYLSSEEDRKKGKKFARYQLG DLLLHLEKKHGEDWGKVYDEAWERIDKKVEGLSKHIKLEEE RRSEDAQSKAALTDWLRAKASFVIEGLKEADKDEFCRCELK LQKWYGDLRGKPFAIEAENSILDISGFSKQYNCAFIWQKDGV KKLNLYLIINYFKGGKLRFKKIKPEAFEANRFYTVINKKSGEIV PMEVNFNFDDPNLIILPLAFGKRQGREFIWNDLLSLETGSLK LANGRVIEKTLYNRRTRQDEPALFVALTFERREVLDSSNIKP MNLIGVDRGENIPAVIALTDPEGCPLSRFKDSLGNPTHILRIG ESYKEKQRTIQAKKEVEQRRAGGYSRKYASKAKNLADDMV RNTARDLLYYAVTQDAMLIFENLSRGFGRQGKRTFMAERQ YTRMEDWLTAKLAYEGLSKTYLSKTLAQYTSKTCSNCGFTIT SADYDRVLEKLKKTATGWMTTINGKELKVEGQITYYNRRKR QNVVKDLSVELDRLSEESVNNDISSWTKGRSGEALSLLKKR FSHRPVQEKFVCLNCGFETHADEQAALNIARSWLFLRSQEY KKYQTNKTTGNTDKRAFVETWQSFYRKKLKEVWKPAVTSP KKKRKV (SEQ ID NO: 484) |
| CasX 490 | (SEQ ID NO: 485) | MAPKKKRKVSRQEIKRINKIRRRLVKDSNTKKAGKTGPMKTL LVRVMTPDLRERLENLRKKPENIPQPISNTSRANLNKLLTDY TEMKKAILHVYWEEFQKDPVGLMSRVAQPASKKIDQNKLKP EMDEKGNLTTAGFACSQCGQPLFVYKLEQVSEKGKAYTNY FGRCNVAEHEKLILLAQLKPEKDSDEAVTYSLGKFGQRALD FYSIHVTKESTHPVKPLAQIAGNRYASGPVGKALSDACMGTI ASFLSKYQDIIIEHQKVVKGNQKRLESLRELAGKENLEYPSV TLPPQPHTKEGVDAYNEVIARVRMWVNLNLWQKLKLSRDD AKPLLRLKGFPSFPLVERQANEVDWWDMVCNVKKLINEKKE DGKVFWQNLAGYKRQEALRPYLSSEEDRKKGKKFARYQLG DLLKHLEKKHGEDWGKVYDEAWERIDKKVEGLSKHIKLEEE RRSEDAQSKAALTDWLRAKASFVIEGLKEADKDEFCRCELK LQKWYGDLRGKPFAIEAENSILDISGFSKQYNCAFIWQKDGV KKLNLYLIINYFKGGKLRFKKIKPEAFEANRFYTVINKKSGEIV PMEVNFNFDDPNLIILPLAFGKRQGREFIWNDLLSLETGSLK LANGRVIEKTLYNRRTRQDEPALFVALTFERREVLDSSNIKP MNLIGVDRGENIPAVIALTDPEGCPLSRFKDSLGNPTHILRIG ESYKEKQRTIQAKKEVEQRRAGGYSRKYASKAKNLADDMV RNTARDLLYYAVTQDAMLIFENLSRGFGRQGKRTFMAERQ YTRMEDWLTAKLAYEGLSKTYLSKTLAQYTSKTCSNCGFTIT SADYDRVLEKLKKTATGWMTTINGKELKVEGQITYYNRRKR QNVVKDLSVELDRLSEESVNNDISSWTKGRSGEALSLLKKR FSHRPVQEKFVCLNCGFETHADEQAALNIARSWLFLRSQEY KKYQTNKTTGNTDKRAFVETWQSFYRKKLKEVWKPAVTSP KKKRKV (SEQ ID NO: 486) |
| CasX 491 | (SEQ ID NO: 487) | MAPKKKRKVSRQEIKRINKIRRRLVKDSNTKKAGKTGPMKTL LVRVMTPDLRERLENLRKKPENIPQPISNTSRANLNKLLTDY TEMKKAILHVYWEEFQKDPVGLMSRVAQPASKKIDQNKLKP EMDEKGNLTTAGFACSQCGQPLFVYKLEQVSEKGKAYTNY FGRCNVAEHEKLILLAQLKPEKDSDEAVTYSLGKFGQRALD FYSIHVTKESTHPVKPLAQIAGNRYASGPVGKALSDACMGTI ASFLSKYQDIIIEHQKVVKGNQKRLESLRELAGKENLEYPSV TLPPQPHTKEGVDAYNEVIARVRMWVNLNLWQKLKLSRDD AKPLLRLKGFPSFPLVERQANEVDWWDMVCNVKKLINEKKE DGKVFWQNLAGYKRQEALRPYLSSEEDRKKGKKFARYQLG DLLLHLEKKHGEDWGKVYDEAWERIDKKVEGLSKHIKLEEE RRSEDAQSKAALTDWLRAKASFVIEGLKEADKDEFCRCELK LQKWYGDLRGKPFAIEAENSILDISGFSKQYNCAFIWQKDGV KKLNLYLIINYFKGGKLRFKKIKPEAFEANRFYTVINKKSGEIV PMEVNFNFDDPNLIILPLAFGKRQGREFIWNDLLSLETGSLK LANGRVIEKTLYNRRTRQDEPALFVALTFERREVLDSSNIKP MNLIGVDRGENIPAVIALTDPEGCPLSRFKDSLGNPTHILRIG ESYKEKQRTIQAKKEVEQRRAGGYSRKYASKAKNLADDMV RNTARDLLYYAVTQDAMLIFENLSRGFGRQGKRTFMAERQ YTRMEDWLTAKLAYEGLSKTYLSKTLAQYTSKTCSNCGFTIT SADYDRVLEKLKKTATGWMTTINGKELKVEGQITYYNRYKR QNVVKDLSVELDRLSEESVNNDISSWTKGRSGEALSLLKKR FSHRPVQEKFVCLNCGFETHADEQAALNIARSWLFLRSQEY KKYQTNKTTGNTDKRAFVETWQSFYRKKLKEVWKPAVTSP KKKRKV (SEQ ID NO: 488) |

TABLE 11-continued

| Sequences of CasX 395 and 485-491 | | |
|---|---|---|
| Construct | DNA Sequence | Amino Acid Sequence |
| CasX 494 | (SEQ ID NO: 489) | MAPKKKRKVSRQEIKRINKIRRRLVKDSNTKKAGKTGPMKTL LVRVMTPDLRERLENLRKKPENIPQPISNTSRANLNKLLTDY TEMKKAILHVYWEEFQKDPVGLMSRVAQPASKKIDQNKLKP EMDEKGNLTTAGFACSQCGQPLFVYKLEQVSEKGKAYTNY FGRCNVAEHEKLILLAQLKPEKDSDEAVTYSLGKFGQRALD FYSIHVTRESNHPVKPLEQIGGNSCASGPVGKALSDACMGA VASFLTKYQDIILEHQKVIKKNEKRLANLKDIASANGLAFPKIT LPPQPHTKEGIEAYNNVVAQIVIWVNLNLWQKLKIGRDEAKP LQRLKGFPSFPLVERQANEVDWWDMVCNVKKLINEKKEDG KVFWQNLAGYKRQEALRPYLSSEEDRKKGKKFARYQLGDL LLHLEKKHGEDWGKVYDEAWERIDKKVEGLSKHIKLEEERR SEDAQSKAALTDWLRAKASFVIEGLKEADKDEFCRCELKLQ KWYGDLRGKPFAIEAENSILDISGFSKQYNCAFIWQKDGVKK LNLYLIINYFKGGKLRFKKIKPEAFEANRFYTVINKKSGEIVPM EVNFNFDDPNLIILPLAFGKRQGREFIWNDLLSLETGSLKLAN GRVIEKTLYNRRTRQDEPALFVALTFERREVLDSSNIKPMNLI GVDRGENIPAVIALTDPEGCPLSRFKDSLGNPTHILRIGESYK EKQRTIQAKKEVEQRRAGGYSRKYASKAKNLADDMVRNTA RDLLYYAVTQDAMLIFENLSRGFGRQGKRTFMAERQYTRM EDWLTAKLAYEGLSKTYLSKTLAQYTSKTCSNCGFTITSADY DRVLEKLKKTATGWMTTINGKELKVEGQITYYNRYKRQNVV KDLSVELDRLSEESVNNDISSWTKGRSGEALSLLKKRFSHR PVQEKFVCLNCGFETHADEQAALNIARSWLFLRSQEYKKYQ TNKTTGNTDKRAFVETWQSFYRKKLKEVWKPAVTSPKKKR KV (SEQ ID NO: 490) |

Example 6: Generation of RNA Guides

For the generation of RNA single guides and spacers, templates for in vitro transcription were generated by performing PCR with Q5 polymerase (NEB M0491) according to the recommended protocol, with template oligos for each backbone and amplification primers with the T7 promoter and the spacer sequence. The DNA primer sequences for the T7 promoter, guide and spacer for guides and spacers are presented in Table 12, below. The template oligos, labeled "backbone fwd" and "backbone rev" for each scaffold, were included at a final concentration of 20 nM each, and the amplification primers (T7 promoter and the unique spacer primer) were included at a final concentration of 1 uM each. The sg2, sg32, sg64, and sg174 guides correspond to SEQ TD NOS: 5, 2104, 2106, and 2238, respectively, with the exception that sg2, sg32, and sg64 were modified with an additional 5' G to increase transcription efficiency (compare sequences in Table 12 to Table 2). The 7.37 spacer targets beta2-microglobulin (B2M). Following PCR amplification, templates were cleaned and isolated by phenol-chloroform-isoamyl alcohol extraction followed by ethanol precipitation.

In vitro transcriptions were carried out in buffer containing 50 mM Tris pH 8.0, 30 mM $MgCl_2$, 0.01% Triton X-100, 2 mM spermidine, 20 mM DTT, 5 mM NTPs, 0.5 GM template, and 100 μg/mL T7 RNA polymerase. Reactions were incubated at 37° C. overnight. 20 units of DNase I (Promega #M6101)) were added per 1 mL of transcription volume and incubated for one hour. RNA products were purified via denaturing PAGE, ethanol precipitated, and resuspended in 1× phosphate buffered saline. To fold the sgRNAs, samples were heated to 70' C for 5 min and then cooled to room temperature. The reactions were supplemented to 1 mM final $MgCl_2$ concentration, heated to 50° C. for 5 min and then cooled to room temperature. Final RNA guide products were stored at −80° C.

TABLE 12

| Sequences for generation of guide RNA | | |
|---|---|---|
| Primer | Primer sequence | RNA product |
| T7 promoter primer | GAAATTAATACGACTCACTATA (SEQ ID NO: 491) | Used for all |
| sg2 backbone fwd | GAAATTAATACGACTCACTATA GGTACTGGCGCTTTTATCTCAT TACTTTGAGAGCCATCACCAGC GACTATGTCGTATGGGTAAAG (SEQ ID NO: 492) | GGUACUGGCGCU UUUAUCUCAUUA CUUUGAGAGCCA UCACCAGCGACU AUGUCGUAUGGG |
| sg2 backbone rev | CTTTGATGCTTCTTATTTATCG GATTTCTCTCCGATAAATAAGC GCTTTACCCATACGACATAGTC GCTGGTGATGGC (SEQ ID NO: 493) | UAAAGCGCUUAU UUAUCGGAGAGA AAUCCGAUAAAU AAGAAGCAUCAA AGGGCCGAGAUG |
| sg2.7.37 spacer primer | CGGAGCGAGACATCTCGGCCCT TTGATGCTTCTTATTTATCGGA TTTCTCTCCG (SEQ ID NO: 494) | UCUCGCUCCG (SEQ ID NO: 504) |
| sg32 backbone fwd | GAAATTAATACGACTCACTATA GGTACTGGCGCTTTTATCTCAT TACTTTGAGAGCCATCACCAGC GACTATGTCGTATGGGTAAAGC GC (SEQ ID NO: 495) | GGUACUGGCGCU UUUAUCUCAUUA CUUUGAGAGCCA UCACCAGCGACU AUGUCGUAUGGG |
| sg32 backbone rev | CTTTGATGCTTCCCTCCGAAGA GGGCGCTTTACCCATACGACAT AG (SEQ ID NO: 496) | UAAAGCGCCCUC UUCGGAGGGAAG CAUCAAAGGGCC GAGAUGUCUCG (SEQ ID |
| sg32.7.37 spacer primer | CGGAGCGAGACATCTCGGCCCT TTGATGCTTCCCTCCGAAGAG (SEQ ID NO: 497) | NO: 505) |
| sg64 backbone fwd | GAAATTAATACGACTCACTATA GGTACTGGCGCCTTTATCTCAT TACTTTGAGAGCCATCACCAGC GACTATGTCGTATGGGTAAAGC GC (SEQ ID NO: 498) | GGUACUGGCGCC UUUAUCUCAUUA CUUUGAGAGCCA UCACCAGCGACU AUGUCGUAUGGG |

TABLE 12-continued

Sequences for generation of guide RNA

| Primer | Primer sequence | RNA product |
|---|---|---|
| sg64 backbone rev | CTTTGATGCTTCTTACGGACCGAAGTCCGTAAGCGCTTTACCCATACGACATAG (SEQ ID NO: 499) | UAAAGCGCUUACGGACUUCGGUCCGUAAGAAGCAUCAAAGGGCCGAGA |
| sg64.7.37 spacer primer | CGGAGCGAGACATCTCGGCCCTTTGATGCTTCTTACGGACCGAAG(SEQ ID NO: 500) | UGUCUCGCUCCG (SEQ ID NO: 506) |
| sg174 backbone fwd | GAAATTAATACGACTCACTATAACTGGCGCTTTTATCTGATTACTTTGAGAGCCATCACCAGCGACTATGTCGTAGTGGGTAAAGCT (SEQ ID NO: 501) | ACUGGCGCUUUUAUCUgAUUACUUUGAGAGCCAUCACCAGCGACUAUGUCGUAgUGGGUA |
| sg174 backbone rev | CTTTGATGCTCCCTCCGAAGAGGGAGCTTTACCCACTACGACATAGTCGC (SEQ ID NO: 502) | AAGCUCCCUCUUCGGAGGGAGCAUCAAAGGGCCGAGAUGUCUCGCUCC |
| sg174.7.37 spacer primer | CGGAGCGAGACATCTCGGCCCTTTGATGCTCCCTCC (SEQ ID NO: 503) | G (SEQ ID NO: 507) |

Example 7: RNP Assembly

Purified wild-type and RNP of CasX and single guide RNA (sgRNA) were either prepared immediately before experiments or prepared and snap-frozen in liquid nitrogen and stored at −80° C. for later use. To prepare the RNP complexes, the CasX protein was incubated with sgRNA at 1:1.2 molar ratio. Briefly, sgRNA was added to Buffer #1 (25 mM NaPi, 150 mM NaCl, 200 mM trehalose, 1 mM MgCl2), then the CasX was added to the sgRNA solution, slowly with swirling, and incubated at 37° C. for 10 min to form RNP complexes. RNP complexes were filtered before use through a 0.22 m Costar 8160 filters that were pre-wet with 200 μl Buffer #1. If needed, the RNP sample was concentrated with a 0.5 ml Ultra 100-Kd cutoff filter, (Millipore part #UFC510096), until the desired volume was obtained. Formation of competent RNP was assessed as described in Example 14.

Example 8: Assessing Binding Affinity to the Guide RNA

Purified wild-type and improved CasX will be incubated with synthetic single-guide RNA containing a 3' Cy7.5 moiety in low-salt buffer containing magnesium chloride as well as heparin to prevent non-specific binding and aggregation. The sgRNA will be maintained at a concentration of 10 pM, while the protein will be titrated from 1 pM to 100 pM in separate binding reactions. After allowing the reaction to come to equilibrium, the samples will be run through a vacuum manifold filter-binding assay with a nitrocellulose membrane and a positively charged nylon membrane, which bind protein and nucleic acid, respectively. The membranes will be imaged to identify guide RNA, and the fraction of bound vs unbound RNA will be determined by the amount of fluorescence on the nitrocellulose vs nylon membrane for each protein concentration to calculate the dissociation constant of the protein-sgRNA complex. The experiment will also be carried out with improved variants of the sgRNA to determine if these mutations also affect the affinity of the guide for the wild-type and mutant proteins. We will also perform electromobility shift assays to qualitatively compare to the filter-binding assay and confirm that soluble binding, rather than aggregation, is the primary contributor to protein-RNA association.

Example 9: Assessing Binding Affinity to the Target DNA

Purified wild-type and improved CasX will be complexed with single-guide RNA bearing a targeting sequence complementary to the target nucleic acid. The RNP complex will be incubated with double-stranded target DNA containing a PAM and the appropriate target nucleic acid sequence with a 5' Cy7.5 label on the target strand in low-salt buffer containing magnesium chloride as well as heparin to prevent non-specific binding and aggregation. The target DNA will be maintained at a concentration of 1 nM, while the RNP will be titrated from 1 pM to 100 pM in separate binding reactions. After allowing the reaction to come to equilibrium, the samples will be run on a native 5% polyacrylamide gel to separate bound and unbound target DNA. The gel will be imaged to identify mobility shifts of the target DNA, and the fraction of bound vs unbound DNA will be calculated for each protein concentration to determine the dissociation constant of the RNP-target DNA ternary complex.

Example 10: Editing of Gene Targets PCSK9, PMP22, TRAC, SOD1, B2M and HTT

The purpose of this study was to evaluate the ability of the CasX variant 119 and gNA variant 174 to edit nucleic acid sequences in six gene targets.

Materials and Methods

Spacers for all targets except B2M and SOD1 were designed in an unbiased manner based on PAM requirements (TTC or CTC) to target a desired locus of interest. Spacers targeting B2M and SOD1 had been previously identified within targeted exons via lentiviral spacer screens carried out for these genes. Designed spacers for the other targets were ordered from Integrated DNA Technologies (IDT) as single-stranded DNA (ssDNA) oligo pairs. ssDNA spacer pairs were annealed together and cloned via Golden Gate cloning into a base mammalian-expression plasmid construct that contains the following components: codon optimized Cas X 119 protein+NLS under an EF1A promoter, guide scaffold 174 under a U6 promoter, carbenicillin and puromycin resistance genes. Assembled products were transformed into chemically-competent *E. coli*, plated on Lb-Agar plates (LB: Teknova Cat #L9315, Agar: Quartzy Cat #214510) containing carbenicillin and incubated at 37° C. Individual colonies were picked and miniprepped using Qiagen Qiaprep spin Miniprep Kit (Qiagen Cat #27104) following the manufacturer's protocol. The resulting plasmids were sequenced through the guide scaffold region via Sanger sequencing (Quintara Biosciences) to ensure correct ligation.

HEK 293T cells were grown in Dulbecco's Modified Eagle Medium (DMEM; Corning Cellgro, #10-013-CV) supplemented with 10% fetal bovine serum (FBS; Seradigm, #1500-500), 100 Units/ml penicillin and 100 mg/ml streptomycin (100×-Pen-Strep; GIBCO #15140-122), sodium pyruvate (100×, Thermofisher #11360070), non-essential amino acids (100× Thermofisher #11140050), HEPES buffer (100× Thermofisher #15630080), and 2-mercaptoethanol (1000× Thermofisher #21985023). Cells were passed every 3-5 days using TryplE and maintained in an incubator at 37° C. and 5% CO2.

On day 0, HEK293T cells were seeded in 96-well, flat-bottom plates at 30 k cells/well. On day 1, cells were transfected with 100 ng plasmid DNA using Lipofectamine 3000 according to the manufacturer's protocol. On day 2, cells were switched to FB medium containing puromycin. On day 3, this media was replaced with fresh FB medium containing puromycin. The protocol after this point diverged depending on the gene of interest. Day 4 for PCSK9, PMP22, and TRAC: cells were verified to have completed selection and switched to FB medium without puromycin. Day 4 for B2M, SOD1, and HTT: cells were verified to have completed selection and passed 1:3 using TryplE into new plates containing FB medium without puromycin. Day 7 for PCSK9, PMP22, and TRAC: cells were lifted from the plate, washed in dPBS, counted, and resuspended in Quick Extract (Lucigen, QE09050) at 10,000 cells/μl. Genomic DNA was extracted according to the manufacturer's protocol and stored at −20° C. Day 7 for B2M, SOD1, and HTT: cells were lifted from the plate, washed in dPBS, and genomic DNA was extracted with the Quick-DNA Miniprep Plus Kit (Zymo, D4068) according to the manufacturer's protocol and stored at −20° C.

NGS Analysis: Editing in cells from each experimental sample was assayed using next generation sequencing (NGS) analysis. All PCRs were carried out using the KAPA HiFi HotStart ReadyMix PCR Kit (KR0370). The template for genomic DNA sample PCR was 5 μl of genomic DNA in QE at 10 k cells/μL for PCSK9, PMP22, and TRAC. The template for genomic DNA sample PCR was 400 ng of genomic DNA in water for B2M, SOD1, and HTT. Primers were designed specific to the target genomic location of interest to form a target amplicon. These primers contain additional sequence at the 5' ends to introduce Illumina read and 2 sequences. Further, they contain a 7 nt randomer sequence that functions as a unique molecular identifier (UMI). Quality and quantification of the amplicon was assessed using a Fragment Analyzer DNA analyzer kit (Agilent, dsDNA 35-1500 bp). Amplicons were sequenced on the Illumina Miseq according to the manufacturer's instructions. Resultant sequencing reads were aligned to a reference sequence and analyzed for indels. Samples with editing that did not align to the estimated cut location or with unexpected alleles in the spacer region were discarded.

Results

Figure 9:
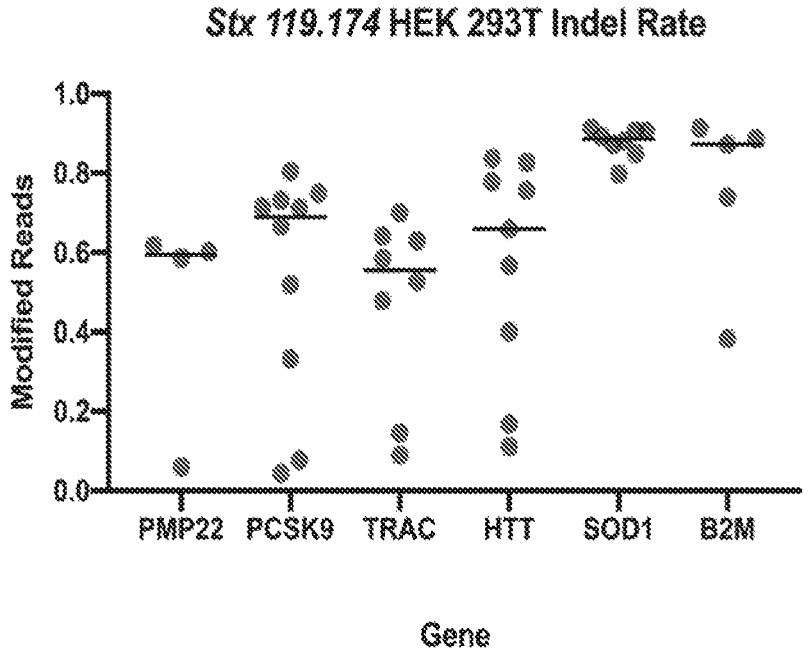
FIG. 9 shows the results of an editing assay of 6 target genes in HEK293T cells, as described in Example 10. Each dot represents results using an individual spacer.
Figure 10:
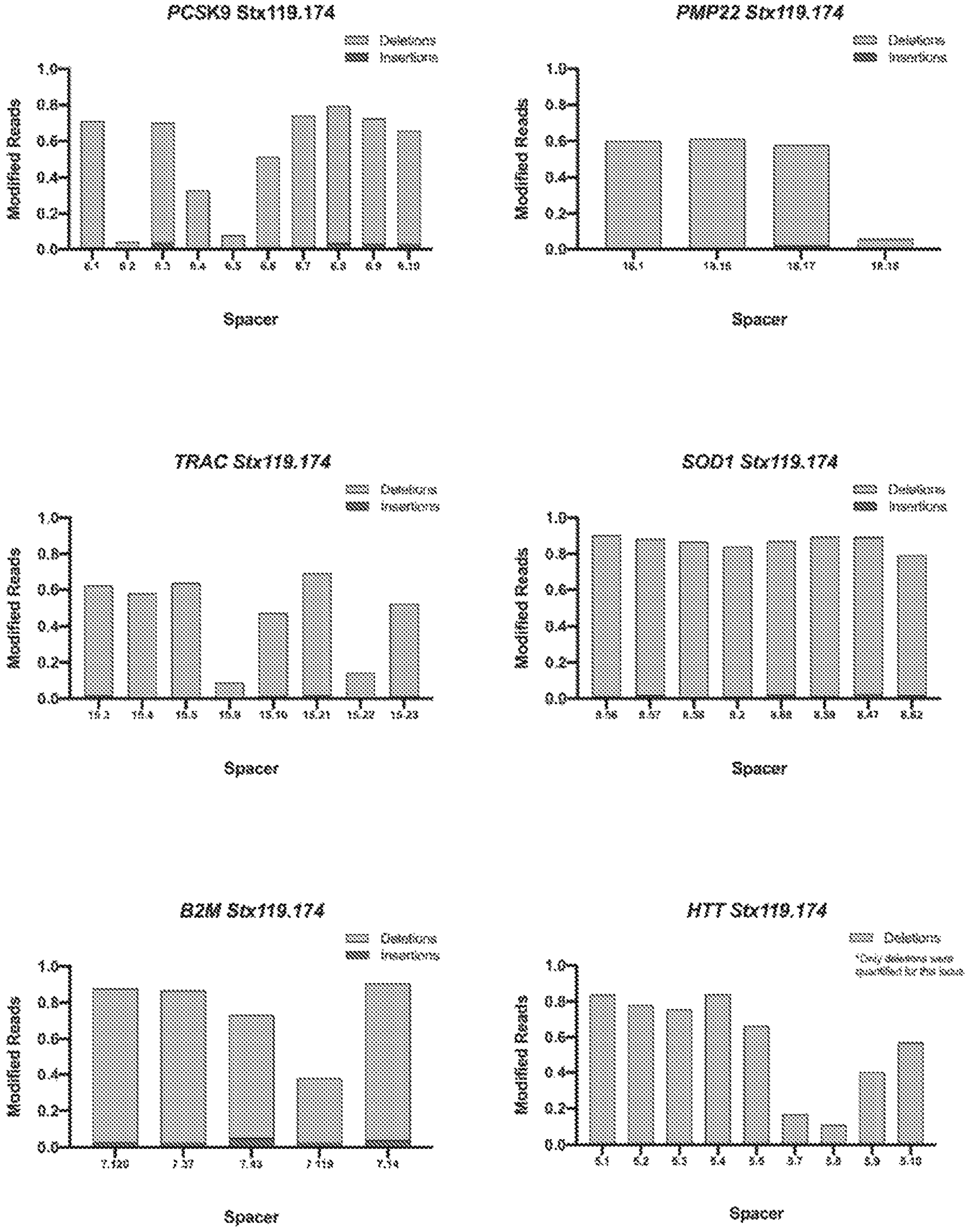
FIG. 10 shows the results of an editing assay of 6 target genes in HEK293T cells, with individual bars representing the results obtained with individual spacers, as described in Example 10.
Figure 11:
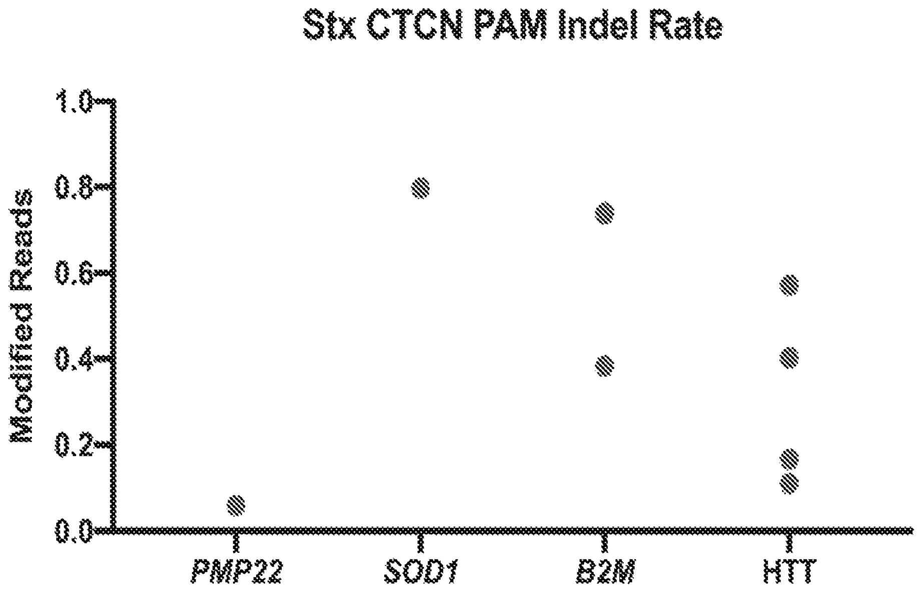
FIG. 11 shows the results of an editing assay of 4 target genes in HEK293T cells, as described in Example 10. Each dot represents results using an individual spacer utilizing a CTC PAM.

In order to validate the editing effected by the CasX:gNA 119.174 at a variety of genetic loci, a clonal plasmid transfection experiment was performed in HEK 293T cells. Multiple spacers (Table 13, listing the encoding DNA and the RNA sequences of the actual gNA spacers) were designed and cloned into an expression plasmid encoding the CasX 119 nuclease and guide 174 scaffold. HEK 293T cells were transfected with plasmid DNA, selected with puromycin, and harvested for genomic DNA six days post-transfection. Genomic DNA was analyzed via next generation sequencing (NGS) and aligned to a reference DNA sequence for analysis of insertions or deletions (indels). CasX:gNA 119.174 was able to efficiently generate indels across the 6 target genes, as shown in FIGS. 9 and 10. Indel rates varied between spacers, but median editing rates were consistently at 60% or higher, and in some cases, indel rates as high as 91% were observed. Additionally, spacers with non-canonical CTC PAMs were demonstrated to be able to generate indels with all tested target genes (FIG. 11).

The results demonstrate that the CasX variant 119 and gNA variant 174 can consistently and efficiently generate indels at a wide variety of genetic loci in human cells. The unbiased selection of many of the spacers used in the assays shows the overall effectiveness of the 119.174 RNP molecules to edit genetic loci, while the ability to target to spacers with both a TTC and a CTC PAM demonstrates its increased versatility compared to reference CasX that edit only with the TTC PAM.

TABLE 13

Spacer sequences targeting each genetic locus.

| Gene | Spacer | PAM | Spacer DNA Sequence | Spacer RNA Sequence |
|---|---|---|---|---|
| PCSK9 | 6.1 | TTC | GAGGAGGACGGCCTG GCCGA (SEQ ID NO: 508) | GAGGAGGACGGCCUGG CCGA (SEQ ID NO: 552) |
| PCSK9 | 6.2 | TTC | ACCGCTGCGCCAAGGT GCGG (SEQ ID NO: 509) | ACCGCUGCGCCAAGGU GCGG (SEQ ID NO: 553) |
| PCSK9 | 6.4 | TTC | GCCAGGCCGTCCTCCT CGGA (SEQ ID NO: 510) | GCCAGGCCGUCCUCCU CGGA (SEQ ID NO: 554) |
| PCSK9 | 6.5 | TTC | GTGCTCGGGTGCTTCG GCCA (SEQ ID NO: 511) | GUGCUCGGGUGCUUCG GCCA (SEQ ID NO: 555) |
| PCSK9 | 6.3 | TTC | ATGGCCTTCTTCCTGG CTTC (SEQ ID NO: 512) | AUGGCCUUCUUCCUGG CUUC (SEQ ID NO: 556) |
| PCSK9 | 6.6 | TTC | GCACCACCACGTAGGT GCCA (SEQ ID NO: 513) | GCACCACCACGUAGGU GCCA (SEQ ID NO: 557) |
| PCSK9 | 6.7 | TTC | TCCTGGCTTCCTGGTG AAGA (SEQ ID NO: 514) | UCCUGGCUUCCUGGUG AAGA (SEQ ID NO: 558) |
| PCSK9 | 6.8 | TTC | TGGCTTCCTGGTGAAG ATGA (SEQ ID NO: 515) | UGGCUUCCUGGUGAAG AUGA (SEQ ID NO: 559) |
| PCSK9 | 6.9 | TTC | CCAGGAAGCCAGGAA GAAGG (SEQ ID NO: 516) | CCAGGAAGCCAGGAAG AAGG (SEQ ID NO: 560) |
| PCSK9 | 6.10 | TTC | TCCTTGCATGGGGCCA GGAT (SEQ ID NO: 517) | UCCUUGCAUGGGGCCA GGAU (SEQ ID NO: 561) |
| PMP22 | 18.16 | TTC | GGCGGCAAGTTCTGCT CAGC (SEQ ID NO: 518) | GGCGGCAAGUUCUGCU CAGC (SEQ ID NO: 562) |
| PMP22 | 18.17 | TTC | TCTCCACGATCGTCAG CGTG (SEQ ID NO: 519) | UCUCCACGAUCGUCAG CGUG (SEQ ID NO: 563) |
| PMP22 | 18.18 | CTC | ACGATCGTCAGCGTGA GTGC (SEQ ID NO: 520) | ACGAUCGUCAGCGUGA GUGC (SEQ ID NO: 564) |
| PMP22 | 18.1 | TTC | CTCTAGCAATGGATCG TGGG (SEQ ID NO: 521) | CUCUAGCAAUGGAUCG UGGG (SEQ ID NO: 565) |
| TRAC | 15.3 | TTC | CAAACAAATGTGTCAC AAAG (SEQ ID NO: 522) | CAAACAAAUGUGUCAC AAAG (SEQ ID NO: 566) |

TABLE 13-continued

Spacer sequences targeting each genetic locus.

| Gene | Spacer | PAM | Spacer DNA Sequence | Spacer RNA Sequence |
|---|---|---|---|---|
| TRAC | 15.4 | TTC | GATGTGTATATCACAGACAA (SEQ ID NO: 523) | GAUGUGUAUAUCACAGACAA (SEQ ID NO: 567) |
| TRAC | 15.5 | TTC | GGAATAATGCTGTTGTTGAA (SEQ ID NO: 524) | GGAAUAAUGCUGUUGUUGAA (SEQ ID NO: 568) |
| TRAC | 15.9 | TTC | AAATCCAGTGACAAGTCTGT (SEQ ID NO: 525) | AAAUCCAGUGACAAGUCUGU (SEQ ID NO: 569) |
| TRAC | 15.10 | TTC | AGGCCACAGCACTGTTGCTC (SEQ ID NO: 526) | AGGCCACAGCACUGUUGCUC (SEQ ID NO: 570) |
| TRAC | 15.21 | TTC | AGAAGACACCTTCTTCCCCA (SEQ ID NO: 527) | AGAAGACACCUUCUUCCCCA (SEQ ID NO: 571) |
| TRAC | 15.22 | TTC | TCCCCAGCCCAGGTAAGGGC (SEQ ID NO: 528) | UCCCCAGCCCAGGUAAGGGC (SEQ ID NO: 572) |
| TRAC | 15.23 | TTC | CCAGCCCAGGTAAGGGCAGC (SEQ ID NO: 529) | CCAGCCCAGGUAAGGGCAGC (SEQ ID NO: 573) |
| HTT | 5.1 | TTC | AGTCCCTCAAGTCCTTCCAG (SEQ ID NO: 530) | AGUCCCUCAAGUCCUUCCAG (SEQ ID NO: 574) |
| HTT | 5.2 | TTC | AGCAGCAGCAGCAGCAGCAG (SEQ ID NO: 531) | AGCAGCAGCAGCAGCAGCAG (SEQ ID NO: 575) |
| HTT | 5.3 | TTC | TCAGCCGCCGCCGCAGGCAC (SEQ ID NO: 532) | UCAGCCGCCGCCGCAGGCAC (SEQ ID NO: 576) |
| HTT | 5.4 | TTC | AGGGTCGCCATGGCGGTCTC (SEQ ID NO: 533) | AGGGUCGCCAUGGCGGUCUC (SEQ ID NO: 577) |
| HTT | 5.5 | TTC | TCAGCTTTTCCAGGGTCGCC (SEQ ID NO: 534) | UCAGCUUUUCCAGGGUCGCC (SEQ ID NO: 578) |
| HTT | 5.7 | CTC | GCCGCAGCCGCCCCCGCCGC (SEQ ID NO: 535) | GCCGCAGCCGCCCCCGCCGC (SEQ ID NO: 579) |
| HTT | 5.8 | CTC | GCCACAGCCGGGCCGGGTGG (SEQ ID NO: 536) | GCCACAGCCGGGCCGGGUGG (SEQ ID NO: 580) |
| HTT | 5.9 | CTC | TCAGCCACAGCCGGGCCGGG (SEQ ID NO: 537) | UCAGCCACAGCCGGGCCGGG (SEQ ID NO: 581) |
| HTT | 5.10 | CTC | CGGTCGGTGCAGCGGCTCCT (SEQ ID NO: 538) | CGGUCGGUGCAGCGGCUCCU (SEQ ID NO: 582) |
| SOD1 | 8.56 | TTC | CCACACCTTCACTGGTCCAT (SEQ ID NO: 539) | CCACACCUUCACUGGUCCAU (SEQ ID NO: 583) |
| SOD1 | 8.57 | TTC | TAAAGGAAAGTAATGGACCA (SEQ ID NO: 540) | UAAAGGAAAGUAAUGGACCA (SEQ ID NO: 584) |
| SOD1 | 8.58 | TTC | CTGGTCCATTACTTTCCTTT (SEQ ID NO: 541) | CUGGUCCAUUACUUUCCUUU (SEQ ID NO: 585) |
| SOD1 | 8.2 | TTC | ATGTTCATGAGTTTGGAGAT (SEQ ID NO: 542) | AUGUUCAUGAGUUUGGAGAU (SEQ ID NO: 586) |
| SOD1 | 8.68 | TTC | TGAGTTTGGAGATAATACAG (SEQ ID NO: 543) | UGAGUUUGGAGAUAAUACAG (SEQ ID NO: 587) |
| SOD1 | 8.59 | TTC | ATAGACACATCGGCCACACC (SEQ ID NO: 544) | AUAGACACAUCGGCCACACC (SEQ ID NO: 588) |
| SOD1 | 8.47 | TTC | TTATTAGGCATGTTGGAGAC (SEQ ID NO: 545) | UUAUUAGGCAUGUUGGAGAC (SEQ ID NO: 589) |
| SOD1 | 8.62 | CTC | CAGGAGACCATTGCATCATT (SEQ ID NO: 546) | CAGGAGACCAUUGCAUCAUU (SEQ ID NO: 590) |
| B2M | 7.120 | TTC | GGCCTGGAGGCTATCCAGCG (SEQ ID NO: 547) | GGCCUGGAGGCUAUCCAGCG (SEQ ID NO: 591) |
| B2M | 7.37 | TTC | GGCCGAGATGTCTCGCTCCG (SEQ ID NO: 548) | GGCCGAGAUGUCUCGCUCCG (SEQ ID NO: 592) |
| B2M | 7.43 | CTC | AGGCCAGAAAGAGAGAGTAG (SEQ ID NO: 549) | AGGCCAGAAAGAGAGAGUAG (SEQ ID NO: 593) |
| B2M | 7.119 | CTC | CGCTGGATAGCCTCCAGGCC (SEQ ID NO: 550) | CGCUGGAUAGCCUCCAGGCC (SEQ ID NO: 594) |
| B2M | 7.14 | TTC | TGAAGCTGACAGCATTCGGG (SEQ ID NO: 551) | UGAAGCUGACAGCAUUCGGG (SEQ ID NO: 595) |

Example 11: Assessing Differential PAM Recognition In Vitro

Purified wild-type and engineered CasX variants will be complexed with single-guide RNA bearing a fixed targeting sequence. The RNP complexes will be added to buffer containing MgCl2 at a final concentration of 100 nM and incubated with 5' Cy7.5-labeled double-stranded target DNA at a concentration of 10 nM. Separate reactions will be carried out with different DNA substrates containing different PANMs adjacent to the target nucleic acid sequence. Aliquots of the reactions will be taken at fixed time points and quenched by the addition of an equal volume of 50 mM EDTA and 9500 formamide. The samples will be run on a denaturing polyacrylamide gel to separate cleaved and uncleaved DNA substrates. The results will be visualized and the rate of cleavage of the non-canonical PAMs by the CasX variants will be determined.

Example 12: Assessing Nuclease Activity for Double-Strand Cleavage

Purified wild-type and engineered CasX variants will be complexed with single-guide RNA bearing a fixed PM22 targeting sequence. The RNP complexes will be added to buffer containing $MgCl_2$ at a final concentration of 100 nM and incubated with double-stranded target DNA with a 5' Cy7.5 label on either the target or non-target strand at a concentration of 10 nM. Aliquots of the reactions will be taken at fixed time points and quenched by the addition of an equal volume of 50 mM EDTA and 95% formamide. The samples will be run on a denaturing polyacrylamide gel to separate cleaved and uncleaved DNA substrates. The results will be visualized and the cleavage rates of the target and non-target strands by the wild-type and engineered variants will be determined. To more clearly differentiate between changes to target binding vs the rate of catalysis of the nucleolytic reaction itself, the protein concentration will be titrated over a range from 10 nM to 1 uM and cleavage rates will be determined at each concentration to generate a pseudo-Michaelis-Menten fit and determine the kcat* and KM*. Changes to KM* are indicative of altered binding, while changes to kcat* are indicative of altered catalysis.

Example 13: Assessing Target Strand Loading for Cleavage

Purified wild-type and engineered CasX 119 will be complexed with single-guide RNA bearing a fixed PM22 targeting sequence. The RNP complexes will be added to buffer containing MgCl2 at a final concentration of 100 nM and incubated with double-stranded target DNA with a 5' Cy7.5 label on the target strand and a 5' Cy5 label on the non-target strand at a concentration of 10 nM. Aliquots of the reactions will be taken at fixed time points and quenched by the addition of an equal volume of 50 mM EDTA and 95% formamide. The samples will be run on a denaturing polyacrylamide gel to separate cleaved and uncleaved DNA substrates. The results will be visualized and the cleavage rates of both strands by the variants will be determined. Changes to the rate of target strand cleavage but not non-target strand cleavage would be indicative of improvements to the loading of the target strand in the active site for cleavage. This activity could be further isolated by repeating the assay with a dsDNA substrate that has a gap on the non-target strand, mimicking a pre-cleaved substrate. Improved cleavage of the non-target strand in this context would give further evidence that the loading and cleavage of the target strand, rather Example 14: CasX:gNA In Vitro Cleavage Assays 1. Determining Cleavage-Competent Fractions for Protein Variants Compared to Wild-Type Reference CasX The ability of CasX variants to form active RNP compared to reference CasX was determined using an in vitro cleavage assay. The beta-2 microglobulin (B2M) 7.37 target for the cleavage assay was created as follows. DNA oligos with the sequence TGAAGCTGACAGCATTCGGGCCGAGATGTCTCGCTCCGTGGCCTTAGCTGTGCTC GCGCT (non-target strand, NTS (SEQ ID NO: 596)) and TGAAGCTGACAGCATTCGGGCCGAGATGTCTCGCTCCGTGGCCTTAGCTGTGCTC GCGCT (target strand, TS (SEQ ID NO: 597)) were purchased with 5' fluorescent labels (LI-COR IRDye 700 and 800, respectively). dsDNA targets were formed by mixing the oligos in a 1:1 ratio in 1× cleavage buffer (20 mM Tris HCl pH 7.5, 150 mM NaCl, 1 mM TCEP, 5% glycerol, 10 mM $MgCl_2$), heating to 95° C. for 10 minutes, and allowing the solution to cool to room temperature.

CasX RNPs were reconstituted with the indicated CasX and guides (see graphs) at a final concentration of 1 μM with 1.5-fold excess of the indicated guide unless otherwise specified in 1× cleavage buffer (20 mM Tris HCl pH 7.5, 150 mM NaCl, 1 mM TCEP, 5% glycerol, 10 mM $MgCl_2$) at 37° C. for 10 min before being moved to ice until ready to use. The 7.37 target was used, along with sgRNAs having spacers complementary to the 7.37 target.

Figure 12:
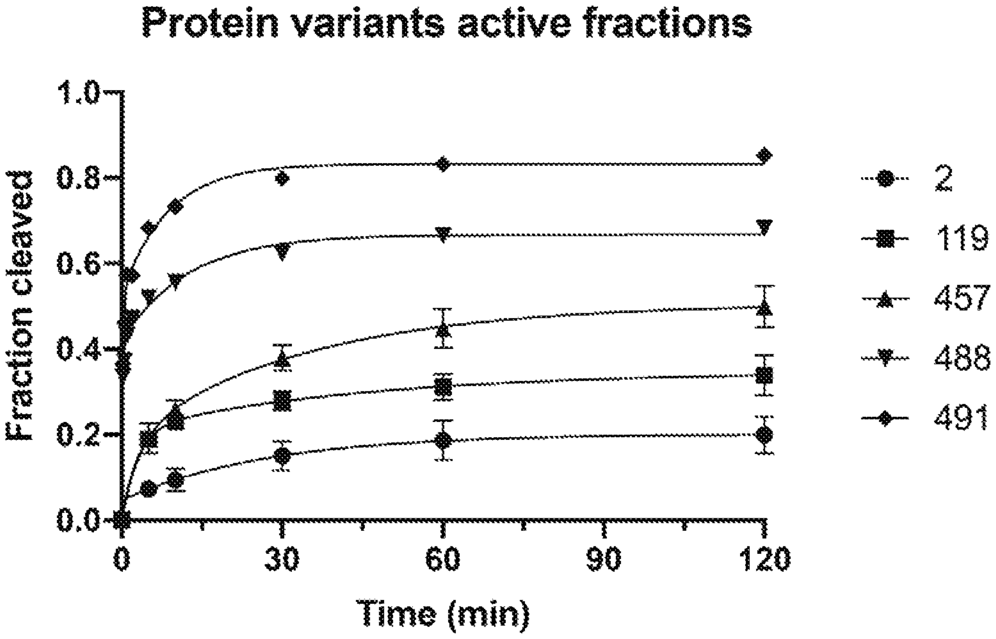
FIG. 12 is a graph of the results of an assay for the quantification of active fractions of RNP formed by sgRNA174 and the CasX variants, as described in Example 14. Equimolar amounts of RNP and target were co-incubated and the amount of cleaved target was determined at the indicated timepoints. Mean and standard deviation of three independent replicates are shown for each timepoint. The biphasic fit of the combined replicates is shown. "2" refers to the reference CasX protein of SEQ ID NO:2.

Cleavage reactions were prepared with final RNP concentrations of 100 nM and a final target concentration of 100 nM. Reactions were carried out at 37° C. and initiated by the addition of the 7.37 target DNA. Aliquots were taken at 5, 10, 30, 60, and 120 minutes and quenched by adding to 95% formamide, 20 mM EDTA. Samples were denatured by heating at 95° C. for 10 minutes and run on a 10% urea-PAGE gel. The gels were either imaged with a LI-COR Odyssey CLx and quantified using the LI-COR Image Studio software or imaged with a Cytiva Typhoon and quantified using the Cytiva IQTL software. The resulting data were plotted and analyzed using Prism. We assumed that CasX acts essentially as a single-turnover enzyme under the assayed conditions, as indicated by the observation that sub-stoichiometric amounts of enzyme fail to cleave a greater-than-stoichiometric amount of target even under extended time-scales and instead approach a plateau that scales with the amount of enzyme present. Thus, the fraction of target cleaved over long time-scales by an equimolar amount of RNP is indicative of what fraction of the RNP is properly formed and active for cleavage. The cleavage traces were fit with a biphasic rate model, as the cleavage reaction clearly deviates from monophasic under this concentration regime, and the plateau was determined for each of three independent replicates. The mean and standard deviation were calculated to determine the active fraction (Table 14). The graphs are shown in FIG. 12.

Apparent active (competent) fractions were determined for RNPs formed for CasX2+guide 174+7.37 spacer, CasX119+guide 174+7.37 spacer, CasX457+guide 174+7.37 spacer, CasX488+guide 174+7.37 spacer, and CasX491+guide 174+7.37 spacer. The determined active fractions are shown in Table 14. All CasX variants had higher active fractions than the wild-type CasX2, indicating that the engineered CasX variants form significantly more active and stable RNP with the identical guide under tested conditions compared to wild-type CasX. This may be due to an increased affinity for the sgRNA, increased stability or solubility in the presence of sgRNA, or greater stability of a cleavage-competent conformation of the engineered CasX:sgRNA complex. An increase in solubility of the RNP was indicated by a notable decrease in the observed precipitate formed when CasX457, CasX488, or CasX491 was added to the sgRNA compared to CasX2.

Figure 13:
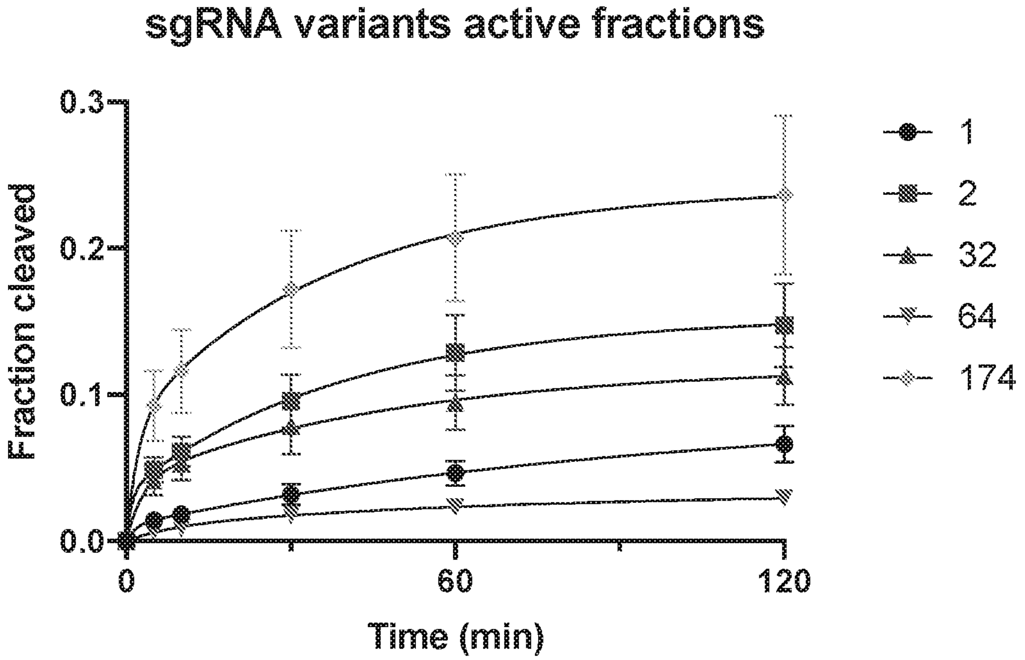
FIG. 13 shows the quantification of active fractions of RNP formed by CasX2 and the modified sgRNAs, as described in Example 14. Equimolar amounts of RNP and target were co-incubated and the amount of cleaved target was determined at the indicated timepoints. Mean and standard deviation of three independent replicates are shown for each timepoint. The biphasic fit of the combined replicates is shown.

2. In Vitro Cleavage Assays—Determining $k_{cleave}$ for CasX Variants Compared to Wild-Type Reference CasX Cleavage-competent fractions were also determined using the same protocol for CasX2.2.7.37, CasX2.32.7.37, CasX2.64.7.37, and CasX2.174.7.37 to be 16±3%, 13±3%, 5±2%, and 22±5%, as shown in FIG. 13 and Table 14.

Figure 14:
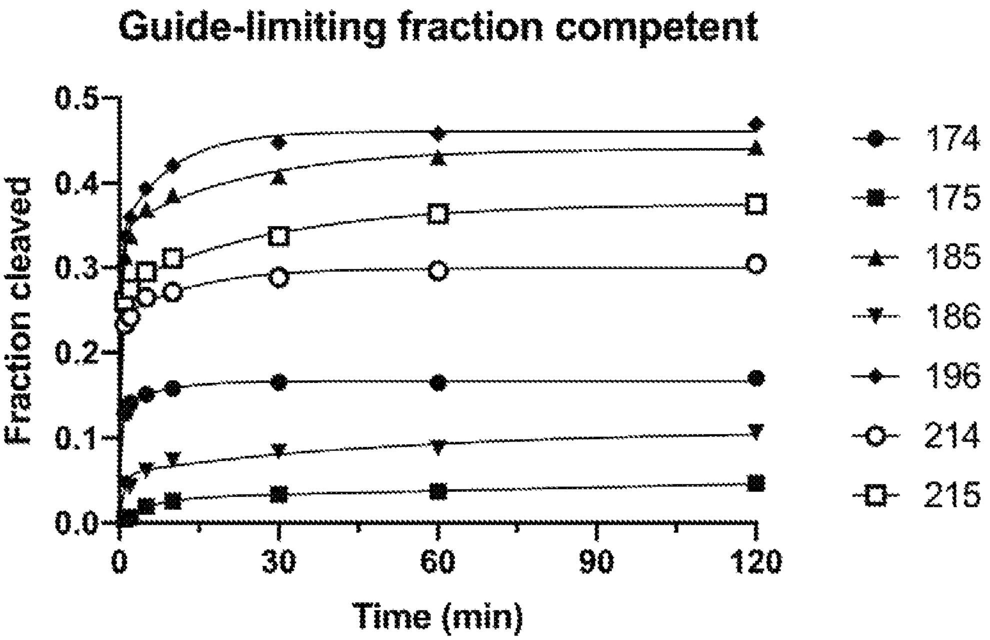
FIG. 14 shows the quantification of active fractions of RNP formed by CasX 491 and the modified sgRNAs under guide-limiting conditions, as described in Example 14. Equimolar amounts of RNP and target were co-incubated and the amount of cleaved target was determined at the indicated timepoints. The biphasic fit of the data is shown.

A second set of guides were tested under different conditions to better isolate the contribution of the guide to RNP formation. 174, 175, 185, 186, 196, 214, and 215 guides with 7.37 spacer were mixed with CasX491 at final concentrations of 1 μM for the guide and 1.5 μM for the protein, rather than with excess guide as before. Results are shown in FIG. 14 and Table 14. Many of these guides exhibited additional improvement over 174, with 185 and 196 achieving 44% and 46% competent fractions, respectively, compared with 17% for 174 under these guide-limiting conditions.

The data indicate that both CasX variants and sgRNA variants are able to form a higher degree of active RNP with guide RNA compare to wild-type CasX and wild-type sgRNA.

The apparent cleavage rates of CasX variants 119, 457, 488, and 491 compared to wild-type reference CasX were determined using an in vitro fluorescent assay for cleavage of the target 7.37.

CasX RNPs were reconstituted with the indicated CasX (see FIG. 15) at a final concentration of 1 μM with 1.5-fold excess of the indicated guide in 1× cleavage buffer (20 mM Tris HCl pH 7.5, 150 mM NaCl, 1 mM TCEP, 5% glycerol, 10 mM $MgCl_2$) at 37° C. for 10 min before being moved to ice until ready to use. Cleavage reactions were set up with a final RNP concentration of 200 nM and a final target concentration of 10 nM. Reactions were carried out at 37° C. except where otherwise noted and initiated by the addition of the target DNA. Aliquots were taken at 0.25, 0.5, 1, 2, 5, and 10 minutes and quenched by adding to 95% formamide, 20 mM EDTA. Samples were denatured by heating at 95° C. for 10 minutes and run on a 10% urea-PAGE gel. The gels were imaged with a LI-COR Odyssey CLx and quantified using the LI-COR Image Studio software or imaged with a Cytiva Typhoon and quantified using the Cytiva IQTL software. The resulting data were plotted and analyzed using Prism, and the apparent first-order rate constant of non-target strand cleavage ($k_{cleave}$) was determined for each CasX:sgRNA combination replicate individually. The mean and standard deviation of three replicates with independent fits are presented in Table 14, and the cleavage traces are shown in FIG. 15.

Figure 15:
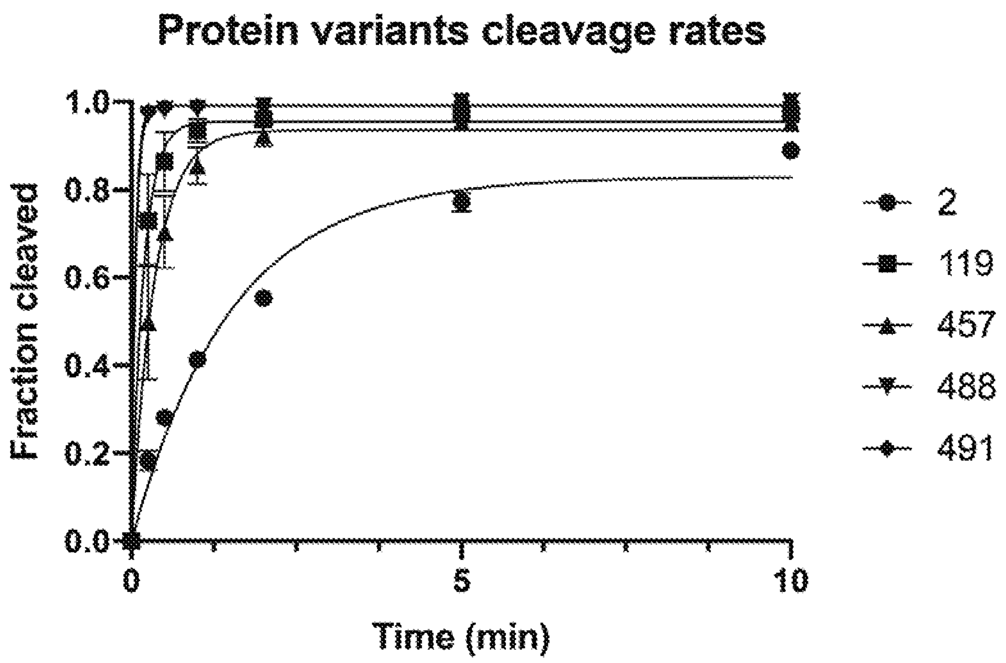
FIG. 15 shows the quantification of cleavage rates of RNP formed by sgRNA174 and the CasX variants, as described in Example 14. Target DNA was incubated with a 20-fold excess of the indicated RNP and the amount of cleaved target was determined at the indicated time points. Mean and standard deviation of three independent replicates are shown for each timepoint, except for 488 and 491 where a single replicate is shown. The monophasic fit of the combined replicates is shown.

Apparent cleavage rate constants were determined for wild-type CasX2, and CasX variants 119, 457, 488, and 491 with guide 174 and spacer 7.37 utilized in each assay (see Table 14 and FIG. 15). All CasX variants had improved cleavage rates relative to the wild-type CasX2. CasX457 cleaved more slowly than 119, despite having a higher competent fraction as determined above. CasX488 and CasX491 had the highest cleavage rates by a large margin; as the target was almost entirely cleaved in the first time-point, the true cleavage rate exceeds the resolution of this assay, and the reported $k_{cleave}$ should be taken as a lower bound.

The data indicate that the CasX variants have a higher level of activity, with $k_{cleave}$ rates reaching at least 30-fold higher compared to wild-type CasX2.

3. In Vitro Cleavage Assays: Comparison of Guide Variants to Wild-Type Guides

Cleavage assays were also performed with wild-type reference CasX2 and reference guide 2 compared to guide variants 32, 64, and 174 to determine whether the variants improved cleavage. The experiments were performed as described above. As many of the resulting RNPs did not approach full cleavage of the target in the time tested, we determined initial reaction velocities ($V_0$) rather than first-order rate constants. The first two timepoints (15 and 30 seconds) were fit with a line for each CasX:sgRNA combination and replicate. The mean and standard deviation of the slope for three replicates were determined.

Figure 16:
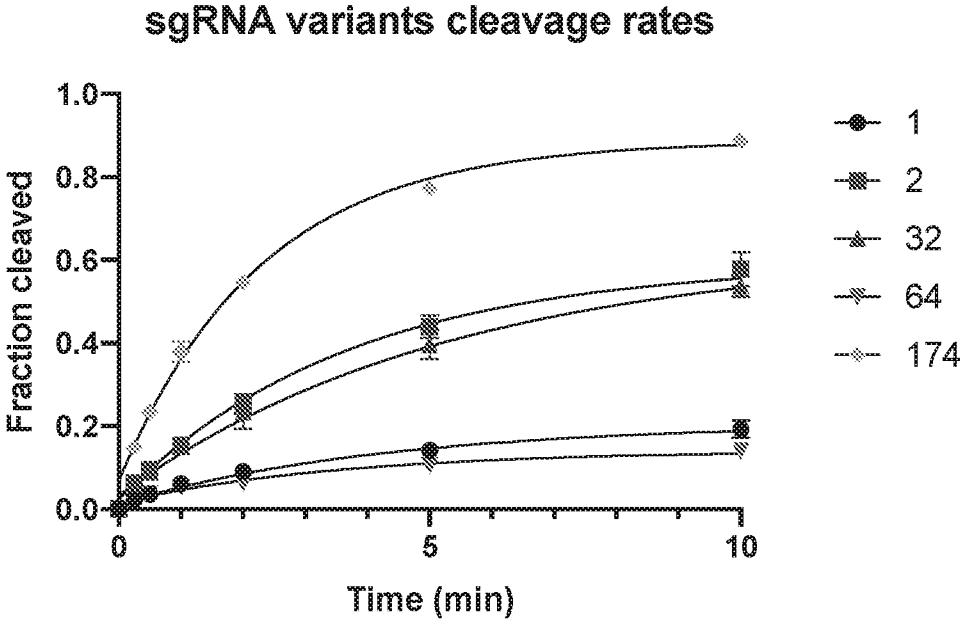
FIG. 16 shows the quantification of cleavage rates of RNP formed by CasX2 and the sgRNA variants, as described in Example 14. Target DNA was incubated with a 20-fold excess of the indicated RNP and the amount of cleaved target was determined at the indicated time points. Mean and standard deviation of three independent replicates are shown for each timepoint. The monophasic fit of the combined replicates is shown.
Figure 17:
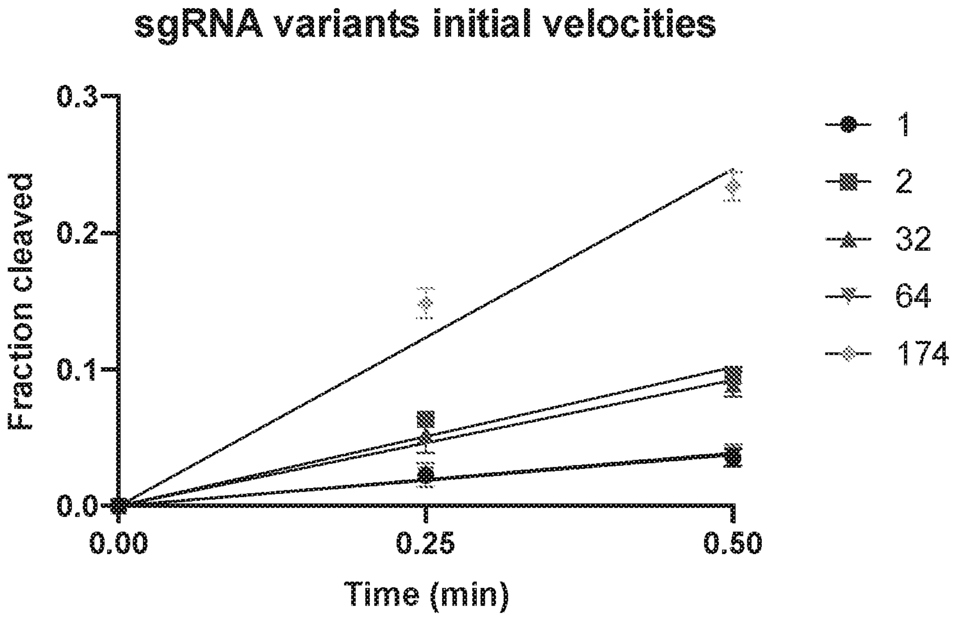
FIG. 17 shows the quantification of initial velocities of RNP formed by CasX2 and the sgRNA variants, as described in Example 14. The first two time-points of the previous cleavage experiment were fit with a linear model to determine the initial cleavage velocity.

Under the assayed conditions, the $V_0$ for CasX2 with guides 2, 32, 64, and 174 were 20.4±1.4 nM/min, 18.4±2.4 nM/min, 7.8±1.8 nM/min, and 49.3±1.4 nM/min (see Table 14 and FIG. 16 and FIG. 17). Guide 174 showed substantial improvement in the cleavage rate of the resulting RNP (~2.5-fold relative to 2, see FIG. 17), while guides 32 and 64 performed similar to or worse than guide 2. Notably, guide 64 supports a cleavage rate lower than that of guide 2 but performs much better in vivo (data not shown). Some of the sequence alterations to generate guide 64 likely improve in vivo transcription at the cost of a nucleotide involved in triplex formation. Improved expression of guide 64 likely explains its improved activity in vivo, while its reduced stability may lead to improper folding in vitro.

Figure 18:
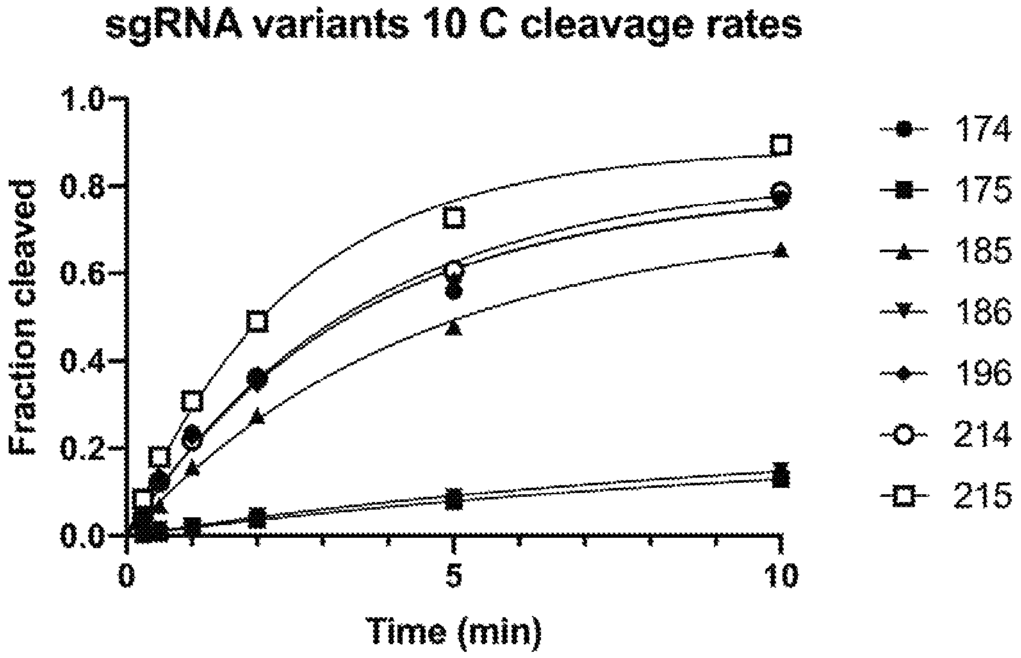
FIG. 18 shows the quantification of cleavage rates of RNP formed by CasX491 and the sgRNA variants, as described in Example 14. Target DNA was incubated with a 20-fold excess of the indicated RNP at 10° C. and the amount of cleaved target was determined at the indicated time points. The monophasic fit of the timepoints is shown.

Additional experiments were carried out with guides 174, 175, 185, 186, 196, 214, and 215 with spacer 7.37 and CasX491 to determine relative cleavage rates. To reduce cleavage kinetics to a range measurable with our assay, the cleavage reactions were incubated at 10° C. Results are in FIG. 18 and Table 14. Under these conditions, 215 was the only guide that supported a faster cleavage rate than 174. 196, which exhibited the highest active fraction of RNP under guide-limiting conditions, had kinetics essentially the same as 174, again highlighting that different variants result in improvements of distinct characteristics.

The data support that, under the conditions of the assay, use of the majority of the guide variants with CasX results in RNP with a higher level of activity than one with the wild-type guide, with improvements in initial cleavage velocity ranging from ~2-fold to >6-fold. Numbers in Table 14 indicate, from left to right, CasX variant, sgRNA scaffold, and spacer sequence of the RNP construct.

TABLE 14

Results of cleavage and RNP formation assays

| RNP Construct | $k_{cleave}$* | Initial velocity* | Competent fraction |
|---|---|---|---|
| 2.2.7.37 | | 20.4 ± 1.4 nM/min | 16 ± 3% |
| 2.32.7.37 | | 18.4 ± 2.4 nM/min | 13 ± 3% |
| 2.64.7.37 | | 7.8 ± 1.8 nM/min | 5 ± 2% |
| 2.174.7.37 | 0.51 ± 0.01 $min^{-1}$ | 49.3 ± 1.4 nM/min | 22 ± 5% |
| 119.174.7.37 | 6.29 ± 2.11 $min^{-1}$ | | 35 ± 6% |
| 457.174.7.37 | 3.01 ± 0.90 $min^{-1}$ | | 53 ± 7% |
| 488.174.7.37 | 15.19 $min^{-1}$ | | 67% |
| 491.174.7.37 | 16.59 $min^{-1}$/0.293 $min^{-1}$ (10° C) | | 83%/17% (guide-limited) |
| 491.175.7.37 | 0.089 $min^{-1}$ (10° C) | | 5% (guide-limited) |
| 491.185.7.37 | 0.227 $min^{-1}$ (10° C) | | 44% (guide-limited) |
| 491.186.7.37 | 0.099 $min^{-1}$ (10° C) | | 11% (guide-limited) |
| 491.196.7.37 | 0.292 $min^{-1}$ (10° C) | | 46% (guide-limited) |
| 491.214.7.37 | 0.284 $min^{-1}$ (10° C) | | 30% (guide-limited) |
| 491.215.7.37 | 0.398 $min^{-1}$ (10° C) | | 38% (guide-limited) |

*Mean and standard deviation

Example 15: Identification of Nicking Variants

Purified modified CasX variants will be complexed with single-guide RNA bearing a fixed targeting sequence. The RNP complexes will be added to buffer containing $MgCl_2$ at a final concentration of 100 nM and incubated with double-stranded target DNA with a 5' fluorescein label on the target strand and a 5' Cy5 label on the non-target strand at a concentration of 10 nM. Aliquots of the reactions will be taken at fixed time points and quenched by the addition of an equal volume of 50 mM EDTA and 95% formamide. The samples will be run on a denaturing polyacrylamide gel to separate cleaved and uncleaved DNA substrates. Efficient cleavage of one strand but not the other would be indicative that the variant possessed single-strand nickase activity.

Example 16: Assessing Improved Expression and Solubility Characteristics of CasX Variants for RNP Production Wild-type and modified CasX variants will be expressed in BL21 (DE3) *E. coli* under identical conditions. All proteins will be under the control of an IPTG-inducible T7 promoter. Cells will be grown to an OD of 0.6 in TB media at 37° C., at which point the growth temperature will be reduced to 16° C. and expression will be induced by the addition of 0.5 mM IPTG. Cells will be harvested following 18 hours of expression. Soluble protein fractions will be extracted and analyzed on an SDS-PAGE gel. The relative levels of soluble CasX expression will be identified by Coomassie staining. The proteins will be purified in parallel according to the protocol above, and final yields of pure protein will be compared. To determine the solubility of the purified protein, the constructs will be concentrated in storage buffer until the protein begins to precipitate. Precipitated protein will be removed by centrifugation and the final concentration of soluble protein will be measured to determine the maximum solubility for each variant. Finally, the CasX variants will be complexed with single guide RNA and concentrated until precipitation begins. Precipitated RNP will be removed by centrifugation and the final concentration of soluble RNP will be measured to determine the maximum solubility of each variant when bound to guide RNA.

Example 17: Assays Used to Measure sgNA and CasX Protein Activity

Several assays were used to carry out initial screens of CasX protein and sgNA Deep Mutational Evolution (DME) libraries and modified mutants, and to measure the activity of select protein and sgNA variants relative to CasX reference sgNAs and proteins. *E. coli* CRISPRi screen:

Briefly, biological triplicates of dead CasX DME Libraries on a chloramphenicol (CM) resistant plasmid with a GFP gNA on a carbenicillin (Carb) resistant plasmid were transformed (at >5× library size) into MG1655 with genetically integrated and constitutively expressed GFP and RFP. Cells were grown overnight in EZ-RDM+Carb, CM and Anhydrotetracycline (aTc) inducer. *E. coli* were FACS sorted based on gates for the top 1% of GFP but not RFP repression, collected, and resorted immediately to further enrich for highly functional CasX molecules. Double sorted libraries were then grown out and DNA was collected for deep sequencing on a highseq. This DNA was also re-transformed onto plates and individual clones were picked for further analysis.

*E. coli* Toxin Selection:

Briefly carbenicillin resistant plasmid containing an arabinose inducible toxin were transformed into *E. coli* cells and made electrocompetent. Biological triplicates of CasX DME Libraries with a toxin targeted gNA on a chloramphenicol resistant plasmid were transformed (at >5× library size) into said cells and grown in LB+CM and arabinose inducer. *E. coli* that cleaved the toxin plasmid survived in the induction media and were grown to mid log and plasmids with functional CasX cleavers were recovered. This selection was repeated as needed. Selected libraries were then grown out and DNA was collected for deep sequencing on a highseq. This DNA was also re-transformed onto plates and individual clones were picked for further analysis and testing.

Figure 19:
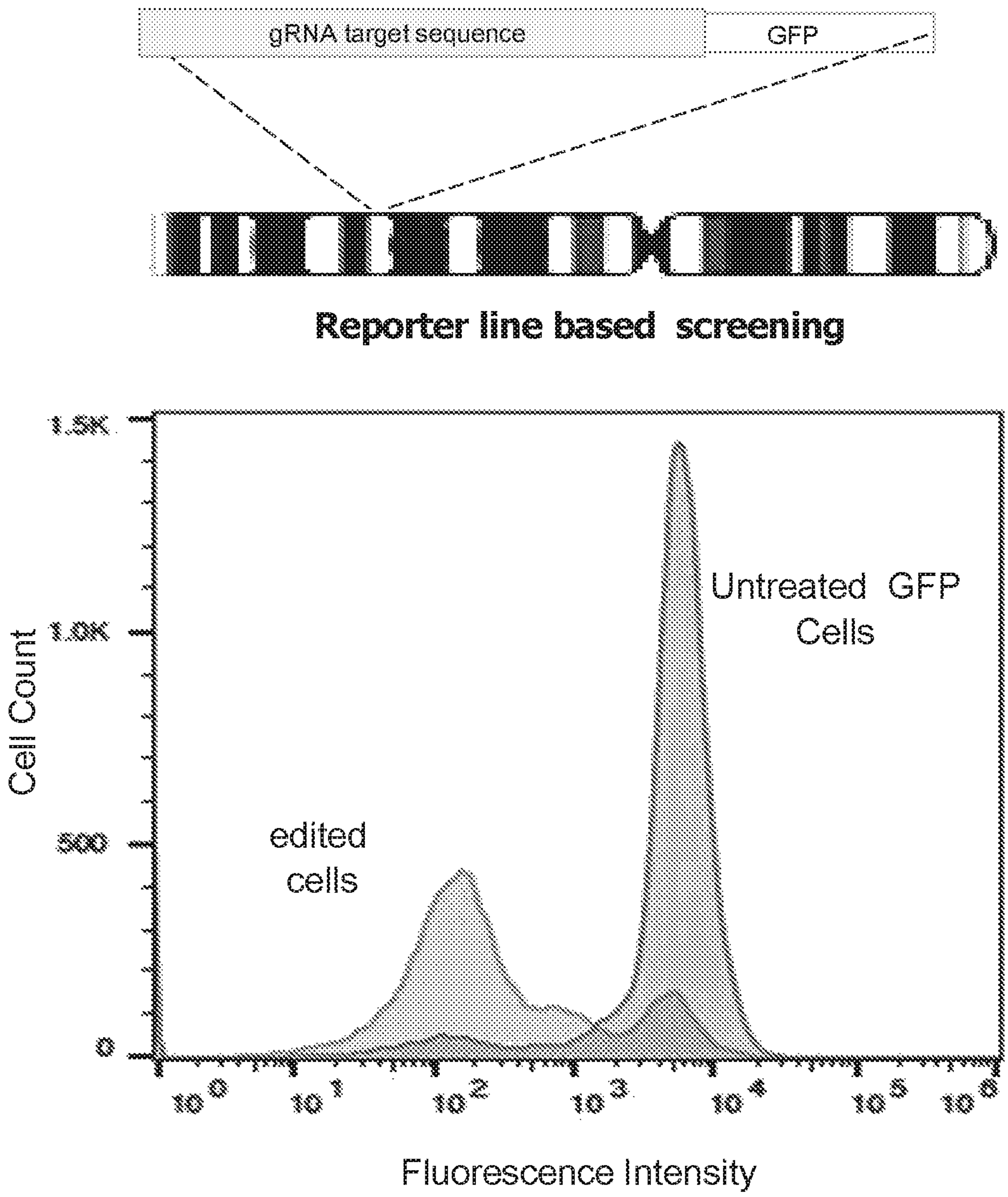
FIG. 19 is a diagram and an example fluorescence activated cell sorting (FACS) plot illustrating an exemplary method for assaying the effectiveness of a reference CasX protein or single guide RNA (sgRNA), or variants thereof, as described in Example 17. A reporter (e.g., GFP reporter) coupled to a gRNA target sequence, complementary to the gRNA spacer, is integrated into a reporter cell line. Cells are transformed or transfected with a CasX protein and/or sgRNA variant, with the spacer motif of the sgRNA complementary to and targeting the gRNA target sequence of the reporter. Ability of the CasX:sgRNA ribonucleoprotein complex to cleave the target sequence is assayed by FACS. Cells that lose reporter expression indicate occurrence of CasX: sgRNA ribonucleoprotein complex-mediated cleavage and indel formation.

Lentiviral Based Screen EGFP Screen:

Lentiviral particles were produced in HEK293 cells at a confluency of 70%-90% at time of transfection. Cells were transfected using polyethylenimine based transfection of plasmids containing a CasX DME library. Lentiviral vectors were co-transfected with the lentiviral packaging plasmid and the VSV-G envelope plasmids for particle production. Media was changed 12 hours post-transfection, and virus harvested at 36-48 hours post-transfection. Viral supernatants were filtered using 0.45 mm membrane filters, diluted in cell culture media if appropriate, and added to target cells HEK cells with an Integrated GFP reporter. Polybrene was supplemented to enhance transduction efficiency, if necessary. Transduced cells were selected for 24-48 hours post-transduction using puromycin and grown for 7-10 days. Cells were then sorted for GFP disruption & collected for highly functional CasX sgNA or protein variants (see FIG. 19). Libraries were then Amplified via PCR directly from the genome and collected for deep sequencing on a highseq. This DNA could also be re-cloned and re-transformed onto plates and individual clones were picked for further analysis.

Example 18: Assaying Editing Efficiency of an HEK EGFP Reporter

To assay the editing efficiency of CasX reference sgNAs and proteins and variants thereof, EGFP HEK293T reporter cells were seeded into 96-well plates and transfected according to the manufacturer's protocol with lipofectamine 3000 (Life Technologies) and 100-200 ng plasmid DNA encoding a reference or CasX variant protein, P2A-puromycin fusion and the reference or variant sgNA. The next day cells were selected with 1.5 μg/ml puromycin for 2 days and analyzed by fluorescence-activated cell sorting (FACS) 7 days after selection to allow for clearance of EGFP protein from the cells. EGFP disruption via editing was traced using an Attune NxT Flow Cytometer and high-throughput autosampler.

Example 19: Cleavage Efficiency of CasX Reference sgRNA

The reference CasX sgRNA of SEQ ID NO:4 (below) is described in WO 2018064371 and U.S. Ser. No. 10/570,415B2, the contents of which are incorporated herein by reference:

(SEQ ID NO: 4)

ACAUCUGGCGCGUUUAUUCCAUUACUUUGGAGCCAGUCCCAGCGACUAUG

UCGUAUGGACGAAGCGCUUAUUUAUCGGAGAGAAACCGAUAAGUAAAACG

CAUCAAAG.

It was found that alterations to the sgRNA reference sequence of SEQ ID NO:4, producing SEQ ID NO:5 (below) were able to improve CasX cleavage efficiency. The sequence is:

(SEQ ID NO: 5)
UACUGGCGCUUUUAUCUCAUUACUUUGAGAGCCAUCACCAGCGACUAUGU

CGUAUGGGUAAAGCGCUUAUUUAUCGGAGAGAAAUCCGAUAAAUAAGAAG

CAUCAAAG.

To assay the editing efficiency of CasX reference sgRNAs and variants thereof, EGFP HEK293T reporter cells were seeded into 96-well plates and transfected according to the manufacturer's protocol with lipofectamine 3000 (Life Technologies) and 100-200 ng plasmid DNA encoding a reference CasX protein, P2A-puromycin fusion and the sgRNA. The next day cells were selected with 1.5 μg/ml puromycin for 2 days and analyzed by fluorescence-activated cell sorting (FACS) 7 days after selection to allow for clearance of EGFP protein from the cells. EGFP disruption via editing was traced using an Attune NxT Flow Cytometer and high-throughput autosampler.

When testing cleavage of an EGFP reporter by CasX reference and sgNA variants, the following spacer target sequences were used:

E6 (TGTGGTCGGGGTAGCGGCTG (SEQ ID NO: 17))
and

E7 (TCAAGTCCGCCATGCCCGAA (SEQ ID NO: 18)).

Figure 20:
FIG. 20 shows results of gene editing in an EGFP disruption assay, as described in Example 19. Editing was measured by indel formation and GFP disruption in HEK293 cells carrying a GFP reporter.

An example of the increased cleavage efficiency of the sgRNA of SEQ ID NO:5 compared to the sgRNA of SEQ ID NO:4 is shown in FIG. 20. Editing efficiency of SEQ ID NO: 5 was improved 176% compared to SEQ ID NO: 4. Accordingly, SEQ ID NO: 5 was chosen as reference sgRNA for DME and additional sgNA variant design, described below.

Example 20: Design, Creation and Evaluation of gNA Variants with Improved Target Cleavage Guide nucleic acid (gNA) variants were designed and tested in order to assess improvements in cleavage activity relative to reference gNAs. These guides were discovered via DME or rational design and replacement or addition of guide parts such as the extended stem or the addition of ribozymes at the termini, as described herein.

Experimental design: All guides were tested In HEK293T or a HEK293T reporter line as follows. Mammalian cells were maintained in a 37° C. incubator, at 5% CO2. HEK293T Human kidney cells and derivatives thereof were grown in Dulbecco's Modified Eagle Medium (DMEM; Corning Cellgro, #10-013-CV) supplemented with 10% fetal bovine serum (FBS; Seradigm, #1500-500), and 100 Units/ml penicillin and 100 mg/ml streptomycin (100×-Pen-Strep; GIBCO #15140-122), and can additionally include sodium pyruvate (100×, Thermofisher #11360070), Non-essential amino acids (100× Thermofisher #11140050), HEPES buffer (100× Thermofisher #15630080), and 2-mercaptoethanol (1000× Thermofisher #21985023). Cells were seeded at 20-30 thousand cells per well into 96-well plates and transfected using 0.25-1 uL of Lipofectamine 3000 (Thermo Fisher Scientific #L3000008), 50-500 ng of a plasmid containing CasX and the reference or variant CasX guide targeting the reporter or target gene following the manufacturer's protocol. 24-72 hours later the media was changed and 0.3-3.0 ug/ml puromycin (Sigma #P8833) was added to select for transformation. 24-96 hours following selection the cells were analyzed by flow cytometry and gated for the appropriate forward and side scatter, selected for single cells and then gated for green fluorescent protein (GFP) or antibody reporter expression (Attune Nxt Flow Cytometer, Thermo Fisher Scientific) to quantify the expression levels of fluorophores. At least 10,000 events were collected for each sample. For the HEK293T-GFP genome editing reporter cell line, flow cytometry was used to quantify the percentage of GFP-negative (edited) cells and the number of cells with GFP disruption for each variant was compared to the reference guide to generate a fold change measurement.

Figure 21:
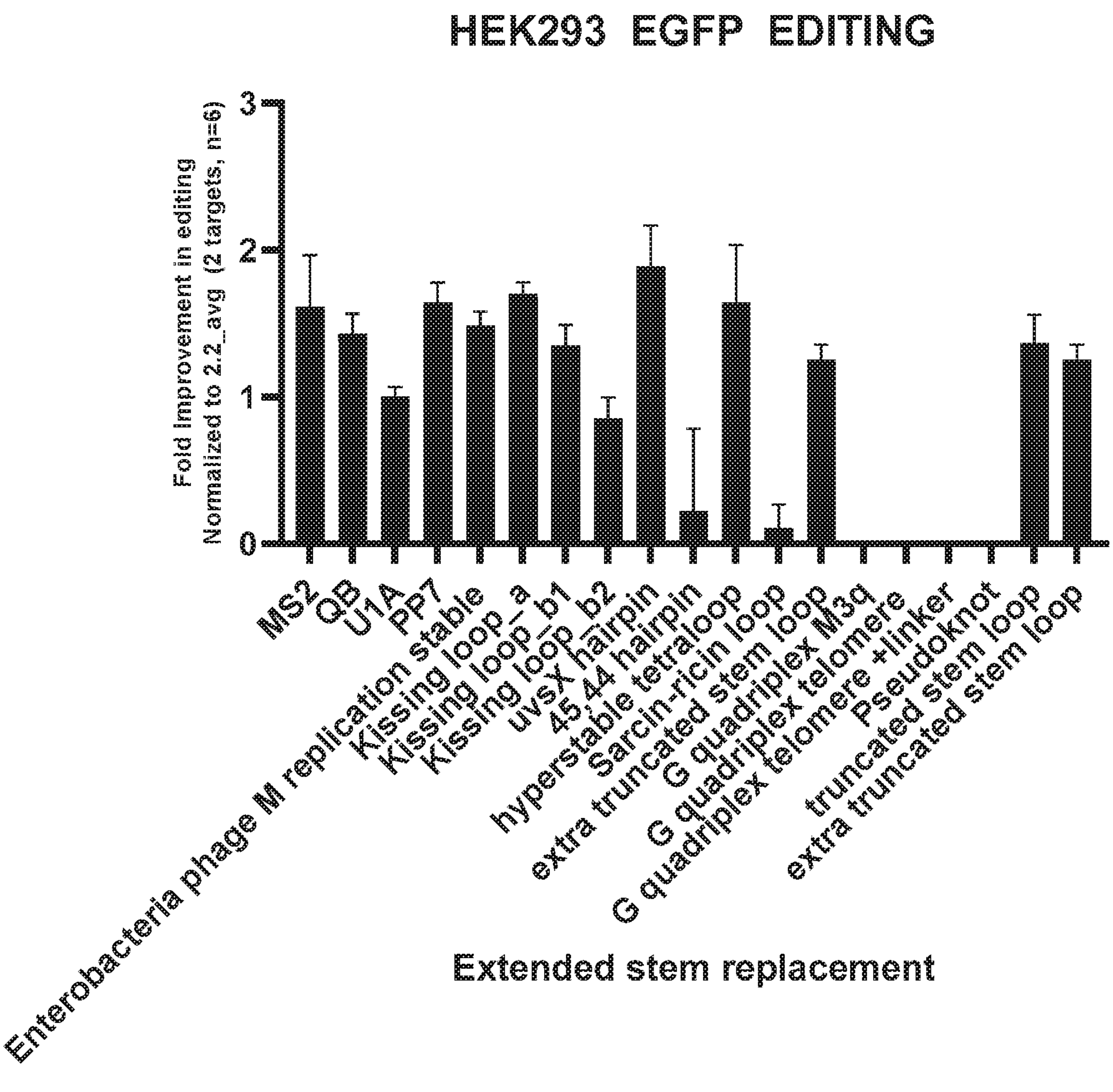
FIG. 21 shows results of gene editing in an EGFP disruption assay where further editing improvements were obtained in the sgRNA scaffold of SEQ ID NO:5 by swapping the extended stem loop sequence (indicated in the X-axis) for additional sequences to generate the scaffolds whose sequences are shown in Table 2, as described in Example 20.
Figure 22:
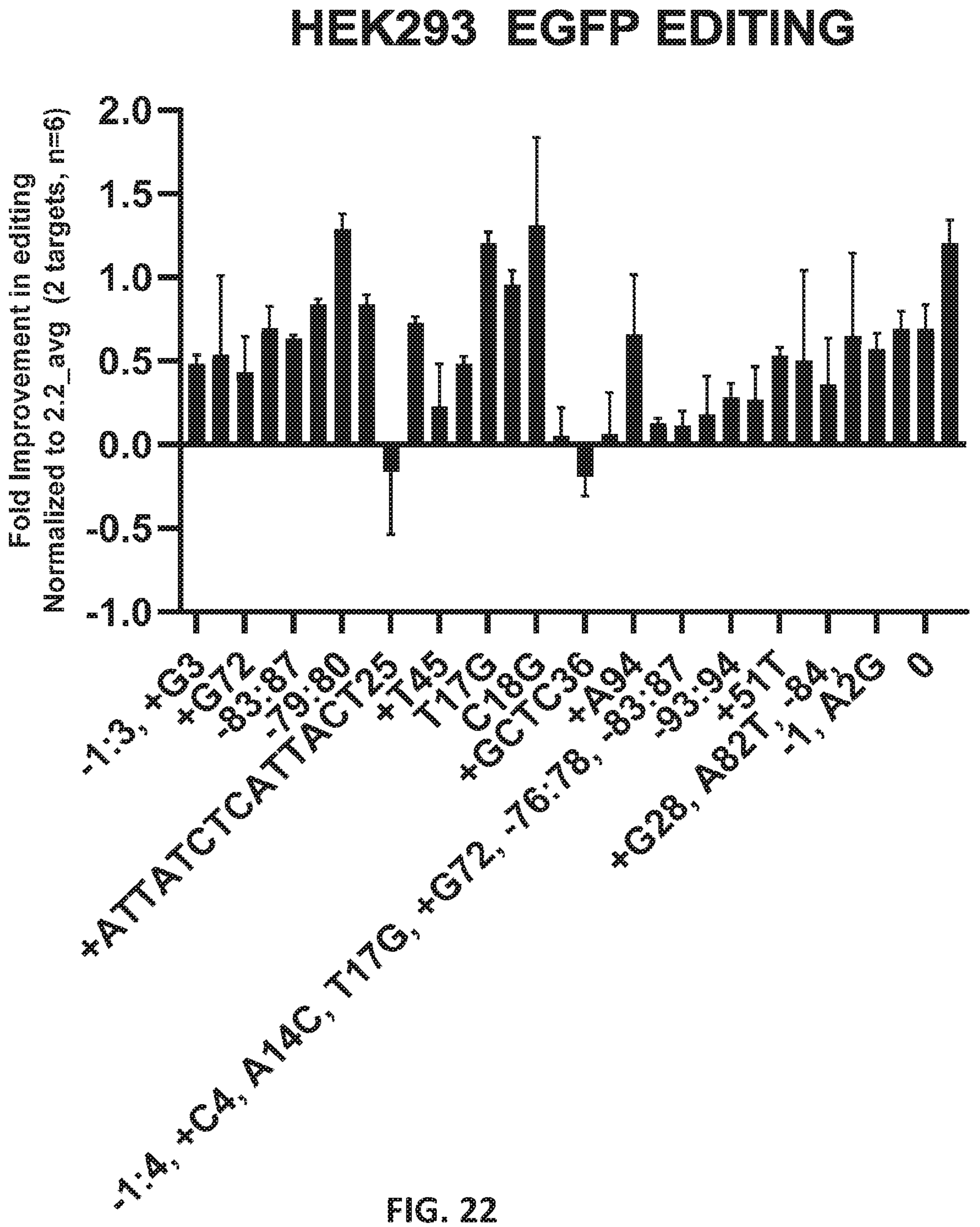
FIG. 22 is a graph showing the fold improvement of sgRNA variants generated by DME mutations normalized to SEQ ID NO:5 as the CasX reference sgRNA, as described in Example 20.
Figure 23:
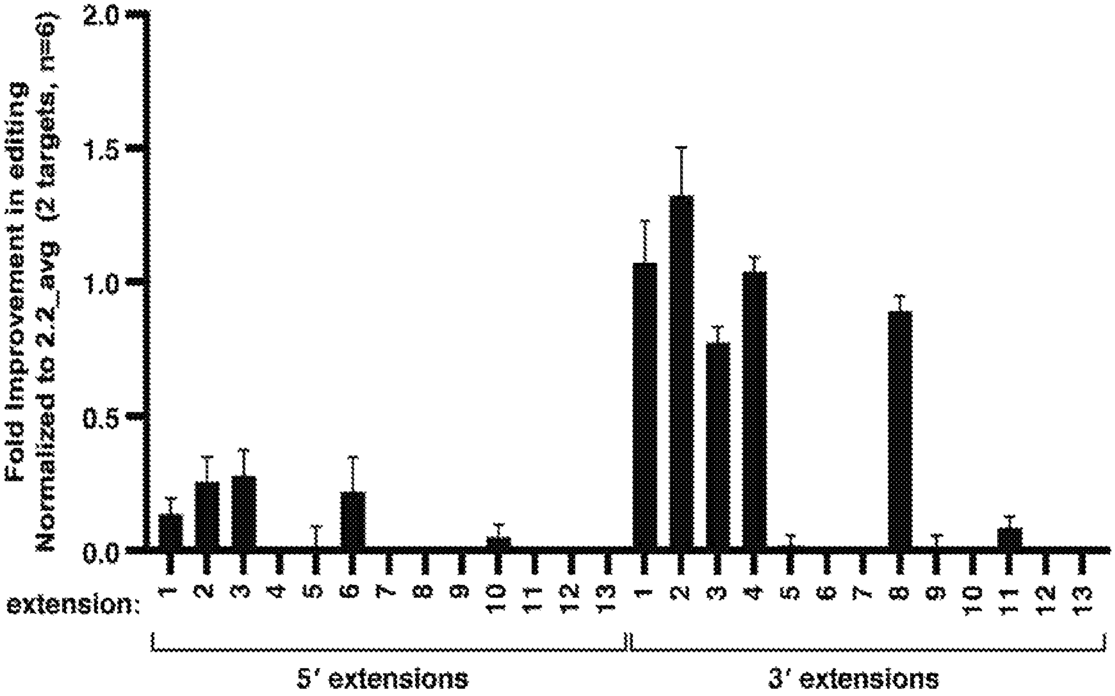
FIG. 23 is a graph showing the fold improvement normalized to the SEQ ID NO:5 reference CasX sgRNA of variants created by both combining (stacking) scaffold stem mutations showing improved cleavage, DME mutations showing improved cleavage, and using ribozyme appendages showing improved cleavage (the appendages and their sequences are listed in Table 15 in Example 20). The resulting sgRNA variants yield 2-fold or greater improvement in cleavage compared to SEQ ID NO:5 in this assay. EGFP editing assays were performed with spacer target sequences of E6 (TGTGGTCGGGGTAGCGGCTG (SEQ ID NO: 17)) and E7 (TCAAGTCCGCCATGCCCGAA (SEQ ID NO: 18)) described in Example 19.

Results: Results from the sgNA variants generated via DME were measured and compared to the reference gNA of SEQ ID NO: 4 are presented in FIG. 22, with most variants showing improvements from 0.1 to nearly 1.5-fold compared to the reference gNA. Results of the variants generated via rational design and replacement or addition of guide parts (such as the extended stem or the addition of ribozymes at the termini) are shown in FIGS. 21 and 23 respectively; again showing improvements with many of the constructs. The additions to the variants, along with their encoding sequences, portrayed by number in FIG. 23 are listed in Table 15, below. We observed that single mutations such as the C18G improve guide activity when compared to the reference. Additionally, rationally swapping in different stem loops for the extended stem loop, such as MS2, QB, PP7, UvsX, etc. improved activity when compared to the reference guide, as does truncating the original extended stem loop. Finally, we demonstrate that while most ribozymes disrupt activity, the addition of a 3' HDV to the reference guide RNA can improve activity up to 20-50%.

TABLE 15

Extensions added to 3' and 5" ends of gNA

| Extension Number | Extension Name | Extension Encoding Sequence |
|---|---|---|
| 1 | HDV antigenomic ribozyme | GGGTCGGCATGGCATCTCCACCTCCTCG CGGTCCGACCTGGGCATCCGAAGGAGGA CGCACGTCCACTCGGATGGCTAAGGGAG AGCCA (SEQ ID NO: 598) |
| 2 | HDV genomic ribozyme | GGCCGGCATGGTCCCAGCCTCCTCGCTG GCGCCGGCTGGGCAACATTCCGAGGGGA CCGTCCCCTCGGTAATGGCGAATGGGAC CC (SEQ ID NO: 599) |
| 3 | HDV ribozyme (v1) | GATGGCCGGCATGGTCCCAGCCTCCTCG CTGGCGCCGGCTGGGCAACACCTTCGGG TGGCGAATGGGAC (SEQ ID NO: 600) |
| 4 | HDV ribozyme (v2) | TTTTGGCCGGCATGGTCCCAGCCTCCTC GCTGGCGCCGGCTGGGCAACATGCTTCG GCATGGCGAATGGGACCCCGGG (SEQ ID NO: 601) |
| 5 | Hatchet | CATTCCTCAGAAAATGACAAACCTGTGG GGCGTAAGTAGATCTTCGGATCTATGAT CGTGCAGACGTTAAAATCAGGT (SEQ ID NO: 602) |
| 6 | env25 pistol ribozyme (with CUUCGG loop) | CGTGGTTAGGGCCACGTTAAATAGTTGC TTAAGCCCTAAGCGTTGATCTTCGGATC AGGTGCAA (SEQ ID NO: 603) |

TABLE 15-continued

| Extensions added to 3' and 5" ends of gNA | | |
|---|---|---|
| Extension Number | Extension Name | Extension Encoding Sequence |
| 7 | HH15 Minimal Hammerhead ribozyme | GGGAGCCCCGCTGATGAGGTCGGGGAGA CCGAAAGGGACTTCGGTCCCTACGGGGC TCCC (SEQ ID NO: 604) |
| 8 | sTRSV WT viral Hammerhead ribozyme | CCTGTCACCGGATGTGCTTTCCGGTCTG ATGAGTCCGTGAGGACGAAACAGG (SEQ ID NO: 605) |
| 9 | Hammerhead ribozyme | CGACTACTGATGAGTCCGTGAGGACGAA ACGAGTAAGCTCGTCTAGTCGCGTGTAG CGAAGCA (SEQ ID NO: 606) |
| 10 | Hammerhead ribozyme, smaller scar | CGACTACTGATGAGTCCGTGAGGACGAA ACGAGTAAGCTCGTCTAGTCG (SEQ ID NO: 607) |
| 11 | Hammerhead ribozyme, guide scaffold scar | CCAGTACTGATGAGTCCGTGAGGACGAA ACGAGTAAGCTCGTCTACTGGCGCTTTT ATCTCAT (SEQ ID NO: 608) |
| 12 | Twisted Sister 1 | ACCCGCAAGGCCGACGGCATCCGCCGCC GCTGGTGCAAGTCCAGCCGCCCCTTCGG GGGCGGGCGCTCATGGGTAAC (SEQ ID NO: 609) |
| 13 | Env-9 Twister | GGCAATAAAGCGGTTACAAGCCCGCAAA AATAGCAGAGTAATGTCGCGATAGCGCG GCATTAATGCAGCTTTATTG (SEQ ID NO: 610) |
| 14 | RBMX recruiting motif | CCACCCCCACCACCACCCCCACCCCCAC CACCACCC (SEQ ID NO: 611) |

Conclusions: The results support the conclusion that DME and rational design can be used to improve the performance of the gNAs and that many of these variant RNAs can now be used with the targeting sequences as a component of the CasX:gNA systems described herein to edit target nucleic acid sequences.

Example 21: CasX Editing of B2M Locus

Goal: Experiments were performed in order to identify optimal CasX and gNA molecules to edit the B2M locus Materials and Methods:

1. Generating B2M Targeting Constructs:

In order to generate the B2M targeting constructs, the codon-optimized CasX 2 (construct 2.2) and construct 119.64 molecules (CasX sequence in Table 16; guide sequences are listed in Tables 1 and 2) and fused NLS (referred to as "StX" herein), guide scaffold, and non-targeting targeting sequences were cloned, using the encoding DNA sequences, into a mammalian expression plasmid (pStX) using standard cloning methods. pStX includes a selection marker for both puromycin and carbenicillin. Sequences encoding the targeting sequences that target the gene of interest were designed based on StX PAM locations (Table 17, listing the RNA targeting sequences; plasmids were created with the corresponding DNA encoding sequences). Targeting sequence DNA was ordered as single-stranded DNA (ssDNA) oligos (Integrated DNA Technologies) consisting of the targeting sequence and the reverse complement of this sequence. These two oligos were annealed together and cloned into pStx individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C2984I), plated on Lb-Agar plates (LB: Teknova Cat #L9315, Agar: Quartzy Cat #214510) containing carbenicillin. Individual colonies were picked and miniprepped using Qiagen Qiaprep spin Miniprep Kit (Qiagen Cat #27104) and following the manufacturer's protocol. The resultant plasmids were sequenced using Sanger sequencing to ensure correct ligation. SaCas9 and SpyCas9 control plasmids were prepared similarly to pStx plasmids described above, with the protein and guide regions of pStx exchanged for the respective protein and guide. Targeting sequences for SaCas9 and SpyCas9 were either obtained from the literature or were rationally designed according to established methods.

2. Assessing B2M Editing Activity in Mammalian Cell Lines:

Activity of the two StX variants were assessed in mammalian cells, including human embryonic kidney (HEK293T) cells and human T lymphocyte cells (Jurkats). Mammalian cells were maintained in a 37° C. incubator at 5% CO2. HEK293T cells and derivatives thereof were grown in Dulbecco's Modified Eagle Medium (DMEM; Corning Cellgro, #10-013-CV) supplemented with 10% fetal bovine serum (FBS; Seradigm, #1500-500), and 100 Units/ml penicillin and 100 mg/ml streptomycin (100×-Pen-Strep; GIBCO #15140-122), and can additionally include sodium pyruvate (100×, Thermofisher #11360070), non-essential amino acids (100× Thermofisher #11140050), HEPES buffer (100× Thermofisher #15630080), and 2-mercaptoethanol (1000× Thermofisher #21985023). Jurkats and K562s were cultured in RPMI medium supplemented with 10% fetal bovine serum (FBS; Seradigm, #1500-500), and 100 units/ml penicillin and 100 mg/ml streptomycin (100×-Pen-Strep; GIBCO #15140-122), and can additionally include sodium pyruvate (100×, Thermofisher #11360070), non-essential amino acids (100× Thermofisher #11140050), HEPES buffer (100× Thermofisher #15630080), and 2-mercaptoethanol (1000× Thermofisher #21985023). Adherent cells, such as HEK293 Ts, were seeded at 20-30 thousand cells per well into 96-well plates and transfected using 0.25-1 uL of Lipofectamine 3000 (Thermo Fisher Scientific #L3000008), 50-500 ng of a plasmid containing CasX and the reference or variant CasX guide targeting the reporter or target gene following the manufacturer's protocol. Alternatively, suspension cells such as Jurkats were nucleofected with 0.5-4.0 ug plasmid DNA/200 k cells using Lonza 4D-nucleofector following manufacturer's protocol. After nucleofection, suspension cells such as Jurkats were cultured in 96 well plates. 24-72 hours later the media was changed and 0.3-3.0 ug/ml puromycin (Sigma #P8833) was added to select for transformation. The following controls, or a combination thereof, were used for each transfection or nucleofection experiment: StX molecules with non-targeting targeting sequences, Sa.Cas9 and/or SpyCas9 targeting B2M, and Sa.Cas9 and Spy.Cas9 with non-targeting targeting sequences. 24-96 hours following selection, or later, the cells were analyzed by flow cytometry and gated for the appropriate forward and side scatter, selected for single cells and then gated for antibody reporter expression (Attune Nxt Flow Cytometer, Thermo Fisher Scientific) to quantify the expression levels of fluorophores. At least 10,000 events were collected for each sample. The data were then used to calculate the percentage of antibody-label negative (edited) cells.

Additionally, editing in cells from each experimental sample were assayed using T7E1 and NGS. For this, a subset of cells from each experimental sample was lysed and genomic DNA extracted using Quikextract solution (Lucigen Cat #QE09050) following the manufacturer's protocol. For T7E1, genomic DNA is first amplified via PCR with primers at the target genomic location of interest. This amplified DNA was then processed following the New England Biolabs T7E1 protocol and analyzed by gel electrophoresis.

3. NGS Analysis

For NGS analysis, genomic DNA was amplified via PCR with primers specific to the target genomic location of interest to form a target amplicon. These primers contain additional sequence at the 5' ends to introduce Illumina read1 and 2 sequences. Further, they contain a 16 nt randomer sequence that functions as a unique molecular identifier (UMI). Quality and quantification of the amplicon was assessed using a Fragment Analyzer DNA analyzer kit (Agilent, dsDNA 35-1500 bp). Amplicons were sequenced on the Illumina Miseq according to manufacturer's instructions.

Raw fastq files from sequencing were processed as follows: (1) the sequences were trimmed for quality and for adapter sequences using the program cutadapt (v. 2.1); (2) the sequences from read 1 and read 2 were merged into a single insert sequence using the program flash2 (v2.2.00); (3) inserts with the same UMI sequence were merged into a single sequence. In a first step, a single consensus sequence was generated from all individual inserts with the same UMI, using a per-base voting strategy. In a second step, the individual inserts were compared to the consensus sequence. If more than 67% of inserts exactly match the consensus sequence, the consensus sequence was taken for that UMI. If not, the individual insert with the highest sequencing quality is taken for that UMI; and (4) the consensus insert sequences were run through the program CRISPResso2 (v 2.0.29), along with the expected amplicon sequence and the targeting sequence. This program quantifies the percent of reads that are modified in a window around the 3' end of the targeting sequence (20 bp window centered at −3 bp from 3' end of targeting sequence). The percent modified of an StX molecule was quantified by the total percent of reads that contain insertions and/or deletions in this window.

TABLE 16

Sequences of Stx CasX Constructs

| Construct | Amino Acid Sequence |
|---|---|
| 2.2 | QEIKRINKIRRRLVKDSNTKKAGKTGPMKTLLVRVMTPDLRERLENLRKKPENIPQPISNTSRANLNKLLTDYTEMKKAILHVYWEEFQKDPVGLMSRVAQPAPKNIDQRKLIPVKDGNERLTSSGFACSQCCQPLYVYKLEQVNDKGKPHTNYFGRCNVSEHERLILLSPHKPEANDELVTYSLGKFGQRALDFYSIHVTRESNHPVKPLEQIGGNSCASGPVGKALSDACMGAVASFLTKYQDIILEHQKVIKKNEKRLANLKDIASANGLAFPKITLPPQPHTKEGIEAYNNVVAQIVIWVNLNLWQKLKIGRDEAKPLQRLKGFPSFPLVERQANEVDWWDMVCNVKKLINEKKEDGKVFWQNLAGYKRQEALLPYLSSEEDRKKGKKFARYQFGDLLLHLEKKHGEDWGKVYDEAWERIDKKVEGLSKHIKLEEERRSEDAQSKAALTDWLRAKASFVIEGLKEADKDEFCRCELKLQKWYGDLRGKPFAIEAENSILDISGFSKQYNCAFIWQKDGVKKLNLYLIINYFKGGKLRFKKIKPEAFEANRFYTVINKKSGEIVPMEVNFNFDDPNLIILPLAFGKRQGREFIWNDLLSLETGSLKLANGRVIEKTLYNRRTRQDEPALFVALTFERREVLDSSNIKPMNLIGIDRGENIPAVIALTDPEGCPLSRFKDSLGNPTHILRIGESYKEKQRTIQAAKEVEQRRAGGYSRKYASKAKNLADDMVRNTARDLLYYAVTQDAMLIFENLSRGFGRQGKRTFMAERQYTRMEDWLTAKLAYEGLPSKTYLSKTLAQYTSKTCSNCGFTITSADYDRVLEKLKKTATGWMTTINGKELKVEGQITYYNRYKRQNVVKDLSVELDRLSEESVNNDISSWTKGRSGEALSLLKKRFSHRPVQEKFVCLNCGFETHADEQAALNIARSWLFLRSQEYKKYQTNKTTGNTDKRAFVETWQSFYRKKLKEVWKPAV(SEQ ID NO: 612) |
| 119.64 | QEIKRINKIRRRLVKDSNTKKAGKTGPMKTLLVRVMTPDLRERLENLRKKPENIPQPISNTSRANLNKLLTDYTEMKKAILHVYWEEFQKDPVGLMSRVAQPAPKNIDQRKLIPVKDGNERLTSSGFACSQCCQPLYVYKLEQVNDKGKPHTNYFGRCNVSEHERLILLSPHKPEANDELVTYSLGKFGQRALDFYSIHVTRESNHPVKPLEQIGGNSCASGPVGKALSDACMGAVASFLTKYQDIILEHQKVIKKNEKRLANLKDIASANGLAFPKITLPPQPHTKEGIEAYNNVVAQIVIWVNLNLWQKLKIGRDEAKPLQRLKGFPSFPLVERQANEVDWWDMVCNVKKLINEKKEDGKVFWQNLAGYKRQEALRPYLSSEEDRKKGKKFARYQFGDLLLHLEKKHGEDWGKVYDEAWERIDKKVEGLSKHIKLEEERRSEDAQSKAALTDWLRAKASFVIEGLKEADKDEFCRCELKLQKWYGDLRGKPFAIEAENSILDISGFSKQYNCAFIWQKDGVKKLNLYLIINYFKGGKLRFKKIKPEAFEANRFYTVINKKSGEIVPMEVNFNFDDPNLIILPLAFGKRQGREFIWNDLLSLETGSLKLANGRVIEKTLYNRRTRQDEPALFVALTFERREVLDSSNIKPMNLIGIDRGENIPAVIALTDPEGCPLSRFKDSLGNPTHILRIGESYKEKQRTIQAKKEVEQRRAGGYSRKYASKAKNLADDMVRNTARDLLYYAVTQDAMLIFENLSRGFGRQGKRTFMAERQYTRMEDWLTAKLAYEGLSKTYLSKTLAQYTSKTCSNCGFTITSADYDRVLEKLKKTATGWMTTINGKELKVEGQITYYNRYKRQNVVKDLSVELDRLSEESVNNDISSWTKGRSGEALSLLKKRFSHRPVQEKFVCLNCGFETHADEQAALNIARSWLFLRSQEYKKYQTNKTTGNTDKRAFVETWQSFYRKKLKEVWKPAV(SEQ ID NO: 613) |

TABLE 17

HLA1 Editing by CasX or Cas9 with Targeting Sequences

| Nuclease | Name* | Sequence | % HLA Negative* |
|---|---|---|---|
| CasX | TTC 7 | UCCAUCCGACAUUGAAGUUG (SEQ ID NO: 614) | 0 |
| | TTC 8 | AUCUCUU-GUAC UACAC UGAA (SEQ ID NO: 615) | 0 |
| | TTC 9 | GUGUAGUACAAGAGAUAGAA (SEQ ID NO: 616) | 6.00 |
| | TTC 10 | CACGGCAGGCAUACUCAUCU (SEQ ID NO: 617) | 0 |
| | TTC 11 | UAGAUCGAGACAUGUAAGCA (SEQ ID NO: 618) | 9.67 |

TABLE 17-continued

HLA1 Editing by CasX or Cas9 with Targeting Sequences

| Nuclease | Name* | Sequence | % HLA Negative* |
|---|---|---|---|
| | TTC 12 | AAUUUACAUACUCUGC UUAG (SEQ ID NO: 619) | 0 |
| | TTC 13 | AAGCAGAGUAUGUAAA UUGG (SEQ ID NO: 620) | 0.33 |
| | TTC 14 | UGAAGCUGACAGCAUU CGGG (SEQ ID NO: 621) | 4.67 |
| | TTC 16 | GGUUUACUCACGUCAU CCAG (SEQ ID NO: 622) | 2.33 |
| | TTC 17 | CUCUCCAUUCUUCAGU AAGU (SEQ ID NO: 623) | 0 |
| | TTC 18 | GACUUGUCUUUCAGCA AGGA (SEQ ID NO: 624) | 0.67 |
| | TTC 19 | CCCCCACUGAAAAAGA UGAG (SEQ ID NO: 625) | 0 |
| | TTC 20 | UAGAUCGAGACAUGUA AGCA (SEQ ID NO: 626) | 6.67 |
| | TTC 21 | CCACUGUCUUUUUCAU AGAU (SEQ ID NO: 627) | 0 |
| | TTC 22 | UUGCUAACCUUUUUCU UUUC (SEQ ID NO: 628) | 3.00 |
| | TTC 23 | UUUCUUUUCAGGUUUG AAGA (SEQ ID NO: 629) | 0 |
| | TTC 24 | UUUCAGGUUUGAAGAU GCCG (SEQ ID NO: 630) | 0 |
| | TTC 25 | GGUUUGAAGAUGCCG CAUUU (SEQ ID NO: 631) | 0 |
| | TTC 26 | AACCUGAAAAGAAAAG AAAA (SEQ ID NO: 632) | 0 |
| | TTC 27 | UCCAAUCCAAAUGCGG CAUC (SEQ ID NO: 633) | 0 |
| | TTC 28 | UGGUCAAAUAAACAAA GCUG (SEQ ID NO: 634) | 0 |
| | TTC 29 | CAUUUUCCAGAUUAGG AAUC (SEQ ID NO: 635) | 0 |
| | TTC 30 | GGAAUGCCCGCCAGC GCGAC (SEQ ID NO: 636) | 0 |

TABLE 17-continued

HLA1 Editing by CasX or Cas9 with Targeting Sequences

| Nuclease | Name* | Sequence | % HLA Negative* |
|---|---|---|---|
| | TTC 31 | UGAAGCUGACAGCAUU CGGG (SEQ ID NO: 637) | 0 |
| | TTC 32 | CAAGGUCAAAAACUUA CCUC (SEQ ID NO: 638) | 1.67 |
| | TTC 34 | UUUCUUUUCAGGUUUG AAGA (SEQ ID NO: 639) | 0 |
| | TTC 35 | AGGCAUAGUUUUAUAC CUGA (SEQ ID NO: 640) | 0 |
| | TTC 37 | GGCCGAGAUGUCUCG CUCCG (SEQ ID NO: 641) | 11.00 |
| | CTC 38 | AUGUUUGAUGUAUCUG AGCA (SEQ ID NO: 642) | 0 |
| | CTC 39 | GAUACAUCAAACAUGG AGAC (SEQ ID NO: 643) | 0 |
| | CTC 40 | AUGAUGCUGCUUACAU GUCU (SEQ ID NO: 644) | 0 |
| | CTC 41 | CGUCAUCCAGCAGAGA AUGG (SEQ ID NO: 645) | 0 |
| | CTC 42 | GCUGGAUGACGUGAG UAAAC (SEQ ID NO: 646) | 0 |
| | CTC 43 | AGGCCAGAAAGAGAGA GUAG (SEQ ID NO: 647) | 3.67 |
| | CTC 44 | ACUGUCUUUUUCAUAG AUCG (SEQ ID NO: 648) | 0 |
| | CTC 45 | AGGUCAAAAACUUACC UCCA (SEQ ID NO: 649) | 0 |
| | CTC 46 | AUGAUGCUGCUUACAU GUCU (SEQ ID NO: 650) | 0 |
| | CTC 47 | ACUUAUAUUAAACGCG UGCC (SEQ ID NO: 651) | 0 |
| | ATC 48 | CGGCCCGAAUGCUGU CAGCU (SEQ ID NO: 652) | 0 |
| | ATC 49 | AGCGUGAGUCUCUCCU ACCC (SEQ ID NO: 653) | 0 |
| | ATC 50 | UUGGAGUACCUGAGGA AUAU (SEQ ID NO: 654) | 0 |

TABLE 17-continued

HLA1 Editing by CasX or Cas9 with Targeting Sequences

| Nuclease | Name* | Sequence | % HLA Negative* |
|---|---|---|---|
| | ATC 52 | AUCCGACAUUGAAGUUGACU (SEQ ID NO: 655) | 0 |
| | ATC 53 | GACAUUGAAGUUGACUUACU (SEQ ID NO: 656) | 0 |
| | ATC 54 | CUUGUACUACACUGAAUUCA (SEQ ID NO: 657) | 0 |
| | ATC 55 | UUUUCAGUGGGGGUGAAUUC (SEQ ID NO: 658) | 0 |
| | ATC 56 | UGGGCUGUGACAAAGUCACA (SEQ ID NO: 659) | 0 |
| | ATC 57 | AGACAUGUAAGCAGCAUCAU (SEQ ID NO: 660) | 0 |
| | ATC 58 | UCAAACCUGAAAAGAAAAGA (SEQ ID NO: 661) | 0 |
| | ATC 59 | AAAUGCGGCAUCUUCAAACC (SEQ ID NO: 662) | 0 |
| | ATC 60 | AAUCCAAAUGCGGCAUCUUC (SEQ ID NO: 663) | 0 |
| | ATC 61 | GAGCAGGUUGCUCCACAGGU (SEQ ID NO: 664) | 0 |
| | ATC 62 | UAAAACUUGAUGUGUUAUCU (SEQ ID NO: 665) | 0 |
| | ATC 63 | AACAUCAACAUCUUGGUCAG (SEQ ID NO: 666) | 0 |
| | ATC 64 | CGGCCCGAAUGCUGUCAGCU (SEQ ID NO: 667) | 0 |
| | GTC 65 | UGAUUGGCUGGGCACGCGUU (SEQ ID NO: 668) | 0 |
| | GTC 66 | CGCUCCGUGGCCUUAGCUGU (SEQ ID NO: 669) | 0 |
| | GTC 67 | AAUAAACAAAGCUGGCCAUC (SEQ ID NO: 670) | 0 |
| | GTC 68 | UAUAAGAUUCAUAUUUACUU (SEQ ID NO: 671) | 0 |
| | ATT 69 | GGGCCGAGAUGUCUCGCUCC (SEQ ID NO: 672) | 0 |
| | CTT 70 | AAUGUCGGAUGGAUGAAACC (SEQ ID NO: 673) | 0 |
| | CTT 71 | GCUGUGCUCGCGCUACUCUC (SEQ ID NO: 674) | 0 |
| | CTT 72 | CUGGCCUGGAGGCUAUCCAG (SEQ ID NO: 675) | 0 |
| | CTT 73 | CCAUUCUCUGCUGGAUGACG (SEQ ID NO: 676) | 0 |
| | CTT 74 | CUGAAGAAUGGAGAGAGAAU (SEQ ID NO: 677) | 0 |
| | CTT 75 | CCUCCAUGAUGCUGCUUACA (SEQ ID NO: 678) | 0 |
| | CTT 76 | CAAUUUACAUACUCUGCUUA (SEQ ID NO: 679) | 0 |
| | CTT 77 | CACUCAAAGCUUGUUAAGAU (SEQ ID NO: 680) | 0 |
| | CTT 78 | ACAAGCUUUGAGUGCAAGAG (SEQ ID NO: 681) | 0 |
| Cas9 | SaCas9 79 | UCGGCCCGAAUGCUGUCAGCUUC (SEQ ID NO: 682) | 6.30 |
| | SaCas9 80 | GCCACGGAGCGAGACAUCUCGGC (SEQ ID NO: 683) | 49.46 |
| | SaCas9 81 | GGAUAGCCUCCAGGCCAGAAAGA (SEQ ID NO: 684) | 69.53 |
| | SaCas9 82 | UUCUGGCCUGGAGGCUAUCCAGC (SEQ ID NO: 685) | 69.70 |
| | SaCas9 83 | CGGGAGGGUAGGAGAGACUCACG (SEQ ID NO: 686) | 31.56 |
| | SaCas9 84 | AACCUGAAUCUUUGGAGUACCUG (SEQ ID NO: 687) | 76.00 |
| | SaCas9 85 | UGACGUGAGUAAACCUGAAUCUU (SEQ ID NO: 688) | 1.69 |
| | SaCas9 86 | UCUGCUGGAUGACGUGAGUAAAC (SEQ ID NO: 689) | 6.93 |
| | SaCas9 87 | AGGUUUACUCACGUCAUCCAGCA (SEQ ID NO: 690) | 30.26 |

TABLE 17-continued

HLA1 Editing by CasX or Cas9 with Targeting Sequences

| Nuclease | Name* | Sequence | % HLA Negative* |
|---|---|---|---|
| | SaCas9 88 | CUUUCCAUUCUCUGCUGGAUGAC (SEQ ID NO: 691) | 1.89 |
| | SaCas9 90 | CAGAGAAUGGAAAGUCAAAUUUC (SEQ ID NO: 692) | 1.05 |
| | SaCas9 91 | AAAUUUCCUGAAUUGCUAUGUGU (SEQ ID NO: 693) | 43.46 |
| | SaCas9 92 | CAGUAAGUCAACUUCAAUGUCGG (SEQ ID NO: 694) | 24.13 |
| | SaCas9 93 | CCGACAUUGAAGUUGACUUACUG (SEQ ID NO: 695) | 18.03 |
| | SaCas9 95 | GUUGACUUACUGAAGAAUGGAGA (SEQ ID NO: 696) | 79.06 |
| | SaCas9 96 | CCAGUCCUUGCUGAAAGACAAGU (SEQ ID NO: 697) | 33.70 |
| | SaCas9 97 | GUCUUUCUAUCUCUUGUACUACA (SEQ ID NO: 698) | 7.20 |
| | SaCas9 98 | UGAAUUCACCCCCACUGAAAAAG (SEQ ID NO: 699) | 64.33 |
| | SaCas9 99 | CAUACUCAUCUUUUUCAGUGGGG (SEQ ID NO: 700) | 4.57 |
| | SaCas9 100 | CAGGCAUACUCAUCUUUUUCAGU (SEQ ID NO: 701) | 0.90 |
| | SaCas9 101 | UGUCACAGCCCAAGAUAGUUAAG (SEQ ID NO: 702) | 49.33 |
| | SaCas9 102 | UUUCAGGUUUGAAGAUGCCGCAU (SEQ ID NO: 703) | 0.76 |
| | SaCas9 103 | UUCAGGUUUGAAGAUGCCGCAUU (SEQ ID NO: 704) | 0.30 |
| | SaCas9 104 | GGUUUGAAGAUGCCGCAUUUGGA (SEQ ID NO: 705) | 2.11 |
| | SaCas9 105 | UGAAGAUGCCGCAUUUGGAUUGG (SEQ ID NO: 706) | 1.82 |
| | SaCas9 106 | UAAAUUUUCCCCCAAAUUCUAAG (SEQ ID NO: 707) | 1.28 |
| | SaCas9 108 | UCGGCCCGAAUGCUGUCAGCUUC (SEQ ID NO: 708) | 2.13 |
| | SaCas9 109 | GCCACGGAGCGAGACAUCUCGGC (SEQ ID NO: 709) | 0.86 |
| | SpyCas9 110 | GGAUAGCCUCCAGGCCAGAAAGA (SEQ ID NO: 710) | 87.64 |

*Mean value of at least 3 replicate assays

Figure 24:
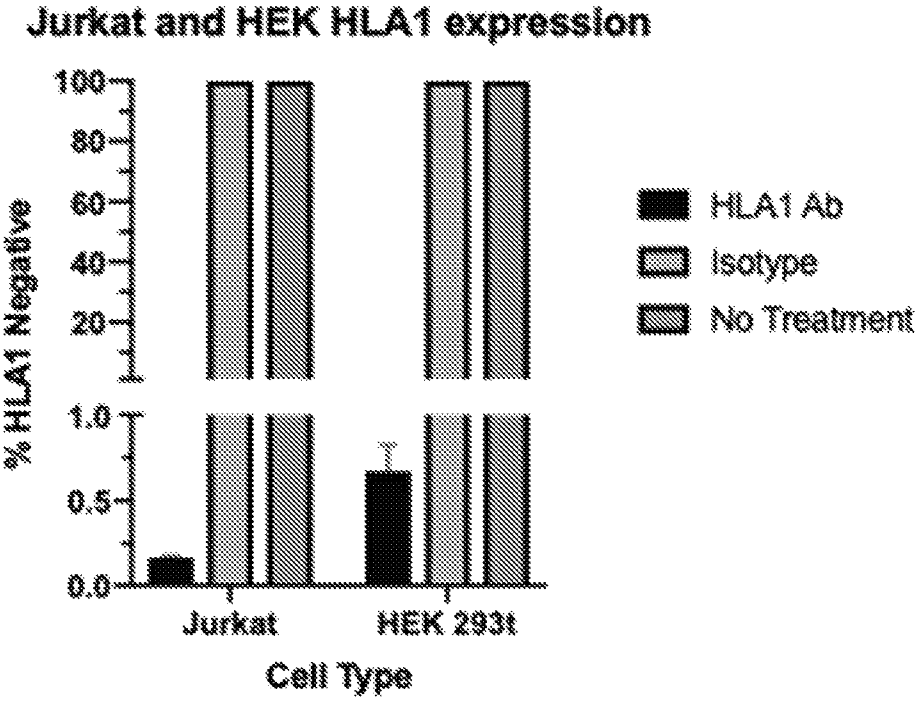
FIG. 24 is a graph showing the expression levels of HLA1 in Jurkat and HEK 293T, as described in Example 21. Cells were analyzed via flow cytometry using a fluorescent antibody targeting HLA1.
Figure 25:
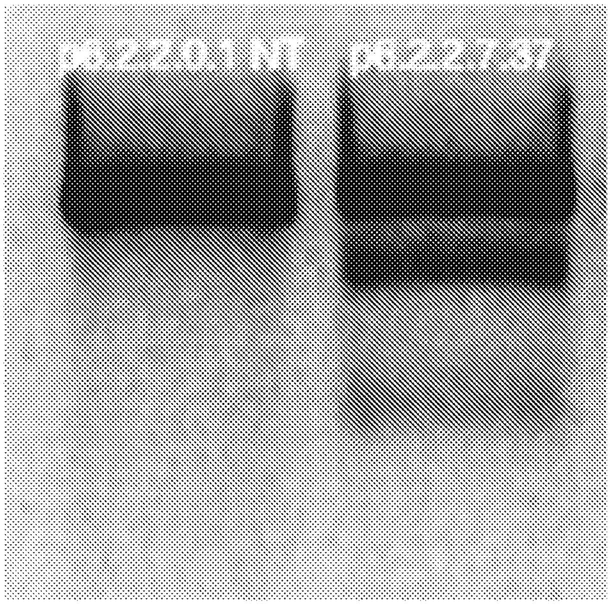
FIG. 25 is an agarose gel showing T7E1 of HEK 293T genomic DNA treated with Stx 2.2, as described in Example 21. Editing is occurring at the B2M locus with a targeting spacer (p6.2.2.7.37), but not with a nontargeting spacer (p6.2.2.0.1).

Results:

The level of HLA1 expression was first assessed in multiple human cell lines (FIG. 24). The basis of this assay is the reduction in the level of HLA1 expression due to the knockout of B2M, an essential structural protein of HLAL. The T7E1 assay verified editing of the B2M locus in HEK cells (FIG. 25). We screened for this using a fluorescent antibody specific to HLA 1. An initial screen in HEK293T cells of 68 B2M targeting sequences (see Table 17) with various PAM specificities were tested with our initial Stx molecule 2.2 using SpyCas9 as a control, and a) similar screen was then performed with 26 B2M targeting sequences compatible (see Table 17) with SaCas9 to establish controls for this target with the SaCas9 molecule. The results of the editing assay are presented in Table 17, expressed as the percent change in HLA1 expression.

Figure 26:
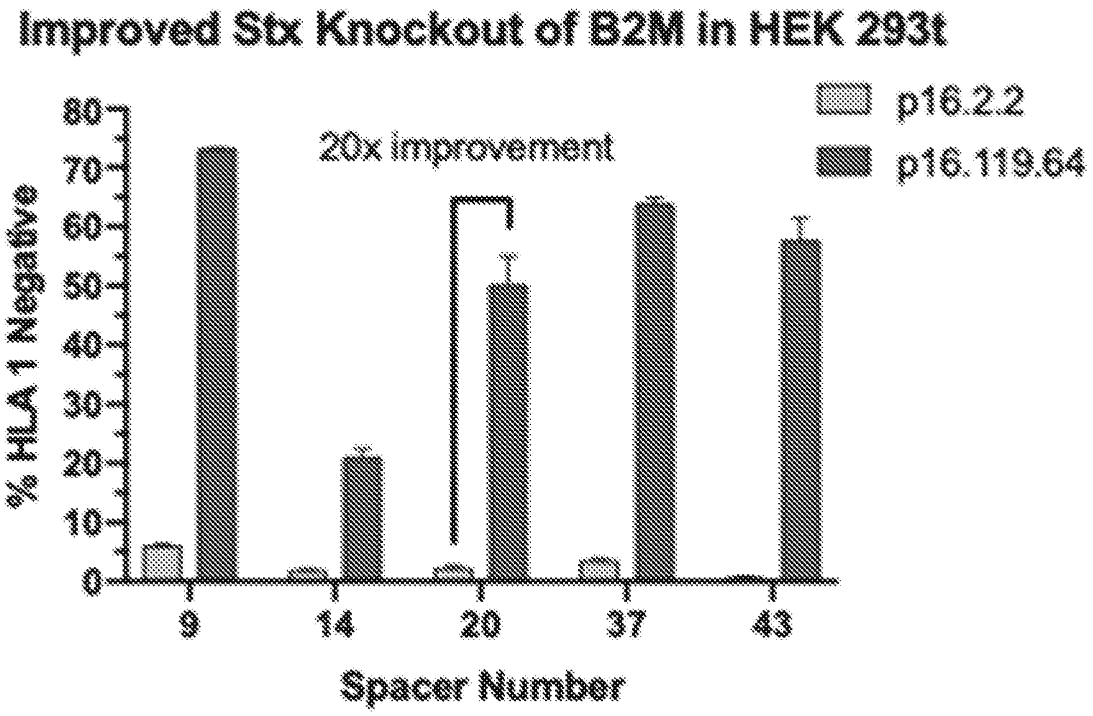
FIG. 26 is a graph showing the relative improvement in edited (knock-out) of B2M in HEK 293T cells using Stx molecule 119.64 (numbers refer to CasX and guide, respectively), compared to Stx 2.2, as described in Example 21.
Figure 27:
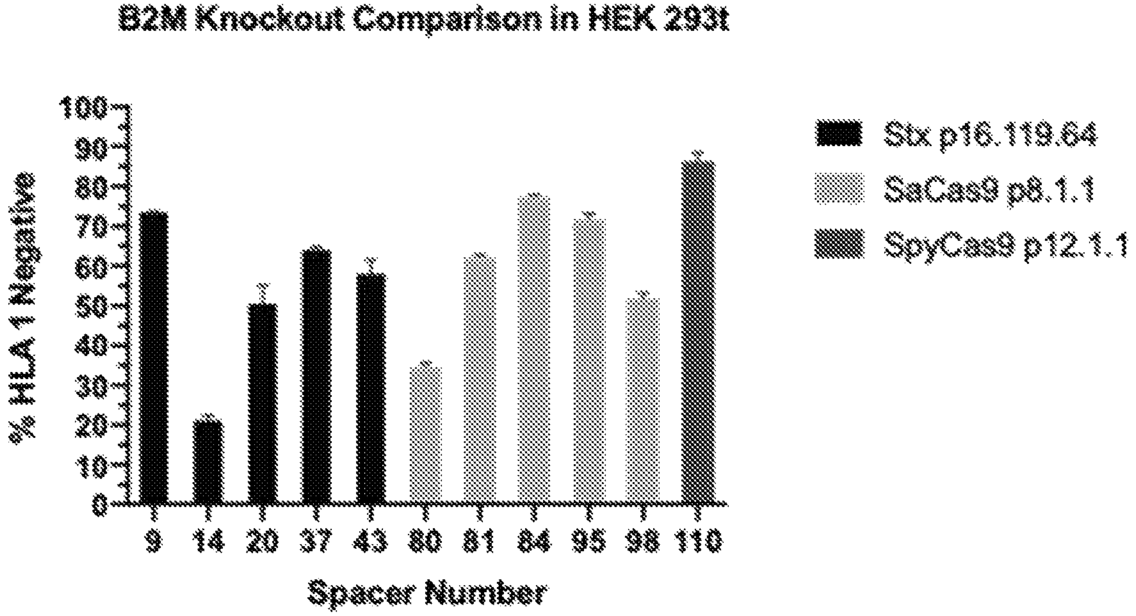
FIG. 27 is a graph showing the comparison in edited (knock-out) of B2M in HEK 293T cells using Stx 119.64 in comparison with the five high-performing SaCas9 spacers, showing comparable levels of editing, as described in Example 21.
Figure 28:
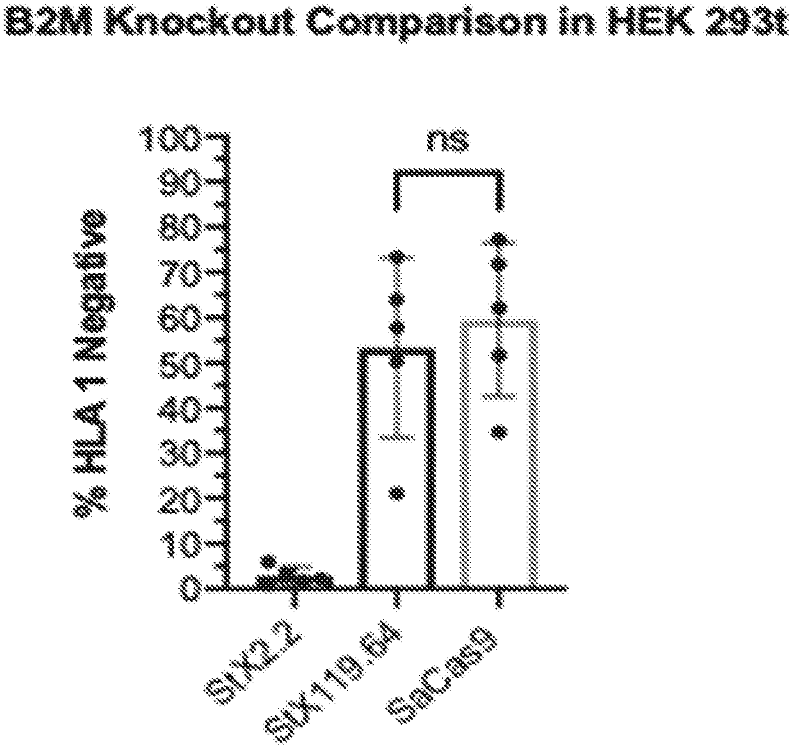
FIG. 28 is a graph showing the relative improvement in edited (knock-out) of B2M in HEK 293T cells using Stx molecule 119.64.7 (numbers refer to CasX, guide, and spacer, respectively) compared to Stx 2.2, with results comparable to SaCas9, as described in Example 21.
Figure 29:
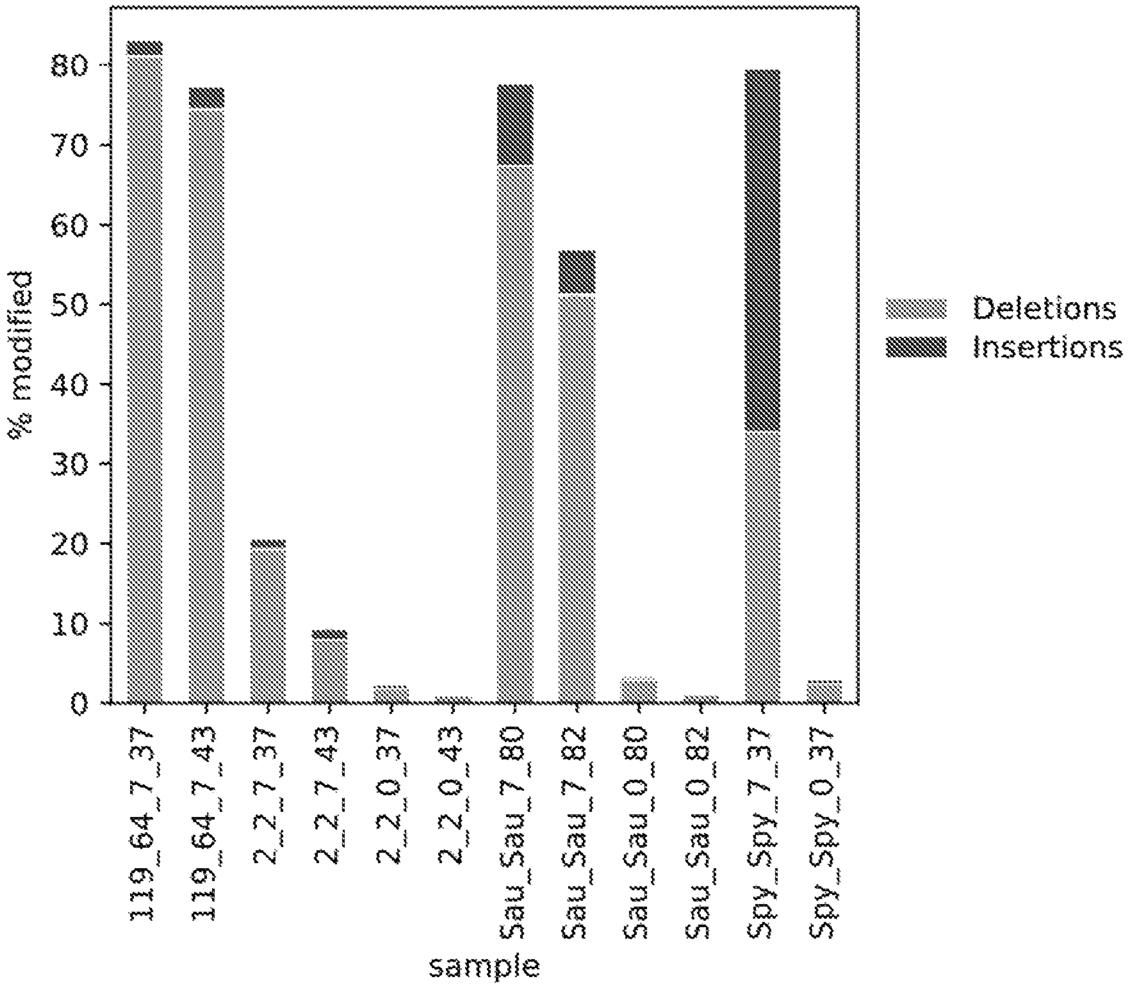
FIG. 29 is a graph showing NGS analysis of percentage editing of the HEK 293T B2M locus, with up to 80% modification with Stx 119.64, as described in Example 21.

The Stx 119.64 variant shows substantial improvement over Stx 2.2, editing at the endogenous B2M locus in HEK cells with up to 20-fold higher efficiency as measured via flow cytometry in HEK293T cells (FIG. 26). A comparison of Stx 119.64 with the five best SaCas9 spacers targeting endogenous B2M in HEK 293T cells shows comparable levels of editing (FIGS. 27 and 28). NGS analysis of HEK 293tTB2M locus shows up to 80% modification with Stx 119.64 (FIG. 29). These modifications are predominantly deletions, in contrast to SpyCas9 which are primarily insertions.

Conclusions: The results support that the editing performance of Stx CasX can be improved by selective mutations introduced into the sequence of Stx 2.2.

Example 22: Genetic Disruption of B2M in Cells Genetically Engineered to Express a Chimeric Antigen Receptor (CAR) and TCR Primary human CD4+ and CD8+ T cells will be isolated by immunoaffinity-based selection from human PBMC samples obtained from healthy donors. The resulting cells will be stimulated by culturing with an anti-CD3/anti-CD28 reagent in media containing human serum, IL-2 (100 U/mL), IL-7 (10 ng/mL) and IL-15 (5 ng/mL) at 37° C. prior to engineering with a chimeric antigen receptor (CAR) by lentiviral transduction for 24-48 hours. The cells will be transduced using a lentiviral vector containing a nucleic acid molecule encoding an exemplary anti-CD19 CAR and a nucleic acid encoding a truncated EGFR (EGFRt), for use as a surrogate marker for transduction, separated by a sequence encoding a T2A ribosome switch. The CAR will include an anti-CD19 scFv (such as an anti-CD19 sequence of Table 5 wherein the VH and VL are joined by short linkers), an Ig-derived spacer, a human CD28-derived transmembrane domain, a human 4-1BB-derived intracellular signaling domain and a human CD3 zeta-derived signaling domain.

For introduction of the engineered T cell receptor (TCR), the cells will be transduced using a lentiviral vector containing a nucleic acid molecule encoding a human full length T-cell receptor a chain linked to an anti-CD19 sequence of Table 5 (which may be the same or different compared to the CAR anti-CD19 sequence) by a linker sequence, and further containing an intracellular signaling domain of CD3 epsilon or CD3 gamma.

Following transduction, the cells will be cultured for 36-48 hours in media containing human serum and IL-2 (50 U/mL), IL-7 (5 ng/mL) and IL-15 (0.5 ng/mL). The cells will then be electroporated with RNP prepared using the B2M-targeted gNA with the targeting sequence GUGUAGUACAAGAGAUAGAA (TTC 9 of Table 17 (SEQ ID NO: 616)) and CasX 119 with guide 174. The cells then will be cultured in the same media containing IL-2, IL-7 and IL-15 at the same concentrations, overnight at 30° C., and then at 37° C. through day 12-15 post-electroporation.

CAR and B2M Expression

Cell surface expression of B2M, TCR and CAR expression (as indicated via the surrogate marker) will be assessed on day 12 after electroporation, following a 24 hour restimulation with beads conjugated with anti-CD3/anti-CD28 antibodies. Cells will be stained with anti-EGFR antibody to verify CAR expression (as indicated by surface expression of the surrogate marker, EGFRt), an anti-TCR alpha to verify TCR expression, and an anti-B2M antibody to verify and knock-down expression of B2M on the surface by flow cytometry. By flow cytometry, the majority of cells would be expected to show reduced expression of B2M, i and expression of the CAR-expressing populations (as indicated by the EGFRt marker), and expression of the TCR in the TCR-expressing populations.

Phenotypic characteristics of the modified engineered CD4+ and CD8+ T cells also will be assessed by flow cytometry assessing surface expression of various markers, including those indicative of phenotype, differentiation state and/or activation state. Cells will be stained with antibodies specific for -C motif chemokine receptor 7 (CCR7), 4-1BB, TIM-3, CD27, CD45RA, C-D45RO, Lag-3, (CD62L, CD25 and CD69 in addition to those for recognizing B2M and the EGFRt marker (surrogate for CAR expression) as described above.

Example 23: Cytotoxicity Assay

JVM-2 cells (human chronic B-cell leukemia cell line expressing CD19) and the CAR-T cell line of Example 22 will be cultured in RPMI 1640 (Life Technologies, Rockville, MD) supplemented with 10% FCS (Bio Whittaker, Walkersville, MD), 100 IU/mL penicillin, and 100 μg/mL streptomycin (Life Technologies). Cytotoxicity will be measured in a standard $^{51}$Cr-release assay. CAR-T cells will be seeded with Chromium 51 ($^{51}$Cr)-labeled target cells (5×103 cells per well) at various effector/target cell ratios in 96-well U-bottomed microtiter plates (triplicate wells per sample). Plates will be incubated for 6 hours at 37° C., 5% CO2. $^{51}$Cr-release will be measured in 100 μL supernatant using a liquid scintillation counter. Maximum release will be obtained from detergent-released target cell counts and spontaneous release from target cell counts in the absence of effector cells. Cellular cytotoxicity will be calculated as follows: % specific lysis=[(experimental release−spontaneous release)/(maximum release−spontaneous release)]. It is expected that the data will confirm the ability of the CAR-T cells to effect lysis on the CD19+ target cells.

Example 24: Editing at B2M Locus

Materials and Methods

CasX variants 119, 488, and 491 were expressed and purified as described in the Examples above. Single guide RNAs with scaffold 174 and spacers 7.9 (having sequence GUGUAGUACAAGAGAUAGAA (SEQ ID NO: 616)) and 7.37 (having sequence GGCCGAGAUGUCUCGCUCCG (SEQ ID NO: 592)) were transcribed and purified as described in the Examples, above. Individual RNPs were assembled by mixing protein with a 1.2-fold molar excess of guide in buffer containing 25 mM sodium phosphate buffer (pH 7.25), 150 mM NaCl, 1 mM $MgCl_2$, and 200 mM trehalose (Buffer 1). RNPs were incubated at 37° C. for 10 minutes and then purified via size exclusion chromatography. The concentration of the RNP was determined following purification using the Pierce 660 nm protein assay.

Purified RNPs were tested for editing at the B2M locus in Jurkat cells. RNPs were delivered by electroporation using the Lonza 4-D nucleofector system. 700,000 cells were resuspended in 20 uL of Lonza buffer P3 and added to RNP diluted in Buffer 1 to the appropriate concentration and a final volume of 5 uL, unless otherwise specified. Cells were electroporated using the Lonza 96-well shuttle system using the protocol EH-115. Cells were recovered in pre-equilibrated RPMI and then each electroporation condition was split into three wells of a 96-well plate. Media was changed on days 1 and 4 following the nucleofection. On day 7 post-nucleofection, cells were stained with a fluorescent anti-HLA 1 antibody and assessed for elimination of surface HLA using an Attune Nxt flow cytometer. If next-generation sequencing was carried out, half of the cells from each condition were passaged for an additional three days before harvesting. Genomic DNA was isolated and the relevant regions of the B2M gene (exon 1 for 7.37, exon 2 for 7.9) were PCR amplified and sequenced using an Illumina MiSeq. The resulting sequence reads were analyzed for editing profiles using Crispresso.

Results

Figure 30:
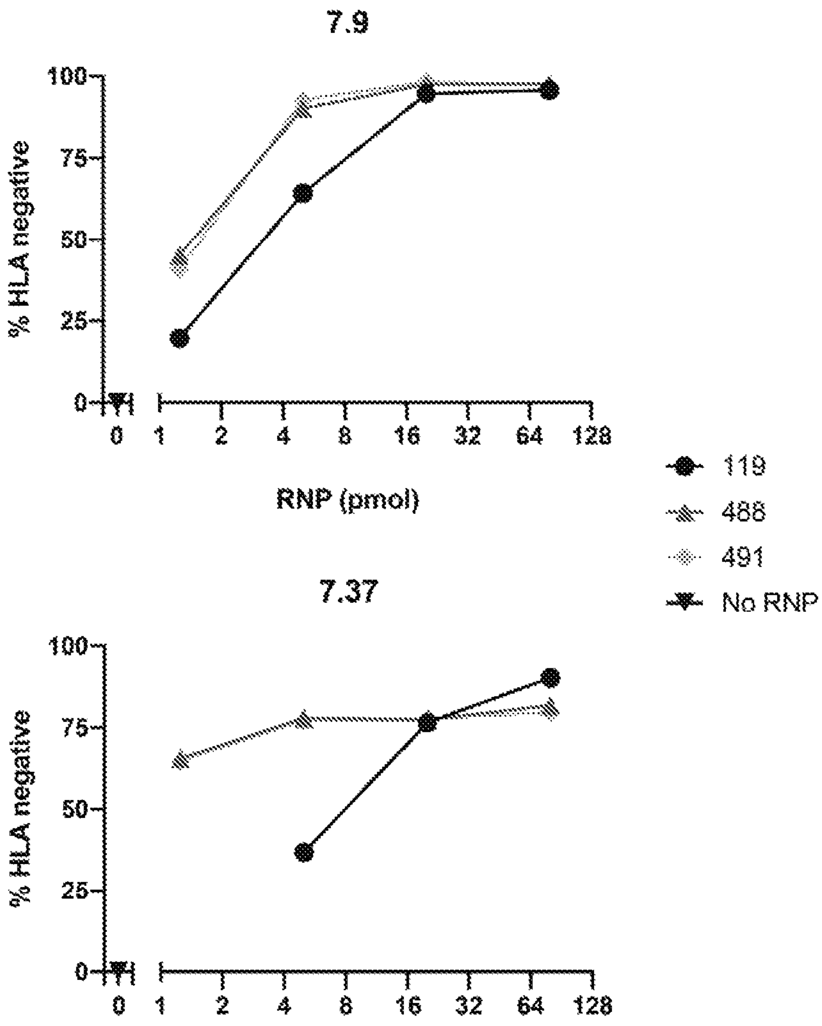
FIG. 30 shows the results of RNP-mediated editing at the B2M locus, as described in Example 24. Jurkat cells were electroporated with the indicated dose and variant of CasX with a guide with either spacer 7.9 or 7.37. HLA knockdown was determined with antibody staining and flow cytometry.
Figure 31:
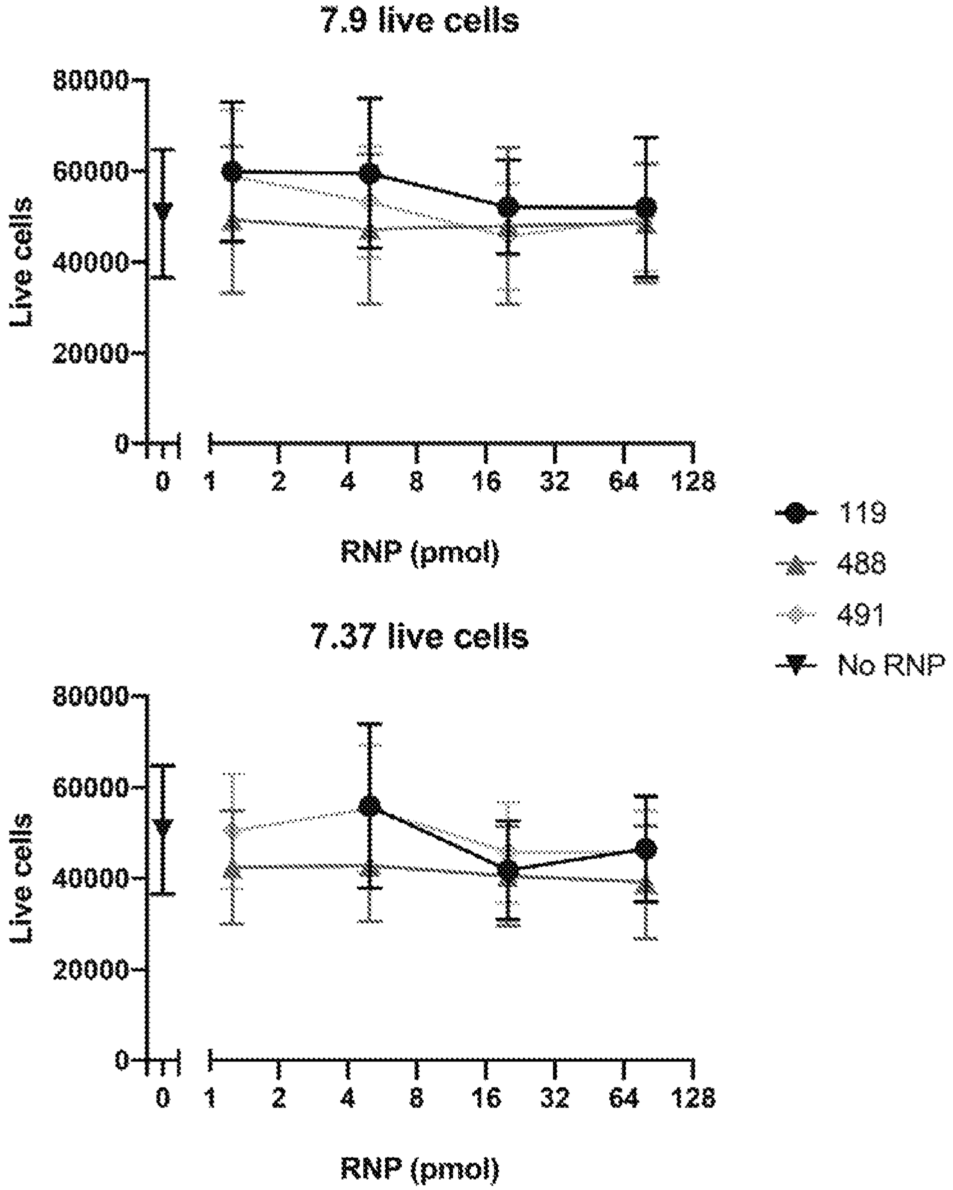
FIG. 31 shows the results of cell viability assays following electroporation of CasX RNPs, as described in Example 24, with spacer 7.9 (top) and 7.37 (bottom). Live cells were counted via DAPI staining and flow cytometry at the time of HLA knockdown analysis.

CasX RNPs composed of either CasX variant 119, 488, or 491 and B2M-targeting guides 174.7.9 or 174.7.37 were nucleofected into Jurkat cells at doses of 1.25, 5, 20, and 80 pmol per 25 uL nucleofection condition. The 1.25 pmol dose for RNP 119.174.7.37 was omitted due to space constraints. RNPs targeting 7.9 eliminated surface HLA in >90% of cells for all protein variants at 20 and 80 pmol doses (FIG. 30). At lower doses CasX 488 and 491 RNPs outperformed CasX 119 RNPs. The 7.37-targeting RNPs appeared to have an editing ceiling of ~80%, with a substantial decrease in editing for 119 at the 5 pmol dose but relatively little decline in editing at even the lowest dose for 488 and 491 (FIG. 30). Across all doses, performance of 488 and 491-based RNPs were nearly identical. None of the RNPs exhibited pronounced RNP-dependent toxicity, as measured by the number of viable cells following treatment with RNP vs a buffer-only control (FIG. 31). 491 potentially had better viability than 488, though the differences were small relative to the standard deviation of the measurement, and it also has better production characteristics (data not shown), making it the preferred candidate for future RNP editing experiments.

Figure 32:
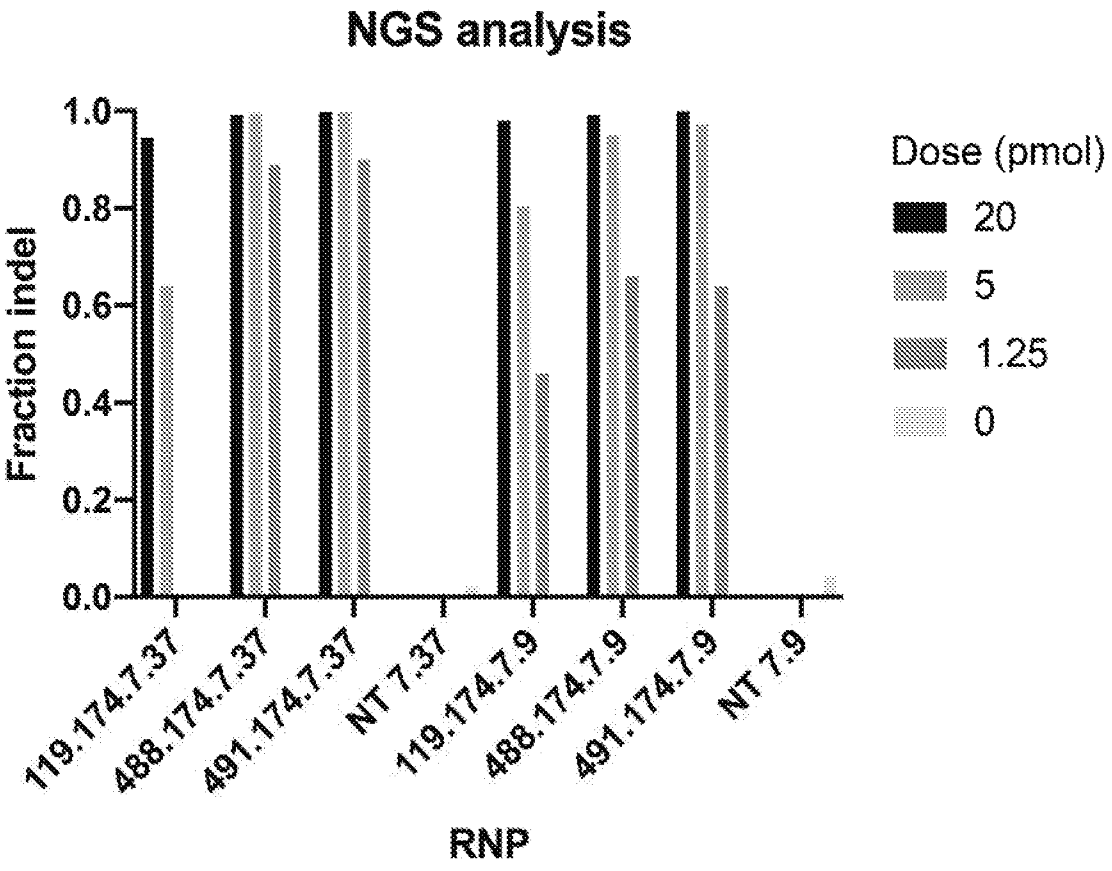
FIG. 32 shows the results of NGS analysis of RNP-mediated editing at the B2M locus, as described in Example 24. Jurkat cells were electroporated with the indicated dose of RNP and analyzed for indel formation via NGS.

To validate the phenotypic knockdown of HLA, deep sequencing of the targeted regions of B2M was performed for the 1.25, 5, and 20 pmol doses of each RNP. The 488.174.7.9 (CasX 488, gNA 174 and spacer 7.9) and 491.174.7.9 (CasX 491, gNA 174 and spacer 7.9) RNPs produced indels in >99% of B2M loci at the 20 pmol dose and in 95% and 97% of B2M loci at the 5 pmol dose, respectively (FIG. 32). The corresponding 7.37 RNPs resulted in >99% indels at both the 20 pmol dose and the 5 pmol dose, indicating that many of the edits at this location still result in functional B2M production and cause the apparent ceiling on phenotypic knockout. The NGS data is consistent with the phenotypic analysis in showing consistently higher editing with 488 and 491 relative to 119-based RNPs, as well as demonstrating efficient editing with very low doses of RNP, in the picomolar range.

Example 25. NHEJ and HDR at TRAC locus

Methods and Materials

RNPs composed of CasX variant 491 and either gRNA 174.15.3 or 174.15.5 were assembled and purified as described above. Templates for homology-directed repair were generated by PCR-amplifying homology arms from human genomic DNA corresponding to roughly 500 bp on either side of the cut site and an eGFP sequence with flanking P2A and T2A self-cleaving peptide sequences (primers used are in Table 18). The fragments were combined using overlap extension PCR, such that the resulting template included the P2A-eGFP-T2A construct in-frame with TRAC. The assembled template sequence was then cloned into a plasmid backbone using PstI and HindIII restriction sites. To produce double-stranded DNA templates, the appropriate plasmid was PCR-amplified using the indicated primers and the product was purified by phenol-chloroform extraction and ethanol precipitation. To produce single-stranded DNA templates, the plasmid was PCR-amplified using the same primers but with one of the two containing a 5' phosphate. The resulting product was purified and digested using lambda exonuclease, which degrades the strand with the 5' phosphate, yielding predominantly ssDNA of the desired strand. The ssDNA product was purified by phenol-chloroform extraction and ethanol precipitation.

Electroporations were carried out largely as described above, except that template DNA diluted in water to the desired concentration for a final volume of 2 uL was added to reactions where appropriate. 50 pmol of RNP was used, and template DNA amounts were varied from 2 to 8 ug for dsDNA and 1 to 4 ug for ssDNA. Seven days post-nucleofection, cells were stained using fluorescent anti-TCR α/β antibodies and assessed for TCR knockout and GFP expression using an Attune Nxt flow cytometer. Jurkat cells have a significant TCR negative population in the absence of editing at the locus. To correct for this, we assumed that cells not expressing TCR were edited at the TRAC locus at a comparable rate to cells with regular TCR expression and presentation and applied the formula E, $=(\mathrm{TCRNeg}_{Obs}-\mathrm{TCRNeg}_{ctrl})/(1-\mathrm{TCRNeg}_{ctrl})$, where E, is corrected editing, $\mathrm{TCRNeg}_{Obs}$ is the fraction of TCR negative cells observed, and $\mathrm{TCRNeg}_{ctrl}$ is the average fraction of TCR negative cells observed in buffer-only controls. No correction was applied to GFP+ cells, though it is possible that silencing of the TCRα locus results in an underestimation of our HDR efficiency.

TABLE 18

Primers used for HDR template generation

| Primer | DNA Sequence |
|---|---|
| 15.3 left homology arm FWD | AGAGAGCTGCAGTGGCCAAGATTGATAGCTT GTGCCTG (SEQ ID NO: 711) |
| 15.3 left homology arm REV | AGAGATCCCCTGCCCTCTCCGGATCCGGACG ACACATTTGTTTGAGAATCAAAATCGGTG (SEQ ID NO: 712) |
| 15.3 right homology arm FWD | GCCGGCGACGTGGAGGAGAACCCCGGCCCCA GTAAGGATTCTGATGTGTATATCACAGAC (SEQ ID NO: 713) |
| 15.3 right homology arm REV | GAGAGAAAGCTTGGGTTTTGGTGGCAATGGA TAAGG (SEQ ID NO: 714) |
| 15.5 left homology arm FWD | AGAGAGCTGCAGGCATCTGGACTCCAGCCTG GG (SEQ ID NO: 715) |
| 15.5 left homology arm REV | GTAAGGAGAGATCCCCTGCCCTCTCCGGATC CGGAATTTGCACATGCAAAGTCAGATTTG (SEQ ID NO: 716) |
| 15.5 right homology arm FWD | CAGGCCGGCGACGTGGAGGAGAACCCCGGCC CCAGTAACAGCATTATTCCAGAAGACACC (SEQ ID NO: 717) |
| 15.5 right homology arm REV | GAGAGAAAGCTTAACTCAGTTGGAGAGACTG AGG (SEQ ID NO: 718) |
| eGFP FWD | GGAGAGGGCAGGGGATCTCTCCTTACTTGTG GCGACGTGGAGGAGAACCCCGGCCCCATGGT GAGCAAGGGCGAGGAG (SEQ ID NO: 719) |
| eGFP REV | GGGGTTCTCCTCCACGTCGCCGGCCTGCTTC AGCAGGCTGAAGTTGGTGGCTCCGGATCCGG ACTTGTACAGCTCGTCCATGCCG (SEQ ID NO: 720) |
| 15.3 amplification FWD | TGGCCAAGATTGATAGCTTG (SEQ ID NO: 721) |
| 15.3 amplification REV | GGGTTTTGGTGGCAATGG (SEQ ID NO: 722) |
| 15.5 amplification FWD | GCATCTGGACTCCAGCCTGGG (SEQ ID NO: 723) |
| 15.5 amplification REV | AACTCAGTTGGAGAGACTGAGG (SEQ ID NO: 724) |

Results

Figure 33:
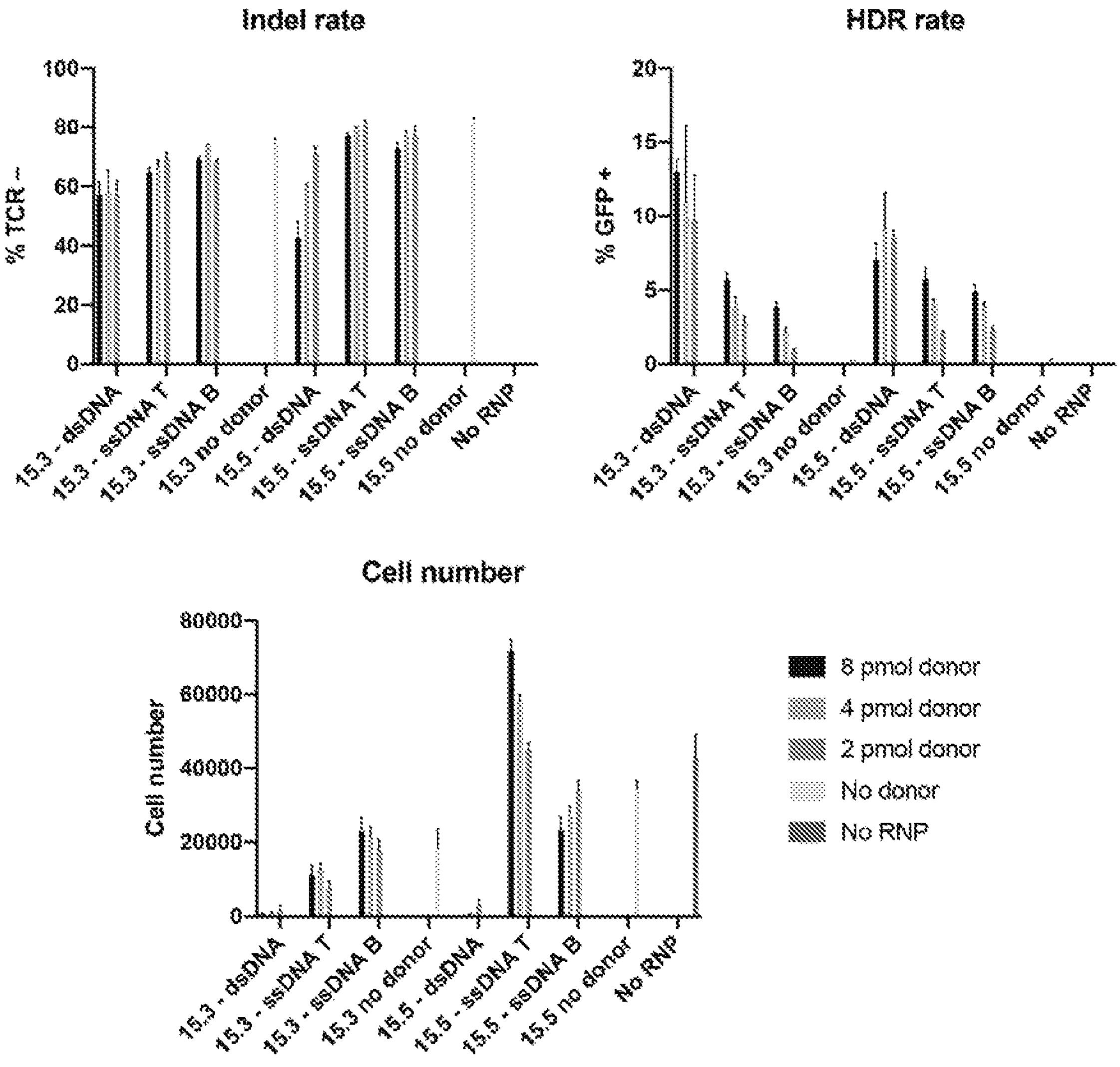
FIG. 33 shows the results of indel and HDR rates by editing at the TRAC locus analyzed for loss of surface expression of TCR a/p, which indicates indel formation, expression of GFP, which indicates HDR, and number of viable cells, as described in Example 25. "T" and "B" indicate whether the ssDNA is the top or bottom strand relative to the direction of the TRAC gene.

TRAC-targeting RNPs in the absence of donor eliminated surface TCR a/3 in 75% and 83% of cells with a 50 pmol dose of spacer 15.3 and 15.5, respectively (FIG. 33). dsDNA appeared to generate the highest HDR rate, reaching over 10%, but also led to the death of nearly all the cells. ssDNA had a much lower effect on viability, in some cases appearing to increase viability relative to no donor and buffer-only controls. HDR rates with ssDNA varied with dose of both RNP and donor from 1%-6%, with the highest rates being achieved with spacer 15.5 and the top strand of the donor DNA. For both spacers, the donor DNA derived from the top strand of the template resulted in higher levels of HDR, though it is not yet clear whether this is a consistent characteristic of ssDNA templates in this system.

Example 26. Simultaneous Editing at B2M and TRAC Loci

Methods and Materials

RNPs were assembled as described above with CasX 491 and guides 174.7.9, 174.7.37, and 174.15.3. RNPs were purified using anion exchange, rather than size-exclusion chromatography.

Electroporations were carried out largely as described above. Co-electroporations of RNPs targeting B2M and TRAC were carried out by mixing equimolar amounts of each RNP in a final volume of 5 uL. RNP doses were made in 2-fold dilutions from 20 pmol to 0.3725 pmol for each RNP alone, and from 20 pmol to 0.625 pmol for the co-electroporation conditions. Molar amounts refer to the individual RNPs, rather than the combined amount of both RNPs in a condition. When measuring TRAC knockout only, a background correction was applied as described above. When determining the fraction of double-knockouts, we assumed that editing at TRAC and B2M were independent of each other and the TCR state of the cell and applied the formula $DblNeg_c=(DblNeg_{obs}-TCRNeg_{ctrl}*HLANeg_{obs})/(1-TCRNeg_{ctrl})$, where $DblNeg_c$ is the corrected double negative fraction, $DblNeg_{obs}$ is the observed TCR-/HLA-fraction for a given sample, $TCRNeg_{ctrl}$ is the total TCR—fraction in the buffer only control, and $HLANeg_{obs}$ is the observed total HLA—fraction for a given sample.

Results

Figure 34:
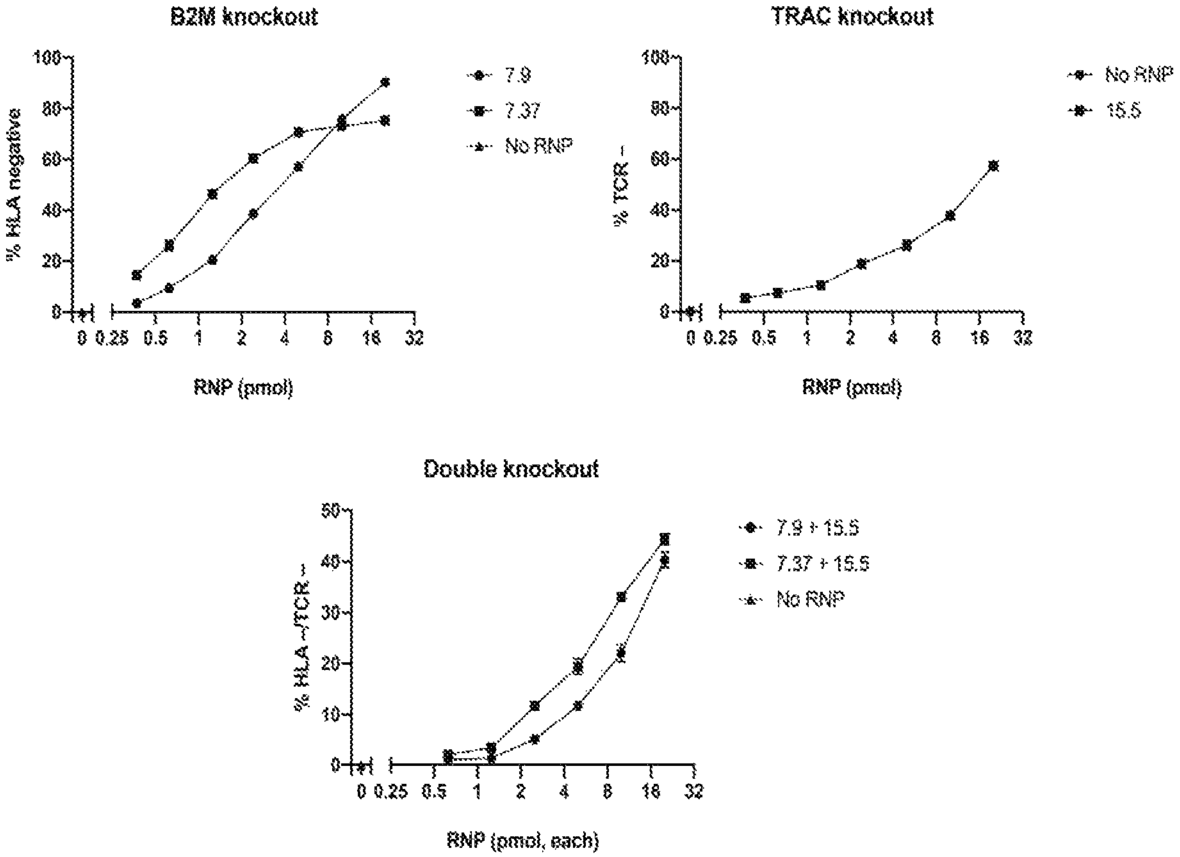
FIG. 34 shows the results of co-editing of B2M and TRAC loci, as described in Example 26. Jurkat cells were electroporated with the indicated dose of RNP, and editing of B2M and TRAC was identified by staining for HLA-1 and TCR a/P and detected by flow cytometry.

Editing at B2M and TRAC showed a good dose response across varying RNP levels. Editing at the TRAC locus was generally lower than at the B2M locus, with a maximum editing rate of 57% (FIG. 34). Double-knockout rates reached 45% at the highest RNP dose. The double-knockout rates at each dose are consistent with the expectation that the two loci are edited independently. The rate of co-editing could likely continue to be improved by increasing the dose of TRAC-targeting RNP to compensate for the reduced efficiency of editing at that site.

SEQUENCE LISTING

The patent contains a lengthy sequence listing. A copy of the sequence listing is available in electronic form from the USPTO web site (https://seqdata.uspto.gov/docdetail?docId=US12551560B2). An electronic copy of the sequence listing will also be available from the USPTO upon request and payment of the fee set forth in 37 CFR 1.19(b)(3).

What is claimed is:

1. A system comprising a CasX protein and a first guide nucleic acid (gNA), wherein the first gNA comprises a targeting sequence complementary to a target nucleic acid sequence of a gene encoding a first protein involved in antigen processing, antigen presentation, antigen recognition, and/or antigen response, wherein the first gNA has a scaffold comprising the sequence of SEQ ID NO: 2238, or a sequence having at least about 70% sequence identity thereto.

2. The system of claim 1, wherein the first protein is an immune cell surface marker or an immune checkpoint protein.

3. The system of claim 1, wherein the first protein is an intracellular protein.

4. The system of claim 1, wherein the first protein is selected from the group consisting of beta-2-microglobulin (B2M), T cell receptor alpha chain constant region (TRAC), class II major histocompatibility complex transactivator (CIITA), T cell receptor beta constant 1 (TRBC1), T cell receptor beta constant 2 (TRBC2), human leukocyte antigen A (HLA-A), human leukocyte antigen B (HLA-B), TGFβ Receptor 2 (TGFβRII), programmed cell death 1 (PD-1), cytokine inducible SH2 (CISH), lymphocyte activating 3 (LAG-3), T cell immunoreceptor with Ig and ITIM domains (TIGIT), adenosine A2a receptor (ADORA2A), killer cell lectin like receptor C1 (NKG2A), cytotoxic T-lymphocyte-associated protein 4 (CTLA-4), T-cell immunoglobulin and mucin domain 3 (TIM-3), and 2B4 (CD244).

5. The system of claim 1, further comprising a second gNA wherein the second gNA has a scaffold comprising the sequence of SEQ ID NO: 2238, or a sequence having at least about 70% sequence identity thereto, and wherein the second gNA comprises a targeting sequence complementary to a target nucleic acid sequence of an immune cell gene encoding a second protein selected from the group consisting of beta-2-microglobulin (B2M), T cell receptor alpha chain constant region (TRAC), class II major histocompatibility complex transactivator (CIITA), T cell receptor beta constant 1 (TRBC1), T cell receptor beta constant 2 (TRBC2), human leukocyte antigen A (HLA-A), human leukocyte antigen B (HLA-B), TGFβRII, PD-1, CISH, LAG-3, TIGIT, ADORA2A, NKG2A, CTLA-4, TIM-3, and CD244, wherein the second protein is different from the first protein.

6. The system of claim 5, wherein the first and/or the second gNA is a guide RNA (gRNA).

7. The system of claim 1, wherein the CasX protein comprises the sequence of SEQ ID NO: 138, or a sequence having at least about 90% sequence identity thereto.

8. The system of claim 1, wherein the CasX protein is a chimeric CasX protein comprising protein domains from two or more different CasX proteins.

9. The system of claim 1, wherein the CasX protein further comprises one or more nuclear localization signals (NLS).

10. The system of claim 1, wherein the CasX protein is capable of forming a ribonuclear protein complex (RNP) with the gNA and wherein an RNP of the CasX protein and the gNA exhibits at least one or more improved characteristics as compared to an RNP of a reference CasX protein of SEQ ID NO:2 and a reference gNA comprising a sequence of any one of SEQ ID NOS: 4-16, wherein the improved characteristics are selected from the group consisting of increased PAM versatility, increased editing activity; improved editing efficiency; and improved RNP stability.

11. The system of claim 10, wherein the RNP comprising the CasX protein and the gNA exhibits greater editing efficiency and/or binding of a target sequence in a cellular assay system comprising a protospacer on a target DNA strand complementary to the gNA and a non-target DNA strand with a PAM sequence, wherein any one of the PAM sequences TTC, ATC, GTC, or CTC is located 1 nucleotide 5' to the non-target strand of the protospacer, when compared to the editing efficiency and/or binding of an RNP comprising a reference CasX protein of SEQ ID NO:2 and a reference gNA comprising the sequence of any one of SEQ ID NOS: 4-16 in a comparable assay system.

12. The system of claim 1, further comprising a donor template nucleic acid.

13. A polynucleotide comprising a sequence that encodes the CasX protein and/or gNA of claim 1.

14. A vector comprising the polynucleotide of claim 13.

15. A method of modifying a target nucleic acid sequence of a gene in cells, wherein the gene encodes a protein involved in antigen processing, antigen presentation, antigen recognition, and/or antigen response, comprising introducing into each cell the system of claim 1 wherein the target nucleic acid sequence of the cells is modified by the CasX protein.

16. The method of claim 15, wherein the cells are modified by introduction of a polynucleotide encoding a chimeric antigen receptor (CAR) with binding affinity for a disease antigen, optionally a tumor cell antigen, and/or are modified by introduction of a polynucleotide encoding an engineered T cell receptor (TCR) comprising a binding domain with binding affinity for a disease antigen, optionally a tumor cell antigen.

17. The method of claim 16, wherein the tumor cell antigen is selected from the group consisting of Cluster of Differentiation 19 (CD19), cluster of differentiation 3 (CD3), CD3d molecule (CD3D), CD3g molecule (CD3G), CD3e molecule (CD3E), CD247 molecule (CD3Z), CD8a molecule (CD8), CD7 molecule (CD7), membrane metalloendopeptidase (CD10), membrane spanning 4-domains A1 (CD20), CD22 molecule (CD22), TNF receptor superfamily member 8 (CD30), C-type lectin domain family 12 member A (CLL1), CD33 molecule (CD33), CD34 molecule (CD34), CD38 molecule (CD38), integrin subunit alpha 2b (CD41), Indian blood group CD44 molecule (CD44), CD47 molecule (CD47), integrin alpha 6 (CD49f), neural cell adhesion molecule 1 (CD56), CD70 molecule (CD70), CD74 molecule (CD74), Xg blood group CD99 molecule (CD99), interleukin 3 receptor subunit/alpha (CD123), prominin 1 (CD133), syndecan 1 (CD138), carbonic anhydrase IX (CAIX), CC chemokine receptor 4 (CCR4), ADAM metallopeptidase domain 12 (ADAM12), adhesion G protein-coupled receptor E2 (ADGRE2), alkaline phosphatase placental-like 2 (ALPPL2), alpha 4 Integrin, angiopoietin-2 (ANG2), B-cell maturation antigen (BCMA), CD44V6, carcinoembryonic antigen (CEA), CEAC, CEA cell adhesion molecule 5 (CEACAMS), Claudin 6 (CLDN6), claudin 18 (CLDN18), C-type lectin domain family 12 member A (CLEC12A), mesenchymal-epithelial transition factor (CMET), cytotoxic T-lymphocyte-associated protein 4 (CTLA4), epidermal growth factor receptor 1 (EGFIR), epidermal growth factor receptor variant III (EGFRvIID), epithelial glycoprotein 2 (EGP-2), epithelial cell adhesion molecule (EGP-40 or EpCAM), EPH receptor A2 (EphA2), ectonucleotide pyrophosphatase/phosphodiesterase 3 (ENPP3), erb-b2 receptor tyrosine kinase 2 (ERBB2), erb-b2 receptor tyrosine kinase 3 (ERBB3), erb-b2 receptor tyrosine kinase 4 (ERBB4), folate binding protein (FBP), fetal nicotinic acetylcholine receptor (AChR), folate receptor alpha (FRalpha or FOLR1), G protein-coupled receptor 143 (GPR143), glutamate metabotropic receptor 8 (GRMS8), glypican-3 (GPC3), ganglioside GD2, ganglioside GD3, human epidermal growth factor receptor 1 (HER1), human epidermal growth factor receptor 2 (HER2), human epidermal growth factor receptor 3 (HER3), Integrin B7, intercellular cell-adhesion molecule-1 (CAM-1), human telomerase reverse transcriptase (hTERT), Interleukin-13 receptor a2 (IL-I13R-a2), K-light chain, Kinase insert domain receptor (KDR), Lewis-Y (LeY), chondromodulin-1 (LECT1), LI cell adhesion molecule (L1CAM), Lysophosphatidic acid receptor 3 (LPAR3), melanoma-associated antigen 1 (MAGE-A1), mesothelin (MSLN), mucin 1 (MUC1), mucin 16 (MUC16), melanoma-associated antigen 3 (MAGE-A3), tumor protein p53 (p53), Melanoma Antigen Recognized by T cells 1 (MART1), glycoprotein 100 (GPI100), Proteinase3 (PR1), ephrin-A receptor 2 (EphA2), Natural killer group 2D ligand (NKG2D ligand), New York esophageal squamous cell carcinoma 1 (NY-ESO-1), oncofetal antigen (h5T4), prostate-specific membrane antigen (PSMA), programmed death ligand 1 (PDL-1), receptor tyrosine kinase-like orphan receptor 1 (ROR1), trophoblast glycoprotein (TPBG), tumor-associated glycoprotein 72 (TAG-72), tumor-associated calcium signal transducer 2 (TROP-2), tyrosinase (TYR), survivin, vascular endothelial growth factor receptor 2 (VEGF-R2), Wilms tumor-1 (WT-1), leukocyte immunoglobulin-like receptor B2 (LILRB2), Preferentially Expressed Antigen In Melanoma (PRAME), T cell receptor beta constant 1 (TRBC1), TRBC2, and T-cell immunoglobulin mucin-3 (TIM-3).

18. The method of claim 17, wherein the CAR and/or the TCR comprises an antigen binding domain selected from the group consisting of a linear antibody, single domain antibody (sdAb), and single-chain variable fragment (scFv).

19. The method of claim 18, wherein the antigen binding domain is an scFv comprising variable heavy (VH) and variable light (VL) and/or heavy chain and light chain CDRs selected from the group consisting of the sequences set forth in SEQ ID NOs: 217-436, or comprising one or more amino acid modifications wherein the scFv retains binding affinity to the tumor antigen, and wherein the modification is selected from the group consisting of a substitution, deletion, and insertion.

20. The method of claim 15, wherein the cells are human cells.

21. The method of claim 15, wherein the cells are selected from the group consisting of progenitor cells, hematopoietic stem cells, and pluripotent stem cells.

22. The method of claim 15, wherein the cells are immune cells.

23. The method of claim 22, wherein the immune cells are selected from the group consisting of T cells, tumor infiltrating lymphocytes, NK cells, B cells, monocytes, macrophages, and dendritic cells.

24. The method of claim 23, wherein the T cells are selected from the group consisting of CD4+ T cells, CD8+ T cells, cytotoxic T cells, terminal effector T cells, memory T cells, naive T cells, regulatory T cells, natural killer T cells, gamma-delta T cells, cytokine-induced killer (CIK) T cells, tumor infiltrating lymphocytes, and a combination thereof.

25. The method of claim 15, wherein the modifying comprises introducing an insertion, deletion, substitution, duplication, or inversion of one or more nucleotides in the target nucleic acid sequence of the cells, resulting in a knock-down or knock-out of a gene in the cells of the population encoding one or more proteins selected from the group consisting of B2M, TRAC, CIITA, TRBC1, TRBC2, HLA-A, HLA-B, TGFBRII, PD-1, CISH, LAG3, TIGIT, ADORA2A, NKG2A, CTLA-4, TIM-3, and CD244, wherein the cells of the population have been modified such that at least about 50% of the cells do not express a detectable level of the one or more proteins in comparison to a cell that has not been modified.

26. The method of claim 15, wherein the method comprises insertion of a donor template into one or more break site(s) of the target nucleic acid sequence of the cells, wherein the insertion of the donor template is mediated by homology-directed repair (HDR) or homology-independent targeted integration (HITT).

27. The method of claim 26, wherein insertion of the donor template results in a knock-down or knock-out of one or more genes in the cells encoding one or more proteins selected from the group consisting of B2M, TRAC, CITA, TRBC1, TRBC2, HLA-A, HLA-B, TGFBRII, PD-1, CISH, LAG-3, TIGIT, ADORA2A, NKG2A, CTLA-4, TIM-3, and CD244.

28. The method of claim 15, wherein the method is conducted ex vivo on the population of cells.

29. The method of claim 15, wherein the method is conducted in vivo in a subject.

30. The method of claim 29, wherein the subject is a human or a non-human primate.

31. A population of cells modified ex vivo by the method of claim 15.

32. A method of providing anti-tumor immunity in a subject, the method comprising administering to the subject a therapeutically effective amount of the population of cells of claim 31.

33. The method of claim 32, wherein the administering of the therapeutically effective amount of the population of cells results in an improvement in a clinical parameter or endpoint in the subject selected from one or more of tumor shrinkage as a complete, partial or incomplete response; time-to-progression, time to treatment failure, biomarker response; progression-free survival; disease free-survival; time to recurrence; time to metastasis; time of overall survival; improvement of quality of life; and improvement of symptoms.

34. A method of treating a subject in need thereof, comprising administering to the subject a therapeutically effective amount of the population of cells of claim 31.

35. The method of claim 34, wherein the subject has cancer or an autoimmune disease.

36. The method of claim 35, wherein the cancer expresses a tumor cell antigen.

37. The method of claim 36, wherein the cells express a CAR, wherein the CAR has a specific binding affinity to the tumor cell antigen.

* * * * *